US008551984B2

(12) United States Patent
Altman et al.

(10) Patent No.: US 8,551,984 B2
(45) Date of Patent: Oct. 8, 2013

(54) AMINOPYRIMIDINES AS SYK INHIBITORS

(75) Inventors: Michael D. Altman, Needham, MA (US); Brian M. Andresen, Sharon, MA (US); Kenneth L. Arrington, Revere, MA (US); Jason Burch, Westmount (CA); Kaleen Konrad Childers, Newton, MA (US); Bernard Cote, Notre-Dame-de-l'Ile-Perrot (CA); Maria Emilia Di Francesco, Brookline, MA (US); Anthony Donofrio, Cambridge, MA (US); Kristina Dupont-Gaudet, Vaudreuil-Dorion (CA); John Michael Ellis, Needham, MA (US); Christian Fischer, Natick, MA (US); Daniel Guay, Lachine (CA); David Joseph Guerin, Natick, MA (US); Andrew M. Haidle, Cambridge, MA (US); Solomon Kattar, Arlington, MA (US); Sandra Lee Knowles, Boston, MA (US); Chaomin Li, Boston, MA (US); Jongwon Lim, Lexington, MA (US); Michelle R. Machacek, Brookline, MA (US); Alan B. Northrup, Reading, MA (US); Brendan M. O'Boyle, Boston, MA (US); Ryan D. Otte, Natick, MA (US); Michael H. Reutershan, Brookline, MA (US); Eric Romeo, Alliston, MA (US); Adam J. Schell, Newton, MA (US); Tony Siu, Brookline, MA (US); Kerrie B. Spencer, Woonsocket, RI (US); Brandon M. Taoka, Brookline, MA (US); B. Wesley Trotter, Newton Highland, MA (US); Hua Zhou, Acton, MA (US)

(73) Assignees: Merck Sharp & Dohme Corp., Rahway, NJ (US); Merck Canada Inc., Kirkland, Quebec (CA)

( * ) Notice: Subject to any disclaimer, the term of this patent is extended or adjusted under 35 U.S.C. 154(b) by 126 days.

(21) Appl. No.: 12/968,608

(22) Filed: Dec. 15, 2010

(65) Prior Publication Data
US 2011/0245205 A1 Oct. 6, 2011

Related U.S. Application Data

(60) Provisional application No. 61/287,267, filed on Dec. 17, 2009.

(51) Int. Cl.
*C07D 417/12* (2006.01)
*A61K 31/497* (2006.01)

(52) U.S. Cl.
USPC ............. 514/212.08; 514/217.06; 514/235.8; 514/252.02; 514/252.19; 514/275; 540/524; 540/601; 544/122; 544/238; 544/295; 544/296; 544/331

(58) Field of Classification Search
USPC ................. 540/524, 601; 544/122, 238, 295, 544/296, 331; 514/212.08, 217.06, 235.8, 514/252.02, 252.19, 275
See application file for complete search history.

(56) References Cited

U.S. PATENT DOCUMENTS

| 7,449,458 | B2 | 11/2008 | Bhamidipati et al. |
| 7,485,724 | B2 | 2/2009 | Singh et al. |
| 7,538,108 | B2 | 5/2009 | Singh et al. |
| 7,557,210 | B2 | 7/2009 | Singh et al. |
| 2008/0139535 | A1 | 6/2008 | Anandan et al. |

FOREIGN PATENT DOCUMENTS

| EP | 1854793 A1 | 11/2007 |
| WO | 02/096905 A1 | 12/2002 |
| WO | 02/102313 A2 | 12/2002 |
| WO | 2004/005283 A1 | 1/2004 |
| WO | 2004/087698 A2 | 10/2004 |
| WO | 2006/129100 A1 | 7/2006 |
| WO | 2007/117692 A2 | 10/2007 |
| WO | 2008/024634 A1 | 2/2008 |
| WO | 2008/073687 A2 | 6/2008 |
| WO | 2004/087699 A2 | 10/2008 |
| WO | 2008/137605 A1 | 11/2008 |
| WO | 2009/012421 A1 | 1/2009 |
| WO | 2009/032861 A1 | 3/2009 |
| WO | 2009/103032 A1 | 8/2009 |
| WO | 2009/122180 A1 | 10/2009 |
| WO | 2009/145856 A1 | 12/2009 |
| WO | 2011/075515 A1 | 6/2011 |
| WO | WO 2011/086086 | * 7/2011 |

OTHER PUBLICATIONS

Pearce et al., Failure modes in anticancer drug discovery and development, Cancer Drug Design and Discovery Edited by Stephen Neidle, Chapter 18, pp. 424-435 (2008).*
Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Pamuk et al., Spleen tyrosine kinase inhibition in the treatment of autoimmune, allergic and autoinflammatory diseases, Arthritis Research & Therapy, (2010), 12:222, pp. 1-11.*
Written Opinion issued by the International Searching Authority in connection with PCT International Application No. PCT/US2010/060454, filed Dec. 15, 2010.

(Continued)

*Primary Examiner* — Deepak Rao
(74) *Attorney, Agent, or Firm* — Eric A. Meade; Valerie J. Camara

(57) ABSTRACT

The present invention provides novel pyrimidine amines of formula (I) which are potent inhibitors of spleen tyrosine kinase, and are useful in the treatment and prevention of diseases mediated by said enzyme, such as asthma, COPD and rheumatoid arthritis.

40 Claims, No Drawings

(56) References Cited

OTHER PUBLICATIONS

Matsubara, S., et al., "Inhibition of Spleen Tyrosine Kinase Prevents Mast Cell Activation and Airway Hyperresponsiveness", American Journal of Respiratory and Critical Care Medicine, 2006, vol. 173, pp. 56-63.

Penton, P.C., et al., "Spleen Tyrosine Kinase Inhibition Attenuates Airway Hyperresponsiveness and pollution-induced enhanced airway response in a chronic mouse model of asthma", Journal of Allergy Clinical Immunology, Feb. 2013, vol. 131, No. 2, pp. 512-520.

Krishnan, S., et al., "Differential Expression and Molecular Associations of Syk in Systemic Lupus Erythematosus T Cells," The Journal of Immunology, 2008, vol. 181, pp. 8145-8152.

Deng, G., et al., "Suppression of Skin and Kidney Disease by Inhibition of Spleen Tyrosine Kinase in Lupus-Prone Mice," Arthritis & Rheumatism, Jul. 2010, vol. 62, No. 7, pp. 2086-2092.

Translation of Official Action mailed Nov. 9, 2012 in Japanese Patent Application No. 2012-544746.

\* cited by examiner

AMINOPYRIMIDINES AS SYK INHIBITORS

BACKGROUND OF THE INVENTION

Spleen Tyrosine Kinase (Syk) is a protein tyrosine kinase which has been described as a key mediator of immunoreceptor signalling in a host of inflammatory cells including mast cells, B-cells, macrophages and neutrophils. These immunoreceptors, including Fc receptors and the B-cell receptor, are important for both allergic diseases and antibody-mediated autoimmune diseases and thus pharmacologically interfering with Syk could conceivably treat these disorders.

Allergic rhinitis and asthma are diseases associated with hypersensitivity reactions and inflammatory events involving a multitude of cell types including mast cells, eosinophils, T cells and dendritic cells. Following exposure to allergen, high affinity immunoglobulin receptors for IgE and IgG become cross-linked and activate downstream processes in mast cells and other cell types leading to the release of pro-inflammatory mediators and airway spasmogens. In the mast cell, for example, IgE receptor cross-linking by allergen leads to release of mediators including histamine from pre-formed granules, as well as the synthesis and release of newly synthesized lipid mediators including prostaglandins and leukotrienes.

Syk kinase is a non-receptor linked tyrosine kinase which is important in transducing the downstream cellular signals associated with cross-linking Fc.epsilon.R1 and or Fc.epsilon.R1 receptors, and is positioned early in the signalling cascade. In mast cells, for example, the early sequence of Fc.epsilon.R1 signalling following allergen cross-linking of receptor-IgE complexes involves first Lyn (a Src family tyrosine kinase) and then Syk. Inhibitors of Syk activity would therefore be expected to inhibit all downstream signalling cascades thereby alleviating the immediate allergic response and adverse events initiated by the release of pro-inflammatory mediators and spasmogens (Wong et al 2004, Expert Opin. Investig. Drugs (2004) 13 (7) 743-762).

Recently, it has been shown that the Syk kinase inhibitor R112 (Rigel), dosed intranasally in a phase I/II study for the treatment of allergic rhinitis, gave a statistically significant decrease in $PGD_2$, a key immune mediator that is highly correlated with improvements in allergic rhinorrhea, as well as being safe across a range of indicators, thus providing the first evidence for the clinical safety and efficacy of a topical Syk kinase inhibitor. (Meltzer, Eli O.; Berkowitz, Robert B.; Grossbard, Elliott B, Journal of Allergy and Clinical Immunology (2005), 115(4), 791-796). In a more recent phase II clinical trial for allergic rhinitis (Clinical Trials.gov Identifier NCT0015089), R112 was shown as having a lack of efficacy versus placebo.

Rheumatoid Arthritis (RA) is an auto-immune disease affecting approximately 1% of the population. It is characterised by inflammation of articular joints leading to debilitating destruction of bone and cartilage. Recent clinical studies with Rituximab, which causes a reversible B cell depletion, (J. C. W. Edwards et al 2004, New Eng. J. Med. 350: 2572-2581) have shown that targeting B cell function is an appropriate therapeutic strategy in auto-immune diseases such as RA. Clinical benefit correlates with a reduction in auto-reactive antibodies (or Rheumatoid. Factor) and these studies suggest that B cell function and indeed auto-antibody production are central to the ongoing pathology in the disease.

Studies using cells from mice deficient in the Spleen Tyrosine Kinase (Syk) have demonstrated a non-redundant role of this kinase in B cell function. The deficiency in Syk is characterised by a block in B cell development (M. Turner et al 1995 Nature 379: 298-302 and Cheng et al 1995, Nature 378: 303-306). These studies, along with studies on mature B cells deficient in Syk (Kurasaki et al 2000, Immunol. Rev. 176:19-29), demonstrate that Syk is required for the differentiation and activation of B cells. Hence, inhibition of Syk in RA patients is likely block B cell function and thereby reduce Rheumatoid Factor production. In addition to the role of Syk in B cell function, and of further relevance to the treatment of RA, is the requirement for Syk activity in Fc receptor (FcR) signalling. FcR activation by immune complexes in RA has been suggested to contribute to the release of multiple pro-inflammatory mediators.

The present invention relates to novel compounds, which are inhibitors of Syk kinase activity. These compounds therefore have potential therapeutic benefit in the treatment of disorders associated with inappropriate Syk activity, in particular in the treatment and prevention of disease states mediated by Syk. Such disease states may include inflammatory, allergic and autoimmune diseases, for example, asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, idiopathic thrombocytopenic purpura (ITP), multiple sclerosis, cancer, HIV and lupus.

SUMMARY OF THE INVENTION

The present invention provides novel compounds that are potent inhibitors of SYK as well as pharmaceutical compositions containing them. As SYK inhibitors compounds of the present invention are useful in the treatment and prevention of diseases and disorders mediated by the SYK protein; such diseases and disorders include, but are not limited to, asthma, COPD, rheumatoid arthritis, cancer and idiopathic thrombocytopenic purpura.

DETAILED DESCRIPTION OF THE INVENTION

The present invention provides compounds of formula I and pharmaceutically acceptable salts thereof:

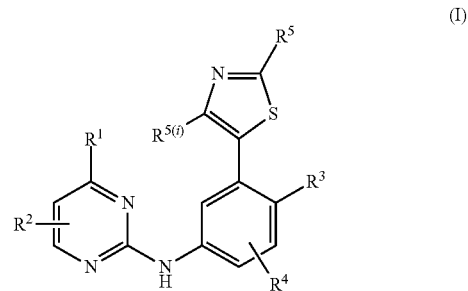

(I)

wherein:
$R^1$ is selected from the group consisting of (a) hydrogen, (b) halogen, (c) CN, (d) $C_{1-6}$ alkyl optionally substituted with one or more groups independently selected from the group consisting of $OR^a$, $C_{3-6}$cycloalkyl, and halogen, (e) $C_{2-6}$ alkenyl optionally substituted with $OC_{1-6}$alkyl, (f) $C_{2-6}$ alkynyl, (g) $C_{3-6}$ cycloalkyl, (h) OH, (i) —O—$C_{1-6}$ alkyl optionally substituted with one or more groups independently selected from (i) aryl, (ii) 5- or 6-membered heteroaryl optionally substituted with one or more groups independently selected from $C_{1-6}$ alkyl, (iii) 4- to 8-membered heterocyclyl optionally substituted with one or more groups independently selected from oxo, halogen, $C_{1-6}$ alkyl, (iv) —$CO_2R^a$, (v) —$CONR^bR^c$, (vi) —$NR^bR^c$, and (vii) —$OR^a$, (j) -A-X, wherein A is a bond or O, X is selected from the group consisting of (i) 4- to 8-membered heterocyclyl optionally substituted with one or more groups independently selected from halogen, $C_{1-6}$ alkyl, —$C_{1-6}$ haloalkyl, —$C_{1-6}$ hydroxyalkyl, $COR^a$, $CO_2R^a$, (ii) $C_{3-6}$ cycloalkyl optionally substituted with one or more groups independently selected from $C_{1-6}$ alkyl, —$OR^a$, —$CO_2R^a$, —$NR^bR^c$, and (iii) heteroaryl optionally substituted with a benzyl which is optionally substituted with $OR^a$, (k) O—$CH_2C\equiv$C-pyrimidinyl, (l) —$S(O)_n$—$C_{1-6}$ alkyl, (m) —$COR^a$, (n) —$CO_2R^a$, (o) —$CONR^bR^c$, and (p) —$NR^bR^c$;

$R^2$ is selected from the group consisting of (a) H, (b) halogen, (c) $C_{1-6}$ alkyl, (d) O—$C_{1-6}$ alkyl, (e) $C_{1-6}$ haloalkyl and (f) O—$C_{1-6}$ haloalkyl; or $R^1$ and $R^2$ on adjacent carbon atoms together represent $(CH_2)_{3-4}$;

$R^3$ is H, halogen, $OR^a$, or $C_{1-4}$alkyl, $R^4$ is selected from the group consisting of (a) H, (b) halogen, (c) $C_{1-6}$ alkyl optionally substituted with one or more groups independently selected from (i) halogen, (ii) $OR^a$, (iii) OC(O) $R^a$, (iv) $NR^bR^c$, (v) NHC(O)$R^a$, and (vi) NHC(O)$NHR^b$; (d) $C_{2-6}$ alkenyl, (e) $C_{2-6}$ alkynyl, (f) $C_{3-6}$ cycloalkyl, (g) $OR^a$, (h) $NO_2$, (i) $NR^bR^c$, (j) NHC(O)$R^a$, (k) NHC(O)$NHR^b$, and (l) NHC(O)NHC(O)$NR^bR^c$;

$R^5$ is selected from the group consisting of (a) H, (b) halogen, (c) $C_{1-8}$alkyl, $C_{2-6}$alkenyl, $C_{2-6}$ alkynyl, each of which is optionally substituted with one or more groups independently selected from $R^y$, (d) $C_{3-12}$ carbocycle, or a carbon-linked 3- to 12-membered heterocyclyl each optionally substituted with one or more groups independently selected from $R^z$, (e) heteroaryl optionally substituted with $C_{1-3}$ alkyl (optionally substituted with one or more OH or CN or heterocycle), (f) —C(O)$R^a$, (g) —C(O)$_2R^a$, and (h) —C(O)$NR^bR^c$, $R^{5(i)}$ is selected from the group consisting of H and $C_{1-3}$alkyl;

$R^a$ is selected from the group consisting of (a) H, (b) $C_{1-6}$ alkyl optionally substituted with one or more groups independently selected from (i) halogen, (ii) CN, (iii) OH, (iv) OC1-4alkyl, (v) heterocyclyl optionally substituted with oxo, (vi) C(O) $C_{1-6}$alkyl optionally substituted with OH, (vii) $CO_2H$, (viii) $CO_2C_{1-6}$alkyl, (ix) $CONR^{b(i)}R^c(i)$, (x) $SO_2C_{1-6}$alkyl, (xi) —$NR^{b(i)}R^{c(i)}$, (xii) $NR^b(i)$ C(O)$NR^{b(i)}R^{c(i)}$, (xiii) phenyl, and (xiv) heteroaryl optionally substituted with OH, (c) $C_{2-6}$alkenyl, (d) $C_{3-6}$ cycloalkyl optionally substituted with one or more groups independently selected from (i) OH, (ii) $CO_2H$, (iii) $CO_2C_{1-6}$alkyl, (iv) $CONR^{b(i)}R^{c(i)}$, (e) phenyl optionally substituted with one or more groups independently selected from (i) $C_{2-6}$alkynyl, (ii) CN, (iii) halogen, (iv) OH, (v) OC(O)$C_{1-6}$alkyl, (vi) $CO_2H$, (vii) $CO_2C_{1-6}$alkyl, (f) heteroaryl optionally substituted with one or more groups independently selected from $C_{1-6}$alkyl, $C_{1-6}$haloalkyl, $(CH_2)_{0-2}CO_2H$, OH, halogen, phenyl optionally substituted with $CO_2H$, and (g) heterocyclyl optionally substituted with oxo, $R^b$ and $R^c$ are independently selected from the group consisting of (a) H, (b) $C_{1-6}$ alkyl optionally substituted with one or more groups independently selected from (i) $OR^a$, (ii) halogen, (iii) heterocyclyl optionally substituted with oxo, OH, $C_{1-6}$ alkyl (optionally substituted with OH), (iv) $C_{3-6}$ cycloalkyl optionally substituted with one or two groups selected from $C_{1-4}$alkyl, $CH_2OH$, $CONR^{b(i)}R^{c(i)}$, and $CO_2R^a$, (v) heteroaryl optionally substituted with $C_{1-6}$alkyl optionally substituted with OH, $CO_2H$ or heteroaryl optionally substituted with a heteroaryl, (vi) $SO_2NR^{b(i)}R^{c(i)}$, (vii) $SO_2C_{1-4}$alkyl, (viii) $CONR^{b(i)}R^c(i)$, (ix) $NR^{b(i)}R^{c(i)}$, (x) $CO_2R^a$, (xi) aryl optionally substituted with one or more groups selected from halogen, $OR^a$, $C_{1-6}$alkyl (optionally substituted with halogen, heterocycle (optionally substituted with oxo), or $OR^a$), $SO_2NH_2$, and heteroaryl optionally substituted with $CH_2OH$, (xii) $SO_3H$, (xiii) $R^b(OCONR^{b(i)}R^{c(i)}$, (xiv) CN, and (xv) NHC(O)$R^a$, (c) $C_{3-6}$ alkenyl optionally substituted with F; (d) $C_{3-6}$ cycloalkyl (optionally fused to a benzene ring) optionally substituted with one or more groups independently selected from (i) $C_{1-4}$alkyl, (ii) $OR^a$, (iii) $CH_2OH$, (iv) $CO_2R^a$, and (v) $CONR^{b(i)}R^{c(i)}$, (e) aryl optionally substituted with one or two groups independently selected from (i) $C_{1-6}$alkyl (optionally substituted with $OR^a$), (ii) CN, (iii) ORE, (iv) halogen, and (v) $OCOC_{1-4}$alkyl; (f) heteroaryl optionally substituted with one or more groups independently selected from (i) $OR^a$, (ii) $CO_2R^a$ and (iii) $C_{1-6}$ alkyl optionally substituted with OH, (g) heterocyclyl optionally substituted with one or more groups independently selected from (i) oxo, (ii) OH and (iii) $C_{1-6}$ alkyl, or $R^b$, $R^c$ and the nitrogen atom to which they are attached together form a 5-, 6- or 7-membered heterocycle having 0 or 1 additional heteroatom selected from 0, P(O)($C_{1-6}$alkyl), S(O)$_n$ and N—$R^x$, and optionally substituted with one or more groups independently selected from (a) oxo, (b) thioxo, (c) $C_{1-6}$ alkyl optionally substituted with one or more groups independently selected from (i) $OR^a$, (ii) $CO_2R^a$, (iii) OP(O) $(C_{1-6}$alkyl)$_2$, (iv) aryl, and (v) halogen, (d) $OR^a$, (e) C(O)$R^a$, (f) C(O)$_2R^a$, (g) $CONR^{b(i)}R^{c(i)}$, (h) P(O)(OH)$_2$, (i) $SO_2R^a$, and (j) CN, or $R^b$, $R^c$ and the nitrogen atom to which they are attached together form

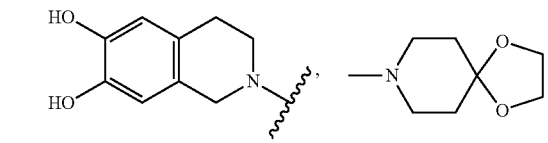

wherein W is CH or N;

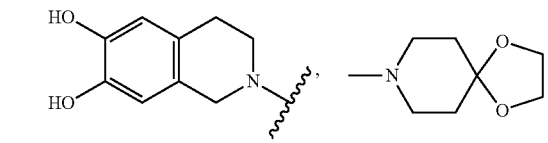

$R^b(i)$ and $R^{c(i)}$ are independently selected from the group consisting of (a) H and (b) $C_{1-6}$ alkyl optionally substituted with OH, $CO_2H$ or $CO_2C_{1-6}$alkyl; or $R^b(i)$, $R^{c(i)}$ and the nitrogen atom to which they are attached together form a 5- or 6-membered heterocycle having 0 or 1 additional heteroatom selected from O, S and N—$R^x$, and optionally substituted with one or more groups independently selected from oxo, $R^u$ is selected from the group consisting of (a) $C_{1-6}$ alkyl optionally substituted with one to three groups selected from halogen, OH, $SO_2R^a$, $CONR^bR^c$, $NR^bR^c$, phenyl, heterocyclyl and heteroaryl, (b) $C_{3-8}$ cycloalkyl optionally substituted with OH, $CO_2R^a$, —COM-12, (c) heterocycle optionally substituted with oxo, (d) aryl optionally substituted with $C_{2-6}$alkynyl, CN, halogen, $OR^a$, and (e) heteroaryl optionally substituted with OH;

$R^x$ is selected from the group consisting of (a) H, (b) $C_{1-6}$ alkyl optionally substituted with heterocycle, (c) phenyl optionally substituted with OH or $OC_{1-4}$alkyl, (d) —C(O)—$C_{1-6}$ alkyl, (e) —C(O)$_2$—$C_{1-6}$ alkyl, (f) —C(O)$NH_2$, —C(O)NH—$C_{1-6}$ alkyl, —C(O)N($C_{1-6}$ alkyl)$_2$, (g) —C(O)$_2$NHC(O)NH$_2$, —C(O)$_2$NHC(O)NH—$C_{1-6}$ alkyl, —C(O)$_2$NHC(O)N($C_{1-6}$ alkyl)$_2$, (h) —SO$_2$—$C_{1-6}$ alkyl (optionally substituted with halogen), —SO$_2$-heteroaryl (optionally substituted with alkyl), (i) —S(O)$_2$NH$_2$, —S(O)$_2$NH—$C_{1-6}$ alkyl, —S(O)$_2$N($C_{1-6}$ alkyl)$_2$, and (j) —SO$_2$NHC(O)$_2$—$C_{1-6}$ alkyl;

$R^y$ is selected from the group consisting of (a) aryl optionally substituted with one or more groups independently selected from (i) halogen, (ii) $C_{1-6}$alkyl optionally substituted with OH or CO$_2$R$^a$, (iii) $C_{2-6}$alkenyl optionally substituted with CO$_2$R$^a$, (iv) phenyl optionally substituted with CO$_2$R$^a$, (v) COR$^a$, (vi) CO$_2$R$^a$, (vii) CONR$^b$R$^c$, (viii) OR$^a$, (ix) S(O)$_n$R$^a$, (x) SO$_2$NR$^b$R$^c$, (xi) SO$_2$NHC(O)R$^a$, (xii) NO$_2$, and (xiii) NHC(O)R$^a$, (b) heteroaryl optionally substituted with one or more groups independently selected from (i) halogen, (ii) $C_{1-6}$ alkyl optionally substituted with CO$_2$R$^a$, (iii) $C_{3-6}$ cycloalkyl, (iv) aryl optionally substituted with CO$_2$R$^a$, (v) CONR$^b$R$^c$, (vi) OR$^a$, (vii) SO$_2$R$^a$, and (viii) CO$_2$R$^a$, (c) $C_{3-8}$ cycloalkyl optionally substituted with one or more groups independently selected from (i) $C_{1-6}$ alkyl, (ii) CO$_2$R$^a$, and (iii) NR$^b$R$^c$, (d) $C_{6-8}$cycloalkenyl (optionally substituted with CO$_2$R$^a$), (e) halogen, (f) CN, (g) —C(O)R$^a$, (h) —C(O)$_2$R$^a$, (i) C(O)CO$_2$R$^a$, (j) —C(O)NR$^b$R$^c$, (k) —C(O)NHC(O)NR$^b$R$^c$, (l) —OR$^a$, (m) OC(O)R$^a$, (n) —NR$^b$R$^c$, (o) —NHC(O)R$^u$, (p) —NHC(O)NR$^b$R$^c$, (q) —NHC(O)NHC(O)NH$_2$, (r) —NHSO$_m$R$^a$, (s) —NHSO$_2$NR$^b$R$^c$, (t) SO$_n$R$^a$, (u) —SO$_2$NR$^b$R$^c$, (v) —SO$_2$NHC(O)R$^a$, (w) —SO$_2$NHC(O)$_2$R$^a$, (x) SO$_3$H, (y) —P(O)(OR$^a$)$_2$, (z) CONHOH, and (aa) heterocyclyl optionally substituted with one or more groups independently selected from oxo, thioxo, $C_{1-6}$alkyl, and CO$_2$R$^a$;

$R^z$ is selected from the group consisting of (a) a group selected from $R^y$, (b) $C_{1-6}$ alkyl optionally substituted with one or more groups independently selected from halogen, NR$^b$R$^c$, OR$^a$, CN, phenyl (optionally substituted with $C_{1-6}$alkanoic acid), CONR$^b$R$^c$C, and —CO$_2$R$^a$, (c) oxo, and (d) =NOR$^a$;

m is 1 or 2, n is 0, 1 or 2.

In one group of formula (I) are compounds wherein R$^2$ and R$^{5(i)}$ are each hydrogen. In a second group of formula (I) are compounds wherein R$^2$, R$^3$ and R$^{5(i)}$ are each hydrogen.

In another group of formula (I) [Group R5-I] are compounds wherein R$^5$ is selected from (a) $C_{1-8}$ alkyl, optionally substituted with one or more groups independently selected from R$^y$, and (b) $C_{3-12}$ carbocycle or 3- to 12-membered heterocyclyl each optionally substituted with one or more groups independently selected from R$^z$.

In another group of formula (I) [Group R5-II] are compounds wherein R$^5$ is selected from:

[I] $C_{1-8}$alkyl;

[II] $C_{1-8}$haloalkyl;

wherein said alkyl and haloalkyl are each optionally substituted with one to four groups independently selected from (A) $C_{3-4}$cycloalkyl optionally substituted with one or two groups independently selected from OH, benzyloxy and $C_{1-3}$alkyl; (B) phenyl optionally substituted with one or two groups independently selected from (i) O—$C_{1-3}$alkyl optionally substituted with CO$_2$R$^{a(a)}$, (CH$_2$)$_{0-1}$CO$_2$H, (iii) SO$_2$CH$_3$, and (iv) C(O)C$_{1-3}$alkyl; (C) heteroaryl optionally substituted with one or two groups independently selected from $C_{1-3}$alkyl, halogen, OC$_{1-3}$alkyl, (CH$_2$)$_{0-2}$CO$_2$H, SO$_2$CH$_3$ and SO$_2$Ph; (D) heterocycle optionally substituted with one or two groups independently selected from oxo and CO$_2$R$^{a(a)}$, $C_{1-3}$alkyl, and halogen, (E) CN, (F) OR$^{a(a)}$, (G) OC(O)C$_{1-4}$alkyl, (H) COC$_{1-4}$alkyl, (I) CO$_2$R$^{a(a)}$, (J) CONR$^{a(a)}$R$^{a(a)}$, (K) CO-4-morpholinyl, (L) NR$^{b(a)}$R$^c$C(a), (M) NHC(O)NH$_2$, (N)NHSO$_2$C$_{1-4}$alkyl, (O)NH SO$_2$C$_{1-4}$haloalkyl, (P)NHSO$_2$NH$_2$, (O)SO$_2$NH$_2$, (R)SO$_2$C$_{1-4}$alkyl;

[III] $C_{3-10}$ carbocycle, and

[IV] 4- to 10-membered heterocyclyl;

wherein said carbocycle and heterocyclyl are each optionally substituted with one to six groups independently selected from (A1) $C_{1-6}$alkyl, (A2) $C_{1-6}$haloalkyl wherein each (A1) and (A2) is optionally substituted with one or two groups independently selected from OH, CN, NH$_2$, CONH$_2$ and CO$_2$R$^{a(a)}$, (B) aminocyclopropyl, (C1) $C_{3-6}$cycloalkyl, (C2) $C_{6-8}$cyclohexenyl, each of (C1) and (C2) is optionally substituted with CO$_2$R$^{a(a)}$; (D) phenyl optionally substituted with one or two groups independently selected from fluoro, methyl and CO$_2$R$^{a(a)}$, (E) benzyl, (F) heteroaryl selected from pyridyl optionally substituted with CO$_2$R$^{a(a)}$ and 1,3,4-oxadiazolyl optionally substituted with methyl, (G) halogen, (H) CN, (I) OH, (J) OC$_{1-4}$alkyl optionally substituted with OH, (K) oxo, (L1) COC$_{1-4}$alkyl, (L2) COC$_{1-4}$haloalkyl, each (L1) and (L2) is optionally substituted with one to three groups independently selected form OR$^{a(a)}$, CN, NR$^{a(a)}$R$^{a(a)}$, NHCONH$_2$, CO$_2$R$^{a(a)}$, CONR$^{a(a)}$R$^{a(a)}$, SO$_2$CH$_3$, heteroaryl optionally substituted with OH, and heterocyclyl optionally substituted with oxo, (M) COPh optionally substituted with one or two groups selected from ethynyl, CN, F, OH, CO$_2$R$^{a(a)}$ and OC(O)CH$_3$, (N)C(O)-heteroaryl optionally substituted with one or two groups independently selected from halogen, OH, CF$_3$ and $C_{1-4}$alkyl, (O)C(O)-heterocycle optionally substituted with oxo, (P) CO—$C_{3-6}$cycloalkyl optionally substituted with a group selected from OH and CO$_2$R$^{a(a)}$, (Q) CO$_2$R$^{a(a)}$, (R) COCO$_2$R$^{a(a)}$, (S) C(O)NR$^{b(a)}$R$^{c(a)}$, (T1) NR$^{a(a)}$R$^{a(a)}$, (T2) 1-pyrrolidinyl optionally substituted with oxo, (U) NHC(O)C$_{1-3}$alkyl optionally substituted with one or two OH groups, SO$_2$CH$_3$, CONR$^{a(a)}$R$^{a(a)}$, imidazolyl, pyridyl, pyrazolyl, triazolyl, tetrazolyl, pyrimidinyl, 2-oxotetrahydrofuranyl, tetrahydrofuranyl, tetrahydropyranyl and phenyl, (V) NHC(O)—Y, (W) NHC(O)NH$_2$, (X) NHC(O)NHC(O)NH$_2$, (Y) NHSO$_2$NH$_2$, (Z1) NHSO$_2$C$_{1-3}$alkyl, (Z2) NHSO$_2$C$_{1-3}$haloalkyl, (AA1) SO$_2$C$_{1-4}$alkyl, (AA2) SO$_2$C$_{1-4}$haloalkyl, (BB) SO$_2$Ph, (CC)SO$_2$-heteroaryl optionally substituted with $C_{1-4}$alkyl, (DD) SO$_2$NH$_2$, (EE) SO$_2$NHCOC$_{1-4}$alkyl, (FF) SO$_2$NHCO$_2$C$_{1-4}$alkyl, (GG) SO$_3$H, (HH) hydroxyimino; (II) 1,3,4-oxadiazole-2(3H)-one and 1,2,4-oxadiazole-5(4H)-one, (JJ) P(O)(OEt)$_2$;

R$^{a(a)}$ is H or $C_{1-4}$alkyl,

R$^{b(a)}$ and R$^{c(a)}$ are independently selected from (A) H, (B) optionally benzofused $C_{3-6}$cycloalkyl optionally substituted with OH, (C) heteroaryl selected from imidazolyl, pyridyl and indolyl, (D) tetrahydrofuranyl, (E) benzyl, (F) phenyl optionally substituted with one or two groups selected from (CH$_2$)$_{0-2}$OH and F, (G1) $C_{1-4}$alkyl and (G2) $C_{1-4}$haloalkyl, wherein (G1) and (G2) are each optionally substituted with one to three groups independently selected from (i) OH, (ii) $C_{3-6}$cycloalkyl optionally substituted with one or two groups independently selected from $C_{1-4}$alkyl, CONH$_2$, CO$_2$H and CH$_2$OH, (iii) 1-carboxy-$C_{3-6}$cycloalkyl, (iv) CONH$_2$, (v) SO$_2$NH$_2$, (vi) SO$_2$C$_{1-4}$alkyl, (vii) optionally benzofused 4- to 7-membered heterocyclyl optionally substituted with one or two groups independently selected from oxo, (CH$_2$)$_{0-2}$OH, and $C_{1-4}$alkyl, (viii) a 5- to 10-membered monocyclic or bicyclic heteroaryl optionally substituted with one or two groups independently selected from carboxy, (CH$_2$)$_{0-2}$OH, and $C_{1-4}$-alkyl, (ix) CN, (x) OC$_{1-4}$alkyl, (xi) CO$_2$H, (xii) NR$^{a(a)}$C(O)C$_{1-4}$alkyl, (xiii) phenyl optionally substituted with one or two groups selected from (CH$_2$)$_{0-2}$OH, SO$_2$NH$_2$, CF$_3$, F and Cl, (xiv) OPh, (xv) 1-pyrrolidinyl optionally substituted with oxo, (xvi) 1-imidazolidinyl optionally substituted with oxo, (xvii) 1-piperidinyl optionally substituted with oxo, and (xviii) 4-morpholinyl; or $R^{b(a)}$ and $R^{c(a)}$ together with the nitrogen atom to which they are attached form a 6- or 7-membered heterocycle having 0 to 1 additional heteroatom selected from N, O and S, wherein said heterocycle is optionally substituted with one or two groups independently selected from oxo, CN, $(CH_2)_{0-2}OH$, acetyl, benzyl, $SO_2C_{1-4}$alkyl, $CONH_2$, methoxymethyl, carboxymethyl, $CO_2R^{a(a)}$ and $C_{1-4}$alkyl;

Y is selected from $CH(OH)CF_3$, $CH_2CH(NH_2)CF_3$, $C_{4-6}$cycloalkyl (optionally substituted with OH or $CO_2R^{a(a)}$), imidazolyl, pyridyl (optionally substituted with OH), pyrazolyl, triazolyl, tetrazolyl, pyrimidinyl, phenyl (optionally substituted with one or two groups selected from OH, F, CN and ethynyl), a heterocycle selected from imidazolidinyl, tetrahydrofuranyl, tetrahydropyranyl, piperidinyl, each of which is optionally substituted with oxo.

In one subset of [Group R5-II] $R^5$ is $C_{3-10}$ carbocycle selected from cyclopropyl, cyclobutyl, cyclopentyl, cyclohexyl, cyclohexenyl, cycloheptyl, cycloheptenyl, bicyclo [3.3.0]octyl, bicyclo[4.1.0]heptyl, decalinyl, indanyl, octahydroindenyl, bicyclo[2.2.1]heptyl, bicyclo[2.2.2]octyl, bicyclo[3.3.1]nonyl, bicyclo[3.2.1]octyl, tetrahydronaphthyl, spiro[3.3]heptyl, spiro[2.5]octyl, dispiro[2.1.2.3]decyl, adamantyl, and tricyclo[2.2.1.0$^{2,6}$]heptyl. In one aspect within this subset, the carbocycle is selected from cyclopropyl, cyclobutyl, cyclopentyl, cyclohexyl and cycloheptyl; and in one embodiment thereof, the carbocycle is cyclohexyl. In another aspect of within this subset, the carbocycle is substituted with one to three groups independently selected from hydroxymethyl, aminomethyl, OH, OCH$_3$, OCH$_2$CH$_2$OH, oxo, F, CN, 1,3,4-oxadiazolyl, 1,3,4-oxadiazole-2(3H)-one, 1,2,4-oxadiazole-5(4H)-one, $CO_2R^{a(a)}$, $CONR^{b(a)}R^{c(a)}$, $NR^{a(a)}R^{a(a)}$, NHC(O)C$_{1-3}$alkyl (optionally substituted with OH), NHC(O)NH$_2$, NHC(O)NHC(O)NH$_2$, NHC(O)(1-C(O) NH$_2$-cPr), NHSO$_2$NH$_2$, NHSO$_2$C$_{1-3}$alkyl and NHSO$_2$ C$_{1-3}$haloalkyl, and optionally further substituted with one to four methyl groups. In one embodiment thereof, the substituted carbocycle is cyclohexyl substituted with one to three groups selected from F, OH, CO$_2$H, CONH$_2$, CONHR$^{b(a)}$, NH$_2$, NHC(O)C$_{1-3}$alkyl optionally substituted with OH, and optionally substituted with one or two methyl groups.

In another subset of [Group R5-II] $R^5$ is 4- to 10-membered heterocyclyl selected from oxetanyl, tetrahydrofuranyl, tetrahydropyranyl, tetrahydrothiopyranyl, azetidinyl, pyrrolidinyl, piperidinyl, azepanyl, tetrahydropyridyl, tetrahydroazepinyl, 8-azabicyclo[3.2.1]-octyl, 7-azabicyclo[2.2.1] heptyl, 1,3-dioxanyl, 3-azabicyclo[3.2.0]heptyl, 1,4-dioxospiro[4.5]decyl, 1-azaspiro[4.5]decyl and 3-oxa-9-azabicyclo[3.3.1]nonyl. In one aspect within this subset, the heterocyclyl is selected from azetidinyl, pyrrolidinyl, piperidinyl and azepanyl; and in one embodiment thereof the heterocyclyl is azepanyl. In another aspect within this subset, the heterocycle is substituted with one to three groups selected from hydroxymethyl, aminomethyl, OH, OCH$_3$, OCH$_2$CH$_2$OH, oxo, F, CN, CO$_2$R$^{a(a)}$, CONR$^{b(a)}$R$^{c(a)}$, NR$^{a(a)}$R$^{a(a)}$, NHC(O)C$_{1-3}$alkyl (optionally substituted with OH), NHC(O)NH$_2$, NHC(O)NHC(O)NH$_2$, NHC(O)(1-C(O) NH$_2$-cPr), NHSO$_2$NH$_2$, NHSO$_2$C$_{1-3}$alkyl and NHSO$_2$ C$_{1-3}$haloalkyl, and optionally further substituted with one to four methyl groups. In one embodiment thereof the substituted heterocycle is hydroxy-substituted azepan-2-one.

In another subset of [Group R5-II] $R^5$ is C$_{1-6}$alkyl optionally substituted with one to three groups independently selected from (A) C$_{3-4}$cycloalkyl; (B) phenyl optionally substituted with one or two groups independently selected from (i) OCH$_3$ optionally substituted with CO$_2$H, (CH$_2$)$_{0-1}$CO$_2$H, (iii) SO$_2$CH$_3$, and (iv) C(O)CH$_3$; (C) heteroaryl selected from pyrrolyl, pyrazolyl, imidazolyl, furyl, thienyl, thiazolyl, triazolyl, 1,2,4-oxadiazolyl, pyridyl, and pyrazinyl, each optionally substituted with one or two groups independently selected from CH$_3$, halogen, OCH$_3$, (CH$_2$)$_{0-2}$CO$_2$H, SO$_2$CH$_3$ and SO$_2$Ph; (D) OR$^{a(a)}$, (E) NR$^{b(a)}$R$^{c(a)}$, (F) NHC(O) NH$_2$, (G) NHSO$_2$CH$_3$, (H) CO$_2$R$^{a(a)}$, (I) NHSO$_2$NH$_2$, (J) CONR$^{a(a)}$R$^{a(a)}$, (K) SO$_2$NH$_2$ and (L) SO$_2$CH$_3$.

In another subset of [Group R5-II] $R^5$ is C$_{1-6}$-fluoroalkyl optionally substituted with one or two hydroxy groups.

In another group of formula (I) [Group R5-III] are compounds having the formula (Ia) or a pharmaceutically acceptable salt thereof:

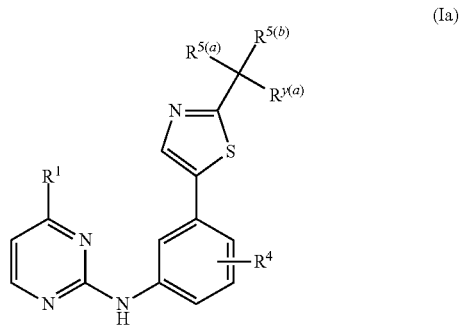

(Ia)

wherein $R^1$ and $R^4$ are as defined under formula (I);

$R^{5(a)}$ and $R^{5(b)}$ are each independently selected from the group consisting of (a) H, (b) C$_{1-8}$alkyl optionally substituted with one or more groups independently selected from R$^y$; and (c) a group selected from R$^y$; or $R^{5(a)}$, $R^{5(b)}$ and the carbon to which they are both attached together form a C$_{3-12}$ carbocycle or 3- to 12-membered heterocyclyl each optionally substituted with one or more groups independently selected from R$^z$;

$R^{y(a)}$ is selected from the group consisting of hydroxymethyl, aminomethyl, OR$^a$, CO$_2$R$^a$, CONR$^b$R$^c$, SO$_2$NR$^b$R$^c$, SO$_2$R$^a$, SO$_2$NHC(O)R$^a$, NHC(O)R$^u$, NHC(O)NH$_2$, NHC(O)NHC (O)NH$_2$, NHSO$_m$R$^a$, NHSO$_2$NR$^b$R$^c$, NR$^b$R$^c$, 1,3,4-oxadiazolyl, CN and halogen.

In a subset of formula (Ia) are compounds wherein R$^{y(a)}$ is aminomethyl, OH, OCH$_3$, OCH$_2$CH$_2$OH, F, CN, CO$_2$R$^{a(a)}$, CONR$^{b(a)}$R$^{c(a)}$, NR$^{a(a)}$R$^{a(a)}$, NHC(O)C$_{1-3}$alkyl (optionally substituted with OH), NHC(O)NH$_2$, NHC(O)NHC(O)NH$_2$, NHC(O)(1-C(O)NH$_2$-cPr), SO$_2$NH$_2$, SO$_2$CH$_3$, SO$_2$NHC(O) CH$_3$, NHSO$_2$NH$_2$, NHSO$_2$C$_{1-3}$alkyl, or NHSO$_2$C$_{1-3}$haloalkyl, and at least one of R$^{5(a)}$ and R$^{5(b)}$ is other than H.

In another subset of formula (Ia) are compounds wherein R$^{5(a)}$, R$^{5(b)}$ and the carbon to which they are both attached together form a C$_{3-10}$ carbocycle. In one aspect within this subset are compounds wherein R$^{y(a)}$ is OH. In another aspect are compounds wherein R$^{5(a)}$, R$^{5(b)}$ and the carbon to which they are both attached together form a carbocycle selected from cyclopropyl, cyclobutyl, cyclopentyl, cyclohexyl, cyclohexenyl, cycloheptyl, cycloheptenyl, bicyclo[3.3.0]octane, indane, bicyclo[3.3.1]nonane, decalin, tetrahydronaphthalene, spiro[3.3]heptane, bicyclo[3.1.0]hexane, adamantane, tricyclo[2.2.1.0$^{2,6}$]heptane, and dispiro[2.1.2.3]decane.

In another subset of formula (Ia) are compounds wherein R$^{y(a)}$ is aminomethyl, OH, OCH$_3$, OCH$_2$CH$_2$OH, F, CN, 1,3, 4-oxadiazolyl, CO$_2$R$^{a(a)}$, CONR$^{b(a)}$R$^{c(a)}$, NR$^{a(a)}$R$^{a(a)}$, NHC (O)C$_{1-3}$alkyl (optionally substituted with OH), NHC(O)NH$_2$, NHC(O)NHC(O)NH$_2$, NHC(O)(1-C(O)NH$_2$-cPr), SO$_2$NH$_2$, SO$_2$CH$_3$, SO$_2$NHC(O)CH$_3$, NHSO$_2$NH$_2$, NHSO$_2$C$_{1-3}$alkyl, or NHSO$_2$C$_{1-3}$haloalkyl, and R$^{5(a)}$, R$^{5(b)}$ and the carbon to which they are both attached together form a monocyclic C$_{3-8}$ cycloalkyl optionally substituted with a group selected from the group consisting of (a) C$_{1-4}$ alkyl optionally substituted with one or more groups independently selected from OH, NH$_2$, CN, CO$_2$R$^{a(a)}$ and CONH$_2$, (b) halogen, (c) CN, (d) —C(O)R$^{a(a)}$, (e) —C(O)$_2$R$^{a(a)}$, (f) —C(O)NR$^{b(a)}$R$^{c(a)}$, (g) —OR$^{a(a)}$, (h) —OC(O)R$^{a(a)}$, (i) —NR$^{b(a)}$R$^{c(a)}$, —NHC(O)C$_{1-3}$alkyl (optionally substituted with OH), (k) —NHSO$_2$C$_{1-3}$alkyl, (l) —NHSO$_2$NH$_2$, (m) oxo, (n) phenyl, (o) hydroxyimino, (p) 1-aminocyclopropyl, (q) 1,3,4-oxadiazole-2(3H)-one, and (r) 1,2,4-oxadiazole-5(4H)-one, and optionally further substituted with one to four methyl groups. In one aspect are compounds wherein R$^{y(a)}$ is OH, F, OCH$_3$, CONH$_2$ and CN. In another aspect are compounds wherein R$^{5(a)}$, R$^{5(b)}$ and the carbon to which they are both attached together form a cyclohexyl ring optionally substituted with a group selected from —CO$_2$H, —CO$_2$C$_{1-4}$alkyl, C(O)NH$_2$, CONHC$_{1-3}$ alkyl optionally substituted with NR$^{b(a)}$R$^{c(a)}$, and —NHC(O)C$_{1-3}$alkyl (optionally substituted with OH), and optionally further substituted with one or two methyl groups.

In another subset of formula (Ia) are compounds wherein R$^{y(a)}$ is aminomethyl, OH, OCH$_3$, OCH$_2$CH$_2$OH, F, CN, 1,3,4-oxadiazolyl, CO$_2$R$^{a(a)}$, CONR$^{b(a)}$R$^{c(a)}$, NR$^{a(a)}$R$^{a(a)}$, NHC(O)C$_{1-3}$alkyl (optionally substituted with OH), NHC(O)NH$_2$, NHC(O)NHC(O)NH$_2$, NHC(O)(1-C(O)NH$_2$-cPr), SO$_2$NH$_2$, SO$_2$CH$_3$, SO$_2$NHC(O)CH$_3$, NHSO$_2$NH$_2$, NHSO$_2$C$_{1-3}$alkyl, or NHSO$_2$C$_{1-3}$haloalkyl, and R$^{5(a)}$, R$^{5(b)}$ and the carbon to which they are both attached together form (a) a monocyclic 4- to 6-membered heterocyclyl having a ring O or S, and optionally substituted with one or two groups selected from the group consisting of oxo and methyl, or (b) a monocyclic 4- to 7-membered heterocyclyl having a ring N—H or N—R$^y$(b) group, and optionally substituted with one or two groups selected from oxo, methyl, trifluoromethyl, and CO$_2$R$^{a(a)}$, wherein R$^y$(b) is selected from (ia) C$_{1-3}$ alkyl optionally substituted with one or more groups independently selected from OH, NH$_2$, CN, CO$_2$R$^{a(a)}$ and CONH$_2$, (ib) C$_{1-3}$haloalkyl (optionally substituted with NH$_2$ or OH), (iia) COC$_{1-4}$alkyl or C(O)C$_{1-4}$haloalkyl (where alkyl and haloalkyl is each optionally substituted with OR$^{a(a)}$, CN, CO$_2$R$^{a(a)}$, CONR$^{a(a)}$R$^{a(a)}$, NR$^{a(a)}$R$^{a(a)}$, SO$_2$CH$_3$, heterocyclyl optionally substituted with oxo, heteroaryl optionally substituted with OH), (iib) CO-phenyl (optionally substituted with one or two groups selected from ethynyl, CO$_2$R$^{a(a)}$, CN, F and OH), (iic) CO-heteroaryl (optionally substituted with methyl, Cl, CF$_3$), (iid) CO-heterocyclyl (optionally substituted with oxo), (iie) CO—C$_{3-6}$cycloalkyl (optionally substituted with OH or CO$_2$R$^{a(a)}$), (iii) C$_{0-3}$alkyl-CO$_2$R$^{a(a)}$, (iva) CONR$^{a(a)}$R$^{a(a)}$, (ivb) CONH-phenyl (optionally substituted with one or two groups selected from C$_{1-4}$alkyl, OC(O)C$_{1-3}$alkyl, CN, and Cl), (ivc) CONH—C$_{3-6}$cycloalkyl, (v) SO$_2$NH$_2$, (vi) SO$_2$NHCO$_2$R$^{a(a)}$, (viia) SO$_2$C$_{1-3}$alkyl, (viib) SO$_2$C$_{1-3}$haloalkyl, (viic) SO$_2$Ph, (viid) SO$_2$-heteroaryl (optionally substituted with methyl), (viii) SO$_3$H. In one aspect within this subset are compounds wherein R$^{5(a)}$, R$^{5(b)}$ and the carbon to which they are both attached together form pyrrolidinyl, oxetanyl, piperidinyl and azepanyl. Within said aspect is an embodiment in which R$^{y(a)}$ is OH.

R$^{a(a)}$, R$^{b(a)}$, R$^{c(a)}$ in the above subsets are as defined in [Group R5-II].

In another group of formula (I) [Group R5-IV] are compounds of formula I(b) or a pharmaceutically acceptable salt thereof:

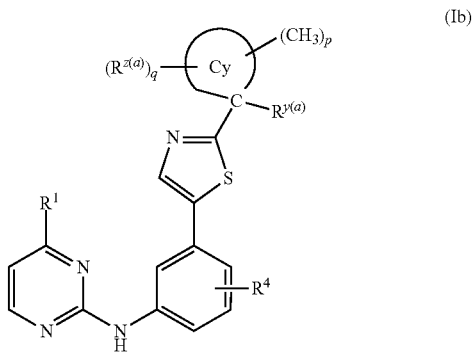

(Ib)

wherein R$^1$ and R$^4$ are as defined under formula (I);
Cy is a C$_{3-7}$ monocyclic carbocycle or a 4- to 7-membered monocyclic heterocycle having a heteroatom selected from N, S or O;
R$^{y(a)}$ is defined under formula Ia;
R$^{z(a)}$ is selected from (A) C$_{1-4}$ alkyl optionally substituted with one to three groups independently selected from OH, NH$_2$, CN, CO$_2$R$^{a(a)}$ and CONH$_2$, (B) C$_{1-3}$-fluoroalkyl, (C) halogen, (D) CN, (E) COC$_{1-4}$alkyl (optionally substituted with one or two groups independently selected from OR$^{a(a)}$, CN, CO$_2$R$^{a(a)}$, CONR$^{a(a)}$R$^{a(a)}$, and NR$^{a(a)}$R$^{a(a)}$), (F) CO-phenyl (optionally substituted with one or two groups independently selected from ethynyl, CO$_2$R$^{a(a)}$, CN, F and OH), (G) CO—C$_{3-6}$cycloalkyl (optionally substituted with OH or CO$_2$R$^{a(a)}$), (H) C$_{0-3}$alkyl-CO$_2$R$^{a(a)}$, (I) —C(O)NR$^{b(a)}$R$^{c(a)}$, (J) —OR$^{a(a)}$, (K) —OC(O)R$^{a(a)}$, (L) —NR$^{b(a)}$R$^{c(a)}$, (M) —NHC(O)C$_{1-4}$alkyl (optionally substituted with one to three OH or a CONR$^{a(a)}$R$^{a(a)}$), (N) —NHSO$_2$C$_{1-3}$alkyl, (O) —NHSO$_2$NH$_2$, (P) oxo, (Q) 1,3,4-oxadiazole-2(3H)-one, (R) 1,2,4-oxadiazole-5(4H)-one, (S) SO$_2$NH$_2$, (T) SO$_2$C$_{1-3}$alkyl, (U) SO$_2$C$_{1-3}$haloalkyl, and (V) SO$_2$Ph;
R$^{a(a)}$, R$^{b(a)}$ and R$^{c(a)}$ are as defined in Group [R5-II];
p is 0 to 4; and
q is 0, 1 or 2.

In one subset of formula (Ib) are compounds wherein
p is 0 to 4;
q is 0, 1 or 2;
Cy is selected from C$_{4-7}$cycloalkyl, oxetanyl, pyrrolidinyl, piperidinyl, and azepanyl;
R$^1$ is selected from H, C$_{1-4}$alkyl, C$_{1-4}$haloalkyl, C$_{3-6}$cycloalkyl, and OC$_{1-4}$alkyl;
R$^4$ is selected from H, C$_{1-4}$alkyl, and C$_{3-4}$cycloalkyl;
R$^{y(a)}$ is aminomethyl, OH, OCH$_3$, OCH$_2$CH$_2$OH, F, CN, CO$_2$R$^{a(a)}$, CONR$^{b(a)}$R$^c$(a), NR$^{a(a)}$R$^{a(a)}$, NHC(O)C$_{1-3}$alkyl (optionally substituted with OH), NHC(O)NH$_2$, NHSO$_2$NH$_2$, NHSO$_2$C$_{1-3}$alkyl, or NHSO$_2$C$_{1-3}$haloalkyl;
R$^{z(a)}$ is selected from (A) C$_{1-4}$ alkyl optionally substituted with one to three groups independently selected from OH, NH$_2$, CN, CO$_2$R$^{a(a)}$ and CONH$_2$, (B) C$_{1-3}$-fluoroalkyl, (C) halogen, (D) CN, (B) COC$_{1-4}$alkyl (optionally substituted with one or two groups independently selected from OR$^{a(a)}$, CN, CO$_2$R$^{a(a)}$, CONR$^{a(a)}$R$^{a(a)}$, and NR$^{a(a)}$R$^{a(a)}$), (F) CO-phenyl (optionally substituted with one or two groups independently selected from ethynyl, CO$_2$R$^{a(a)}$, CN, F and OH), (G) CO—C$_{3-6}$cycloalkyl (optionally substituted with OH or CO$_2$R$^{a(a)}$), (H)C$_{0-3}$alkyl-CO$_2$R$^{a(a)}$, (I) —C(O)NR$^{b(a)}$R$^{c(a)}$, (J) —OR$^{a(a)}$, (K) —OC(O)R$^{a(a)}$, (L) —NR$^{b(a)}$R$^{c(a)}$, (M) —NHC(O)C$_{1-4}$alkyl (optionally substituted with one to three OH or a CONR$^{a(a)}$R$^{a(a)}$), (N) —NHSO$_2$C$_{1-3}$alkyl, (O) —NHSO$_2$NH$_2$, (P) oxo, (Q) 1,3,4-oxadiazole-2(3H)-one, (R) 1,2,4-oxadiazole-5(4H)-one, (S) $SO_2NH_2$, (T) $SO_2$$C_{1-3}$alkyl, (U) $SO_2C_{1-3}$haloalkyl, and (V) $SO_2Ph$;

$R^{a(a)}$ is H or $C_{1-4}$alkyl;

$R^{b(a)}$ and $R^{c(a)}$ are independently selected from (A) H, (B) $C_{3-6}$cycloalkyl optionally substituted with OH, (C) heteroaryl selected from imidazolyl, pyridyl and indolyl, (D) tetrahydrofuranyl, (E) benzyl, (F) phenyl optionally substituted with one or two groups independently selected from $(CH_2)_{0-2}OH$ and F, (G1) $C_{1-4}$alkyl and (G2) $C_{1-4}$haloalkyl, wherein (G1) and (G2) are each optionally substituted with one to three groups independently selected from (i) OH, (ii) $C_{3-6}$cycloalkyl optionally substituted with one or two groups independently selected from $C_{1-4}$alkyl, $CONH_2$, $CO_2H$ and $CH_2OH$, (iii) $CONH_2$, (iv) $SO_2NH_2$, (v) $SO_2C_{1-4}$alkyl, (vi) 4- to 7-membered monocyclic heterocyclyl optionally substituted with one or two groups independently selected from oxo, $(CH_2)_{0-2}OH$, and $C_{1-4}$-alkyl, (vii) a 5- or 6-membered heteroaryl optionally substituted with one or two groups independently selected from carboxy, $(CH_2)_{0-2}OH$, and $C_{1-4}$alkyl, (viii) CN, (x) $OC_{1-4}$alkyl, (ix) $CO_2H$, (xii) $NR^{a(a)}C(O)C_{1-4}$alkyl, (x) phenyl optionally substituted with one or two groups independently selected from $(CH_2)_{0-2}OH$, $SO_2NH_2$, $CF_3$, F and Cl, (xi) 1-pyrrolidinyl optionally substituted with oxo, (xii) 1-imidazolidinyl optionally substituted with oxo, (xiii) piperidinyl optionally substituted with oxo, and (xiv) 4-morpholinyl; or $R^{b(a)}$ and $R^{c(a)}$ together with the nitrogen atom to which they are attached form a 6- or 7-membered heterocycle having 0 to 1 additional heteroatom selected from N, O and S, wherein said heterocycle is optionally substituted with one or two groups independently selected from oxo, CN, $(CH_2)_{0-2}OH$, acetyl, benzyl, $SO_2C_{1-4}$alkyl, $CONH_2$, methoxymethyl, carboxymethyl, $CO_2R^{a(a)}$ and $C_{1-4}$alkyl.

In another subset of formula (Ib) are compounds wherein Cy is cyclohexyl. In one aspect the cyclohexyl is substituted with a group selected from $CO_2R^{a(a)}$, $CONR^{b(a)}R^{c(a)}$ and $NHC(O)C_{1-4}$alkyl optionally substituted with OH, and said cyclohexyl is optionally further substituted with one or two methyl groups.

In another subset of formula (Ib) are compounds wherein Cy is piperidinyl. In one aspect the nitrogen atom of piperidinyl is substituted with a group selected from (i) $COC_{1-4}$alkyl (optionally substituted with $OR^{a(a)}$, CN, $CO_2R^{a(a)}$, $CONR^{a(a)}R^{a(a)}$, and $NR^{a(a)}R^{a(a)}$), (ii) CO-phenyl (optionally substituted with one or two groups independently selected from ethynyl, $CO_2R^{a(a)}$, CN, F and OH), (iii) CO—$C_{3-6}$cycloalkyl (optionally substituted with OH or $CO_2R^{a(a)}$), (iv) $C_{0-3}$alkyl-$CO_2R^{a(a)}$, (v) $CONR^{a(a)}R^{a(a)}$, (vi) CONH-phenyl (optionally substituted with one or two groups independently selected from $C_{1-4}$alkyl, CN, and Cl), (vii) CONH—$C_{3-6}$cycloalkyl, (viii) $SO_2NH_2$, (ix) $SO_2C_{1-3}$alkyl, (x) $SO_2C_{1-3}$haloalkyl, and (xi) $SO_2Ph$.

In another subset of formula (Ib) are compounds wherein Cy is azepanyl. In one aspect azepanyl is substituted with an oxo group at the 2-position of the ring.

In another subset of formula (Ib) are compounds wherein $R^{y(a)}$ is OH. In one aspect Cy is cyclohexyl. In one embodiment thereof cyclohexyl is substituted with a group selected from selected from $CO_2R^{a(a)}$, $CONHR^b(a)$ and $NHC(O)$ $C_{1-4}$alkyl optionally substituted with OH, and said cyclohexyl is optionally further substituted with one or two methyl groups. In another aspect Cy is 2-oxoazepanyl.

In another subset of formula (Ib) are compounds wherein $R^{y(a)}$ is $CONH_2$. In one aspect Cy is cyclohexyl. In one embodiment thereof cyclohexyl is substituted with a group selected from selected from $CO_2R^{a(a)}$, $CONHR^{b(a)}$ and NHC(O)$C_{1-4}$alkyl optionally substituted with OH, and said cyclohexyl is optionally further substituted with one or two methyl groups.

In another group of formula (I) [Group R5-V] are compounds of formula I(c) or a pharmaceutically acceptable salt thereof:

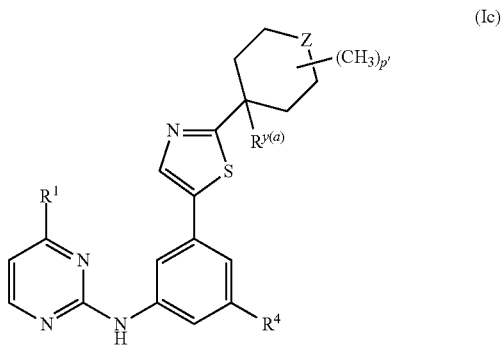

(Ic)

wherein
Z is —$CR^{z(b)}R^{z(c)}$—, —$N(R^{z(d)})$—, —$CH_2$—$N(R^{z(d)})$—, or $NHC(O)$—;

p' is 0 to 3, with the proviso that p is 0 when Z is —NHC(O)—;

$R^{z(b)}$ is selected from (A) H, (B) $C_{1-4}$ alkyl optionally substituted with one to three groups independently selected from OH, $NH_2$, CN, $CO_2R^{a(a)}$ and $CONH_2$, (C) halogen, (D) CN, (E) —$C(O)R^{a(a)}$, (F) —$C(O)_2R^{a(a)}$, (G) —$C(O)NR^{b(a)}R^{c(a)}$, (H) —$OR^{a(a)}$, (I) —$OC(O)R^{a(a)}$, (J) —$NR^{b(a)}R^{c(a)}$, (K) —$NHC(O)C_{1-4}$alkyl (optionally substituted with OH), (L) —$NHSO_2C_{1-3}$alkyl, (M) —$NHSO_2NH_2$, (N) 1,3,4-oxadiazole-2(3H)-one, and (O) 1,2,4-oxadiazole-5(4H)-one;

$R^{z(c)}$ is H or methyl;

$R^{z(d)}$ is selected from (A) H, (B) $C_{1-3}$ alkyl optionally substituted with a group selected from $CO_2R^{a(a)}$ and $CONH_2$, (C) $C_{1-3}$-fluoroalkyl, (D) $COC_{1-4}$alkyl (optionally substituted with one or two groups independently selected from $OR^{a(a)}$, CN, $CO_2R^{a(a)}$, $CONR^{a(a)}R^{a(a)}$, and $NR^{a(a)}R^{a(a)}$), (E) CO-phenyl (optionally substituted with one or two groups independently selected from ethynyl, $CO_2R^{a(a)}$, CN, F and OH), (F) CO—$C_{3-6}$cycloalkyl (optionally substituted with OH or $CO_2R^{a(a)}$), (G) $C_{0-3}$alkyl-$CO_2R^{a(a)}$, (H) $CONR^{a(a)}R^{a(a)}$, (I) CONH-phenyl (optionally substituted with one or two groups independently selected from $C_{1-4}$alkyl, CN, and Cl), (J) CONH—$C_{3-6}$cycloalkyl, (K) $SO_2NH_2$, (L) $SO_2C_{1-3}$alkyl, (M) $SO_2C_{1-3}$haloalkyl, and (N) $SO_2Ph$; and $R^1$ is selected from H, $C_{1-4}$alkyl, $C_{1-4}$haloalkyl, $C_{3-6}$cycloalkyl, and $OC_{1-4}$alkyl;

$R^4$ is selected from H, $C_{1-4}$alkyl, and $C_{3-4}$cycloalkyl;

$R^{y(a)}$ is aminomethyl, OH, $OCH_3$, $OCH_2CH_2OH$, F, CN, $CO_2R^{a(a)}$, $CONR^{b(a)}R^{c(a)}$, $NR^{a(a)}R^{a(a)}$, $NHC(O)C_{1-3}$alkyl (optionally substituted with OH), $NHC(O)NH_2$, $NHSO_2NH_2$, $NHSO_2C_{1-3}$alkyl, or $NHSO_2C_{1-3}$haloalkyl;

$R^{a(a)}$ is H or $C_{1-4}$alkyl;

$R^{b(a)}$ and $R^{c(a)}$ are independently selected from (A) H, (B) $C_{3-6}$cycloalkyl optionally substituted with OH, (C) heteroaryl selected from imidazolyl, pyridyl and indolyl, (D) tetrahydrofuranyl, (E) benzyl, (F) phenyl optionally substituted with one or two groups independently selected from $(CH_2)_{0-2}OH$ and F, (G1) $C_{1-4}$alkyl and (G2) $C_{1-4}$haloalkyl, wherein (G1) and (G2) are each optionally substituted with one to three groups independently selected from (i) OH, (ii) $C_{3-6}$cycloalkyl optionally substituted with one or two groups independently selected from $C_{1-4}$alkyl, $CONH_2$, $CO_2H$ and CH$_2$OH, (iii) CONH$_2$, (iv) SO$_2$NH$_2$, (v) SO$_2$C$_{1-4}$alkyl, (vi) 4- to 7-membered monocyclic heterocyclyl optionally substituted with one or two groups independently selected from oxo, (CH$_2$)$_{0-2}$OH, and C$_{1-4}$alkyl, (vii) a 5- or 6-membered heteroaryl optionally substituted with one or two groups independently selected from carboxy, (CH$_2$)$_{0-2}$OH, and C$_{1-4}$alkyl, (viii) CN, (x) OC$_{1-4}$alkyl, (ix) CO$_2$H, (xii) NR$^{a(a)}$C(O)C$_{1-4}$alkyl, (x) phenyl optionally substituted with one or two groups independently selected from (CH$_2$)$_{0-2}$OH, SO$_2$NH$_2$, CF$_3$, F and Cl, (xi) 1-pyrrolidinyl optionally substituted with oxo, (xii) 1-imidazolidinyl optionally substituted with oxo, (xiii) 1-piperidinyl optionally substituted with oxo, and (xiv) 4-morpholinyl; or R$^{b(a)}$ and R$^{c(a)}$ together with the nitrogen atom to which they are attached form a 6- or 7-membered heterocycle having 0 to 1 additional heteroatom selected from N, O and S, wherein said heterocycle is optionally substituted with one or two groups independently selected from oxo, CN, (CH$_2$)$_{0-2}$OH, acetyl, benzyl, SO$_2$C$_{1-4}$alkyl, CONH$_2$, methoxymethyl, carboxymethyl, CO$_2$R$^{a(a)}$ and C$_{1-4}$alkyl.

In one subset of formula (Ic) are compounds wherein R$^{y(a)}$ is aminomethyl, OH, OCH$_3$, OCH$_2$CH$_2$OH, F, CN, CO$_2$R$^{a(a)}$, CONR$^{b(a)}$R$^{c(a)}$, NR$^{a(a)}$R$^{a(a)}$, NHC(O)C$_{1-3}$alkyl (optionally substituted with OH), NHC(O)NH$_2$, SO$_2$NH$_2$, SO$_2$CH$_3$, NHSO$_2$NH$_2$, NHSO$_2$C$_{1-3}$alkyl, or NHSO$_2$C$_{1-3}$haloalkyl.

In another subset of formula (Ic) are compounds wherein Z is —N(R$^{z(d)}$)—, and p' is 0. In one embodiment thereof R$^{y(a)}$ is OH.

In another subset of formula (Ic) are compounds wherein Z is —NHC(O)—. In one embodiment thereof. R$^{y(a)}$ is OH.

In another subset of formula (Ic) are compounds wherein Z is —CHR$^{z(b)}$, and p' is 0, 1 or 2. In one embodiment thereof R$^{y(a)}$ is OH. In another embodiment thereof R$^{y(a)}$ is CONH$_2$.

In another subset of formula (Ic) are compounds wherein Z is —CHR$^{z(b)}$, p' is 0, 1 or 2, and R$^{y(a)}$ is OH or CONH$_2$. In one embodiment thereof. R$^z$(b) is —C(O)$_2$R$^{a(a)}$; preferably R$^z$(b) is —C(O)$_2$H. In another embodiment R$^z$(b) is —C(O)NHR$^b$(a); preferably R$^z$(b) is —C(O)NH$_2$ or —C(O)NH(CH$_2$)$_3$-(2-oxo-1-pyrrolidinyl). In another embodiment thereof. R$^z$(b) is —NHC(O)C$_{1-4}$alkyl (optionally substituted with OH).

In another group of formula (I) [Group R5-VI] R$^5$ is CONR$^b$R$^c$ or C(O)R$^a$.

In another group of formula (I) [Group R5-VII] R$^5$ is a group other than H.

In another group of formula (I) [Group R5-VIII] R$^5$ is a group other than H or halogen.

For compounds of formulas (I), (Ia), and (Ib) as well as various applicable groups, subsets, aspects and embodiments mentioned above, there is one group [Group R1] in which R$^1$ is (a) C$_{1-6}$ alkyl optionally substituted with one or more groups independently selected from the group consisting of OR$^a$, C$_{3-6}$cycloalkyl, and halogen, (b) C$_{3-6}$cycloalkyl, (c) OH, (d) —O—C$_{1-6}$ alkyl optionally substituted with one or more groups independently selected from (i) aryl, (ii) 5- or 6-membered heteroaryl optionally substituted with one or more groups independently selected from C$_{1-6}$ alkyl, (iii) 4- to 8-membered heterocyclyl optionally substituted with one or more groups independently selected from oxo, halogen, C$_{1-6}$ alkyl, (iv) —CO$_2$R$^a$, (v) —CONR$^b$R$^c$, (vi) —NR$^b$R$^c$, (vii) —NH-heterocycle (piperidine) optionally substituted with alkyl, and (viii) —OR$^a$, and (e) —O—X, wherein X is selected from the group consisting of (i) 4- to 8-membered heterocyclyl optionally substituted with one or more groups independently selected from halogen, C$_{1-6}$ alkyl, —C$_{1-6}$ haloalkyl, COR$^a$, CO$_2$R$^a$, and (ii) C$_{3-6}$ cycloalkyl optionally substituted with one or more groups independently selected from C$_{1-6}$ alkyl, OR$^a$, benzyl, CO$_2$R$^a$, NR$^b$R$^c$.

In one subset of [Group R1] are compounds wherein R$^1$ is C$_{1-6}$ alkyl optionally substituted with one or more groups independently selected from the group consisting of OR$^a$, C$_{3-6}$cycloalkyl, and halogen. In one aspect thereof R$^1$ is C$_{1-4}$alkyl; examples thereof are methyl, ethyl, isopropyl, and t-butyl. In another aspect thereof R$^1$ is C$_{1-4}$alkyl substituted with one or two hydroxy groups; examples thereof are CH(OH)CH$_3$, CH(OH)CH$_2$OH, C(CH$_3$)$_2$OH, CH$_2$C(CH$_3$)$_2$OH. In another aspect thereof R$^1$ is C$_{1-4}$haloalkyl, particularly C$_{1-3}$-fluoroalkyl; examples thereof are difluoromethyl, trifluoromethyl, 2-fluoroethyl and 1-fluoroethyl. In another aspect thereof R$^1$ is C$_{1-4}$-alkyl substituted with C$_{3-6}$cycloalkyl and optionally with a second group selected from OH and halogen; examples thereof are —CH(OH)-cPr, —CH(F)-cPr, —C(OH)(CH$_3$)-cPr.

In another subset of [Group R1] are compounds wherein R$^1$ is C$_{3-6}$cycloalkyl. In one aspect thereof R$^1$ is cyclopropyl.

In another subset of [Group R1] are compounds wherein R$^1$ is —O—X wherein X is selected from (a) C$_{4-6}$cycloalkyl optionally substituted with one to two groups independently selected from C__3alkyl, OH, OC$_{1-3}$alkyl, benzyl, CO$_2$H, CO$_2$C$_{1-4}$alkyl, NH$_2$, NHC$_{1-3}$alkyl, and N(C$_{1-3}$alkyl)$_2$; and (b) a heterocycle selected from azetidinyl, pyrrolidinyl, piperidinyl, azepanyl, tetrahydrofuranyl, tetrahydropyranyl, wherein said heterocycle is optionally substituted with one to two groups independently selected from C$_{1-3}$alkyl, halogen, C$_{1-3}$haloalkyl, CO$_2$H, CO$_2$C$_{1-4}$alkyl.

In another subset of [Group R1] are compounds wherein R$^1$ is —O—C$_{1-6}$ alkyl optionally substituted with one to two groups independently selected from (i) phenyl, (ii) 5- or 6-membered heteroaryl selected from pyridyl, imidazolyl, pyrimidinyl, pyrazolopyridine, pyrazolyl, isoxazolyl, triazolyl, tetrazolyl, each of which is optionally substituted with one or two methyl groups, (iii) 4- to 8-membered heterocyclyl selected from 1,4-dioxanyl, tetrahydropyranyl, tetrahydrofuranyl, pyrrolidinyl, azetidinyl, piperidinyl, azepanyl, morpholinyl, 2,3-dihydroindolyl, 1,4-diazepanyl, piperazinyl, oxazolidinyl, optionally substituted with one or more groups independently selected from oxo, fluoro and methyl, (iv) —CO$_2$H or CO$_2$C$_{1-4}$alkyl, (v) —CONH$_2$ (vi) —NH$_2$, —NHC$_{1-4}$alkyl, 4-morpholinyl, 1-pyrrolidinyl, 1,4-diazepan-1-yl, oxazolidin-3-yl, each ring being optionally substituted with one or two groups selected from oxo, methyl and fluoro; (vii) —NH-piperidine optionally substituted with methyl, (viii) OH or OC$_{1-4}$alkyl.

In another subset of [Group R1] are compounds wherein R$^1$ is —O—C$_{1-4}$alkyl; examples thereof are methoxy, ethoxy and isopropoxy.

In another subset of [Group R1] are compounds wherein R$^1$ is selected from —O—(CH$_2$)$_{1-2}$-"ring" and "ring" is selected from phenyl, 2-, 3- and 4-pyridyl, 1,4-dioxan-2-yl, 4-tetrahydropyranyl, 3-tetrahydrofuranyl, 4-piperidinyl, 3-azetidinyl, 3-oxo-4-morpholinyl, 3,4-difluoro-1-pyrrolizinyl, 1-methyl-2-imidazolyl, 4-imidazolyl, 3-tetrahydropyranyl, 4-pyrimidinyl, pyrazolo[1,5-a]pyrimidin-7-yl, 4-methyl-4-pyrazolyl, 3-isoxazolyl, 4-azepanyl, 1,2,3-triazol-1-yl, 2,3-dihydro-2-indolyl, 1-methyl-5-pyrazolyl, 1-methyl-2-pyrrolidinyl, 1,4-diazepan-1-yl, 1,4-dimethyl-2-piperazinyl, 5-tetrazolyl, 1-methyl-2-oxo-4-pyrrolidinyl, 3-methyl-3-piperidinyl, 4-methyl-2-morpholinyl, 5-methyl-2-oxo-3-oxazolidinyl, 2-oxo-1-pyrrolidinyl.

In another subset of [Group R1] are compounds wherein R$^1$ is selected from —O—(CH$_2$)$_{2-3}$—OH, O—(CH$_2$)$_{2-3}$—

OCH$_3$, O—(CH$_2$)$^{2-3}$—OCH$_2$Ph, O—(CH$_2$)$_{2-3}$—NHCH$_3$, O—C$_{1-3}$alkyl substituted with CO$_2$H, CO$_2$C$_{1-3}$alkyl or CONH$_2$ group.

In another subset of [Group R1] are compounds wherein R$^1$ is selected from H, C$_{1-4}$alkyl, C$_{1-4}$haloalkyl, C$_{3-6}$cycloalkyl, and OC$_{1-4}$alkyl. Examples of R$^1$ include H, methyl, isopropyl, difluoromethyl, trifluoromethyl, 1-fluoroethyl, cyclopropyl and isopropyloxy.

For compounds of formulas (I), (Ia), and (Ib) as well as various applicable groups, subsets, aspects and embodiments mentioned above, there is one group [Group R4] of compounds wherein R$^4$ is selected from H, halogen, C$_{1-3}$alkyl (optionally substituted with OH, OCH$_3$, OCOCH$_3$, NH$_2$, NHCONH$_2$ or NHCOCH$_3$), C$_{1-3}$haloalkyl, C$_{3-4}$cycloalkyl, NR$^{b(a)}$R$^{c(a)}$, NHCOC$_{1-3}$alkyl, NHCOC$_{3-6}$cycloalkyl, NHCONHR$^{b(a)}$. In one embodiment, R$^4$ is H. In another embodiment, R$^4$ is C$_{1-4}$alkyl, preferably methyl. In another embodiment R$^4$ is C$_{3-4}$cycloalkyl, preferably cyclopropyl.

In another group of formula (I) are compounds having the formula I(d) or a pharmaceutically acceptable salt thereof:

(Id)

wherein p' is 0, 1 or 2;

R$^{y(a)}$ is selected from OH, OCH$_3$, F, CN and CONH$_2$;

R$^{z(b)}$ is selected from (a) C$_{1-4}$ alkyl optionally substituted with one or more groups independently selected from OFT, NH$_2$, CN, CO$_2$R$^{a(a)}$ and CONH$_2$, (b) CN, (c) —C(O)$_2$R$^{a(a)}$, (d) —C(O)NHR$^{b(a)}$, (e) —NHC(O)C$_{1-4}$alkyl (optionally substituted with OH), (f) 1,3,4-oxadiazole-2(3H)-one, and (g) 1,2,4-oxadiazole-5(4H)-one;

R$^1$ is selected from H, methyl, isopropyl, difluoromethyl, trifluoromethyl, 1-fluoroethyl, cyclopropyl and isopropyloxy;

R$^4$ is selected from H, methyl and cyclopropyl;

R$^{a(a)}$ is H or C$_{1-4}$ alkyl;

R$^{b(a)}$ is H, C$_{1-4}$ alkyl optionally substituted 2-oxo-1-pyrrolidinyl.

In one subset of formula (Id) are compounds wherein R$^{y(a)}$ is OH.

In another subset of formula (Id) are compounds wherein R$^z$(b) is CO$_2$H, CONH$_2$, CONH(CH$_2$)$_3$-(2-oxo-1-pyrrolidinyl), or NHC(O)CH$_2$OH.

In another group of formula (I) are compounds having the formula I(e) or a pharmaceutically acceptable salt thereof:

(Ie)

wherein

R$^{y(a)}$ is selected from OH, NH$_2$, OCH$_2$CH$_2$OH, and aminomethyl,

R$^1$ is selected from H, methyl, isopropyl, difluoromethyl, trifluoromethyl, 1-fluoroethyl, cyclopropyl and isopropyloxy; and R$^4$ is selected from H, methyl and cyclopropyl.

In one subset of formula (Ie) R$^{y(a)}$ is OH.

Representative compounds of the present invention are as follows (each compound is intended to include pharmaceutically acceptable salts thereof):

1-[5-(2-fluoro-5-{[4-(trifluoromethyl)pyrimidin-2-yl]amino}phenyl)-1,3-thiazol-2-yl]cyclobutanol;
1-[5-(2-methoxy-5-{[4-(trifluoromethyl)pyrimidin-2-yl]amino}phenyl)-1,3-thiazol-2-yl]cyclobutanol;
1-[5-(2-chloro-5-{[4-(trifluoromethyl)pyrimidin-2-yl]amino}phenyl)-1,3-thiazol-2-yl]cyclobutanol;
1-{5-[2-(trifluoromethoxy)-5-{[4-(trifluoromethyl)pyrimidin-2-yl]amino}phenyl]-1,3-thiazol-2-yl}cyclobutanol;
1-{5-[2-(benzyloxy)-5-{[4-(trifluoromethyl)pyrimidin-2-yl]amino}phenyl]-1,3-thiazol-2-yl}cyclobutanol;
2-[2-(1-(hydroxycyclobutyl)-1,3-thiazol-5-yl]-4-{[4-(trifluoromethyl)pyrimidin-2-yl]amino}phenol;
1-[5-(2-methyl-5-{[4-(trifluoromethyl)pyrimidin-2-yl]amino}phenyl)-1,3-thiazol-2-yl]cyclobutanol;
1-{5-[3-(trifluoromethyl)-5-{[4-(trifluoromethyl)pyrimidin-2-yl]amino}phenyl]-1,3-thiazol-2-yl}cyclobutanol;
1-[5-(3-chloro-5-{[4-(trifluoromethyl)pyrimidin-2-yl]amino}phenyl)-1,3-thiazol-2-yl]cyclobutanol;
2-[5-(3-{[4-(trifluoromethyl)pyrimidin-2-yl]amino}phenyl)-1,3-thiazol-2-yl]propan-2-ol;
1-[5-(3-methyl-5-{[4-(trifluoromethyl)pyrimidin-2-yl]amino}phenyl)-1,3-thiazol-2-yl]cyclobutanol;
1,1,1-trifluoro-2-[5-(3-{[4-(trifluoromethyl)pyrimidin-2-yl]amino}phenyl)-1,3-thiazol-2-yl]propan-2-ol;
1,1,1,3,3,3-hexafluoro-2-[5-(3-{[4-(trifluoromethyl)pyrimidin-2-yl]amino}phenyl)-1,3-thiazol-2-yl]propan-2-ol;
2-[5-(3-bromo-5-{[4-(trifluoromethyl)pyrimidin-2-yl]amino}phenyl)-1,3-thiazol-2-yl]propan-2-ol;
cyclopropyl[5-(3-{[4-(trifluoromethyl)pyrimidin-2-yl]amino}phenyl)-1,3-thiazol-2-yl]methanol;
1-[5-(3-{[4-(trifluoromethyl)pyrimidin-2-yl]amino}phenyl)-1,3-thiazol-2-yl]cycloheptanol;
3,3-dimethyl-2-[5-(3-{[4-(trifluoromethyl)pyrimidin-2-yl]amino}phenyl)-1,3-thiazol-2-yl]butan-2-ol;
2-methyl-1-[5-(3-{[4-(trifluoromethyl)pyrimidin-2-yl]amino}phenyl)-1,3-thiazol-2-yl]cyclopentanol;
1-acetyl-4-[5-(3-{[4-(trifluoromethyl)pyrimidin-2-yl]amino}phenyl)-1,3-thiazol-2-yl]piperidin-4-ol;

2,2-difluoro-1-phenyl-1-[5-(3-{[4-(trifluoromethyl)pyrimidin-2-yl]amino}phenyl)-1,3-thiazol-2-yl]ethanol;
3-(dimethylamino)-2,2-dimethyl-1-[5-(3-[4-(trifluoromethyl)pyrimidin-2-yl]amino)phenyl)-1,3-thiazol-2-yl]propan-1-ol;
1,1,1-trifluoro-2-[5-(3-{[4-(trifluoromethyl)pyrimidin-2-yl]amino}phenyl)-1,3-thiazol-2-yl]butan-2-ol;
1,1-difluoro-2-[5-(3-{[4-(trifluoromethyl)pyrimidin-2-yl]amino}phenyl)-1,3-thiazol-2-yl]propan-2-ol;
1-cyclohexyl-2,2,2-trifluoro-1-[5-(3-{[4-(trifluoromethyl)pyrimidin-2-yl]amino}phenyl)-1,3-thiazol-2-yl]ethanol;
1-[1-(phenylsulfonyl)-1H-pyrrol-3-yl]-1-[5-(3-{[4-(trifluoromethyl)pyrimidin-2-yl]amino}phenyl)-1,3-thiazol-2-yl]ethanol;
1-(5-bromopyridin-2-yl)-2,2-difluoro-1-[5-(3-{[4-(trifluoromethyl)pyrimidin-2-yl]amino}phenyl)-1,3-thiazol-2-yl]ethanol;
1-(4-fluorophenyl)-3-[5-(3-{[4-(trifluoromethyl)pyrimidin-2-yl]amino}phenyl)-1,3-thiazol-2-yl]pyrrolidin-3-ol;
1-(dimethylamino)-2-[5-(3-{[4-(trifluoromethyl)pyrimidin-2-yl]amino}phenyl)-1,3-thiazol-2-yl]propan-2-ol;
cyclopentyl[5-(3-{[4-(trifluoromethyl)pyrimidin-2-yl]amino}phenyl)-1,3-thiazol-2-yl]m ethanol;
ethyl (1R,5S)-3-hydroxy-3-[5-(3-{[4-(trifluoromethyl)pyrimidin-2-yl]amino}phenyl)-1,3-thiazol-2-yl]-8-azabicyclo[3.2.1]octane-8-carboxylate;
1-(1-methyl-1H-pyrrol-3-yl)-1-[5-(3-{[4-(trifluoromethyl)pyrimidin-2-yl]amino}phenyl)-1,3-thiazol-2-yl]ethanol;
furan-3-yl[5-(3-{[4-(trifluoromethyl)pyrimidin-2-yl]amino}phenyl)-1,3-thiazol-2-yl]methanol;
furan-3-yl[5-(3-{[4-(trifluoromethyl)pyrimidin-2-yl]amino}phenyl)-1,3-thiazol-2-yl]methanone;
pyridin-3-yl[5-(3-{[4-(trifluoromethyl)pyrimidin-2-yl]amino}phenyl)-1,3-thiazol-2-yl]methanol;
(1-methyl-1H-pyrazol-5-yl)[5-(3-{[4-(trifluoromethyl)pyrimidin-2-yl]amino}phenyl)-1,3-thiazol-2-yl]methanol;
isoxazol-3-yl[5-(3-{[4-(trifluoromethyl)pyrimidin-2-yl]amino}phenyl)-1,3-thiazol-2-yl]methanone;
[1-(1-methylethyl)-1H-pyrazol-4-yl][5-(3-{[4-(trifluoromethyl)pyrimidin-2-yl]amino}phenyl)-1,3-thiazol-2-yl]methanol;
1-pyridin-3-yl-1-[5-(3-{[4-(trifluoromethyl)pyrimidin-2-yl]amino}phenyl)-1,3-thiazol-2-yl]ethanol;
1-pyrazin-2-yl-1-[5-(3-{[4-(trifluoromethyl)pyrimidin-2-yl]amino}phenyl)-1,3-thiazol-2-yl]ethanol;
1-cyclobutyl-1-[5-(3-{[4-(trifluoromethyl)pyrimidin-2-yl]amino}phenyl)-1,3-thiazol-2-yl]ethanol;
2,4-dimethyl-3-[5-(3-{[4-(trifluoromethyl)pyrimidin-2-yl]amino}phenyl)-1,3-thiazol-2-yl]pentan-3-ol;
3-hydroxy-3-[5-(3-{[4-(trifluoromethyl)pyrimidin-2-yl]amino}phenyl)-1,3-thiazol-2-yl]butyl acetate;
1-cyclopropyl-4-[5-(3-{[4-(trifluoromethyl)pyrimidin-2-yl]amino}phenyl)-1,3-thiazol-2-yl]piperidin-4-ol;
3-{2-hydroxy-2-[5-(3-{[4-(trifluoromethyl)pyrimidin-2-yl]amino}phenyl)-1,3-thiazol-2-yl]cyclohexyl}propanenitrile;
ethyl 1-{1-hydroxy-1-[5-(3-{[4-(trifluoromethyl)pyrimidin-2-yl]amino}phenyl)-1,3-thiazol-2-yl]ethyl}cyclopropanecarboxylate;
1,3,4-oxadiazol-2-yl(pyridin-3-yl)[5-(3-{[4-(trifluoromethyl)pyrimidin-2-yl]amino}phenyl)-1,3-thiazol-2-yl]methanol;
ethyl 4-hydroxy-4-[5-(3-{[4-(trifluoromethyl)pyrimidin-2-yl]amino}phenyl)-1,3-thiazol-2-yl]piperidine-1-carboxylate;
1-(1-methylethyl)-4-[5-(3-{[4-(trifluoromethyl)pyrimidin-2-yl]amino}phenyl)-1,3-thiazol-2-yl]piperidin-4-ol;
4-hydroxy-4-[5-(3-{[4-(trifluoromethyl)pyrimidin-2-yl]amino}phenyl)-1,3-thiazol-2-yl]hexan-3-one;
(3aR,5s,6aS)-5-hydroxy-5-[5-(3-{[4-(trifluoromethyl)pyrimidin-2-yl]amino}phenyl)-1,3-thiazol-2-yl]hexahydropentalen-2(1H)-one;
1-[5-(methylsulfonyl)thiophen-2-yl]-1-[5-(3-{[4-(trifluoromethyl)pyrimidin-2-yl]amino}phenyl)-1,3-thiazol-2-yl]ethanol;
2,2,6,6-tetra methyl-4-[5-(3-{[4-(trifluoromethyl)pyrimidin-2-yl]amino}phenyl)-1,3-thiazol-2-yl]tetrahydro-2H-thiopyran-4-ol;
pyridin-2-yl(1,3-thiazol-2-yl)[5-(3-{[4-(trifluoromethyl)pyrimidin-2-yl]amino}phenyl)-1,3-thiazol-2-yl]methanol;
9-benzyl-7-[5-(3-{[4-(trifluoromethyl)pyrimidin-2-yl]amino}phenyl)-1,3-thiazol-2-yl]-3-oxa-9-azabicyclo[3.3.1]nonan-7-ol;
1-(phenylcarbonyl)-4-[5-(3-{[4-(trifluoromethyl)pyrimidin-2-yl]amino}phenyl)-1,3-thiazol-2-yl]piperidin-4-ol;
3,3,4,4,5,5,5-heptafluoro-2-[5-(3-{[4-(trifluoromethyl)pyrimidin-2-yl]amino}phenyl)-1,3-thiazol-2-yl]pentan-2-ol;
2-[5-(3-{[4-(trifluoromethyl)pyrimidin-2-yl]amino}phenyl)-1,3-thiazol-2-yl]-7-azabicyclo[2.2.1]heptan-2-ol;
3-[5-(3-{[4-(trifluoromethyl)pyrimidin-2-yl]amino}phenyl)-1,3-thiazol-2-yl]oxetan-3-ol;
3-[5-(3-methyl-5-{[4-(trifluoromethyl)pyrimidin-2-yl]amino}phenyl)-1,3-thiazol-2-yl]oxetan-3-ol;
4-[5-(3-methyl-5-{[4-(trifluoromethyl)pyrimidin-2-yl]amino}phenyl)-1,3-thiazol-2-yl]tetrahydro-2H-pyran-4-ol;
1-methoxy-2-[5-(3-methyl-5-{[4-(trifluoromethyl)pyrimidin-2-yl]amino}phenyl)-1,3-thiazol-2-yl]propan-2-ol;
2-[5-(3-methyl-5-{[4-(trifluoromethyl)pyrimidin-2-yl]amino}phenyl)-1,3-thiazol-2-yl]propan-2-ol;
1-fluoro-2-[5-(3-methyl-5-{[4-(trifluoromethyl)pyrimidin-2-yl]amino}phenyl)-1,3-thiazol-2-yl]propan-2-ol;
1,3-difluoro-2-[5-(3-methyl-5-{[4-(trifluoromethyl)pyrimidin-2-yl]amino}phenyl)-1,3-thiazol-2-yl]propan-2-ol;
1-(1-methyl-1H-1,2,4-triazol-5-yl)-1-[5-(3-methyl-5-{[4-(trifluoromethyl)pyrimidin-2-yl]amino}phenyl)-1,3-thiazol-2-yl]ethanol;
1-(5-methyl-1,2,4-oxadiazol-3-yl)-1-[5-(3-methyl-5-{[4-(trifluoromethyl)pyrimidin-2-yl]amino}phenyl)-1,3-thiazol-2-yl]ethanol;
dicyclopropyl[5-(3-methyl-5-{[4-(trifluoromethyl)pyrimidin-2-yl]amino}phenyl)-1,3-thiazol-2-yl]methanol;
2,2-dimethyl-5-[5-(3-methyl-5-{[4-(trifluoromethyl)pyrimidin-2-yl]amino}phenyl)-1,3-thiazol-2-yl]-1,3-dioxan-5-ol;
2-[5-(3-methyl-5-{[4-(trifluoromethyl)pyrimidin-2-yl]amino}phenyl)-1,3-thiazol-2-yl]propane-1,2,3-triol;
8-[5-(3-methyl-5-{[4-(trifluoromethyl)pyrimidin-2-yl]amino}phenyl)-1,3-thiazol-2-yl]-1,4-dioxaspiro[4.5]decan-8-ol;
3-(1H-imidazol-4-yl)-1-[5-(3-methyl-5-{[4-(trifluoromethyl)pyrimidin-2-yl]amino}phenyl)-1,3-thiazol-2-yl]propan-1-ol;
8-(5-{3-[(4-methoxypyrimidin-2-yl)amino]-5-methylphenyl}-1,3-thiazol-2-yl)-1,4-dioxaspiro[4.5]decan-8-ol;
2-(5-{3-methyl-5-[(4-methylpyrimidin-2-yl)amino]phenyl}-1,3-thiazol-2-yl)propane-1,2,3-triol;
3-[5-(3-{[4-(trifluoromethyl)pyrimidin-2-yl]amino}phenyl)-1,3-thiazol-2-yl]pentane-1,3,5-triol;
2-[5-(3-{[4-(trifluoromethyl)pyrimidin-2-yl]amino}phenyl)-1,3-thiazol-2-yl]propane-1,2-diol;
2-[5-(3-{[4-(trifluoromethyl)pyrimidin-2-yl]amino}phenyl)-1,3-thiazol-2-yl]propane-1,2-diol;

2-[5-(3-{[4-(trifluoromethyl)pyrimidin-2-yl]amino}phenyl)-1,3-thiazol-2-yl]propane-1,2-diol;
2-methyl-3-[5-(3-methyl-5-{[4-(trifluoromethyl)pyrimidin-2-yl]amino}phenyl)-1,3-thiazol-2-yl]butane-2,3-diol;
2-[5-(3-methyl-5-{[4-(trifluoromethyl)pyrimidin-2-yl]amino}phenyl)-1,3-thiazol-2-yl]propane-1,2-diol;
2-[5-(3-methyl-5-{[4-(trifluoromethyl)pyrimidin-2-yl]amino}phenyl)-1,3-thiazol-2-yl]propane-1,2-diol;
2-[5-(3-methyl-5-{[4-(trifluoromethyl)pyrimidin-2-yl]amino}phenyl)-1,3-thiazol-2-yl]propane-1,2-diol;
2,2,2-trifluoro-1-[5-(3-methyl-5-{[4-(trifluoromethyl)pyrimidin-2-yl]amino}phenyl)-1,3-thiazol-2-yl]ethanol;
2,2,2-trifluoro-1-[5-(3-{[4-(trifluoromethyl)pyrimidin-2-yl]amino}phenyl)-1,3-thiazol-2-yl]ethanone;
2,2,2-trifluoro-1-[5-(3-{[4-(trifluoromethyl)pyrimidin-2-yl]amino}phenyl)-1,3-thiazol-2-yl]ethanol;
2,2,2-trifluoro-1-[5-(3-methyl-5-{[4-(trifluoromethyl)pyrimidin-2-yl]amino}phenyl)-1,3-thiazol-2-yl]ethanol;
2,2,2-trifluoro-1-[5-(3-methyl-5-{[4-(trifluoromethyl)pyrimidin-2-yl]amino}phenyl)-1,3-thiazol-2-yl]ethanol;
2,2,2-trifluoro-1-[5-(3-methyl-5-{[4-(trifluoromethyl)pyrimidin-2-yl]amino}phenyl)-1,3-thiazol-2-yl]ethanone;
ethyl 3,3,3-trifluoro-2-hydroxy-2-[5-(3-methyl-5-{[4-(trifluoromethyl)pyrimidin-2-yl]amino}phenyl)-1,3-thiazol-2-yl]propanoate;
3,3,3-trifluoro-2-[5-(3-methyl-5-{[4-(trifluoromethyl)pyrimidin-2-yl]amino}phenyl)-1,3-thiazol-2-yl]propane-1,2-diol;
3,3,3-trifluoro-2-[5-(3-methyl-5-{[4-(trifluoromethyl)pyrimidin-2-yl]amino}phenyl)-1,3-thiazol-2-yl]propane-1,2-diol;
3,3,3-trifluoro-2-[5-(3-methyl-5-{[4-(trifluoromethyl)pyrimidin-2-yl]amino}phenyl)-1,3-thiazol-2-yl]propane-1,2-diol;
2,2,4,4-tetramethyl-1-[5-(3-{[4-(trifluoromethyl)pyrimidin-2-yl]amino}phenyl)-1,3-thiazol-2-yl]cyclobutane-1,3-diol;
4-hydroxy-4-[5-(3-methyl-5-{[4-(trifluoromethyl)pyrimidin-2-yl]amino}phenyl)-1,3-thiazol-2-yl]cyclohexanone;
cis-1-[5-(3-methyl-5-{[4-(trifluoromethyl)pyrimidin-2-yl]amino}phenyl)-1,3-thiazol-2-yl]cyclohexane-1,4-diol;
trans-1-[5-(3-methyl-5-{[4-(trifluoromethyl)pyrimidin-2-yl]amino}phenyl)-1,3-thiazol-2-yl]cyclohexane-1,4-diol;
trans-1-methyl-4-[5-(3-methyl-5-{[4-(trifluoromethyl)pyrimidin-2-yl]amino}phenyl)-1,3-thiazol-2-yl]cyclohexane-1,4-diol;
cis-1-methyl-4-[5-(3-methyl-5-{[4-(trifluoromethyl)pyrimidin-2-yl]amino}phenyl)-1,3-thiazol-2-yl]cyclohexane-1,4-diol;
5-hydroxy-5-[5-(3-methyl-5-{[4-(trifluoromethyl)pyrimidin-2-yl]amino}phenyl)-1,3-thiazol-2-yl]azepan-2-one;
5-Hydroxy-5-(5-{3-[(4-methoxypyrimidin-2-yl)amino]-5-methylphenyl}-1,3-thiazol-2-yl)-azepan-2-one;
Cyclopropyl[5-(3-{[4-(trifluoromethyl)pyrimidin-2-yl]amino}phenyl)-1,3-thiazol-2-yl]methanone;
1-Cyclopropyl-2,2,2-trifluoro-1-[5-(3-{[4-(trifluoromethyl)pyrimidin-2-yl]amino}phenyl)-1,3-thiazol-2-yl]ethanol;
N-(3-methyl-5-[2-(1-methylethyl)-1,3-thiazol-5-yl]phenyl)-4-(trifluoromethyl)pyrimidin-2-amine;
N-[3-(2-cyclobutyl-1,3-thiazol-5-yl)-5-methylphenyl]-4-(trifluoromethyl)pyrimidin-2-amine;
tert-butyl 4-{1-hydroxy-1-[5-(3-{[4-(trifluoromethyl)pyrimidin-2-yl]amino}phenyl)-1,3-thiazol-2-yl]ethyl}piperidine-1-carboxylate;
1-(piperidin-4-yl)-1-[5-(3-{[4-(trifluoromethyl)pyrimidin-2-yl]amino}phenyl)-1,3-thiazol-2-yl]ethanol;
dicyclopropyl[5-(3-{[4-(trifluoromethyl)pyrimidin-2-yl]amino}phenyl)-1,3-thiazol-2-yl]methanol;
1-[5-(3-{[4-(trifluoromethyl)pyrimidin-2-yl]amino}phenyl)-1,3-thiazol-2-yl]cyclopentanol;
1-cyclopropyl-1-[5-(3-{[4-(trifluoromethyl)pyrimidin-2-yl]amino}phenyl)-1,3-thiazol-2-yl]ethanol;
1,1,1-trifluoro-2-[5-(3-methyl-5-{[4-(trifluoromethyl)pyrimidin-2-yl]amino}phenyl)-1,3-thiazol-2-yl]propan-2-ol;
1-[5-(3-{[4-(trifluoromethyl)pyrimidin-2-yl]amino}phenyl)-1,3-thiazol-2-yl]ethanol;
N-(3-[2-(1-hydroxycyclobutyl)-1,3-thiazol-5-yl]-5-{[4-(trifluoromethyl)pyrimidin-2-yl]amino}phenyl)acetamide;
1-[5-(3-amino-5-{[4-(trifluoromethyl)pyrimidin-2-yl]amino}phenyl)-1,3-thiazol-2-yl]cyclobutanol;
N-(3-[2-(1-hydroxycyclobutyl)-1,3-thiazol-5-yl]-5-{[4-(trifluoromethyl)pyrimidin-2-yl]amino}phenyl)butanamide;
N-(3-[2-(1-hydroxycyclobutyl)-1,3-thiazol-5-yl]-5-{[4-(trifluoromethyl)pyrimidin-2-yl]amino}phenyl)cyclopropanecarboxamide;
1-[5-(3-nitro-5-{[4-(trifluoromethyl)pyrimidin-2-yl]amino}phenyl)-1,3-thiazol-2-yl]cyclobutanol;
1-cyclopentyl-3-(3-[2-(1-hydroxycyclobutyl)-1,3-thiazol-5-yl]-5-{[4-(trifluoromethyl)pyrimidin-2-yl]amino}phenyl)urea;
1-ethyl-3-(3-[2-(1-hydroxycyclobutyl)-1,3-thiazol-5-yl]-5-{[4-(trifluoromethyl)pyrimidin-2-yl]amino}phenyl)urea;
1-(3-[2-(1-hydroxycyclobutyl)-1,3-thiazol-5-yl]-5-{[4-(trifluoromethyl)pyrimidin-2-yl]amino}phenyl)urea;
1-(3-[2-(1-hydroxycyclobutyl)-1,3-thiazol-5-yl]-5-{[4-(trifluoromethyl)pyrimidin-2-yl]amino}phenyl)-3-methylurea;
1-(3-[2-(1-hydroxycyclobutyl)-1,3-thiazol-5-yl]-5-{[4-(trifluoromethyl)pyrimidin-2-yl]amino}phenyl)-3-(1-methylethyl)urea;
N-(3-[2-(1-hydroxycyclobutyl)-1,3-thiazol-5-yl]-5-{[4-(trifluoromethyl)pyrimidin-2-yl]amino}phenyl)dicarbonimidic diamide;
4-[5-(3-[(ethyl carbamoyl)amino]-5-{[4-(trifluoromethyl)pyrimidin-2-yl]amino}phenyl)-1,3-thiazol-2-yl]cyclohexanecarboxamide;
2-methyl-2-[5-(3-{[4-(trifluoromethyl)pyrimidin-2-yl]amino}phenyl)-1,3-thiazol-2-yl]propan-1-ol;
N-{3-[2-(tetrahydrofuran-2-yl)-1,3-thiazol-5-yl]phenyl}-4-(trifluoromethyl)pyrimidin-2-amine;
N-{3-[2-(4-methylmorpholin-2-yl)-1,3-thiazol-5-yl]phenyl}-4-(trifluoromethyl)pyrimidin-2-amine;
N-(3-{2-[(methylsulfonyl)methyl]-1,3-thiazol-5-yl}phenyl)-4-(trifluoromethyl)pyrimidin-2-amine;
N-{3-[2-(1-methyl-1H-pyrazol-4-yl)-1,3-thiazol-5-yl]phenyl}-4-(trifluoromethyl)pyrimidin-2-amine;
N-{3-[2-(tetrahydrofuran-3-yl)-1,3-thiazol-5-yl]phenyl}-4-(trifluoromethyl)pyrimidin-2-amine;
N-{3-[2-(morpholin-4-ylmethyl)-1,3-thiazol-5-yl]phenyl}-4-(trifluoromethyl)pyrimidin-2-amine;
N-{3-[2-(2,3-dihydro-1H-inden-1-yl)-1,3-thiazol-5-yl]phenyl}-4-(trifluoromethyl)pyrimidin-2-amine;
4-(diethylamino)-2-[5-(3-{[4-(trifluoromethyl)pyrimidin-2-yl]amino}phenyl)-1,3-thiazol-2-yl]butan-2-ol;
N-{3-[2-(3,3-difluorocyclobutyl)-1,3-thiazol-5-yl]phenyl}-4-(trifluoromethyl)pyrimidin-2-amine;
3-{[5-(3-{[4-(trifluoromethyl)pyrimidin-2-yl]amino}phenyl)-1,3-thiazol-2-yl]methyl}-1,3-oxazolidin-2-one;
methyl trans-4-[5-(3-{[4-(trifluoromethyl)pyrimidin-2-yl]amino}phenyl)-1,3-thiazol-2-yl]cyclohexanecarboxylate;

trans-N-(2-hydroxyethyl)-4-[5-(3-{[4-(trifluoromethyl)pyrimidin-2-yl]amino}phenyl)-1,3-thiazol-2-yl]cyclohexanecarboxamide;
trans-N-cyclopropyl-4-[5-(3-{[4-(trifluoromethyl)pyrimidin-2-yl]amino}phenyl)-1,3-thiazol-2-yl]cyclohexanecarboxamide;
4-[5-(3-{[4-(trifluoromethyl)pyrimidin-2-yl]amino}phenyl)-1,3-thiazol-2-yl]pyrrolidin-2-one;
N-{3-[2-(1,4-dioxan-2-yl)-1,3-thiazol-5-yl]phenyl}-4-(trifluoromethyl)pyrimidin-2-amine;
1-{2-[5-(3-{[4-(trifluoromethyl)pyrimidin-2-yl]amino}phenyl)-1,3-thiazol-2-yl]ethyl}pyrrolidine-2-thione;
1-methyl-5-[5-(3-{[4-(trifluoromethyl)pyrimidin-2-yl]amino}phenyl)-1,3-thiazol-2-yl]piperidin-2-one;
N-{3-[2-(1-methylazepan-2-yl)-1,3-thiazol-5-yl]phenyl}-4-(trifluoromethyl)pyrimidin-2-amine;
trans-4-[5-(3-{[4-(trifluoromethyl)pyrimidin-2-yl]amino}phenyl)-1,3-thiazol-2-yl]cyclohexanecarboxylic acid;
trans-N-cyclopropyl-4-[5-(3-{[4-(trifluoromethyl)pyrimidin-2-yl]amino}phenyl)-1,3-thiazol-2-yl]cyclohexanecarboxamide;
trans-4-[5-(3-{[4-(trifluoromethyl)pyrimidin-2-yl]amino}phenyl)-1,3-thiazol-2-yl]cyclohexanecarboxamide;
dicyclopropyl{5-[3-(morpholin-4-yl)-5-{[4-(trifluoromethyl)pyrimidin-2-yl]amino}phenyl]-1,3-thiazol-2-yl}methanol;
1-[5-(3-morpholin-4-yl-5-{[4-(trifluoromethyl)pyrimidin-2-yl]amino}phenyl)-1,3-thiazol-2-yl]ethanol;
N-{3-[2-(2-methyl-1,3-dioxolan-2-yl)-1,3-thiazol-5-yl]-5-morpholin-4-ylphenyl}-4-(trifluoromethyl)pyrimidin-2-amine;
1-[5-(3-morpholin-4-yl-5-{[4-(trifluoromethyl)pyrimidin-2-yl]amino}phenyl)-1,3-thiazol-2-yl]ethanone;
1-[5-(3-[4-(methylsulfonyl)piperazin-1-yl]-5-{[4-(trifluoromethyl)pyrimidin-2-yl]amino}phenyl)-1,3-thiazol-2-yl]cyclobutanol;
1-[5-(3-morpholin-4-yl-5-{[4-(trifluoromethyl)pyrimidin-2-yl]amino}phenyl)-1,3-thiazol-2-yl]cyclobutanol;
1-cyclopropyl-1-[5-(3-morpholin-4-yl-5-{[4-(trifluoromethyl)pyrimidin-2-yl]amino}phenyl)-1,3-thiazol-2-yl]ethanol;
1,1,1-trifluoro-2-[5-(3-morpholin-4-yl-5-{[4-(trifluoromethyl)pyrimidin-2-yl]amino}phenyl)-1,3-thiazol-2-yl]propan-2-ol;
(cis)Tert-butyl 4-fluoro-4-[5-(3-methyl-5-{[4-(trifluoromethyl)pyrimidin-2-yl]amino}phenyl)-1,3-thiazol-2-yl]cyclohexanecarboxylate;
(trans)Tert-butyl 4-fluoro-4-[5-(3-methyl-5-{[4-(trifluoromethyl)pyrimidin-2-yl]amino}phenyl)-1,3-thiazol-2-yl]cyclohexanecarboxylate;
4-fluoro-4-[5-(3-methyl-5-{[4-(trifluoromethyl)pyrimidin-2-yl]amino}phenyl)-1,3-thiazol-2-yl]cyclohexanecarboxylic acid;
trans-4-fluoro-4-[5-(3-methyl-5-{[4-(trifluoromethyl)pyrimidin-2-yl]amino}phenyl)-1,3-thiazol-2-yl]cyclohexanecarboxylic acid;
N-{3-[2-(1-fluorocyclobutyl)-1,3-thiazol-5-yl]-5-morpholin-4-ylphenyl}-4-(trifluoromethyl)pyrimidin-2-amine;
N-{3-[2-(1-fluorocyclobutyl)-1,3-thiazol-5-yl]phenyl}-4-(trifluoromethyl)pyrimidin-2-amine;
ethyl cis-4-fluoro-4-[5-(3-{[4-(trifluoromethyl)pyrimidin-2-yl]amino}phenyl)-1,3-thiazol-2-yl]cyclohexanecarboxylate;
ethyl trans-4-fluoro-4-[5-(3-{[4-(trifluoromethyl)pyrimidin-2-yl]amino}phenyl)-1,3-thiazol-2-yl]cyclohexanecarboxylate;
trans-4-fluoro-4-[5-(3-{[4-(trifluoromethyl)pyrimidin-2-yl]amino}phenyl)-1,3-thiazol-2-yl]cyclohexanecarboxylic acid;
1-[5-(3-[(2,2,2-trifluoroethyl)amino]-5-{[4-(trifluoromethyl)pyrimidin-2-yl]amino}phenyl)-1,3-thiazol-2-yl]cyclobutanol;
2,2-difluoro-1-[5-(3-[(2,2,2-trifluoroethyl)amino]-5-{[4-(trifluoromethyl)pyrimidin-2-yl]amino}phenyl)-1,3-thiazol-2-yl]ethanol;
1,1,1-trifluoro-2-[5-(3-[(2,2,2-trifluoroethyl)amino]-5-{[4-(trifluoromethyl)pyrimidin-2-yl]amino}phenyl)-1,3-thiazol-2-yl]propan-2-ol;
1-{5-[3-(difluoromethyl)-5-{[4-(trifluoromethyl)pyrimidin-2-yl]amino}phenyl]-1,3-thiazol-2-yl}cyclobutanol;
2-{5-[3-(difluoromethyl)-5-{[4-(trifluoromethyl)pyrimidin-2-yl]amino}phenyl]-1,3-thiazol-2-yl}propan-2-ol;
2-[5-(3-ethynyl-5-{[4-(trifluoromethyl)pyrimidin-2-yl]amino}phenyl)-1,3-thiazol-2-yl]propan-2-ol;
2-[5-(3-ethyl-5-{[4-(trifluoromethyl)pyrimidin-2-yl]amino}phenyl)-1,3-thiazol-2-yl]propan-2-ol;
2-[5-(3-cyclopropyl-5-{[4-(trifluoromethyl)pyrimidin-2-yl]amino]phenyl)-1,3-thiazol-2-yl]propan-2-ol;
ethyl 4-hydroxy-4-[5-(3-methyl-5-{[4-(trifluoromethyl)pyrimidin-2-yl]amino}phenyl)-1,3-thiazol-2-yl]cyclohexanecarboxylate;
trans-4-hydroxy-4-[5-(3-methyl-5-{[4-(trifluoromethyl)pyrimidin-2-yl]amino}phenyl)-1,3-thiazol-2-yl]cyclohexanecarboxylic acid;
cis-4-hydroxy-4-[5-(3-methyl-5-{[4-(trifluoromethyl)pyrimidin-2-yl]amino}phenyl)-1,3-thiazol-2-yl]cyclohexanecarboxylic acid;
trans-4-hydroxy-4-[5-(3-{[4-(trifluoromethyl)pyrimidin-2-yl]amino}phenyl)-1,3-thiazol-2-yl]cyclohexanecarboxylic acid;
cis-4-hydroxy-4-[5-(3-{[4-(trifluoromethyl)pyrimidin-2-yl]amino}phenyl)-1,3-thiazol-2-yl]cyclohexanecarboxylic acid;
ethyl cis-4-hydroxy-4-[5-(3-{[4-(trifluoromethyl)pyrimidin-2-yl]amino}phenyl)-1,3-thiazol-2-yl]cyclohexanecarboxylate;
ethyl trans-4-hydroxy-4-[5-(3-{[4-(trifluoromethyl)pyrimidin-2-yl]amino}phenyl)-1,3-thiazol-2-yl]cyclohexanecarboxylate;
ethyl 4-hydroxy-4-[5-(3-methyl-5-{[4-(trifluoromethyl)pyrimidin-2-yl]amino}phenyl)-1,3-thiazol-2-yl]cyclohexanecarboxylate;
cis-4-hydroxy-4-[5-(3-methyl-5-{[4-(trifluoromethyl)pyrimidin-2-yl]amino}phenyl)-1,3-thiazol-2-yl]cyclohexanecarboxylic acid;
ethyl trans-4-hydroxy-4-[5-(3-methyl-5-{[4-(trifluoromethyl)pyrimidin-2-yl]amino}phenyl)-1,3-thiazol-2-yl]cyclohexanecarboxylate;
trans-4-hydroxy-4-[5-(3-methyl-5-{[4-(trifluoromethyl)pyrimidin-2-yl]amino}phenyl)-1,3-thiazol-2-yl]cyclohexanecarboxylic acid;
cis-4-hydroxy-4-(5-{3-[(4-methoxypyrimidin-2-yl)amino]-5-methylphenyl}-1,3-thiazol-2-yl)cyclohexanecarboxylic acid;
trans-4-hydroxy-4-(5-{3-[(4-methoxypyrimidin-2-yl)amino]-5-methylphenyl}-1,3-thiazol-2-yl)cyclohexanecarboxylic acid;
trans-4-hydroxy-4-(5-{3-[(4-methoxypyrimidin-2-yl)amino]-5-methylphenyl}-1,3-thiazol-2-yl)-1-methylcyclohexanecarboxylic acid;

cis-4-hydroxy-4-(5-{3-[(4-methoxypyrimidin-2-yl)amino]-5-methylphenyl}-1,3-thiazol-2-yl)-1-methylcyclohexanecarboxylic acid;

cis-4-hydroxy-4-(5-{3-methyl-5-[(4-methylpyrimidin-2-yl)amino]phenyl}-1,3-thiazol-2-yl)cyclohexanecarboxylic acid;

trans-4-hydroxy-4-(5-(3-methyl-5-[(4-methylpyrimidin-2-yl)amino]phenyl)-1,3-thiazol-2-yl)cyclohexanecarboxylic acid;

4-hydroxy-4-[5-(3-methyl-5-{[4-(trifluoromethyl)pyrimidin-2-yl]amino}phenyl)-1,3-thiazol-2-yl]-1-phenylcyclohexanecarboxylic acid;

trans-4-hydroxy-1-methyl-4-[5-(3-{[4-trifluoromethyl)pyrimidin-2-yl]amino}phenyl)-1,3-thiazol-2-yl]cyclohexanecarboxylic acid;

cis-4-hydroxy-1-methyl-4-[5-(3-{[4-trifluoromethyl)pyrimidin-2-yl]amino}phenyl)-1,3-thiazol-2-yl]cyclohexanecarboxylic acid;

ethyl cis-4-hydroxy-1-methyl-4-[5-(3-methyl-5-{[4-trifluoromethyl)pyrimidin-2-yl]amino}phenyl)-1,3-thiazol-2-yl]cyclohexanecarboxylate;

ethyl trans-4-hydroxy-1-methyl-4-[5-(3-methyl-5-{[4-trifluoromethyl)pyrimidin-2-yl]amino}phenyl)-1,3-thiazol-2-yl]cyclohexanecarboxylate;

trans-4-hydroxy-1-methyl-4-[5-(3-methyl-5-{[4-(trifluoromethyl)pyrimidin-2-yl]amino}phenyl)-1,3-thiazol-2-yl]cyclohexanecarboxylic acid;

cis-4-hydroxy-1-methyl-4-[5-(3-methyl-5-{[4-(trifluoromethyl)pyrimidin-2-yl]amino}phenyl)-1,3-thiazol-2-yl]cyclohexanecarboxylic acid;

methyl 1-(acetylamino)-4-hydroxy-4-[5-(3-methyl-5-{[4-(trifluoromethyl)pyrimidin-2-yl]amino}phenyl)-1,3-thiazol-2-yl]cyclohexanecarboxylate;

1-(acetylamino)-4-hydroxy-4-[5-(3-methyl-5-{[4-trifluoromethyl)pyrimidin-2-yl]amino}phenyl)-1,3-thiazol-2-yl]cyclohexanecarboxylic acid;

9-hydroxy-9-[5-(3-methyl-5-{[4-(trifluoromethyl)pyrimidin-2-yl]amino}phenyl)-1,3-thiazol-2-yl]bicyclo[3.3.1]nonane-3-carboxylic acid;

3-hydroxy-3-[5-(3-methyl-5-{[4-(trifluoromethyl)pyrimidin-2-yl]amino}phenyl)-1,3-thiazol-2-yl]cyclobutanecarboxylic acid;

3-hydroxy-3-[5-(3-methyl-5-{[4-(trifluoromethyl)pyrimidin-2-yl]amino}phenyl)-1,3-thiazol-2-yl]cyclopentanecarboxylic acid;

ethyl 4-[5-(3-methyl-5-{[4-(trifluoromethyl)pyrimidin-2-yl]amino}phenyl)-1,3-thiazol-2-yl]cyclohex-3-ene-1-carboxylate;

ethyl 4-[5-(3-methyl-5-{[4-(trifluoromethyl)pyrimidin-2-yl]amino}phenyl)-1,3-thiazol-2-yl]cyclohexanecarboxylate;

4-[5-(3-methyl-5-{[4-(trifluoromethyl)pyrimidin-2-yl]amino}phenyl)-1,3-thiazol-2-yl]cyclohexanecarboxylic acid;

ethyl 4-[5-(3-{[4-(trifluoromethyl)pyrimidin-2-yl]amino}phenyl)-1,3-thiazol-2-yl]cyclohex-3-ene-1-carboxylate;

ethyl 4-[5-(3-methyl-5-{[4-(trifluoromethyl)pyrimidin-2-yl]amino}phenyl)-1,3-thiazol-2-yl]cyclohex-3-ene-1-carboxylate;

ethyl 4-[5-(3-methyl-5-{[4-(trifluoromethyl)pyrimidin-2-yl]amino}phenyl)-1,3-thiazol-2-yl]cyclohexanecarboxylate;

4-[5-(3-methyl-5-{[4-(trifluoromethyl)pyrimidin-2-yl]amino}phenyl)-1,3-thiazol-2-yl]cyclohex-3-ene-1-carboxylic acid;

trans-4-[5-(3-{[4-(trifluoromethyl)pyrimidin-2-yl]amino}phenyl)-1,3-thiazol-2-yl]cyclohexanecarboxylic acid;

methyl trans-4-[5-(3-{[4-(trifluoromethyl)pyrimidin-2-yl]amino}phenyl)-1,3-thiazol-2-yl]cyclohexanecarboxylate;

cis-4-hydroxy-4-[5-(3-methyl-5-{[4-(trifluoromethyl)pyrimidin-2-yl]amino}phenyl)-1,3-thiazol-2-yl]cyclohexanecarbonitrile;

trans-4-hydroxy-4-[5-(3-methyl-5-{[4-(trifluoromethyl)pyrimidin-2-yl]amino}phenyl)-1,3-thiazol-2-yl]cyclohexanecarbonitrile;

trans-4-hydroxy-4-[5-(3-methyl-5-{[4-(trifluoromethyl)pyrimidin-2-yl]amino}phenyl)-1,3-thiazol-2-yl]cyclohexanecarboxamide;

cis-4-hydroxy-4-[5-(3-methyl-5-{[4-(trifluoromethyl)pyrimidin-2-yl]amino}phenyl)-1,3-thiazol-2-yl]cyclohexanecarboxamide;

ethyl 4-[5-(3-{(tert-butoxycarbonyl)[4-(trifluoromethyl)pyrimidin-2-yl]amino}-5-methylphenyl)-1,3-thiazol-2-yl]-4-hydroxycyclohexanecarboxylate;

2-({3-[2-(cis-4-Carboxy-1-methoxycyclohexyl)-1,3-thiazol-5-yl]-5-methylphenyl}amino)-4-(trifluoromethyl)pyrimidin-1-ium trifluoroacetate;

cis-4-methoxy-4-[5-(3-methyl-5-{[4-(trifluoromethyl)pyrimidin-2-yl]amino}phenyl)-1,3-thiazol-2-yl]cyclohexanecarboxylic acid;

2-({3-[2-(trans-4-Carboxy-1-methoxycyclohexyl)-1,3-thiazol-5-yl]-5-methylphenyl}amino)-4-(trifluoromethyl)pyrimidin-1-ium trifluoroacetate;

trans-4-methoxy-4-[5-(3-methyl-5-{[4-(trifluoromethyl)pyrimidin-2-yl]amino}phenyl)-1,3-thiazol-2-yl]cyclohexanecarboxylic acid;

4-methoxy-4-[5-(3-methyl-5-{[4-(trifluoromethyl)pyrimidin-2-yl]amino}phenyl)-1,3-thiazol-2-yl]cyclohexanecarboxylic acid;

1-amino-4-hydroxy-4-[5-(3-methyl-5-{[4-(trifluoromethyl)pyrimidin-2-yl]amino}phenyl)-1,3-thiazol-2-yl]cyclohexanecarboxylic acid;

(1S,4R)-4-hydroxy-2,2-dimethyl-4-[5-(3-methyl-5-{[4-(trifluoromethyl)pyrimidin-2-yl]amino}-phenyl)-1,3-thiazol-2-yl]cyclohexanecarboxylic acid;

(1S,4R)-4-hydroxy-2,2-dimethyl-4-{5-[3-($^2H_3$)methyl-5-{[4-(trifluoromethyl)pyrimidin-2-yl]amino}phenyl]-1,3-thiazol-2-yl}cyclohexanecarboxylic acid; ~

(1R,4S)-4-hydroxy-2,2-dimethyl-4-{5-[3-($^2H_3$)methyl-5-{[4-(trifluoromethyl)pyrimidin-2-yl]amino}phenyl]-1,3-thiazol-2-yl}cyclohexanecarboxylic acid;

(1S,4R)-4-hydroxy-2,2-dimethyl-4-{5-[3-($^2H_2$)methyl-5-[4-(trifluoromethyl)pyrimidin-2-yl]-amino}phenyl]-1,3-thiazol-2-yl)-cyclohexane-carboxylic acid;

(1R,4S)-4-hydroxy-2,2-dimethyl-4-{5-[3-($^2H_2$)methyl-5-{[4-(trifluoromethyl)pyrimidin-2-yl]amino}phenyl]-1,3-thiazol-2-yl}cyclohexane-carboxylic acid;

tert-butyl 4-hydroxy-4-[5-(3-methyl-5-{[4-(trifluoromethyl)pyrimidin-2-yl]amino}phenyl)-1,3-thiazol-2-yl]piperidine-1-carboxylate;

4-[5-(3-methyl-5-{[4-(trifluoromethyl)pyrimidin-2-yl]amino}phenyl)-1,3-thiazol-2-yl]piperidin-4-ol;

4-hydroxy-4-[5-(3-methyl-5-{[4-(trifluoromethyl)pyrimidin-2-yl]amino}phenyl)-1,3-thiazol-2-yl]piperidine-1-carboxamide;

tert-butyl({4-hydroxy-4-[5-(3-methyl-5-[4-(trifluoromethyl)pyrimidin-2-yl]amino}phenyl)-1,3-thiazol-2-yl]piperidin-1-yl sulfonyl)carbamate;

4-hydroxy-4-[5-(3-methyl-5-{[4-(trifluoromethyl)pyrimidin-2-yl]amino}phenyl)-1,3-thiazol-2-yl]piperidine-1-sulfonamide;

4-[5-(3-methyl-5-([4-(trifluoromethyl)pyrimidin-2-yl]amino)phenyl)-1,3-thiazol-2-yl]-1-(phenylsulfonyl)piperidin-4-ol;

1-{4-hydroxy-4-[5-(3-methyl-5-{[4-(trifluoromethyl)pyrimidin-2-yl]amino}phenyl)-1,3-thiazol-2-yl]piperidin-1-yl}ethanone;

4-hydroxy-N-methyl-4-[5-(3-methyl-5-{[4-(trifluoromethyl)pyrimidin-2-yl]amino}phenyl)-1,3-thiazol-2-yl]piperidine-1-carboxamide;

2-{3-Hydroxy-3-[5-(3-methyl-5-{[4-(trifluoromethyl)pyrimidin-2-yl]amino}phenyl)-1,3-thiazol-2-yl]azetidin-1-yl}-2-methylpropanoic acid;

2-[(2-{3-Hydroxy-3-[5-(3-methyl-5-{[4-(trifluoromethyl)pyrimidin-2-yl]amino}phenyl)-1,3-thiazol-2-yl]azetidin-1-yl}-2-methylpropanoyl)oxy]-2-methylpropanoic acid;

Methyl{[4-hydroxy-4-(5-{3-[(4-methoxypyrimidin-2-yl)amino]-5-methylphenyl}-1,3-thiazol-2-yl)piperidin-1-yl]sulfonyl}carbamate;

4-Chloro-4-(5-{3-[(4-methoxypyrimidin-2-yl)amino]-5-methylphenyl}-1,3-thiazol-2-yl)-piperidine-1-sulfonamide;

1-[(1-methylethyl)sulfonyl]-4-[5-(3-methyl-5-{[4-(trifluoromethyl)pyrimidin-2-yl]amino}phenyl)-1,3-thiazol-2-yl]piperidin-4-ol;

4-[5-(3-methyl-5-{[4-(trifluoromethyl)pyrimidin-2-yl]amino}phenyl)-1,3-thiazol-2-yl]-1-[(trifluoromethyl)sulfonyl]piperidin-4-ol;

1-[(1-methyl-1H-imidazol-4-yl)sulfonyl]-4-[5-(3-methyl-5-{[4-(trifluoromethyl)pyrimidin-2-yl]amino}phenyl)-1,3-thiazol-2-yl]piperidin-4-ol;

4-[5-(3-methyl-5-{[4-(trifluoromethyl)pyrimidin-2-yl]amino}phenyl)-1,3-thiazol-2-yl]-1-propanoylpiperidin-4-ol;

1-(hydroxyacetyl)-4-[5-(3-methyl-5-{[4-(trifluoromethyl)pyrimidin-2-yl]amino}phenyl)-1,3-thiazol-2-yl]piperidin-4-ol;

3-{4-hydroxy-4-[5-(3-methyl-5-{[4-(trifluoromethyl)pyrimidin-2-yl]amino}phenyl)-1,3-thiazol-2-yl]piperidin-1-yl}-3-oxopropanenitrile;

1-(N,N-dimethylglycyl)-4-[5-(3-methyl-5-{[4-(trifluoromethyl)pyrimidin-2-yl]amino)phenyl)-1,3-thiazol-2-yl]piperidin-4-ol;

4-[5-(3-methyl-5-([4-(trifluoromethyl)pyrimidin-2-yl]amino}phenyl)-1,3-thiazol-2-yl]-1-(pyridin-3-ylcarbonyl)piperidin-4-ol;

4-[5-(3-methyl-5-{[4-(trifluoromethyl)pyrimidin-2-yl]amino}phenyl)-1,3-thiazol-2-yl]-1-(pyridin-2-ylcarbonyl)piperidin-4-ol;

1-(2-{4-hydroxy-4-[5-(3-methyl-5-{[4-(trifluoromethyl)pyrimidin-2-yl]amino}phenyl)-1,3-thiazol-2-yl]piperidin-1-yl}-2-oxoethyl)pyrrolidin-2-one;

1-(cyclopropylcarbonyl)-4-[5-(3-methyl-5-{[4-(trifluoromethyl)pyrimidin-2-yl]amino}phenyl)-1,3-thiazol-2-yl]piperidin-4-ol;

N-cyclohexyl-4-hydroxy-4-[5-(3-methyl-5-{[4-(trifluoromethyl)pyrimidin-2-yl]amino}phenyl)-1,3-thiazol-2-yl]piperidine-1-carboxamide;

4-hydroxy-N-(1-methylethyl)-4-[5-(3-methyl-5-{[4-(trifluoromethyl)pyrimidin-2-yl]amino)phenyl)-1,3-thiazol-2-yl]piperidine-1-carboxamide;

4-hydroxy-4-[5-(3-methyl-5-[4-(trifluoromethyl)pyrimidin-2-yl]amino}phenyl)-1,3-thiazol-2-yl]-N-propylpiperidine-1-carboxamide;

4-hydroxy-N,N-dimethyl-4-[5-(3-methyl-5-{[4-(trifluoromethyl)pyrimidin-2-yl]amino}phenyl)-1,3-thiazol-2-yl]piperidine-1-carboxamide;

3-hydroxy-3-[5-(3-methyl-5-{[4-(trifluoromethyl)pyrimidin-2-yl]amino}phenyl)-1,3-thiazol-2-yl]pyrrolidine-1-carboxamide;

3-hydroxy-3-[5-(3-methyl-5-{[4-(trifluoromethyl)pyrimidin-2-yl]amino}phenyl)-1,3-thiazol-2-yl]pyrrolidine-1-carboxamide;

3-hydroxy-3-[5-(3-methyl-5-{[4-(trifluoromethyl)pyrimidin-2-yl]amino}phenyl)-1,3-thiazol-2-yl]azetidine-1-carboxamide;

tert-butyl 3-hydroxy-3-[5-(3-methyl-5-{[4-(trifluoromethyl)pyrimidin-2-yl]amino}phenyl)-1,3-thiazol-2-yl]pyrrolidine-1-carboxylate;

3-[5-(3-methyl-5-{[4-(trifluoromethyl)pyrimidin-2-yl]amino}phenyl)-1,3-thiazol-2-yl]pyrrolidin-3-ol;

4-hydroxy-4-[5-(3-methyl-5-{[4-(trifluoromethyl)pyrimidin-2-yl]amino}phenyl)-1,3-thiazol-2-yl]piperidine-1-sulfonamide;

3-hydroxy-3-[5-(3-methyl-5-{[4-(trifluoromethyl)pyrimidin-2-yl]amino}phenyl)-1,3-thiazol-2-yl]pyrrolidine-1-sulfonamide;

3-hydroxy-3-[5-(3-methyl-5-{[4-(trifluoromethyl)pyrimidin-2-yl]amino}phenyl)-1,3-thiazol-2-yl]pyrrolidine-1-carboxamide;

tert-butyl({3-hydroxy-3-[5-(3-methyl-5-{[4-(trifluoromethyl)pyrimidin-2-yl]amino}phenyl)-1,3-thiazol-2-yl]pyrrolidin-1-yl}sulfonyl)carbamate;

N-(dimethylcarbamoyl)-4-hydroxy-4-(5-{3-[(4-methoxypyrimidin-2-yl)amino]-5-methylphenyl}-1,3-thiazol-2-yl)piperidine-1-carboxamide;

methyl{[4-hydroxy-4-(5-{3-[(4-methoxypyrimidin-2-yl)amino]-5-methylphenyl}-1,3-thiazol-2-yl)piperidin-1-yl]sulfonyl}carbamate;

3-hydroxy-3-(5-{3-[(4-methoxypyrimidin-2-yl)amino]-5-methylphenyl}-1,3-thiazol-2-yl)pyrrolidine-1-carboxamide;

4-hydroxy-4-(5-{3-[(4-methoxypyrimidin-2-yl)amino]-5-methylphenyl}-1,3-thiazol-2-yl)piperidine-1-carboxamide;

3-(5-(3-{[4-methoxypyrimidin-2-yl)amino]-5-methylphenyl}-1,3-thiazol-2-yl)pyrrolidin-3-ol;

4-(5-{3-[(4-methoxypyrimidin-2-yl)amino]-5-methylphenyl}-1,3-thiazol-2-yl)piperidin-4-ol;

1-[5-(3-methyl-5-{[4-(propan-2-yl)pyrimidin-2-yl]amino}phenyl)-1,3-thiazol-2-yl]cyclobutanol;

1-(5-{3-methyl-5-[(4-methylpyrimidin-2-yl)amino]phenyl}-1,3-thiazol-2-yl)cyclobutanol;

1-(5-{3-[(4-ethylpyrimidin-2-yl)amino]-5-methylphenyl}-1,3-thiazol-2-yl)cyclobutanol;

1-(5-{3-[(4-cyclopropylpyrimidin-2-yl)amino]-5-methylphenyl}-1,3-thiazol-2-yl)cyclobutanol;

1-[5-(3-methyl-5-{[4-(methyl sulfanyl)pyrimidin-2-yl]amino}phenyl)-1,3-thiazol-2-yl]cyclobutanol;

2-(5-{3-[(4-cyclopropyl-5-fluoropyrimidin-2-yl)amino]-5-fluorophenyl}-1,3-thiazol-2-yl)propane-1,2-diol;

2-(5-{3-[(4-cyclopropyl-5-fluoropyrimidin-2-yl)amine]-5-methylphenyl}-1,3-thiazol-2-yl)-3,3,3-trifluoropropane-1,2-diol;

N-{3-[2-(3-aminooxetan-3-yl)-1,3-thiazol-5-yl]-5-methylphenyl}-4-(trifluoromethyl)pyrimidin-2-amine;

N-{3-[5-(3-methyl-5-{[4-(trifluoromethyl)pyrimidin-2-yl]amino}phenyl)-1,3-thiazol-2-yl]-oxetan-3-yl}methanesulfonamide;

2-methyl-N-{3-[5-(3-methyl-5-{[4-(trifluoromethyl)pyrimidin-2-yl]amino}phenyl)-1,3-thiazol-2-yl]oxetan-3-yl}propane-2-sulfonamide;

N-{3-[2-(1-aminocyclobutyl)-1,3-thiazol-5-yl]-5-methylphenyl}-4-(trifluoromethyl)pyrimidin-2-amine;

1,1,1-trifluoro-N-{3-[5-(3-methyl-5-{[4-(trifluoromethyl)pyrimidin-2-yl]amino}phenyl)-1,3-thiazol-5-yl]oxetan-3-yl}methanesulfonamide;

2,2,2-trifluoro-N-{1-[5-(3-methyl-5-{[4-(trifluoromethyl) pyrimidin-2-yl]amino}phenyl)-1,3-thiazol-2-yl] cyclobutyl}ethanesulfonamide;
1-fluoro-N-{1-[5-(3-methyl-5-{[4-(trifluoromethyl)pyrimidin-2-yl]amino}phenyl)-1,3-thiazol-2-yl] cyclobutyl}methanesulfonamide;
2,2,2-trifluoro-N-{3-[5-(3-methyl-5-{[4-(trifluoromethyl) pyrimidin-2-yl]amino}phenyl)-1,3-thiazol-2-yl]oxetan-3-yl}ethanesulfonamide;
N-{dicyclopropyl[5-(3-methyl-5-{[4-(trifluoromethyl)pyrimidin-2-yl]amino}phenyl)-1,3-thiazol-2-yl] methyl}methanesulfonamide;
1,1-difluoro-N-{3-[5-(3-methyl-5-{[4-(trifluoromethyl)pyrimidin-2-yl]amino}phenyl)-1,3-thiazol-2-yl]oxetan-3-yl}methanesulfinamide;
N-{3-[5-(3-{[4-(trifluoromethyl)pyrimidin-2-yl] amino}phenyl)-1,3-thiazol-2-yl]oxetan-3-yl}methanesulfonamide;
N-{dicyclopropyl[5-(3-methyl-5-{[4-(trifluoromethyl)pyrimidin-2-yl]amino}phenyl)-1,3-thiazol-2-yl]methyl}-2-methylpropane-2-sulfinamide;
N-{1-[5-(3-methyl-5-{[4-(trifluoromethyl)pyrimidin-2-yl] amino}phenyl)-1,3-thiazol-2-yl] cyclobutyl}methanesulfonamide;
N-{3-[2-(1-amino-1-methylethyl)-1,3-thiazol-5-yl]-5-methylphenyl}-4-(trifluoromethyl)pyrimidin-2-amine;
N-{1-methyl-1-[5-(3-methyl-5-{[4-(trifluoromethyl)pyrimidin-2-yl]amino}phenyl)-1,3-thiazol-2-yl] ethyl}methanesulfonamide;
1,1,1-trifluoro-N-{1-[5-(3-methyl-5-{[4-(trifluoromethyl) pyrimidin-2-yl]amino}phenyl)-1,3-thiazol-2-yl] cyclobutyl}methanesulfonamide;
N-{3-[2-(1-aminocyclobutyl)-1,3-thiazol-5-yl]-5-methylphenyl}-4-cyclopropylpyrimidin-2-amine;
N-{3-[2-(1-aminocyclobutyl)-1,3-thiazol-5-yl]-5-methylphenyl}-4-cyclopropylpyrimidin-2-amine;
N-{3-[2-(1-aminocyclobutyl)-1,3-thiazol-5-yl]-5-methylphenyl}pyrimidin-2-amine;
N-{3-[2-(1-aminocyclobutyl)-1,3-thiazol-5-yl]-5-methylphenyl}-4-methoxypyrimidin-2-amine;
N-[3-methyl-5-(1,3-thiazol-5-yl)phenyl]-4-(piperidin-4-yloxy)pyrimidin-2-amine;
N-{3-[5-(3-methyl-5-{[4-(trifluoromethyl)pyrimidin-2-yl] amino}phenyl)-1,3-thiazol-2-yl]oxetan-3-yl}sulfuric diamide;
N-{1-[5-(3-methyl-5-{[4-(trifluoromethyl)pyrimidin-2-yl] amino}phenyl)-1,3-thiazol-2-yl]cyclobutyl}sulfamide;
N-{dicyclopropyl[5-(3-methyl-5-{[4-(trifluoromethyl)pyrimidin-2-yl]amino}phenyl)-1,3-thiazol-2-yl] methyl}sulfamide;
1-{1-[5-(3-methyl-5-{[4-(trifluoromethyl)pyrimidin-2-yl] amino}phenyl)-1,3-thiazol-2-yl]cyclobutyl}urea;
1-{3-[5-(3-methyl-5-{[4-(trifluoromethyl)pyrimidin-2-yl] amino}phenyl)-1,3-thiazol-2-yl]oxetan-3-yl}urea;
1-{dicyclopropyl[5-(3-methyl-5-{[4-(trifluoromethyl)pyrimidin-2-yl]amino}phenyl)-1,3-thiazol-2-yl]methyl}urea;
1-[1-(5-{3-[(4-cyclopropylpyrimidin-2-yl)amino]-5-methylphenyl}-1,3-thiazol-2-yl)cyclobutyl]urea;
1-(1-{5-[3-methyl-5-(pyrimidin-2-ylamino)phenyl]-1,3-thiazol-2-yl}cyclobutyl)urea;
1-[1-(5-{3-[(4-methoxypyrimidin-2-yl)amino]-5-methylphenyl-1,3-thiazol-2-yl)cyclobutyl]urea;
1-{1-[5-(3-methyl-5-{[4-(piperidin-4-yloxy)pyrimidin-2-yl]amino}phenyl)-1,3-thiazol-2-yl]cyclobutyl}urea;
N-[1-(5-{3-[(4-cyclopropyl-5-fluoropyrimidin-2-yl)amino]-5-methylphenyl}-1,3-thiazol-2-yl)cyclobutyl]urea trifluoroacetate;
N-[1-(5-{3-[(4-cyclopropyl-5-fluoropyrimidin-2-yl)amino]-5-fluorophenyl}-1,3-thiazol-2-yl)cyclobutyl]urea;
N-{dicyclopropyl[5-(3-methyl-5-{[4-(trifluoromethyl)pyrimidin-2-yl]amino}phenyl)-1,3-thiazol-2-yl] methyl}dicarbonimidic diamide;
N-{3-[5-(3-methyl-5-{[4-(trifluoromethyl)pyrimidin-2-yl] amino}phenyl)-1,3-thiazol-2-yl]oxetan-3-yl}dicarbonimidic diamide;
N-[1-(5-{3-[(4-methoxypyrimidin-2-yl)amino]-5-methylphenyl}-1,3-thiazol-2-yl)cyclobutyl]dicarbonimidic diamide;
N-(1-{5-[3-methyl-5-(pyrimidin-2-ylamino)phenyl]-1,3-thiazol-2-yl}cyclobutyl)dicarbonimidic diamide;
N-[1-(5-{3-[(4-cyclopropylpyrimidin-2-yl)amino]-5-methylphenyl}-1,3-thiazol-2-yl)cyclobutyl]dicarbonimidic diamide;
N-{1-[5-(3-methyl-5-{[4-(piperidin-4-yloxy)pyrimidin-2-yl]amino}phenyl)-1,3-thiazol-2-yl] cyclobutyl}dicarbonimidic diamide;
N-{1-[5-(3-methyl-5-{[4-(trifluoromethyl)pyrimidin-2-yl] amino}phenyl)-1,3-thiazol-2-yl]cyclobutyl}acetamide;
N-{3-[5-(3-methyl-5-{[4-(trifluoro ethyl)pyrimidin-2-yl] amino}phenyl)-1,3-thiazol-2-yl]oxetan-3-yl}acetamide;
N-{dicyclopropyl[5-(3-methyl-5-{[4-(trifluoromethyl)pyrimidin-2-yl]amino}phenyl)-1,3-thiazol-2-yl] methyl}cyclopropane-1,1-dicarboxamide;
N-{3-[5-(3-methyl-5-{[4-(trifluoromethyl)pyrimidin-2-yl] amino}phenyl)-1,3-thiazol-2-yl]oxetan-3-yl}cyclopropane-1,1-dicarboxamide;
2-({3-methyl-5-[2-(1,1,1-trifluoro-2-hydroxypropan-2-yl)-1,3-thiazol-5-yl]phenyl}amino)-pyrimidine-4-carboxylic acid;
2-({3-[2-(1-hydroxycyclobutyl)-1,3-thiazol-5-yl]-5-methylphenyl}amino)pyrimidine-5-carboxylic acid;
1-[5-(3-{[4-(trifluoromethyl)pyrimidin-2-yl] amino}phenyl)-1,3-thiazol-2-yl]cyclobutanol;
[2-({3-methyl-5-[2-(1,1,1-trifluoro-2-hydroxypropan-2-yl)-1,3-thiazol-5-yl]phenyl}amino)-pyrimidin-4-yl](piperazin-1-yl)methanone;
1,1,1-trifluoro-2-[5-(3-methyl-5-{[4-(morpholin-4-ylcarbonyl)pyrimidin-2-yl]amino}phenyl)-1,3-thiazol-2-yl]propan-2-ol;
2-[5-(3-nitro-5-{[4-(trifluoromethyl)pyrimidin-2-yl] amino}phenyl)-1,3-thiazol-2-yl]propane-2-sulfonamide;
2-[5-(3-amino-5-{[4-(trifluoromethyl)pyrimidin-2-yl] amino}phenyl)-1,3-thiazol-2-yl]propane-2-sulfonamide;
N-(3-{2-(2-sulfamoylpropan-2-yl)-1,3-thiazol-5-yl}-5-{[4-(trifluoromethyl)pyrimidin-2-yl]amino}phenyl)acetamide;
N-(3-methyl-5-{2-[2-(methylsulfonyl)propan-2-yl]-1,3-thiazol-5-yl}phenyl)-4-(trifluoromethyl)pyrimidin-2-amine;
N-({1-[5-(3-methyl-5-[4-(trifluoromethyl)pyrimidin-2-yl] amino}phenyl)-1,3-thiazol-2-yl]-cyclobutyl sulfonyl)acetamide;
2-[5-(3-methyl-5-{[4-(trifluoromethyl)pyrimidin-2-yl] amino}phenyl)-1,3-thiazol-2-yl]propane-2-sulfonamide;
1-[5-(3-methyl-5-{[4-(trifluoromethyl)pyrimidin-2-yl] amino}phenyl)-1,3-thiazol-2-yl]cyclobutanesulfonamide;
N-(3-methyl-5-{2-[1-(methylsulfonyl)cyclobutyl]-1,3-thiazol-5-yl}phenyl)-4-(trifluoromethyl)pyrimidin-2-amine;
N-(3-{2-[1-(methylsulfonyl)cyclobutyl]-1,3-thiazol-5-yl}-5-nitrophenyl)-4-(trifluoromethyl)pyrimidin-2-amine;
5-{2-[1-(methylsulfonyl)cyclobutyl]-1,3-thiazol-5-yl}-N-[4-(trifluoromethyl)pyrimidin-2-yl]benzene-1,3-diamine;

N-(3-{2-[1-(methylsulfonyl)cyclobutyl]-1,3-thiazol-5-yl}-5-{[4-(trifluoromethyl)pyrimidin-2-yl]amino}phenyl)acetamide;

N-(3-{2-[2-(methylsulfonyl)propan-2-yl]-1,3-thiazol-5-yl}phenyl)-4-(trifluoromethyl)pyrimidin-2-amine;

2-[5-(3-{[4-(trifluoromethyl)pyrimidin-2-yl]amino}phenyl)-1,3-thiazol-2-yl]propane-2-sulfonamide;

2-(5-{3-[(4-methoxypyrimidin-2-yl)amino]-5-methylphenyl}-1,3-thiazol-2-yl)propane-2-sulfonamide;

1-[5-(3-methyl-5-{[4-(trifluoromethyl)pyrimidin-2-yl]amino}phenyl)-1,3-thiazol-2-yl]methanesulfonamide;

1-[5-(3-{[4-(trifluoromethyl)pyrimidin-2-yl]amino}phenyl)-1,3-thiazol-2-yl]methanesulfonamide;

1-(5-{3-{[(4-methoxypyrimidin-2-yl)amino]-5-methylphenyl}-1,3-thiazol-2-yl)methanesulfonamide;

Methyl(2R)-2-methyl-3-[5-(3-methyl-5-{[4-(trifluoromethyl)pyrimidin-2-yl]amino}phenyl)-1,3-thiazol-2-yl]propanoate;

Methyl 2,2-dimethyl-3-[5-(3-methyl-5-{[4-(trifluoromethyl)pyrimidin-2-yl]amino}phenyl)-1,3-thiazol-2-yl]propanoate;

2,2-dimethyl-3-[5-(3-methyl-5-{[4-(trifluoromethyl)pyrimidin-2-yl]amino}phenyl)-1,3-thiazol-2-yl]propanoic acid;

N-(3-methyl-5-{2-[2-methyl-2-(1,3,4-oxadiazol-2-yl)propyl]-1,3-thiazol-5-yl}phenyl)-4-(trifluoromethyl)pyrimidin-2-amine;

ethyl 3-[5-(3-methyl-5-{[4-(trifluoromethyl)pyrimidin-2-yl]amino}phenyl)-1,3-thiazol-2-yl]propanoate;

3-[5-(3-methyl-5-{[4-(trifluoromethyl)pyrimidin-2-yl]amino}phenyl)-1,3-thiazol-2-yl]propanamide;

3-[5-(3-methyl-5-{[4-(trifluoromethyl)pyrimidin-2-yl]amino}phenyl)-1,3-thiazol-2-yl]propanoic acid;

N,N-dimethyl-3-[5-(3-methyl-5-{[4-(trifluoromethyl)pyrimidin-2-yl]amino}phenyl)-1,3-thiazol-2-yl]propanamide;

N-{3-methyl-5-[2-(3-morpholin-4-yl-3-oxopropyl)-1,3-thiazol-5-yl]phenyl}-4-(trifluoromethyl)pyrimidin-2-amine;

N-(2-hydroxyethyl)-3-[5-(3-methyl-5-{[4-(trifluoromethyl)pyrimidin-2-yl]amino}phenyl)-1,3-thiazol-2-yl]propanamide;

N-(3-methyl-5-{2-[2-(1,3,4-oxadiazol-2-yl)ethyl]-1,3-thiazol-5-yl}phenyl)-4-(trifluoromethyl)pyrimidin-2-amine;

N-(3-methyl-5-{2-[2-(5-methyl-1,3,4-oxadiazol-2-yl)ethyl]-1,3-thiazol-5-yl}phenyl)-4-(trifluoromethyl)pyrimidin-2-amine;

N-(3-{2-[2-(5-cyclopropyl-1,3,4-oxadiazol-2-yl)ethyl]-1,3-thiazol-5-yl}-5-methylphenyl)-4-(trifluoromethyl)pyrimidin-2-amine;

2,2-dimethyl-3-[5-(3-methyl-5-{[4-(trifluoromethyl)pyrimidin-2-yl]amino}phenyl)-1,3-thiazol-2-yl]propanamide;

N,N,2,2-tetramethyl-3-[5-(3-methyl-5-{[4-(trifluoromethyl)pyrimidin-2-yl]amino}phenyl)-1,3-thiazol-2-yl]propanamide;

2-methyl-4-[5-(3-methyl-5-{[4-(trifluoromethyl)pyrimidin-2-yl]amino}phenyl)-1,3-thiazol-2-yl]butan-2-ol;

tent-Butyl 2-methyl-2-[5-(3-methyl-5-{[4-(trifluoromethyl)pyrimidin-2-yl]amino}phenyl)-1,3-thiazol-2-yl]propanoate;

N-(3-methyl-5-{2-[2-(1,3,4-oxadiazol-2-yl)propan-2-yl]-1,3-thiazol-5-yl}phenyl)-4-(trifluoromethyl)pyrimidin-2-amine;

tert-butyl 1-[5-(3-methyl-5-{[4-(trifluoromethyl)pyrimidin-2-yl]amino}phenyl)-1,3-thiazol-2-yl]cyclopropanecarboxylate;

1-[5-(3-methyl-5-{[4-(trifluoromethyl)pyrimidin-2-yl]amino}phenyl)-1,3-thiazol-2-yl]cyclopropanecarboxylic acid;

N-(3-methyl-5-{2-[1-(1,3,4-oxadiazol-2-yl)cyclopropyl]-1,3-thiazol-5-yl}phenyl)-4-(trifluoromethyl)pyrimidin-2-amine;

2-methyl-2-[5-(3-methyl-5-{[4-(trifluoromethyl)pyrimidin-2-yl]amino}phenyl)-1,3-thiazol-2-yl]propanamide;

N,N,2-trimethyl-2-[5-(3-methyl-5-{[4-(trifluoromethyl)pyrimidin-2-yl]amino}phenyl)-1,3-thiazol-2-yl]propanamide;

N-{3-[2-(1,1-dimethyl-2-morpholin-4-yl-2-oxoethyl)-1,3-thiazol-5-yl]-5-methylphenyl}-4-(trifluoromethyl)pyrimidin-2-amine;

N-(3-methyl-5-{2-[1-methyl-1-(5-methyl-1,3,4-oxadiazol-2-yl)ethyl]-1,3-thiazol-5-yl}phenyl)-4-(trifluoromethyl)pyrimidin-2-amine;

N,N-dimethyl-1-[5-(3-methyl-5-{[4-(trifluoromethyl)pyrimidin-2-yl]amino}phenyl)-1,3-thiazol-2-yl]cyclopropanecarboxamide;

N-methyl-1-[5-(3-methyl-5-{[4-(trifluoromethyl)pyrimidin-2-yl]amino}phenyl)-1,3-thiazol-2-yl]cyclopropanecarboxamide;

1-[5-(3-methyl-5-{[4-(trifluoromethyl)pyrimidin-2-yl]amino}phenyl)-1,3-thiazol-2-yl]cyclopropanecarboxamide;

N-(3-methyl-5-{2-[1-(5-methyl-1,3,4-oxadiazol-2-yl)cyclopropyl]-1,3-thiazol-5-yl}phenyl)-4-(trifluoromethyl)pyrimidin-2-amine;

5-(3-methyl-5-{[4-(trifluoromethyl)pyrimidin-2-yl]amino}phenyl)-1,3-thiazole-2-carboxylic acid;

N-[(2R)-2,3-dihydroxypropyl]-5-(3-methyl-5-{[4-(trifluoromethyl)pyrimidin-2-yl]amino}-phenyl)-1,3-thiazole-2-carboxamide;

N-(1-methylethyl)-5-(3-methyl-5-{[4-(trifluoromethyl)pyrimidin-2-yl]amino}phenyl)-1,3-thiazole-2-carboxamide;

N-{3-methyl-5-[2-(pyrrolidin-1-ylcarbonyl)-1,3-thiazol-5-yl]phenyl}-4-(trifluoromethyl)pyrimidin-2-amine;

5-(3-methyl-5-{[4-(trifluoromethyl)pyrimidin-2-yl]amino}phenyl)-1,3-thiazole-2-carboxamide;

N-(2,3-dihydroxypropyl)-5-(3-methyl-5-{[4-(trifluoromethyl)pyrimidin-2-yl]amino}phenyl)-1,3-thiazole-2-carboxamide;

N-[(2R)-2,3-dihydroxypropyl]-5-(3-methyl-5-{[4-(trifluoromethyl)pyrimidin-2-yl]amino}phenyl)-1,3-thiazole-2-carboxamide;

N-[2-(methylsulfonyl)ethyl]-5-(3-methyl-5-{[4-(trifluoromethyl)pyrimidin-2-yl]amino}phenyl)-1,3-thiazole-2-carboxamide;

N-(2-hydroxyethyl)-N-methyl-5-(3-methyl-5-{[4-(trifluoromethyl)pyrimidin-2-yl]amino}phenyl)-1,3-thiazole-2-carboxamide;

N-(2-hydroxypropyl)-5-(3-methyl-5-{[4-(trifluoromethyl)pyrimidin-2-yl]amino}phenyl)-1,3-thiazole-2-carboxamide;

N-(2-hydroxy-1-methylethyl)-5-(3-methyl-5-{[4-(trifluoromethyl)pyrimidin-2-yl]amino}phenyl)-1,3-thiazole-2-carboxamide;

N-[1-(hydroxymethyl)cyclopropyl]-5-(3-methyl-5-{[4-(trifluoromethyl)pyrimidin-2-yl]amino}phenyl)-1,3-thiazole-2-carboxamide;

N-[1-(hydroxymethyl)propyl]-5-(3-methyl-5-{[4-(trifluoromethyl)pyrimidin-2-yl]amino}phenyl)-1,3-thiazole-2-carboxamide;

N-(2-hydroxy-2-methylpropyl)-5-(3-methyl-5-{[4-(trifluoromethyl)pyrimidin-2-yl]amino}phenyl)-1,3-thiazole-2-carboxamide;

4-{[5-(3-methyl-5-{[4-(trifluoromethyl)pyrimidin-2-yl]amino}phenyl)-1,3-thiazol-2-yl]carbonyl}piperazin-2-one;

N-(3-methyl-5-{2-[(4-methylpiperazin-1-yl)carbonyl]-1,3-thiazol-5-yl}phenyl)-4-(trifluoromethyl)pyrimidin-2-amine;

N-[2-hydroxy-1-(hydroxymethyl)-1-methylethyl]-5-(3-methyl-5-{[4-(trifluoromethyl)pyrimidin-2-yl]amino}phenyl)-1,3-thiazole-2-carboxamide;

N-[(1-methyl-1H-pyrazol-4-yl)methyl]-5-(3-methyl-5-{[4-(trifluoromethyl)pyrimidin-2-yl]amino}phenyl)-1,3-thiazole-2-carboxamide;

N-[(1-methyl-1H-imidazol-5-yl)methyl]-5-(3-methyl-5-{[4-(trifluoromethyl)pyrimidin-2-yl]amino}phenyl)-1,3-thiazole-2-carboxamide;

N-[2-(1H-imidazol-4-yl)ethyl]-5-(3-methyl-5-{[4-(trifluoromethyl)pyrimidin-2-yl]amino}phenyl)-1,3-thiazole-2-carboxamide;

1-methyl-4-{[5-(3-methyl-5-{[4-(trifluoromethyl)pyrimidin-2-yl]amino}phenyl)-1,3-thiazol-2-yl]carbonyl}piperazin-2-one;

N-[1-(hydroxymethyl)cyclopentyl]-5-(3-methyl-5-{[4-(trifluoromethyl)pyrimidin-2-yl]amino}phenyl)-1,3-thiazole-2-carboxamide;

N-{3-[2-(3,4-dihydropyrrolo[1,2-a]pyrazin-2(1H)-ylcarbonyl)-1,3-thiazol-5-yl]-5-methylphenyl}-4-(trifluoromethyl)pyrimidin-2-amine;

1,3-dimethyl-4-{[5-(3-methyl-5-{[4-(trifluoromethyl)pyrimidin-2-yl]amino}phenyl)-1,3-thiazol-2-yl]carbonyl}piperazin-2-one;

N-(3-{2-[(4-acetylpiperazin-1-yl)carbonyl]-1,3-thiazol-5-yl}-5-methylphenyl)-4-(trifluoromethyl)pyrimidin-2-amine;

N-[2-(1,3-dioxolan-2-yl)ethyl]-N-methyl-5-(3-methyl-5-{[4-(trifluoromethyl)pyrimidin-2-yl]amino}phenyl)-1,3-thiazole-2-carboxamide;

N-[(1-methyl-1H-1,2,4-triazol-5-yl)methyl]-5-(3-methyl-5-{[4-(trifluoromethyl)pyrimidin-2-yl]amino}phenyl)-1,3-thiazole-2-carboxamide;

N-(2-fluoroprop-2-en-1-yl)-5-(3-methyl-5-{[4-(trifluoromethyl)pyrimidin-2-yl]amino}phenyl)-1,3-thiazole-2-carboxamide;

3-methyl-4-{[5-(3-methyl-5-{[4-(trifluoromethyl)pyrimidin-2-yl]amino}phenyl)-1,3-thiazol-2-yl]carbonyl}morpholin-2-ol;

N-(1,4-dioxan-2-ylmethyl)-5-(3-methyl-5-{[4-(trifluoromethyl)pyrimidin-2-yl]amino}phenyl)-1,3-thiazole-2-carboxamide;

N-{3-[2-(5,6-dihydroimidazo[1,2-a]pyrazin-7(8H)-ylcarbonyl)-1,3-thiazol-5-yl]-5-methylphenyl}-4-(trifluoromethyl)pyrimidin-2-amine;

N-methyl-N-[(1-methyl-1H-imidazol-2-yl)methyl]-5-(3-methyl-5-{[4-(trifluoromethyl)-pyrimidin-2-yl]amino}phenyl)-1,3-thiazole-2-carboxamide;

N-(dicyclopropylmethyl)-N-methyl-5-(3-methyl-5-{[4-(trifluoromethyl)pyrimidin-2-yl]amino}phenyl)-1,3-thiazole-2-carboxamide;

2-(4-{[5-(3-methyl-5-{[4-(trifluoromethyl)pyrimidin-2-yl]amino}phenyl)-1,3-thiazol-2-yl]carbonyl}morpholin-2-yl)ethanol;

N-(1,4-dioxan-2-ylmethyl)-N-methyl-5-(3-methyl-5-{[4-(trifluoromethyl)pyrimidin-2-yl]amino}phenyl)-1,3-thiazole-2-carboxamide;

[(3R)-1-{[5-(3-methyl-5-{[4-(trifluoromethyl)pyrimidin-2-yl]amino}phenyl)-1,3-thiazol-2-yl]carbonyl}pyrrolidin-3-yl]methanol;

3-methyl-1-{[5-(3-methyl-5-{[4-(trifluoromethyl)pyrimidin-2-yl]amino}phenyl)-1,3-thiazol-2-yl]carbonyl}pyrrolidin-3-ol;

N-(2-hydroxy-3-methoxypropyl)-5-(3-methyl-5-{[4-(trifluoromethyl)pyrimidin-2-yl]amino}-phenyl)-1,3-thiazole-2-carboxamide;

N-(3-methyl-5-{2-[(1-oxido-1,4-thiazepan-4-yl)carbonyl]-1,3-thiazol-5-yl}-phenyl)-4-(trifluoromethyl)pyrimidin-2-amine;

N-(1H-imidazol-2-ylmethyl)-5-(3-methyl-5-{[4-(trifluoromethyl)pyrimidin-2-yl]amino}phenyl)-1,3-thiazole-2-carboxamide;

N-(3-{2-[(1,1-dioxidothiomorpholin-4-yl)carbonyl]-1,3-thiazol-5-yl}-5-methylphenyl)-4-(trifluoromethyl)pyrimidin-2-amine;

N-(2,3-dihydroxypropyl)-N-methyl-5-(3-methyl-5-{[4-(trifluoromethyl)pyrimidin-2-yl]amino}phenyl)-1,3-thiazole-2-carboxamide;

N-methyl-N-[2-(methylsulfonyl)ethyl]-5-(3-methyl-5-{[4-(trifluoromethyl)pyrimidin-2-yl]amino}phenyl)-1,3-thiazole-2-carboxamide;

N-ethyl-N-methyl-5-(3-methyl-5-{[4-(trifluoromethyl)pyrimidin-2-yl]amino}phenyl)-1,3-thiazole-2-carboxamide;

N,N-bis(2-hydroxyethyl)-5-(3-methyl-5-{[4-(trifluoromethyl)pyrimidin-2-yl]amino}phenyl)-1,3-thiazole-2-carboxamide;

N-methyl-N-[2-(methylamino)-2-oxoethyl]-5-(3-methyl-5-{[4-(trifluoromethyl)pyrimidin-2-yl]amino}phenyl)-1,3-thiazole-2-carboxamide;

N-[3-methyl-5-(2-{[4-(2,2,2-trifluoroethyl)piperazin-1-yl]carbonyl}-1,3-thiazol-5-yl)phenyl]-4-(trifluoromethyl)pyrimidin-2-amine;

[(3S)-1-{[5-(3-methyl-5-{[4-(trifluoromethyl)pyrimidin-2-yl]amino}phenyl)-1,3-thiazol-2-yl]carbonyl}pyrrolidin-3-yl]methanol;

N-[(2S)-2,3-dihydroxypropyl]-5-(3-methyl-5-{[4-(trifluoromethyl)pyrimidin-2-yl]amino}-phenyl)-1,3-thiazole-2-carboxamide;

5-(3-{[4-(trifluoromethyl)pyrimidin-2-yl]amino}phenyl)-1,3-thiazole-2-carboxamide;

5-[({[5-(3-methyl-5-{[4-(trifluoromethyl)pyrimidin-2-yl]amino}phenyl)-1,3-thiazol-2-yl]-methyl}amino)methyl]pyrrolidin-2-one;

N-(3-methyl-5-{2-[(pyrimidin-5-ylamino)methyl]-1,3-thiazol-5-yl}phenyl)-4-(trifluoromethyl)-pyrimidin-2-amine;

1,1-difluoro-3-({[5-(3-methyl-5-{[4-(trifluoromethyl)pyrimidin-2-yl]amino}phenyl)-1,3-thiazol-2-yl]methyl}amino)propan-2-ol;

5-[({[5-(3-methyl-5-{[4-(trifluoromethyl)pyrimidin-2-yl]amino}phenyl)-1,3-thiazol-2-yl]methyl}amino)methyl]-2,4-dihydro-3H-1,2,4-triazol-3-one;

5-[(methyl{[5-(3-methyl-5-{[4-(trifluoromethyl)pyrimidin-2-yl]amino}phenyl)-1,3-thiazol-2-yl]methyl}amino)methyl]-2,4-dihydro-3H-1,2,4-triazol-3-one;

N-[3-(2-{[(1,1-dioxidotetrahydrothiophen-3-yl)amino]methyl}-1,3-thiazol-5-yl)-5-methyl-phenyl]-4-(trifluoromethyl)pyrimidin-2-amine;

N-{3-methyl-5-[2-({[(3-methyloxetan-3-yl)methyl]amino}methyl)-1,3-thiazol-5-yl]phenyl}-4-(trifluoromethyl)pyrimidin-2-amine;

N-[3-(2-{[(dicyclopropylmethyl)(methyl)amino]methyl}-1,3-thiazol-5-yl)-5-methylphenyl]-4-(trifluoromethyl)pyrimidin-2-amine;

N-[3-(2-{[(2-fluoroprop-2-en-1-yl)amino]methyl}-1,3-thiazol-5-yl)-5-methylphenyl]-4-(trifluoromethyl)pyrimidin-2-amine;

N-[3-methyl-5-(2-{[(1-pyridin-2-ylethyl)amino]methyl}-1,
3-thiazol-5-yl)phenyl]-4-(trifluoromethyl)pyrimidin-2-
amine;
N-{3-methyl-5-[2-({[1-(1-methylethyl)-1H-1,2,3-triazol-4-
yl]amino}methyl)-1,3-thiazol-5-yl]phenyl}-4-(trifluo-
romethyl)pyrimidin-2-amine;
2-({[5-(3-methyl-5-{[4-(trifluoromethyl)pyrimidin-2-yl]
amino}phenyl)-1,3-thiazol-2-yl]methyl}amino)ethane-
sulfonamide;
3-methyl-1-{[5-(3-methyl-5-{[4-(trifluoromethyl)pyrimi-
din-2-yl]amino}phenyl)-1,3-thiazol-2-yl]
methyl}piperidin-3-ol;
3-methyl-1-{[5-(3-methyl-5-{[4-(trifluoromethyl)pyrimi-
din-2-yl]amino}phenyl)-1,3-thiazol-2-yl]
methyl}pyrrolidin-3-ol;
N-(3-methyl-5-{2-[(1-oxidothiomorpholin-4-yl)methyl]-1,
3-thiazol-5-yl}phenyl)-4-(trifluoromethyl)pyrimidin-2-
amine;
N-(3-methyl-5-{2-[(1-oxido-1,4-thiazepan-4-yl)methyl]-1,
3-thiazol-5-yl}phenyl)-4-(trifluoromethyl)pyrimidin-2-
amine;
4-methyl-1-{[5-(3-methyl-5-{[4-(trifluoromethyl)pyrimi-
din-2-yl]amino}phenyl)-1,3-thiazol-2-yl]
methyl}piperidin-4-ol;
2-(methyl{[5-(3-methyl-5-{[4-(trifluoromethyl)pyrimidin-
2-yl]amino}phenyl)-1,3-thiazol-2-yl]methyl}amino)etha-
nol;
2,2'-({[5-(3-methyl-5-{[4-(trifluoromethyl)pyrimidin-2-yl]
amino}phenyl)-1,3-thiazol-2-yl]methyl}imino)diethanol;
2-methyl-2-({[5-(3-methyl-5-{[4-(trifluoromethyl)pyrimi-
din-2-yl]amino}phenyl)-1,3-thiazol-2-yl]methyl}amino)
propane-1,3-diol;
2-({[5-(3-methyl-5-{[4-(trifluoromethyl)pyrimidin-2-yl]
amino}phenyl)-1,3-thiazol-2-yl]methyl}amino)propan-1-
ol;
2-({[5-(3-methyl-5-{[4-(trifluoromethyl)pyrimidin-2-yl]
amino}phenyl)-1,3-thiazol-2-yl]methyl}amino)butan-1-
ol;
1-({[5-(3-methyl-5-{[4-(trifluoromethyl)pyrimidin-2-yl]
amino}phenyl)-1,3-thiazol-2-yl]methyl}amino)propan-2-
ol;
2-({[5-(3-methyl-5-{[4-(trifluoromethyl)pyrimidin-2-yl]
amino}phenyl)-1,3-thiazol-2-yl]methyl}amino)ethanol;
3-({[5-(3-methyl-5-{[4-(trifluoromethyl)pyrimidin-2-yl]
amino}phenyl)-1,3-thiazol-2-yl]methyl}amino)propan-1-
ol;
4-({[5-(3-methyl-5-{[4-(trifluoromethyl)pyrimidin-2-yl]
amino}phenyl)-1,3-thiazol-2-yl]methyl}amino)butan-1-
ol;
1-({[5-(3-methyl-5-{[4-(trifluoromethyl)pyrimidin-2-yl]
amino}phenyl)-1,3-thiazol-2-yl]methyl}amino)cyclopro-
panecarboxylic acid;
N~2~-{[5-(3-methyl-5-{[4-(trifluoromethyl)pyrimidin-2-
yl]amino}phenyl)-1,3-thiazol-2-yl]methyl}glycinamide;
N~3~-{[5-(3-methyl-5-{[4-(trifluoromethyl)pyrimidin-2-
yl]amino}phenyl)-1,3-thiazol-2-yl]methyl}-beta-alanina-
mide;
N-(3-{2-[(4-acetylpiperazin-1-yl)methyl]-1,3-thiazol-5-yl}-
5-methylphenyl)-4-(trifluoromethyl)-pyrimidin-2-amine;
1-{[5-(3-methyl-5-{[4-(trifluoromethyl)pyrimidin-2-yl]
amino}phenyl)-1,3-thiazol-2-yl]methyl}-1,4-diazepan-5-
one;
4-{[5-(3-methyl-5-{[4-(trifluoromethyl)pyrimidin-2-yl]
amino}phenyl)-1,3-thiazol-2-yl]methyl}piperazin-2-one;
N-{3-methyl-5-[2-({[2-(methylsulfonyl)ethyl]
amino}methyl)-1,3-thiazol-5-yl]phenyl}-4-(trifluorom-
ethyl)pyrimidin-2-amine;
N-{3-methyl-5-[2-({methyl[2-(methylsulfonyl)ethyl]
amino}methyl)-1,3-thiazol-5-yl]phenyl}-4-(trifluorom-
ethyl)pyrimidin-2-amine;
4-{[5-(3-methyl-5-{[4-(trifluoromethyl)pyrimidin-2-yl]
amino}phenyl)-1,3-thiazol-2-yl]methyl}-1,4-diazepan-2-
one;
N-[3-(2-{[(1-ethyl-1H-1,2,3-triazol-4-yl)amino]methyl}-1,
3-thiazol-5-yl)-5-methylphenyl]-4-(trifluoromethyl)pyri-
midin-2-amine;
1-({[5-(3-methyl-5-{[4-(trifluoromethyl)pyrimidin-2-yl]
amino}phenyl)-1,3-thiazol-2-yl]methyl}amino)cyclobu-
tanecarboxylic acid;
3-(methyl{[5-(3-methyl-5-{[4-(trifluoromethyl)pyrimidin-
2-yl]amino}phenyl)-1,3-thiazol-2-yl]methyl}amino)pro-
pane-1,2-diol;
3-({[5-(3-methyl-5-{[4-(trifluoromethyl)pyrimidin-2-yl]
amino}phenyl)-1,3-thiazol-2-yl]methyl}amino)azepan-2-
one;
4-[2-({[5-(3-methyl-5-{[4-(trifluoromethyl)pyrimidin-2-yl]
amino}phenyl)-1,3-thiazol-2-yl]methyl}amino)ethyl]pip-
erazin-2-one;
N-methyl-2-({[5-(3-methyl-5-{[4-(trifluoromethyl)pyrimi-
din-2-yl]amino}phenyl)-1,3-thiazol-2-yl]methyl}amino)
ethanesulfonamide;
5-({[5-(3-methyl-5-{[4-(trifluoromethyl)pyrimidin-2-yl]
amino}phenyl)-1,3-thiazol-2-yl]methyl}amino)-1H-
pyrazole-3-carboxylic acid;
2-methyl-1-({[5-(3-methyl-5-{[4-(trifluoromethyl)pyrimi-
din-2-yl]amino}phenyl)-1,3-thiazol-2-yl]methyl}amino)
propan-2-ol;
N-[3-methyl-5-(2-[4-(methylsulfonyl)piperazin-1-yl]me-
thyl)-1,3-thiazol-5-yl)phenyl]-4-(trifluoromethyl)pyrimi-
din-2-amine;
2-[3-methyl-5-({[5-(3-methyl-5-{[4-(trifluoromethyl)pyri-
midin-2-yl]amino}phenyl)-1,3-thiazol-2-yl]
methyl}amino)-1H-pyrazol-1-yl]ethanol;
3-({[5-(3-methyl-5-{[4-(trifluoromethyl)pyrimidin-2-yl]
amino}phenyl)-1,3-thiazol-2-yl]methyl}-amino)pyrroli-
din-2-one;
4-({[5-(3-methyl-5-[4-(trifluoromethyl)pyrimidin-2-yl]
amino}phenyl)-1,3-thiazol-2-yl]methyl)amino)pyrroli-
din-2-one;
3-({1-[5-(3-methyl-5-{[4-(trifluoromethyl)pyrimidin-2-yl]
amino}phenyl)-1,3-thiazol-2-yl]ethyl}-amino)pyrrolidin-
2-one;
N-(3-{2-[1-(dimethylamino)ethyl]-1,3-thiazol-5-yl}-5-me-
thylphenyl)-4-(trifluoromethyl)-pyrimidin-2-amine;
4-({1-[5-(3-methyl-5-{[4-(trifluoromethyl)pyrimidin-2-yl]
amino}phenyl)-1,3-thiazol-2-yl]ethyl}-amino)pyrrolidin-
2-one;
[5-(3-methyl-5-{[4-(trifluoromethyl)pyrimidin-2-yl]
amino}phenyl)-1,3-thiazol-2-yl]methanol;
N-{3-[2-(bromomethyl)-1,3-thiazol-5-yl]-5-methylphenyl}-
4-(trifluoromethyl)pyrimidin-2-amine;
Ethyl 3-{[5-(3-methyl-5-{[4-(trifluoromethyl)pyrimidin-2-
yl]amino}phenyl)-1,3-thiazol-2-yl]-methyl}-2-oxopyrro-
lidine-3-carboxylate;
3-{[5-(3-methyl-5-{[4-(trifluoromethyl)pyrimidin-2-yl]
amino}phenyl)-1,3-thiazol-2-yl]methyl}-2-oxopyrroli-
dine-3-carboxylic acid;
3-{[5-(3-methyl-5-{[4-(trifluoromethyl)pyrimidin-2-yl]
amino}phenyl)-1,3-thiazol-2-yl]methyl}-1,3-oxazolidin-
2-one;
1-{[5-(3-methyl-5-{[4-(trifluoromethyl)pyrimidin-2-yl]
amino}phenyl)-1,3-thiazol-2-yl]methyl}pyrrolidin-2-
one;

ethyl 3-{[5-(3-methyl-5-{[4-(trifluoromethyl)pyrimidin-2-yl]amino}phenyl)-1,3-thiazol-2-yl]methyl}-2-oxopyrrolidine-3-carboxylate;

1-methyl-3-[5-(3-methyl-5-{[4-(trifluoromethyl)pyrimidin-2-yl]amino}phenyl)-1,3-thiazol-2-yl]methyl}imidazolidin-2-one;

3-{[5-(3-methyl-5-{[4-(trifluoromethyl)pyrimidin-2-yl]amino}phenyl)-1,3-thiazol-2-yl]methyl}-2-oxopyrrolidine-3-carboxylic acid;

1-[5-(3-{[4-(azetidin-3-yloxy)pyrimidin-2-yl]amino)-5-methylphenyl)-1,3-thiazol-2-yl]cyclobutanol;

1-[5-(3-methyl-5-[4-(oxetan-3-yloxy)pyrimidin-2-yl]amino}phenyl)-1,3-thiazol-2-yl]cyclobutanol;

1-[5-(3-methyl-5-{[4-(pyridin-4-ylmethoxy)pyrimidin-2-yl]amino}phenyl)-1,3-thiazol-2-yl]cyclobutanol;

1-[5-(3-methyl-5-{[4-(pyridin-3-ylmethoxy)pyrimidin-2-yl]amino}phenyl)-1,3-thiazol-2-yl]cyclobutanol;

1-[5-(3-methyl-5-[4-(pyridin-2-ylmethoxy)pyrimidin-2-yl]amino)phenyl)-1,3-thiazol-2-yl]cyclobutanol;

1-[5-(3-{[4-(1,4-dioxan-2-ylmethoxy)pyrimidin-2-yl]amino}-5-methylphenyl)-1,3-thiazol-2-yl]cyclobutanol;

1-{5-[3-methyl-5-({4-[2-(tetrahydro-2H-pyran-4-yl)ethoxy]pyrimidin-2-yl}amino)phenyl]-1,3-thiazol-2-yl}cyclobutanol;

1-[5-(3-{[5-fluoro-4-(tetrahydrofuran-3-yloxy)pyrimidin-2-yl]amino}-5-methylphenyl)-1,3-thiazol-2-yl]cyclobutanol;

1-[5-(3-methyl-5-{[4-(tetrahydro-2H-pyran-4-ylmethoxy)pyrimidin-2-yl]amino}phenyl)-1,3-thiazol-2-yl]cyclobutanol;

1-{5-[3-methyl-5-({4-[(3R)-tetrahydrofuran-3-yloxy]pyrimidin-2-yl}amino)phenyl]-1,3-thiazol-2-yl}cyclobutanol;

1-{5-[3-({4-[2-(benzyloxy)ethoxy]pyrimidin-2-yl}amino)-5-methylphenyl]-1,3-thiazol-2-yl}cyclobutanol;

1-{5-[3-methyl-5-({4-[(3S)-tetrahydrofuran-3-yloxy]pyrimidin-2-yl}amino)phenyl]-1,3-thiazol-2-yl}cyclobutanol;

1-{5-[3-({4-[4-(benzyloxy)butoxy]pyrimidin-2-yl}amino)-5-methylphenyl]-1,3-thiazol-2-yl}cyclobutanol;

1-[5-(3-{[4-(3-methoxypropoxy)pyrimidin-2-yl]amino}-5-methylphenyl)-1,3-thiazol-2-yl]-cyclobutanol;

1-{5-[3-({4-[3-(benzyloxy)propoxy]pyrimidin-2-yl}amino)-5-methylphenyl]-1,3-thiazol-2-yl}-cyclobutanol;

1-[5-(3-{[4-(2-methoxyethoxy)pyrimidin-2-yl]amino}-5-methylphenyl)-1,3-thiazol-2-yl]cyclobutanol;

1-[5-(3-methyl-5-{[4-(tetrahydrofuran-3-ylmethoxy)pyrimidin-2-yl]amino}phenyl)-1,3-thiazol-2-yl]cyclobutanol;

ethyl 4-{[2-({3-[2-(1-hydroxycyclobutyl)-1,3-thiazol-5-yl]-5-methylphenyl}amino)pyrimidin-4-yl]oxy}cyclohexanecarboxylate;

1-[5-(3-methyl-5-{[4-(tetrahydro-2H-pyran-4-yloxy)pyrimidin-2-yl]amino}phenyl)-1,3-thiazol-2-yl]cyclobutanol;

1-{5-[3-({4-[(4-aminocyclohexyl)oxy]pyrimidin-2-yl}amino)-5-methylphenyl]-1,3-thiazol-2-yl}cyclobutanol;

1-{5-[3-({4-[(3-amino-8-oxabicyclo[3.2.1]oct-6-yl)oxy]pyrimidin-2-yl}amino)-5-methylphenyl]-1,3-thiazol-2-yl}cyclobutanol;

1-{5-[3-methyl-5-({4-[(7-methylazepan-4-yl)oxy]pyrimidin-2-yl}amino)phenyl]-1,3-thiazol-2-yl}cyclobutanol;

1-[5-(3-{[4-(azepan-4-yloxy)pyrimidin-2-yl]amino}-5-methylphenyl)-1,3-thiazol-2-yl]cyclobutanol;

(2R)-2-{[2-({3-[2-(1-hydroxycyclobutyl)-1,3-thiazol-5-yl]-5-methylphenyl}amino)pyrimidin-4-yl]oxy}propanoic acid;

1-{5-[3-methyl-5-({4-[2-(methylamino)ethoxy]pyrimidin-2-yl}amino)phenyl]-1,3-thiazol-2-yl}cyclobutanol;

1-[5-(3-methyl-5-{[4-(piperidin-4-ylmethoxy)pyrimidin-2-yl]amino}phenyl)-1,3-thiazol-2-yl]cyclobutanol;

tert-butyl 2-{[2-({3-[2-(1-hydroxycyclobutyl)-1,3-thiazol-5-yl]-5-methylphenyl}amino)-pyrimidin-4-yl]oxy}-2-methylpropanoate;

2-[5-(3-{[4-(benzyloxy)pyrimidin-2-yl]amino}-5-methylphenyl)-1,3-thiazol-2-yl]-1,1,1-trifluoropropan-2-ol;

1-[5-(3-methyl-5-{[4-(piperidin-3-yloxy)pyrimidin-2-yl]amino}phenyl)-1,3-thiazol-2-yl]-cyclobutanol;

1-[5-(3-{[4-(azetidin-3-ylmethoxy)pyrimidin-2-yl]amino}-5-methylphenyl)-1,3-thiazol-2-yl]-cyclobutanol;

1-[5-(3-{[4-(azetidin-3-yloxy)pyrimidin-2-yl]amino}-5-methylphenyl)-1,3-thiazol-2-yl]-cyclobutanol;

1-[5-(3-methyl-5-{[4-(tetrahydrofuran-3-yloxy)pyrimidin-2-yl]amino}phenyl)-1,3-thiazol-2-yl]-cyclobutanol;

1-[5-(3-{[4-(cyclobutyloxy)pyrimidin-2-yl]amino}-5-methylphenyl)-1,3-thiazol-2-yl]-cyclobutanol;

1-[5-(3-{[4-(cyclopentyloxy)pyrimidin-2-yl]amino}-5-methylphenyl)-1,3-thiazol-2-yl]-cyclobutanol;

1-[5-(3-{[4-(cyclohexyloxy)pyrimidin-2-yl]amino}-5-methylphenyl)-1,3-thiazol-2-yl]-cyclobutanol;

1-methyl-4-{[2-({3-methyl-5-[2-(2,2,2-trifluoro-1-hydroxy-1-methylethyl)-1,3-thiazol-5-yl]phenyl}amino)pyrimidin-4-yl]oxy}cyclohexanol;

2-(5-{3-[(4-{[4-(benzyloxy)cyclohexyl]oxy}pyrimidin-2-yl)amino]-5-methylphenyl}-1,3-thiazol-2-yl)-1,1,1-trifluoropropan-2-ol;

1,1,1-trifluoro-2-(5-{3-[(4-{[3-fluoropiperidin-4-yl]oxy}pyrimidin-2-yl)amino]-5-methylphenyl}-1,3-thiazol-2-yl)propan-2-ol;

tert-butyl 3-fluoro-4-{[2-({3-methyl-5-[2-(2,2,2-trifluoro-1-hydroxy-1-methylethyl)-1,3-thiazol-5-yl]phenyl}amino)pyrimidin-4-yl]oxy}piperidine-1-carboxylate;

1,1,1-trifluoro-2-[5-(3-methyl-5-{[4-(piperidin-4-yloxy)pyrimidin-2-yl]amino}phenyl)-1,3-thiazol-2-yl]propan-2-ol;

1,1,1-trifluoro-2-(5-{3-[(4-{[3-fluoropiperidin-4-yl]oxy}pyrimidin-2-yl)amino]-5-methyl-phenyl}-1,3-thiazol-2-yl)propan-2-ol;

1,1,1-trifluoro-2-{5-[3-methyl-5-({4-[(3R)-pyrrolidin-3-yloxy]pyrimidin-2-yl}amino)phenyl]-1,3-thiazol-2-yl}propan-2-ol;

1,1,1-trifluoro-2-{5-[3-methyl-5-({4-[(3S)-pyrrolidin-3-yloxy]pyrimidin-2-yl}amino)phenyl]-1,3-thiazol-2-yl}propan-2-ol;

1-[5-(3-methyl-5-{[4-(piperidin-4-yloxy)pyrimidin-2-yl]amino}phenyl)-1,3-thiazol-2-yl]-cyclobutanol;

1-[5-(3-{[4-(piperidin-4-yloxy)pyrimidin-2-yl]amino}phenyl)-1,3-thiazol-2-yl]ethanol;

2-{[2-({3-[2-(1-hydroxycyclobutyl)-1,3-thiazol-5-yl]-5-methylphenyl}amino)pyrimidin-4-yl]oxy}-2-methylpropanoic acid;

4-{[2-({3-methyl-5-[2-(1,1,1-trifluoro-2-hydroxypropan-2-yl)-1,3-thiazol-5-yl]phenyl}amino)-pyrimidin-4-yl]oxy}cyclohexanol;

4-{[2-({3-[2-(1-hydroxycyclobutyl)-1,3-thiazol-5-yl]-5-methylphenyl}amino)pyrimidin-4-yl]oxy}cyclohexanecarboxylic acid;

2-(5-{3-[(4-chloropyrimidin-2-yl)amino]-5-methylphenyl}-1,3-thiazol-2-yl)-1,1,1-trifluoropropan-2-ol;

2-{[2-({3-methyl-5-[2-(1,1,1-trifluoro-2-hydroxypropan-2-yl)-1,3-thiazol-5-yl]phenyl}amino)-pyrimidin-4-yl]oxy}acetamide;

1,1,1-trifluoro-2-(5-{3-methyl-5-[(5-methylpyrimidin-2-yl)amino]phenyl}-1,3-thiazol-2-yl)propan-2-ol;

1-(5-{3-[(4-methoxypyrimidin-2-yl)amino]-5-methylphenyl}-1,3-thiazol-2-yl)cyclobutanol;
1,1,1-trifluoro-2-(5-{3-[(4-methoxypyrimidin-2-yl)amino]-5-methylphenyl}-1,3-thiazol-2-yl)-propan-2-ol;
1-(5-{3-methyl-5-[(4-methylpyrimidin-2-yl)amino]phenyl}-1,3-thiazol-2-yl)cyclobutanol;
1-{5-[3-methyl-5-(pyrimidin-2-ylamino)phenyl]-1,3-thiazol-2-yl}cyclobutanol;
1,1,1-trifluoro-2-(5-{3-[(5-fluoropyrimidin-2-yl)amino]-5-methylphenyl}-1,3-thiazol-2-yl)-propan-2-ol;
1,1,1-trifluoro-2-(5-{3-[(5-methoxypyrimidin-2-yl)amino]-5-methylphenyl}-1,3-thiazol-2-yl)-propan-2-ol;
1-(5-{3-[(5-fluoropyrimidin-2-yl)amino]-5-methylphenyl}-1,3-thiazol-2-yl)cyclobutanol;
1-(5-{3-[(5-chloropyrimidin-2-yl)amino]-5-methylphenyl}-1,3-thiazol-2-yl)cyclobutanol;
1-(5-{3-[(5-ethylpyrimidin-2-yl)amino]-5-methylphenyl}-1,3-thiazol-2-yl)cyclobutanol;
2-(5-{3-[(5-cyclopropylpyrimidin-2-yl)amino]-5-methylphenyl}-1,3-thiazol-2-yl)-1,1,1-trifluoropropan-2-ol;
2-({3-[2-(1-hydroxycyclobutyl)-1,3-thiazol-5-yl]-5-methylphenyl}amino)pyrimidine-4-carbonitrile;
1,1,1-trifluoro-2-{5-[3-methyl-5-(pyrimidin-2-ylamino)phenyl]-1,3-thiazol-2-yl}propan-2-ol;
1-[5-(3-methyl-5-{[4-(methylsulfanyl)pyrimidin-2-yl]amino}phenyl)-1,3-thiazol-2-yl]-Cyclobutanol;
1-(5-{3-[(5-chloro-4-methoxypyrimidin-2-yl)amino]-5-methylphenyl}-1,3-thiazol-2-yl)-cyclobutanol;
1-(5-{3-[(5-chloro-4-methylpyrimidin-2-yl)amino]-5-methylphenyl}-1,3-thiazol-2-yl)cyclobutanol;
1-(5-{3-[(4-ethenylpyrimidin-2-yl)amino]-5-methylphenyl}-1,3-thiazol-2-yl)cyclobutanol;
1-[2-({3-[2-(1-hydroxycyclobutyl)-1,3-thiazol-5-yl]-5-methylphenyl}amino)pyrimidin-4-yl]ethane-1,2-diol;
1-[2-({3-methyl-5-[2-(1,1,1-trifluoro-2-hydroxypropan-2-yl)-1,3-thiazol-5-yl]phenyl}amino)pyrimidin-4-yl]ethanone;
1-(5-{3-[(4-cyclobutylpyrimidin-2-yl)amino]-5-methylphenyl}-1,3-thiazol-2-yl)cyclobutanol;
1-(5-{3-[(4-cyclopentylpyrimidin-2-yl)amino]-5-methylphenyl}-1,3-thiazol-2-yl)cyclobutanol;
1-(5-{3-[(4-cyclohexylpyrimidin-2-yl)amino]-5-methylphenyl}-1,3-thiazol-2-yl)cyclobutanol;
1-(5-{3-[(4-ethoxypyrimidin-2-yl)amino]-5-methylphenyl}-1,3-thiazol-2-yl)cyclobutanol;
1-{5-[3-methyl-5-({4-[(1-methyl-1H-imidazol-2-yl)methoxy]pyrimidin-2-yl}amino)phenyl]-1,3-thiazol-2-yl}cyclobutanol;
1-[5-(3-{[4-(1H-imidazol-4-ylmethoxy)pyrimidin-2-yl]amino}-5-methylphenyl)-1,3-thiazol-2-yl]cyclobutanol;
4-(2-{[2-({3-[2-(1-hydroxycyclobutyl)-1,3-thiazol-5-yl]-5-methylphenyl}amino)pyrimidin-4-yl]oxy}ethyl)morpholin-3-one;
1-[5-(3-methyl-5-{[4-(tetrahydro-2H-pyran-3-ylmethoxy)pyrimidin-2-yl]amino}phenyl)-1,3-thiazol-2-yl]cyclobutanol;
1-(5-{3-[(4-{2-[(3S,4S)-3,4-difluoropyrrolidin-1-yl]ethoxy}pyrimidin-2-yl)amino]-5-methyl-phenyl}-1,3-thiazol-2-yl)cyclobutanol;
1-[5-(3-{[4-(2-amino-1-pyrimidin-4-ylethoxy)pyrimidin-2-yl]amino}-5-methylphenyl}-1,3-thiazol-2-yl]cyclobutanol;
1-[5-(3-methyl-5-{[4-(pyrazolo[1,5-a]pyridin-7-ylmethoxy)pyrimidin-2-yl]amino}phenyl)-1,3-thiazol-2-yl]cyclobutanol;

1-{5-[3-methyl-5-({4-[2-(1-methyl-1H-pyrazol-4-yl)ethoxy]pyrimidin-2-yl}amino)phenyl]-1,3-thiazol-2-yl}cyclobutanol;
1-[5-(3-{[4-(isoxazol-3-ylmethoxy)pyrimidin-2-yl]amino}-5-methylphenyl)-1,3-thiazol-2-yl]-cyclobutanol;
1-[5-(3-{[4-(azepan-4-yloxy)pyrimidin-2-yl]amino}-5-methylphenyl)-1,3-thiazol-2-yl]-cyclobutanol;
1-[5-(3-{[4-(azepan-4-yloxy)pyrimidin-2-yl]amino}-5-methylphenyl)-1,3-thiazol-2-yl]-cyclobutanol;
1-{5-[3-methyl-5-({4-[2-(2H-1,2,3-triazol-2-yl)ethoxy]pyrimidin-2-yl}amino)phenyl]-1,3-thiazol-2-yl}cyclobutanol;
1-{5-[3-methyl-5-({4-[2-(1H-1,2,3-triazol-1-yl)ethoxy]pyrimidin-2-yl}amino)phenyl]-1,3-thiazol-2-yl}cyclobutanol;
1-(5-{3-methyl-5-[(4-{2-[(1-methylpiperidin-4-yl)amino]ethoxy)pyrimidin-2-yl)amino]phenyl}-1,3-thiazol-2-yl)cyclobutanol;
1-[5-(3-{[4-(2,3-dihydro-1H-indol-2-ylmethoxy)pyrimidin-2-yl]amino}-5-methylphenyl)-1,3-thiazol-2-yl]cyclobutanol;
1-{5-[3-methyl-5-({4-[(1-methyl-1H-pyrazol-5-yl)methoxy]pyrimidin-2-yl}amino)phenyl]-1,3-thiazol-2-yl}cyclobutanol;
1-{5-[3-methyl-5-({4-[2-(1-methylpyrrolidin-2-yl)ethoxy]pyrimidin-2-yl}amino)phenyl]-1,3-thiazol-2-yl}cyclobutanol;
1-{5-[3-({4-[2-(1,4-diazepan-1-yl)ethoxy]pyrimidin-2-yl}amino)-5-methylphenyl]-1,3-thiazol-2-yl}cyclobutanol;
1-{5-[3-({4-[(1,4-dimethylpiperazin-2-yl)methoxy]pyrimidin-2-yl}amino)-5-methylphenyl]-1,3-thiazol-2-yl}cyclobutanol;
1-{5-[3-methyl-5-({4-[2-(1H-tetrazol-5-yl)ethoxy]pyrimidin-2-yl}amino)phenyl]-1,3-thiazol-2-yl}cyclobutanol;
1-{5-[3-methyl-5-({4-[(3-pyrimidin-5-ylprop-2-yn-1-yl)oxy]pyrimidin-2-yl}amino)phenyl]-1,3-thiazol-2-yl}cyclobutanol;
4-([2-({3-[2-(1-hydroxycyclobutyl)-1,3-thiazol-5-yl]-5-methylphenyl}amino)pyrimidin-4-yl]oxy)methyl)-1-methylpyrrolidin-2-one;
1-{5-[3-methyl-({4-[(3-methylpiperidin-3-yl)methoxy]pyrimidin-2-yl}amino)phenyl]-1,3-thiazol-2-yl}cyclobutanol;
1-{5-[3-methyl-5-({4-[2-(4-methylmorpholin-2-yl)ethoxy]pyrimidin-2-yl}amino)phenyl]-1,3-thiazol-2-yl}cyclobutanol;
1-{5-[3-methyl-5-({4-[(2,2,6,6-tetramethylpiperidin-4-yl)oxy]pyrimidin-2-yl}amino)phenyl]-1,3-thiazol-2-yl}cyclobutanol;
3-(2-{[2-({3-[2-(1-hydroxycyclobutyl)-1,3-thiazol-5-yl]-5-methylphenyl}amino)pyrimidin-4-yl]oxy}propyl)-5-methyl-1,3-oxazolidin-2-one;
3-(2-{([2-({3-[2-(1-hydroxycyclobutyl)-1,3-thiazol-5-yl]-5-methylphenyl}amino)pyrimidin-4-yl]oxy}ethoxy)phenol;
1-[5-(3-methyl-5-{[4-(3-pyridin-3-ylpropoxy)pyrimidin-2-yl]amino}phenyl)-1,3-thiazol-2-yl]cyclobutanol;
1-(2-{[2-({3-[2-(1-hydroxycyclobutyl)-1,3-thiazol-5-yl]-5-methylphenyl}amino)pyrimidin-4-yl]oxy}ethyl)pyrrolidin-2-one;
1-[5-(3-{[4-(4-hydroxybutoxy)pyrimidin-2-yl]amino}-5-methylphenyl)-1,3-thiazol-2-yl]-cyclobutanol;
1-{5-[3-({4-[(1R,4R,5S)-2-azabicyclo[2.2.1]hept-5-yloxy]pyrimidin-2-yl}amino)-5-methyl-phenyl]-1,3-thiazol-2-yl}cyclobutanol;

1-{5-[3-({4-[(1R,4R,5R)-2-azabicyclo[2.2.1]hept-5-yloxy]pyrimidin-2-yl}amino)-5-methyl-phenyl]-1,3-thiazol-2-yl}cyclobutanol;

1-[5-(3-{[4-(2-hydroxyethoxy)pyrimidin-2-yl]amino}-5-methylphenyl)-1,3-thiazol-2-yl]-cyclobutanol;

1-[5-(3-{[4-(3-hydroxypropoxy)pyrimidin-2-yl]amino}-5-methylphenyl)-1,3-thiazol-2-yl]-cyclobutanol;

1-(5-{3-[(4-ethoxypyrimidin-2-yl)amino]-5-methylphenyl}-1,3-thiazol-2-yl)cyclobutanol;

1-[5-(3-methyl-5-{[4-(1-methylethoxy)pyrimidin-2-yl]amino}phenyl)-1,3-thiazol-2-yl]-cyclobutanol;

1-[5-(3-methyl-5-{[4-(methylsulfinyl)pyrimidin-2-yl]amino}phenyl)-1,3-thiazol-2-yl]-cyclobutanol;

1-[5-(3-methyl-5-{[4-(methylsulfonyl)pyrimidin-2-yl]amino}phenyl)-1,3-thiazol-2-yl]-cyclobutanol;

1-[5-(3-{[4-(ethylsulfanyl)pyrimidin-2-yl]amino}-5-methylphenyl)-1,3-thiazol-2-yl]-cyclobutanol;

1-[5-(3-{[4-(butylsulfanyl)pyrimidin-2-yl]amino}-5-methylphenyl)-1,3-thiazol-2-yl]-cyclobutanol;

1-[5-(3-methyl-5-{[4-(propylsulfanyl)pyrimidin-2-yl]amino}phenyl)-1,3-thiazol-2-yl]-cyclobutanol;

1-{5-[3-methyl-5-({4-[(1-methylethyl)sulfanyl]pyrimidin-2-yl}amino)phenyl]-1,3-thiazol-2-yl}cyclobutanol;

1-{5-[3-({4-[(2-hydroxyethyl)sulfanyl]pyrimidin-2-yl}amino)-5-methylphenyl]-1,3-thiazol-2-yl}cyclobutanol;

1-{5-[3-({4-[(3-hydroxypropyl)sulfanyl]pyrimidin-2-yl}amino)-5-methylphenyl]-1,3-thiazol-2-yl}cyclobutanol;

1-{5-[3-({4-[(4-hydroxybutyl)sulfanyl]pyrimidin-2-yl}amino)-5-methylphenyl]-1,3-thiazol-2-yl}cyclobutanol;

tert-butyl 4-{[2-({3-(acetylamino)-5-[2-(1-hydroxycyclobutyl)-1,3-thiazol-5-yl]phenyl}-1.0 amino)pyrimidin-4-yl]oxy}piperidine-1-carboxylate;

N-(3-[2-(1-hydroxycyclobutyl)-1,3-thiazol-5-yl]-5-{[4-(piperidin-4-yloxy)pyrimidin-2-yl]-amino}phenyl)acetamide;

1-cyclohexyl-3-(3-[2-(1-hydroxycyclobutyl)-1,3-thiazol-5-yl]-5-{[4-(piperidin-4-yloxy)-pyrimidin-2-yl]amino}phenyl)urea;

1-(5-{3-amino-5-[(4-{[1-(2,2,2-trifluoroethyl)piperidin-4-yl]oxy}pyrimidin-2-yl)amino]phenyl}-1,3-thiazol-2-yl)cyclobutanol;

N-[3-({4-[(1-acetylpiperidin-4-yl)oxy]pyrimidin-2-yl}amino)-5-[2-(1-hydroxycyclobutyl)-1,3-thiazol-5-yl]phenyl]acetamide;

1-(5-{3-amino-5-[(4-{[1-(trifluoroacetyl)piperidin-4-yl]oxy}pyrimidin-2-yl)amino]phenyl}-1,3-thiazol-2-yl)cyclobutanol;

1-{5-[3-({4-[(1-acetylpiperidin-4-yl)oxy}pyrimidin-2-yl}amino)-5-aminophenyl]-1,3-thiazol-2-yl]cyclobutanol;

2,2,2-trifluoro-N-(3-[2-(1-hydroxycyclobutyl)-1,3-thiazol-5-yl]-5-{[4-(tetrahydro-2H-pyran-4-yloxy)pyrimidin-2-yl]amino}phenyl)acetamide;

N-(3-[2-(1-hydroxycyclobutyl)-1,3-thiazol-5-yl]-5-{[4-(tetrahydro-2H-pyran-4-yloxy)pyrimidin-2-yl]amino}phenyl)acetamide;

1-[5-(3-amino-5-{[4-(tetrahydro-2H-pyran-4-yloxy)pyrimidin-2-yl]amino}phenyl)-1,3-thiazol-2-yl]cyclobutanol;

tert-butyl 3-{[2-({3-amino-5-[2-(1-hydroxycyclobutyl)-1,3-thiazol-5-yl]phenyl}amino)pyrimidin-4-yl]oxy}azetidine-1-carboxylate;

1-(3-[2-(1-hydroxycyclobutyl)-1,3-thiazol-5-yl]-5-{[4-(piperidin-4-yloxy)pyrimidin-2-yl]-amino}phenyl)urea;

1-[5-(3-amino-5-{[4-(piperidin-4-yloxy)pyrimidin-2-yl]amino}phenyl)-1,3-thiazol-2-yl]-cyclobutanol;

ethyl 3-{[2-({3-amino-5-[2-(1-hydroxycyclobutyl)-1,3-thiazol-5-yl]phenyl}amino)pyrimidin-4-yl]oxy}azetidine-1-carboxylate; and 1-[5-(3-amino-5-{[4-(azetidin-3-yloxy)pyrimidin-2-yl]amino}phenyl)-1,3-thiazol-2-yl]-cyclobutanol.

Cis-4-(aminomethyl)-1-(5-{3-methyl-5-[(4-methylpyrimidin-2-yl)amino]phenyl}-1,3-thiazol-2-yl)cyclohexanol;

Trans-4-(aminomethyl)-1-(5-{3-methyl-5-[(4-methylpyrimidin-2-yl)amino]phenyl}1,3-thiazol-2-yl)cyclohexanol;

4-(aminomethyl)-1-[5-(3-methyl-5-{[4-(trifluoromethyl)pyrimidin-2-yl]amino}phenyl)-1,3-thiazol-2-yl]cyclohexanol;

4-(2-aminoethyl)-1-[5-(3-methyl-5-{[4-(trifluoromethyl)pyrimidin-2-yl]amino}phenyl)-1,3-thiazol-2-yl]cyclohexanol;

trans-4-(hydroxymethyl)-1-[5-(3-methyl-5-{[4-(trifluoromethyl)pyrimidin-2-yl]amino}phenyl)-1,3-thiazol-2-yl]cyclohexanol;

4-(hydroxymethyl)-1-[5-(3-methyl-5-{[4-(trifluoromethyl)pyrimidin-2-yl]amino}phenyl)-1,3-thiazol-2-yl]cyclohexanol;

cis-4-(hydroxymethyl)-1-[5-(3-methyl-5-{[4-(trifluoromethyl)pyrimidin-2-yl]amino}phenyl)-1,3-thiazol-2-yl]cyclohexanol;

4-(hydroxymethyl)-1-(5-{3-methyl-5-[(4-methylpyrimidin-2-yl)amino]phenyl}-1,3-thiazol-2-yl)cyclohexanol;

1-amino-4-hydroxy-4-(5-{3-methyl-5-[(4-methylpyrimidin-2-yl)amino]phenyl}-1,3-thiazol-2-yl)cyclohexanecarboxylic acid;

Cis-[3-hydroxy-1-methyl-3-(5-{3-methyl-5-[(4-methylpyrimidin-2-yl)amino]phenyl}-1,3-thiazol-2-yl)cyclohexyl]acetic acid;

Trans-[3-hydroxy-1-methyl-3-(5-{3-methyl-5-[(4-methylpyrimidin-2-yl)amino]phenyl}-1,3-thiazol-2-yl)cyclohexyl]acetic acid;

ethyl 4-(5-{3-[(5-fluoropyrimidin-2-yl)amino]-5-methylphenyl}-1,3-thiazol-2-yl)-4-hydroxy-1-methylcyclohexanecarboxylate;

{cis-4-hydroxy-4-[5-(3-methyl-5-{[4-(trifluoromethyl)pyrimidin-2-yl]amino}phenyl)-1,3-thiazol-2-yl]cyclohexyl}acetic acid;

{trans-4-hydroxy-4-[5-(3-methyl-5-{[4-(trifluoromethyl)pyrimidin-2-yl]amino}phenyl)-1,3-thiazol-2-yl]cyclohexyl}acetic acid;

7-[5-(3-methyl-5-{[4-(trifluoromethyl)pyrimidin-2-yl]amino}phenyl)-1,3-thiazol-2-yl]-spiro[2.5]octane-4,7-diol;

methyl(4-hydroxy-2-(1-methylethyl)-4-(5-{3-methyl-5-[(4-methylpyrimidin-2-yl)amino]phenyl}-1,3-thiazol-2-yl)cyclohexanecarboxylate;

methyl 4-(5-{3-[(5-chloropyrimidin-2-yl)amino]-5-methylphenyl}-1,3-thiazol-2-yl)-4-hydroxy-2,2-dimethylcyclohexanecarboxylate;

Cis-4-(1-aminocyclopropyl)-1-[5-(3-methyl-5-{[4-(trifluoromethyl)pyrimidin-2-yl]amino}phenyl)-1,3-thiazol-2-yl]cyclohexanol;

Trans-4-(1-aminocyclopropyl)-1-[5-(3-methyl-5-{[4-(trifluoromethyl)pyrimidin-2-yl]amino}phenyl)-1,3-thiazol-2-yl]cyclohexanol;

ethyl 3-hydroxy-3-[5-(3-methyl-5-{[4-(trifluoromethyl)pyrimidin-2-yl]amino}phenyl)-1,3-thiazol-2-yl]cyclohexanecarboxylate;

(1R)-{(3S)-3-hydroxy-1-methyl-3-[5-(3-methyl-5-{[4-(trifluoromethyl)pyrimidin-2-yl]amino}phenyl)-1,3-thiazol-2-yl]cyclohexyl}acetic acid;

(1R)-{(3R)-3-hydroxy-1-methyl-3-[5-(3-methyl-5-{[4-(trifluoromethyl)pyrimidin-2-yl]amino}phenyl)-1,3-thiazol-2-yl]cyclohexyl}acetic acid;
ethyl 4-hydroxy-4-(5-{3-methyl-5-[(4-methylpyrimidin-2-yl)amino]phenyl}-3-thiazol-2-yl)-2-phenylcyclohexanecarboxylate;
methyl 4-hydroxy-2-(1-methylethyl)-4-[5-(3-methyl-5-{[4-(trifluoromethyl)pyrimidin-2-yl]amino}phenyl)-1,3-thiazol-2-yl]cyclohexanecarboxylate;
3-{4-hydroxy-4-[5-(3-methyl-5-{[4-(trifluoromethyl)pyrimidin-2-yl]amino}phenyl)-1,3-thiazol-2-yl]cyclohexyl}-2,2-dimethylpropanoic acid;
Ethyl 4-hydroxy-4-(5-{3-methyl-5-[(4-methylpyrimidin-2-yl)amino]phenyl}-1,3-thiazol-2-yl)-2-(2-methylphenyl)cyclohexanecarboxylate;
ethyl 2-(4-fluorophenyl)-4-hydroxy-4-(5-{3-methyl-5-[(4-methylpyrimidin-2-yl)amino]phenyl}-1,3-thiazol-2-yl)cyclohexanecarboxylate;
N-{cis-4-hydroxy-4-[5-(3-methyl-5-{[4-(trifluoromethyl)pyrimidin-2-yl]amino}phenyl)-1,3-thiazol-2-yl]cyclohexyl}-2-(1H-imidazol-1-yl)acetamide;
(2R)—N-{cis-4-hydroxy-4-[5-(3-methyl-5-{[4-(trifluoromethyl)pyrimidin-2-yl]amino}phenyl)-1,3-thiazol-2-yl]cyclohexyl}-5-oxotetrahydrofuran-2-carboxamide;
N-{cis-4-hydroxy-4-[5-(3-methyl-5-{[4-(trifluoromethyl)pyrimidin-2-yl]amino}phenyl)-1,3-thiazol-2-yl]cyclohexyl}-5-oxotetrahydrofuran-2-carboxamide;
N-{cis-4-hydroxy-4-[5-(3-methyl-5-{[4-(trifluoromethyl)pyrimidin-2-yl]amino}phenyl)-1,3-thiazol-2-yl]cyclohexyl}-2-pyridin-3-ylacetamide;
4-(dimethylamino)-1-[5-(3-methyl-5-{[4-(trifluoromethyl)pyrimidin-2-yl]amino}phenyl)-1,3-thiazol-2-yl]cyclohexanol;
5-hydroxy-5-(5-{3-methyl-5-[(4-methylpyrimidin-2-yl)amino]phenyl}-1,3-thiazol-2-yl)azepan-2-one;
1-cyclopropyl-4-[5-(3-methyl-5-{[4-(trifluoromethyl)pyrimidin-2-yl]amino}phenyl)-1,3-thiazol-2-yl]piperidin-4-ol;
1-(2-methylphenyl)-4-[5-(3-methyl-5-{[4-(trifluoromethyl)pyrimidin-2-yl]amino}phenyl)-1,3-thiazol-2-yl]piperidin-4-ol;
1-(3-fluorophenyl)-4-[5-(3-methyl-5-{[4-(trifluoromethyl)pyrimidin-2-yl]amino}phenyl)-1,3-thiazol-2-yl]piperidin-4-ol;
1-(2-fluorophenyl)-4-[5-(3-methyl-5-{[4-(trifluoromethyl)pyrimidin-2-yl]amino}phenyl)-1,3-thiazol-2-yl]piperidin-4-ol;
1-(4-fluorophenyl)-4-[5-(3-methyl-5-{[4-(trifluoromethyl)pyrimidin-2-yl]amino}phenyl)-1,3-thiazol-2-yl]piperidin-4-ol;
5-{4-hydroxy-4-[5-(3-methyl-5-{[4-(trifluoromethyl)pyrimidin-2-yl]amino}phenyl)-1,3-thiazol-2-yl]piperidin-1-yl}-5-oxopentanoic acid;
1-tert-butyl 2-methyl 4-hydroxy-4-[5-(3-methyl-5-{[4-(trifluoromethyl)pyrimidin-2-yl]amino}phenyl)-1,3-thiazol-2-yl]piperidine-1,2-dicarboxylate;
tert-butyl 4-hydroxy-4-[5-(3-methyl-5-{[4-(trifluoromethyl)pyrimidin-2-yl]amino}phenyl)-1,3-thiazol-2-yl]-2-(trifluoromethyl)piperidine-1-carboxylate;
4-hydroxy-4-[5-(3-methyl-5-{[4-(trifluoromethyl)pyrimidin-2-yl]amino}phenyl)-1,3-thiazol-2-yl]butanenitrile;
1-[5-(3-methyl-5-{[4-(trifluoromethyl)pyrimidin-2-yl]amino}phenyl)-1,3-thiazol-2-yl]pent-4-en-1-ol;
2-[5-(3-methyl-5-{[4-(trifluoromethyl)pyrimidin-2-yl]amino}phenyl)-1,3-thiazol-2-yl]hex-5-en-2-ol;
4-hydroxy-4-[5-(3-methyl-5-{[4-(trifluoromethyl)pyrimidin-2-yl]amino}phenyl)-1,3-thiazol-2-yl]butanamide;
4-amino-2-[5-(3-methyl-5-{[4-(trifluoromethyl)pyrimidin-2-yl]amino}phenyl)-1,3-thiazol-2-yl]pentan-2-ol;
5-amino-2-[5-(3-methyl-5-{[4-(trifluoromethyl)pyrimidin-2-yl]amino}phenyl)-1,3-thiazol-2-yl]pentan-2-ol;
5-hydroxy-5-[5-(3-methyl-5-{[4-(trifluoromethyl)pyrimidin-2-yl]amino}phenyl)-1,3-thiazol-2-yl]hexanoic acid;
methyl 3-hydroxy-2,2-dimethyl-3-[5-(3-methyl-5-{[4-(trifluoromethyl)pyrimidin-2-yl]amino}phenyl)-1,3-thiazol-2-yl]butanoate;
2-methyl-1-[5-(3-methyl-5-{[4-(trifluoromethyl)pyrimidin-2-yl]amino}phenyl)-1,3-thiazol-2-yl]-1-pyridin-2-ylpropan-1-ol;
1-(3-methoxythiophen-2-yl)-1-[5-(3-methyl-5-{[4-(trifluoromethyl)pyrimidin-2-yl]amino}-phenyl)-1,3-thiazol-2-yl]ethanol;
1-(4-{1-hydroxy-1-[5-(3-methyl-5-{[4-(trifluoromethyl)pyrimidin-2-yl]amino}phenyl)-1,3-thiazol-2-yl]ethyl}phenyl)ethanone;
methyl 4-{hydroxy[5-(3-methyl-5-{[4-(trifluoromethyl)pyrimidin-2-yl]amino}phenyl)-1,3-thiazol-2-yl]methyl}benzoate;
3-{1-hydroxy-1-[5-(3-methyl-5-{[4-(trifluoromethyl)pyrimidin-2-yl]amino}phenyl)-1,3-thiazol-2-yl]ethyl}benzoic acid;
3-{(1S)-1-hydroxy-1-[5-(3-methyl-5-{[4-(trifluoromethyl)pyrimidin-2-yl]amino}phenyl)-1,3-thiazol-2-yl]ethyl}benzoic acid;
3-{(1R)-1-hydroxy-1-[5-(3-methyl-5-{[4-(trifluoromethyl)pyrimidin-2-yl]amino}phenyl)-1,3-thiazol-2-yl]ethyl}benzoic acid;
1-[5-(3-methyl-5-{[4-(trifluoromethyl)pyrimidin-2-yl]amino}phenyl)-1,3-thiazol-2-yl]-1-(4-nitrophenyl)ethanol;
1-[4-(methylsulfanyl)phenyl]-1-[5-(3-methyl-5-{[4-(trifluoromethyl)pyrimidin-2-yl]amino}phenyl)-1,3-thiazol-2-yl]ethanol;
(4-{1-hydroxy-1-[5-(3-methyl-5-{[4-(trifluoromethyl)pyrimidin-2-yl]amino}phenyl)-1,3-thiazol-2-yl]ethyl}phenyl)acetic acid;
(4-{(1S)-1-hydroxy-1-[5-(3-methyl-5-{[4-(trifluoromethyl)pyrimidin-2-yl]amino}phenyl)-1,3-thiazol-2-yl]ethyl}phenyl)acetic acid;
(4-{(1R)-1-hydroxy-1-[5-(3-methyl-5-{[4-(trifluoromethyl)pyrimidin-2-yl]amino}phenyl)-1,3-thiazol-2-yl]ethyl}phenyl)acetic acid;
4-{2-hydroxy-2-[5-(3-methyl-5-{[4-(trifluoromethyl)pyrimidin-2-yl]amino}phenyl)-1,3-thiazol-2-yl]propyl}benzoic acid;
2,2-dimethoxy-1-[5-(3-methyl-5-{[4-(trifluoromethyl)pyrimidin-2-yl]amino}phenyl)-1,3-thiazol-2-yl]-1-pyridin-2-ylethanol;
(5-{1-hydroxy-1-[5-(3-methyl-5-{[4-(trifluoromethyl)pyrimidin-2-yl]amino}phenyl)-1,3-thiazol-2-yl]ethyl}thiophen-3-yl)acetic acid;
4-{1-hydroxy-1-[5-(3-methyl-5-{[4-(trifluoromethyl)pyrimidin-2-yl]amino}phenyl)-1,3-thiazol-2-yl]ethyl}-2-methoxybenzoic acid;
4-{(1S)-1-hydroxy-1-[5-(3-methyl-5-{[4-(trifluoromethyl)pyrimidin-2-yl]amino}phenyl)-1,3-thiazol-2-yl]ethyl}-2-methoxybenzoic acid;
4-{(1R)-1-hydroxy-1-[5-(3-methyl-5-{[4-(trifluoromethyl)pyrimidin-2-yl]amino}phenyl)-1,3-thiazol-2-yl]ethyl}-2-methoxybenzoic acid;
(3-(1-hydroxy-1-[5-(3-methyl-5-{[4-(trifluoromethyl)pyrimidin-2-yl]amino}phenyl)-1,3-thiazol-2-yl]ethyl)phenoxy)acetic acid;

(1S)-1-(6-bromopyridin-3-yl)-1-[5-(3-methyl-5-{[4-(trifluoromethyl)pyrimidin-2-yl]amino}phenyl)-1,3-thiazol-2-yl]ethanol;

(1R)-1-(6-bromopyridin-3-yl)-1-[5-(3-methyl-5-{[4-(trifluoromethyl)pyrimidin-2-yl]amino}phenyl)-1,3-thiazol-2-yl]ethanol;

1-(6-bromopyridin-3-yl)-1-[5-(3-methyl-5-{[4-(trifluoromethyl)pyrimidin-2-yl]amino}phenyl)-1,3-thiazol-2-yl]ethanol;

1-(5-bromopyridin-2-yl)-1-[5-(3-methyl-5-{[4-(trifluoromethyl)pyrimidin-2-yl]amino}phenyl)-1,3-thiazol-2-yl]ethanol;

methyl 4-{1-hydroxy-1-[5-(3-methyl-5-{[4-(trifluoromethyl)pyrimidin-2-yl]amino}phenyl)-1,3-thiazol-2-yl]ethyl}-2-methoxybenzoate;

4-(1-hydroxy-1-[5-(3-methyl-5-{[4-(trifluoromethyl)pyrimidin-2-yl]amino}phenyl)-1,3-thiazol-2-yl]ethyl)-N,N-dimethylbenzenesulfonamide;

5-{1-hydroxy-1-[5-(3-methyl-5-{[4-(trifluoromethyl)pyrimidin-2-yl]amino}phenyl)-1,3-thiazol-2-yl]ethyl}-3-methylthieno[2,3-b]pyridine-2-carboxylic acid;

3'-{1-hydroxy-1-[5-(3-methyl-5-{[4-(trifluoromethyl)pyrimidin-2-yl]amino}phenyl)-1,3-thiazol-2-yl]ethyl}biphenyl-3-carboxylic acid;

4-{2-hydroxy-2-[5-(3-methyl-5-{[4-(trifluoromethyl)pyrimidin-2-yl]amino}phenyl)-1,3-thiazol-2-yl]-2-phenylethyl}benzoic acid;

N-[(4-{1-hydroxy-1-[5-(3-methyl-5-{[4-(trifluoromethyl)pyrimidin-2-yl]amino}phenyl)-1,3-thiazol-2-yl]ethyl}phenyl)sulfonyl]acetamide;

1-(4-{1-hydroxy-1-[5-(3-methyl-5-{[4-(trifluoromethyl)pyrimidin-2-yl]amino}phenyl)-1,3-thiazol-2-yl]ethyl}phenyl)-5-oxopyrrolidine-3-carboxylic acid;

4-[1-hydroxy-1-(5-{3-[(4-methoxypyrimidin-2-yl)amino]-5-methylphenyl}-1,3-thiazol-2-yl)ethyl]benzoic acid;

4-(5-{3-methyl-5-[(4-methylpyrimidin-2-yl)amino]phenyl}-1,3-thiazol-2-yl)-1-azatricyclo[3.3.1.1~3,7~]decan-4-ol;

2-[5-(3-methyl-5-{[4-(trifluoromethyl)pyrimidin-2-yl]amino}phenyl)-1,3-thiazol-2-yl]bicyclo[4.1.0]heptan-2-ol;

6-[5-(3-methyl-5-{[4-(trifluoromethyl)pyrimidin-2-yl]amino}phenyl)-1,3-thiazol-2-yl]-3-azabicyclo[3.2.0]heptan-6-ol;

5-hydroxy-5-[5-(3-methyl-5-{[4-(trifluoromethyl)pyrimidin-2-yl]amino}phenyl)-1,3-thiazol-2-yl]hexahydropentalen-2(1H)-one;

4-hydroxy-4-(5-{3-methyl-5-[(4-methylpyrimidin-2-yl)amino]phenyl}-1,3-thiazol-2-yl)-decahydronaphthalene-1-carboxylic acid;

4-hydroxy-4-(5-{3-methyl-5-[(4-methylpyrimidin-2-yl)amino]phenyl}-1,3-thiazol-2-yl)decahydronaphthalene-1-carboxylic acid;

cis-8-hydroxy-8-[5-(3-methyl-5-{[4-(trifluoromethyl)pyrimidin-2-yl]amino}phenyl)-1,3-thiazol-2-yl]-1-azaspiro[4.5]decan-2-one;

trans-8-hydroxy-8-[5-(3-methyl-5-{[4-(trifluoromethyl)pyrimidin-2-yl]amino}phenyl)-1,3-thiazol-2-yl]-1-azaspiro[4.5]decan-2-one;

3a,5-dihydroxy-7a-methyl-5-[5-(3-methyl-5-{[4-(trifluoromethyl)pyrimidin-2-yl]amino}phenyl)-1,3-thiazol-2-yl]octahydro-1H-inden-1-one;

{5-hydroxy-5-[5-(3-methyl-5-{[4-(trifluoromethyl)pyrimidin-2-yl]amino}phenyl)-1,3-thiazol-2-yl]octahydropentalen-2-yl}acetic acid;

6,6-dimethyl-7-[5-(3-methyl-5-{[4-(trifluoromethyl)pyrimidin-2-yl]amino}phenyl)-1,3-thiazol-2-yl]-1,4-dioxaspiro[4.5]decan-7-ol;

4-(5-{3-methyl-5-[(4-methylpyrimidin-2-yl)amino]phenyl}-1,3-thiazol-2-yl)tricyclo[3.3.1.1~3,7~]decane-1,4-diol;

Cis-4-hydroxy-4-(5-{3-methyl-5-[(4-methylpyrimidin-2-yl)amino]phenyl}-1,3-thiazol-2-yl)tricyclo[3.3.1.1~3,7~]decane-1-carboxylic acid;

Trans-4-hydroxy-4-(5-{3-methyl-5-[(4-methylpyrimidin-2-yl)amino]phenyl}-1,3-thiazol-2-yl)tricyclo[3.3.1.1~3,7~]decane-1-carboxylic acid;

3-hydroxy-4,7,7-trimethyl-3-(5-{3-methyl-5-[(4-methylpyrimidin-2-yl)amino]phenyl}-1,3-thiazol-2-yl)bicyclo[2.2.1]heptane-1-carboxylic acid;

5-hydroxy-5-[5-(3-methyl-5-{[4-(trifluoromethyl)pyrimidin-2-yl]amino}phenyl)-1,3-thiazol-2-yl]tricyclo[2.2.1.0$^{2,6}$]heptane-3-carboxylic acid;

4-methyl-3-[5-(3-methyl-5-{[4-(trifluoromethyl)pyrimidin-2-yl]amino}phenyl)-1,3-thiazol-2-yl]bicyclo[2.2.2]octane-1,3-diol;

4-[5-(3-methyl-5-{[4-(trifluoromethyl) pyrimidin-2-yl]amino}phenyl)-1,3-thiazol-2-yl]tricyclo[3.3.1.1$^{3,7}$]decane-1,4-diol;

4-hydroxy-4-[5-(3-methyl-5-{[4-(trifluoromethyl)pyrimidin-2-yl]amino}phenyl)-1,3-thiazol-2-yl]tricyclo[3.3.1.1$^{3,7}$]decane-2-carboxylic acid;

3-hydroxy-4,7,7-trimethyl-3-[5-(3-methyl-5-{[4-(trifluoromethyl)pyrimidin-2-yl]amino}phenyl)-1,3-thiazol-2-yl]bicyclo[2.2.1]heptane-1-carboxylic acid;

Cis-N-{4-hydroxy-4-[5-(3-methyl-5-{[4-(trifluoromethyl)pyrimidin-2-yl]amino}phenyl)-1,3-thiazol-2-yl]tricyclo[3.3.1.1$^{3,7}$]dec-1-yl}acetamide;

Trans-N-{4-hydroxy-4-[5-(3-methyl-5-{[4-(trifluoromethyl)pyrimidin-2-yl]amino}phenyl)-1,3-thiazol-2-yl]tricyclo[3.3.1.1$^{3,7}$]dec-1-yl}acetamide;

5-bromo-2-hydroxy-2-[5-(3-methyl-5-{[4-(trifluoromethyl)pyrimidin-2-yl]amino}phenyl)-1,3-thiazol-2-yl]bicyclo[2.2.1]heptane-7-carboxylic acid;

1-[5-(3-methyl-5-{[4-(trifluoromethyl)pyrimidin-2-yl]amino}phenyl)-1,3-thiazol-2-yl]cyclohept-2-en-1-ol;

9-[5-(3-methyl-5-{[4-(trifluoromethyl)pyrimidin-2-yl]amino}phenyl)-1,3-thiazol-2-yl]dispiro[2.1.2.3]decane-4,9-diol;

ethyl 4-hydroxy-2,3-dimethyl-4-[5-(3-methyl-5-{[4-(trifluoromethyl)pyrimidin-2-yl]amino}phenyl)-1,3-thiazol-2-yl]cyclohexanecarboxylate;

4,4,5-trimethyl-5-(5-{3-methyl-5-[(4-methylpyrimidin-2-yl)amino]phenyl}-1,3-thiazol-2-yl)dihydrofuran-2(3H)-one;

4-[5-(3-methyl-5-{[4-(trifluoromethyl)pyrimidin-2-yl]amino}phenyl)-1,3-thiazol-2-yl]-4-oxobutanenitrile;

5-[5-(3-methyl-5-{[4-(trifluoromethyl)pyrimidin-2-yl]amino}phenyl)-1,3-thiazol-2-yl]dihydrofuran-2(3H)-one;

4,4,5-trimethyl-5-[5-(3-methyl-5-{[4-(trifluoromethyl)pyrimidin-2-yl]amino}phenyl)-1,3-thiazol-2-yl]dihydrofuran-2(3H)-one;

6-hydroxy-1-[5-(3-methyl-5-{[4-(trifluoromethyl)pyrimidin-2-yl]amino}phenyl)-1,3-thiazol-2-yl]hexane-1,4-dione;

2-(5-{3-[(5-fluoro-4-methylpyrimidin-2-yl)amino]-5-methylphenyl}-1,3-thiazol-2-yl)propane-1,2-diol;

(2R)-2-(5-{3-[(5-fluoro-4-methylpyrimidin-2-yl)amino]-5-methylphenyl}-1,3-thiazol-2-yl)propane-1,2-diol;

(2S)-2-(5-{3-[(5-fluoro-4-methylpyrimidin-2-yl)amino]-5-methylphenyl}-1,3-thiazol-2-yl)propane-1,2-diol;

2-(5-{3-[(5-chloropyrimidin-2-yl)amino]-5-methylphenyl}-1,3-thiazol-2-yl)propane-1,2-diol;
(2R)-2-(5-{3-[(5-chloropyrimidin-2-yl)amino]-5-methylphenyl}-1,3-thiazol-2-yl)propane-1,2-diol;
(2S)-2-(5-{3-[(5-chloropyrimidin-2-yl)amino]-5-methylphenyl}-1,3-thiazol-2-yl)propane-1,2-diol;
2-(5-{3-[(5-chloro-4-methylpyrimidin-2-yl)amino]-5-methyl phenyl}-1,3-thiazol-2-yl)propane-1,2-diol;
2-(5-{3-[(5-fluoro-4-methoxypyrimidin-2-yl)amino]-5-methylphenyl}-1,3-thiazol-2-yl)propane-1,2-diol;
2-(5-{3-[(4-cyclopropyl-5-fluoropyrimidin-2-yl)amino]-5-methylphenyl}-1,3-thiazol-2-yl)propane-1,2-diol;
(2R)-2-(5-{3-[(4-cyclopropyl-5-fluoropyrimidin-2-yl)amino]-5-methylphenyl}-1,3-thiazol-2-yl)propane-1,2-diol;
(2S)-2-(5-{3-[(4-cyclopropyl-5-fluoropyrimidin-2-yl)amino]-5-methylphenyl}-1,3-thiazol-2-yl)propane-1,2-diol;
2-(5-{3-[(5-chloro-4-methoxypyrimidin-2-yl)amino]-5-methylphenyl}-1,3-thiazol-2-yl)propane-1,2-diol;
2-(5-{3-[(5-chloropyrimidin-2-yl)amino]-5-methylphenyl}-1,3-thiazol-2-yl)propane-1,2,3-triol;
cis-1-(5-{3-[(5-fluoro-4-methylpyrimidin-2-yl)amino]-5-methylphenyl}-1,3-thiazol-2-yl)cyclohexane-1,4-diol;
cis-1-(5-{3-[(5-chloro-4-methylpyrimidin-2-yl)amino]-5-methylphenyl}-1,3-thiazol-2-yl)cyclohexane-1,4-diol;
cis-1-(5-{3-[(5-fluoro-4-methoxypyrimidin-2-yl)amino]-5-methylphenyl}-1,3-thiazol-2-yl)cyclohexane-1,4-diol;
cis-1-(5-{3-[(4-cyclopropyl-5-fluoropyrimidin-2-yl)amino]-5-methylphenyl}-1,3-thiazol-2-yl)cyclohexane-1,4-diol;
cis-1-(5-{3-[(5-chloro-4-methoxypyrimidin-2-yl)amino]-5-methylphenyl}-1,3-thiazol-2-yl)cyclohexane-1,4-diol;
(1S,4R)-3,3-dimethyl-1-[5-(3-methyl-5-{[4-(trifluoromethyl)pyrimidin-2-yl]amino}phenyl)-1,3-thiazol-2-yl]cyclohexane-1,4-diol;
(1R,4S)-3,3-dimethyl-1-[5-(3-methyl-5-{[4-(trifluoromethyl)pyrimidin-2-yl]amino}phenyl)-1,3-thiazol-2-yl]cyclohexane-1,4-diol;
4-(5-{3-[(5-fluoro-4-methylpyrimidin-2-yl)amino]-5-methylphenyl}-1,3-thiazol-2-yl)-4-hydroxycyclohexanone;
3-hydroxy-2,2-dimethyl-3-[5-(3-methyl-5-{[4-(trifluoromethyl)pyrimidin-2-yl]amino}phenyl)-1,3-thiazol-2-yl]cyclohexanone;
cis-2,2-dimethyl-1-[5-(3-methyl-5-{[4-(trifluoromethyl)pyrimidin-2-yl]amino}phenyl)-1,3-thiazol-2-yl]cyclohexane-1,3-diol;
trans-2,2-dimethyl-1-[5-(3-methyl-5-{[4-(trifluoromethyl)pyrimidin-2-yl]amino}phenyl)-1,3-thiazol-2-yl]cyclohexane-1,3-diol;
1-[4-(1-hydroxyethyl)phenyl]-1-[5-(3-methyl-5-{[4-(trifluoromethyl)pyrimidin-2-yl]amino}phenyl)-1,3-thiazol-2-yl]ethanol;
2-(4-{1-hydroxy-1-[5-(3-methyl-5-{[4-(trifluoromethyl)pyrimidin-2-yl]amino}phenyl)-1,3-thiazol-2-yl]ethyl}phenyl)propan-2-ol;
(5S)-5-hydroxy-5-[5-(3-methyl-5-{[4-(1-methylethyl)pyrimidin-2-yl]amino}phenyl)-1,3-thiazol-2-yl]azepan-2-one;
(5R)-5-hydroxy-5-[5-(3-methyl-5-{[4-(1-methylethyl)pyrimidin-2-yl]amino}phenyl)-1,3-thiazol-2-yl]azepan-2-one;
(5S)-5-hydroxy-5-{5-[3-(methoxymethyl)-5-{[4-(trifluoromethyl)pyrimidin-2-yl]amino}phenyl]-1,3-thiazol-2-yl}azepan-2-one;
4-[5-(3-methyl-5-{[4-(trifluoromethyl)pyrimidin-2-yl]amino}phenyl)-1,3-thiazol-2-yl]-5,6-dihydropyridin-2(1H)-one;
4-[5-(3-methyl-5-{[4-(trifluoromethyl)pyrimidin-2-yl]amino}phenyl)-1,3-thiazol-2-yl]-1,5,6,7-tetrahydro-2H-azepin-2-one;
tert-butyl cis-4-hydroxy-4-[5-(3-methyl-5-{[4-(1-methylethyl)pyrimidin-2-yl]amino}phenyl)-1,3-thiazol-2-yl]cyclohexanecarboxylate;
tert-butyl cis-4-hydroxy-4-[5-(3-methyl-5-{[4-(1-methylethoxy)pyrimidin-2-yl]amino}phenyl)-1,3-thiazol-2-yl]cyclohexanecarboxylate;
[cis-4-hydroxy-4-(5-{3-methyl-5-[(4-methylpyrimidin-2-yl)amino]phenyl}-1,3-thiazol-2-yl)cyclohexyl]acetic acid;
[trans-4-hydroxy-4-(5-{3-methyl-5-[(4-methylpyrimidin-2-yl)amino]phenyl}-1,3-thiazol-2-yl)cyclohexyl]acetic acid;
(4-hydroxy-4-[5-(3-methyl-5-{[4-(trifluoromethyl)pyrimidin-2-yl]amino}phenyl)-1,3-thiazol-2-yl]cyclohexyl)acetic acid;
(4-{4-hydroxy-4-[5-(3-methyl-5-{[4-(trifluoromethyl)pyrimidin-2-yl]amino}phenyl)-1,3-thiazol-2-yl]cyclohexyl}phenyl)acetic acid;
cis-4-(5-{3-[(5-fluoropyrimidin-2-yl)amino]-5-methylphenyl}-1,3-thiazol-2-yl)-4-hydroxy-1-methylcyclohexanecarboxylic acid;
trans-4-(5-{3-[(5-fluoropyrimidin-2-yl)amino]-5-methylphenyl}-1,3-thiazol-2-yl)-4-hydroxy-1-methylcyclohexanecarboxylic acid;
trans-4-[5-(3-chloro-5-{[4-(trifluoromethyl)pyrimidin-2-yl]amino}phenyl)-1,3-thiazol-2-yl]-4-hydroxycyclohexanecarboxylic acid;
3-{4-hydroxy-4-[5-(3-methyl-5-{[4-(trifluoromethyl)pyrimidin-2-yl]amino}phenyl)-1,3-thiazol-2-yl]cyclohexyl}propanoic acid;
cis-3-{4-hydroxy-4-[5-(3-methyl-5-{[4-(trifluoromethyl)pyrimidin-2-yl]amino}phenyl)-1,3-thiazol-2-yl]cyclohexyl}propanoic acid;
trans-3-{4-hydroxy-4-[5-(3-methyl-5-{[4-(trifluoromethyl)pyrimidin-2-yl]amino}phenyl)-1,3-thiazol-2-yl]cyclohexyl}propanoic acid;
cis-4-(5-{3-[(4-cyclopropyl-5-fluoropyrimidin-2-yl)amino]-5-methylphenyl}-1,3-thiazol-2-yl)-4-hydroxycyclohexanecarboxylic acid;
trans-4-(5-{3-[(4-cyclopropyl-5-fluoropyrimidin-2-yl)amino]-5-methylphenyl}-1,3-thiazol-2-yl)-4-hydroxycyclohexanecarboxylic acid;
ethyl 3-{4-hydroxy-4-[5-(3-methyl-5-{[4-(trifluoromethyl)pyrimidin-2-yl]amino}phenyl)-1,3-thiazol-2-yl]cyclohexyl}propanoate;
(1S,4R)-4-hydroxy-4-(5-{3-[(4-methoxypyrimidin-2-yl)amino]-5-methylphenyl}-1,3-thiazol-2-yl)-2,2-dimethylcyclohexanecarboxylic acid;
(1R,4S)-4-hydroxy-4-(5-{3-[(4-methoxypyrimidin-2-yl)amino]-5-methylphenyl}-1,3-thiazol-2-yl)-2,2-dimethylcyclohexanecarboxylic acid;
4-hydroxy-2,2-dimethyl-4-(5-{3-methyl-5-[(4-methylpyrimidin-2-yl)amino]phenyl}-1,3-thiazol-2-yl)cyclohexanecarboxylic acid;
methyl(1R,4S)-4-hydroxy-2,2-dimethyl-4-[5-(3-{[4-(trifluoromethyl)pyrimidin-2-yl]-amino}phenyl)-1,3-thiazol-2-yl]cyclohexanecarboxylate;
(1R,2S,4S)-4-hydroxy-2-methyl-4-[5-(3-methyl-5-{[4-(trifluoromethyl)pyrimidin-2-yl]-amino}phenyl)-1,3-thiazol-2-yl]cyclohexanecarboxylic acid;
(1S,2R,4R)-4-hydroxy-2-methyl-4-[5-(3-methyl-5-{[4-(trifluoromethyl)pyrimidin-2-yl]-amino}phenyl)-1,3-thiazol-2-yl]cyclohexanecarboxylic acid;

{(1R,3R)-3-hydroxy-3-[5-(3-methyl-5-{[4-(trifluoromethyl)pyrimidin-2-yl]amino}phenyl)-1,3-thiazol-2-yl]cyclopentyl}acetic acid;
{(1S,3R)-3-hydroxy-3-[5-(3-methyl-5-{[4-(trifluoromethyl)pyrimidin-2-yl]amino}phenyl)-1,3-thiazol-2-yl]cyclopentyl}acetic acid;
{(1S,3S)-3-hydroxy-3-[5-(3-methyl-5-{[4-(trifluoromethyl)pyrimidin-2-yl]amino}phenyl)-1,3-thiazol-2-yl]cyclopentyl}acetic acid;
{(1R,3S)-3-hydroxy-3-[5-(3-methyl-5-{[4-(trifluoromethyl)pyrimidin-2-yl]amino}phenyl)-1,3-thiazol-2-yl]cyclopentyl}acetic acid;
(1R,2S,4S)-4-hydroxy-2-methyl-4-(5-{3-methyl-5-[(4-methylpyrimidin-2-yl)amino]phenyl}-1,3-thiazol-2-yl)cyclohexanecarboxylic acid;
(1S,2R,4R)-4-hydroxy-2-methyl-4-(5-{3-methyl-5-[(4-methylpyrimidin-2-yl)amino]phenyl}-1,3-thiazol-2-yl)cyclohexanecarboxylic acid;
(1S,2S,4R)-4-hydroxy-2-(1-methylethyl)-4-[5-(3-methyl-5-{[4-(trifluoromethyl)pyrimidin-2-yl]-amino}phenyl)-1,3-thiazol-2-yl]cyclohexanecarboxylic acid;
(1S,2S,4R)-4-hydroxy-2-(1-methylethyl)-4-(5-{3-methyl-5-[(4-methylpyrimidin-2-yl)amino]-phenyl}-1,3-thiazol-2-yl)cyclohexanecarboxylic acid;
(1S,2S,4R)-4-hydroxy-2-(1-methylethyl)-4-[5-(3-methyl-5-{[4-(trifluoromethyl)pyrimidin-2-yl]-amino}phenyl)-1,3-thiazol-2-yl]cyclohexanecarboxylic acid;
(1R,2R,4S)-4-hydroxy-2-(1-methylethyl)-4-[5-(3-methyl-5-{[4-(trifluoromethyl)pyrimidin-2-yl]-amino}phenyl)-1,3-thiazol-2-yl]cyclohexanecarboxylic acid;
(1S,2S,4R)-4-hydroxy-2-(1-methylethyl)-4-(5-{3-methyl-5-[(4-methylpyrimidin-2-yl)amino]phenyl}-1,3-thiazol-2-yl)cyclohexanecarboxylic acid;
(1R,2R,4S)-4-hydroxy-2-(1-methylethyl)-4-(5-{3-methyl-5-[(4-methylpyrimidin-2-yl)amino]-phenyl}-1,3-thiazol-2-yl)cyclohexanecarboxylic acid;
(1R,2R,4S)-4-hydroxy-2-methoxy-4-[5-(3-methyl-5-{[4-(trifluoromethyl)pyrimidin-2-yl]amino}-phenyl)-1,3-thiazol-2-yl]cyclohexanecarboxylic acid;
(1R,2S,4S)-4-hydroxy-2-methoxy-4-[5-(3-methyl-5-{[4-(trifluoromethyl)pyrimidin-2-yl]amino}-phenyl)-1,3-thiazol-2-yl]cyclohexanecarboxylic acid;
4-{3-hydroxy-3-[5-(3-methyl-5-{[4-(trifluoromethyl)pyrimidin-2-yl]amino}phenyl)-1,3-thiazol-2-yl]cyclohexyl}benzoic acid;
3-{3-hydroxy-3-[5-(3-methyl-5-{[4-(trifluoromethyl)pyrimidin-2-yl]amino}phenyl)-1,3-thiazol-2-yl]cyclohexyl}benzoic acid;
2-[4-({2-hydroxy-2-[5-(3-methyl-5-{[4-(trifluoromethyl)pyrimidin-2-yl]amino}phenyl)-1,3-thiazol-2-yl]cyclopentyl}methyl)phenyl]propanoic acid;
4-hydroxy-2,2-dimethyl-4-[5-(3-methyl-5-{[4-(trifluoromethyl)pyrimidin-2-yl]amino}phenyl)-1,3-thiazol-2-yl]cyclopentanecarboxylic acid;
4-hydroxy-2,2-dimethyl-4-[5-(3-methyl-5-{[4-(trifluoromethyl)pyrimidin-2-yl]amino}phenyl)-1,3-thiazol-2-yl]cycloheptanecarboxylic acid;
4-(5-{3-[(5-fluoropyrimidin-2-yl)amino]-5-methylphenyl}-1,3-thiazol-2-yl)-4-hydroxy-2,2-dimethylcyclohexanecarboxylic acid;
4-(5-{3-[(5-chloropyrimidin-2-yl)amino]-5-methylphenyl}-1,3-thiazol-2-yl)-4-hydroxy-2,2-dimethylcyclohexanecarboxylic acid;
4-(5-{3-[(5-fluoropyrimidin-2-yl)amino]-5-methylphenyl}-1,3-thiazol-2-yl)-4-hydroxy-2,2-dimethylcyclohexanecarboxylic acid;
(1S,2S)-4-hydroxy-4-(5-{3-methyl-5-[(4-methylpyrimidin-2-yl)amino]phenyl}-1,3-thiazol-2-yl)-2-phenylcyclohexanecarboxylic acid;
(1S,2S)-4-hydroxy-4-(5-{3-methyl-5-[(4-methylpyrimidin-2-yl)amino]phenyl}-1,3-thiazol-2-yl)-2-(2-methylphenyl)cyclohexanecarboxylic acid;
(1S,2S)-4-hydroxy-4-(5-{3-methyl-5-[(4-methylpyrimidin-2-yl)amino]phenyl}-1,3-thiazol-2-yl)-2-thiophen-3-ylcyclohexanecarboxylic acid;
(1S,2S)-2-(4-fluorophenyl)-4-hydroxy-4-(5-{3-methyl-5-[(4-methylpyrimidin-2-yl)amino]-phenyl}-1,3-thiazol-2-yl)cyclohexanecarboxylic acid;
(1R,4S)-4-[5-(3-cyclopropyl-5-{[4-(trifluoromethyl)pyrimidin-2-yl]amino}phenyl)-1,3-thiazol-2-yl]-4-hydroxy-2,2-dimethylcyclohexanecarboxylic acid;
(1S,4R)-4-[5-(3-cyclopropyl-5-{[4-(trifluoromethyl)pyrimidin-2-yl]amino}phenyl)-1,3-thiazol-2-yl]-4-hydroxy-2,2-dimethylcyclohexanecarboxylic acid;
methyl 4-hydroxy-4-{5-[3-(hydroxymethyl)-5-{[4-(trifluoromethyl)pyrimidin-2-yl]amino}-phenyl]-1,3-thiazol-2-yl}-2,2-dimethylcyclohexanecarboxylate;
4-hydroxy-4-{5-[3-(hydroxymethyl)-5-{[4-(trifluoromethyl)pyrimidin-2-yl]amino}phenyl]-1,3-thiazol-2-yl}-2,2-dimethylcyclohexanecarboxylic acid;
methyl(1S,4R)-4-hydroxy-2,2-dimethyl-4-(5-{3-methyl-5-[(4-methylpyrimidin-2-yl)amino]-phenyl}-1,3-thiazol-2-yl)cyclohexanecarboxylate;
3-hydroxy-3-[5-(3-methyl-5-{[4-(trifluoromethyl)pyrimidin-2-yl]amino}phenyl)-1,3-thiazol-2-yl]cyclohexanecarboxylic acid;
(1S,4S)-4-hydroxy-2,2-dimethyl-4-[5-(3-methyl-5-{[4-(trifluoromethyl)pyrimidin-2-yl]amino}-phenyl)-1,3-thiazol-2-yl]cyclohexanecarboxylic acid;
(1S,4R)-4-hydroxy-2,2-dimethyl-4-[5-(3-{[4-(trifluoromethyl)pyrimidin-2-yl]amino}phenyl)-1,3-thiazol-2-yl]cyclohexanecarboxylic acid;
(1R,4S)-4-hydroxy-2,2-dimethyl-4-[5-(3-{[4-(trifluoromethyl)pyrimidin-2-yl]amino}phenyl)-1,3-thiazol-2-yl]cyclohexanecarboxylic acid;
methyl 4-(5-{3-[(4-cyclopropyl-5-fluoropyrimidin-2-yl)amino]-5-methylphenyl}-1,3-thiazol-2-yl)-4-hydroxy-2,2-dimethylcyclohexanecarboxylate;
methyl 4-{5-[3-(difluoromethyl)-5-{[4-(trifluoromethyl)pyrimidin-2-yl]amino}phenyl]-1,3-thiazol-2-yl}-4-hydroxy-2,2-dimethylcyclohexanecarboxylate;
methyl 4-(5-{3-[(4-cyclopropylpyrimidin-2-yl)amino]-5-methylphenyl}-1,3-thiazol-2-yl)-4-hydroxy-2,2-dimethylcyclohexanecarboxylate;
4-(5-{3-[(4-cyclopropylpyrimidin-2-yl)amino]-5-methylphenyl}-1,3-thiazol-2-yl)-4-hydroxy-2,2-dimethylcyclohexanecarboxylic acid;
4-{5-[3-(difluoromethyl)-5-{[4-(trifluoromethyl)pyrimidin-2-yl]amino}phenyl]-1,3-thiazol-2-yl}-4-hydroxy-2,2-dimethylcyclohexanecarboxylic acid;
(1R,4S)-4-(5-{3-[(4-cyclopropylpyrimidin-2-yl)amino]-5-methylphenyl}-1,3-thiazol-2-yl)-4-hydroxy-2,2-dimethylcyclohexanecarboxylic acid;
(1R,4S)-4-{5-[3-(difluoromethyl)-5-{[4-(trifluoromethyl)pyrimidin-2-yl]amino}phenyl]-1,3-thiazol-2-yl}-4-hydroxy-2,2-dimethylcyclohexanecarboxylic acid;
(1S,4R)-4-{5-[3-(difluoromethyl)-5-{[4-(trifluoromethyl)pyrimidin-2-yl]amino}phenyl]-1,3-thiazol-2-yl}-4-hydroxy-2,2-dimethylcyclohexanecarboxylic acid;
(1R,4S)-4-[5-(3-fluoro-5-{[4-(trifluoromethyl)pyrimidin-2-yl]amino}phenyl)-1,3-thiazol-2-yl]-4-hydroxy-2,2-dimethylcyclohexanecarboxylic acid;

(1R,4R)-4-(5-{3-[(4-cyclopropyl-5-fluoropyrimidin-2-yl)
    amino]-5-methylphenyl}-1,3-thiazol-2-yl)-4-hydroxy-2,
    2-dimethylcyclohexanecarboxylic acid;
(1R,4S)-4-(5-{3-[(4-cyclopropyl-5-fluoropyrimidin-2-yl)
    amino]-5-methylphenyl}-1,3-thiazol-2-yl)-4-hydroxy-2,
    2-dimethylcyclohexanecarboxylic acid;
(1R,4S)-4-(5-{3-[(4-cyclopropylpyrimidin-2-yl)amino]-5-
    methylphenyl}-1,3-thiazol-2-yl)-4-hydroxy-2,2-dimethylcyclohexanecarboxylic acid;
(1S,4R)-4-[5-(3-fluoro-5-{[4-(trifluoromethyl)pyrimidin-2-
    yl]amino}phenyl)-1,3-thiazol-2-yl]-4-hydroxy-2,2-dimethylcyclohexanecarboxylic acid;
methyl 4-[5-(3-cyclopropyl-5-{[4-(trifluoromethyl)pyrimidin-2-yl]amino}phenyl)-1,3-thiazol-2-yl]-4-hydroxy-2,2-dimethylcyclohexanecarboxylate;
4-hydroxy-4-{5-[3-(1-hydroxy-1-methylethyl)-5-{[4-(trifluoromethyl)pyrimidin-2-yl]amino}-phenyl]-1,3-thiazol-2-yl}-2,2-dimethylcyclohexanecarboxylic acid;
4-[5-(3-cyclopropyl-5-{[4-(trifluoromethyl)pyrimidin-2-yl]
    amino}phenyl)-1,3-thiazol-2-yl]-4-hydroxy-2,2-dimethylcyclohexanecarboxylic acid;
methyl(1S,4R)-4-hydroxy-4-{5-[3-(hydroxymethyl)-5-{[4-
    (trifluoromethyl)pyrimidin-2-yl]-amino}phenyl]-1,3-
    thiazol-2-yl}-2,2-dimethylcyclohexanecarboxylate;
(1S,4R)-4-hydroxy-4-{5-[3-(hydroxymethyl)-5-{[4-(trifluoromethyl)pyrimidin-2-yl]amino}-phenyl]-1,3-thiazol-2-yl}-2,2-dimethylcyclohexanecarboxylic acid;
methyl(1S,4R)-4-[5-(3-[(acetyloxy)methyl]-5-{[4-(trifluoromethyl)pyrimidin-2-yl]amino}-phenyl)-1,3-thiazol-2-yl]-4-hydroxy-2,2-dimethylcyclohexanecarboxylate;
4-hydroxy-2,2,3-trimethyl-4-[5-(3-methyl-5-{[4-(trifluoromethyl)pyrimidin-2-yl]amino}phenyl)-1,3-thiazol-2-yl]cyclohexanecarboxylic acid;
4-(5-{3-[(5-fluoro-4-methylpyrimidin-2-yl)amino]-5-methylphenyl}-1,3-thiazol-2-yl)-4-hydroxy-2,2,3-trimethylcyclohexanecarboxylic acid;
4-hydroxy-2,2,3-trim ethyl-4-[5-(3-methyl-5-{[4-(trifluoromethyl)pyrimidin-2-yl]amino}phenyl)-1,3-thiazol-2-yl]cyclohexanecarboxylic acid;
4-hydroxy-2,3-dimethyl-4-[5-(3-methyl-5-{[4-(trifluoromethyl)pyrimidin-2-yl]amino}phenyl)-1,3-thiazol-2-yl]cyclohexanecarboxylic acid;
4-hydroxy-2,3-dimethyl-4-[5-(3-methyl-5-{[4-(trifluoromethyl)pyrimidin-2-yl]amino}phenyl)-1,3-thiazol-2-yl]cyclohexanecarboxylic acid;
3-ethyl-4-hydroxy-2-methyl-4-[5-(3-methyl-5-{[4-(trifluoromethyl)pyrimidin-2-yl]amino}-phenyl)-1,3-thiazol-2-yl]cyclohexanecarboxylic acid;
8-(5-{3-methyl-5-[(4-methylpyrimidin-2-yl)amino]phenyl}-1,3-thiazol-2-yl)-1,4-dioxaspiro[4.5]decan-8-ol;
5-hydroxy-5-(5-{3-methyl-5-[(4-methylpyrimidin-2-yl)
    amino]phenyl}-1,3-thiazol-2-yl)-bicyclo[2.2.2]octane-2-carboxylic acid;
4-hydroxy-4-(5-{3-methyl-5-[(4-methylpyrimidin-2-yl)
    amino]phenyl}-1,3-thiazol-2-yl)tricyclo[3.3.1.1$^{3,7}$]decane-1-carboxylic acid;
6-hydroxy-6-[5-(3-methyl-5-{[4-(trifluoromethyl)pyrimidin-2-yl]amino}phenyl)-1,3-thiazol-2-yl]spiro[3.3]heptane-2-carboxylic acid;
3-hydroxy-3-[5-(3-methyl-5-{[4-(trifluoromethyl)pyrimidin-2-yl]amino}phenyl)-1,3-thiazol-2-yl]bicyclo[3.2.1]
    octane-8-carboxylic acid;
2-hydroxy-2-[5-(3-methyl-5-{[4-(trifluoromethyl)pyrimidin-2-yl]amino}phenyl)-1,3-thiazol-2-yl]bicyclo[3.1.0]
    hexane-6-carboxylic acid;
3-hydroxy-3-[5-(3-methyl-5-{[4-(trifluoromethyl)pyrimidin-2-yl]amino}phenyl)-1,3-thiazol-2-yl]bicyclo[3.1.0]
    hexane-6-carboxylic acid;
ethyl 3-hydroxy-3-[5-(3-methyl-5-{[4-(trifluoromethyl)pyrimidin-2-yl]amino}phenyl)-1,3-thiazol-2-yl]bicyclo
    [3.1.0]hexane-6-carboxylate;
3-[5-(3-methyl-5-{[4-(trifluoromethyl)pyrimidin-2-yl]
    amino}phenyl)-1,3-thiazol-2-yl]azetidin-3-ol;
tert-butyl 3-hydroxy-3-[5-(3-methyl-5-{[4-(trifluoromethyl)
    pyrimidin-2-yl]amino}phenyl)-1,3-thiazol-2-yl]azetidine-1-carboxylate;
2-{4-hydroxy-4-[5-(3-methyl-5-{[4-(trifluoromethyl)pyrimidin-2-yl]amino}phenyl)-1,3-thiazol-2-yl]piperidin-1-yl}pyridine-3-carboxylic acid;
ethyl 2-{4-hydroxy-4-[5-(3-methyl-5-[4-(trifluoromethyl)
    pyrimidin-2-yl]amino}phenyl)-1,3-thiazol-2-yl]piperid
    pyridine-3-carboxylate;
5-hydroxy-2,2-d methyl-5-[5-(3-methyl-5-{[4-(trifluoromethyl)pyrimidin-2-yl]amino}phenyl)-1,3-thiazol-2-yl]
    hexanoic acid;
(5R)-5-hydroxy-2,2-dimethyl-5-[5-(3-methyl-5-{[4-(trifluoromethyl)pyrimidin-2-yl]amino}phenyl)-1,3-thiazol-2-yl]hexanoic acid;
(5S)-5-hydroxy-2,2-dimethyl-5-[5-(3-methyl-5-{[4-(trifluoromethyl)pyrimidin-2-yl]amino}phenyl)-1,3-thiazol-2-yl]hexanoic acid;
methyl 5-hydroxy-2,2-dimethyl-5-[5-(3-methyl-5-{[4-(trifluoromethyl)pyrimidin-2-yl]amino}-phenyl)-1,3-thiazol-2-yl]hexanoate;
(3E)-5-hydroxy-2,2-dimethyl-5-[5-(3-methyl-5-{[4-(trifluoromethyl)pyrimidin-2-yl]amino}-phenyl)-1,3-thiazol-2-yl]hex-3-enoic acid;
methyl(3E)-5-hydroxy-2,2-dimethyl-5-[5-(3-methyl-5-{[4-
    (trifluoromethyl)pyrimidin-2-yl]amino}phenyl)-1,3-thiazol-2-yl]hex-3-enoate;
2-(2-hydroxy-2-[5-(3-methyl-5-{[4-(trifluoromethyl)pyrimidin-2-yl]amino}phenyl)-1,3-thiazol-2-yl]propoxy)-2-methylpropanoic acid;
methyl 2-{2-hydroxy-2-[5-(3-methyl-5-{[4-(trifluoromethyl)pyrimidin-2-yl]amino}phenyl)-1,3-thiazol-2-yl]
    propoxy}-2-methylpropanoate;
4-hydroxy-2,2-dimethyl-4-[5-(3-methyl-5-{[4-(trifluoromethyl)pyrimidin-2-yl]amino}phenyl)-1,3-thiazol-2-yl]
    pentanoic acid;
4-hydroxy-4-[5-(3-methyl-5-{[4-(trifluoromethyl)pyrimidin-2-yl]amino}phenyl)-1,3-thiazol-2-yl]pentanoic acid;
(2-{1-hydroxy-1-[5-(3-methyl-5-{[4-(trifluoromethyl)pyrimidin-2-yl]amino}phenyl)-1,3-thiazol-2-yl]
    ethyl}phenoxy)acetic acid;
(4-{1-hydroxy-1-[5-(3-methyl-5-{[4-(trifluoromethyl)pyrimidin-2-yl]amino}phenyl)-1,3-thiazol-2-yl]
    ethyl}phenoxy)acetic acid;
2-(4-{1-hydroxy-1-[5-(3-methyl-5-{[4-(trifluoromethyl)pyrimidin-2-yl]amino}phenyl)-1,3-thiazol-2-yl]
    ethyl}phenoxy)propanoic acid;
4-[(4-{1-hydroxy-1-[5-(3-methyl-5-{[4-(trifluoromethyl)
    pyrimidin-2-yl]amino}phenyl)-1,3-thiazol-2-yl]
    ethyl}phenyl)amino]-4-oxobutanoic acid;
5-[(4-{1-hydroxy-1-[5-(3-methyl-5-{[4-(trifluoromethyl)
    pyrimidin-2-yl]amino}phenyl)-1,3-thiazol-2-yl]
    ethyl}phenyl)amino]-5-oxopentanoic acid;
4-{1-hydroxy-1-[5-(3-methyl-5-{[4-(trifluoromethyl)pyrimidin-2-yl]amino}phenyl)-1,3-thiazol-2-yl]
    ethyl}benzoic acid;
methyl 4-{1-hydroxy-1-[5-(3-methyl-5-{[4-(trifluoromethyl)pyrimidin-2-yl]amino}phenyl)-1,3-thiazol-2-yl]
    ethyl}benzoate;

4-{2-hydroxy-2-[5-(3-methyl-5-{[4-(trifluoromethyl)pyrimidin-2-yl]amino}phenyl)-1,3-thiazol-2-yl]propyl}benzoic acid;

3-(4-{1-hydroxy-1-[5-(3-methyl-5-{[4-(trifluoromethyl)pyrimidin-2-yl]amino}phenyl)-1,3-thiazol-2-yl]ethyl}-3,5-dimethyl-1H-pyrazol-1-yl)propanoic acid;

5-{1-hydroxy-1-[5-(3-methyl-5-{[4-(trifluoromethyl)pyrimidin-2-yl]amino]phenyl)-1,3-thiazol-2-yl]ethyl}thiophene-2-carboxylic acid;

5-{(1R)-1-hydroxy-1-[5-(3-methyl-5-{[4-(trifluoromethyl)pyrimidin-2-yl]amino}phenyl)-1,3-thiazol-2-yl]ethyl}thiophene-2-carboxylic acid;

5-{(1S)-1-hydroxy-1-[5-(3-methyl-5-{[4-(trifluoromethyl)pyrimidin-2-yl]amino}phenyl)-1,3-thiazol-2-yl]ethyl}thiophene-2-carboxylic acid;

1-{2-hydroxy-1,1-dimethyl-2-[5-(3-methyl-5-{[4-(trifluoromethyl)pyrimidin-2-yl]amino}phenyl)-1,3-thiazol-2-yl]ethyl}piperidine-4-carboxylic acid;

(2E)-3-(4-{cyclopropyl(hydroxy)[5-(3-methyl-5-{[4-(trifluoromethyl)pyrimidin-2-yl]amino}-phenyl)-1,3-thiazol-2-yl]methyl}phenyl)prop-2-enoic acid;

5-hydroxy-5-[5-(3-methyl-5-{[4-(trifluoromethyl)pyrimidin-2-yl]amino}phenyl)-1,3-thiazol-2-yl]-5-pyridin-4-ylpentanoic acid;

(2-methyl-3-{[5-(3-methyl-5-{[4-(trifluoromethyl)pyrimidin-2-yl]amino}phenyl)-1,3-thiazol-2-yl]carbonyl}-1H-indol-1-yl)acetic acid;

3-(3-{[5-(3-methyl-5-{[4-(trifluoromethyl)pyrimidin-2-yl]amino}phenyl)-1,3-thiazol-2-yl]-carbonyl}-1H-indol-1-yl)propanoic acid;

4-(2-[5-(3-methyl-5-{[4-(trifluoromethyl)pyrimidin-2-yl]amino) phenyl)-1,3-thiazol-2-yl]-carbonyl}-1H-pyrrol-1-yl)benzoic acid;

3,3,5-trimethyl-5-[5-(3-methyl-5-{[4-(trifluoromethyl)pyrimidin-2-yl]amino}phenyl)-1,3-thiazol-2-yl]dihydrofuran-2(3H)-one;

7-hydroxy-7-[5-(3-methyl-5-{[4-(trifluoromethyl)pyrimidin-2-yl]amino}phenyl)-1,3-thiazol-2-yl]spiro[2.5]octane-4-carboxylic acid;

3-[5-(3-methyl-5-{[4-(trifluoromethyl)pyrimidin-2-yl]amino}phenyl)-1,3-thiazol-2-yl]cyclopent-2-en-1-one;

3-[5-(3-methyl-5-{[4-(trifluoromethyl)pyrimidin-2-yl]amino}phenyl)-1,3-thiazol-2-yl]cyclohex-2-en-1-one;

3-[5-(3-methyl-5-{[4-(trifluoromethyl)pyrimidin-2-yl]amino}phenyl)-1,3-thiazol-2-yl]-cyclohexanone;

3-[5-(3-methyl-5-{[4-(trifluoromethyl)pyrimidin-2-yl]amino}phenyl)-1,3-thiazol-2-yl]cyclohept-2-en-1-one;

3-[5-(3-methyl-5-{[4-(trifluoromethyl)pyrimidin-2-yl]amino}phenyl)-1,3-thiazol-2-yl]-cycloheptanone;

Methyl 2,2-dimethyl-4-[5-(3-methyl-5-{[4-(trifluoromethyl)pyrimidin-2-yl]amino}phenyl)-1,3-thiazol-2-yl]cyclohex-3-ene-1-carboxylate;

Methyl 6,6-dimethyl-4-[5-(3-methyl-5-{[4-(trifluoromethyl)pyrimidin-2-yl]amino}phenyl)-1,3-thiazol-2-yl]cyclohex-3-ene-1-carboxylate;

4-[5-(3-methyl-5-{[4-(trifluoromethyl)pyrimidin-2-yl]amino}phenyl)-1,3-thiazol-2-yl]piperidin-2-one;

5-[5-(3-methyl-5-[4-(trifluoromethyl)pyrimidin-2-yl]amino)phenyl)-1,3-thiazol-2-yl]-1,3,4,7-tetrahydro-2H-azepin-2-one;

4-[5-(3-methyl-5-{[4-(trifluoromethyl)pyrimidin-2-yl]amino}phenyl)-2-yl]azepan-2-one;

5-[5-(3-methyl-5-{[4-(trifluoromethyl)pyrimidin-2-yl]amino}phenyl)-1,3-thiazol-2-yl]azepan-2-one;

N-{3-[2-(1,4-dioxaspiro[4.5]dec-8-yl)-1,3-thiazol-5-yl]-5-methylphenyl}-4-(trifluoromethyl)pyrimidin-2-amine;

(1R,4R)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid;

(1R,4R)-4-hydroxy-4-{5-[3-($^2$H$_3$)methyl-5-{[4-(trifluoromethyl)pyrimidin-2-yl]amino}phenyl]-1,3-thiazol-2-yl}cyclohexanecarboxylic acid;

tert-butyl (4R)-4-hydroxy-4-[5-(3-methyl-5-{[4-(trifluoromethyl)pyrimidin-2-yl]amino}phenyl)-1,3-thiazol-2-yl]azepane-1-carboxylate;

tert-butyl (4S)-4-hydroxy-4-[5-(3-methyl-5-{[4-(trifluoromethyl)pyrimidin-2-yl]amino}phenyl)-1,3-thiazol-2-yl]azepane-1-carboxylate;

4-[5-(3-methyl-5-{[4-(trifluoromethyl)pyrimidin-2-yl]amino}phenyl)-1,3-thiazol-2-yl]-2-(trifluoromethyl)piperidin-4-ol;

Methyl 4-hydroxy-4-[5-(3-methyl-5-{[4-(trifluoromethyl)pyrimidin-2-yl]amino}phenyl)-1,3-thiazol-2-yl]piperidine-2-carboxylate;

tert-butyl({4-hydroxy-4-[5-(3-methyl-5-{[4-(trifluoromethyl)pyrimidin-2-yl]amino}phenyl)-1,3-thiazol-2-yl]azepan-1-yl}sulfonyl)carbamate;

4-hydroxy-4-[5-(3-methyl-5-{[4-(trifluoromethyl)pyrimidin-2-yl]amino}phenyl)-1,3-thiazol-2-yl]azepane-1-sulfonamide;

(4R)-4-hydroxy-4-[5-(3-methyl-5-{[4-(trifluoromethyl)pyrimidin-2-yl]amino}phenyl)-1,3-thiazol-2-yl]azepane-1-sulfonamide;

(4S)-4-hydroxy-4-[5-(3-methyl-5-{[4-(trifluoromethyl)pyrimidin-2-yl]amino]phenyl)-1,3-thiazol-2-yl]azepane-1-sulfonamide;

2-fluoro-5-hydroxy-N-{cis-4-hydroxy-4-[5-(3-methyl-5-{[4-(trifluoromethyl)pyrimidin-2-yl]amino}phenyl)-1,3-thiazol-2-yl]cyclohexyl}benzamide;

3-fluoro-4-hydroxy-N-{cis-4-hydroxy-4-[5-(3-methyl-5-{[4-(trifluoromethyl)pyrimidin-2-yl]amino}phenyl)-1,3-thiazol-2-yl]cyclohexyl}benzamide;

3-amino-4,4,4-trifluoro-N-{cis-4-hydroxy-4-[5-(3-methyl-5-{[4-(trifluoromethyl)pyrimidin-2-yl]amino}phenyl)-1,3-thiazol-2-yl]cyclohexyl}butanamide;

methyl 4-({cis-4-hydroxy-4-[5-(3-methyl-5-{[4-(trifluoromethyl)pyrimidin-2-yl]amino}phenyl)-1,3-thiazol-2-yl]cyclohexyl}carbamoyl)cyclohexanecarboxylate;

(4R)-4-hydroxy-4-[5-(3-methyl-5-{[4-(trifluoromethyl)pyrimidin-2-yl]amino}phenyl)-1,3-thiazol-2-yl]azepane-1-carboxamide;

(4S)-4-hydroxy-4-[5-(3-methyl-5-{[4-(trifluoromethyl)pyrimidin-2-yl]amino}phenyl)-1,3-thiazol-2-yl]azepane-1-carboxamide;

1-(hydroxyacetyl)-4-[5-(3-methyl-5-{[4-(trifluoromethyl)pyrimidin-2-yl]amino}phenyl)-1,3-thiazol-2-yl]azepan-4-ol;

(4R)-1-(hydroxyacetyl)-4-[5-(3-methyl-5-{[4-(trifluoromethyl)pyrimidin-2-yl]amino}phenyl)-1,3-thiazol-2-yl]azepan-4-ol;

(4S)-1-(hydroxyacetyl)-4-[5-(3-methyl-5-{[4-(trifluoromethyl)pyrimidin-2-yl]amino}phenyl)-1,3-thiazol-2-yl]azepan-4-ol;

(4R)-4-[5-(3-methyl-5-{[4-(trifluoromethyl)pyrimidin-2-yl]amino}phenyl)-1,3-thiazol-2-yl]-1-(4H-1,2,4-triazol-3-ylcarbonyl)azepan-4-ol;

(4S)-4-[5-(3-methyl-5-{[4-(trifluoromethyl)pyrimidin-2-yl]amino}phenyl)-1,3-thiazol-2-yl]-1-(4H-1,2,4-triazol-3-ylcarbonyl)azepan-4-ol;

2-fluoro-5-hydroxy-N-{cis-4-hydroxy-4-[5-(3-methyl-5-{[4-(trifluoromethyl)pyrimidin-2-yl]amino}phenyl)-1,3-thiazol-2-yl]cyclohexyl}benzamide;

3-fluoro-4-hydroxy-N-{cis-4-hydroxy-4-[5-(3-methyl-5-{[4-(trifluoromethyl)pyrimidin-2-yl]amino}phenyl)-1,3-thiazol-2-yl]cyclohexyl}benzamide;
3-amino-4,4,4-trifluoro-N-{cis-4-hydroxy-4-[5-(3-methyl-5-{[4-(trifluoromethyl)pyrimidin-2-yl]amino}phenyl)-1,3-thiazol-2-yl]cyclohexyl}butanamide;
methyl 4-({cis-4-hydroxy-4-[5-(3-methyl-5-{[4-(trifluoromethyl)pyrimidin-2-yl]amino}phenyl)-1,3-thiazol-2-yl]cyclohexyl}carbamoyl)cyclohexanecarboxylate;
(4R)-4-hydroxy-4-[5-(3-methyl-5-{[4-(trifluoromethyl)pyrimidin-2-yl]amino}phenyl)-1,3-thiazol-2-yl]azepane-1-carboxamide;
(4S)-4-hydroxy-4-[5-(3-methyl-5-{[4-(trifluoromethyl)pyrimidin-2-yl]amino}phenyl)-1,3-thiazol-2-yl]azepane-1-carboxamide;
1-(hydroxyacetyl)-4-[5-(3-methyl-5-{[4-(trifluoromethyl)pyrimidin-2-yl]amino}phenyl)-1,3-thiazol-2-yl]azepan-4-ol;
(4R)-1-(hydroxyacetyl)-4-[5-(3-methyl-5-{[4-(trifluoromethyl)pyrimidin-2-yl]amino}phenyl)-1,3-thiazol-2-yl]azepan-4-ol;
(4S)-1-(hydroxyacetyl)-4-[5-(3-methyl-5-{[4-(trifluoromethyl)pyrimidin-2-yl]amino}phenyl)-1,3-thiazol-2-yl]azepan-4-ol;
(4R)-4-[5-(3-methyl-5-{[4-(trifluoromethyl)pyrimidin-2-yl]amino}phenyl)-1,3-thiazol-2-yl]-1-(4H-1,2,4-triazol-3-ylcarbonyl)azepan-4-ol;
(4S)-4-[5-(3-methyl-5-{[4-(trifluoromethyl)pyrimidin-2-yl]amino}phenyl)-1,3-thiazol-2-yl]-1-(4H-1,2,4-triazol-3-ylcarbonyl)azepan-4-ol;
4-hydroxy-4-[5-(3-methyl-5-{[4-(trifluoromethyl)pyrimidin-2-yl]amino}phenyl)-1,3-thiazol-2-yl]azepane-1-sulfonic acid;
(2R)-2-hydroxy-N-{cis-4-hydroxy-4-[5-(3-methyl-5-{[4-(trifluoromethyl)pyrimidin-2-yl]-amino}phenyl)-1,3-thiazol-2-yl]cyclohexyl}propanamide;
(2S)-2-hydroxy-N-{cis-4-hydroxy-4-[5-(3-methyl-5-{[4-(trifluoromethyl)pyrimidin-2-yl]amino}phenyl)-1,3-thiazol-2-yl]cyclohexyl}propanamide;
N-{cis-4-hydroxy-4-[5-(3-methyl-5-{[4-(trifluoromethyl)pyrimidin-2-yl]amino}phenyl)-1,3-thiazol-2-yl]cyclohexyl}propanediamide;
N-{cis-4-hydroxy-4-[5-(3-methyl-5-{[4-(trifluoromethyl)pyrimidin-2-yl]amino}phenyl)-1,3-thiazol-2-yl]cyclohexyl}-1H-imidazole-2-carboxamide;
N-{cis-4-hydroxy-4-[5-(3-methyl-5-{[4-(trifluoromethyl)pyrimidin-2-yl]amino}phenyl)-1,3-thiazol-2-yl]cyclohexyl}-1H-imidazole-4-carboxamide;
N-{cis-4-hydroxy-4-[5-(3-methyl-5-{[4-(trifluoromethyl)pyrimidin-2-yl]amino}phenyl)-1,3-thiazol-2-yl]cyclohexyl}-1H-1,2,3-triazole-4-carboxamide;
3-hydroxy-N-{cis-4-hydroxy-4-[5-(3-methyl-5-{[4-(trifluoromethyl)pyrimidin-2-yl]amino}phenyl)-1,3-thiazol-2-yl]cyclohexyl}cyclobutanecarboxamide;
N-{cis-4-hydroxy-4-[5-(3-methyl-5-{[4-(trifluoromethyl)pyrimidin-2-yl]amino}phenyl)-1,3-thiazol-2-yl]cyclohexyl}butanediamide;
N-{cis-4-hydroxy-4-[5-(3-methyl-5-{[4-(trifluoromethyl)pyrimidin-2-yl]amino}phenyl)-1,3-thiazol-2-yl]cyclohexyl}benzamide;
N-{cis-4-hydroxy-4-[5-(3-methyl-5-{[4-(trifluoromethyl)pyrimidin-2-yl]amino}phenyl)-1,3-thiazol-2-yl]cyclohexyl}-2-(1H-imidazol-4-yl)acetamide;
N-{cis-4-hydroxy-4-[5-(3-methyl-5-{[4-(trifluoromethyl)pyrimidin-2-yl]amino}phenyl)-1,3-thiazol-2-yl]cyclohexyl}-2-(1H-1,2,4-triazol-1-yl)acetamide;
N-{cis-4-hydroxy-4-[5-(3-methyl-5-{[4-(trifluoromethyl)pyrimidin-2-yl]amino}phenyl)-1,3-thiazol-2-yl]cyclohexyl}-2-(1H-1,2,3-triazol-1-yl)acetamide;
N-{cis-4-hydroxy-4-[5-(3-methyl-5-{[4-(trifluoromethyl)pyrimidin-2-yl]amino}phenyl)-1,3-thiazol-2-yl]cyclohexyl}-2-(1H-tetrazol-1-yl)acetamide;
N-{cis-4-hydroxy-4-[5-(3-methyl-5-{[4-(trifluoromethyl)pyrimidin-2-yl]amino}phenyl)-1,3-thiazol-2-yl]cyclohexyl}cyclohexanecarboxamide;
N-{cis-4-hydroxy-4-[5-(3-methyl-5-{[4-(trifluoromethyl)pyrimidin-2-yl]amino}phenyl)-1,3-thiazol-2-yl]cyclohexyl}-2-oxoimidazolidine-4-carboxamide;
N-{cis-4-hydroxy-4-[5-(3-methyl-5-{[4-(trifluoromethyl)pyrimidin-2-yl]amino}phenyl)-1,3-thiazol-2-yl]cyclohexyl}tetrahydro-2H-pyran-2-carboxamide;
N-{cis-4-hydroxy-4-[5-(3-methyl-5-{[4-(trifluoromethyl)pyrimidin-2-yl]amino}phenyl)-1,3-thiazol-2-yl]cyclohexyl}-2-(tetrahydrofuran-3-yl)acetamide;
N-{cis-4-hydroxy-4-[5-(3-methyl-5-{[4-(trifluoromethyl)pyrimidin-2-yl]amino}phenyl)-1,3-thiazol-2-yl]cyclohexyl}tetrahydro-2H-pyran-3-carboxamide;
N-{cis-4-hydroxy-4-[5-(3-methyl-5-{[4-(trifluoromethyl)pyrimidin-2-yl]amino}phenyl)-1,3-thiazol-2-yl]cyclohexyl}-2-(tetrahydrofuran-2-yl)acetamide;
3-hydroxy-2-(hydroxymethyl)-N-{cis-4-hydroxy-4-[5-(3-methyl-5-{[4-(trifluoromethyl)pyrimidin-2-yl]amino}phenyl)-1,3-thiazol-2-yl]cyclohexyl}-2-methylpropanamide;
N-{cis-4-hydroxy-4-[5-(3-methyl-5-{[4-(trifluoromethyl)pyrimidin-2-yl]amino}phenyl)-1,3-thiazol-2-yl]cyclohexyl}-2-pyridin-2-ylacetamide;
N-{cis-4-hydroxy-4-[5-(3-methyl-5-{[4-(trifluoromethyl)pyrimidin-2-yl]amino}phenyl)-1,3-thiazol-2-yl]cyclohexyl}-2-(methylsulfonyl)acetamide;
N-{cis-4-hydroxy-4-[5-(3-methyl-5-{[4-(trifluoromethyl)pyrimidin-2-yl]amino}phenyl)-1,3-thiazol-2-yl]cyclohexyl}-2-pyrimidin-2-ylacetamide;
5-hydroxy-N-{cis-4-hydroxy-4-[5-(3-methyl-5-{[4-(trifluoromethyl)pyrimidin-2-yl]amino}phenyl)-1,3-thiazol-2-yl]cyclohexyl}pyridine-2-carboxamide;
6-hydroxy-N-{cis-4-hydroxy-4-[5-(3-methyl-5-{[4-(trifluoromethyl)pyrimidin-2-yl]amino}phenyl)-1,3-thiazol-2-yl]cyclohexyl}pyridine-2-carboxamide;
N-{cis-4-hydroxy-4-[5-(3-methyl-5-{[4-(trifluoromethyl)pyrimidin-2-yl]amino}phenyl)-1,3-thiazol-2-yl]cyclohexyl}-3-(1H-pyrazol-4-yl)propanamide;
N-{cis-4-hydroxy-4-[5-(3-methyl-5-{[4-(trifluoromethyl)pyrimidin-2-yl]amino}phenyl)-1,3-thiazol-2-yl]cyclohexyl}-3-(1H-1,2,4-triazol-1-yl)propanamide;
(2S)—N-{cis-4-hydroxy-4-[5-(3-methyl-5-{[4-(trifluoromethyl)pyrimidin-2-yl]amino}phenyl)-1,3-thiazol-2-yl]cyclohexyl}-6-oxopiperidine-2-carboxamide;
N-{cis-4-hydroxy-4-[5-(3-methyl-5-{[4-(trifluoromethyl)pyrimidin-2-yl]amino}phenyl)-1,3-thiazol-2-yl]cyclohexyl}-2-(tetrahydro-2H-pyran-4-yl)acetamide;
3,3,3-trifluoro-2-hydroxy-N-{cis-4-hydroxy-4-[5-(3-methyl-5-{[4-(trifluoromethyl)pyrimidin-2-yl]amino}phenyl)-1,3-thiazol-2-yl]cyclohexyl}propanamide;
N'-{cis-4-hydroxy-4-[5-(3-methyl-5-{[4-(trifluoromethyl)pyrimidin-2-yl]amino}phenyl)-1,3-thiazol-2-yl]cyclohexyl}-N,N-dimethylbutanediamide;
4-ethynyl-N-{cis-4-hydroxy-4-[5-(3-methyl-5-{[4-(trifluoromethyl)pyrimidin-2-yl]amino}phenyl)-1,3-thiazol-2-yl]cyclohexyl}benzamide;

4-cyano-N-{cis-4-hydroxy-4-[5-(3-methyl-5-[4-(trifluoromethyl)pyrimidin-2-yl]amino}phenyl)-1,3-thiazol-2-yl]cyclohexyl benzamide;
2,2-bis(hydroxymethyl)-N-{cis-4-hydroxy-4-[5-(3-methyl-5-{[4-(trifluoromethyl)pyrimidin-2-yl]amino}phenyl)-1,3-thiazol-2-yl]cyclohexyl}butanamide;
2-fluoro-5-hydroxy-N-{cis-4-hydroxy-4-[5-(3-methyl-5-{[4-(trifluoromethyl)pyrimidin-2-yl]amino}phenyl)-1,3-thiazol-2-yl]cyclohexyl}benzamide;
3-fluoro-4-hydroxy-N-{cis-4-hydroxy-4-[5-(3-methyl-5-[4-(trifluoromethyl)pyrimidin-2-yl]amino}phenyl)-1,3-thiazol-2-yl]cyclohexyl benzamide;
3-amino-4,4,4-trifluoro-N-{cis-4-hydroxy-4-[5-(3-methyl-5-{[4-(trifluoromethyl)pyrimidin-2-yl]amino}phenyl)-1,3-thiazol-2-yl]cyclohexyl}butanamide;
methyl 4-({cis-4-hydroxy-4-[5-(3-methyl-5-{[4-(trifluoromethyl)pyrimidin-2-yl]amino}phenyl)-1,3-thiazol-2-yl]cyclohexyl}carbamoyl)cyclohexanecarboxylate;
(4R)-4-hydroxy-4-[5-(3-methyl-5-{[4-(trifluoromethyl)pyrimidin-2-yl]amino}phenyl)-1,3-thiazol-2-yl]azepane-1-carboxamide;
(4S)-4-hydroxy-4-[5-(3-methyl-5-{[4-(trifluoromethyl)pyrimidin-2-yl]amino}phenyl)-1,3-thiazol-2-yl]azepane-1-carboxamide;
1-(hydroxyacetyl)-4-[5-(3-methyl-5-{[4-(trifluoromethyl)pyrimidin-2-yl]amino}phenyl)-1,3-thiazol-2-yl]azepan-4-ol;
(4R)-1-(hydroxyacetyl)-4-[5-(3-methyl-5-{[4-(trifluoromethyl)pyrimidin-2-yl]amino}phenyl)-1,3-thiazol-2-yl]azepan-4-ol;
(4S)-1-(hydroxyacetyl)-4-[5-(3-methyl-5-{[4-(trifluoromethyl)pyrimidin-2-yl]amino}phenyl)-1,3-thiazol-2-yl]azepan-4-ol;
(4R)-4-[5-(3-methyl-5-{[4-(trifluoromethyl)pyrimidin-2-yl]amino}phenyl)-1,3-thiazol-2-yl]-1-(4H-1,2,4-triazol-3-ylcarbonyl)azepan-4-ol;
(4S)-4-[5-(3-methyl-5-{[4-(trifluoromethyl)pyrimidin-2-yl]amino}phenyl)-1,3-thiazol-2-yl]-1-(4E-1,2,4-triazol-3-ylcarbonyl)azepan-4-ol;
N-butyl-4-hydroxy-4-[5-(3-methyl-5-{[4-(trifluoromethyl)pyrimidin-2-yl]amino}phenyl)-1,3-thiazol-2-yl]piperidine-1-carboxamide;
4-hydroxy-N-(4-methylphenyl)-4-[5-(3-methyl-5-{[4-(trifluoromethyl)pyrimidin-2-yl]amino}phenyl)-1,3-thiazol-2-yl]piperidine-1-carboxamide;
4-hydroxy-N-(3-methylphenyl)-4-[5-(3-methyl-5-{[4-(trifluoromethyl)pyrimidin-2-yl]amino}phenyl)-1,3-thiazol-2-yl]piperidine-1-carboxamide;
N-(4-cyanophenyl)-4-hydroxy-4-[5-(3-methyl-5-{[4-(trifluoromethyl)pyrimidin-2-yl]amino}phenyl)-1,3-thiazol-2-yl]piperidine-1-carboxamide;
N-(2,5-dimethylphenyl)-4-hydroxy-4-[5-(3-methyl-5-{[4-(trifluoromethyl)pyrimidin-2-yl]amino}phenyl)-1,3-thiazol-2-yl]piperidine-1-carboxamide;
N-(2,4-dimethylphenyl)-4-hydroxy-4-[5-(3-methyl-5-{[4-(trifluoromethyl)pyrimidin-2-yl]amino}phenyl)-1,3-thiazol-2-yl]piperidine-1-carboxamide;
4-hydroxy-N-[4-(1-methylethyl)phenyl]-4-[5-(3-methyl-5-{[4-(trifluoromethyl)pyrimidin-2-yl]amino}phenyl)-1,3-thiazol-2-yl]piperidine-1-carboxamide;
N-(5-chloro-2-methylphenyl)-4-hydroxy-4-[5-(3-methyl-5-{[4-(trifluoromethyl)pyrimidin-2-yl]amino}phenyl)-1,3-thiazol-2-yl]piperidine-1-carboxamide;
N-(3-chloro-2-methylphenyl)-4-hydroxy-4-[5-(3-methyl-5-{[4-(trifluoromethyl)pyrimidin-2-yl]amino}phenyl)-1,3-thiazol-2-yl]piperidine-1-carboxamide;
4-hydroxy-N-methyl-4-[5-(3-methyl-5-{[4-(trifluoromethyl)pyrimidin-2-yl]amino}phenyl)-1,3-thiazol-2-yl]azepane-1-carboxamide;
(4R)-4-hydroxy-N-methyl-4-[5-(3-methyl-5-{[4-(trifluoromethyl)pyrimidin-2-yl]amino}phenyl)1,3-thiazol-2-yl]azepane-1-carboxamide;
(4S)-4-hydroxy-N-methyl-4-[5-(3-methyl-5-{[4-(trifluoromethyl)pyrimidin-2-yl]amino}phenyl)1,3-thiazol-2-yl]azepane-1-carboxamide;
4-hydroxy-4-[5-(3-methyl-5-{[4-(trifluoromethyl)pyrimidin-2-yl]amino}phenyl)-1,3-thiazol-2-yl]j-N-prop-2-en-1-ylazepane-1-carboxamide;
4-hydroxy-4-[5-(3-methyl-5-{[4-(trifluoromethyl)pyrimidin-2-yl]amino}phenyl)-1,3-thiazol-2-yl]-N-propylazepane-1-carboxamide;
4-hydroxy-N-(1-methylethyl)-4-[5-(3-methyl-5-{[4-(trifluoromethyl)pyrimidin-2-yl]amino}phenyl)-1,3-thiazol-2-yl]azepane-1-carboxamide;
ethyl N-({4-hydroxy-4-[5-(3-methyl-5-{[4-(trifluoromethyl)pyrimidin-2-yl]amino}phenyl)-1,3-thiazol-2-yl]azepan-1-yl}carbonyl)glycinate;
ethyl 4-[({4-hydroxy-4-[5-(3-methyl-5-{[4-(trifluoromethyl)pyrimidin-2-yl]amino}phenyl)-1,3-thiazol-2-yl]azepan-1-yl}carbonyl)amino]butanoate;
methyl{4-hydroxy-4-[5-(3-methyl-5-{[4-(trifluoromethyl)pyrimidin-2-yl]amino}phenyl)-1,3-thiazol-2-yl]piperidin-1-yl}acetate;
methyl 3-{4-hydroxy-4-[5-(3-methyl-5-{[4-(trifluoromethyl)pyrimidin-2-yl]amino}phenyl)-1,3-thiazol-2-yl]piperidin-1-yl}propanoate;
methyl 2-{4-hydroxy-4-[5-(3-methyl-5-{[4-(trifluoromethyl)pyrimidin-2-yl]amino}phenyl)-1,3-thiazol-2-yl]piperidin-1-yl}propanoate;
methyl 4-{4-hydroxy-4-[5-(3-methyl-5-{[4-(trifluoromethyl)pyrimidin-2-yl]amino}phenyl)-1,3-thiazol-2-yl]piperidin-1-yl}butanoate;
1-(2-fluoroethyl)-4-[5-(3-methyl-5-{[4-(trifluoromethyl)pyrimidin-2-yl]amino}phenyl)-1,3-thiazol-2-yl]azepan-4-ol;
{4-hydroxy-4-[5-(3-methyl-5-{[4-(trifluoromethyl)pyrimidin-2-yl]amino}phenyl)-1,3-thiazol-2-yl]azepan-1-yl}acetic acid;
3-{4-hydroxy-4-[5-(3-methyl-5-{[4-(trifluoromethyl)pyrimidin-2-yl]amino}phenyl)-1,3-thiazol-2-yl]azepan-1-yl}propanoic acid;
(4R)-4-[5-(3-methyl-5-{[4-(trifluoromethyl)pyrimidin-2-yl]amino}phenyl)-1,3-thiazol-2-yl]-1-(2,2,2-trifluoroethyl)azepan-4-ol;
(4S)-4-[5-(3-methyl-5-{[4-(trifluoromethyl)pyrimidin-2-yl]amino}phenyl)-1,3-thiazol-2-yl]-1-(2,2,2-trifluoroethyl)azepan-4-ol;
4-[5-(3-methyl-5-{[4-(trifluoromethyl)pyrimidin-2-yl]amino}phenyl)-1,3-thiazol-2-yl]-1-(2,2,2-trifluoroethyl)azepan-4-o l;
methyl 3-{4-hydroxy-4-[5-(3-methyl-5-{[4-(trifluoromethyl)pyrimidin-2-yl]amino}phenyl)-1,3-thiazol-2-yl]azepan-1-yl}propanoate;
tert-butyl (4-hydroxy-4-[5-(3-methyl-5-{[4-(trifluoromethyl)pyrimidin-2-yl]amino}phenyl)-1,3-thiazol-2-yl]azepan-1-yl)acetate;
3-(5-{3-methyl-5-[(4-methylpyrimidin-2-yl)amino]phenyl}-1,3-thiazol-2-yl)pyrrolidin-3-ol;
3-[5-(3-{[4-(trifluoromethyl)pyrimidin-2-yl]amino}phenyl)-1,3-thiazol-2-yl]pyrrolidin-3-ol;
3-hydroxy-3-(5-{3-methyl-5-[(4-methylpyrimidin-2-yl)amino]phenyl}-1,3-thiazol-2-yl)pyrrolidine-1-carboxamide;

(3S)-3-hydroxy-3-(5-{3-methyl-5-[(4-methylpyrimidin-2-yl)amino]phenyl}-1,3-thiazol-2-yl)pyrrolidine-1-carboxamide;

(3R)-3-hydroxy-3-(5-{3-methyl-5-[(4-methylpyrimidin-2-yl)amino]phenyl}-1,3-thiazol-2-yl)pyrrolidine-1-carboxamide;

3-(5-{3-[(5-fluoro-4-methylpyrimidin-2-yl)amino]-5-methylphenyl}-1,3-thiazol-2-yl)-3-hydroxypyrrolidine-1-carboxamide;

3-(5-{3-[(5-chloro-4-methylpyrimidin-2-yl)amino]-5-methylphenyl}-1,3-thiazol-2-yl)-3-hydroxypyrrolidine-1-carboxamide;

3-(5-{3-[(5-fluoro-4-methoxypyrimidin-2-yl)amino]-5-methylphenyl}-1,3-thiazol-2-yl)-3-hydroxypyrrolidine-1-carboxamide;

3-hydroxy-3-[5-(3-{[4-(trifluoromethyl)pyrimidin-2-yl]amino}phenyl)-1,3-thiazol-2-yl]pyrrolidine-1-carboxamide;

1-(2-hydroxyethyl)-3-[5-(3-methyl-5-{[4-(trifluoromethyl)pyrimidin-2-yl]amino}phenyl)-1,3-thiazol-2-yl]pyrrolidin-3-ol;

2-{3-hydroxy-3-[5-(3-methyl-5-{[4-(trifluoromethyl)pyrimidin-2-yl]amino}phenyl)-1,3-thiazol-2-yl]pyrrolidin-1-yl}acetamide;

1-(hydroxyacetyl)-3-[5-(3-methyl-5-{[4-(trifluoromethyl)pyrimidin-2-yl]amino}phenyl)-1,3-thiazol-2-yl]pyrrolidin-3-ol;

{3-hydroxy-3-[5-(3-methyl-5-{[4-(trifluoromethyl)pyrimidin-2-yl]amino}phenyl)-1,3-thiazol-2-yl]pyrrolidin-1-yl}acetic acid;

2-{3-hydroxy-3-[5-(3-methyl-5-{[4-(trifluoromethyl)pyrimidin-2-yl]amino}phenyl)-1,3-thiazol-2-yl]pyrrolidin-1-yl}-2-oxoacetamide;

methyl{3-hydroxy-3-[5-(3-methyl-5-{[4-(trifluoromethyl)pyrimidin-2-yl]amino}phenyl)-1,3-thiazol-2-yl]pyrrolidin-1-yl}acetate;

{3-hydroxy-3-[5-(3-methyl-5-{[4-(trifluoromethyl)pyrimidin-2-yl]amino}phenyl)-1,3-thiazol-2-yl]pyrrolidin-1-yl}(oxo)acetic acid;

3-{3-hydroxy-3-[5-(3-methyl-5-{[4-(trifluoromethyl)pyrimidin-2-yl]amino}phenyl)-1,3-thiazol-2-yl]pyrrolidin-1-yl}-3-oxopropanamide;

methyl{3-hydroxy-3-[5-(3-methyl-5-{[4-(trifluoromethyl)pyrimidin-2-yl]amino}phenyl)-1,3-thiazol-2-yl]pyrrolidin-1-yl}(oxo)acetate;

3-{3-hydroxy-3-[5-(3-methyl-5-{[4-(trifluoromethyl)pyrimidin-2-yl]amino}phenyl)-1,3-thiazol-2-yl]pyrrolidin-1-yl}-3-oxopropane-1,2-diol;

1-(5-(3-[(4-tert-butylpyrimidin-2-yl)amino]-5-methylphenyl)-1,3-thiazol-2-yl)cyclobutanol;

N-{3-[2-(3-aminooxetan-3-yl)-1,3-thiazol-5-yl]-5-methylphenyl}-5-chloro-4-methoxypyrimidin-2-amine;

N-[3-(5-{3-[(5-fluoro-4-methylpyrimidin-2-yl)amino]-5-methylphenyl}-1,3-thiazol-2-yl)oxetan-3-yl]sulfuric diamide;

N-[3-(5-{3-[(5-chloro-4-methoxypyrimidin-2-yl)amino]-5-methylphenyl}-1,3-thiazol-2-yl)oxetan-3-yl]sulfuric diamide;

1-[1-(5-{3-[(5-chloro-4-methoxypyrimidin-2-yl)amino]-5-methylphenyl}-1,3-thiazol-2-yl)-cyclobutyl]urea;

1-{4-[5-(3-methyl-5-{[4-(trifluoromethyl)pyrimidin-2-yl]amino}phenyl)-1,3-thiazol-2-yl]-7-oxoazepan-4-yl}urea;

N-{4-[5-(3-methyl-5-{[4-(trifluoromethyl)pyrimidin-2-yl]amino}phenyl)-1,3-thiazol-2-yl]-7-oxoazepan-4-yl}dicarbonimidic diamide;

N-{4-[5-(3-{[5-chloro-4-(trifluoromethyl)pyrimidin-2-yl]amino}-5-methylphenyl)-1,3-thiazol-2-yl]-7-oxoazepan-4-yl}dicarbonimidic diamide;

N-[1-(5-{3-[(5-chloro-4-methoxypyrimidin-2-yl)amino]-5-methylphenyl}-1,3-thiazol-2-yl)-cyclobutyl]dicarbonimidic diamide;

2-(5-{3-[(4-tert-butylpyrimidin-2-yl)amino]-5-methylphenyl}-1,3-thiazol-2-yl)propane-2-sulfonamide;

2-[5-(3-methyl-5-{[4-(1-methylethyl)pyrimidin-2-yl]amino}phenyl)-1,3-thiazol-2-yl]propane-2-sulfonamide;

4-[5-(3-methyl-5-{[4-(trifluoromethyl)pyrimidin-2-yl]amino}phenyl)-1,3-thiazol-2-yl]-7-oxoazepane-4-carboxamide;

N-[2-hydroxy-1-(hydroxymethyl)ethyl]-5-(3-methyl-5-{[4-(trifluoromethyl)pyrimidin-2-yl]-amino}phenyl)-1,3-thiazole-2-carboxamide;

N-[2-hydroxy-1,1-bis(hydroxymethyl)ethyl]-5-(3-methyl-5-{[4-(trifluoromethyl)pyrimidin-2-yl]-amino}phenyl)-1,3-thiazole-2-carboxamide;

N-[5-(3-methyl-5-{[4-(trifluoromethyl)pyrimidin-2-yl]amino}phenyl)-1,3-thiazol-2-yl]-carbonyl)-beta-alanine;

1-{[5-(3-methyl-5-{[4-(trifluoromethyl)pyrimidin-2-yl]amino}phenyl)-1,3-thiazol-2-yl]-carbonyl}pyrrolidin-3-ol;

N-{3-[bis(2-hydroxyethyl)amino]propyl}-5-(3-methyl-5-{[4-(trifluoromethyl)pyrimidin-2-yl]-amino}phenyl)-1,3-thiazole-2-carboxamide;

(3R,4S)-1-{[5-(3-methyl-5-[4-(trifluoromethyl)pyrimidin-2-yl]amino}phenyl)-1,3-thiazol-2-yl]-carbonyl)pyrrolidine-3,4-diol;

1-{[5-(3-methyl-5-{[4-(trifluoromethyl)pyrimidin-2-yl]amino}phenyl)-1,3-thiazol-2-yl]-carbonyl}piperidine-4-carboxylic acid;

4-({[5-(3-methyl-5-{[4-(trifluoromethyl)pyrimidin-2-yl]amino}phenyl)-1,3-thiazol-2-yl]-carbonyl}amino)cyclohexanecarboxylic acid;

(2R,3R)-2-hydroxy-3-({[5-(3-methyl-5-{[4-(trifluoromethyl)pyrimidin-2-yl]amino}phenyl)-1,3-thiazol-2-yl]carbonyl}amino)-3-phenylpropanoic acid;

4-hydroxy-1-{[5-(3-methyl-5-{[4-(trifluoromethyl)pyrimidin-2-yl]amino}phenyl)-1,3-thiazol-2-yl]carbonyl}proline;

methyl 4-hydroxy-1-{[5-(3-methyl-5-{[4-(trifluoromethyl)pyrimidin-2-yl]amino}phenyl)-1,3-thiazol-2-yl]carbonyl}prolinate;

4-hydroxy-1-{[5-(3-methyl-5-{[4-(trifluoromethyl)pyrimidin-2-yl]amino}phenyl)-1,3-thiazol-2-yl]carbonyl}piperidine-4-carboxylic acid;

methyl(4R)-4-hydroxy-1-{[5-(3-methyl-5-{[4-(trifluoromethyl)pyrimidin-2-yl]amino}phenyl)-1,3-thiazol-2-yl]carbonyl}-D-prolinate;

(4R)-4-hydroxy-1-{[5-(3-methyl-5-[4-(trifluoromethyl)pyrimidin-2-yl]amino}phenyl)-1,3-thiazol-2-yl]carbonyl)-D-proline;

N-{3-[2-(aminomethyl)-1,3-thiazol-5-yl]-5-methylphenyl}-4-(trifluoromethyl)pyrimidin-2-amine;

3-({[5-(3-methyl-5-{[4-(trifluoromethyl)pyrimidin-2-yl]amino}phenyl)-1,3-thiazol-2-yl]methyl}amino)propane-1,2-diol;

2-[2-({[5-(3-methyl-5-{[4-(trifluoromethyl)pyrimidin-2-yl]amino}phenyl)-1,3-thiazol-2-yl]methyl}amino)ethoxy]ethanol;

(2S,3S)-2-({[5-(3-methyl-5-{[4-(trifluoromethyl)pyrimidin-2-yl]amino}phenyl)-1,3-thiazol-2-yl]methyl}amino)butane-1,3-diol;

(2R,3R)-2-({[5-(3-methyl-5-{[4-(trifluoromethyl)pyrimidin-2-yl]amino}phenyl)-1,3-thiazol-2-yl]methyl}amino)butane-1,3-diol;

4-methyl-4-({[5-(3-methyl-5-{[4-(trifluoromethyl)pyrimidin-2-yl]amino}phenyl)-1,3-thiazol-2-yl]methyl}amino)pentan-2-ol;

{3-[({[5-(3-methyl-5-{[4-(trifluoromethyl)pyrimidin-2-yl]amino}phenyl)-1,3-thiazol-2-yl]methyl}amino)methyl]oxetan-3-yl}methanol;

2-(hydroxymethyl)-2-({[5-(3-methyl-5-{[4-(trifluoromethyl)pyrimidin-2-yl]amino}phenyl)-1,3-thiazol-2-yl]methyl}amino)propane-1,3-diol;

N-[3-(2-{[(1,4-dioxan-2-ylmethyl)(methyl)amino]methyl}-1,3-thiazol-5-yl)-5-methylphenyl]-4-(trifluoromethyl)pyrimidin-2-amine;

{4-[({[5-(3-methyl-5-{[4-(trifluoromethyl)pyrimidin-2-yl]amino}phenyl)-1,3-thiazol-2-yl]methyl}amino)methyl]tetrahydro-2H-pyran-4-yl}methanol;

1-methyl-4-[2-({[5-(3-methyl-5-{[4-(trifluoromethyl)pyrimidin-2-yl]amino}phenyl)-1,3-thiazol-2-yl]methyl}amino)ethyl]piperidin-4-ol;

2,2'-{[3-({[5-(3-methyl-5-{[4-(trifluoromethyl)pyrimidin-2-yl]amino}phenyl)-1,3-thiazol-2-yl]methyl}amino)propyl]imino}diethanol;

2-[(2-hydroxyethyl) {[5-(3-methyl-5-{[4-(trifluoromethyl)pyrimidin-2-yl]amino}phenyl)-1,3-thiazol-2-yl]methyl}amino]ethanesulfonic acid;

4-({[5-(3-methyl-5-{[4-(trifluoromethyl)pyrimidin-2-yl]amino}phenyl)-1,3-thiazol-2-yl]methyl}amino)tetrahydrofuran-3-ol;

4-(methyl{[5-(3-methyl-5-{[4-(trifluoromethyl)pyrimidin-2-yl]amino}phenyl)-1,3-thiazol-2-yl]methyl}amino)tetrahydrofuran-3-ol;

[2-methyl-2-({[5-(3-methyl-5-{[4-(trifluoromethyl)pyrimidin-2-yl]amino}phenyl)-1,3-thiazol-2-yl]methyl}amino)cyclohexyl]methanol;

[3-({[5-(3-methyl-5-{[4-(trifluoromethyl)pyrimidin-2-yl]amino}phenyl)-1,3-thiazol-2-yl]methyl}amino)-7-oxabicyclo[2.2.1]hept-2-yl]methanol;

4-({[5-(3-methyl-5-[4-(trifluoromethyl)pyrimidin-2-yl]amino}phenyl)-1,3-thiazol-2-yl]methyl)amino)tetrahydrothiophene-3-ol 1,1-dioxide;

4-(ethyl{[5-(3-methyl-5-{[4-(trifluoromethyl)pyrimidin-2-yl]amino}phenyl)-1,3-thiazol-2-yl]methyl}amino)tetrahydrothiophene-3-ol 1,1-dioxide;

2-[(1,1-dioxidotetrahydrothiophen-3-yl){[5-(3-methyl-5-{[4-(trifluoromethyl)pyrimidin-2-yl]amino}phenyl)-1,3-thiazol-2-yl]methyl}amino]ethanol;

4-[(2-hydroxyethyl){[5-(3-methyl-5-{[4-(trifluoromethyl)pyrimidin-2-yl]amino}phenyl)-1,3-thiazol-2-yl]methyl}amino]tetrahydrothiophene-3-ol 1,1-dioxide;

1-methyl-3-{[5-(3-methyl-5-{[4-(trifluoromethyl)pyrimidin-2-yl]amino}phenyl)-1,3-thiazol-2-yl]methyl}urea;

1-ethyl-3-{[5-(3-methyl-5-{[4-(trifluoromethyl)pyrimidin-2-yl]amino}phenyl)-1,3-thiazol-2-yl]methyl}urea;

1-(1-methylethyl)-3-{[5-(3-methyl-5-{[4-(trifluoromethyl)pyrimidin-2-yl]amino}phenyl)-1,3-thiazol-2-yl]methyl}urea;

ethyl N-({[5-(3-methyl-5-{[4-(trifluoromethyl)pyrimidin-2-yl]amino}phenyl)-1,3-thiazol-2-yl]methyl}carbamoyl)alaninate;

1-{[5-(3-methyl-5-{[4-(trifluoromethyl)pyrimidin-2-yl]amino}phenyl)-1,3-thiazol-2-yl]methyl}piperidine-3-carboxamide;

2-(4-{[5-(3-methyl-5-{[4-(trifluoromethyl)pyrimidin-2-yl]amino}phenyl)-1,3-thiazol-2-yl]methyl}morpholin-2-yl)ethanol;

(4-{[5-(3-methyl-5-{[4-(trifluoromethyl)pyrimidin-2-yl]amino}phenyl)-1,3-thiazol-2-yl]methyl}-1,4-oxazepan-2-yl)methanol;

N-[3-(2-{[2-(methoxymethyl)morpholin-4-yl]methyl}-1,3-thiazol-5-yl)-5-methylphenyl]-4-(trifluoromethyl)pyrimidin-2-amine;

(4-{[5-(3-methyl-5-{[4-(trifluoromethyl)pyrimidin-2-yl]amino}phenyl)-1,3-thiazol-2-yl]methyl}morpholin-2-yl)acetic acid;

(1-{[5-(3-methyl-5-{[4-(trifluoromethyl)pyrimidin-2-yl]amino}phenyl)-1,3-thiazol-2-yl]methyl}pyrrolidin-2-yl)phosphonic acid;

(1-{[5-(3-methyl-5-{[4-(trifluoromethyl)pyrimidin-2-yl]amino}phenyl)-1,3-thiazol-2-yl]methyl}azetidin-3-yl)methyl dimethylphosphinate;

N-[3-methyl-5-(2-{[4-(1-methylethyl)-4-oxido-1,4-azaphosphinan-1-yl]methyl}-1,3-thiazol-5-yl)phenyl]-4-(trifluoromethyl)pyrimidin-2-amine;

1-[2-({3-[2-(1-hydroxycyclobutyl)-1,3-thiazol-5-yl]-5-methylphenyl}amino)pyrimidin-4-yl]-1,3-diazepan-4-one;

(1R,4S)-4-(5-{3-[(4,6-dimethylpyrimidin-2-yl)amino]-5-methylphenyl}-1,3-thiazol-2-yl)-4-hydroxy-2,2-dimethylcyclohexanecarboxylic acid;

(1S,4R)-4-(5-{3-[(4,6-dimethylpyrimidin-2-yl)amino]-5-methylphenyl}-1,3-thiazol-2-yl)-4-hydroxy-2,2-dimethylcyclohexanecarboxylic acid;

cis-1-[5-(3-{[4-methoxy-5-(trifluoromethyl)pyrimidin-2-yl]amino}-5-methylphenyl)-1,3-thiazol-2-yl]cyclohexane-1,4-diol;

methyl(1R,4S)-4-(5-{3-[(4,6-dimethylpyrimidin-2-yl)amino]-5-methylphenyl}-1,3-thiazol-2-yl)-4-hydroxy-2,2-dimethylcyclohexanecarboxylate;

(1S,4R)-4-hydroxy-4-(5-{3-[(4-methoxy-5-methylpyrimidin-2-yl)amino]-5-methylphenyl}-1,3-thiazol-2-yl)-2,2-dimethylcyclohexanecarboxylic acid;

(1S,4R)-4-hydroxy-4-(5-{3-({4-[(1R)-1-hydroxyethyl]pyrimidin-2-yl}amino)-5-methylphenyl]-1,3-thiazol-2-yl}-2,2-dimethylcyclohexanecarboxylic acid;

(1S,4R)-4-hydroxy-4-(5-{3-({4-[(1S)-1-hydroxyethyl]pyrimidin-2-yl}amino)-5-methylphenyl]-1,3-thiazol-2-yl}-2,2-dimethylcyclohexanecarboxylic acid;

(1S,4R)-4-[5-(3-{[4-(dimethylamino)-5-methylpyrimidin-2-yl]amino}-5-methylphenyl)-1,3-thiazol-2-yl]-4-hydroxy-2,2-dimethylcyclohexanecarboxylic acid;

(1S,4R)-4-hydroxy-4-[5-(3-{[4-(1-hydroxy-1-methylethyl)pyrimidin-2-yl]amino}-5-methylphenyl)-1,3-thiazol-2-yl]-2,2-dimethylcyclohexanecarboxylic acid;

(1S,4R)-4-{5-[3-({4-[(R)-cyclopropyl(hydroxy)methyl]pyrimidin-2-yl}amino)-5-methylphenyl]-1,3-thiazol-2-yl}-4-hydroxy-2,2-dimethylcyclohexanecarboxylic acid;

(1S,4R)-4-{5-[3-({4-[(S)-cyclopropyl(hydroxy)methyl]pyrimidin-2-yl}amino)-5-methylphenyl]-1,3-thiazol-2-yl}-4-hydroxy-2,2-dimethylcyclohexanecarboxylic acid;

(1S,4R)-4-{5-[3-({4-[cyclopropyl(fluoro)methyl]pyrimidin-2-yl}amino)-5-methylphenyl]-1,3-thiazol-2-yl}-4-hydroxy-2,2-dimethylcyclohexanecarboxylic acid;

(1S,4R)-4-{5-[3-({4-[(R)-cyclopropyl(fluoro)methyl]pyrimidin-2-yl}amino)-5-methylphenyl]-1,3-thiazol-2-yl}-4-hydroxy-2,2-dimethylcyclohexanecarboxylic acid;

(1S,4R)-4-{5-[3-({4-[(S)-cyclopropyl(fluoro)methyl]pyrimidin-2-yl}amino)-5-methylphenyl]-1,3-thiazol-2-yl}-4-hydroxy-2,2-dimethyl cyclohexanecarboxylic acid;

(1S,4R)-4-hydroxy-4-{5-[3-({4-[(1E)-3-hydroxy-3-methylbut-1-en-1-yl]pyrimidin-2-yl}amino)-5-methylphenyl]-1,3-thiazol-2-yl}-2,2-dimethyl cyclohexanecarboxylic acid;

(1S,4R)-4-[5-(3-{[4-(1-cyclopropyl-1-hydroxyethyl)pyrimidin-2-yl]amino}-5-methylphenyl)-1,3-thiazol-2-yl]-4-hydroxy-2,2-dimethylcyclohexanecarboxylic acid;

(1S,4R)-4-{5-[3-({4-[(1R)-1-cyclopropyl-1-hydroxyethyl]pyrimidin-2-yl}amino)-5-methylphenyl]-1,3-thiazol-2-yl}-4-hydroxy-2,2-dimethylcyclohexanecarboxylic acid;

(1S,4R)-4-{5-[3-({4-[(1S)-1-cyclopropyl-1-hydroxyethyl]pyrimidin-2-yl}amino)-5-methylphenyl]-1,3-thiazol-2-yl}-4-hydroxy-2,2-dimethylcyclohexanecarboxylic acid;

methyl 4-hydroxy-4-{[5-(3-{[4-methoxy-5-(trifluoromethyl)pyrimidin-2-yl]amino}-5-methylphenyl]-1,3-thiazol-2-yl}-2,2-dimethylcyclohexanecarboxylate;

(1S,4R)-4-{5-[3-(6,7-dihydro-5H-cyclopenta[d]pyrimidin-2-ylamino)-5-methylphenyl]-1,3-thiazol-2-yl}-4-hydroxy-2,2-dimethylcyclohexanecarboxylic acid;

methyl(1S,4R)-4-{5-[3-(6,7-dihydro-5H-cyclopenta[d]pyrimidin-2-ylamino)-5-methylphenyl]-1,3-thiazol-2-yl}-4-hydroxy-2,2-dimethylcyclohexanecarboxylate;

ethyl 4-(5-{3-[(4-tert-butylpyrimidin-2-yl)amino]-5-methylphenyl}-1,3-thiazol-2-yl)-4-hydroxy-2-methylcyclohexanecarboxylate;

methyl(1S,4R)-4-hydroxy-2,2-dimethyl-4-[5-(3-methyl-5-{[4-(1-methylethyl)pyrimidin-2-yl]amino}phenyl)-1,3-thiazol-2-yl]cyclohexanecarboxylate;

methyl(1S,4R)-4-(5-{3-[(4-tert-butyl pyrimidin-2-yl)amino]-5-methylphenyl-1,3-thiazol-2-yl}-4-hydroxy-2,2-dimethylcyclohexanecarboxylate;

methyl(1S,4R)-4-hydroxy-2,2-dimethyl-4-[5-(3-methyl-5-{[4-(1-methylethoxy)pyrimidin-2-yl]amino}phenyl)-1,3-thiazol-2-yl]cyclohexanecarboxylate;

methyl(1S,4R)-4-(5-{3-[(4-ethenylpyrimidin-2-yl)amino]-5-methylphenyl}-1,3-thiazol-2-yl)-4-hydroxy-2,2-dimethylcyclohexanecarboxylate;

methyl(1S,4R)-4-(5-{3-[(4-cyclobutylpyrimidin-2-yl)amino]-5-methylphenyl}-1,3-thiazol-2-yl)-4-hydroxy-2,2-dimethylcyclohexanecarboxylate;

methyl(1S,4R)-4-(5-{3-[(4-carbamoylpyrimidin-2-yl)amino]-5-methylphenyl}-1,3-thiazol-2-yl)-4-hydroxy-2,2-dimethylcyclohexanecarboxylate;

tert-butyl cis-4-hydroxy-4-{5-[3-({4-[1-(4-methoxybenzyl)-1H-1,2,3-triazol-4-yl]pyrimidin-2-yl}amino)-5-methylphenyl]-1,3-thiazol-2-yl}cyclohexanecarboxylate;

4-hydroxy-4-[5-(3-{[4-methoxy-5-(trifluoromethyl)pyrimidin-2-yl]amino}-5-methylphenyl)-1,3-thiazol-2-yl]-2,2-dimethylcyclohexanecarboxylic acid;

(1S,4R)-4-hydroxy-4-[5-(3-{[4-methoxy-5-(trifluoromethyl)pyrimidin-2-yl]amino}-5-methylphenyl)-1,3-thiazol-2-yl]-2,2-dimethylcyclohexanecarboxylic acid;

tert-butyl 4-hydroxy-4-{5-[3-({4-[(1E)-3-methoxyprop-1-en-1-yl]pyrimidin-2-yl}amino)-5-methylphenyl]-1,3-thiazol-2-yl}cyclohexanecarboxylate;

4-hydroxy-4-{5-[3-({4-[(1E)-3-methoxyprop-1-en-1-yl]pyrimidin-2-yl}amino)-5-methylphenyl]-1,3-thiazol-2-yl}cyclohexanecarboxylic acid;

(1S,4R)-4-[5-(3-{[5-bromo-4-(trifluoromethyl)pyrimidin-2-yl]amino}-5-methylphenyl)-1,3-thiazol-2-yl]-4-hydroxy-2,2-dimethylcyclohexanecarboxylic acid;

(1R,4S)-4-[5-(3-{[5-bromo-4-(trifluoromethyl)pyrimidin-2-yl]amino}-5-methylphenyl)-1,3-thiazol-2-yl]-4-hydroxy-2,2-dimethylcyclohexanecarboxylic acid;

(5R)-5-[5-(2-bromo-3-methyl-5-{[4-(trifluoromethyl)pyrimidin-2-yl]amino}phenyl)-1,3-thiazol-2-yl]-5-hydroxyazepan-2-one;

(5S)-5-[5-(2-bromo-3-methyl-5-{[4-(trifluoromethyl)pyrimidin-2-yl]amino}phenyl)-1,3-thiazol-2-yl]-5-hydroxyazepan-2-one;

2,6-anhydro-3,4-dideoxy-5-C-[5-(3-methyl-5-{[4-(trifluoromethyl)pyrimidin-2-yl]amino}phenyl)-1,3-thiazol-2-yl]hexonic acid;

cis-4-fluoro-4-(5-{3-[(4-methoxypyrimidin-2-yl)amino]-5-methylphenyl}-1,3-thiazol-2-yl)cyclohexanecarboxylic acid;

cis-4-hydroxy-4-[5-(3-{[4-(2-methoxyethoxy)pyrimidin-2-yl]amino}-5-methylphenyl)-1,3-thiazol-2-yl]cyclohexanecarboxylic acid;

methyl-4-hydroxy-2-methyl-4-(5-{3-methyl-5-[(4-methylpyrimidin-2-yl)amino]phenyl}-1,3-thiazol-2-yl)cyclohexanecarboxylate;

4-hydroxy-2,5-dimethyl-4-(5-{3-methyl-5-[(4-methylpyrimidin-2-yl)amino]phenyl}-1,3-thiazol-2-yl)cyclohexanecarboxylic acid;

ethyl 4-hydroxy-2,5-dimethyl-4-(5-{3-methyl-5-[(4-methylpyrimidin-2-yl)amino]phenyl}-1,3-thiazol-2-yl)cyclohexanecarboxylate;

methyl(1R,2R,4S)-4-hydroxy-2-methyl-4-(5-{3-methyl-5-[(4-methylpyrimidin-2-yl)amino]phenyl}-1,3-thiazol-2-yl)cyclohexanecarboxylate;

ethyl (1R,2S,4R,5R)-4-hydroxy-2,5-dimethyl-4-(5-{3-methyl-5-[(4-methylpyrimidin-2-yl)amino]phenyl}-1,3-thiazol-2-yl)cyclohexanecarboxylate;

ethyl (1R,2S,4R,5R)-4-hydroxy-2,5-dimethyl-4-(5-{3-methyl-5-[(4-methylpyrimidin-2-yl)amino]phenyl}-1,3-thiazol-2-yl)cyclohexanecarboxylate;

(1R,2S,4R,5S)-4-hydroxy-2,5-dimethyl-4-[5-(3-methyl-5-{[4-(trifluoromethyl)pyrimidin-2-yl]amino}phenyl)-1,3-thiazol-2-yl]cyclohexanecarboxylic acid;

(1R,2S,4R,5R)-4-hydroxy-2,5-dimethyl-4-[5-(3-methyl-5-{[4-(trifluoromethyl)pyrimidin-2-yl]amino}phenyl)-1,3-thiazol-2-yl]cyclohexanecarboxylic acid;

(1R,2S,4R,5S)-4-hydroxy-2,5-dimethyl-4-[5-(3-methyl-5-{[4-(trifluoromethyl)pyrimidin-2-yl]amino}phenyl)-1,3-thiazol-2-yl]cyclohexanecarboxylic acid;

(1R,2S,4R,5R)-4-hydroxy-2,5-dimethyl-4-[5-(3-methyl-5-{[4-(trifluoromethyl)pyrimidin-2-yl]amino}phenyl)-1,3-thiazol-2-yl]cyclohexanecarboxylic acid;

(1R,2S,4R,5R)-4-hydroxy-2,5-dimethyl-4-[5-(3-methyl-5-{[4-(trifluoromethyl)pyrimidin-2-yl]amino}phenyl)-1,3-thiazol-2-yl]cyclohexanecarboxylic acid;

ethyl(1R,2S,4R,5S)-4-hydroxy-2,5-dimethyl-4-[5-(3-methyl-5-{[4-(trifluoromethyl)pyrimidin-2-yl]amino}phenyl)-1,3-thiazol-2-yl]cyclohexanecarboxylate;

ethyl(1R,2S,4R,5S)-4-hydroxy-2,5-dimethyl-4-[5-(3-methyl-5-{[4-(trifluoromethyl)pyrimidin-2-yl]amino}phenyl)-1,3-thiazol-2-yl]cyclohexanecarboxylate;

methyl(1R,2R,4R)-4-hydroxy-2-methyl-4-(5-{3-methyl-5-[(4-methylpyrimidin-2-yl)amino]phenyl}-1,3-thiazol-2-yl)cyclohexanecarboxylate;

ethyl(1R,2S,4R,5S)-4-hydroxy-2,5-dimethyl-4-[5-(3-methyl-5-{[4-(trifluoromethyl)pyrimidin-2-yl]amino}phenyl)-1,3-thiazol-2-yl]cyclohexanecarboxylate;

ethyl(1R,2S,4R,5R)-4-hydroxy-2,5-dimethyl-4-[5-(3-methyl-5-{[4-(trifluoromethyl)pyrimidin-2-yl]amino}phenyl)-1,3-thiazol-2-yl]cyclohexanecarboxylate;

(1s,2R,4r,6S)-4-hydroxy-2,6-dimethyl-4-(5-{3-methyl-5-[(4-methylpyrimidin-2-yl)amino]phenyl}-1,3-thiazol-2-yl)cyclohexanecarboxylic acid;

(1r,2R,4s,6S)-4-hydroxy-2,6-dimethyl-4-(5-{3-methyl-5-[(4-methylpyrimidin-2-yl)amino]phenyl}-1,3-thiazol-2-yl)cyclohexanecarboxylic acid;

1-methylethyl (1s,2R,4r,6S)-4-hydroxy-2,6-dimethyl-4-(5-{3-methyl-5-[(4-methylpyrimidin-2-yl)amino]phenyl}-1,3-thiazol-2-yl)cyclohexanecarboxylate;

1-methylethyl (1r,2R,4s,6S)-4-hydroxy-2,6-dimethyl-4-(5-{3-methyl-5-[(4-methylpyrimidin-2-yl)amino]phenyl}-1,3-thiazol-2-yl)cyclohexanecarboxylate;

1-methylethyl (1r,2R,4r,6S)-4-hydroxy-2,6-dimethyl-4-(5-{3-methyl-5-[(4-methylpyrimidin-2-yl)amino]phenyl}-1,3-thiazol-2-yl)cyclohexanecarboxylate;

(1s,2R,4s,6S)-4-hydroxy-2,6-dimethyl-4-[5-(3-methyl-5-{[4-(trifluoromethyl)pyrimidin-2-yl]amino}phenyl)-1,3-thiazol-2-yl]cyclohexanecarboxylic acid;

(1r,2R,4s,6S)-4-hydroxy-2,6-dimethyl-4-[5-(3-methyl-5-{[4-(trifluoromethyl)pyrimidin-2-yl]amino}phenyl)-1,3-thiazol-2-yl]cyclohexanecarboxylic acid;

1-methyl ethyl (1s,2R,4r,6S)-4-hydroxy-2,6-dimethyl-4-[5-(3-methyl-5-{[4-(trifluoromethyl)pyrimidin-2-yl]amino}phenyl)-1,3-thiazol-2-yl]cyclohexanecarboxylate;

1-methylethyl 4-hydroxy-2,6-dimethyl-4-[5-(3-methyl-5-{[4-(trifluoromethyl)pyrimidin-2-yl]amino}phenyl)-1,3-thiazol-2-yl]cyclohexanecarboxylate;

ethyl 4-hydroxy-3,5-dimethyl-4-(5-{3-methyl-5-[(4-methylpyrimidin-2-yl)amino]phenyl}-1,3-thiazol-2-yl)cyclohexanecarboxylate;

4-hydroxy-3,5-dimethyl-4-[5-(3-methyl-5-{[4-(trifluoromethyl)pyrimidin-2-yl]amino}phenyl)-3-thiazol-2-yl]cyclohexanecarboxylic acid;

ethyl 4-hydroxy-3,5-dimethyl-4-[5-(3-methyl-5-{[4-(trifluoromethyl)pyrimidin-2-yl]amino}phenyl)-1,3-thiazol-2-yl]cyclohexanecarboxylate;

5-(5-{3-[(5-fluoro-4-methylpyrimidin-2-yl)amino]-5-methylphenyl}-1,3-thiazol-2-yl)-5-hydroxyazepan-2-one;

5-(5-{3-[(4-cyclopropylpyrimidin-2-yl)amino]-5-methylphenyl}-1,3-thiazol-2-yl)-5-hydroxyazepan-2-one;

5-[5-(3-{[4-(1-fluoroethyl)pyrimidin-2-yl]amino}-5-methylphenyl)-1,3-thiazol-2-yl]-5-hydroxyazepan-2-one;

4-(5-{3-[(4-ethylpyrimidin-2-yl)amino]-5-methylphenyl}-1,3-thiazol-2-yl)-4-hydroxy-2-methylcyclohexanecarboxylic acid;

5-[5-(3-{[4-(1-fluoroethyl)pyrimidin-2-yl]amino}-5-methylphenyl)-1,3-thiazol-2-yl]-5-hydroxyazepan-2-one;

5-(5-{3-[(5-chloro-4-methoxypyrimidin-2-yl)amino]-5-methylphenyl}-1,3-thiazol-2-yl)-5-hydroxyazepan-2-one;

5-(5-{3-[(5-fluoro-4-methoxypyrimidin-2-yl)amino]-5-methylphenyl}-1,3-thiazol-2-yl)-5-hydroxyazepan-2-one;

5-[5-(3-{[4-(difluoromethyl)pyrimidin-2-yl]amino}-5-methylphenyl)-1,3-thiazol-2-yl]-5-hydroxyazepan-2-one;

5-hydroxy-5-[5-(3-{[4-(trifluoromethyl)pyrimidin-2-yl]amino}phenyl)-1,3-thiazol-2-yl]azepan-2-one;

5-(5-{3-[(4-tert-butylpyrimidin-2-yl)amino]-5-methylphenyl}-1,3-thiazol-2-yl)-5-hydroxyazepan-2-one;

5-hydroxy-5-[5-(3-methyl-5-{[4-(1-methylethoxy)pyrimidin-2-yl]amino}phenyl)-1,3-thiazol-2-yl]azepan-2-one;

5-(5-{3-[(5-chloro-4-methoxypyrimidin-2-yl)amino]-5-methylphenyl}-1,3-thiazol-2-yl)-5-hydroxyazepan-2-one;

5-hydroxy-5-(5-{3-methyl-5-[(4-thiophen-2-ylpyrimidin-2-yl)amino]phenyl}-1,3-thiazol-2-yl)azepan-2-one;

4-(5-{3-[(4-cyclopropylpyrimidin-2-yl)amino]-5-methylphenyl}-1,3-thiazol-2-yl)azepan-4-ol;

4-[5-(3-methyl-5-{[4-(1-methylethyl)pyrimidin-2-yl]amino}phenyl)-1,3-thiazol-2-yl]azepan-4-ol;

(4S)-4-(5-{3-[(5-chloro-4-methoxypyrimidin-2-yl)amino]-5-methylphenyl}-1,3-thiazol-2-yl)azepan-4-ol;

(4R)-4-(5-{3-[(5-chloro-4-methoxypyrimidin-2-yl)amino]-5-methylphenyl}-1,3-thiazol-2-yl)azepan-4-ol;

tert-butyl (4R)-4-(5-{3-[(4-cyclopropylpyrimidin-2-yl)amino]-5-methylphenyl}-1,3-thiazol-2-yl)-4-hydroxyazepane-1-carboxylate;

tert-butyl (4S)-4-(5-{3-[(4-cyclopropylpyrimidin-2-yl)amino]-5-methylphenyl}-1,3-thiazol-2-yl)-4-hydroxyazepane-1-carboxylate;

tert-butyl 4-hydroxy-4-[5-(3-methyl-5-{[4-(1-methylethyl)pyrimidin-2-yl]amino}phenyl)-1,3-thiazol-2-yl]azepane-1-carboxylate;

tert-butyl (4R)-4-hydroxy-4-[5-(3-methyl-5-{[4-(1-methylethyl)pyrimidin-2-yl]amino}phenyl)-1,3-thiazol-2-yl]azepane-1-carboxylate;

tert-butyl (4S)-4-hydroxy-4-[5-(3-methyl-5-{[4-(1-methylethyl)pyrimidin-2-yl]amino}phenyl)-1,3-thiazol-2-yl]azepane-1-carboxylate;

tert-butyl (4S)-4-(5-{3-[(5-chloro-4-methoxypyrimidin-2-yl)amino]-5-methylphenyl}-1,3-thiazol-2-yl)-4-hydroxyazepane-1-carboxylate;

tert-butyl (4R)-4-(5-{3-[(5-chloro-4-methoxypyrimidin-2-yl)amino]-5-methylphenyl}-1-thiazol-2-yl)-4-hydroxyazepane-1-carboxylate;

4-hydroxy-4-(5-{3-[(4-methoxypyrimidin-2-yl)amino]-5-methylphenyl}1,3-thiazol-2-yl)-2-methylcyclohexanecarboxylic acid;

4-{1-[5-(3-methyl-5-{[4-(trifluoromethyl)pyrimidin-2-yl]amino}phenyl)-1,3-thiazol-2-yl]ethenyl}benzoic acid;

methyl 4-{1-[5-(3-methyl-5-{[4-(trifluoromethyl)pyrimidin-2-yl]amino}phenyl)-1,3-thiazol-2-yl]ethenyl}benzoate;

4-{1-[5-(3-methyl-5-{[4-(trifluoromethyl)pyrimidin-2-yl]amino}phenyl)-1,3-thiazol-2-yl]cyclopropyl}benzoic acid;

methyl 4-{(E)-2-[5-(3-methyl-5-{[4-(trifluoromethyl)pyrimidin-2-yl]amino}phenyl)-1,3-thiazol-2-yl]ethenyl}benzoate;

4-{1-methyl-1-[5-(3-methyl-5-{[4-(trifluoromethyl)pyrimidin-2-yl]amino}phenyl)-1,3-thiazol-2-yl]ethyl}benzoic acid;

6-{1-hydroxy-1-[5-(3-methyl-5-{[4-(trifluoromethyl)pyrimidin-2-yl]amino}phenyl)-1,3-thiazol-2-yl]ethyl}pyridine-3-carboxylic acid;

4-{difluoro[5-(3-methyl-5-{[4-(trifluoromethyl)pyrimidin-2-yl]amino}phenyl)-1,3-thiazol-2-yl]methyl}benzoic acid;

methyl 4-{1-[5-(3-methyl-5-{[4-(trifluoromethyl)pyrimidin-2-yl]amino}phenyl)-1,3-thiazol-2-yl]cyclopropyl}benzoate;

methyl 4-{1-methyl-1-[5-(3-methyl-5-{[4-(trifluoromethyl)pyrimidin-2-yl]amino}phenyl)-1,3-thiazol-2-yl]ethyl}benzoate;

methyl 4-{difluoro[5-(3-methyl-5-{[4-(trifluoromethyl)pyrimidin-2-yl]amino}phenyl)-1,3-thiazol-2-yl]methyl}benzoate;

4-hydroxy-4-(5-{3-[(4-methoxypyrimidin-2-yl)amino]-5-methylphenyl}-1,3-thiazol-2-yl)-2-methylcyclohexanecarboxylic acid;

(1S,2R,4R)-4-(5-{3-[(5-fluoro-4-methylpyrimidin-2-yl)amino]-5-methylphenyl}-1,3-thiazol-2-yl)-4-hydroxy-2-methylcyclohexanecarboxylic acid;

(1R,2S,4S)-4-(5-{3-[(5-fluoro-4-methylpyrimidin-2-yl)amino]-5-methylphenyl}-1,3-thiazol-2-yl)-4-hydroxy-2-methylcyclohexanecarboxylic acid;

cis-4-hydroxy-4-[5-(3-{[4-(3-methoxypropoxy)pyrimidin-2-yl]amino}-5-methylphenyl)-1,3-thiazol-2-yl]cyclohexanecarboxylic acid;

4-(5-{3-[(4-cyclopropylpyrimidin-2-yl)amino]-5-methylphenyl}-1,3-thiazol-2-yl)-4-hydroxy-2-methylcyclohexanecarboxylic acid;

4-hydroxy-2-methyl-4-[5-(3-methyl-5-{[4-(1-methylethyl)pyrimidin-2-yl]amino}phenyl)-1,3-thiazol-2-yl]cyclohexanecarboxylic acid;

4-(5-{3-[(5-chloro-4-methylpyrimidin-2-yl)amino]-5-methylphenyl}-1,3-thiazol-2-yl)-4-hydroxy-2-methylcyclohexanecarboxylic acid;

cis-4-[5-(3-chloro-5-{[4-(trifluoromethyl)pyrimidin-2-yl]amino}phenyl)-1,3-thiazol-2-yl]-4-hydroxycyclohexanecarboxylic acid;

4-(5-{3-[(5-fluoro-4-methoxypyrimidin-2-yl)amino]-5-methylphenyl}-1,3-thiazol-2-yl)-4-hydroxy-2-methylcyclohexanecarboxylic acid;

ethyl (1S,2R,4R)-4-(5-{3-[(4-ethylpyrimidin-2-yl)amino]-5-methylphenyl}-1,3-thiazol-2-yl)-4-hydroxy-2-methylcyclohexanecarboxylate;

ethyl (1R,2S,4S)-4-(5-{3-[(4-ethylpyrimidin-2-yl)amino]-5-methylphenyl}-1,3-thiazol-2-yl)-4-hydroxy-2-methylcyclohexanecarboxylate;

4-(5-{3-[(4-cyclopropyl-5-fluoropyrimidin-2-yl)amino]-5-methylphenyl}-1,3-thiazol-2-yl)-4-hydroxy-2-methylcyclohexanecarboxylic acid;

(1S,2R,4R)-4-(5-{3-[(5-chloro-4-methoxypyrimidin-2-yl)amino]-5-methylphenyl}-1,3-thiazol-2-yl)-4-hydroxy-2-methylcyclohexanecarboxylic acid;

(1R,2S,4S)-4-(5-{3-[(5-chloro-4-methoxypyrimidin-2-yl)amino]-5-methylphenyl}-1,3-thiazol-2-yl)-4-hydroxy-2-methylcyclohexanecarboxylic acid;

4-hydroxy-4-[5-(3-{[4-(2-methoxyethoxy)pyrimidin-2-yl]amino}-5-methylphenyl)-1,3-thiazol-2-yl]-2-methylcyclohexanecarboxylic acid;

4-hydroxy-2-methyl-4-(5-{3-methyl-5-[(4-methylpyrimidin-2-yl)amino]phenyl}-1,3-thiazol-2-yl)cyclohexanecarboxylic acid;

4-hydroxy-4-[5-(3-{[4-(3-methoxypropoxy)pyrimidin-2-yl]amino}-5-methylphenyl)-1,3-thiazol-2-yl]-2-methylcyclohexanecarboxylic acid;

4-hydroxy-4-{5-[3-(methoxymethyl)-5-{[4-(trifluoromethyl)pyrimidin-2-yl]amino}phenyl]-1,3-thiazol-2-yl}-2-methylcyclohexanecarboxylic acid;

ethyl-4-hydroxy-4-[5-(3-{[4-(2-methoxyethoxy)pyrimidin-2-yl]amino}-5-methylphenyl)-1,3-thiazol-2-yl]-2-methylcyclohexanecarboxylate;

ethyl-4-hydroxy-2,5-dimethyl-4-[5-(3-methyl-5-{[4-(trifluoromethyl)pyrimidin-2-yl]amino}phenyl)-1,3-thiazol-2-yl]cyclohexanecarboxylate;

ethyl-4-hydroxy-4-[5-(3-{[4-(3-methoxypropoxy)pyrimidin-2-yl]amino}-5-methylphenyl)-1,3-thiazol-2-yl]-2-methylcyclohexanecarboxylate;

(1S,4R)-4-(5-{3-[(4-ethylpyrimidin-2-yl)amino]-5-methylphenyl}-1,3-thiazol-2-yl)-4-hydroxy-2,2-dimethylcyclohexanecarboxylic acid;

4-hydroxy-2-methyl-4-(5-{3-methyl-5-[(4-methylpyrimidin-2-yl)amino]phenyl}-3-thiazol-2-yl)cyclohexanecarboxylic acid;

methyl(1S,4R)-4-(5-{3-[(4-cyanopyrimidin-2-yl)amino]-5-methylphenyl}-1,3-thiazol-2-yl)-4-hydroxy-2,2-dimethylcyclohexanecarboxylate;

(1S,4R)-4-(5-{3-[(4-cyclopropylpyrimidin-2-yl)amino]-5-methylphenyl}-1,3-thiazol-2-yl)-4-hydroxy-2,2-dimethylcyclohexanecarboxylic acid;

(1S,4R)-4-hydroxy-2,2-dimethyl-4-[5-(3-methyl-5-{[4-(1-methylethyl)pyrimidin-2-yl]amino}phenyl)-1,3-thiazol-2-yl]cyclohexanecarboxylic acid;

methyl(1S,4R)-4-(5-{3-[(4-ethylpyrimidin-2-yl)amino]-5-methylphenyl}-1,3-thiazol-2-yl)-4-hydroxy-2,2-dimethylcyclohexanecarboxylate;

methyl(1R,4S)-4-hydroxy-4-(5-{3-[(4-methoxypyrimidin-2-yl)amino]-5-methylphenyl}-1,3-thiazol-2-yl)-2,2-dimethylcyclohexanecarboxylate;

methyl(1S,4R)-4-hydroxy-4-(5-{3-[(4-methoxypyrimidin-2-yl)amino]-5-methylphenyl}-1,3-thiazol-2-yl)-2,2-dimethylcyclohexanecarboxylate;

methyl(1S,4R)-4-(5-{3-[(4-cyclopropylpyrimidin-2-yl)amino]-5-methylphenyl}-1,3-thiazol-2-yl)-4-hydroxy-2,2-dimethylcyclohexanecarboxylate;

4-(5-{3-[(4-cyclopropyl-5-fluoropyrimidin-2-yl)amino]-5-methylphenyl}-1,3-thiazol-2-yl)-4-hydroxy-2,2-dimethylcyclohexanecarboxylic acid;

(1S,4R)-4-(5-{3-[(4-cyclopropyl-5-fluoropyrimidin-2-yl)amino]-5-methylphenyl}-1,3-thiazol-2-yl)-4-hydroxy-2,2-dimethylcyclohexanecarboxylic acid;

4-[5-(3-chloro-5-{[4-(trifluoromethyl)pyrimidin-2-yl]amino}phenyl)-1,3-thiazol-2-yl]-4-hydroxy-2,2-dimethylcyclohexanecarboxylic acid;

4-hydroxy-2-methyl-4-(5-{3-methyl-5-[(4-methylpyrimidin-2-yl)amino]phenyl}-1,3-thiazol-2-yl)cyclohexanecarboxylic acid;

(1S,4R)-4-[5-(3-chloro-5-{[4-(trifluoromethyl)pyrimidin-2-yl]amino}phenyl)-1,3-thiazol-2-yl]-4-hydroxy-2,2-dimethylcyclohexanecarboxylic acid;

(1R,4S)-4-[5-(3-chloro-5-{[4-trifluoromethyl)pyrimidin-2-yl]amino}phenyl)-1,3-thiazol-2-yl]-4-hydroxy-2,2-dimethylcyclohexanecarboxylic acid;

(1S,4R)-4-hydroxy-4-{5-[3-(methoxymethyl)-5-{[4-(trifluoromethyl)pyrimidin-2-yl]amino}phenyl]-1,3-thiazol-2-yl}-2,2-dimethylcyclohexanecarboxylic acid;

methyl 4-[5-(3-chloro-5-{[4-(trifluoromethyl)pyrimidin-2-yl]amino}phenyl)-1,3-thiazol-2-yl]-4-hydroxy-2,2-dimethylcyclohexanecarboxylate;

(1S,4R)-4-hydroxy-2,2-dimethyl-4-[5-(3-methyl-5-{[4-(trifluoromethyl)(6-$^2$H)pyrimidin-2-yl]amino}phenyl)-1,3-thiazol-2-yl]cyclohexanecarboxylic acid;

methyl(1S,4R)-4-hydroxy-2,2-dimethyl-4-[5-(3-methyl-5-{[4-(trifluoromethyl)(6-$^2$H)pyrimidin-2-yl]amino}phenyl)-1,3-thiazol-2-yl]cyclohexanecarboxylate;

4-hydroxy-2,3-dimethyl-4-(5-{3-methyl-5-[(4-methylpyrimidin-2-yl)amino]phenyl}-1,3-thiazol-2-yl)cyclohexanecarboxylic acid;

ethyl 4-hydroxy-2,3-dimethyl-4-(5-{3-methyl-5-[(4-methylpyrimidin-2-yl)amino]phenyl}-1,3-thiazol-2-yl)cyclohexanecarboxylate;

4-hydroxy-2,3-dimethyl-4-[5-(3-methyl-5-{[4-(trifluoromethyl)pyrimidin-2-yl]amino}phenyl)-1,3-thiazol-2-yl]cyclohexanecarboxylic acid;

ethyl 4-hydroxy-2,3-dimethyl-4-[5-(3-methyl-5-{[4-(trifluoromethyl)pyrimidin-2-yl]amino}phenyl)-1,3-thiazol-2-yl]cyclohexanecarboxylate;

4-hydroxy-3-methyl-4-(5-{3-methyl-5-[(4-methylpyrimidin-2-yl)amino]phenyl}-1,3-thiazol-2-yl)cyclohexanecarboxylic acid;

ethyl 4-hydroxy-3-methyl-4-(5-{3-methyl-5-[(4-methylpyrimidin-2-yl)amino]phenyl}-1,3-thiazol-2-yl)cyclohexanecarboxylate;

4-hydroxy-3-methyl-4-[5-(3-methyl-5-{[4-(trifluoromethyl)pyrimidin-2-yl]amino}phenyl)-1,3-thiazol-2-yl]cyclohexanecarboxylic acid;

ethyl 4-hydroxy-3-methyl-4-[5-(3-methyl-5-{[4-(trifluoromethyl)pyrimidin-2-yl]amino}phenyl)-1,3-thiazol-2-yl]cyclohexanecarboxylate;

3,4-dihydroxy-4-(5-{3-methyl-5-[(4-methylpyrimidin-2-yl)amino]phenyl}yl)cyclohexanecarboxylic acid;

4-hydroxy-3,3-dimethyl-4-(5-{3-methyl-5-[(4-methylpyrimidin-2-yl)amino]phenyl}-1,3-thiazol-2-yl)cyclohexanecarboxylic acid;

N-{3-methyl-5-[2-(1H-pyrazol-4-yl)-1,3-thiazol-5-yl]phenyl}-4-(trifluoromethyl)pyrimidin-2-amine;

N-{3-methyl-5-[2-(4,5,6,7-tetrahydropyrazolo[1,5-a]pyridin-3-yl)-1,3-thiazol-5-yl]phenyl}-4-(trifluoromethyl)pyrimidin-2-amine;

N-{3-methyl-5-[2-(1H-pyrazol-5-yl)-1,3-thiazol-5-yl]phenyl}-4-(trifluoromethyl)pyrimidin-2-amine;

N-[3-methyl-5-(2-pyridin-3-yl-1,3-thiazol-5-yl)phenyl]-4-(trifluoromethyl)pyrimidin-2-amine;

N-[3-methyl-5-(2-pyridin-4-yl-1,3-thiazol-5-yl)phenyl]-4-(trifluoromethyl)pyrimidin-2-amine;

N-[3-methyl-5-(2-thiophen-2-yl-1,3-thiazol-5-yl)phenyl]-4-(trifluoromethyl)pyrimidin-2-amine;

N-[3-methyl-5-(2-thiophen-3-yl-1,3-thiazol-5-yl)phenyl]-4-(trifluoromethyl)pyrimidin-2-amine;

N-[3-(2-furan-2-yl-1,3-thiazol-5-yl)-5-methylphenyl]-4-(trifluoromethyl)pyrimidin-2-amine;

N-{3-methyl-5-[2-(1H-pyrrol-2-yl)-1,3-thiazol-5-yl]phenyl}-4-(trifluoromethyl)pyrimidin-2-amine;

N-(3-methyl-5-{2-[1-(tetrahydro-2H-pyran-4-yl)-1H-pyrazol-4-yl]-1,3-thiazol-5-yl}phenyl)-4-(trifluoromethyl)pyrimidin-2-amine;

3-{4-[5-(3-methyl-5-{[4-(trifluoromethyl)pyrimidin-2-yl]amino}phenyl)-1,3-thiazol-2-yl]-1H-pyrazol-1-yl}propanenitrile;

2-{4-[5-(3-methyl-5-{[4-(trifluoromethyl)pyrimidin-2-yl]amino}phenyl)-1,3-thiazol-2-yl]-1H-pyrazol-1-yl}ethanol;

3-{4-[5-(3-methyl-5-{[4-(trifluoromethyl)pyrimidin-2-yl]amino}phenyl)-1,3-thiazol-2-yl]-1H-pyrazol-1-yl}propan-1-ol;

(2R)-3-{-4-[5-(3-methyl-5-{[4-trifluoromethyl)pyrimidin-2-yl]amino}phenyl)-1,3-thiazol-2-yl]-1H-pyrazol-1-yl}propane-1,2-diol;

2-methyl-1-{4-[5-(3-methyl-5-{[4-trifluoromethyl)pyrimidin-2-yl]amino}phenyl)-1,3-thiazol-2-yl]-1H-pyrazol-1-yl}propan-2-ol;

4-hydroxy-2-{-4-[5-(3-methyl-5-{[4-trifluoromethyl)pyrimidin-2-yl]amino}phenyl)-1,3-thiazol-2-yl]-1H-pyrazol-1-yl}butanoic acid;

5-({4-[5-(3-methyl-5-{[4-trifluoromethyl)pyrimidin-2-yl]amino}phenyl)-1,3-thiazol-2-yl]-1H-pyrazol-1-yl}methyl)-1,3-oxazolidin-2-one;

cis-1-(5-{3-[(4,6-dimethylpyrimidin-2-yl)amino]-5-methylphenyl}-1,3-thiazol-2-yl)cyclohexane-1,4-diol;

tert-butyl cis-4-[5-(3-{[4-(1-fluoroethyl)pyrimidin-2-yl]amino}-5-methylphenyl)-1,3-thiazol-2-yl]-4-hydroxycyclohexanecarboxylate;

tert-butyl cis-4-(5-{3-[(5-fluoro-4-methoxypyrimidin-2-yl)amino]-5-methylphenyl}-1,3-thiazol-2-yl)-4-hydroxycyclohexanecarboxylate;

tert-butyl cis-4-(5-{3-[(4-tert-butylpyrimidin-2-yl)-amino]-5-methylphenyl}-1,3-thiazol-2-yl)-4-hydroxycyclohexanecarboxylate;

(1S,4R)4-{5-[3-({4-[(1R)-1-fluoroethyl]pyrimidin-2-yl}amino)-5-methylphenyl]-1,3-thiazol-2-yl}-4-hydroxy-2,2-dimethylcyclohexanecarboxylic acid;

(1S,4R)4-{5-[3-({4-[(1S)-1-fluoroethyl]pyrimidin-2-yl}amino)-5-methylphenyl]-1,3-thiazol-2-yl}-4-hydroxy-2,2-dimethylcyclohexanecarboxylic acid;

cis-4-hydroxy-4-[5-(3-methyl-5-{[44-pentafluoroethyl)pyrimidin-2-yl]amino}phenyl)-1,3-thiazol-2-yl]cyclohexanecarboxylic acid;

tert-butyl cis-4-(5-{3-[(5-chloro-4-methoxypyrimidin-2-yl)amino]-5-methylphenyl}-1,3-thiazol-2-yl)-4-hydroxycyclohexanecarboxylate;

tert-butyl cis-4-hydroxy-4-(5-{3-methyl-5-[(4-thiophen-2-ylpyrimidin-2-yl)amino]phenyl}thiazol-2-yl)cyclohexanecarboxylate;

tert-butyl cis-4-hydroxy-4-[5-(3-methyl-5-{[4-pentafluoroethyl)pyrimidin-2-yl]amino}phenyl)-1,3-thiazol-2-yl]cyclohexanecarboxylate;

cis-4-hydroxy-4-{5-[3-({-4-[1-(4-methoxybenzyl)-1H-1,2,3-triazol-4-yl]pyrimidin-2-yl}amino)-5-methylphenyl]-1,3-thiazol-2-yl}cyclohexanecarboxylic acid;

(1R,2S,4S)-4-[5-(3-{[4-difluoromethyl)pyrimidin-2-yl]amino}-5-methylphenyl)-1,3-thiazol-2-yl]-4-hydroxy-2-methylcyclohexanecarboxylic acid;

(1S,2R,4R)-4-[5-(3-{[4-difluoromethyl)pyrimidin-2-yl]amino}-5-methylphenyl)-1,3-thiazol-2-yl]-4-hydroxy-2-methylcyclohexanecarboxylic acid;

cis-4-(5-{3-[(5-fluoro-4-methylpyrimidin-2-yl)amino]-5-methylphenyl}-1,3-thiazol-2-yl)-4-hydroxycyclohexanecarboxylic acid;

4-(5-{3-[(4-tert-butylpyrimidin-2-yl)amino]-5-methylphenyl}-1,3-thiazol-2-yl)-4-hydroxy-2-methylcyclohexanecarboxylic acid;

4-hydroxy-2-methyl-4-[5-(3-methyl-5-{[4-(1-methylethoxy)pyrimidin-2-yl]amino}phenyl)-1,3-thiazol-2-yl]cyclohexanecarboxylic acid;

methyl-4-(5-{3-[(5-fluoropyrimidin-2-yl)amino]-5-methylphenyl}-1,3-thiazol-2-yl)-4-hydroxy-2,2-dimethylcyclohexanecarboxylate;

4-(5-{3-[(5-fluoro-4-hydroxypyrimidin-2-yl)amino]-5-methylphenyl}-1,3-thiazol-2-yl)-4-hydroxy-2,2-dimethylcyclohexanecarboxylic acid;

2-[(3-{2-[(1S,4R)-4-carboxy-1-hydroxy-3,3-dimethylcyclohexyl]-1,3-thiazol-5-yl}-5-methylphenyl)amino]pyrimidine-4-carboxylic acid;

methyl 4-(5-{3-[(5-fluoro-4-methylpyrimidin-2-yl)amino]-5-methylphenyl}-1,3-thiazol-2-yl)-4-hydroxy-2,2-dimethylcyclohexanecarboxylate;

4-(5-{3-[(5-chloro-4-methylpyrimidin-2-yl)amino]-5-methylphenyl}-1,3-thiazol-2-yl)-4-hydroxy-2,2-dimethylcyclohexanecarboxylic acid;

(1R,4S)-4-(5-{3-[(5-chloro-4-methylpyrimidin-2-yl)amino]-5-methylphenyl}-1,3-thiazol-2-yl)-4-hydroxy-2,2-dimethylcyclohexanecarboxylic acid;

(1S,4R)-4-(5-{3-[(5-fluoro-4-methoxypyrimidin-2-yl)amino]-5-methylphenyl}-1,3-thiazol-2-yl)-4-hydroxy-2,2-dimethylcyclohexanecarboxylic acid;

cis-4-hydroxy-4-[5-(3-methyl-5-{[4-(1-methylethyl)pyrimidin-2-yl]amino}phenyl)-1,3-thiazol-2-yl]cyclohexanecarboxylic acid;

4-(5-{3-[(5-chloro-4-hydroxypyrimidin-2-yl)amino]-5-methylphenyl}-1,3-thiazol-2-yl)-4-hydroxy-2,2-dimethylcyclohexanecarboxylic acid;

(1S,4R)-4-[5-(3-{[4-(difluoromethyl)pyrimidin-2-yl]amino}-5-methylphenyl)-1,3-thiazol-2-yl]-4-hydroxy-2,2-dimethylcyclohexanecarboxylic acid;

(1S,4R)-4-(5-{3-[(4-cyclobutylpyrimidin-2-yl)amino]-5-methylphenyl}-1,3-thiazol-2-yl)-4-hydroxy-2,2-dimethylcyclohexanecarboxylic acid;

4-(5-{3-[(4-tert-butylpyrimidin-2-yl)amino]-5-methylphenyl}-1,3-thiazol-2-yl)-4-hydroxy-2,2-dimethylcyclohexanecarboxylic acid;

(1S,4R)-4-hydroxy-2,2-dimethyl-4-[5-(3-methyl-5-{[4-(1-methylethoxy)pyrimidin-2-yl]amino}phenyl)-1,3-thiazol-2-yl]cyclohexanecarboxylic acid;
methyl 4-(5-{3-[(5-chloro-4-methylpyrimidin-2-yl)amino]-5-methylphenyl}-1,3-thiazol-2-yl)-4-hydroxy-2,2-dimethylcyclohexanecarboxylate;
methyl-4-(5-{3-[(5-fluoro-4-methoxypyrimidin-2-yl)amino]-5-methylphenyl}-1,3-thiazol-2-yl)-4-hydroxy-2,2-dimethylcyclohexanecarboxylate;
4-(5-{3-[(5-chloro-4-methoxypyrimidin-2-yl)amino]-5-methylphenyl}-1,3-thiazol-2-yl)-4-hydroxy-2,2-dimethylcyclohexanecarboxylic acid;
(1S,4R)-4-hydroxy-2,2-dimethyl-4-[5-(4-methyl-3-{[4-(trifluoromethyl)pyrimidin-2-yl]amino}phenyl)-1,3-thiazol-2-yl]cyclohexanecarboxylic acid;
methyl-4-(5-{3-[(5-chloro-4-methoxypyrimidin-2-yl)amino]-5-methylphenyl}-1,3-thiazol-2-yl)-4-hydroxy-2,2-dimethylcyclohexanecarboxylate;
cis-4-(5-{3-[(5-chloro-4-methylpyrimidin-2-yl)amino]-5-methylphenyl}-1,3-thiazol-2-yl)-4-hydroxycyclohexanecarboxylic acid;
1,3-thiazol-2-yl)propan-2-ol;
8-(5-{3-[(5-fluoro-4-methylpyrimidin-2-yl)amino]-5-methylphenyl}-1,3-thiazol-2-yl)-1,4-dioxaspiro[4.5]decan-8-ol;
8-(5-{3-[(5-chloro-4-methoxypyrimidin-2-yl)amino]-5-methylphenyl}-1,3-thiazol-2-yl)-1,4-dioxaspiro[4.5]decan-8-ol;
cis-4-(5-{3-[(5-fluoro-4-methoxypyrimidin-2-yl)amino]-5-methylphenyl}-1,3-thiazol-2-yl)-4-hydroxycyclohexanecarboxylic acid;
cis-4-(5-{3-[(4-tert-butylpyrimidin-2-yl)amino]-5-methylphenyl}-1,3-thiazol-2-yl)-4-hydroxycyclohexanecarboxylic acid;
cis-4-hydroxy-4-[5-(3-methyl-5-{[4-(1-methylethoxy)pyrimidin-2-yl]amino}phenyl)-1,3-thiazol-2-yl]cyclohexanecarboxylic acid;
cis-4-(5-{3-[(5-chloro-4-methoxypyrimidin-2-yl)amino]-5-methylphenyl}-1,3-thiazol-2-yl)-4-hydroxycyclohexanecarboxylic acid;
cis-4-hydroxy-4-(5-{3-methyl-5-[(4-thiophen-2-ylpyrimidin-2-yl)amino]phenyl}-1,3-thiazol-2-yl)cyclohexanecarboxylic acid;
(1S,3S)-3-hydroxy-3-[5-(3-methyl-5-{[4-(trifluoromethyl)pyrimidin-2-yl]amino}phenyl)-1,3-thiazol-2-yl]cyclopentanecarboxamide;
(1R,3R)-3-hydroxy-3-[5-(3-methyl-5-{[4-(trifluoromethyl)pyrimidin-2-yl]amino}phenyl)-1,3-thiazol-2-yl]cyclopentanecarboxamide;
(1R,3S)-3-hydroxy-3-[5-(3-methyl-5-{[4-(trifluoromethyl)pyrimidin-2-yl]amino}phenyl)-1,3-thiazol-2-yl]cyclopentanecarboxamide;
(1S,3R)-3-hydroxy-3-[5-(3-methyl-5-{[4-(trifluoromethyl)pyrimidin-2-yl]amino}phenyl)-1,3-thiazol-2-yl]cyclopentanecarboxamide;
4-hydroxy-2-methyl-4-(5-{3-methyl-5-[(4-methylpyrimidin-2-yl)amino]phenyl}-1,3-thiazol-2-yl)cyclohexanecarboxamide;
cis-4-hydroxy-2,2-dimethyl-4-(5-{3-methyl-5-[(4-methylpyrimidin-2-yl)amino]phenyl}-1,3-thiazol-2-yl)cyclohexanecarboxamide;
cis-4-hydroxy-4-[5-(3-methyl-5-{[4-(1-methylethyl)pyrimidin-2-yl]amino}phenyl)-1,3-thiazol-2-yl]cyclohexanecarboxamide;
cis-4-(5-{3-[(4-tert-butylpyrimidin-2-yl)amino]-5-methylphenyl}-1,3-thiazol-2-yl)-4-hydroxycyclohexanecarboxamide;
4-hydroxy-2-methyl-4-[5-(3-methyl-5-{[4-(1-methylethyl)pyrimidin-2-yl]amino}phenyl)-1,3-thiazol-2-yl]cyclohexanecarboxamide;
cis-4-hydroxy-4-[5-(3-methyl-5-{[4-(1-methylethoxy)pyrimidin-2-yl]amino}phenyl)-1,3-thiazol-2-yl]cyclohexanecarboxamide;
(1S,4R)-4-hydroxy-4-(5-{3-[(4-methoxypyrimidin-2-yl)amino]-5-methylphenyl}-1,3-thiazol-2-yl)-2,2-dimethylcyclohexanecarboxamide;
4-hydroxy-4-[5-(3-{[4-(2-hydroxyethoxy)pyrimidin-2-yl]amino}-5-methylphenyl)-1,3-thiazol-2-yl]cyclohexanecarboxamide;
cis-4-hydroxy-N-methyl-4-[5-(3-methyl-5-{[4-(trifluoromethyl)pyrimidin-2-yl]amino}phenyl)-1,3-thiazol-2-yl]cyclohexanecarboxamide;
cis-N,4-dihydroxy-4-[5-(3-methyl-5-{[4-(trifluoromethyl)pyrimidin-2-yl]amino}phenyl)-1,3-thiazol-2-yl]cyclohexanecarboxamide;
cis-4-hydroxy-N,N-dimethyl-4-[5-(3-methyl-5-{[4-(trifluoromethyl)pyrimidin-2-yl]amino}phenyl)-1,3-thiazol-2-yl]cyclohexanecarboxamide;
N-(cyanomethyl)-4-hydroxy-4-[5-(3-methyl-5-{[4-(trifluoromethyl)pyrimidin-2-yl]amino}phenyl)-1,3-thiazol-2-yl]cyclohexanecarboxamide;
cis-4-(azetidin-1-ylcarbonyl)-1-[5-(3-methyl-5-{[4-(trifluoromethyl)pyrimidin-2-yl]amino}phenyl)-1,3-thiazol-2-yl]cyclohexanol;
4-hydroxy-N-(1-methylethyl)-4-[5-(3-methyl-5-{[4-(trifluoromethyl)pyrimidin-2-yl]amino}phenyl)-1,3-thiazol-2-yl]cyclohexanecarboxamide;
N-ethyl-4-hydroxy-N-methyl-4-[5-(3-methyl-5-{[4-(trifluoromethyl)pyrimidin-2-yl]amino}phenyl)-1,3-thiazol-2-yl]cyclohexanecarboxamide;
4-hydroxy-N-(2-hydroxyethyl)-4-[5-(3-methyl-5-{[4-(trifluoromethyl)pyrimidin-2-yl]amino}phenyl)-1,3-thiazol-2-yl]cyclohexanecarboxamide;
N-(cyclopropylmethyl)-4-hydroxy-4-[5-(3-methyl-5-{[4-(trifluoromethyl)pyrimidin-2-yl]amino}phenyl)-1,3-thiazol-2-yl]cyclohexanecarboxamide;
cis-1-[5-(3-methyl-5-{[4-(trifluoromethyl)pyrimidin-2-yl]amino}phenyl)-1,3-thiazol-2-yl]-4-(pyrrolidin-1-ylcarbonyl)cyclohexanol;
4-hydroxy-N-(2-methoxyethyl)-4-[5-(3-methyl-5-{[4-(trifluoromethyl)pyrimidin-2-yl]amino}phenyl)-1,3-thiazol-2-yl]cyclohexanecarboxamide;
N-({4-hydroxy-4-[5-(3-methyl-5-{[4-(trifluoromethyl)pyrimidin-2-yl]amino}phenyl)-1,3-thiazol-2-yl]cyclohexyl}carbonyl)glycine;
cis-4-hydroxy-N-1H-imidazol-2-yl-4-[5-(3-methyl-5-{[4-(trifluoromethyl)pyrimidin-2-yl]amino}phenyl)-1,3-thiazol-2-yl]cyclohexanecarboxamide;
cis-N-(2-cyanoethyl)-4-hydroxy-N-methyl-4-[5-(3-methyl-5-{[4-(trifluoromethyl)pyrimidin-2-yl]amino}phenyl)-1,3-thiazol-2-yl]cyclohexanecarboxamide;
cis-1-[5-(3-methyl-5-{[4-(trifluoromethyl)pyrimidin-2-yl]amino}phenyl)-1,3-thiazol-2-yl]-4-(morpholin-4-ylcarbonyl)cyclohexanol;
cis-N-(3-amino-3-oxopropyl)-4-hydroxy-4-[5-(3-methyl-5-{[4-(trifluoromethyl)pyrimidin-2-yl]amino}phenyl)-1,3-thiazol-2-yl]cyclohexanecarboxamide;
4-hydroxy-N-(3-methoxypropyl)-4-[5-(3-methyl-5-{[4-(trifluoromethyl)pyrimidin-2-yl]amino}phenyl)-1,3-thiazol-2-yl]cyclohexanecarboxamide;
N-(2,3-dihydroxypropyl)-4-hydroxy-4-[5-(3-methyl-5-{[4-(trifluoromethyl)pyrimidin-2-yl]amino}phenyl)-1,3-thiazol-2-yl]cyclohexanecarboxamide;

4-hydroxy-N-[2-hydroxy-1-(hydroxymethyl)ethyl]-4-[5-(3-methyl-5-{[4-(trifluoromethyl)pyrimidin-2-yl]amino}phenyl)-1,3-thiazol-2-yl]cyclohexanecarboxamide;

4-hydroxy-4-[5-(3-methyl-5-{[4-(trifluoromethyl)pyrimidin-2-yl]amino}phenyl)-1,3-thiazol-2-yl]-N-pyridin-4-ylcyclohexanecarboxamide;

4-hydroxy-4-[5-(3-methyl-5-{[4-(trifluoromethyl)pyrimidin-2-yl]amino}phenyl)-1,3-thiazol-2-yl]-N-pyridin-2-ylcyclohexanecarboxamide;

4-hydroxy-4-[5-(3-methyl-5-{[4-(trifluoromethyl)pyrimidin-2-yl]amino}phenyl)-1,3-thiazol-2-yl]-N-pyridin-3-ylcyclohexanecarboxamide;

1-({cis-4-hydroxy-4-[5-(3-methyl-5-{[4-(trifluoromethyl)pyrimidin-2-yl]amino}phenyl)-1,3-thiazol-2-yl]cyclohexyl}carbonyl)pyrrolidine-3-carbonitrile;

cis-4-hydroxy-N-(1H-imidazol-2-ylmethyl)-4-[5-(3-methyl-5-{[4-(trifluoromethyl)pyrimidin-2-yl]amino}phenyl)-1,3-thiazol-2-yl]cyclohexanecarboxamide;

cis-4-hydroxy-4-[5-(3-methyl-5-{[4-(trifluoromethyl)pyrimidin-2-yl]amino}phenyl)-1,3-thiazol-2-yl]-N-(1H-pyrazol-5-ylmethyl)cyclohexanecarboxamide;

cis-N-(2-cyanoethyl)-N-ethyl-4-hydroxy-4-[5-(3-methyl-5-{[4-(trifluoromethyl)pyrimidin-2-yl]amino}phenyl)-1,3-thiazol-2-yl]cyclohexanecarboxamide;

cis-4-hydroxy-N-(isoxazol-4-ylmethyl)-4-[5-(3-methyl-5-{[4-(trifluoromethyl)pyrimidin-2-yl]amino}phenyl)-1,3-thiazol-2-yl]cyclohexanecarboxamide;

cis-4-hydroxy-4-[5-(3-methyl-5-{[4-(trifluoromethyl)pyrimidin-2-yl]amino}phenyl)-1,3-thiazol-2-yl]-N-(1,3-oxazol-4-ylmethyl)cyclohexanecarboxamide;

cis-4-hydroxy-N-(isoxazol-5-ylmethyl)-4-[5-(3-methyl-5-{[4-(trifluoromethyl)pyrimidin-2-yl]amino}phenyl)-1,3-thiazol-2-yl]cyclohexanecarboxamide;

N-cyclohexyl-4-hydroxy-4-[5-(3-methyl-5-{[4-(trifluoromethyl)pyrimidin-2-yl]amino 1-phenyl)-1,3-thiazol-2-yl]cyclohexanecarboxamide;

cis-4-hydroxy-4-[5-(3-methyl-5-[4-(trifluoromethyl)pyrimidin-2-yl]amino}phenyl)-1,3-thiazol-2-yl]-N-(1,2,4-oxadiazol-3-ylmethyl)cyclohexanecarboxamide;

4-[(4-methylpiperazin-1-yl)carbonyl]-1-[5-(3-methyl-5-{[4-(trifluoromethyl)pyrimidin-2-yl]amino}phenyl)-1,3-thiazol-2-yl]cyclohexanol;

1-({4-hydroxy-4-[5-(3-methyl-5-{[4-(trifluoromethyl)pyrimidin-2-yl]amino}phenyl)-1,3-thiazol-2-yl]cyclohexyl}carbonyl)piperidin-4-ol;

cis-4-hydroxy-N-methyl-4-[5-(3-methyl-5-{[4-(trifluoromethyl)pyrimidin-2-yl]amino}phenyl)-1,3-thiazol-2-yl]-N-(tetrahydrofuran-3-yl)cyclohexanecarboxamide;

cis-N-[2-(acetylamino)ethyl]-4-hydroxy-4-[5-(3-methyl-5-{[4-(trifluoromethyl)pyrimidin-2-yl]amino}phenyl)-1,3-thiazol-2-yl]cyclohexanecarboxamide;

4-hydroxy-N,N-bis(2-hydroxyethyl)-4-[5-(3-methyl-5-[4-(trifluoromethyl)pyrimidin-2-yl]amino)phenyl)-1,3-thiazol-2-yl]cyclohexanecarboxamide;

N-benzyl-4-hydroxy-4-[5-(3-methyl-5-{[4-(trifluoromethyl)pyrimidin-2-yl]amino}phenyl)-1,3-thiazol-2-yl]cyclohexanecarboxamide;

4-hydroxy-4-[5-(3-methyl-5-{[4-(trifluoromethyl)pyrimidin-2-yl]amino}phenyl)-1,3-thiazol-2-yl]-N-(pyridin-3-ylmethyl)cyclohexanecarboxamide;

4-hydroxy-4-[5-(3-methyl-5-{[4-(trifluoromethyl)pyrimidin-2-yl]amino}phenyl)-1,3-thiazol-2-yl]-N-(pyridin-4-ylmethyl)cyclohexanecarboxamide;

4-hydroxy-4-[5-(3-methyl-5-{[4-(trifluoromethyl)pyrimidin-2-yl]amino}phenyl)-1,3-thiazol-2-yl]-N-(pyridin-2-ylmethyl)cyclohexanecarboxamide;

4-hydroxy-N-(4-hydroxyphenyl)-4-[5-(3-methyl-5-{[4-(trifluoromethyl)pyrimidin-2-yl]amino}phenyl)-1,3-thiazol-2-yl]cyclohexanecarboxamide;

cis-4-hydroxy-N-(2-hydroxyphenyl)-4-[5-(3-methyl-5-{[4-(trifluoromethyl)pyrimidin-2-yl]amino}phenyl)-1,3-thiazol-2-yl]cyclohexanecarboxamide;

cis-4-hydroxy-4-[5-(3-methyl-5-{[4-(trifluoromethyl)pyrimidin-2-yl]amino}phenyl)-1,3-thiazol-2-yl]-N-(pyrimidin-5-ylmethyl)cyclohexanecarboxamide;

cis-4-hydroxy-4-[5-(3-methyl-5-{[4-(trifluoromethyl)pyrimidin-2-yl]amino}phenyl)-1,3-thiazol-2-yl]-N-(pyridazin-3-ylmethyl)cyclohexanecarboxamide;

1-({cis-4-hydroxy-4-[5-(3-methyl-5-{[4-(trifluoromethyl)pyrimidin-2-yl]amino}phenyl)-1,3-thiazol-2-yl]cyclohexyl}carbonyl)piperidine-4-carbonitrile;

1-({cis-4-hydroxy-4-[5-(3-methyl-5-{[4-(trifluoromethyl)pyrimidin-2-yl]amino}phenyl)-1,3-thiazol-2-yl]cyclohexyl}carbonyl)piperidine-3-carbonitrile;

cis-4-hydroxy-N-(6-hydroxypyridin-3-yl)-4-[5-(3-methyl-5-{[4-(trifluoromethyl)pyrimidin-2-yl]amino}phenyl)-1,3-thiazol-2-yl]cyclohexanecarboxamide;

cis-N-(4-fluorophenyl)-4-hydroxy-4-[5-(3-methyl-5-{[4-(trifluoromethyl)pyrimidin-2-yl]amino}phenyl)-1,3-thiazol-2-yl]cyclohexanecarboxamide;

4-hydroxy-4-[5-(3-methyl-5-{[4-(trifluoromethyl)pyrimidin-2-yl]amino}phenyl)-1,3-thiazol-2-yl]-N-(thiophen-2-ylmethyl)cyclohexanecarboxamide;

4-hydroxy-4-[5-(3-methyl-5-{[4-(trifluoromethyl)pyrimidin-2-yl]amino}phenyl)-1,3-thiazol-2-yl]-N-(2-pyrrolidin-1-ylethyl)cyclohexanecarboxamide;

cis-4-hydroxy-N-[(3-hydroxyisoxazol-5-yl)methyl]-4-[5-(3-methyl-5-{[4-(trifluoromethyl)pyrimidin-2-yl]amino}phenyl)-1,3-thiazol-2-yl]cyclohexanecarboxamide;

cis-4-hydroxy-N-(isothiazol-5-ylmethyl)-4-[5-(3-methyl-5-{[4-(trifluoromethyl)pyrimidin-2-yl]amino}phenyl)-1,3-thiazol-2-yl]cyclohexanecarboxamide;

cis-4-hydroxy-4-[5-(3-methyl-5-{[4-(trifluoromethyl)pyrimidin-2-yl]amino}phenyl)-1,3-thiazol-2-yl]-N-(1,3,4-thiadiazol-2-ylmethyl)cyclohexanecarboxamide;

cis-N-{2-[acetyl(methyl)amino]ethyl}-4-hydroxy-4-[5-(3-methyl-5-{[4-(trifluoromethyl)pyrimidin-2-yl]amino}phenyl)-1,3-thiazol-2-yl]cyclohexanecarboxamide;

N-benzyl-4-hydroxy-N-methyl-4-[5-(3-methyl-5-{[4-(trifluoromethyl)pyrimidin-2-yl]amino}phenyl)-1,3-thiazol-2-yl]cyclohexanecarboxamide;

4-hydroxy-4-[5-(3-methyl-5-{[4-(trifluoromethyl)pyrimidin-2-yl]amino}phenyl)-1,3-thiazol-2-yl]-N-(2-phenylethyl)cyclohexanecarboxamide;

cis-4-hydroxy-N-(3-hydroxybenzyl)-4-[5-(3-methyl-5-{[4-(trifluoromethyl)pyrimidin-2-yl]amino}phenyl)-1,3-thiazol-2-yl]cyclohexanecarboxamide;

cis-4-hydroxy-N-[4-(hydroxymethyl)phenyl]-4-[5-(3-methyl-5-{[4-(trifluoromethyl)pyrimidin-2-yl]amino}phenyl)-1,3-thiazol-2-yl]cyclohexanecarboxamide;

cis-4-hydroxy-N-[3-(hydroxymethyl)phenyl]-4-[5-(3-methyl-5-{[4-(trifluoromethyl)pyrimidin-2-yl]amino}phenyl)-1,3-thiazol-2-yl]cyclohexanecarboxamide;

cis-4-hydroxy-N-(2-hydroxybenzyl)-4-[5-(3-methyl-5-{[4-(trifluoromethyl)pyrimidin-2-yl]amino}phenyl)-1,3-thiazol-2-yl]cyclohexanecarboxamide;

4-hydroxy-N-(4-hydroxybenzyl)-4-[5-(3-methyl-5-{[4-(trifluoromethyl)pyrimidin-2-yl]amino}phenyl)-1,3-thiazol-2-yl]cyclohexanecarboxamide;

cis-N-(2,4-dihydroxyphenyl)-4-hydroxy-4-[5-(3-methyl-5-{[4-(trifluoromethyl)pyrimidin-2-yl]amino}phenyl)-1,3-thiazol-2-yl]cyclohexanecarboxamide;

cis-N-(4-fluorobenzyl)-4-hydroxy-4-[5-(3-methyl-5-{[4-(trifluoromethyl)pyrimidin-2-]amino}phenyl)-1,3-thiazol-2-yl]cyclohexanecarboxamide;

cis-4-hydroxy-4-[5-(3-methyl-5-{[4-(trifluoromethyl)pyrimidin-2-yl]amino}phenyl)-1,3-thiazol-2-yl]-N-[2-(2-oxopyrrolidin-1-yl)ethyl]cyclohexanecarboxamide;

cis-4-hydroxy-4-[5-(3-methyl-5-{[4-(trifluoromethyl)pyrimidin-2-yl]amino}phenyl)-1,3-thiazol-2-yl]-N-[2-(2-oxoimidazolidin-1-yl)ethyl]cyclohexanecarboxamide;

4-hydroxy-4-[5-(3-methyl-5-{[4-(trifluoromethyl)pyrimidin-2-yl]amino}phenyl)-1,3-thiazol-2-yl]-N-(2-morpholin-4-ylethyl)cyclohexanecarboxamide;

cis-N-[4-(acetylamino)butyl]-4-hydroxy-4-[5-(3-methyl-5-{[4-(trifluoromethyl)pyrimidin-2-yl]amino}phenyl)-1,3-thiazol-2-yl]cyclohexanecarboxamide;

cis-4-hydroxy-N-1H-indol-5-yl-4-[5-(3-methyl-5-{[4-(trifluoromethyl)pyrimidin-2-yl]amino}phenyl)-1,3-thiazol-2-yl]cyclohexanecarboxamide;

4-hydroxy-4-[5-(3-methyl-5-{[4-(trifluoromethyl)pyrimidin-2-yl]amino}phenyl)-1,3-thiazol-2-yl]-N-(3-phenylpropyl)cyclohexanecarboxamide;

4-hydroxy-4-[5-(3-methyl-5-{[4-(trifluoromethyl)pyrimidin-2-yl]amino}phenyl)-1,3-thiazol-2-yl]-N-(2-phenoxyethyl)cyclohexanecarboxamide;

cis-4-hydroxy-N-[4-(hydroxymethyl)benzyl]-4-[5-(3-methyl-5-{[4-(trifluoromethyl)pyrimidin-2-yl]amino}phenyl)-1,3-thiazol-2-yl]cyclohexanecarboxamide;

cis-N-(3,4-dihydroxybenzyl)-4-hydroxy-4-[5-(3-methyl-5-{[4-(trifluoromethyl)pyrimidin-2-yl]amino}phenyl)-1,3-thiazol-2-yl]cyclohexanecarboxamide;

cis-N-(4-chlorobenzyl)-4-hydroxy-4-[5-(3-methyl-5-{[4-(trifluoromethyl)pyrimidin-2-yl]amino}phenyl)-1,3-thiazol-2-yl]cyclohexanecarboxamide;

4-hydroxy-4-[5-(3-methyl-5-[4-(trifluoromethyl)pyrimidin-2-yl)amino]phenyl)-1,3-thiazol-2-yl]-N-[3-(2-oxopyrrolidin-1-yl)propyl]cyclohexanecarboxamide;

cis-4-hydroxy-4-[5-(3-methyl-5-{[4-(trifluoromethyl)pyrimidin-2-yl]amino}phenyl)-1,3-thiazol-2-yl]-N-[2-(2-oxopiperidin-1-yl)ethyl]cyclohexanecarboxamide;

cis-N-(4-carbamoylcyclohexyl)-4-hydroxy-4-[5-(3-methyl-5-{[4-(trifluoromethyl)pyrimidin-2-yl]amino}phenyl)-1,3-thiazol-2-yl]cyclohexanecarboxamide;

4-[({4-hydroxy-4-[5-(3-methyl-5-{[4-(trifluoromethyl)pyrimidin-2-yl]amino}phenyl)-1,3-thiazol-2-yl]cyclohexyl}carbonyl)amino]cyclohexanecarboxylic acid;

methyl 4-({cis-4-hydroxy-4-[5-(3-methyl-5-{[4-(trifluoromethyl)pyrimidin-2-yl]amino}phenyl)-1,3-thiazol-2-yl]cyclohexyl}carbonyl)piperazine-1-carboxylate;

4-hydroxy-4-[5-(3-methyl-5-{[4-(trifluoromethyl)pyrimidin-2-yl]amino}phenyl)-1,3-thiazol-2-yl]-N-(1,2,3,4-tetrahydronaphthalen-1-yl)cyclohexanecarboxamide;

cis-4-hydroxy-N-(imidazo[1,2-a]pyridin-2-ylmethyl)-4-[5-(3-methyl-5-{[4-(trifluoromethyl)pyrimidin-2-yl]amino}phenyl)-1,3-thiazol-2-yl]cyclohexanecarboxamide;

4-hydroxy-N-(2-hydroxy-2,3-dihydro-1H-inden-1-yl)-4-[5-(3-methyl-5-{[4-(trifluoromethyl)pyrimidin-2-yl]amino}phenyl)-1,3-thiazol-2-yl]cyclohexanecarboxamide;

cis-4-hydroxy-4-[5-(3-methyl-5-{[4-(trifluoromethyl)pyrimidin-2-yl]amino}phenyl)-1,3-thiazol-2-yl]-N-[(3-oxo-2,3-dihydro-1H-isoindol-4-yl)methyl]cyclohexanecarboxamide;

cis-4-hydroxy-4-[5-(3-methyl-5-{[4-(trifluoromethyl)pyrimidin-2-yl]amino}phenyl)-1,3-thiazol-2-yl]-N-[(3-oxo-2,3-dihydro-1H-isoindol-5-yl)methyl]cyclohexanecarboxamide;

cis-4-hydroxy-4-[5-(3-methyl-5-{[4-(trifluoromethyl)pyrimidin-2-yl]amino}phenyl)-1,3-thiazol-2-yl]-N-[(1-oxo-2,3-dihydro-1H-isoindol-4-yl)methyl]cyclohexanecarboxamide;

cis-4-hydroxy-4-[5-(3-methyl-5-{[4-(trifluoromethyl)pyrimidin-2-yl]amino}phenyl)-1,3-thiazol-2-yl]-N-[(1-oxo-2,3-dihydro-1H-isoindol-5-yl)methyl]cyclohexanecarboxamide;

4-hydroxy-4-[5-(3-methyl-5-{[4-(trifluoromethyl)pyrimidin-2-yl]amino}phenyl)-1,3-thiazol-2-yl]-N-[4-(trifluoromethyl)benzyl]cyclohexanecarboxamide;

cis-4-hydroxy-4-[5-(3-methyl-5-{[4-(trifluoromethyl)pyrimidin-2-yl]amino}phenyl)-1,3-thiazol-2-yl]-N-[(3-pyridin-2-ylisoxazol-5-yl)methyl]cyclohexanecarboxamide;

4-[(4-benzylpiperidin-1-yl)carbonyl]-1-[5-(3-methyl-5-{[4-(trifluoromethyl)pyrimidin-2-yl]amino}phenyl)-1,3-thiazol-2-yl]cyclohexanol;

cis-4-hydroxy-4-[5-(3-methyl-5-{[4-(trifluoromethyl)pyrimidin-2-yl]amino}phenyl)-1,3-thiazol-2-yl]-N-[(2-oxo-1,2,3,4-tetrahydroquinolin-7-yl)methyl]cyclohexanecarboxamide;

cis-4-hydroxy-4-[5-(3-methyl-5-{[4-(trifluoromethyl)pyrimidin-2-yl]amino}phenyl)-1,3-thiazol-2-yl]-N-(4-sulfamoylbenzyl)cyclohexanecarboxamide;

cis-4-hydroxy-N-{4-[4-(hydroxymethyl)-1H-pyrazol-1-yl]benzyl}-4-[5-(3-methyl-5-{[4-(trifluoromethyl)pyrimidin-2-yl]amino}phenyl)-1,3-thiazol-2-yl]cyclohexanecarboxamide;

cis-4-hydroxy-4-[5-(3-methyl-5-{[4-(trifluoromethyl)pyrimidin-2-yl]amino}phenyl)-1,3-thiazol-2-yl]-N-(4-{[(4R)-2-oxo-1,3-oxazolidin-4-yl]methyl}benzyl)cyclohexanecarboxamide;

cis-4-hydroxy-4-[5-(3-methyl-5-{[4-(trifluoromethyl)pyrimidin-2-yl]amino}phenyl)-1,3-thiazol-2-yl]-N-{[6-(2,2,2-trifluoroethoxy)pyridin-3-yl]methyl}cyclohexanecarboxamide;

N-(cyanomethyl)-4-hydroxy-2-methyl-4-(5-{3-methyl-5-[(4-methylpyrimidin-2-yl)amino]phenyl}-1,3-thiazol-2-yl)cyclohexanecarboxamide;

4-(5-{3-[(4-tert-butylpyrimidin-2-yl)amino]-5-methylphenyl}-1,3-thiazol-2-yl)-4-hydroxy-2-methylcyclohexanecarboxamide;

4-hydroxy-2-methyl-4-[5-(3-methyl-5-{[4-(1-methylethoxy)pyrimidin-2-yl]amino}phenyl)-1,3-thiazol-2-yl]cyclohexanecarboxamide;

4-hydroxy-2-methyl-4-[5-(3-methyl-5-{[4-(trifluoromethyl)pyrimidin-2-yl]amino}phenyl)-1,3-thiazol-2-yl]cyclohexanecarboxamide;

N-(cyanomethyl)-4-hydroxy-2-methyl-4-[5-(3-methyl-5-{[4-(1-methylethyl)pyrimidin-2-yl]amino}phenyl)-1,3-thiazol-2-yl]cyclohexanecarboxamide;

4-hydroxy-2-methyl-4-(5-{3-methyl-5-[(4-methylpyrimidin-2-yl)amino]phenyl}-1,3-thiazol-2-yl)-N-(pyridin-3-ylmethyl)cyclohexanecarboxamide;

4-hydroxy-2-methyl-4-[5-(3-methyl-5-{[4-(1-methylethyl)pyrimidin-2-yl]amino}phenyl)-1,3-thiazol-2-yl]-N-(pyridin-3-ylmethyl)cyclohexanecarboxamide;

4-hydroxy-2-methyl-4-(5-{3-methyl-5-[(4-methylpyrimidin-2-yl)amino]phenyl}-1,3-thiazol-2-yl)-N-[3-(2-oxopyrrolidin-1-yl)propyl]cyclohexanecarboxamide;

(1S,4R)-4-hydroxy-4-(5-{3-[(4-methoxypyrimidin-2-yl)amino]-5-methylphenyl}-1,3-thiazol-2-yl)-2,2-dimethylcyclohexanecarboxamide;

(1S,4R)-4-(5-{3-[(4-cyclopropylpyrimidin-2-yl)amino]-5-methylphenyl}-1,3-thiazol-2-yl)-4-hydroxy-2,2-dimethylcyclohexanecarboxamide;

(1S,4R)-4-hydroxy-2,2-dimethyl-4-[5-(3-methyl-5-{[4-(1-methyl ethyl)pyrimidin-2-yl]amino}phenyl)-1,3-thiazol-2-yl]cyclohexanecarboxamide;

(1S,4R)-4-hydroxy-4-{5-[3-({4-[(1S)-1-hydroxyethyl]pyrimidin-2-yl}amino)-5-methylphenyl]-1,3-thiazol-2-yl}-2,2-dimethylcyclohexanecarboxamide;

(1S,4R)-4-hydroxy-4-{5-[3-({4-[(1R)-1-hydroxyethyl]pyrimidin-2-yl}amino)-5-methylphenyl]-1,3-thiazol-2-yl}-2,2-dimethylcyclohexanecarboxamide;

(1S,4R)-4-{5-[3-({4-[(1S)-1-fluoroethyl]pyrimidin-2-yl}amino)-5-methylphenyl]-1,3-thiazol-2-yl}-4-hydroxy-2,2-dimethylcyclohexanecarboxamide;

(1S,4R)-4-{5-[3-({4-[(1R)-1-fluoroethyl]pyrimidin-2-yl}amino)-5-methylphenyl]-1,3-thiazol-2-yl}-4-hydroxy-2,2-dimethylcyclohexanecarboxamide;

N-(cyanomethyl)-4-hydroxy-2,2-dimethyl-4-(5-{3-methyl-5-[(4-methylpyrimidin-2-yl)amino]phenyl}-1,3-thiazol-2-yl)cyclohexanecarboxamide;

(1S,4R)-4-(5-{3-[(4-tert-butylpyrimidin-2-yl)amino]-5-methylphenyl}-1,3-thiazol-2-yl)-4-hydroxy-2,2-dimethylcyclohexanecarboxamide;

(1S,4R)-4-hydroxy-2,2-dimethyl-4-[5-(3-methyl-5-{[4-(1-methylethoxy)pyrimidin-2-yl]amino}phenyl)-1,3-thiazol-2-yl]cyclohexanecarboxamide;

(1S,4R)-4-hydroxy-4-[5-(3-{[4-(1-hydroxy-1-methylethyl)pyrimidin-2-yl]amino}-5-methylphenyl)-1,3-thiazol-2-yl]-2,2-dimethylcyclohexanecarboxamide;

4-hydroxy-4-[5-(3-{[4-(2-hydroxyethoxy)pyrimidin-2-yl]amino}-5-methylphenyl)-1,3-thiazol-2-yl]-2,2-dimethylcyclohexanecarboxamide;

(1S,4R)-4-hydroxy-4-[5-(3-{[4-(2-hydroxyethoxy)pyrimidin-2-yl]amino}-5-methylphenyl)-1,3-thiazol-2-yl]-2,2-dimethylcyclohexanecarboxamide;

(1R,4S)-4-hydroxy-4-[5-(3-{[4-(2-hydroxyethoxy)pyrimidin-2-yl]amino}-5-methylphenyl)-1,3-thiazol-2-yl]-2,2-dimethylcyclohexanecarboxamide;

(1R,4S)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxamide;

(1S,4R)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxamide;

(1S,4R)—N-(cyanomethyl)-4-hydroxy-4-(5-{3-[(4-methoxypyrimidin-2-yl)amino]-5-methylphenyl}-1,3-thiazol-2-yl)-2,2-dimethylcyclohexanecarboxamide;

(1S,4R)-4-hydroxy-4-(5-{3-[(4-methoxypyrimidin-2-yl)amino]-5-methylphenyl}-1,3-thiazol-2-yl)-2,2-dimethyl-N-(pyridin-3-ylmethyl)cyclohexanecarboxamide;

(1S,4R)-4-hydroxy-2,2-dimethyl-4-(5-{3-methyl-5-[(4-methylpyrimidin-2-yl)amino]phenyl}-1,3-thiazol-2-yl)-N-[3-(2-oxopyrrolidin-1-yl)propyl]cyclohexanecarboxamide;

(1S,4R)-4-hydroxy-2,2-dimethyl-4-[5-(3-methyl-5-{[4-(trifluoromethyl)pyrimidin-2-yl]amino}phenyl)-1,3-thiazol-2-yl]-N-pyridin-3-ylcyclohexanecarboxamide;

(1S,4R)-4-hydroxy-4-(5-{3-[(4-methoxypyrimidin-2-yl)amino]-5-methylphenyl}-1,3-thiazol-2-yl)-2,2-dimethyl-N-[3-(2-oxopyrrolidin-1-yl)propyl]cyclohexanecarboxamide;

(1S,4R)-4-hydroxy-2,2-dimethyl-4-[5-(3-methyl-5-{[4-(trifluoromethyl)pyrimidin-2-yl]amino}phenyl)-1,3-thiazol-2-yl]-N-[3-(2-oxopyrrolidin-1-yl)propyl]cyclohexanecarboxamide;

(1S,4R)-4-hydroxy-4-{5-[3-(hydroxymethyl)-5-{[4-(trifluoromethyl)pyrimidin-2-yl]amino}phenyl]-1,3-thiazol-2-yl}-2,2-dimethylcyclohexanecarboxamide;

4-hydroxy-4-{5-[3-(methoxymethyl)-5-{[4-(trifluoromethyl)pyrimidin-2-yl]amino}phenyl]-1,3-thiazol-2-yl}-2-methylcyclohexanecarboxamide;

(1S,4R)-4-hydroxy-4-{5-[3-(methoxymethyl)-5-{[4-(trifluoromethyl)pyrimidin-2-yl]amino}phenyl]-1,3-thiazol-2-yl}-2,2-dimethylcyclohexanecarboxamide;

(1S,4R)-4-[5-(3-chloro-5-{[4-(trifluoromethyl)pyrimidin-2-yl]amino}phenyl)-1,3-thiazol-2-yl]-4-hydroxy-2,2-dimethylcyclohexanecarboxamide;

cis-4-[4-(3-chloro-5-{[4-(trifluoromethyl)pyrimidin-2-yl]amino}phenyl)-1,3-thiazol-2-yl]-4-hydroxycyclohexanecarboxamide;

4-[5-(3-[(acetylamino)methyl]-5-{[4-(trifluoromethyl)pyrimidin-2-yl]amino}phenyl)-1,3-thiazol-2-yl]-4-hydroxy-2,2-dimethylcyclohexanecarboxamide;

2-({cis-4-hydroxy-4-[5-(3-methyl-5-{[4-(trifluoromethyl)pyrimidin-2-yl]amino}phenyl)-1,3-thiazol-2-yl]cyclohexyl}carbonyl)-1,2,3,4-tetrahydroisoquinoline-6,7-diol;

4-{[4-(3-methoxyphenyl)piperazin-1-yl]carbonyl}-1-[5-(3-methyl-5-{[4-(trifluoromethyl)pyrimidin-2-yl]amino}phenyl)-1,3-thiazol-2-yl]cyclohexanol;

cis-4-(1,4-dioxa-8-azaspiro[4.5]dec-8-ylcarbonyl)-1-[5-(3-methyl-5-{[4-(trifluoromethyl)pyrimidin-2-yl]amino}phenyl)-1,3-thiazol-2-yl]cyclohexanol;

3-hydroxy-3-[4-(3-methyl-5-{[4-(trifluoromethyl)pyrimidin-2-yl]amino}phenyl)-1,3-thiazol-2-yl]cyclobutanecarboxamide;

4-hydroxy-4-(5-{3-methyl-5-[(4-methylpyrimidin-2-yl)amino]phenyl}-1,3-thiazol-2-yl)decahydronaphthalene-1-carboxamide;

trans-4-hydroxy-1-methyl-4-[5-(3-methyl-5-{[4-(trifluoromethyl)pyrimidin-2-yl]amino}phenyl)-1,3-thiazol-2-yl]cyclohexanecarboxamide;

4-[5-(3-methyl-5-{[4-(trifluoromethyl)pyrimidin-2-yl]amino}phenyl)-1,3-thiazol-2-yl]cyclohexanecarboxamide;

4-[5-(3-methyl-5-{[4-(trifluoromethyl)pyrimidin-2-yl]amino}phenyl)-1,3-thiazol-2-yl]cyclohexanecarboxamide;

2-{4-hydroxy-4-[5-(3-methyl-5-{[4-(trifluoromethyl)pyrimidin-2-yl]amino}phenyl)-1,3-thiazol-2-yl]piperidin-1-yl}pyridine-3-carboxamide;

4-{4-hydroxy-4-[5-(3-methyl-5-{[4-(trifluoromethyl)pyrimidin-2-yl]amino}phenyl)-1,3-thiazol-2-yl]piperidin-1-yl}butanamide;

2-{4-hydroxy-4-[4-(3-methyl-5-{[4-(trifluoromethyl)pyrimidin-2-yl]amino}phenyl)-1,3-thiazol-2-yl]cyclohexyl}acetamide;

2-{cis-4-hydroxy-4-[4-(3-methyl-5-{[4-(trifluoromethyl)pyrimidin-2-yl]amino}phenyl)-1,3-thiazol-2-yl]cyclohexyl}acetamide;

2-{trans-4-hydroxy-4-[4-(3-methyl-5-{[4-(trifluoromethyl)pyrimidin-2-yl]amino}phenyl)-1,3-thiazol-2-yl]cyclohexyl}acetamide;

3-{(4-hydroxy-4-[5-(3-methyl-5-{[4-(trifluoromethyl)pyrimidin-2-yl]amino}phenyl)-1,3-thiazol-2-yl]cyclohexyl}propanamide;
3-{(4-hydroxy-4-[5-(3-methyl-5-{[4-(trifluoromethyl)pyrimidin-2-yl]amino}phenyl)-1,3-thiazol-2-yl]cyclohexyl}propanamide;
3-{4-hydroxy-4-[5-(3-methyl-5-{[4-(1-methylethyl)pyrimidin-2-yl]amino}phenyl)-1,3-thiazol-2-yl]azepan-1-yl}-3-oxopropanamide;
3-[5-(3-{[4-(2-hydroxyethoxy)pyrimidin-2-yl]amino}-5-methylphenyl)-1,3-thiazol-2-yl]propanamide;
N-[1-(hydroxymethyl)propyl]-3-[5-(3-methyl-5-{[4-(trifluoromethyl)pyrimidin-2-yl]amino}phenyl)-1,3-thiazol-2-yl]propanamide;
ethyl N-{3-[5-(3-methyl-5-{[4-(trifluoromethyl)pyrimidin-2-yl]amino}phenyl)-1,3-thiazol-2-yl]propanoyl}glycinate;
methyl N-{3-[5-(3-methyl-5-{[4-(trifluoromethyl)pyrimidin-2-yl]amino}phenyl)-1,3-thiazol-2-yl]propanoyl}alaninate;
methyl N-{3-[5-(3-methyl-5-{[4-(trifluoromethyl)pyrimidin-2-yl]amino}phenyl)-1,3-thiazol-2-yl]propanoyl}-beta-alaninate;
methyl N-{3-[5-(3-methyl-5-{[4-(trifluoromethyl)pyrimidin-2-yl]amino}phenyl)-1,3-thiazol-2-yl]propanoyl}leucinate;
4-{(1S)-1-hydroxy-1-[5-(3-methyl-5-{[4-(trifluoromethyl)pyrimidin-2-yl]amino}phenyl)-1,3-thiazol-2-yl]ethyl}benzamide;
4-{(1R)-1-hydroxy-1-[5-(3-methyl-5-{[4-(trifluoromethyl)pyrimidin-2-yl]amino}phenyl)-1,3-thiazol-2-yl]ethyl}benzamide;
(1S,4R)-4-[5-(2-bromo-3-methyl-5-{[4-(trifluoromethyl)pyrimidin-2-yl]amino}phenyl)-1,3-thiazol-2-yl]-4-hydroxy-2,2-dimethylcyclohexanecarboxamide;
Ethyl(1R,4S)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylate;
Methyl(1R,4S)-4-hydroxy-2,2-dimethyl-4-[5-(3-methyl-5-{[4-(trifluoromethyl)pyrimidin-2-yl]-amino}phenyl)-1,3-thiazol-2-yl]cyclohexanecarboxylate;
tert-butyl 4-hydroxy-4-[5-(3-[4-(3-methoxypropyl)pyrimidin-2-yl]amino)-5-methylphenyl)-1,3-thiazol-2-yl]cyclohexanecarboxylate;
(1S,4R)-4-{5-[3-(aminomethyl)-5-{[4-(trifluoromethyl)pyrimidin-2-yl]amino}phenyl]-1,3-thiazol-2-yl}-4-hydroxy-2,2-dimethylcyclohexanecarboxylic acid;
(1S,4R)-4-[5-(3-[(carbamoylamino)methyl]-5-{[4-(trifluoromethyl)pyrimidin-2-yl]amino}phenyl)-1,3-thiazol-2-yl]-4-hydroxy-2,2-dimethylcyclohexanecarboxylic acid;
(1S,4R)-4-[5-(3-[(acetylamino)methyl]-5-{[4-(trifluoromethyl)pyrimidin-2-yl]amino}phenyl)-1,3-thiazol-2-yl]-4-hydroxy-2,2-dimethylcyclohexanecarboxylic acid;
5-(aminomethyl)-5-[5-(3-methyl-5-{[4-(trifluoromethyl)pyrimidin-2-yl]amino}phenyl)-1,3-thiazol-2-yl]azepan-2-one;
5-(2-hydroxyethoxy)-5-[5-(3-methyl-5-[4-(trifluoromethyl)pyrimidin-2-yl]amino)phenyl)-1,3-thiazol-2-yl]azepan-2-one;
1-[5-(3-methyl-5-{[4-(trifluoromethyl)pyrimidin-2-yl]amino}phenyl)-1,3-thiazol-2-yl]cyclohexanecarbonitrile;
1-[5-(3-methyl-5-{[4-(trifluoromethyl)pyrimidin-2-yl]amino}phenyl)-1,3-thiazol-2-yl]cyclohexanecarboxamide;
N-[3-(2-cyclohexyl-1,3-thiazol-5-yl)-5-methylphenyl]-4-(trifluoromethyl)pyrimidin-2-amine;
1-[4-(methylsulfonyl)phenyl]-1-[5-(3-methyl-5-{[4-(trifluoromethyl)pyrimidin-2-yl]amino}phenyl)-1,3-thiazol-2-yl]ethanol;
N-{3-[2-(4-fluorotetrahydro-2H-thiopyran-4-yl)-1,3-thiazol-5-yl]-5-methylphenyl}-4-(trifluoromethyl)pyrimidin-2-amine;
N-{3-[2-(3,6-dihydro-2H-thiopyran-4-yl)-1,3-thiazol-5-yl]-5-methylphenyl}-4-(trifluoromethyl)pyrimidin-2-amine;
N-{3-[2-(4-fluoro-1,1-dioxidotetrahydro-2H-thiopyran-4-yl)-1,3-thiazol-5-yl]-5-methylphenyl}-4-(trifluoromethyl)pyrimidin-2-amine;
N-{3-[2-(1,1-dioxido-3,6-dihydro-2H-thiopyran-4-yl)-1,3-thiazol-5-yl]-5-methylphenyl}-4-(trifluoromethyl)pyrimidin-2-amine;
N-{3-[2-(4-fluorotetrahydro-2H-thiopyran-4-yl)-1,3-thiazol-5-yl]-5-methylphenyl}-4-(trifluoromethyl)pyrimidin-2-amine;
N-{3-[2-(1,1-dioxidotetrahydro-2H-thiopyran-4-yl)-1,3-thiazol-5-yl]-5-methylphenyl}-4-(trifluoromethyl)pyrimidin-2-amine;
(1S,4R)-4-methoxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid;
Cis-5,5-dimethyl-1-[5-(3-methyl-5-{[4-(trifluoromethyl)pyrimidin-2-yl]amino}phenyl)-1,3-thiazol-2-yl]-2-oxabicyclo[2.2.2]octan-3-one;
Trans-1,4-dihydroxy-4-[5-(3-methyl-5-{[4-(trifluoromethyl)pyrimidin-2-yl]amino}phenyl)-1,3-thiazol-2-yl]cyclohexanecarboxylic acid;
cis-1,4-dihydroxy-4-[5-(3-methyl-5-{[4-(trifluoromethyl)pyrimidin-2-yl]amino}phenyl)-1,3-thiazol-2-yl]cyclohexanecarboxylic acid;
1-{Cis-4-hydroxy-4-[5-(3-methyl-5-{[4-(trifluoromethyl)pyrimidin-2-yl]amino}phenyl)-1,3-thiazol-2-yl]cyclohexyl}pyrrolidin-2-one;
4,5-dihydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid;
7-[5-(3-methyl-5-{[4-(trifluoromethyl)pyrimidin-2-yl]amino}phenyl)-1,3-thiazol-2-yl]spiro[2.5]octane-4,7-diol;
9-[5-(3-methyl-5-{[4-(trifluoromethyl)pyrimidin-2-yl]amino}phenyl)-1,3-thiazol-2-yl]dispiro[2.1.2.3]decane-4,9-diol;
3-[5-(3-methyl-5-{[4-(trifluoromethyl)pyrimidin-2-yl]amino}phenyl)-1,3-thiazol-2-yl]azepan-2-one;
(1S)-4-{1,2-dihydroxy-1-[5-(3-methyl-5-{[4-(trifluoromethyl)pyrimidin-2-yl]amino}phenyl)-1,3-thiazol-2-yl]ethyl}benzoic acid;
(1R)-4-{1,2-dihydroxy-1-[5-(3-methyl-5-{[4-(trifluoromethyl)pyrimidin-2-yl]amino}phenyl)-1,3-thiazol-2-yl]ethyl}benzoic acid;
4-{(Cis)-1,2-dihydroxy-2-[5-(3-methyl-5-{[4-(trifluoromethyl)pyrimidin-2-yl]amino}phenyl)-1,3-thiazol-2-yl]ethyl}benzoic acid;
Methyl 4-{(E)-2-[5-(3-methyl-5-{[4-(trifluoromethyl)pyrimidin-2-yl]amino}phenyl)-1,3-thiazol-2-yl]ethenyl}benzoate;
4-{2-[5-(3-methyl-5-{[4-(trifluoromethyl)pyrimidin-2-yl]amino}phenyl)-1,3-thiazol-2-yl]ethyl}benzoic acid;
5-{1-Hydroxy-1-[5-(3-methyl-5-{[4-(trifluoromethyl)pyrimidin-2-yl]amino}phenyl)-1,3-thiazol-2-yl]ethyl}pyridine-2-carboxylic acid;
6-{1-Hydroxy-1-[5-(3-methyl-5-[4-(trifluoromethyl)pyrimidin-2-yl]amino}phenyl)-1,3-thiazol-2-yl]ethyl)pyridine-3-carboxylic acid;

cis-4-fluoro-4-[5-(3-methyl-5-{[4-(trifluoromethyl)pyrimidin-2-yl]amino}phenyl)-1,3-thiazol-2-yl]cyclohexanecarboxylic acid;

trans-4-fluoro-4-[5-(3-methyl-5-{[4-(trifluoromethyl)pyrimidin-2-yl]amino}phenyl)-1,3-thiazol-2-yl]cyclohexanecarboxylic acid;

(1S,4R)-4-Hydroxy-2,2-dimethyl-4-{5-[3-methyl-5-(4-ethyl-pyrimidin-2-ylamino)-phenyl]-1,3-thiazol-2-yl}-cyclohexanecarboxylic acid;

N-(3-{2-[(E)-2-Methoxyethenyl]-1,3-thiazol-5-yl}-5-methylphenyl)-4-(trifluoromethyl)pyrimidin-2-amine;

N-(3-{2-[(Z)-2-Methoxyethenyl]-1,3-thiazol-5-yl}-5-methylphenyl)-4-(trifluoromethyl)pyrimidin-2-amine;

2,2-Dimethyl-4-[5-(3-methyl-5-{[4-(trifluoromethyl)pyrimidin-2-yl]amino}phenyl)-1,3-thiazol-2-yl]cyclohexanecarboxamide;

Diethyl{cis-1,4-dihydroxy-4-[5-(3-methyl-5-{[4-(trifluoromethyl)pyrimidin-2-yl]amino}phenyl)-1,3-thiazol-2-yl]cyclohexyl}phosphonate;

Diethyl{trans-1,4-dihydroxy-4-[5-(3-methyl-5-{[4-(trifluoromethyl)pyrimidin-2-yl]amino}phenyl)-1,3-thiazol-2-yl]cyclohexyl}phosphonate;

(3E)-3-(Hydroxyimino)-2,2-dimethyl-1-[5-(3-methyl-5-{[4-(trifluoromethyl)pyrimidin-2-yl]amino}phenyl)-1,3-thiazol-2-yl]cyclohexanol;

1-{5-[3-({4-[1-(2-hydroxy-2-methylpropyl)-1,1-pyrazol-4-yl]pyrimidin-2-yl}amino)-5-methylphenyl]-1,3-thiazol-2-yl}cyclobutanol;

2-[5-(3-{[4-(2-hydroxyethoxy)pyrimidin-2-yl]amino}-5-methylphenyl)-1,3-thiazol-2-yl]propane-1,2,3-triol;

4-hydroxy-4-[5-(3-{[4-(2-hydroxyethoxy)pyrimidin-2-yl]amino}-5-methylphenyl)-1,3-thiazol-2-yl]-2,2-dimethylcyclohexanecarboxylic acid;

4,5-dihydroxy-5-[5-(3-methyl-5-{[4-(trifluoromethyl)pyrimidin-2-yl]amino}phenyl)-1,3-thiazol-2-yl]azepan-2-one;

5,6-dihydroxy-5-[5-(3-methyl-5-{[4-(trifluoromethyl)pyrimidin-2-yl]amino}phenyl)-1,3-thiazol-2-yl]azepan-2-one;

4,5-dihydroxy-5-[5-(3-methyl-5-{[4-(trifluoromethyl)pyrimidin-2-yl]amino}phenyl)-1,3-thiazol-2-yl]azepan-2-one;

5,6-dihydroxy-5-[5-(3-methyl-5-{[4-(trifluoromethyl)pyrimidin-2-yl]amino}phenyl)-1,3-thiazol-2-yl]azepan-2-one;

5-amino-5-[5-(3-methyl-5-{[4-(trifluoromethyl)pyrimidin-2-yl]amino}phenyl)-1,3-thiazol-2-yl]azepan-2-one;

5-{cis-4-hydroxy-4-[5-(3-methyl-5-{[4-(trifluoromethyl)pyrimidin-2-yl]amino}phenyl)-1,3-thiazol-2-yl]cyclohexyl}-1,3,4-oxadiazol-2(3H)-one;

3-{cis-4-hydroxy-4-[5-(3-methyl-5-{[4-(trifluoromethyl)pyrimidin-2-yl]amino}phenyl)-1,3-thiazol-2-yl]cyclohexyl}-1,2,4-oxadiazol-5(4H)-one;

(1S,4R)-4-hydroxy-2,2-dimethyl-4-[5-(3-methyl-5-{[4-(propan-2-yloxy)pyrimidin-2-yl]amino}phenyl)-1,3-thiazol-2-yl]cyclohexanecarboxamide cis-4-hydroxy-4-[5-(3-methyl-5-{[4-(trifluoromethyl)pyrimidin-2-yl]amino}phenyl)-1,3-thiazol-2-yl]-N-[3-(2-oxopyrrolidin-1-yl)propyl]cyclohexanecarboxamide (1S,4R)-4-hydroxy-2,2-dimethyl-4-[5-(3-methyl-5-{[4-(propan-2-yloxy)pyrimidin-2-yl]amino}phenyl)-1,3-thiazol-2-yl]cyclohexanecarboxamide (1S,4R)-4-(5-{3-cyclopropyl-5-[(4-methylpyrimidin-2-yl)amino]phenyl}-1,3-thiazol-2-yl)-4-hydroxy-2,2-dimethylcyclohexanecarboxylic acid (1S,4R)-4-(5-{3-cyclopropyl-5-[(4-methylpyrimidin-2-yl)amino]phenyl}-1,3-thiazol-2-yl)-4-hydroxy-2,2-dimethylcyclohexanecarboxylic acid (1R,4S)-4-(5-{3-[(5-fluoro-4-methylpyrimidin-2-yl)amino]-5-methylphenyl}-1,3-thiazol-2-yl)-4-hydroxy-2,2-dimethylcyclohexanecarboxylic acid (1S,4R)-4-(5-{3-[(5-fluoro-4-methylpyrimidin-2-yl)amino]-5-methylphenyl}-1,3-thiazol-2-yl)-4-hydroxy-2,2-dimethylcyclohexanecarboxylic acid (1S,4R)-4-[5-(2-bromo-3-methyl-5-{[4-(trifluoromethyl)pyrimidin-2-yl]amino}phenyl)-1,3-thiazol-2-yl]-4-hydroxy-2,2-dimethylcyclohexanecarboxylic acid trans-4-(5-{3-[(4-cyclopropylpyrimidin-2-yl)amino]-5-methylphenyl}-1,3-thiazol-2-yl)-4-hydroxycyclohexanecarboxylic acid cis-4-(5-{3-[(4-cyclopropylpyrimidin-2-yl)amino]-5-methylphenyl}-1,3-thiazol-2-yl)-4-hydroxycyclohexanecarboxylic acid cis-4-[(hydroxyacetyl)amino]-1-[5-(3-methyl-5-{[4-(trifluoromethyl)pyrimidin-2-yl]amino}phenyl)-1,3-thiazol-2-yl]cyclohexanecarboxamide.

Preferred compounds include:

(1R,4S)-4-[5-(3-cyclopropyl-5-{[4-(trifluoromethyl)pyrimidin-2-yl]amino}phenyl)-1,3-thiazol-2-yl]-4-hydroxy-2,2-dimethylcyclohexanecarboxylic acid;

(1S,4R)-4-[5-(3-cyclopropyl-5-{[4-(trifluoromethyl)pyrimidin-2-yl]amino}phenyl)-1,3-thiazol-2-yl]-4-hydroxy-2,2-dimethylcyclohexanecarboxylic acid;

(1S,4R)-4-hydroxy-2,2-dimethyl-4-{5-[3-methyl-5-(4-methyl-pyrimidin-2-ylamino)-phenyl]-1,3-thiazol-2-yl}-cyclohexanecarboxylic acid;

(1S,4R)-4-[5-(3-{[4-(difluoromethyl)pyrimidin-2-yl]amino}-5-methylphenyl)-1,3-thiazol-2-yl]-4-hydroxy-2,2-dimethylcyclohexanecarboxylic acid;

trans-4-hydroxy-4-[5-(3-methyl-5-{[4-(trifluoromethyl)pyrimidin-2-yl]amino}phenyl)-1,3-thiazol-2-yl]cyclohexanecarboxylic acid;

cis-4-hydroxy-4-[5-(3-methyl-5-{[4-(trifluoromethyl)pyrimidin-2-yl]amino}phenyl)-1,3-thiazol-2-yl]cyclohexanecarboxylic acid;

5-hydroxy-5-[5-(3-methyl-5-{[4-(trifluoromethyl)pyrimidin-2-yl]amino}phenyl)-1,3-thiazol-2-yl]azepan-2-one;

cis-4-[(hydroxyacetyl)amino]-1-[5-(3-methyl-5-{[4-(trifluoromethyl)pyrimidin-2-yl]amino}phenyl)-1,3-thiazol-2-yl]cyclohexanecarboxamide; and (1S,4R)-4-hydroxy-2,2-dimethyl-4-[5-(3-methyl-5-{[4-(trifluoromethyl)pyrimidin-2-yl]amino}phenyl)-1,3-thiazol-2-yl]-N-[3-(2-oxopyrrolidin-1-yl)propyl]cyclohexanecarboxamide;

(1S,4R)-4-hydroxy-2,2-dimethyl-4-[5-(3-methyl-5-{[4-(trifluoromethyl)pyrimidin-2-yl]amino}-phenyl)-1,3-thiazol-2-yl]cyclohexanecarboxylic acid;

(1R,4S)-4-hydroxy-2,2-dimethyl-4-[5-(3-methyl-5-{[4-(trifluoromethyl)pyrimidin-2-yl]amino}-phenyl)-1,3-thiazol-2-yl]cyclohexanecarboxylic acid;

(1S,4S)-4-hydroxy-2,2-dimethyl-4-[5-(3-methyl-5-{[4-(trifluoromethyl)pyrimidin-2-yl]amino}-phenyl)-1,3-thiazol-2-yl]cyclohexanecarboxylic acid;

(1R,4R)-4-hydroxy-2,2-dimethyl-4-[5-(3-methyl-5-{[4-(trifluoromethyl)pyrimidin-2-yl]amino}-phenyl)-1,3-thiazol-2-yl]cyclohexanecarboxylic acid;

(1R,4S)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxamide;

(1S,4R)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxamide;

(1S,4R)4-{5-[3-({4-[(1R)-1-fluoroethyl]pyrimidin-2-yl}amino)-5-methylphenyl]-1,3-thiazol-2-yl}-4-hydroxy-2,2-dimethylcyclohexanecarboxylic acid;

(1S,4R)4-{5-[3-({4-[(1S)-1-fluoroethyl]pyrimidin-2-yl}amino)-5-methylphenyl]-1,3-thiazol-2-yl}-4-hydroxy-2,2-dimethylcyclohexanecarboxylic acid;

or a pharmaceutically acceptable salt thereof.

In the application various terms are as defined below:

"Alkyl" refers to a straight- or branched-chain hydrocarbon radical having the specified number of carbon atoms. Examples of "alkyl" include, but are not limited to, methyl, ethyl, n-propyl, isopropyl, n-butyl, isobutyl, t-butyl, n-pentyl, isopentyl, and the like.

"Alkenyl" refers to a straight- or branched-chain hydrocarbon radical having at least one carbon-carbon double bond, and having the specified number of carbon atoms. Examples of "alkenyl" include, but are not limited to ethenyl, propenyl, n-butenyl, 3-methylbut-2-enyl and n-pentenyl.

"Alkynyl" refers to a straight- or branched-chain hydrocarbon radical having at least one carbon-carbon triple bond, and having the specified number of carbon atoms. Examples of "alkynyl" include, but are not limited to ethynyl, propynyl, 2-butynyl and 3-methylbutynyl.

"Carbocycle" refers to a non-aromatic saturated or partially unsaturated monocyclic ring in which all ring atoms are carbon, and the ring being isolated or fused (including ortho-fused, spiro-fused and bridged) to one or two such ring or to a benzene ring. In the case of a polycyclic carbocycle, the attachment point may be on any ring. Examples of carbocycles include, but are not limited to, cyclopropyl, cyclobutyl, cyclopentyl, cyclohexyl, cyclohexenyl, cycloheptyl, cycloheptenyl, bicyclo[3.3.0]octane, indane, bicyclo[3.3.1]nonane, decalin, tetrahydronaphthalene, spiro[3.3]heptane, bicyclo[3.1.0]hexane, adamantane, tricyclo[2.2.1.0$^{2,6}$]heptane, dispiro[2.1.2.3]decane.

"Cycloalkyl" refers to a saturated ring containing the specified number of ring carbon atoms, and no heteroatom. In a like manner the term "$C_{3-8}$ cycloalkyl" refers to a saturated ring having from 3 to 8 ring carbon atoms. Exemplary "cycloalkyl" groups useful in the present invention include, but are not limited to, cyclopropyl, cyclobutyl, cyclopentyl, cyclohexyl, cycloheptyl and cyclooctyl.

"Halogen" or "halo" refers to fluorine, chlorine, bromine, or iodine.

"Haloalkyl" refers to an alkyl group as defined above in which one and up to all hydrogen atoms are replaced by a halogen; halogen is as defined herein. Examples of such branched or straight chained haloalkyl groups useful in the present invention, include, but are not limited to, methyl, ethyl, propyl, isopropyl, isobutyl and n-butyl substituted independently with one or more halos, e.g., fluoro, chloro, bromo and iodo. Examples of "haloalkyl" include, but are not limited to, fluoromethyl, difluoromethyl, trifluoromethyl, 1-fluoroethyl, 2-fluoroethyl, 2,2-difluoroethyl, 2,2,2-trifluoroethyl, and perfluoro-n-propyl.

"Hydroxyalkyl" refers to an alkyl group as defined above in which one hydrogen on each carbon atom may be replaced by a hydroxy group. Examples of "hydroxyalkyl" include, but are not limited to, hydroxymethyl, hydroxyethyl, propane-1,2-diol.

"Heterocyclic" or "heterocyclyl" refers to a non-aromatic saturated or partially unsaturated monocyclic ring in which one to three ring atoms are independently selected from N, S and O, and the ring being isolated or fused (including ortho-fused, spiro-fused and bridged) to one or two other rings, wherein the latter is selected from heterocycle (as defined above), carbocycle, benzene and heteroaryl. In the case of a polycyclic heterocycle, the attachment point may be on any ring. A carbon-linked heterocycle is attached via a ring carbon atom. Examples of heterocycle include, but are not limited to, aziridine, azetidine, pyrrolidine, piperidine, piperazine, morpholine, thiomorpholine, imidazolidine, oxazolidine, thiazolidine, dihydroazepine, tetrahydroazepine, azepane, diazepane, dihydro-diazepine, tetrahydro-diazepine, oxetane, tetrahydrofuran, dihydropyran, pyran, tetrahydropyran, tetrahydrothiophen, tetrahydrothiopyran, dihydrothiopyran, tetrahydroquinoline, tetrahydroisoquinoline, 1,3-dioxane, 1,4-dioxane, 1,3-dioxolane, 8-azabicyclo[3.2.1]octane, 9-azabicyclo[3.3.1]nonane, 7-azabicyclo[2.2.1]heptane, 2-oxabicyclo[2.2.2]octane, 1,4-dioxaspiro[4.5]decane, 1-azaspiro[5.4]decane, 1,4-dioxa-8-azaspiro[4.5]decane, 1-azatricyclo[3.3.1.1$^{3,7}$]decane, tetrahydro-pyrazolo[1,5-a]pyridine.

"Heteroaryl" refers to aromatic monocyclic groups and fused bicyclic aromatic rings containing 1, 2, 3 or 4 heteroatoms selected from N, O and S. Examples of heteroaryl groups include, but are not limited to, furan, thiophene, pyrrole, imidazole, pyrazole, triazole, tetrazole, thiazole, isothiazole, oxazole, isoxazole, oxadiazole, thiadiazole, pyridine, pyridazine, pyrazine, pyrimidine, quinoline, isoquinoline, benzofuran, benzoxazole, benzothiazole, naphthyridine, benzothiophene, benzimidazole, thieno[2,3-b]pyridine, pyrazolo[1,5-a]pyridine, imidazo[1,2-a]pyridine, indole and indazole.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

As used herein, the term "optionally" means that the subsequently described event(s) may or may not occur, and includes both event(s), which occur, and events that do not occur.

As used herein, the term "substituted with one or more groups" refers to substitution with the named substituent or substituents, multiple degrees of substitution, up to replacing all hydrogen atoms with the same or different substituents, being allowed unless the number of substituents is explicitly stated. Where the number of substituents is not explicitly stated, one or more is intended.

Each variable is independently defined each time it occurs within the generic structural formula definitions. For example, when there is more than one $R^{z(a)}$ substituents on the Cy ring, each substituent is independently selected at each occurrence, and each substituent can be the same or different from the other(s). As another example, for the group $NR^{a(a)}R^{a(a)}$, each occurrence of the two $R^{a(a)}$ groups may be the same or different.

As used herein, where the notation "$C_0$" or "$(CH_2)_0$" modifies a substituent, it indicates a bond between the substituent and the rest of the molecule. Thus, the term "$CO_{0-3}$ alkyl-$CO_2H$" means the carboxy group is either directly attached to the rest of the molecule, or there is an intervening $C_{1-3}$alkyl group therebetween.

The term "Syk inhibitor", is used to mean a compound which inhibits the Syk enzyme.

The term "Syk mediated disease" or a "disorder or disease or condition mediated by inappropriate Syk activity" is used to mean any disease state mediated or modulated by Syk kinase mechanisms. Such disease states may include inflammatory, allergic and autoimmune diseases, for example, asthma, chronic obstructive pulmonary disease (COPD), adult respiratory distress syndrome (ARDs), ulcerative colitis, Crohns disease, bronchitis, dermatitis, allergic rhinitis, psoriasis, scleroderma, urticaria, rheumatoid arthritis, multiple sclerosis, cancer, HIV and lupus, in particular, asthma, chronic obstructive pulmonary disease (COPD), adult respiratory distress syndrome (ARDs), allergic rhinitis and rheumatoid arthritis.

As used herein, "a compound of the invention" means a compound of formula (I) or a salt, solvate or physiologically functional derivative thereof.

As used herein, the term "solvate" refers to a complex of variable stoichiometry formed by a solute (in this invention, a compound of formula (I), or a salt thereof) and a solvent. Such solvents for the purpose of the invention may not interfere with the biological activity of the solute. Examples of suitable solvents include, but are not limited to, water, acetone, methanol, ethanol and acetic acid. Preferably the solvent used is a pharmaceutically acceptable solvent. Examples of suitable pharmaceutically acceptable solvents include water, ethanol and acetic acid. Most preferably the solvent is water.

As used herein, the term "physiologically functional derivative" refers to a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. Prodrugs are such derivatives, and a discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The compounds of formula (I) may have the ability to crystallize in more than one form, a characteristic known as polymorphism, and it is understood that such polymorphic forms ("polymorphs") are within the scope of formula (I). Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention.

It is also noted that the compounds of Formula (I) may form tautomers. It is understood that all tautomers and mixtures of tautomers of the compounds of the present invention are included within the scope of the compounds of the present invention. Some of the compounds described herein contain olefinic double bonds, and unless specified otherwise, are meant to include both E and Z geometric isomers.

Whilst the embodiments for each variable have generally been listed above separately for each variable, this invention also includes those compounds in which several or each embodiment in formula (I) is selected from each of the embodiments listed above. Therefore, this invention is intended to include all combinations of embodiments for each variable.

The compounds of the present invention may be in the form of and/or may be administered as a pharmaceutically acceptable salt. For a review on suitable salts see Berge et al, J. Pharm. Sci. 1977, 66, 1-19. Typically, the salts of the present invention are pharmaceutically acceptable salts. Salts encompassed within the term "pharmaceutically acceptable salts" refer to non-toxic salts of the compounds of this invention. Suitable pharmaceutically acceptable salts can include acid or base additions salts.

A pharmaceutically acceptable acid addition salt can be formed by reaction of a compound of formula (I) with a suitable inorganic or organic acid (such as hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated, for example, by crystallisation and filtration. A pharmaceutically acceptable acid addition salt of a compound of formula (I) can comprise or be, for example, a hydrobromide, hydrochloride, sulfate, nitrate, phosphate, succinate, maleate, formarate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

A pharmaceutically acceptable base salt can be formed by reaction of a compound of formula (I) with a suitable inorganic or organic base. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Other, non-pharmaceutically acceptable, salts, e.g. oxalates or trifluoroacetates, may also be used, for example, in the isolation of compounds of the invention, and are included within the scope of this invention.

The invention includes within its scope all possible stoichiometric and non-stoichiometric forms of the compounds of formula (I).

In the compounds of formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates The compounds of formula (I) and salts, solvates and physiologically functional derivatives thereof are believed to be inhibitors of Syk activity, and thus be potentially useful in the treatment of diseases and conditions associated with inappropriate Syk activity.

Compound of formula I or its pharmaceutically acceptable salts and pharmaceutical compositions can be used to treat or prevent a variety of conditions or diseases mediated by Spleen tyrosine kinase (SYK). Such conditions and diseases include, but are not limited to: (1) arthritis, including rheumatoid arthritis, juvenile arthritis, psoriatic arthritis and osteoarthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia including idiopathic thrombopenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenic purpura, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g. precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors) myelomas including multiple myeloma, myeloproliferative disorders kidney cancer, lung cancer, muscle cancer, bone cancer, bladder cancer, brain cancer, melanoma including oral and metastatic melanoma, Kaposi's sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; (14) low grade scarring including scleroderma, increased fibrosis, keloids, post-surgical scars, pulmonary fibrosis, vascular spasms, migraine, reperfusion injury, and post-myocardial infarction.

The invention thus provides compounds of formula (I) and salts, solvates and physiologically functional derivatives thereof for use in therapy, and particularly in the treatment of diseases and conditions mediated by inappropriate Syk activity. The inappropriate Syk activity referred to herein is any Syk activity that deviates from the normal Syk activity expected in a particular mammalian subject. Inappropriate Syk activity may take the form of, for instance, an abnormal increase in activity, or an aberration in the timing and or control of Syk activity. Such inappropriate activity may result then, for example, from overexpression or mutation of the protein kinase leading to inappropriate or uncontrolled activation.

In a further embodiment, the present invention is directed to methods of regulating, modulating, or inhibiting Syk for the prevention and/or treatment of disorders related to unregulated Syk activity.

In a further embodiment, the present invention provides a method of treatment of a mammal suffering from a disorder mediated by Syk activity, which comprises administering to said mammal an effective amount of a compound of formula (I) or a pharmaceutically acceptable salt, solvate, or a physiologically functional derivative thereof.

In a further embodiment, the present invention provides for the use of a compound of formula (I), or a pharmaceutically acceptable salt or solvate thereof, or a physiologically functional derivative thereof, in the preparation of a medicament for the treatment of a disorder mediated by Syk activity.

In a further embodiment said disorder mediated by Syk activity is asthma. In a further embodiment said disorder is rheumatoid arthritis. In yet another embodiment, said disorder is cancer. In a further embodiment said disorder is ocular conjunctivitis.

Yet another aspect of the present invention provides a method for treating diseases caused by or associated with Fe receptor signaling cascades, including FceRI and/or FcgRI-mediated degranulation as a therapeutic approach towards the treatment or prevention of diseases characterized by, caused by and/or associated with the release or synthesis of chemical mediators of such Fc receptor signaling cascades or degranulation. In addition, Syk is known to play a critical role in immunotyrosine-based activation motif (ITAM) singaling, B cell receptor signaling, T cell receptor singaling and is an essential component of integrin beta (1), beta (2), and beta (3) signaling in neutrophils. Thus, compounds of the present invention can be used to regulate Fe receptor, ITAM, B cell receptor and integrin singaling cascades, as well as the cellular responses elicited through these signaling cascades. Non-limiting examples of cellular responses that may be regulated or inhibited include respiratory burst, cellular adhesion, cellular degranulation, cell spreading, cell migration, phagocytosis, calcium ion flux, platelet aggregation and cell maturation.

While it is possible that, for use in therapy, a compound of formula (I), as well as salts, solvates and physiological functional derivatives thereof, may be administered as the raw chemical, it is possible to present the active ingredient as a pharmaceutical composition. Accordingly, the invention further provides a pharmaceutical composition, which comprises a compound of formula (I) and salts, solvates and physiological functional derivatives thereof, and one or more pharmaceutically acceptable carriers, diluents, or excipients. The compounds of the formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing a compound of the formula (I), or salts, solvates and physiological functional derivatives thereof, with one or more pharmaceutically acceptable carriers, diluents or excipients.

Pharmaceutical compositions of the present invention may be presented in unit dose forms containing a predetermined amount of active ingredient per unit dose. Such a unit may contain, for example, 5 μg to 1 g, preferably 1 mg to 700 mg, more preferably 5 mg to 100 mg of a compound of the formula (I), depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, or parenteral (including intravenous and intramuscular) route. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, COPD or ARDS.

In a further embodiment, the present invention provides a pharmaceutical composition adapted for administration by the ocular route, for treating, diseases of the eye, for example, conjunctivitis.

In a further embodiment, the present invention provides a pharmaceutical composition adapted for administration by the parenteral (including intravenous) route, for treating, for example, cancer.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release, for example, by coating or embedding particulate material in polymers, wax or the like.

The compounds of formula (I), and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Dosage forms for inhaled administration may conveniently be formulated as aerosols or dry powders.

For compositions suitable and/or adapted for inhaled administration, it is preferred that the compound or salt of formula (I) is in a particle-size-reduced form, and more preferably the size-reduced form is obtained or obtainable by micronisation. The preferable particle size of the size-reduced (e.g. micronised) compound or salt or solvate is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of formula (I) or salt or solvate thereof (preferably in particle-size-reduced form, e.g. in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of formula (I) or salt thereof. The lactose is preferably lactose hydrate e.g. lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g. 10-1000 microns e.g.

30-1000 microns) in diameter, and/or 50% or more of the lactose particles being less than 500 microns (e.g. 10-500 microns) in diameter. More preferably, the particle size of the lactose is defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g. about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition can be administered by inhalation via the device such as the DISKUS® device (GlaxoSmithKline). Other dry powder inhalers are well known to those of ordinary skill in the art, and many such devices are commercially available, with representative devices including Aerolizer® (Novartis), Airmax™ (WAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler (Schering-Plough), Turbuhaler® (AstraZeneca), Ultrahaler® (Aventis), and the like.

Dosage forms for ocular administration may be formulated as solutions or suspensions with excipients suitable for ophthalmic use.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurised aerosols, nebulizers or insufflators.

For pharmaceutical compositions suitable and/or adapted for intranasal administration, the compound of formula (I) or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

The following are examples of representative pharmaceutical dosage forms for the compounds of this invention:

| Injectable Suspension (I.M.) | mg/ml |
|---|---|
| Compound of Formula Ia | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
|---|---|
| Compound of Formula Ia | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula Ia | 25 |
| Lactose Powder | 573.5 |
| Magnesium Stearate | 1.5 |
| | 600 |

| Aerosol | Per canister |
|---|---|
| Compound of Formula Ia | 24 mg |
| Lecithin, NF Liquid Concentrate | 1.2 mg |
| Trichlorofluoromethane, NF | 4.025 gm |
| Dichlorodifluoromethane, NF | 12.15 gm |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian However, an effective amount of a compound of formula (I) for the treatment of diseases or conditions associated with inappropriate Syk activity, will generally be in the range of 5 µg to 100 mg/kg body weight of recipient (mammal) per day and more usually in the range of 5 µg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of formula (I) per se.

Compounds of the present invention, and their salts and solvates, and physiologically functional derivatives thereof, may be employed alone or in combination with other therapeutic agents for the treatment of diseases and conditions associated with inappropriate Syk activity. Combination therapies according to the present invention thus comprise the administration of at least one compound of formula (I) or a pharmaceutically acceptable salt or solvate thereof, or a physiologically functional derivative thereof, and the use of at least one other pharmaceutically active agent. The compound(s) of formula (I) and the other pharmaceutically active agent(s) may be administered together or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect.

For the treatment of the inflammatory diseases, rheumatoid arthritis, psoriasis, inflammatory bowel disease, COPD, asthma and allergic rhinitis a compound of formula I may be combined with one or more other active agents such, as: (1) TNF-α inhibitors such as infliximab (Remicade®), etanercept (Enbrel®), adalimumab (Humira®), certolizumab pegol (Cimzia®), and golimumab (Simponi®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, etodolac, azapropazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof, (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast, cilomilast, AWD-12-281 (Elbion), and PD-168787 (Pfizer); (8) antihistaminic H1 receptor antagonists such as cetirizine, levocetirizine, loratadine, desloratadine, fexofenadine, astemizole, azelastine, levocabastine, olopatidine, methapyrilene and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, (R,R)-glycopyrrolate, pirenzepine, and telenzepine; (11) β-adrenoceptor agonists such as metaproterenol, isoproterenol, isoprenaline, albuterol, formoterol (particularly the fumarate salt), salmeterol (particularly the xinafoate salt), terbutaline, orciprenaline, bitolterol mesylate, fenoterol, and pirbuterol, or methylxanthanines such as theophylline and aminophylline, sodium cromoglycate; (12) insulin-like growth factor type I (IGF-1) mimetic; (13) glucocorticosteroids, especially inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate; (14) kinase inhibitors such as inhibitors of the Janus Kinases (JAK 1 and/or JAK2 and/or JAK 3 and/or TYK2), p38 MAPK and IKK2; (15) B-cell targeting biologics such as rituximab (Rituxan®); (16) selective costimulation modulators such as abatacept (Orencia); (17) interleukin inhibitors, such as IL-1 inhibitor anakinra (Kineret) and IL-6 inhibitor tocilizumab (Actemra).

The present invention also provides for so-called "triple combination" therapy, comprising a compound of formula (I) or a pharmaceutically acceptable salt thereof together with beta$_2$-adrenoreceptor agonist and an anti-inflammatory corticosteroid. Preferably this combination is for treatment and/or prophylaxis of asthma, COPD or allergic rhinitis. The beta$_2$-adrenoreceptor agonist and/or the anti-inflammatory corticosteroid can be as described above and/or as described in WO 03/030939 A1. Representative examples of such a "triple" combination are a compound of formula (I) or a pharmaceutically acceptable salt thereof in combination with the components of Advair® (salmeterol xinafoate and fluticasone propionate), Symbicort® (budesonide and formoterol fumarate), or Dulera® (mometasone furoate and formoterol). fumarate).salmeterol or a pharmaceutically acceptable salt thereof (e.g. salmeterol xinafoate) and fluticasone propionate.

For the treatment of treatment cancer a compound of Formula I may be combined with one or more of an anticancer agents. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: (1) estrogen receptor modulator such as diethylstibestral, tamoxifen, raloxifene, idoxifene, LY353381, LY117081, toremifene, fluoxymestero, and SH646; (2) other hormonal agents including aromatase inhibitors (e.g., aminoglutethimide, tetrazole anastrozole, letrozole and exemestane), luteinizing hormone release hormone (LHRH) analogues, ketoconazole, goserelin acetate, leuprolide, megestrol acetate and mifepristone; (3) androgen receptor modulator such as finasteride and other 5α-reductase inhibitors, nilutamide, flutamide, bicalutamide, liarozole, and abiraterone acetate; (4) retinoid receptor modulator such as bexarotene, tretinoin, 13-cis-retinoic acid, 9-cis-retinoic acid, α-difluoromethylomithine, ILX23-7553, trans-N-(4'-hydroxyphenyl) retinamide, and N-4-carboxyphenyl retinamide; (5) antiproliferative agent such asantisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, fluoromethylene-2'-deoxycytidine, N6-[4-deoxy-4-[N2-[2(E),4 (E)-tetradeca-dienoyl]glycylamino]-L-glycero-B-L-mannoheptopyranosyl]adenine, aplidine, ecteinascidin, troxacitabine, aminopterin, 5-fluorouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone; (6) prenyl-protein transferase inhibitor including farnesyl-protein transferase (FPTase), geranylgeranyl-protein transferase type I (GGPTase-I), and geranylgeranyl-protein transferase type-II (GGPTase-II, also called Rab GGPTase); (7) HMG-CoA reductase inhibitor such as lovastatin, simvastatin, pravastatin, atorvastatin, fluvastatin and rosuvastatin; (8) angiogenesis inhibitor such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, steroidal anti-inflammatories, carboxyamidotriazole, combretastatin A-4, squalamine, 6-O-chloroacetyl-carbonyl)-fumagillol, thalidomide, angiostatin, troponin-1, angiotensin IT antagonists, heparin, carboxypeptidase U inhibitors, and antibodies to VEGF, endostatin, ukrain, ranpirnase, IM862, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, and 3-[(2,4-dimethylpyrrol-5-yl)methylene]-2-indolinone (SU5416); (9) PPAR-γ agonists, PPAR-δ agonists, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and (2R)-7-(3-(2-chloro-4-(4-fluorophenoxy)phenoxy)propoxy)-2-ethylchromane-2-carboxylic acid (disclosed in U.S. Ser. No. 60/235,708 and 60/244,697); (9) inhibitor of inherent multidrug resistance including inhibitors of p-glycoprotein (P-gp), such as LY335979, XR9576, OC144-093, R101922, VX853 and PSC833 (vaispodar); (10) inhibitor of cell proliferation and survival signaling such as inhibitors of EGFR (for example gefitinib and erlotinib), inhibitors of ERB-2 (for example trastuzumab), inhibitors of IGF1R such as MK-0646 (dalotuzumab), inhibitors of CD20 (rituximab), inhibitors of cytokine receptors, inhibitors of MET, inhibitors of PI3K family kinase (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573); (11) a bisphosphonate such as etidronate, pamidronate, alendronate, risedronate, zoledronate, ibandronate, incadronate or cimadronate, clodronate, EB-1053, minodronate, neridronate, piridronate and tiludronate; (12) γ-secretase inhibitors, (13) agents that interfere with receptor tyrosine kinases (RTKs) including inhibitors of c-Kit, Eph, PDGF, Flt3 and c-Met; (14) agent that interferes with a cell cycle checkpoint including inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032; (15) BTK inhibitors such as PCI32765, AVL-292 and AVL-101; (16) PARP inhibitors including iniparib, olaparib, AGO14699, ABT888 and MK4827; (16) ERK inhibitors; (17) mTOR inhibitors such as sirolimus, ridaforolimus, temsirolimus, everolimus; (18) cytotoxic/cytostatic agents.

"Cytotoxic/cytostatic agents" refer to compounds which cause cell death or inhibit cell proliferation primarily by interfering directly with the cell's functioning or inhibit or interfere with cell mycosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, eiS-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin.

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, 2,3-(methylenedioxy)-5-methyl-7-hydroxy-8-methoxybenzo[c]- phenanthridinium, 5-(3-aminopropylamino)-7,10-dihydroxy-2-(2-hydroxyethylaminomethyl)-6H-pyrazolo[4,5,1-de]acridin-6-one, N-[1-[2-(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, vorinostat, trichostatin A, oxamflatin, PXD101, MG98, valproic acid and scriptaid.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2,4-tetradecadienoyl]glycylamino]-L-glycero-B-L-mannoheptopyranosyl]adenine, aplidine, ecteinascidin, troxacitabine, aminopterin, 5-fluorouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone.

Non-limiting examples of suitable agents used in cancer therapy that may be combined with compounds of formula I include, but are not limited to, abarelix; aldesleukin; alemtuzumab; alitretinoin; allopurinol; altretamine; amifostine; anastrozole; arsenic trioxide; asparaginase; azacitidine; bendamustine; bevacuzimab; bexarotene; bleomycin; bortezomib; busulfan; calusterone; capecitabine; carboplatin; carmustine; cetuximab; chlorambucil; cisplatin; cladribine; clofarabine; cyclophosphamide; cytarabine; dacarbazine; dactinomycin, actinomycin D; dalteparin; darbepoetin alfa; dasatinib; daunorubicin; degarelix; denileukin diftitox; dexrazoxane; docetaxel; doxorubicin; dromostanolone propionate; eculizumab; Elliott's B Solution; eltrombopag; epirubicin; epoetin alfa; erlotinib; estramustine; etoposide phosphate; etoposide; everolimus; exemestane; filgrastim; floxuridine; fludarabine; fluorouracil; fulvestrant; gefitinib; gemcitabine; gemtuzumab ozogamicin; goserelin acetate; histrelin acetate; hydroxyurea; ibritumomab tiuxetan; idarubicin; ifosfamide; imatinib mesylate; interferon alfa 2a; interferon alfa-2b; irinotecan; ixabepilone; lapatinib; lenalidomide; letrozole; leucovorin; leuprolide acetate; levamisole; lomustine; meelorethamine, nitrogen mustard; megestrol acetate; melphalan, L-PAM; mercaptopurine; mesna; methotrexate; methoxsalen; mitomycin C; mitotane; mitoxantrone; nandrolone phenpropionate; nelarabine; nilotinib; Nofeturnomab; ofatumumab; oprelvekin; oxaliplatin; paclitaxel; palifermin; pamidronat; panitumumab; pazopanib; pegademase; pegaspargase; Pegfilgrastim; pemetrexed disodium; pentostatin; pipobroman; plerixafor; plicamycin, mithramycin); porfimer sodium; pralatrexate; procarbazine; quinacrine; Rasburicase; raloxifene hydrochloride; Rituximab; romidepsin; romiplostim; sargramostim; sargramostim; satraplatin; sorafenib; streptozocin; sunitinib maleate; tamoxifen; temozolomide; temsirolimus; teniposide; testolactone; thioguanine; thiotepa; topotecan; toremifene; tositumomab; trastuzumab; tretinoin; uracil mustard; valrubicin; vinblastine; vincristine; vinorelbine; vorinostat; and zoledronate.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of protecting groups as well as the reaction conditions and order of reaction steps shall be consistent with the preparation of compounds of Formula (I). Those skilled in the art will recognize if a stereocenter exists in compounds of Formula (I). Accordingly, the present invention includes all possible stereoisomers and includes not only mixtures of stereoisomers (such as racemic compounds) but the individual stereoisomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994).

The following abbreviations are used in the schemes and examples: Ac=Acetyl; AcOH=Acetic acid; Bn=benzyl; Boc (t-Boc)=t-butyloxycarbonyl; BOP=(Benzotriazol-1-yloxy)- tris(dimethylamino)phosphonium hexafluorophosphate; DAST=(Diethylamino)sulfur trifluoride; dba=dibenzylideneacetone; DCE=1,2-diehloroethane; DCM=Dichloromethane; Dibal/Dibal-H=Diisobutylaluminum hydride; DIPEA/DIEA=Diisopropylethylamine; DMAP=N,N-dimethyl-aminopyridine; DME=1,2-dimethoxyethane; DIVIF=Dimethyl formamide; DMSO=Dimethyl-sulfoxide; Dppf=1,1'-Bis(diphenylphosphino)ferrocene; EDC=N-(3-Dimethylaminopropyl)-N'-ethylcarbodiimide; EtOAc=Ethyl acetate; HATU=N,N,N',N'-Tetramethyl-O-(7-azabenzotriazol-1-yl) uronium hexafluorophosphate; Imps=Hexamethyldisilazane; HOBT=1-Hydroxybenzotriazole; IPA=Isopropyl alcohol; LDA=Lithium diisopropylamide; mCPBa=Meta-chloroperoxybenzoic acid; Ms=Methanesulfonyl (mesyl); MTBE=Methyl t-butyl ether; NBS=N-bromo-succinimide; Ph=phenyl; TBAF=t-butylammonium fluoride; TBDMS/TBS=t-butyl dimethylsilyl; TFA=Trifluoroacetic/trifluoroacetate; THF=Tetrahydrofuran; TLC=Thin-layer chromatography; TMS=Trimethylsilyl; Ts=Toluenesulfonyl (tolyl); TSA=p-toluenesulfonic acid. Abbreviations for alkyl/cycloalkyl groups: Me=methyl, Et=ethyl, nPr=n-propyl, iPr=isopropyl, nBu=n-butyl, t-Bu=tertiary butyl, cPr=cyclopropyl, cBu=cyclobutyl, cPen=cyclopentyl, cHex=cyclohexyl, cHept=cycloheptyl.

In the following Schemes, A and B are appropriate groups as defined for R5 in Formula (I), and may be e.g., optionally substituted alkyl, or A, B and the carbon to which they are attached form an optionally substituted carbocyclyl or heterocyclyl group.

SCHEME 1

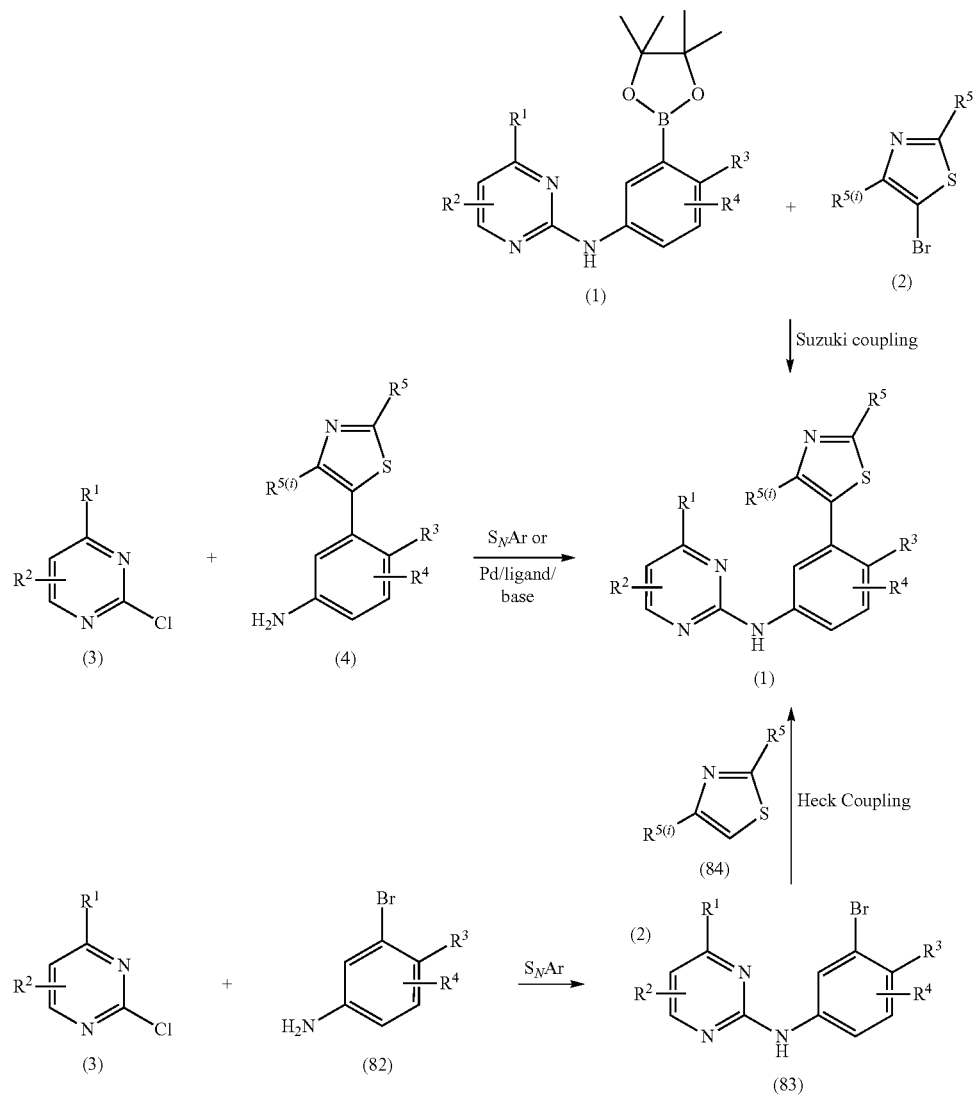

Compounds of formula (I) may be prepared by Suzuki coupling of boronic esters (1) with a thiazole bromides (2). Boronic esters (1) can be obtained by reacting 2-chloropyrimidines (3) and 3-bromoanilines (82) to form the corresponding N-(3-bromophenyl)-pyrimidine-2-amines (83), followed by Miyaura coupling with bis(pinacolato)diboron. Compounds of formula (I) can also be obtained by reacting 2-chloropyrimidines (3) and thiazole-substituted anilines (4) in the presence of a Pd catalyst or alternatively an S$_N$Ar reaction.

Thiazole-substituted anilines (4), in turn, may be formed under Suzuki coupling conditions using a bromothiazole and nitrophenyl boronic ester, followed by reduction of the nitro group to an amino group using standard conditions known to reduce nitroaromatic compounds to anilines such as Pd-catalyzed hydrogenation. Compounds of formula (I) may also be formed by the Heck reaction between bromo-substituted anilines (83) with substituted thiazoles (84). Bromo-substituted anilines (83) can be prepared by $S_NAr$ reaction between 2-chloropyrimidines (3) and substituted bromo-anilines (82).

Compounds of formula (I) can also be prepared from compounds (5). Thiazole (5) is treated with a strong base such as LDA, and then with ketones or aldehydes to afford alcohols (6); with esters followed by $NaBH_4$ to give secondary alcohols (7); with sulfimines to provide sulfinamides (9), which can be cleaved under acidic conditions provided amines (10). Alcohols (7) can be further oxidized, for example with Dess-Martin periodinane, to give the corresponding ketones (8).

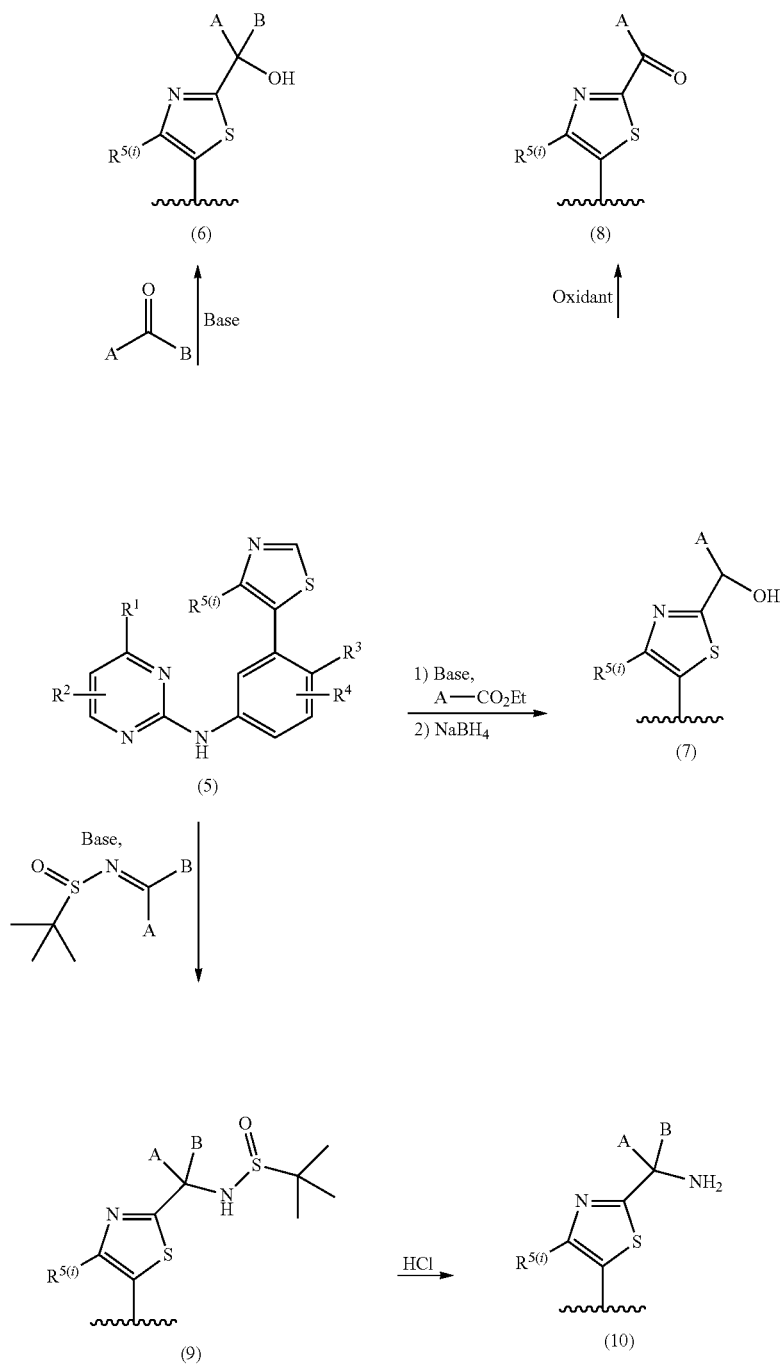

SCHEME 2

SCHEME 3

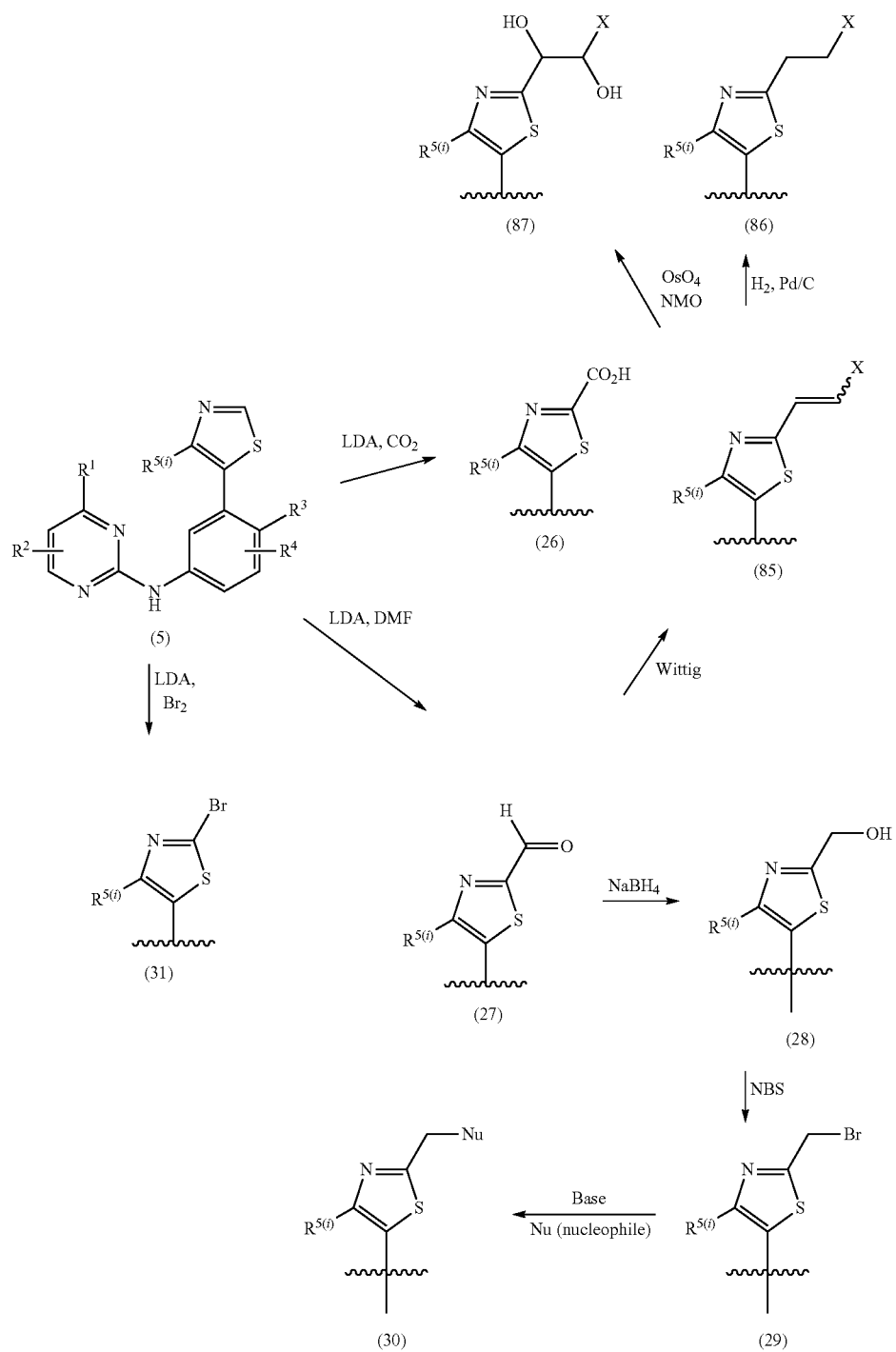

X is H or Alkyl Optionally Substituted as Provided in Formula (I)

Treatment of thiazoles (5) with strong base such as LDA followed by carbon dioxide provides acids (26), which can be converted to amides using conventional amide coupling methodologies. Treatment of thiazoles (5) with strong base such as LDA followed by dimethylformamide provides formylated compounds (27), which can be converted to bromides (29) via the primary alcohol (28). Bromides (28) can react with various nucleophilic species to provide compounds of type (30). Treatment of thiazoles (5) with strong base such as LDA followed by bromine provides bromides (31). The aldehydes (27) can be converted to the corresponding olefins (85) by Wittig reaction. The olefins (85) can then be hydrogenated with $H_2$ and Pd/C to afford saturated compounds (86) or dihydroxylated by the action of $OsO_4$ and NMO to afford diols (87).

SCHEME 4

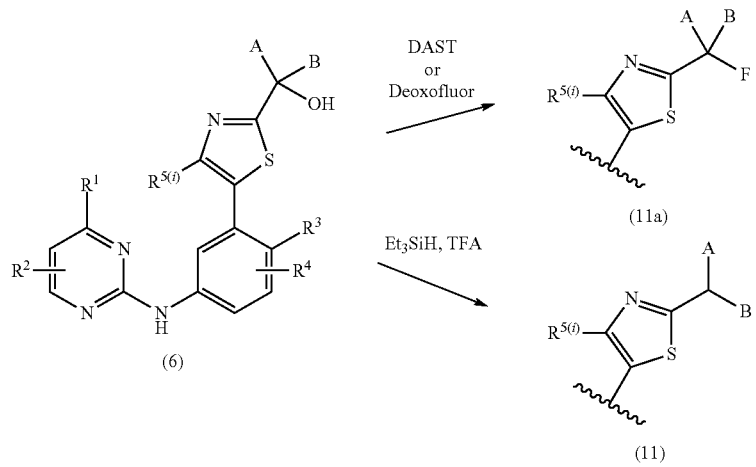

Various functionalized thiazole compounds in the previous Schemes can be further elaborated. Alcohols (6) can be fluorinated using a fluorinating agent such as DAST or deoxofluor to provide compounds (11a), or treated with triethylsilane/TFA to afford deoxygenated compounds (11). Ketones (8) can be converted to trifluoromethyl alcohols (12) by treatment with TMSCF$_3$ and TBAF. Reductive amination of ketones (8) provides amines (13).

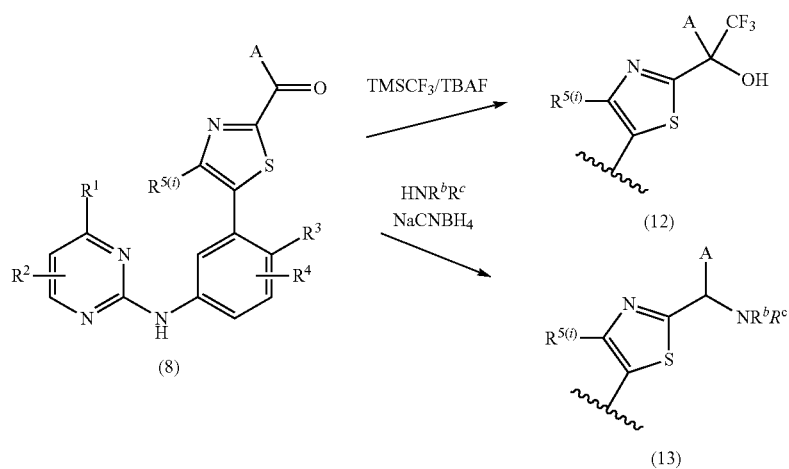

SCHEME 5

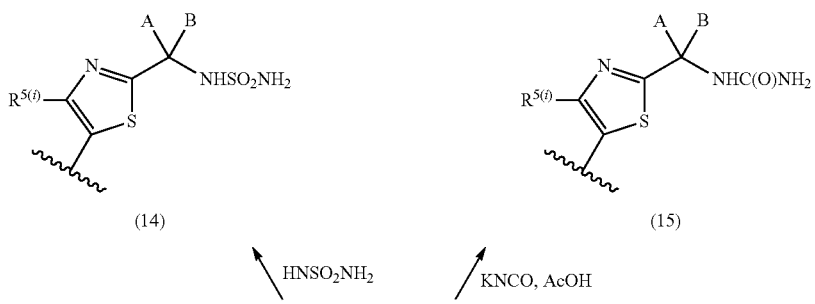

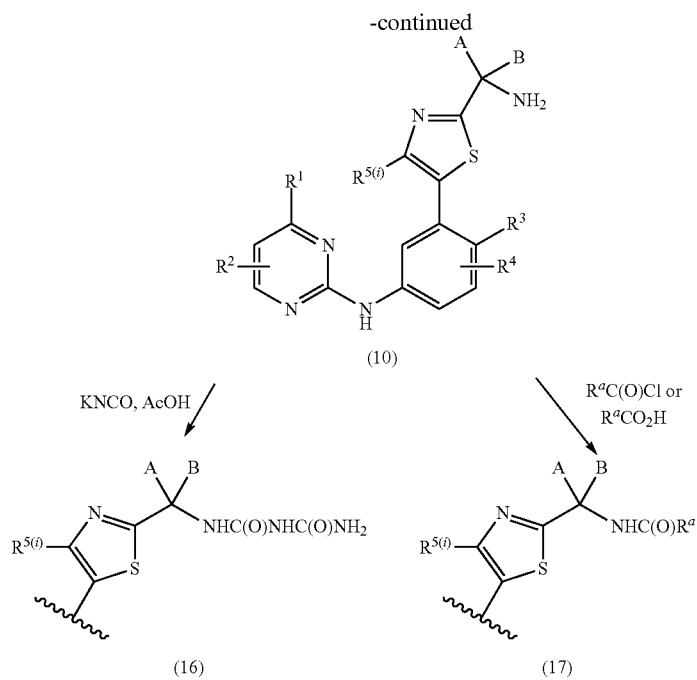
Amines (10) can be treated (a) with sulfamide to provide compounds (14); (b) with potassium cyanate in the presence of acetic acid to provide ureas (15), as well as compounds (16); (c) with acylating agents such as acid chlorides and carboxylic acids with a coupling agent to provide amides (17).
SCHEME 6
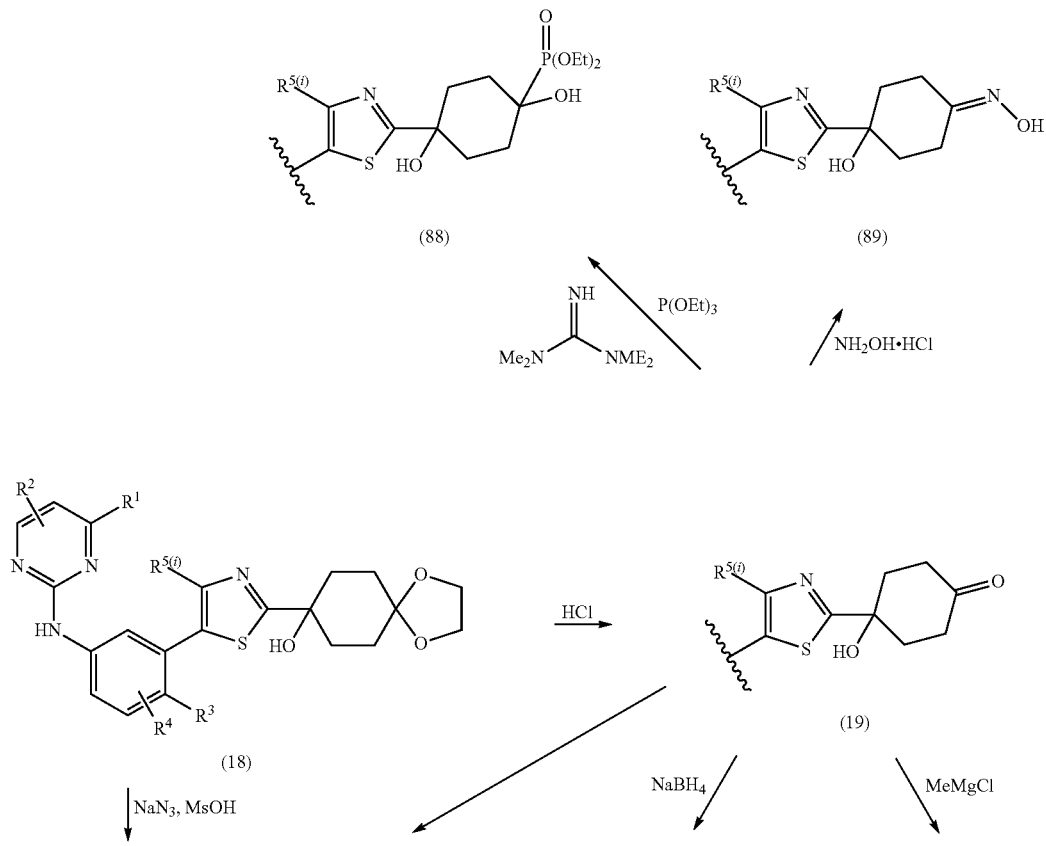

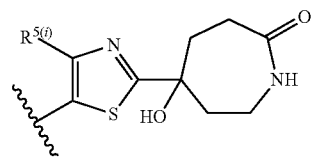
(21)

-continued
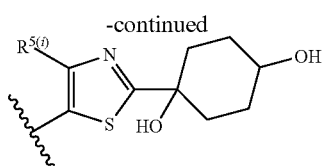
(20)

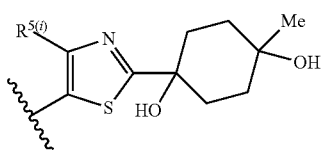
(22)

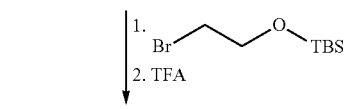

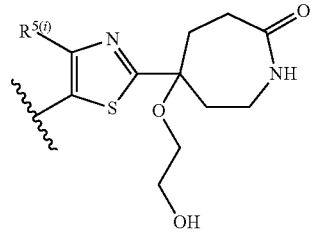
(90)

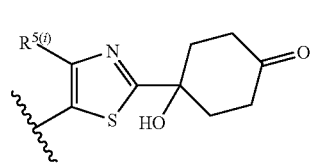
(19)

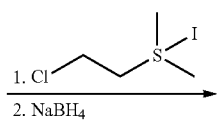

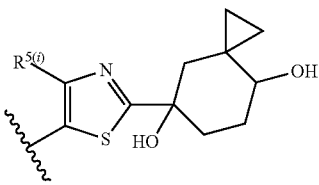
(91)

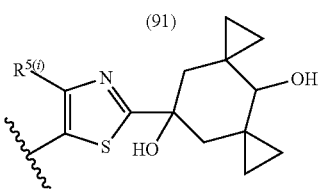
(92)

Ketals (18), prepared from compounds (5) and 1,4-dioxaspiro[4.5]decan-8-one, can be treated with HCl to afford ketones (19), which can then be reduced with sodium borohydride or treated with methyl Grignard to afford diols (20) or (22), respectively. Alternatively, ketals (18) or ketones (19) are treated with sodium azide and methanesulfonic acid to provided the rearranged lactam (21). Ketones (19) can be reacted with tetramethyl guanidine and triethylphosphite to give phosphonate esters (88). The ketones (19) can also be reacted with hydroxylamine to form the oximes (89). Alternatively, ketones (19) can be reacted with 1-chloro-2-[iodo(dimethyl)-λ$^4$-sulfanyl]ethane to give spirocycles (91) and (92) after sodium borohydride reduction. Alkylation of compounds (21) followed by deprotection of the intermediate silyl ether yields alcohols (90).

SCHEME 7

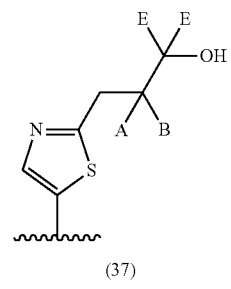

-continued

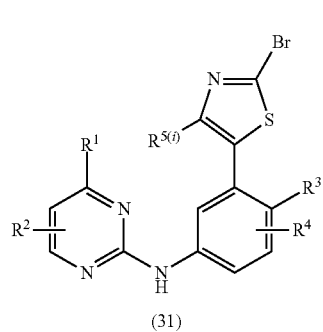 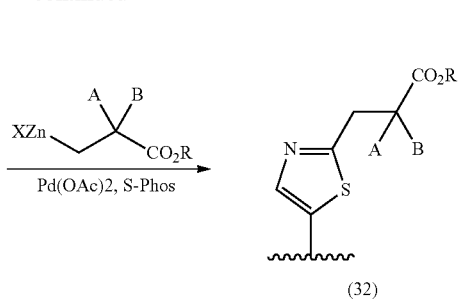

(31) (32)

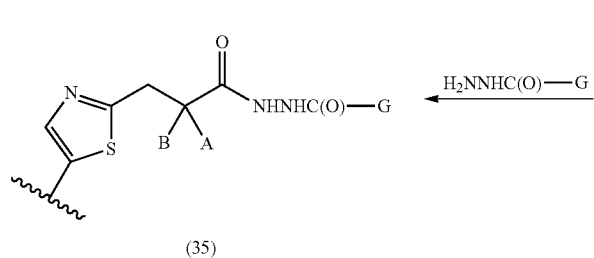

(35) (33)

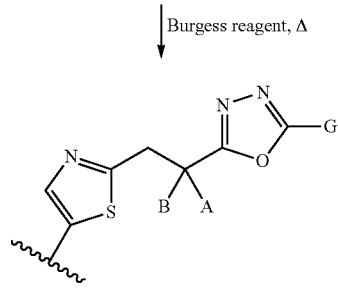 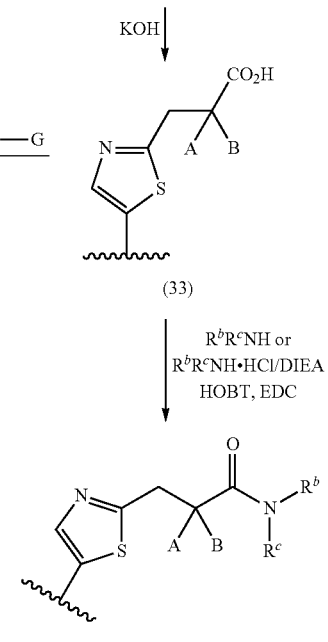

(36) (34)

Negishi coupling of bromides (31) with alkylzinc halides affords the esters (32), which can be hydrolyzed to provide the acids (33). Acids (33) can react with amines or acylhydrazines to provide amides (34) or hydrazides (35), respectively. Compounds (35) can be heated with Burgess reagent to yield 1,3,4-oxadiazoles (36). The addition of Grignard reagents to esters (32) afford access to tertiary alcohols (37).

SCHEME 8

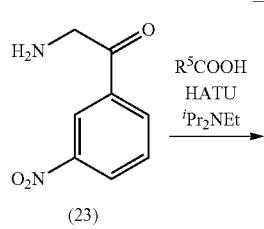

(23)

-continued

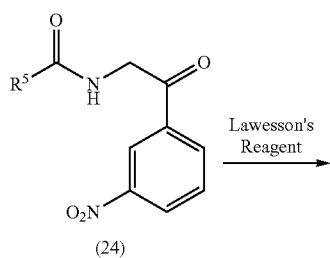

(24)

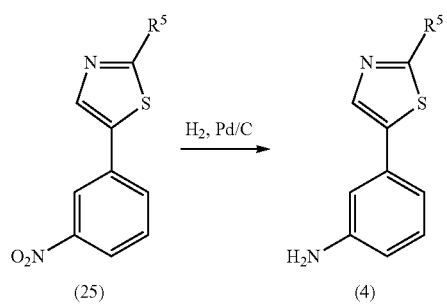

(25) (4)

Compounds (4) can be prepared from 2-amino-1-(3-nitrophenyl)ethanone (23). Amide coupling with an acid provides compounds (24), which are treated with Lawesson's reagent resulting in the formation of nitrophenyls (25). Palladium-mediated reduction of nitroarenes (25) by hydrogen yields anilines (4).

Various functionalized bromothiazoles can be prepared as shown in Scheme 8, starting from 2-bromothiazole (38), Formation of the thiazole Grignard and addition to various ketones affords alcohols (39). Bromination of (39) with $Br_2$ gives bromothiazoles (40), which are reacted with methyl 3-mercaptopropionate under Lewis acidic conditions to pro-

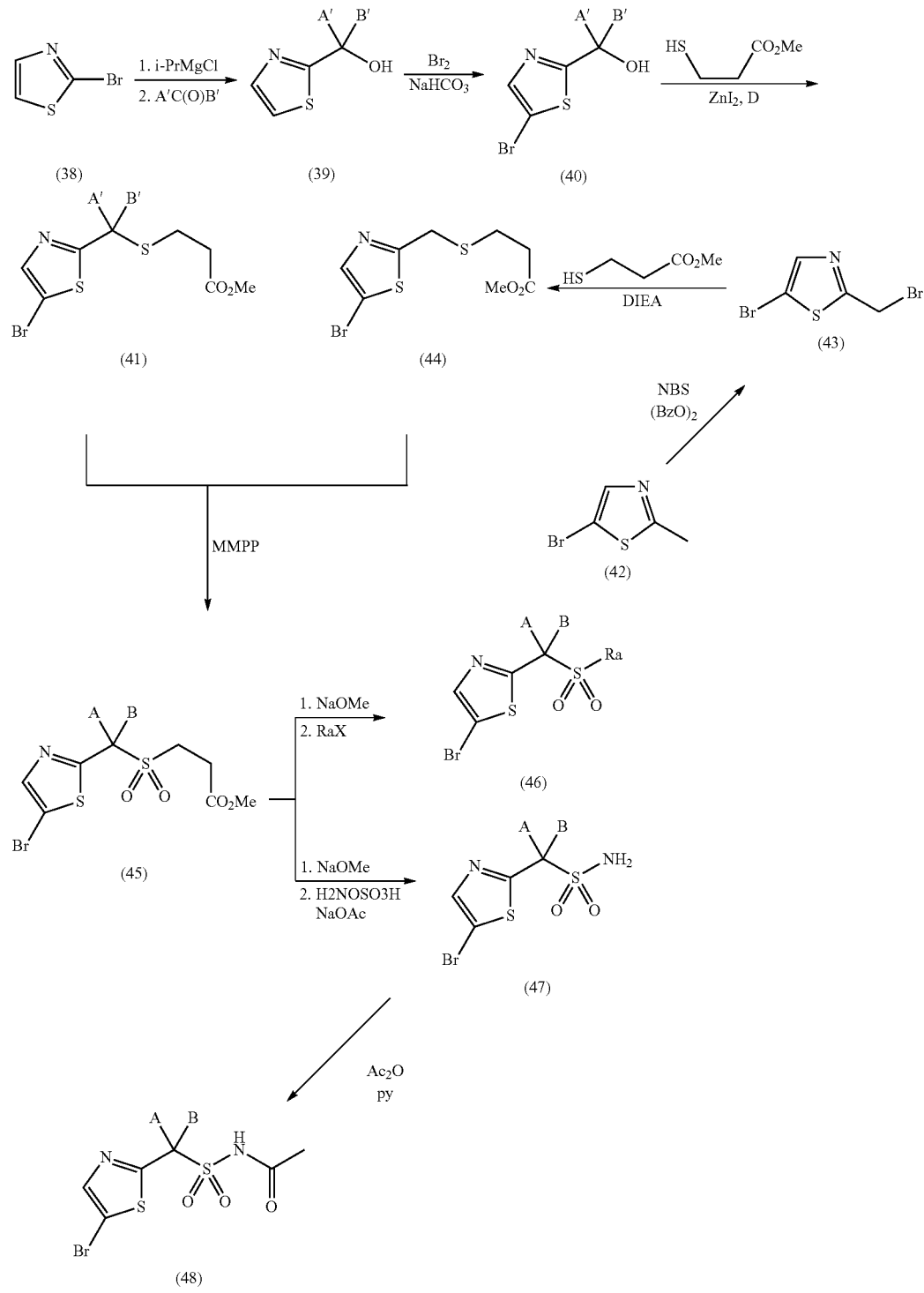

SCHEME 9 vide (41). Radical bromination of 5-bromo-2-methylthiazole (42) gives (43), followed by reaction with methyl 3-mercaptopropionate affords compound (44). Oxidation of (41) and (44) to their respective sulfones (45) is followed by conversion to either the primary sulfonamide (47) (with hydroxylamine-O-sulfonic acid) or sulfone (46) (with alkyl halides) via the sulfinate following the method of as described in Baskin, J. M.; Wang, Z. *Tetrahedron Lett.* 2002, 43, 8479. Further elaboration of (47) with acetic anhydride allowed access to acyl sulfonamides (48).

SCHEME 10

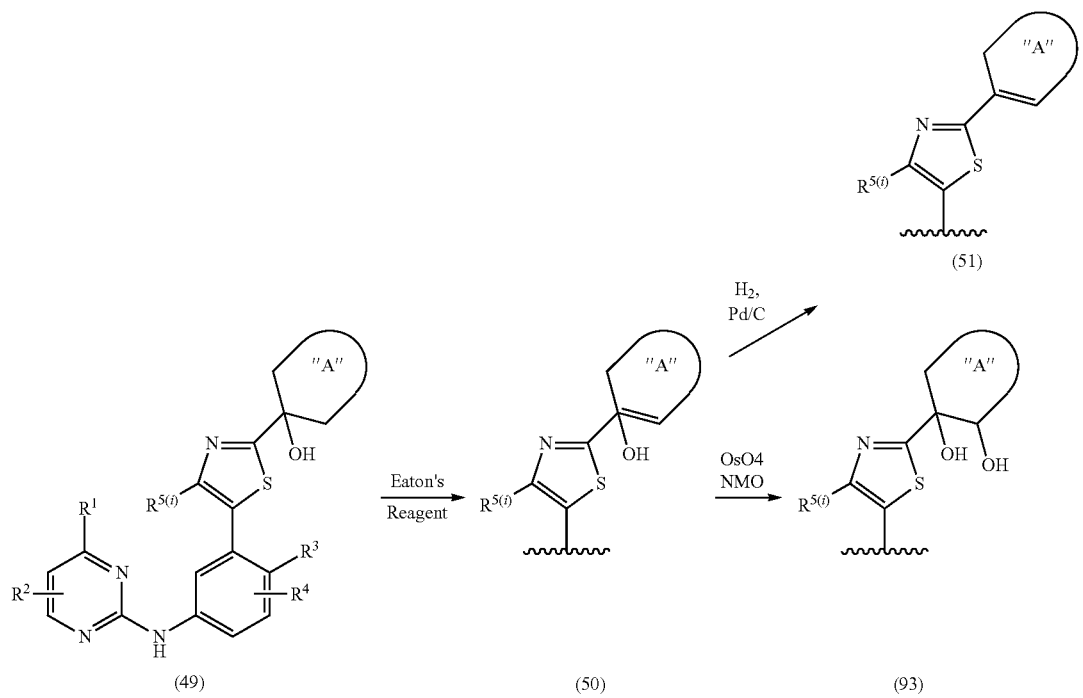

Ring "A" is an Optionally Substituted Carbocycle or Heterocycle as Defined in Formula (I)

Dehydration of compounds (49) with Eaton's reagent provides the cycloalkenes (50), which yield the saturated compounds (51) or the diols (93) following hydrogenation or dihydroxylation, respectively.

SCHEME 11

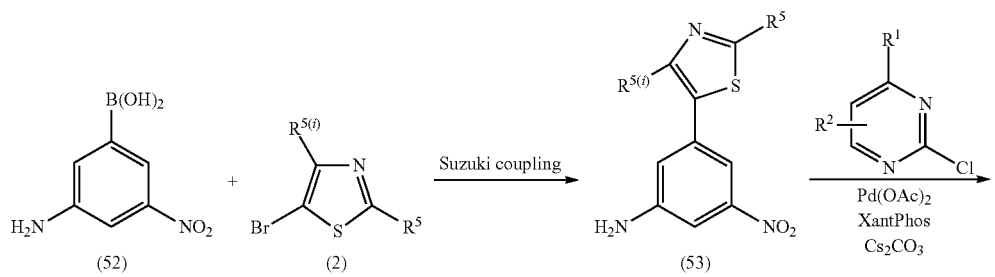

-continued

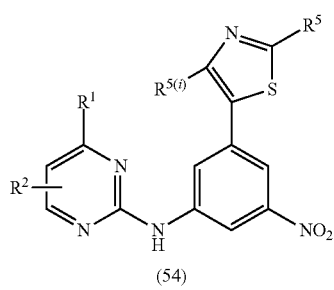
(54)

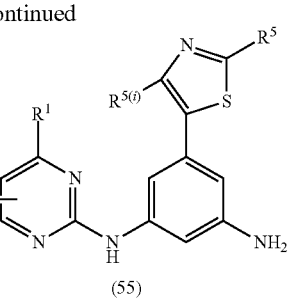
(55)

H₂, Pd/C

R$^a$NCO

R$^a$C(O)Cl

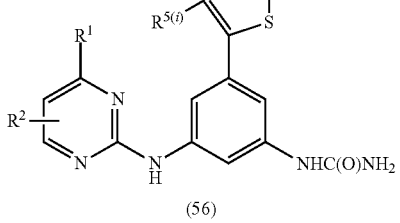
(56)

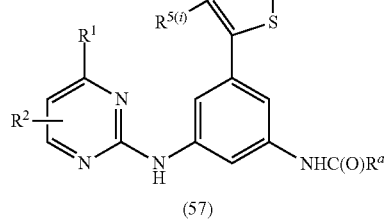
(57)

Suzuki coupling of a thiazole bromides (2) with (3-amino-5-nitrophenyl)boronic acid (52) affords biaryl compounds (53). Palladium catalyzed coupling of compounds (53) with 2-chloropyrimidines provides nitroarenes (54), which are reduced to provide anilines (55). Acylation with acyl chlorides provides amides (57), and reactions of isocyanates provide ureas (56).

SCHEME 12

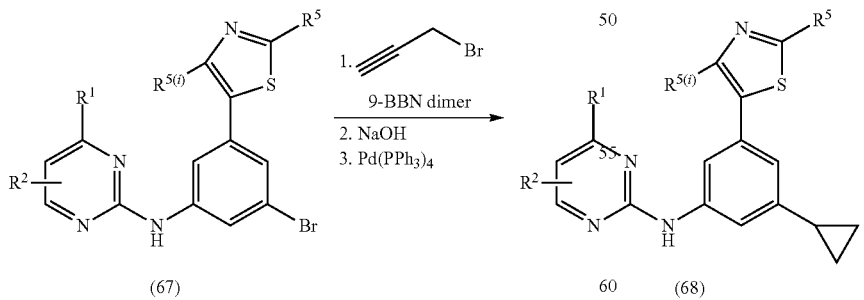

-continued

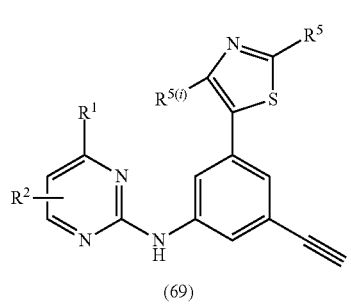
(69)

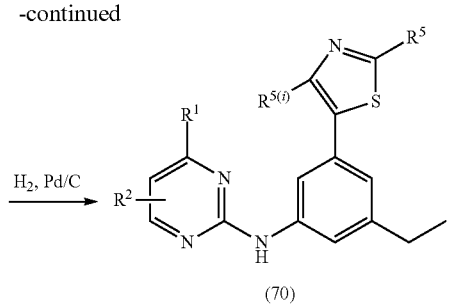
(70)

The bromides (67) are subjected to Sonogashira coupling with TMS-acetylene and subsequent silyl deprotection yields the acetylene compounds (69), which are reduced to yield compounds (70). Palladium-mediated coupling of (67) with cyclopropylboronate (prepared according to literature; see: J. A.; Huertas, R.; Leon-Colon, G. *Tetrahedron Lett.* 2000, 41, 4251-4255) provides the cyclopropyl compound (68).

SCHEME 13

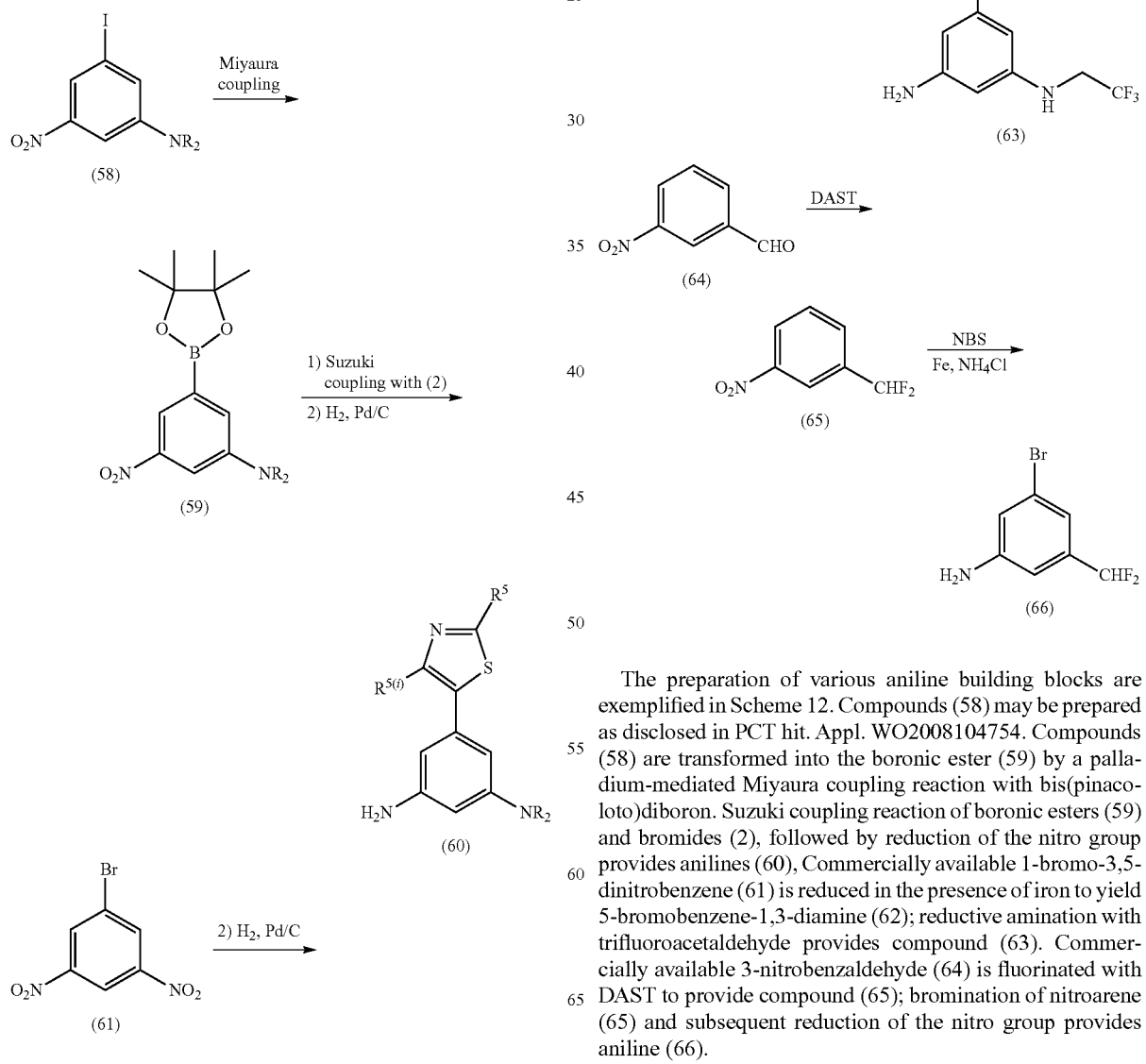

The preparation of various aniline building blocks are exemplified in Scheme 12. Compounds (58) may be prepared as disclosed in PCT hit. Appl. WO2008104754. Compounds (58) are transformed into the boronic ester (59) by a palladium-mediated Miyaura coupling reaction with bis(pinacoloto)diboron. Suzuki coupling reaction of boronic esters (59) and bromides (2), followed by reduction of the nitro group provides anilines (60), Commercially available 1-bromo-3,5-dinitrobenzene (61) is reduced in the presence of iron to yield 5-bromobenzene-1,3-diamine (62); reductive amination with trifluoroacetaldehyde provides compound (63). Commercially available 3-nitrobenzaldehyde (64) is fluorinated with DAST to provide compound (65); bromination of nitroarene (65) and subsequent reduction of the nitro group provides aniline (66).

SCHEME 14

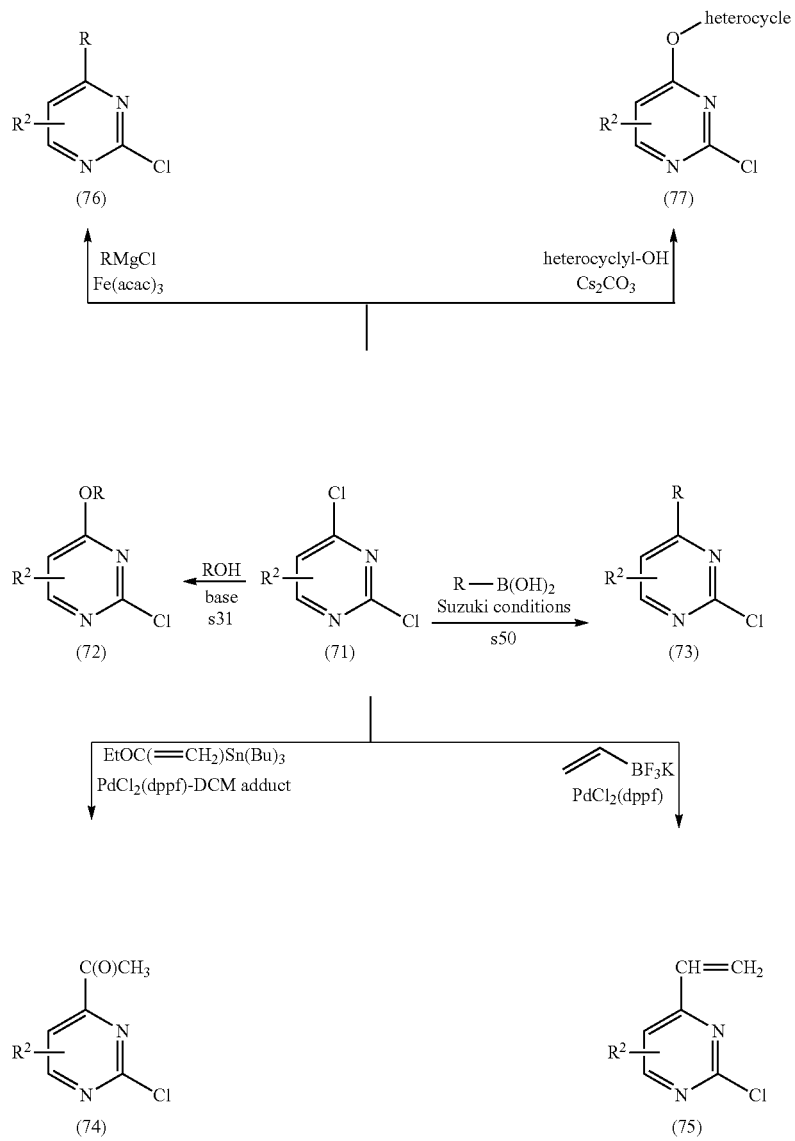

R is e.g., lower alkyl, cycloalkyl

Preparation of 2-chloropyrimidine building blocks starting with 2,4-dichloropyrimidines (71) is illustrated in Scheme 13. Pyrimidine functionalization via Suzuki coupling yields substituted 2-chloropyrimidines (73), while a base mediated $S_NAr$ reaction with substituted alcohol nucleophile provides ethers (72). Reaction of compounds (71) with commercially available vinyl potassium trifluoroborate provided olefin adducts (75). Stille coupling of compounds (71) with commercially available tributyl(1-ethoxyethenyl)stannane provided ketones (74). Compounds (71) are transformed into compounds (74) via an iron-catalyzed Grignard addition, and into compounds (77) by the action of an alcohol and base. Compounds (76) are prepared by an iron promoted coupling of Grignard reagents with compounds (71)

SCHEME 15

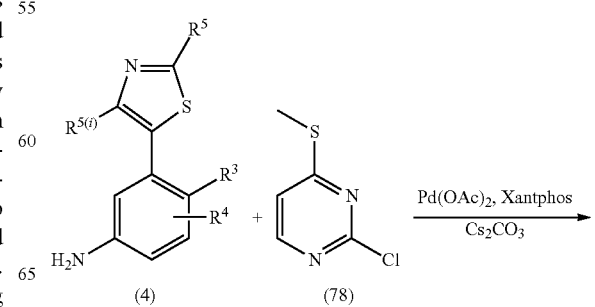

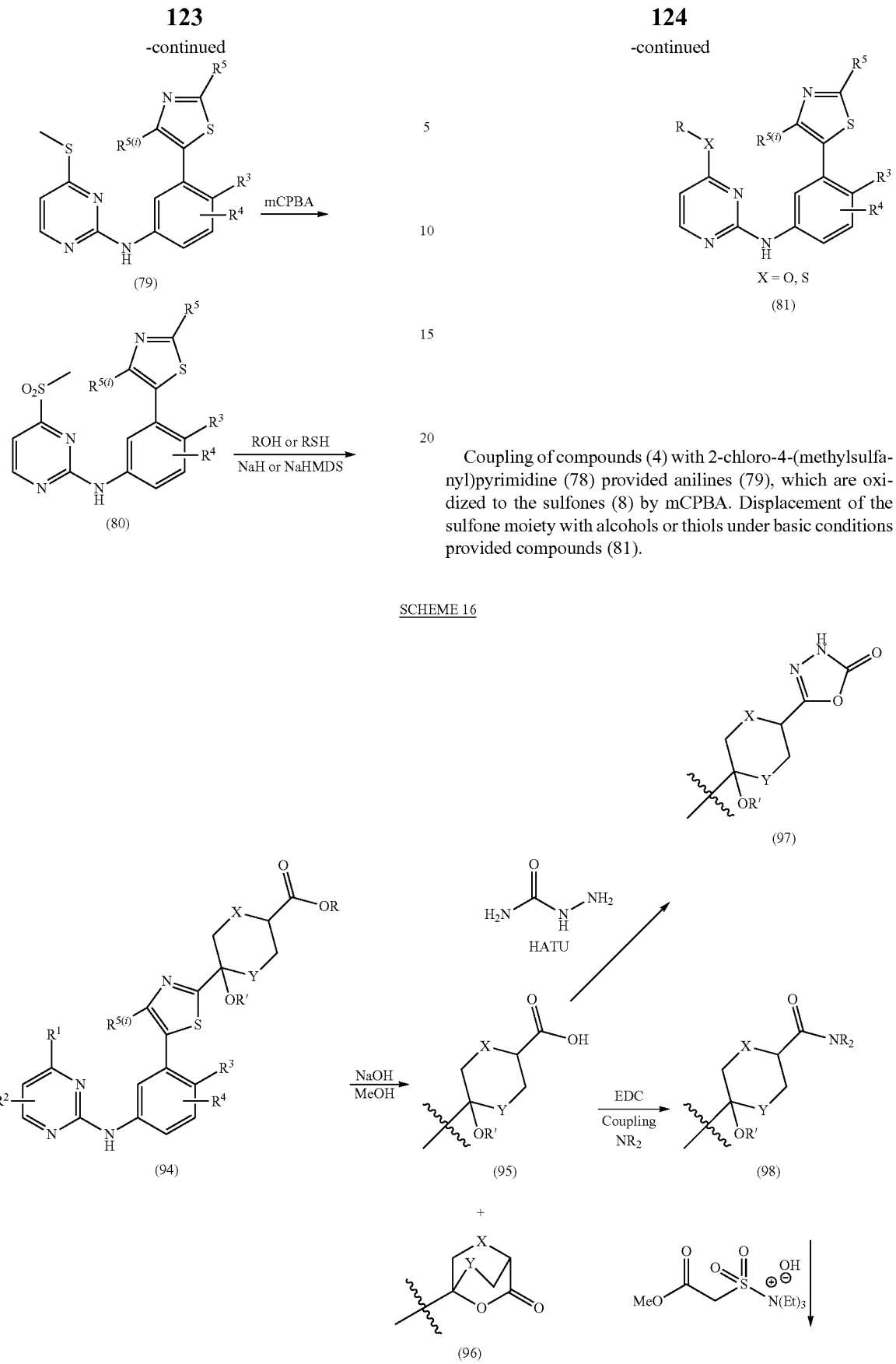
Coupling of compounds (4) with 2-chloro-4-(methylsulfanyl)pyrimidine (78) provided anilines (79), which are oxidized to the sulfones (8) by mCPBA. Displacement of the sulfone moiety with alcohols or thiols under basic conditions provided compounds (81).
SCHEME 16

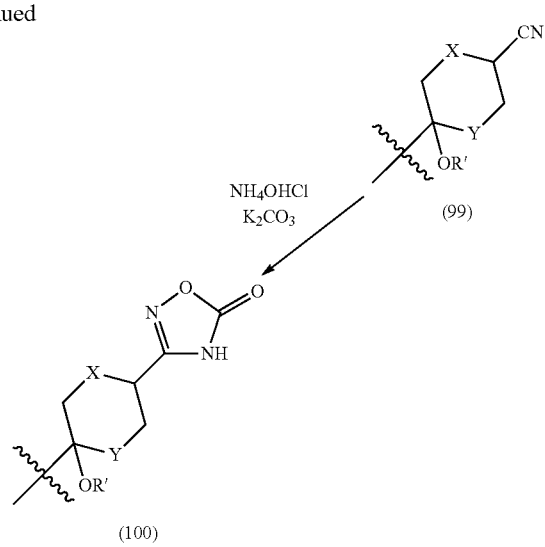

R' is H or Me; X and Y are independently a bond, CH₂, CH(CH₃) or C(CH₃)₂

Saponfication of esters (94) yields acids (95) and the lactones (96). Reaction of acids (95) with hydrazine carboxamide yields the 1,3,4-oxadiazoles (97). Alternatively, amide coupling with acids (95) yields amides (98). Dehydration of the amides (98) with a sulfamoyl salt affords the nitriles (99). Cyclization of the nitriles (99) with ammonium hydroxide yields the 1,2,4-oxadiazoles (100).

SCHEME 17

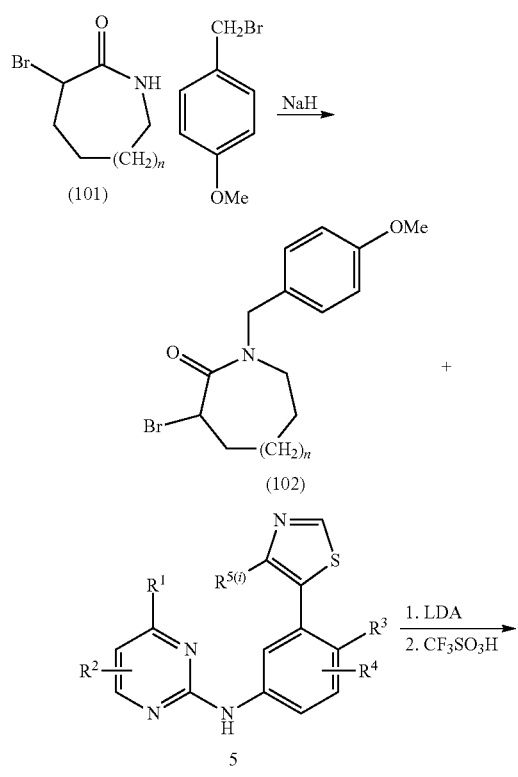

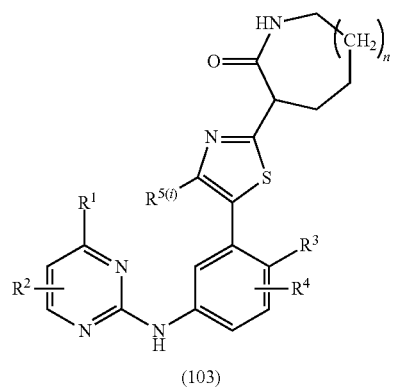

n is e.g., 0 or 1

Alkylation of bromolactams (101) with 1-(bromomethyl)-4-methoxybenzene gives compounds (102). Deprotonation of thiazole (5) with LDA followed by the addition of 3-bromo azepariones (102) gives (103) after deprotection under acidic conditions.

SCHEME 18

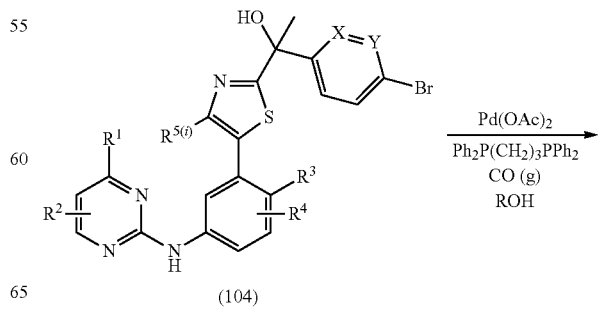

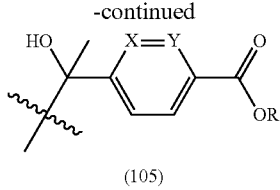

(105)

X, Y = CH or N

SCHEME 20

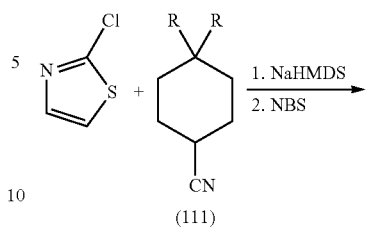

Carbonylation of (104) in the presence of carbon monoxide and a palladium catalyst yields (105).

SCHEME 19

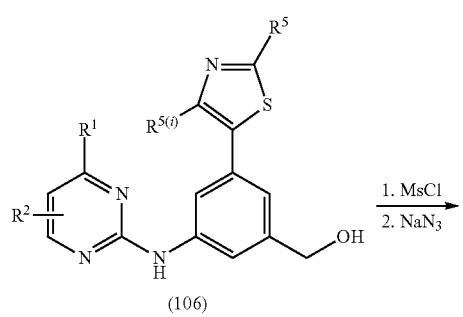

(106)

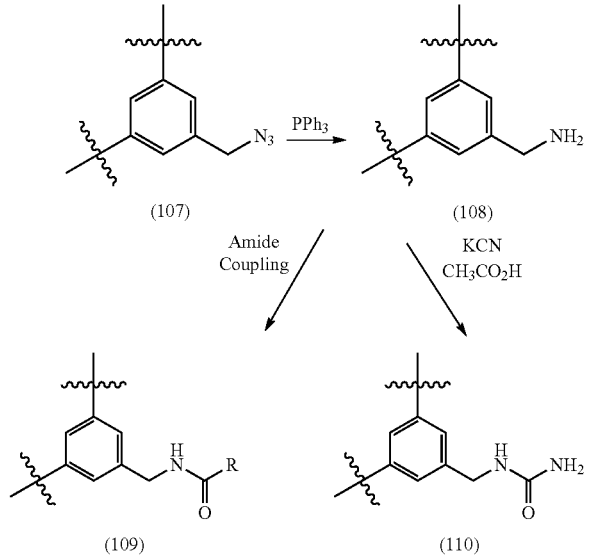

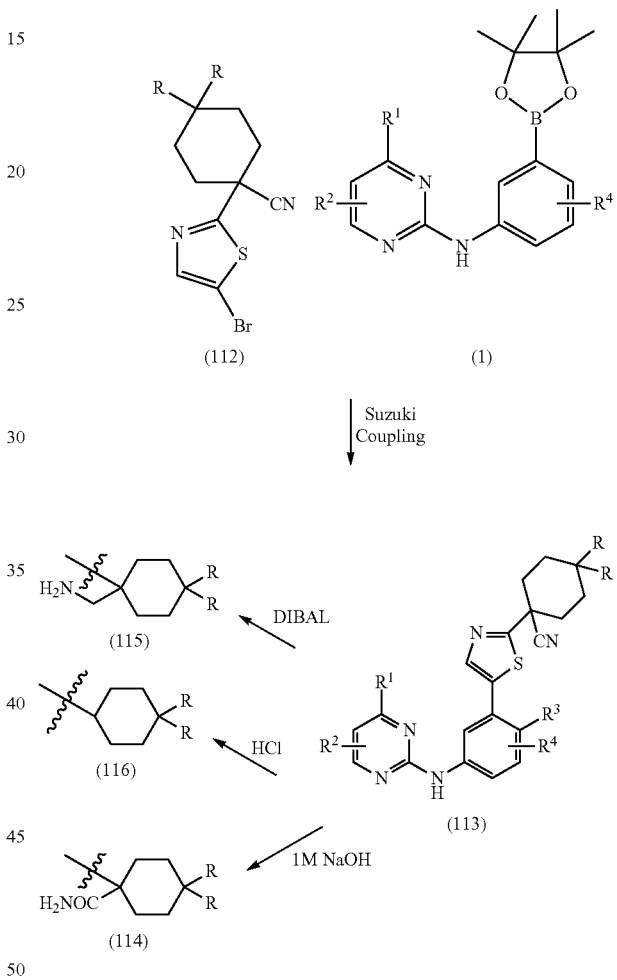

Primary alcohols (106) are activated with MsCl and the resulting methansulfonates are displaced with azide to produce azides (107). Reduction of azides (107) with triphenylphosphine gives the corresponding amines (108). Amide coupling of (108) by the action of an amine and an appropriate coupling reagent gives amides (109). Reaction of amines (108) with potassium cyanide gives the ureas (110).

In Scheme 20 the two R groups and the carbon to which they are attached represent a ketal such as 1,3-dioxolane. 2-Chlorothiazole is reacted with (111) in the presence of NaHMDS followed by bromination provides (112). Suzuki coupling of (1) with (112) yields (113). Hydrolysis of (113) gives (114). The nitrile (113) is reduced with DIBAL to give the amine (115) or reacted with hydrochloric acid to give the cyclohexyl compound (116). The ketal can be converted into the ketone, which may be further elaborated into appropriate functional groups.

SCHEME 21

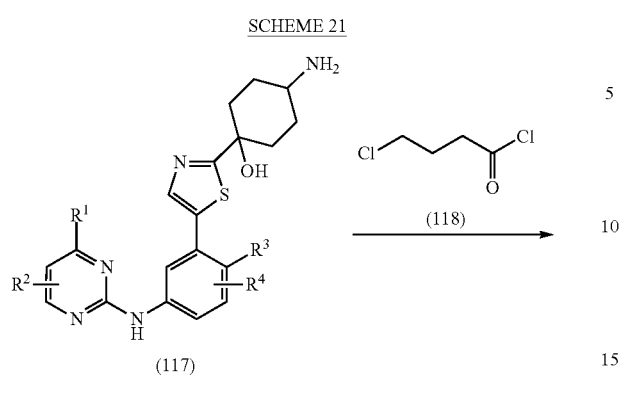

(117) + (118) →

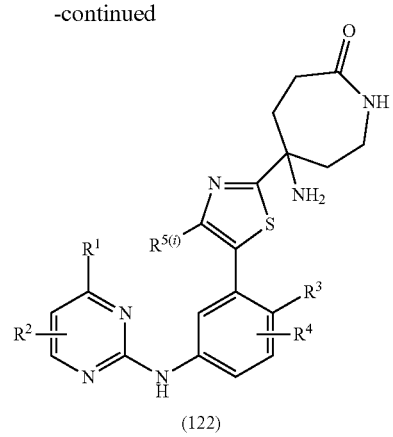

(122)

Reaction of amines (117) with acid chloride (118) gives lactams (119).

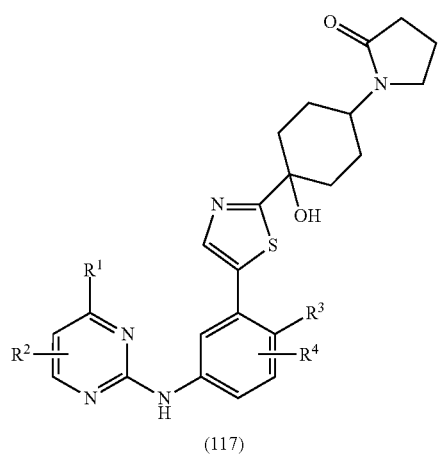

(119)

SCHEME 22

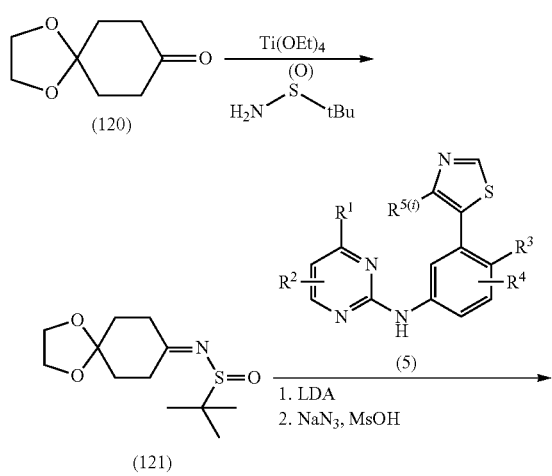

Ketone (120) is reacted with t-butyl sulfonamide in the presence of titanium ethoxide to afford (121). Deprotonation of compound (5) with LDA followed by the addition of (121) and then ring expansion by the action of acid and azide gives (122).

Compounds of formula I, as well as intermediates for their synthesis, can be prepared according to the procedures described in the Schemes, Preparation of Intermediates, and Examples herein, using appropriate materials and are further exemplified by the following specific intermediates and examples. The compounds exemplified are representative of the invention, and are not to be construed as limiting the scope of the invention in any manner. The examples further illustrate details for the preparation of the compounds of the present invention. Those skilled in the art will readily understand that known variations of protecting groups, of reagents, as well as of the conditions and processes of the following preparative procedures, can be used to prepare intermediates and compounds of the instant invention. It is also understood that whenever a chemical reagent is not commercially available, such a chemical reagent can be readily prepared by those skilled in the art by either following or adapting known methods described in the literature. All temperatures are degrees Celsius unless otherwise noted. Mass spectra (MS) were measured either by electrospray ion-mass spectroscopy (ESI) or by atmospheric pressure chemical ionization mass spectroscopy (APCI).

PREPARATION OF INTERMEDIATES

Intermediate 1:
1-(5-bromo-1,3-thiazol-2-yl)cyclobutanol

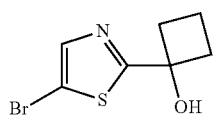

Step 1

Isopropylmagnesium chloride/lithium chloride complex (1.3 M in THF, 582 mL, 756 mmol) was cooled to 0° C. Thiazole (53.2 mL, 749 mmol) was added over 15 minutes, resulting in an orange/red solution. Stirred for 20 min at 0° C., then removed cooling bath and allowed to warm to rt. Stirred an additional 2 h, then retooled to 0° C. Cyclobutanone (53.3 mL, 713 mmol) was added over 50 min, Removed the cooling bath and allowed to warm to rt and stirred 20 min at that temperature. The reaction mixture was cooled to 0° C. and saturated aqueous ammonium chloride was slowly added. The mixture was diluted with EtOAc, the layers separated and the organic portion washed with water. The aqueous layer was washed with ethyl acetate. The combined organic portions were dried over MgSO$_4$ and concentrated in vacuo to provide 127.5 g of material containing 1-(1,3-thiazol-2-yl)cyclobutanol, which was used without further purification.

Step 2

The product of Step 1 (171.9 g, 1.107 mol) was dissolved in DMF (860 mL) and cooled to 0° C. Added NBS (236 g, 1.327 mol) and stirred 1 h at 0° C. Removed the cooling bath and allowed to warm to rt. Followed by LC until the starting material was consumed. The solution was poured into cooled water (2 L) containing Na$_2$SO$_3$ (30 g), washing with MTBE (1 L). The mixture was stirred 10 min, then diluted with MTBE (1.5 L) and water (500 mL). Separated the layers and washed the organic portion with water (2 L). The aqueous portions were extracted with MTBE (2 L). The combined organic extracts were dried over MgSO$_4$ and concentrated in vacuo to provide an orange oil. Diluted in hexanes at 50° C. (1 L). Stirred while slowly allowing to cool. Added seed crystals, and crystallization began around 35° C. Stirred overnight at rt. Cooled to −20° C. and stirred 20 min. Filtered, washing with hexane at −20° C. Dried under a nitrogen bag to provide 1-(5-bromo-1,3-thiazol-2-yl)cyclobutanol (172.9 g, 739 mmol, 67%). The filtrate and all remaining material in the flask was diluted in CH$_2$Cl$_2$ and concentrated in vacuo. Hexane added, concentrated to ~300 mL cooled to rt and seed crystals were added. Began to crystallize. Cooled to −10° C. and filtered, washing with hexane at −10° C. Second crop of crystals allowed to air dry providing 1-(5-bromo-1,3-thiazol-2-yl)cyclobutanol (38.8 g, 166 mmol, 15%). The mother liquor from the second filtration was concentrated and purified by column chromatography on silica gel (Biotage EtOAc/Hex) then dried under vacuum to provide 1-(5-bromo-1,3-thiazol-2-yl)cyclobutanol (10.6 g, 45 mmol, 4%). Overall, obtained 1-(5-bromo-1,3-thiazol-2-yl)cyclobutanol (222 g, 948 mmol, 86%). $^1$H NMR (400 MHz, CDCl$_3$): δ 7.58 (s, 1H); 3.56 (br s, 1H); 2.69-2.60 (m, 2H); 2.47-2.36 (m, 2H); 2.09-1.87 (m, 2H).

Intermediate 2: N-(3-bromo-5-methylphenyl)-4-(trifluoromethyl)pyrimidin-2-amine

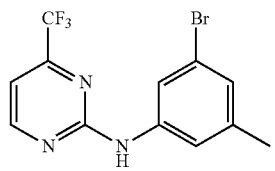 [SMILES: Cc1cc(Br)cc(Nc2nccc(C(F)(F)F)n2)c1]

A solution of 3-bromo-5-methylaniline (162.5 g, 873.66 mmol) in 1,4-dioxane (2 L) was prepared, and 2-chloro-4-(trifluoromethyl)pyrimidine (182 g, 994.54 mmol) and methanesulfonic acid (97.5 g, 1.02 mol) were added sequentially. The resulting solution was heated to reflux overnight. The resulting mixture was cooled and concentrated in vacuo. The residue was diluted with 2 L of water, then adjusted to pH 7-8 with aqueous sodium bicarbonate solution, followed by extraction with EtOAc (2×2 L) The organic layers were combined, washed with water (2×2 L), dried over anhydrous sodium sulfate and concentrated in vacuo. This resulted in N-(3-bromo-5-methylphenyl)-4-(trifluoromethyl)pyrimidin-2-amine (200 g, 602 mmol, 69%) as a light yellow solid. MS (ESI): [M+H]$^+$ 334.0. $^1$H NMR (400 MHz, CDCl$_3$): δ 8.68 (d, J=4.9 Hz, 1H); 7.79 (s, 1H); 7.30 (s, 2H); 7.10-7.06 (m, 2H); 2.36 (s, 3H).

Intermediate 3: N-[3-methyl-5-(4,4,5,5-tetramethyl-1,3,2-dioxaborolan-2-yl)phenyl]-4-(trifluoromethyl)pyrimidin-2-amine

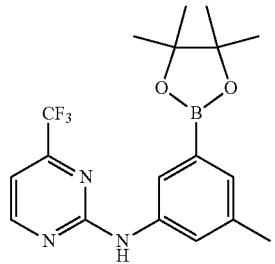 [SMILES: Cc1cc(Nc2nccc(C(F)(F)F)n2)cc(B2OC(C)(C)C(C)(C)O2)c1]

To a solution of Intermediate 2 (250 g, 753.01 mmol,) in 1,4-dioxane (3 L) was added 4,4,5,5-tetramethyl-2-(4,4,5,5-tetramethyl-1,3,2-dioxaborolan-2-yl)-1,3,2-dioxaborolane (225 g, 885.83 mmol), KOAc (225 g, 2.30 mol) and Pd(dppf)Cl$_2$ (19 g, 25.23 mmol). The resulting solution was heated to reflux overnight. The solid was filtered. The filtrate was decolorized by passing through a silica gel column. The fractions were collected and concentrated in vacuo. This resulted in 110 g pure and 150 g crude product. The crude product was decolorized again with active carbon to provide an additional 125 g of pure product. This resulted in N-[3-methyl-5-(4,4,5,5-tetramethyl-1,3,2-dioxaborolan-2-yl)phenyl]-4-(trifluoromethyl)pyrimidin-2-amine (235 g, 620 mmol, 82%) as a white solid. MS APCI: [M+H]$^+$ m/z 380. $^1$H NMR (400 MHz, CDCl$_3$, ppm): 1.350 (12H, s), 2.386 (3H, s), 6.993-7.006 (1H, d, J=5.2 Hz), 7.385-7.427 (2H, s), 7.636 (1H, s), 7.753 (1H, s), 8.608-8.621 (1H, d, J=5.2 Hz).

Intermediate 4: N-[3-methyl-5-(1,3-thiazol-5-yl)phenyl]-4-(trifluoromethyl)pyrimidin-2-amine

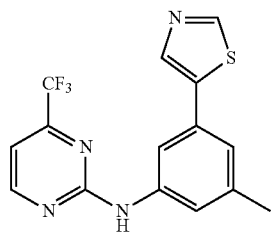 [SMILES: Cc1cc(Nc2nccc(C(F)(F)F)n2)cc(-c2cncs2)c1]

To a solution of Intermediate 3 (80 g, 211.08 mmol) in 1,4-dioxane (800 mL) was added 5-bromo-1,3-thiazole (28 g, 171.78 mmol), Pd(dppf)Cl$_2$ (8 g, 10.62 mmol) and a solution of sodium carbonate (44.7 g, 421.70 mmol) in water (447 mL). The resulting solution was heated to reflux for 1 hour. Then it was allowed to cool and concentrated in vacuo. The residue was diluted with EtOAc (500 mL) and filtered. The filtrate was washed with brine (2×300 mL) and water (2×300 mL). The organic layer was dried over anhydrous sodium sulfate and concentrated in vacuo. The crude product was recrystallized from EtOAc:DCM in the ratio of 1:5 to get 34 g of product. The mother liquor was applied onto a silica gel column and eluted with dichloromethane/ethyl acetate (2:1). This resulted in N-[3-methyl-5-(1,3-thiazol-5-yl)phenyl]-4-(trifluoromethyl)pyrimidin-2-amine (42 g, 125 mmol, 73%) as a pale yellow solid. MS APCI: [M+H]$^+$ m/z 337. $^1$H NMR (400 MHz, CD$_3$COCD$_3$, ppm): 2.413 (3H, s), 7.250-7.263 (2H, m), 7.636 (1H, s), 8.204-8.213 (2H, m), 8.834-8.846 (1H, d, J=4.8 Hz), 8.970 (1H, s), 9.210 (1H, br). rhSYK activity=+++.

Intermediate 5: N-(3-bromophenyl)-4-(trifluoromethyl)pyrimidin-2-amine

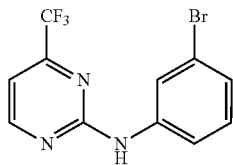 [SMILES: FC(F)(F)c1ccnc(Nc2cccc(Br)c2)n1]

A solution of 3-bromoaniline (250 g, 1.46 mol) in 1,4-dioxane (2.5 L) was prepared, and 2-chloro-4-(trifluoromethyl)pyrimidine (267 g, 1.47 mol) and methanesulfonic acid (155 g, 1.61 mol) were added sequentially. The resulting solution was heated to 100° C. overnight. The resulting mixture was cooled and concentrated in vacuo. The residue was adjusted to pH 7-8 with aqueous sodium bicarbonate solution. The solid was filtered, and the filtrate was extracted with EtOAc (4×500 mL) The organic layers were combined, washed with water (2×2 L), dried over anhydrous sodium sulfate and concentrated in vacuo. This resulted in N-(3-bromophenyl)-4-(trifluoromethyl)pyrimidin-2-amine (200 g, 629 mmol, 43%) as a light yellow solid. MS APCI: [M+3]$^+$ m/z 319. $^1$H NMR (500 MHz, CDCl$_3$): δ 8.68 (d, J=4.9 Hz, 1H); 7.95 (s, 1H); 7.53-7.50 (m, 1H); 7.44 (br s, 1H); 7.22 (m, 2H); 7.08 (d, J=4.9 Hz, 1H).

Intermediate 6: N-[3-(4,4,5,5-tetramethyl-1,3,2-dioxaborolan-2-yl)phenyl]-4-(trifluoromethyl)pyrimidin-2-amine

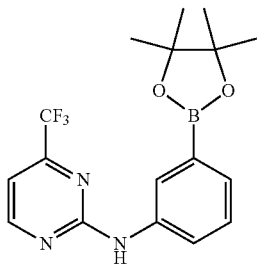 [SMILES: CC1(C)OB(c2cccc(Nc3nccc(C(F)(F)F)n3)c2)OC1(C)C]

To a solution of Intermediate 5 (200 g, 631 mmol,) in 1,4-dioxane (2 L) was added 4,4,5,5-tetramethyl-2-(4,4,5,5-tetramethyl-1,3,2-dioxaborolan-2-yl)-1,3,2-dioxaborolane (177 g, 697 mmol), KOAc (187 g, L91 mol) and Pd(dppf)C12 (24 g, 32 mmol). The resulting solution was heated to 100° C. for 2 h. The reaction was allowed to cool, and the solid was filtered. The filtrate was concentrated in vacuo. The residue was applied onto a silica gel column and eluted with ethyl acetate/petroleum ether (1:10). This resulted in N-[3-(4,4,5,5-tetramethyl-1,3,2-dioxaborolan-2-yl)phenyl]-4-(trifluoromethyl)pyrimidin-2-amine (140 g, 384 mmol, 61%) as a white solid. MS APCI: [M+H]$^+$ m/z 366. $^1$H NMR (400 MHz, DMSO-d6, ppm): 1300 (12H, s), 7.237-7.249 (1H, m), 7.331-7.342 (2H, m), 7.882-7.910 (1H, m), 8.000 (1H, s), 8.796-8.806 (1H, m), 10.130 (1H, s).

Intermediate 7: N-[3-(1,3-thiazol-5-yl)phenyl]-4-(trifluoromethyl)pyrimidin-2-amine

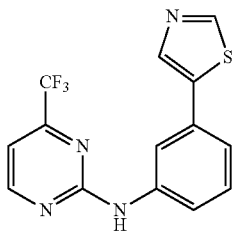 [SMILES: FC(F)(F)c1ccnc(Nc2cccc(-c3cncs3)c2)n1]

Pd(dppf)Cl$_2$ (1.01 g, 1.23 mmol) and Intermediate 6 (9.0 g, 25 mmol) were combined in a flask and were evacuated and back-filled with nitrogen (×3). Added 2-Me THF (90 mL), 5-bromothiazole (4.45 g, 27.1 mmol), and aqueous sodium carbonate (24.7 mL, 49.3 mmol) sequentially. Sealed the flask and heated to 80° C. for 15 h. The brown solution was allowed to cool to rt, then diluted with water and EtOAc. The layers were separated, and the aqueous portion was extracted with EtOAc (2×). The combined organic portions were washed with saturated aqueous NaHCO$_3$, then Brine, then dried over Na$_2$SO$_4$ and concentrated in vacuo. Trituration with CH$_2$Cl$_2$ and collection of the beige solid via filtration provided 5.94 g of the desired product. The mother liquor was concentrated in vacuo and subsequent purification via silica gel column chromatography (CH$_2$Cl$_2$-40% EtOAc:CH$_2$Cl$_2$) provided an additional 1.41 g of the desired product. In total, N-[3-(1,3-thiazol-5-yl)phenyl]-4-(trifluoromethyl)pyrimidin-2-amine (7.35 g, 22.8 mmol, 93%) was isolated as a beige solid. MS APCI: [M+H]$^+$ m/z 323. $^1$H NMR (600 MHz, DMSO-D$_6$, ppm) δ 10.32 (s, 1H), 9.06 (s, 1H), 8.82 (d, J=4.8, 1H), 8.20 (d, J=8.2, 1H), 8.20 (s, 1H), 7.64 (d, J=7.5, 1H), 7.40-7.31 (m, 2H), 7.27 (d, J=4.9, 1H). rhSYK activity=++.

Intermediate 8: 4-(3-iodo-5-nitrophenyl)morpholine

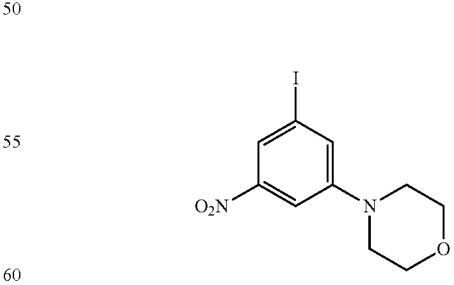

To a solution of 1-fluoro-3-iodo-5-nitrobenzene (4.0 g, 15 mmol) in DMSO (7.5 mL) was added morpholine (3.26 mL, 37.5 mmol), and the mixture (which instantly became purple) was heated to 130° C. for 30 min in the microwave. Purification was attempted by directly loading the mixture onto a silica gel column (80 g; load neat w/CH$_2$Cl$_2$ rinse; 100:0 to 60:40 hexanes:EtOAc over 35 minutes) but the mixture crashed at the top of the column and not all the mixture could be loaded. Nonetheless, after an initial spike in pressure, purification was possible, and the residual material was purified in a second purification (24 g; load w/CH₂Cl₂; 100:0 to 60:40 hexanes:EtOAc over 20 minutes). Concentration of the combined fractions from the two purifications provided 4-(3-iodo-5-nitrophenyl)morpholine (4.01 g, 12.0 mmol, 80%) as a bright yellow solid. ¹H NMR (400 MHz, CDCl₃): δ 7.99 (s, 1H); 7.67 (s, 1H); 7.47 (s, 1H); 3.89 (m, 4H); 3.26 (m, 4H).

Intermediate 9: N-[3-(2-bromo-1,3-thiazol-5-yl)-5-methylphenyl]-4-(trifluoromethyl)-pyrimidin-2-amine

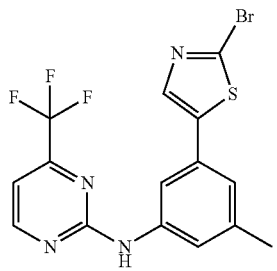 [SMILES: Cc1cc(Nc2nccc(C(F)(F)F)n2)cc(-c2cnc(Br)s2)c1]

Lithium diisopropylamide (1.8 M in THF/heptane/ethylbenzene, 11.4 mL, 20.5 mmol) was cooled to −70° C. Intermediate 4 (2.3 g, 6.8 mmol) in THF (23 mL) was added slowly over 15 minutes, keeping the temperature at −65° C. The reaction was allowed to stir for 30 minutes following the addition and then bromine (0.53 mL, 10.3 mmol) was added. The reaction was stirred for 30 minutes and then quenched with 20 mL of water and warmed to rt. The reaction was diluted with EtOAc (50 mL). The layers were separated and the organic portion was washed with Na₂SO₃ (10% aqueous), brine, dried over MgSO₄ and concentrated in vacuo. Purification via column chromatography (ISCO, dry load with silica gel, Hexane-50% EtOAc:Hexane) to provide N-[3-(2-bromo-1,3-thiazol-5-yl)-5-methylphenyl]-4-(trifluoromethyl)pyrimidin-2-amine (1.88 g, 4.53 mmol, 66%). MS APCI: [M+H]⁺ m/z 414.8, 416.8. ¹H NMR (600 MHz, CDCl₃) δ 8.64 (d, 4.9, 1H), 7.88 (s, 1H), 7.74 (s, 1H), 7.33 (s, 1H), 7.05 (t, J=6.4, 1H), 7.01 (s, 1H), 2.38 (s, 3H).

Intermediate 10: N-[3-bromo-5-(4,4,5,5-tetramethyl-1,3,2-dioxaborolan-2-yl)phenyl]-4-(trifluoromethyl)pyrimidin-2-amine

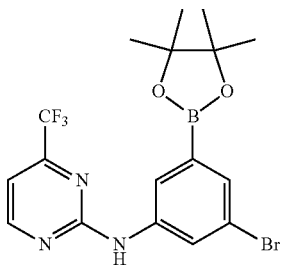 [SMILES: CC1(C)OB(c2cc(Br)cc(Nc3nccc(C(F)(F)F)n3)c2)OC1(C)C]

Step 1

To a solution of 3,5-dibromoanaline (4.47 g, 17.8 mmol) and 2-chloro-4-(trifluoromethyl)pyrimidine (2.36 mL, 19.6 mmol) was added p-toluenesulfonic acid (4.06 g, 21.4 mmol), resulting in the formation of a thick suspension. This mixture was heated to 100° C. overnight, during which it became a deep red solution. The mixture was diluted with 200 mL EtOAc and washed with 200 mL sat. NaHCO₃ (aq) and 200 mL brine. The organic layer was dried (Na₂SO₄) and concentrated in vacuo. Purification by chromatography on silica gel (220 g; load w/toluene; 100:0 to 85:15 hexanes:EtOAc over 45 minutes) provided N-(3,5-dibromophenyl)-4-(trifluoromethyl)pyrimidin-2-amine (5.85 g, 14.7 mmol, 83%) as a light yellow solid. MS APCI: [M+H]⁺ m/z 397.8. ¹H NMR (400 MHz, CDCl₃): δ 8.72 (d, J=4.9 Hz, 1H); 7.84 (s, 2H); 7.39 (s, 1H); 7.34 (s, 1H); 7.14 (d, J=4.9 Hz, 1H).

Step 2

To a solution of the product of Step 1 (2.0 g, 5.0 mmol) in DMSO (10.1 mL) were added 4,4,5,5-tetramethyl-2-(4,4,5,5-tetramethyl-1,3,2-dioxaborolan-2-yl)-1,3,2-dioxaborolane (1.4 g, 5.5 mmol), KOAc (1.48 g, 15.1 mmol) and Pd(dppf)Cl₂ (123 mg, 0.151 mmol), and the mixture was heated to 125° C. for 30 minutes in the microwave. The mixture was diluted with 100 mL EtOAc and washed with 2×100 mL 1:1 H₂O:brine. The organic layer was dried (Na₂SO₄) and concentrated in vacuo. Purification by Chromatography on silica gel (80 g; load w/CH₂Cl₂; 100:0 to 70:30 hexanes:EtOAc over 40 minutes) provided N-[3-bromo-5-(4,4,5,5-tetramethyl-1,3,2-dioxaborolan-2-yl)phenyl]-4-(trifluoromethyl)pyrimidin-2-amine (755 mg, 1.70 mmol, 34%) as an off-white solid. ¹H NMR (500 MHz, DMSO-d₆) δ 8.86 (d, J=4.9, 1H), 8.25 (s, 1H), 7.96 (s, 1H), 7.36 (s, 1H), 7.32 (d, J=4.9, 1H), 1.34 (s, 12H).

Intermediate 11: N-[3-bromo-5-(1,3-thiazol-5-yl)phenyl]-4-(trifluoromethyl)pyrimidin-2-amine

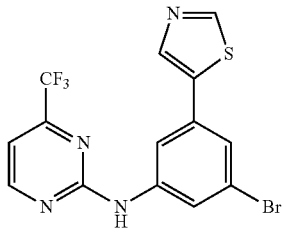 [SMILES: FC(F)(F)c1ccnc(Nc2cc(Br)cc(-c3cncs3)c2)n1]

A solution of Pd(OAc)₂ (19 mg, 0.085 mmol) and butyl di-1-adamantyl phosphine (61 mg, 0.18 mmol) in THF (12.8 mL) was stirred for 15 min. Intermediate 10 (755 mg, 1.70 mmol), 5-bromo-1,3-thiazole (760 μL, 8.50 mmol), potassium fluoride (296 mg, 5.10 mmol), and water (4.25 mL) were then added, and the mixture was heated to 75° C. overnight. After cooling to rt, the mixture was diluted with 100 mL EtOAc and washed with 100 mL brine. A bright yellow solid remained undissolved on the walls of the separatory funnel, which was thus rinsed with 100 mL THF. The combined organic extracts were dried (Na₂SO₄) and concentrated in vacuo. Purification by Chromatography on silica gel (40 g; dry load; 100:0 to 50:50 hexanes:EtOAc over 25 minutes) provided N-[3-bromo-5-(1,3-thiazol-5-yl)phenyl]-4-(trifluoromethyl)pyrimidin-2-amine (449 mg, 1.12 mmol, 66%) as an off-white solid. MS APCI: [M+H]⁺ m/z 403.0. ¹H NMR (400 MHz, (CD₃)₂CO): δ 9.46 (s, 1H); 9.03 (s, 1H); 8.89 (d, J=4.9 Hz, 1H); 8.32-8.26 (m, 2H); 8.16 (s, 1H); 7.59 (s, 1H); 7.33 (d, J=4.9 Hz, 1H). rhSYK activity=++

Intermediate 12: N-[3-nitro-5-(4,4,5,5-tetramethyl-1,3,2-dioxaborolan-2-yl)phenyl]-4-(trifluoromethyl)pyrimidin-2-amine

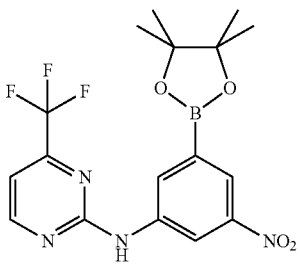 [SMILES: CC1(C)OB(c2cc(Nc3nccc(C(F)(F)F)n3)cc([N+](=O)[O-])c2)OC1(C)C]

A solution of 3-nitro-5-(4,4,5,5-tetramethyl-1,3,2-dioxaborolan-2-yl)aniline (9.09 g, 34.4 mol) and 2-chloro-4-(trifluoromethyl)pyrimidine (6.1 g, 33.4 mmol) in 1,4-dioxane (67 mL) was prepared. Methanesulfonic acid (2.17 mL, 33.4 mmol) was added. The resulting solution was heated to 110° C. overnight. The resulting mixture was cooled and aqueous sodium bicarbonate solution was added. Extracted with EtOAc. Washed with brine, dried over anhydrous sodium sulfate, filtered through a plug of silica gel, and concentrated in vacuo. The resultant brown solid was triturated with hexanes, and the solid was filtered and dried in a vacuum oven for two days to provide N-[3-nitro-5-(4,4,5,5-tetramethyl-1,3,2-dioxaborolan-2-yl)phenyl]-4-(trifluoromethyl)pyrimidin-2-amine (11.7 g, 28.5 mmol, 85%). MS APCI: [M+H]⁺ m/z 411.1. ¹H NMR (600 MHz, CDCl₃) δ 9.00 (t, J=2.2 Hz, 1H), 8.71 (d, J=4.9 Hz, 1H), 8.32 (d, J=1.9 Hz, 1H), 8.01 (d, J=1.7 Hz, 1H), 7.55 (s, 1H), 7.11 (d, J=4.9 Hz, 1H), 1.35 (s, 12H).

Intermediate 13: N-[3-(4,4,5,5-tetramethyl-1,3,2-dioxaborolan-2-yl)-5-(trifluoromethyl)phenyl]-4-(trifluoromethyl)pyrimidin-2-amine

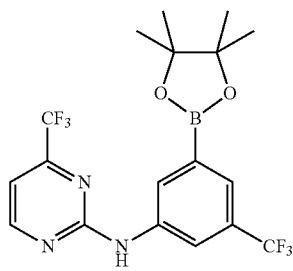 [SMILES: CC1(C)OB(c2cc(Nc3nccc(C(F)(F)F)n3)cc(C(F)(F)F)c2)OC1(C)C]

Step 1

To a solution of 2-chloro-4-trifluoromethylpyrimidine (1.224 g, 6.71 mmol) and 3-bromo-5-(trifluoromethyl)aniline (1.4 g, 5.83 mmol) in dioxane (20 ml) was added p-toluenesulfonic acid monohydrate (1.220 g, 6.42 mmol). An immediate white suspension formed. The tube was sealed and the slurry was stirred and heated at 100° C. for 24 h. The now clear solution was diluted with ethyl acetate and diethyl ether and washed with saturated NaHCO₃ (aq.). The organic fraction was dried over MgSO₄ and concentrated in vacuo. Product was further purified by column chromatography on silica gel, eluting with ethyl acetate/hexane with a gradient 0-30% to afford N-[3-bromo-5-(trifluoromethyl)phenyl]-4-(trifluoromethyl)pyrimidin-2-amine (2.252 g, 87%) as a light beige solid. MS APCI: [M+H]⁺ m/z 386.0. ¹H NMR (400 MHz, CDCl₃): δ 8.75 (d, J=4.9 Hz, 1H); 8.09 (s, 1H); 7.94 (s, 1H); 7.52-7.43 (m, 2H); 7.17 (d, J=4.9 Hz, 1H). rhSYK activity=+.

Step 2

To a solution of the product of Step 1 (790 mg, 2.046 mmol) in degassed DMSO (9.0 mL) were added PdCl₂ (dppf), 4,4,4',4',5,5,5',5'-octamethyl-2,2'-bi-1,3,2-dioxaborolane (572 mg, 2.251 mmol) and potassium acetate (602 mg, 6.14 mmol). Nitrogen was bubbled through the mixture for 2 min and then the tube was sealed and heated at 125° C. in the microwave. The reaction mixture was diluted with ethyl acetate and water. The layers were separated, and the aqueous fraction was extracted with ethyl acetate. The combined organic fractions were washed with water, brine and dried over MgSO₄. Product was further purified by column chromatography on silica gel, eluting with ethyl acetate/hexane with a gradient 0-50% to afford N-[3-(4,4,5,5-tetramethyl-1,3,2-dioxaborolan-2-yl)-5-(trifluoromethyl)phenyl]-4-(trifluoromethyl)pyrimidin-2-amine (886 mg, 80%) as a solid. ¹H NMR (400 MHz, CDCl₃): δ 8.70 (d, J=4.9 Hz, 1H); 8.41 (s, 1H); 7.93 (d, J=2.2 Hz, 1H); 7.79 (s, 1H); 7.43 (s, 1H); 7.10 (d, J=4.9 Hz, 1H); 1.38 (s, 12H).

Intermediate 14: 1-(5-Bromo-1,3-thiazol-2-yl)-2,2-difluoroethanol

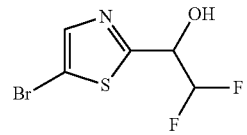 [SMILES: OC(c1ncc(Br)s1)C(F)F]

Step 1

This procedure is based on literature, see: Krasovskiy, A.; Krasovskaya, V.; Knochel, P. *Angew. Chem. Int. Ed.* 2006, 45, 2958. Thiazole (5.7 mL, 80 mmol) in THF (100 mL) was added to a stirred, cooled (0° C.) solution of isopropylmagnesium chloride-lithium chloride (1.18 M in THF, 74.9 mL, 88 mmol) in THF (75 mL) then the mixture was stirred at room temperature for 1 hour. Then the solution was cooled to −20° C. and ethyl difluoroacetate (9.29 ml, 88 mmol) was added. The mixture was stirred for 10 minutes at −20° C., then 10 minutes at room temperature. The mixture was diluted with ethyl acetate (200 mL), washed with aqueous ammonium chloride (saturated, 200 mL), dried (MgSO₄), filtered and the solvent was evaporated under reduced pressure. The residue was purified by column chromatography on silica gel (chromatography on silica gel, 0-90% ethyl acetate in hexanes) to give 2,2-difluoro-1-(1,3-thiazol-2-yl)ethanone (12 g, 73.6 mmol, 92% yield) as a yellow oil. MS ESI: [M+H]⁺ m/z 164.0.

Step 2

To a solution of the product of Step 1 (3 g, 18.39 mmol) in chloroform (90 mL) and methanol (22.5 mL) at 0° C. was added sodium borohyride (3.53 g, 18.49 mmol), portionwise. The reaction was then allowed to warm to room temperature and was diluted with a saturated aqueous sodium bicarbonate solution (200 mL). The aqueous layer was extracted with diethyl ether (2×100 mL) and the combined organic fractions were dried ($Na_2SO_4$), filtered and the solvent was evaporated under reduced pressure. 2,2-Difluoro-1-(1,3-thiazol-2-yl) ethanol was carried forward as an oil without further purification in the next step. MS ESI: $[M+H]^+$ m/z 166.0.

Step 3

Bromine (7.58 mL, 147 mmol) was added dropwise to a stirred mixture of the product of Step 2 (3.04 g, 18.39 mmol) and sodium acetate (15.10 g, 184 mmol) in acetic acid (92 mL) and the mixture was stirred at 80° C. for 12 hrs and then over the weekend at room temperature. The solvent was removed by evaporation ($Na_2S_2O_3$ trap). The residue was diluted with water:brine (1:1) and the aqueous phase was extracted 3× with ethyl acetate. The combined organics were washed with brine, dried ($Na_2SO_4$) and were concentrated. The resultant residue was purified by column chromatography on silica gel (chromatography on silica gel, 0-70% ethyl acetate in hexanes) to give 1-(5-bromo-1,3-thiazol-2-yl)-2,2-difluoroethanol (1.4 g, 5.74 mmol, 31.2% yield). $^1$H NMR (500 MHz, $CDCl_3$): δ 7.73 (s, 1H); 6.04 (td, J=55.0, 3.3 Hz, 1H); 5.15-5.09 (m, 1H).

Intermediate 15: 1-[5-(3-amino-5-methylphenyl)-1,3-thiazol-2-yl]cyclobutanol

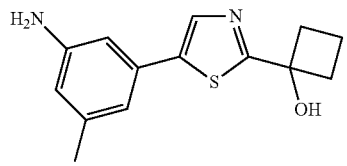 [SMILES: Cc1cc(N)cc(-c2cnc(C3(O)CCC3)s2)c1]

Step 1

Dioxane (720 mL) in a 1 L three-necked round bottom flask was degassed for 30 min. 3-Bromo-5-methylaniline (60 g, 193 mmol), (bispinacolato)diboron (96 g, 377 mmol), potassium acetate (42.7 g, 435 mmol), X-Phos (8.3 g, 17.41 mmol) and $Pd_2 dba_3$ (3.99 g, 4.35 mmol) were added to the degassed solvent under $N_2(g)$. After stirring for 10 min at room temperature, the reaction mixture was heated to an internal temperature of 80° C. After ca. 4 hours, the heating mantle was removed and replaced with an ice water bath. The reaction mixture was cooled to 30° C., and was then filtered through a pad of celite (washing with 500 mL of MTBE). This was transferred to a 4 L separatory funnel containing 500 mL pH 8 phosphate buffer, 500 mL brine, and an additional 500 mL of MTBE. The layers were cut and the organic washed with 1 L of a 1:1 mixture of brine and water. The aqueous layers were combined and sequentially back extracted with a second 500 mL portion of MTBE. The combined organics were treated with 100 g of $MgSO_4$ and the resulting mixture stirred for 20 min. This was then filtered and concentrated in vacuo. The resultant residue was purified by chromatography on silica gel (Biotage, 0-25% ethyl acetate in hexanes) to yield 3-methyl-5-(4,4,5,5-tetramethyl-1,3,2-dioxaborolan-2-yl)aniline (66 g, 255 mmol, 88%) as a light orange solid. MS APCI: $[M+H]^+$ m/z 234.2.

Step 2

To 500 mL three-necked round bottom flask were added 2-methyl THF (720 mL) and an aqueous solution of sodium carbonate (2 M, 367 mL, 734 mmol). The solution was degassed for 30 min. The product of Step 1 (90 g, 367 mmol), Intermediate 1 (86 g, 367 mmol) and $PdCl_2(dppf)$ (8.05 g, 11 mmol) were added to the degassed solution under $N_2(g)$. The resulting mixture was stirred for 5 min at room temperature and was then heated to 80° C. After ca. 9 hours, the heating mantle was removed and the reaction was cooled to 30° C. The reaction mixture was filtered through a pad of SolkaFloc employing water (500 mL) and ethyl acetate (500 mL) to complete the transfer. The filtrate was then transferred to a separatory funnel, using an additional 500 mL ethyl acetate and 250 mL brine to complete the transfer. The layers were cut, the organic washed with a mixture of water and brine (500 mL and 250 mL, respectively), and then the aqueous was back extracted with ethyl acetate (400 mL). The organics were combined, dried over $MgSO_4$ (100 g), filtered, and concentrated in vacuo to yield a brown crystalline solid. This material was recrystallized from hot ethyl acetate (250 mL at 60° C.), using hexanes as a counter-solvent (750 mL) to yield 1-[5-(3-amino-5-methylphenyl)-1,3-thiazol-2-yl]cyclobutanol (88 g, 338 mmol, 92%). MS APCI: $[M+H]^+$ m/z 261.2. $^1$H NMR (500 MHz, DMSO-$D_6$) δ 7.87 (s, 1H), 6.59 (s, 1H), 6.58 (s, 1H), 6.45 (s, 1H), 6.34 (s, 1H), 5.14 (s, 2H), 2.52-2.48 (m, 2H), 2.31 (q, J=9.3, 2H), 2.17 (s, 3H), 1.93-1.80 (m, 2H).

Intermediate 16:
3-Methyl-5-(1,3-thiazol-5-yl)aniline

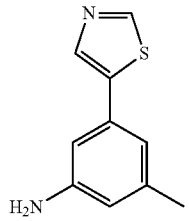

3-Methyl-5-(4,4,5,5-tetramethyl-1,3,2-dioxaborolan-2-yl)aniline (20.98 g, 90 mmol), 5-bromothiazole (8.85 mL, 99 mmol), and sodium carbonate (90 mL, 180 mmol) were combined in a flask. 2-Methyl-THF (326 mL) was added and the flask was degassed with $N_2$ for 1.5 h before 1,1'-bis(diphenylphosphino)ferrocene-palladium(II) dichloride dichloromethane complex (3.67 g, 4.50 mmol) was added. The reaction was heated to 100° C. overnight and was then cooled to room temperature. The reaction mixture was filtered though a pad of Celite, washing with ethyl acetate. The layers were separated and the aqueous layer was back-extracted with ethyl acetate, dried over $Na_2SO_4$, and concentrated. The residue was purified by chromatography (0-40% ethyl acetate in hexanes). 3-Methyl-5-(1,3-thiazol-5-yl)aniline was isolated as a yellowish brown solid (15.33 g, 81 mmol, 90%). MS ESI: $[M+H]^+$ m/z 191.1. $^1$H NMR (500 MHz, $CDCl_3$) δ 8.71 (s, 1H), 8.02 (s, 1H), 6.80 (s, 1H), 6.71 (s, 1H), 6.50 (s, 1H), 3.71 (s, 2H), 1.79 (s, 3H).

Intermediate 17: 2-[5-(3-amino-5-methylphenyl)-1,3-thiazol-2-yl]-1,1,1-trifluoropropan-2-ol

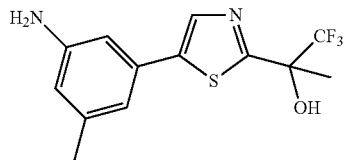 [SMILES: Cc1cc(N)cc(-c2cnc(C(C)(O)C(F)(F)F)s2)c1]

To diisopropylamine (18.73 ml, 131 mmol) in THF (263 mL) at −78° C. was added n-butyllithium (2.5 M in hexanes, 54.7 ml, 137 mmol). The reaction was aged for 30 minutes at −40° C. before cooling to −78° C. Intermediate 16 (10 g, 52.6 mmol) was added as a solution in 5 mL THF at −78° C. and was then warmed to 0° C. over 2 hours. The reaction was once again cooled to −78° C. before adding 1,1,1-trifluoroacetone (14.85 mL, 158 mmol) as a solution in 5 mL THF at −78° C. The reaction was allowed to warm to room temperature slowly, and was diluted with water and DCM. The layers were separated and the organic layer was dried over sodium sulfate and was concentrated in vacuo. The resultant residue was purified on silica gel (0-30% ethyl acetate in hexanes) to yield a yellow oil which solidified in hexanes overnight. The yellow to off-white solid was sonicated and filtered to yield 2-[5-(3-amino-5-methylphenyl)-1,3-thiazol-2-yl]-1,1,1-trifluoropropan-2-ol (11.69 g, 38.7 mmol, 73.6%). MS APCI: [M+H]$^+$ m/z 303.0. $^1$H NMR (500 MHz, CDCl$_3$) δ 7.85 (s, 1H), 6.76 (s, 1H), 6.67 (s, 1H), 6.52 (s, 1H), 4.53 (br s, 2H), 2.29 (s, 3H), 1.83 (s, 3H).

Intermediate 18: 4-methyl-N-[3-methyl-5-(4,4,5,5-tetramethyl-1,3,2-dioxaborolan-2-yl)phenyl]pyrimidin-2-amine

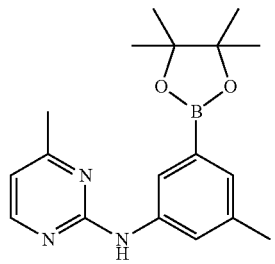 [SMILES: Cc1cc(Nc2nccc(C)n2)cc(B2OC(C)(C)C(C)(C)O2)c1]

Step 1

Acetic acid (0.234 mL, 4.08 mmol) was added to 2-chloro-4-methylpyrimidine (0.5 g, 3.89 mmol) and 3-bromo-5-methylaniline (1.096 g, 3.89 mmol) suspended in dioxane (7.78 mL). The reaction was heated to 120° C. overnight. Then, the reaction was cooled to room temperature and was directly purified by column chromatography on silica gel eluting with ethyl acetate/hexanes to give N-(3-bromo-5-methylphenyl)-4-methylpyrimidin-2-amine (1.08 g, 3.89 mmol, quant.) as a white solid. MS ESI: [M+H]$^+$ m/z 278.0 and 280.0.

Step 2

A 40 mL vial was charged with the product of Step 1 (500 mg, 1.798 mmol), bis(pinacolato)diboron (502 mg, 1.977 mmol), 1,1′-bis(diphenylphosphino)ferrocene-palladium(II) dichloride dichloromethane complex (44.0 mg, 0.054 mmol) and potassium acetate (529 mg, 5.39 mmol). The solid mixture was dissolved with DMSO (7.19 mL) and was heated to 120° C. After stirring for 2 h, the mixture was cooled to room temperature. The reaction was diluted with ethyl acetate, washed with a saturated aqueous solution of NaHCO$_3$ and brine. The organics were dried over anhydrous sodium sulfate, filtered and concentrated under reduced pressure. The residue was purified by column chromatography on silica gel eluting with ethyl acetate in hexanes to give 4-methyl-N-[3-methyl-5-(4,4,5,5-tetramethyl-1,3,2-dioxaborolan-2-yl)phenyl]pyrimidin-2-amine (331 mg, 1.018 mmol, 56.6% yield) as an orange oil. MS ESI: [M+H]$^+$ m/z 326.2. $^1$H NMR (500 MHz, DMSO-D$_6$) δ 9.40 (s, 1H), 8.31 (d, J=5.0 Hz, 1H), 7.77 (s, 2H), 7.07 (s, 1H), 6.70 (d, J=5.0 Hz, 1H), 2.33 (s, 3H), 2.26 (s, 3H), 1.27 (s, 12H).

Intermediate 19: 4-methyl-N-[3-methyl-5-(1,3-thiazol-5-yl)phenyl]pyrimidin-2-amine

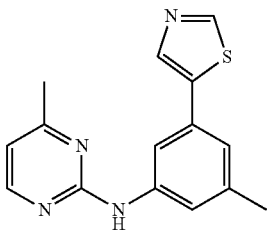 [SMILES: Cc1cc(Nc2nccc(C)n2)cc(-c2cncs2)c1]

A microwave vial was charged with Intermediate 18 (218 mg, 0.670 mmol), 5-bromo-1,3-thiazole (59.9 μL, 0.670 mmol), Pd$_2$(dba)$_3$ (30.7 mg, 0.034 mmol), X-Phos (32.0 mg, 0.067 mmol) and cesium carbonate (437 mg, 1.341 mmol). The system was purged and flushed with Ar(g) four times before adding dioxane (918 μL) and water (92 μL). Again, the system was purged and flushed five times before sealing the vial and heating at 100° C. LCMS showed ~60% desired product, ~35% de-borolated product and remaining unreacted starting material. The reaction mixture was diluted with ethyl acetate, filtered through a celite plug and concentrated. The resultant residue was purified by column chromatography on silica gel (Biotage, 0-20% ethyl acetate in hexanes) to afford 4-methyl-N-[3-methyl-5-(1,3-thiazol-5-yl)phenyl]pyrimidin-2-amine (105 mg, 0.372 mmol, 55.5%). MS ESI: [M+H]$^+$ m/z 283.0. $^1$H NMR (500 MHz, DMSO-D$_6$) δ 9.60 (s, 1H), 9.04 (s, 1H), 8.35 (d, J=6.6, 1H), 8.18 (s, 1H), 8.04 (s, 1H), 7.54 (s, 1H), 7.10 (s, 1H), 6.75 (d, J=6.3, 1H), 2.37 (s, 3H), 2.30 (s, 3H).

Intermediate 20: 4-methoxy-N-[3-methyl-5-(4,4,5,5-tetramethyl-1,3,2-dioxaborolan-2-yl)phenyl]pyrimidin-2-amine

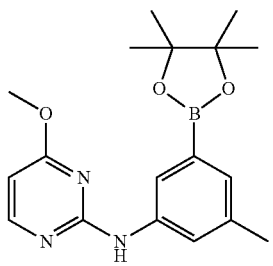 [SMILES: COc1ccnc(Nc2cc(C)cc(B3OC(C)(C)C(C)(C)O3)c2)n1]

Step 1

A 10-20 mL microwave vial was charged with 2-chloro-4-methoxypyrimidine (0.835 g, 5.78 mmol), 3-bromo-5-methylaniline (1.075 g, 5.78 mmol), acetic acid (0.347 mL, 6.06 mmol) and dioxane (11.55 mL). The system was purged and flushed with Ar(g) three times before sealing and heating to 120° C. for 3 hours. The mixture was cooled and stirred overnight. The light brown solids were collected by filtration and were dried in a vacuum oven overnight to yield N-(3-bromo-5-methylphenyl)-4-methoxypyrimidin-2-amine (1.7 g, 5.78 mmol, 100% yield) as a tan solid. MS ESI: [M+H]+ m/z 296.0.

Step 2

A 10-20 mL microwave vial was charged with the product of Step 1 (1.6 g, 5.44 mmol), bispinacolatodiboron (1.519 g, 5.98 mmol), 1,1'-bis(diphenylphosphino)ferrocene-palladium(II)-dichloride dichloromethane complex (0.133 g, 0.163 mmol), potassium acetate (1.602 g, 16.32 mmol) and DMSO (10.88 mL). The system was flushed and purged five times with Ar(g) before sealing the vial and heating to 120° C. for 1 hour. The reaction was the cooled to room temperature, diluted with ethyl acetate, filtered through a celite plug and was concentrated to dryness. The resultant residue was purified by column chromatography on silica gel (Biotage, 5-60% ethyl acetate in hexanes) to afford 4-methoxy-N-[3-methyl-5-(4,4,5,5-tetramethyl-1,3,2-dioxaborolan-2-yl)phenyl]pyrimidin-2-amine (900 mg, 2.64 mmol, 48.5% yield) as a tan solid. MS ESI: [M+H]+ m/z 342.1. $^1$H NMR (500 MHz, DMSO-$d_6$) δ 9.46 (s, 1H), 8.17 (d, J=5.8, 1H), 8.04 (s, 1H), 7.62 (s, 1H), 7.06 (s, 1H), 6.25 (d, J=5.8, 1H), 3.92 (s, 3H), 2.26 (s, 3H), 1.26 (s, 12H).

Intermediate 21: 4-methoxy-N-[3-methyl-5-(1,3-thiazol-5-yl)phenyl]pyrimidin-2-amine

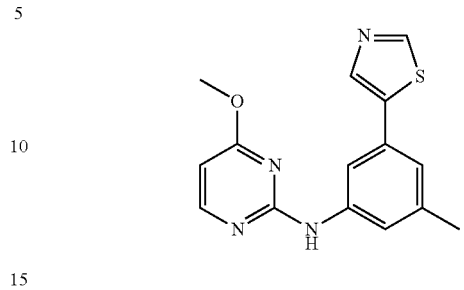

To a round-bottom flask were added 2-chloro-4-methoxypyrimidine (1.58 g, 10.93 mmol), Intermediate 20 (2 g, 10.51 mmol), cesium carbonate (6.85 g, 21.02 mmol) and degassed dioxane (105 mL). The system was flushed and purged with Ar(g) and palladium(II) acetate (0.236 g, 1.051 mmol) and Xantphos (0.912 g, 1.577 mmol) were added. The system was flushed and purged again three times with Ar(g) and then was heated to 90° C. for 2 hours. The reaction was cooled to ambient temperature and the solvent was removed under reduced pressure and the residue was directly purified by column chromatography on silica gel (0 to 100%, 10:1 ethyl acetate: methanol in hexanes) to afford 4-methoxy-N-[3-methyl-5-(1,3-thiazol-5-yl)phenyl]-pyrimidin-2-amine (3.1 g, 10.39 mmol, 99%). MS ESI: [M+H]+ m/z 299.1. $^1$H NMR (600 MHz, CDCl$_3$) δ 8.72 (s, 1H), 8.13 (d, J=5.7, 1H), 8.06 (s, 1H), 7.91 (s, 1H), 7.29 (s, 1H), 7.25 (s, 1H), 7.05 (s, 1H), 6.21 (d, J=5.7, 1H), 3.98 (s, 3H), 2.37 (s, 3H).

Intermediate 22: 1-[5-(3-amino-5-nitrophenyl)-1,3-thiazol-2-yl]cyclobutanol

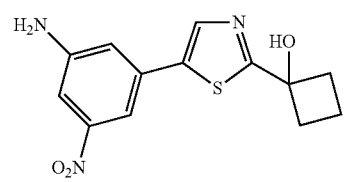 [SMILES: Nc1cc(-c2cnc(C3(O)CCC3)s2)cc([N+](=O)[O-])c1]

To a solution of commercially available (3-amino-5-nitrophenyl)boronic acid (18 g, 99 mmol) and Intermediate 1 (25.5 g, 109 mmol) in DME (360 mL) were added tetrakis(triphenyl-phosphine)palladium(0) (5.72 g, 4.95 mmol) and 2M Na$_2$CO$_3$(aq) (148 mL, 297 mmol), and the mixture was degassed and then heated to 85° C. for 5 hours. After cooling to room temperature, the mixture was diluted with ethyl acetate (500 mL) and filtered through Celite (ethyl acetate rinse). The filtrate was washed with brine (300 mL), dried (Na$_2$SO$_4$) and concentrated in vacuo. The impure material was split into two batches, and each purified by Chromatography on silica gel (70:30 to 0:100 hexanes:ethyl acetate) then the product fractions from the two purifications were combined and concentrated in vacuo to provide 26.53 g (91 mmol, 92%) of 1-[5-(3-amino-5-nitrophenyl)-1,3-thiazol-2-yl]cyclobutanol as a green solid. MS ESI: [M+H]+m/z 292.0. $^1$H NMR (DMSO-$d_6$): δ 8.15 (1H, s), 7.54 (1H, s), 7.33 (1H, s), 7.14 (1H, s), 6.58 (1H, s), 6.00 (2H, s), 2.56-2.47 (2H, m), 2.39-2.29 (2H, m), 1.95-1.83 (2H, m).

Intermediate 23: 1-[5-(3-aminophenyl)-1,3-thiazol-2-yl]ethanol

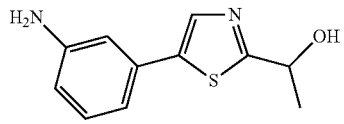

Step 1

To a solution of 2-acetylthiazole (3.0 mL, 28.9 mmol) in ethanol (50 mL) at room temperature, under nitrogen, were added triethyl orthoformate (48.2 mL, 289 mmol) and p-TSA (550 mg, 2.89 mmol). The mixture was stirred at reflux for 18 h to give ~90% conversion. Additional p-TSA (4.73 g, 24.87 mmol) was added that the reaction was refluxed for 5 more hours to completion. The reaction mixture was cooled to room temperature and was poured in 500 mL of saturated aqueous NaHCO$_3$. The aqueous layer was extracted with ethyl acetate (3×). The combined organics were washed with saturated aqueous NaHCO$_3$ and brine, dried (sodium sulfate) and concentrated to give an amber liquid (13.2 g). Chromatography on silica gel (CombiFlash, 5-20% ethyl acetate in hexanes) afforded 2-(1,1-diethoxyethyl)-1,3-thiazole (3.54 g, 17.59 mmol, 60.8% yield) as a colorless liquid.

Step 2

To a solution of the product of Step 1 (3.54 g, 17.59 mmol) in THF (60 mL) at −78° C., under nitrogen, was added n-butyllithium (1.6 M, 11.54 mL, 18.47 mmol) dropwise at such a rate that internal temperature was maintained below −65° C. (addition over 15 min). The mixture was stirred at −78° C. for 30 min and a solution of carbon tetrabromide (6.42 g, 19.35 mmol) in THF (20 mL) was added dropwise at such a rate that internal temperature was maintained below −65° C. (addition over 15 min). After 30 min at −78° C., the temperature was allowed to reach 0° C. and the reaction was quenched by the addition of saturated aqueous NH$_4$Cl after 30 min. The aqueous layer was extracted with ethyl acetate (3×). The combined organics were washed with water and brine, dried (sodium sulfate) and concentrated to give a pale yellow liquid (8 g). Chromatography on silica gel (chromatography on silica gel, 5-30%, ethyl acetate in hexanes) afforded 5-bromo-2-(1,1-diethoxyethyl)-1,3-thiazole (989 mg, 3.53 mmol, 20.07% yield) as a colorless liquid.

Step 3

To a solution of the product of Step 2 (981 mg, 3.50 mmol) in dichloromethane (4 mL) at room temperature, under nitrogen, were added trifluoroacetic acid (6.204 mL, 81 mmol) and water (208 µL, 11.55 mmol). The mixture was stirred at room temperature for 18 h. The solvent was removed under reduced pressure. The residue was dissolved in dichloromethane and was washed with 5% aqueous sodium bicarbonate (3×) and brine, dried (sodium sulfate) and concentrated to give 1-(5-bromo-1,3-thiazol-2-yl)ethanone (654 mg, 3.17 mmol, 91% yield) as a yellow solid that was used without further purification.

Step 4

The product of Step 3 (300 mg, 1.456 mmol), 3-aminophenylboronic acid monohydrate (271 mg, 1.747 mmol), tetrakis(triphenylphosphine)palladium(0) (84 mg, 0.073 mmol), DME (9 mL) and sodium carbonate (2 M, 2.184 mL, 4.37 mmol) were successively introduced in a 10-20 mL reaction vial under nitrogen. The mixture was stirred under microwave irradiation at 140° C. for 20 min, cooled to room temperature and was diluted with water. The aqueous layer was extracted with ethyl acetate (3×). The combined organics were washed with water and brine, dried (sodium sulfate) and concentrated to give a beige solid (419 mg). Chromatography on silica gel (CombiFlash, 5-25% ethyl acetate in dichloromethane) afforded 1-[5-(3-aminophenyl)-1,3-thiazol-2-yl]ethanone (252 mg, 1.155 mmol, 79% yield) as a yellow solid.

Step 5

To a solution of the product of Step 4 (179 mg, 0.820 mmol) in THF (3 mL) and methanol (1 mL) at 0° C., under nitrogen, was added sodium borohydride (62.1 mg, 1.640 mmol). The mixture was allowed to warm to room temperature and was stirred for 1 h, before being quenched by the addition of 25% aqueous NH$_4$OAc. The aqueous layer was extracted with ethyl acetate (3×). The combined organics were washed with water and brine, dried (Na$_2$SO$_4$) and concentrated to give a colorless gum (177 mg). Chromatography on silica gel (CombiFlash, 40-90% ethyl acetate in dichloromethane) afforded 1-[5-(3-aminophenyl)-1,3-thiazol-2-yl]ethanol (151 mg, 0.685 mmol, 84% yield) as a white solid. $^1$H NMR (400 MHz, CDCl$_3$): δ 7.84 (s, 1 H); 7.20 (t, J=7.8 Hz, 1H); 6.97 (d, 7.7 Hz, 1H); 6.88 (s, 1H); 6.68 (dd, J=8.0, 2.2 Hz, 1H); 5.20-5.12 (m, 1H); 3.78 (s, 2H); 2.96 (d, J=4.6 Hz, 1H); 1.69 (d, J=6.5 Hz, 3H).

Intermediate 24: Methyl 2,2-dimethyl-4-oxocyclohexanecarboxylate

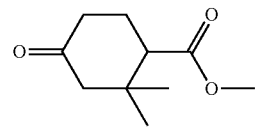

Step 1

Methyl 3-oxobutanoate (232 g, 2.00 mol) and paraformaldehyde (30 g, 999.00 mmol) were combined, and to the mixture was added piperidine (10 g, 117.44 mmol). The resulting solution was stirred for 2 h at 0° C. The solution was heated to 60° C. for 2 h. Extracted with Et$_2$O (3×), and the organic layers were combined and dried over Na$_2$SO$_4$. Filtered and concentrated in vacuo. This resulted in 370 g (crude) of dimethyl 2-methyl-6-oxocyclohex-1-ene-1,3-dicarboxylate as a brown oil. MS: [M+H]$^+$ m/z 227.

Step 2

To a solution of sodium methanolate (90 g, 1.67 mol) in methanol (300 mL) was added the product of Step 1 (150 g, 663.04 mmol) in methanol (150 mL) dropwise with stirring over 30 min. The resulting solution was heated to 80° C. for 30 min. and the mixture was concentrated in vacuo. The reaction mixture was then quenched by the addition of H$_2$O/ice (120 mL), then diluted with acetic acid (130 mL). The resulting solution was extracted with Et$_2$O (3×), and the organic layers were combined and dried over Na$_2$SO$_4$, filtered and concentrated in vacuo. The final product was purified by distillation under reduced pressure (5 mm Hg) and the fraction was collected at 110~120° C. This resulted in 100 g (88%) of methyl 2-methyl-4-oxocyclohex-2-enecarboxylate as a yellow oil. MS: [M+H]+ m/z 169.

Step 3

Copper iodide (121.8 g, 639.54 mmol) was added to Et$_2$O (800 mL). Methyllithium (1.6 M in diethyl ether, 800 mL, 1.28 mol) was added dropwise at −40° C. over 3 h. Added a solution of the product of Step 2 (53.8 g, 319.88 mmol) in Et$_2$O (400 mL) at −40° C. over 2 min. The resulting solution was stirred 5 h at −20° C. Quenched via the addition of saturated aqueous ammonium chloride (2.5 L). Extracted with EtOAc (3×2 L). The combined organic extracts were dried over Na$_2$SO$_4$, filtered, and concentrated in vacuo. The residue was purified by eluting through a silica gel column with a 1:20 EtOAc/PE solvent system. This resulted in 45 g (73%) of methyl 2,2-dimethyl-4-oxocyclohexanecarboxylate as a yellow oil. MS: [M+H]+ m/z 185. $^1$H NMR (600 MHz, CDCl$_3$) δ 3.49 (s, 3H), 2.43-2.40 (m, 1H), 2.35-2.29 (m, 1H), 2.21-2.17 (m, 1H), 2.11-2.04 (m, 1H), 2.00-1.96 (m, 1H), 1.91-1.85 (m, 1H), 0.85 (s, 3H), 0.77 (s, 3H).

Intermediate 25: Racemic cis-methyl 4-(5-bromo-1,3-thiazol-2-yl)-4-hydroxy-2,2-dimethylcyclohexanecarboxylate

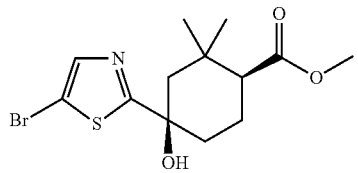 [SMILES: COC(=O)[C@H]1CC[C@](O)(c2ncc(Br)s2)CC1(C)C]

Step 1 n-Butyllithium (2.2 mL, 5.5 mmol, 2.5 M solution in hexanes) was added dropwise over 12 minutes to a solution of thiazole (0.515 g, 6.05 mmol) in tetrahydrofuran (15 mL) at −78° C. After 30 minutes, the opaque yellow suspension was transferred over 5 minutes via a dry ice-cooled cannula to a solution of Intermediate 24 (1.013 g, 5.5 mmol) in tetrahydrofuran (15 mL) at −78° C. The resulting yellow solution was kept at −78° C. for 1 hour, moved to a 0° C. bath for 15 minutes, and then cooled back to −78° C. Aqueous saturated ammonium chloride solution (10 mL) was added and the mixture was allowed to warm to room temperature. The biphasic mixture was partitioned between ethyl acetate (50 mL) and water (5 mL); the layers were separated and the aqueous layer was extracted with ethyl acetate (15 mL). The combined organic layers were washed with brine, dried over sodium sulfate, filtered, and concentrated. The crude material was purified via silica gel chromatography (Biotage 100 g SNAP column, 90:10 to 65:35 hexane:ethyl acetate) to afford racemic cis-methyl 4-hydroxy-2,2-dimethyl-4-(1,3-thiazol-2-yl)cyclohexanecarboxylate as a white solid (1.08 g, 73% yield). MS APCI: [M+H]+ m/z 270.1.

Step 2

To a solution of the product of Step 1 (0.35 g, 1.3 mmol) in N,N-dimethylformamide (1.9 mL) was added N-bromosuccinimide (0.254 g, 1.429 mmol). After three hours an additional portion of N-bromosuccinimide (0.046 g, 0.258 mmol) was added. After an additional hour, the reaction mixture was partitioned between ethyl acetate (25 mL), aqueous saturated sodium thiosulfate (10 mL), and water (5 mL). The layers were separated, and the organic layer was washed with water (3×5 mL) and brine (10 mL), dried over sodium sulfate, filtered, and concentrated. The crude reaction was purified via silica gel chromatography (Biotage 100 g SNAP column, 95:5 to 75:25 hexane:ethyl acetate) to afford racemic cis-methyl 4-(5-bromo-1,3-thiazol-2-yl)-4-hydroxy-2,2-dimethylcyclohexanecarboxylate as a white solid (286.8 mg, 63% yield). MS APCI: [M+H]+ m/z 348.0, 350.0. $^1$H NMR (500 MHz, CDCl$_3$): δ 7.58 (s, 1H); 3.69 (s, 3H); 2.45 (s, 1H); 2.36 (m, 1H); 2.21 (m, 1H); 1.94 (m, 3H); 1.75 (m, 2H); 1.19 (s, 3H); 1.06 (s, 3H).

Intermediate 26: 5-Bromo-2-(1-methoxycyclobutyl)-1,3-thiazole

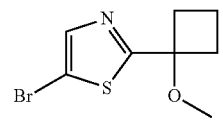

Sodium hydride (60% dispersion in mineral oil) (47.0 mg, 1.175 mmol) was added to a 0° C. solution of Intermediate 1 (250 mg, 1.068 mmol) in DMF (3 mL) and THF (3 mL) and the mixture was allowed to react for 1 hour. Methyl iodide (0.080 ml, 1.281 mmol) was added and the mixture further reacted for 2 hours. The reaction mixture was poured in dilute aqueous NH$_4$Cl and extracted twice with diethyl ether. The organic fraction was concentrated and the residue was passed through a plug of silica eluting with 1:10 ethyl acetate:hexane to yield 2-bromo-5-(1-methoxycyclobutyl)-1,3-thiazole (225 mg, 85%). $^1$H NMR (500 MHz, (CD$_3$)$_2$CO): δ 7.73 (s, 1H); 3.19 (s, 3H); 2.54-2.40 (m, 4H); 1.92-1.82 (m, 2H).

Intermediate 27: 2-chloro-4-ethylpyrimidine

Ethylmagnesium bromide (1.0 M in THF, 71.4 mL, 71.4 mmol) was added dropwise to a −78° C. solution of 2,4-dichloropyrimidine (10 g, 67.1 mmol) in THF (125 mL). After stirring for 1 h, saturated aqueous NH$_4$Cl was added at −78° C. and the reaction was allowed to come to room temperature with stirring. Then, the reaction mixture was extracted with ethyl acetate. The organic layer was washed with saturated aqueous NaHCO$_3$, then dried over anhydrous sodium sulfate, filtered and concentrated under reduced pressure. The residue was purified by column chromatography on silica gel eluting with ethyl acetate and hexanes to provide 2-chloro-4-ethylpyrimidine (5.031 g, 18.70 mmol, 27.9%) as a 53:47 regioisomeric mixture.

Intermediate 28: 2-chloro-4-(methylsulfanyl)pyrimidine

Sodium thiomethoxide (5.18 g, 73.8 mmol) was added slowly portion-wise via powder addition funnel to a stirring solution of 2,4-dichloropyrimidine (10 g, 67.1 mmol) in THF (150 mL) at room temperature. After stirring overnight, the reaction was taken up in ethyl acetate, washed with water, brine, dried over anhydrous sodium sulfate, filtered and concentrated under reduced pressure. The residue was purified by column chromatography on silica gel eluting with ethyl acetate and hexanes to give 2-chloro-4-(methylsulfanyl)pyrimidine (10.127 g, 47.3 mmol, 70.4%) as a white solid.

Intermediate 29: 2-chloro-4-cyclopropylpyrimidine 2,4-Dichloropyrimidine (15 g, 101 mmol), cyclopropylboronic acid (8.65 g, 101 mmol), PdCl$_2$(dppf)-CH$_2$Cl$_2$ adduct (8.22 g, 10.07 mmol), and potassium phosphate (53.4 g, 252 mmol) were combined in a 1 L round-bottom flask. THF (503 mL) was added and the suspension was heated to reflux with stifling overnight. The reaction was then cooled to room temperature, concentrated to ~100 mL under reduced pressure, extracted with ethyl acetate, washed with saturated aqueous NaHCO$_3$, brine, dried over anhydrous sodium sulfate, filtered and concentrated under reduced pressure. The residue was purified by column chromatography on silica gel eluting with ethyl acetate in hexanes to give 2-chloro-4-cyclopropylpyrimidine (10.124 g, 58.3 mmol, 57.9%) as an 89:11 mixture of regioisomers.

Intermediate 30: N-[3-fluoro-5-(4,4,5,5-tetramethyl-1,3,2-dioxaborolan-2-yl)phenyl]-4-(trifluoromethyl)pyrimidin-2-amine

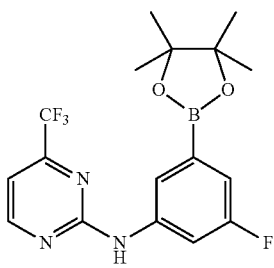 [SMILES: CC1(C)OB(c2cc(F)cc(Nc3nccc(C(F)(F)F)n3)c2)OC1(C)C]

To a flask containing 3-fluoro-5-(4,4,5,5-tetramethyl-1,3,2-dioxaborolan-2-yl)aniline (3.3 g, 14.00 mmol) and 2-chloro-4-(trifluoromethyl)pyrimidine (2.94 g, 16.10 mmol) were added dioxane (44 mL) and methanesulfonic acid (1.55 g, 16.10 mmol) and the reaction was heated at 100° C. overnight. The reaction was cooled, diluted with ethyl acetate, washed with water, dried over magnesium sulfate, filtered and concentrated. Flash chromatography was used for purification to yield. N-[3-fluoro-5-(4,4,5,5-tetramethyl-1,3,2-dioxaborolan-2-yl)phenyl]-4-(trifluoromethyl)pyrimidin-2-amine (4.10 g, 10.70 mmol, 76% yield). MS ESI: [M+H]$^+$ m/z 384. $^1$H NMR (500 MHz, DMSO-d$_6$) δ 10.41 (s, 1H), 8.85 (d, J=4.9, 1H), 7.92 (dt, J=2.3, 12.1, 1H), 7.77 (d, J=1.5, 1H), 7.32 (d, J=4.9, 1H), 6.98 (dd, J=2.2, 8.4, 1H), 1.28 (s, 12H).

Intermediate 31: 5-fluoro-4-methoxy-N-[3-methyl-5-(4,4,5,5-tetramethyl-1,3,2-dioxaborolan-2-yl)phenyl]pyrimidin-2-amine

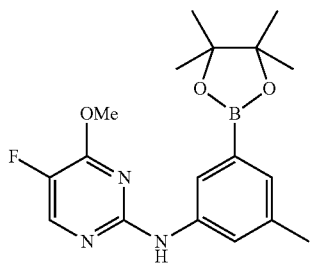 [SMILES: COc1nc(Nc2cc(C)cc(B3OC(C)(C)C(C)(C)O3)c2)ncc1F]

To a flask containing 2-chloro-5-fluoro-4-methoxypyrimidine (0.32 g, 1.97 mmol) and 3-methyl-5-(4,4,5,5-tetramethyl-1,3,2-dioxaborolan-2-yl)aniline (0.40 g, 1.72 mmol) were added dioxane (17 mL) and methanesulfonic acid (0.13 mL, 1.97 mmol). The reaction was heated at 100° C. overnight. The reaction was then cooled to room temperature, diluted with ethyl acetate, washed with water, dried over magnesium sulfate, filtered and concentrated. Flash chromatography was used for purification to yield 5-fluoro-4-methoxy-N-[3-methyl-5-(4,4,5,5-tetramethyl-1,3,2-dioxaborolan-2-yl)phenyl]pyrimidin-2-amine (0.31 g, 0.86 mmol, 50% yield). MS ESI: [M+H]$^+$ m/z 360. $^1$H NMR (500 MHz, DMSO-d$_6$) δ 9.51 (s, 1H), 8.27 (d, J=3.2, 1H), 8.00 (s, 1H), 7.57 (s, 1H), 7.07 (s, 1H), 4.01 (s, 3H), 2.25 (s, 3H), 1.26 (s, 12H).

Intermediate 32: 4-methyl-N-[3-(4,4,5,5-tetramethyl-1,3,2-dioxaborolan-2-yl)phenyl]pyrimidin-2-amine

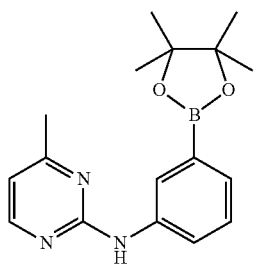 [SMILES: Cc1ccnc(Nc2cccc(B3OC(C)(C)C(C)(C)O3)c2)n1]

To a flask containing 3-(4,4,5,5-tetramethyl-1,3,2-dioxaborolan-2-yl)aniline (1.50 g, 6.85 mmol) and 2-chloro-4-methylpyrimidine (1.01 g, 7.87 mmol) were added dioxane (69 mL) and methanesulfonic acid (0.51 mL, 7.87 mmol). The reaction was heated at 100° C. overnight. The reaction was then cooled to room temperature, diluted with ethyl acetate, washed with water, dried over magnesium sulfate, filtered and concentrated. Flash chromatography was used for purification to yield 4-methyl-N-[3-(4,4,5,5-tetramethyl-1,3,2-dioxaborolan-2-yl)phenyl]pyrimidin-2-amine (1.23 g, 3.95 mmol, 58% yield).

MS ESI: [M+H]$^+$ m/z 312. $^1$H NMR (500 MHz, DMSO-d$_6$) δ 9.48 (s, 1H), 8.30 (d, J=5.0, 1H), 7.98 (d, J=8.0, 1H), 7.95 (s, 1H), 7.29-7.20 (m, 2H), 6.71 (d, J=5.0, 1H), 2.33 (s, 3H), 1.28 (s, 12H).

Intermediate 33: 4-(2-methoxyethoxy)-N-[3-methyl-5-(4,4,5,5-tetramethyl-1,3,2-dioxaborolan-2-yl)phenyl]pyrimidin-2-amine

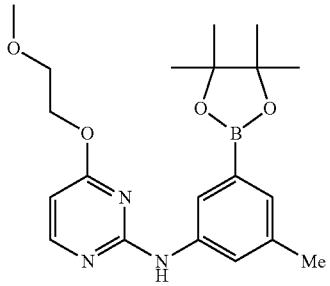 [SMILES: COCCOc1ccnc(Nc2cc(C)cc(B3OC(C)(C)C(C)(C)O3)c2)n1]

2-Chloro-4-(2-methoxyethoxy)pyrimidine (91 mg, 0.485 mmol) and 3-methyl-5-(4,4,5,5-tetramethyl-1,3,2-dioxaborolan-2-yl)aniline (113 mg, 0.485 mmol) were dissolved in Dioxane (4 ml), and methanesulfonic acid (0.033 ml, 0.509 mmol) was added. The mixture was heated to 100° C. for 18 h. The mixture was allowed to cool to room temperature, quenched with saturated aqueous sodium bicarbonate and extracted with EtOAc (2×). The combined organics were dried over $Na_2SO_4$, filtered and concentrated in vacuo to obtained 4-(2-methoxyethoxy)-N-[3-methyl-5-(4,4,5,5-tetramethyl-1,3,2-dioxaborolan-2-yl)phenyl]pyrimidin-2-amine (160 mg, 86%) as a brown solid. MS APCI: $[M+H]^+$ m/z 386. $^1$H NMR (500 MHz, $CDCl_3$) δ 8.08 (d, J=5.8, 1H), 7.93 (s, 1H), 7.48 (s, 1H), 7.34 (s, 1H), 6.26 (d, J=6.0, 1H), 4.58 (m, 2H), 3.77 (m, 2H), 3.42 (s 3H), 2.37 (s, 3H), 1.34 (s, 12H).

Intermediate 34: 4-(3-methoxypropoxy)-N-[3-methyl-5-(4,4,5,5-tetramethyl-1,3,2-dioxaborolan-2-yl)phenyl]pyrimidin-2-amine

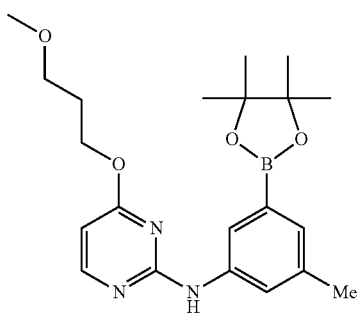 [SMILES: COCCCOc1ccnc(Nc2cc(C)cc(B3OC(C)(C)C(C)(C)O3)c2)n1]

Step 1

2,4-Dichloropyrimidine (250 mg, 1.678 mmol), 3-methoxy-1-propanol (0.193 ml, 2.014 mmol), and cesium carbonate (929 mg, 2.85 mmol) were combined in DMF (5 ml). The suspension was heated to 80° C. for 15 h. The mixture was allowed to cool to room temperature, diluted with brine and extracted with EtOAc (3×). The organic layer was dried over $Na_2SO_4$ and concentrated in vacuo. Purification via flash chromatography (5-15% EtOAc:Hexanes) gave 2-chloro-4-(3-methoxypropoxy)pyrimidine (112 mg, 33%) as a colorless oil. MS ESI: $[M+H]^+$ m/z 203.

Step 2

The product of Step 1 (107 mg, 0.528 mmol) and 3-methyl-5-(4,4,5,5-tetramethyl-1,3,2-dioxaborolan-2-yl)aniline (123 mg, 0.528 mmol) were dissolved in Dioxane (4 ml), and methanesulfonic acid (0.036 ml, 0.554 mmol) was added. The mixture was heated to 100° C. for 18 h. The mixture was allowed to cool to room temperature, quenched with saturated aqueous sodium bicarbonate and extracted with EtOAc (2×). The combined organic layers were dried over $Na_2SO_4$ and concentrated in vacuo to afford 4-(3-methoxypropoxy)-N-[3-methyl-5-(4,4,5,5-tetramethyl-1,3,2-dioxaborolan-2-yl)phenyl]pyrimidin-2-amine (165 mg, 78%) as a brown solid. MS ESI: $[M+H]^+$ m/z 400. $^1$H NMR (500 MHz, $CDCl_3$) δ 8.09 (d, J=5.8, 1H), 7.82 (s, 1H), 7.59 (s, 1H), 7.32 (s, 1H), 6.17 (d, J=4.4, 1H), 4.48 (t, J=5.8, 2H), 3.53 (t, J=5.5, 2H), 3.34 (s, 3H), 2.37 (s, 3H), 2.05 (dd, J=3.3, 9.4, 2H), 1.34 (s, 12H).

Intermediate 35: 4-Ethyl-N-[3-methyl-5-(4,4,5,5-tetramethyl-1,3,2-dioxaborolan-2-yl)phenyl]pyrimidin-2-amine

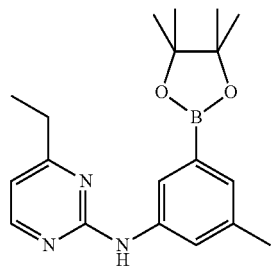 [SMILES: CCc1ccnc(Nc2cc(C)cc(B3OC(C)(C)C(C)(C)O3)c2)n1]

Step 1

To a 1 L 3 neck flask containing 3-bromo-5-methylaniline (60 g, 290 mmol), bis(pinacolato)diboron (96 g, 377 mmol), 2-dicyclohexylphosphino-2',4',6'-triisopropylbiphenyl (8.3 g, 17.4 mmol), palladium dibenzylideneacetone (3.99 g, 4.35 mmol), and potassium acetate (42.7 g, 435 mmol) was added 1,4-dioxane (720 mL) that had been degassed via sparging with nitrogen for 30 minutes. After flushing the flask with nitrogen for 2 minutes, the reaction was heated to an internal temperature of 80° C. for 4 hours. Upon cooling, the reaction mixture was filtered through a pad of Celite, and then the Celite was washed with methyl tert-butyl ether (500 mL). The resulting solution was diluted with methyl tert-butyl ether (500 mL), pH 8 phosphate buffer (500 mL), and brine (500 mL). The layers were separated and the organic layer was washed with a half-saturated brine solution (1 L). The aqueous layers, which were kept separately, were sequentially back extracted with methy tert-butylether (500 mL). The combined organics were dried over magnesium sulfate, filtered, and concentrated. The crude material was purified by silica gel flash chromatography (0-90% ethyl acetate/hexanes) and the resulting light orange solid was dried overnight under nitrogen to give 3-methyl-5-(4,4,5,5-tetramethyl-1,3,2-dioxaborolan-2-yl)aniline (67.7 g, 255 mmol, 88% yield, 90% purity). MS ESI: $[M+H]^+$ m/z 234.1.

Step 2

A solution of 2-chloro-4-ethyl pyrimidine (0.98 g, 7.00 mmol), the product of Step 1 (1.794 g, 7.70 mmol), and methanesulfonic acid (0.50 mL, 7.70 mmol) in 1,4-dioxane (30 mL) was sealed in a 100 mL screw-top pressure flask and heated at 110° C. for 15 hours. The flask was cooled, an additional portion of 2-chloro-4-ethyl pyrimidine (0.145 g, 1.05 mmol) was added, and the flask was resealed and heated for another 6.5 hours. The reaction mixture was cooled, diluted with ethyl acetate (70 mL), washed with saturated aqueous sodium bicarbonate solution (25 mL) and brine (25 mL), dried over sodium sulfate, filtered, and concentrated. The resulting reddish brown solid 4-ethyl-N-[3-methyl-5-(4,4,5,5-tetramethyl-1,3,2-dioxaborolan-2-yl)phenyl]pyrimidin-2-amine (3.44 g as a 80:20 w/w mixture with 1,4-dioxane) was used without further purification. MS ESI: [M+H]$^+$ m/z 340.1

Intermediate 36: N-[3-Cyclopropyl-5-(4,4,5,5-tetramethyl-1,3,2-dioxaborolan-2-yl)phenyl]-4-methylpyrimidin-2-amine

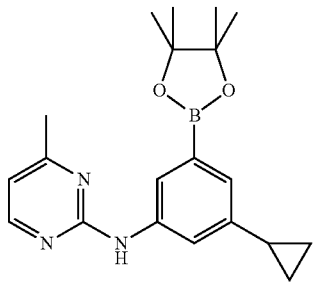 [SMILES: Cc1ccnc(Nc2cc(B3OC(C)(C)C(C)(C)O3)cc(C3CC3)c2)n1]

Step 1

A solution of 3,5-dibromoaniline (2.93 g, 11.67 mmol), 2-chloro-4-methylpyrimidine (1.5 g, 11.67 mmol), and acetic acid (0.701 mL, 12.25 mmol) in 1,4-dioxane (23.5 mL) was sealed in a pressure vessel under an argon atmosphere and heated at 120° C. for 17 hours. After being cooled to room temperature, the reaction mixture was partitioned between ethyl acetate (100 mL) and saturated aqueous sodium bicarbonate solution (40 mL). The layers were separated, and the organic layer was washed with brine, dried over sodium sulfate, filtered, and concentrated. Silica gel flash chromatography (10% to 30% ethyl acetate/hexanes) afforded N-(3,5-dibromophenyl)-4-methylpyrimidin-2-amine (3.6 g, 9.97 mmol, 85% yield, 95% purity) as a light yellow solid. MS ESI: [M+H]$^+$ m/z 343.8.

Step 2

A mixture of 1,4-dioxane (40 mL) and aqueous sodium carbonate (2 M, 10.50 mL, 20.99 mmol) was sparged with argon for 15 minutes and then poured into a flask containing the product of Step 1 (3.6 g, 9.97 mmol, 85% yield, 95% purity) and PdCl$_2$(dppf)-CH$_2$Cl$_2$ adduct (0.686 g, 0.840 mmol). Cyclopropyl boronic acid (1.037 g, 12.07 mmol) was added followed by a condenser and the whole system was placed under argon via five vacuum/argon flush cycles. The reaction mixture was heated to reflux for 18 hours and then cooled to room temperature and diluted with ethyl acetate (100 mL) and saturated aqueous sodium bicarbonate. The layers were separated, and the organic layer was washed with brine, dried over sodium sulfate, filtered, and concentrated. The residue was purified via reverse phase HPLC (45-80% acetonitrile/water with a 0.10% TPA buffer). The fractions containing the desired product were diluted with ethyl acetate and saturated aqueous sodium bicarbonate. The organic layer was separated, dried over magnesium sulfate, filtered and concentrated to give N-(3-bromo-5-cyclopropylphenyl)-4-methylpyrimidin-2-amine (443.6 mg, 1.31 mmol, 13% yield) as a brown oil. MS ESI: [M+H]$^+$ m/z 306.0.

Step 3

A solution of the product of Step 2 (443.6 mg, 1.458 mmol), Bis(pinacoloato)diboron (407 mg, 1.604 mmol), PdCl$_2$(dppf)-CH$_2$Cl$_2$ adduct (119 mg, 0.146 mmol), and potassium acetate (429 mg, 4.37 mmol) in dimethylsulfoxide was heated under argon in a microwave for 10 minutes at 150° C. The reaction mixture was diluted with diethyl ether (40 mL), ethyl acetate (40 mL), and saturated aqueous sodium bicarbonate solution (30 mL) and then filtered to remove any solids that did not dissolve. The layers were separated and the organic layer was washed with water (3×25 mL) and brine (25 mL), dried over sodium sulfate, filtered, and concentrated. The resulting crude product was purified via silica gel chromatography (5-30% ethyl acetate/hexanes) to provide N-[3-cyclopropyl-5-(4,4,5,5-tetramethyl-1,3,2-dioxaborolan-2-yl)phenyl]-4-methylpyrimidin-2-amine (186.1 mg, 0.53 mmol, 36% yield, about 75% pure) as a white solid. The material was used in subsequent steps in this crude form. MS ESI: [M+H]$^+$ m/z 352.2.

Intermediate 37: N-[3-(methoxymethyl)-5-(4,4,5,5-tetramethyl-1,3,2-dioxaborolan-41)phenyl]-4-(trifluoromethyl)pyrimidin-2-amine

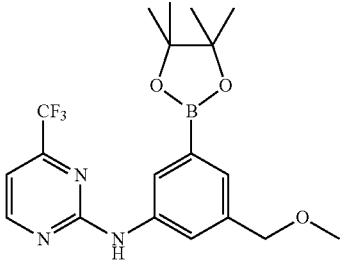 [SMILES: COCc1cc(Nc2nccc(C(F)(F)F)n2)cc(B2OC(C)(C)C(C)(C)O2)c1]

Step 1

To a solution of (3-bromo-5-nitrophenyl)methanol (500 mg, 2.155 mmol) in DMF (7.2 mL) was added iodomethane (0.40 mL, 6.46 mmol. The solution was cooled to 0° C. before NaH (60% dispersion in mineral oil, 172 mg, 4.31 mmol) was added. The reaction was stirred at 0° C. and allowed to come to room temperature. After 2 hours the reaction was quenched with water and ethyl acetate was then added. Extraction was done with ethyl acetate (3×). The combined organic layer was dried over magnesium sulfate and then filtered. Ethyl acetate was then removed in vacuo to afford 1-bromo-3-(methoxymethyl)-5-nitrobenzene (470 mg, 1.910 mmol, 89% yield) as a yellow solid. $^1$H NMR (500 MHz, DMSO-d$_6$) δ 8.25 (s, 1H), 8.13 (s, 1H), 7.96 (s, 1H), 4.53 (s, 2H), 3.33 (s, 3H).

Step 2

To a solution of the product of Step 1 (470 mg, 1.910 mmol) in (EtOH/water) (8.5 mL/4.2 mL) were added iron (533 mg, 9.55 mmol) and ammonium chloride (51 mg, 0.955 mmol). The reaction was stirred at 90° C. for about 4 hours. The reaction was then allowed to come to room temperature and diluted with ethyl acetate. The solution was then filtered through Celite and organic solvent was then removed in vacuo. Flash chromatography (hexane/ethyl acetate: 70/30) was used for purification to afford 3-bromo-5-(methoxymethyl)aniline (258 mg, 1.194 mmol, 62.5% yield). MS ESI: [M+H]$^+$ m/z=216.0.

Step 3

To a solution of the product of Step 2 (258 mg, 1.194 mmol) in dioxane (3.8 mL) were added 2-chloro-4-(trifluoromethyl) pyrimidine (251 mg, 1.373 mmol) and methanesulfonic acid (0.07 mL, 1.015 mmol). The reaction was then stirred overnight at 100° C. The reaction was then cooled, diluted with ethyl acetate and then washed with brine solution. The organic layer was collected, dried over magnesium sulfate and then filtered. Ethyl acetate was then removed in vacuo. Flash chromatography (hexane/ethyl acetate: 70/30) was used for purification to afford N-[3-bromo-5-(methoxymethyl)phenyl]-4-(trifluoromethyl)pyrimidin-2-amine as an off-white solid (314 mg, 0.867 mmol, 72.6% yield). MS ESI: [M+H]$^+$ m/z=362.0.

Step 4

To a solution of the product of Step 3 (200 mg, 0.552 mmol) in dioxane (2.8 ml) were added Bis(pinacolato)diboron (210 mg, 0.828 mmol), potassium acetate (108 mg, 1.105 mmol), X-phos (26.5 mg, 0.055 mmol) and palladium(II) acetate (6.20 mg, 0.029 mmol). Nitrogen was bubbled into the reaction for about 5 minutes and reaction was then sealed and stirred overnight at 90° C. The reaction was then cooled to room temperature and diluted with ethyl acetate. The solution was then filtered through Celite and organic solvent was removed in vacuo to afford N-[3-(methoxymethyl)-5-(4,4,5,5-tetramethyl-1,3,2-dioxaborolan-2-yl)phenyl]-4-(trifluoromethyl)pyrimidin-2-amine as a brown oil. 100% yield was assumed and no further purification was done on this material. MS ESI: [M+H]$^+$ m/z=410.2.

Intermediate 38: (5-Fluoro-4-methyl-pyrimidin-2-yl)-[3-methyl-5-(4,4,5,5-tetramethyl-[1,3,2]dioxaborolan-2-yl)-phenyl]-amine

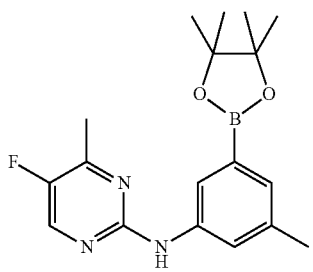 [SMILES: Cc1cc(Nc2ncc(F)c(C)n2)cc(B2OC(C)(C)C(C)(C)O2)c1]

To a solution of 2-chloro-5-fluoro-4-methyl-pyrimidine (4.00 g, 27.3 mmol) and 3-methyl-5-(4,4,5,5-tetramethyl-[1,3,2]dioxaborolan-2-yl)-phenylamine (8.27 g, 35.5 mmol) in dioxane (40.7 mL) was added methanesulfonic acid (1.77 ml, 27.3 mmol) dropwise during which the reaction exothermed 15.7° C. Subsequently the reaction mixture was heated to 100° C. and allowed to stir over the weekend. The mixture was cooled to room temperature and was diluted with saturated aqueous NaHCO$_3$ and extracted with ethyl acetate. The organic extracts were washed with brine and dried over MgSO$_4$, filtered and concentrated in vacuo. Purification by flash chromatography provided (5-fluoro-4-methyl-pyrimidin-2-yl)-[3-methyl-5-(4,4,5,5-tetramethyl-[1,3,2]dioxaborolan-2-yl)-phenyl]-amine (5.87 g, 17.1 mmol) MS ESI: [M+H]$^+$ m/z 344.1. $^1$H NMR (500 MHz, DMSO-d$_6$) δ 9.50 (s, 1H), 838 (d, J=1.6, 1H), 7.81-7.62 (m, 2H), 7.07 (s, 1H), 2.36 (d, J=2.3, 3H), 2.26 (s, 3H), 1.27 (s, 12H).

Intermediate 39: (4-Difluoromethyl-pyrimidin-2-yl)-[3-methyl-5-(4,4,5,5-tetramethyl-[1,3,2]dioxaborolan-2-yl)-phenyl]-amine

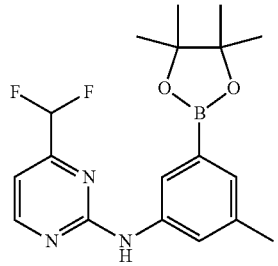 [SMILES: Cc1cc(Nc2nccc(C(F)F)n2)cc(B2OC(C)(C)C(C)(C)O2)c1]

Step 1

To a solution of difluoroacetic anhydride (50 g, 287 mmol) in CH$_2$Cl$_2$ (300 mL) cooled to −20° C. was added DMAP (0.351 g, 2.87 mmol) followed by the addition of ethyl vinyl ether (13.8 mL, 144 mmol) at such a rate that the internal temperature did not exceed −10° C. When complete the flask was stirred at 0° C. for 12 h before slowly warming to room temperature over the next 6 h. Water along with CH$_2$Cl$_2$ were added, the layers separated and the organic washed sequentially with aqueous saturated NaHCO$_3$ and then brine. The organic layer was dried with MgSO$_4$, filtered, concentrated in vacuo. The residue was subsequentually taken up in EtOH (162 mL), immersed in an ice water bath and then urea (17.25 g, 287 mmol) followed by conc. HCl (43 mL) were added at such a rate that the internal temperature did not exceed 20° C. When the addition was complete, the cooling bath was removed and the resulting mixture stirred for 18 h before concentration in vacuo. EtOH was added and the mixture concentrated a second time, then repeated 2× with EtOAc. The residue was diluted with EtOAc (100 mL), the heterogenous mixture stirred for 10 min and then the solvent decanted This was repeated twice more then the light brown solid was dried under vacuum for 48 h before dilution with phosphous oxychloride (215 mL, 2310 mmol). The resulting suspension was heated to 105° C. for 90 min during which time it was observed to become homogenous. The reaction mixture was cooled to room temperature, poured carefully into a 4 L cooled flask containing 2 L of ice and a temperature probe. The mixture was stirred for 1 h until the exotherm had ceased at which time the contents were transferred to a separatory funnel with additional CH$_2$Cl$_2$. The layers were cut, the aqueous layer extracted with CH$_2$Cl$_2$ (2×), then the combined organics were dried with MgSO$_4$, filtered and concentrated in vacuo (200 Torr, 40° C.) to an orange oil. The product was placed under vacuum for 1 min to yield 2-chloro-4-difluoromethyl-pyrimidine (31 g, 62.5 wt % solution in CH$_2$Cl$_2$ by ¹H NMR, 118 mmol). ¹H NMR (600 MHz, CDCl₃) δ 8.82 (d, J=5.0, 1H), 7.57 (d, J=5.0, 1H), 6.51 (t, J=54.4, 1H).

Step 2

The product of Step 1 (4.75 g, 23 mmol) and 3-bromo-5-methylaniline (5.59 g, 30 mmol) were diluted with dioxane (33 mL) to which AcOH (1.32 mL, 23 mmol) was added. The resulting mixture was heated to reflux and kept stirring for 30 h after which it was recooled to room temperature, diluted with CH₂Cl₂ and absorbed on silica prior to purification by flash chromatography to afford N-(3-bromo-5-methylphenyl)-4-(difluoromethyl)pyrimidin-2-amine (5.2 g, 16.6 mmol). ¹H NMR (600 MHz, CDCl₃) δ 8.58 (d, J=4.9, 1H), 7.75 (s, 1H), 7.32 (s, 1H), 7.21 (s, 1H), 7.06-6.92 (m, 2H), 6.50-6.27 (m, 1H), 2.30 (s, 3H).

Step 3

The product of Step 2 (0.5 g, 1.6 mmol), bis(pinacolato)diboron (0.465 g, 1.83 mmol), potassium acetate (0.469 g, 4.78 mmol) and PdCl₂(dppf)-CH₂Cl₂ adduct (0.065 g, 0.08 mmol) were diluted with degassed dioxane (3.5 mL) and heated to reflux for 2 h then retooled to room temperature. The mixture was diluted with CH₂Cl₂ and water was added. The layers were cut, the organic dried with MgSO₄, filtered and concentrated in vacuo, and the crude residue purified by flash chromatography to afford (4-difluoromethyl-pyrimidin-2-yl)-[3-methyl-5-(4,4,5,5-tetramethyl-[1,3,2]dioxaborolan-2-yl)-phenyl]-amine (550 mg, 1.52 mmol) MS ESI: [M+H]⁺ m/z 362.1. ¹H NMR (600 MHz, CDCl₃) δ 8.56 (d, J=4.1, 1H), 7.74 (s, 1H), 7.59 (s, 1H), 7.45 (s, 1H), 7.35 (s, 1H), 6.94 (d, J=4.2, 1H), 6.38 (t, J=55.0, 1H), 2.36 (s, 3H), 1.33 (s, 12H).

Intermediate 40: 2-[3-(1,3-thiazol-5-yl)-5-{[4-(trifluoromethyl)pyrimidin-2-yl]amino}phenyl]propan-2-ol

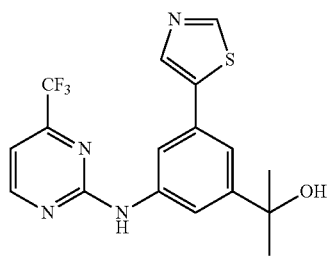 [SMILES: CC(C)(O)c1cc(Nc2nccc(C(F)(F)F)n2)cc(-c2cncs2)c1]

Step 1

To a flask containing methyl 3-amino-5-iodobenzoate (500 mg, 1.81 mmol) was added a solution of 2-chloro-4-(trifluoromethyl)pyrimidine (379 mg, 2.08 mmol) in dioxane (5.6 mL). Methanesulfonic acid (199 mg, 2.08 mmol) was added and the reaction was heated at 100° C. overnight. The reaction was cooled, diluted with ethyl acetate, washed with water, dried over magnesium sulfate, filtered and concentrated. Flash chromatography was used for purification to yield methyl 3-iodo-5-{[4-(trifluoromethyl)pyrimidin-2-yl]amino}benzoate (538 mg, 1.27 mmol, 71% yield). MS ESI: [M+H]⁺ m/z 424.0.

Step 2

To a flask containing the product of Step 1 (538 mg, 1.27 mmol), (bispinacolato)diboron (646 mg, 2.54 mmol), tricyclohexylphosphine (36 mg, 0.13 mmol), Pd₂(dba)₃ (29 mg, 0.03 mmol) and potassium acetate (200 mg, 2.03 mmol) was added previously degassed dioxane (12 mL). The solution was evacuated and then purged with argon 5 times and then heated at 95° C. overnight. The reaction was cooled, diluted with ethyl acetate, washed with water, dried over magnesium sulfate, filtered and concentrated. Flash chromatography was used for purification to yield methyl 3-(4,4,5,5-tetramethyl-1,3,2-dioxaborolan-2-yl)-5-{[4-(trifluoromethyl)pyrimidin-2-yl]amino}benzoate (391 mg, 0.92 mmol, 73% yield). MS ESI: [M+H]⁺ m/z 424.1.

Step 3

To a flask containing the product of Step 2 (391 mg, 0.92 mmol), dicyclohexyl[2',4',6'-tri(propan-2-yl)biphenyl-2-yl]phosphane (44 mg, 0.092 mmol), Pd₂(dba)₃ (42 mg, 0.046 mmol), cesium carbonate (602 mg, 1.85 mmol) was added a solution of 5-bromothiazole in a degassed mixture of dioxane (8.4 mL) and water (840 µL). The solution was evacuated and then purged with argon 5 times and then heated at 90° C. overnight. The reaction was cooled, diluted with ethyl acetate, washed with water, dried over magnesium sulfate, filtered and concentrated. Flash chromatography was used for purification to yield methyl 3-(1,3-thiazol-5-yl)-5-{[4-(trifluoromethyl)pyrimidin-2-yl]amino}benzoate (254 mg, 0.67 mmol, 72% yield). MS ESI: [M+H]⁺ m/z 381.0.

Step 4

To a flask containing the product of Step 3 (254 mg, 0.67 mmol) was added THF (6.7 mL). The solution was cooled to 0° C. and then methylmagnesium chloride (3.0M in Et₂O, 1.1 mL, 3.3 mmol) was added and the reaction was stirred for one hour. After one hour, more methylmagnesium chloride (3.0M in Et₂O, 1.1 mL, 3.3 mmol) was added and the reaction was stirred for 30 minutes. The reaction was then diluted with ethyl acetate and carefully quenched with water and then diluted with water. The organic layer was separated, dried over magnesium sulfate, filtered and concentrated. Flash chromatography was used for purification to yield 2-[3-(1,3-thiazol-5-yl)-5-{[4-(trifluoromethyl)pyrimidin-2-yl]amino}phenyl]propan-2-ol (188 mg, 0.49 mmol, 74% yield). MS ESI: [M+H]⁺ m/z 381. ¹H NMR (500 MHz, DMSO-d₆) δ 10.26 (s, 1H), 9.07 (s, 1H), 8.82 (d, J=4.8, 1H), 8.20 (s, 1H), 8.03 (s, 1H), 7.79 (s, 1H), 7.45 (s, 1H), 7.28 (d, J=4.9, 1H), 5.12 (s, 1H), 1.46 (s, 6H).

Intermediate 41: N-[3-cyclopropyl-5-(1,3-thiazol-5-yl)phenyl]-4-(trifluoromethyl)pyrimidin-2-amine

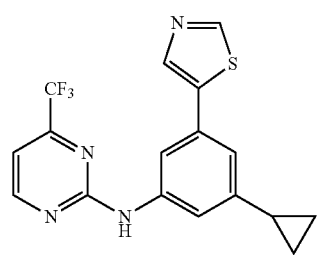 [SMILES: FC(F)(F)c1ccnc(Nc2cc(-c3cncs3)cc(C3CC3)c2)n1]

To a flask were added N-[3-(bromomethyl)-5-(1,3-thiazol-5-yl)phenyl]-4-(trifluoromethyl)-pyrimidin-2-amine (523 mg, 1.30 mmol), cyclopropyl boronic acid (336 mg, 3.91 mmol), potassium phosphate (968 mg, 4.56 mmol), Pd(OAc)₂ (15 mg, 0.07 mmol) and tricyclo-hexylphosphine (37 mg, 0.13 mmol). Degassed toluene (10 mL) and water (0.5 mL) were added and the solution was evacuated and then purged with argon 5 times. The mixture was then heated in the microwave at 130° C. for 30 minutes. The reaction was diluted with ethyl acetate, washed with water, dried over magnesium sulfate, filtered and concentrated. Flash chromatography was used for purification to yield N-[3-cyclopropyl-5-(1,3-thiazol-5-yl)phenyl]-4-(trifluoromethyl)pyrimidin-2-amine (384 mg, 1.06 mmol, 81% yield). MS ESI: [M+H]⁺ m/z 363. ¹H NMR (500 MHz, DMSO-d₆) δ 10.23 (s, 1H), 9.06 (s, 1H), 8.83 (d, J=4.8, 1H), 8.23 (s, 1H), 7.92 (s, 1H), 7.41 (s, 1H), 7.28 (d, J=4.9, 1H), 7.12 (s, 1H), 2.03-1.80 (m, 1H), 1.05-0.92 (m, 2H), 0.78-0.61 (m, 2H).

Intermediate 42: N-[3-({[tert-butyl(dimethyl)silyl]oxy}methyl)-5-(1,3-thiazol-5-yl)phenyl]-4-(trifluoromethyl)pyrimidin-2-amine

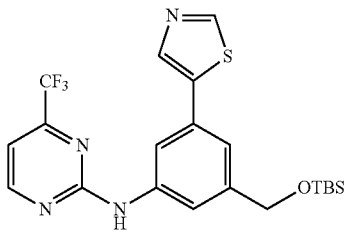 [SMILES: CC(C)(C)[Si](C)(C)OCc1cc(Nc2nccc(C(F)(F)F)n2)cc(-c2cncs2)c1]

Step 1

To a flask containing methyl 3-amino-5-iodobenzoate (250 mg, 0.90 mmol) was added THF (9.0 mL). The solution was cooled to 0° C. and lithium aluminum hydride (1.0M in THF, 1.8 mL, 1.8 mmol) was added slowly and the reaction was allowed to warm to room temperature. Once complete by TLC, the reaction was quenched carefully with water and then diluted with ethyl acetate. The organic layer was extracted, dried over magnesium sulfate, filtered and concentrated. Flash chromatography was used for purification to yield [3-(aminomethyl)-5-iodophenyl]methanol (109 mg, 0.44 mmol, 49% yield). MS ESI: [M+H]⁺ m/z 250.0.

Step 2

To a flask containing the product of Step 1 (109 mg, 0.44 mmol) was added a solution of 2-chloro-4-(trifluoromethyl)pyrimidine (92 mg, 0.50 mmol) in dioxane (1.4 mL). Methanesulfonic acid was added (0.02 mL, 0.37 mmol) and the reaction was heated at 100° C. overnight. The reaction was then cooled to room temperature, diluted with ethyl acetate, washed with brine, dried over magnesium sulfate, filtered and concentrated. Flash chromatography was used for purification to yield (3-iodo-5-{[4-(trifluoromethyl)pyrimidin-2-yl]amino}phenyl)methanol (90 mg, 0.23 mmol, 52% yield). MS ESI: [M+H]⁺ m/z 396.0.

Step 3

To a flask containing the product of Step 2 (2.79 g, 7.06 mmol) in AMY (71 mL) were added tert-butyldimethylsilyl chloride (1.60 g, 10.59 mmol), imidazole (0.96 g, 14.12 mmol) and DMAP (86 mg, 0.71 mmol). After two hours, The reaction was diluted with water and ethyl acetate. The organic layer was separated, dried over magnesium sulfate, filtered and concentrated. Column chromatography on silica gel was used for purification to yield N-[3-({[tert-butyl(dimethyl)silyl]oxy}methyl)-5-iodophenyl]-4-(trifluoromethyl)pyrimidin-2-amine (3.46 g, 6.79 mmol, 96% yield). MS ESI: [M+H]⁺ m/z 510.0.

Step 4

To a flask was added the product of Step 3 (3.46 g, 6.79 mmol), (bispinacolato)diboron (2.59 g, 10.19 mmol), dicyclohexyl[2',4',6'-tri(propan-2-yl)biphenyl-2-yl]phosphane (324 mg, 0.68 mmol), Pd(OAc)₂ (76 mg, 0.34 mmol) and potassium acetate (1.33 g, 13.59 mmol) was added previously degassed dioxane (68 mL). The solution was evacuated and then purged with argon 5 times and then heated at 85° C. overnight. The solution was cooled, diluted with ethyl acetate, washed with water, dried over magnesium sulfate, filtered and concentrated. Flash chromatography was used for purification to yield N-[3-({[tert-butyl(dimethyl)silyl]oxy}methyl)-5-(4,4,5,5-tetramethyl-1,3,2-dioxaborolan-2-yl)phenyl]-4-(trifluoromethyl)pyrimidin-2-amine (2.75 g, 5.40 mmol, 79% yield). MS ESI: [M+H]⁺ m/z 510.2.

Step 5

To a flask containing the product of Step 4 (750 mg, 1.47 mmol), dicyclohexyl[2',4',6'-tri(propan-2-yl)biphenyl-2-yl]phosphane (70 mg, 0.15 mmol), Pd₂(dba)₃ (67 mg, 0.074 mmol), cesium carbonate (959 mg, 2.94 mmol) was added a solution of 5-bromothiazole in a degassed mixture of dioxane (2.7 mL) and water (2704). The solution was evacuated and then purged with argon 5 times and then heated at 90° C. overnight. The reaction was cooled, diluted with ethyl acetate, washed with water, dried over magnesium sulfate, filtered and concentrated. Flash chromatography was used for purification to yield N-[3-({[tert-butyl(dimethyl)silyl]oxy}-methyl)-5-(1,3-thiazol-5-yl)phenyl]-4-(trifluoromethyl)pyrimidin-2-amine (414 mg, 0.89 mmol, 60% yield). MS ESI: [M+H]⁺ m/z 381. ¹H NMR (500 MHz, DMSO-d₆) δ 10.38 (s, 1H), 9.07 (s, 1H), 8.81 (d, J=4.9, 1H), 8.17 (s, 1H), 8.09 (s, 1H), 7.69 (s, 1H), 7.28 (d, J=4.9, 1H), 7.26 (s, 1H), 4.72 (s, 2H), 0.91 (s, 9H), 0.09 (s, 6H).

Intermediate 43: 4-cyclopropyl-N-[3-methyl-5-(1,3-thiazol-5-yl)phenyl]pyrimidin-2-amine

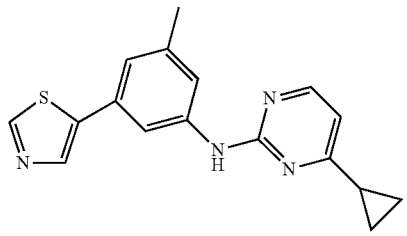 [SMILES: Cc1cc(Nc2nccc(C3CC3)n2)cc(-c2cncs2)c1]

To a solution of 4-cyclopropyl-N-(3-methyl-5-(4,4,5,5-tetramethyl-1,3,2-dioxaborolan-2-yl)phenyl)pyrimidin-2-amine (750 mg, 2.14 mmol) in 2-methyl tetrahydrofuran (10.7 mL) were added 5-bromothiazole (406 mg, 2.35 mmol), PdCl₂(dppf)-CH₂Cl₂ (87 mg, 0.11 mmol), and aqueous sodium carbonate (2 M, 2.14 mL). The reaction was sealed and purged with N₂ for 5 minutes. The reaction was stirred at 80° C. for 16 h and cooled to room temperature. Water was added and extracted with EtOAc (3×). The combined organic layers were dried (magnesium sulfate), concentrated, and purified by flash chromatography to afford 4-cyclopropyl-N-[3-methyl-5-(1,3-thiazol-5-yl)phenyl]pyrimidin-2-amine (600 mg, 1.95 mmol, 91% yield) as an off-white solid. MS ESI: [M+H]$^+$ m/z 309.1. $^1$H NMR (500 MHz, DMSO-d$_6$) δ 9.49 (s, 1H), 9.06 (s, 1H), 8.26 (d, 5.0, 1H), 8.19 (s, 1H), 8.04 (s, 1H), 7.43 (s, 1H), 7.10 (s, 1H), 6.82 (d, J=5.0, 1H), 2.29 (s, 3H), 2.00 (m, 1H), 1.17-0.93 (m, 4H).

Intermediate 44: 4-isopropyl-N-(3-methyl-5-(thiazol-5-yl)phenyl)pyrimidin-2-amine

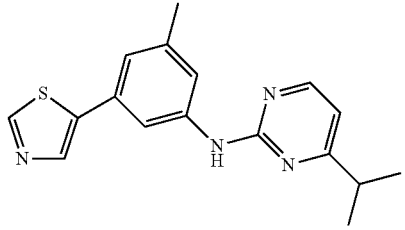 [SMILES: Cc1cc(Nc2nccc(C(C)C)n2)cc(-c2cncs2)c1]

To a solution of 4-isopropyl-N-(3-methyl-5-(4,4,5,5-tetramethyl-1,3,2-dioxaborolan-2-yl)phenyl)pyrimidin-2-amine (500 mg, 1.42 mmol) in 2-methyl tetrahydrofuran (7.1 mL) were added 5-bromothiazole (318 mg, 1.84 mmol), PdCl$_2$(dppf)-CH$_2$Cl$_2$ (58 mg, 0.07 mmol), and aqueous sodium carbonate (2 M, 1.42 mL). The reaction was sealed and purged with N$_2$ for 5 minutes. The reaction was stirred at 80° C. for 16 h and cooled to room temperature. Water was added and extracted with EtOAc (3×). The combined organic layers were dried over magnesium sulfate, concentrated in vacuo, and purified by flash chromatography to give 4-isopropyl-N-(3-methyl-5-(thiazol-5-yl)phenyl)pyrimidin-2-amine (366 mg, 1.18 mmol, 83% yield) as an off-white solid. MS ESI: [M+H]$^+$ m/z 311.1. $^1$H NMR (500 MHz, DMSO-d$_6$) δ 9.59 (s, 1H), 9.05 (s, 1H), 8.38 (d, J=4.7, 1H), 8.19 (s, 1H), 8.13 (s, 1H), 7.51 (s, 1H), 7.11 (s, 1H), 6.77 (d, J=5.1, 1H), 2.87 (m, 1H), 2.30 (s, 3H), 1.25 (d, J=6.8, 6H).

Intermediate 45: 2-{[3-methyl-5-(1,3-thiazol-5-yl)phenyl]amino}pyrimidine-4-carboxylic acid trifluoroacetate

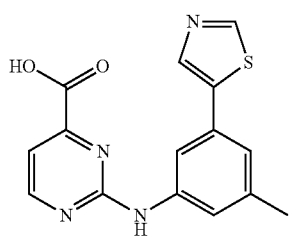 [SMILES: Cc1cc(Nc2nccc(C(=O)O)n2)cc(-c2cncs2)c1]

To a solution of 2-chloropyrimidine-4-carboxylic acid (417 mg, 2.6 mmol) and 3-methyl-5-(1,3-thiazol-5-yl)aniline (500 mg, 2.6 mmol) in degassed 1,4 dioxane (11 mL) were added Pd(OAc)$_2$ (59 mg, 0.26 mmol), Xantphos (228 mg, 0.39 mmol) and Cs$_2$CO$_3$ (2.6 g, 7.9 mmol) and the reaction was heated to 100° C. for 30 minutes. After cooling, the reaction was partitioned between 100 mL each of dichloromethane and pH 1 buffer. The layers were separated and the organic phase was dried over anhydrous MgSO$_4$, filtered, and concentrated under reduced pressure. Purification by reverse phase HPLC (35-70% acetonitrile gradient using water with a 0.1% trifluoroacetic acid buffer) afforded 2-{[3-methyl-5-(1,3-thiazol-5-yl)phenyl]amino}pyrimidine-4-carboxylic acid trifluoroacetate (20 mg, 1.8%) as a colorless oil. MS ESI: [M+H]$^+$ m/z 313.0.

Intermediate 46: 3-methyl-N-[3-(pentafluoroethyl)phenyl]-5-(1,3-thiazol-5-yl)aniline

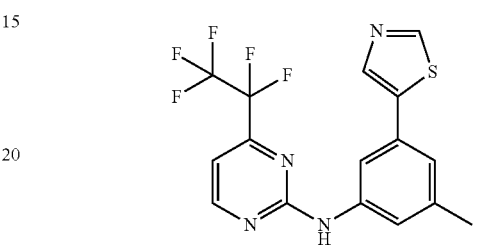

To a solution of 2-chloro-4-(pentafluoroethyl)pyrimidine (61 mg, 0.26 mmol) and 3-methyl-5-(1,3-thiazol-5-yl)aniline (50 mg, 0.26 mmol) in degassed 1,4-dioxane (1.1 mL) were added Xantphos (23 mg, 0.039 mmol), Pd(OAc)$_2$ (5.9 mg, 0.026 mmol) and Cs$_2$CO$_3$ (172 mg, 0.53 mmol) and the reaction was heated to 100° C. for 30 minutes. After cooling, the reaction was partitioned between EtOAc (10 mL) and saturated aqueous sodium bicarbonate. The layers were separated and the aqueous phase was extracted EtOAc (10 mL). The combined organic phases were washed with saturated aqueous sodium chloride (10 mL), dried over anhydrous MgSO$_4$, filtered and concentrated under reduced pressure. Purification on silica (20-60% ethyl acetate in hexanes) afforded 3-methyl-N-[3-(pentafluoroethyl)phenyl]-5-(1,3-thiazol-5-yl)aniline (13 mg, 13%) as a colorless foam. MS ESI: [M+H]$^+$ m/z 387.0.

Intermediate 47: 4-[1-(4-methoxybenzyl)-1H-1,2,3-triazol-4-yl]-N-[3-methyl-5-(1,3-thiazol-5-yl)phenyl]pyrimidin-2-amine

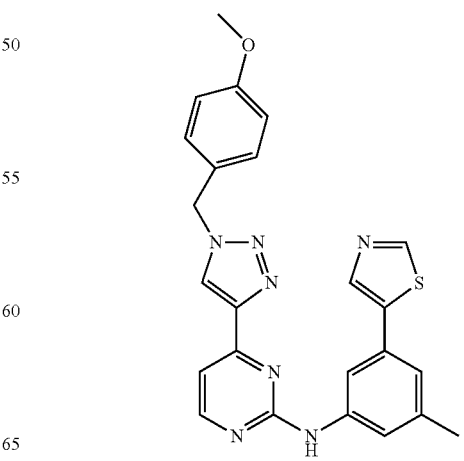

Step 1

To a solution of 2-chloro-4-ethynylpyrimidine (200 mg, 1.4 mmol) and 1-(azidomethyl)-4-methoxybenzene (0.5 M in t-butanol, 2.9 mL, 1.44 mmol) in 1:1 water tBuOH (7.2 mL) was added copper(II) sulfate pentahydrate (36 mg, 0.14 mmol) and sodium ascorbate (143 mg, 0.72 mmol) and the reaction was stirred at room temperature for 2 hrs. The reaction was then partitioned between water (50 mL) and EtOAc (50 mL). The layers were separated and the aqueous phase was extracted once with EtOAc (50 mL). The combined organic phases were washed with saturated aqueous sodium chloride (50 mL), dried over anhydrous MgSO$_4$, filtered, and concentrated under reduced pressure. Purification on silica (30-50% ethyl acetate in hexanes) afforded 2-chloro-4-[1-(4-methoxybenzyl)-1H-1,2,3-triazol-4-yl]pyrimidine (256 mg, 59%) as a white solid.

Step 2

To a solution of 3-methyl-5-(1,3-thiazol-5-yl)aniline (63 mg, 0.33 mmol) and the product of Step 1 (100 mg, 0.33 mmol) in degassed 1,4-dioxane (1.3 mL) were added Pd(OAc)$_2$ (7.4 mg, 0.033 mmol), Xantphos (29 mg, 0.050 mmol) and Cs$_2$CO$_3$ (216 mg, 0.66 mmol) and the reaction was heated to 100° C. for 30 minutes. After cooling, the reaction was partitioned between EtOAc (10 mL) and saturated aqueous sodium bicarbonate (10 mL). The layers were separated, and the aqueous phase was extracted with EtOAc (10 mL). The combined organic phases were washed with saturated aqueous sodium chloride (10 mL), dried over anhydrous MgSO$_4$, filtered, and concentrated under reduced pressure. Purification on silica (30-70% ethyl acetate in hexanes) afforded 4-[1-(4-methoxybenzyl)-1H-1,2,3-triazol-4-yl]-N-[3-methyl-5-(1,3-thiazol-5-yl)phenyl]pyrimidin-2-amine (50 mg, 33%) as a colorless foam. MS ESI: [M+H]$^+$ m/z 456.1.

Intermediate 48: 5-Chloro-N-[3-methyl-5-(1,3-thiazol-5-yl)phenyl]pyrimidin-2-amine

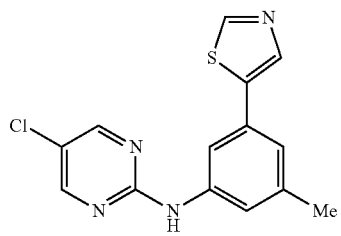 [SMILES: Cc1cc(Nc2ncc(Cl)cn2)cc(-c2cncs2)c1]

A flask containing 2,5-dichloropyrimidine (2 g, 13.42 mmol), 3-methyl-5-(1,3-thiazol-5-yl)aniline (2.55 g, 13.42 mmol), PdOAc$_2$ (0.603 g, 2.68 mmol), Xantphos (2.330 g, 4.03 mmol), and cesium carbonate (8.75 g, 26.8 mmol) was degassed for 5 min. Dioxane (89 ml) was added and argon was bubbled through the mixture for 15 min. The temperature was increased to 110° C. and the reaction was stirred 14 h at that temperature. The cooled reaction was diluted with brine and water and extracted three times with CH$_2$Cl$_2$. The organic layer was concentrated under reduced pressure and purified by flash chromatography (0-70% EtOAc:Hexanes) to give 5-chloro-N-[3-methyl-5-(1,3-thiazol-5-yl)phenyl]pyrimidin-2-amine (2.95 g, 73%) as a white solid. MS ESI: [M+H]$^+$ m/z 303. $^1$H NMR (500 MHz, CDCl$_3$) δ 8.75 (s, 1H), 8.37 (s, 2H), 8.08 (s, 1H), 7.71 (s, 1H), 7.33 (s, 1H), 7.09 (s, 1H), 2.40 (s, 3H). rhSYK activity=++.

Intermediate 49: 5-Fluoro-4-ethyl-N-[3-methyl-5-(1,3-thiazol-5-yl)phenyl]pyrimidin-2-amine

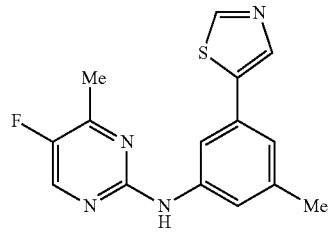 [SMILES: Cc1cc(Nc2ncc(F)c(C)n2)cc(-c2cncs2)c1]

2-Chloro-5-fluoro-4-methylpyrimidine (500 mg, 3.41 mmol), 3-methyl-5-(1,3-thiazol-5-yl)aniline (649 mg, 3.41 mmol), PdOAc$_2$ (77 mg, 0.341 mmol), Xantphos (296 mg, 0.512 mmol), and cesium carbonate (2223 mg, 6.82 mmol) were combined in a flask and degassed with Argon. Dioxane (12 mL) was added and the solution was degassed with Argon for 5 min. The mixture was heated to 100° C. for 2 h and then allowed to cool to room temperature. The mixture was diluted with Brine and EtOAc. The layers were separated and the aqueous portion was re-extracted with EtOAc. The combined organic layers were dried over Na$_2$SO$_4$ and concentrated in vacuo. Purification via silica gel flash chromatography (0-40% EtOAc:CH$_2$Cl$_2$) afforded 5-fluoro-4-methyl-N-[3-methyl-5-(1,3-thiazol-5-yl)phenyl]pyrimidin-2-amine (588 mg, 57%) as a beige solid. MS ESI: [M+H]$^+$ m/z 301. $^1$H NMR (500 MHz, CDCl$_3$) δ 8.75 (s, 1H), 8.33 (s, 2H), 8.09 (s, 1H), 7.74 (s, 1H), 7.33 (s, 1H), 7.08 (s, 1H), 2.40 (s, 3H). rhSYK activity=+++.

Intermediate 50: 5-Fluoro-N-[3-methyl-5-(1,3-thiazol-5-yl)phenyl]pyrimidin-2-amine

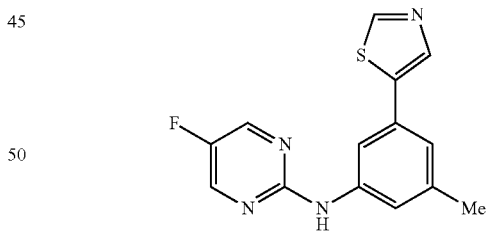

2-Chloro-5-fluoropyrimidine (0.443 ml, 3.58 mmol), 3-methyl-5-(1,3-thiazol-5-yl)aniline (682 mg, 3.58 mmol), PdOAc$_2$ (80 mg, 0.358 mmol), Xantphos (311 mg, 0.538 mmol), and cesium carbonate (2336 mg, 7.17 mmol) were combined in a flask and degassed with Argon. Dioxane (12 mL) was added and the mixture was degassed with Argon for 5 min. The mixture was then heated to 100° C. for 2 h. The reaction was cooled to room temperature, diluted with brine and EtOAc. The layers were separated and the aqueous portion re-extracted with EtOAc. The combined organics were dried over Na$_2$SO$_4$, filtered and concentrated in vacuo. Purification via silica gel flash chromatography (0-40% EtOAc: CH$_2$Cl$_2$) afforded 5-fluoro-N-[3-methyl-5-(1,3-thiazol-5-yl)

phenyl]pyrimidin-2-amine (947 mg, 92%) as a beige solid. MS ESI: [M+H]+ m/z 287. rhSYK activity=++.

Intermediate 51: 4-Cyclopropyl-5-fluoro-N-[3-methyl-5-(1,3-thiazol-5-yl)phenyl]pyrimidin-2-amine

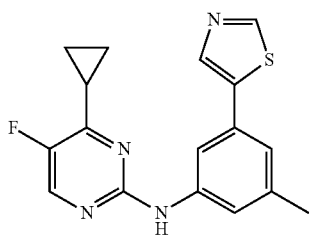 [SMILES: Cc1cc(Nc2ncc(F)c(C3CC3)n2)cc(-c2cncs2)c1]

Step 1

5-Fluoro-2,4-dichloropyrimidine (5 g, 29.9 mmol), cyclopropyl boronic acid (2.57 g, 29.9 mmol), potassium phosphate tribasic (15.89 g, 74.9 mmol) and PdCl$_2$(dppf)-dichloromethane adduct (1.22 g, 1.50 mmol) were added to a dry flask. The flask was degassed with argon and then tetrahydrofuran (150 ml) was added. The reaction mixture was degassed with argon for five minutes, and then heated to 67° C. After 12 hours, the reaction mixture was cooled to room temperature, diluted with ethyl acetate (1000 mL), washed with brine, dried over magnesium sulfate, filtered and concentrated. The residue was purified by flash chromatography on silica gel (EtOAc/hexane gradient) to afford 2-chloro-4-cyclopropyl-5-fluoropyrimidine (4.1 g, 23.8 mmol, 79% yield). MS ESI: [M+H]+ m/z 172.9. $^1$H NMR (500 MHz, DMSO-d$_6$) δ 8.66 (d, J=2.0 Hz, 1H); 2.34-2.26 (m, 1H); 1.26-1.20 (m, 2H); 1.12-1.08 (m, 2H).

Step 2

3-Methyl-5-(1,3-thiazol-5-yl)aniline (0.250 g, 1.31 mmol), the product of Step 1 (0.227 g, 1.31 mmol), palladium (II) acetate (0.0295 g, 0.131 mmol), xantphos (0.114 g, 0.197 mmol), and cesium carbonate (0.856 g, 2.63 mmol) were added to a dry flask. The flask was degassed with argon and then dioxane (4.4 ml) was added. The reaction mixture was degassed with argon for 5 minutes, and then heated to 100° C. After 2 hours, the reaction mixture was cooled to room temperature, diluted with ethyl acetate, washed with brine, dried over magnesium sulfate, filtered, and concentrated. The residue was purified by flash chromatography on silica gel (EtOAc/dichloromethane gradient) to afford 4-cyclopropyl-5-fluoro-N-[3-methyl-5-(1,3-thiazol-5-yl)phenyl]pyrimidin-2-amine (0.390 g, 1.20 mmol, 91% yield). MS ESI: [M+H]+ m/z 326.8. $^1$H NMR (500 MHz, DMSO-d$_6$) δ 9.59 (s, 1H); 9.06 (s, 1H); 8.38 (d, J=2.5 Hz, 1H); 8.19 (s, 1H); 7.94 (s, 1H); 7.39 (s, 1H); 7.10 (s, 1H); 2.29 (s, 3H); 2.28-2.23 (m, 1H); 1.18-1.14 (m, 4H).

Intermediate 52: N-[3-fluoro-5-(1,3-thiazol-5-yl)phenyl]-4-(trifluoromethyl)pyrimidin-2-amine

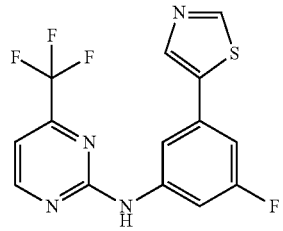 [SMILES: Fc1cc(Nc2nccc(C(F)(F)F)n2)cc(-c2cncs2)c1]

Step 1

3-bromo-5-fluoroaniline (2.23 g, 11.7 mmol), bispinacolatodiboron (3.28 g, 12.9 mmol), Pd$_2$(dba)$_3$ (0.269 g, 0.293 mmol), tricyclohexylphosphine (0.329 g, 1.17 mmol), and potassium acetate (1.84 g, 18.8 mmol) were added to a dry flask. The flask was degassed with argon and then dioxane (25 mL) was added. The reaction mixture was degassed again with argon for five minutes, and then heated to 95° C. After 12 hours, the reaction mixture was cooled, diluted with ethyl acetate, filtered through celite, and concentrated. The residue was purified by flash chromatography (EtOAc/hexane gradient) to afford 3-fluoro-5-(4,4,5,5-tetramethyl-1,3,2-dioxaborolan-2-yl)aniline (2.66 g, 11.2 mmol, 96% yield). MS ESI: [M+H]+ m/z 238.1. $^1$H NMR (500 MHz, DMSO-d$_6$) δ 6.74 (d, J=2.0 Hz, 1H); 6.44-6.36 (m, 2H); 5.40 (s, 2H); 1.25 (s, 12H).

Step 2

The product of Step 1 (2.66 g, 11.2 mmol), 2-bromo-1,4-thiazole (1.00 ml, 11.2 mmol), Pd$_2$(dba)$_3$ (0.514 g, 0.561 mmol), X-phos (0.535 g, 1.122 mmol), and cesium carbonate (7.31 g, 22.4 mmol) were added to a dry flask. The flask was degassed with argon, then dioxane (25 ml) and water (2.5 ml) were added. The reaction mixture was degassed with argon for five minutes, and then heated to 95° C. After 16 hours, the reaction mixture was cooled, diluted with ethyl acetate, filtered through celite, and concentrated. The residue was purified by flash chromatography (EtOAc/hexane gradient) to afford 3-fluoro-5-(1,3-thiazol-5-yl)aniline (2.27 g, 9.49 mmol, 85% yield). MS APCI: [M+H]+ m/z 195.1. $^1$H NMR (500 MHz, DMSO-d$_6$) δ 9.02 (s, 1H); 8.18 (s, 1H); 6.66-6.62 (m, 1H); 6.61-6.59 (m, 1H); 6.29-6.26 (m, 1H); 5.58 (s, 2H).

Step 3

The product of Step 2 (0.93 g, 4.79 mmol), 2-chloro-4-(trifluoromethyl)pyrimidine (0.874 g, 4.79 mmol), palladium (II) acetate (0.107 g, 0.479 mmol), xantphos (0.416 g, 0.718 mmol), and cesium carbonate (3.12 g, 9.58 mmol) were added to a dry flask. The flask was degassed with argon, and then dioxane (20 ml) was added. The reaction mixture was degassed with argon for five minutes, and then heated to 90° C. After 2 hours, the reaction mixture was cooled, diluted with ethyl acetate, filtered through celite, and concentrated. The residue was purified by column chromatography on silica gel (EtOAc/hexane gradient) to afford solids. The solids were dissolved in hot ethyl acetate (25 mL) and then triturated with hexanes (50 mL) while cooling. After 2 hours, the mixture was filtered to afford N-[3-fluoro-5-(1,3-thiazol-5-yl)phenyl]-4-(trifluoromethyl)pyrimidin-2-amine (1.18 g, 3.47 mmol, 72% yield). MS ESI: [M+H]⁺ m/z 341.1. ¹H NMR (500 MHz, DMSO-d₆) δ 10.52 (s, 1H); 9.10 (s, 1H); 8.87 (d, J=4.0 Hz, 1H); 8.31 (s, 1H); 7.93 (s, 1H); 7.66-7.62 (m, 1H); 7.35 (d, J=4.5 Hz, 1H); 7.28 (dt, J=8.0 Hz, 1.5 Hz, 1H).

Intermediate 53: 2-chloro-4-[(1E)-3-methoxyprop-1-en-1-yl]pyrimidine

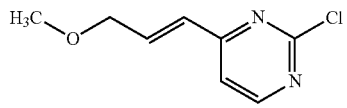

A microwave vessel was charged with 2,4-dichloropyrimidine (500 mg, 3.36 mmol), 3-acetoxy-1-propenylboronic acid pinacol ester (997 mg, 5.03 mmol) and solid potassium phosphate tribasic (2.14 g, 10.1 mmol), which were then suspended in 2-methyltetrahydrofuran (4 ml) and water (1 ml). The vessel was deoxygenated three times, then Palladium(II) acetate (37.7 mg, 0.17 mmol) and 2-dicyclohexylphosphino-2',6'-dimethoxybiphenyl (138 mg, 0.34 mmol) were introduced and the dark mixture was heated under microwave irradiation at 125° C. for 15 min. The reaction mixture was diluted with saturated aqueous NaHCO₃ (80 ml) and extracted with EtOAc (2×75 ml). The combined organic layers were dried over MgSO₄ and concentrated. The crude orange oil was purified by flash column chromatography (SiO₂: 100% Hex to 100% EtOAc), which afforded 2-chloro-4-[(1E)-3-methoxyprop-1-en-1-yl]pyrimidine (623 mg, 3.21 mmol, 96% yield) as an orange-red solid. MS ESI: [M+H]⁺ m/z 185.1.

Intermediate 54: 2-chloro-4-(propan-2-yloxy)pyrimidine

To a solution of 2,4-dichloropyrimidine (5.0 g, 34 mmol) in 2-propanol (84 mL) was added Cs₂CO₃ (12 g, 37 mmol) and the mixture was stirred at rt for 16 h. The reaction was then heated to 65° C. for 3 h, after which time the reaction was filtered and concentrated. Purification on silica using a gradient solvent system of 0-10% EtOAc/Hexanes furnished 2-chloro-4-(propan-2-yloxy)pyrimidine (2.4 g, 41%) as a colorless oil. ¹H NMR (500 MHz, CDCl₃) δ 8.23 (d, J=5.7, 1H), 6.56 (d, J=5.7, 1H), 5.38 (hept, J=6.2, 1H), 1.34 (d, J=6.2, 6H).

Intermediate 55: 4-tert-butyl-2-chloropyrimidine

To a dry flask containing 2-chloropyrimidine (1.0 g, 8.7 mmol) was added anhydrous Et₂O (8.7 mL) and the solution was cooled to −30° C. tBuLi (1.7 M solution in n-pentane, 5.7 mL, 9.6 mmol) was added dropwise and the reaction was held at −30° C. for 30 min. The reaction was warmed to 0° C. and stirred at that temperature for 30 min, at which time the reaction was quenched by dropwise addition of a solution of acetic acid (0.60 mL, 10.5 mmol) in THF (3 mL) and water (1 mL). The reaction was maintained at 0° C. and a solution of DDQ (2.38 g, 10.5 mmol) in THF (8.7 mL) was added. After 15 minutes, NaOH (1 M, 1 mL) and water (10 mL) were added, and the dark reaction mixture was transferred to a separatory funnel containing EtOAc (50 mL) and water (50 mL). The layers were separated and the aqueous layer was extracted once with EtOAc (50 mL). The combined organic phases were washed with saturated aqueous sodium chloride (50 mL), dried over anhydrous MgSO₄, filtered and concentrated under reduced pressure. Adsorption of the oily black residue on silica, followed by chromatography on silica using a gradient solvent system of 5→30% EtOAc/hexanes furnished 4-tert-butyl-2-chloropyrimidine (1.00 g, 67%) as a pale yellow oil. ¹H NMR (500 MHz, CDCl₃) δ 8.49 (d, J=5.2, 1H), 7.24 (d, J=5.2, 1H), 1.33 (s, 9H).

Intermediate 56: 2-chloro-4-methoxy-5-(trifluoromethyl)pyrimidine

A solution of 2,4-dichloro-5-(trifluoromethyl)pyrimidine (0.625 ml, 4.61 mmol), sodium methoxide (0.124 g, 2.304 mmol) in MeOH (23 ml) was prepared. The solution was stirred at room temperature. After 50 minutes, additional NaOMe (110 mg) was added. After a total of two hours, the reaction was diluted with ethyl acetate and transferred to a separatory funnel. The organic layer was washed with saturated aqueous NaHCO₃ and brine. The organic layer was dried over Na₂SO₄, filtered and concentrated. Flash chromatography (5-25% EtOAc/hexanes) afforded 2-chloro-4-methoxy-5-(trifluoromethyl)pyrimidine (118.9 mg, 0.503 mmol, 10.92% yield). ¹H NMR (500 MHz, DMSO-d₆) δ 8.86 (s, 1H), 4.07 (s, 3H).

Intermediate 57: methyl 2-chloropyrimidine-4-carboxylate

To a solution of 2-chloropyrimidine-4-carboxylic acid (1.0 g, 6.31 mmol) in 1:1 benzene (5 mL) and MeOH (5 mL) at 0° C. was added trimethylsilyl-diazomethane (2.0 M solution in hexanes, 3.78 mL, 7.57 mmol) dropwise. The solution was left to stir for 14 hr and concentrated to dryness. Flash chromatography on silica (0-100% EtOAc/hexanes) afforded methyl 2-chloropyrimidine-4-carboxylate (980 mg, 5.68 mmol, 90% yield) as a yellow oil. MS ESI: [M+H]⁺ m/z 173.0. ¹H NMR (500 MHz, CDCl₃) δ 8.88 (dd, J=1.5, 4.9, 1H), 7.96 (dd, J=1.5, 4.9, 1H), 4.04 (d, J=1.5, 3H).

Intermediate 58: 2-(2-chloropyrimidin-4-yl)propan-2-ol

To a solution of THF (0.25 mL) and toluene (1 mL) at −20° C. under a nitrogen atmosphere was added methyl magnesium chloride (3.0 M in THF, 1 mL, 2.90 mmol) followed by t-BuOH (0.050 mL in 0.750 mL THF, 0.579 mmol) and left to stir for 30 min at 0° C. The solution was cooled back down to −20° C. and methyl 2-chloropyrimidine-4-carboxylate (100 mg, 0.58 mmol) in THF (1 mL) was added. The solution was warmed to room temperature and stirred for an additional 30 min. The solution was diluted with EtOAc, washed with brine, dried with MgSO₄, filtered, and concentrated to dryness to afford 2-(2-chloropyrimidin-4-yl)propan-2-ol (71 mg, 0.41 mmol, 71% yield. MS ESI: [M+H]⁺ m/z 173.1. ¹H NMR (500 MHz, CDCl₃) δ 8.60 (dd, J=1.8, 5.1, 1H), 7.44 (d, J=5.1 1H), 1.56 (d, J=1.8, 6H).

Intermediate 59: 2-chloro-N-methoxy-N-methylpyrimidine-4-carboxamide

To a solution of 2-chloropyrimidine-4-carboxylic acid (3.95 g, 24.9 mmol) and N-methoxymethanamine hydrogen chloride salt (2.43 g, 24.9 mmol) in dichloromethane (15 mL) were added triethylamine (6.95 mL, 50 mmol) and (benzotriazol-1-yloxy)tripyrrolidino-phosphonium hexafluorophosphate (13 g, 24.91 mmol) and stirred for 4 hr. The solution was diluted with EtOAc, washed with brine, dried with MgSO₄, filtered, and concentrated to dryness. Purification on silica gel by flash chromatography (0-100% EtOAc/hexanes) afforded 2-chloro-N-methoxy-N-methylpyrimidine-4-carboxamide (3.30 g, 16.37 mmol, 66% yield). MS ESI: [M+H]$^+$ m/z 202.0. $^1$H NMR (500 MHz, CDCl$_3$) δ 8.75 (d, J=4.6, 1H), 7.48 (d, J=4.6, 1H), 3.77 (s, 3H), 3.35 (s, 3H).

Intermediate 60: 1-(2-chloropyrimidin-4-yl)ethanone

To a solution of 2-chloro-N-methoxy-N-methylpyrimidine-4-carboxamide (75 mg, 0.372 mmol) in THF (3 mL) at −78° C. under a nitrogen atmosphere was added methyl magnesium chloride (3.0 M in THF, 0.124 mL, 0.372 mmol) dropwise. The solution was warmed to room temperature for 1 hr. The solution was diluted with EtOAc, washed with 1 N the organic layer was neutralized with saturated aqueous NaHCO$_3$, dried with MgSO$_4$, filtered, and concentrated to dryness. Purification on silica gel by flash chromatography (0-100% EtOAc/hexanes) afforded 1-(2-chloropyrimidin-4-yl)ethanone (45 mg, 0.29 mmol, 77% yield). $^1$H NMR (500 MHz, CDCl$_3$) δ 8.86 (d, J=4.9, 1H), 7.83 (d, J=4.9, 1H), 2.71 (s, 3H).

Intermediate 61: 1-(2-chloropyrimidin-4-yl)ethanol

To a solution of 1-(2-chloropyrimidin-4-yl)ethanone (600 mg, 3.83 mmol) in MeOH (5 mL) at 0° C. was added sodium borohydride (145 mg, 3.83 mmol) and stirred for 30 min. The solution was diluted with EtOAc, washed with brine, dried with MgSO$_4$, filtered, and concentrated to dryness to afford 1-(2-chloropyrimidin-4-yl)ethanol (220 mg, 1.39 mmol, 36% yield). MS ESI: [M+H]$^+$ m/z 159.0. $^1$H NMR (500 MHz, CDCl$_3$) δ 8.60 (d, J=5.1, 1H), 7.39 (d, J=5.1, 1H), 4.87 (q, J=6.6, 1H), 1.53 (m, 3H).

Intermediate 62: 2-chloro-4-(1-fluoroethyl)pyrimidine

To a solution of 1-(2-chloropyrimidin-4-yl)ethanol (150 mg, 0.950 mmol) in dichloromethane (3 mL) at 0° C. was added diethylaminosulfur trifluoride (183 mg, 1.14 mmol) dropwise and stirred for 3 hr. The solution was diluted with dichloromethane, washed with saturated aqueous NaHCO$_3$, dried with MgSO$_4$, and concentrated to dryness. Purification on silica gel by flash chromatography (0-50% EtOAc/hexanes) afforded 2-chloro-4-(1-fluoroethyl)pyrimidine (75 mg, 0.467 mmol, 49% yield) as a yellow oil. MS ESI: [M+H]$^+$ m/z 161.0. $^1$H NMR (500 MHz, CDCl$_3$) δ 8.67 (d, J=4.2, 1H), 7.46 (d, J=4.2, 1H), 5.58 (dq, J=6.7, 48, 1H), 1.74-1.57 (m, 3H).

Intermediate 63: (2-chloropyrimidin-4-yl)(cyclopropyl)methanone

To a solution of 2-chloro-N-methoxy-N-methylpyrimidine-4-carboxamide (893 mg, 4.43 mmol) in THF (9 mL) at −78° C. under nitrogen atmosphere was added cyclopropyl magnesium bromide (0.5 M in THF, 13.3 mL, 6.64 mmol) dropwise. The solution was warmed to 0° C. and stirred for an additional 30 min. The solution was diluted with EtOAc, washed with brine, dried with MgSO$_4$, filtered, and concentrated to dryness. Purification on silica gel by flash chromatography (0-100% EtOAc/hexanes) afforded (2-chloropyrimidin-4-yl)(cyclopropyl)methanone (360 mg, 1.97 mmol, 45% yield) as a colorless oil. MS ESI: [M+H]$^+$ m/z 183.1. $^1$H NMR (500 MHz, CDCl$_3$) δ 8.85 (d, J=4.9, 1H); 7.82 (d, J=4.9, 1H), 3.45-3.31 (m, 1H), 1.30 (m, 2H), 1.22 (m, 2H).

Intermediate 64: 1-(2-chloropyrimidin-4-yl)-1-cyclopropylethanol

To a solution of (2-chloropyrimidin-4-yl)(cyclopropyl)methanone (175 mg, 0.958 mmol) in THF (3 mL) at −78° C. under a nitrogen atmosphere was added methyl magnesium chloride (3.0 M in diethyl ether, 0.380 mL, 1.15 mmol) dropwise. The solution was warmed to room temperature and stirred for an additional 30 min. The solution was diluted with EtOAc, washed with brine, dried with MgSO$_4$, filtered, and concentrated to dryness to afford 1-(2-chloropyrimidin-4-yl)-1-cyclopropylethanol (115 mg, 0.579 mmol, 60% yield). MS ESI: [M+H]$^+$ m/z 199.1. $^1$H NMR (500 MHz, CDCl$_3$) δ 8.60 (d, J=5.2, 1H), 7.43 (d, J=5.2, 1H), 3.43 (s, 1H), 1.52 (s, 3H), 1.26 (m, 1H), 0.60 (m, 1H), 0.50 (m, 1H), 0.40 (m, 1H), 0.30 (m, 1H).

Intermediate 65: (2-chloropyrimidin-4-yl)(cyclopropyl)methanol

To a solution of (2-chloropyrimidin-4-yl)(cyclopropyl)methanone (150 mg, 0.821 mmol) in MeOH (3 mL) at 0° C. was added sodium borohydride (31 mg, 0.821 mmol) and stirred for 30 min. The solution was diluted with EtOAc, washed with brine, dried with MgSO$_4$, filtered, and concentrated to dryness to afford (2-chloropyrimidin-4-yl)(cyclopropyl)methanol (150 mg, 0.812 mmol, 99% yield). MS ESI: [M+H]$^+$ m/z 185.1. $^1$H NMR (500 MHz, CDCl$_3$) δ 8.60 (d, J=4.0, 1H), 7.41 (d, J=4.0, 1H), 4.12 (d, J=7.9, 1H), 1.12 (m, 1H), 0.64 (m, 2H), 0.56 (m, 2H).

Intermediate 66: 2-chloro-4-[cyclopropyl(fluoro)methyl]pyrimidine

To a solution of (2-chloropyrimidin-4-yl)(cyclopropyl)methanol (75 mg, 0.406 mmol) in dichloromethane (2 mL) at 0° C. was added diethylaminosulfur trifluoride (66 mg, 0.410 mmol) and stirred for 30 min. The solution was concentrated to dryness and purified by flash chromatography on silica gel (0-100% EtOAc/hexanes) to afford 2-chloro-4-[cyclopropyl(fluoro)methyl]pyrimidine (20 mg, 0.107 mmol, 26% yield) as a colorless oil. MS ESI: [M+H]$^+$ m/z 187.1. $^1$H NMR (500 MHz, CDCl$_3$) δ 8.67 (d, J=5.0, 1H), 7.43 (d, J=5.0, 1H), 4.93 (dd, J=7.4, 47.5, 1H), 1.13 (m, 1H), 0.70-0.60 (m, 4H).

Intermediate 67: trimethyl[(2-methylbut-3-yn-2-yl)oxy]silane

To a solution of 2-methylbut-3-yn-2-ol (140 g, 1.67 mol) was added DMAP (20 g 0.17 mol), Et$_3$N (927 ml, 3.33 mol) and TMS-Cl (289 g, 2.66 mol) at 5 degree under a nitrogen atmosphere. After being stirred one hour, the mixture was washed with water, dried (MgSO$_4$), filtered, concentrated, and distilled to obtain trimethyl[(2-methylbut-3-yn-2-yl)oxy]silane (150 g, 0.96 mol).

Intermediate 68: (3E)-2-methyl-4-(4,4,5,5-tetramethyl-1,3,2-dioxaborolan-2-yl)but-3-en-2-ol

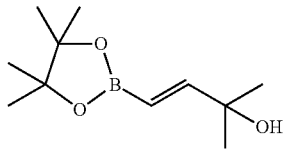

A suspension of dicyclohexylborane (80 ml, 0.08 mol) in THF evaporated under reduced pressure to afford the neat dicyclohexylborane. Pinacolborane (102.2 g, 0.81 mol) and trimethyl[(2-methylbut-3-yn-2-yl)oxy]silane (115 g, 0.74 mol) were added at 0° C. and the mixture was stirred for 2 h and bubbled air through the solution for 2 hr at room temperature. The mixture was diluted with THF and citric acid (16 g, 0.083 mol) was added. The solution was stirred at room temperature for 1 hour and solvent was concentrated and extracted with ether. The organic layer was washed with a saturated aqueous solution of $NaHCO_3$ four times and dried over $Na_2SO_4$. After filtration and concentration, an oil was obtained. Purification by flash chromatography afforded (3E)-2-methyl-4-(4,4,5,5-tetramethyl-1,3,2-dioxaborolan-2-yl)but-3-en-2-ol. $^1$H NMR (300 MHz, $CDCl_3$): 1.26 (s, 12H), 1.3 (s, 6H), 5.57-5.63 (d, J=18, 1H), 6.68-6.74 (d, J=18 Hz, 1H).

Intermediate 69: (3E)-4-(2-chloropyrimidin-4-yl)-2-methylbut-3-en-2-ol

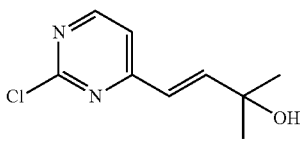

To a solution of 2,4-dichloropyrimidine (71 mg, 0.476 mmol) in dioxane (4 mL) and sodium carbonate (2M in water, 0.25 mL, 0.5 mmol) were added (3E)-2-methyl-4-(4,4,5,5-tetramethyl-1,3,2-dioxaborolan-2-yl)but-3-en-2-ol (100 mg, 0.476 mmol) and tetrakis triphenylphosphine palladium(0) (55 mg, 0.048 mmol). The solution was degassed by bubbling nitrogen gas and heated to 90° C. for 2 hr. The solution was diluted with EtOAc, washed with brine, dried with $MgSO_4$, filtered, and concentrated to dryness. The residue was purified by flash chromatography on silica gel (0-100% EtOAc/hexanes) to afford (3E)-4-(2-chloropyrimidin-4-yl)-2-methylbut-3-en-2-ol as a colorless oil. MS ESI: $[M+H]^+$ m/z 199.1. $^1$H NMR (500 MHz, $CDCl_3$) δ 8.52 (d, J=5.1, 1H) 7.24 (d, J=15.6, 1H) 7.12 (d, J=5.1, 1H) 6.60 (d, J=15.6, 1H); 1.22 (s, 6H).

Intermediate 70: 2-chloro-4-(difluoromethyl)pyrimidine as a yellow oil

Into a 500-mL 3-necked round-bottom flask, purged and maintained with an inert atmosphere of nitrogen, was placed a solution of 2-chloropyrimidine-4-carbaldehyde (15.0 g, 104 mmol, 1.00 equiv, 98%) in dichloromethane (200 mL). This was followed by the addition of Bis[(2-methoxyethyl)amino] sulfur trifluoride (46.0 g, 208 mmol, 2.00 equiv, 100%) dropwise with stirring at 0° C. over 30 min. The resulting solution was stirred for 2 h at 0° C., then quenched by the addition of 50 mL of water. The resulting solution was extracted with 3×100 mL of dichloromethane. The organic layers were combined, dried over anhydrous sodium sulfate and concentrated under vacuum. The residue was applied onto a silica gel column and eluted with DCM/Pentane (2:1) to afford 2-chloro-4-(difluoromethyl)pyrimidine (2.38 g, 14% yield) as a yellow oil. GC-MS ESI: $[M+H]^+$ m/z 164. $^1$H-NMR (300 MHz, $CDCl_3$): 8.87 (t, 1H), 7.61 (d, 1H), 6.55 (m, 1H). $^{19}$F-NMR (300 MHz, $CDCl_3$): −119.37

Intermediate 71: tert-butyl 4-[5-(3-amino-5-methylphenyl)-1,3-thiazol-2-yl]-4-hydroxycyclohexanecarboxylate

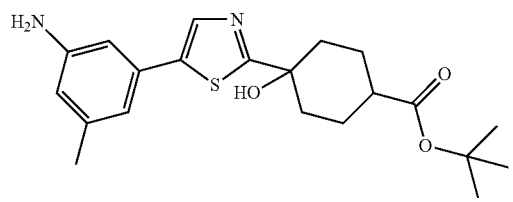 [SMILES: Cc1cc(N)cc(-c2cnc(C3(O)CCC(C(=O)OC(C)(C)C)CC3)s2)c1]

Step 1

To a flask containing TI-IF (82 mL) was added isopropylmagnesium chloride/lithium chloride (1.2 M in THF, 37.7 mL, 45 mmol). A solution of thiazole (3.5 g, 41 mmol) in THF (20 mL) was added slowly. The reaction was stirred for one hour. A solution of tert-butyl 4-oxocyclohexanecarboxylate (12.23 g, 62 mmol) in THF (20 mL) was added and the reaction was stirred for 3 hours. The reaction was then quenched slowly with saturated ammonium chloride and diluted with ethyl acetate. The organic layer was separated, dried over magnesium sulfate, filtered and concentrated. Flash chromatography was used for purification to yield tert-butyl 4-hydroxy-4-(1,3-thiazol-2-yl)cyclohexanecarboxylate (9.25 g, 33 mmol, 79% yield). MS ESI: $[M+H]^+$ m/z 284.1.

Step 2

To a flask containing the product of Step 1 (925 g, 33 mmol) was added DMF (36 mL) and then n-bromosuccinimide (6.97 g, 32 mmol). The reaction was allowed to stir until complete by LCMS. The reaction was diluted with water and ethyl acetate. The organic layer was separated, dried over magnesium sulfate, filtered and concentrated. Flash chromatography was used for purification to yield tert-butyl 4-(5-bromo-1,3-thiazol-2-yl)-4-hydroxycyclohexane-carboxylate (9.24 g, 25.5 mmol, 78% yield). MS ESI: $[M+H]^+$ m/z 364.0.

Step 3

To a flask containing 3-methyl-5-(4,4,5,5-tetramethyl-1,3,2-dioxaborolan-2-yl)aniline (1.6 g, 6.96 mmol), the product of Step 2 (2.52 g, 6.96 mmol), dicyclohexyl[2',4',6'-tri(propan-2-yl)biphenyl-2-yl]phosphane (0.33 g, 0.70 mmol), $Pd_2(dba)_3$ (0.32 g, 0.35 mmol), cesium carbonate (6.80 g, 20.9 mmol) was added a degassed mixture of dioxane (23 mL) and water (2.3 mL). The solution was evacuated and then purged with argon 5 times and then heated at 100° C. overnight. The reaction was then cooled to room temperature, diluted with ethyl aceate, washed with aqueous saturated sodium bicarbonate, dried over magnesium sulfate, filtered and concentrated. Flash chromatography was used for purification to yield tert-butyl 4-[5-(3-amino-5-methylphenyl)-1,3-thiazol-2-yl]-4-hydroxycyclohexanecarboxylate. MS ESI: [M+H]+ m/z 389.

Intermediate 72: ethyl 4-[5-(3-amino-5-methylphenyl)-1,3-thiazol-2-yl]-4-hydroxy-2-methylcyclohexanecarboxylate

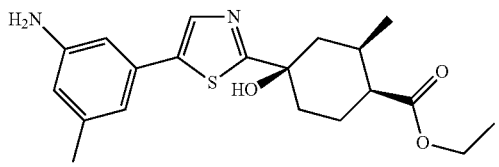 [SMILES: CCOC(=O)[C@H]1CC[C@](O)(c2ncc(-c3cc(C)cc(N)c3)s2)C[C@H]1C]

To a round bottom flask containing 3-methyl-5-(4,4,5,5-tetramethyl-1,3,2-dioxaborolan-2-yl)aniline (402 mg, 1.7 mmol), ethyl 4-(5-bromo-1,3-thiazol-2-yl)-4-hydroxy-2-methylcyclohexanecarboxylate (400 mg, L1 mmol), $Pd_2(dba)_3$ (105 mg, 0.11 mmol), X-phos (55 mg, 0.11 mmol) and $Cs_2CO_3$ (1.12 g, 3.45 mmol) was added 4.3 mL of degassed 10:1 1,4 dioxane/$H_2O$. The reaction was heated to 100° C. for 16 h, then cooled and partitioned between EtOAc (50 mL) and saturated aqueous sodium bicarbonate (50 mL). The layers were separated and the aqueous phase was extracted once with EtOAc (50 mL). The combined organic phases were washed with brine (50 mL), dried over anhydrous $MgSO_4$, filtered and concentrated under reduced pressure. Purification of the resulting residue on silica furnished ethyl 4-[5-(3-amino-5-methylphenyl)-1,3-thiazol-2-yl]-4-hydroxy-2-methylcyclohexanecarboxylate (344 mg, 80%) as a colorless foam. MS BSI: [M+H]+ m/z 375.2.

Intermediate 73: 2-[5-(3-amino-5-methylphenyl)-1,3-thiazol-2-yl]propane-2-sulfonamide

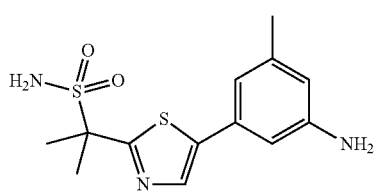 [SMILES: Cc1cc(N)cc(-c2cnc(C(C)(C)S(N)(=O)=O)s2)c1]

2-(5-Bromo-1,3-thiazol-2-yl)propane-2-sulfonamide (1.223 g, 4.29 mmol), 3-methyl-5-(4,4,5,5-tetramethyl-1,3,2-dioxaborolan-2-yl)aniline (1.00 g, 4.29 mmol), tris(dibenzylideneacetone)-dipalladium(0) (0.196 g, 0.214 mmol), X-phos (0.204 g, 0.429 mmol), and cesium carbonate (4.19 g, 12.87 mmol) were combined in a flask, sealed and purged with $N_2$ (3×). Degassed dioxane (15 mL) and water (1.5 mL) were added and the reaction mixture was heated at 100° C. for 16 hrs. The reaction was diluted with water and extracted with EtOAc (2×). The combined organic layers were washed with brine, dried ($MgSO_4$) and evaporated. Flash chromatography ($SiO_2$, dry load, gradient elution 0 to 75% EtOAc in $CH_2Cl_2$) afforded 2-[5-(3-amino-5-methylphenyl)-1,3-thiazol-2-yl] propane-2-sulfonamide (0.302 g, 0.97 mmol, 22.6% yield) as a tan foam. MS ESI: [M+H]+ m/z 312.1. $^1$H NMR (500 MHz, DMSO-$d_6$) δ 7.92 (s, 1H), 6.99 (m, 2H), 6.59 (m, 2H), 6.34 (s, 1H), 5.18 (br s, 2H), 2.15 (s, 3H), 1.75 (s, 6H).

Intermediate 74: cis-methyl-4-[5-(3-amino-5-methylphenyl)-1,3-thiazol-2-yl]-4-hydroxy-2,2-dimethyl-cyclohexanecarboxylate

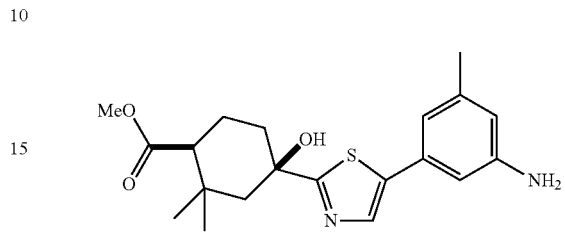

cis-Methyl 4-(5-bromo-1,3-thiazol-2-yl)-4-hydroxy-2,2-dimethylcyclohexanecarboxylate (1.372 g, 3.94 mmol), 3-methyl-5-(4,4,5,5-tetramethyl-1,3,2-dioxaborolan-2-yl)aniline (0.918 g, 3.94 mmol), cesium carbonate (3.85 g, 11.82 mmol), X-Phos (0.188 g, 0.394 mmol) and $Pd_2(dba)_3$ (0.180 g, 0.197 mmol) were placed in a flask and evacuated/purged with $N_2$ three times. Dioxane (13 mL) and water (1.3 mL) were degassed by undersurface $N_2$ bubbling and added to the reaction vessel. The resulting reaction mixture was stirred at 100° C. for 16 hrs and then diluted with EtOAc (25 mL), washed with saturated aqueous $NaHCO_3$ (25 mL), brine (25 mL), dried over $Na_2SO_4$, filtered and concentrated under reduced pressure. The residue was purified by flash chromatography (2% to 12% EtOAc in hexanes) to give cis-methyl-4-[5-(3-amino-5-methylphenyl)-1,3-thiazol-2-yl]-4-hydroxy-2,2-dimethylcyclohexanecarboxylate (1.33 g, 3.54 mmol, 90% yield) as an orange foam. MS ESI: [M+H]+ m/z 375.1. $^1$H NMR (500 MHz, $CD_3OD$) δ 7.80 (s, 1H), 6.78-6.74 (m, 2H), 6.53 (br s, 1H), 3.68 (s, 3H), 2.45-2.36 (m, 2H), 2.25-2.12 (m, 4H), 2.01-1.94 (m, 2H), 1.76-1.62 (m, 2H), 1.19 (s, 3H), 1.04 (s, 3H).

Intermediate 75: 8-[5-(3-amino-5-methylphenyl)-1,3-thiazol-2-yl]-1,4-dioxaspiro[4.5]decan-8-ol

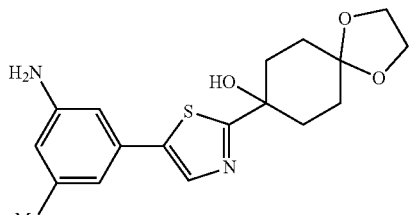

Step 1

Thiazole (25.0 mL, 352 mmol) was diluted with THF (300 mL) and cooled to −780° C. n-BuLi (220 mL, 352 mmol) was added at such a rate that the internal temperature did not exceed −65 C. A yellow slurry formed and the addition took 40 min. The reaction was aged for 20 min then 1,4-dioxaspiro [4.5]decan-8-one (50 g, 320 mmol) was added as a solution in THF (420 mL) dropwise via addition funnel. After 2 h, the reaction was quenched with water, the cooling bath removed and the mixture stirred until the internal temperature reached 0° C. The mixture was diluted with EtOAc and the layers were separated followed by extraction of the aqueous portion with EtOAc. The combined organics were dried with MgSO$_4$, filtered, and concentrated to a viscous orange oil. EtOAc was added and concentrated to 100 mL. Hexanes was added dropwise via an addition funnel. The mixture was stirred for 1 h then cooled to −10° C. and filtered. The white cake was washed with hexanes (2×) then dried under a nitrogen bag to afford 8-(1,3-thiazol-2-yl)-1,4-dioxaspiro[4.5]decan-8-ol (66 g, 85%) as a white solid.

Step 2

The product of Step 1 (60.5 g, 251 mmol) was diluted with DMF (365 mL). N-bromosuccinimide (49.1 g, 276 mmol) was added, and the solution was heated to 50° C. and stirred for 2 h. The reaction was removed from heat and cooled to 45° C. and H$_2$O (600 mL) containing 15.8 g Na$_2$SO$_3$ was added dropwise affording a solid. The mixture was stirred at room temperature for 1 h, then filtered and washed 2× with H$_2$O (300 mL). The cake was dried overnight under a nitrogen bag to afford 8-(5-bromo-1,3-thiazol-2-yl)-1,4-dioxaspiro[4.5]decan-8-ol (68.2 g, 85%) as a white solid.

Step 3

3-methyl-5-(4,4,5,5-tetramethyl-1,3,2-dioxaborolan-2-yl)aniline (2.00 g, 8.58 mmol), the product of Step 2 (2.75 g, 8.58 mmol), X-Phos (0.409 g, 0.858 mmol), cesium carbonate (8.39 g, 25.7 mmol), and Pd$_2$(dba)$_3$ (0.393 g, 0.429 mmol) were placed in a flask flushed with Argon. Degassed Dioxane (30 ml) and Water (3 mL) were added and the reaction was heated to 100° C. for 40 h. The reaction was then cooled to room temperature, quenched with saturated aqueous sodium bicarbonate and extracted with EtOAc (3×). The combined organics were dried over Na$_2$SO$_4$ and concentrated in vacuo. Purification via flash chromatography (40%-100% EtOAc:hexanes) afforded 8-[5-(3-amino-5-methylphenyl)-1,3-thiazol-2-yl]-1,4-dioxaspiro[4.5]decan-8-ol (1.93 g, 65%) as a brown foam. MS ESI: [M+H]$^+$ m/z 347.

Intermediate 76: 2-[5-(3-amino-5-methylphenyl)-1,3-thiazol-2-yl]-1-{[tert-butyl(dimethyl)silyl]oxy}propan-2-ol

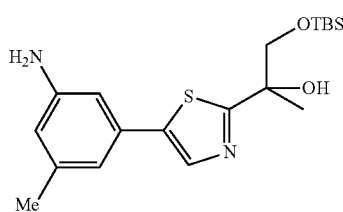 [SMILES: Cc1cc(N)cc(-c2cnc(C(C)(O)CO[Si](C)(C)C(C)(C)C)s2)c1]

Step 1

Isopropylmagnesium chloride-lithium chloride complex (2.98 ml, 3.88 mmol) was dissolved in THF (4 mL). Thiazole (0.252 ml, 3.52 mmol) in THF (2 mL) was added slowly. After 1 h, 1-(tert-butyldimethylsilyloxy)-2-propanone (0.816 ml, 423 mmol) in THF (2 mL) was added and the reaction was stirred for 3 h at room temperature. The reaction was quenched with saturated ammonium chloride and extracted with EtOAc (3×). The combined organics were dried over Na$_2$SO$_4$, filtered and concentrated in vacuo. Purification via silica gel column chromatography (5%-10% EtOAc:hexanes) afforded 1-{[tert-butyl(dimethyl)silyl]oxy}-2-(1,3-thiazol-2-yl)propan-2-ol (383 mg, 40%) as a yellow oil. MS ESI: [M+H]$^+$ m/z 274.

Step 2

The product of Step 1 (364 mg, 1.331 mmol) was dissolved in DMF (2 ml). N-bromosuccinimide (284 mg, 1.597 mmol) was added, and the solution was maintained 2 h at rt. Water was added and the mixture extracted with EtOAc (3×). The combined organics were dried over Na$_2$SO$_4$ and concentrated in vacuo. Purification via silica gel column chromatography (0%-10% EtOAc:hexanes) afforded 2-(5-bromo-1,3-thiazol-2-yl)-1-{[tert-butyl(dimethyl)silyl]oxy}propan-2-ol (104 mg, 22%) as a white solid. MS ESI: [M+H]$^+$ m/z 352, 354.

Step 3

3-methyl-5-(4,4,5,5-tetramethyl-1,3,2-dioxaborolan-2-yl)aniline (69 mg, 0.296 mmol), the product of Step 2 (104 mg, 0.296 mmol), X-Phos (14.11 mg, 0.030 mmol), cesium carbonate (289 mg, 0.888 mmol), and Pd$_2$(dba)$_3$ (13.55 mg, 0.015 mmol) were placed in a flask flushed with Ar. Degassed Dioxane (1.2 ml) and Water (0.12 ml) were added and heated to 110° C. for 5.5 h. The reaction was allowed to cool to room temperature and then quenched with saturated aqueous sodium bicarbonate and extracted with EtOAc (3×). The combined organics were dried over Na$_2$SO$_4$, filtered and concentrated in vacuo. Purification via silica gel column chromatography (10-30% EtOAc:hexanes) afforded 2-[5-(3-amino-5-methylphenyl)-1,3-thiazol-2-yl]-1-{[tert-butyl(dimethyl)silyl]oxy}propan-2-ol (82 mg, 73%) as a brown oil. MS ESI: [M+H]$^+$ m/z 379.

Intermediate 77: 4-[5-(3-amino-5-methylphenyl)-1,3-thiazol-2-yl]-4-hydroxy-2,2,3-trimethylcyclohexanecarboxylic acid

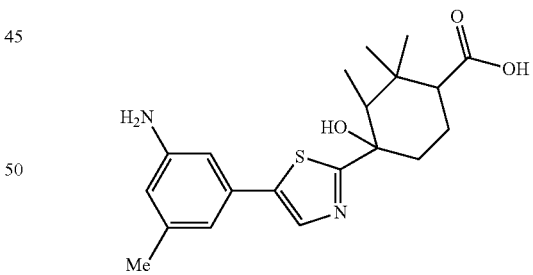

Lithium diisopropylamide (5110 µl, 9.20 mmol) was added to a −78° C. solution of 3-methyl-5-(1,3-thiazol-5-yl)aniline (500 mg, 2.63 mmol) in THF (7 mL). The reaction was allowed to warm to −60° C. while aging for 30 min. The solution was cooled to −78° C. and 2,2,3-trimethyl-4-oxocyclohexanecarboxylic acid (600 mg, 3.26 mmol) in THF (6 mL) was added portionwise, maintaining an internal temperature below −65° C. After 5 min at −78° C. the reaction was warmed to room temperature, diluted with EtOAc and washed with aqueous saturated ammonium chloride (3×). The combined aqueous portion was extracted with 10% IPA:CHCl$_3$ (3×). The combined organic layers were dried under reduced pressure to yield 4-[5-(3-amino-5-methylphenyl)-1,3-thiazol-2-yl]-4-hydroxy-2,2,3-trimethylcyclohexanecarboxylic acid (121 mg, 12%) as a yellow oil. MS ESI: [M+H]+ m/z 375.

Intermediate 78: Cis-1-[5-(3-amino-5-methylphenyl)-1,3-thiazol-2-yl]cyclohexane-1,4-diol

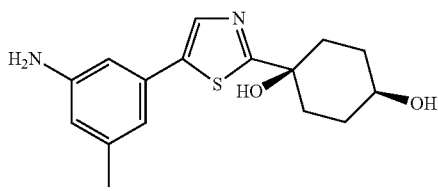 [SMILES: Cc1cc(N)cc(-c2cnc([C@]3(O)CC[C@@H](O)CC3)s2)c1]

Step 1

Thiazole (25.02 mL, 352 mmol) was diluted with THF (300 mL) and cooled to −78° C. n-BuLi (1.6 M, 220 mL, 532 mmol) was added at such a rate that the internal temperature did not exceed −65° C. The mixture was aged for 20 min, then 1,4-dioxaspiro[4.5]decan-8-one (50 g, 320 mmol) was added as a solution in THF (420 mL) drop wise via addition funnel. The mixture was stirred for 2 h and then quenched with water. The flask was removed from the cooling bath and stirred until it reached 0° C. The mixture was transferred to a separatory funnel with EtOAc and brine and then extracted with EtOAc. The combined organics were dried with MgSO4, filtered and concentrated to an orange viscous oil. The oil was diluted with EtOAc and concentrated to ~100 mL. A stir bar was added to the flask and hexanes was added drop wise via addition funnel. The mixture was stirred for 1 h then cooled to −10° C. and filtered. The filtrate was washed with hexanes (2×) and dried to afforded 8-(1,3-thiazol-2-yl)-1,4-dioxaspiro[4.5]decan-8-ol (66 g, 274 mmol, 85% yield).

Step 2

The product of Step 1 (60.5 g, 251 mmol) was diluted with DMF (5 mL). To this solution, NBS (49.1 g, 276 mmol) was added. The reaction was heated to 50° C. for 2 h. The reaction was cooled to 45° C. and H2O (600 mL) containing Na2SO3 (15.8 g, 125 mmol) was added drop wise. The reaction was stirred at room temperature for 1 h then filtered and washed with H2O (2×, 300 mL). The filtrate was dried under nitrogen to afford 8-(5-bromo-1,3-thiazol-2-yl)-1,4-dioxaspiro[4.5]decan-8-ol (68.15 g, 213 mmol, 85% yield).

Step 3

The product of Step 2 (15 g, 46.8 mmol) was diluted with THF (10 mL). HCl (6 N, 78 mL) was added and stirred at 60° C. for 3 h. The reaction was cooled to RT and NaOH (6 N, 78 mL) was added. The reaction was diluted with EtOAc. The layers were separated and the aqueous layer back extracted with EtOAc (2×). The combined organic layers were dried (MgSO4) and evaporated. The residue was diluted with EtOAc to transfer and concentrated to ~20 mL where hexanes (60 mL) was added drop wise. The slurry was cooled to room temperature, stirred for 1 h then filtered, washed with hexanes (2×15 mL) and dried to afford 4-(5-bromo-1,3-thiazol-2-yl)-4-hydroxycyclohexanone (11.25 g, 40.8 mmol, 87% yield).

Step 4

The product of Step 3 (6.5 g, 23.54 mmol) was diluted with THF (10 mL) then cooled to −76° C. LiBH4 (2M in THF, 14.1, mL, 28.2 mmol) was added drop wise, keeping internal temp <−75° C. The reaction was stirred for 1 h and quenched with aqueous saturated NH4Cl. The reaction was diluted with EtOAc. The layers were separated and the aqueous layer was back extracted with EtOAc (2×). The combined organic layers were dried over Na2SO4, filtered and concentrated in vacuo. Flash chromatography and drying under high vacuum afforded cis-1-(5-bromo-1,3-thiazol-2-yl)cyclohexane-1,4-diol (5.2 g, 18.69 mmol, 79% yield) as a white solid.

Step 5

A vial was charged with 3-methyl-5-(4,4,5,5-tetramethyl-1,3,2-dioxaborolan-2-yl)aniline (0.84 g, 3.60 mmol), the product of Step 4 (1.002 g, 3.60 mmol), cesium carbonate (3.52 g, 10.81 mmol), Pd2(dba)3 (0.165 g, 0.180 mmol), x-phos (0.172 g, 0.360 mmol), dioxane (14.62 ml) and water (1.462 ml). The mixture was reacted under Argon at 110° C. for 5 hours. The reaction was diluted with ethyl acetate and transferred to a reparatory funnel. The organic layer was washed with aqueous saturated NaHCO3 and brine. The organic layer was dried over Na2SO4, filtered and concentrated. The crude residue was purified by flash chromatography on silica (0-20% MeOH/DCM) to afford cis-1-[5-(3-amino-5-methylphenyl)-1,3-thiazol-2-yl]cyclohexane-1,4-diol (871.5 mg, 2.86 mmol, 79% yield). MS ESI: [M+H]+ m/z 305.1.

Intermediate 79: methyl(1S,4R)-4-(5-{3-[(acetyloxy)methyl]-5-aminophenyl}-1,3-thiazol-2-yl)-4-hydroxy-2,2-dimethylcyclohexanecarboxylate

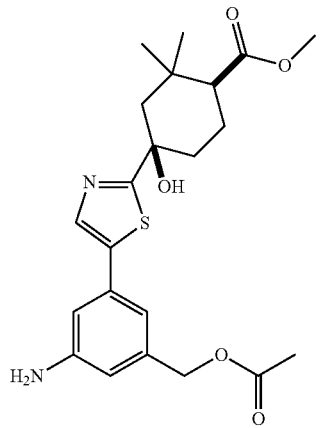 [SMILES: COC(=O)[C@H]1CC[C@](O)(c2ncc(-c3cc(N)cc(COC(C)=O)c3)s2)CC1(C)C]

Step 1

A solution of 3-bromo-5-nitrobenzyl alcohol (5 g, 21.5 mmol), in N,N-dimethylformamide (5 mL) was treated with tert-butyldimethylsilyl chloride (4.9 g, 32.3 mmol) and imidazole (2.5 g, 36.6 mmol) and stirred at room temperature for 14 h. The reaction was quenched with water and extracted with ethyl acetate (2×). The organic layer was dried over sodium sulfate, filtered, and concentrated. Purification by flash chromatography on silica (0-75% ethyl acetate inhexanes) afforded [(3-bromo-5-nitrobenzyl)oxy](tert-butyl)dimethylsilane (7.32 g, 20.1 mmol, 93% yield) as a yellow oil.

Step 2

To a solution of the product of Step 1 (7.25 g, 21 mmol) dissolved in dioxane (50 mL) was added bis(pinacolato)diboron (8 g, 31 mmol) and potassium acetate (6.2 g, 63 mmol). After deoxygenation, the solution was charged with 1,1'-Bis(diphenylphosphino)ferrocene-palladium(II) dichloride dichloromethane complex (0.86 g, 1.05 mmol). The mixture was heated to 90° C. for 15 h. The reaction was cooled to room temperature and quenched with saturated aqueous sodium bicarbonate. The mixture was extracted with ethyl acetate (2×). The combined organic layers were washed with brine, dried over sodium sulfate, filtered, and concentrated. Purification by flash chromatography (0-75% ethyl acetate in hexanes) afforded tert-butyl(dimethyl){[3-nitro-5-(4,4,5,5-tetramethyl-1,3,2-dioxaborolan-2-yl)benzyl]oxy}silane (8.9 g, 18.1 mmol, 80% yield) as an orange oily solid. $^1$H NMR (500 MHz, CDCl$_3$) δ 8.51 (s, 1H), 8.33 (s, 1H), 7.98 (s, 1H), 4.81 (s, 2H), 1.35 (d, J=6.8, 12H), 0.99-0.93 (m, 9H), 0.12 (m, 6H).

Step 3

To a stirring solution of the product of Step 2 (7.91 g, 20.1 mmol) in dioxane (30 mL) and water (4 mL) was added methyl(1S,4R)-4-(5-bromo-1,3-thiazol-2-yl)-4-hydroxy-2,2-dimethylcyclohexanecarboxylate (5 g, 14.4 mmol) and cesium carbonate (14 g, 43.1 mmol). The solution was deoxygenated, then tris(dibenzylideneacetone)dipalladium(0) (0.66 g, 0.72 mmol) and 2-(dicyclohexylphosphino)-2',4',6'-triisopropylbiphenyl (0.68 g, 1.44 mmol) were added and the mixture was stirred at 100° C. for 15 h. The mixture was cooled to room temperature and quenched with 1:1 saturated aqueous sodium bicarbonate:brine. The mixture was extracted with ethyl acetate, and the organic layer was dried over sodium sulfate, filtered, and concentrated. Purification by flash chromatography on silica gel (0-50% ethyl acetate in hexanes) afforded methyl(1S,4R)-4-{5-[3-({[tert-butyl(dimethyl)silyl]oxy}methyl)-5-nitrophenyl]-1,3-thiazol-2-yl}-4-hydroxy-2,2-dimethylcyclohexanecarboxylate (4.4 g, 7.82 mol, 54% yield) as an orange oil. MS ESI: [M+H]$^+$ m/z 535.2.

Step 4

To a solution of the product of Step 3 (4.4 g, 8.23 mmol) in acetonitrile (20 mL) was added triethylamine trihydrofluoride (4 mL, 24.7 mmol). The mixture was stirred for 5 h at room temperature, then quenched with saturated aqueous sodium bicarbonate. The mixture was extracted with ethyl acetate (2×), and the combined organics were dried over sodium sulfate, filtered, and concentrated to give methyl(1S,4R)-4-hydroxy-4-{5-[3-(hydroxymethyl)-5-nitrophenyl]-1,3-thiazol-2-yl}-2,2-dimethylcyclohexanecarboxylate (3.5 g, 7.9 mmol, 96% yield) as an orange-maroon oily foam. MS ESI: [M+H]$^+$ m/z 421.1.

Step 5

To a solution of the product of Step 4 (194 mg, 0.46 mmol) dissolved in dichloromethane (1.8 mL) at −20° C. was added acetyl chloride (34 µL, 0.48 mmol) and triethylamine (129 µL, 0.92 mmol). The reaction was warmed to room temperature and stirred for 2.5 h. The reaction was quenched with saturated aqueous sodium bicarbonate, and extracted with dichloromethane (3×). The combined organic layers were washed with brine, then dried over sodium sulfate, filtered, and concentrated to afford methyl(1S,4R)-4-(5-{3-[(acetyloxy)methyl]-5-nitrophenyl}-1,3-thiazol-2-yl)-4-hydroxy-2,2-dimethylcyclohexanecarboxylate (203 mg, 0.39 mmol, 86% yield) as a yellow foam. MS ESI: [M+H]$^+$ m/z 463.1.

Step 6

To a solution of the product of Step 5 (200 mg, 0.43 mmol) dissolved in ethanol (3.7 mL) and water (0.57 mL) was added iron (72.4 mg, 1.29 mmol). Saturated aqueous ammonium chloride (0.57 mL) was added and heated the mixture to 70° C. The reaction was stirred for 8 h at 70° C., then cooled to room temperature, diluted with ethyl acetate, and filtered. The filter cake was washed with 1:1 ethanol:ethyl acetate, and then the filtrate was washed with 1:1 water:saturated aqueous sodium bicarbonate. The filtrate was extracted with ethyl acetate (3×) and the combined organic layers were washed with brine, and then dried over sodium sulfate, filtered, and concentrated to give methyl(1S,4R)-4-(5-{3-[(acetyloxy)methyl]-5-aminophenyl}-1,3-thiazol-2-yl)-4-hydroxy-2,2-dimethylcyclohexanecarboxylate (186.5 mg, 0.43 mmol, 100% yield) as a yellow foam. MS ESI: [M+H]$^+$ m/z 433.2.

Intermediate 80: 4-(5-Bromo-thiazol-2-yl)-4-hydroxy-trans-2-methyl-cyclohexanecarboxylic acid methyl ester

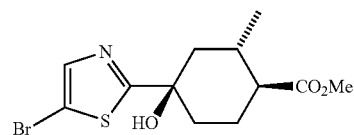 [SMILES: COC(=O)[C@H]1CC[C@](O)(c2ncc(Br)s2)C[C@@H]1C]

Step 1

To a cooled (−78° C.) solution of trans-2-methyl-4-oxo-cyclohexanecarboxylic acid methyl ester (13 g, 76 mmol) and thiazole (10.9 mL, 153 mmol) in THF (130 mL) was added nBuLi (2.5 M in Hex, 30.6 mL, 76 mmol) dropwise at such a rate that the internal temperature was maintained <−70° C. The reaction mixture was stirred for 30 min, MeOH (3.1 mL, 76 mmol) was introduced, and the reaction warmed to room temperature where it was diluted with water and EtOAc. The layers were separated; the organic layer dried with MgSO$_4$, filtered and adsorbed to silica gel by concentrating in vacuo. The crude residue was purified by flash chromatography to afford trans-4-hydroxy-trans-2-methyl-4-thiazol-2-yl-cyclohexanecarboxylic acid methyl ester (4.1 g, 16 mmol) along with the other diastereomer (7.0 g, 27 mmol).

Step 2

To a solution of the product of Step 1 (4.1 g, 16 mmol) in DMF (30 mL) was added NBS (3.43 g, 19.3 mmol). After the initial exotherm had subsided the reaction mixture was heated to 50° C. and stirred for 1 h. It was then cooled to room temperature and water (280 mL containing 7 g of sodium sulfite) was added followed by EtOAc. The layers were cut and the aqueous layer was extracted EtOAc (2×). The combined organics were washed with H$_2$O, dried with MgSO$_4$, filtered and adsorbed to silica gel by concentration in vacuo. The crude residue was purified by flash chromatography to afford 4-(5-bromo-thiazol-2-yl)-trans-4-hydroxy-trans-2- methyl-cyclohexanecarboxylic acid methyl ester (4.75 g, 16.1 mmol), MS ESI: [M+H]⁺ m/z 333.9.

Intermediate 81: propan-2-yl-4-(5-bromo-1,3-thiazol-2-yl)-4-hydroxy-2,6 dimethylcyclohexanecarboxylate

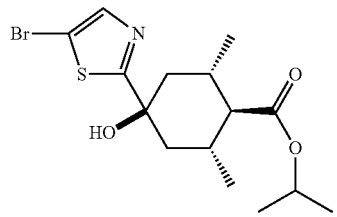 [SMILES: CC(C)OC(=O)[C@H]1[C@H](C)C[C@](O)(c2ncc(Br)s2)C[C@@H]1C]

Step 1

Propan-2-yl 2,6-dimethyl-4-oxocyclohex-2-ene-1-carboxylate (20 g, 95.1 mmol) was prepared according to a literature procedure (*J. Org. Chem.* 2007, 72(4), 1458-1453) using isopropyl acetoacetate in place of ethyl acetoacetate and diluted with EtOH (300 mL). To the resulting solution under a nitrogen blanket was added 5% Pd/C (0.8 g) after which the vessel was shaken under an initial hydrogen pressure of 50 psi for 2 h. The reaction contents were then filtered through celite using additional EtOH, concentrated in vacuo and purified by flash chromatography to afford propan-2-yl 2,6-dimethyl-4-oxocyclohexanecarboxylate (5.2 g, 24.5 mmol).

Step 2

The product of Step 1 (5.2 g, 24.5 mmol) was diluted with THF (50 mL) to which thiazole (2.63 mL, 36.7 mmol) was added. The resulting solution was cooled to −78° C. and nBuLi (2.5 M in Hex, 10.3 mL, 25.7 mmol) was added dropwise at such a rate to keep the internal temperature <−65° C. When the addition was completed, the reaction mixture was stirred for a further 1 h then quenched by the addition of water and brought to room temperature. EtOAc was added, the layers separated and the organic layer was dried with MgSO₄, filtered, concentrated in vacuo and the crude residue purified by flash chromatography to afford propan-2-yl-4-hydroxy-2,6-dimethyl-4-(1,3-thiazol-2-yl)cyclohexanecarboxylate (2.0 g, 6.7 mmol).

Step 3

To a solution of the product of Step 2 (2.0 g, 6.7 mmol) in DMF (16 mL) was added NBS (1.38 g, 7.73 mmol) and the resulting solution heated to 55° C. After 60 min the reaction was cooled and a solution of sodium sulfite (500 mg) in water (30 mL) was added followed by EtOAc. The layers were separated, the aqueous layer was back extracted with EtOAc (2×). The combined organics were dried over MgSO₄, filtered, and concentrated in vacuo. The crude residue was purified by flash chromatography to afford propan-2-yl-4-(5-bromo-1,3-thiazol-2-yl)-4-hydroxy-2,6 dimethylcyclohexanecarboxylate (2.2 g, 5.85 mmol) MS ESI: [M+H]⁺ m/z 375.9.

Intermediate 82: propan-2-yl-4-(5-bromo-1,3-thiazol-2-yl)-4-hydroxy-2,6 dimethylcyclohexanecarboxylate

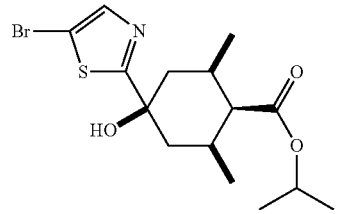 [SMILES: CC(C)OC(=O)[C@@H]1[C@H](C)C[C@@](O)(c2ncc(Br)s2)C[C@@H]1C]

Step 1

Propan-2-yl 2,6-dimethyl-4-oxocyclohex-2-ene-1-carboxylase (20 g, 95.1 mmol) was prepared according to a literature procedure (*J. Org. Chem.* 2007, 72(4), 1458-1453) using isopropyl acetoacetate in place of ethyl acetoacetate and diluted with EtOH (300 mL). To the resulting solution under a nitrogen blanket was added 5% Pd/C (0.8 g) after which the vessel was shaken under an initial hydrogen pressure of 50 psi for 2 h. The reaction contents were then filtered through celite using additional EtOH, concentrated in vacuo and purified by flash chromatography to afford propan-2-yl 2,6-dimethyl-4-oxocyclohexanecarboxylate (6.4 g, 30.1 mmol).

Step 2

The product of Step 1 (6.4 g, 30.1 mmol) was diluted with THF (65 mL) to which thiazole (3.24 mL, 45.2 mmol) was added. The resulting solution was cooled to −78° C. and nBuLi (2.5 M in Hex, 12.7 mL, 31.7 mmol) was added dropwise at such a rate to keep the internal temperature <−65° C. When the addition was completed, the reaction mixture was stirred for a further 1 h then quenched by the addition of water and brought to room temperature. EtOAc was added, the layers separated and the organic layer was dried with MgSO₄, filtered, concentrated in vacuo and the crude residue purified by flash chromatography to afford all-cis-propan-2-yl-4-hydroxy-2,6-dimethyl-4-(1,3-thiazol-2-yl)cyclohexanecarboxylate (4.45 g, 15.0 mmol).

Step 3

To a solution of all-cis-propan-2-yl-4-hydroxy-2,6-dimethyl-4-(1,3-thiazol-2-yl)cyclohexanecarboxylate (4.4 g, 14.8 mmol) in DMF (34 mL) was added NBS (3.03 g, 17.0 mmol) and the resulting solution heated to 55° C. After 60 min the reaction was cooled and a solution of sodium sulfite (500 mg) in water (30 mL) was added followed by EtOAc. The layers were separated and the aqueous layer was back extracted with EtOAc (2×). The combined organics were dried with MgSO₄, filtered, and concentrated in vacuo. The crude residue was purified by flash chromatography to give impure product. The product was swirled up in some hexanes, filtered and washed with more hexanes to afford all-cis-propan-2-yl-4-(5-bromo-1,3-thiazol-2-yl)-4-hydroxy-2,6 dimethylcyclohexanecarboxylate (2.4 g, 6.38 mmol) MS ESI: [M+H]⁺ m/z 375.9.

Intermediate 83: 2,6-anhydro-5-C-(5-bromo-1,3-thiazol-2-yl)-3,4-dideoxyhexonate

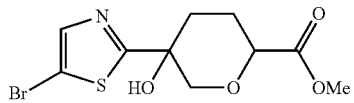 [SMILES: COC(=O)C1CCC(O)(c2ncc(Br)s2)CO1]

Step 1

Methyl 2,6-anhydro-3,4-dideoxy-L-erythro-hexonate (prepared as described in Okada, M. et al. Macromolecules, 1986, 19, 953; 500 mg, 3.12 mmol) was dissolved in $CH_2Cl_2$ (20 mL) and Dess Martin Periodinane (1986 mg, 4.68 mmol) was added. The reaction was stirred at room temperature for 2 h and then diluted with $Na_2S_2O_3$ (10% solution in water) and aqueous saturated $NaHCO_3$ and extracted with $CH_2Cl_2$ (2×). The combined organic layers were washed with brine, dried ($MgSO_4$) and evaporated. Flash chromatography ($SiO_2$, gradient elution 0 to 50% EtOAc in hexanes) afforded methyl 5-oxotetrahydro-2-pyran-2H-carboxylate (441 mg, 2.79 mmol, 89%) as a colorless oil.

Step 2

2-Bromothiazole (0.136 ml, 1.524 mmol) was dissolved in THF (10 mL) and cooled to −20° C. Isopropylmagnesium chloride (2.0 M in THF, 0.80 ml, 1.60 mmol) was added dropwise. After stirring for 1 hr (−10° C. to 0° C.), the reaction was cooled to −78° C. and the product of Step 1 (265 mg, 1.677 mmol) in THF (2 ml) was added dropwise. The reaction was stirred for 30 min at −78° C., then warmed to room temperature. After stirring 1 hr at room temperature, the reaction was quenched with saturated $NH_4Cl$ and extracted with EtOAc (2×). The combined organic layers were dried over $MgSO_4$ and concentrated under reduced pressure. The residue was purified by flash chromatography ($SiO_2$, gradient elution 10 to 100% EtOAc in hexanes) to give methyl 2,6-anhydro-3,4-dideoxy-5-C-1,3-thiazol-2-ylhexonate (59 mg, 0.24 mmol, 15.9%) as a diastereomeric mixture (colorless gum). MS ESI: $[M+H]^+$ m/z 244.0.

Step 3

The product of Step 2 (180 mg, 0.740 mmol) was dissolved in DMF (5 mL) and N-bromosuccinimide (165 mg, 0.925 mmol) was added. The reaction was stirred at room temperature for 8 h. Two further aliquots of N-bromosuccinimide (65.8 mg, 0.370 mmol and 132 mg, 0.740 mmol) were added over a period of 72 hrs to achieve complete conversion of the starting material. The mixture was diluted with water and extracted with EtOAc (2×). The combined organic layers were washed with 10% $Na_2S_2O_3$ and brine, dried over $MgSO_4$ and evaporated. Flash chromatography ($SiO_2$, gradient elution, 0 to 50% EtOAc in hexanes) provided methyl 2,6-anhydro-5-C-(5-bromo-1,3-thiazol-2-yl)-3,4-dideoxy-hexonate (134 mg, 0.416 mmol, 56.2%) as a ca 2:1 mixture of diastereomers as determined by $^1$H-NMR. MS ESI: $[M+H]^+$ m/z 323.9. Major diastereoisomer $^1$H NMR (500 MHz, $CDCl_3$) δ 7.61 (s, 1H), 4.30 (m, 1H), 4.11 (m, 1H), 3.79 (s, 3H), 3.62 (m, 1H), 3.52 (br s, 1H), 2.24-2.18 (m, 2H), 2.09-2.03 (m, 2H).

Intermediate 84(a): ethyl 4-hydroxy-3-methyl-4-(1,3-thiazol-2-yl)cyclohexanecarboxylate

Intermediate 84(b): ethyl 4-hydroxy-3,5-dimethyl-4-(1,3-thiazol-2-yl)cyclohexanecarboxylate

Intermediate 84(c): ethyl 4-hydroxy-3,3-dimethyl-thiazol-2-yl)cyclohexanecarboxylate

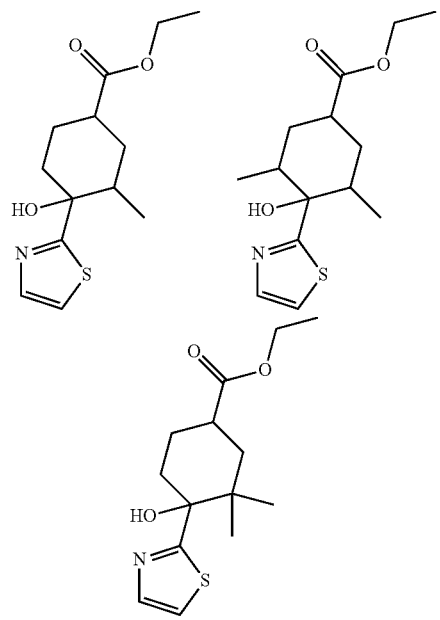

Step 1

Lithium bis(trimethylsilyl)amide (41.1 ml, 41.1 mmol) was added to a −78° C. solution of ethyl 4-oxocyclohexanecarboxylate (7 g, 41.1 mmol) in THF (153 ml) making sure that the temperature never exceeded −70° C. After the addition, the reaction was aged for 30 min before slowly adding iodomethane (15 ml, 240 mmol). The reaction was aged below −70° C. for 10 min before slowly warming to room temperature over the course of 1 h. The reaction was then heated to 50° C. for 5 h. The heating source was removed, and the reaction was aged at rt for 14 h. The solution was mixed with water and extracted three times with EtOAc. The combined organic layer was dried under reduced pressure to obtain a dark red oil (9 g). The crude product was used directly in the next step without further purification.

Step 2

The crude dark red oil (9 g) from the previous step was mixed with thiazole (4.41 mL, 61.7 mmol) in THF (150 mL) and cooled to −78° C. n-Butyllithium (2.5 M, 16.46 ml, 41.1 mmol) was added, and the solution was maintained at −78° C. for 1 h, then allowed to warm to rt. The reaction was quenched with water and extracted three times with $CH_2Cl_2$. The combined organic layer was dried under reduced pressure and purified by silica gel column chromatography (5-100% EtOAc:Hexanes) to give ethyl 4-hydroxy-3-methyl-4-(1,3-thiazol-2-yl)cyclohexanecarboxylate (2.69 g, 24%) as a brown oil and a mixture of ethyl 4-hydroxy-3,5-dimethyl-4-

(1,3-thiazol-2-yl)cyclohexanecarboxylate and ethyl 4-hydroxy-3,3-dimethyl-4-(1,3-thiazol-2-yl)cyclohexanecarboxylate (1.09 g, 9%) as a brown oil. MS ESI: [M+H]⁺ m/z 270 (for 84a)+284 (for 84 b/c)

Intermediate 85: ethyl 4-(5-bromo-1,3-thiazol-2-yl)-4-hydroxy-3-methylcyclohexanecarboxylate

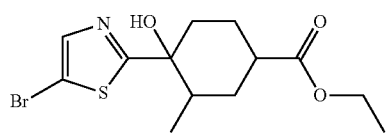 [SMILES: CCOC(=O)C1CCC(O)(c2ncc(Br)s2)C(C)C1]

N-bromosuccinimide (2.222 g, 12.48 mmol) was added to solution of Intermediate 84(a) (2.69 g, 9.99 mmol) in DMF (10.51 ml). The reaction was aged at room temperature for 2 h. The reaction was then quenched with aqueous saturated sodium bicarbonate and mixed with water. The mixture was extracted with CH₂Cl₂ (3×). The combined organic layers were concentrated under reduced pressure and purified by silica gel flash chromatography (0-30% EtOAc:Hexanes) to give ethyl 4-(5-bromo-1,3-thiazol-2-yl)-4-hydroxy-3-methylcyclohexanecarboxylate (2.27 g, 65%) as a yellow oil. MS ESI: [M+H]⁺ m/z 348, 350.

Intermediate 86(a): ethyl 4-(5-bromo-1,3-thiazol-2-yl)-4-hydroxy-3,5-dimethylcyclohexanecarboxylate Intermediate 86(b): ethyl 4-(5-bromo-1,3-thiazol-2-yl)-4-hydroxy-3,3-dimethylcyclohexanecarboxylate

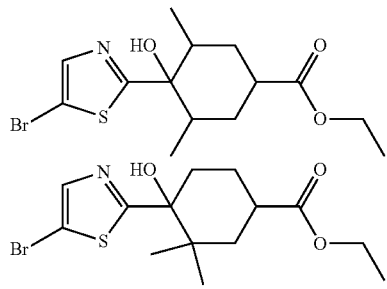

N-bromosuccinimide (1.01 g, 5.64 mmol) was added to solution of Intermediate 84(b) and Intermediate 84(c) (1.09 g, 3.85 mmol) in DMF (5.94 ml). The reaction was aged at rt for 2 h and then quenched with aqueous saturated sodium bicarbonate and mixed with water. The mixture was extracted three times with CH₂Cl₂. The combined organic layers were concentrated under reduced pressure and purified by flash chromatography (0-40% Et₂O:Heptane) to give ethyl 4-(5-bromo-1,3-thiazol-2-yl)-4-hydroxy-3,5-dimethylcyclohexanecarboxylate and ethyl 4-(5-bromo-1,3-thiazol-2-yl)-4-hydroxy-3,3-dimethylcyclohexanecarboxylate (1.04 g, 75%) as a yellow oil. MS ESI: [M+H]⁺ m/z 362, 364. 240 mg of this material was further purified using chiral HPLC (5% EtOH:Heptane) to give ethyl 4-(5-bromo-1,3-thiazol-2-yl)-4-hydroxy-3,5-dimethylcyclohexanecarboxylate (71 mg, 30%) (MS ESI: [M+H]⁺ m/z 362, 364) as a yellow oil and ethyl 4-(5-bromo-1,3-thiazol-2-yl)-4-hydroxy-3,3-dimethylcyclohexanecarboxylate (110 mg, 46%) (MS ESI: [M+H]⁺ m/z 362, 364) as a yellow oil.

Intermediate 87: Methyl 4-[2-(5-bromo-1,3-thiazol-2-yl)propan-2-yl]benzoate

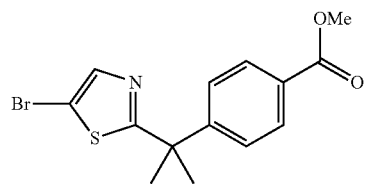 [SMILES: COC(=O)c1ccc(C(C)(C)c2ncc(Br)s2)cc1]

Step 1

2-Bromothiazole (2.72 ml, 30.5 mmol) was taken up in THF (60 ml) and cooled to −20° C. Isopropylmagnesium chloride (16.00 ml, 32.0 mmol) was added drop wise. After stirring for 1 h (−10° C. to 0° C.), the reaction was cooled to −78° C., and methyl 4-formylbenzoate (5.50 g, 33.5 mmol) in THF (10 ml) was added drop wise. The reaction was stirred for 30 min at −78° C., then warmed to room temperature. After 1 h at room temperature, the reaction was quenched with aqueous saturated NH₄Cl and extracted with EtOAc (2×). The combined organic layers were dried over MgSO₄ and concentrated in vacuo. The residue was purified by flash chromatography (10-75% EtOAc/hexanes) to provide methyl 4-[hydroxy(1,3-thiazol-2-yl)methyl]benzoate (7.29 g, 29.2 mmol, 96% yield) as an off-white solid. MS ESI: [M+H]⁺ m/z 250.0.

Step 2

The product of Step 1 (4.00 g, 16.05 mmol) was taken up in DCE (80 ml) with triethylsilane (25.6 ml, 160 mmol), and trifluoroacetic acid (24.72 ml, 321 mmol) was added. The reaction was stirred at reflux overnight. The reaction was diluted with toluene and evaporated to dryness. The residue was taken back up in EtOAc, washed with aqueous saturated NaHCO₃ and brine, dried over MgSO₄, filtered and concentrated. Flash chromatography (0-50% EtOAc/hexanes) afforded methyl 4-(1,3-thiazol-2-ylmethyl)benzoate (3.13 g, 13.42 mmol, 84% yield) as a pale yellow gum that crystallized upon standing. MS ESI: [M+H]⁺ m/z 234.1.

Step 3

Sodium hydride (1.072 g, 26.8 mmol) was suspended in THF (7 ml)/DMF (7 ml) under nitrogen and cooled to 0° C. The compound of Step 2 (1.25 g, 5.36 mmol) in THF (4 ml)/DMF (4 ml) was added drop wise. The ice bath was removed, and the dark red suspension was stirred at room temperature for 1 h. The mixture was then cooled back down to 0° C., and iodomethane (1.675 ml, 26.8 mmol) was added in one portion. The reaction was allowed to warm to room temperature and stirred for 3 h. It was then quenched with aqueous saturated NH₄Cl and water and extracted with EtOAc (2×). The combined organic layers were washed with brine, dried over MgSO₄, filtered and concentrated in vacuo. Flash chromatography (0-50% EtOAc/hexanes) afforded methyl 4-[2-(1,3-thiazol-2-yl)propan-2-yl]benzoate (1.066 g, 4.08 mmol, 76% yield) as a colorless gum that crystallized upon standing. MS ESI: [M+H]⁺ m/z 262.1.

Step 4

The compound of Step 3 (880 mg, 3.37 mmol) was dissolved in DMF (17 ml), and N-bromosuccinimide (779 mg, 4.38 mmol) was added. The reaction was stirred at room temperature overnight. Additional N-bromosuccinimide (599 mg, 3.37 mmol) was added. After 8 h at room temperature, the reaction was diluted with $Na_2S_2O_3$ (10% solution in water), and extracted with EtOAc (2×). The combined organic layers were washed with brine, dried over $MgSO_4$, filtered and concentrated in vacuo. Flash chromatography (0-20% EtOAc/hexanes) afforded methyl 4-[2-(5-bromo-1,3-thiazol-2-yl)propan-2-yl]benzoate (1.057 g, 3.11 mmol, 92% yield) as a colorless gum. MS ESI: [M+H]⁺ m/z 342.0. ¹H NMR (500 MHz, DMSO-$d_6$) δ 7.91-7.89 (m, 1H), 7.89-7.87 (m, 1H), 7.79 (s, 1H), 7.49-7.47 (m, 1H), 7.47-7.45 (m, 1H), 3.81 (s, 3H), 1.75 (s, 6H).

Intermediate 88: Methyl 4-[1-(5-bromo-1,3-thiazol-2-yl)cyclopropyl]bonzoate

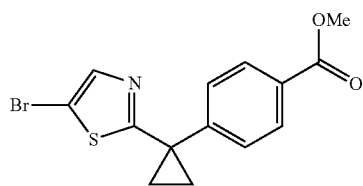 [SMILES: COC(=O)c1ccc(C2(c3ncc(Br)s3)CC2)cc1]

Step 1

Zinc dust, <10 micron (2.227 g, 34.1 mmol) was suspended in THF (5 ml), and 1,2-dibromoethane (0.090 ml, 1.048 mmol) was added. The mixture was stirred for 10 min at 70° C. It was then cooled to room temperature, and TMS-Cl (0.100 ml, 0.786 mmol) was added. After 30 min at room temperature, the activated zinc was cooled to 0° C., and methyl 4-(bromomethyl)benzoate) (6.00 g, 26.2 mmol) in THF (20 ml) was added drop-wise over 75 min (~2 mL every ~5-7 min). After stirring for another 1 h at 0° C., another portion of THF (25 ml) was added to dilute to ~0.5 M. The gray suspension was allowed to stand so the remaining zinc solid would settle, and the supernatant was used as bromo[4-(methoxycarbonyl)benzyl]zinc (0.5 M in THF). Palladium (II) acetate (103 mg, 0.457 mmol), and 2-dicylochexylphosphino-2',6'-dimethoxy-1',1',biphenyl (375 mg, 0.915 mmol) were combined in a flask, sealed, and flushed with nitrogen (2×). Degassed THF (15 ml), 2-bromothiazole (0.408 ml, 4.57 mmol), and the freshly prepared 0.5 M bromo[4-(methoxycarbonyl)benzyl]zinc in THF (27.4 ml, 13.72 mmol) were added, and the reaction was stirred at room temperature overnight. The reaction was diluted with saturated $NH_4Cl$ and water before being extracted with EtOAc (2×). The combined organic layers were washed with brine, dried over $MgSO_4$, filtered and concentrated in vacuo. Flash chromatography (0-50% EtOAc/hexanes) afforded methyl 4-(1,3-thiazol-2-ylmethyl)benzoate (1.06 g, 4.54 mmol, 99%) as a yellow oil that crystallized upon standing. MS ESI: [M+H]⁺ m/z 234.0.

Step 2

Sodium hydride (0.857 g, 21.43 mmol) was suspended in THF (6 ml)/DMF (6 ml) under nitrogen and cooled to 0° C. The product of Step 1 (1.00 g, 4.29 mmol) in THF (3 ml)/DMF (3 ml) was added drop-wise. The ice bath was removed, and the dark red suspension was stirred at room temperature for 30 min. The mixture was then cooled back down to 0° C., and 1,2-dibromoethane (1.478 ml, 17.15 mmol) was added in one portion. The reaction was allowed to warm to room temperature and stirred for 2 h. The green suspension was then quenched with saturated $NH_4Cl$ and water and extracted with EtOAc (2×). The combined organic layers were washed with brine, dried over $MgSO_4$, filtered and evaporated. Flash chromatography (0-30% $Et_2O$/hexanes) afforded methyl 4-[1-(1,3-thiazol-2-yl)cyclopropyl]benzoate (342 mg, 1.319 mmol, 30.8%) as a colorless gum. MS ESI: [M+H]⁺ m/z 260.0.

Step 3

The product of Step 2 (459 mg, 1.770 mmol) was dissolved in DMF (10 ml), and N-bromosuccinimide (473 mg, 2.65 mmol) was added. The reaction was stirred at room temperature overnight. The reaction was diluted with $Na_2S_2O_3$ (10% solution in water) and extracted with EtOAc (2×). The combined organic layers were washed with brine, dried over $MgSO_4$, filtered and concentrated in vacuo. Flash chromatography (0-25% EtOAc/hexanes) afforded methyl 4-[1-(5-bromo-1,3-thiazol-2-yl)cyclopropyl]benzoate (523 mg, 1.546 mmol, 87% yield) as a colorless solid. MS ESI: [M+H]⁺ m/z 339.9. ¹H NMR (500 MHz, DMSO-$d_6$) δ 7.95 (d, J=8.1, 2H), 7.71 (s, 1H), 7.57 (d, J=8.1, 2H), 3.84 (s, 3H), 1.79-1.56 (m, 2H), 1.55-1.39 (m, 2H).

Intermediate 89: Methyl 4-[1-(5-bromo-1,3-thiazol-2-yl)ethenyl]benzoate

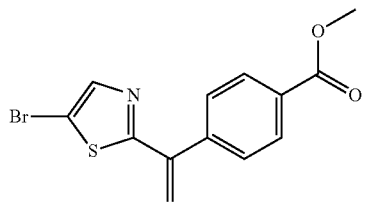 [SMILES: C=C(c1ccc(C(=O)OC)cc1)c1ncc(Br)s1]

Step 1

A flask was charged with 2-bromothiazole (1.386 ml, 15.55 mmol) and THF (30.6 ml) and then sealed and purged with Argon. The solution was cooled to −20° C. and isopropylmagnesium chloride (2 M, 8.16 ml, 16.32 mmol) was added drop wise. The reaction was stirred for 1 hour and then warmed to 0° C. After stirring for 60 minutes, the solution was cooled to −78° C. and methyl 4-acetylbenzoate (3.05 g, 17.10 mmol) in THF (5.11 ml) was added drop wise. The reaction stirred for an additional 30 minutes at −78° C. then warmed to room temperature. After stirring for 1 hour, the reaction was quenched with aqueous saturated $NH_4Cl$ and extracted with ethyl acetate (2×). The combined organics were dried over $Na_2SO_4$, filtered and concentrated. The crude mixture was purified by flash chromatography on silica (10-75% ethyl acetate/hexanes). The mixed fractions were combined, concentrated and re-purified by column chromatography on silica (10-75% ethyl acetate/hexanes). The desired fractions were combined and concentrated to afford methyl 4-[1-hydroxy-1-(1,3-thiazol-5-yl)ethyl]benzoate (2.54 g, 9.65 mmol, 62.0% yield). MS ESI: [M+H]⁺ m/z 264.0.

Step 2

N-bromosuccinimide (0.933 g, 5.24 mmol) was added to a solution of the product of Step 1 (1.15 g, 4.37 mmol) and DMF (8.73 ml). The resulting solution was stirred overnight at room temperature. The reaction was diluted with ethyl acetate and transferred to a separatory funnel. The organic layer was washed with aqueous saturated NaHCO₃ and brine. The organic layer was dried over Na₂SO₄, filtered and concentrated. Flash chromatography (0-65% EtOAc/hexanes) afforded methyl 4-[1-(5-bromo-1,3-thiazol-2-yl)-1-hydroxyethyl]benzoate (863 mg, 2.52 mmol, 57.7% yield) as a yellow solid. MS ESI: [M+H]⁺ m/z 343.9.

Step 3

A vial was charged with the product of Step 2 (0.86 g, 2.51 mmol) and Eaton's reagent (15.16 ml, 95 mmol). The resulting solution was stirred at 60° C. for 1 hour. The reaction was cooled, carefully neutralized with aqueous saturated NaHCO₃ and then extracted with ethyl acetate (2×). The combined organic layers were dried over Na₂SO₄, filtered and concentrated. Flash chromatography (10-65% EtOAc/hexanes) afforded methyl 4-[1-(5-bromo-1,3-thiazol-2-yl)ethenyl]benzoate (799 mg, 2.465 mmol, 98% yield). MS ESI: [M+H]⁺ m/z 325.9.

Intermediate 90: 4-(5-Bromo-thiazol-2-yl)-4-hydroxy-2-methyl-cyclohexanecarboxylic acid ethyl ester

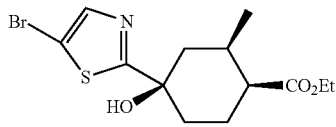 [SMILES: CCOC(=O)[C@H]1CC[C@](O)(c2ncc(Br)s2)C[C@H]1C]

Step 1

To a cooled (-78° C.) solution of cis-2-methyl-4-oxo-cyclohexanecarboxylic acid ethyl ester (22 g, 119 mmol) and thiazole (16.9 mL, 239 mmol) in THF (154 mL) was added nBuLi (1.6 M in Hex, 74.6 mL, 119 mmol) dropwise at such a rate that the internal temperature was maintained <-65° C. The reaction mixture was stirred for 30 min, MeOH (4.83 mL, 119 mmol) was introduced, and the reaction warmed to room temperature where it was diluted with water and EtOAc. The layers were separated, the organic layer dried with MgSO₄, filtered and concentrated in vacuo. The crude residue was purified by flash chromatography to afford 4-hydroxy-2-methyl-4-thiazol-2-yl-cyclohexanecarboxylic acid ethyl ester (21 g, 78 mmol).

Step 2

To a solution of the product of Step 1 (20 g, 74.3 mmol) in DMF (140 mL) was added NBS (15.9 g, 89 mmol). After the initial exotherm had subsided the reaction mixture was heated to 50° C. and stirred for 1 h. It was then cooled to room temperature and water (280 mL containing 7 g of sodium sulfite) was added followed by EtOAc. The layers were cut and the aqueous layer was back extracted with EtOAc (2×), and then the combined organics washed with H₂O. The organic layer was dried with MgSO₄, filtered and concentrated in vacuo. The crude residue was purified by flash chromatography to afford 4-(5-bromo-thiazol-2-yl)-4-hydroxy-2-methyl-cyclohexanecarboxylic acid ethyl ester (20 g, 57.4 mmol), MS ESI: [M+H]⁺ m/z 347.9.

Intermediate 91: 4-(5-Bromo-thiazol-2-yl)-4-hydroxy-2,5-dimethyl-cyclohexanecarboxylic acid ethyl ester

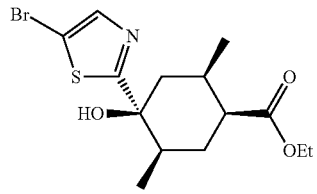 [SMILES: CCOC(=O)[C@H]1C[C@@H](C)[C@](O)(c2ncc(Br)s2)C[C@H]1C]

Step 1 cis-2-Methyl-4-oxo-cyclohexanecarboxylic acid ethyl ester (25 g, 136 mmol) was dissolved in tetrahydrofuran (250 mL) and cooled to -78° C. in a dry ice/acetone bath. Lithium hexamethyldisilazide (136 mL, 136 mmol) was added dropwise over one hour, keeping the internal temperature of the reaction under -70° C. The reaction was aged for 30 minutes at -78° C., and then methyl iodide (9.33 mL, 149 mmol) was added. The reaction was aged for 2 hours and then warmed to room temperature and stirred over night, at which point TLC analysis (KMnO₄ staining) indicated complete consumption of the starting ester. The reaction was diluted with water (200 mL) and ethyl acetate (200 mL), and extracted with ethyl acetate (3×100 mL). The organic extracts were washed with brine (100 mL) and dried over MgSO₄, filtered and concentrated in vacuo to an orange residue. The crude mixture was taken up in tetrahydrofuran (250 mL) and cooled to -78° C. with a dry ice/acetone bath. Thiazole (14.6 mL, 204 mmol) was added, followed by n-butyllithium (54.3 mL, 136 mmol) dropwise, keeping the internal temperature below -70° C. The reaction was aged for 1.25 hours, then quenched with water (100 mL) and warmed to room temperature. The solution was extracted with ethyl acetate (3×100 mL) and the organic extracts were washed with brine (100 mL) and dried over MgSO₄, filtered and concentrated in vacuo. Purification by flash chromatography yielded a 4:6 mixture of two isomers of 4-hydroxy-2,5-dimethyl-4-thiazol-2-yl-cyclohexanecarboxylic acid ethyl ester (4.6 g, 16.1 mmol) and impure fractions that were purified a second time by flash chromatography which provided 4-hydroxy-2,5-dimethyl-4-thiazol-2-yl-cyclohexanecarboxylic acid ethyl ester (3.84 g (13.6 mmol) as a colorless oil. MS ESL: [M+H]⁺ m/z 284.2.

Step 2

To a solution of the product of Step 1 (3.84 g, 8.54 mmol) in dimethylformamide (33.5 mL) was added N-bromosuccinimide (1.75 g, 9.82 mmol) and the solution stirred at 55° C. for 3 hours. A solution of sodium sulfite (0.538 g, 4.27 mmol) in water (60 mL) was added dropwise to the reaction. The mixture was diluted with ethyl acetate (100 mL) and washed the organic extract with water (2×100 mL). The combined aqueous layers were back extracted with ethyl acetate (3×100 mL) and the combined organic extracts were dried over MgSO₄, filtered and concentrated in vacuo. Purification by flash chromatography provided a solid, which was triturated with hexanes, to give 4-(5-bromo-thiazol-2-yl)-4-hydroxy-2,5-dimethyl-cyclohexanecarboxylic acid ethyl ester (1.07 g, 2.95 mmol). MS ESI: [M+H]⁺ m/z 362.1.

Intermediate 92: 445-Bromo-thiazol-2-yl)-4-hydroxy-2,3-dimethyl-cyclohexanecarboxylic acid ethyl ester

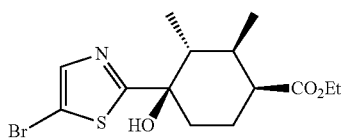 [SMILES: CCOC(=O)[C@H]1CC[C@](O)(c2ncc(Br)s2)[C@H](C)[C@H]1C]

To a DMF (15.6 mL) solution of a 4:6 mixture of two isomers of 4-hydroxy-2,5-dimethyl-4-thiazol-2-yl-cyclohexanecarboxylic acid ethyl ester (1.2 g, 4.03 mmol) was added NBS (0.83 g, 4.64 mmol). The resulting solution was heated to 55° C. for 1 h, then cooled to room temperature and a solution of sodium sulfite (0.54 g, 4.27 mmol) in water (30 mL) was added. The mixture was diluted with EtOAc and the layers separated. The aqueous layer was back extracted with EtOAc (2×). The combined organics were washed with brine, dried over MgSO₄, filtered and concentrated in vacuo. The crude residue was purified by flash chromatography to afford a 4:6 mixture of geometrical isomers of 4-(5-bromo-thiazol-2-yl)-4-hydroxy-2,3-dimethyl-cyclohexanecarboxylic acid ethyl ester (700 mg, 1.93 mmol). This was further separated by SFC to afford 4-(5-bromo-thiazol-2-yl)-4-hydroxy-2,3-dimethyl-cyclohexanecarboxylic acid ethyl ester as shown above. ¹H NMR (600 MHz, CDCl₃): δ 7.51 (s, 1H), 4.08 (m, 2H), 2.68 (q, J=4.5 Hz, 1H), 2.34 (m, 1H), 2.26 (m, 1H), 2.20 (dd, J=9.5, 6.7 Hz, 1H), 2.09 (td, J=13.1, 2.5 Hz, 1H), 1.94 (dt, J=13.1, 3.4, 1H), 1.85 (dq, J=15.0, 3.6 Hz, 1H), 1.22 (t, J=7.5 Hz, 3H), 0.98 (d, J=6.7 Hz, 3H), 0.75 (d, J=6.7 Hz, 3H).

Intermediate 93: propan-2-yl-4-(5-bromo-1,3-thiazol-2-yl)-4-hydroxy-2,6-dimethylcyclohexanecarboxylate

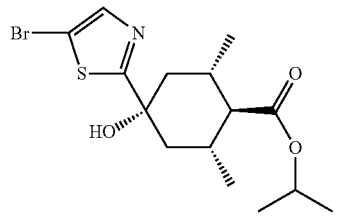 [SMILES: CC(C)OC(=O)[C@H]1[C@H](C)C[C@@](O)(c2ncc(Br)s2)C[C@@H]1C]

Step 1

Propan-2-yl 2,6-dimethyl-4-oxocyclohex-2-ene-1-carboxylate (20 g, 95.1 mmol) was prepared according to a literature procedure (*J. Org. Chem.*, 2007, 72(4), 1458-1453) using isopropyl acetoacetate in place of ethyl acetoacetate and diluted with EtOH (300 mL). To the resulting solution under a nitrogen blanket was added 5% Pd/C (0.8 g) after which the vessel was shaken under an initial hydrogen pressure of 50 psi for 2 h. The reaction contents were then filtered through celite using additional EtOH, concentrated in vacuo and purified by flash chromatography to afford propan-2-yl 2,6-dimethyl-4-oxocyclohexanecarboxylate (5.2 g, 24.5 mmol).

Step 2

The product of Step 1 (5.2 g, 24.5 mmol) was diluted with THF (50 mL) to which thiazole (2.63 mL, 36.7 mmol) was added. The resulting solution was cooled to −78° C. and nBuLi (2.5 M in Hex, 10.3 mL, 25.7 mmol) was added dropwise at such a rate to keep the internal temperature <−65° C. When the addition was complete, the reaction mixture was stirred for a further 1 h then quenched by the addition of water and brought to room temperature. EtOAc was added, the layers separated and the organic dried with MgSO₄, filtered, concentrated in vacuo and the crude residue purified by flash chromatography to afford propan-2-yl-4-hydroxy-2,6-dimethyl-4-(1,3-thiazol-2-yl)cyclohexanecarboxylate (1.4 g, 4.7 mmol).

Step 3

To a solution of the product of Step 2 (1.4 g, 4.7 mmol) in DMF (15 mL) was added NBS (0.963 g, 5.41 mmol) and the resulting solution heated to 55° C. After 60 min the reaction was cooled and a solution of sodium sulfite (500 mg) in water (30 mL) was added followed by EtOAc. The layers were separated, the aqueous layer was back extracted twice with EtOAc and the combined organics were dried with MgSO₄, filtered, and concentrated in vacuo. The crude residue was purified by flash chromatography to afford propan-2-yl-4-(5-bromo-1,3-thiazol-2-yl)-4-hydroxy-2,6 dimethylcyclohexanecarboxylate (1.04 g, 2.76 mmol) MS ESI: [M+H]⁺ m/z 375.9.

Intermediate 94: tert-butyl (4R)-4-(5-bromo-1,3-thiazol-2-yl)-4-hydroxyazepane-1-carboxylate

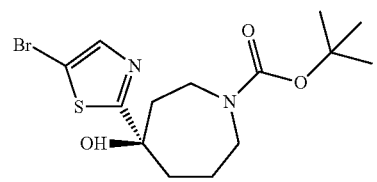 [SMILES: CC(C)(C)OC(=O)N1CCC[C@](O)(c2ncc(Br)s2)CC1]

Step 1

Azepan-4-one (40.0 g, 267 mmol) in DCM (320 mL) was treated with triethylamine (27.0 g, 225 mmol) and then Boc₂O (88.0 g, 401 mmol) was added slowly using an ice water bath to maintain the temperature at 10-20° C. Additional triethylamine (27.0 g, 225 mmol) was then added and the solution was stirred for 12 hours. The reaction was then treated with saturated aqueous NH₄Cl (180 mL) and EtOAc (250 mL). The aqueous layer was extracted with EtOAc (150 mL) and the organic layer was concentrated and purified by flash chromatography on silica gel to afford tert-butyl 4-oxoazepane-1-carboxylate as a viscous oil (45.9 g, 233 mmol).

Step 2

Thiazole (21.3 g, 250 mmol) in THF (160 mL) was cooled to −70° C. and then n-BuLi (100 mL, 250 mmol) was added slowly over 5 minutes, keeping the temperature at −60° C. or lower. The resulting slurry was stirred for 45 minutes at this temperature and then the product of Step 1 (48.55 g, 228 mmol) in THF (50 mL) was added dropwise, maintaining the temperature at −60° C. The solution was stirred for one hour and then the cooling bath removed. At −20° C., 2M HCl (114 mL) was added and upon warming to RT the homogeneous solution was diluted with EtOAc (150 mL). The phases were separated and the aqueous layer was extracted with EtOAc (150 mL). The combined organic layers were washed with aqueous saturated NaHCO$_3$ (150 mL), brine (150 mL) and then concentrated to a thick syrup. This was dissolved in EtOAc (140 mL) and then treated with hexane (210 mL) and the slurry filtered to afford tert-butyl 4-hydroxy-4-(1,3-thiazol-2-yl)azepane-1-carboxylate as a white solid (68.0 g, 220 mmol) and the material was then subjected to chiral chromatography to afford tert-butyl (4R)-4-hydroxy-4-(1,3-thiazol-2-yl)azepane-1-carboxylate (14.5 g, 48.6 mmol).

Step 3

The product of Step 2 (14.5 g, 48.6 mmol) was dissolved in DMF (58 mL) and then treated with NBS (11.24 g, 63.2 mmol) and warmed to 40° C. for 3 hours. The reaction was quenched with Na$_2$SO$_3$ (3.0 g, 24.30 mmol) in H$_2$O (50 mL) and the solution was then extracted with EtOAc (100 mL), washed with brine (50 mL) and then chromatographed on silica gel to afford tert-butyl (4R)-4-(5-bromo-1,3-thiazol-2-yl)-4-hydroxyazepane-1-carboxylate (18.3 g, 46 mmol). MS ESI: [M+H-tBu]$^+$ m/z 320.

Intermediate 95: ethyl cis-4-(5-bromo-1,3-thiazol-2-yl)-4-hydroxycyclohexanecarboxylate

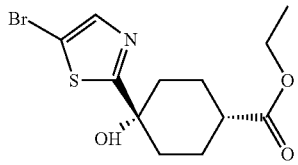

Step 1

Isopropylmagnesium chloride/lithium chloride complex (1.3 M, 119 mL, 154 mmol) was added to a flask and cooled to 0° C. and then diluted with 50 mL THF. Thiazole (13.0 g, 154 mmol) was added over 30 minutes making sure the temperature did not exceed 5° C. The orange slurry was stirred for 45 minutes and then cooled to −20° C. and ethyl 4-oxocyclohexane-carboxylate (25.0 g, 147 mmol) in THF (25 mL) was added and then stirred for 50 minutes. The solution was cooled to 5° C. and then quenched with HCl (2 M, 100 mL) and extracted with EtOAc (250 mL). The organic layer was washed with aqueous saturated NaHCO$_3$ solution (100 mL), brine (100 mL), evaporated and purified by flash chromatography on silica gel to afford ethyl 4-hydroxy-4-(1,3-thiazol-2-yl)cyclohexanecarboylate as an oil (23.6 g, 92 mmol).

Step 2

The product of Step 1 (23.5 g, 92 mmol) was dissolved in DMF (94 mL) and then treated with NBS (19.66 g, 110 mmol) and stirred at RT for 10 hours. The reaction was then treated with Na$_2$SO$_3$ (5.8 g, 465 mmol) in H$_2$O (150 mL) and then extracted with EtOAc (100 mL) and the oil was purified by flash chromatography on silica gel to afford ethyl 4-(5-bromo-1,3-thiazol-2-yl)-4-hydroxycyclohexanecarboxylate as an oil (31 g, 77 mmol), which was subjected to chiral chromatography to afford ethyl cis-4-(5-bromo-1,3-thiazol-2-yl)-4-hydroxycyclohexane-carboxylate as an oil (15 g, 33 mmol). MS ESI: [M+H]$^+$ m/z 333.

Intermediate 96: 5-(5-bromo-1,3-thiazol-2-yl)-5-hydroxyazepan-2-one

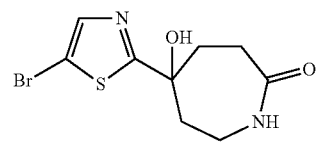

Step 1

To a solution of 8-(1,3-thiazol-2-yl)-1,4-dioxaspiro[4.5]decan-8-ol (15.0 g, 62.2 mmol) in DMF (75 mL) was added NBS (6.9 g, 55 mmol) and the solution warmed to 45° C. for 8 hours. The solution was treated with Na$_2$SO$_3$ (3.9 g, 31 mmol) in H$_2$O (150 mL) and the resulting slurry was filtered and washed with water (70 mL) to afford 8-(5-bromo-1,3-thiazol-2-yl)-1,4-dioxaspiro[4.5]decan-8-ol as a white solid (16.8 g, 52.5 mmol).

Step 2

The product of Step 1 (3.0 g, 9.4 mmol) was dissolved in 30 mL of 1:1 THF:HCl (3N) and heated at 50° C. for 8 hours and the solution neutralized with solid KHCO$_3$ and then EtOAc (100 mL) and water (20 mL) were added. The aqueous layer was then extracted with EtOAc (50 mL) and the combined organic layers were washed with brine (50 mL), evaporated to a slurry which was treated with hexanes (20 mL). Filtration and drying afforded 4-(5-bromo-1,3-thiazol-2-yl)-4-hydroxycyclohexanone as a white solid (2.1 g, 7.7 mmol).

Step 3

To the product of Step 2 (10 g, 36.2 mmol) in THF (60.0 mL) was added hydroxylaminehydrochloride (5.0 g, 72.4 mmol) in water (7.0 mL) and Na$_2$CO$_3$ (2 M, 36.2 mL) added. The solution was stirred for 30 minutes and the resulting slurry was heated to 50° C. for 8 hours and then allowed to cool to RT over 12 hours. To the slurry was added H$_2$O (240.0 mL). Slow filtration afforded 1-(5-bromo-1,3-thiazol-2-yl)4-hydroxyimino)cyclohexnanol as a white solid (10.15 g, 35 mmol).

Step 4

The product of Step 3 (10.0 g, 34.3 mmol) was suspended in acetonitrile (75.0 mL) and then TsCl (7.2 g, 37.8 mmol) and DABCO (4.2 g, 37.8 mmol) were added, maintaining the temperature at 20° C. with an ice/water bath. The slurry was stirred for 5 hours and then H$_2$O (10.0 mL) added. The slurry was filtered slowly and washed with water. The liquors were concentrated and the residue dissolved with heating in MeOH (25 mL). Filtration afforded 5-(5-bromo-1,3-thiazol-2-yl)-5- hydroxyazepan-2-one as a white solid (4.0 g combined, 23 mmol) as a white solid. MS ESI: [M+H]+ m/z 291.

Intermediate 97: ethyl 3-oxobicyclo[3.1.0]hexane-6-carboxylate

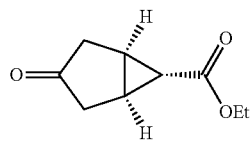 [SMILES: CCOC(=O)[C@H]1[C@@H]2CC(=O)C[C@@H]21]

Step 1

To a flask was added tert-butyl(cyclopent-3-en-1-yloxy)dimethylsilane (0.5 g, 2.52 mmol) and rhodium(II) acetate dimer (22 mg, 0.05 mmol). The flask was evacuated and purged 5 times with argon. Dichloromethane (8.4 mL) was added and the flask was evacuated and purged 5 times with argon. In a separate flask, ethyl diazoacetate (0.37 mL, 3.02 mmol) was added. The flask was evacuated and purged with argon five times. Dichloromethane (8.4 mL) was added and the solution was added to the first flask via syringe pump over a six hour time period and then allowed to stir overnight. The mixture was filtered over a pad of celite and then concentrated. Flash chromatography was used for purification to yield ethyl 3-{[tert-butyl(dimethyl)silyl]oxy}bicyclo[3.1.0]hexane-6-carboxylate (524 mg, 1.84 mmol, 73% yield). $^1$H NMR (500 MHz, CDCl$_3$) δ 4.13-4.03 (m, 2H), 2.37-2.20 (m, 1H), 2.20-2.12 (m, 1H), 2.11-1.96 (m, 1H), 1.94-1.70 (m, 4H), 1.35-1.14 (m, 4H), 0.89-0.79 (m, 9H), 0.05--0.11 (m, 6H).

Step 2

To a solution of the product of Step 1 (524 mg, 1.84 mmol) in THF (4.6 mL) was added TBAF (1.0 M in THF, 4.6 mL, 4.6 mmol). The reaction was heated at 50° C. for one hour. The reaction was cooled to room temperature, diluted with ethyl acetate, washed with water, dried over magnesium sulfate, filtered and concentrated. The reaction mixture containing ethyl 3-hydroxybicyclo[3.1.0]hexane-6-carboxylate was taken on to the next step without further purification.

Step 3

To a solution of the product of Step 2 (389 mg, 2.3 mmol) in dichloromethane (5.7 mL) was added Dess-Martin periodinane (1.9 g, 4.57 mmol). The reaction was stirred overnight at room temperature. The reaction was then diluted with dichloromethane, washed with saturated sodium bicarbonate, dried over magnesium sulfate, filtered and concentrated. Flash chromatography was used for purification to yield ethyl 3-oxobicyclo[3.1.0]hexane-6-carboxylate (191 mg, 1.14 mmol, 50% yield) as the major product. $^1$H NMR (500 MHz, CDCl$_3$) δ 4.14 (q, J=7.1, 2H), 2.71-2.67 (m, 2H), 2.66-2.63 (m, 1H), 2.31 (s, 1H), 2.27 (s, 1H), 2.21-2.14 (m, 2H), 1.31-1.22 (m, 3H).

Intermediate 98: N-[(4-acetylphenyl)sulfonyl]acetamide

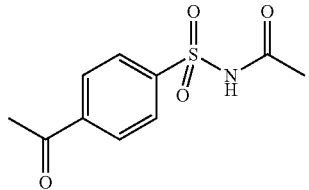 [SMILES: CC(=O)NS(=O)(=O)c1ccc(C(C)=O)cc1]

A solution of 4-acetylbenzenesulfonamide (0.726 g, 3.64 mmol), acetic anhydride (0.7 ml, 7.42 mmol) and DMAP (22.26 mg, 0.182 mmol) in pyridine (0.7 ml) was stirred at room temperature 16 hrs. The volatiles were removed under reduced pressure, the residue was taken up in toluene (5 mL) and concentrated again (3×). The residue was dissolved in EtOAc (20 mL), washed with brine (20 mL), dried over Na$_2$SO$_4$, filtered and concentrated in vacuo. The solid residue was triturated in Et$_2$O and filtered to give N-[(4-acetylphenyl)sulfonyl]acetamide (670 mg, 2.78 mmol, 76% yield) as a pale yellow solid. MS ESI: [M+Na]+ m/z 264.0. $^1$H NMR (500 MHz, DMSO-d$_6$) δ 12.25 (s, 1H), 8.13 (d, J=9.9, 2H), 8.01 (d, J=9.9, 2H), 2.62 (s, 3H), 1.91 (s, 3H).

Intermediate 99: Ethyl[5-oxooctahydropentalen-2-yl]acetate

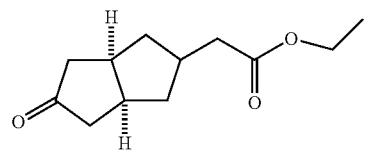

Step 1

To a of solution cis-tetrahydropentalene-2,5-(1H,3H)-dione (2.99 g, 21.6 mmol) and 2,2-dimethylpropane-1,3-diol (2.254 g, 21.6 mmol) in toluene (70 mL) was added p-toluenesulfonic acid monohydrate (0.206 g, 1.08 mmol) and the mixture was heated at 110° C. for 24 hrs with a Dean Stark apparatus. The reaction mixture was cooled to room temperature, poured over solid K$_2$CO$_3$, stirred 5 mins then filtered and concentrated under reduced pressure. The residue was purified by flash chromatography (12 to 100% EtOAc in hexanes) to give 5,5-dimethyltetrahydro-1'H-spiro[1,3-dioxane-2,2'-pentalen]-5'(3'H)-one (2.224 g, 9.92 mmol, 45.8% yield) as a colorless oil which solidified upon standing. MS ESI: [M+H]+ m/z 225.7.

Step 2

Sodium hydride (60% dispersion in mineral oil, 134 mg, 3.34 mmol) was suspended in THF (2 mL) and cooled to 0° C. Triethylphopsphonoacetate (0.55 g, 2.45 mmol) was added dropwise and the mixture was stirred at 0° C. for 30 min. The product of Step 1 (500 mg, 2.229 mmol) was added dropwise as a solution in THF (0.5 mL) and the reaction mixture was stirred 16 hrs while warming from 0° C. to room temperature. The mixture was partitioned between EtOAc and water, the organic layer dried over Na$_2$SO$_4$, concentrated under reduced pressure and the residue was purified by flash chromatography (7 to 60% EtOAc in hexanes) to give ethyl[5,5-dimethyltetrahydro-1'H-spiro[1,3-dioxane-2,2'-pentalen]-5'(3'H)-ylidene]ethanoate (460 mg, 1.563 mmol, 70.1% yield) as a colorless oil. MS ESI: [M+Na]$^+$ m/z 295.7.

Step 3

A mixture of the product of Step 2 (400 mg, 1.359 mmol) and 10% Pd—C-50% wet (85 mg, 0.799 mmol) in EtOAc (8.0 mL) was stirred 16 hrs at room temperature under a hydrogen atmosphere. The catalyst was then filtered off and the volatiles were removed under reduced pressure to give ethyl[5,5-dimethylhexahydro-1'H-spiro[1,3-dioxane-2,2'-pentalen]-5'-yl]acetate as a colorless oil. MS ESI: [M+Na]$^+$ m/z 297.7.

Step 4

A solution of the product of Step 3 (400 mg, 1.350 mmol) in acetone (8.0 mL) and water (8.00 mL) was stirred at room temperature 16 hrs with p-toluenesulfonic acid monohydrate (257 mg, 1.35 mmol). The volatiles were removed under reduced pressure and the residue was partitioned between EtOAc and brine. The separated organic layer was dried over Na$_2$SO$_4$, filtered and concentrated under reduced pressure. Flash chromatography (10 to 60% EtOAc in hexanes) afforded ethyl[5-oxooctahydropentalen-2-yl]acetate (38 mg, 0.181 mmol, 13.4% yield) as a colorless oil. $^1$H NMR (500 MHz, CDCl$_3$) δ 4.14-4.09 (m, 2H), 2.73-2.71 (m, 2H), 2.53-2.47 (m, 2H), 2.37-2.32 (m, 3H), 2.29-2.25 (m, 2H), 2.08-2.02 (m, 2H), 1.27-1.24 (m, 3H).

Intermediate 100: methyl(cis)-4-oxo-2-(propan-2-yl)cyclohexanecarboxylate

Step 1

Methyl isobutyryl acetate (7.20 g, 49.9 mmol) and sodium methoxide (0.896 g, 4.14 mmol) were cooled to 0° C. Methyl vinyl ketone (4.12 ml, 49.9 mmol) was added dropwise, and the solution was allowed to warm to rt and stirred 1 h at that temperature.

Acetic acid (0.249 ml, 434 mmol) was added, followed by a mixture of MeOH (6.75 ml):Water (750 μL), and finally a solution of pyrrolidine (0.349 ml, 4.21 mmol) in acetic acid (0.309 ml, 5.39 mmol). The resultant solution was heated to reflux (115° C.) for 2 h. The reaction was allowed to cool to room temperature and then diluted with Et$_2$O and water. The layers were separated and the aqueous portion extracted again with Et$_2$O (1×). The combined organic layers were dried over Na$_2$SO$_4$ and concentrated in vacuo to afford methyl 4-oxo-2-(propan-2-yl)cyclohex-2-ene-1-carboxylate (5.11 g, 52%) as a yellow oil, which was used in the subsequent step without further purification.

Step 2

The product of Step 1 (5.11 g, 26.0 mmol) was dissolved in MeOH (80 ml). Palladium on carbon (0.416 g, 0.391 mmol) was added, and the flask was fitted with a hydrogen balloon. The flask was evacuated and backfilled with hydrogen (3×) and stirred 15 h at room temperature. The reaction was then filtered through Celite and the celite was washed with EtOAc. The filtrate was concentrated in vacuo. Purification via silica gel flash chromatography (0-15% EtOAc:Hexanes) gave methyl(cis)-4-oxo-2-(propan-2-yl)cyclohexanecarboxylate (2.63 g, 51%) as a colorless oil.

Intermediate 101: methyl 2,2-dimethyl-4-oxocycloheptanecarboxylate

TMS-Diazomethane (5.97 ml, 11.94 mmol) was added to a stirred, cooled −30° C. mixture of methyl 2,2-dimethyl-4-oxocyclohexanecarboxylate (2 g, 10.86 mmol) and BF$_3$—OEt$_2$ (1.513 ml, 11.94 mmol) in CH$_2$Cl$_2$ (65.0 ml). The reaction was aged at −30° C. for 2 h. The reaction was then quenched with water and allowed to warm to room temperature. The mixture was extracted three times with CH$_2$Cl$_2$ and the combined organic layers were concentrated under reduced pressure. The remaining residue was purified by flash chromatography (0-100% EtOAc:Hexanes) to afford a mixture of regioisomers, including methyl 2,2-dimethyl-4-oxo-cycloheptanecarboxylate (992 mg, 18%) as a yellow oil. $^1$H NMR (500 MHz, CDCl$_3$) δ 3.67-3.57 (m, 3H), 2.76 (d, J=12.9, 0.4H), 2.61 (ddd, J=3.1, 8.0, 15.5, 0.6H), 2.55-2.27 (m, 4H), 1.96-1.50 (m, 4H), 0.95 (m, 6H).

Intermediate 102: Ethyl(trans)-4-oxo-2-phenylcyclohexanecarboxylate

Step 1

A 20-liter round-bottomed flask equipped with a magnetic stir bar was charged with dichloromethane (10 volumes), trans-cinnamic acid (1 eq) and 4-dimethylaminopyridine (0.1 eq). The mixture was cooled to an internal temperature of 0° C., followed by the addition of pentafluorophenol (1.3 eq). 1-(3-Dimethylaminopropyl)-3-ethylcarbodiimide hydrochloride (1.2 eq) was added in portions over 30 minutes, maintaining the internal temperature below 50C. The reaction was allowed to warm to room temperature, then stirred for 18 h, or until judged complete by TLC. Water (10 volumes) was added and the reaction was stirred vigorously. The organic phase was retained, washed with dilute acetic acid (1%, 10 volumes), dilute sodium bicarbonate solution (0.5M, 10 volumes) and brine (10 volumes). The organic phase was dried over magnesium sulfate and evaporated in vacuo to give pentafluorophenyl-trans-cinnamate as a pale, low melting solid (90% yield).

Step 2

A 20-liter pressure vessel capable of standing pressures up to 5 bar was charged with pentafluorophenyl-trans-cinnamate, toluene (3 volumes), 2-trimethylsilyloxy-2,4-butadiene (3 eq), hydroquinone (0.01 eq) and then pressurized to 3 bar with nitrogen. The vessel was heated to an internal temperature of 140° C. for 24 h, or until the reaction was judged complete by NMR. The reaction was evaporated in vacuo, resolubilized in methanol (10 volumes) and evaporated in vacuo a second time to give pentafluorophenyl-(4-oxo-2-phenyl cyclohexane) carboxylate as a crude sticky solid. This product was used in the next step without purification.

Step 3

A 10-liter round-bottomed flask equipped with a magnetic stir bar was charged with pentafluorophenyl-(4-oxo-2-phenylcyclohexane) carboxylate and THF (10 volumes). Sodium hydroxide (3.4 eq) was added and the reaction stirred vigorously for 18 h, or until judged complete by TLC. The solvent was evaporated in vacuo. The resulting residue was taken up into water (10 volumes) and the pH adjusted to 7 with hydrochloric acid (conc). The aqueous phase was then washed with tert-butyl methyl ether (2×10 volumes). The pH was adjusted to 1 with hydrochloric acid, then the aqueous phase was extracted with dichloromethane (2×10 volumes). The combined organic extracts were dried over magnesium sulfate and evaporated in vacuo to give 4-oxo-2-phenyl cyclohexane carboxylic acid as a beige solid. A typical yield of approximately 40% for steps two and three combined was obtained. Purities were approximately 95% as determined by proton NMR.

Step 4

Sulfuric acid (0.073 ml, 1.375 mmol) was added to a mixture of (trans)-4-oxo-2-phenylcyclohexanecarboxylic acid (1.5 g, 6.87 mmol) in EtOH (15 ml). The reaction was aged at 77° C. for 14 h. The cooled reaction was quenched with NaOH (1N) and extracted three times with $CH_2Cl_2$. The combined organic layers were dried under reduced pressure and purified via silica gel column chromatography (0-40% EtOAc:Hexanes) to afford ethyl(trans)-4-oxo-2-phenylcyclohexanecarboxylate (526 mg, 31%) as a colorless oil. MS ESI: $[M+H]^+$ m/z 247.

Intermediate 103: Ethyl(trans)-2-(2-methylphenyl)-4-oxocyclohexanecarboxylate

The title compound was prepared in a manner analogous of that described for Intermediate 102. MS ESI: $[M+H]^+$ m/z 261. $^1$H NMR (500 MHz, $CDCl_3$) δ 7.29-7.22 (m, 1H), 7.21-7.15 (m, 1H), 7.15-7.07 (m, 2H), 3.97-3.85 (m, 2H), 3.64-3.53 (m, 1H), 3.09 (td, J=3.5, 11.3, 1H), 2.60-2.39 (m, 4H), 2.37-2.28 (m, 4H), 2.10-1.98 (m, 1H), 0.95 (t, 7.1, 3H).

Intermediate 104: Ethyl(trans)-2-(4-fluorophenyl)-4-oxocyclohexanecarboxylate

The title compound was prepared in a manner analogous of that described for Intermediate 102. MS ESI: $[M+H]^+$ m/z 265. $^1$H NMR (500 MHz, $CDCl_3$) δ 7.18 (dd, J=5.3, 8.5, 2H), 6.99 (t, J=8.6, 2H), 3.98-3.87 (m, 2H), 3.27 (td, J=4.9, 11.8, 1H), 2.93 (td, J=3.6, 11.3, 1H), 2.62-2.40 (m, 4H), 2.34-2.25 (m, 1H), 2.09-1.95 (m, 1H), 0.98 (m, 3H).

Intermediate 105: Ethyl(trans)-4-oxo-2-(thiophen-3-yl)cyclohexanecarboxylate

The title compound was prepared in a manner analogous of that described for Intermediate 102. $^1$H NMR (500 MHz, $CDCl_3$) δ 7.27 (dd, J=3.1, 4.5, 1H), 7.02 (d, J=2.6, 1H), 6.97 (d, J=5.0, 1H), 4.05-3.94 (m, 2H), 3.56-3.42 (m, 1H), 2.91 (td, J=3.6, 10.3, 1H), 2.67 (dd, J=4.7, 14.7, 1H), 2.61-2.48 (m, 2H), 2.48-2.36 (m, 1H), 2.22 (ddd, J=4.1, 9.8, 13.8, 1H), 2.09-1.95 (m, 1H), 1.07 (dd, J=6.5, 7.1, 3H).

Intermediate 106: Methyl 2-methyl-2-(2-oxopropoxy)propanoate

Step 1

To a solution of 3-bromo-2-methylpropene (1.280 mL, 12.70 mmol) and methyl 2-1.5 hydroxy isobutyrate (1.466 mL, 12.70 mmol) in N,N-dimethylformamide (30 mL) was added sodium hydride (60% dispersion in mineral oil, 0.508 g, 12.70 mmol). After 75 minutes, the reaction mixture was partitioned between diethyl ether (100 mL) and saturated aqueous sodium bicarbonate solution (30 mL). The layers were separated and the organic layer was washed with water (3×25 mL) and brine (25 mL), dried over sodium sulfate, filtered, and concentrated to afford methyl 2-methyl-2-[(2-methylprop-2-en-1-yl)oxy]propanoate (1.73 g, 10 mmol) of a clear oil which was used directly in the subsequent step.

Step 2

To a solution of the product of Step 1 (1.73 g, 10 mmol) in 1,4-dioxane (75 mL) and water (25 mL) was added osmium tetroxide (4 wt % in water, 0.392 mL, 0.05 mmol), 2,6-lutidine (2.329 mL, 20 mmol), and sodium periodate (8.56 g, 40 mmol). After stirring for 14 hours, a large amount of white precipitate had built up. The reaction mixture was then partitioned between diethyl ether (100 mL) and water (25 mL). The layers were separated and the aqueous layer was extracted with diethyl ether (2×50 mL). The combined organic layers were washed with saturated aqueous sodium bicarbonate solution (50 mL) and brine (50 mL), dried over sodium sulfate, filtered, and concentrated to provide methyl 2-methyl-2-(2-oxopropoxy)propanoate as a brown oil (1.74 g, 10 mmol), which was used without further purification. $^1$H NMR (500 MHz, $CDCl_3$) δ 4.02 (s, 2H), 3.73 (s, 3H), 2.22 (s, 3H), 1.48 (s, 6H).

Intermediate 107: Methyl(3E)-2,2-dimethyl-5-oxohex-3-enoate

To a solution of dimethyl(2-oxopropyl)phosphonate (4.09 mL, 30 mmol) in tetrahydrofuran (200 mL) at 0° C. was added potassium tert-butoxide (3.22 g, 28.7 mmol). After 15 minutes, the reaction flask was moved to a 20° C. water bath and then a solution of methyl 2,2-dimethyl-3-oxopropanoate (3.39 g, 26 mmol) in tetrahydrofuran (10 mL) was added. After 20 hours, the opaque reaction mixture was partitioned between diethyl ether (100 mL) and water (100 mL). The layers were separated and the aqueous layer was extracted with diethyl ether (1×100 mL, 1×50 mL). The combined organic layers were washed with saturated aqueous sodium bicarbonate solution and brine, dried over sodium sulfate, filtered, and concentrated. The residue was purified by silica gel flash column chromatography (0-4% methanol/dichloromethane gradient) to afford methyl(3E)-2,2-dimethyl-5-oxohex-3-enoate (2.21 g, 12.21 mmol, 47% yield) as a light yellow oil. $^1$H NMR (500 MHz, $CDCl_3$) δ 6.95 (d, J=16.3, 1H), 6.09 (d, J=16.3, 1H), 3.71 (s, 3H), 2.29 (s, 3H), 1.37 (d, J=2.3, 6H).

Intermediate 108: Methyl 4-acetyl-2-methoxybenzoate

A flask was charged with methyl 4-bromo-2-methoxybenzoate (250 mg, 1.020 mmol), vinyl butyl ether (131 μl, 1.020 mmol), potassium carbonate (169 mg, 1.224 mmol), 1,3-(bis (diphenylphosophine)propane (25.2 mg, 0.061 mmol) and palladium (II) acetate (6.87 mg, 0.031 mmol). The flask was sealed and 3 evacuation/argon purges were performed. DMF (4554 μl) and Water (546 μl) were added and the reaction was heated in a microwave at 122° C. for 75 minutes. Additional vinyl butyl ether (131 μl, 1.020 mmol) was added and the reaction was heated an additional 30 minutes in a MW at 122° C. Once complete the reaction was stirred overnight at 100° C. with conventional heating. The reaction was then cooled. HCl (5%, 8 mL) was added and the mixture was stirred for 30 minutes and then diluted with ethyl acetate and transferred to a separatory funnel. The organic layer was washed with aqueous saturated $NaHCO_3$, brine, dried over $Na_2SO_4$, filtered and concentrated. Flash chromatography (0-50% EtOAc/hexanes) afforded methyl 4-acetyl-2-methoxybenzoate (54.4 mg, 0.261 mmol, 25.6% yield). MS ESI: [M+H]+ m/z 200.1. $^1$H NMR (600 MHz, DMSO-$d_6$) δ 7.70 (d, J=7.9, 1H), 7.57 (dd, J=1.1, 7.9, 1H), 7.53 (s, 1H), 3.86 (s, 3H), 3.78 (s, 3H), 2.49-2.44 (m, 3H).

Intermediate 109: 7-(aminomethyl)isoindolin-1-one hydrochloride

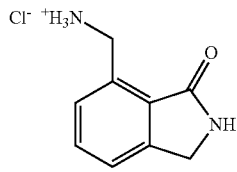 [SMILES: [Cl-] ; [NH3+]Cc1cccc2c1C(=O)NC2]

A mixture of 3-oxoisoindoline-4-carbonitrile (80.0 g, 506 mmol, 1.00 equiv) and Raney Ni (50 g) in CF$_3$COOH (1400 ml) was stirred overnight under a hydrogen atmosphere at room temperature. The solid was filtered out. The filtrate was concentrated under vacuum. The residue was washed with 400 mL of diethylether, then added 300 ml of 37% HCl and stirred for an additional 30 min at room temperature. The resulting mixture was concentrated under vacuum. The solid was dried in an oven under reduced pressure. This resulted in 62 g (76%) of 7-(aminomethyl)isoindolin-1-one hydrochloride as a colorless solid. LC ESI: [M+H]+ m/z 162. $^1$H-NMR (400 MHz, DMSO-$d_6$): 4.40-4.44 (m, 4H), 7.57 (m, 1H), 7.74 (m, 2H), 8.22 (br s, 2H), 9.08 (br s, 1H).

Intermediate 110: 4-(aminomethyl)-2,3-dihydro-1H-isoindol-1-one oxalate

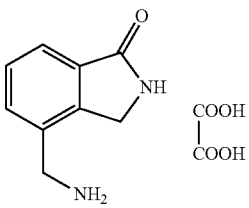

A 2000-mL 3-necked round-bottom flask purged and maintained with an inert atmosphere of nitrogen was added 2,2,2-trifluoroacetic acid (700 mL), then added Raney Ni (17.0 g, 288 mmol, 0.91 equiv) in portions. This was followed by the addition of 1-oxoisoindoline-4-carbonitrile (50.0 g, 316 mmol, 1.00 equiv). The resulting mixture was then flushed and stirred for 48 hours under a hydrogen atmosphere at room temperature. The solid was filtered out. The filtrate was concentrated under vacuum. The residue was applied onto a silica gel column and eluted with methanol/DCM (18:1→2:1). The collected fraction was diluted with 500 ml of water, then adjusted to pH 12 with sodium hydroxide (6.07 g). The resulting mixture was concentrated under vacuum. The residue was dissolved in 2500 ml of tetrahydrofuran. The solid was filtered out. The filtrate was concentrated under vacuum. The residue was dissolved in DCM/MeOH (10:1), then added 13.6 g oxalic acid. The resulting mixture was stirred for 1.5 hours. The solid was collected by filtration. This resulted in 45 g (56%) of 4-(aminomethyl)-2,3-dihydro-1H-isoindol-1-one oxalate as a colorless solid. LC ESI: [M+H]+ m/z 252. $^1$H-NMR (400 MHz, D$_2$O): 4.25 (s, 2H), 4.55 (s, 2H), 7.58-7.62 (m, 1H), 7.66-7.69 (m, 1H), 7.78-7.80 (d, J=7.6 Hz, 1H).

Intermediate 111: 6-(aminomethyl)-2,3-dihydro-1H-isoindol-1-one oxalate

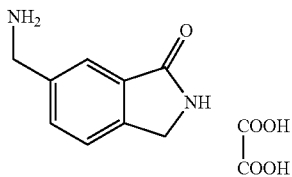

A 2000-mL 3-necked round-bottom flask purged and maintained with an inert atmosphere of nitrogen was added 2,2,2-trifluoroacetic acid (700 mL). This was followed by the addition of Raney Ni (17.0 g, 288 mmol, 0.91 equiv.) in portions. To this was added 3-oxoisoindoline-5-carbonitrile (50.0 g, 316 mmol, 1.00 equiv.) The resulting mixture was stirred for 48 hours at room temperature under a hydrogen atmosphere. The solid was filtered out. The filtrate was concentrated under vacuum. The residue was applied onto a silica gel column and eluted with methanol/CH$_2$Cl$_2$ (18:1→2:1). The collected fraction was diluted with 500 mL of water, then adjusted to pH 12 with sodium hydroxide (6.07 g). The resulting mixture was concentrated under vacuum. The residue was dissolved in 2500 mL of tetrahydrofuran. The solid was filtered out. The filtrate was concentrated under vacuum. The residue was dissolved in CH$_2$Cl$_2$/MeOH (10:1), then added 13.6 g of oxalic acid. The resulting mixture was stirred for 1.5 hours. The solid was collected by filtration. This resulted in 45 g (56% yield) of 6-(aminomethyl)-2,3-dihydro-1H-isoindol-1-one oxalate as a colorless solid. LC ESI: [M+H]+ m/z 163. $^1$H-NMR (400 MHz, D$_2$O): 4.23 (s, 2H), 4.46 (s, 2H), 7.63 (m, 2H), 7.75 (s, 1H).

Intermediate 112: 6-(aminomethyl)-2,3-dihydro-1H-isoindol-1-one

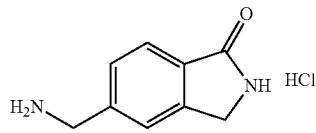 [SMILES: NCc1ccc2c(c1)CNC2=O ; Cl]

Step 1

A mixture of 6-bromo-2,3-dihydro-1H-isoindol-1-one (150 g, 0.71 mol), Pd(OAc)$_2$ (7.92 g, 0.036 mol), PPh$_3$ (27.9 g, 0.106 mol), Zn(CN)$_2$ (124.6 g, 1.065 mol) and 500 ml of DMF was stirred at 100° C. overnight. Cooled to rt, the solvent was removed and the residue was dissolved in EtOAc. The solid was removed and the filtrate was washed with brine, dried over Na$_2$SO$_4$, evaporated to afford the crude product, which was purified by flash column chromatography on silica gel to afford 3-oxo-2,3-dihydro-1H-isoindole-5-carbonitrile (87.5 g, 78% yield).

Step 2

To a mixture of the product of Step 1 (80 g, 0.51 mol), NiCl₂ (13 g, 0.10 mol), (Boc)₂O (222.4 g, 1.02 mol) and 800 ml of MeOH was added in portions NaBH₄ (136 g, 3.57 mol) at 0° C. and the mixture was stirred at rt overnight. After removal of the solvent the solid was dissolved in a mixture of citric acid (100 g) and 1 L of water. The aqueous layer was extracted with EtOAc three times, dried over Na₂SO₄, evaporated to afford crude product, which was purified by flash column chromatography on silica gel to afford text-butyl[(3-oxo-2,3-dihydro-1H-isoindol-5-yl)methyl]carbamate (100 g, 75% yield.).

Step 3

A mixture of the product of Step 2 (100 g, 0.38 mol) and HCl (dissolved in MeOH, 3 M, 500 ml) was stirred overnight. Removal of the solvent gave a solid which was washed with Et₂O and dried to afford 6-(aminomethyl)-2,3-dihydro-1H-isoindol-1-one (57 g, 76% yield). $^1$H-NMR (300 MHz, D₂O) δ: 7.69-7.67 (m, 1H), 7.52 (s, 1H), 7.45-7.43 (m, 1H), 4.39 (s, 2H), 4.17 (s, 2H).

Intermediate 113: 6-(aminomethyl)-3,4-dihydroquinolin-2(1H)-one hydrochloride

Step 1

To an ice cooled solution of 2-oxo-1,2,3,4-tetrahydroquinoline-6-carbonitrile (100 g) in dry MeOH (4000 ml) was added Boc₂O (253 g) and NiCl₂.6H₂O (27.7 g), followed by the careful addition of NaBH₄ (154.7 g), the mixture was stirred for 2 h at 0° C., and then the mixture was stirred overnight at RT. The solvent was evaporated and the residue was suspended in ethyl acetate (5000 ml), washed with 10% aqueous citric acid (5000 ml), followed by NaHCO₃ (5000 ml), the organic layer was dried over Na₂SO₄, filtered and evaporated. The residue was purified by column chromatography (PE:EA=2:1) to afford tert-butyl[(2-oxo-1,2,3,4-tetrahydroquinolin-6-yl)methyl]carbamate (65 g).

Step 2

500 ml of 3 N HCl in dioxane was added to the mixture of 40 g of the product of Step 1 in 500 ml of DCM and the solution was stirred overnight at RT. The solvent was evaporated, and the residue was washed with Et₂O (1000 ml) to afford 6-(aminomethyl)-3,4-dihydroquinolin-2(1H)-one hydrochloride (30 g, 95% yield). $^1$H-NMR (300 MHz, DMSO-d₆) δ: 10.17 (s, 1H), 7.28-7.23 (m, 2H), 6.88-6.86 (m, 1H), 3.90 (s, 2H), 2.89-2.84 (m, 2H), 2.53-2.42 (m, 2H).

Intermediate 114: azetidin-3-ylmethyl dimethylphosphinate TFA salt

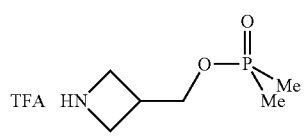

Step 1

Diisopropyl ethyl amine (124.28 g, 0.961 mol) was added dropwise to stirred solution of compound text-butyl 3-(hydroxymethyl)azetidine-1-carboxylate (150 g, 0.80 mol) in dichloromethane (500 mL) at 0° C. Dimethyl phosphinyl chloride (90 g, 0.80 mol) in dichloromethane (300 mL) was added to above reaction mixture over a period of 90 min at same temperature. Then, the reaction mixture was warmed to room temperature and continued stirring for 2 h. After completion of the reaction, the mixture was diluted with water (300 mL). The layers were separated. The organic layer was washed with brine (300 ml), dried over sodium sulfate and concentrated. The resultant concentrated product was purified via column chromatography on silica gel using chloroform/methanol (95/5) to afford tert-butyl 3-{[(dimethylphosphoryl)oxy]methyl}azetidine-1-carboxylate (146.8 g, 68.3%) as brown liquid.

Step 2

Trifluoroacetic acid (120 mL) was added dropwise to the product of Step 1 (80 g) in dichloromethane (120 mL) at 0° C. over a period of 30 min. The reaction mixture was stirred at room temperature for 2 h. After completion of reaction, reaction mixture was concentrated to remove excess trifluoroacetic acid under vacuum to afford azetidin-3-ylmethyl dimethylphosphinate TFA salt (90 g) as brown liquid. LC ESI: [M+H]⁺ m/z 164.2; HPLC purity; >97%. $^1$H NMR (400 MHz, CD₃OD) S: 1.62 (s, 3H), 1.65 (s, 3H), 3.23-3.27 (m, 1H), 4.02 (dd, J=7.7, 11.1 Hz, 2H), 4.11-4.19 (m, 4H).

Intermediate 116: 4-(propan-2-yl)-1,4-azaphosphinane 4-oxide oxalate salt

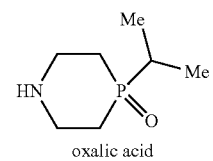

oxalic acid

Step 1

A 20 L four-necked round bottom flask fitted with an overhead stirrer and dropping funnel, flame dried and cooled in a stream of nitrogen, was charged with isopropyl phosphonic dichloride (350.0 g, 2173 mmol) in THF (5000 mL). The mixture was cool to −78° C. and vinyl magnesium bromide (5217 mL, 5217 mmol, 1M in THF) was added dropwise over 4 h. The reaction mixture was stirred at −78° C. for additional 30 minutes. After completion, the reaction mixture was poured into cold saturated aqueous NH₄Cl (3.5 L) and extracted with dichloromethane (4×1000 L). The organic layers were combined, washed with brine (2×15000 mL), dried over sodium sulfate and concentrated in vacuo to give diethenyl(propan-2-yl)phosphane oxide (250 g, 80%) as light-brown oil.

Step 2

A 20 L four-necked round bottom flask fitted with an overhead stirrer and reflux condenser, flame dried and cooled in a stream of nitrogen, was charged with the product of Step 1 (250 g, 1734 mmol), THF (2500 mL), water (2500 mL) and benzyl amine (297.3 g, 2774 mmol). The reaction mixture was heated at 85° C. for 16 h. After completion, THF was removed under reduced pressure. The aqueous layer was extracted with ether to remove the excess of benzyl amine and later with dichloromethane (2×2500 mL). The combined dichloromethane layers were washed with brine (2×1000 mL), dried over sodium sulfate and concentrated to give 1-benzyl-4-(propan-2-yl)-1,4-azaphosphinane 4-oxide (273 g, 63%) as brown oil.

Step 3

A 10 L auto clave was charged with the product of Step 2 (200.0 g, 796.8 mmol), ethanol (4000 mL) and oxalic acid dihydrate (100.4 g, 797.0 mmol) in water (1000 ml). To the reaction mixture was added palladium on carbon (10% w/w, 99.6 g) and stirred at room temperature under $H_2$ pressure (50 psi) for 16 h. After completion, the reaction mixture filtered and concentrated. Obtained solid was triturated with hot ethanol (250 mL) and kept in a cold room for 90 minutes, filtered, washed with diethylether and hexane to give 4-(propan-2-yl)-1,4-azaphosphinane 4-oxide oxalate salt (105 g, 53%) as a colorless solid. Mp 223-224° C. LC ESI: [M]$^+$ m/z 162. HPLC (ELSD method)=99.9%.

Intermediate 117: ethyl 7-oxospiro[2.5]octane-4-carboxylate

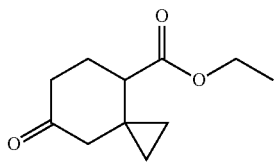

Step 1

2-(Trimethylsiloxy)-1,3-butadiene (900 mg, 6.33 mmol) and ethyl cyclopropylideneacetate (2195 mg, 17.40 mmol) were combined in toluene (3 ml) and heated to 130° C. for 14 h. The mixture was then allowed to cool to room temperature and concentrated in vacuo to yield ethyl 7-[(trimethylsilyl)oxy]spiro[2.5]oct-6-ene-4-carboxylate that was used without further purification in the subsequent reaction.

Step 2

The product of Step 1 (1.698 g, 6.33 mmol) was dissolved in methanol (6 ml). Potassium fluoride (0.404 g, 6.96 mmol) was added, and the solution was maintained at room temperature for 1 hour. The solution was concentrated in vacuo. Purification via silica gel column chromatography (0-25% EtOAc:Hexanes) afforded ethyl 7-oxospiro[2.5]octane-4-carboxylate (251 mg, 20%) as a colorless oil. $^1$H NMR (500 MHz, CDCl$_3$) δ 4.27-4.14 (m, 2H), 2.90 (d, J=14.9, 1H), 2.66 (ddd, J=5.6, 11.4, 16.8, 1H), 2.42-2.25 (m, 2H), 2.15-2.04 (m, 2H), 1.68 (d, J=14.9, 1H), 1.34-1.26 (m, 3H), 0.76-0.67 (m, 1H), 0.50-0.40 (m, 2H), 0.40-0.31 (m, 1H).

Intermediate 118: N-(3-{2-[amino(dicyclopropyl)methyl]-1,3-thiazol-5-yl}-5-methylphenyl)-4-(trifluoromethyl)pyrimidin-2-amine

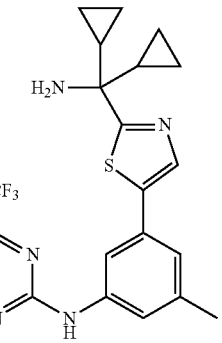

Step 1

A 20-mL microwave vial containing a solution of dicyclopropyl ketone (0.778 ml, 6.81 mmol), (R)-2-methylpropane-2-sulfinamide (0.825 g, 6.81 mmol), and titanium ethoxide (1.427 ml, 6.81 mmol) in tetrahydrofuran (13.5 mL) under argon was heated in a microwave for 5 minutes at 150° C. and then again at 160° C. for an additional 5 minutes. The reaction mixture was poured into brine (14 mL), the resulting slurry filtered through Celite, and the two resulting layers were separated. The aqueous layer was extracted with ethyl acetate, and the combined organic layers were dried over sodium sulfate, filtered, and concentrated. The crude material was purified by silica gel flash chromatography (10-50% ethyl acetate/hexanes) to afford (R)—N-(dicyclopropylmethylidene)-2-methylpropane-2-sulfinamide (0.325 g, 1.52 mmol, 22% yield). MS ESI: [M+H]$^+$ m/z 214.1.

Step 2

To a solution of lithium diisopropylamide (1.8 M, 2.12 mL, 3.81 mmol) in tetrahydrofuran (5 mL) at −78° C. was added a solution of N-[3-methyl-5-(1,3-thiazol-5-yl)phenyl]-4-(trifluoromethyl)pyrimidin-2-amine (Intermediate 24, 564 mg, 1.68 mmol) in tetrahydrofuran (5 mL) over 8 minutes. After 40 minutes, a solution of (R)—N-(dicyclopropylmethylidene)-2-methylpropane-2-sulfinamide (0.325 g, 1.52 mmol) in tetrahydrofuran (4 mL) was added all at once. After 90 minutes, acetic acid (0.275 mL) was added and the reaction mixture was partitioned between ethyl acetate (45 mL) and saturated aqueous sodium bicarbonate solution (20 mL). The layers were separated and the organic layer was washed with brine (20 mL), dried over sodium sulfate, filtered, and concentrated. Purification of the crude material using silica gel flash chromatography (ethyl acetate/hexanes) yielded (R)—N-{dicyclopropyl[5-(3-methyl-5-{[4-(trifluoromethyl)pyrimidin-2-yl]amino}phenyl)-1,3-thiazol-2-yl]methyl}-2-methylpropane-2-sulfinamide (638.6 mg, 1.16 mmol, 76% yield) as a yellow film. MS ESI: [MH] m/z 550.1.

Step 3

To a solution of (R)—N-{dicyclopropyl[5-(3-methyl-5-{[4-(trifluoromethyl)pyrimidin-2-yl]amino}phenyl)-1,3-thiazol-2-yl]methyl}-2-methylpropane-2-sulfinamide (125 mg, 0.227 mmol) in methanol (2 mL) was added hydrochloric acid (4 M in 1,4-dioxane, 0.227 mL, 0.910 mmol). After 45 minutes, the reaction mixture was partitioned between ethyl acetate (20 mL) and saturated aqueous sodium bicarbonate solution (20 mL). The layers were separated and the organic layer was washed with brine, dried over sodium sulfate, filtered, and concentrated to afford N-(3-{2-[amino(dicyclopropyl)methyl]-1,3-thiazol-5-yl}-5-methylphenyl)-4-(trifluoromethyl)pyrimidin-2-amine (100 mg, 0.224 mmol, 99% yield) which was used without purification. MS ESI: [M+H]$^+$ m/z 429.0.

Intermediate 119: Ethyl 4-[5-(3-{(tert-butoxycarbonyl)[4-(trifluoromethyl)pyrimidin-2-yl]amino}-5-methylphenyl)-1,3-thiazol-2-yl]-4-hydroxycyclohexanecarboxylate

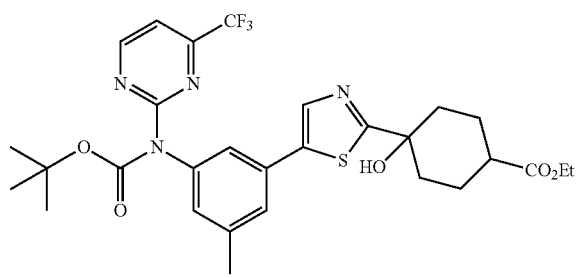 [SMILES: CCOC(=O)C1CCC(O)(c2ncc(-c3cc(C)cc(N(C(=O)OC(C)(C)C)c4nccc(C(F)(F)F)n4)c3)s2)CC1]

To ethyl 4-hydroxy-4-[5-(3-methyl-5-{[4-(trifluoromethyl)pyrimidin-2-yl]amino}phenyl)-1,3-thiazol-2-yl]cyclohexanecarboxylate (Example 32, 0.15 g, 0.29 mmol) in THF (1.4 mL) was added di-tert-butyl-dicarbonate (0.069 mg, 0.32 mmol), 4-dimethylaminopyridine (0.04 g, 0.03 mmol), and triethylamine (0.043 g, 0.43 mmol). The reaction was heated at 50° C. overnight. The reaction was cooled, diluted with dichloromethane and washed with water. The organic layer was extracted two more times with dichloromethane and the organic layers were combined, dried over magnesium sulfate, filtered and concentrated. Purification by silica gel chromatography was used to give ethyl 4-[5-(3-{(tert-butoxycarbonyl)[4-(trifluoromethyl)-pyrimidin-2-yl]amino}-5-methylphenyl)-1,3-thiazol-2-yl]-4-hydroxycyclohexanecarboxylate (0.15 mg, 85% yield). MS ESI: [M+H]$^+$ m/z 607.2. $^1$H NMR (500 MHz, CDCl$_3$) δ 8.81 (d, J=5.5, 1H), 7.78 (s, 1H), 7.39-7.29 (m, 1H), 7.27 (d, J=5.6, 1H), 7.19 (s, 7.02 (s, 1H), 4.31-3.95 (m, 2H), 2.64-2.49 (m, 1H), 2.37 (s, 3H), 2.30-2.18 (m, 1H), 2.13-1.87 (m, 6H), 1.87-1.74 (m, 1H), 1.49 (s, 9H), 1.26-1.23 (m, 4H). rhSYK activity=+

Example 1

1-[5-(2-fluoro-5-{[4-(trifluoromethyl)pyrimidin-2-yl]amino}phenyl)-1,3-thiazol-2-yl]cyclobutanol

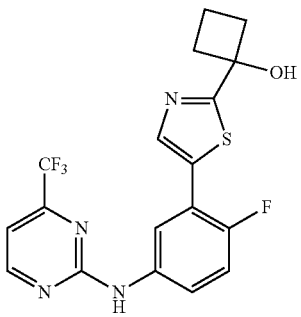 [SMILES: OC1(c2ncc(-c3cc(Nc4nccc(C(F)(F)F)n4)ccc3F)s2)CCC1]

Step 1

To 3-bromo-4-fluoroaniline (0.76 g, 4.0 mmol) and 2-chloro-4-(trifluoromethyl)pyrimidine (0.73 g, 4.0 mmol) was added dioxane (13.33 mL) and p-TSA (0.761 g, 4.0 mmol). The reaction was sealed and was heated at reflux overnight. The reaction was cooled to room temperature and was diluted with ethyl acetate, washed with saturated aqueous NaHCO$_3$, and the organic was dried over sodium sulfate and filtered before concentration. The crude product was purified by flash chromatography (25:75 ethyl acetate:hexanes) to afford N-(3-bromo-4-fluorophenyl)-4-(trifluoromethyl)pyrimidin-2-amine (1.2 g, 3.57 mmol, 89%) as a pale yellowish solid. $^1$H NMR (500 MHz, CDCl$_3$): δ 8.68 (d, J=4.9 Hz, 1H); 7.99-7.96 (m, 1H); 7.51 (d, J=8.4 Hz, 1H); 7.29 (s, 1H); 7.14 (t, J=8.5 Hz, 1H); 7.10 (d, J=4.9 Hz, 1H). rhSYK activity=+

Step 2

To the product of Step 1 (0.336 g, 1 mmol) was added bis(pinacolato)diboron (0.267 g, 1.05 mmol), potassium acetate (0.294 mmol, 3.0 mmol), PdCl$_2$(dppf)-dichloromethane adduct (0.082 g, 0.1 mmol) and DMSO (3.33 mL). The reaction vessel was sealed and heated at 100° C. until the reaction was complete (by TLC analysis). The reaction was cooled to room temperature, diluted with ethyl acetate and washed with water (3 times), and dried over sodium sulfate. After filtration and solvent evaporation the crude product was purified by flash chromatography (ethyl acetate in hexanes) to afford N-[4-fluoro-3-(4,4,5,5-tetramethyl-1,3,2-dioxaborolan-2-yl)phenyl]-4-(trifluoromethyl)pyrimidin-2-amine (383 mg, 1.0 mmol, quant. yield).

Step 3

To a solution of the product of Step 2 (383 mg, 1.0 mmol) in DMF (2 mL) and aqueous sodium carbonate (2 M, 1.5 mL, 3.0 mmol) in a microwave vial was added Intermediate 1 (234 mg, 1.0 mmol), and PdCl$_2$(dppf)-dichloromethane adduct (82 mg, 0.1 mmol) under dry nitrogen. The vial was sealed and the reaction was heated in a microwave at 85° C. for 2 hours. The reaction was cooled to room temperature, diluted with ethyl acetate, washed with water, then brine and was dried over sodium sulfate. The organic was concentrated after filtration and was purified by flash chromatography (25:75 ethyl acetate:hexanes) to afford 1-[5-(2-fluoro-5-{[4-(trifluoromethyl)pyrimidin-2-yl]amino}phenyl)-1,3-thiazol-2-yl]cy-clobutanol as an off-white foamy solid (102 mg, 0.249 mmol, 24.9%). $^{1}$H NMR (500 MHz, CDCl$_{3}$): δ 8.66 (d, J=4.9 Hz, 1H); 8.07 (s, 1H); 8.03 (d, J=6.1 Hz, 1H); 7.82 (s, 1H); 7.50 (dt, J=8.8, 3.4 Hz, 1H); 7.16 (t, J=9.6 Hz, 1H); 7.07 (d, J=4.9 Hz, 1H); 4.07 (s, 1H); 2.77-2.70 (m, 2H); 2.59-2.49 (m, 2H); 2.13-1.98 (m, 2H). rhSYK activity=++

The following examples were prepared in an analogous manner of that described in Example 1 using commercially available or known functionalized bromoanilines in step 1. Compounds were isolated as the free base.

TABLE 1

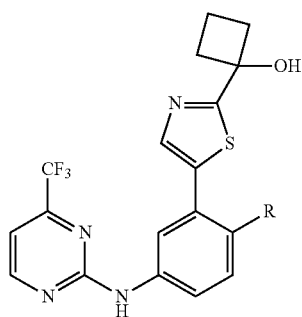

| Example | R | rhSYK Activity | [M + H] + Obs'd |
|---|---|---|---|
| 1-1 | —OCH$_{3}$ | +++ | 423.1 |
| 1-2 | Cl | ++ | 427.1 |
| 1-3 | —OCF$_{3}$ | ++ | 477.1 |
| 1-4 | —OCH$_{2}$Ph | ++ | 499.1 |
| 1-5 | —OH | +++ | 409.1 |
| 1-6 | —CH$_{3}$ | +++ | 407.1 |

Example 2

1-{5-[3-(trifluoromethyl)-5-{[4-(trifluoromethyl)pyrimidin-2-yl]amino}phenyl]-1,3-thiazol-2-yl}cyclobutanol

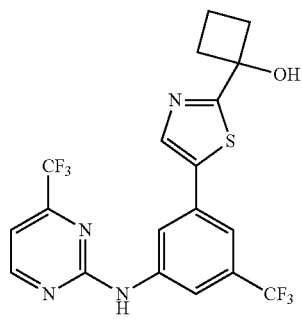 [SMILES: OC1(c2ncc(-c3cc(Nc4nccc(C(F)(F)F)n4)cc(C(F)(F)F)c3)s2)CCC1]

A solution of palladium(II) acetate (2.55 mg, 0.011 mmol) and butyldi-1-adamantyl phosphine (CataCXium A, 8.14 mg, 0.023 mmol) in THF (1.42 mL) was stirred for 10 min while nitrogen was bubbled through gently. Intermediate 13 (100 mg, 0.189 mmol), Intermediate 1 (51.0 mg, 0.218 mmol), potassium fluoride (33.0 mg, 0.568 mmol) and water (473 μl) were added. The tube was sealed (screw cap) and heated overnight at 85° C. The reaction was cooled to room temperature and diluted with ethyl acetate. After decanting the solids and extraction with ethyl acetate, the organic layer was washed with brine and dried over MgSO$_{4}$. Filtration and subsequent solvent evaporation gave a residue which was purified by chromatography on silica gel (5-50% ethyl acetate in hexanes) to give 75 mg (86%) of 1-{5-[3-(trifluoromethyl)-5-{[4-(trifluoromethyl)pyrimidin-2-yl]amino}phenyl]-1,3-thiazol-2-yl}cyclobutanol as a grey solid. MS ESI [M+H]$^{+}$ 461.1. $^{1}$H NMR (400 MHz, DMSO-d$_{6}$): δ 10.67 (s, 1H); 8.93 (d, J=4.9 Hz, 1H); 8.33 (s, 1H); 8.24 (s, 1H); 8.17 (s, 1H); 7.68 (s, 1H); 7.41 (d, J=4.9 Hz, 1H); 6.62 (s, 1H); 2.59-2.48 (m, 2H); 2.42-2.31 (m, 2H); 1.98-1.87 (m, 2H). rhSYK activity=++

Example 3

1-[5-(3-chloro-5-{[4-(trifluoromethyl)pyrimidin-2-yl]amino}phenyl)-1,3-thiazol-2-yl]cyclobutanol

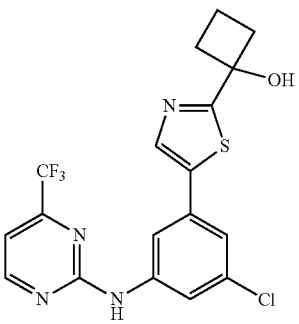 [SMILES: OC1(c2ncc(-c3cc(Cl)cc(Nc4nccc(C(F)(F)F)n4)c3)s2)CCC1]

Step 1

A 20 mL microwave vial was charged with a stir bar, 1-bromo-3-chloro-5-nitrobenzene (1.182 g, 5.0 mmol), bis (pinacolato)diboron (1.397 mg, 5.5 mmol), PdCl$_{2}$ (dppf) dichloromethane adduct (204 mg, 0.25 mmol), potassium acetate (1.472 g, 15.0 mmol) and DMSO (10.00 mL). The vial was sealed and heated in a microwave at 120° C. for 30 minutes. The reaction mixture was diluted with ethyl acetate and washed twice with water, brine, and then dried over Na₂SO₄ to give 2,3-dimethylbutane-2,3-diol 2-(3-chloro-5-nitrophenyl)-4,4,5,5-tetramethyl-1,3,2-dioxaborolane (1:1) (1.7 g, 85%) after filtration and solvent evaporation. The crude product mixture was used as is in the next reaction.

Step 2

The product of Step 1 (1.6 g, 3.98 mmol), Intermediate 1 (839 mg, 3.58 mmol), PdCl₂ (dppf)-dichloromethane adduct (163 mg, 0.199 mmol), sodium carbonate (2M in water) (5.97 mL, 11.95 mmol), and DMF (39.8 mL) were heated at 100° C. for 2 hours under nitrogen. The reaction mixture was diluted with ethyl acetate and water, the solids were filtered and the organic fraction was washed with water, brine and dried over Na₂SO₄. Filtration and solvent evaporation gave a residue which was further purified by column chromatography on silica gel, eluting with ethyl acetate/hexane with a gradient 30-50% to afford 1-[5-(3-chloro-5-nitrophenyl)-1,3-thiazol-2-yl]cyclobutanol (610 mg, 49.3%).

Step 3

Water (2.617 mL) and ethanol (5.235 mL) were added to the product of Step 2 (610 mg, 49.3%), followed by ammonium chloride (52.5 mg, 0.981 mmol) and then iron (548 mg, 9.81 mmol) and the reaction was heated to 80° C. for 1 hour. The reaction mixture was filtered and diluted with ethyl acetate before washing with water, filtering off solids and drying over Na₂SO₄. Filtration and solvent evaporation gave a residue which was further purified by column chromatography on silica gel, eluting with ethyl acetate/hexane with a gradient 40-50% to afford 1-[5-(3-amino-5-chlorophenyl)-1,3-thiazol-2-yl]cyclobutanol (460 mg, 83%).

Step 4

The product of Step 3 (460 mg, 1.720 mmol), 2-chloro-4-(trifluoromethyl)pyrimidine (314 mg, 1.638 mmol), Xantphos (284 mg, 0.492 mmol), palladium (II) acetate (73.6 mg, 0.328 mmol), cesium carbonate (1.068 g, 3.28 mmol) and dioxane (12.3 mL) were heated at 90° C. for 90 minutes. The reaction mixture was diluted with ethyl acetate, washed with water and dried over Na₂SO₄. Filtration and solvent evaporation gave a residue which was further purified by column chromatography on silica gel, eluting with 40% ethyl acetate in hexane to afford 1-[5-(3-chloro-5-{[4-(trifluoromethyl)pyrimidin-2-yl]amino}phenyl)-1,3-thiazol-2-yl]cyclobutanol as a brown solid (390 mg, 55.8%). ¹H NMR (500 MHz, CDCl₃): δ 8.71 (d, J=4.7 Hz, 1H); 7.92 (s, 1H); 7.85 (s, 1H); 7.78 (s, 1H); 7.69 (s, 1H); 7.25 (s, 1H); 7.13 (d, J=4.8 Hz, 1H); 3.81 (s, 1H); 2.73 (s, 2H); 2.58-2.47 (m, 2H); 2.13-1.97 (m, 2H) MS APCI: [M+H]⁺ m/z 427.1. rhSYK activity=++

Example 4

2-[5-(3-methyl-5-{[4-(trifluoromethyl)pyrimidin-2-yl]amino}phenyl)-1,3-thiazol-2-yl]propan-2-ol

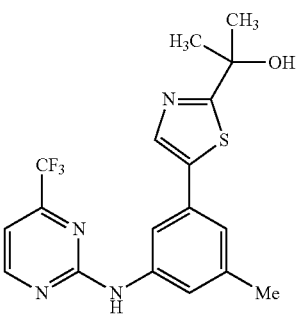 [SMILES: Cc1cc(Nc2nccc(C(F)(F)F)n2)cc(-c2cnc(C(C)(C)O)s2)c1]

INTERMEDIATE 4 (100 mg, 0.297 mmol) in THF (1.5 mL) was added slowly to LDA (496 μL, 0.892 mmol) precooled to −78° C. over 5 min with stirring. The reaction mixture was left to stir for 30 min and treated with acetone (32.7 pt, 0.446 mmol). After 1 h, the reaction mixture was treated with 5 mL sat NH₄Cl and allowed to warm to room temperature. The mixture was extracted with EtOAc, and the organic layer washed with saturated aqueous NaHCO₃. The organic layer was dried over anhydrous Na₂SO₄, filtered, concentrated, and purified by flash chromatography to give 2-[5-(3-methyl-5-{[4-(trifluoromethyl)pyrimidin-2-yl]amino}phenyl)-1,3-thiazol-2-yl]propan-2-ol (95 mg, 0.241 mmol, 81% yield) as a colorless oil. APCI: [M+H]⁺ m/z 395.0. ¹H NMR (500 MHz, DMSO-d₆) δ 10.25 (s, 8.83 (d, J=4.9, 1H), 7.95 (s, 1H), 7.92 (s, 1H), 7.45 (s, 1H), 7.28 (d, J=4.9, 1H), 7.14 (s, 1H), 6.03 (s, 1H), 2.31 (s, 3H), 1.51 (s, 6H). rhSYK activity=+++

The following compounds were prepared in an analogous manner to that described in Example 4. Entries in this and all subsequent Tables without explicit reported stereochemistry (absolute or relative) are either single isomers of unknown configuration or a mixture of isomers. Indicators of relative stereochemistry (cis or trans) refer to the relative relationship of the corresponding substituents with the highest CIP priority respectively. In the Table below, 2,2-dimethyl-5-[5-(3-methyl-5-{[4-(trifluoromethyl)pyrimidin-2-yl]amino}phenyl)-1,3-thiazol-2-yl]-1,3-dioxan-5-ol and 2,2-dimethyl-5-(5-[3-methyl-5-[(4-methylpyrimidin-2-yl)amino]phenyl]-1,3-thiazol-2-yl)-1,3-dioxan-5-ol were treated with HCl to afford the corresponding triols, and 3-(1H-imidazol-4-yl)-1-[5-(3-methyl-5-{[4-(trifluoromethyl)pyrimidin-2-yl]amino}phenyl)-1,3-thiazol-2-yl]propan-1-ol was obtained by treating the corresponding 1-trityl-imidazole adduct with AcOH.

TABLE 4A

[Structure: pyrimidine (with R¹ at position 5) linked via NH to a phenyl ring (with R² substituent), which is connected to a thiazole bearing a C(R³)(R⁴)OH group]

| Ex. | R¹ | R² | R³/R⁴ | rhSYK Activity | [M + H]+ Obs'd | Form(s) |
|---|---|---|---|---|---|---|
| 4A-1 | 4-CF₃ | H | CH₃/CH₃ | +++ | 381.0 | Free Base |
| 4A-2 | 4-CF₃ | H | CH₃/CF₃ | +++ | 435.0 | Free Base |
| 4A-3 | 4-CF₃ | H | CF₃/CF₃ | +++ | 489.0 | Free Base |
| 4A-4 | 4-CF₃ | Br | CH₃/CH₃ | +++ | 458.9 | Free Base |
| 4A-5 | 4-CF₃ | H | H/cPr | +++ | 393.0 | Free Base |
| 4A-6 | 4-CF₃ | H | CH₃/t-Bu | ++ | 423.3 | Free Base |
| 4A-7 | 4-CF₃ | H | CHF₂/Ph | ++ | 479.1 | Free Base |
| 4A-8 | 4-CF₃ | H | H/—C(CH₃)₂CH₂N(CH₃)₂ | ++ | 452.2 | Free Base |
| 4A-9 | 4-CF₃ | H | —CH₂CH₃/CF₃ | +++ | 449.1 | Free Base |
| 4A-10 | 4-CF₃ | H | CH₃/CHF₂ | +++ | 417.1 | Free Base |
| 4A-11 | 4-CF₃ | H | CF₃/cHex | + | 503.2 | Free Base |
| 4A-12 | 4-CF₃ | H | CH₃/1-PhSO₂-3-pyrrolyl | ++ | 572.3 | Free Base |
| 4A-13 | 4-CF₃ | H | CHF₂/5-Br-2-pyridyl | ++ | 557.9 | Free Base |
| 4A-14 | 4-CF₃ | H | CH₃/—CH₂N(CH₃)₂ | ++ | 424.3 | Free Base |
| 4A-15 | 4-CF₃ | H | H/cPen | ++ | 421.3 | Free Base |
| 4A-16 | 4-CF₃ | H | CH₃/1-Me-3-pyrrolyl | +++ | 428.3 (M − H₂O + H) | Free Base |
| 4A-17 | 4-CF₃ | H | H/3-furyl | +++ | 419.3 | Free Base |
| 4A-18 | 4-CF₃ | H | H/3-pyridyl | ++ | 430.3 | Free Base |
| 4A-19 | 4-CF₃ | H | H/1-Me-5-pyrazolyl | ++ | 433.3 | Free Base |
| 4A-20 | 4-CF₃ | H | H/1-iPr-4-pyrazolyl | ++ | 461.1 | Free Base |
| 4A-21 | 4-CF₃ | H | CH₃/3-pyridyl | +++ | 444.3 | Free Base |
| 4A-22 | 4-CF₃ | H | CH₃/2-pyrazinyl | +++ | 445.3 | Free Base |
| 4A-23 | 4-CF₃ | H | CH₃/cBu | +++ | 421.3 | Free Base |
| 4A-24 | 4-CF₃ | H | iPr/iPr | ++ | 437.2 | Free Base |
| 4A-25 | 4-CF₃ | H | CH₃/—CH₂CH₂OC(O)CH₃ | ++ | 453.3 | Free Base |
| 4A-26 | 4-CF₃ | H | CH₃/1-CO₂Et-cPr | ++ | 479.0 | Free Base |
| 4A-27 | 4-CF₃ | H | 3-pyridyl/1,3,4-oxadiazol-2-yl | ++ | 498.1 | Free Base |
| 4A-28 | 4-CF₃ | H | Et/C(O)Et | ++ | 437.1 | Free Base |
| 4A-29 | 4-CF₃ | H | CH₃/5-SO₂CH₃-2-thienyl | ++ | 527.0 | Free Base |
| 4A-30 | 4-CF₃ | H | 2-pyridyl/2-thiazolyl | ++ | 513.0 | Free Base |
| 4A-31 | 4-CF₃ | H | CH₃/n-C₃F₇ | + | 535.0 | Free Base |
| 4A-32 | 4-CF₃ | CH₃ | CH₃/—CH₂OCH₃ | +++ | 425.0 | Free Base |
| 4A-33 | 4-CF₃ | CH₃ | CH₃/—CH₂F | +++ | 413.0 | Free Base |
| 4A-34 | 4-CF₃ | CH₃ | —CH₂F/—CH₂F | +++ | 431.0 | Free Base |
| 4A-35 | 4-CF₃ | CH₃ | CH₃/1-Me-1,2,4-triazol-5-yl | +++ | 461.7 | Free Base |
| 4A-36 | 4-CF₃ | CH₃ | CH₃/5-Me-1,2,4-oxadiazol-3-yl | +++ | 462.7 | Free Base |
| 4A-37 | 4-CF₃ | CH₃ | cPr/cPr | +++ | 447.1 | Free Base |
| 4A-38 | 4-CF₃ | CH₃ | —CH₂OH/—CH₂OH | +++ | 427.0 | Free Base |
| 4A-39 | 4-CH₃ | CH₃ | —CH₂OH/—CH₂OH | +++ | 373.1 | Free Base |
| 4A-40 | 4-CF₃ | CH₃ | H/—CH₂CH₂-4-imidazolyl | +++ | 461.0 | Free Base |
| 4A-41 | 4-CF₃ | CH₃ | H/CH₂CH₂CN | +++ | 420.1 | Free Base |
| 4A-42 | 4-CF₃ | CH₃ | H/CH₂CH₂CH=CH₂ | +++ | 421.1 | Free Base |
| 4A-43 | 4-CF₃ | CH₃ | CH₃/CH₂CH₂CH=CH₂ | +++ | 435.1 | Free Base |
| 4A-44 | 4-CF₃ | CH₃ | H/CONH₂ | +++ | 438.1 | Free Base |
| 4A-45 | 4-CF₃ | CH₃ | CH₃/CH₂CH(NH₂)CH₃ | +++ | 438.1 | TFA Salt |
| 4A-46 | 4-CF₃ | CH₃ | CH₃/(CH₂)₃NH₂ | +++ | 438.1 | TFA Salt |
| 4A-47 | 4-CF₃ | CH₃ | CH₃/(CH₂)₃CO₂H | +++ | 467.0 | Formate Salt |
| 4A-48 | 4-CF₃ | CH₃ | CH₃/C(CH₃)₂CO₂CH₃ | +++ | 481.1 | Free Base |
| 4A-49 | 4-CF₃ | CH₃ | iPr/2-pyridyl | ++ | 486 | Formate Salt |
| 4A-50 | 4-CF₃ | CH₃ | CH₃/3-OCH₃-2-thienyl | +++ | 493 | Formate Salt |
| 4A-51 | 4-CF₃ | CH₃ | CH₃/4-C(O)CH₃—Ph | +++ | 499.1 | Free Base |
| 4A-52 | 4-CF₃ | CH₃ | H/4-CO₂CH₃—Ph | ++ | 501.0 | Free Base |
| 4A-53 | 4-CF₃ | CH₃ | CH₃/3-CO₂H—Ph | +++ | 501.1 | Free Base |
| 4A-54 | 4-CF₃ | CH₃ | CH₃/3-CO₂H—Ph (enantiomer 1) | +++ | 501.1 | Free Base |

TABLE 4A-continued

| Ex. | R¹ | R² | R³/R⁴ | rhSYK Activity | [M + H]+ Obs'd | Form(s) |
|---|---|---|---|---|---|---|
| 4A-55 | 4-CF₃ | CH₃ | CH₃/3-CO₂H—Ph (enantiomer 2) | +++ | 501.1 | Free Base |
| 4A-56 | 4-CF₃ | CH₃ | CH₃/4-NO₂—Ph | ++ | 502 | Free Base |
| 4A-57 | 4-CF₃ | CH₃ | CH₃/4-SCH₃—Ph | ++ | 503.1 | TFA Salt |
| 4A-58 | 4-CF₃ | CH₃ | CH₃/4-CH₂CO₂H—Ph | +++ | 515.1 | Free Base |
| 4A-59 | 4-CF₃ | CH₃ | CH₃/4-CH₂CO₂H—Ph (enantiomer 1) | +++ | 515.0 | Free Base |
| 4A-60 | 4-CF₃ | CH₃ | CH₃/4-CH₂CO₂H—Ph (enantiomer 2) | +++ | 515.1 | Free Base |
| 4A-61 | 4-CF₃ | CH₃ | CH₃/ CH₂-(4-CO₂H)—Ph | +++, +++ | 515.1 | Free Base, Formate Salt |
| 4A-62 | 4-CF₃ | CH₃ | CH(OCH₃)₂/2-pyridyl | +++ | 518 | Formate Salt |
| 4A-63 | 4-CF₃ | CH₃ | CH₃/4-CH₂CO₂H-2-thienyl | +++ | 521.0 | Ammonium Salt |
| 4A-64 | 4-CF₃ | CH₃ | CH₃/4-CO₂H-3-OCH₃—Ph | +++ | 531.1 | Free Base |
| 4A-65 | 4-CF₃ | CH₃ | CH₃/4-CO₂H-3-OCH₃—Ph (enantiomer 1) | +++ | 531.1 | Free Base |
| 4A-66 | 4-CF₃ | CH₃ | CH₃/4-CO₂H-3-OCH₃—Ph (enantiomer 2) | +++ | 531.1 | Free Base |
| 4A-67 | 4-CF₃ | CH₃ | CH₃/3-OCH₂CO₂H—Ph | +++ | 531.0 | Ammonium Salt |
| 4A-68 | 4-CF₃ | CH₃ | CH₃/6-Br-3-pyridyl (enantiomer 1) | +++ | 536.0 | Free Base |
| 4A-69 | 4-CF₃ | CH₃ | CH₃/6-Br-3-pyridyl (enantiomer 2) | +++ | 536.0 | Free Base |
| 4A-70 | 4-CF₃ | CH₃ | CH₃/6-Br-3-pyridyl | +++ | 536.0 | Free Base |
| 4A-71 | 4-CF₃ | CH₃ | CH₃/5-Br-3-pyridyl | +++ | 536.0 | Free Base |
| 4A-72 | 4-CF₃ | CH₃ | CH₃/4-CO₂CH₃-3-OCH₃—Ph | ++ | 545.1 | Free Base |
| 4A-73 | 4-CF₃ | CH₃ | CH₃/4-SO₂N(CH₃)₂—Ph | ++ | 564.1 | TFA Salt |
| 4A-74 | 4-CF₃ | CH₃ | CH₃/ 3-methyl-2-CO₂H-thieno[2,3-b]pyridin-5-yl | +++ | 572.0 | Ammonium Salt |
| 4A-75 | 4-CF₃ | CH₃ | CH₃/3-(3-CO₂H—Ph)—Ph | +++ | 577.0 | Formate Salt |
| 4A-76 | 4-CF₃ | CH₃ | CH₃/CH₂-(4-CO₂H)—Ph | +++ | 577.1 | Formate Salt |
| 4A-77 | 4-CF₃ | CH₃ | CH₃/CH₂-(4-SO₂NH—C(O)CH₃)—Ph | +++, +++ | 578.1 | Free Base, TFA Salt |
| 4A-78 | 4-CF₃ | CH₃ | CH₃/ 4-(4-CO₂H-2-oxopyrrolidin-1-yl)—Ph | +++ | 584.1 | Ammonium Salt |
| 4A-79 | 4-OCH₃ | CH₃ | CH₃/4-CO₂H—Ph | +++ | 463.1 | Free Base |

TABLE 4B

| Ex. | R¹ | R² | R³ | rhSYK Activity | [M + H]+ Obs'd | Form(s) |
|---|---|---|---|---|---|---|
| 4B-1 | CF₃ | CH₃ | 1-OH-cBu | +++ | 407.1 | Free Base |
| 4B-2 | CF₃ | H | 1-OH-2-CH₃-cPen | +++ | 421.3 | Free Base |
| 4B-3 | CF₃ | H | N-CO₂Et (bicyclic with OH) | ++ | 520.3 | Free Base |
| 4B-4 | CF₃ | H | C(O)-3-furyl | ++ | 417.3 | Free Base |
| 4B-5 | CF₃ | H | C(O)-3-isoxazolyl | +++ | 418.2 | Free Base |
| 4B-6 | CF₃ | H | 1-OH-2-(CH₂CH₂CN)-cHex | ++ | 474.2 | Free Base |
| 4B-7 | CF₃ | H | (bicyclic ketone with OH) | ++ | 461.1 | Free Base |
| 4B-8 | CF₃ | H | (tetramethyl thiopyran with OH) | + | 495.1 | Free Base |
| 4B-9 | CF₃ | H | (N-Bn oxa-aza bicyclic with OH) | + | 554.1 | Free Base |
| 4B-10 | CF₃ | H | (azabicyclic with OH) | ++ | 434.1 | Free Base |
| 4B-11 | CF₃ | H | (HO-oxetane-cyclobutane) | +++ | 395.0 | Free Base |
| 4B-12 | CF₃ | CH₃ | (HO-oxetane-cyclobutane) | +++ | 409.1 | Free Base |

TABLE 4B-continued

| Ex. | R¹ | R² | R³ | rhSYK Activity | [M + H]+ Obs'd | Form(s) |
|---|---|---|---|---|---|---|
| 4B-13 | $CF_3$ | $CH_3$ | 4-hydroxy-tetrahydropyran-4-yl | +++ | 437.1 | Free Base |
| 4B-14 | $CF_3$ | $CH_3$ | 5-hydroxy-2,2-dimethyl-1,3-dioxan-5-yl | +++ | 467.1 | Free Base |
| 4B-15 | $CF_3$ | $CH_3$ | 8-hydroxy-1,4-dioxaspiro[4.5]dec-8-yl | +++ | 493.1 | Free Base |
| 4B-16 | $OCH_3$ | $CH_3$ | 8-hydroxy-1,4-dioxaspiro[4.5]dec-8-yl | +++ | 455.2 | Free Base |
| 4B-17 | $CH_3$ | $CH_3$ | hydroxy-azaadamantyl | ++ | 434.2 | TFA Salt |
| 4B-18 | $CF_3$ | $CH_3$ | hydroxy-bicyclo[4.1.0]heptyl | +++ | 447 | Formate Salt |
| 4B-19 | $CF_3$ | $CH_3$ | hydroxy-azabicyclo | +++ | 478.2 | TFA Salt |
| 4B-20 | $CF_3$ | $CH_3$ | hydroxy-oxo-bicyclo[3.3.0] | +++ | 475.1 | TFA Salt |

TABLE 4B-continued

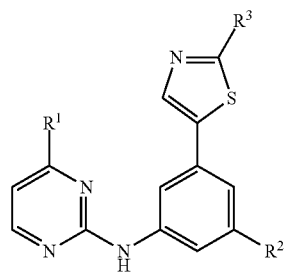

| Ex. | R¹ | R² | R³ | rhSYK Activity | [M + H]+ Obs'd | Form(s) |
|---|---|---|---|---|---|---|
| 4B-21 | $CH_3$ | $CH_3$ | (decalin with CO₂H and OH) | +++ | 479.2 | TFA Salt |
| 4B-22 | $CH_3$ | $CH_3$ | (decalin with CO₂H and OH) (isomer 1) | +++ | 479.2 | Free Base |
| 4B-23 | $CH_3$ | $CH_3$ | (decalin with CO₂H and OH) (isomer 2) | +++ | 479.2 | Free Base |
| 4B-24 | $CF_3$ | $CH_3$ | (spirocyclohexane-pyrrolidinone with OH) (cis) | +++ | 504.1 | Free Base |
| 4B-25 | $CF_3$ | $CH_3$ | (spirocyclohexane-pyrrolidinone with OH) (trans) | +++ | 504.1 | Free Base |
| 4B-26 | $CF_3$ | $CH_3$ | (hydrindanone with 2 OH and $CH_3$) | +++ | 519.2 | TFA Salt |

TABLE 4B-continued

| Ex. | R¹ | R² | R³ | rhSYK Activity | [M + H]+ Obs'd | Form(s) |
|---|---|---|---|---|---|---|
| 4B-27 | $CF_3$ | $CH_3$ | (bicyclic diol with $CO_2H$) | +++ | 519.1 | Free Base |
| 4B-28 | $CF_3$ | $CH_3$ | (dioxolane cyclohexane with HO, $H_3C$, $CH_3$) | ++ | 521.1 | Free Base |
| 4B-29 | $CH_3$ | $CH_3$ | (adamantane diol) | +++ | 449.2 | TFA Salt |
| 4B-30 | $CH_3$ | $CH_3$ | (adamantane with HO, $CO_2H$) (isomer 1) | +++, +++ | 477.2 | TFA Salt, Ammonium Salt |
| 4B-31 | $CH_3$ | $CH_3$ | (adamantane with HO, $CO_2H$) (isomer 2) | +++, +++ | 477.2 | TFA Salt, Ammonium Salt |
| 4B-32 | $CH_3$ | $CH_3$ | (bicyclic with $H_3C$, $CH_3$, $CH_3$, HO, $CO_2H$) (isomer 1) | +++ | 479.2 | TFA Salt |

TABLE 4B-continued

| Ex. | R¹ | R² | R³ | rhSYK Activity | [M + H]+ Obs'd | Form(s) |
|---|---|---|---|---|---|---|
| 4B-33 | CH₃ | CH₃ | (isomer 2) | +++ | 479.2 | TFA Salt |
| 4B-34 | CH₃ | CH₃ | (isomer 3) | +++ | 479.2 | Free Base |
| 4B-35 | CH₃ | CH₃ | (isomer 4) | +++ | 479.2 | Free Base |
| 4B-36 | CF₃ | CH₃ |  | +++ | 489.1 | TFA Salt |
| 4B-37 | CF₃ | CH₃ | (isomer 1) | +++ | 489.1 | Free Base |
| 4B-38 | CF₃ | CH₃ | (isomer 2) | +++ | 489.1 | Free Base |
| 4B-39 | CF₃ | CH₃ | (isomer 3) | +++ | 489.1 | Free Base |

TABLE 4B-continued

| Ex. | R¹ | R² | R³ | rhSYK Activity | [M + H]+ Obs'd | Form(s) |
|---|---|---|---|---|---|---|
| 4B-40 | $CF_3$ | $CH_3$ | (isomer 4) | +++ | 489.1 | TFA Salt |
| 4B-41 | $CF_3$ | $CH_3$ |  | +++ | 491.1 | TFA Salt |
| 4B-42 | $CF_3$ | $CH_3$ |  | +++ | 503.2 | TFA Salt |
| 4B-43 | $CF_3$ | $CH_3$ |  | +++ | 531.2 | TFA Salt |
| 4B-44 | $CF_3$ | $CH_3$ | (isomer 1) | +++ | 531.2 | Free Base |
| 4B-45 | $CF_3$ | $CH_3$ | (isomer 2) | +++ | 531.2 | Free Base |
| 4B-46 | $CF_3$ | $CH_3$ | (isomer 3) | +++ | 531.2 | TFA Salt |

TABLE 4B-continued
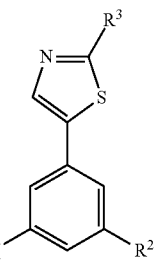
| Ex. | R¹ | R² | R³ | rhSYK Activity | [M + H]+ Obs'd | Form(s) |
|---|---|---|---|---|---|---|
| 4B-47 | $CF_3$ | $CH_3$ | 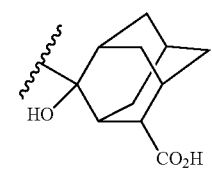 (isomer 4) | +++ | 531.2 | TFA Salt |
| 4B-48 | $CF_3$ | $CH_3$ | 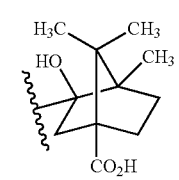 | +++ | 533.2 | TFA Salt |
| 4B-49 | $CF_3$ | $CH_3$ | 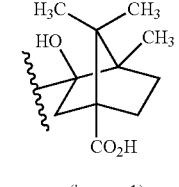 (isomer 1) | +++ | 533.2 | Free Base |
| 4B-50 | $CF_3$ | $CH_3$ | 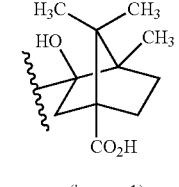 (isomer 2) | +++ | 533.2 | Free Base |
| 4B-51 | $CF_3$ | $CH_3$ | 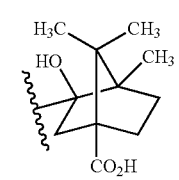 (cis) | +++ | 544.2 | TFA Salt |
| 4B-52 | $CF_3$ | $CH_3$ | 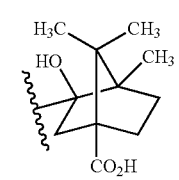 (trans) | +++ | 544.2 | TFA Salt |

TABLE 4B-continued

| Ex. | R¹ | R² | R³ | rhSYK Activity | [M + H]+ Obs'd | Form(s) |
|---|---|---|---|---|---|---|
| 4B-53 | CF₃ | CH₃ | (Isomer 1) | +++ | 570.1 | TFA Salt |
| 4B-54 | CF₃ | CH₃ | (Isomer 2) | +++ | 570.1 | TFA Salt |
| 4B-55 | CF₃ | CH₃ | | +++ | 447.2 | Free Base |
| 4B-56 | CF₃ | CH₃ | | +++ | 485 is observed mass | Free Base |
| 4B-57 | CF₃ | CH₃ | | +++ | 535 | Free Base |
| 4B-58 | CH₃ | CH₃ | | +++ | 409.1 | TFA Salt |

TABLE 4B-continued

| Ex. | R¹ | R² | R³ | rhSYK Activity | [M + H]+ Obs'd | Form(s) |
|---|---|---|---|---|---|---|
| 4B-59 | $CF_3$ | $CH_3$ | $C(O)CH_2CH_2CN$ | +++ | 418.2 | Free Base |
| 4B-60 | $CF_3$ | $CH_3$ | (5-oxotetrahydrofuran-2-yl) | +++ | 421.1 | Free Base |
| 4B-61 | $CF_3$ | $CH_3$ | (3,3,4-trimethyl-5-oxotetrahydrofuran-2-yl) | +++ | 463.1 | TFA Salt |
| 4B-62 | $CF_3$ | $CH_3$ | $C(O)CH_2CH_2C(O)CH_2CH_2OH$ | ++ | 465.1 | Free Base |

TABLE 4C

| Ex. | R¹* | X | R³/R⁴ | rhSYK Activity | [M + H]+ Obs'd | Form(s) |
|---|---|---|---|---|---|---|
| R² = H | | | | | | |
| 4C-1 | $CF_3$ | $CH_2CH_2$ | H/H | +++ | 435.1 | Free base |
| R² = $CH_3$ | | | | | | |
| 4C-2 | $CH_3$ | $CH_2$ | H/$CH_2NH_2$ (cis) | +++ | 410.2 | TFA Salt |
| 4C-3 | $CH_3$ | $CH_2$ | H/$CH_2NH_2$ (trans) | +++ | 410.2 | TFA Salt |
| 4C-4 | $CF_3$ | $CH_2$ | H/$CH_2NH_2$ | +++, +++ | 464.2 | Free Base, TFA Salt |
| 4C-5 | $CF_3$ | $CH_2$ | H/$CH_2CH_2NH_2$ | +++ | 478.2 | TFA Salt |
| 4C-6 | $CF_3$ | $CH_2$ | H/$CH_2OH$ (trans) | +++ | 465.2 | Free Base |
| 4C-7 | $CF_3$ | $CH_2$ | H/$CH_2OH$ | +++ | 465.2 | Free Base |
| 4C-8 | $CF_3$ | $CH_2$ | H/$CH_2OH$ (cis) | +++ | 465.2 | Free Base |
| 4C-9 | $CH_3$ | $CH_2$ | H/$CH_2OH$ | +++ | 411.2 | Free Base |
| 4C-10 | $CH_3$ | $CH_2$ | $NH_2$/$CO_2H$ | +++ | 440.0 | TFA Salt |

TABLE 4C-continued

| Ex. | R¹* | X | R³/R⁴ | rhSYK Activity | [M + H]+ Obs'd | Form(s) |
|---|---|---|---|---|---|---|
| 4C-11 | CH₃ | CH₂ | CH₃/CH₂CO₂H (isomer 1) | +++ | 453.1 | TFA Salt |
| 4C-12 | CH₃ | CH₂ | CH₃/CH₂CO₂H (isomer 2) | +++ | 453.1 | TFA Salt |
| 4C-13 | 5-F | CH₂ | CH₃/CH₂CO₂CH₂CH₃ | ++ | 471 | Free Base |
| 4C-14 | CF₃ | CH₂ | H/CH₂CO₂H (cis) | +++ | 493.1 | Free Base |
| 4C-15 | CF₃ | CH₂ | H/CH₂CO₂H (trans) | +++ | 493.1 | Free Base |
| 4C-16 | CF₃ | (cyclopropylidene) | H/OH | +++ | 477 | Free Base |
| 4C-17 | CH₃ | CH(iPr) | H/CO₂CH₃ | +++ | 481.1 | Free Base |
| 4C-18 | 5-Cl | C(CH₃)₂ | H/CO₂CH₃ | + | 487 | Free Base |
| 4C-19 | CF₃ | CH₂ | H/1-(NH₂)cPr (cis) | +++ | 490.2 | TFA Salt |
| 4C-20 | CF₃ | CH₂ | H/1-(NH₂)cPr (trans) | +++ | 490.2 | TFA Salt |
| 4C-21 | CF₃ | CH(CO₂Et) | H/H | ++ | 507.1, 507.2 | Free Base |
| 4C-22 | CF₃ | C(CH₃)(CH₂CO₂H) | H/H (1R, 3S) | +++ | 507.1 | TFA Salt |
| 4C-23 | CF₃ | C(CH₃)(CH₂CO₂H) | H/H (1R, 3R) | +++ | 507.1 | TFA Salt |
| 4C-24 | CH₃ | CHPh | H/CO₂Et | ++ | 529 | Free Base |
| 4C-25 | CF₃ | CH(iPr) | H/CO₂CH₃ | ++ | 535.0 | Free Base |
| 4C-26 | CF₃ | CH₂ | H/CH₂C(CH₃)₂CO₂H | +++ | 535.2 | TFA Salt |
| 4C-27 | CH₃ | CH(2-CH₃—Ph) | H/CO₂Et | ++ | 543 | Free Base |
| 4C-28 | CH₃ | CH(4-F—Ph) | H/CO₂Et | ++ | 547 | Free Base |
| 4C-29 | CF₃ | CH₂ | H/HN(O)C—CH₂—(imidazol-1-yl) (cis) | +++, +++ | 558.2 | Free Base Formate Salt |
| 4C-30 | CF₃ | CH₂ | H/HN(O)C-(γ-butyrolactone) (R) | +++ | 562.2 | Free Base |
| 4C-31 | CF₃ | CH₂ | H/HN(O)C-(γ-butyrolactone) | +++ | 562.2 | Formate Salt |
| 4C-32 | CF₃ | CH₂ | H/HN(O)C—CH₂-(pyridin-2-yl) (cis) | +++, +++ | 569.2 | Free Base, Formate Salt |
| 4C-33 | CF₃ | CH₂ | H/N(CH₃)₂ | +++ | 478 | Formate Salt |

*R¹ is on the 4-position of the pyrimidine ring, unless otherwise specified.

TABLE 4D

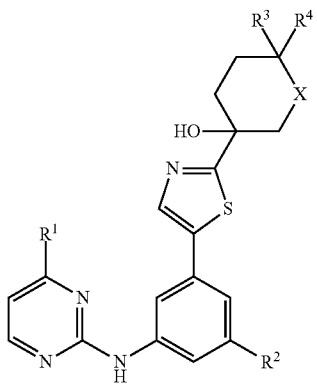

| Ex. | R¹ | R² | X | R³ | rhSYK Activity | [M + H]+ Obs'd | Form(s) |
|---|---|---|---|---|---|---|---|
| 4D-1 | CF₃ | H | CH₂ | C(O)CH₃ | +++ | 464.3 | Free Base |
| 4D-2 | CF₃ | H | Bond | 4-F—Ph | + | 502.3 | Free Base |
| 4D-3 | CF₃ | H | CH₂ | cPr | +++ | 462.2 | Free Base |
| 4D-4 | CF₃ | H | CH₂ | CO₂Et | +++ | 494.1 | Free Base |
| 4D-5 | CF₃ | H | CH₂ | iPr | ++ | 464.1 | Free Base |
| 4D-6 | CF₃ | H | CH₂ | C(O)Ph | +++ | 526.1 | Free Base |
| 4D-7 | CH₃ | CH₃ | CH₂C(O) (lactam formed) | H | +++ | 410.2 | Free Base |
| 4D-8 | CF₃ | CH₃ | CH₂ | cPr | +++ | 476 | Formate Salt |
| 4D-9 | CF₃ | CH₃ | CH₂ | 2-CH₃—Ph | ++ | 526 | Formate Salt |
| 4D-10 | CF₃ | CH₃ | CH₂ | 3-F—Ph | ++ | 530 | Formate Salt |
| 4D-11 | CF₃ | CH₃ | CH₂ | 2-F—Ph | ++ | 530 | Formate Salt |
| 4D-12 | CF₃ | CH₃ | CH₂ | 4-F—Ph | +++ | 530 | Formate Salt |
| 4D-13 | CF₃ | CH₃ | CH₂ | C(O)(CH₂)₃CO₂H | +++ | 550.1 | Formate Salt |
| 4D-14 | CF₃ | CH₃ | CH(CO₂CH₃) | CO₂C(CH₃)₃ | ++ | 594.1 | Free Base |
| 4D-15 | CF₃ | CH₃ | CH(CF₃) | CO₂C(CH₃)₃ | ++ | 604.1 | Free Base |

Example 5

3-[5-(3-{[4-(trifluoromethyl)pyrimidin-2-yl]amino}phenyl)-1,3-thiazol-2-yl]pentane-1,3,5-triol

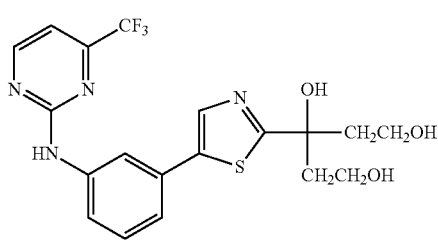

Step 1

To a stirred solution of 1,5-dihydroxypentan-3-one (300 mg, 2.54 mmol) in DMF (12.7 mL) was added imidazole (864 mg, 12.7 mmol), followed by TBDMSCl (919 mg, 6.09 mmol). The reaction mixture was stirred overnight at room temperature. Another portion of imidazole (864 mg, 12.7 mmol) and TBDMSCl (919 mg, 6.09 mmol) were added to the solution and the reaction mixture was stirred 24 h. The reaction was quenched with sat. NaHCO₃ and the aqueous layer was extracted with Et₂O (×3). The combined organics were washed with brine, dried (Na₂SO₄) and concentrated after filtration. The residue was purified by flash chromatography to give 2,2,3,3,11,11,12,12-octamethyl-4,10-dioxa-3,11-disilamidecan-7-one (795 mg, 2.293 mmol, 90% yield) as a colorless oil.

Step 2 n-Butyl lithium (0.372 mL, 0.931 mmol) was added to a stirred, cooled 0° C. mixture of diisopropylamine (0.139 mL, 0.977 mmol) in THF (1.55 mL) and the mixture was stirred at 0° C. for 30 min and then cooled to −78° C. To the cooled −78° C. LDA solution was added a solution of Intermediate 7 (100 mg, 0.310 mmol) in THF (1 mL) and the reaction mixture was stirred at that temperature for 30 minutes. At −78° C. was then added the product of Step 1 (323 mg, 0.931 mmol) and the reaction mixture was stirred overnight (temperature was allowed to reach slowly to room temperature). The reaction mixture was filtered through a pre-packed celite pad with DCM and the filtrate was concentrated. The residue was purified by flash chromatography to give 2,2,3,3,11,11,12,12-octamethyl-7-[5-(3-{[4-(trifluoromethyl)pyrimidin-2-yl]amino}phenyl)-1,3-thiazol-2-yl]-4,10-dioxa-3,11-disilamidecan-7-ol (323 mg, 0.931 mmol) as a yellow oil. APCI: [M+H]+ m/z 669.2.

Step 3

To a solution of the product of Step 2 (196 mg, 0.293 mmol) in THF (3 mL) was added TBAF (1 M in THF, 1.465 mL, 1.465 mmol) and the solution was stirred overnight at room temperature. Solvent was removed by evaporation and the residue was purified by flash chromatography to give 3-[5-(3-{[4-(trifluoromethyl)pyrimidin-2-yl]amino}phenyl)-1,3-thiazol-2-yl]pentane-1,3,5-triol (79.8 mg, 0.181 mmol, 61.8% yield) as an off-white fluffy solid. APCI: [M+H]+ m/z 441.1. $^1$H NMR (500 MHz, acetone-$d_6$): δ 9.30 (1H, s), 8.86 (1H, d, J=4.89 Hz), 8.34-8.32 (1H, m), 8.06 (1H, s), 7.84-7.79 (1H, m), 7.47-7.41 (1H, m), 7.39 (1H, dt, J=7.76, 1.40 Hz), 7.27 (1H, d, J=4.88 Hz), 6.00 (1H, s), 4.04 (2H, t, J=4.74 Hz), 3.77-3.68 (4H, m), 2.25-2.19 (4H, m). rhSYK activity=++

The following examples were prepared in an analogous manner of that described in Example 5.

TABLE 5

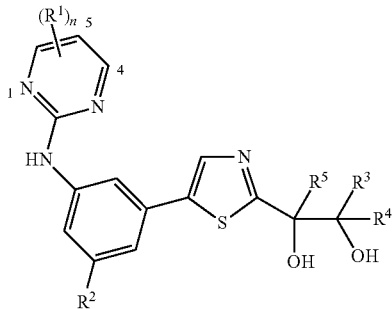

n is 1 or 2, and in the following Table, unless otherwise specified, n is 1 and $R^1$ is attached to the 4-position of the pyrimidine ring.

| Ex | $R^1$ | $R^2$ | $R^3/R^4$ | rhSYK Activity | [M + H]+ Observed | Form(s) |
|---|---|---|---|---|---|---|
| $R^5$ = $CH_3$ | | | | | | |
| 5-1 | 4-$CF_3$ | H | H/H | +++ | 397.0 | Free Base |
| 5-2 | 4-$CF_3$ | H (Enantiomer 1) | H/H | +++ | 397.0 | Free Base |
| 5-3 | 4-$CF_3$ | H (Enantiomer 2) | H/H | +++ | 397.0 | Free Base |
| 5-4 | 4-$CF_3$ | $CH_3$ | $CH_3/CH_3$ | +++ | 439.0 | Free Base |
| 5-5 | 4-$CF_3$ | $CH_3$ (Enantiomer 1) | H/H | +++ | 411.0 | Free Base |
| 5-6 | 4-$CF_3$ | $CH_3$ (Enantiomer 2) | H/H | +++ | 411.0 | Free Base |
| 5-7 | 4-$CF_3$ | $CH_3$ | H/H | +++ | 411.1 | Free Base |
| 5-8 | 4-$CH_3$, 5-F | $CH_3$ | H/H | +++ | 375 | Free Base |
| 5-9 | 4-$CH_3$, 5-F | $CH_3$ (Enantiomer 1) | H/H | +++ | 375 | Free Base |
| 5-10 | 4-$CH_3$, 5-F | $CH_3$ (Enantiomer 2) | H/H | +++ | 375 | Free Base |
| 5-11 | 5-Cl | $CH_3$ | H/H | ++ | 377 | Free Base |
| 5-12 | 5-Cl | $CH_3$ (Enantiomer 1) | H/H | +++ | 377 | Free Base |
| 5-13 | 5-Cl | $CH_3$ (Enantiomer 2) | H/H | ++ | 377 | Free Base |
| 5-14 | 4-$CH_3$, 5-F | $CH_3$ | H/H | +++ | 391 | Free Base |
| 5-15 | 4-$OCH_3$, 5-F | $CH_3$ | H/H | +++ | 391 | Free Base |
| 5-16 | 4-cPr, 5-F | $CH_3$ | H/H | +++ | 401.1 | Free Base |
| 5-17 | 4-cPr, 5-F | $CH_3$ (Enantiomer 1) | H/H | +++ | 401.1 | Free Base |
| 5-18 | 4-cPr, 5-F | $CH_3$ (Enantiomer 2) | H/H | +++ | 401.1 | Free Base |
| 5-19 | 4-$OCH_3$, 5-Cl | $CH_3$ | H/H | +++ | 407 | Free Base |
| $R^5$ = $CH_2OH$ | | | | | | |
| 5-20 | 5-Cl | $CH_3$ | H/H | ++ | 393 | Free Base |

Example 6

2,2,2-trifluoro-1-[5-(3-methyl-5-{[4-(trifluoromethyl)pyrimidin-2-yl]amino}phenyl)-1,3-thiazol-2-yl]ethanol

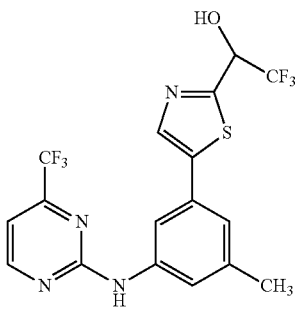 [SMILES: Cc1cc(Nc2nccc(C(F)(F)F)n2)cc(-c2cnc(C(O)C(F)(F)F)s2)c1]

Step 1

INTERMEDIATE 4 (500 mg, 1.487 mmol) in THF (7.4 mL) was added slowly to LDA (1.8 M, 2478 μL, 4.46 mmol) pre-cooled to −78° C. over 5 min with stirring. The reaction mixture was left to stir for 30 min then treated with ethyl trifluoroacetate (0.27 mL, 2.2 mmol). After 1 h, the reaction was quenched by adding 5 mL of saturated aqueous NH₄Cl solution, and the mixture was warmed to room temperature. The mixture was extracted with ethyl acetate, and washed with saturated NaHCO₃ solution. The organic layer was dried over anhydrous Na₂SO₄, filtered, concentrated, and purified by flash chromatography to give 2,2,2-trifluoro-1-[5-(3-methyl-5-{[4-(trifluoromethyl)pyrimidin-2-yl]amino}phenyl)-1,3-thiazol-2-yl]ethane-1,1-diol (513 mg, 1.139 mmol, 77% yield) as a colorless oil. APCI: [M+H]⁺ m/z 451.0.

Step 2

Sodium borohydride (41.6 mg, 1.099 mmol) was added to the product of Step 1 (450 mg, 0.999 mmol) in MeOH (3.3 mL) at 0° C. After stirring for 3 h, the reaction was poured into a separatory funnel containing ethyl acetate and saturated aqueous NaHCO₃. The layers were separated and the organic layer was washed with water, brine, dried over anhydrous sodium sulfate, and concentrated. The residue was purified by flash chromatography to give 2,2,2-trifluoro-1-[5-(3-methyl-5-{[4-(trifluoromethyl)pyrimidin-2-yl]amino}phenyl)-1,3-thiazol-2-yl]ethanol (394.6 mg, 0.908 mmol, 91% yield) as a white solid. APCI: [M+H]⁺ m/z 435.1. $^1$H NMR (500 MHz, DMSO-$d_6$) δ 10.28 (s, 1H), 8.84 (d, J=4.9, 1H), 8.12 (s, 1H), 8.02 (s, 1H), 7.86 (d, J=6.0, 1H), 7.48 (s, 1H), 7.29 (d, J=4.9, 1H), 7.22 (s, 1H), 5.52 (dd, J=6.7, 13.1, 1H), 2.32 (s, 3H). rhSYK activity=+++

The following examples were prepared in an analogous manner of that described in Example 6. Reduction of the ethyl ester was carried out with LiBH₄ in THF.

TABLE 6

| Ex. | R¹ | R2 | rhSYK Activity | [M + H]+ Observed | Form(s) |
|---|---|---|---|---|---|
| 6-1 | H | —C(O)CF₃ | +++ | 419.0 | Free Base |
| 6-2 | H | —CH(OH)CF₃ | +++ | 421.1 | Free Base |
| 6-3 | CH₃ | —CH(OH)CF₃ (Enantiomer 1) | +++ | 435.0 | Free Base |
| 6-4 | CH₃ | —CH(OH)CF₃ (Enantiomer 2) | +++ | 435.0 | Free Base |
| 6-5 | CH₃ | —C(O)CF₃ | +++ | 451.0 (M + H₂O + H) | Free Base |
| 6-6 | CH₃ | —C(OH)(CF₃)CO₂Et | +++ | 507.0 | Free Base |
| 6-7 | CH₃ | —C(OH)(CF₃)CH₂OH | +++ | 465.0 | Free Base |
| 6-8 | CH₃ | —C(OH)(CF₃)CH₂OH (Enantiomer 1) | +++ | 465.0 | Free Base |
| 6-9 | CH₃ | —C(OH)(CF₃)CH₂OH (Enantiomer 2) | +++ | 465.0 | Free Base |
| 6-10 | H | (structure) | ++ | 465.1 | Free Base |

Example 7

4-hydroxy-4-[5-(3-methyl-5-{[4-(trifluoromethyl)pyrimidin-2-yl]amino}phenyl)-1,3-thiazol-2-yl]cyclohexanone

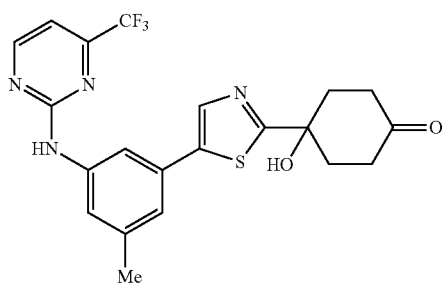 [SMILES: Cc1cc(Nc2nccc(C(F)(F)F)n2)cc(-c2cnc(C3(O)CCC(=O)CC3)s2)c1]

To a stirred solution of 8-[5-(3-methyl-5-{[4-(trifluoromethyl)pyrimidin-2-yl]amino}phenyl)-1,3-thiazol-2-yl]-1,4-dioxaspiro[4.5]decan-8-ol (Example 4B-15, 785 mg, 1.59 mmol) in THF (6 mL) was added HCl (6 M, 5.3 mL, 32 mmol) and the reaction was left to stir for 6 h. The mixture was brought to pH 8 with saturated aqueous sodium bicarbonate, extracted with ethyl acetate (×3), and the combined organic portion was washed with saturated aqueous sodium bicarbonate. The solution was dried over Na$_2$SO$_4$, filtered, concentrated, and purified by flash chromatography to afford 4-hydroxy-4-[5-(3-methyl-5-{[4-(trifluoromethyl)pyrimidin-2-yl]amino}phenyl)-1,3-thiazol-2-yl]cyclohexanone (625 mg, 1.39 mmol) as a white foam. APCI: [M+H]$^+$ m/z 449.1. $^1$H NMR (600 MHz, CDCl$_3$) δ 8.64 (d, J=4.9, 1H), 7.90 (s, 1H), 7.86 (s, 1H), 7.46 (s, 1H), 7.26 (s, 1H), 7.06 (s, 1H), 7.04 (d, J=4.9, 1H), 2.92-2.82 (m, 2H), 2.49-2.29 (m, 6H), 2.38 (s, 3H). rhSYK activity=+++

Examples 8(1) and 8(2)

cis-1-[5-(3-methyl-5-{[4-(trifluoromethyl)pyrimidin-2-yl]amino}phenyl)-1,3-thiazol-2-yl]-cyclohexane-1,4-diol trans-1-[5-(3-methyl-5-{[4-(trifluoromethyl)pyrimidin-2-yl]amino}phenyl)-1,3-thiazol-2-yl]-cyclohexane-1,4-diol

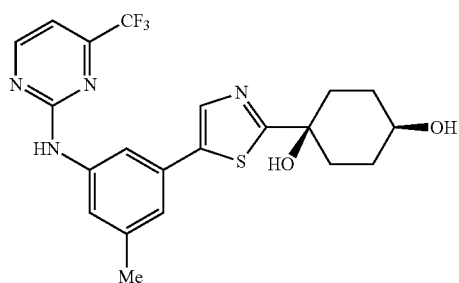

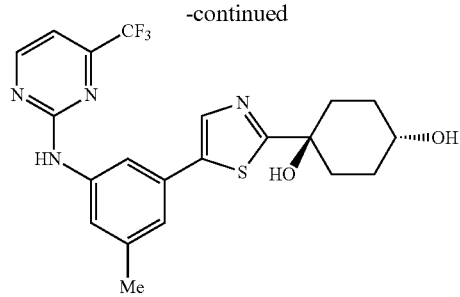

To a stirred solution of 4-hydroxy-4-[5-(3-methyl-5-{[4-(trifluoromethyl)pyrimidin-2-yl]amino}-phenyl)-1,3-thiazol-2-yl]cyclohexanone (500 mg, 1.115 mmol) in MeOH (11 mL) was added sodium borohydride (63.3 mg, 1.672 mmol) at −20° C. and the reaction was aged for 20 min. The mixture was treated with water and extracted with ethyl acetate. The combined organics were dried, filtered, concentrated, and purified by flash chromatography to afford cis-1-[5-(3-methyl-5-{[4-(trifluoromethyl)pyrimidin-2-yl]amino}phenyl)-1,3-thiazol-2-yl]cyclohexane-1,4-diol (250 mg, 0.56 mmol). APCI: [M+H]$^+$ m/z 451.1. $^1$H NMR (600 MHz, CDCl$_3$) δ 8.63 (d, J=4.9, 1H), 7.89-7.79 (m, 2H), 7.45 (s, 1H), 7.26 (s, 1H), 7.06 (s, 1H), 7.02 (d, J=4.9, 1H), 3.81-3.72 (m, 1H), 2.98 (s, 1H), 2.37 (s, 3H), 2.11-1.72 (m, 8H). rhSYK activity=+++ trans-1-[5-(3-methyl-5-{[4-(trifluoromethyl)pyrimidin-2-yl]amino}phenyl)-1,3-thiazol-2-yl]-cyclohexane-1,4-diol (40 mg, 0.09 mmol) APCI: [M+H]$^+$ m/z 451.1. $^1$H NMR (600 MHz, CDCl$_3$) δ 8.63 (d, J=4.9, 1H), 7.88-7.79 (m, 2H), 7.46 (s, 1H), 7.27 (s, 1H), 7.06 (s, 1H), 7.02 (d, J=4.9, 1H), 3.67 (t, J=6.3, 1H), 3.56 (m, 1H), 2.43-1.62 (m, 8H), 2.37 (s, 3H). rhSYK activity=+++

Compounds in the following Table(s) were prepared in an analogous manner of that described in Example 8(1)/8(2):

TABLE 8A

| Example | R$^1$ | R$^2$ | R$^3$/R$^{3a}$ | R$^4$/R$^{4a}$ | rhSYK Activity | [M + H]+ Observed | Form(s) |
|---|---|---|---|---|---|---|---|
| 8A-1 | CH$_3$ | F | H/H | H/OH (cis) | +++ | 415 | Free Base |
| 8A-2 | CH$_3$ | Cl | H/H | H/OH (cis) | +++ | 431 | Free Base |
| 8A-3 | OCH$_3$ | F | H/H | H/OH (cis) | +++ | 431 | Free Base |

TABLE 8A-continued

| Example | R¹ | R² | R³/R³ᵃ | R⁴/R⁴ᵃ | rhSYK Activity | [M + H]+ Observed | Form(s) |
|---|---|---|---|---|---|---|---|
| 8A-4 | cPr | F | H/H | H/OH (cis) | +++ | 441.1 | Free Base |
| 8A-5 | OCH₃ | Cl | H/H | H/OH (cis) | +++ | 447 | Free Base |
| 8A-6 | CF₃ | H | CH₃/CH₃ | H/OH (1S, 4R) | +++ | 479.1 | Free Base |
| 8A-7 | CF₃ | H | CH₃/CH₃ | H/OH (1R, 4S) | +++ | 479.1 | Free Base |
| 8A-8 | CH₃ | F | H/H | =O | +++ | 413 | Free Base |

TABLE 8B

| Example | R | rhSYK Activity | [M + H]+ Obs'd | Form(s) |
|---|---|---|---|---|
| 8B-1 | (CH₃, HO, cyclohexanone with methyl) | +++ | 477.1 | Free Base |
| 8B-2 | (CH₃, OH, HO, cyclohexane) (cis) | +++ | 479.1 | Free Base |
| 8B-3 | (CH₃, OH, HO, cyclohexane) (trans) | +++ | 479.1 | Free Base |
| 8B-4 | C(OH)(CH₃)(4-CH(OH)CH₃—Ph) | +++ | 501 | Free Base |

Example 9(1) and 9(2)

trans-1-methyl-4-[5-(3-methyl-5-{[4-(trifluoromethyl)pyrimidin-2-yl]amino}phenyl)-1,3-thiazol-2-yl]cyclohexane-1,4-diol cis-1-methyl-4-[5-(3-methyl-5-{[4-(trifluoromethyl)pyrimidin-2-yl]amino}phenyl)-1,3-thiazol-2-yl]cyclohexane-1,4-diol

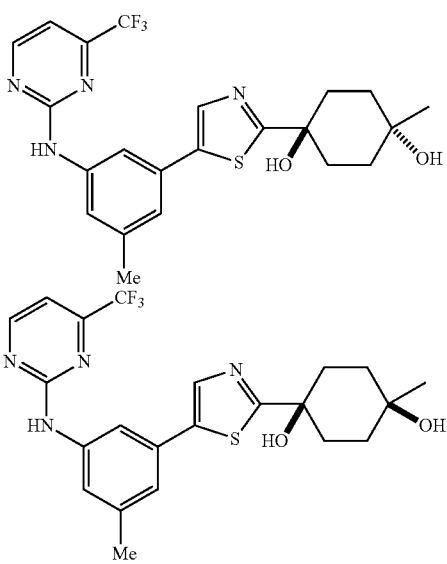

To a stirred solution of 4-hydroxy-4-[5-(3-methyl-5-{[4-(trifluoromethyl)pyrimidin-2-yl]amino}-phenyl)-1,3-thiazol-2-yl]cyclohexanone (104 mg, 0.232 mmol) in THF (4 mL) was added MeMgCl (3.0 M, 0.464 mL, 1.39 mmol) at 0° C. The resultant orange suspension was stirred for t h at 0° C., treated with saturated aqueous ammonium chloride, and extracted with ethyl acetate (×3). The combined organics were dried over Na₂SO₄, filtered, and concentrated in vacuo. Purification by flash chromatography gave:

trans-1-methyl-4-[5-(3-methyl-5-{[4-(trifluoromethyl)pyrimidin-2-yl]amino}phenyl)-1,3-thiazol-2-yl]cyclohexane-1,4-diol (6 mg, 0.013 mmol) as a white solid. APCI: [M+H]⁺ m/z 465.1. ¹H NMR (600 MHz, DMSO-d₆) δ 10.22 (s, 1H), 8.81 (d, J=4.9, 1H), 7.92 (s, 1H), 7.90 (s, 1H), 7.43 (s, 1H), 7.25 (d, J=4.9, 1H), 712 (s, 1H), 5.74 (s, 1H), 4.03 (s, 1H), 2.29 (s, 3H), 2.21 (td, J=3.9, 13.3, 2H), 1.71-1.36 (m, 6H), 1.10 (s, 3H). rhSYK activity=+++)

cis-1-methyl-4-[5-(3-methyl-5-{[4-(trifluoromethyl)pyrimidin-2-yl]amino}phenyl)-1,3-thiazol-2-yl]cyclohexane-1,4-diol (23 mg, 0.050 mmol) as a colorless oil. APCI: [M+H]⁺ m/z 465.1. ¹H NMR (500 MHz, DMSO-d₆) δ 10.25 (s, 1H), 8.83 (d, J=4.8, 1H), 7.94 (s, 1H), 7.92 (s, 1H), 7.45 (s, 1H), 7.27 (d, J=4.9, 1H), 7.13 (s, 1H), 2.31 (s, 3H), 1.96-1.40 (m, 8H), 1.13 (s, 3H). rhSYK activity=+++.

The following compound was prepared as the free base in an analogous manner of that described in Example 9(1)/9(2):

| Example | Structure | rhSYK Activity | [M + H]+ Obs'd |
|---|---|---|---|
| 9.1 | 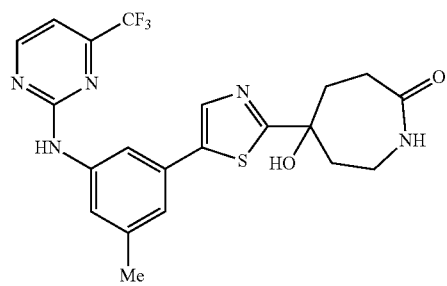 [SMILES: Cc1cc(Nc2nccc(C(F)(F)F)n2)cc(-c2cnc(C3(O)CCNC(=O)CC3)s2)c1] | ++ | 515 |

Example 10

5-hydroxy-5-[5-(3-methyl-5-{[4-(trifluoromethyl)pyrimidin-2-yl]amino}phenyl)-1,3-thiazol-2-yl]azepan-2-one

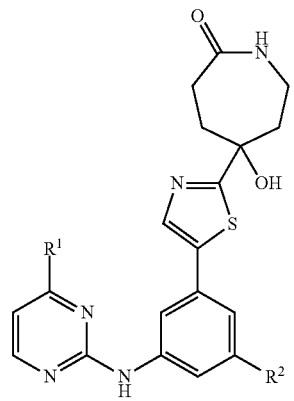

A mixture of 8-[5-(3-methyl-5-{[4-(trifluoromethyl)pyrimidin-2-yl]amino}phenyl)-1,3-thiazol-2-yl]-1,4-dioxaspiro[4.5]decan-8-ol (60 mg, 0.122 mmol), sodium azide (23.76 mg, 0.365 mmol) and methanesulfonic acid (95 L, 1.462 mmol) in CHCl₃ (1.2 mL) was heated at 65° C. for 1 h and cooled to room temperature. The mixture was treated with water, and extracted with ethyl acetate. The combined organics were dried, filtered, concentrated and purified by flash chromatography to afford 5-hydroxy-5-[5-(3-methyl-5-{[4-(trifluoromethyl)pyrimidin-2-yl]amino}phenyl)-1,3-thiazol-2-yl]azepan-2-one (36 mg, 0.078 mmol). APCI: [M+H]⁺ m/z 464.2. ¹H NMR (600 MHz, CDCl₃): δ 8.63 (d, J=4.9, 1H), 7.89 (s, 1H), 7.83 (s, 1H), 7.62 (s, 1H), 7.26 (s, 1H), 7.05 (s, 1H), 7.03 (d, J=4.9, 1H), 6.21 (s, 1H), 3.81 (s, 1H), 3.46 (s, 1H), 3.21-3.03 (m, 2H), 2.41 (dd, J=7.5, 14.4, 1H), 2.37 (s, 3H), 2.24 (t, J=13.3, 1H), 2.18-2.04 (m, 3H). rhSYK activity=+++

The following compounds were prepared as the free base in an analogous manner of that described in Example 10:

TABLE 10

A

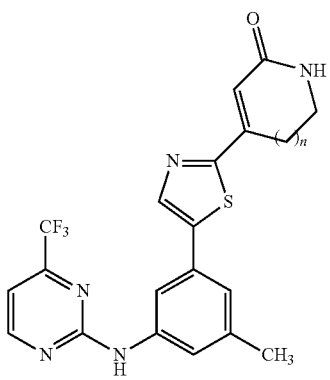

Formula A

| Example | R¹ | R² | rhSYK Activity | [M + H]+ Observed |
|---|---|---|---|---|
| 10A-1 | OCH₃ | CH₃ | +++ | 426.2 |
| 10A-2 | CH(CH₃)₂ (Enantiomer 1) | CH₃ | +++ | 438.2 |
| 10A-3 | CH(CH₃)₂ (Enantiomer 2) | CH₃ | +++ | 438.2 |
| 10A-4 | CF₃ | CH₂OCH₃ | +++ | 494.1 |

Formula B

| Example | n | rhSYK Activity | [M + H]+ Obs'd |
|---|---|---|---|
| 10B-1 | 1 | +++ | 432.1 |
| 10B-2 | 2 | +++ | 446.1 |

Example 11

Cyclopropyl[5-(3-{[4-(trifluoromethyl)pyrimidin-2-yl]amino}phenyl)-1,3-thiazol-2-yl]methanone

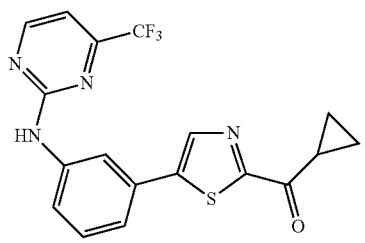 [SMILES: O=C(c1ncc(-c2cccc(Nc3nccc(C(F)(F)F)n3)c2)s1)C1CC1]

Dess-Martin periodinane (110 mg, 0.260 mmol) was added to a stirred, cooled (room temperature) mixture of cyclopropyl[5-(3-{[4-(trifluoromethyl)pyrimidin-2-yl]amino}phenyl)-1,3-thiazol-2-yl]methanol (Example 4A-5, 85 mg, 0.217 mmol) in dichloromethane (0.72 mL) and the mixture was stirred at room temperature for 30 min. The mixture was cooled, diluted with ethyl acetate, washed with aqueous sodium sulfite then brine, dried (MgSO$_4$), filtered, and concentrated. The residue was purified by flash chromatography to give cyclopropyl[5-(3-{[4-(trifluoromethyl)pyrimidin-2-yl]amino}phenyl)-1,3-thiazol-2-yl]methanone (43 mg, 0.110 mmol, 50.8%) as a colorless solid. APCI: [M+H]$^+$ m/z 391.0. $^1$H NMR (400 MHz, CDCl$_3$): δ 8.71 (d, J=4.90, 1H), 8.26 (s, 1H), 8.24 (s, 1H), 7.58-7.50 (m, 2H), 7.46 (t, J=7.87, 1H), 7.42-7.38 (m, 1H), 7.13 (d, J=4.91, 1H), 3.28-3.23 (m, 1H), 1.39-1.34 (m, 2H), 1.22-1.17 (m, 2H). rhSYK activity=+++

Example 12

1-Cyclopropyl-2,2,2-trifluoro-1-[5-(3-{[4-(trifluoromethyl)pyrimidin-2-yl]amino}phenyl)-1,3-thiazol-2-yl]ethanol

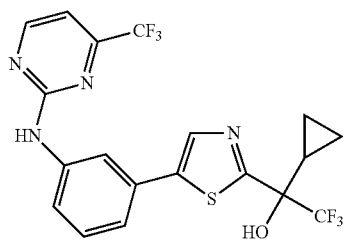 [SMILES: OC(c1ncc(-c2cccc(Nc3nccc(C(F)(F)F)n3)c2)s1)(C1CC1)C(F)(F)F]

TBAF (1 M, 3.71 μL, 3.71 μmol) was added to a stirred, cooled (0° C.) mixture of cyclopropyl[5-(3-{[4-(trifluoromethyl)pyrimidin-2-yl]amino}phenyl)-1,3-thiazol-2-yl]methanone (29 mg, 0.074 mmol) and (trifluoromethyl)trimethylsilane (14.24 μL, 0.089 mmol) in tetrahydrofuran (0.2 mL) and the mixture was stirred at room temperature for 4 h. Additional TMSCF$_3$ (20 μL) and tetramethyammonium fluoride (0.811 mg, 7.43 mop were added and the mixture was left to stir overnight. Additional TMSCF$_3$ (22 μL) and KOtBu (1M in THF, 74 μL) were added to the mixture and left to stir for 2 days. The mixture was treated with TBAF (74 μL), ether and HCl, and extracted with ethyl acetate. The combined organics were concentrated, and purified by flash chromatography to give 1-cyclopropyl-2,2,2-trifluoro-1-[5-(3-{[4-(trifluoromethyl)-pyrimidin-2-yl]amino}phenyl)-1,3-thiazol-2-yl]ethanol (23 mg, 0.050 mmol, 67.2% yield). APCI: [M+H]$^+$ m/z 461.1. $^1$H NMR (400 MHz, CDCl$_3$): δ 8.72 (d, J=4.9 Hz, 1H); 8.19 (s, 1H); 7.97 (s, 1H); 7.52 (d, J=8.3 Hz, 1H); 7.48-7.40 (m, 2H); 7.32 (d, J=7.8 Hz, 1H); 7.12 (d, J=4.9 Hz, 1H); 4.53 (s, 1H); 1.58-1.51 (m, 1H); 1.01-0.94 (m, 1H); 0.77-0.67 (m, 1H); 0.59-0.51 (m, 2H). rhSYK activity=+++

Example 13

N-{3-methyl-5-[2-(1-methylethyl)-1,3-thiazol-5-yl]phenyl}-4-(trifluoromethyl)pyrimidin-2-amine

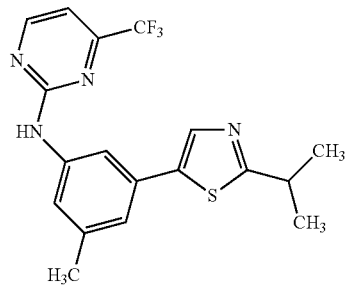 [SMILES: Cc1cc(Nc2nccc(C(F)(F)F)n2)cc(-c2cnc(C(C)C)s2)c1]

To a stirred solution of 2-[5-(3-methyl-5-{[4-(trifluoromethyl)pyrimidin-2-yl}amino]phenyl)-1,3-thiazol-2-yl]propan-2-ol (Example 4, 58 mg, 0.15 mmol) in DCM (1.5 mL) were added Et$_3$SiH (0.18 mL, 1.1 mmol) and TFA (0.17 mL, 2.2 mmol). The reaction mixture was heated to 60° C. for 3 hr. Additional Et$_3$SiH (0.18 mL) and TFA (0.11 mL) were added and the reaction was then heated to 80° C. for 1 d. The mixture was cooled to room temperature, diluted with ethyl acetate (75 mL) and washed with saturated aqueous NRHCO$_3$ solution, water, and brine. The solution was dried over anhydrous sodium sulfate, concentrated, and purified by flash chromatography to give N-{3-methyl-5-[2-(1-methylethyl)-1,3-thiazol-5-yl]phenyl}-4-(trifluoromethyl)pyrimidin-2-amine (31.7 mg, 0.084 mmol, 57.3% yield) as a white solid. APCI: [M+H]$^+$ m/z 379.1. $^1$H NMR (500 MHz, DMSO-d$_6$) δ 10.25 (s, 1H), 8.83 (d, J=4.9, 1H), 7.98 (s, 1H), 7.93 (s, 1H), 7.44 (s, 1H), 7.28 (d, J=4.9, 1H), 7.14 (s, 1H), 3.27 (dt, J=6.9, 13.7, 1H), 2.31 (s, 3H), 1.34 (d, J=6.9, 6H). rhSYK activity=+++

The following examples were prepared in an analogous manner of that described in Examples 13:

| Example | Structure | hSYK Activity | [M + H]+ obs'd | Form(s) |
|---|---|---|---|---|
| 13-1 | (cyclobutyl-thiazole-phenyl-CH3, CF3-pyrimidin-2-ylamino) | ++ | 391.1 | Free Base |

Example 14 cis-4-[(hydroxyacetyl)amino]-1-[5-(3-methyl-5-{[4-(trifluoromethyl)pyrimidin-2-yl]amino}phenyl)-1,3-thiazol-2-yl]cyclohexanecarboxamide

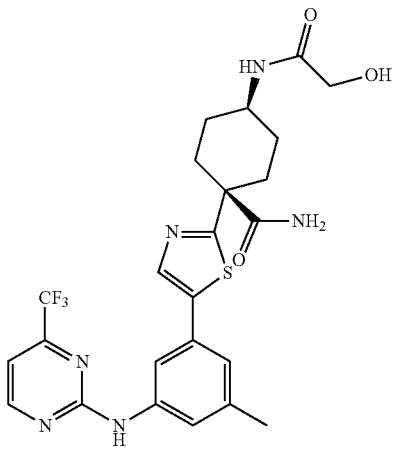 [SMILES: Cc1cc(Nc2nccc(C(F)(F)F)n2)cc(-c2cnc([C@]3(C(N)=O)CC[C@@H](NC(=O)CO)CC3)s2)c1]

Step 1

To a solution of ethyl 4-oxocyclohexanecarboxylate (5.0 g, 40.6 mmol) in benzene (20 ml) were added ethylene glycol (2.83 ml, 50.8 mmol) and catalytic sulfuric acid (772 mg, 4.1 mmol) and the mixture was refluxed under a Dean-Stark trap for 18 h. The mixture was cooled to 23° C., diluted with saturated aqueous NaHCO$_3$ (85 ml) and extracted with EtOAc (2×75 ml). The organic layer was dried over Na$_2$SO$_4$, filtered and concentrated and the crude product was purified via flash column chromatography to afford 1,4-dioxaspiro[4.5]decane-8-carbonitrile (6.15 g, 34.9 mmol, 86% yield) as a colorless oil. $^1$H NMR (500 MHz, CDCl$_3$): δ 3.85-3.3.80 (m, 4H), 2.61-2.53 (m, 1H), 1.90-1.77 (m, 4H), 1.75-1.69 (m, 2H), 1.56-1.48 (m, 2H).

Step 2

To a solution of 1,4-dioxaspiro[4.5]decane-8-carbonitrile (3 g, 17.9 mmol) in anhydrous toluene (95 ml) at 0° C., was added sodium bis(trimethylsilyl)amide (1M in toluene, 21.5 ml, 21.5 mmol). The resulting orange solution was maintained at 0° C. for 1 h, before introducing a solution of 2-chlorotriazole (2.14 g, 17.9 mmol) in anhydrous toluene (10 ml) via cannulation. The residual dark brown solution was allowed to slowly warm to 23° C. over 16 h. The reaction was diluted with saturated aqueous NH$_4$Cl (100 ml) and extracted with EtOAc (2×80 ml). The combined organic layers were washed with brine (100 ml), dried over Na$_2$SO$_4$, filtered and concentrated in vacuo. The crude oil was purified via flash column chromatography (SiO$_2$: 100% Hex to 80:20 Hex:EtOAc) to provide 8-(1,3-thiazol-2-yl)-1,4-dioxaspiro[4.5]decane-8-carbonitrile (1.78 g, 6.74 mmol, 37.5% yield) as a fluffy, off-white solid. MS ESI: [M+H]$^+$ m/z 251.1. $^1$H NMR (500 MHz, CDCl$_3$): δ 7.79 (d, 1H, J=3.2 Hz), 7.35 (d, 1H, J=3.5 Hz), 4.01-3.95 (m, 4H), 2.44-2.31 (m, 4H), 2.09-2.03 (m, 2H), 1.89-1.86 (m, 2H).

Step 3

To a solution of 8-(1,3-thiazol-2-yl)-1,4-dioxaspiro[4.5]decane-8-carbonitrile (1.78 g, 7.11 mmol) in anhydrous DMF (25 ml) was added N-bromosuccinimide (1.52 g, 8.53 mmol). The solution was heated at 50° C. for 2 h. The reaction was cooled to 23° C. then diluted with saturated aqueous NaS$_2$O$_3$ (175 ml) and extracted with EtOAc (2×130 ml). The combined organic layers were washed with brine (150 ml), dried over Na$_2$SO$_4$, filtered and concentrated. The crude yellow oil was purified via flash column chromatography (SiO$_2$: 100% Hex to 60:40 Hex:EtOAc), to afford 8-(5-bromo-1,3-thiazol-2-yl)-1,4-dioxaspiro[4.5]decane-8-carbonitrile (1.43 g, 4.13 mmol, 58% yield) as an off-white solid. MS ESI: [M+H]$^+$ m/z 331.1. $^1$H NMR (500 MHz, CDCl$_3$): δ 7.66 (s, 1H), 4.01-3.93 (m, 4H), 2.39-2.26 (m, 4H), 2.07-2.01 (m, 2H), 1.88-1.86 (m, 2H).

Step 4

N-[3-methyl-5-(4,4,5,5-tetramethyl-1,3,2-dioxaborolan-2-yl)phenyl]-4-(trifluoromethyl)pyrimidin-2-amine (1.60 g, 4.22 mmol), 8-(5-bromo-1,3-thiazol-2-yl)-1,4-dioxaspiro[4.5]decane-8-carbonitrile (1.40 g, 4.22 mmol), cesium carbonate (4.12 g, 12.6 mmol), Pd$_2$(dba)$_3$ (193 mg, 0.21 mmol) and X-Phos (201 mg, 0.42 mmol) were added to a flame-dried flask, deoxygenated, and diluted with anhydrous 1,4-dioxane (15 ml) and water (1.5 ml). The resulting dark mixture was heated to 100° C. for 5 h. The reaction mixture was diluted with 1:1 saturated aqueous NaHCO$_3$: brine (100 ml) and extracted with EtOAc (2×85 ml). The organic layers were dried over Na$_2$SO$_4$, filtered and concentrated. The crude dark maroon oil was purified via flash column chromatography (SiO$_2$: 100% Hex to 60:40 Hex:EtOAc) which afforded 8-[5-(3-methyl-5-{[4-(trifluoromethyl)pyrimidin-2-yl]amino}phenyl)-1,3-thiazol-2-yl]-1,4-dioxaspiro[4.5]decane-8-carbonitrile (1.77 g, 3.35 mmol, 79% yield) as an off-white solid. MS ESI: [M+H]$^+$ m/z 502.1. $^1$H NMR (500 MHz, CD$_3$OD): δ 11.1 (s, 1H), 9.65 (d, 1H, J=4.9 Hz), 8.93 (s, 1H), 8.83 (s, 1H), 8.30 (s, 1H), 8.10 (d, 1H, J=4.9 Hz), 8.02 (s, 1H), 4.73-4.72 (m, 4H), 3.21-3.18 (m, 2H), 3.13 (s, 3H), 3.01-2.97 (m, 2H), 2.69-2.61 (m, 4H). rhSYK activity=+++

Step 5

To a solution of 8-[5-(3-methyl-5-{[4-(trifluoromethyl)pyrimidin-2-yl]amino}phenyl)-1,3-thiazol-2-yl]-1,4-dioxaspiro[4.5]decane-8-carbonitrile (250 mg, 0.50 mmol) in anhydrous DMSO (4 ml) were added potassium carbonate (172 mg, 1.25 mmol) and hydrogen peroxide (218 μL, 2.49 mmol). The resulting solution was stirred at 70° C. for 1.5 h, cooled to room temperature and diluted with water (70 ml) and washed with EtOAc (2×60 ml). The combined organic layers were dried over Na$_2$SO$_4$, filtered and concentrated. The crude oil was triturated with diethyl ether and hexanes, and the resulting tan solid was collected via filtration and air dried to provide 8-[5-(3-methyl-5-{[4-(trifluoromethyl)pyrimidin-2-yl]amino}phenyl)-1,3-thiazol-2-yl]-1,4-dioxaspiro[4.5]decane-8-carboxamide (171 mg, 0.31 mmol, 63% yield) as a tan solid. MS ESI: [M+H]$^+$ m/z 520.1. $^1$H NMR (500 MHz, CD$_3$OD): δ 11.0 (s, 1H), 9.64 (d, 1H, J=4.9 Hz), 8.79 (s, 1H), 8.76 (bs, 1H), 8.28 (bs, 1H), 8.12-8.05 (m, 3H), 7.97 (s, 1H), 4.68-4.64 (m, 4H), 3.23-3.15 (m, 2H), 3.12 (s, 3H), 2.95-2.85 (m, 2H), 2.44-2.38 (m, 4H).

Step 6

To a suspension of 8-[5-(3-methyl-5-{[4-(trifluoromethyl)pyrimidin-2-yl]amino}phenyl)-1,3-thiazol-2-yl]-1,4-dioxaspiro[4.5]decane-8-carboxamide (700 mg, 1.35 mmol) in anhydrous THF (2 ml) and was added concentrated HCl (5.53 ml, 67.4 mmol). The resulting dark yellow solution was stirred at 23° C. for 6 h. The mixture was diluted with saturated aqueous NaHCO$_3$ (80 ml) and extracted with EtOAc (2×70 ml). The combined organic layers were dried over Na$_2$SO$_4$, filtered and concentrated. The crude oil was triturated with hexanes and diethyl ether which afforded 1-[5-(3-methyl-5-{[4-(trifluoromethyl)pyrimidin-2-yl]amino}phenyl)-1,3-thiazol-2-yl]-4-oxocyclohexanecarboxamide (683 mg, 1.01 mmol, 74.6%) as an tan solid. MS APCI: [M+H]$^+$ m/z 476.1.

Step 7

To a solution of 1-[5-(3-methyl-5-{[4-(trifluoromethyl)pyrimidin-2-yl]amino}phenyl)-1,3-thiazol-2-yl]-4-oxocyclohexanecarboxamide (683 mg, 1.44 mmol) in anhydrous MeOH (6 ml) were added ammonium acetate (221 mg, 2.87 mmol) and sodium cyanoborohydride (95 mg, 1.508 mmol). The resulting mixture was stirred at 23° C. for 6 d. The reaction was quenched with 0.5M NaOH (100 ml) and extracted with EtOAc (2×75 ml). The combined organic layers were washed with water, dried over Na$_2$SO$_4$, filtered and concentrated to an orange oil, which was purified via reverse-phase HPLC (C$_{18}$ column, Acetonitrile/Water gradient with 0.1% TFA present). Purification yielded a mixture of diastereomers, which were separated via separation on a chiral stationary phase (SFC, 35%/65% Methanol/CO$_2$ (no other modifiers) to provide both cis-4-amino-1-[5-(3-methyl-5-{[4-(trifluoromethyl)pyrimidin-2-yl]amino}phenyl)-1,3-thiazol-2-yl]cyclohexanecarboxamide (92 mg, 0.18 mmol, 29% yield) and trans-4-amino-1-[5-(3-methyl-5-{[4-(trifluoromethyl)pyrimidin-2-yl]amino}phenyl)-1,3-thiazol-2-yl]cyclohexanecarboxamide (103 mg, 0.21 mmol, 32% yield) as off-white solids. MS ESI: [M+H]$^+$ m/z 477.1. For molecule A, rhSYK activity=+++; for molecule B, rhSYK activity=+++

Step 8

To a solution of cis-4-amino-1-[5-(3-methyl-5-{[4-(trifluoromethyl)pyrimidin-2-yl]amino}phenyl)-1,3-thiazol-2-yl]cyclohexanecarboxamide (30 mg, 0.06 mmol) in anhydrous DMF (1.5 ml) were added sequentially glycolic acid (7.18 mg, 0.09 mmol), EDC (18.1 mg, 0.09 mmol), HOBT (14.5 mg, 0.09 mmol), and Et$_3$N (0.03 ml, 0.19 mmol). The mixture was stirred at 23° C. for 16 h, then diluted with water (55 ml) and washed with EtOAc (2×40 ml). The combined organic layers were dried over Na$_2$SO$_4$, filtered and concentrated. The crude product was purified via reverse-phase HPLC (Acetonitrile/Water gradient with 0.1% TFA present) and the fractions containing product were diluted with saturated aqueous NaHCO$_3$ (50 ml) and washed with EtOAc (45 ml). The organic layer was dried over Na$_2$SO$_4$, filtered and concentrated to afford cis-4-[(hydroxyacetyl)amino]-1-[5-(3-methyl-5-{[4-(trifluoromethyl)pyrimidin-2-yl]amino}phenyl)-1,3-thiazol-2-yl]cyclohexanecarboxamide (16.5 mg, 0.03 mmol, 47% yield) as an off-white solid. MS ESI: [M+H]$^+$ m/z 535.1. $^1$H NMR (500 MHz, DMSO) δ 10.26 (s, 1H), 8.83 (d, J=4.9, 1H), 7.96 (s, 1H), 7.94 (s, 1H), 7.55 (d, J=8.2, 1H), 7.45 (m, 2H), 7.32-7.22 (m, 2H), 7.14 (s, 1H), 5.29 (t, J=5.9, 1H), 3.75 (d, J=6.0, 2H), 3.70-3.60 (m, 1H), 2.67-2.58 (m, 2H), 2.31 (s, 3H), 1.82-1.68 (m, 4H), 1.54-1.41 (m, 2H). rhSYK activity=+++

Examples 15(1) and 15(2)

tert-butyl 4-{1-hydroxy-1-[5-(3-{[4-(trifluoromethyl)pyrimidin-2-yl]amino}phenyl)-1,3-thiazol-2-yl]ethyl}piperidine-1-carboxylate 1-(piperidin-4-yl)-1-[5-(3-{[4-(trifluoromethyl)pyrimidin-2-yl]amino}phenyl)-1,3-thiazol-2-yl]ethanol

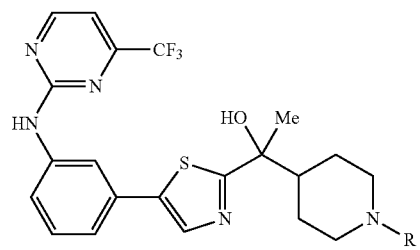

Example 15 (1): R = BOC; Example 15 (2): R = H

Step 1 n-Butyl lithium (0.281 mL, 0.702 mmol) was added dropwise to a stirred, cooled (−78° C.) mixture of thiazole (0.050 mL, 0.702 mmol) in THF (2.55 mL) and the mixture was stirred at −78° C. for 30 min. A solution of 4-acetyl-piperidine-1-carboxylic acid tert-butyl ester in THF (0.638 mL) was then added dropwise. Temperature was maintained at −78° C. for 30 min and then allowed to reach room temperature. The reaction was quenched with saturated NH$_4$Cl solution and extracted with EtOAc (×2). The combined organics were washed with brine, dried (Na$_2$SO$_4$) and concentrated. The residue was purified by flash chromatography to give tert-butyl 4-[1-hydroxy-1-(1,3-thiazol-2-yl)ethyl]piperidine-1-carboxylate (180 mg, 0.576 mmol, 90%) as a colorless oil.

Step 2

Bromine (0.071 mL, 1.383 mmol) was added dropwise to a stirred mixture of the product of Step 1 (180 mg, 0.576 mmol) and sodium acetate (236 mg, 2.88 mmol) in acetic acid (2.31 mL), and the mixture was stirred at room temperature for 2 h. Acetic acid was removed by evaporation under vacuum and the residue was treated with saturated NaHCO$_3$ solution, and extracted with ethyl acetate (×3). The combined organic fractions were washed with brine, dried (Na$_2$SO$_4$), concentrated, and purified by flash chromatography to give tert-butyl 4-[1-(5-bromo-1,3-thiazol-2-yl)-1-hydroxyethyl]piperidine-1-carboxylate (87 mg, 0.222 mmol, 38.6%). APCI: [M+H]$^+$ m/z 379.1.

Step 3

The product of Step 2 (87 mg, 0.222 mmol), 3-aminophenylboronic acid monohydrate (41.3 mg, 0.267 mmol), Pd(Ph$_3$P)$_4$ (12.85 mg, 0.011 mmol) and Na$_2$CO$_3$ (0.333 mL, 0.667 mmol) were stirred in DME at 100° C. overnight under N$_2$. The reaction mixture was filtered through a pre-pack pad of celica with dichloromethane. The filtrate was concentrated and the residue was purified by flash chromatography to give tert-butyl 4-{1-[5-(3-aminophenyl)-1,3-thiazol-2-yl]-1-hydroxyethyl}piperidine-1-carboxylate (82.4 mg, 0.204 mmol, 92%) as a yellow oil.

Step 4

2-Chloro-4-(trifluoromethyl)pyrimidine (0.030 mL, 0.245 mmol), the product of Step 3 (82.4 mg, 0.204 mmol), Cs$_2$CO$_3$ (133 mg, 0.408 mmol), palladium(II) acetate (2.292 mg, 10.21 μmol) and Xantphos (17.72 mg, 0.031 mmol) were stirred in Dioxane (4.0 mL) at 105° C. overnight under N$_2$. The reaction mixture was filtered through a celite pre-pack column with CH$_2$Cl$_2$ and small amount of 2-MeTHF. The filtrate was concentrated and the residue was purified by flash chromatography to give tert-butyl 4-{1-hydroxy-1-[5-(3-{[4-(trifluoromethyl)-pyrimidin-2-yl]amino}phenyl)-1,3-thiazol-2-yl]ethyl}piperidine-1-carboxylate (Example 15(1), 74 mg, 0.135 mmol, 66%). APCI: [M-Boc+H]$^+$ m/z 450.1. $^1$H NMR (CDCl$_3$): δ 8.67 (d, J=4.91, 1H), 8.07 (s, 1H), 7.90 (s, 1H), 7.66 (s, 1H), 7.52 (d, J=8.22, 1H), 7.39 (t, J=7.91, 1H), 7.30-7.25 (m, 1H), 7.08 (d, J=4.91, 1H), 4.19-4.09 (m, 2H), 3.31 (s, 1H), 2.75-2.57 (m, 2H), 1.95 (td, J=12.01, 3.49, 1H), 1.87-1.73 (m, 1H), 1.67 (s, 3H), 1.60-1.49 (m, 1H), 1.45 (s, 9H), 1.50-1.32 (m, 1H). rhSYK activity=++

Step 5

To a stirred solution of the product of Step 4 (18.2 mg, 0.033 mmol) in dichloromethane (1 mL) was added TEA (1.00 mL, 12.98 mmol) and the mixture was stirred at room temperature.

The solvent was removed by evaporation and stripped with ethyl acetate. The residue was concentrated and dried under high-vacuum to afford 1-(piperidin-4-yl)-1-[5-(3-{[4-(trifluoromethyl)pyrimidin-2-yl]amino}phenyl)-1,3-thiazol-2-yl]ethanol (Example 15(2), 12.5 mg, 0.018 mmol) as a TFA salt. APCI: [M+H]$^+$ m/z 450.1. $^1$H NMR (500 MHz, DMSO-d$_6$): δ 10.34 (1H, s), 8.86 (1H, d, J=4.89 Hz), 8.43 (2H, broad s), 8.14 (1H, s), 8.01 (1H, s), 7.67 (1H, d, J=8.10 Hz), 7.39 (1H, t, 7.88 Hz), 7.34-7.29 (2H, m), 3.18-3.02 (2H, m), 2.61-2.54 (2H, m), 1.92-1.77 (2H, m), 1.51 (3H, s), 1.55-1.41 (1H, m), 1.38-1.22 (1H, m). rhSYK activity=+++

The following examples were prepared in an analogous manner of that described in Examples 15(1)/15(2). 1-[5-(3-{[4-(Trifluoromethyl)pyrimidin-2-yl]amino}phenyl)-1,3-thiazol-2-yl]ethanol (Example 15-5) was prepared by coupling INTERMEDIATE 23 to 2-chloro-4-(trifluoromethyl)pyrimidine under microwave irradiation (K$_2$CO$_3$, DMF, 160° C., 20 min).

TABLE 15

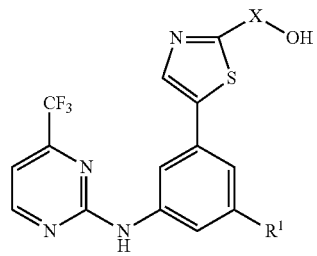

| Example | R$^1$ | X | rhSYK Activity | [M + H]+ Observed | Form(s) |
|---|---|---|---|---|---|
| 15-1 | H | C(cPr)$_2$ | +++ | 415.1 (M − H$_2$O + H) | Free Base |
| 15-2 | H | (spirocyclopentyl) | +++ | 407.1 | Free Base |
| 15-3 | H | C(CH$_3$)(cPr) | +++ | 389.1 (M − H$_2$O + H) | Free Base |
| 15-4 | CH$_3$ | C(CH$_3$)(CF$_3$) | +++ | 449.0 | TFA Salt |
| 15-5 | H | CHCH$_3$ | +++ | 367.0 | Free Base |

Example 16

N-(3-[2-(1-hydroxycyclobutyl)-1,3-thiazol-5-yl]-5-{[4-(trifluoromethyl)pyrimidin-2-yl]amino}phenyl) acetamide

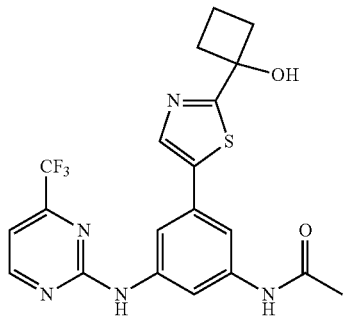 [SMILES: CC(=O)Nc1cc(Nc2nccc(C(F)(F)F)n2)cc(-c2cnc(C3(O)CCC3)s2)c1]

Step 1

To a solution of the compound of Example 18 (290 mg, 0.663 mmol) in DMF (2 mL) was added imidazole (99 mg, 1.46 mmol) and TBSCl (110 mg, 0.729 mmol). The mixture was stirred for 3 days at room temperature, then the mixture was diluted with ethyl acetate (100 mL) and washed with 1:1 H$_2$O:brine (2×100 mL). The organic extracts were dried (Na$_2$SO$_4$) filtered, and concentrated in vacuo. Purification by chromatography on silica gel (100:0 to 60:40 hexanes:ethyl acetate) provided 252 mg (0.457 mmol, 69%) of N-{3-[2-(1-{[tert-butyl-(dimethyl)silyl]oxy}cyclobutyl)-1,3-thiazol-5-yl]-5-nitrophenyl}-4-(trifluoromethyl)pyrimidin-2-amine as a bright yellow solid.

Step 2

To a solution of the product of Step 1 (252 mg, 0.457 mmol) in ethyl acetate (5 mL) was added 10% Pd/C (97 mg, 0.091 mmol), then the vessel headspace was purged with H₂(g) and the mixture was stirred under an atmosphere of H₂ (g) (1 atm) for 2 hours. Due to incomplete reaction (as evidenced by LCMS analysis), the headspace was purged with N₂, additional catalyst (~100 mg) was added and the vessel was again purged with H₂ and stirred under H₂ balloon overnight. The catalyst was deactivated by addition of dichloromethane, then the mixture was filtered through Celite (ethyl acetate rinse) and concentrated in vacuo to provide 219 mg (0.420 mmol, 92%) of 5-[2-(1-{[tert-butyl(dimethyl)silyl]oxy}cyclobutyl)-1,3-thiazol-5-yl]-N-[4-(trifluoromethyl)pyrimidin-2-yl]benzene-1,3-diamine as a brown foam.

Step 3, Part A

To a solution of the product of Step 3 (100 mg, 0.192 mmol) in dichloromethane (2 mL) were added Et₃N (67 µL, 0.48 mmol) and AcCl (20 µL, 0.29 mmol) as solutions in dichloromethane. After 2 hours, the mixture was diluted with ethyl acetate (100 mL) and washed with brine (100 mL). The organic extracts were dried (Na₂SO₄) and concentrated in vacuo. Part B: The residue was dissolved in THF (2 mL), TBAF (576 µL, 1.0 M; 0.576 mmol) was added and the mixture was stirred at room temperature for 90 minutes. The mixture was concentrated in vacuo, then purified by chromatography on silica gel (50:50 to 0:100 hexanes:ethyl acetate), which provided the desired alcohol contaminated with ~1-2% of the free aniline remaining from incomplete acylation in the first step. Trituration with dichloromethane provided 28 mg (0.062 mmol, 32%) of N-(3-[2-(1-hydroxycyclobutyl)-1,3-thiazol-5-yl]-5-{[4-(trifluoromethyl)-pyrimidin-2-yl]amino}phenyl)acetamide as a white solid. MS APCI: [M+H]⁺ m/z 450.0. ¹H NMR (400 MHz, d₆-acetone): δ 9.31 (br s, 2H); 8.83 (d, J=4.9 Hz, 1H); 8.10 (s, 1H); 8.01 (s, 1H); 7.95 (s, 1H); 7.73 (s, 1H); 7.25 (d, J=4.9 Hz, 1H); 5.51 (s, 1H); 2.74-2.64 (m, 2H); 2.48-2.37 (m, 2H); 2.12 (s, 3H); 2.04-1.91 (m, 2H). rhSYK activity=+++

The following examples were prepared in an analogous manner of that described in Example 16.

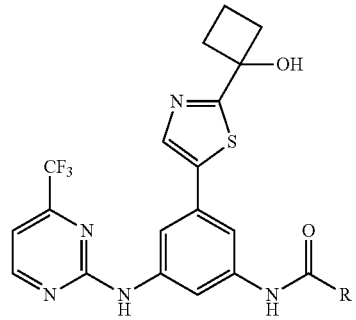

| Example | R | rhSYK Activity | [M +H ]+ Observed | Form(s) |
|---|---|---|---|---|
| 16-1 | nPr | +++ | 478.1 | Free Base |
| 16-2 | cPr | +++ | 476.1 | Free Base |

Example 17

1-[5-(3-amino-5-{[4-(trifluoromethyl)pyrimidin-2-yl]amino}phenyl)-1,3-thiazol-2-yl]cyclobutanol

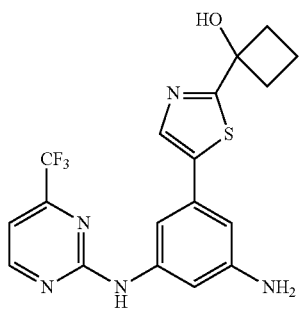 [SMILES: Nc1cc(Nc2nccc(C(F)(F)F)n2)cc(-c2cnc(C3(O)CCC3)s2)c1]

The title compound was obtained by deacylating the product of Example 16, step 2. MS APCI [M+H]⁺ m/z 408.1. ¹H NMR (400 MHz, CDCl₃) δ 8.67 (d, J=4.9, 1H), 7.87 (s, 1H), 7.46 (s, 1H), 7.10 (s, 1H), 7.06 (d, J=4.9, 1H), 6.62 (s, 1H), 3.86 (s, 2H), 3.50 (s, 1H), 2.72 (ddd, J=13.1, 6.9, 3.6, 2H), 2.52 (dt, J=10.8, 9.4 2H), 2.27-1.91 (m, 2H). rhSYK Activity: +++

Example 18

1-[5-(3-nitro-5-{[4-(trifluoroethyl)pyrimidin-2-yl]amino}phenyl)-1,3-thiazol-2-yl]cyclobutanol

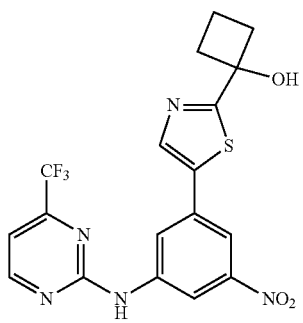 [SMILES: O=[N+]([O-])c1cc(Nc2nccc(C(F)(F)F)n2)cc(-c2cnc(C3(O)CCC3)s2)c1]

A mixture of 2-chloro-4-(trifluoromethyl)pyrimidine (2.04 mL, 16.9 mmol), Intermediate 22 (4.69 g, 16.1 mmol), cesium carbonate (10.5 g, 32.2 mmol), XantPhos (1.40 g, 2.41 mmol) and Pd(OAc)₂ (0.361 g, 1.61 mmol) in dixoane (100 mL) was heated to 100° C. overnight. Upon completion the reaction was cooled to room temperature and was diluted with ethyl acetate (100 mL) and filtered through Celite. After in vacuo concentration, purification by chromatography on silica gel (70:30 to 20:80 hexanes:ethyl acetate) provided 4.23 g (9.67 mmol, 60%) of 1-[5-(3-nitro-5-{[4-(trifluoromethyl)pyrimidin-2-yl]amino}phenyl)-1,3-thiazol-2-yl]cyclobutanol as a bright yellow solid. MS APCI: [M+H]⁺ m/z 438.0. ¹H NMR (400 MHz, Acetone): δ 9.74 (s, 1H); 8.96 (s, 1H); 8.85 (s, 1H); 8.60 (s, 1H); 8.24 (s, 1H); 8.15 (s, 1H); 7.40 (s, 1H); 5.64 (s, 1H); 2.86 (s, 2H); 2.72 (s, 2H); 2.47 (d, J=11.2 Hz, 2H). rhSYK=++.

Example 19

1-cyclopentyl-3-(3-[2-(1-hydroxycyclobutyl)-1,3-thiazol-5-yl]-5-{[4-(trifluoromethyl)pyrimidin-2-yl]amino}phenyl)urea

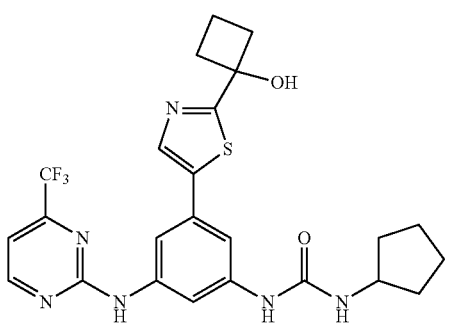 [SMILES: O=C(Nc1cc(Nc2nccc(C(F)(F)F)n2)cc(-c2cnc(C3(O)CCC3)s2)c1)NC1CCCC1]

Step 1

To a solution of N-{3-[2-(1-{[tert-butyl(dimethyl)silyl]oxy}cyclobutyl)-1,3-thiazol-5-yl]-5-nitrophenyl}-4-(trifluoromethyl)pyrimidin-2-amine (Example 16, step 1, 1.00 g, 1.81 mmol) in THF (9 mL) was added triethylamine (379 µL, 2.72 mmol), DMAP (22 mg, 0.18 mmol) then $Boc_2O$ (435 mg; 1.99 mmol) and the mixture was stirred overnight at room temperature. The mixture was diluted with ethyl acetate (100 mL) and washed with $H_2O$ (100 mL) and brine (100 L). The organic extracts were dried ($Na_2SO_4$) and concentrated in vacuo. Purification by chromatography on silica gel (100:0 to 40:60, hexanes:ethyl acetate) provided 1.13 g (1.73 mmol, 96%) of tert-butyl {3-[2-(1-{[tert-butyl(dimethyl)silyl]oxy}cyclobutyl)-1,3-thiazol-5-yl]-5-nitrophenyl}[4-(trifluoromethyl)pyrimidin-2-yl]carbamate as an off-white foam.

Step 2

To a solution of the product of Step 1 (200 mg, 0.307 mmol) in ethyl acetate (1.5 mL) was added 10% Pd/C (65 mg, 0.061 mmol), and the vessel headspace was evacuated and purged with $H_2$. The mixture was stirred under an atmosphere of $H_2$ (balloon) for 3 hours, at which point LCMS analysis indicated incomplete reaction. The headspace was evacuated and purged with $N_2$, then 100 mg additional catalyst was added and the headspace evacuated again and purged with $H_2$. The catalyst was deactivated by adding dichloromethane, then the mixture was filtered through a pre-packed Celite cartridge (ethyl acetate rinse) and concentrated in vacuo. Purification by chromatography on silica gel (80:20 to 0:100, hexanes:ethyl acetate) provided 112 mg (0.180 mmol, 59%) of tert-butyl {3-amino-5-[2-(1-{[tert-butyl(dimethyl)silyl]oxy}cyclobutyl)-1,3-thiazol-5-yl]phenyl}[4-(trifluoromethyl)pyrimidin-2-yl]carbamate as a colorless oil.

Step 3

To a solution of the product of Step 2 (56 mg; 0.090 mmol) in THF (0.9 mL) was added triethylamine (38 µL; 0.27 mmol) followed by the isocyanatocyclopentane (31 µL; 0.27 mmol), then the mixture was stirred at room temperature overnight, at which point LC-UV analysis indicated ~70% conversion to the desired urea. Additional $Et_3N$ and isocyanate (0.27 mmol each) were added, and the mixture was heated to 50° C. for 3 hours, at which point LC-UV indicated complete conversion. The mixture was diluted with ethyl acetate (30 mL) and washed with water (30 mL) and brine (30 mL). The organic extracts were dried ($Na_2SO_4$) and concentrated in vacuo. Purification by chromatography on silica gel (90:10 to 40:60, hexanes:ethyl acetate) provided 57 mg (0.078 mmol, 86%) of tert-butyl (3-[2-(1-{[tert-butyl(dimethyl)silyl]oxy}cyclobutyl)-1,3-thiazol-5-yl]-5-[(cyclopentylcarbamoyl)amino]phenyl) [4-(trifluoromethyl)pyrimidin-2-yl]carbamate as a white foam.

Step 4

To a solution of the product of Step 3 (56 mg, 0.076 mmol) in dichloromethane (1 mL) was added TEA (1 mL) and the mixture was stirred for 60 minutes at room temperature. The mixture was concentrated in vacuo, then the residue was diluted with ethyl acetate (30 mL) and washed with sat. $NaHCO_3(aq)$ (30 mL) and brine (30 mL). The organic extracts were dried ($Na_2SO_4$) and concentrated in mew. The residue was dissolved in THF (1 mL), TBAF (228 lit, 1.0 M; 0.228 mmol) was added, and the mixture was stirred overnight at room temperature. The mixture was concentrated in vacuo, and the residue purified by chromatography on silica gel (100:0 to 80:20, ethyl acetate: EtOH) provided 9 mg (0.017 mmol, 28%) of the desired 1-cyclopentyl-3-(3-[2-(1-hydroxycyclobutyl)-1,3-thiazol-5-yl]-5-{[4-(trifluoromethyl)pyrimidin-2-yl]amino}phenyl)urea as a white solid. MS APCI: $[M+H]^+$ m/z 519.1. $^1H$ NMR (400 MHz, $d_6$-acetone): δ 9.22 (s, 1H); 8.81 (d, J=4.9 Hz, 1H); 8.00-7.90 (m, 3H); 7.78 (s, 1H); 7.66 (s, 1H); 7.23 (d, J=4.9 Hz, 1H); 5.90 (d, J=7.0 Hz, 1H); 5.49 (s, 1H); 4.17-4.08 (m, 1H); 2.79-2.59 (m, 2H); 2.49-2.37 (m, 2H); 2.06-1.88 (m, 4H); 1.82-1.48 (m, 4H); 1.51-1.42 (m, 2H). rhSYK activity=+++

The following examples were prepared in an analogous manner of that described in Examples 18/19.

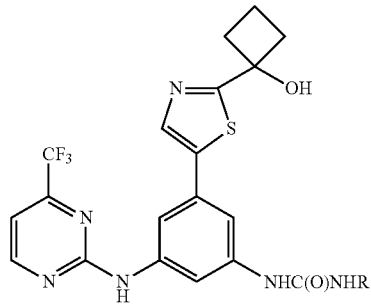

| Example | R | rhSYK Activity | [M + H]+ Observed | Form(s) |
|---|---|---|---|---|
| 19-1 | Et | +++ | 479.1 | Free Base |
| 19-2 | H | +++ | 451.1 | Free Base |
| 19-3 | Me | +++ | 465.1 | Free Base |
| 19-4 | iPr | +++ | 493.1 | Free Base |
| 19-5 | —C(O)NH$_2$ | +++ | 494.1 | Free Base |

Examples 20(1) and 20(2)

4-[5-(3-[(ethylcarbamoyl)amino]-5-{[4-(trifluoromethyl)pyrimidin-2-yl]amino}phenyl)-1,3-thiazol-2-yl]cyclohexanecarboxamide

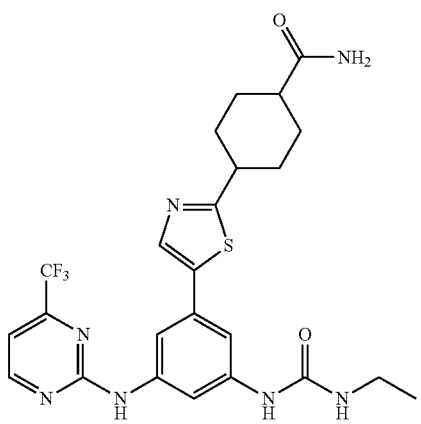 [SMILES: CCNC(=O)Nc1cc(Nc2nccc(C(F)(F)F)n2)cc(-c2cnc(C3CCC(C(N)=O)CC3)s2)c1]

Step 1

To a solution of ethyl 4-[5-(3-[(ethylcarbamoyl)amino]-5-{[4-(trifluoromethyl)pyrimidin-2-yl]amino}phenyl)-1,3-thiazol-2-yl]cyclohexanecarboxylate (2.030 g, 3.70 mmol) in tetrahydrofuran (13.45 mL) and methanol (5.045 mL) was added aqueous 1N LiOH (11.10 mL, 11.10 mmol). The resulting solution was stirred 2 h at room temperature and 2 h at 50° C. The reaction was cooled to ambient temperature and was then quenched with HCl (11.10 mL, 11.10 mmol) and then diluted with aqueous 25% $NH_4OAc$ (to pH=7). The mixture was extracted with 2-Me-THF. The combined organic fractions were washed with brine, dried ($Na_2SO_4$), and filtered. The solvent was evaporated under reduced pressure and the resultant residue was purified by column chromatography on silica gel (Combiflash, 0-100% ethanol in dichloromethane) to give a brown oil-solid. The residue was triturated in hot ethyl acetate. Diethyl ether was added and the product was isolated by filtration. The solid was dried to give 4-[5-(3-[(ethylcarbamoyl)amino]-5-{[4-(trifluoromethyl)pyrimidin-2-yl]amino}phenyl)-1,3-thiazol-2-yl]cyclohexanecarboxylic acid (396 mg, 0.741 mmol, 20.02% yield) as a mixture of the syn and anti diastereoisomers. MS APCI: [M+H]+ m/z 535.1.

Step 2

The product of Step 1 (396 mg, 0.741 mmol) was dissolved in Mg (3.50 mL). To this solution was added HATU (563 mg, 1.482 mmol) and DIPEA (0.776 mL, 4.44 mmol), followed by ammonium chloride (119 mg, 2.222 mmol). Reaction was complete after stirring 1 hour at room temperature. The reaction mixture was diluted with saturated $NaHCO_3$(aq) and 2-MeTHF. The phases were separated and the organic layer was washed with brine, dried over sodium sulfate, filtered, and concentrated to dryness. The mixture of syn and anti iomers was diluted in DMSO was purified by reversed phase HPLC ($C_{18}$ column; MeCN/water with 0.1% TFA added) to yield:

Example 20(1): Diastereoisomer 1 (20 mg, 0.037 mmol, 5.06% yield): fast eluting on Polar RP—100 mm×21 mm—, eluting with 0.6% HCOOH/MeCN. MS APCI: [M+H]+ m/z 534.2. ¹H NMR (400 MHz, DMSO-$d_6$): δ 10.24 (s, 1H); 8.83 (d, J=4.9 Hz, 1H); 8.54 (s, 1H); 7.85 (s, 1H); 7.76 (s, 1H); 7.56 (s, 1H); 7.50 (s, 1H); 7.29 (d, J=4.9 Hz, 1H); 7.24 (s, 1H); 6.71 (s, 1H); 6.16 (t, J=5.6 Hz, 1H); 3.17-3.07 (m, 2H); 3.01-2.92 (m, 1H); 2.22-2.11 (m, 3H); 1.93-1.82 (m, 2H); 1.59-1.44 (m, 4H); 1.07 (t, J=7.2 Hz, 3H). rhSYK activity=+++ Example 20(2): Diastereoisomer 2 (20 mg, 0.037 mmol, 5.06% yield): slow eluting on Polar RP—100 mm×21 mm, eluting with 0.6% HCOOH/MeCN MS APCI: [M+H]+ m/z 534.2. ¹H NMR (400 MHz, DMSO-$d_6$): δ 10.24 (s, 1H); 8.83 (d, J=4.9 Hz, 1H); 8.69 (s, 1H); 7.85 (s, 1H); 7.77 (s, 1H); 7.56 (s, 1H); 7.53 (s, 1H); 7.28 (d, J=4.9 Hz, 1H); 7.21 (s, 1H); 6.71 (s, 1H); 6.35-6.26 (m, 1H); 3.23-3.15 (m, 1H); 3.17-3.07 (m, 2H); 2.36-2.27 (m, 1H); 2.12-2.00 (m, 2H); 1.91-1.75 (m, 4H); 1.67-1.55 (m, 2H); 1.06 (t, J=7.1 Hz, 3H). rhSYK activity=+++

Example 21

2-methyl-2-[5-(3-{[4-(trifluoromethyl)pyrimidin-2-yl]amino}phenyl)-1,3-thiazol-2-yl]propan-1-ol

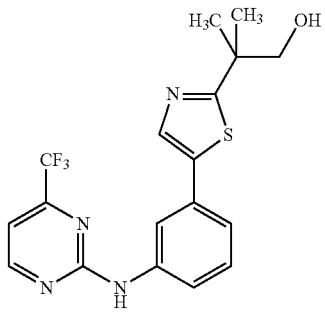 [SMILES: CC(C)(CO)c1ncc(-c2cccc(Nc3nccc(C(F)(F)F)n3)c2)s1]

Step 1

To a solution of 2-amino-1-(3-nitrophenyl)ethanone HCl salt (300 mg, 138 mmol) and 3-{[tert-butyl(diphenyl)silyl]oxy}-2,2-dimethylpropanoic acid (543 mg, 1.52 mmol) in DMF (1.3 mL) was added HATU (579 mg, 1.52 mmol) and the mixture was cooled to 0° C. Hunig's base (726 µL, 4.15 mmol) was added, and the mixture was stirred for two hours at this temperature. The mixture was diluted with ethyl acetate (30 mL), then washed with 1:1 water:saturated $NaHCO_3$(aq) (30 mL) and 1:1 water:brine (2×30 mL). The aqueous fractions were further extracted with ethyl acetate (30 mL), then the combined organic extracts were dried ($Na_2SO_4$) and concentrated in vacuo. Purification by chromatography on silica gel (100:0 to 50:50, hexanes:ethyl acetate) provided 680 mg of 3-{[tert-butyl(diphenyl)silyl]oxy}-2,2-dimethyl-N-[2-(3-nitrophenyl)-2-oxoethyl]propanamide (1.31 mmol, 95%) as a white solid.

Step 2

To a solution of the product of Step 1 (680 mg, 1.31 mmol) in toluene (6.5 mL) was added Lawesson's reagent (530 mg, 1.31 mmol) and the mixture was heated to 100° C. for 20 hours and then cooled to rt then the mixture was concentrated in vacuo. Purification by chromatography on silica gel (100:0 to 50:50, hexanes:ethyl acetate) provided 461 mg (0.892 mmol, 68%) of 2-(1-{[tert-butyl(diphenyl)silyl]oxy}-2-methylpropan-2-yl)-5-(3-nitrophenyl)-1,3-thiazole as a colorless viscous oil.

Step 3

To a solution of the product of Step 2 (461 mg, 0.892 mmol) in ethyl acetate (9 mL) was added Pd/C (10 wt %, 190 mg, 0.178 mmol), and the reaction vessel was charged with $H_2$ (balloon) and stirred overnight, at which point LCMS analysis indicated complete conversion. Dichloromethane was added to deactivate the catalyst, and the mixture was filtered through a pad of Celite (ethyl acetate rinse) and concentrated in vacuo to provided 393 mg (0.807 mmol, 91%) of 3-[2-(1-{[tert-butyl(diphenyl)silyl]oxy}-2-methylpropan-2-yl)-1,3-thiazol-5-yl]aniline as a light yellow oil.

Step 4

To a suspension of the product of Step 3 (393 mg, 0.807 mmol), cesium carbonate (526 mg; 1.62 mmol), XantPhos (70.1 mg, 0.121 mmol) and palladium(II) acetate (18 mg; 0.081 mmol) in dioxane (5 mL) was added the 2-chloro-4-(trifluoromethyl)pyrimidine (102 μL; 0.848 mmol). The reaction was stirred at 100° C. overnight. After dilution with ethyl acetate (100 mL), the mixture was filtered through celite and concentrated in vacuo. Purification by chromatography on silica gel (100:0 to 50:50, hexanes:ethyl acetate) provided 327 mg (0.517 mmol, 64%) of N-{3-[2-(1-{[tert-butyl(diphenyl)silyl]oxy}-2-methylpropan-2-yl)-1,3-thiazol-5-yl]phenyl}-4-(trifluoromethyl)pyrimidin-2-amine as an off-white foam.

Step 5

To a solution of the product of Step 4 (327 mg, 0.517 mmol) in THF (3 mL) was added TBAF (1.0 M, 1.55 mL, 1.55 mmol), and the mixture stirred at room temperature for 2 weeks at which point LCMS showed complete conversion. The mixture was concentrated in vacuo, then the residue purified by chromatography on silica gel (60:40 to 0:100, hexanes:ethyl acetate) to provide 162 mg (0.411 mmol, 79%) of 2-methyl-2-[5-(3-{[4-(trifluoromethyl)pyrimidin-2-yl]amino}phenyl)-1,3-thiazol-2-yl]propan-1-ol as a white solid. MS APCI: [M+H]$^+$ m/z 395.0. $^1$H NMR (400 MHz, CDCl$_3$): δ 8.67 (d, J=4.9 Hz, 1H); 8.07 (s, 1H); 7.85 (s, 1H); 7.63 (s, 1H); 7.49 (d, J=8.2 Hz, 1H); 7.37 (t, J=7.9 Hz, 1H); 7.26 (d, J=7.7 Hz, 1H); 7.07 (d, J=4.9 Hz, 1H); 3.79 (s, 2H); 1.48 (s, 6H). rhSYK activity=+++

The following examples were prepared in an analogous manner of that described in Example 21.

TABLE 21

| Example | R | rhSYK Activity | [M + H]+ Observed | Form(s) |
|---|---|---|---|---|
| 21-1 | 2-tetrahydrofuranyl | +++ | 393.1 | Free Base |
| 21-2 | 4-Me-2-morpholinyl | +++ | 422.1 | Free Base |
| 21-3 | —CH$_2$SO$_2$CH$_3$ | +++ | 415.0 | Free Base |
| 21-4 | 1-Me-4-pyrazolyl | +++ | 403.1 | Free Base |
| 21-5 | 3-tetrahydrofuranyl | +++ | 393.1 | Free Base |
| 21-6 | 4-morpholinylmethyl | +++ | 422.1 | Free Base |
| 21-7 | 2,3-dihydro-1-indenyl | + | 439.1 | Free Base |
| 21-8 | —C(OH)(CH$_3$)CH$_2$CH$_2$N(Et)$_2$ | ++ | 466.1 | Free Base |
| 21-9 | 3,3-diF—cBu | ++ | 413.0 | Free Base |
| 21-10 | 2-oxo-3-oxazolidinylmethyl | +++ | 422.0 | Free Base |
| 21-11 | trans-4-CO$_2$CH$_3$—cHex | ++ | 463.1 | Free Base |
| 21-12 | trans-4-(CONHCH$_2$CH$_2$OH)—cHex | +++ | 492.1 | Free Base |
| 21-13 | trans-4-(CONH—cPr)—cHex | +++ | 488.1 | Free Base |
| 21-14 | 2-oxo-4-pyrrolidinyl | +++ | 406.0 | Free Base |
| 21-15 | 1,4-dioxan-2-yl | +++ | 409.1 | Free Base |
| 21-16 | —CH$_2$CH$_2$-(2-thioxo-1-pyrrolidinyl) | +++ | 450.1 | Free Base |
| 21-17 | 1-Me-2-oxo-5-piperidinyl | +++ | 434.1 | Free Base |
| 21-18 | 1-Me-2-azepanyl | ++ | 434.1 | Formate Salt |

Example 22

Trans-4-[5-(3-{[4-(trifluoromethyl)pyrimidin-2-yl]amino}phenyl)-1,3-thiazol-2-yl]cyclohexanecarboxylic acid

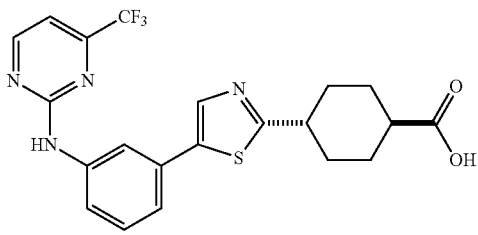

To a solution of methyl trans-4-[5-(3-{[4-(trifluoromethyl)pyrimidin-2-yl]amino}phenyl)-1,3-thiazol-2-yl]cyclohexanecarboxylate (Example 21-11, 91 mg, 0.197 mmol) in tetrahydrofuran (2.00 mL) and methanol (0.75 mL) was added aqueous 1N LiOH (0.590 mL, 0.590 mmol). The resultant solution was stirred 20 minutes at room temperature and then 30 minutes at 50° C. The solution cooled to room temperature and was quenched with HCl (0.571 mL, 0.571 mmol) and then aqueous 25% NH$_4$OAc solution (to pH-7). The mixture was extracted with 2-Me-THF.

The combined organic fractions were washed with brine, dried (Na$_2$SO$_4$), and were filtered before concentration to dryness. The residue was triturated in hot ethyl acetate. The product was collected by filtration (wash with ethyl acetate, then ether and then hexanes) to yield trans-4-[5-(3-{[4-(trifluoromethyl)pyrimidin-2-yl]amino}phenyl)-1,3-thiazol-2-yl]cyclohexanecarboxylic acid (37.6 mg 0.084 mmol, 43%) as a yellowish solid. MS APCI [M+H]⁺ m/z 449.1. ¹H NMR (400 MHz, DMSO) δ 12.12 (s, 1H), 10.34 (s, 1H), 8.86 (d, J=4.9, 1H), 8.15 (s, 1H), 7.99 (s, 1H), 7.66 (d, J=8.0, 1H), 7.39 (t, J=7.9, 1H), 7.35-7.29 (m, 2H), 3.07-2.89 (m, 1H), 2.30 (ddd, J=11.5, 6.8, 2.5, 1H), 2.16 (d, J=10.4, 2H), 2.09-1.96 (m, 2H), 1.66-1.41 (m, 4H). rhSYK Activity: +++

Example 23 trans-N-cyclopropyl-4-[5-(3-{[4-(trifluoromethyl)pyrimidin-2-yl]amino}phenyl)-1,3-thiazol-2-yl]cyclohexanecarboxamide

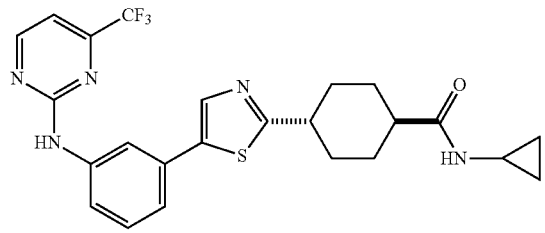

trans-4-[5-(3-{[4-(Trifluoromethyl)pyrimidin-2-yl]amino}phenyl)-1,3-thiazol-2-yl]cyclohexane-carboxylic acid (27 mg, 0.060 mmol) was dissolved in DMF (0.60 mL). To this solution was added HATU (24.04 mg, 0.063 mmol), DIPEA (0.063 mL, 0.361 mmol), followed by cyclopropylamine (3.44 mg, 0.060 mmol). The reaction was complete after stirring 1 hour at room temperature. The reaction mixture was diluted with saturated NaHCO₃ and 2-Me-THF. The phases were separated and aqueous was extracted twice with ethyl acetate. The combined organics were washed with brine, dried over sodium sulfate and were concentrated in vacuo. The residue was purified by column chromatography on silica gel (Combiflash, 0-50% EtOH in DCM) to yield trans-N-cyclopropyl-4-[5-(3-{[4-(trifluoromethyl)pyrimidin-2-yl]amino}phenyl)-1,3-thiazol-2-yl]cyclohexanecarboxamide (10.9 mg, 0.022 mmol, 37.1% yield) as an off-white solid. MS APCI: [M+H]⁺ m/z 488.1. ¹H NMR (400 MHz, DMSO-d₆): δ 10.33 (s, 1H); 8.85 (d, J=4.8 Hz, 1H); 8.16 (s, 1H); 7.99 (s, 1H); 7.82 (d, J=4.2 Hz, 1H); 7.65 (d, J=8.0 Hz, 1H); 7.38 (t, J=7.9 Hz, 1H); 7.34-7.28 (m, 2H); 3.04-2.92 (m, 1H); 2.64-2.59 (m, 1H); 2.21-2.06 (m, 3H); 1.87-1.77 (m, 2H); 1.61-1.40 (m, 4H); 0.63-0.57 (m, 2H); 0.42-0.34 (m, 2H), rhSYK activity=+++

Compounds in the following Table were prepared in a manner analogous of that described in Example 23:

| Example | Structure | hSYK Activity | [M + H]⁺ obs'd | Form(s) |
|---|---|---|---|---|
| 23-1 | 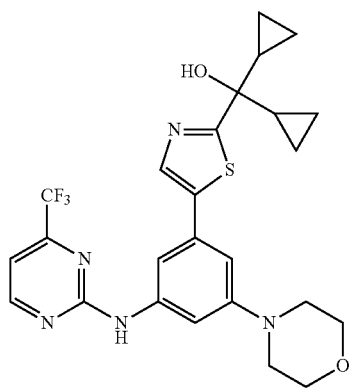 [SMILES: OC(c1ncc(-c2cc(Nc3nccc(C(F)(F)F)n3)cc(N3CCOCC3)c2)s1)(C1CC1)C1CC1] (trans) | +++ | 448.1 | Free Base |

Example 24 dicyclopropyl{5-[3-(morpholin-4-yl)-5-{[4-(trifluoromethyl)pyrimidin-2-yl]amino}phenyl]-1,3-thiazol-2-yl}methanol

Step 1 n-Butyllithium (2.5 M in hexanes, 0.953 mL, 2.38 mmol) was added to a stirred, cooled −78° C. mixture of thiazole (0.169 mL, 2.383 mmol) in THF (5.0 mL) and the mixture was stirred at −78° C. for 15 min. A solution of the dicyclopropylmethanone (250 mg, 2.27 mmol) in THF (3.0 mL) was added dropwise and the mixture was stirred 30 mill at −78° C. and then the temperature was allowed to reach room temperature. The reaction was quenched by addition of water and the mixture was extracted with ethyl acetate (3×). The combined organic fractions were washed with brine, dried (Na₂SO₄), filtered and the solvent was evaporated under reduced pressure. The residue was purified by chromatography on silica gel (0-100% ethyl acetate in hexanes) to give dicyclopropyl(1,3-thiazol-2-yl)methanol (412 mg, 2.110 mmol, 93% yield). MS APCI: [M-OH]+ m/z 179.0.

Step 2

Bromine (0.271 mL, 5.26 mmol) was added dropwise to a stirred mixture of the product of Step 1 (411 mg, 2.10 mmol)

and NaOAc (863 mg; 10.5 mmol) in acetic acid (9.17 mL) and the mixture was stirred at room temperature for 4 h. The reaction was quenched with brine and the aqueous layer was extracted with ethyl acetate (3×). The combined organics were washed with brine, dried (sodium sulfate), filtered, and concentrated. The residue was purified by chromatography on silica gel (0-100% ethyl acetate in hexanes) to give (5-bromo-1,3-thiazol-2-yl)(dicyclopropyl)methanol (329 mg, 1.20 mmol, 57% yield) as an off-white solid. MS APCI: [M-OH]+ m/z 255.9

Step 3

To a solution of 4-(3-iodo-5-nitrophenyl)morpholine (Intermediate 8, 1.00 g, 2.99 mmol) and bis(pinacolato)diboron (0.836 g, 3.29 mmol) in DMSO (13 mL) was added Pd(dppf)Cl$_2$ (0.110 g, 0.150 mmol) and KOAc (0.881 g, 8.98 mmol) and the mixture was degassed with N$_2$. The mixture was then irradiated to 125° C. in the microwave for 30 minutes. After cooling to room temperature, the mixture was diluted with 1:1 water:brine, and extracted with ethyl acetate. The organic layer was washed with 1:1 water:brine (4×), dried (sodium sulfate), filtered, and concentrated in vacuo to provide 1.36 g of 4-[3-nitro-5-(4,4,5,5-tetramethyl-1,3,2-dioxaborolan-2-yl)phenyl]morpholine as a green-brown solid which was used directly without further purification.

Step 4

A solution of the product of Step 2 (239 mg, 0.872 mmol), crude product of Step 3 (320 mg, ~0.96 mmol), Pd(dppf)Cl$_2$ (31.9 mg, 0.044 mmol) and Na$_2$CO$_3$ (aq) (2.0 M, 1.3 mL, 2.6 mmol) in DME (4.4 mL) was irradiated to 130° C. in the microwave for 35 minutes. The reaction mixture was filtered through a celite pad with dichloromethane and the filtrate was concentrated. The residue was purified twice by chromatography on silica gel (0-100% ethyl acetate in hexanes then 0-60% dichloromethane in ethyl acetate) to give the desired dicyclopropyl{5-[3-(morpholin-4-yl)-5-nitrophenyl]-1,3-thiazol-2-yl}methanol (239 mg, 0.595 mmol, 68% yield) as a yellow solid. MS APCI: [M-OH]+ m/z 385.1.

Step 5

To a solution of the product of Step 4 (239 mg, 0.595 mmol) in ethyl acetate (5.4 mL)/acetic acid (0.54 mL) was added Pd/C (10 wt %, 60 mg, 0.056 mmol) and the reaction flask was purged with N$_2$ and then H$_2$. The reaction was stirred for 4 hr at room temperature under H$_2$ (balloon; 25 mg of Pd/C were added after 2 h to complete the reaction) and then filtered through a microfilter (Glass Acrodisc 25 mm) and was washed with dichloromethane. The filtrate was concentrated, stripped with toluene (3×) and then dried under vacuum overnight to provide 221 mg (0.595 mmol, quant. yield) of {5-[3-amino-5-(morpholin-4-yl)phenyl]-1,3-thiazol-2-yl}(dicyclopropyl)methanol as a fluffy solid of sufficient purity to be used directly. MS APCI: [M+H]$^+$ m/z 372.1.

Step 6

To a solution of 2-chloro-4-(trifluoromethyl)pyrimidine (0.079 mL, 0.654 mmol) and the product of Step 5 (221 mg, 0.595 mmol) in dioxane (4.0 mL) was added cesium carbonate (388 mg, 1.190 mmol), Pd(OAc)$_2$ (6.68 mg, 0.030 mmol) and XantPhos (51.6 mg, 0.089 mmol) and the mixture was heated to 125° C. for 2 hours. After cooling to room temperature, 1.5 mL of water was added and the reaction mixture was filtered through a celite column with dichloromethane. The filtrate was concentrated and the residue was purified by chromatography on silica gel (0-100% ethyl acetate in hexanes). The yellow residue was triturated in diethyl ether (with trace dichloromethane) to give dicyclopropyl{5-[3-(morpholin-4-yl)-5-{[4-(trifluoromethyl)pyrimidin-2-yl]amino}phenyl]-1,3-thiazol-2-yl}methanol (165 mg, 0.319 mmol, 54% yield) as an off-white solid. MS APCI: [M+H]$^+$ m/z 518.1. $^1$H NMR (400 MHz, DMSO-d$_6$): δ 10.17 (s, 1H); 8.84 (d, J=4.9 Hz, 1H); 7.98 (s, 1H); 7.57 (s, 1H); 7.40 (s, 1H); 7.28 (d, J=4.9 Hz, 1H); 6.89 (s, 1H); 5.38 (s, 1H); 3.77 (t, J=4.3 Hz, 4H); 3.17 (t, J=4.4 Hz, 4H); 1.41-1.33 (m, 2H); 0.54-0.38 (m, 6H); 0.32-0.24 (m, 2H). rhSYK activity=+++

The following examples were prepared in an analogous manner of that described in Example 24.

TABLE 24

| Example | X | R | rhSYK Activity | [M + H]+ Observed | Form(s) |
|---|---|---|---|---|---|
| 24-1 | O | —CH(OH)CH$_3$ | +++ | 452.1 | Free Base |
| 24-2 | O | 2-Me-1,3-dioxolan-2-yl | +++ | 494.1 | Free Base |
| 24-3 | O | —C(O)CH$_3$ | +++ | 450.1 | Free Base |
| 24-4 | N—SO$_2$CH$_3$ | 1-OH—cBu | +++ | 555.1 | Free Base |
| 24-5 | O | 1-OH—cBu | +++ | 478.2 | Free Base |
| 24-6 | O | —C(OH)(cPr)CH$_3$ | +++ | 492.1 | Free Base |
| 24-7 | O | —C(OH)(CF$_3$)CH$_3$ | +++ | 520.1 | Free Base |

Example 25

(1S,4R)-4-hydroxy-2,2-dimethyl-4-[5-(3-methyl-5-{[4-(trifluoromethyl)pyrimidin-2-yl]amino}phenyl)-1,3-thiazol-2-yl]-N-[3-(2-oxopyrrolidin-1-yl)propyl]cyclohexanecarboxamide

Example 26 cis-4-Fluoro-4-[5-(3-methyl-5-{[4-(trifluoromethyl)pyrimidin-2-yl]amino}phenyl)-1,3-thiazol-2-yl]cyclohexanecarboxylic acid

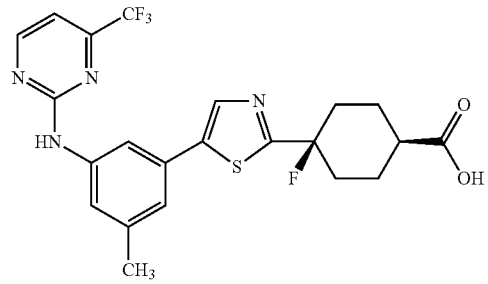 [SMILES: Cc1cc(Nc2nccc(C(F)(F)F)n2)cc(-c2cnc([C@]3(F)CC[C@@H](C(=O)O)CC3)s2)c1]

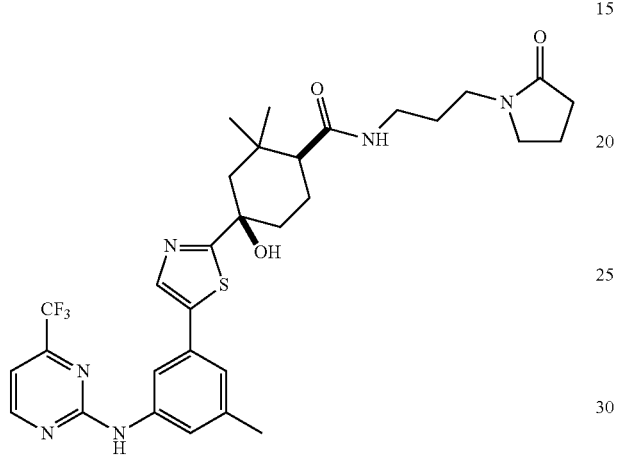

To (1S,4R)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid (102 mg, 0.20 mmol), N-(3-aminopropyl)-2-pyrrolidinone (85 µL, 0.60 mmol), EDC (58 mg, 0.30 mmol), and HOBt (46 mg, 0.30 mmol) was added N,N-dimethylformamide (2 mL) and triethylamine (140 µL, 1.01 mmol). The mixture was stirred at room temperature for 16 h, quenched with 1:1 water:brine, and extracted with EtOAc. The organic layer was washed with 1:1 water:brine (3×). The organic layer was dried over magnesium sulfate, filtered and purified by reverse phase HPLC (C-18, eluting with a 45:55 to 80:20 gradient of acetonitrile:water+0.1% TFA). The combined fractions were diluted with ethyl acetate and dichloromethane and washed with saturated aqueous sodium bicarbonate solution. The organic layer was separated, dried over magnesium sulfate, filtered and concentrated to afford the title compound (97 mg, 0.15 mmol, 76% yield) as a white solid. MS ESI: [M+H]$^+$ m/z 631.2. $^1$H NMR (500 MHz, DMSO-d$_6$) δ 10.25 (s, 1H), 8.83 (d, J=4.9, 1H), 7.93 (s, 1H), 7.92 (s, 1H), 7.68 (t, J=5.6, 1H), 7.46 (s, 1H), 7.28 (d, J=4.9, 1H), 7.14 (s, 1H), 5.86 (s, 1H), 3.29 (s, 1H), 3.24-3.12 (m, 2H), 3.12-3.03 (m, 1H), 2.99-2.88 (m, 1H), 2.31 (s, 3H), 2.19 (m, 2H), 2.02 (m, 2H), 1.86 (m, 5H), 1.66-1.50 (m, 3H), 1.40 (m, 1H), 1.11 (s, 3H), 0.92 (s, 3H).

Step 1

To solution of tert-butyl 4-hydroxy-4-[5-(3-methyl-5-{[4-(trifluoromethyl)pyrimidin-2-yl]amino}phenyl)-1,3-thiazol-2-yl]cyclohexanecarboxylate (400 mg, 0.748 mmol) in dichloromethane (3.74 mL) and ethanol (2.2 µL, 0.037 mmol) was added Deoxofluor (690 µL, 3.74 mmol). The reaction was complete after stirring for one hour at room temperature. The reaction was diluted with ethyl acetate, washed with water, dried over magnesium sulfate, filtered and concentrated. Column chromatography was used for purification to provide the two isomers of tert-butyl 4-fluoro-4-[5-(3-methyl-5-{[4-(trifluoromethyl)pyrimidin-2-yl]amino}-phenyl)-1,3-thiazol-2-yl]cyclohexanecarboxylate. Cis-isomer (141 mg, 0.210 mmol, 28.1%). MS ESI: [M+H]$^+$ m/z 537.2. $^1$H NMR (500 MHz, DMSO-d$_6$) δ 10.28 (s, 1H), 8.83 (d, J=5.2, 1H), 8.07 (d, 2.9, 1H), 8.03 (s, J=8.3, 1H), 7.47 (s, 1H), 7.29 (d, J=5.1, 1H), 7.20 (s, 1H), 2.32 (s, 5H), 2.20-1.93 (m, 3H), 1.93-1.78 (m, 2H), 1.76-1.57 (m, 2H), 1.40 (s, 9H). Trans-isomer (175 mg, 0.326 mmol, 43.6%). MS ESI: [M+H]$^+$ m/z 537.2. $^1$H NMR (500 MHz, DMSO-d$_6$) δ 10.29 (s, 1H), 8.83 (d, J=5.3, 1H), 8.10 (s, 1H), 8.03 (s, 1H), 7.47 (s, 1H), 7.29 (d, J=5.2, 1H), 7.20 (s, 1H), 2.53 (s, 3H), 2.32 (s, 4H), 2.08-1.93 (m, 2H), 1.93-1.82 (m, 2H), 1.84-1.61 (m, 1H), 1.39 (s, 9H).

Step 2

To a solution of cis-tert-butyl 4-fluoro-4-[5-(3-methyl-5-{[4-(trifluoromethyl)pyrimidin-2-yl]amino}phenyl)-1,3-thiazol-2-yl]cyclohexanecarboxylate (67 mg, 0.125 mmol) in dichloromethane (2.50 mL) was added 2,6-lutidine (145 µL, 1.249 mmol) and tert-butyldimethylsilyl trifluoromethanesulfonate (860 µL, 3.75 mmol). The reaction was complete after 1 hour at room temperature. The reaction was diluted with ethyl acetate, washed with water, dried over magnesium sulfate, filtered and concentrated. Column chromatography was used for purification to yield a mixture of the fluoro carboxylic acid and the des-fluoro carboxylic acid. SEC was then used for further purification (Berger Multigram II SFC, column: Chiral Technology OJ 2.1×25 cm, 5 uM, mobile phase: 40% to 60% methanol in CO$_2$(1), flow rate: 70 mL/min, 7.5 min run time) to yield cis-4-fluoro-4-[5-(3-methyl-5-{[4-(trifluoromethyl)-pyrimidin-2-yl]amino}phenyl)-1,3-thiazol-2-yl]cyclohexanecarboxylic acid (17 mg, 0.035 mmol, 28.3%). MS ESI: [M+H]$^+$ m/z 481.1. $^1$H NMR (600 MHz, DMSO-d$_6$) δ 10.26 (s, 1H), 8.82 (d, J=4.9, 1H), 8.06 (d, J=2.8, 1H), 8.00 (s, 1H), 7.45 (s, 1H), 7.27 (d, J=4.9, 1H), 7.18 (s, 1H), 2.40 (t, J=12.1, 1H), 2.30 (s, 3H), 2.16 (t, J=11.8, 2H), 2.05 (dtd, J=4.4, 14.0, 40.0, 2H), 1.91 (d, J=13.3, 2H), 1.68 (tt, J=6.5, 12.9, 2H). rhSYK activity=+++

The following examples were prepared in an analogous manner of that described in Example 26.

TABLE 26

| Example | R | X | rhSYK Activity | [M + H]+ Observed | Form(s) |
|---|---|---|---|---|---|
| 26-1 | CH3 | (trans) —CH₂—CH(CO₂H)—CH₂— | +++ | 481.1 | Free Base |
| 26-2 | 4-morpholinyl | —CH₂— | ++ | 480.1 | Free Base |
| 26-3 | H | —CH₂— | ++ | 395.0 | Free Base |
| 26-4 | H | (cis) —CH₂CH(CO₂Et)—CH₂— | ++ | 495.1 | Free Base |
| 26-5 | H | (trans) —CH₂CH(CO₂Et)—CH₂— | + | 495.1 | Free Base |
| 25-6 | H | (trans) —CH₂CH(CO₂H)—CH₂— | +++ | 467.0 | Free Base |

Example 27

1-[5-(3-[(2,2,2-trifluoroethyl)amino]-5-{[4-(trifluoromethyl)pyrimidin-2-yl]amino}phenyl)-1,3-thiazol-2-yl]cyclobutanol

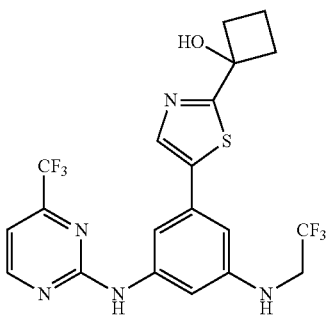 [SMILES: OC1(c2ncc(-c3cc(NCC(F)(F)F)cc(Nc4nccc(C(F)(F)F)n4)c3)s2)CCC1]

Step 1

Ammonium chloride (5.20 g, 97 mmol) was added to a stirred, cooled (room temperature) mixture of 1-bromo-3,5-dinitrobenzene (20 g, 81 mmol) and iron (54.3 g, 972 mmol) in ethanol:water (2:1) and the mixture was stirred at 80° C. for 1 h. The heterogeneous reaction was filtered on celite while hot, concentrated, and diluted with brine. The product was extracted with ethyl acetate, the organic layer washed with brine and dried over Na₂SO₄. The residue was dissolved in boiling ethyl acetate (~75 mL), a bit of hexanes was added to form a layer on top of ethyl acetate (~7.5 mL) and the mixture was left to crystallize overnight. The crystals were filtered, washed with diethyl ether and air-dried to give 5.77 g of 5-bromobenzene-1,3-diamine as a grey solid. MS ESI: [M+H]⁺ m/z 187.0 and 189.0.

Step 2

Trifluoroacetic acid was added to a stirred, cooled (0° C.) mixture of the bromobenzene-1,3-diamine (3.00 g, 16.0 mmol) and sodium cyanoborohydride (2.02 g, 32.1 mmol) in dichloromethane (note: gas evolution) at 0° C. Then, trifluoroacetaldehyde (2.79 g, 24.06 mmol) was added and the mixture was stirred at room temperature for 45 min. The mixture was cooled to 0° C., aqueous sodium carbonate (2M) was added until basic pH was achieved and no more gas evolution was observed then the mixture was extracted with ethyl acetate. The combined organic fractions were washed with brine, dried over Na₂SO₄, filtered and the solvent was evaporated under reduced pressure. The residue was purified by chromatography on silica gel (0-70% ethyl acetate in hexanes) to give 5-bromo-N-(2,2,2-trifluoroethyl)benzene-1,3-diamine (1.51 g, 5.61 mmol, 35% yield) as a yellow oil that crystallized upon standing. MS ESI: [M+H]⁺ m/z 269.1.

Step 3

Aqueous HCl (1.0 M, 1.5 mL, 1.5 mmol) was added to a stirred mixture of the product of Step 2 (0.80 g, 2.97 mmol) and 2-chloro-4-trifluoromethylpyrimidine (8.0 mL, 66.2 mmol) in DMSO and the mixture was stirred at 100° C. for 2 h. The mixture was cooled, water was added and the mixture was extracted with Et₂O (3×). The combined organic fractions were washed with HCl, water, aqueous copper sulfate and brine, dried (MgSO₄), filtered and the solvent was evaporated under reduced pressure. The residue was purified by column chromatography (0-60% ethyl acetate in hexanes) to give 5-bromo-N-(2,2,2-trifluoroethyl)-N'-[4-(trifluoromethyl)-pyrimidin-2-yl]benzene-1,3-diamine (622 mg, 1.50 mmol, 50% yield) as a off-white solid. MS ESI: [M+H]⁺ m/z 416.9.

Step 4

A mixture of the product of Step 3 (500 mg, 1.204 mmol), PdCl₂(dppf)-dichloromethane adduct (49.2 mg, 0.060 mmol), potassium acetate (355 mg, 3.61 mmol) and bis(pinacolato)diboron (321 mg, 1.26 mmol) in dioxane (3.0 mL) was degassed (alternating vacuum-N₂ cycles). The mixture was heated to 85° C. and stirred overnight. LCMS analysis indicated incomplete reaction, and thus the mixture was cooled down to room temperature, diluted with diethyl ether and filtered on celite and the solvent was evaporated under reduced pressure. This impure material was redissolved in dioxane (3.0 mL) and additional bis(pinacolato)diboron (244 mg, 0.960 mmol), potassium acetate (353 mg, 3.60 mmol), Pd$_2$dba$_3$ (27.5 mg, 0.030 mmol) and 2-dicyclohexylphosphino-2',4',6'-tri-isopropyl-1,1'-biphenyl (57.2 mg, 0.120 mmol) were added. The septum was replaced with a screwcap and the mixture stirred at 110° C. for 30 min. The mixture was cooled, Et$_2$O and hexanes were added, and then was filtered on celite and washed with Et$_2$O. The volatiles were removed under partial vacuum, and the residue was then triturated in hexanes. The residue was purified by column chromatography (20-50% ethyl acetate in hexanes) to give 5-(4,4,5,5-tetramethyl-1,3,2-dioxaborolan-2-yl)-N-(2,2,2-trifluoroethyl)-N'-[4-(trifluoromethyl)pyrimidin-2-yl]benzene-1,3-diamine (354 mg, 0.766 mmol, 64%) as a colorless solid. MS ESI: [M+H]$^+$ m/z 463.1.

Step 5

A mixture of the product of Step 4 (50 mg, 0.108 mmol), PdCl$_2$(dppf) (as the dichloromethane adduct; 4.42 mg, 5.41 µmol) and Intermediate 1 (27.9 mg, 0.119 mmol) was degassed (alternating vacuum-N$_2$ cycles). Dioxane (0.3 mL) and Na$_2$CO$_3$ (2.0 M, 162 µL, 0.325 mmol) were added. The mixture was degassed again and stirred at 85° C. for 2 hrs. The mixture was cooled to room temperature, diluted with ethyl acetate and gravity filtered on celite. After in vacuo concentration, the residue was purified by Chromatography on silica gel (0-100% ethyl acetate in hexanes) then briefly triturated in hexanes to give the 1-[5-(3-[(2,2,2-trifluoroethyl)amino]-5-{[4-(trifluoromethyl)pyrimidin-2-yl]amino}phenyl)-1,3-thiazol-2-yl]cyclobutanol (36.4 mg, 0.074 mmol, 69% yield) as a white solid. MS ESI: [M+H]$^+$ m/z 490.0. $^1$H NMR (500 MHz, CD$_3$OD) δ 8.73 (d, J=4.9, 1H), 7.92 (s, 1H), 7.43 (s, 1H), 7.31 (s, 1H), 7.15 (d, J=4.9, 1H), 6.69 (s, 1H), 3.88 (q, 9.2, 2H), 2.79-2.67 (m, 2H), 2.67-2.36 (m, 2H), 2.12-1.92 (m, 2H).

rhSYK activity=+++

The following examples were prepared in an analogous manner of that described in Example 27.

TABLE 27

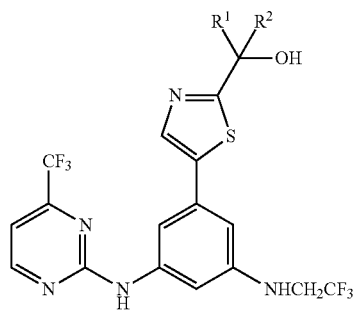

| Example | R$^1$/R$^2$ | rhSYK Activity | [M + H]+ Observed | Form(s) |
|---|---|---|---|---|
| 27-1 | H/CF$_2$H | +++ | 500.0 | Free Base |
| 27-2 | CH$_3$/CF$_3$ | +++ | 532.0 | Free Base |

Example 28

1-{5-[3-(difluoromethyl)-5-{[4-(trifluoromethyl) pyrimidin-2-yl]amino}phenyl]-1,3-thiazol-2-yl}cyclobutanol

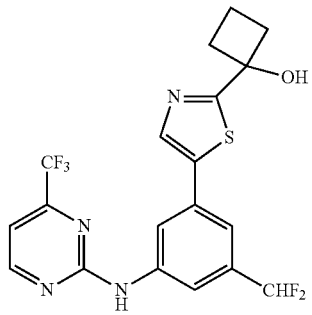 [SMILES: OC1(c2ncc(-c3cc(Nc4nccc(C(F)(F)F)n4)cc(C(F)F)c3)s2)CCC1]

Step 1

DAST (16.5 mL, 125 mmol) was added dropwise to a −78° C. solution of 3-nitrobenzaldehyde (3.78 g, 25 mmol) in dichloromethane (20 mL). The mixture was stirred for 15 min and then allowed to warm to room temperature. After 4 hrs, TLC showed incomplete conversion, so the mixture was cooled again to −78° C. and additional DAST (16.5 mL, 125 mmol) was added. The mixture was allowed to warm to room temperature and was stirred overnight. The mixture was poured in ice and dilute NH$_4$OH(aq) and extracted 2× with dichloromethane. The combined organic extracts were washed with brine and dried over sodium sulfate. Filtration and solvent evaporation gave a residue which was passed over a short plug of silica eluting with 10% ethyl acetate in hexanes to yield 1-(difluoromethyl)-3-nitrobenzene (4.3 g, 24.8 mmol, 99%).

Step 2

1-(Difluoromethyl)-3-nitrobenzene (866 mg, 5.00 mmol) was added to cold conc. H$_2$SO$_4$ and then NBS (890 mg, 5.00 mmol) was added. The mixture was warmed to room temperature for 30 minutes then 50-60° C. for 1 h. The mixture was then poured in water and ice and extracted diethyl ether twice. The organic layer was washed with dilute aqueous NaHCO$_3$ and brine. Purification by chromatography on silica gel (0-15% ethyl acetate in hexanes) yielded 1-bromo-3-(difluoromethyl)-5-nitrobenzene (710 Mg, 2.82 mmol, 56.3%).

Step 3

Iron (1.99 g, 35.7 mmol) was added to a vigorously stirred mixture of 1-bromo-3-(difluoromethyl)-5-nitrobenzene (1.80 g, 7.14 mmol) and NH$_4$Cl (0.191 g, 3.57 mmol) in ethanol (30 mL) and water (15 mL). The mixture was heated to 95° C. for 2 h. It was then diluted with ethyl acetate while still hot and filtered over Celite. The filtrate was washed with dilute aqueous NaHCO$_3$ and brine. After solvent evaporation the residue was purified through a silica plug, eluting with 1:5 ethyl acetate:hexanes to yield 3-bromo-5-(difluoromethyl) aniline (1.3 g, 5.86 mmol, 82%).

Step 4

Acetic acid (1.01 mL, 17.6 mmol) was added to a mixture of 3-bromo-5-(difluoromethyl)aniline (1.30 g, 5.86 mmol) and 2-chloro-4-(trifluoromethyl)pyrimidine (2.14 g, 11.7 mmol) in dioxane (5.0 mL). The mixture was heated to 105° C. for 16 hrs then cooled to room temperature. The mixture was diluted with ethyl acetate, washed with dilute aqueous NaHCO$_3$, brine and dried. The residue was purified by chromatography on silica gel (0-15% ethyl acetate in hexanes) to yield N-[3-bromo-5-(difluoromethyl)phenyl]-4-(trifluoromethyl)pyrimidin-2-amine (741 mg, 2.01 mmol, 34%).

Step 5

Pd(dppf)Cl$_2$-dichloromethane adduct (82 mg, 0.101 mmol) was added to a degassed mixture of bis(pinacolato)diboron (537 mg, 2.114 mmol), potassium acetate (593 mg, 6.04 mmol) and the product of Step 4 (741 mg, 2.013 mmol) in dioxane (15 mL). The mixture was heated to 105° C. for 16 h, then cooled to room temperature and concentrated in vacuo. The residue was purified by column chromatography (1:3 ethyl acetate:hexanes) to yield N-[3-(difluoromethyl)-5-(4,4,5,5-tetramethyl-1,3,2-dioxaborolan-2-yl)phenyl]-4-(trifluoromethyl)-pyrimidin-2-amine (684 mg, 1.648 mmol, 82%).

Step 6

Pd(dppf)Cl$_2$-DCM adduct (50 mg, 0.061 mmol) was added to a degassed mixture of the product of Step 5 (0.342 g, 0.824 mmol) and Intermediate 1 (212 mg, 0.906 mmol) in DMF (6.0 mL) and Na$_2$CO$_3$ (2.0 M, 1.24 mL, 2.47 mmol). The mixture was heated to 85° C. for 3 hrs. After cooling to room temperature, the residue was purified by chromatography (25:75 to 50:50, ethyl acetate:hexanes). The product was triturated in hexanes (trace diethyl ether) to yield 1-{5-[3-(difluoromethyl)-5-[4-(trifluoromethyl)pyrimidin-2-yl]amino}phenyl]-1,3-thiazol-2-yl)-cyclobutanol (129 mg, 0.292 mmol, 35%). MS ESI: [M+H]$^+$ m/z 443.1. $^1$H NMR (400 MHz, (CD$_3$)$_2$CO): δ 9.53 (s, 1H); 8.91 (d, J=4.9 Hz, 1H); 8.45 (s, 1H); 8.14-8.10 (m, 2H); 7.58 (s, 1H); 7.34 (d, J=4.9 Hz, 1H); 6.99 (t, J=56.1 Hz, 1H); 5.60 (s, 1H); 2.75-2.66 (m, 2H); 2.51-2.41 (m, 2H); 2.06-1.96 (m, 2H). rhSYK activity=+++

Compounds in the following Table(s) were prepared in an analogous manner of that described in Example 28:

| Example | Structure | hSYK Activity | [M + H]+ obs'd | Form(s) |
|---|---|---|---|---|
| 28-1 | 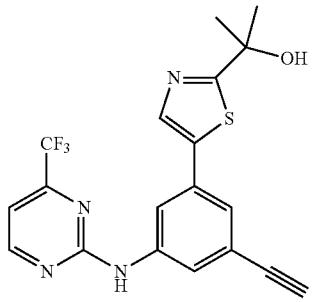 [SMILES: C#Cc1cc(Nc2nccc(C(F)(F)F)n2)cc(-c2cnc(C(C)(C)O)s2)c1] | +++ | 431.1 | Free Base |

Example 29

2-[5-(3-ethynyl-5-{[4-(trifluoromethyl)pyrimidin-2-yl]amino}phenyl)-1,3-thiazol-2-yl]propan-2-ol

Step 1

A solution of diisopropylamine (0.220 mL, 1.545 mmol) in 4 mL THF was cooled to 0° C., then n-BuLi (2.5 M in hexanes, 0.598 mL, 1.495 mmol) was added dropwise. The mixture was stirred at this temperature for 15 minutes, then cooled to −78° C. Intermediate II (200 mg, 0.498 mmol) was then added dropwise as a solution in 1.0 mL THF, and the mixture stirred for 30 minutes. Acetone (0.110 mL, 1.495 mmol) was then added, and the mixture was stirred at −78° C. for 30 minutes, then allowed to warm to room temperature. The reaction was quenched by the addition of ~1 mL brine, then the mixture was diluted with ethyl acetate (100 mL) and washed with brine (100 mL). The organic extracts were dried (sodium sulfate) filtered, and concentrated in vacuo. Purification by chromatography on silica gel (80:20 to 40:60, hexanes:ethyl acetate) provided 141 mg (0.307 mmol, 61.6%) of 2-[5-(3-bromo-5-{[4-(trifluoromethyl)pyrimidin-2-yl]amino}phenyl)-1,3-thiazol-2-yl]propan-2-ol as an off-white solid.

Step 2

A solution of the product of Step 1 (50 mg, 0.109 mmol), trimethylsilylacetylene (30.6 μL, 0.218 mmol), DIPEA (57 μL, 0.33 mmol), CuI (4.2 mg, 0.022 mmol) and Pd(PPh$_3$)$_4$ (12.6 mg, 0.011 mmol) in DMF (2.0 mL) was heated to 85° C. overnight. After cooling to room temperature, the mixture was diluted with ethyl acetate (30 mL) and washed with 1:1 water:brine (2×30 mL). The aqueous layers were further extracted with ethyl acetate (30 mL), then the combined organic extracts were dried (Na$_2$SO$_4$), filtered, and concentrated in vacuo. Purification by chromatography on silica gel (100:0 to 50:50, hexanes:ethyl acetate) provided 35 mg (0.073 mmol, 68%) of 2-[5-(3-{[4-(trifluoromethyl)pyrimidin-2-yl]amino}-5-[(trimethylsilyl)ethynyl]phenyl)-1,3-thiazol-2-yl]propan-2-ol as a yellow oil.

Step 3

To a solution of the product of Step 2 (35 mg, 0.073 mmol) in THF (1.0 mL) was added TBAF (1.0 M in THF, 0.44 mL, 0.44 mmol) and the mixture was stirred at room temperature for 90 minutes. The mixture was concentrated in vacuo, then purified by chromatography on silica gel (80:20 to 30:70, hexanes:ethyl acetate) to provide 22 mg (0.054 mmol, 74%)

of 2-[5-(3-ethynyl-5-{[4-(trifluoromethyl)pyrimidin-2-yl]amino}phenyl)-1,3-thiazol-2-yl]propan-2-ol as a white solid. MS ESI: [M+H]$^+$ m/z 405.1. $^1$H NMR (400 MHz, CDCl$_3$): δ 8.68 (d, J=4.9 Hz, 1H); 8.06 (s, 1H); 7.88 (s, 1H); 7.69-7.59 (m, 2H); 7.38 (s, 1H); 7.09 (d, J=4.9 Hz, 1H); 3.20 (s, 1H); 2.05 (s, 1H); 1.73 (s, 6H). rhSYK activity=+++

Example 30

2-[5-(3-ethyl-5-{[4-(trifluoromethyl)pyrimidin-2-yl]amino}phenyl)-1,3-thiazol-2-yl]propan-2-ol

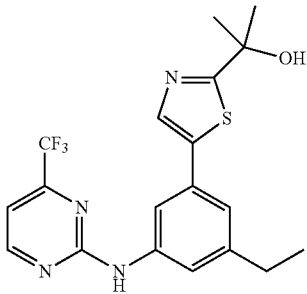 [SMILES: CCc1cc(Nc2nccc(C(F)(F)F)n2)cc(-c2cnc(C(C)(C)O)s2)c1]

To a solution of 2-[5-(3-ethynyl-5-{[4-(trifluoromethyl)pyrimidin-2-yl]amino}phenyl)-1,3-thiazol-2-yl]propan-2-ol (19 mg, 0.047 mmol) in ethyl acetate (1 mL) was added Pd/C (10 wt %, 10.0 mg, 9.4 µmol), and the reaction vessel was then purged with H2 and stirred under an atmosphere of H$_2$ (balloon) overnight. The catalyst was deactivated by addition of dichloromethane, then the mixture was filtered through Celite (ethyl acetate rinse) and concentrated in vacuo. The residue was then purified by preparative HPLC (50-90% CH$_3$CN in 15 mM NH$_4$HCO$_3$(aq)) which provided 12 mg (0.029 mmol, 63%) of 2-[5-(3-ethyl-5-{[4-(trifluoromethyl)pyrimidin-2-yl]amino}phenyl)-1,3-thiazol-2-yl]propan-2-ol as a white solid. MS ESI: [M+H]+ m/z 409.1. $^1$H NMR (400 MHz, (CD$_3$)$_2$CO): δ 9.20 (s, 1H); 8.82 (d, J=4.9 Hz, 1H); 8.12 (s, 1H); 7.94 (s, 1H); 7.67 (s, 1H); 7.25-7.20 (m, 2H); 5.02 (s, 1H); 2.70 (q, J=7.6 Hz, 2H); 1.63 (s, 6H); 1.28 (t, J=7.6 Hz, 3H). rhSYK activity=+++

Example 31

2-[5-(3-cyclopropyl-5-{[4-(trifluoromethyl)pyrimidin-2-yl]amino}phenyl)-1,3-thiazol-2-yl]propan-2-ol

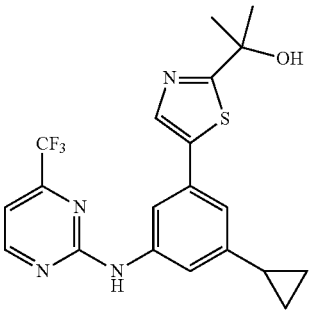 [SMILES: CC(C)(O)c1ncc(-c2cc(Nc3nccc(C(F)(F)F)n3)cc(C3CC3)c2)s1]

Step 1

This procedure is based on literature, see: Soderquist, J. A.; Huertas, R.; Leon-Colon, G. *Tetrahedron Lett.* 2000, 41, 4251-4255. To a suspension of 9-BBN dimer (1.22 g, 5.00 mmol) in THF (5.0 mL) was added 3-bromoprop-1-yne (0.555 mL, 5.00 mmol), and this mixture was heated to reflux for 2 hours. After cooling to room temperature, a NaOH solution (3 M, 5.00 mL, 15.0 mmol), which had been degassed by bubbling N$_2$ for 15 minutes, was added and stirring was continued for an additional 2 hours. The resulting solution was used directly (~0.5 M) in the next step without further manipulation.

Step 2

To a mixture of 2-[5-(3-bromo-5-{[4-(trifluoromethyl)pyrimidin-2-yl]amino}phenyl)-1,3-thiazol-2-yl]propan-2-ol (Example 4A-4, 50 mg, 0.109 mmol) and tetrakis(triphenylphosphine)palladium(0) (13 mg, 11 µmol) was added the sodium (cyclooctane-1,5-diyl-κ$^2$C$^1$,C$^5$)(cyclopropyl)hydroxyborate(1-) solution (0.5 M, 650 µL, 0.327 mmol) from Step 1, and the mixture was heated to 75° C. overnight. The mixture was diluted with ethyl acetate (100 mL), dried (Na$_2$SO$_4$) and filtered through celite. After in vacuo concentration, purification by chromatography on silica gel (80:20 to 30:70 hexanes:Ethyl acetate over 20 minutes) provided the desired product contaminated by a minor by-product (~10%). Further purification by prep LCMS (50-90% CH$_3$CN in NH$_4$CO$_3$(aq)) provided 15 mg (0.036 mmol, 33%) of 2-[5-(3-cyclopropyl-5-{[4-(trifluoromethyl)pyrimidin-2-yl]amino}phenyl)-1,3-thiazol-2-yl]propan-2-ol as a white solid. MS ESI: [M+H]$^+$ m/z 421.1. $^1$H NMR (400 MHz, (CD$_3$)$_2$CO)): δ 9.17 (s, 1H); 8.81 (d, J=4.9 Hz, 1H); 8.03 (s, 1H); 7.93 (s, 1H); 7.54 (s, 1H); 7.22 (d, J=4.9 Hz, 1H); 7.11 (s, 1H); 2.03-1.93 (m, 1H); 1.63 (s, 6H); 1.04-0.94 (m, 2H); 0.80-0.75 (m, 2H). rhSYK activity=+++

Examples 32 ethyl 4-hydroxy-4-[5-(3-methyl-5-{[4-(trifluoromethyl)pyrimidin-2-yl]amino}phenyl)-1,3-thiazol-2-yl]cyclohexanecarboxylate

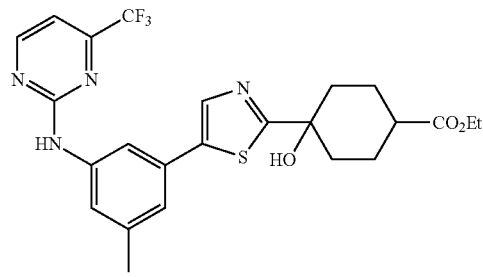 [SMILES: CCOC(=O)C1CCC(O)(c2ncc(-c3cc(C)cc(Nc4nccc(C(F)(F)F)n4)c3)s2)CC1]

Tetrahydrofuran was placed in a flask and cooled to −78° C. Lithium diisopropylamide (9.91 mL, 17.84 mmol) was added and the mixture was allowed to cool to −78° C. Intermediate 4 (2.0 g, 5.95 mmol) was dissolved in tetrahydrofuran (60 mL) and added to the reaction mixture in one portion and stirred for 30 minutes. Ethyl 4-oxocyclohexanecarboxylate (1.52 g, 8.92 mmol) was dissolved in tetrahydrofuran (60 mL) and added in one portion. After 1 hour, the reaction was quenched with saturated ammonium chloride and allowed to warm to room temperature. The solution was diluted with ethyl acetate. The organic layer was separated, dried over magnesium sulfate, filtered and concentrated. Silica gel chromatography was used for purification to yield a 1:1 mixture of diastereomers of ethyl 4-hydroxy-4-[5-(3-methyl-5-{[4-(trifluoromethyl)-pyrimidin-2-yl]amino}phenyl)-1,3-thiazol-2-yl]cyclohexanecarboxylate (1.96 g, 65.1%). MS ESI: [M+H]$^+$ m/z 507.2. $^1$H NMR (500 MHz, DMSO-d$_6$) δ 10.25 (s, 1H), 8.83 (d, J=5.2, 1H), 8.02-7.85 (m, 2H), 7.46 (s, 1H), 7.27 (d, J=5.0, 1H), 7.14 (s, 1H), 5.97 (m, 1H), 4.12-4.01 (m, 2H), 2.62-2.54 (m, 1H), 2.31 (s, 3H), 2.12-1.99 (m, 1H), 1.93-1.58 (m, 7H), 1.24-1.05 (m, 3H). rhSYK activity=+++

Examples 33(1) and 33(2)

trans-4-hydroxy-4-[5-(3-methyl-5-[4-(trifluoromethyl)pyrimidin-2-yl amino]phenyl)-1,3-thiazol-2-yl]cyclohexanecarboxylic acid cis-4-hydroxy-4-[5-(3-methyl-5-{[4-(trifluoromethyl)pyrimidin-2-yl]amino}phenyl)-1,3-thiazol-2-yl]cyclohexanecarboxylic acid

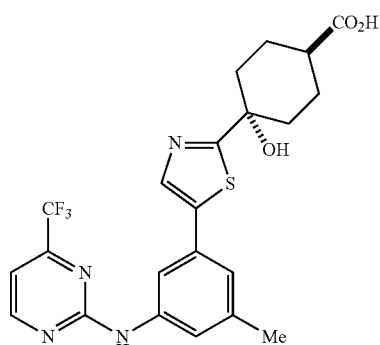

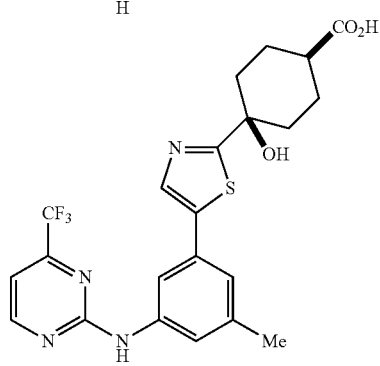

Part A:
Ethyl 4-hydroxy-4-[5-(3-methyl-5-{[4-(trifluoromethyl)pyrimidin-2-yl]amino}phenyl)-1,3-thiazol-2-yl]cyclohexanecarboxylate (3.72 g, 7.3 mmol) was suspended in methanol (42 mL) and sodium hydroxide (1M in water, 15 mL) was added. The solution was split between 3 20-mL microwave tubes. The reaction was irradiated at 100° C. in the microwave for 15 minutes. Upon completion, the solution was acidified with HCl (1M in water, 18 mL). The solution was extracted with ethyl acetate and a small amount of 9:1 CHCl$_3$:isopropanol. The organic layer was separated, dried over magnesium sulfate, filtered and concentrated.

Part B:
Supercritical fluid separation was used for purification with an OJ-H 2.1×25 cm, 5 column. The mobile phase used was a 3:7 methanol/CO$_2$ with a flow rate of 70 mL/min with a 7 minute run time, to yield:

Isomer 1: trans-4-hydroxy-4-[5-(3-methyl-5-{[4-(trifluoromethyl)pyrimidin-2-yl]amino}phenyl)-1,3-thiazol-2-yl]cyclohexanecarboxylic acid (1.11 g, 32% yield). MS ESI: [M+H]$^+$ m/z 479.1. $^1$H NMR (600 MHz, DMSO-d$_6$) δ 10.23 (s, 1H), 8.81 (d, J=4.9, 1H), 8.00-7.75 (m, 2H), 7.44 (s, 1H), 7.25 (d, J=4.9, 1H), 7.12 (s, 1H), 5.92 (s, 1H), 2.62 (s, 1H), 2.29 (s, 3H), 2.11-1.95 (m, 2H), 1.92-1.75 (m, 4H), 1.71-1.54 (m, 2H). rhSYK activity=+++

Isomer 2: cis-4-hydroxy-4-[5-(3-methyl-5-{[4-(trifluoromethyl)pyrimidin-2-yl]amino}phenyl)-1,3-thiazol-2-yl]cyclohexanecarboxylic acid (1.13 g, 32%). MS ESI: [M+H]$^+$ m/z 479.1. $^1$H NMR (500 MHz, DMSO-d$_6$) δ 12.1 (s, 1H), 10.25 (s, 1H), 8.83 (d, J=5.2, 1H), 8.04-7.83 (m, 2H), 7.46 (s, 1H), 7.27 (d, J=5.0, 1H), 7.15 (s, 1H), 5.95 (s, 1H), 2.31 (s, 3H), 2.13-1.99 (m, 1H), 1.91-1.73 (m, 2H), 1.71-1.53 (m, 6H). rhSYK activity=+++

Examples 33(1)-NA

Sodium cis-4-hydroxy-4-[5-(3-methyl-5-{[4-(trifluoromethyl)pyrimidin-2-yl]amino}phenyl)-1,3-thiazol-2-yl]cyclohexanecarboxylate cis-4-Hydroxy-4-[5-(3-methyl-5-{[4-(trifluoromethyl)pyrimidin-2-yl]amino}phenyl)-1,3-thiazol-2-yl]cyclohexanecarboxylic acid (15 mg, 0.031 mmol) was dissolved in acetonitrile (272 μL) and water (54 μL). Sodium hydroxide (31 μL, 0.031 mmol) was added, and the mixture was heated to 40° C. for 1 h. The reaction was allowed to cool to room temperature, before freezing and lyophilization to dryness to afford sodium cis-4-hydroxy-4-[5-(3-methyl-5-{[4-(trifluoromethyl)-pyrimidin-2-yl]amino}phenyl)-1,3-thiazol-2-yl]cyclohexanecarboxylate. MS ESI: [M+H]$^+$ m/z 479.1. $^1$H NMR (500 MHz, DMSO-d$_6$) δ 10.25 (s, 1H), 8.83 (s, 1H), 8.06-7.73 (m, 2H), 7.46 (s, 1H), 7.27 (s, 1H), 7.13 (s, 1H), 5.89-5.60 (m, 1H), 2.31 (s, 3H), 1.91-1.54 (m, 9H). rhSYK activity=+++

Examples 33(1)-K

Potassium cis-4-hydroxy-4-[5-(3-methyl-5-{[4-(trifluoromethyl)pyrimidin-2-yl]amino}phenyl)-1,3-thiazol-2-yl]cyclohexanecarboxylate cis-4-Hydroxy-4-[5-(3-methyl-5-{[4-(trifluoromethyl)pyrimidin-2-yl]amino}phenyl)-1,3-thiazol-2-yl]cyclohexanecarboxylic acid (15 mg, 0.031 mmol) was dissolved in acetonitrile (272 μL) and water (54 μL). Potassium hydroxide (31 μL, 0.031 mmol) was added, and the mixture was heated to 40° C. for 1 h. The reaction was allowed to cool to room temperature, before freezing and lyophilization to dryness to afford potassium cis-4-hydroxy-4-[5-(3-methyl-5-{[4-(trifluoromethyl)pyrimidin-2-yl]amino}phenyl)-1,3-thiazol-2-yl]cyclohexanecarboxylate. MS ESI: [M+H]$^+$ m/z 479.1. $^1$H NMR (500 MHz, DMSO-d$_6$) δ 10.25 (s, 1H), 8.83 (d, J=4.9, 1H), 7.99-7.83 (m, 2H), 7.46 (s, 1H), 7.27 (d, J=4.9, 1H), 7.13 (s, 1H), 5.88-5.63 (m, 1H), 2.31 (s, 3H), 1.88-1.59 (m, 9H). rhSYK activity=+++

Examples 33(2)-NA

Sodium trans-4-hydroxy-4-[5-(3-methyl-5-{[4-(trifluoromethyl)pyrimidin-2-yl]amino}phenyl)-1,3-thiazol-2-yl]cyclohexanecarboxylate trans-4-Hydroxy-4-[5-(3-methyl-5-{[4-(trifluoromethyl)pyrimidin-2-yl]amino}phenyl)-1,3-thiazol-2-yl]cyclohexanecarboxylic acid (15 mg, 0.031 mmol) was dissolved in acetonitrile (272 μL) and water (54 μL). Sodium hydroxide (31 μL, 0.031 mmol) was added, and the mixture was heated to 40° C.

for 1 h. The reaction was allowed to cool to room temperature, before freezing and lyophilization to dryness to afford sodium trans-4-hydroxy-4-[5-(3-methyl-5-{[4-(trifluoromethyl)pyrimidin-2-yl]amino}phenyl)-1,3-thiazol-2-yl]cyclohexanecarboxylate. MS ESI: [M+H]+ m/z 479.1. $^1$H NMR (500 MHz, DMSO-$d_6$) δ 10.25 (s, 1H), 8.83 (d, J=4.9, 1H), 8.04-7.76 (m, 2H), 7.46 (s, 1H), 7.27 (d, J=4.9, 1H), 7.14 (s, 1H), 5.68 (s, 1H), 2.31 (s, 3H), 2.21-1.96 (m, 3H), 1.90-1.63 (m, 4H), 1.62-1.42 (m, 2H). rhSYK activity=+++

Examples 33(2)-K

Potassium trans-4-hydroxy-4-[5-(3-methyl-5-{[4-(trifluoromethyl)pyrimidin-2-yl]amino}phenyl)-1,3-thiazol-2-yl]cyclohexanecarboxylate trans-4-Hydroxy-4-[5-(3-methyl-5-{[4-(trifluoromethyl)pyrimidin-2-yl]amino}phenyl)-1,3-thiazol-2-yl]cyclohexanecarboxylic acid (15 mg, 0.031 mmol) was dissolved in acetonitrile (272 mL) and water (54 μL). Potassium hydroxide (31 μL, 0.031 mmol) was added, and the mixture was heated to 40° C. for 1 h. The reaction was allowed to cool to room temperature, before freezing and lyophilization to dryness to afford potassium trans-4-hydroxy-4-[5-(3-methyl-5-{[4-(trifluoromethyl)pyrimidin-2-yl]amino}phenyl)-1,3-thiazol-2-yl]cyclohexanecarboxylate. MS ESI: [M+H]+ m/z 479.1. $^1$H NMR (500 MHz, DMSO-$d_6$) δ 10.25 (s, 1H), 8.83 (d, J=4.9, 1H), 8.02-7.78 (m, 2H), 7.46 (s, 1H), 7.27 (d, J=4.9, 1H), 7.14 (s, 1H), 5.69 (s, 1H), 2.31 (s, 3H), 2.19-2.07 (m, 2H), 1.99-1.85 (m, 1H), 1.81-1.60 (m, 4H), 1.57-1.42 (m, 2H). rhSYK activity=+++

Compounds in the following Tables 33A to 33D were prepared in an analogous manner as that described in Examples 32-33.

TABLE 33-A

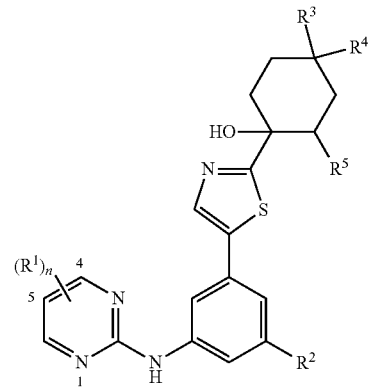

A

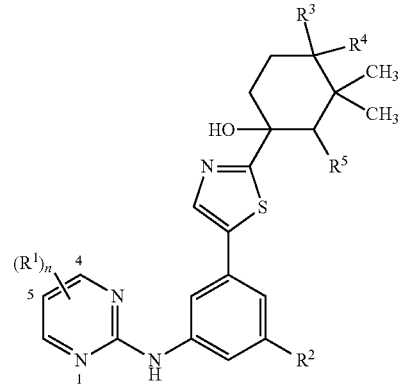

B n is 1 or 2, and in the following Tables, unless otherwise specified, n is 1 and $R^1$ is attached to the 4-position of the pyrimidine ring.

| Ex. | $R^1$ | $R^2$ | $R^3/R^4$ | rhSYK Activity | [M + H]+ Obs'd | Form(s) |
|---|---|---|---|---|---|---|
| Formula A; $R^5$ = H | | | | | | |
| 33A-1 | 4-c-Pr, 5-F | CH$_3$ | H/CO$_2$H (cis) | +++ | 469.2 | Free Base |
| 33A-2 | 4-c-Pr, 5-F | CH$_3$ | H/CO$_2$H (trans) | +++ | 469.3 | Free Base |

TABLE 33-A-continued

| | | | | | | |
|---|---|---|---|---|---|---|
| 33A-3 | 5-F | $CH_3$ | $CH_3/CO_2H$ (cis) | +++ | 443 | TFA Salt |
| 33A-4 | 5-F | $CH_3$ | $CH_3/CO_2H$ (trans) | +++ | 443 | TFA Salt |
| 33A-5 | 4-$CF_3$ | $CH_3$ | $H/CO_2Et$ | +++ | 507.2 | Free Base |
| 33A-6 | 4-$CF_3$ | $CH_3$ | $H/CO_2H$ (cis) | +++ | 479.1 | Free Base |
| 33A-7 | 4-$CF_3$ | $CH_3$ | $H/CO_2Et$ (trans) | +++ | 507.2 | Free Base |
| 33A-8 | 4-$CF_3$ | $CH_3$ | $H/CO_2H$ (trans) | +++ | 479.1 | Free Base |
| 33A-9 | 4-$CF_3$ | $CH_3$ | $Ph/CO_2H$ | +++ | 555.2 | Free Base |
| 33A-10 | 4-$CF_3$ | $CH_3$ | $CH_3/CO_2Et$ (cis) | +++ | 521.1 | Free Base |
| 33A-11 | 4-$CF_3$ | $CH_3$ | $CH_3/CO_2Et$ (trans) | ++ | 521.1 | Free Base |
| 33A-12 | 4-$CF_3$ | $CH_3$ | $CH_3/CO_2H$ (trans) | +++ | 493.1 | Free Base |
| 33A-13 | 4-$CF_3$ | $CH_3$ | $CH_3/CO_2H$ (cis) | +++ | 493.1 | Free Base |
| 33A-14 | 4-$CF_3$ | $CH_3$ | $CO_2Me/NHC(O)CH_3$ | +++ | 550.1 | Free Base |
| 33A-15 | 4-$CF_3$ | $CH_3$ | $CO_2H/NHC(O)CH_3$ | +++ | 536.1 | TFA Salt |
| 33A-16 | 4-$CF_3$ | $CH_3$ | $H/CH2CO_2H$ (trans) | +++ | 493 | Formate Salt |
| 33A-17 | 4-$CF_3$ | $CH_3$ | $H/4-(CO2H)Ph$ | +++ | 570 | Ammonium Salt |
| 33A-18 | 4-$CF_3$ | $CH_3$ | $H/CH_2CH_2CO_2H$ | +++ | 507.2 | Free Base |
| 33A-19 | 4-$CF_3$ | $CH_3$ | $H/CH_2CH_2CO_2H$ (cis) | +++ | 507.2 | Free Base |
| 33A-20 | 4-$CF_3$ | $CH_3$ | $H/CH_2CH_2CO_2H$ (trans) | +++ | 507.2 | Free Base |
| 33A-21 | 4-$CF_3$ | $CH_3$ | $H/CH_2CH_2CO_2CH_2CH_3$ | +++ | 535.2 | Free Base |
| 33A-22 | 4-$CF_3$ | Cl | $H/CO_2H$ (trans) | +++ | 499.1 | Free Base |
| 33A-23 | 4-$CF_3$ | H | $H/CO_2H$ (trans) | +++ | 465.0 | Free Base |
| 33A-24 | 4-$CF_3$ | H | $H/CO_2H$ (cis) | +++ | 465.0 | Free Base |
| 33A-25 | 4-$CF_3$ | H | $H/CO_2Et$ (cis) | +++ | 493.1 | Free Base |
| 33A-26 | 4-$CF_3$ | H | $H/CO_2Et$ (trans) | ++ | 493.1 | Free Base |
| 33A-27 | 4-$CF_3$ | H | $CH_3/CO_2H$ (trans) | +++ | 479.1 | Free Base |
| 33A-28 | 4-$CF_3$ | H | $CH_3/CO_2H$ (cis) | +++ | 479.1 | Free Base |
| 33A-29 | 4-iPr | $CH_3$ | $H/CO_2C(CH_3)_3$ (cis) | ++ | 509.2 | Free Base |
| 33A-30 | 4-$CH_3$ | $CH_3$ | $H/CO_2H$ (cis) | +++ | 425.1 | Free Base |
| 33A-31 | 4-$CH_3$ | $CH_3$ | $H/CO_2H$ (trans) | +++ | 425.1 | Free Base |
| 33A-32 | 4-$CH_3$ | $CH_3$ | $H/CH2CO_2H$ (cis) | +++ | 439.1 | Free Base |
| 33A-33 | 4-$CH_3$ | $CH_3$ | $H/CH2CO_2H$ (trans) | +++ | 439.0 | Free Base |
| 33A-34 | 4-O—iPr | $CH_3$ | $H/CO_2C(CH_3)_3$ (cis) | ++ | 525.2 | Free Base |
| 33A-35 | 4-$OCH_3$ | $CH_3$ | $H/CO_2H$ (cis) | +++ | 441.1 | Free Base |
| 33A-36 | 4-$OCH_3$ | $CH_3$ | $H/CO_2H$ (trans0 | +++ | 441.1 | Free Base |
| 33A-37 | 4-$OCH_3$ | $CH_3$ | $CH_3/CO_2H$ (cis) | +++ | 455.1 | Free Base |
| 33A-38 | 4-$OCH_3$ | $CH_3$ | $CH_3/CO_2H$ (trans) | +++ | 455.1 | Free Base |

Formula B; $R^5$ = H

| | | | | | | |
|---|---|---|---|---|---|---|
| 33A-39 | 4-c-Pr, 5-F | $CH_3$ | $H/CO_2CH_3$ | +++ | 511.2 | Free Base |
| 33A-40 | 4-c-Pr, 5-F | $CH_3$ | $H/CO_2H$ (isomer 1) | +++ | 497.2 | Free Base |
| 33A-41 | 4-c-Pr, 5-F | $CH_3$ | $H/CO_2H$ (isomer 2) | +++ | 497.2 | TFA Salt |
| 33A-42 | 4-c-Pr, 5-F | $CH_3$ | $H/CO_2H$ (isomer 3) | +++ | 479.2 | TFA Salt |
| 33A-43 | 5-Cl | $CH_3$ | $H/CO_2H$ (isomer 1) | +++ | 473 | Free Base |
| 33A-44 | 5-Cl | $CH_3$ | $H/CO_2H$ (isomer 2) | +++ | 473 | Free Base |
| 33A-45 | 5-F | $CH_3$ | $H/CO_2H$ | ++ | 457 | Free Base |
| 33A-46 | 5-F | $CH_3$ | $H/CO_2H$ (enantiomer 1) | ++ | 457 | TFA Salt |
| 33A-47 | 5-F | $CH_3$ | $H/CO_2H$ (enantiomer 2) | +++ | 457 | TFA Salt |
| 33A-48 | $CF_3$ | $C(OH)CH_3)_2$ | $H/CO_2H$ | +++ | 551.2 | TFA Salt |
| 33A-49 | $CF_3$ | $CH_2OC(O)CH_3$ | $H/CO_2CH_3$ | +++ | 579.2 | Free Base |
| 33A-50 | $CF_3$ | $CH_2OH$ | $H/CO_2CH_3$ (enantiomer 1) | +++ | 537.1 | Free Base |
| 33A-51 | $CF_3$ | $CH_2OH$ | $H/CO_2H$ (enantiomer 1) | +++ | 523.2 | Free Base |
| 33A-52 | $CF_3$ | $CH_2OH$ | $H/CO_2CH_3$ (enantiomer 2) | +++ | 537.1 | Free Base |
| 33A-53 | $CF_3$ | $CH_2OH$ | $H/CO_2H$ (enantiomer 2) | +++ | 523.2 | Free Base |
| 33A-54 | $CF_3$ | $CH_3$ | $H/CO_2H$ (trans) | +++ | 507 | Free Base |
| 33A-55 | $CF_3$ | $CHF_2$ | $H/CO_2CH_3$ | ++ | 557.2 | Free Base |
| 33A-56 | $CF_3$ | $CHF_2$ | $H/CO_2H$ | +++ | 543.1 | Free Base |
| 33A-57 | $CF_3$ | $CHF_2$ | $H/CO_2H$ (enantiomer 1) | +++ | 543.1 | Free Base |
| 33A-58 | $CF_3$ | $CHF_2$ | $H/CO_2H$ (enantiomer 2) | +++ | 543.1 | Free Base |
| 33A-59 | $CF_3$ | c-Pr | $H/CO_2H$ (enantiomer 1) | +++ | 533.2 | Free Base |
| 33A-60 | $CF_3$ | c-Pr | $H/CO_2H$ (enantiomer 2) | +++, +++ | 533.2 | Free Base, TFA Salt |
| 33A-61 | $CF_3$ | c-Pr | $H/CO_2CH_3$ | +++ | 547.2 | Free Base |

TABLE 33-A-continued

| | | | | | | |
|---|---|---|---|---|---|---|
| 33A-62 | CF$_3$ | c-Pr | H/CO$_2$H | +++ | 533.2 | TFA Salt |
| 33A-63 | CF$_3$ | F | H/CO$_2$H (enantiomer 1) | +++ | 511.1 | Free Base |
| 33A-64 | CF$_3$ | F | H/CO$_2$H (enantiomer 2) | +++ | 511.1 | TFA Salt |
| 33A-65 | CF$_3$ | H | H/CO$_2$CH$_3$ | ++ | 507.1 | Free Base |
| 33A-66 | CF$_3$ | H | H/CO$_2$H (cis, enantiomer 1) | +++ | 493 | Free Base |
| 33A-67 | CF$_3$ | H | H/CO$_2$H (cis, enantiomer 2) | +++ | 493 | Free Base |
| 33A-68 | CH$_3$ | CH$_3$ | H/CO$_2$H (cis) | +++ | 452.1 | Free Base |
| 33A-69 | CH$_3$ | CH$_3$ | H/CO$_2$CH$_3$ (cis) | +++ | 467.2 | Free Base |
| 33A-70 | c-Pr | CH$_3$ | H/CO$_2$CH$_3$ | +++ | 493.2 | Free Base |
| 33A-71 | c-Pr | CH$_3$ | H/CO$_2$H | +++ | 479.2 | Free Base |
| 33A-72 | OCH$_3$ | CH$_3$ | H/CO$_2$H (isomer 1) | +++ | 469.1 | Free Base |
| 33A-73 | OCH$_3$ | CH$_3$ | H/CO$_2$H (isomer 2) | +++ | 469.1 | Free Base |
| Formula B; R$^5$ = CH$_3$ | | | | | | |
| 33A-74 | 4-CH$_3$, 5-F | CH$_3$ | H/CO$_2$H | +++ | 485 | Free Base |
| 33A-75 | CF$_3$ | CH$_3$ | H/CO$_2$H | +++ | 521 | Free Base |
| 33A-76 | CF$_3$ | CH$_3$ | H/CO$_2$H (isomer 1) | +++ | 421 | Free Base |
| 33A-77 | CF$_3$ | CH$_3$ | H/CO$_2$H (isomer 2) | +++ | 521 | Free Base |
| 33A-78 | CF$_3$ | CH$_3$ | H/CO$_2$H (isomer 3) | +++ | 521 | Free Base |

TABLE 33B

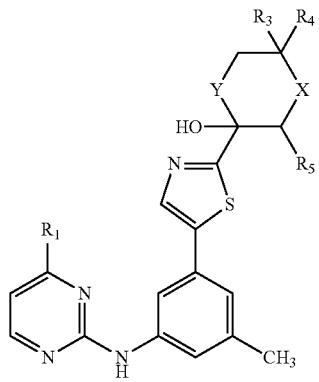

| Ex. | X | Y | R$^3$/R$^4$ | rhSYK Activity | [M + H]+ Obs'd | Form(s) |
|---|---|---|---|---|---|---|
| R$^1$ = CF$_3$, R$^5$ = H | | | | | | |
| 33B-1 | Bond | Bond | H/CO$_2$H | +++ | 451.0 | Ammonium salt |
| 33B-2 | Bond | CH[CH$_2$-(4-(2-propanoic acid)-Ph)] | H/H | +++ | 583 | Ammonium Salt |
| 33B-3 | C(CH$_3$)$_2$ | Bond | H/CO$_2$H | +++ | 493 | Free Base |
| 33B-4 | C(CH$_3$)$_2$ | Bond | H/CO$_2$H (isomer 2) | +++ | 493 | Free Base |
| 33B-5 | C(CH$_3$)$_2$ | Bond | H/CO$_2$H (isomer 4) | +++ | 493 | Free Base |
| 33B-6 | C(CH$_3$)$_2$ | Bond | H/CO$_2$H (isomer 1) | +++ | 493 | Free Base |
| 33B-7 | C(CH$_3$)$_2$ | Bond | H/CO$_2$H (isomer 3) | +++ | 493 | Free Base |
| 33B-8 | C(CH$_3$)$_2$ | CH$_2$CH$_2$ | H/CO$_2$H | +++ | 521 | Free Base |
| 33B-9 | C(CH$_3$)$_2$ | CH$_2$CH$_2$ | H/CO$_2$H (isomer 1) | +++ | 521 | Free Base |
| 33B-10 | C(CH$_3$)$_2$ | CH$_2$CH$_2$ | H/CO$_2$H (isomer 2) | +++ | 521 | Free Base |
| 33B-11 | C(CH$_3$)$_2$ | CH$_2$CH$_2$ | H/CO$_2$H (isomer 3) | +++ | 521 | Free Base |
| 33B-12 | C(CH$_3$)$_2$ | CH$_2$CH$_2$ | H/CO$_2$H (isomer 4) | +++ | 521 | Free Base |
| 33B-13 | CH(OCH$_3$) | CH$_2$ | H/CO$_2$H | +++ | 509 | Free Base |
| 33B-14 | CH(OCH$_3$) | CH$_2$ | H/CO$_2$H (cis, cis) | +++ | 509 | Free Base |

TABLE 33B-continued

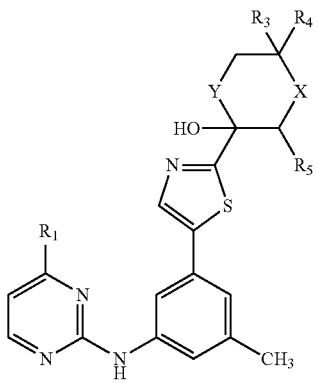

| Ex. | X | Y | $R^3/R^4$ | rhSYK Activity | [M + H]+ Obs'd | Form(s) |
|---|---|---|---|---|---|---|
| 33B-15 | CH(4-CO$_2$H—Ph) | CH$_2$ | H/H (isomer 1) | +++ | 555 | Formate Salt |
| 33B-16 | CH(4-CO$_2$H—Ph) | CH$_2$ | H/H (isomer 2) | +++ | 555 | Formate Salt |
| 33B-17 | [spiro-cyclopropyl] | CH$_2$ | H/CO$_2$H | +++ | 505 | Free Base |
| 33B-18 | CH(CH$_3$) | CH$_2$ | H/CO$_2$H (isomer 1) | +++ | 493.1 | Free Base |
| 33B-19 | CH(CH$_3$) | CH$_2$ | H/CO$_2$H (isomer 2) | +++ | 493.2 | TFA Salt |
| 33B-20 | CH(CH$_3$) | CH$_2$ | H/CO$_2$H (isomer 3) | +++, +++ | 493.1 | Free Base, TFA Salt |
| 33B-21 | CH(CO$_2$H) | CH$_2$ | H/H | +++ | 479.1 | Free Base |
| 33B-24 | CH(iPr) | CH$_2$ | H/CO$_2$H | +++ | 521 | Free Base |
| 33B-22 | CH(iPr) | CH$_2$ | H/CO$_2$H (enantiomer 1) | +++ | 521 | Free Base |
| 33B-23 | CH(iPr) | CH$_2$ | H/CO$_2$H (enantiomer 2) | +++ | 521 | Free Base |
| 33B-24 | CH$_2$ | bond | H/CO$_2$H | +++ | 465.0 | Ammonium salt |
| 33B-25 | CH$_2$ | bond | H/CH$_2$CO$_2$H (trans, enantiomer 1)) | +++ | 479 | Free Base |
| 33B-26 | CH$_2$ | bond | H/CH$_2$CO$_2$H (cis, enantiomer 1) | +++ | 479 | Free Base |
| 33B-27 | CH$_2$ | bond | H/CH$_2$CO$_2$H (trans, enantiomer 2) | +++ | 479 | Free Base |
| 33B-28 | CH$_2$ | bond | H/CH$_2$CO$_2$H (cis, enantiomer 2) | +++ | 479 | Free Base |

$R^1 = CH_3, R^5 = H$

| 33B-29 | CH(2-CH$_3$—Ph) | CH$_2$ | H/CO$_2$H | +++ | 515 | Free Base |
| 33B-30 | CH(3-thienyl) | CH$_2$ | H/CO$_2$H | ++ | 507 | Free Base |
| 33B-31 | CH(4-F—Ph) | CH$_2$ | H/CO$_2$H | +++ | 519 | Free Base |
| 33B-32 | CH(CH$_3$) | CH$_2$ | H/CO$_2$H (isomer 1) | +++ | 439.2 | Free Base |
| 33B-33 | CH(CH$_3$) | CH$_2$ | H/CO$_2$H (isomer 2) | +++ | 439.2 | Free Base |
| 33B-34 | CH(iPr) | CH$_2$ | H/CO$_2$H | +++ | 467 | Free Base |
| 33B-35 | CH(iPr) | CH$_2$ | H/CO$_2$H (isomer 1) | +++ | 467 | Free Base |
| 33B-36 | CH(iPr) | CH$_2$ | H/CO$_2$H (isomer 2) | +++ | 467 | Free Base |
| 33B-37 | CH(Ph) | CH$_2$ | H/CO$_2$H | +++ | 501 | Free Base |

$R^1 = CF_3, R^5 = CH_3$

TABLE 33B-continued

| Ex. | X | Y | $R^3/R^4$ | rhSYK Activity | [M + H]+ Obs'd | Form(s) |
|---|---|---|---|---|---|---|
| 33B-38 | CH(CH$_3$) | CH$_2$ | H/CO$_2$H (isomer 1) | +++ | 507 | TFA Salt |
| 33B-39 | CH(CH$_3$) | CH$_2$ | H/CO$_2$H (isomer 2) | +++ | 507 | Free Base |

$R^1 = CF_3, R^5 = CH_2CH_3$

| Ex. | X | Y | $R^3/R^4$ | rhSYK Activity | [M + H]+ Obs'd | Form(s) |
|---|---|---|---|---|---|---|
| 33B-40 | CH(CH$_3$) | CH$_2$ | H/CO$_2$H | +++ | 521 | TFA Salt |
| 33B-41 | CH(CH$_3$) | CH$_2$ | H/CO$_2$H (isomer 1) | +++ | 521 | TFA Salt |
| 33B-42 | CH(CH$_3$) | CH$_2$ | H/CO$_2$H (isomer 2) | +++ | 521 | TFA Salt |

TABLE 33C

| Ex. | $R^1$ | $R^3$ | rhSYK Activity | [M + H]+ Obs'd | Form(s) |
|---|---|---|---|---|---|
| 33C-1 | CF$_3$ | (spiro bicyclobutane with HO$_2$C– and –OH) | +++ | 491.1 | Free Base |
| 33C-2 | CF$_3$ | (bicyclic with HO$_2$C– and –OH) | +++ | 505 | Free Base |
| 33C-3 | CF$_3$ | (bicyclo with HO– and –CO$_2$H) | +++ | 519.2 | Ammonium salt |

TABLE 33C-continued

| Ex. | R¹ | R³ | rhSYK Activity | [M + H]+ Obs'd | Form(s) |
|---|---|---|---|---|---|
| 33C-4 | CH₃ | (2-acyl-1-(4-carboxyphenyl)pyrrole) | +++ | 550 | Ammonium Salt |
| 33C-5 | CH₃ | (3,3,5-trimethyl-γ-butyrolactone) | +++ | 463.0 | Free Base |
| 33C-6 | CF₃ | (hydroxy-bicyclic cyclopentane-CO₂H) | +++ | 477.1 | Free Base |
| 33C-7 | CF₃ | (hydroxy-bicyclic cyclopentane-CO₂H) isomer 1 | +++ | 477.1 | Free Base |
| 33C-8 | CF₃ | (hydroxy-bicyclic cyclopentane-CO₂H) isomer 2 | +++ | 477.1 | Free Base |
| 33C-9 | CF₃ | (HO-bicyclic cyclopentane-CO₂H) isomer 1 | +++ | 477.1 | Free Base |
| 33C-10 | CF₃ | (HO-bicyclic cyclopentane-CO₂H) isomer 2 | +++ | 477.1 | Free Base |

TABLE 33C-continued

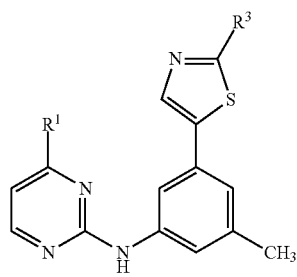

| Ex. | R¹ | R³ | rhSYK Activity | [M + H]+ Obs'd | Form(s) |
|---|---|---|---|---|---|
| 33C-11 | CF₃ | (cyclopropane-fused cyclopentane with HO and CO₂CH₂CH₃) isomer 1 | +++ | 505.1 | Free Base |
| 33C-12 | CF₃ | (cyclopropane-fused cyclopentane with HO and CO₂CH₂CH₃) isomer 2 | +++ | 505.1 | Free Base |
| 33C-13 | CF₃ | (azetidine with HN and OH) | +++ | 408.1 | TFA Salt |
| 33C-14 | CF₃ | (H₃C)₃CO-C(O)-N-azetidine-OH | ++ | 508.1 | Free Base |
| 33C-15 | CF₃ | (piperidine with HO, linked to pyridine with HO₂C) | +++ | 557 | Formate Salt |
| 33C-16 | CF₃ | (piperidine with HO, linked to pyridine with CO₂CH₂CH₃) | ++ | 585 | Formate Salt |
| 33C-17 | CH₃ | (dioxolane-spiro-cyclohexane with OH) | +++ | 439.2 | Free Base |
| 33C-18 | CH₃ | (bicyclic with OH and HO₂C) (isomer 1) | +++ | 451.1 | TFA Salt |

TABLE 33C-continued

[Structure: pyrimidine with R¹ at 4-position, NH-linked to 3-methylphenyl bearing thiazole with R³ at 2-position]

| Ex. | R¹ | R³ | rhSYK Activity | [M + H]+ Obs'd | Form(s) |
|---|---|---|---|---|---|
| 33C-19 | CH₃ | [bicyclic structure with OH, HO₂C] (isomer 2) | +++ | 451.0 | TFA Salt |
| 33C-20 | CH₃ | 1-CO₂H-4-OH-tricyclo[3.3.1.1³,⁷]decan-4-yl | +++, +++ | 477.2, 477.2 | TFA Salt, Ammonium Salt |
| 33C-21 | CH₃ | [2-methyl-1-(carboxymethyl)indol-3-yl ketone] | +++ | 552 | Ammonium Salt |
| 33C-22 | CH₃ | [1-(2-carboxyethyl)indol-3-yl ketone] | ++ | 552 | Ammonium Salt |

TABLE 33D

[Structure: 4-(CF₃)-pyrimidine, NH-linked to 3-methylphenyl bearing thiazole with C(R³)(R⁴)(OH) at 2-position]

| Ex. | R³/R⁴ | rhSYK Activity | [M + H]+ Obs'd | Form(s) |
|---|---|---|---|---|
| 33D-1 | CH₃/(CH₂)₂C(CH₃)₂CO₂H | +++ | 495.1 | TFA Salt |
| 33D-2 | CH₃/(CH₂)₂C(CH₃)₂CO₂H (enantiomer 1) | +++ | 495.1 | Free Base |
| 33D-3 | CH₃/(CH₂)₂C(CH₃)₂CO₂H (enantiomer 2) | +++ | 495.1 | Free Base |
| 33D-4 | CH₃/(CH₂)₂C(CH₃)₂CO₂CH₃ | +++ | 509.1 | Free Base |
| 33D-5 | CH₃/(E)-CH=CHC(CH₃)₂CO₂H | +++ | 493.1 | Free Base |
| 33D-6 | CH₃/(E)-CH=CHC(CH₃)₂CO₂CH₃ | +++ | 507.1 | Free Base |
| 33D-7 | CH₃/CH₂OC(CH₃)₂CO₂H | +++ | 497.1 | Free Base |
| 33D-8 | CH₃/CH₂OC(CH₃)₂CO₂CH₃ | +++ | 511.1 | Free Base |

TABLE 33D-continued

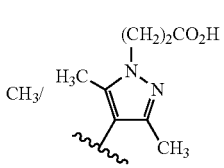

| Ex. | $R^3/R^4$ | rhSYK Activity | [M+H]+ Obs'd | Form(s) |
|---|---|---|---|---|
| 33D-9 | $CH_3/CH_2C(CH_3)_2CO_2H$ | +++ | 481.1 | Free Base |
| 33D-10 | $CH_3/CH_2CH_2CO_2H$ | +++ | 453.1 | Potassium Salt |
| 33D-11 | $CH_3/2\text{-}(OCH_2CO_2H)Ph$ | +++ | 531 | Ammonium Salt |
| 33D-12 | $CH_3/4\text{-}(OCH_2CO_2H)Ph$ | +++ | 531 | Ammonium Salt |
| 33D-13 | $CH_3/4\text{-}(OCH(CH_3)CO_2H)Ph$ | +++ | 545 | Ammonium Salt |
| 33D-14 | $CH_3/4\text{-}(NHC(O)(CH_2)_2CO_2H)Ph$ | +++ | 572 | Ammonium Salt |
| 33D-15 | $CH_3/4\text{-}(NHC(O)(CH_2)_3CO_2H)Ph$ | +++ | 586 | Ammonium Salt |
| 33D-16 | $CH_3/4\text{-}(CO_2H)Ph$ | +++ | 501.0 | Free Base |
| 33D-17 | $CH_3/4\text{-}(CO_2CH_3)Ph$ | +++ | 515.0 | Free Base |
| 33D-18 | $CH_3/CH_2\text{-}4\text{-}(CO_2H)Ph$ | +++ | 515 | Free Base, Formate Salt |
| 33D-19 | 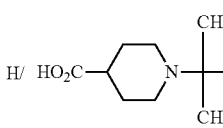 | +++ | 547 | Formate Salt |
| 33D-20 | $CH_3/5\text{-}(CO_2H)\text{-}2\text{-thienyl}$ | +++ | 507.0 | Free Base |
| 33D-21 | $CH_3/5\text{-}(CO_2H)\text{-}2\text{-thienyl}$ (enantiomer 1) | +++ | 507.0 | Free Base |
| 33D-22 | $CH_3/5\text{-}(CO_2H)\text{-}2\text{-thienyl}$ (enantiomer 2) | +++ | 507.0 | Free Base |
| 33D-23 | 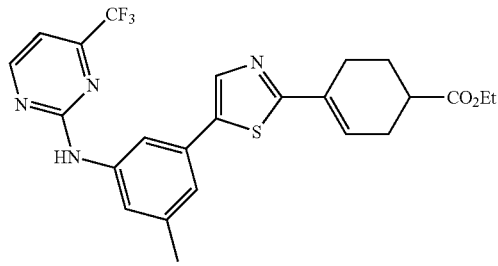 | +++ | 536 | Formate Salt |
| 33D-24 | $cPr/4\text{-}((E)\text{-}CH=CHCO_2H)Ph$ | +++ | 553 | Ammonium Salt |
| 33D-25 | $4\text{-pyridyl}/(CH_2)_3CO_2H$ | +++ | 530 | Formate Salt |

Examples 34 ethyl 4-[5-(3-methyl-5-{[4-(trifluoromethyl)pyrimidin-2-yl]amino}phenyl)-1,3-thiazol-2-yl]cyclohex-3-ene-1-carboxylate

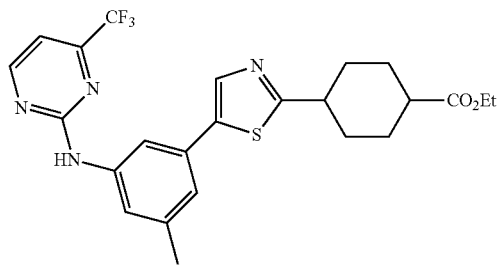 [SMILES: CCOC(=O)C1CCC(c2ncc(-c3cc(C)cc(Nc4nccc(C(F)(F)F)n4)c3)s2)CC1]

To a flask containing ethyl 4-hydroxy-4-[5-(3-methyl-5-{[4-(trifluoromethyl)pyrimidin-2-yl]amino}phenyl)-1,3-thiazol-2-yl]cyclohexanecarboxylate (Example 32, 0.18 g, 0.345 mmol) was added Eaton's Reagent (1.3 mL) and the mixture was heated at 60° C. for 2 hours. The reaction was cooled and added dropwise to saturated sodium bicarbonate. After stirring for 2 minutes, the aqueous solution was extracted three times with ethyl acetate. The combined organics were dried under reduced pressure and purified by silica gel chromatography to yield ethyl 4-[5-(3-methyl-5-{[4-(trifluoromethyl)pyrimidin-2-yl]amino}phenyl)-1,3-thiazol-2-yl]-cyclohex-3-ene-1-carboxylate (0.14 g, 82% yield). MS ESI: [M+H]+ m/z 489.1. $^1$H NMR (500 MHz, CDCl$_3$) δ 8.65 (d, J=5.2, 1H), 7.96-7.79 (m, 2H), 7.46 (s, 1H), 7.26 (s, 1H), 7.14-6.95 (m, 2H), 6.65 (s, 1H), 4.28-3.96 (m, 2H), 2.90-2.75 (m, 1H), 2.75-2.60 (m, 1H), 2.62-2.47 (m, 3H), 2.39 (s, 3H), 2.26-2.10 (m, 1H), 1.95-1.70 (m, 1H), 1.39-1.17 (m, 3H). rhSYK activity=++

Examples 35 ethyl 4-[5-(3-methyl-5-{[4-(trifluoromethyl)pyrimidin-2-yl]amino}phenyl)-1,3-thiazol-2-yl]cyclohexanecarboxylate To ethyl 4-[5-(3-methyl-5-{[4-(trifluoromethyl)pyrimidin-2-yl]amino}phenyl)-1,3-thiazol-2-yl]-cyclohex-3-ene-1-carboxylate (0.15 g, 0.31 mmol) was added ethanol (2 mL) and argon was bubbled through the solution for 5 minutes. The flask was then purged/filled with argon three times. 10% Palladium on carbon (0.33 mg) was added to the flask and the flask was purged/filled with argon three times. A hydrogen balloon was added to the top of the flask and the reaction was purged/filled with argon three times. The reaction was stirred for 72 hours. Upon completion, the reaction was filtered carefully through celite and the celite pad was washed with methanol (70 mL). The filtrate was concentrated under reduced pressure and the solid was purified by silica gel chromatography to yield ethyl 4-[5-(3-methyl-5-{[4-(trifluoromethyl)-pyrimidin-2-yl]amino}phenyl)-1,3-thiazol-2-yl]cyclohexanecarboxylate (0.73 g, 49% yield). MS ESI: [M+H]+ m/z 491.1. $^1$H NMR (500 MHz, CDCl$_3$) δ 8.63 (d, J=5.3, 1H), 7.96-7.73 (m, 2H), 7.64 (s, 1H), 7.25 (s, 1H), 7.13-6.92 (m, 2H), 4.24-3.99 (m, 2H), 3.23-3.02 (m, 1H), 2.73-2.57 (m, 1H), 2.49 (s, 3H) 2.32-2.21 (m, 1H), 2.23-2.07 (m, 2H), 2.02-1.81 (m, 3H), 1.79-1.64 (m, 1H), 1.64-1.52 (m, 1H), 1.39-1.08 (m, 3H). rhSYK activity=++

Examples 36

4-[5-(3-methyl-5-{[4-(trifluoromethyl)pyrimidin-2-yl]amino}phenyl)-1,3-thiazol-2-yl]cyclohexanecarboxylic acid (HCl salt)

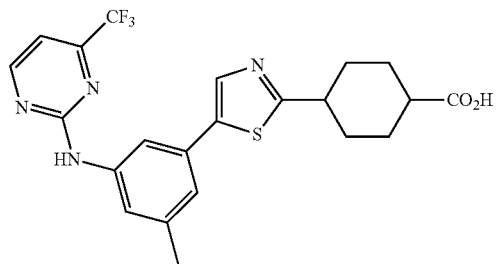 [SMILES: Cc1cc(Nc2nccc(C(F)(F)F)n2)cc(-c2cnc(C3CCC(C(=O)O)CC3)s2)c1]

Step 3

To ethyl 4-[5-(3-methyl-5-{[4-(trifluoromethyl)pyrimidin-2-yl]amino}phenyl)-1,3-thiazol-2-yl]cyclohexanecarboxylate (0.60 g, 0.12 mmol) in tetrahydrofuran (0.61 mL) was added potassium hydroxide (1.2 mL, 1 M in methanol) and the reaction was stirred overnight at room temperature. Upon completion, the reaction was diluted with dichloromethane and washed twice with hydrochloric acid (2 M in water). The organic layer was dried under reduced pressure to give 2-({3-[2-(4-carboxycyclohexyl)-1,3-thiazol-5-yl]-5-methylphenyl}amino)-4-(trifluoromethyl)pyrimidin-1-ium chloride (0.060 g, 85% yield). MS ESI: [M+H]$^+$ m/z 463.1. $^1$H NMR (500 MHz, DMSO-d$_6$) δ 10.25 (s, 1H), 8.83 (d, J=5.2, 1H), 8.06-7.81 (m, 2H), 7.44 (s, 1H), 7.27 (d, J=5.8, 1H), 7.14 (s, 1H), 2.30 (s, 3H), 2.14-2.04 (m, 1H), 2.03-1.83 (m, 4H), 1.82-1.61 (m, 3H), 1.55-1.33 (m, 2H). rhSYK activity=+++

The following examples were prepared in an analogous manner of that described in Examples 34-36.

TABLE 36A

| Example | R$^1$ | X | R$^2$/R$^{2'}$ or R$^2$+R$^{2'}$ | ---- | rhSYK Activity | [M + H]+ Obs'd | Form(s) |
|---|---|---|---|---|---|---|---|
| R$^3$ = R$^{3'}$ = H | | | | | | | |
| 36A-1 | H | CHCO$_2$Et | H/H | double | ++ | 475.1 | Free Base |
| 36A-2 | CH$_3$ | CHCO$_2$Et | H/H | single | ++ | 491.1 | Free Base |
| 36A-3 | CH$_3$ | CHCO$_2$H | H/H | double | +++ | 461.1 | Chloride Salt |
| 36A-4 | H | CHCO$_2$H (trans) | H/H | single | +++ | 449.1 | Free Base |
| 36A-5 | H | CHCO$_2$Me (trans) | H/H | single | ++ | 463.1 | Free Base |
| 36A-6 | CH$_3$ | Bond | =O | double | +++ | 417.1 | Free Base |
| 36A-7 | CH$_3$ | CH$_2$ | =O | double | +++ | 431.1 | Free Base |
| 36A-8 | CH$_3$ | CH$_2$ | =O | single | +++ | 433.1 | Free Base |
| 36A-9 | CH$_3$ | CH$_2$CH$_2$ | =O | double | +++ | 445.1 | Free Base |
| 36A-10 | CH$_3$ | CH$_2$CH$_2$ | =O | single | +++ | 447.1 | Free Base |
| 36A-11 | CH$_3$ | CHCO$_2$CH$_3$ | CH$_3$/CH$_3$ | double | ++ | 503.1 | Free Base |
| 36A-12 | CH$_3$ | (dioxolane) | H/H | single | ++ | 477.1 | Free Base |
| R$^3$ = R$^{3'}$ = CH$_3$ | | | | | | | |
| 36A-13 | CH$_3$ | CHCO$_2$Et | H/H | double | ++ | 503.1 | Free Base |

TABLE 36B

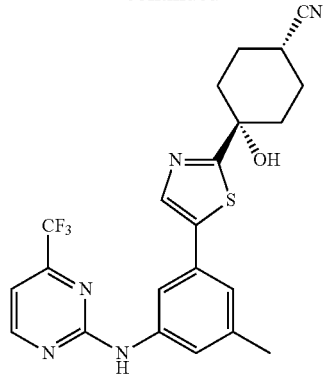

| Example | R | rhSYK Activity | [M + H]+ Obs'd | Form(s) |
|---|---|---|---|---|
| 36B-1 | ![piperidinone] | +++ | 434.1 | Free Base |
| 36B-2 | ![azepinone unsaturated] | +++ | 446.1 | Free Base |
| 36B-3 | ![azepanone] | +++ | 448.1 | Free Base |
| 36B-4 | ![azepanone isomer] | +++ | 448.1 | Free Base |

Examples 37(1) and 37(2)

cis-4-hydroxy-4-[5-(3-methyl-5-{[4-(trifluoromethyl)pyrimidin-2-yl]amino}phenyl)-1,3-thiazol-2-yl]cyclohexanecarbonitrile trans-4-hydroxy-4-[5-(3-methyl-5-{[4-(trifluoromethyl)pyrimidin-2-yl]amino}phenyl)-1,3-thiazol-2-yl]cyclohexanecarbonitrile

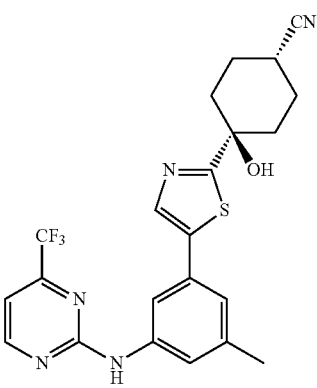

To a flask was added tetrahydrofuran (3.0 mL) and the flask was cooled to −78° C. Lithium diisopropylamide (1.0 mL, 1.78 mmol) was added and the mixture was cooled to −78° C. Intermediate 4 (0.20 g, 0.60 mmol) was dissolved in tetrahydrofuran (3.0 mL) and added to the reaction mixture in one portion and stirred for 30 minutes. 4-oxocyclohexanecarbonitrile (0.073 g, 0.60 mmol) was dissolved in THF (3.0 mL) and then added over a period of five minutes and the solution was then allowed to warm to room temperature. The reaction was diluted with ethyl acetate, washed with saturated ammonium chloride, dried over magnesium sulfate, filtered and concentrated. Column chromatography was used to yield:

cis-4-hydroxy-4-[5-(3-methyl-5-{[4-(trifluoromethyl)pyrimidin-2-yl]amino}phenyl)-1,3-thiazol-2-yl]cyclohexanecarbonitrile (0.72 g, 26%) Analysis for cis isomer: MS ESI: [M+H]+ m/z 460.1. $^1$H NMR (600 MHz, DMSO-d$_6$) δ 10.23 (s, 1H), 8.81 (d, J=4.9, 1H), 7.93 (m, 2H), 7.44 (s, 1H), 7.26 (d, J=4.9, 1H), 7.13 (s, 1H), 6.11 (s, 1H), 2.82 (s, 1H), 2.29 (s, 3H), 1.99-1.72 (m, 8H). rhSYK activity=+++ trans-4-hydroxy-4-[5-(3-methyl-5-{[4-(trifluoromethyl)pyrimidin-2-yl]amino}phenyl)-1,3-thiazol-2-yl]cyclohexanecarbonitrile (0.78 g, 29%). MS ESI: [M+H]+ m/z 460.1. IE NMR (600 MHz, DMSO-d$_6$) δ 10.23 (s, 1H), 8.81 (d, J=4.9, 1H), 8.00-7.89 (m, 2H), 7.45 (s, 1H), 7.25 (d, J=4.9, 1H), 7.14 (s, 1H), 6.11 (s, 1H), 3.13 (s, 1H), 2.30 (s, 3H), 2.07 (m, 2H), 2.00-1.89 (m, 2H), 1.77 (m, 4H). rhSYK activity=+++

Examples 38(1) and 38(2)

trans-4-hydroxy-4-[5-(3-methyl-5-{[4-(trifluoromethyl)pyrimidin-2-yl]amino}phenyl)-1,3-thiazol-2-yl]cyclohexanecarboxamide cis-4-hydroxy-4-[5-(3-methyl-5-{[4-(trifluoromethyl)pyrimidin-2-yl]amino}phenyl)-1,3-thiazol-2-yl]cyclohexanecarboxamide

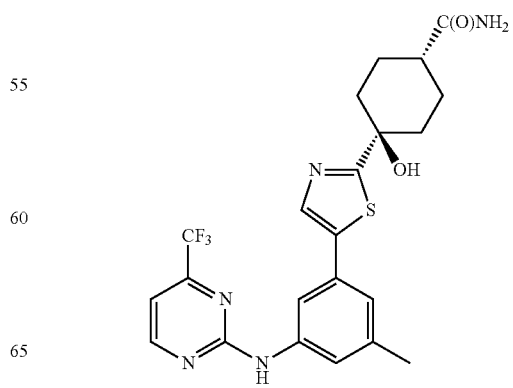

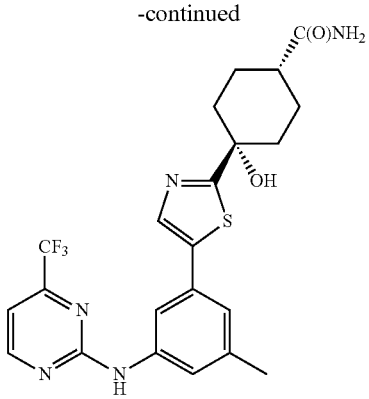

To trans-4-hydroxy-4-[5-(3-methyl-5-{[4-(trifluoromethyl)pyrimidin-2-yl]amino}phenyl)-1,3-thiazol-2-yl]cyclohexanecarbonitrile (0.78 g, 0.17 mmol) was added DMSO (1.4 mL). Potassium carbonate (0.13 mg, 0.92 mmol) and 30% hydrogen peroxide (0.17 mL, 1.70 mmol) were added and the reaction was heated at 70° C. Upon completion, the solution was cooled and filtered. The filtrate was purified by reverse phase HPLC (10-100% acetonitrile gradient with water over 12 minutes with a 0.05% trifluoroacetic acid buffer) to yield trans-4-hydroxy-4-[5-(3-methyl-5-{[4-(trifluoromethyl)pyrimidin-2-yl]amino}phenyl)-1,3-thiazol-2-yl]cyclohexane-carboxamide (0.040 g, 49%). MS ESI: [M+H]⁺ m/z 478.1. ¹H NMR (500 MHz, CD₃OD) δ 8.72 (d, J=5.3, 1H), 8.03 (s, 1H), 7.90 (s, 1H), 7.45 (s, 1H), 7.22-6.90 (m, 2H), 2.57-2.40 (m, 3H), 2.38 (s, 3H), 2.00-1.69 (m, 6H). rhSYK activity=+++

In an analogous manner of that described above, cis-4-hydroxy-4-[5-(3-methyl-5-{[4-(trifluoromethyl)pyrimidin-2-yl]amino}phenyl)-1,3-thiazol-2-yl]cyclohexanecarboxamide was prepared as the free base. [M+H]+ Observed: 478.1. rhSYK Activity: +++

Example 39

3-{cis-4-Hydroxy-4-[5-(3-methyl-5-{[4-(trifluoromethyl)pyrimidin-2-yl]amino}phenyl)-1,3-thiazol-2-yl]cyclohexyl}-1,2,4-oxadiazol-5(4H)-one

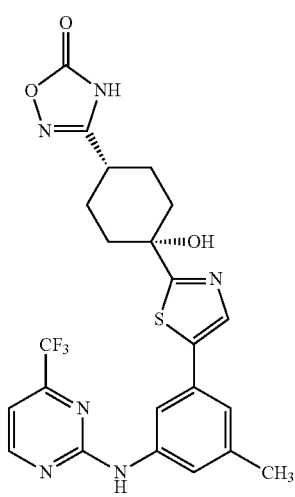 [SMILES: Cc1cc(Nc2nccc(C(F)(F)F)n2)cc(-c2cnc([C@]3(O)CC[C@@H](c4noc(=O)[nH]4)CC3)s2)c1]

Step 1 cis-4-Hydroxy-4-[5-(3-methyl-5-{[4-(trifluoromethyl)pyrimidin-2-yl]amino}phenyl)-1,3-thiazol-2-yl]cyclohexanecarboxylic acid (500 mg, 1.05 mmol), ammonium chloride (112 mg, 2.09 mmol), O-(7-azabenzotriazol-1-yl)-N,N,N',N'-tetramethyluronium hexafluorophosphate (795 mg, 2.09 mmol), and diisopropylethylamine (730 µl, 4.18 mmol) were taken-up in dimethylformamide (4.2 mL) under argon. The vessel was sealed and stirred at 65° C. for 4 hours. Upon cooling, the reaction mixture was diluted with water, and the resulting precipitate was collected via filtration. The solids were washed with water and diethyl ether and dried in vacuo overnight to afford cis-4-hydroxy-4-[5-(3-methyl-5-{[4-(trifluoromethyl)pyrimidin-2-yl]amino}-phenyl)-1,3-thiazol-2-yl]cyclohexanecarboxamide (437.6 mg, 0.916 mmol, 88% yield) as a white solid. MS ESI: [M+H]⁺ m/z 478.1.

Step 2

In a dry vessel, the product from Step 1 (350 mg, 0.733 mmol) was taken-up in dichloromethane (4.9 mL) and tetrahydrofuran (2.4 mL) under argon. (Methoxycarbonyl-sulfamoyl)triethylammonium hydroxide, inner salt (218 mg, 0.916 mmol) was added, and the resulting mixture was sealed and stirred at room temperature for 18 hours. Another portion of (methoxycarbonylsulfamoyl)triethylammonium hydroxide, inner salt (218 mg, 0.916 mmol) was then added, and the resulting mixture was sealed and stirred at room temperature for 18 hours. The reaction mixture was quenched with water and directly concentrated. Reverse-phase HPLC purification (water-acetonitrile, trifluoroacetic acid modifier) afforded cis-4-hydroxy-4-[5-(3-methyl-5-{[4-(trifluoromethyl)pyrimidin-2-yl]amino}phenyl)-1,3-thiazol-2-yl]cyclohexane-carbonitrile (28.6 mg, 0.062 mmol, 8.5% yield) as a white solid. MS ESI: [M+H]⁺ m/z 460.1.

Step 3

The product from Step 2 (25 mg, 0.054 mmol), hydroxylamine hydrochloride (18.90 mg, 0.272 mmol), and potassium carbonate (41.4 mg, 0.299 mmol) were taken-up in ethanol (0.5 mL) under argon. The vessel was sealed and stirred at 80° C. for 18 hours. The reaction mixture was directly concentrated, and the solids were taken-up in tetrahydrofuran (0.5 mL). Triethylamine (22.8 µl, 0.163 mmol) was added, and the mixture was cooled to 0° C. Carbonyldiimidazole (13.2 mg, 0.082 mmol) was added, and the resulting mixture was allowed to warm to room temperature over 18 hours. The reaction was quenched with trifluoroacetic acid and diluted with 1 ml DMSO. The resulting mixture was filtered and directly subjected to reverse-phase HPLC (water-acetonitrile, trifluoroacetic acid modifier). This purification afforded the title compound (14.7 mg, 0.028 mmol, 52% yield) as a white solid. MS ESI: [M+H]⁺ m/z 519.1. ¹H NMR (500 MHz, dmso) δ 12.23 (s, 1H), 10.26 (s, 1H), 8.83 (d, J=4.8, 1H), 7.94 (d, J=10.8, 2H), 7.46 (s, 1H), 7.28 (d, 4.9, 1H), 7.15 (s, 1H), 6.06 (s, 1H), 2.68 (m, 1H), 2.31 (s, 3H), 2.03-1.79 (m, 8H). rhSYK. activity=+++

Example 40(1) and 40(2)

2-({3-[2-(cis-4-Carboxy-1-methoxycyclohexyl)-1,3-thiazol-5-yl]-5-methylphenyl}amino)-4-(trifluoromethyl)pyrimidin-1-ium trifluoroacetate 2-({3-[2-(trans-4-Carboxy-1-methoxycyclohexyl)-1,3-thiazol-5-yl]-5-methylphenyl}amino)-4-(trifluoromethyl)pyrimidin-1-ium trifluoroacetate

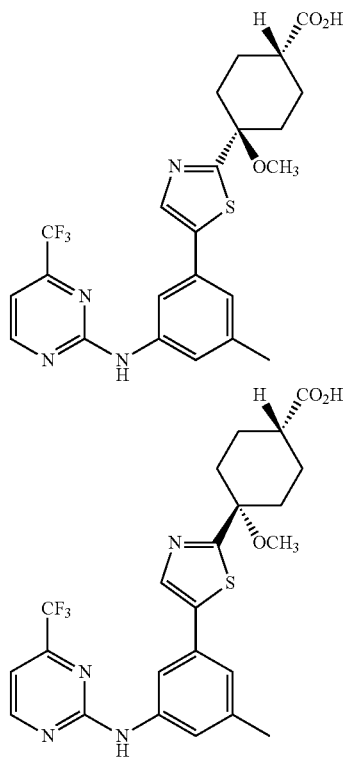

Step 1

To a solution of ethyl 4-[5-(3-{(tert-butoxycarbonyl)[4-(trifluoromethyl)pyrimidin-2-yl]amino}-5-methylphenyl)-1,3-thiazol-2-yl]-4-hydroxycyclohexanecarboxylate (0.148 g, 0.24 mmol) and DMF (1.2 mL) was added iodomethane (0.042 g, 0.29 mmol). The solution was cooled to 0° C. and then 60% sodium hydride in mineral oil (0.011 g, 0.27 mmol) was added and the reaction was allowed to warm up overnight. The next morning, iodomethane (1.14 g, 8.03 mmol) was added and the mixture was cooled to 0° C. Sodium hydride in mineral oil (60%, 0.011 g, 0.27 mmol) was added and the reaction was allowed to warm to room temperature. The reaction was complete after warming. The solution was cooled to 0° C. and carefully quenched with methanol and then water. The mixture was extracted with dichloromethane. The organic layer was washed three times with water, dried over magnesium sulfate, filtered and concentrated. Purification by silica gel chromatography was used to yield ethyl 4-[5-(3-{(tert-butoxycarbonyl)[4-(trifluoromethyl)pyrimidin-2-yl]amino}-5-methylphenyl)-1,3-thiazol-2-yl]-4-methoxycyclohexanecarboxylate. MS ESI: [M+H]$^+$ m/z 621.2.

Step 2

To the product of Step 1 (0.15 g, 0.243 mmol) in dichloromethane (2 mL) was added trifluoroacetic acid (1.48 g, 12.98 mmol) and the reaction was stirred until complete. The reaction was diluted with water and the mixture extracted three times with dichloromethane. The combined organic layers were dried over magnesium sulfate; filtered and concentrated to give ethyl 4-methoxy-4-[5-(3-methyl-5-{[4-(trifluoromethyl)pyrimidin-2-yl]amino}phenyl)-1,3-thiazol-2-yl]cyclohexanecarboxylate. MS ESI: [M+H]$^+$ m/z 521.2.

Step 3

To the product of Step 2 (0.13, 0.24 mmol) in methanol (1 mL) was added potassium hydroxide (1M in water, 0.24 mL, 0.24 mmol) and the reaction was stirred at room temperature overnight. The reaction was quenched with hydrochloric acid (2N in water) and the solution was extracted 3 times with dichloromethane. The combined organic layer was concentrated and the residue was subject to purification by supercritical fluid chromatography with an OJ-H 2.1×25 cm, 5 μM column. The mobile phase was a 2:8 methanol/CO$_2$ with a flow rate of 70 mL/min with a 12 minute run time to yield: 2-({3-[2-(cis-4-Carboxy-1-methoxycyclohexyl)-1,3-thiazol-5-yl]-5-methylphenyl}amino)-4-(trifluoromethyl)pyrimidin-1-ium trifluoroacetate (0.03 g, 19% yield). MS ESI: [M+H]$^+$ m/z 493.1. $^1$H NMR (500 MHz, CDCl$_3$) δ 8.64 (s, 1H), 7.93 (m, 2H), 7.28 (s, 1H), 7.12 (s, 1H), 7.07 (d, J=4.9, 1H), 3.27, (s, 3H), 2.41 (s, 3H), 2.29 (m, 1H), 1.96 (m, 8H). rhSYK activity=+++. 2-(3-[2-(trans-4-Carboxy-1-methoxycyclohexyl)-1,3-thiazol-5-yl]-5-methylphenyl)amino)-4-(trifluoromethyl)pyrimidin-1-ium trifluoroacetate (0.02 g, 15% yield). MS ESI: [M+H]$^+$ m/z 493.1. $^1$H NMR (600 MHz, CDCl$_3$) δ 8.58 (s, 1H), 7.92 (s, 1H), 7.83 (s, 1H), 7.41 (s, 1H), 7.08 (s, 1H), 7.04 (d, J=5.0, 1H), 3.16 (s, 3H), 2.64 (s, 1H), 2.37 (s, 3H), 2.05-1.89 (m, 8H). rhSYK activity=+++.

Example 41

1-amino-4-hydroxy-4-[5-(3-methyl-5-{[4-(trifluoromethyl)pyrimidin-2-yl]amino}phenyl)-1,3-thiazol-2-yl]cyclohexanecarboxylic acid

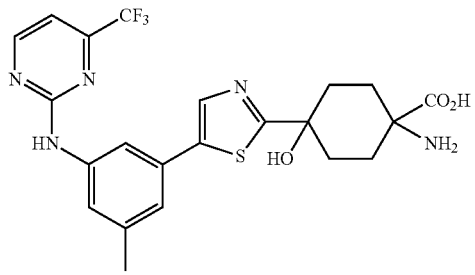 [SMILES: Cc1cc(Nc2nccc(C(F)(F)F)n2)cc(-c2cnc(C3(O)CCC(N)(C(=O)O)CC3)s2)c1]

Step 1

1-{[(9H-Fluoren-9-yloxy)carbonyl]amino}-4-hydroxy-4-[5-(3-methyl-5-{[4-(trifluoromethyl)pyrimidin-2-yl]amino}phenyl)-1,3-thiazol-2-yl]cyclohexanecarboxylic acid (0.079 g, 0.11 mmol) was dissolved in DMF (1.0 mL). Piperidine (0.086 g, 1.01 mmol) was added. After 15 minutes, the reaction mixture was directly purified by reverse phase HPLC to yield 1-amino-4-hydroxy-4-[5-(3-methyl-5-{[4-(trifluoromethyl)pyrimidin-2-yl]amino}phenyl)-1,3-thiazol-2-yl]cyclohexanecarboxylic acid (0.005 g, 0.01 mmol) as its TFA salt. MS ESI: [M+H]⁺ m/z 494.1. ¹H NMR (600 MHz, CD₃OD) δ 8.70 (d, J=4.9, 1H), 8.04 (s, 1H), 7.94-7.80 (m, 2H), 7.69 (d, J=7.6, 1H), 7.52-7.42 (m, 1H), 7.42-7.34 (m, 1H), 7.18-7.00 (m, 2H), 2.60-2.42 (m, 2H), 2.36 (s, 3H), 2.28-2.07 (m, 4H), 2.05-1.89 (m, 2H). rhSYK activity=+++. The starting material was prepared generally following the procedures described in Examples 32 and 33 using commercially available 1-{[{9H-fluoren-9-ylmethoxy)carbonyl]amino}-4-oxocyclohexanecarboxylic acid.

Examples 42(1) and 42(2) and 42(3) and 42(4)

(1S,4R)-4-hydroxy-2,2-dimethyl-4-[5-(3-methyl-5-{[4-(trifluoromethyl)pyrimidin-2-yl]amino}-phenyl)-1,3-thiazol-2-yl]cyclohexanecarboxylic acid (1R,4S)-4-hydroxy-2,2-dimethyl-4-[5-(3-methyl-5-{[4-(trifluoromethyl)pyrimidin-2-yl]amino}-phenyl)-1,3-thiazol-2-yl]cyclohexanecarboxylic acid (1S,4S)-4-hydroxy-2,2-dimethyl-4-[5-(3-methyl-5-{[4-(trifluoromethyl)pyrimidin-2-yl]amino}-phenyl)-1,3-thiazol-2-yl]cyclohexanecarboxylic acid (1R,4R)-4-hydroxy-2,2-dimethyl-4-[5-(3-methyl-5-{[4-(trifluoromethyl)pyrimidin-2-yl]amino}-phenyl)-1,3-thiazol-2-yl]cyclohexanecarboxylic acid

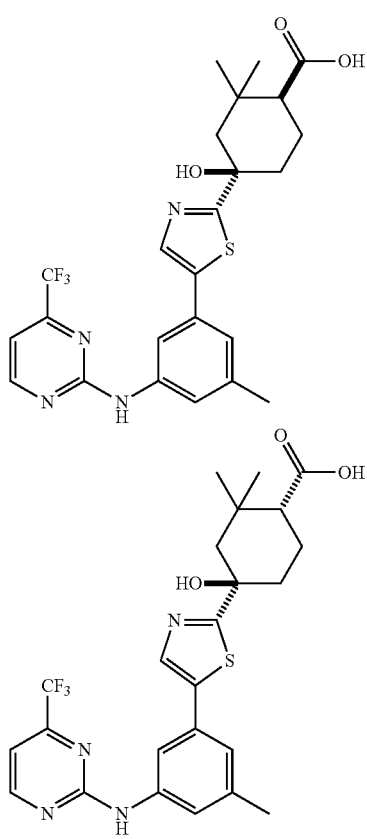

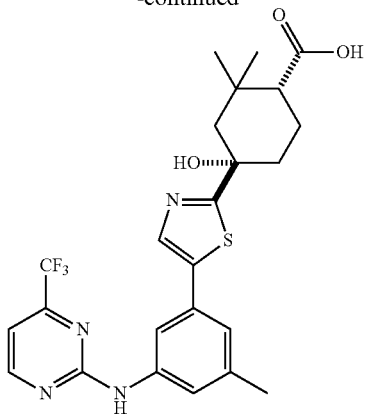

Method 1

Lithium diisopropylamide (1.31 M, 10.0 mL, 13.1 mmol) was cooled to −78° C. and N-[3-methyl-5-(1,3-thiazol-5-yl)phenyl]-4-(trifluoromethyl)pyrimidin-2-amine (Intermediate 4, 2.0 g, 5.95 mmol) in THF (20 mL) was added portionwise. While stirring at −78° C. additional lithium diisopropylamide (1.31 M, 4.55 mL, 5.95 mmol) was added. In a separate flask, lithium diisopropylamide (1.31 M, 10.0 mL, 13.1 mmol) was cooled to 0° C. and 2,2-dimethyl-4-oxo-cyclohexanecarboxylic acid (2.02 g, 11.9 mmol) in THF (20 mL) was added. The resulting solution of the carboxylate anion was transferred via cannula to the previously prepared thiazole anion solution, maintaining an internal reaction temperature below −68° C. The resultant mixture was stirred at −78° C. for 1 h, then methanol (5 mL) was added and the reaction mixture allowed to warm to room temperature. The reaction mixture was poured into water (200 mL) and extracted with MTBE (2×). The layers were separated and the aqueous portion was acidified to pH=3 with 2 N aqueous HCl then extracted with ethyl acetate (2×). The combined organic portions were dried over anhydrous Na₂SO₄, filtered and concentrated in vacuo to provide a yellow foam. The foam was then purified and the enantiomers separated via supercritical fluid chromatography (30% MeOH:CO₂) to give (1S,4R)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid (Example 42(1), 12.9 g, 25.5 mmol, 21%) as a yellow solid. MS ESI: [M+H]⁺ m/z 507.1. ¹H NMR (500 MHz, DMSO-d₆) δ 12.13-11.86 (br s, 1H), 10.24 (s, 1H), 8.82 (m, 1H), 7.94 (s, 1H), 7.92 (s, 1H), 7.46 (s, 1H), 7.27 (m, 1H), 7.14 (s, 1H), 5.89 (s, 1H), 2.31 (s, 3H), 2.16 (d, J=12.7, 1H), 2.02 (m, 1H), 1.86

(m, 3H), 1.64 (d, J=13.8, 1H), 1.57 (d, J=13.1, 1H), 1.11 (s, 3H), 0.99 (s, 3H). rhSYK activity=+++.

(1R,4S)-4-hydroxy-2,2-dimethyl-4-[5-(3-methyl-5-{[4-(trifluoromethyl)pyrimidin-2-yl]amino}-phenyl)-1,3-thiazol-2-yl]cyclohexanecarboxylic acid, (1S,4S)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid and (1R,4R)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid (Examples 42(2), 42(3), 42(4)) were prepared in an analogous manner of that described above for the (1S,4R) isomer. MS ESI: [M+H]+ m/z 507. rhSYK Activity: +++

Method 2 for the Preparation of Example 42(1)

Step 1: Methyl(1S)-2,2-dimethyl-4-oxocyclohexanecarboxylate

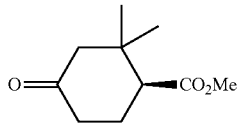

NADPH-dependent ketoreductase KRED-119 (668 mg, 3% w/w, available from Codexis, Inc., Redwood City, Calif.), NADP (668 mg, 3% w/w), glucose dehydrogenase CDX-901 (668 mg, 3% w/w, available from Codexis, Inc., Redwood City, Calif.) and D-(+)-glucose (11.16 g, 61.9 mmol) were dissolved in $KH_2PO_4/K_2HPO_4$ buffer solution (0.1 M aqueous, pH=6.8, 445 mL) at ambient temperature. In a separate flask, racemic methyl 2,2-dimethyl-4-oxocyclo-hexanecarboxylate (Intermediate 24, 22.26 g, 113 mmol) was dissolved in DMSO (6 mL) and the resulting solution was added to the $KH_2PO_4/K_2HPO_4$ buffered solution described above. The pH of the combined mixture was adjusted to 6.9 with 17.6 M aqueous NaOH solution and the reaction mixture stirred for 19 h at pH 6.9. The pH was adjusted to 4 using 11.7 M HCl (aq.) solution and the reaction mixture was stirred for 30 minutes, and then MTBE (100 mL), 2-propanol (100 mL) and sodium chloride (40.0 g) were added. The phases were separated and the organic layer was filtered through a pad of Solka Floc 200. The aqueous layer and the residual aqueous layer from the filtrate were combined and then extracted with MTBE (100 mL). The combined organic layers were concentrated in vacuo to 100 mL, and treated twice with sodium bisulfite (7.03 g, 67.6 mmol) and water (100 mL), each time the biphasic mixture was stirred vigorously for 30 min. The combined aqueous phase was treated with potassium carbonate (22.0 g, 159.2 mmol) then diluted with MTBE (100 mL) and the layers were separated. The combined organic layers were concentrated in vacuo to afford (1S)-2,2-dimethyl-4-oxocyclohexanecarboxylate (9.66 g, 96.2% ee) as an oil. MS ESI: M+. m/z 184. $^1$H NMR (400 MHz, CDCl$_3$) δ 3.73 (s, 3H), 2.62 (t, J=6.6, 1H), 2.57 (m, 1H), 2.44 (dd, J=13.7, 1.8, 1H), 2.29 (m, 1H), 2.19 (d, J=13.7, 1H), 2.11 (m, 2H), 1.07 (s, 3H), 1.00 (s, 3H).

Step 2: (1S,4R)-4-hydroxy-2,2-dimethyl-4-(1,3-thiazol-2-yl)cyclohexanecarboxylic acid hydrate

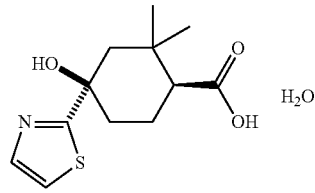

To a solution of methyl(1S)-2,2-dimethyl-4-oxocyclohexanecarboxylate (10 g, 54.28 mmol)) in THF (16.3 g) was added additional THF (184 mL) followed by thiazole (6.93 g, 81.42 mmol). The resulting solution was then cooled to −78° C. Boron trifluoride diethyletherate (9.24 g, 65.14 mmol) was added over 24 minutes and the resulting mixture aged at −78° C. for 5 minutes. n-Butyllithium (2.5M in hexanes, 20.05 g, 71.98 mmol) was added to the mixture subsurface over 4 hours and the mixture was aged for 15 mins. Sodium hydroxide (1M aqueous solution, 54.3 mL, 54.3 mmol) was added followed by MTBE (54 mL) and the mixture was warmed to 20° C. The aqueous layer was separated and the organic layer was washed with a half saturated aqueous solution of sodium chloride (54 mL) resulting in a light yellow solution of methyl (1S,4R)-4-hydroxy-2,2-dimethyl-4-(1,3-thiazol-2-yl)cyclohexanecarboxylate, which was then concentrated under partial vacuum to a low volume. Methanol (124 mL) was added and the solution concentrated to an oil under partial vacuum. The solution was then diluted with methanol (124 mL) and heated to 40° C. A solution of 1M sodium hydroxide (92 mL, 92.0 mmol) was added over 5 minutes and the resulting mixture heated to 50° C. then aged for 16 hours before being cooled to 20° C. The solution was washed three times with dichloromethane (124 mL, 62 mL, 62 mL) and the aqueous methanol solution of the product was crystallised by addition of 6M aqueous HCl (15.3 mL, 92 mmol) over 30 mins. The slurry was aged for 2 hours then the mixture was concentrated under partial vacuum to a total volume of 124 mL. The solid was collected by filtration and washed with water-methanol (1:1 v:v, 62 mL) then water (62 mL) to give the title compound (11.44 g, 41.86 mmol, 99.9% ee) as a pale yellow solid. MS ESI: [M+H]+ 256.1 NMR (400 MHz, DMSO-d$_6$): 11.89-12.09 (br s, 1H), 7.67 (d, J=3.5 Hz, 1H), 7.53 (d, J=3.5 Hz, 1H), 5.79 (s, 1H), 3.36 (br s, 2H), 2.13-2.20 (m, 2H), 1.95-2.09 (m, 1H), 1.76-1.91 (m, 3H), 1.53-1.65 (m, 2H), 1.11 (s, 3H), 0.99 (s, 3H).

Step 3: N-(3-bromo-5-methylphenyl)-4-(trifluoromethyl)pyrimidin-2-amine

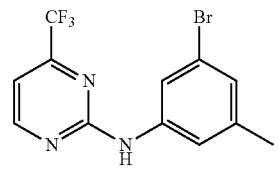 [SMILES: Cc1cc(Br)cc(Nc2nccc(C(F)(F)F)n2)c1]

To a solution of 3-bromo-5-methylaniline (45.77 g, 246 mmol) in toluene (500 ml) were sequentially added 2-chloro-4-(trifluoromethyl)pyrimidine (53.9 g, 295 mmol) and methanesulfonic acid (28.4 g, 295 mmol). The resulting solution was heated to 105° C. overnight. The resulting mixture was cooled, diluted with water (500 mL) and adjusted to pH 14 via addition of a concentrated aqueous sodium hydroxide solution (26.6 g of a solution containing 320 mmol of sodium hydroxide). The resulting solution was extracted with MTBE (500 mL), the layers separated, and the organic layer subsequently washed with water (300 ml) then 50% saturated brine solution (200 mL). The organic layer was concentrated in vacuo to 200 ml resulting in product crystallization. To the slurry was added heptane (660 mL) over 40 minutes followed by a 2 hr aging at 20° C. The solid was isolated via filtration, washed with heptane (200 mL) and dried in a vacuum oven at 40° C. overnight to provide the title compound (69.5 g, 209 mmol) as a light yellow solid. MS ESI: [M+H]$^+$ m/z 334.0. $^1$H NMR (400 MHz, CDCl$_3$): δ 8.68 (d, J=4.9 Hz, 1H); 7.79 (s, 1H); 7.30 (s, 2H); 7.10-7.06 (m, 2H); 2.36 (s, 3H).

Step 4. (1S,4R)-4-hydroxy-2,2-dimethyl-4-[5-(3-methyl-5-{[4-(trifluoromethyl)pyrimidin-2-yl]-amino}phenyl)-1,3-thiazol-2-yl]cyclohexanecarboxylic acid A mixture of the product of Step 2 (8.5 g, 31.2 mmol), the product of Step 3 (11 g, 33.4 mmol), palladium(II) acetate (0.15 g, 0.68 mmol), pivalic acid (3.5 g, 35.3 mmol), potassium carbonate (15.1 g, 109 mmol) and diadamantyl n-butyl phosphine (0.74 g, 2.1 mmol) was purged with nitrogen. Dimethyl acetamide (60 ml) was added and the suspension was purged with nitrogen. The mixture was stirred at 120° C. for 20 hours, cooled and poured into water (90 ml) and MTBE (40 ml). The aqueous phase was separated and washed with MTBE (2×). The aqueous phase was acidified with 6N HCl to pH<1 and extracted with MTBE (1×). The organic phase was washed with water (2×) then MBTE was distilled off to concentrate the solution.

Acetonitrile was added to the residue resulting in crystallization of the title compound, which was isolated by filtration and dried in vacuo. The crude product was recrystallised from MeCN: THF (3:1) to give (1S,4R)-4-hydroxy-2,2-dimethyl-4-[5-(3-methyl-5-{[4-(trifluoromethyl)-pyrimidin-2-yl]amino}phenyl)-1,3-thiazol-2-yl]cyclohexanecarboxylic acid (11.9 g, 23.4 mmol) as a yellow solid.

MS ESI: [M+H]$^+$ m/z 507.1. $^1$H NMR (400 MHz, DMSO-d$_6$) δ 12.03-11.95 (br s, 1H), 10.24 (s, 1H), 8.84 (d, J=4.7, 1H), 7.94 (s, 1H), 7.92 (s, 1H), 7.46 (s, 1H), 7.27 (d, J=4.8, 1H), 7.13 (s, 1H), 5.89 (s, 1H), 2.32 (s, 3H), 2.16 (d, 12.7, 1H), 2.10-1.95 (m, 1H), 1.86 (m, 3H), 1.65 (d, J=13.8, 1H), 1.59 (d, J=13.1, 1H), 1.13 (s, 3H), 1.01 (s, 3H). rhSYK Activity: +++

Example 42(1)-NA

Sodium (1S,4R)-4-hydroxy-2,2-dimethyl-4-[5-(3-methyl-5-{[4-(trifluoromethyl)pyrimidin-2-yl]-amino}phenyl)-1,3-thiazol-2-yl]cyclohexanecarboxylate Method 1

(1S,4R)-4-Hydroxy-2,2-dimethyl-4-[5-(3-methyl-5-{[4-(trifluoromethyl)pyrimidin-2-yl]amino}-phenyl)-1,3-thiazol-2-yl]cyclohexanecarboxylic acid (9.8 mg, 0.019 mmol) was dissolved in acetonitrile (20 μL) and water (20 μL). Sodium hydroxide (19 μL, 0.019 mmol) was added, and the mixture was heated to 35° C. for 10 min. The mixture was allowed to cool to rt, diluted with water, froze to a solid, and lyophilized to dryness to afford sodium (1S,4R)-4-hydroxy-2,2-dim ethyl-4-[5-(3-methyl-5-{[4-(trifluoromethyl)pyrimidin-2-yl]amino}phenyl)-1,3-thiazol-2-yl]-cyclohexanecarboxylate.

Method 2

(1S,4R)-4-Hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid (7.15 g, 14.12 mmol) was dissolved in tetrahydrofuran (35 ml). Sodium hydroxide (10 M, 1.383 ml, 13.83 mmol) was added, and the mixture was aged for 15 minutes. Ethyl acetate (50 ml) was slowly added over 45 minutes and the mixture was aged for 1 hr at 20° C. A further aliquot of ethyl acetate (25 ml) was added and 55 ml of solvent was removed in vacuo. The slurry was filtered and washed with ethyl acetate (35 ml). The solid was dried in vacuo at 70° C. to afford the title compound (7.02 g, 13.28 mmol).

MS ESI: [M+H]$^+$ m/z 507.1. $^1$H NMR (400 MHz, DMSO-d$_6$) δ 10.24 (s, 1H), 8.83 (d, J=4.9, 1H), 7.91 (s, 1H), 7.89 (s, 1H), 7.48 (s, 1H), 7.27 (d, J=4.9, 1H), 7.12 (s, 1H), 5.82 (br s, 1H), 2.31 (s, 3H), 1.96-1.85 (m, 1H), 1.84-1.68 (m, 4H), 1.60-1.45 (m, 2H), 1.12 (s, 3H), 1.01 (s, 31-1). rhSYK activity=+++

Example 42(1)-K

Potassium (1S,4R)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylate (1S,4R)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid (9.8 mg, 0.019 mmol) was dissolved in acetonitrile (20 μL) and water (20 μL). Potassium hydroxide (19 μL, 0.019 mmol) was added, and the mixture was heated to 35° C. for 10 min. The mixture was allowed to cool to room temperature, diluted with water, froze to a solid, and lyophilized to dryness to afford potassium (1S,4R)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylate. MS ESI: [M+H]$^+$ m/z 507.1. $^1$H NMR (500 MHz, DMSO-d$_6$) δ 10.24 (s, 1H), 8.83 (d, J=4.9, 1H), 7.91 (s, 1H), 7.88 (s, 1H), 7.46 (s, 1H), 7.27 (d, J=4.9, 1H), 7.12 (s, 1H), 5.97 (s, 2H), 2.31 (s, 3H), 1.92-1.82 (m, 2H), 1.81-1.65 (m, J=13.8, 5H), 1.54-1.48 (m, 1H), 1.47-1.39 (m, 1H), 1.05 (s, 3H), 0.95 (s, 3H). rhSYK activity=+++

Examples 43(1) and 43(2)

(1S,4R)-4-hydroxy-2,2-dimethyl-4-{5-[3-($^2$H$_3$)methyl-5-{[4-(trifluoromethyl)pyrimidin-2-yl]amino}phenyl]-1,3-thiazol-2-yl}cyclohexanecarboxylic acid (1R,4S)-4-hydroxy-2,2-dimethyl-4-{5-[3-($^2$H$_3$)methyl-5-[4-(trifluoromethyl)pyrimidin-2-yl]amino}phenyl]-1,3-thiazol-2-yl)cyclohexanecarboxylic acid

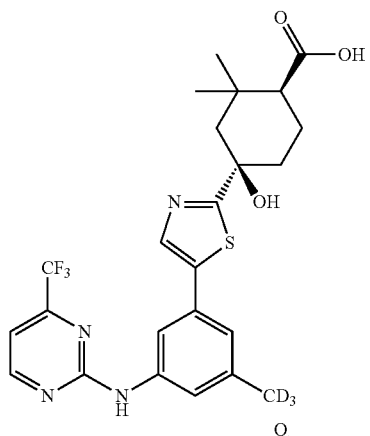

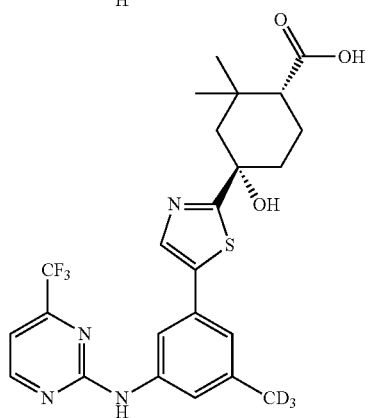

Step 1

A solution of methyl 3-bromo-5-nitrobenzoate (5 g, 19.23 mmol) in THF (48 mL) was cooled to 0° C. and purged with Argon. Lithium aluminum deuteride in THF (1 M, 11.54 mL, 11.54 mmol) was added dropwise, by addition funnel, over 20 minutes. The reaction mixture was stirred for 10 minutes. Sodium sulfate decahydrate was slowly added until the mixture stopped bubbling. The solids were filtered off and the solution was concentrated to afford crude (3-bromo-5-nitrophenyl)($^2$H$_2$)methanol (3.7 g, 15.81 mmol, 82%) as a light brown solid. $^1$H NMR (500 MHz, DMSO-d$_6$) δ 8.23 (s, 1H), 8.16 (s, 1H), 7.94 (s, 1H), 5.56 (s, 1H).

Step 2

A solution of (3-bromo-5-nitrophenyl)($^2$H$_2$)methanol (3.7 g, 15.81 mmol) and Et$_3$N (3.31 mL, 23.71 mmol) in DCM (79 mL) was cooled to 0° C. and purged with Argon. Methansulfonyl chloride (1.478 mL, 18.97 mmol) was added drop wise and the mixture was stirred for 10 minutes. The mixture was diluted with ethyl acetate, washed with saturated NaHCO$_3$, followed by brine, dried (Na$_2$SO$_4$), filtered and concentrated. The residue was purified by column chromatography on silica (10-100% ethyl acetate in hexanes) and concentrated to afford (3-bromo-5-nitrophenyl)($^2$H$_2$)methyl methanesulfonate (3.5 g, 11.21 mmol, 70.9%) as a light brown solid.

Step 3

A solution of (3-bromo-5-nitrophenyl)($^2$H$_2$)methyl methanesulfonate (2 g, 6.41 mmol) in THF (16 mL) was cooled to 0° C. and purged with Argon. 1M Lithium aluminum deuteride in THF (3.20 mL, 3.20 mmol) was added drop wise by an addition funnel over 15 minutes. The reaction mixture was stirred for 10 minutes and then ground sodium sulfate decahydrate was added until the mixture stopped bubbling. The solids were filtered and the solution was concentrated. The residue was purified by column chromatography on silica (0-50% ethyl acetate in hexanes) to afford 1-bromo-3-($^2$H$_3$)methyl-5-nitrobenzene (400 mg, 1.826 mmol, 28.5%). $^1$H NMR (500 MHz, CDCl$_3$) δ 8.19 (s, 1H), 7.98 (s, 1H), 7.66 (s, 1H).

Step 4

To a solution of 1-bromo-3-($^2$H$_3$)methyl-5-nitrobenzene (390 mg, 1.780 mmol) in anhydrous EtOH (11.10 mL), tin(I) chloride dihydrate (1707 mg, 7.57 mmol) was added. The mixture was stirred at 70° C. under Argon for 30 minutes. The solution was cooled to room temperature and the pH was adjusted to 7-8 by addition of saturated aqueous sodium carbonate before being extracted with ethyl acetate. The combined organic phases were washed with brine, dried (Na$_2$SO$_4$), filtered and concentrated to afford crude 3-bromo-5-($^2$H$_3$)methylaniline (321 mg, 1.698 mmol, 95%). MS ESI: [M+H]+ m/z 191.0.

Step 5

A solution of 2-chloro-4-(trifluoromethyl)pyrimidine (204 µL, 1.687 mmol), 3-bromo-5-($^2$H$_3$)methylaniline (319 mg, 1.687 mmol) and AcOH (101 µL, 1.687 mmol) were dissolved in dioxane (4.5 mL). The reaction mixture was heated to 120° C. under Argon overnight. The mixture was cooled, diluted with ethyl acetate, washed with saturated sodium bicarbonate, followed by brine, dried (Na$_2$SO$_4$), filtered and concentrated. The residue was purified by column chromatography on silica (0-30% ethyl acetate in hexanes) to afford N-[3-bromo-5-($^2$H$_3$)methylphenyl]-4-(trifluoromethyl)pyrimidin-2-amine (320 mg, 0.955 mmol, 56.6%) as a pale yellow solid. MS ESI: [M+H]+ m/z 335.0.

Step 6

A vial was charged with N-[3-bromo-5-($^2$H$_3$)methylphenyl]-4-(trifluoromethyl)pyrimidin-2-amine (0.3 g, 0.895 mmol), bis(pinacolato)diboron (0.250 g, 0.985 mmol), 1,1'- bis(diphenylphosphino)ferrocene-palladium(II)dichloride dichloromethane complex (0.022 g, 0.027 mmol), potassium acetate (0.264 g, 2.69 mmol) and DMSO (1.8 mL). The resulting reaction mixture was heated to 120° C. under Argon for 2 hours. The mixture was cooled, diluted with ethyl acetate, washed with saturated sodium bicarbonate, followed by brine, dried ($Na_2SO_4$), filtered and concentrated to afford crude N-[3-($^2H_3$)methyl-5-(4,4,5,5-tetramethyl-1,3,2-dioxaborolan-2-yl)phenyl]-4-(trifluoromethyl)pyrimidin-2-amine (284 mg, 0.706 mmol, 79%) as a light brown solid. MS ESI: [M+H]+ m/z 383.1.

Step 7

A vial was charged with N-[3-($^2H_3$)methyl-5-(4,4,5,5-tetramethyl-1,3,2-dioxaborolan-2-yl)phenyl]-4-(trifluoromethyl)pyrimidin-2-amine (50 mg, 0.131 mmol), racemic Intermediate 25 (7 mg, 0.131 mmol), $Pd_2(dba)_3$ (5.99 mg, 6.54 µmol), X-phos (6.24 mg, 0.013 mmol) and cesium carbonate (85 mg, 0.262 mmol). Dioxane (500 µL) and water (50 µL) were added. The resulting reaction mixture was heated to 90° C. under Argon for 4.5 hours. The mixture was cooled, diluted with ethyl acetate, washed with saturated $NaHCO_3$, followed by brine, dried ($Na_2SO_4$), filtered and concentrated. The residue was purified by column chromatography on silica (10-80% ethyl acetate in hexanes) to afford methyl(4R)-4-hydroxy-2,2-dimethyl-4-{5-[3-($^2H_3$)methyl-5-{[4-(trifluoromethyl)pyrimidin-2-yl]amino}phenyl]-1,3-thiazol-2-yl}cyclohexanecarboxylate (35 mg, 0.067 mmol, 51.1%). MS ESI: [M+H]+ m/z 524.2.

Step 8

A microwave vial was charged with racemic cis-methyl-4-hydroxy-2,2-dimethyl-4-{5-[3-($^2H_3$)methyl-5-{[4-(trifluoromethyl)pyrimidin-2-yl]amino}phenyl]-1,3-thiazol-2-yl}cyclohexanecarboxylate (35 mg, 0.067 mmol), MeOH (400ł) and NaOH (134 µL, 0.134 mmol). The resulting suspension was irradiated in a microwave at 100° C. for 78 minutes. The pH was adjusted to 3-4 with 1M HCl, diluted with water and 10% IPA/$CHCl_3$. The aqueous layer was extracted with 10% IPA/$CHCl_3$. The combined organic phases were washed with water, dried ($Na_2SO_4$), filtered and concentrated to afford racemic cis-4-hydroxy-2,2-dimethyl-4-{5-[3-($2H_3$)methyl-5-{[4-(trifluoromethyl)-pyrimidin-2-yl]amino}phenyl]-1,3-thiazol-2-yl}cyclohexanecarboxylic acid (29 mg). The racemic mixture was purified via super-critical fluid chromatography (30% MeOH:$CO_2$) to give (1S,4R)-4-hydroxy-2,2-dimethyl-4-{5-[3-($^2H_3$)methyl-5-{[4-(trifluoromethyl)pyrimidin-2-yl]amino}phenyl]-1,3-thiazol-2-yl}cyclohexanecarboxylic acid (8.9 mg, 0.017 mmol, 29.%, rhSYK activity=+++) and (1R,4S)-4-hydroxy-2,2-dimethyl-4-{5-[3-(2H$_3$)methyl-5-{[4-(trifluoromethyl)pyrimidin-2-yl]amino}phenyl]-1,3-thiazol-2-yl}cyclohexanecarboxylic acid (9.8 mg, 0.019 mmol, 32.7% yield). MS ESI: [M+H]+ m/z 510.1. $^1$H NMR (500 MHz, DMSO-$d_6$) δ 10.25 (s, 1H), 8.83 (d, J=4.8, 1H), 7.93 (m, 2H), 7.45 (s, 1H), 7.28 (d, J=4.8, 1H), 7.14 (s, 1H), 5.89 (s, 1H), 2.16 (d, J=12.7, 1H), 2.02 (m, 1H), 1.86 (m, 3H), 1.72-1.53 (m, 2H), 1.11 (s, 3H), 0.99 (s, 3H). rhSYK activity=+++

Compounds in the following Table(s) were prepared in a manner analogous of that described in Example 43:

| Example | Structure | rhSYK Activity | [M + H]+ Obs'd | Form(s) |
|---|---|---|---|---|
| 43-1 | 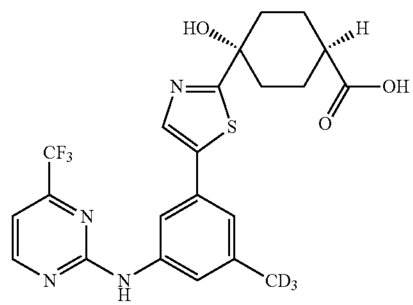 [SMILES: [2H]C([2H])([2H])c1cc(Nc2nccc(C(F)(F)F)n2)cc(-c2cnc([C@]3(O)CC[C@H](C(=O)O)CC3)s2)c1] | +++ | 482.1 | Free Base |

Examples 44(1) and 44(2)

(1S,4R)-4-hydroxy-2,2-dimethyl-4-{5-[3-($^2H_2$)methyl-5-{[4-(trifluoromethyl)pyrimidin-2-yl]-amino}phenyl]-1,3-thiazol-2-yl}-cyclohexane-carboxylic acid (1R,4S)-4-hydroxy-2,2-dimethyl-4-{5-[3-($^2H_2$)methyl-5-{[4-(trifluoromethyl)pyrimidin-2-yl]amino}phenyl]-1,3-thiazol-2-yl}cyclohexane-carboxylic acid

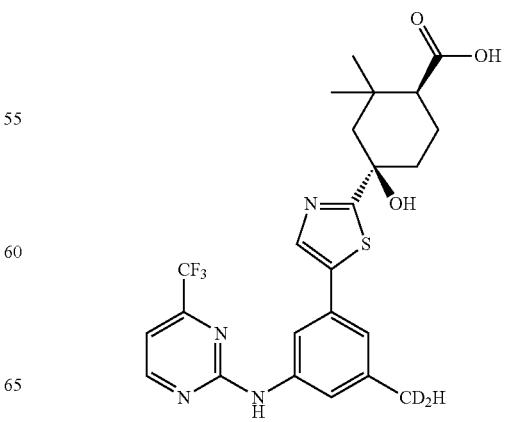

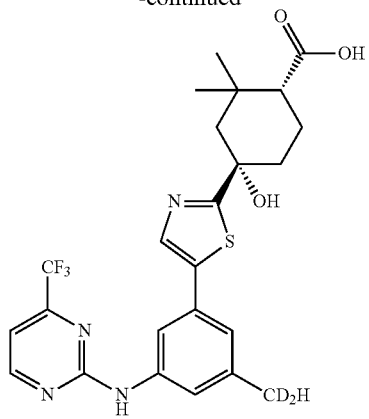

The title compounds were prepared as the free base in an analogous manner of that described in Example 43 using LiAlH₄ in step 3. For both compounds [M+H]+ Observed: 509.1 and rhSYK Activity: +++

Example 45 text-butyl 4-hydroxy-4-[5-(3-methyl-5-{[4-(trifluoromethyl)pyrimidin-2-yl]amino}phenyl)-1,3-thiazol-2-yl]piperidine-1-carboxylate

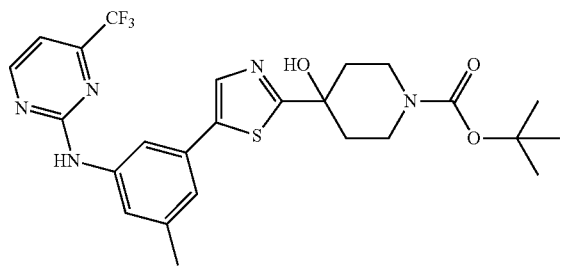 [SMILES: Cc1cc(Nc2nccc(C(F)(F)F)n2)cc(-c2cnc(C3(O)CCN(C(=O)OC(C)(C)C)CC3)s2)c1]

At −78° C., INTERMEDIATE 4 (200 mg, 0.595 mmol) in THF (3.0 mL) was added to LDA (892 µL, 1.784 mmol) and the reaction aged for 10 min followed by addition of tert-butyl 4-oxo-piperidine-1-carboxylate (474 mg, 2.379 mmol). The reaction was allowed to slowly warm to −20° C. over 4 hrs. To the mixture was added saturated aqueousammonium chloride solution and the product was extracted with ethyl acetate. The organic layer was washed with water and brine. The combined organic layer was dried, filtered and solvent reduced by rotovap. The residue was purified by column chromatography on silica gel (0-50% ethyl acetate in DCM) to give 260 mg (0.485 mmol, 82%) tert-butyl-4-hydroxy-4-[5-(3-methyl-5-{[4-(trifluoromethyl)pyrimidin-2-yl]amino}phenyl)-1,3-thiazol-2-yl]piperidine-1-carboxylate as off-white solid. MS ESI: [M+H]+ m/z 536.2. ¹H NMR (600 MHz, CDCl₃): δ 8.60 (d, J=4.8 Hz, 1H); 7.81 (appr s, 2H); 7.74 (br s, 1H); 7.28 (s, 1H); 7.02 (s, 1H); 7.00 (d, J=4.8 Hz, 1H); 4.0 (br s, 2H); 3.28 (br s, 2H); 2.34 (s, 3H); 2.09 (m, 2H); 1.88 (m, 2H); 1.41 (s, 9H). rhSYK=++

Compounds in the following Table(s) were prepared as the free base in an analogous manner of that described in Example 45:

TABLE 45

| Ex. | Structure | rhSYK Activity | [M + H]+ Obs'd |
|---|---|---|---|
| 45-1 | Enantiomer 1 | ++ | 550.2 |
| 45-2 | Enantiomer 2 | ++ | 550.2 |

Example 46

4-[5-(3-methyl-5-{[4-(trifluoromethyl)pyrimidin-2-yl]amino}phenyl)-1,3-thiazol-2-yl]piperidin-4-ol

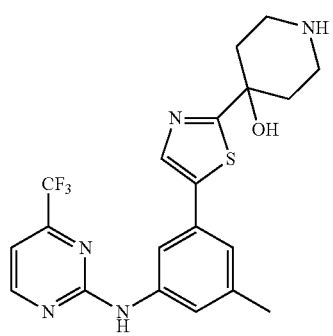 [SMILES: Cc1cc(Nc2nccc(C(F)(F)F)n2)cc(-c2cnc(C3(O)CCNCC3)s2)c1]

To text-butyl 4-hydroxy-4-[5-(3-methyl-5-{[4-(trifluoromethyl)pyrimidin-2-yl]amino}phenyl)-1,3-thiazol-2-yl]piperidine-1-carboxylate (50 mg, 0.093 mmol) in DCM (1 mL) was added 144 uL TFA (20 eq) and the reaction stirred at rt for 4 h. To the mixture was added saturated aqueous NaHCO₃ and extracted with ethyl acetate. The organic layer was washed with water and brine. The combined organic layer was dried, filtered. The solvent was reduced in vacuo to give 40 mg (0.092 mmol, 98%) of 4-[5-(3-methyl-5-{[4-(trifluoromethyl)pyrimidin-2-yl]amino}phenyl)-1,3-thiazol-2-yl]piperidin-4-ol. MS ESI: [M+H]⁺ m/z 436.2. ¹H NMR (600 MHz, DMSO-d₆): δ 8.81 (d, J=4.7 Hz, 1H); 7.93 (m, 2H), 7.44 (s, 1H); 7.25 (d, J=4.9 Hz, 1H); 7.13 (s, 1H); 5.97 (br s, 1H), 2.78-2.98 (m, 4H); 2.29 (s, 3H); 1.93-1.98 (m, 2H), 1.63-1.65 (m, 2H). rhSYK activity=+++

Compounds in the following Table(s) were prepared in a manner analogous of that described in Examples 45/46:

TABLE 46

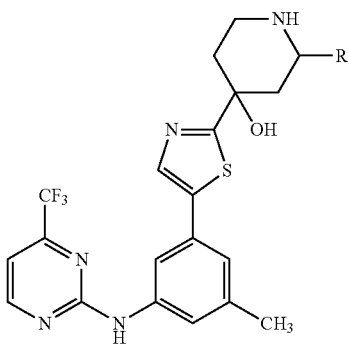

| Ex. | R | rhSYK Activity | [M + H]+ Obs'd | Form(s) |
|---|---|---|---|---|
| 46-1 | $CF_3$ | +++ | 504.1 | Free Base |
| 46-2 | $CO_2CH_3$ | +++ | 494.1 | Free Base |

Example 47

4-hydroxy-4-[5-(3-methyl-5-{[4-(trifluoromethyl)pyrimidin-2-yl]amino}phenyl)-1,3-thiazol-2-yl]piperidine-1-carboxamide

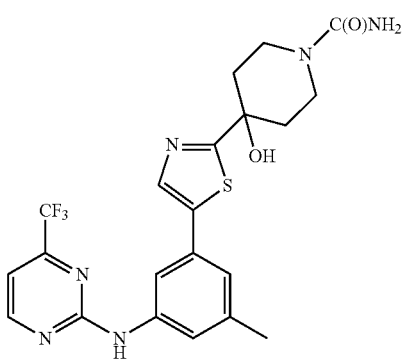

To 15 mg (0.034 mmol) of 4-[5-(3-methyl-5-{[4-(trifluoromethyl)pyrimidin-2-yl]amino}-phenyl)-1,3-thiazol-2-yl]piperidin-4-ol in THF/Water (3:1, 1 mL) was added 4.2 mg (0.052 mmol, 1.5 eq) of potassium cyanate and 2N hydrochloric acid (22 µL, 1.3 eq). The mixture was heated at 50° C. for 6 h and then another 1.5 eq of potassium cyanate and 1.5 eq HCl added and the mixture stirred at 50° C. overnight. The reaction was diluted with saturated aqueous $NaHCO_3$ and was partitioned with ethyl acetate. The organic layer was washed with water and dried, filtered and solvent removed under reduced pressure. The residue was purified by column chromatography on silica gel (0-100% ethyl acetate in hexanes) to give 12 mg (0.025 mmol, 73%) of 4-hydroxy-4-[5-(3-methyl-5-{[4-(trifluoromethyl)pyrimidin-2-yl]amino}phenyl)-1,3-thiazol-2-yl]piperidine-1-carboxamide as off-white solid. MS ESI: [M+H]⁺ m/z 479.2. ¹H NMR (600 MHz, $CD_3OD$): δ 8.68 (d, J=4.8 Hz, 1H); 7.99 (s, 1H); 7.87 (s, 1H); 7.40 (s, 1H); 7.10 (m, 2H); 3.91 (m, \2H); 3.28 (m, 2H); 2.34 (s, 3H); 2.16 (m, 2H); 1.83 (m, 2H). rhSYK activity=+++

Example 48 tert-butyl({4-hydroxy-4-[5-(3-methyl-5-{[4-(trifluoromethyl)pyrimidin-2-yl]amino}phenyl)-1,3-thiazol-2-yl]piperidin-1-yl}sulfonyl)carbamate

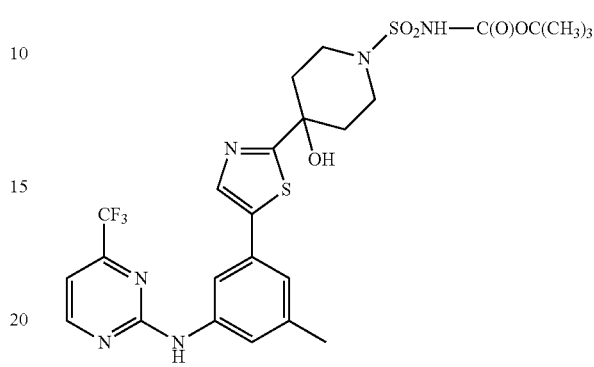

At 0° C., chlorosulfonyl isocyanate (14.95 µL, 0.172 mmol) in DCM (0.6 mL) was added to tert-butanol (16.47 µL, 0.172 mmol), after stirred for 30 min, 4-[5-(3-methyl-5-{[4-(trifluoromethyl)-pyrimidin-2-yl]amino}phenyl)-1,3-thiazol-2-yl]piperidin-4-ol (50 mg, 0.115 mmol) and triethylamine (48.0 µL, 0.344 mmol) were added and the reaction aged for 20 min and ice bath removed. After stirred for 2 h, the crude reaction mixture was directly subject to column chromatography on silica gel (0-100% ethyl acetate in hexanes) to afforded 58 mg (0.094 mmol, 82%) tert-butyl({4-hydroxy-4-[5-(3-methyl-5-{[4-(trifluoromethyl)pyrimidin-2-yl]amino}-phenyl)-1,3-thiazol-2-yl]piperidin-1-yl}sulfonyl)carbamate. MS ESI: [M+H]⁺ m/z 615.1. ¹H NMR (600 MHz, $CDCl_3$): δ 8.64 (d, J=4.8 Hz, 1H); 7.87 (s, 1H); 7.84 (s, 1H); 7.31 (s, 1H); 7.03 (s, 1H); 7.01 (d, J=4.8 Hz, 1H); 3.81 (d, J=12 Hz, 2H); 3.47 (m, 2H); 2.36 (s, 3H); 2.25 (m, 2H); 2.00 (d, J=12 Hz, 2H); 1.50 (s, 9H). rhSYK activity=+++

Example 49

4-hydroxy-4-[5-(3-methyl-5-{[4-(trifluoromethyl)pyrimidin-2-yl]amino}phenyl)-1,3-thiazol-2-yl]piperidine-1-sulfonamide

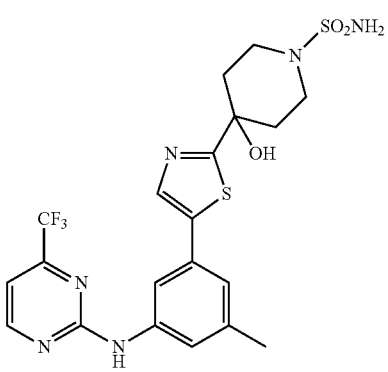 [SMILES: Cc1cc(Nc2nccc(C(F)(F)F)n2)cc(-c2cnc(C3(O)CCN(S(N)(=O)=O)CC3)s2)c1]

To a solution of tert-butyl({4-hydroxy-4-[5-(3-methyl-5-{[4-(trifluoromethyl)pyrimidin-2-yl]amino}phenyl)-1,3-thiazol-2-yl]piperidin-1-yl}sulfonyl)carbamate (45 mg, 0.073 mmol) in DCM (0.7 mL) was added TFA (0.120 mL, 1.5 mmol) and the reaction was stirred at room temperature for 80 min, then more TFA (0.120 mL, 1.5 mmol) was added. After 90 min most volatiles were removed by $N_2$ flow and vacuum. The residue was diluted with saturated aqueous NaHCO$_3$ and ethyl acetate. The combined organic layers were dried and evaporated to give 4-hydroxy-4-[5-(3-methyl-5-{[4-(trifluoromethyl)pyrimidin-2-yl]amino}phenyl)-1,3-thiazol-2-yl]piperidine-1-sulfonamide (31 mg, 0.06 mmol, 82% yield). MS ESI: [M+H]$^+$ m/z 515.2. $^1$H NMR (600 MHz, CDCl$_3$): δ 8.59 (d, J=4.8 Hz, 1H); 7.87 (s, 1H); 7.81 (s, 1H); 7.25 (s, 1H); 7.02 (s, 1H); 7.00 (d, J=4.8 Hz, 1H); 3.59 (d, J=12 Hz, 2H); 3.14 (m, 2H); 2.34 (s, 3H); 2.26 (m, 2H); 1.94 (d, J=12 Hz, 2H). rhSYK activity=+++

Example 50

4-[5-(3-methyl-5-{[4-(trifluoromethyl)pyrimidin-2-yl]amino}phenyl)-1,3-thiazol-2-yl]-1-(phenylsulfonyl)piperidin-4-ol

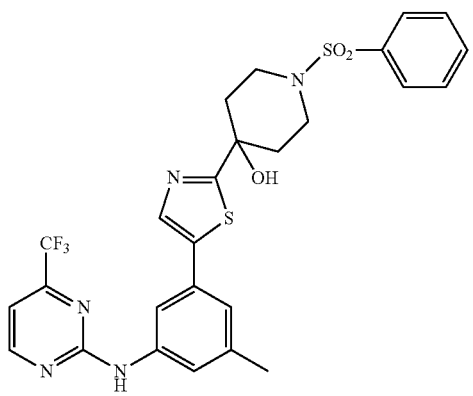

4-[5-(3-Methyl-5-{[4-(trifluoromethyl)pyrimidin-2-yl]amino}phenyl)-1,3-thiazol-2-yl]piperidin-4-ol (Example 46, 50 mg, 0.115 mmol) was dissolved in CH$_2$Cl$_2$ (1 mL). N,N-diisopropylethylamine (50 μL, 0.287 mmol) and benzenesulfonyl chloride (29 μL, 0.230 mmol) were added sequentially. The solution was stirred overnight at room temperature, then concentrated in vacuo on a Genevac. The resultant residue was dissolved in DMSO and purified via HPLC (48-82% CH$_3$CN:H$_2$O) to provide 4-[5-(3-methyl-5-{[4-(trifluoromethyl)pyrimidin-2-yl]amino}phenyl)-1,3-thiazol-2-yl]-1-(phenylsulfonyl)piperidin-4-ol. MS ESI: [M+H]$^+$ m/z 576.1. $^1$H NMR (600 MHz, DMSO-d$_6$) δ 10.21 (s, 1H), 8.80 (d, J=5.2 Hz, 1H), 7.93 (d, J=9.2 Hz, 2H), 7.75 (dd, J=8.7, 10.3 Hz, 2H), 7.73 (s, 1H), 7.65 (t, J=8.1 Hz, 1H), 7.43 (s, 1H), 7.25 (d, J=5.1 Hz, 1H), 7.12 (s, 1H), 6.10 (s, 1H), 3.54 (d, J=12.3 Hz, 1H), 2.58 (t, J=12.3 Hz, 2H), 2.54-2.37 (m, 1H), 2.28 (s, 3H), 2.08 (t, J=16.1 Hz, 2H), 1.80 (d, J=14.6 Hz, 2H). rhSYK activity=++

Example 51

1-{4-hydroxy-4-[5-(3-methyl-5-{[4-(trifluoromethyl)pyrimidin-2-yl]amino}phenyl)-1,3-thiazol-2-yl]piperidin-1-yl}ethanone

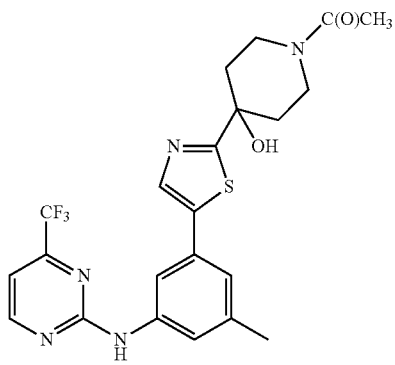

To a mixture of acetic acid (9 μL, 0.15 mmol) and Si-carbonyl diimidazole (266 mg, 0.287 mmol) was added a solution of 4-[5-(3-methyl-5-{[4-(trifluoromethyl)pyrimidin-2-yl]amino}phenyl)-1,3-thiazol-2-yl]piperidin-4-ol (Example 46, 50 mg, 0.115 mmol) and hydroxybenzotriazole (26 mg, 0.17 mmol) dissolved in N,N-dimethylformamide, and the resultant suspension was shaken in a Bohdan block overnight at room temperature. The reaction mixture was filtered and concentrated in vacuo, and the resultant residue was dissolved in DMSO and purified via HPLC (30-64% CH$_3$CN:H$_2$O) to provide 1-{4-hydroxy-4-[5-(3-methyl-5-{[4-(trifluoromethyl)pyrimidin-2-yl]amino}phenyl)-1,3-thiazol-2-yl]piperidin-1-yl}ethanone. MS EST: [M+H]$^+$ m/z 478.1. $^1$H NMR (600 MHz, DMSO-d$_6$) δ 10.23 (s, 1H), 8.81 (d, J=5.2 Hz, 1H), 7.95 (s, 2H), 7.44 (s, 1H), 7.26 (d, J=5.1 Hz, 1H), 7.14 (s, 1H), 6.30 (s, 1H), 4.25-3.99 (m, 1H), 3.73 (m, 1H), 3.41-3.34 (m, 1H), 3.07-2.97 (m, 1H), 2.47 (s, 3H), 2.32 (s, 3H), 2.25-2.14 (m, 1H), 1.93 (m, 2H), 1.75 (m, 1H). rhSYK activity=+++

Example 52

4-hydroxy-N-methyl-4-[5-(3-methyl-5-{[4-(trifluoromethyl)pyrimidin-2-yl]amino}phenyl)-1,3-thiazol-2-yl]piperidine-1-carboxamide

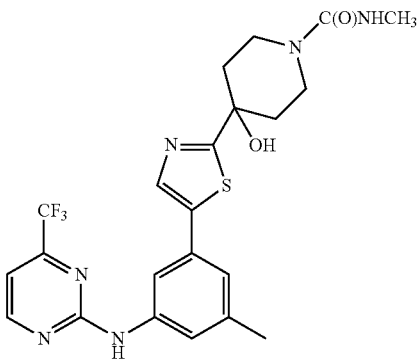

4-[5-(3-Methyl-5-{[4-(trifluoromethyl)pyrimidin-2-yl]amino}phenyl)-1,3-thiazol-2-yl]piperidin-4-ol (Example 46, 50 mg, 0.115 mmol) was dissolved in CH$_2$Cl$_2$ (1 mL). N,N-diisopropylethylamine (30 μL, 0.172 mmol) and methyl isocyanate (7 μL, 0.130 mmol) were added sequentially. The solution was stirred overnight at rt, then concentrated in vacuo on a Genevac. The resultant residue was dissolved in DMSO and purified via HPLC (30-64% CH$_3$CN:H$_2$O) to provide 4-hydroxy-N-methyl-4-[5-(3-methyl-5-{[4-(trifluoromethyl)pyrimidin-2-yl]amino}phenyl)-1,3-thiazol-2-yl]piperidine-1-carboxamide (36 mg, 0.073 mmol). MS ESI: +m/z 493.1. $^1$H NMR (600 MHz, DMSO-d$_6$) δ 10.22 (s, 1H), 8.81 (d, J=5.2 Hz, 1H), 7.93 (s, 2H), 7.44 (s, 1H), 7.25 (d, J=5.1 Hz, 1H), 7.13 (s, 1H), 6.43 (d, J=4.8 Hz, 1H), 6.15 (s, 1H), 3.83-3.74 (m, 2H) (d, J=14.0 Hz, 2H), 3.07 (t, J=14.5 Hz, 2H), 2.53 (s, 3H), 2.29 (s, 3H), 1.98-1.82 (m, 2H), 1.65 (d, J=13.9 Hz, 2H). rhSYK activity=+++

Examples 53(1) and 53(2)

2-{3-Hydroxy-3-[5-(3-methyl-5-{[4-(trifluoromethyl)pyrimidin-2-yl]amino}phenyl)-1,3-thiazol-2-yl]azetidin-1-yl}-2-methylpropanoic acid 2-[(2-{3-Hydroxy-3-[5-(3-methyl-5-{[4-(trifluoromethyl)pyrimidin-2-yl]amino}phenyl)-1,3-thiazol-2-yl]azetidin-1-yl}-2-methylpropanoyl)oxy]-2-methylpropanoic acid

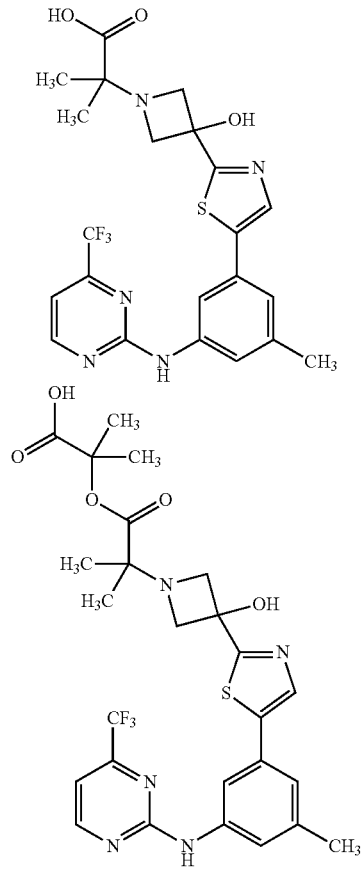

A solution of 3-[5-(3-methyl-5-{[4-(trifluoromethyl)pyrimidin-2-yl]amino}phenyl)-1,3-thiazol-2-yl]azetidin-3-ol (50 mg, 0.123 mmol), 2-bromo-2-methyl propionic acid (20.5 mg, 0.123 mmol), and triethylamine (0.043 mL, 0.307 mmol) in tetrahydrofuran (1 mL) was heated in a microwave for 100 min for 5 min. An additional amount of 2-bromo-2-methyl propionic acid (8 mg, 0.048 mmol), triethylamine (0.060 mL, 0.428 mmol), and tetrahydrofuran (1 mL) were added and the reaction was heated in a microwave oven for an additional 10 min. The reaction was concentrated and then purified by reverse phase HPLC (15% to 50% acetonitrile in water). The fractions containing the desired products were lyophilized to afford: 2-{3-Hydroxy-3-[5-(3-methyl-5-{[4-(trifluoromethyl)pyrimidin-2-yl]amino}phenyl)-1,3-thiazol-2-yl]azetidin-1-yl}-2-methylpropanoic acid (Example 53(1), 32.5 mg). MS ESI: [M+H]$^+$ m/z 494.1. $^1$H NMR (500 MHz, (d$_6$-DMSO): δ 10.30 (s, 1H); 8.85 (d, J=4.9 Hz, 1H); 8.19 (s, H); 8.04 (s, 1H); 7.73 (s, 1H); 7.47 (s, 1H); 7.29 (d, J=4.9 Hz, 1H); 7.22 (s, 1H); 4.82-4.50 (m, 2H); 4.33-4.11 (m, 2H); 2.33 (s, 3H); 1.53 (s, 6H). rhSYK activity=+++2-[(2-{3-Hydroxy-3-[5-(3-methyl-5-{[4-(trifluoromethyl)pyrimidin-2-yl]amino}phenyl)-1,3-thiazol-2-yl]azetidin-1-yl}-2-methylpropanoyl)oxy]-2-methylpropanoic acid (Example 53(2), 8 mg). MS ESI: [M+H]$^+$ m/z 580.2. $^1$H NMR (500 MHz, d$_6$-DMSO): δ 10.29 (s, 1H); 8.83 (d, J=4.6 Hz, 1H); 8.18 (s, 1H); 8.03 (s, 1H); 7.81 (s, 1H); 7.46 (s, 1H); 7.29 (d, J=5.1 Hz, 1H); 7.21 (s, 1H); 4.83 (br s, 1H); 4.72-4.41 (m, 2H); 4.34-4.12 (m, 1H); 2.32 (s, 3H); 1.52 (br s, 12H). rhSYK activity=+++

Examples 54(1) and 54(2)

Methyl{[4-hydroxy-4-(5-{3-[(4-methoxypyrimidin-2-yl)amino]-5-methylphenyl}-1,3-thiazol-2-yl)piperidin-1-yl]sulfonyl}carbamate 4-Chloro-4-(5-{3-[(4-methoxypyrimidin-2-yl)amino]-5-methylphenyl}-1,3-thiazol-2-yl)-piperidine-1-sulfonamide

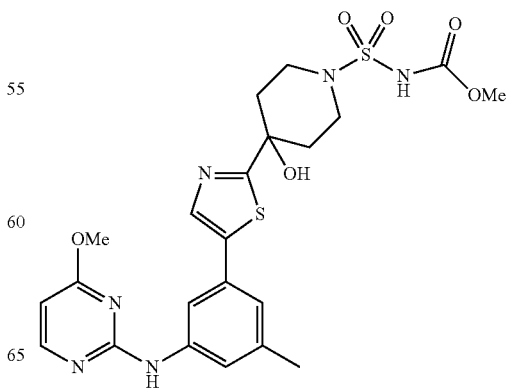

-continued

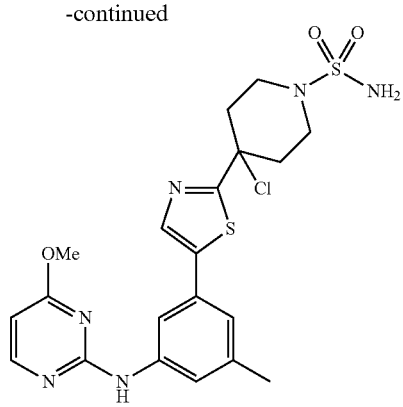

At 0° C., chlorosulfonyl isocyanate (16.38 μL, 0.189 mmol) in dichloromethane was added methanol (7.63 μL, 0.189 mmol). After stirring for 30 min, to the mixture was added 4-(5-{3-[(4-methoxypyrimidin-2-yl)amino]-5-methylphenyl}-1,3-thiazol-2-yl)piperidin-4-ol (50 mg, 0.126 mmol) and triethylamine (52.6 μL, 0.377 mmol). The reaction was aged for 20 min and ice bath removed, and stirred for 3 h. LCMS indicates product formation. The material was directly subject to column chromatography on silica gel (0-100% 10:1 ethyl acetate: methanol in hexanes) to afford:

Methyl{[4-hydroxy-4-(5-{3-[(4-methoxypyrimidin-2-yl)amino]-5-methylphenyl}-1,3-thiazol-2-yl)piperidin-1-yl]sulfonyl}carbamate (7 mg, 0.013 mmol, 10%). MS ESI: [M+H]+ m/z 535.1. $^1$H NMR (600 MHz, CD$_3$OD): δ 8.09 (d, J=6.0 Hz, 1H); 7.91 (s, 1H); 7.88 (s, 1H); 7.38 (s, 1H); 7.08 (s, 1H); 6.23 (d, J=6.0 Hz, 1H); 3.98 (s, 3H); 3.73 (m, 3H); 3.34 (m, 2H); 3.19 (m, 2H); 2.35 (s, 3H); 2.25 (m, 2H); 1.90 (m, 2H). rhSYk activity=+++

4-Chloro-4-(5-{3-[(4-methoxypyrimidin-2-yl)amino]-5-methylphenyl}-1,3-thiazol-2-yl)-piperidine-1-sulfonamide (18 mg, 0.036 mmol, 28%). MS ESI: [M+H]+ m/z 495.2. $^1$H NMR (500 MHz, CD$_3$OD): δ 8.09 (d, J=6.0 Hz, 1H); 7.89 (s, 2H); 7.38 (s, 1H); 7.09 (s, 1H); 6.24 (d, J=6.0 Hz, 1H); 4.37 (m, 1H); 3.99 (s, 3H); 3.97 (m, 1H); 3.68 (m, 1H); 3.36 (m, 1H); 2.35 (s, 3H); 2.19 (m, 2H); 1.94 (m, 2H). rhSYK activity=+++

The following examples were prepared in an analogous manner of that described in Examples 47-54 for N,N-disubstituted urea (Example 47), disubstituted sulfamoyl t-butyl carbamate (Example 48), N,N,N'-trisubstituted sulfuric diamide (Example 49), N,N-disubstituted sulfonamide or sulfamic acid (Example 50), amide (Example 51), N,N,N'-trisubstituted urea (Example 52), N-alkylated azetidine, pyrrolidine, piperidine or azepane (Example 53), and N,N,N'-trisubstituted sulfamoyl carbamate (Example 54).

TABLE 54A

| EX. | R$^1$ | R$^2$ | RHSYK Activity | [M+H]+ Observed | FORM(S) |
|---|---|---|---|---|---|
| N = 1 | | | | | |
| 54A-1 | CF$_3$ | —SO$_2$—iPr | +++ | 542.1 | FORMATE SALT |
| 54A-2 | CF$_3$ | —SO$_2$—CF$_3$ | +++ | 568.1 | FORMATE SALT |
| 54A-3 | CF$_3$ | —SO$_2$-(1-ME-4-IMIDAZOLYL | +++ | 580.1 | FORMATE SALT |
| 54A-4 | CF$_3$ | —C(O)Et | +++ | 492.1 | FORMATE SALT |
| 54A-5 | CF$_3$ | —C(O)CH$_2$OH | +++ | 494.1 | FORMATE SALT |
| 54A-6 | CF$_3$ | —C(O)CH$_2$CN | +++ | 503.1 | FORMATE SALT |
| 54A-7 | CF$_3$ | —C(O)CH$_2$N(CH$_3$)$_2$ | +++ | 521.2 | FORMATE SALT |
| 54A-8 | CF$_3$ | —C(O)-3-pyridyl | +++ | 541.2 | FORMATE SALT |
| 54A-9 | CF$_3$ | —C(O)-2-pyridyl | +++ | 541.2 | FORMATE SALT |
| 54A-10 | CF$_3$ | —C(O)CH-(2-oxo-1-pyrrolidinyl) | +++ | 561.2 | FORMATE SALT |
| 54A-11 | CF$_3$ | —C(O)—c-Pr | +++ | 504.1 | FORMATE SALT |
| 54A-12 | CF$_3$ | —C(O)NHc-Hex | +++ | 561.2 | FORMATE SALT |
| 54A-13 | CF$_3$ | —C(O)NH—iPr | +++ | 521.2 | FORMATE SALT |
| 54A-14 | CF$_3$ | —C(O)NH—nPr | +++ | 521.2 | FORMATE SALT |
| 54A-15 | CF$_3$ | —C(O)N(CH$_3$)$_2$ | +++ | 507.1 | FREE BASE |
| 54A-16 | CF$_3$ | —SO$_2$NH$_2$ | +++ | 515.2 | FREE BASE |
| 54A-17 | OCH$_3$ | —C(O)NHC(O)N(CH$_3$)$_2$ | +++ | 512.1 | FREE BASE |
| 54A-18 | OCH$_3$ | —SO$_2$NHCO$_2$—CH$_3$ | +++ | 535.1 | FREE BASE |
| 54A-19 | OCH$_3$ | —C(O)NH$_2$ | +++ | 441.2 | FREE BASE |
| 54A-20 | OCH$_3$ | H | +++ | 398.2 | FREE BASE |
| 54A-21 | CF$_3$ | —C(O)CH(OH)CH$_3$ (R) | +++ | 508.2 | FORMATE SALT |

TABLE 54A-continued

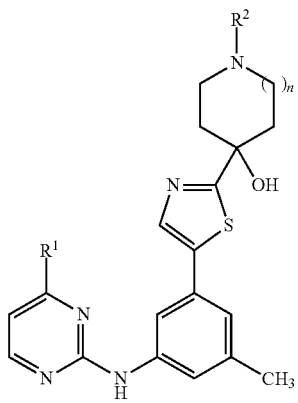

| EX. | R¹ | R² | RHSYK Activity | [M + H]+ Observed | FORM(S) |
|---|---|---|---|---|---|
| 54A-22 | CF₃ | —C(O)CH₂CH₂OH | +++ | 508.2 | FREE BASE |
| 54A-23 | CF₃ | —C(O)CH₂CH₂CN | +++ | 517.2 | FORMATE SALT |
| 54A-24 | CF₃ | —CH₂CF₃ | +++ | 518.1 | FREE BASE |
| 54A-25 | CF₃ | —C(O)CH₂C(O)NH₂ | +++ | 521.2 | FORMATE SALT |
| 54A-26 | CF₃ | —C(O)CH₂C(O)₂H | +++ | 522.1 | FREE BASE |
| 54A-27 | CF₃ | —C(O)CH₂CH(OH)CH₃ | +++ | 522.2 | FREE BASE |
| 54A-28 | CF₃ | —C(O)-2-imidazolyl | +++ | 530.2 | FORMATE SALT |
| 54A-29 | CF₃ | —C(O)-4-imidazolyl | +++ | 530.2 | FORMATE SALT |
| 54A-30 | CF₃ | —C(O)-(1,2,4-triazol-3-yl) | +++ | 531.2 | FREE BASE |
| 54A-31 | CF₃ | —C(O)-(1,2,3-triazol-4-yl) | +++ | 531.2 | FORMATE SALT |
| 54A-32 | CF₃ | —C(O)-3-tetrahydro-furanyl | +++ | 534.2 | FORMATE SALT |
| 54A-33 | CF₃ | —C(O)-(3-OH—cBu) | +++ | 534.2 | FORMATE SALT |
| 54A-34 | CF₃ | —C(O)—Ph | +++ | 540.2 | FORMATE SALT |
| 54A-35 | CF₃ | —C(O)—CH₂-(1-imidazolyl) | +++ | 544.2 | FORMATE SALT |
| 54A-36 | CF₃ | —C(O)—CH₂-(4-imidazolyl) | +++ | 544.2 | FORMATE SALT |
| 54A-37 | CF₃ | —C(O)—CH₂-(1,2,4-triazol-1-yl) | +++ | 545.2 | FORMATE SALT |
| 54A-38 | CF₃ | —C(O)-(5-oxo-2-pyrrolidinyl) (S) | +++ | 547.2 | FORMATE SALT |
| 54A-39 | CF₃ | —C(O)-(2-oxo-4-imidazolidinyl) | +++ | 548.2 | FORMATE SALT |
| 54A-40 | CF₃ | —C(O)CH₂-3-tetrahydrofuranyl | +++ | 548.2 | FORMATE SALT |
| 54A-41 | CF₃ | —C(O)-3-tetrahydropyranyl | +++ | 548.2 | FORMATE SALT |
| 54A-42 | CF₃ | —C(O)CH₂-2-tetrahydrofuranyl | +++ | 548.2 | FORMATE SALT |
| 54A-43 | CF₃ | —C(O)CH₂—CO₂Et | +++ | 550.2 | FREE BASE |
| 54A-44 | CF₃ | —C(O)C(CH₂OH)₂CH₃ | +++ | 552.2 | FORMATE SALT |
| 54A-45 | CF₃ | —C(O)CH₂-3-pyridyl | +++ | 555.2 | FORMATE SALT |
| 54A-46 | CF₃ | —C(O)CH₂-2-pyridyl | +++ | 555.2 | FORMATE SALT |
| 54A-47 | CF₃ | —C(O)CH₂—SO₂CH₃ | +++ | 556.1 | FORMATE SALT |
| 54A-48 | CF₃ | —C(O)CH₂-(5-OH-2-pyridyl) | +++ | 557.2 | FORMATE SALT |
| 54A-49 | CF₃ | —C(O)CH₂-(6-OH-2-pyridyl) | +++ | 557.2 | FORMATE SALT |
| 54A-50 | CF₃ | —C(O)CH₂CH₂-(4-pyrazolyl) | +++ | 558.2 | FORMATE SALT |
| 54A-51 | CF₃ | —C(O)CH₂CH₂-(1,2,4-triazol-1-yl) | +++ | 559.2 | FORMATE SALT |
| 54A-52 | CF₃ | —C(O)-(6-oxo-2-piperidinyl) (S) | +++ | 561.2 | FORMATE SALT |
| 54A-53 | CF₃ | —C(O)CH₂-(4-tetrahydropyranyl) | +++ | 562.2 | FORMATE SALT |
| 54A-54 | CF₃ | —C(O)-(1-CO₂CH₃)—cPr | +++ | 562.2 | FREE BASE |
| 54A-55 | CF₃ | —C(O)-(4-C≡CH)Ph | +++ | 564.2 | FORMATE SALT |
| 54A-56 | CF₃ | —C(O)-(4-CN)Ph | +++ | 565.2 | FORMATE SALT |
| 54A-57 | CF₃ | —C(O)-(3-F, 4-OH)Ph | +++ | 574.2 | FORMATE SALT |
| 54A-58 | CF₃ | —C(O)CH₂—CH(NH₂)CF₃ | +++ | 575.2 | FORMATE SALT |
| 54A-59 | CF₃ | —C(O)-(4-CO₂CH₃)Ph | +++ | 604.2 | FORMATE SALT |
| 54A-60 | CF₃ | —C(O)—CH(OH)CF₃ (racemic) | +++ | 562.1 | FORMATE SALT |
| 54A-61 | CF₃ | (CH₂)₃CH₃ | +++ | 535.2 | FREE BASE |
| 54A-62 | CF₃ | 4-(CH₃)Ph | +++ | 569.2 | FREE BASE |
| 54A-63 | CF₃ | 3-(CH₃)Ph | +++ | 569.2 | FREE BASE |
| 54A-65 | CF₃ | 4-CN—Ph | +++ | 580.1 | FREE BASE |
| 54A-65 | CF₃ | 2,5-di(CH₃)Ph | +++ | 583.2 | FREE BASE |
| 54A-66 | CF₃ | 2,4-di(CH₃)Ph | +++ | 583.2 | FREE BASE |
| 54A-67 | CF₃ | 4-iPr—Ph | +++ | 598,3 | FREE BASE |
| 54A-68 | CF₃ | (2-CH₃-5-Cl)Ph | +++ | 603.1 | FREE BASE |
| 54A-69 | CF₃ | (2-CH₃-4-Cl)Ph | +++ | 603.1 | FREE BASE |
| 54A-70 | CF₃ | CH₂CO₂CH₃ | +++ | 508.2 | FREE BASE |
| 54A-71 | CF₃ | CH₂CH₂CO₂CH₃ | +++ | 522.2 | FREE BASE |
| 54A-72 | CF₃ | CH(CH₃)CO₂CH₃ | +++ | 522.2 | FREE BASE |
| 54A-73 | CF₃ | (CH₂)₃CO₂CH₃ | +++ | 536.2 | FREE BASE |
| N = 2 | | | | | |
| 54A-74 | CF₃ | CH₃ | +++ | 507.2 | FREE BASE |
| 54A-75 | CF₃ | CH₃ (Enantiomer 1) | +++ | 507.2 | FREE BASE |
| 54A-76 | CF₃ | CH₃ (Enantiomer 2) | +++ | 507.2 | FREE BASE |

TABLE 54A-continued

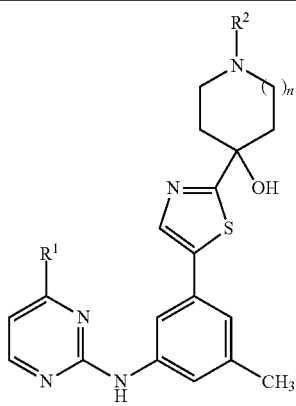

| EX. | R¹ | R² | RHSYK Activity | [M + H]+ Observed | FORM(S) |
|---|---|---|---|---|---|
| 54A-77 | CF₃ | CH₂CH=CH₂ | +++ | 533.2 | TFA SALT |
| 54A-78 | CF₃ | CH₂CH₂CH₃ | +++ | 535.2 | FREE BASE |
| 54A-79 | CF₃ | CH(CH₃)₂ | +++ | 535.2 | FREE BASE |
| 54A-80 | CF₃ | CH₂CO₂Et | +++ | 579.2 | FREE BASE |
| 54A-81 | CF₃ | (CH₂)₃CO₂Et | +++ | 607.2 | TFA SALT |
| 54A-82 | CF₃ | CH₂CH₂F | +++ | 496.2 | TFA SALT |
| 54A-83 | CF₃ | CH₂CO₂H | ++ | 508.2 | TFA SALT |
| 54A-84 | CF₃ | CH₂CH₂CO₂H | +++ | 522.2 | FREE BASE |
| 54A-85 | CF₃ | CH₂CF₃ (Enantiomer 1) | +++ | 532.2 | FREE BASE |
| 54A-86 | CF₃ | CH₂CF₃ (Enantiomer 2) | +++ | 532.2 | FREE BASE |
| 54A-87 | CF₃ | CH₂CF₃ | +++ | 532.2 | TFA SALT |
| 54A-88 | CF₃ | CH₂CH₂CO₂CH₃ | +++ | 536.2 | FORMATE SALT |
| 54A-89 | CF₃ | CH₂CO₂C(CH₃)₃ | +++ | 564.2 | FREE BASE |

TABLE 54B

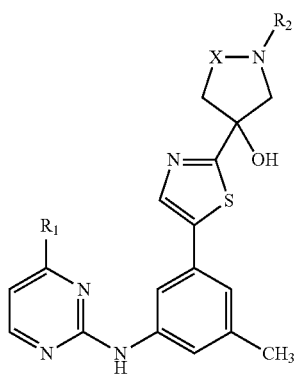

| Ex. | R₁ | R₂ | rhSYK Activity | [M + H]+ Observed | Form(s) |
|---|---|---|---|---|---|
| X = bond | | | | | |
| 54B-1 | CF₃ | —C(O)NH₂ | +++ | 451.1 | Free Base |
| X = CH₂ | | | | | |
| 54B-2 | CF₃ | —C(O)NH₂ (Enantiomer 1) | +++ | 465.1 | Free Base |
| 54B-3 | CF₃ | —C(O)NH₂ (Enantiomer 2) | +++ | 465.1 | Free Base |
| 54B-4 | CF₃ | —C(O)O—tBu | ++ | 522.2 | Free Base |
| 54B-5 | CF₃ | H | +++ | 422.2 | Free Base |
| 54B-6 | CF₃ | —SO₂NH₂ | +++ | 501.1 | Free Base |
| 54B-7 | CF₃ | —C(O)NH₂ | +++ | 465.1 | Free Base |
| 54B-9 | CF₃ | —SO₂NHCO₂—tBu | +++ | 601.1 | Free Base |
| 54B-10 | OCH₃ | —C(O)NH₂ | +++ | 427.2 | Free Base |

TABLE 54B-continued

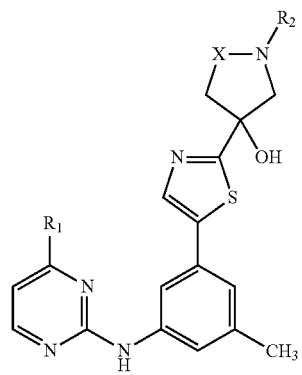

| Ex. | R₁ | R₂ | rhSYK Activity | [M + H]+ Observed | Form(s) |
|---|---|---|---|---|---|
| 54B-11 | OCH₃ | H | +++ | 384.2 | Free Base |
| 54B-12 | CH₃ | H | +++ | 368.2 | Free Base |
| 54B-13 | CH₃ | —C(O)NH₂ (racemic) | +++ | 411.2 | Free Base |
| 54B-14 | CH₃ | —C(O)NH₂ (enantiomer 1) | +++ | 411.2 | Free Base |
| 54B-15 | CH₃ | —C(O)NH₂ (enantiomer 2) | +++ | 411.2 | Free Base |
| 54B-16 | 4-CH₃, 5-F | —C(O)NH₂ | +++ | 429.2 | Free Base |
| 54B-17 | 4-CH₃, 5-Cl | —C(O)NH₂ | +++ | 445.2 | Free Base |
| 548-18 | 4-OCH₃, 5-F | —C(O)NH₂ | +++ | 445.1 | TFA Salt |
| 54B-19 | CF₃ | CH₂CH₂OH | +++ | 466.1 | TFA Salt |

TABLE 54B-continued

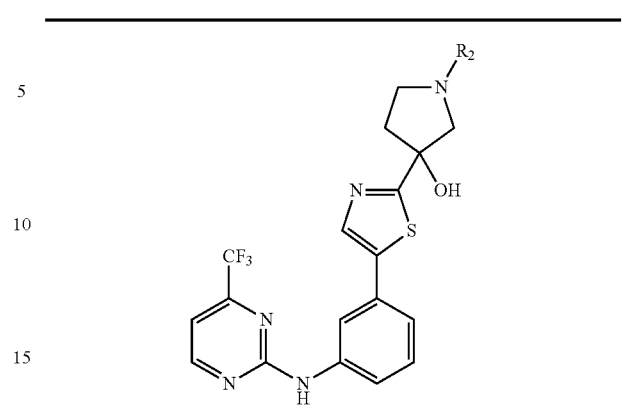

| Ex. | R₁ | R₂ | rhSYK Activity | [M + H]+ Observed | Form(s) |
|---|---|---|---|---|---|
| 54B-20 | CF₃ | CH₂C(O)NH₂ | +++ | 479.1 | TFA Salt |
| 54B-21 | CF₃ | —C(O)CH₂OH | +++ | 480.1 | TFA Salt |
| 54B-22 | CF₃ | —CH₂CO₂H | +++ | 480.2 | TFA Salt |
| 54B-23 | CF₃ | —C(O)C(O)NH₂ | +++ | 493.2 | Free Base |
| 54B-24 | CF₃ | —CH₂CO₂CH₃ | +++ | 494.2 | Free Base |
| 54B-25 | CF₃ | —C(O)CO₂H | +++ | 494.2 | TFA Salt |
| 54B-26 | CF₃ | —C(O)CH₂C(O)NH₂ | +++ | 507.2 | TFA Salt |
| 54B-27 | CF₃ | —C(O)CO₂CH₃ | +++ | 508.2 | Free Base |
| 54B-28 | CF₃ | —C(O)CH(OH)CH₂OH | +++ | 510.2 | TFA Salt |
| 54B-29 | CF₃ | —C(O)-5-isoxazolyl | +++, +++ | 517.2 | Free Base, TFA Salt |
| 54B-30 | CF₃ | —C(O)-(1-OH)—c-Bu | +++ | 520.2 | TFA Salt |
| 54B-31 | CF₃ | —C(O)-(4-CH₃-1,3-oxazol-5-yl) | +++ | 531.2 | TFA Salt |
| 54B-32 | CF₃ | 3-CO₂H—c-Pen | +++ | 534.2 | TFA Salt |
| 54B-33 | CF₃ | 1-CO₂H-cyclohexen-4-yl | +++ | 546.1 | TFA Salt |
| 54B-34 | CF₃ | 3-CO₂CH₃—c-Pen | +++ | 548.2 | Free Base |
| 54B-35 | CF₃ | 3-CO₂CH₃—Ph | ++ | 556.2 | TFA Salt |
| X = CHCO₂H 54B-36) or CHCO₂CH₃ (54B-37) | | | | | |
| 54B-36 | CF₃ | CONH₂ | +++ | 509.2 | TFA Salt |
| 54B-37 | CF₃ | CONH₂ | +++ | 523.2 | Free Base |

TABLE 54C

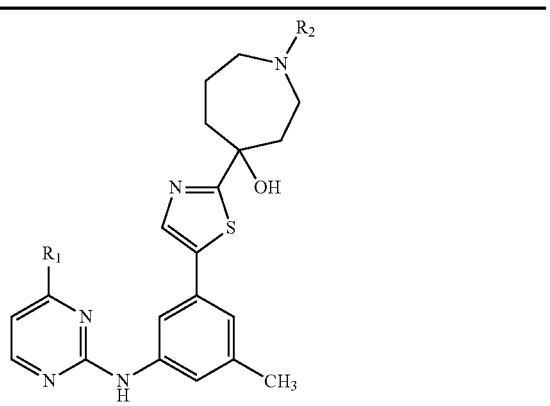

| Ex. | R₂ | rhSYK Activity | [M + H]+ Observed | Form(s) |
|---|---|---|---|---|
| 54C-1 | H | +++ | 408.2 | Free Base |
| 54C-2 | —C(O)NH₂ | +++ | 451.1 | Free Base |

TABLE 54D

| Ex. | R¹ | R² | rhSYK Activity | [M + H]+ Obs'd | Form(s) |
|---|---|---|---|---|---|
| 54D-1 | iPr | H | +++ | 424.2 | Free Base |
| 54D-2 | CF₃ | —C(O)CH₃ | +++ | 492.2 | Free Base |
| 54D-3 | iPr | -(S)—C(O)CH(OH)CH₃ | +++ | 496.2 | Free Base |
| 54D-4 | iPr | —C(O)CH(OH)CH₃ | +++ | 496.2 | Free Base |
| 54D-5 | CF₃ | —C(O)Et | +++ | 506.2 | Free Base |
| 54D-6 | iPr | —C(O)CH₂C(O)NH₂ | +++ | 509.2 | Free Base |
| 54D-7 | iPr | —C(O)CH₂CO₂H | +++ | 510.2 | Free Base |

TABLE 54D-continued

| Ex. | R¹ | R² | rhSYK Activity | [M + H]+ Obs'd | Form(s) |
|---|---|---|---|---|---|
| 54D-8 | iPr | —C(O)CH(OH)CH₂OH | +++ | 512.2 | Free Base |
| 54D-9 | CF₃ | —C(O)CH₂CN | +++ | 517.2 | Free Base |
| 54D-10 | CF₃ | —C(O)—cPr | +++ | 518.2 | Free Base |
| 54D-11 | CF₃ | —C(O)CH₂CH=CH₂ | +++ | 518.2 | Formate Salt |
| 54D-12 | CF₃ | —C(O)CH₂OCH₃ | +++ | 522.2 | Free Base |
| 54D-13 | CF₃ | —C(O)CH₂CH₂OH | +++ | 522.2 | Formate Salt |
| 54D-14 | CF₃ | —C(O)CH(OH)CH₃ | +++ | 522.2 | Formate Salt |
| 54D-15 | iPr | —C(O)CH₂CH₂C(O)NH₂ | +++ | 523.2 | Free Base |
| 54D-16 | CF₃ | —C(O)CH₂CH₂CN | +++ | 531.2 | Free Base |
| 54D-17 | iPr | —C(O)—(CH₃-1,2,3-triazol-5-yl) | +++ | 533.2 | TFA Salt |
| 54D-18 | iPr | —C(O)-(1-CH₃-tetrazol-5-yl) | +++ | 534.2 | TFA Salt |
| 54D-19 | iPr | —C(O)CH₂-(1-tetrazolyl) | +++ | 534.2 | TFA Salt |
| 54D-20 | CF₃ | —C(O)CH₂C(O)NH₂ (enantiomer 1) | +++ | 535.2 | Free Base |
| 54D-21 | CF₃ | —C(O)CH₂C(O)NH₂ (enantiomer 2) | +++ | 535.2 | Free Base |
| 54D-22 | CF₃ | —C(O)CH₂C(O)NH₂ | +++ | 535.2 | Free Base |
| 54D-23 | CF₃ | —C(O)CH₂CH(OH)CH₃ | +++ | 536.2 | Formate Salt |
| 54D-24 | CF₃ | —C(O)CH₂CO₂H | +++ | 536.2 | Formate Salt |
| 54D-25 | CF₃ | —C(O)CH₂CO₂H (Enantiomer 1) | +++ | 536.2 | Free Base |
| 54D-26 | CF₃ | —C(O)CH₂CO₂H (Enantiomer 2) | +++ | 536.2 | Free Base |
| 54D-27 | CF₃ | —C(O)CH(OH)CH₂OH | +++ | 538.2 | Formate Salt |
| 54D-28 | CF₃ | —C(O)CH(OH)CH₂OH (isomer 1) | +++ | 538.2 | Formate Salt |
| 54D-29 | CF₃ | —C(O)CH(OH)CH₂OH (isomer 2) | +++ | 538.2 | Formate Salt |
| 54D-30 | iPr | —C(O)CH₂CO₂Et | +++ | 538.2 | Free Base |
| 54D-31 | iPr | —C(O)C(CH₂OH)₂CH₃ | +++ | 540.3 | TFA Salt |
| 54D-32 | 4-OCH₃, 5-Cl | —C(O)-1,2,3-triazol-5-yl (enantiomer 1) | +++ | 541.2 | Free Base |
| 54D-33 | 4-OCH₃, 5-Cl | —C(O)-1,2,3-triazol-5-yl (enantiomer 2) | +++ | 541.2 | Free Base |
| 54D-34 | CF₃ | —C(O)-2-imidazolyl | +++ | 544.2 | Free Base |
| 54D-35 | CF₃ | —C(O)-(1,2,3-triazol-5-yl) | +++ | 545.2 | Free Base |
| 54D-36 | CF₃ | —C(O)-(1,2,3-triazol-5-yl) (enantiomer 1) | +++, +++ | 545.2 | Free Base, TFA Salt |
| 54D-37 | CF₃ | —C(O)-(1,2,3-triazol-5-yl) (enantiomer 2) | +++ | 545.2 | TFA Salt |
| 54D-38 | CF₃ | —C(O)-(1,2,5-oxadiazol-3-yl) (enantiomer 1) | +++ | 546.2 | TFA Salt |
| 54D-39 | CF₃ | —C(O)-(1,2,5-oxadiazol-3-yl) (enantiomer 2) | +++ | 546.2 | TFA Salt |
| 54D-40 | CF₃ | —C(O)-2-tetrahydrofuranyl | +++ | 548.2 | Formate Salt |
| 54D-41 | CF₃ | —C(O)CH₂CH₂C(O)NH₂ (enantiomer 1) | +++ | 549.2 | TFA Salt |
| 54D-42 | CF₃ | —C(O)CH₂CH₂C(O)NH₂ (enantiomer 2) | +++ | 549.2 | TFA Salt |
| 54D-43 | CF₃ | —C(O)CH₂CH₂CO₂H | +++ | 550.2 | TFA Salt |
| 54D-44 | CF₃ | —C(O)CH₂C(CH₃)₂OH | +++ | 550.2 | Formate Salt |
| 54D-45 | CF₃ | —C(O)—Ph | +++ | 554.2 | Free Base |
| 54D-46 | CF₃ | —C(O)—CH₂-1-imidazolyl | +++ | 558.2 | Free Base |
| 54D-47 | CF₃ | —C(O)—CH₂-4-imidazolyl | +++ | 558.2 | Free Base |
| 54D-48 | CF₃ | —C(O)-(5-CH₃-3-isoxazolyl) | +++ | 559.2 | Formate Salt |
| 54D-49 | CF₃ | —C(O)—CH₂-(1,2,4-triazol-1-yl) | +++ | 559.2 | Free Base |
| 54D-50 | CF₃ | —C(O)-(1-CH₃-1,2,3-triazol-5-yl) (enantiomer 1) | +++ | 559.2 | TFA Salt |
| 54D-51 | CF₃ | —C(O)-(1-CH₃-1,2,3-triazol-5-yl) (enantiomer 2) | +++ | 559.2 | TFA Salt |
| 54D-52 | CF₃ | —C(O)—CH₂-(1,2,3-triazol-1-yl) (enantiomer 1) | +++ | 559.2 | TFA Salt |
| 54D-53 | CF₃ | —C(O)—CH₂-(1,2,3-triazol-1-yl) (enantiomer 2) | +++ | 559.2 | TFA Salt |

TABLE 54D-continued

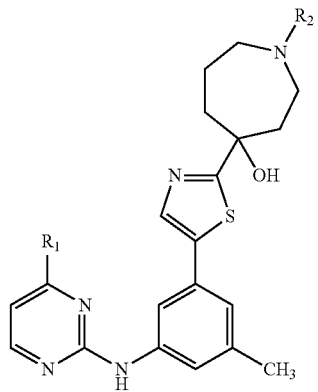

| Ex. | R¹ | R² | rhSYK Activity | [M + H]+ Obs'd | Form(s) |
|---|---|---|---|---|---|
| 54D-54 | $CF_3$ | —C(O)—$CH_2CF_3$ | +++ | 560.2 | Formate Salt |
| 54D-55 | $CF_3$ | —C(O)-(1-$CH_3$-tetrazol-5-yl | +++ | 560.2 | Free Base |
| 54D-56 | $CF_3$ | —C(O)—$CH_2$-(tetrazol-1-yl) | +++ | 560.2 | Free Base |
| 54D-57 | $CF_3$ | —C(O)-(1-$CH_3$-tetrazol-5-yl (enantiomer I) | +++ | 560.2 | TFA Salt |
| 54D-58 | $CF_3$ | —C(O)-(1-$CH_3$-tetrazol-5-yl (enantiomer 2) | +++ | 560.2 | TFA Salt |
| 54D-59 | $CF_3$ | —C(O)—$CH_2$-(tetrazol-5-yl) (enantiomer 1) | +++ | 560.2 | TFA Salt |
| 54D-60 | $CF_3$ | —C(O)—$CH_2$-(tetrazol-5-yl) (enantiomer 2) | +++ | 560.2 | TFA Salt |
| 54D-61 | $CF_3$ | —C(O)-(5-oxo-2-pyrrolidinyl) | +++ | 561.2 | Free Base |
| 54D-62 | $CF_3$ | —C(O)— [1,2,4-triazol-3(2H)-one-5-yl] (enantiomer 1) | +++ | 561.2 | TFA Salt |
| 54D-63 | $CF_3$ | —C(O)— [1,2,4-triazol-3(2H)-one-5-yl] (enantiomer 2) | +++ | 561.2 | TFA Salt |
| 54D-64 | $CF_3$ | —C(O)-(2-oxo-4-imidazolidinyl) | +++ | 562.2 | Free Base |
| 54D-65 | $CF_3$ | —C(O)-2-tetrahydropyranyl | +++ | 562.2 | Free Base |
| 54D-66 | $CF_3$ | —C(O)-(5-oxo-2-tetrahydrofuranyl) | +++ | 562.2 | Free Base |
| 54D-67 | $CF_3$ | —C(O)—$CH_2$-3-tetrahydrofuranyl | +++ | 562.2 | Free Base |
| 54D-68 | $CF_3$ | —C(O)-3-tetrahydropyranyl | +++ | 562.2 | Free Base |
| 54D-69 | $CF_3$ | —C(O)—$CH_2$-3-tetrahydrofuranyl | +++ | 562.2 | Free Base |
| 54D-70 | $CF_3$ | —C(O)-(1-$CO_2H$—cPr) | +++ | 562.2 | Formate Salt |
| 54D-71 | $CF_3$ | —C(O)-(2-$CO_2H$—cPr) | +++ | 562.2 | Formate Salt |
| 54D-72 | $CF_3$ | —C(O)$CH_2CH_2CO_2CH_3$ | +++ | 564.2 | Free Base |
| 54D-73 | $CF_3$ | —C(O)$CH_2CO_2CH_2CH_3$ | +++ | 564.2 | Formate Salt |
| 54D-74 | $CF_3$ | —C(O)$CH_2CO_2CH_2CH_3$ (enantiomer 1) | +++ | 564.2 | Free Base |
| 54D-75 | $CF_3$ | —C(O)$CH_2CO_2CH_2CH_3$ (enantiomer 2) | +++ | 564.2 | Free Base |
| 54D-76 | $CF_3$ | —C(O)$CH_2CH_2NHCONH_2$ | +++ | 564.2 | Free Base |
| 54D-77 | $CF_3$ | —C(O)CH(OH)C($CH_3$)$_2$OH | +++ | 566.2 | Formate Salt |
| 54D-78 | $CF_3$ | —C(O)C($CH_2OH$)$_2CH_3$ | +++ | 566.2 | Free Base |
| 54D-79 | $CF_3$ | —C(O)C($CH_2OH$)$_2CH_3$ (enantiomer 1) | +++ | 566.2 | TFA Salt |
| 54D-80 | $CF_3$ | —C(O)C($CH_2OH$)$_2CH_3$ (enantiomer 2) | +++ | 566.2 | TFA Salt |
| 54D-81 | $CF_3$ | —C(O)$CH_2$-3-pyridyl | +++ | 569.2 | Free Base |
| 54D-82 | $CF_3$ | —C(O)$CH_2$-2-pyridyl | +++ | 569.2 | Free Base |
| 54D-83 | $CF_3$ | —C(O)$CH_2SO_2CH_3$ | +++ | 570.1 | Free Base |
| 54D-84 | $CF_3$ | —C(O)-(4-OH)Ph | +++ | 570.2 | Free Base |
| 54D-85 | $CF_3$ | —C(O)-(5-OH-2-pyridyl) | +++ | 571.2 | Free Base |
| 54D-86 | $CF_3$ | —C(O)-(6-OH-2-pyridyl) | +++ | 571.2 | Free Base |
| 54D-87 | $CF_3$ | —C(O)-(4-OH-2-pyridyl) | +++ | 571.2 | Formate Salt |
| 54D-88 | $CF_3$ | —C(O)$CH_2CH_2$-4-pyrazolyl | +++ | 572.2 | Free Base |

TABLE 54D-continued

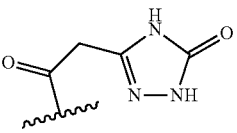

| Ex. | R¹ | R² | rhSYK Activity | [M + H]+ Obs'd | Form(s) |
|---|---|---|---|---|---|
| 54D-89 | CF₃ | —C(O)CH₂CH₂-(1,2,4-triazol-1-yl) | +++ | 573.2 | Free Base |
| 54D-90 | CF₃ | —C(O)CH₂CH₂CF₃ | +++ | 574.2 | Formate Salt |
| 54D-91 | CF₃ | —C(O)CH₂-(2-oxo-1-pyrrolidinyl) | +++ | 575.2 | Formate Salt |
| 54D-92 | CF₃ | —C(O)-(6-oxo-2-piperidinyl) | +++ | 575.2 | Free Base |
| 54D-93 | CF₃ | 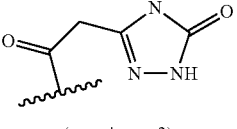 (enantiomer 1) | +++ | 575.2 | TFA Salt |
| 54D-94 | CF₃ | (enantiomer 2) | +++ | 575.2 | TFA Salt |
| 54D-95 | CF₃ | —C(O)-(1-CO₂CH₃)—cPr | +++ | 576.2 | Formate Salt |
| 54D-96 | CF₃ | —C(O)CH₂-4-tetrahydropyranyl | +++ | 576.2 | Free Base |
| 54D-97 | CF₃ | —C(O)CH(OH)CF₃ | +++ | 576.2 | Free Base |
| 54D-98 | CF₃ | —C(O)CH₂CH₂C(O)N(CH₃)₂ | +++ | 577.2 | Free Base |
| 54D-99 | CF₃ | —C(O)-(4-C≡CH)Ph | +++ | 578.2 | Free Base |
| 54D-100 | CF₃ | —C(O)-(4-Cl-1,2,3-triazol-5-yl) (enantiomer 1) | +++ | 579.1 | TFA Salt |
| 54D-101 | CF₃ | —C(O)-(4-Cl-1,2,3-triazol-5-yl) (enantiomer 2) | +++ | 579.1 | TFA Salt |
| 54D-102 | CF₃ | —C(O)C(CH₂OH)₂CH₂CH₃ | +++ | 580.2 | Free Base |
| 54D-103 | CF₃ | —C(O)-(3-F, 4-OH)Ph | +++ | 588.2 | Free Base |
| 54D-104 | CF₃ | —C(O)-(2-F, 5-OH)Ph | +++ | 588.2 | Free Base |
| 54D-105 | CF₃ | —C(O)-(2-Cl-4-pyrimidinyl) | +++ | 590.1 | Free Base |
| 54D-106 | CF₃ | —C(O)-(4-OC(O)CH₃)Ph | +++ | 612.2 | Free Base |
| 54D-107 | CF₃ | —C(O)-(5-CF₃-1,2,3-triazol-4-yl) (enantiomer 1) | +++ | 613.2 | TFA Salt |
| 54D-108 | CF₃ | —C(O)-(5-CF₃-1,2,3-triazol-4-yl) (enantiomer 2) | +++ | 613.2 | TFA Salt |
| 54D-109 | CF₃ | —C(O)-(5-CF₃-1,2,4-triazol-3-yl) (enantiomer 1) | +++ | 613.2 | TFA Salt |
| 54D-110 | CF₃ | —C(O)-(5-CF₃-1,2,4-triazol-3-yl) (enantiomer 2) | +++ | 613.2 | TFA Salt |
| 54D-111 | CF₃ | —C(O)-(4-CO₂CH₃)-cHex | +++ | 618.2 | Free Base |
| 54D-112 | CF₃ | C(O)CH₂C(OH)(CF₃)CO₂CH₃ | +++ | 648.2 | Formate Salt |
| 54D-113 | iPr | —C(O)CH₂C(O)NH₂ | +++ | 509.2 | TFA Salt |
| 54D-114 | CF₃ | SO₂NHCO₂C(CH₃)₃ | +++ | 629.2 | Free Base |
| 54D-115 | CF₃ | SO₂NH₂ | +++ | 529.1 | TFA Salt |
| 54D-116 | CF₃ | SO₂NH₂ (Enantiomer 1) | +++ | 529.1 | Free Base |
| 54D-117 | CF₃ | SO₂NH₂ (Enantiomer 2) | +++ | 529.1 | Free Base |
| 54D-118 | CF₃ | SO₃H | +++ | 530.1 | TFA Salt |
| 54D-119 | CF₃ | C(O)NH₂ (Enantiomer 1) | +++ | 493.1 | Free Base |
| 54D-120 | CF₃ | C(O)NH₂ (Enantiomer 2) | +++ | 493.1 | Free Base |
| 54D-121 | CF₃ | C(O)CH₂OH | +++ | 508.2 | Free Base |
| 54D-122 | CF₃ | C(O)CH₂OH (Enantiomer 1) | +++ | 508.1 | Free Base |
| 54D-123 | CF₃ | C(O)CH₂OH (Enantiomer 2) | +++ | 508.1 | Free Base |

TABLE 54D-continued

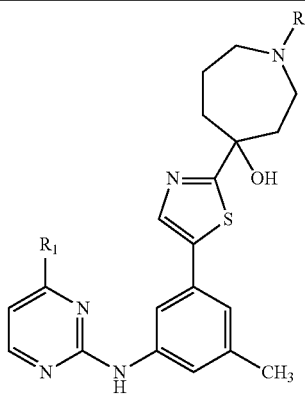

| Ex. | R¹ | R² | rhSYK Activity | [M + H]+ Obs'd | Form(s) |
|---|---|---|---|---|---|
| 54D-124 | $CF_3$ | C(O)-1,2,4-triazol-3-yl (Enantiomer 1) | +++ | 545.2 | Free Base |
| 54D-125 | $CF_3$ | C(O)-1,2,4-triazol-3-yl (Enantiomer 2) | +++ | 545.2 | Free Base |

TABLE 54E

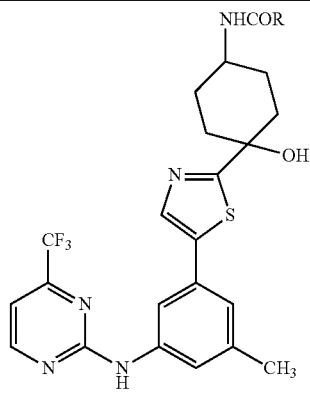

| Ex. | R | rhSYK Activity | [M + H]+ Observed | Form(s) |
|---|---|---|---|---|
| 54E-1 | CH(OH)CH₃ (2R; cis) | +++ | 522.2 | Formate Salt |
| 54E-2 | CH(OH)CH₃ (2S; cis) | +++ | 522.2 | Formate Salt |
| 54E-3 | CH₂C(O)NH₂ | +++ | 535.2 | Formate Salt |
| 54E-4 | 2-imidazolyl (cis) | +++ | 544.2 | Formate Salt |
| 54E-5 | 4-imidazolyl (cis) | +++, +++ | 544.2 | Free Base, Formate Salt |
| 54E-6 | 1,2,3-triazol-4-yl | +++ | 545.2 | Formate Salt |
| 54E-7 | 3-OH—cBu | +++ | 548.2 | Formate Salt |
| 54E-8 | CH₂CH₂C(O)NH₂ (cis) | +++ | 549.2 | Formate Salt |
| 54E-9 | Ph (cis) | +++ | 554.2 | Formate Salt |
| 54E-10 | CH₂-4-imidazolyl (cis) | +++ | 558.2 | Formate Salt |
| 54E-11 | CH₂-1,2,4-triazol-1-yl (cis) | +++ | 559.1 | Formate Salt |
| 54E-12 | CH₂-1,2,3-triazol-1-yl (cis) | +++ | 559.2 | Formate Salt |
| 54E-13 | CH₂-tetrazol-1-yl (cis) | +++ | 560.2 | Formate Salt |
| 54E-14 | cHex (cis) | +++ | 560.2 | Formate Salt |
| 54E-15 | 2-oxo-4-imidazolidinyl | +++ | 562.2 | Formate Salt |
| 54E-16 | 2-tetrahydropyranyl | +++ | 562.2 | Formate Salt |
| 54E-17 | CH₂-2-tetrahydrofuranyl | +++ | 562.2 | Formate Salt |
| 54E-18 | 3-tetrahydrofuranyl | +++ | 562.2 | Formate Salt |
| 54E-19 | CH₂-2-tetrahydrofuranyl | +++ | 562.2 | Formate Salt |
| 54E-20 | C(CH₂OH)₂CH₃ (cis) | +++ | 566.2 | Formate Salt |
| 54E-21 | CH₂-2-pyridyl (cis) | +++ | 569.2 | Formate Salt |
| 54E-22 | CH₂SO₂CH₃ (cis) | +++ | 570.2 | Formate Salt |
| 54E-23 | CH₂-2-pyrimidinyl (cis) | +++ | 570.2 | Formate Salt |
| 54E-24 | 5-OH-2-pyridyl (cis) | +++ | 571.2 | Formate Salt |
| 54E-25 | 6-OH-2-pyridyl (cis) | +++ | 571.2 | Formate Salt |

TABLE 54E-continued

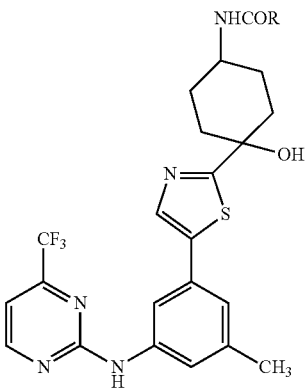

| Ex. | R | rhSYK Activity | [M + H]+ Observed | Form(s) |
|---|---|---|---|---|
| 54E-26 | CH₂CH₂-4-pyrazolyl (cis) | +++ | 572.2 | Formate Salt |
| 54E-27 | CH₂CH₂-1,2,4-triazol-1-yl (cis) | +++ | 573.2 | Formate Salt |
| 54E-28 | 6-oxo-2-piperidinyl (2S; cis) | +++ | 575.2 | Formate Salt |
| 54E-29 | CH₂-4-tetrahydropyranyl | +++ | 576.2 | Formate Salt |
| 54E-30 | CH(OH)CF₃ | +++ | 576.2 | Formate Salt |
| 54E-31 | CH₂CH₂CON(CH₃)₂ (cis) | +++ | 577.2 | Formate Salt |
| 54E-32 | 4-C≡CH—Ph (cis) | +++ | 578.2 | Formate Salt |
| 54E-33 | 4-CN—Ph (cis) | +++ | 579.2 | Formate Salt |
| 54E-34 | C(CH₂OH)₃ | +++ | 580.2 | Formate Salt |
| 54E-35 | (2-F, 5-OH)—Ph (cis) | +++ | 588.2 | Formate Salt |
| 54E-36 | (3-F, 4-OH)—Ph (cis) | +++, +++ | 588.2 | Free Base, Formate Salt |
| 54E-37 | CH₂CH(NH₂)CF₃ | +++ | 589.2 | Formate Salt |
| 54E-38 | 4-(CO₂CH₃)—cHex (cis) | +++ | 618.2 | Formate Salt |

Example 55

5-{cis-4-Hydroxy-4-[5-(3-methyl-5-{[4-(trifluoromethyl)pyrimidin-2-yl]amino}phenyl)-1,3-thiazol-2-yl]cyclohexyl}-1,3,4-oxadiazol-2(3H)-one

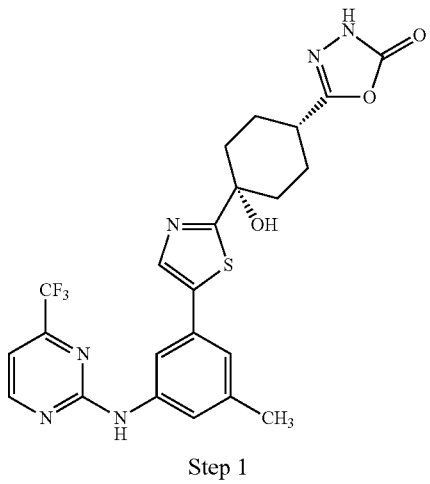

Step 1 cis-4-Hydroxy-4-[5-(3-methyl-5-{[4-(trifluoromethyl)pyrimidin-2-yl]amino}phenyl)-1,3-thiazol-2-yl]cyclohexanecarboxylic acid (150 mg, 0.313 mmol), hydrazinecarboxamide hydrochloride (52.4 mg, 0.470 mmol), O-(7-azabenzotriazol-1-yl)-N,N,N',N'-tetramethyluronium hexafluorophosphate (149 mg, 0.392 mmol), and diisopropylethylamine (164 µl, 0.940 mmol) were taken-up in dimethylformamide (1.3 mL) under argon. The vessel was sealed and stirred at 125° C. for 18 hours. The reaction mixture was cooled to room temperature, filtered, and directly subjected to reverse-phase HPLC (water-acetonitrile, trifluoroacetic acid modifier). This purification afforded 5-{cis-4-hydroxy-4-[5-(3-methyl-5-{[4-(trifluoromethyl)pyrimidin-2-yl]amino}phenyl)-1,3-thiazol-2-yl]cyclohexyl}-1,3,4-oxadiazol-2(3H)-one as a white solid (39.1 mg, 0.075 mmol, 24% yield). MS ESI: [M+H]+ m/z 519.1. ¹H NMR (500 MHz, dmso) δ 12.10 (s, 1H), 10.25 (s, 1H), 8.82 (d, J=4.8, 1H), 8.02-7.88 (m, 2H), 7.45 (s, 1H), 7.27 (d, J=4.9, 1H), 7.15 (s, 1H), 6.06 (s, J=27.1, 1H), 2.67 (s, 1H), 2.31 (s, 3H), 2.09-1.75 (m, 8H). rhSYK activity=+++

Example 56

1-[5-(3-methyl-5-{[4-(propan-2-yl)pyrimidin-2-yl]amino}phenyl)-1,3-thiazol-2-yl]cyclobutanol HCl salt

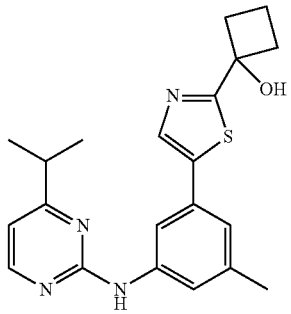 [SMILES: Cc1cc(Nc2nccc(C(C)C)n2)cc(-c2cnc(C3(O)CCC3)s2)c1]

Step 1

Acetic acid (0.192 mL, 3.35 mmol) was added to commercially available 2-chloro-4-(propan-2-yl)pyrimidine (0.5 g, 3.19 mmol) and 3-bromo-5-methylaniline (0.900 g, 3.19 mmol) suspended in dioxane (6.39 mL). Reaction was heated to 120° C. (bath temp) overnight. Then, the reaction was cooled to room temperature and purified by column chromatography on silica gel eluting with ethyl acetate and hexanes to give N-(3-bromo-5-methylphenyl)-4-(propan-2-yl)-pyrimidin-2-amine (959.8 mg, 3.13 mmol, 98%) as a white solid.

Step 2

A 40 mL vial was charged with the product of Step 1 (500 mg, 1.633 mmol), bis(pinacolato)diboron (456 mg, 1.796 mmol), 1,1'-bis(diphenylphosphino)ferrocene-palladium(II) dichloride dichloromethane complex (40.0 mg, 0.049 mmol) and potassium acetate (481 mg, 4.90 mmol). The solid mixture was dissolved with DMSO (6.5 mL) and heated to 120° C. After stirring for 2 h, the mixture was extracted with ethyl acetate, washed with saturated aqueous NaHCO₃, brine, dried over anhydrous sodium sulfate, filtered and concentrated under reduced pressure. The residue was purified by column chromatography on silica gel eluting with ethyl acetate in hexanes to give N-[3 ethyl-5-(4,4,5,5-tetramethyl-1,3,2-dioxaborolan-2-yl)phenyl]-4-(propan-2-yl)pyrimidin-2-amine (249 mg, 0.705 mmol, 43.2% yield) as a white solid.

Step 3

A 2 dram vial was charged with the product of Step 2 (100 mg, 0.283 mmol) 1-(5-bromo-1,3-thiazol-2-yl)cyclobutanol (INTERMEDIATE 1, 72.9 mg, 0.311 mmol), butyldi-1-adamantylphosphine (14.21 mg, 0.040 mmol), palladium(II) acetate (4.45 mg, 0.020 mmol), potassium fluoride (49.3 mg, 0.849 mmol), THF (1166 µL) then water (348 µL). The vial was sealed and then heated to 80° C. overnight. Then, the reaction was cooled to room temperature. The reaction mixture was purified by column chromatography on silica gel eluting with ethyl acetate in hexanes. The fractions were combined, concentrated and redissolved in acetonitrile/water+HCl (1M, 200 uL) and lyophylized to give 1-[5-(3-methyl-5-{[4-(propan-2-yl)pyrimidin-2-yl]amino}phenyl)-1,3-thiazol-2-yl]cyclobutanol HCl salt (16.8 mg, 0.040 mmol, 14.23% yield) as a white solid. MS ESI: [M+H]+ m/z 381.1. ¹H NMR (500 MHz, CDCl₃): δ 9.66 (s, 1H); 8.38 (d, J=5.5 Hz, 1H); 8.02 (s, 1H); 7.97 (s, 1H); 7.50 (s, 1H); 7.07 (m, 1H); 6.79 (m, 1H); 2.90 (m, 1H); 2.53 (m, 2H); 2.33 (m, 21-1); 2.30 (s, 3H); 1.88 (m, 2H); 1.25 (d, J=7 Hz, 6H). rhSYK activity=+++

The following examples were prepared in an analogous manner of that described in Example 56.

TABLE 56

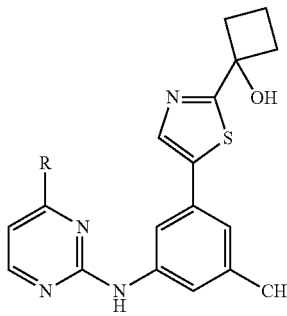

| Example | R | rhSYK Activity | [M + H]+ Observed | Form(s) |
|---|---|---|---|---|
| 56-1 | CH₃ | +++ | 353.1 | HCl salt |
| 56-2 | Et | +++ | 367.1 | HCl salt |
| 56-3 | cPr | +++ | 379.1 | HCl salt |
| 56-4 | S—CH₃ | +++ | 385.1 | HCl salt |
| 56-5 | t-Bu | +++ | 395.2 | Free Base |

Example 57

2-(5-{3-[(4-cyclopropyl-5-fluoropyrimidin-2-yl)amino]-5-fluorophenyl}-1,3-thiazol-2-yl)propane-1,2-diol

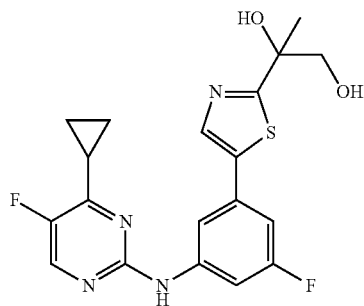 [SMILES: CC(O)(CO)c1ncc(-c2cc(F)cc(Nc3ncc(F)c(C4CC4)n3)c2)s1]

Step 1

3-Bromo-5-fluoroaniline (2.23 g, 11.74 mmol), bispinacolatodiboron (3.28 g, 12.91 mmol), Pd$_2$(dba)$_3$ (0.269 g, 0.293 mmol), tricyclohexylphosphine (0.329 g, 1.174 mmol), and potassium acetate (1.843 g, 18.78 mmol) were added to a dry flask. Degassed with argon, then added dioxane (25 mL). The reaction mixture was degassed again with argon for five minutes, and then heated to 95° C. After 12 hours, the reaction mixture was cooled, diluted with ethyl acetate, filtered through celite, and concentrated. The residue was purified by column chromatography on silica gel, eluting with ethyl acetate and hexanes to afford 3-fluoro-5-(4,4,5,5-tetramethyl-1,3,2-dioxaborolan-2-yl)aniline (2.66 g, 11.2 mmol, 96%). MS ESI: [M+H]⁺ m/z 238.1.

Step 2

The product of Step 1 (2.66 g, 11.22 mmol), 2-bromo-1,4-thiazole (1.003 mL, 11.22 mmol), Pd$_2$(dba)$_3$ (0.514 g, 0.561 mmol), X-phos (0.535 g, 1.122 mmol), and cesium carbonate (7.31 g, 22.44 mmol) were added to a dry flask. Degassed with argon, then added dioxane (25 mL) and water (2.5 mL). The reaction mixture was degassed with argon for five minutes, and then heated to 95° C. After 16 hours, the reaction mixture was cooled, diluted with ethyl acetate, filtered through celite, and concentrated. The residue was purified by column chromatography on silica gel, eluting with ethyl acetate and hexanes to afford 3-fluoro-5-(1,3-thiazol-5-yl)aniline (2.27 g, 9.49 mmol, 85%). MS ESI: [M+H]⁺ m/z 195.1.

Step 3

5-Fluoro-2,4-dichloropyrimidine (5 g, 29.9 mmol), cyclopropyl boronic acid (2.57 g, 29.9 mmol), potassium phosphate tribasic (15.89 g, 74.9 mmol) and PdCl$_2$(dppf)-dichloromethane adduct (1.223 g, 1.497 mmol) were added to a dry flask. The system was degassed with argon, and then tetrahydrofuran (150 mL) was added. The reaction mixture was degassed with argon for five minutes, and then heated to 67° C. After 12 hours, the reaction mixture was diluted with ethyl acetate (1000 mL), washed with brine, dried over magnesium sulfate, filtered and concentrated. The residue was purified by column chromatography on silica gel, eluting with ethyl acetate in hexanes to afford 2-chloro-4-cyclopropyl-5-fluoropyrimidine (4.1 g, 23.8 mmol, 79% yield). MS ESI: [M+H]⁺ m/z 172.9.

Step 4

3-Fluoro-5-(1,3-thiazol-5-yl)aniline (0.91 g, 4.69 mmol), 2-chloro-4-cyclopropyl-5-fluoropyrimidine (0.809 g, 4.69 mmol), palladium(II) acetate (0.105 g, 0.469 mmol), Xantphos (0.407 g, 0.703 mmol), and cesium carbonate (3.05 g, 9.37 mmol) were added to a dry flask. Degassed with argon, and then added dioxane (20 mL). The reaction mixture was degassed with argon for five minutes, and then heated to 90° C. After 2 hours, the reaction mixture was cooled, diluted with ethyl acetate, filtered through celite, and concentrated. The residue was purified by column chromatography on silica gel, eluting with ethyl acetate and hexanes to afford solids. The solids were dissolved in hot ethyl acetate (25 mL) and then triturated with hexanes (50 mL) while cooling. After 2 hours, the mixture was filtered to afford 4-cyclopropyl-5-fluoro-N-[3-fluoro-5-(1,3-thiazol-5-yl)phenyl]pyrimidin-2-amine (1.2 g, 3.6 mmol, 78%). MS ESI: [M+H]⁺ m/z 331.1.

Step 5

LDA (0.757 mL, 1.362 mmol) was added to tetrahydrofuran (4 mL) at −78° C. After 15 minutes at −78° C., a solution of the product of Step 4 (150 mg, 0.454 mmol) in tetrahydrofuran (4 mL) was added dropwise. After 30 minutes at −78° C., a solution of 1-{[tert-butyl(dimethyl)-silyl]oxy}acetone (0.110 mL, 0.568 mmol) in tetrahydrofuran (4 mL) was added dropwise at −78° C. The reaction mixture was allowed to warm to ambient temperature. After 1 hour, the reaction mixture was quenched with saturated ammonium chloride, diluted with ethyl acetate, washed with brine, dried over magnesium sulfate, filtered, and concentrated. The residue was purified by column chromatography on silica gel, eluting with ethyl acetate and hexanes to afford 1-{[tert-butyl(dimethyl)silyl]oxy}-2-(5-{3-[(4-cyclopropyl-5-fluoropyrimidin-2-yl)amino]-5-fluorophenyl}-1,3-thiazol-2-yl)propan-2-ol (150 mg, 0.29 mmol, 64%). MS ESI: [M+H]⁺ m/z 519.2.

Step 6

To a solution of the product of Step 5 (150 mg, 0.289 mmol) in methanol (4 mL) was added HCl (4.0 M in dioxane) (0.072 mL, 0.289 mmol). After 30 minutes, the reaction mixture was concentrated. The residue was purified by preparative HPLC Reverse phase (C-18), eluting with acetonitrile/water 0.05% TFA to give 2-(5-{3-[(4-cyclopropyl-5-fluoropyrimidin-2-yl)-amino]-5-fluorophenyl}-1,3-thiazol-2-yl)propane-1,2-diol (95 mg, 0.24 mmol, 81%). MS ESI: [M+H]$^+$ m/z 405.1. $^1$H NMR (600 MHz, DMSO-d$_6$) 0.83 (s, 1H); 8.41 (s, 1H); 8.01 (s, 1H); 7.75 (s, 1H); 7.53 (d, J=11.4 Hz, 1H); 7.06 (d, J=9.6 Hz, 1H); 5.89 (s, 1H); 4.89 (s, 1H); 3.52 (s, 2H); 2.29-2.22 (m, 1H); 1.43 (s, 3H); 1.20-1.12 (m, 4H). rhSYK activity=+++

Example 58

2-(5-{3-[(4-cyclopropyl-5-fluoropyrimidin-2-yl)amino]-5-methylphenyl}-1,3-thiazol-2-yl)-3,3,3-trifluoropropane-1,2-diol

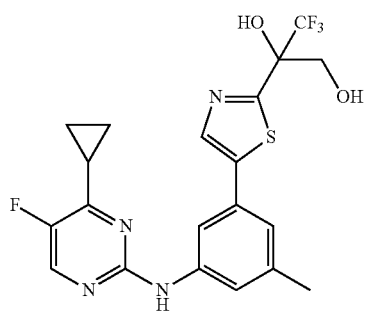 [SMILES: Cc1cc(Nc2ncc(F)c(C3CC3)n2)cc(-c2cnc(C(O)(CO)C(F)(F)F)s2)c1]

To a solution of ethyl 2-(5-{3-[(4-cyclopropyl-5-fluoropyrimidin-2-yl)amino]-5-methylphenyl}-1,3-thiazol-2-yl)-3,3,3-trifluoro-2-hydroxypropanoate (36 mg, 0.073 mmol) in tetrahydrofuran (10 mL) at −78° C. was added DIBAL-H (0.160 mL 0.160 mmol). After 30 minutes, the reaction mixture was warmed to 0° C. After 2 hours, the reaction mixture was quenched with saturated ammonium chloride solution, then diluted with ethyl acetate, washed with brine, dried over magnesium sulfate, filtered, and concentrated. The residue was purified by preparative HPLC Reverse phase (C-18), eluting with acetonitrile/water+0.05% TFA to give 2-(5-{3-[(4-cyclopropyl-5-fluoropyrimidin-2-yl)amino]-5-methylphenyl}-1,3-thiazol-2-yl)-3,3,3-trifluoropropane-1,2-diol (3.5 mg, 0.001 mmol, 10%). MS ESI: [M+H]$^+$ m/z 455.1. $^1$H NMR (500 MHz, DMSO-d$_6$) δ 9.58 (bs, 1H); 8.38 (m, 1H); 8.06 (s, 1H); 7.89 (s, 1H); 7.43 (s, 1H); 7.07 (s, 1H); 3.99 (s, 2H); 2.29 (s, 3H); 2.28-2.23 (m, 1H); 1.18-1.14 (m, rhSYK activity=+++

Example 59

N-{3-[2-(3-aminooxetan-3-yl)-1,3-thiazol-5-yl]-5-methylphenyl}-4-(trifluoromethyl)pyrimidin-2-amine

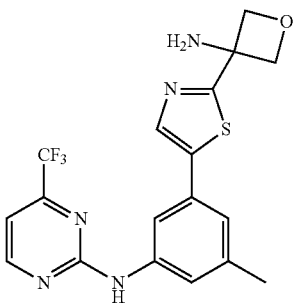 [SMILES: Cc1cc(Nc2nccc(C(F)(F)F)n2)cc(-c2cnc(C3(N)COC3)s2)c1]

Step 1

To a solution of oxetan-3-one (600 mg, 8.33 mmol) and 2-methylpropane-2-sulfinamide (1.01 g, 8.33 mmol) in tetrahydrofuran (14 mL), titanium ethoxide (3.45 mL, 16.65 mmol) was added. The mixture was stirred at 50° C. overnight. The reaction mixture was poured over brine. The suspension was filtered through celite and washed with ethyl acetate. The solution was partitioned between ethyl acetate and brine. The organics were dried (Na$_2$SO$_4$), filtered and concentrated. The residue was purified by column chromatography on silica (0-70% ethyl acetate in hexanes) to afford 2-methyl-N-(oxetan-3-ylidene)propane-2-sulfinamide (692 g, 3.20 mmol, 38% yield) as a clear oil. MS ESI: [M+H]+ m/z 176.1.

Step 2

A solution of lithium diisopropylamine (1.8 M, 4.96 mL, 8.92 mmol) in THF (8 mL) was placed under an Argon atmosphere and was cooled to −78° C. A solution of N-[3-methyl-5-(1,3-thiazol-5-yl)phenyl]-4-(trifluoromethyl)pyrimidin-2-amine (Intermediate 4, 1200 mg, 3.57 mmol) in THF (8 mL) was cooled to −78° C. and added drop wise to the LDA solution. The reaction mixture was stirred 30 minutes at −78° C. The product of Step 1 (625 mg, 3.57 mmol) in THF (8 mL) was added drop wise and the reaction was allowed to warm to room temperature overnight. The mixture was quenched with brine, diluted with ethyl acetate. The organics were washed with saturated NaHCO$_3$, followed by brine, dried (Na$_2$SO$_4$), filtered and concentrated. The residue was purified by column chromatography on silica (20-100% ethyl acetate in hexanes) to afford 2-methyl-N-{3-[5-(3-methyl-5-[[4-(trifluoromethyl)pyrimidin-2-yl]amino}phenyl)-1,3-thiazol-2-yl]oxetan-3-yl]propane-2-sulfinamide (1.10 g, 2.140 mmol, 60.0% yield). MS ESI: [M+H]$^+$ m/z 512.1.

Step 3

To a solution the product of Step 2 (1.01 g, 1.964 mmol) in methanol (9.8 mL), 4M HCl in Dioxane (1.97 mL, 7.86 mmol) was added. The mixture was stirred at room temperature for 15 minutes. The mixture was diluted with ethyl acetate, washed with saturated NaHCO$_3$, followed by brine, dried (Na$_2$SO$_4$), filtered and concentrated. The residue was purified by column chromatography on silica (40-100% ethyl acetate in hexanes) to afford N-{3-[2-(3-aminooxetan-3-yl)-1,3-thiazol-5-yl]-5-methylphenyl}-4-(trifluoromethyl)pyrimidin-2-amine (386.6 mg, 0.954 mmol, 53.5% yield) as a pale yellow solid. MS ESI: [M+H]+ m/z 408.0. $^1$H NMR (500 MHz, DMSO-d$_6$) δ 10.26 (s, 1H), 8.83 (d, J=4.8, 1H), 8.07 (s, 1H), 7.97 (s, 1H), 7.47 (s, 1H), 7.28 (d, J=4.9, 1H), 7.17 (s, 1H), 4.87 (d, J=5.6, 2H), 4.58 (d, J=5.7, 2H), 2.32 (s, 3H).

Example 60

N-{3-[5-(3-methyl-5-{[4-(trifluoromethyl)pyrimidin-2-yl]amino}phenyl)-1,3-thiazol-2-yl]-oxetan-3-yl}methanesulfonamide

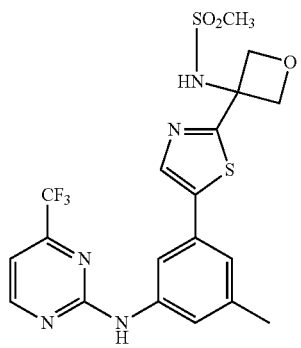 [SMILES: Cc1cc(Nc2nccc(C(F)(F)F)n2)cc(-c2cnc(C3(NS(C)(=O)=O)COC3)s2)c1]

Step 4

To a solution of N-{3-[2-(3-aminooxetan-3-yl)-1,3-thiazol-5-yl]-5-methylphenyl}-4-(trifluoromethyl)pyrimidin-2-amine (200 mg, 0.491 mmol) and Et$_3$N (82 μL, 0.589 mmol) in dichloromethane (3.9 mL), methanesulfonyl chloride (57 μL, 0.736 mmol) was added. The reaction mixture was stirred at room temperature for 95 minutes. The mixture was then diluted with ethyl acetate, washed with saturated NaHCO$_3$, followed by brine, dried (Na$_2$SO$_4$), filtered and concentrated. The residue was purified by column chromatography on silica (10-100% ethyl acetate in hexanes) and lyophilized to afford N-{3-[5-(3-methyl-5-{[4-(trifluoromethyl)-pyrimidin-2-yl]amino}phenyl)-1,3-thiazol-2-yl]oxetan-3-yl}methanesulfonamide (113 mg, 0.233 mmol, 47.4% yield) as a white powder. MS ESI: [M+H]+ m/z 486.0. $^1$H NMR (500 MHz, DMSO-d$_6$) δ 10.28 (s, 1H), 8.83 (m, 2H), 8.11 (s, 1H), 7.99 (s, 1H), 7.50 (s, 1H), 7.29 (m, 1H), 7.21 (s, 1H), 4.91 (dd, J=6.6, 16.1, 4H), 2.98 (s, 3H), 2.33 (s, 3H). rhSYK activity=+++

Example 61

2-methyl-N-{3-[5-(3-methyl-5-{[4-(trifluoromethyl)pyrimidin-2-yl]amino}phenyl)-1,3-thiazol-2-yl]oxetan-3-yl}propane-2-sulfonamide

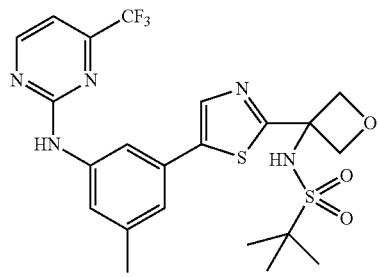 [SMILES: Cc1cc(Nc2nccc(C(F)(F)F)n2)cc(-c2cnc(C3(NS(=O)(=O)C(C)(C)C)COC3)s2)c1]

Step 5

A solution of 2-methyl-N-{3-[5-(3-methyl-5-{([4-(trifluoromethyl)pyrimidin-2-yl]amino}phenyl)-1,3-thiazol-2-yl]oxetan-3-yl}propane-2-sulfinamide (Example 59, Step 2, 75 mg, 0.147 mmol) in dichloromethane (1.5 mL) was cooled to 0° C. m-CPBA (37.8 mg, 0.219 mmol) was added and the resulting mixture was warmed to room temperature. The reaction mixture was diluted with dichloromethane, washed with 2M NaOH (2×), saturated NaHCO$_3$ (1×), brine (1×), dried (Na$_2$SO$_4$), filtered and concentrated. The residue was purified by column chromatography on silica (10-100% ethyl acetate in hexanes) and lyophilized to afford 2-methyl-N-{3-[5-(3-methyl-5-{[4-(trifluoromethyl)pyrimidin-2-yl]amino}phenyl)-1,3-thiazol-2-yl]oxetan-3-yl}propane-2-sulfonamide (45.6 mg, 0.086 mmol, 59.0% yield) as a light yellow solid. MS ESI: [M+H]+ m/z 510.1. $^1$H NMR (500 MHz, dmso) δ 10.29 (s, 1H), 8.83 (d, J=4.9, 1H), 8.29 (s, 1H), 8.09 (s, 1H), 7.95 (s, 1H), 7.53 (s, 1H), 7.28 (d, J=4.9, 1H), 7.18 (s, 1H), 4.90 (dd, 6.6, 33.0, 4H), 2.33 (s, 3H), 1.35 (s, 9H). rhSYK activity=+++

The following examples were prepared in an analogous manner of that described in Examples 59-61.

TABLE 61A

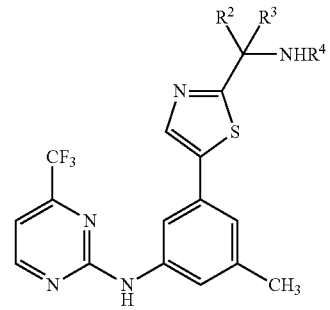

| Example | $R^2/R^3$ | $R^4$ | rhSYK Activity | [M + H]+ Observed | Form(s) |
|---|---|---|---|---|---|
| 61A-1 | cPr/cPr | SO$_2$CH$_3$ | +++ | 524.1 | Free Base |
| 61A-2 | cPr/cPr | SOC(CH$_3$)$_3$ | ++ | 550.1 | Free Base |
| 61A-3 | CH$_3$/CH$_3$ | H | +++ | 394.0 | Free Base |
| 61A-4 | CH$_3$/CH$_3$ | SO$_2$CH$_3$ | +++ | 472.0 | Free Base |

TABLE 61B

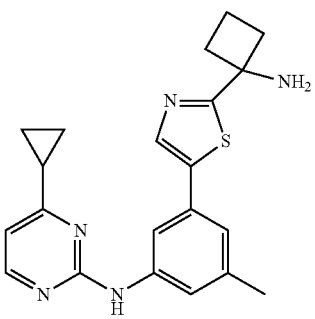 [SMILES: Cc1cc(Nc2nccc(C3CC3)n2)cc(-c2cnc(C3(N)CCC3)s2)c1]

| Example | R¹ | X | R⁴ | rhSYK Activity | [M + H]+ Observed | Form(s) |
|---|---|---|---|---|---|---|
| (R²)ₙ = 4-CF₃ | | | | | | |
| 61B-1 | CH₃ | CH₂ | H | +++ | 406.1 | Free Base |
| 61B-2 | CH₃ | CH₂ | SO₂CH₂CF₃ | +++ | 552.0 | Free Base |
| 61B-3 | CH₃ | CH₂ | SO₂CH₂F | +++ | 502.0 | Free Base |
| 61B-4 | CH₃ | CH₂ | SO₂CH₃ | +++ | 484.0 | Free Base |
| 61B-5 | CH₃ | CH₂ | SO₂CF₃ | +++ | 538.0 | Free Base |
| 61B-6 | CH₃ | O | SO₂CF₃ | +++ | 540.0 | Free Base |
| 61B-7 | CH₃ | O | SO₂CH₂CF₃ | +++ | 554.0 | Free Base |
| 61B-8 | CH₃ | O | SOCHF₂ | +++ | 506.0 | Free Base |
| 61B-9 | H | O | SO₂CH₃ | +++ | 472.0 | Free Base |
| (R²)ₙ = 4-OCH₃, 5-Cl | | | | | | |
| 61B-10 | CH₃ | O | H | +++ | 404.0 | Free Base |

Example 62

N-{3-[2-(1-aminocyclobutyl)-1,3-thiazol-5-yl]-5-methylphenyl}-4-cyclopropylpyrimidin-2-amine hydrochloride

Step 1

A 20 mL microwave vial was charged with 3-methyl-5-(1,3-thiazol-5-yl)aniline (500 mg, 2.63 mmol), cesium carbonate (2.99 g, 9.20 mmol), 2-chloro-4-cyclopropylpyrimidine (Intermediate 29, 406 mg, 2.63 mmol), and dioxane (10.4 mL). The system was purged and flushed with argon (3×) before adding XantPhos (228 mg, 0.394 mmol) and palladium(II) acetate (59 mg, 0.263 mmol). The system was then purged and flushed with argon (3×) before sealing and heating to 100° C. for 2 h. Upon completion the mixture was cooled to room temperature, diluted with ethyl acetate, filtered through celite washing with ethyl acetate, and concentrated under reduced pressure. Purification by column chromatography on silica gel (0-60% ethyl acetate in hexanes) provided 603 mg (1.96 mmol, 74%) of 4-cyclopropyl-N-[3-methyl-5-(1,3-thiazol-5-yl)phenyl]pyrimidin-2-amine as a yellow solid. MS ESI: [M+H]⁺ m/z 309.2.

Step 2

To a solution of the product of Step 1 (250 mg, 0.81 mmol) in tetrahydrofuran (5.0 mL) at −78° C. was added LDA (1.62 mL, 2.0 M, 3.24 mmol). The mixture was stirred for 15 min at −78° C. N-cyclobutylidene-2-methylpropane-2-sulfinamide (169 mg, 0.97 mmol) in tetrahydrofuran (3 mL) was added dropwise at −78° C. and the reaction was allowed to warm to room temperature and stirred over 2 h. The mixture was quenched with aqueous ammonium chloride and the mixture was extracted with ethyl acetate (3×200 mL). The combined organic fractions were washed with brine, dried over sodium sulfate, filtered and the solvent was evaporated under reduced pressure. The residue was purified by column chromatography on silica gel (0-100% ethyl acetate in hexanes) provided 182 mg (0.38 mmol, 47%) of N-[1-(5-{3-[(4-cyclopropylpyrimidin-2-yl)amino]-5-methylphenyl}-1,3-thiazol-2-yl)cyclobutyl]-2-methylpropane-2-sulfinamide. MS ESI: [M+H]⁺ m/z 482.2.

Step 3

To a solution of the product of Step 2 (182 mg, 0.38 mmol) in dioxane (3.8 mL) was added hydrochloric acid 4.0 M in dioxane (0.95 mL, 3.78 mmol) and the mixture was stirred for at room temperature for 2 h. The mixture was concentrated under reduced pressure to provide 170 mg (0.41 mmol, 109%) of N-{3-[2-(1-aminocyclobutyl)-1,3-thiazol-5-yl]-5-methylphenyl}-4-cyclopropylpyrimidin-2-amine hydrochloride. MS ESI: [M+H]⁺ m/z 378.2. ¹H NMR (600 MHz, d6-DMSO) δ 9.54 (s, 1H), 8.95 (s, 2H), 8.25 (d, J=4.8, 1H), 8.16 (s, 1H), 8.10 (s, 1H), 7.40 (s, 1H), 7.11 (s, 1H), 6.83 (d, J=4.8, 1H), 2.66 (m, 2H), 2.57 (m, 2H), 2.28 (s, 3H), 2.14 (m, 1H), 2.03 (m, 2H), 1.10-1.04 (m, 4H). rhSYK activity=+++

The following examples were prepared in an analogous manner of that described in Example 62.

TABLE 62

| Example | R | rhSYK Activity | [M + H]+ Observed | Form(s) |
|---|---|---|---|---|
| 62-1 | H | +++ | 338.2 | Chloride Salt |
| 62-2 | —OCH₃ | +++ | 368.1 | Chloride Salt |

Example 63

N-{3-[5-(3-methyl-5-{[4-(trifluoromethyl)pyrimidin-2-yl]amino}phenyl)-1,3-thiazol-2-yl]oxetan-3-yl}sulfuric diamide

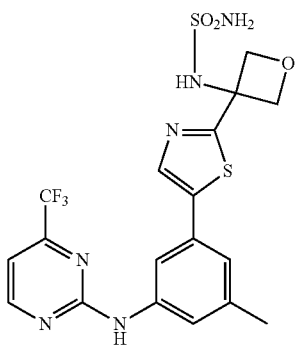 [SMILES: Cc1cc(Nc2nccc(C(F)(F)F)n2)cc(-c2cnc(C3(NS(N)(=O)=O)COC3)s2)c1]

To a solution of N-{3-[2-(3-aminooxetan-3-yl)-1,3-thiazol-5-yl]-5-methylphenyl}-4-(trifluoromethyl)pyrimidin-2-amine (Example 59, 25 mg, 0.061 mmol) in dioxane (600 uL), sulfamide (70 mg, 0.725 mmol) was added. The reaction mixture was stirred at 100° C. The resulting mixture was stirred at 100° C. for 4 days. The mixture was diluted with ethyl acetate, washed with saturated aqueous NaHCO₃, followed by brine, dried (Na₂SO₄), filtered and concentrated. The residue was purified by column chromatography on silica (10-100% ethyl acetate in hexanes) and lyophilized to afford N-{3-[5-(3-methyl-5-{[4-(trifluoromethyl)pyrimidin-2-yl]amino}phenyl)-1,3-thiazol-2-yl]oxetan-3-yl}sulfuric diamide (16.3 mg, 0.034 mmol, 54.6% yield) as a pale yellow solid. MS ESI: [M+H]+ m/z 487.0. $^1$H NMR (500 MHz, DMSO-$d_6$) δ 10.27 (s, 2H), 8.85 (m, 1H), 8.30 (s, 1H), 8.04 (s, 1H), 7.95 (s, 1H), 7.51 (s, 1H), 7.28 (m, 1H), 7.17 (s, 1H), 6.98 (s, 2H), 5.02 (m, 2H), 4.84 (m, 2H), 2.32 (s, 3H). rhSYK activity=+++

Compounds in the following Table(s) were prepared in an analogous manner of that described in Example 63:

TABLE 63

| Example | $R^1$ | $R^2$ | X | rhSYK Activity | [M + H]+ Obs'd | Form(s) |
|---|---|---|---|---|---|---|
| 63-1 | F | CH₃ | oxetane-spiro | +++ | 451.0 | TFA Salt |
| 63-2 | Cl | OCH₃ | oxetane-spiro | +++ | 483.0 | Free Base |
| 63-3 | H | CF₃ | cyclobutane-spiro | +++ | 485.0 | Free Base |
| 63-4 | H | CF₃ | C(cPr)₂ | +++ | 525.1 | Free Base |

Example 64

1-{1-[5-(3-methyl-5-[4-(trifluoromethyl)pyrimidin-2-yl]amino-1-phenyl)-1,3-thiazol-2-yl]cyclobutyl}urea

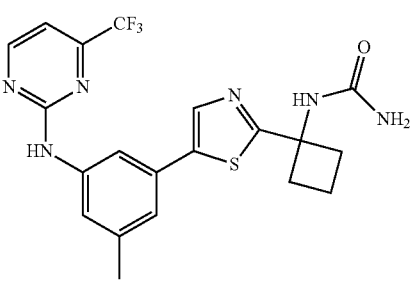 [SMILES: Cc1cc(Nc2nccc(C(F)(F)F)n2)cc(-c2cnc(C3(NC(N)=O)CCC3)s2)c1]

To a solution of N-{3-[2-(1-aminocyclobutyl)-1,3-thiazol-5-yl]-5-methylphenyl}-4-(trifluoromethyl)pyrimidin-2-amine (Example 61E-1, 50 mg, 0.123 mmol) and acetic acid (7 μL, 0.123 mmol) in THF/water (1.6:1, 2.1 mL), potassium cyanate (10 mg, 0.123 mmol) was added. The reaction mixture was stirred overnight at room temperature and then concentrated. The residue was purified by column chromatography on silica (50-100% ethyl acetate in hexanes, 0-20% methanol in dichloromethane) and lyophilized to afford 1-{1-[5-(3-methyl-5-{[4-(trifluoromethyl)pyrimidin-2-yl]amino}phenyl)-1,3-thiazol-2-yl]cyclobutyl}urea (31.3 mg, 0.068 mmol, 54.9%) as a white powder. MS ESI: [M+H]⁺ m/z 449.1. $^1$H NMR (500 MHz, DMSO-$d_6$ δ 10.23 (s, 1H), 8.82 (d, J=4.9, 1H), 7.93 (s, 1H), 7.90 (s, 1H), 7.47 (s, 1H), 7.27 (d, J=4.9, 1H), 7.15-7.00 (m, 2H), 5.58 (s, 2H), 2.63-2.51 (m, 2H), 2.32 (m, 5H), 1.96 (m, 2H). rhSYK activity=+++

The following examples were prepared in an analogous manner of that described in Example 64.

TABLE 64

| Example | R¹ | R² | R³ | X | rhSYK Activity | [M + H]+ Observed | Form(s) |
|---|---|---|---|---|---|---|---|
| 64-1 | CF₃ | H | CH₃ | O | +++ | 451.0 | Free Base |
| 64-2 | cPr | H | CH₃ | CH₂ | +++ | 421.2 | Free Base |
| 64-3 | H | H | CH₃ | CH₂ | +++ | 381.2 | Free Base |
| 64-4 | OCH₃ | H | CH₃ | CH₂ | +++ | 411.2 | Free Base |
| 64-5 | —O-4-piperidyl | H | CH₃ | CH₂ | +++ | 480.3 | Free Base |
| 64-6 | cPr | F | CH₃ | CH₂ | +++ | 438.8 | TFA Salt |
| 64-7 | cPr | F | F | CH₂ | +++ | 443.2 | Free Base |
| 64-8 | OCH₃ | Cl | CH₃ | CH₂ | +++ | 445.1 | Free Base |
| 64-9 | CF₃ | H | CH₃ | —CH₂C(O)NHCH₂— | +++ | 506 | Free Base |

| Example | Structure | rhSYK Activity | [M + H]+ Obs'd | Form(s) |
|---|---|---|---|---|
| 64-10 | 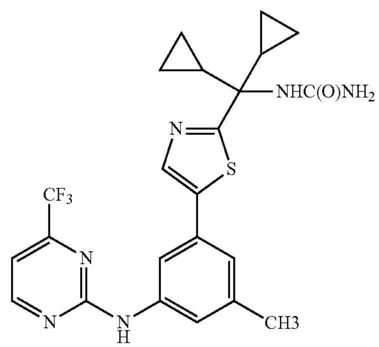 | +++ | 489.1 | Free Base |

Example 65

N-{dicyclopropyl[5-(3-methyl-5-{[4-(trifluoromethyl)pyrimidin-2-yl]amino}phenyl)-1,3-thiazol-2-yl]methyl}dicarbonimidic diamide

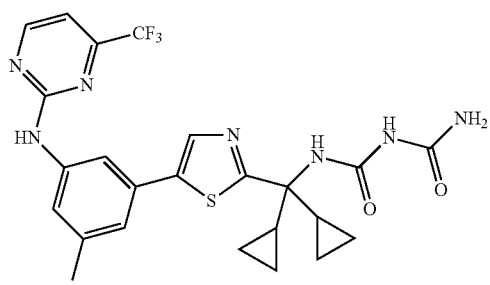 [SMILES: Cc1cc(Nc2nccc(C(F)(F)F)n2)cc(-c2cnc(C(NC(=O)NC(N)=O)(C3CC3)C3CC3)s2)c1]

Step 1

To a solution of N-{3-[2-(amino)(dicyclopropyl)methyl)-1,3-thiazol-5-yl]-5-methylphenyl}-4-(trifluoromethyl)pyrimidin-2-amine (100 mg, 0.224 mmol) and acetic acid (0.013 mL, 0.224 mmol) in THF/water (1.6:1, 2.6 mL), potassium cyanate (18 mg, 0.224 mmol) was added. The reaction mixture was stirred overnight at room temperature. The mixture was then diluted with ethyl acetate, washed with saturated NaHCO₃, followed by brine, dried (Na₂SO₄), filtered and concentrated. The residue was purified by column chromatography on silica (50-100% ethyl acetate in hexanes) and lyophilized to afford N-{dicyclopropyl[5-(3-methyl-5-{[4-(trifluoromethyl)pyrimidin-2-yl]amino}phenyl)-1,3-thiazol-2-yl]methyl}-dicarbonimidic diamide (13.8 mg, 0.026 mmol, 11.6%) as a white powder. MS ESI: [M+H]⁺ m/z 532.1. ¹H NMR (500 MHz, DMSO-d₆) δ 10.24 (s, 1H), 8.83 (d, J=4.9, 1H), 8.02 (s, 1H), 7.89 (s, 1H), 7.43 (s, 1H), 7.28 (d, J=4.9, 1H), 7.13 (s, 1H), 6.25 (s, 1H), 5.53 (s, 2H), 2.31 (s, 3H), 1.66-1.45 (m, 2H), 0.66-0.55 (m, 2H), 0.52-0.41 (m, 2H), 0.41-0.31 (m, 4H). rhSYK activity=+++

The following example was prepared in an analogous manner of that described in Example 65.

TABLE 65

[structure shown: pyrimidine-NH-phenyl(CH3)-thiazole-X-(oxetane or cyclobutane with NHC(O)NHC(O)NH2)]

| Example | R¹ | R² | X | rhSYK Activity | [M+H]+ Observed | Form(s) |
|---|---|---|---|---|---|---|
| 65-1 | CF₃ | H | O | +++ | 494.1 | Free Base |
| 65-2 | —OCH₃ | H | CH₂ | +++ | 454.2 | Free Base |
| 65-3 | H | H | CH₂ | +++ | 424.2 | Free Base |
| 65-4 | cPr | H | CH₂ | +++ | 464.2 | Free Base |
| 65-5 | —O-4-piperidyl | H | CH₂ | +++ | 523.3 | Free Base |
| 65-6 | CF₃ | H | —CH₂C(O)NHCH₂— | +++ | 549.2 | Free Base |
| 65-7 | CF₃ | Cl | —CH₂C(O)NHCH₂— | +++ | 583.1 | Free Base |
| 65-8 | OCH₃ | Cl | CH₂ | +++ | 488.1 | Free Base |

Example 66

N-{1-[5-(3-methyl-5-{[4-(trifluoromethyl)pyrimidin-2-yl]amino}phenyl)-1,3-thiazol-2-yl]cyclobutyl}acetamide

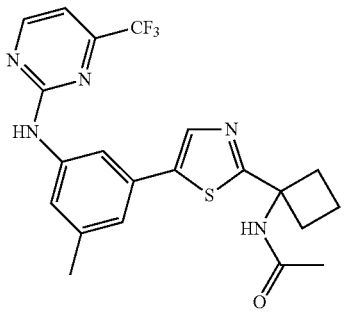 [SMILES: CC(=O)NC1(c2ncc(-c3cc(C)cc(Nc4nccc(C(F)(F)F)n4)c3)s2)CCC1]

To a solution of N-{3-[2-(1-aminocyclobutyl)-1,3-thiazol-5-yl]-5-methylphenyl}-4-(trifluoromethyl)pyrimidin-2-amine (Example 61B-1, 75 mg, 0.185 mmol) and Et₃N (25.8 µL, 0.185 mmol) in THF (1000 µL), acetyl chloride (13.15 µL, 0.185 mmol) was added. The mixture was stirred at room temperature for 70 minutes. Additional acetyl chloride (6 µL) was added to drive the reaction to completion. The mixture was stirred for 10 additional minutes, then diluted with ethyl acetate, washed with saturated NaHCO₃, followed by brine, dried (Na₂SO₄), filtered and concentrated to afford N-{1-[5-(3-methyl-5-{[4-(trifluoromethyl)-pyrimidin-2-yl]amino}phenyl)-1,3-thiazol-2-yl]cyclobutyl}acetamide (80.8 mg, 0.171 mmol, 92%). MS ESI: [M+H]⁺ m/z 480.0. ¹H NMR (500 MHz, DMSO-d₆) δ 10.25 (s, 1H), 8.93 (s, 1H), 8.83 (d, J=4.9 Hz, 1H), 8.00 (s, 1H), 7.94 (s, 1H), 7.42 (s, 1H), 7.28 (d, J=4.9 Hz, 1H), 7.14 (s, 1H), 3.32-2.60 (m, 2H), 2.43-2.41 (m, 2H), 2.31 (s, 3H), 1.99-1.95 (m, 2H), 1.88 (s, 3H). rhSYK activity=+++

Compounds in the following Table(s) were prepared in an analogous matter of that described in Example 66:

| Example | Structure | hSYK Activity | [M+H]+ Obs'd Form(s) |
|---|---|---|---|
| 66-1 | 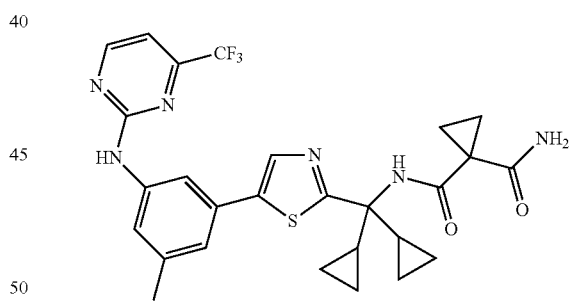 | +++ | 450.0 |

(added as above table)

Example 67

N-{dicyclopropyl[5-(3-methyl-5-{[4-(trifluoromethyl)pyrimidin-2-yl]amino}phenyl)-1,3-thiazol-2-yl]methyl}cyclopropane-1,1-dicarboxamide A flask was charged with 1-carbamoylcyclopropanecarboxylic acid (16.23 mg, 0.126 mmol), N-(3-{2-[amino(dicyclopropyl)methyl]-1,3-thiazol-5-yl}-5-methylphenyl)-4-(trifluoromethyl)-pyrimidin-2-amine (56 mg, 0.126 mmol), BOP (83 mg, 0.189 mmol), DIPEA (43.9 µL, 0.251 mmol) and DMF (10 mL). The reaction was stirred at room temperature for 90 minutes. The mixture was diluted with ethyl acetate, washed with saturated NaHCO₃, followed by brine, dried (Na₂SO₄), filtered, and concentrated to afford N-{dicyclopropyl[5-(3-methyl-5-{[4-(trifluoromethyl)pyrimidin-2-yl]amino}phenyl)-1,3-thiazol-2-yl]methyl}cyclopropane-1,1-dicarboxamide (67.6 mg, 0.121 mmol, 97% yield) as an off white solid. MS ESI: [M+H]⁺ m/z 557.1. ¹H NMR (500 MHz, DMSO-d₆) δ 10.25 (s, 1H), 9.81 (s, 1H), 8.83 (d, 1H), 8.01 (s, 1H), 7.91 (s, 1H), 7.44 (s, 1H), 7.29 (m, 3H), 7.15 (s, 1H), 2.31

(s, 3H), 1.67-1.46 (m, 2H), 1.28-1.20 (m, 4H), 0.7-0.65 (m, 2H), 0.56-0.54 (m, 2H), 0.44-0.38 (m, 4H). rhSYK activity=+++

Compounds in the following Table(s) were prepared in a manner analogous of that described in Example 67:

| Example | Structure | rhSYK Activity | [M + H]+ Obs'd | Form(s) |
|---|---|---|---|---|
| 67-1 | 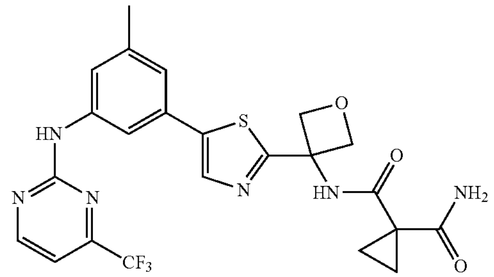 [SMILES: Cc1cc(Nc2nccc(C(F)(F)F)n2)cc(-c2cnc(C3(NC(=O)C4(C(N)=O)CC4)COC3)s2)c1] | +++. | 519.1 | Free Base |

Example 68

2-({3-methyl-5-[2-(1,1,1-trifluoro-2-hydroxypropan-2-yl)-1,3-thiazol-5-yl]phenyl}amino)-pyrimidine-4-carboxylic acid

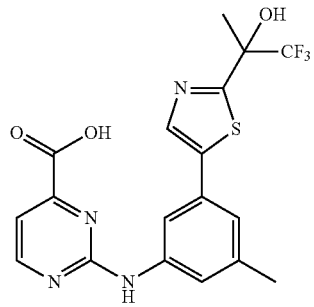 [SMILES: Cc1cc(Nc2nccc(C(=O)O)n2)cc(-c2cnc(C(C)(O)C(F)(F)F)s2)c1]

To 2-chloropyrimidine-4-carboxylic acid (175 mg, 1.104 mmol) in dioxane (2.201 mL) was added 2-[5-(3-amino-5-methylphenyl)-1,3-thiazol-2-yl]-1,1,1-trifluoropropan-2-ol (INTERMEDIATE 17, (334 mg, 1.104 mmol) and acetic acid (69.5 µL, 1.214 mmol). The reaction was heated to 100° C. overnight and was complete by LCMS analysis. The reaction was cooled to room temperature and the solvent was removed under reduced pressure. Remaining acetic acid was azeotroped with toluene (2×5 mL) to yield 2-({3-methyl-5-[2-(1,1,1-trifluoro-2-hydroxypropan-2-yl)-1,3-thiazol-5-yl]phenyl}amino)pyrimidine-4-carboxylic acid as a tan powder. MS ESI: [M+H]+ m/z 425.1. $^1$H NMR (500 MHz, dmso) δ 13.79-13.63 (m, 1H), 10.05 (s, 1H), 8.73 (d, J=5.0, 1H), 8.22-8.14 (m, 1H), 8.10 (s, 1H), 7.65 (s, 1H), 7.56 (s, 1H), 7.32 (d, J=5.0, 1H), 7.12 (s, 1H), 2.31 (s, 3H), 1.76 (s, 3H). rhSYK activity=+

Compounds in the following Table(s) were prepared in a manner analogous of that described in Example 68:

| Example | R¹ | R² | rhSYK Activity | [M + H]+ Obs'd | Form(s) |
|---|---|---|---|---|---|
| 68-1 | 5-CO₂H | CH₃ | ++ | 383.1 | Free Base |
| 68-2 | 4-CF₃ | H | +++ | 393.0 | Free Base |

Example 69

[2-({3-methyl-5-[2-(1,1,1-trifluoro-2-hydroxypropan-2-yl)-1,3-thiazol-5-yl]phenyl}amino)-pyrimidin-4-yl](piperazin-1-yl)methanone

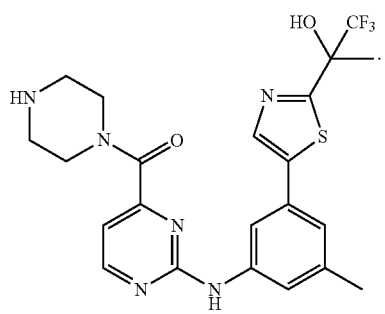 [SMILES: Cc1cc(Nc2nccc(C(=O)N3CCNCC3)n2)cc(-c2cnc(C(C)(O)C(F)(F)F)s2)c1]

To 2-({3-methyl-5-[2-(1,1,1-trifluoro-2-hydroxypropan-2-yl)-1,3-thiazol-5-yl]phenyl}amino)-pyrimidine-4-carboxylic acid (Example 68, 68.9 mg, 0.162 mmol) in a scintillation vial was added DMF (812 μL), tert-butyl piperazine-1-carboxylate (33.4 mg, 0.179 mmol), DIPEA (85 μL, 0.487 mmol) and BOP (108 mg, 0.244 mmol). The reaction was stirred at room temperature for 1 hour before being diluted with water and dichloromethane. The organic was dried over sodium sulfate, filtered and concentrated to dryness. The resultant residue was purified by normal phase chromatography (10% MeOH in DCM: hexanes, 10-100%, linear gradient). Boc deprotection was carried out on the isolated material with 1:1 TFA:dichloromethane (1 mL) at room temperature. Upon completion the reaction was concentrated to dryness and was directly purified by reverse phase chromatography (10-80% MeCN in water, linear gradient) to yield [2-({3-methyl-5-[2-(1,1,1-trifluoro-2-hydroxypropan-2-yl)-1,3-thiazol-5-yl]phenyl}amino)-pyrimidin-4-yl](piperazin-1-yl)methanone as a TEA salt. MS ESI: [M+H]+ m/z 493.1. $^1$H NMR (500 MHz, DMSO-d$_6$) δ 9.91 (s, 1H), 8.87 (s, 2H), 8.67 (d, J=4.8, 1H), 8.08 (s, 1H), 7.83 (s, 1H), 7.57 (s, 1H), 7.16 (s, 1H), 7.00 (s, 1H), 3.82 (s, 2H), 3.67 (s, 2H), 3.21 (s, 2H), 3.08 (s, 2H), 233 (s, 3H), 1.76 (s, 3H). rhSYK activity=+++

Compounds in the following Table(s) were prepared in a manner analogous of that described in Example 69:

| Example | Structure | rhSYK Activity | [M+H]+ Obs'd | Form(s) |
|---|---|---|---|---|
| 69-1 | ![structure] | ++ | 494.1 | TFA Salt |

Example 70

2-[5-(3-nitro-5-{[4-(trifluoromethyl)pyrimidin-2-yl]amino}phenyl)-1,3-thiazol-2-yl]propane-2-sulfonamide

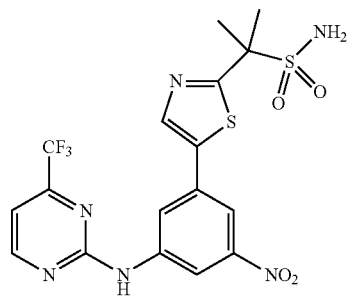

Step 1

2-Bromothiazole (12.00 g, 73.2 mmol) was taken up in THF (150 mL) and cooled to −20° C. Isopropylmagnesium chloride (2.0 M in THF, 38.4 mL, 77 mmol) was added dropwise. After stirring for 1 h (−10° C. to 0° C.), the reaction was cooled to back −20° C., and acetone (5.10 g, 88 mmol) was added dropwise. The reaction was stirred for 30 min at −20° C. then warmed to room temperature. After 2 h at room temperature, the reaction was quenched with saturated NH$_4$Cl and extracted with ethyl acetate (2×). The combined organic layers were washed with brine, dried (MgSO$_4$), and evaporated. The residue was purified by flash chromatography (0-50% ethyl acetate in hexanes) to afford 8.97 g (86%) of 2-(1,3-thiazol-2-yl)propan-2-ol as a pale yellow low-melting solid. MS ESI: [M+H]+ m/z 144.0.

Step 2

The product of Step 1 (8.97 g, 62.6 mmol) was dissolved in CHCl$_3$ (125 mL), and NaHCO$_3$ (5.79 g, 68.9 mmol) was added. Bromine (15.01 g, 94 mmol) was then added dropwise. After stirring for 2 h at room temperature, LC/MS showed a mixture of starting material and product (50% conversion). Additional NaHCO$_3$ (2.89 g, 34.5 mmol), bromine (7.51 g, 47.0 mmol), and methanol (15 mL) were added, and the reaction was stirred for another 2 h at room temperature. The reaction was diluted with 10% Na$_2$S$_2$O$_3$, neutralized with saturated NaHCO$_3$, and extracted with dichloromethane (2×). The combined organic layers were dried (MgSO$_4$), filtered and evaporated. Flash chromatography (0-15% ethyl acetate in toluene) afforded 9.38 g (67%) of 2-(5-bromo-1,3-thiazol-2-yl)propan-2-ol as a white solid. ESI: [M+H]+ m/z 221.9/223.9.

Step 3

The product of Step 2 (9.00 g, 40.5 mmol) was taken up in 1,2-DCE (400 mL) before adding methyl 3-mercaptopropionate (9.74 g, 81 mmol) and zinc iodide (38.8 g, 122 mmol). The reaction was stirred at reflux for 5 h. The suspension was diluted with water and extracted with dichloromethane (2×). The combined organic layers were washed with brine, dried (Na$_2$SO$_4$), filtered and evaporated. Flash chromatography (0-15% ethyl acetate in hexanes) provided methyl 3-{[2-(5-bromo-1,3-thiazol-2-yl)propan-2-yl]sulfanyl}propanoate (12.58 g, 96%) as a colorless oil. ESI: [M+H]+ m/z 323.9/326.0.

Step 4

The product of Step 3 (12.50 g, 38.5 mmol) was taken up in dichloromethane (250 mL)/methanol (125 mL), and magnesium monoperoxyphthalate hexahydrate (35.8 g, 57.8 mmol) was added. The reaction was stirred at room temperature for 2 h. The white slurry was diluted with 10% Na$_2$S$_2$O$_3$ and water and extracted with CH$_2$Cl$_2$ (2×). The combined organic layers were washed with saturated NaHCO$_3$, dried (MgSO$_4$), filtered and evaporated. Flash chromatography (0-40% ethyl acetate in hexanes) afforded 13.12 g (96%) of methyl 3-{[2-(5-bromo-1,3-thiazol-2-yl)propan-2-yl]sulfonyl}propanoate as a white solid. ESI: [M+H]+ m/z 355.9/357.9.

Step 5

The product of Step 4 (2.50 g, 7.02 mmol) was taken up in THF (80 mL) at room temperature, and NaOMe (25% in MeOH, 1.52 g, 7.02 mmol) was added. After 30 min at room temperature, the suspension was evaporated to dryness, pro-

361 viding a white solid. The solid was taken up in water (50 mL), and a solution of NaOAc (3.17 g, 38.6 mmol) and hydroxylamine-O-sulfonic acid (3.97 g, 35.1 mmol) in water (25 mL) was added while cooling the reaction (0° C.). The reaction was vigorously stirred at room temperature overnight (a white solid precipitated after 15-30 min). The reaction was extracted with ethyl acetate (2×). The combined organic layers were washed with brine, dried (MgSO₄), filtered and evaporated. The resulting white residue was triturated with CH₂Cl₂ and filtered to provide 2-(5-bromo-1,3-thiazol-2-yl)propane-2-sulfonamide (1.58 g, 79%) as a white powder. ESI: [M+H]+ m/z 284.9/286.9.

Step 6

The product of Step 5 (174 mg, 0.61 mmol), N-[3-nitro-5-(4,4,5,5-tetramethyl-1,3,2-dioxaborolan-2-yl)phenyl]-4-(trifluoromethyl)pyrimidin-2-amine (INTERMEDIATE 12, 250 mg, 0.61 mmol), and PdCl₂(dppf).CH₂Cl₂ (44.6 mg, 0.061 mmol) were combined in a flask, sealed, and purged with nitrogen (2×). Dioxane (3.6 mL) and 2 M Na₂CO₃ (0.91 mL, 1.83 mmol) were added, and the reaction was purged again with nitrogen (2×). The mixture was stirred in an oil bath at 100° C. for 4 h. The dark brown reaction was diluted with water and extracted with ethyl acetate (2×). The combined organic layers were washed with brine, dried (MgSO₄), filtered and evaporated. Flash chromatography (dry load, 20-100% ethyl acetate in hexanes) afforded 220 mg (74%) of 2-[5-(3-nitro-5-{[4-(trifluoromethyl)pyrimidin-2-yl]amino}phenyl)-1,3-thiazol-2-yl]propane-2-sulfonamide as a yellow solid. ESI: [M+H]⁺ m/z 489.0. ¹H NMR (500 MHz, DMSO-d₆) δ 10.80 (s, 1H), 8.94 (d, J=4.9, 1H), 8.72 (s, 1H), 8.48 (s, 1H), 8.33 (s, 1H), 8.14 (s, 1H), 7.43 (d, J=4.9, 1H), 7.10 (s, 2H), 1.81 (s, 6H). rhSYK activity=++

Compounds in the following Table(s) were prepared in an analogous manner of that described in Example 70:

TABLE 70

| Example | R¹ | rhSYK Activity | [M + H]+ Obs'd | Form(s) |
|---|---|---|---|---|
| 70-1 | t-Bu | +++ | 446.1 | TFA Salt |
| 70-2 | iPr | +++ | 432.1 | TFA Salt |

Example 71

2-[5-(3-amino-5-{[4-(trifluoromethyl)pyrimidin-2-yl]amino}phenyl)-1,3-thiazol-2-yl]propane-2-sulfonamide

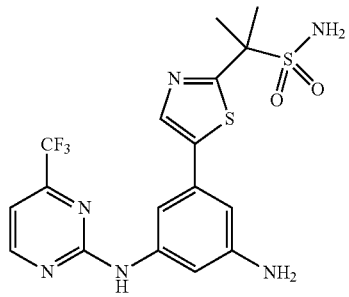 [SMILES: CC(C)(c1ncc(-c2cc(Nc3nccc(C(F)(F)F)n3)cc([N+](=O)[O-])c2)s1)S(N)(=O)=O]

To a suspension of 2-[5-(3-nitro-5-{[4-(trifluoromethyl)pyrimidin-2-yl]amino}phenyl)-1,3-thiazol-2-yl]propane-2-sulfonamide (Example 70, 200 mg, 0.409 mmol) in MeOH (10 mL) was added 3% Pt/0.6% V/C (53 mg, 0.008 mmol). The reaction was sealed, purged with hydrogen, and stirred under a hydrogen balloon at room temperature overnight. A small amount of starting material remained, so additional catalyst (50 mg) was added, and a fresh hydrogen balloon was placed on the reaction. After another 24 h at room temperature, the starting material had been consumed. The reaction was diluted with MeOH, gently heated to dissolve any precipitated product, and filtered through Celite. The filtrate was evaporated, and flash chromatography of the residue (dry load, 20-100% ethyl acetate in hexanes) afforded 2-[5-(3-amino-5-{[4-(trifluoromethyl)pyrimidin-2-yl]amino}phenyl)-1,3-thiazol-2-yl]propane-2-sulfonamide (116 mg, 62%) as an off-white solid. MS ESI: [M+H]+ m/z 459.0. ¹H NMR (500 MHz, DMSO-d₆) δ 10.05 (s, 1H), 8.78 (d, J=4.9, 1H), 7.87 (s, 1H), 7.37 (s, 1H), 7.22 (d, J=4.9, 1H), 7.03 (s, 2H), 6.89 (s, 1H), 6.53 (t, J=1.7, 1H), 5.28 (s, 2H), 1.78 (s, 6H). rhSYK activity=+++

Example 72

N-(3-[2-(2-sulfamoylpropan-2-yl)-1,3-thiazol-5-yl]-5-{[4-(trifluoromethyl)pyrimidin-2-yl]amino}phenyl)acetamide

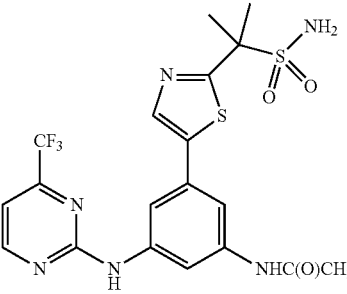

2-[5-(3-Amino-5-{[4-(trifluoromethyl)pyrimidin-2-yl]amino}phenyl)-1,3-thiazol-2-yl]propane-2-sulfonamide (Example 71, 90 mg, 0.196 mmol) was suspended in CH₂Cl₂ (5 mL) with triethylamine (55 μL, 0.393 mmol), and acetyl chloride (28 μL, 0.393 mmol) was added. After stirring for 1 h at room temperature, additional acetyl chloride (28 μL, 0.393 mmol) and triethylamine (55 μL, 0.393 mmol) were added. After another 1 h at room temperature, the suspension was diluted with MeOH, silica was added, and the mixture was evaporated to dryness. Flash chromatography (dry load, 40-100% ethyl acetate in hexanes) afforded N-(3-[2-(2-sulfamoylpropan-2-yl]-1,3-thiazol-5-yl]-5-{[4-(trifluoromethyl)pyrimidin-2-yl]amino}phenyl)acetamide (34 mg, 35%) as a white solid. MS ESI: [M+H]+ m/z 501.0. $^1$H NMR (500 MHz, DMSO-$d_6$) δ 10.35 (s, 1H), 10.07 (s, 1H), 8.82 (d, J=4.9, 1H), 7.94 (s, 1H), 7.91 (s, 1H), 7.83 (s, 1H), 7.61 (s, 1H), 7.29 (d, J=4.9, 1H), 7.05 (s, 2H), 2.05 (s, 3H), 1.79 (s, 6H). rhSYK activity=+++

Example 73

N-(3-methyl-5-{2-[2-(methylsulfonyl)propan-2-yl]-1,3-thiazol-5-yl}phenyl)-4-(trifluoromethyl)pyrimidin-2-amine

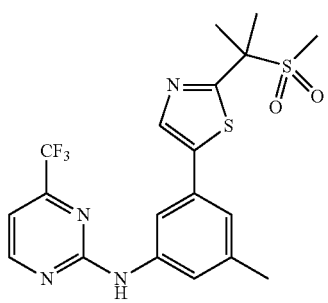 [SMILES: Cc1cc(Nc2nccc(C(F)(F)F)n2)cc(-c2cnc(C(C)(C)S(C)(=O)=O)s2)c1]

Step 1

Methyl 3-{[2-(5-promo-1,3-thiazol-2-yl)propan-2-yl]sulfonyl}propanoate (Example 70, Step 4, 500 mg, 1.403 mmol) was taken up in THF (15 mL) at room temperature, and NaOMe (25% in MeOH, 303 mg, 1.403 mmol) was added. After 30 min at room temperature, the suspension was evaporated to dryness, providing a white solid. The solid was taken back up in DMSO (5 mL), and methyl iodide (398 mg, 2.81 mmol) was added. After stirring for 2 h at room temperature, the reaction was diluted with water and extracted with ethyl acetate (2×). The combined organic layers were washed with brine, dried (MgSO$_4$), filtered and evaporated. Flash chromatography (0-40% ethyl acetate in hexanes) afforded of 5-bromo-2-[2-(methylsulfonyl)propan-2-yl]-1,3-thiazole (372 mg, 93%) as a colorless solid. MS ESI: [M+H]+ m/z 283.9/285.9.

Step 2

The product of Step 1 (112 mg, 0.40 mmol), N-[3-methyl-5-(4,4,5,5-tetramethyl-1,3,2-dioxaborolan-2-yl)phenyl]-4-(trifluoromethyl)pyrimidin-2-amine (Intermediate 3, 150 mg, 0.40 mmol), and PdCl$_2$(dppf)·CH$_2$Cl$_2$ (29 mg, 0.040 mmol) were combined in a flask, sealed, and purged with nitrogen (2×). Dioxane (2.4 mL) and 2 M Na$_2$CO$_3$ (0.59 mL, 1.19 mmol) were added, and the reaction was purged again with nitrogen (2×). The mixture was stirred in an oil bath at 100° C. overnight. The dark brown reaction was diluted with water and extracted with ethyl acetate (2×). The combined organic layers were washed with brine, dried (MgSO$_4$), filtered and evaporated. Flash chromatography (0-50% ethyl acetate in hexanes) afforded N-(3-methyl-5-{2-[2-(methylsulfonyl)propan-2-yl]-1,3-thiazol-5-yl}phenyl)-4-(trifluoromethyl)pyrimidin-2-amine (140 mg, 78%) as a colorless solid. MS ESI: [M+H]+ m/z 457.0. $^1$H NMR (500 MHz, DMSO-$d_6$) δ 10.29 (s, 1H), 8.84 (d, J=4.9, 1H), 8.16 (s, 1H), 8.03 (s, 1H), 7.49 (s, 1H), 7.29 (d, J=4.9, 1H), 7.22 (s, 1H), 2.96 (s, 3H), 2.32 (s, 3H), 1.83 (s, 6H). rhSYK activity=+++

Example 74

N-({1-[5-(3-methyl-5-{[4-(trifluoromethyl)pyrimidin-2-yl]amino}phenyl)-1,3-thiazol-2-yl]-cyclobutyl}sulfonyl)acetamide

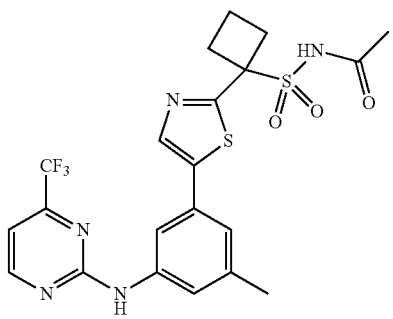 [SMILES: CC(=O)NS(=O)(=O)C1(c2ncc(-c3cc(C)cc(Nc4nccc(C(F)(F)F)n4)c3)s2)CCC1]

Step 1

1-(5-Bromo-1,3-thiazol-2-yl)cyclobutanesulfonamide (110 mg, 0.370 mmol, prepared according to Example 70, Steps 1-5) was taken up in pyridine (5 mL), and acetic anhydride (524 μL, 5.55 mmol) was added. The reaction was stirred at 70° C. overnight. The reaction was concentrated to dryness, diluted with water, acidified with 2 N HCl, and extracted with CH$_2$Cl$_2$ (2×). The combined organic layers were washed with brine, dried (Na$_2$SO$_4$), filtered and evaporated to give N-{[1-(5-bromo-1,3-thiazol-2-yl)cyclobutyl]sulfonyl}acetamide (120 mg, 96%) as a beige solid. MS ESI: [M+H]+ 338.9/340.9.

Step 2

The product of Step 1 (109 mg, 0.322 mmol), N-[3-methyl-5-(4,4,5,5-tetramethyl-1,3,2-dioxaborolan-2-yl)phenyl]-4-(trifluoromethyl)pyrimidin-2-amine (intermediate 3, 122 mg, 0.322 mmol), and PdCl$_2$(dppf)·CH$_2$Cl$_2$ (24 mg, 0.032 mmol) were combined in a vial, sealed, and purged with nitrogen (2×). Dioxane (2.0 mL) and 2 M Na$_2$CO$_3$ (0.48 mL, 0.97 mmol) were added, and the reaction was purged again with nitrogen (2×). The mixture was stirred in an oil bath at 100° C. overnight. The dark brown reaction was diluted with water and extracted with CH$_2$Cl$_2$ (2×). The combined organic layers were dried (Na$_2$SO$_4$), filtered and evaporated. Flash chromatography (dry load, 25-100% ethyl acetate in hexanes, then 0-10% methanol in ethyl acetate) provided an orange-brown residue. The residue was triturated with CH$_2$Cl$_2$, filtered, and dried to afford N-({1-[5-(3-methyl-5-{[4-(trifluoromethyl)pyrimidin-2-yl]amino}-phenyl)-1,3-thiazol-2-yl]cyclobutyl}sulfonyl)acetamide (85 mg, 52%) as a colorless solid. MS ESI: [M+H]+ m/z 512.0. $^1$H NMR (600 MHz, DMSO-$d_6$) δ 11.38 (s, 1H), 10.27 (s, 1H), 8.81 (d, J=4.9, 1H), 8.13 (s, 1H), 8.00 (s, 1H), 7.49 (s, 1H), 7.27 (d, J=4.9, 1H), 7.21 (s, 1H), 3.23-3.06 (m, 2H), 2.76-2.61 (m, 2H), 2.31 (s, 3H), 2.10-1.89 (m, 2H), 1.84 (s, 3H). rhSYK activity=+++

The following examples were prepared in a manner analogous to that described in Examples 72, 73 and 74.

TABLE 74A

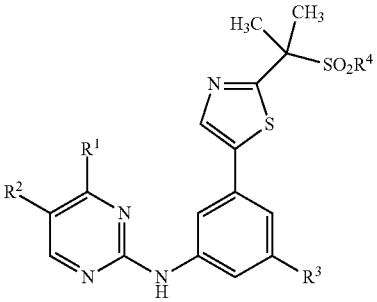

| Example | R¹ | R² | R³ | R⁴ | rhSYK Activity | [M+H]+ Observed | Form(s) |
|---|---|---|---|---|---|---|---|
| 74A-1 | CF₃ | H | CH₃ | NH₂ | +++ | 458.0 | Free Base |
| 74A-2 | CF₃ | H | H | CH₃ | +++ | 443.0 | Free Base |
| 74A-3 | CF₃ | H | H | NH₂ | +++ | 444.0 | Free Base |
| 74A-4 | —OCH₃ | H | CH₃ | NH₂ | +++ | 420.1 | Free Base |
| 74A-5 | CH₃ | F | CH₃ | NH₂ | +++ | 422.1 | Free Base |
| 74A-6 | cPr | F | CH₃ | NH₂ | +++ | 448.0 | Free Base |
| 74A-7 | OCH₃ | Cl | CH₃ | NH₂ | +++ | 454.0 | Free Base |
| 74A-8 | OCH₃ | F | CH₃ | NH₂ | +++ | 438.0 | Free Base |
| 74A-9 | CH₃ | Cl | CH₃ | NH₂ | +++ | 438.0 | Free Base |
| 74A-10 | CF₃ | H | F | NH₂ | ++ | 462.0 | Free Base |
| 74A-11 | CF₃ | H | CHF₂ | NH₂ | +++ | 494.0 | Free Base |
| 74A-12 | CH₃ | H | CH₃ | NH₂ | +++ | 404.0 | Free Base |
| 74A-13 | cPr | H | CH₃ | NH₂ | +++ | 430.1 | Free Base |
| 74A-14 | CF₃ | H | CH₃ | NHCH₂CO₂CH₃ | +++ | 530.1 | Free Base |
| 74A-15 | CF₃ | H | CH₃ | NHCH₂CO₂H | +++ | 516.0 | Free Base |
| 74A-16 | CF₃ | H | CH₃ | NHCH₂NH₂ | +++ | 515.0 | Free Base |

TABLE 74B

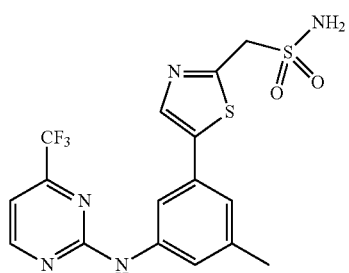

| Example | R³ | R⁴ | rhSYK Activity | [M+H]+ Obs'd | Form(s) |
|---|---|---|---|---|---|
| 74B-1 | CH₃ | NH₂ | +++ | 470.0 | Free Base |
| 74B-2 | CH₃ | CH₃ | +++ | 469.0 | Free Base |
| 74B-3 | NO₂ | CH₃ | + | 500.0 | Free Base |
| 74B-4 | NH₂ | CH₃ | +++ | 470.0 | Free Base |
| 74B-5 | —NHC(O)CH₃ | CH₃ | +++ | 512.0 | Free Base |

Example 75

1-[5-(3-methyl-5-{[4-(trifluoromethyl)pyrimidin-2-yl]amino}phenyl)-1,3-thiazol-2-yl]methanesulfonamide Step 1

5-Bromo-2-methylthiazole (2.00 g, 11.2 mmol) was combined with N-bromosuccinimide (2.20 g, 12.4 mmol) and benzoyl peroxide (0.136 g, 0.56 mmol) in CCl₄ (40 mL). The mixture was stirred at reflux overnight. The brown solution was diluted with CCl₄ and filtered to remove succinimide. The filtrate was concentrated to a brown residue and purified by flash chromatography (0-25% ether in hexanes) to afford 135 g (47%) of 5-bromo-2-(bromomethyl)-1,3-thiazole as a yellow oil. MS ESI: [M+H]+ m/z 257.8.

Step 2

5-Bromo-2-(bromomethyl)-1,3-thiazole (1.34 g, 5.22 mmol) was dissolved in DMF (15 mL). Methyl 3-mercaptopropionate (0.689 g, 5.74 mmol) and DIEA (0.876 g, 6.78 mmol) were added, and the reaction was stirred at room temperature for 3 h. The reaction was diluted with water and extracted with ethyl acetate (2×). The combined organic layers were washed with brine, dried (MgSO₄), filtered and evaporated. Flash chromatography (0-30% ethyl acetate in hexanes) afforded methyl 3-{[(5-bromo-1,3-thiazol-2-yl)

methyl]sulfanyl}propanoate (1.45 g, 94%) as a pale yellow oil. MS BSI: [M+H]⁺ m/z 295.9/297.9.

Step 3

The product of Step 2 (1.45 g, 4.90 mmol) was taken up in CH₂Cl₂ (30 mL)/MeOH (15 mL), and magnesium monoperoxyphthalate hexahydrate (4.54 g, 7.34 mmol) was added. The reaction was stirred at room temperature for 2 h. The yellow slurry was diluted with aqueous 10% Na₂S₂O₃ and water and extracted with CH₂Cl₂ (2×). The combined organic layers were washed with saturated aqueous NaHCO₃, dried (MgSO₄), filtered and evaporated. Flash chromatography (0-50% ethyl acetate in hexanes) afforded methyl 3-{[(5-bromo-1,3-thiazol-2-yl)methyl]sulfonyl}propanoate (1.53 g, 95%) as a white solid. MS ESI: [M+H]+ m/z 327.9/329.9.

Step 4

The product of Step 3 (1.244 g, 3.79 mmol) was taken up in THF (50 mL) at room temperature, and NaOMe (25% in MeOH, 0.819 g, 3.79 mmol) was added. After 30 min at room temperature, the suspension was evaporated to dryness, providing a yellow solid. The solid was taken up in water (25 mL), and a solution of NaOAc (1.710 g, 20.85 mmol) and hydroxylamine-O-sulfonic acid (2.143 g, 18.95 mmol) in water (12.5 mL) was added while cooling the reaction (0° C.). The reaction was vigorously stirred at room temperature overnight. The reaction was extracted with ethyl acetate (2×). The combined organic layers were washed with brine, dried (MgSO₄), filtered and evaporated. Flash chromatography (dry load, 10-100% EtOAc/hexanes) afforded 1-(5-bromo-1,3-thiazol-2-yl)methanesulfonamide (470 mg, 48%) as a colorless solid. MS ESI: [M+H]+ m/z 256.9/258.9.

Step 5

The product of Step 4 (102 mg, 0.396 mmol), N-[3-methyl-5-(4,4,5,5-tetramethyl-1,3,2-dioxaborolan-2-yl)phenyl]-4-(trifluoromethyl)pyrimidin-2-amine (Intermediate 3, 1.50 mg, 0.396 mmol), and PdCl₂(dppf).CH₂Cl₂ (29 mg, 0.040 mmol) were combined in a flask, sealed, and purged with nitrogen (2×). Dioxane (2.4 mL) and aqueous Na₂CO₃ (2 M, 0.593 mL, 1.187 mmol) were added, and the reaction was purged again with nitrogen (2×). The mixture was stirred in an oil bath at 100° C. overnight. The dark brown reaction was diluted with water and extracted with ethyl acetate (2×). The combined organic layers were washed with brine, dried (MgSO₄), filtered and evaporated. Flash chromatography (dry load, 25-100% ethyl acetate in hexanes) provided an orange solid that was triturated with CH₂Cl₂ and filtered to afford 1-[5-(3-methyl-5-{[4-(trifluoromethyl)pyrimidin-2-yl]amino}phenyl)-1,3-thiazol-2-yl]methanesulfonamide (120 mg, 71%) as a colorless solid. MS ESI: [M+H]⁺ m/z 430.0. ¹H NMR (500 MHz, DMSO-d₆) δ 10.28 (s, 1H), 8.83 (d, J=4.9, 1H), 8.09 (s, 1H), 7.98 (s, 1H), 7.50 (s, 1H), 7.28 (d, J=4.9, 1H), 7.20 (s, 1H), 7.17 (s, 2H), 4.73 (s, 2H), 2.32 (s, 3H). rhSYK activity=+++

Compounds in the following Table(s) were prepared in a manner analogous to that described in Example 75:

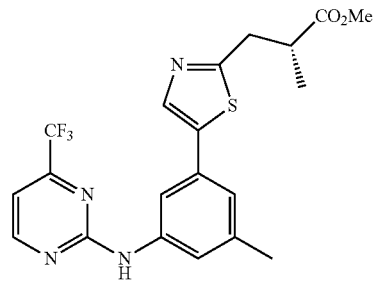 [SMILES: COC(=O)[C@H](C)Cc1ncc(-c2cc(C)cc(Nc3nccc(C(F)(F)F)n3)c2)s1]

| Example | R¹ | R² | rhSYK Activity | [M + H]+ Obs'd | Form(s) |
|---|---|---|---|---|---|
| 75-1 | CF₃ | H | +++ | 416.0 | Free Base |
| 75-2 | OCH₃ | CH₃ | +++ | 392.0 | Free Base |

Example 76

Methyl(2R)-2-methyl-3-[5-(3-methyl-5-{[4-(trifluoromethyl)pyrimidin-2-yl]amino}phenyl)-1,3-thiazol-2-yl]propanoate N-[3-(2-Bromo-1,3-thiazol-5-yl)-5-methylphenyl]-4-(trifluoromethyl)pyrimidin-2-amine (INTERMEDIATE 9, 1.50 g, 3.61 mmol), Pd(OAc)₂ (81 mg, 0.361 mmol), and 2-dicyclohexylphosphino-2',6'-dimethoxy-1,1'-biphenyl (297 mg, 0.722 mmol) were combined in a vial, sealed, and purged with nitrogen (2×). Degassed THF (15 mL) and (S)-(−)-3-methoxy-2-methyl-3-oxopropylzinc bromide (0.5 M in THF, 28.9 mL, 14.45 mmol) were added, and the reaction was stirred at room temperature overnight. The reaction was diluted with saturated aqueous NH₄Cl and water and extracted with ethyl acetate (2×). The combined organic layers were washed with brine, dried (MgSO₄), filtered and evaporated. Flash chromatography (0-50% ethyl acetate in hexanes) afforded methyl (2R)-2-methyl-3-[5-(3-methyl-5-{[4-(trifluoromethyl)pyrimidin-2-yl]amino}phenyl)-1,3-thiazol-2-yl]propanoate (1.37 g, 87%) as a yellow gum. MS ESI: [M+H]+ m/z 437.0. ¹H NMR (600 MHz, DMSO-d₆) δ 10.23 (s, 1H), 8.80 (d, J=4.8, 1H), 7.93 (s, 2H), 7.43 (s, 1H), 7.25 (d, J=4.9, 1H), 7.12 (s, 1H), 3.58 (s, 3H), 3.25 (dd, J=7.8, 15.2, 1H), 3.09 (dd, J=6.2, 15.2, 1H), 3.00-2.91 (m, 1H), 2.29 (s, 3H), 1.15 (d, J=7.0, 3H). rhSYK activity=+++

Example 77

Methyl 2,2-dimethyl-3-[5-(3-methyl-5-{[4-(trifluoromethyl)pyrimidin-2-yl]amino}phenyl)-1,3-thiazol-2-yl]propanoate

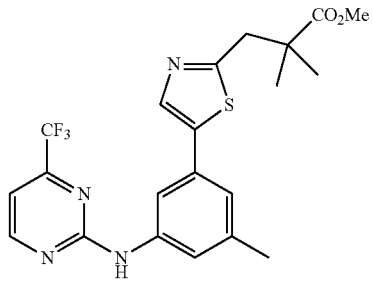 [SMILES: COC(=O)C(C)(C)Cc1ncc(-c2cc(C)cc(Nc3nccc(C(F)(F)F)n3)c2)s1]

Step 1

Methyl(2R)-2-methyl-3-[5-(3-methyl-5-{[4-(trifluoromethyl)pyrimidin-2-yl]amino}-phenyl)-1,3-thiazol-2-yl]propanoate (1.00 g, 2.291 mmol), triethylamine (348 mg, 3.44 mmol), and DMAP (28 mg, 0.229 mmol) were combined in THF (15 mL), and Boc$_2$O (550 mg, 2.52 mmol) was added. The reaction was stirred at room temperature overnight. The reaction was diluted with water and extracted with ethyl acetate (2×). The combined organic layers were washed with brine, dried (Na$_2$SO$_4$), filtered and evaporated. Flash chromatography (0-50% ethyl acetate in hexanes) afforded 1.204 g (98%) of methyl(2R)-3-[5-(3-{(tert-butoxycarbonyl)[4-(trifluoromethyl)pyrimidin-2-yl]amino}-5-methylphenyl)-1,3-thiazol-2-yl]-2-methylpropanoate as a yellow gum. MS ESI: [M+H]+ m/z 537.1.

Step 2

The product from Step 1 (700 mg, 1.305 mmol) and methyl iodide (926 mg, 6.52 mmol) were taken up in THF (18 mL) at room temperature, and LHMDS (1.0 M in THF, 6.52 mL, 6.52 mmol) was added dropwise. After stirring for 1 h at room temperature, the reaction was quenched with saturated NH$_4$Cl and extracted with EtOAc (2×). The combined organic layers were washed with brine, dried (Na$_2$SO$_4$), filtered and evaporated. Flash chromatography (0-50% ethyl acetate in hexanes) afforded methyl 3-[5-(3-{(tert-butoxycarbonyl)[4-(trifluoromethyl)pyrimidin-2-yl]amino}-5-methylphenyl)-1,3-thiazol-2-yl]-2,2-dimethylpropanoate (324 mg, 45%) as a yellow gum. MS ESI: [M+H]+ m/z 551.1.

Step 3

The product from Step 2 (390 mg, 0.708 mmol) was dissolved in CH$_2$Cl$_2$ (8 mL)/TFA (2 mL) and stirred at room temperature for 90 min. The reaction was subsequently diluted with 1,2-DCE and evaporated to dryness. The residue was redissolved in EtOAc, washed with saturated NaHCO$_3$ and brine, dried (Na$_2$SO$_4$), filtered and evaporated. Flash chromatography (0-50% ethyl acetate in hexanes) afforded 293 mg (92%) of methyl 2,2-dimethyl-3-[5-(3-methyl-5-{[4-(trifluoromethyl)pyrimidin-2-yl]amino}phenyl)-1,3-thiazol-2-yl]propanoate as a yellow gum. MS ESI: [M+H]+ m/z 451.0. $^1$H NMR (600 MHz, DMSO-d$_6$) δ 10.23 (s, 1H), 8.80 (d, J=4.9, 1H), 8.00-7.88 (m, 2H), 7.43 (s, 1H), 7.25 (d, J=4.9, 1H), 7.13 (s, 1H), 3.61 (s, 3H), 3.19 (s, 2H), 2.29 (s, 3H), 1.18 (s, 6H). rhSYK activity=+++

Example 78

2,2-dimethyl-3-[5-(3-methyl-5-{[4-(trifluoromethyl)pyrimidin-2-yl]amino}phenyl)-1,3-thiazol-2-yl]propanoic acid (potassium salt and TFA salt)

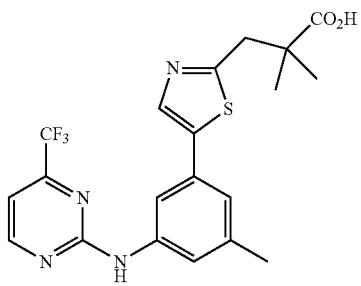 [SMILES: Cc1cc(Nc2nccc(C(F)(F)F)n2)cc(-c2cnc(CC(C)(C)C(=O)O)s2)c1]

Methyl 2,2-dimethyl-3-[5-(3-methyl-5-{[4-(trifluoromethyl)pyrimidin-2-yl]amino}phenyl)-1,3-thiazol-2-yl]propanoate (278 mg, 0.617 mmol) was taken up in MeOH (4 mL)/THF (4 mL), and 1 M KOH (648 µL, 0.648 mmol) was added. The reaction was stirred at room temperature overnight. LC/MS analysis showed only ~40% conversion, so additional 1 M KOH (123 µL, 0.123 mmol) was added, and the reaction was stirred at 50° C. overnight. The reaction was subsequently evaporated to dryness, providing 2,2-dimethyl-3-[5-(3-methyl-5-{[4-(trifluoromethyl)pyrimidin-2-yl]amino}phenyl)-1,3-thiazol-2-yl]propanoic acid (potassium salt) as a yellow solid that was used without purification in subsequent reactions (337 mg, 87% pure, 100% yield). A small portion (40 mg) was purified by reverse phase HPLC (50-100% MeCN/water w/0.025% TFA). Product fractions were combined and evaporated to provide a clean sample of 2,2-dimethyl-3-[5-(3-methyl-5-{[4-(trifluoromethyl)pyrimidin-2-yl]amino}-phenyl)-1,3-thiazol-2-yl]propanoic acid (TFA salt) as an off-white foam (28 mg). MS ESI: [M+H]+ m/z 437.0. $^1$H NMR (600 MHz, DMSO-d$_6$) δ 12.41 (s, 1H), 10.23 (s, 1H), 8.80 (d, J=4.9, 1H), 7.98-7.86 (m, 2H), 7.44 (s, 1H), 7.26 (d, J=4.9, 1H), 7.11 (s, 1H), 3.16 (s, 2H), 2.29 (s, 3H), 1.16 (s, 6H). rhSYK activity=+++

Example 79

N-(3-methyl-5-{2-[2-methyl-2-(1,3,4-oxadiazol-2-yl)propyl]-1,3-thiazol-5-yl}phenyl)-4-(trifluoromethyl)pyrimidin-2-amine

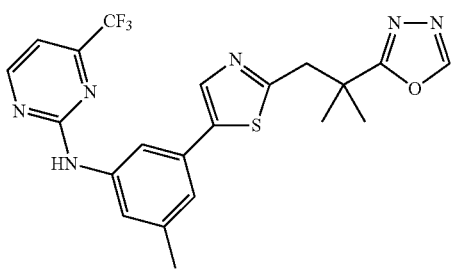 [SMILES: Cc1cc(Nc2nccc(C(F)(F)F)n2)cc(-c2cnc(CC(C)(C)c3nnco3)s2)c1]

Step 1

2,2-Dimethyl-3-[5-(3-methyl-5-{[4-(trifluoromethyl)pyrimidin-2-yl]amino}phenyl)-1,3-thiazol-2-yl]propanoic acid (potassium salt) (87% pure, 100 mg, 0.183 mmol), formic acid hydrazide (22.0 mg, 0.367 mmol), HOBT (56.2 mg, 0.367 mmol), and EDC (70.3 mg, 0.367 mmol) were combined with DMF (4 mL) and DIEA (47.4 mg, 0.367 mmol). The reaction was stirred overnight at room temperature. The reaction was diluted with water and extracted with ethyl acetate (2×). The combined organic layers were washed with brine, dried (MgSO$_4$), filtered and evaporated. Flash chromatography (0-10% methanol in ethyl acetate) afforded N'-formyl-2,2-dimethyl-3-[5-(3-methyl-5-{[4-(trifluoromethyl)pyrimidin-2-yl]amino}phenyl)-1,3-thiazol-2-yl]propanehydrazide (70 mg, 80%) as a yellow gum. BSI: [M+H]+ m/z 479.0.

Step 2

The product from Step 1 (70 mg, 0.146 mmol) was taken up in THF (2.0 mL) in a microwave vial, and Burgess reagent (70 mg, 0.293 mmol) was added. The reaction was heated in the microwave at 100° C. for 30 min. The orange reaction mixture was concentrated to dryness, and the resulting residue was purified by flash chromatography (10-100% ethyl acetate in hexanes) to provide N-(3-methyl-5-{2-[2-methyl-2-(1,3,4-oxadiazol-2-yl)propyl]-1,3-thiazol-5-yl}phenyl)-4-(trifluoromethyl)pyrimidin-2-amine (32 mg, 48%) as a colorless foam. MS ESI: [M+H]+ m/z 461.0. $^1$H NMR (600 MHz, DMSO-d$_6$) δ 10.22 (s, 1H), 9.16 (s, 1H), 8.80 (d, J=4.9, 1H), 7.94-7.83 (m, 2H), 7.42 (s, 1H), 7.25 (d, J=4.9, 1H), 7.08 (s, 1H), 3.39 (s, 2H), 2.27 (s, 3H), 1.43 (s, 6H). rhSYK activity=+++

The following examples were prepared in a manner analogous to that described in Examples 76-79,

TABLE 79

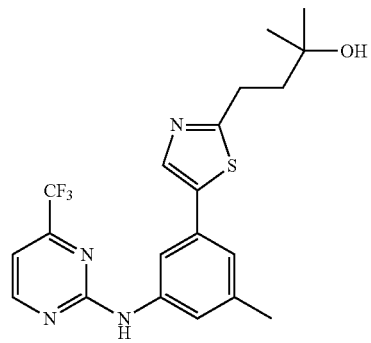 [SMILES: Cc1cc(Nc2nccc(C(F)(F)F)n2)cc(-c2cnc(CCC(C)(C)O)s2)c1]

| Example | A | R | rhSYK Activity | [M + H]+ Observed | Form(s) |
|---|---|---|---|---|---|
| 79-1 | CH$_2$ | —CO$_2$Et | +++ | 437.0 | Free Base |
| 79-2 | CH$_2$ | —CONH$_2$ | +++ | 408.0 | Free Base |
| 79-3 | CH$_2$ | —CO$_2$H | +++ | 409.0 | TFA Salt |
| 79-4 | CH$_2$ | —CON(CH$_3$)$_2$ | +++ | 436.0 | Free Base |
| 79-5 | CH$_2$ | —CO-(4-morpholinyl) | +++ | 478.0 | Free Base |
| 79-6 | CH$_2$ | —C(O)NHCH$_2$CH$_2$OH | +++ | 452.0 | Free Base |
| 79-7 | CH$_2$ | 1,3,4-oxadiaxol-2-yl | +++ | 433.0 | Free Base |
| 79-8 | CH$_2$ | 5-Me-1,3,4-oxadiazol-2-yl | +++ | 447.0 | Free Base |
| 79-9 | CH$_2$ | 5-cPr-1,3,4-oxadiazol-2-yl | +++ | 473.0 | Free Base |
| 79-10 | C(CH$_3$)$_2$ | CONH$_2$ | +++ | 436.0 | Free Base |
| 79-11 | (CH$_3$)$_2$ | CON(CH$_3$)$_2$ | +++ | 464.0 | Free Base |

Example 80

2-methyl-4-[5-(3-methyl-5-{[4-(trifluoromethyl)pyrimidin-2-yl]amino}phenyl)-1,3-thiazol-2-yl]butan-2-ol

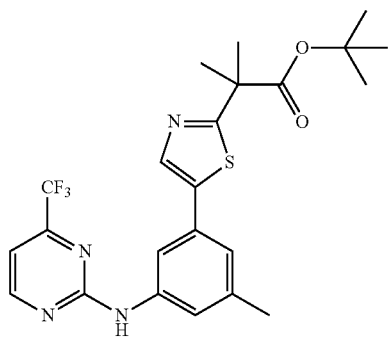 [SMILES: Cc1cc(Nc2nccc(C(F)(F)F)n2)cc(-c2cnc(C(C)(C)C(=O)OC(C)(C)C)s2)c1]

Ethyl 3-[5-(3-methyl-5-{[4-(trifluoromethyl)pyrimidin-2-yl]amino}phenyl)-1,3-thiazol-2-yl]-propanoate (Example 79-1, 100 mg, 0.229 mmol) was taken up in THF (5 mL) and cooled to −78° C. Methylmagnesium bromide (3.0 M in Et$_2$O, 305 µL, 0.916 mmol) was added, and the reaction was stirred at −78° C. for 90 min. It was then warmed to room temperature. After 1 h at room temperature, the reaction was quenched with saturated NH$_4$Cl and extracted with ethyl acetate (2×). The combined organic layers were washed with brine, dried (MgSO$_4$), and evaporated. Column chromatography on silica (20-100% ethyl acetate in hexanes) afforded 2-methyl-4-[5-(3-methyl-5-{[4-(trifluoromethyl)pyrimidin-2-yl]amino}phenyl)-1,3-thiazol-2-yl]butan-2-ol (73 mg, 75%) as a white foam. MS ESI: [M+H]+ m/z 423.1. $^1$H NMR (600 MHz, DMSO-d$_6$) δ 10.22 (s, 1H), 8.81 (d, J=4.8, 1H), 7.93 (s, 1H), 7.89 (s, 1H), 7.42 (s, 1H), 7.25 (d, J=4.8, 1H), 7.11 (s, 1H), 436 (s, 1H), 3.05-2.92 (m, 2H), 2.28 (s, 3H), 1.87-1.73 (m, 2H), 1.11 (s, 6H). rhSYK activity=+++

Example 81 tert-Butyl 2-methyl-2-[5-(3-methyl-5-{[4-(trifluoromethyl)pyrimidin-2-yl]amino}phenyl)-1,3-thiazol-2-yl]propanoate Step 1

Toluene (30 mL) was placed in a nitrogen-flushed flask and degassed with nitrogen (20 min). 2-Chlorothiazole (900 mg, 7.53 mmol) and tert-butyl propionate (1.176 g, 9.03 mmol) were added, and the mixture was cooled to 0° C. NaHMDS (0.6 M in toluene, 30.1 mL, 18.06 mmol) was added. The reaction was stirred for 2 h at 0° C., allowed to warm to room temperature, and stirred for 18 h at room temperature. Methyl iodide (3.85 g, 27.1 mmol) was then added. After 1 h at room temperature, the orange reaction was quenched (under nitrogen) with aqueous saturated NH₄Cl. The mixture was extracted with ethyl acetate (2×), and the combined organic layers were washed with brine, dried (Na₂SO₄), filtered and evaporated. Flash chromatography (0-25% ethyl acetate in hexanes) afforded tert-butyl 2-methyl-2-(1,3-thiazol-2-yl) propanoate (1.06 g, 62%) as a pale yellow oil. MS ESI: [M+H]⁺ m/z 228.1.

Step 2

The product from Step 1 (935 mg, 4.11 mmol) was taken up in CHCl₃ (20 mL) and placed in a cool water bath. NaHCO₃ (380 mg, 4.52 mmol) was added, followed by bromine (1.315 g, 8.23 mmol). After stirring for 2 h at room temperature, some starting material remained, so additional NaHCO₃ (380 mg, 4.52 mmol) and bromine (1.315 g, 8.23 mmol) were added. After another 2 h at room temperature, the reaction was diluted with aqueous 10% Na₂S₂O₃ and aqueous saturated NaHCO₃ and extracted with CH₂Cl₂ (2×). The combined organic layers were washed with brine, dried (Na₂SO₄), and evaporated. Flash chromatography (0-10% ethyl acetate in hexanes) afforded tert-butyl 2-(5-bromo-1,3-thiazol-2-yl)-2-methylpropanoate (1.032 g, 82%) as a colorless oil. MS ESI: [M-t-Bu]+ m/z 249.9/251.9.

Step 3

The product of Step 2 (1.022 g, 3.34 mmol), N-[3-methyl-5-(4,4,5,5-tetramethyl-1,3,2-dioxaborolan-2-yl)phenyl]-4-(trifluoromethyl)pyrimidin-2-amine (INTERMEDIATE 3, 1.15 g, 3.03 mmol), and PdCl₂(dppf).CH₂Cl₂ (222 mg, 0.303 mmol) were combined in a flask, sealed, and purged with nitrogen (2×). Dioxane (18 mL) and 2 M Na₂CO₃ (4.55 mL, 9.10 mmol) were added, and the reaction was purged again with nitrogen (2×). The mixture was stirred in an oil bath at 100° C. overnight. The dark brown reaction was diluted with water and extracted with ethyl acetate (2×). The combined organic layers were washed with brine, dried (Na₂SO₄), filtered and evaporated. Flash chromatography (0-25% ethyl acetate in hexanes) provided tert-butyl 2-methyl-2-[5-(3-methyl-5-{[4-(trifluoromethyl)pyrimidin-2-yl]amino}phenyl)-1,3-thiazol-2-yl]propanoate (968 mg, 67%) as a colorless gum that crystallized into a waxy solid upon standing. MS ESI: [M+H]+ m/z 479.1. ¹H NMR (600 MHz, DMSO-d₆) δ 10.24 (s, 1H), 8.80 (d, J=4.7, 1H), 7.99 (s, 1H), 7.96 (d, J=1.6, 1H), 7.42 (s, 1H), 7.26 (dd, J=1.4, 4.9, 1H), 7.15 (s, 1H), 2.29 (s, 3H), 1.57 (s, 6H), 1.34 (s, 9H). rhSYK activity=++

Example 82

N-(3-methyl-5-{2-[2-(1,3,4-oxadiazol-2-yl)propan-2-yl]-1,3-thiazol-5-yl}phenyl)-4-(trifluoromethyl)pyrimidin-2-amine

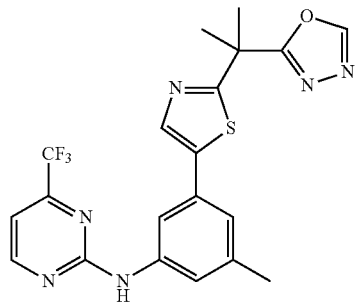 [SMILES: Cc1cc(Nc2nccc(C(F)(F)F)n2)cc(-c2cnc(C(C)(C)c3nnco3)s2)c1]

Step 1 tert-Butyl 2-methyl-2-[5-(3-methyl-5-{[4-(trifluoromethyl)pyrimidin-2-yl]amino}-phenyl)-1,3-thiazol-2-yl]propanoate (400 mg, 0.836 mmol) was taken up in dioxane (8 mL) before adding HCl (4 M in dioxane, 16 mL, 64.0 mmol). The reaction was stirred at room temperature for 4 d (became yellow suspension over time). The yellow suspension was diluted with Et₂O and filtered to isolate 2-methyl-2-[5-(3-methyl-5-{[4-(trifluoromethyl)pyrimidin-2-yl]amino}phenyl)-1,3-thiazol-2-yl]propanoic acid (HCl salt, 375 mg, 98%) as a yellow solid. MS ESI: [M+H]⁺ m/z 423.0.

Step 2

The product from Step 1 (HCl salt, 187 mg, 0.408 mmol), HOBT (125 mg, 0.815 mmol), and EDC (156 mg, 0.815 mmol) were combined with dioxane (5 mL) and stirred for 5 min at room temperature. Formic acid hydrazide (73 mg, 1.223 mmol) and DIEA (105 mg, 0.815 mmol) were subsequently added. The reaction was stirred overnight at room temperature. The reaction was diluted with water and extracted with ethyl acetate (2×). The combined organic layers were washed with brine, dried (Na₂SO₄), filtered and evaporated. Column chromatography on silica (50-100% EtOAc/hexanes) afforded N'-formyl-2-methyl-2-[5-(3-methyl-5-{[4-(trifluoromethyl)pyrimidin-2-yl]amino}phenyl)-1,3-thiazol-2-yl]propanehydrazide (87 mg, 46%) as a colorless solid. MS ESI: [M+H]+ m/z 465.0.

Step 3

The product from Step 2 (80 mg, 0.172 mmol) was taken up in THF (2 mL) in a microwave vial, and Burgess reagent (82 mg, 0.344 mmol) was added. The reaction was irradiated in the microwave at 100° C. for 30 min. The yellow reaction mixture was concentrated to dryness, and the resulting residue was purified by column chromatography on silica (0-100% ethyl acetate in hexanes) to provide N-(3-methyl-5-{2-[2-(1,3,4-oxadiazol-2-yl)propan-2-yl]-1,3-thiazol-5-yl}phenyl)-4-(trifluoromethyl)pyrimidin-2-amine (32 mg, 42%) as an off-white solid. MS ESI: [M+H]+ m/z 447.0. ¹H NMR (600 MHz, DMSO-d₆) δ 10.24 (s, 1H), 9.20 (s, 1H), 8.81 (d, J=4.9, 1H), 7.97 (s, 2H), 7.44 (s, 1H), 7.26 (d, J=4.9, 1H), 7.14 (s, 1H), 2.29 (s, 3H), 1.87 (s, 6H). rhSYK activity=+++

Example 83 tert-butyl 1-[5-(3-methyl-5-{[4-(trifluoromethyl) pyrimidin-2-yl]amino}phenyl)-1,3-thiazol-2-yl]cyclopropanecarboxylate

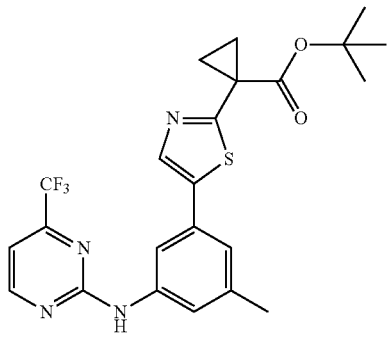 [SMILES: Cc1cc(Nc2nccc(C(F)(F)F)n2)cc(-c2cnc(C3(C(=O)OC(C)(C)C)CC3)s2)c1]

Step 1

Toluene (60 mL) was placed in a nitrogen-flushed flask and degassed with nitrogen (20 min). 2-chlorothiazole (2.00 g, 16.73 mmol) and tert-butyl acetate (2.137 g, 18.40 mmol) were added, and the mixture was cooled to 0° C. NaHMDS (0.6 M in toluene, 61.3 mL, 36.8 mmol) was added. The reaction was stirred for 2 h at 0° C., allowed to warm to room temperature, and stirred for 18 h. The orange reaction was quenched (under nitrogen) with aqueous saturated NH$_4$Cl. The mixture was extracted with ethyl acetate (2×), and the combined organic layers were washed with brine, dried (Na$_2$SO$_4$), filtered and evaporated. Column chromatography on silica (0-25% ethyl acetate in hexanes) afforded tert-butyl (1,3-thiazol-2-yl)acetate (770 mg, 23%) as a pale yellow oil. MS ESI: [M t-Bu]+ m/z 144.0.

Step 2

Sodium hydride (702 mg, 17.56 mmol) was suspended in THF (7 mL)/DMF (7 mL) under nitrogen and cooled to 0° C. The product from Step 1 (875 mg, 4.39 mmol) in THF (3 mL)/DMF (3 mL) was added dropwise. The ice bath was removed, and the yellow-orange suspension was stirred at room temperature for 30 min. The mixture was then cooled back down to 0° C., and 1,2-dibromoethane (2.475 g, 13.17 mmol) was added in one portion. The reaction was allowed to warm to room temperature and stirred for 2 h. It was then quenched with saturated NH$_4$Cl and water and extracted with ethyl acetate (2×). The combined organic layers were washed with brine, dried (Na$_2$SO$_4$), and evaporated. Flash chromatography (0-20% ethyl acetate in hexanes) afforded tert-butyl 1-(1,3-thiazol-2-yl)cyclopropanecarboxylate (866 mg, 88%) as a colorless oil. MS ESI: [M+H]$^+$ m/z 226.1.

Step 3

The product from Step 2 (860 mg, 3.82 mmol) was taken up in CHCl$_3$ (19 mL) and placed in a cool water bath. NaHCO$_3$ (353 mg, 4.20 mmol) was added, followed by bromine (1.22 g, 7.63 mmol). After stirring for 90 min at room temperature, the reaction was diluted with 10% Na$_2$S$_2$O$_3$ and saturated NaHCO$_3$ and extracted with CH$_2$Cl$_2$ (2×). The combined organic layers were washed with brine, dried (Na$_2$SO$_4$), filtered and evaporated. Flash chromatography (0-10% ether in hexanes) afforded tert-butyl 1-(5-bromo-1,3-thiazol-2-yl)cyclopropanecarboxylate (545 mg, 47%) as a colorless oil. MS ESI: [M-t-Bu]+ m/z 247.9/249.9.

Step 4

The product of Step 3 (538 mg, 1.767 mmol), N-[3-methyl-5-(4,4,5,5-tetramethyl-1,3,2-dioxaborolan-2-yl)phenyl]-4-(trifluoromethyl)pyrimidin-2-amine (Intermediate 3, 670 mg, 1.767 mmol), and PdCl$_2$(dppf).CH$_2$Cl$_2$ (129 mg, 0.177 mmol) were combined in a flask, sealed, and purged with nitrogen (2×). Dioxane (11 mL) and 2 M Na$_2$CO$_3$ (2.65 mL, 5.30 mmol) were added, and the reaction was purged again with nitrogen (2×). The mixture was stirred in an oil bath at 100° C. overnight. The dark brown reaction was diluted with water and extracted with ethyl acetate (2×). The combined organic layers were washed with brine, dried (Na$_2$SO$_4$), and evaporated. Flash chromatography (0-20% ethyl acetate in hexanes) afforded of tert-butyl 1-[5-(3-methyl-5-{[4-(trifluoromethyl)pyrimidin-2-yl]amino}phenyl)-1,3-thiazol-2-yl] cyclopropanecarboxylate (555 mg, 66%) as a pale yellow solid. MS ESI: [M+H]+ m/z 477.0. $^1$H NMR (600 MHz, DMSO-d$_6$) δ 10.22 (s, 1H), 8.80 (d, J=4.9, 1H), 7.93 (s, 1H), 7.87 (s, 1H), 7.44 (s, 1H), 7.25 (d, J=4.9, 1H), 7.13 (s, 1H), 2.29 (s, 3H), 1.76-1.61 (m, 4H), 1.44 (s, 9H). rhSYK activity=++

Example 84

1-[5-(3-methyl-5-{[4-(trifluoromethyl)pyrimidin-2-yl]amino}phenyl)-1,3-thiazol-2-yl]cyclopropanecarboxylic acid (TFA salt)

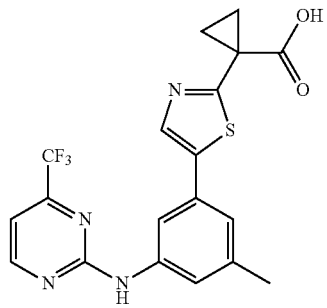 [SMILES: Cc1cc(Nc2nccc(C(F)(F)F)n2)cc(-c2cnc(C3(C(=O)O)CC3)s2)c1]

tert-Butyl 1-[5-(3-methyl-5-{[4-(trifluoromethyl)pyrimidin-2-yl]amino}phenyl)-1,3-thiazol-2-yl]cyclopropanecarboxylate (375 mg, 0.787 mmol) was taken up in CH$_2$Cl$_2$ (12 mL) before adding TFA (3 mL). The reaction was stirred at room temperature overnight. The reaction was evaporated to dryness, and the residue was azeotroped with DCE (3×) to provide 1-[5-(3-methyl-5-{[4-(trifluoromethyl)pyrimidin-2-yl]amino}phenyl)-1,3-thiazol-2-yl]cyclopropanecarboxylic acid (TFA salt) (421 mg, 100%) as a yellow solid. MS ESI: [M+H]+ m/z 421.0. $^1$H NMR (600 MHz, DMSO-d$_6$) δ 13.15 (s, 10.21 (s, 1H)), 8.80 (d, J=4.8, 1H), 7.95 (s, 1H), 7.87 (s, 1H), 7.44 (s, 1H), 7.25 (d, J=4.9, 1H), 7.12 (s, 1H), 2.29 (s, 3H), 1.81-1.62 (m, 4H). rhSYK activity=+++

Example 85

N-(3-methyl-5-{2-[1-(1,3,4-oxadiazol-2-yl)cyclopropyl]-1,3-thiazol-5-yl}phenyl)-4-(trifluoromethyl)pyrimidin-2-amine

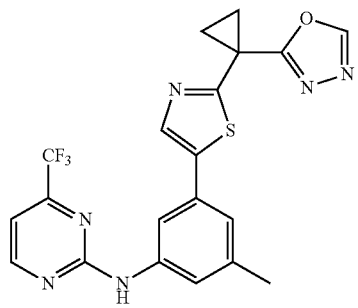 [SMILES: Cc1cc(Nc2nccc(C(F)(F)F)n2)cc(-c2cnc(C3(c4nnco4)CC3)s2)c1]

Step 1

1-[5-(3-Methyl-5-{[4-(trifluoromethyl)pyrimidin-2-yl]amino}phenyl)-1,3-thiazol-2-yl]cyclopropanecarboxylic acid (TEA salt, 110 mg, 0.206 mmol), formic acid hydrazide (37 mg, 0.617 mmol), HOST (95 mg, 0.617 mmol), and EDC (118 mg, 0.617 mmol) were combined with DMF (5 mL) and DMA (80 mg, 0.617 mmol). The reaction was stirred for 3 h at room temperature. It was subsequently diluted with water and extracted with ethyl acetate (2×). The combined organic layers were washed with brine, dried (MgSO$_4$), filtered and evaporated. The residue was triturated with ether and filtered to provide N'-formyl-1-[5-(3-methyl-5-{[4-(trifluoromethyl)pyrimidin-2-yl]amino}phenyl)-1,3-thiazol-2-yl]cyclopropanecarbohydrazide (88 mg, 92%) as a colorless solid. MS ESI: [M+H]$^+$ m/z 463.0.

Step 2

The product from Step 1 (85 mg, 0.184 mmol) was taken up in THF (2 mL) in a microwave vial, and Burgess reagent (88 mg, 0.368 mmol) was added. The reaction was heated in the microwave at 100° C. for 30 min. The yellow reaction mixture was concentrated to dryness, and the resulting residue was purified by flash chromatography (25-100% ethyl acetate in hexanes) to afford N-(3-methyl-5-{2-[1-(1,3,4-oxadiazol-2-yl)cyclopropyl]-1,3-thiazol-5-yl}phenyl)-4-(trifluoromethyl)pyrimidin-2-amine (18 mg, 22%) as a colorless solid. MS ESI: [M+H]+ m/z 445.0. $^1$H NMR (600 MHz, DMSO-d$_6$) δ 10.23 (s, 1H), 9.23 (s, 1H), 8.81 (d, 4.9, 1H), 7.97 (s, 1H), 7.96 (s, 1H), 7.46 (s, 1H), 7.26 (d, J=4.9, 1H), 7.15 (s, 1H), 2.29 (s, 3H), 1.94-1.82 (m, 4H). rhSYK activity=+++

The following examples were prepared in a manner analogous to that described in Examples 82-85.

TABLE 85A

Structure: thiazole bearing a C(CH$_3$)$_2$-R$^3$ group at the 2-position, linked via 5-position to a 3-methylphenyl group attached to NH-pyrimidine-4-CF$_3$.

| Example | R$^3$ | rhSYK Activity | [M + H]+ Observed | Form(s) |
|---|---|---|---|---|
| 85A-1 | —CONH$_2$ | +++ | 422.0 | Free Base |
| 85A-2 | —CONH(CH$_3$)$_2$ | +++ | 450.0 | Free Base |
| 85A-3 | —C(O)-(4-morpholinyl) | +++ | 492.1 | Free Base |
| 85A-4 | 5-Me-1,3,4-oxadiazol-2-yl | +++ | 461.0 | Free Base |

TABLE 85B

Structure: thiazole bearing an R group at the 2-position, linked via 5-position to a 3-methylphenyl group attached to NH-pyrimidine-4-CF$_3$.

| Example | R | rhSYK Activity | [M + H]+ Observed | Form(s) |
|---|---|---|---|---|
| 85B-1 | 1-[C(O)N(CH$_3$)$_2$]cyclopropyl | +++ | 448.0 | Free Base |
| 85B-2 | 1-(CONHCH$_3$)cyclopropyl | +++ | 434.0 | Free Base |
| 85B-3 | 1-(CONH$_2$)cyclopropyl | +++ | 420.0 | Free Base |
| 85B-4 | 1-(5-methyl-1,3,4-oxadiazol-2-yl)cyclopropyl | +++ | 459.0 | Free Base |

Example 86

5-(3-methyl-5-{[4-(trifluoromethyl)pyrimidin-2-yl]amino}phenyl)-1,3-thiazole-2-carboxylic acid

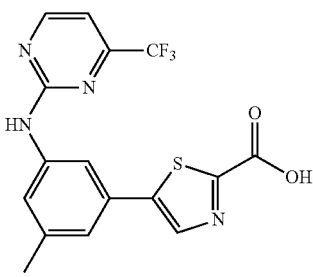 [SMILES: Cc1cc(Nc2nccc(C(F)(F)F)n2)cc(-c2cnc(C(=O)O)s2)c1]

To a solution of INTERMEDIATE 4 (8.0 g, 23.79 mmol) in tetrahydrofuran (80 mL) at −78° C. was added a solution of lithium diisopropylamide (33.0 mL, 59.5 mmol, 1.8 M) via a dropping funnel over 15 minutes. After the reaction mixture had been stirred at −78° C. for 90 minutes, it was poured into a suspension of crushed carbon dioxide$_{(solid)}$ (5.23 g, 119 mmol) in tetrahydrofuran (20 mL). Following another 30 minutes of stirring the mixture was diluted with aqueous hydrogen chloride solution (50 mL, 2 M) and water (50 mL). The solid was then isolated by filtration and washed with water (50 mL), ethyl acetate (100 mL), and dichloromethane (50 mL) in succession before being suction dried overnight. The filtrate produced more solid upon standing, and this material was isolated by filtration, washed with ethyl acetate, and suction dried. The two crops were combined to give 5-(3-methyl-5-{[4-(trifluoromethyl)pyrimidin-2-yl]amino}phenyl)-1,3-thiazole-2-carboxylic acid (5.65 g, 14.9 mmol, 62% yield, 90% purity) as a yellow solid. MS ESI: [M+H]$^+$ m/z 381.0. $^1$H NMR (500 MHz, d$_6$-DMSO): δ 10.31 (s, 1H); 8.85 (d, J=4.9 Hz, 1H); 8.31 (s, 1H); 8.10 (s, 1H); 7.52 (s, 1H); 7.30 (m, 2H); 2.31 (s, 3H). rhSYK activity=+++

Example 87

N-[(2R)-2,3-dihydroxypropyl]-5-(3-methyl-5-{[4-(trifluoromethyl)pyrimidin-2-yl]amino}-phenyl)-1,3-thiazole-2-carboxamide

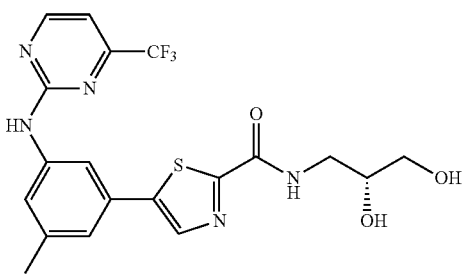 [SMILES: Cc1cc(Nc2nccc(C(F)(F)F)n2)cc(-c2cnc(C(=O)NC[C@@H](O)CO)s2)c1]

To a solution of (2R)-3-aminopropane-1,2-diol (132 mg, 1.446 mmol), 5-(3-methyl-5-{[4-(trifluoromethyl)pyrimidin-2-yl]amino}phenyl)-1,3-thiazole-2-carboxylic acid (500 mg, 1.315 mmol), and triethylamine (0.403 mL, 2.89 mmol) in N,N-dimethylformamide (8 mL) was added benzotriazol-1-yl-oxytripyrrolidinophosphonium hexafluorophosphate (821 mg, 1.578 mmol). After 45 minutes, water (32 mL) was added to the reaction mixture and the resulting yellow solid was collected by filtration; the solid was then purified by trituration using a mixture of methanol (2 mL), ethyl acetate (3 mL), and dichloromethane (3 mL) followed by filtration and drying in vacuo. The mother liquor from the trituration was concentrated and additional product was purified via column chromatography on silica (Biotage 50 g SNAP column, 97.5:2.5 to 85:15 dichloromethane:methanol). The combined material afforded in N-[(2R)-2,3-dihydroxypropyl]-5-(3-methyl-5-{[4-(trifluoromethyl)pyrimidin-2-yl]amino}phenyl)-1,3-thiazole-2-carboxamide (487 mg 82% yield) as a yellow solid. MS ESI: [M+H]$^+$ m/z 454.0. $^1$H NMR (500 MHz, d$_6$-DMSO): δ 10.31 (s, 1H); 8.85 (d, J=4.9 Hz, 1H); 8.53 (t, J=5.9 Hz, 1H); 8.29 (s, 1H); 8.11 (s, 1H); 7.51 (s, 1H); 7.31 (s, 1H); 7.30 (d, J=4.9 Hz, 1H); 4.90 (d, J=5.1 Hz, 1H); 4.64 (t, J=5.7 Hz, 1H); 3.63 (m, 1H); 3.42 (m, 1H); 3.35 (m, 2H); 3.23 (m, 1H); 2.34 (s, 3H). rhSYK activity=+++

The following examples were prepared in an analogous manner of that described in Example 87.

TABLE 87A

| Example | $R^1/R^2$ | rhSYK Activity | [M + H]+ Observed | Form(s) |
|---|---|---|---|---|
| $R^3 = CH_3$ | | | | |
| 87A-1 | H/iPr | ++ | 422.0 | Free Base |
| 87A-2 | H/H | ++ | 380.1 | Free Base |
| 87A-3 | H/—CH$_2$CH(OH)CH$_2$OH | +++ | 454.0 | Free Base |
| 87A-4 | H/—CH$_2$CH(OH)CH$_2$OH (R) | +++ | 454.0 | Free Base |
| 87A-5 | H/—CH$_2$CH$_2$SO$_2$CH$_3$ | +++, +++ | 486.0 | Free Base, Formate Salt |
| 87A-6 | CH$_3$/—CH$_2$CH$_2$OH | +++ | 438.1 | Formate Salt |
| 87A-7 | H/—CH$_2$CH(OH)CH$_3$ | +++ | 438.5 | Formate Salt |
| 87A-8 | H/—CH(CH$_3$)CH$_2$OH | +++ | 438.1 | Formate Salt |
| 87A-9 | H/1-(CH$_2$OH)cPr | +++ | 450.1 | Formate Salt |
| 87A-10 | H/—CH(Et)CH$_2$OH | +++ | 452.1 | Formate Salt |
| 87A-11 | H/—CH$_2$C(CH$_3$)$_2$OH | +++ | 452.1 | Formate Salt |
| 87A-12 | H/—C(CH$_2$OH)$_2$CH$_3$ | +++ | 468.1 | Formate Salt |
| 87A-13 | H/—CH$_2$-(1-Me-4-pyrazolyl) | ++ | 474.1 | Formate Salt |

TABLE 87A-continued

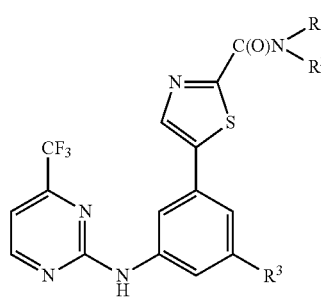

| Example | R¹/R² | rhSYK Activity | [M + H]+ Observed | Form(s) |
|---|---|---|---|---|
| 87A-14 | H/—CH₂-(1-Me-5-imidazolyl) | +++ | 474.1 | Formate Salt |
| 87A-15 | H/—CH₂CH₂-(4-imidazolyl) | +++ | 474.1 | Formate Salt |
| 87A-16 | H/1-(CH₂OH)cPen | + | 478.1 | Formate Salt |
| 87A-17 |  | ++ | 494.1 | Formate Salt |
| 87A-18 | H/—CH₂-(1-Me-1,2,4-triazol-5-yl) | ++ | 475.1 | Formate Salt |
| 87A-19 | H/—CH₂C(=CH₂)F | +++ | 438.1 | Formate Salt |
| 87A-20 | H/—CH₂-(1,4-dioxan-2-yl) | +++ | 480.1 | Formate Salt |
| 87A-21 | CH₃/—CH₂-(1-Me-2-imidazolyl) | +++ | 488.1 | Formate Salt |
| 87A-22 | CH₃/—CH(cPr)₂ | + | 488.2 | Formate Salt |
| 87A-23 | CH₃/—CH₂-(1,4-dioxan-2-yl) | ++ | 494.1 | Formate Salt |
| 87A-24 | H/—CH₂CH(OH)CH₂OCH₃ | +++ | 468.1 | Formate Salt |
| 87A-25 | H/—CH₂-2-imidazolyl | +++ | 460.1 | Formate Salt |
| 87A-26 | CH₃/—CH₂CH(OH)CH₂OH | +++ | 468.1 | Formate Salt |
| 87A-27 | CH₃/—CH₂CH₂SO₂CH₃ | + | 500.1 | Formate Salt |
| 87A-28 | CH₃/Et | ++ | 422.1 | Formate Salt |
| 87A-29 | CH₂CH₂OH/—CH₂CH₂OH | +++ | 468.1 | Formate Salt |
| 87A-30 | CH₃/ CH₂C(O)NHCH₃ | +++ | 465.1 | Formate Salt |
| 87A-31 | H/—CH₂CH(OH)CH₂OH (S) | +++ | 454.1 | Free Base |
| 87A-32 | H/CH(Ph)CH(OH)CO₂H (R,R) | +++ | 544.1 | TFA Salt |
| 87A-33 | H/CH(CH₂OH)₂ | +++ | 454.1 | TFA Salt |
| 87A-34 | H/C(CH₂OH)₃ | +++ | 484.0 | TFA Salt |
| 87A-35 | H/CH₂CH₂CO₂H | +++ | 452.1 | TFA Salt |
| 87A-36 | H/(CH₂)₃N(CH₂CH₂OH)₂ | +++ | 525.2 | TFA Salt |
| 87A-37 | H/4-CO₂H-cHex | +++ | 506.1 | TFA Salt |

TABLE 87A-continued

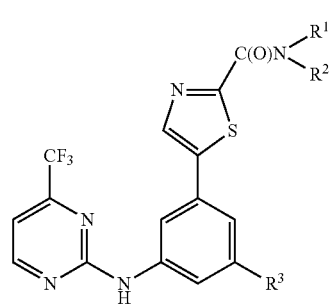

| Example | R¹/R² | rhSYK Activity | [M + H]+ Observed | Form(s) |
|---|---|---|---|---|
| R₃ = H ||||| 
| 87A-38 | H/H | +++ | 363.9* | Free Base |

*[M − H]+ was measured instead of [M + H]+

TABLE 87B

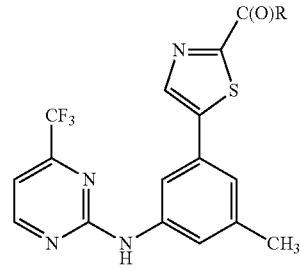

| Example | R | rhSYK Activity | [M + H]+ Observed | Form(s) |
|---|---|---|---|---|
| 87B-1 | 1-pyrrolidinyl | ++ | 434.0 | Free Base |
| 87B-2 | 3-oxo-1-piperazinyl | ++ | 463.1 | Formate Salt |
| 87B-3 | 4-Me-1-piperazinyl | ++ | 463.1 | Formate Salt |
| 87B-4 | 4-Me-3-oxo-1-piperazinyl | +++ | 477.1 | Formate Salt |
| 87B-5 | 2,4-diMe-3-oxo-1-piperazinyl | ++ | 491.1 | Formate Salt |
| 87B-6 | [bicyclic pyrrolo-piperazine] | +++ | 485.1 | Formate Salt |
| 87B-7 | [piperazinyl-N-C(O)CH₃] | ++ | 491.1 | Formate Salt |

TABLE 87B-continued

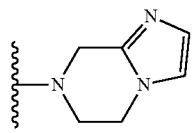 [SMILES: *N1CCn2ccnc2C1]

| Example | R | rhSYK Activity | [M+H]+ Observed | Form(s) |
|---|---|---|---|---|
| 87B-8 | 2-OH-3-Me-4-morpholinyl | +++ | 480.1 | Formate Salt |
| 87B-9 | 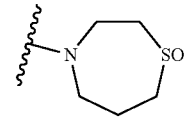 | +++ | 486.1 | Formate Salt |
| 87B-10 | 2-(—CH₂CH₂OH)-4-morpholinyl | +++ | 494.1 | Formate Salt |
| 87B-11 | 3-(CH₂OH)pyrrolidin-1-yl (R) | +++ | 464.1 | Formate Salt |
| 87B-12 | 3-Me-3-OH-pyrrolidin-1-yl | +++ | 464.1 | Formate Salt |
| 87B-13 | 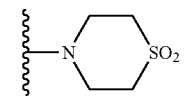 | +++ | 496.1 | Formate Salt |
| 87B-14 | 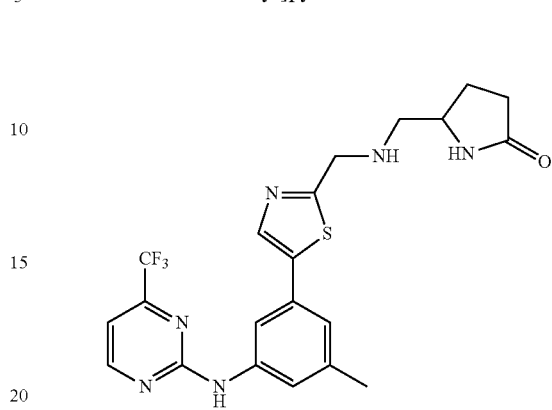 | ++ | 498.1 | Formate Salt |
| 87B-15 | 4-CH₂CF₃-1-piperazinyl | + | 531.1 | Formate Salt |
| 87B-16 | 3-CH₂OH-1-pyrrolidinyl (S) | +++ | 464.1 | Formate Salt |
| 87B-17 | 3-OH-1-pyrrolidinyl | +++ | 450.1 | TFA Salt |
| 87B-18 | 3,4-diOH-1-pyrrolidinyl (cis) | +++ | 466.1 | TFA Salt |
| 87B-19 | 4-CO₂H-1-piperidinyl | +++ | 492.1 | Free Base |
| 87B-20 | 2-CO₂H-4-OH-1-pyrrolidinyl | +++ | 494.1 | TFA Salt |
| 87B-21 | 2-CO₂CH₃-4-OH-1-pyrrolidinyl | +++ | 508.1 | TFA Salt |
| 87B-22 | 4-CO₂H-4-OH-1-piperidinyl | +++ | 508.1 | TFA Salt |
| 87B-23 | 2-CO₂CH₃-4-OH-1-pyrrolidinyl (2R,4R) | +++ | 508.1 | Free Base |
| 87B-24 | 2-CO₂H-4-OH-1-pyrrolidinyl (2R,4R) | +++ | 494.1 | TFA Salt |

Example 88

5-[({[5-(3-methyl-5-{[4-(trifluoromethyl)pyrimidin-2-yl]amino}phenyl)-1,3-thiazol-2-yl]-methyl}amino)methyl]pyrrolidin-2-one

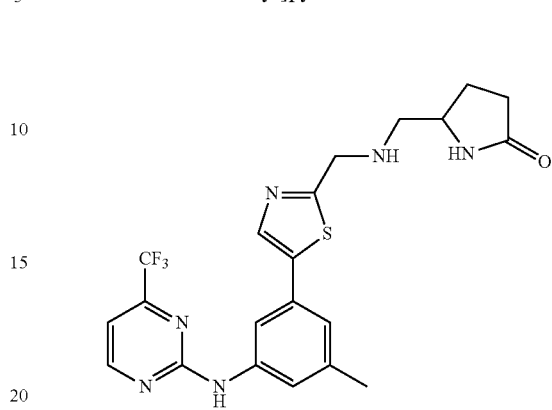

Step 1

To a flask was added tetrahydrofuran (60 mL) and the solution was cooled to −78° C. Lithium diisopropylamide (19.8 mL, 35.7 mmol) was added and the mixture was allowed to cool to −78° C. INTERMEDIATE 4 (4.0 g, 11.90 mmol) was dissolved in THF (60 mL) and added in portion. The solution was stirred for 30 minutes. DMF (1.30 g, 17.84 mmol) was dissolved in THF (60 mL) and added over a period of five minutes. The solution was then allowed to warm to room temperature. The reaction mixture was then diluted with ethyl acetate, washed with saturated ammonium chloride, dried over magnesium sulfate, filtered and concentrated. The solid was purified by silica gel column chromatography to yield 5-(3-methyl-5-{[4-(trifluoromethyl)pyrimidin-2-yl]amino}phenyl)-1,3-thiazole-2-carbaldehyde (3.5 g, 81%). MS ESI: [M+H]⁺ m/z 364.8. ¹H NMR (500 MHz, DMSO-d₆) δ 10.36 (s, 1H), 9.91 (s, 1H), 8.86 (d, J=5.3, 1H), 8.57 (s, 1H), 8.19 (s, 1H), 7.54 (s, 1H), 7.38 (s, 1H), 7.31 (d, J=5.2, 1H), 2.35 (s, 3H).

Step 2

To a flask was added 4 Å molecular sieves (200 mgs) and the product from Step 1 (0.050 g, 0.14 mmol), 5-(aminomethyl)pyrrolidin-2-one (0.016 g, 0.21 mmol) and a 95:5 solution of DMF: acetic acid (1.4 mL). The mixture was stirred overnight. Resin-bound sodium cyanoborohydride (0.44 g, 0.41 mmol, 0.93 mmol/g loading) was added and the reaction was stirred for 72 hours. The mixture was filtered and purified by reverse phase HPLC (12-100% acetonitrile gradient with water over 6 minutes with 0.1% formic acid buffer) to yield 5-[({[5-(3-methyl-5-{[4-(trifluoromethyl)pyrimidin-2-yl]amino}phenyl)-1,3-thiazol-2-yl]methyl}amino)-methyl]pyrrolidin-2-one (0.016 g, 25%). MS ESI: [M+H]⁺ m/z 463.1. ¹H NMR (600 MHz, DMSO-d₆) δ 10.22 (s, 1H), 8.81 (d, J=5.2, 1H), 7.96 (s, 2H), 7.61 (s, 1H), 7.42 (s, 1H), 7.26 (d, J=5.1, 1H), 7.14 (s, 1H), 4.03 (s, 2H), 3.63 (s, 1H), 2.74-2.53 (m, 1H), 2.47 (m, 1H), 2.29 (s, 3H), 2.20-1.98 (m, 3H), 1.80-1.59 (m, 1H). rhSYK activity=+++

The following examples were prepared in an analogous manner of that described in Example 88. In cases where the reductive amination was carried out with a ketone, the reaction was heated to 80° C. after the addition of sodium cyanoborohydride (step 2).

TABLE 88A

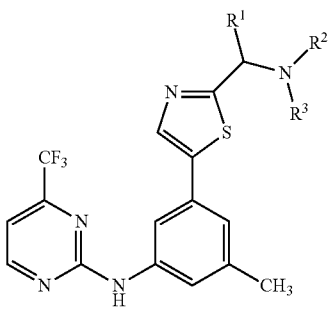

| Example | R¹ | R²/R³ | rhSYK Activity | [M + H]+ Observed | Form(s) |
|---|---|---|---|---|---|
| 88A-1 | H | H/5-Pyrimidinyl | +++ | 444.1 | Formate Salt |
| 88A-2 | H | H/—CH$_2$CH(OH)CHF$_2$ | +++ | 460.1 | Formate Salt |
| 88A-3 | H | H/—CH$_2$-(3-oxo-2,4-dihydro-1,2,4-triazol-5-yl) | +++ | 463.1 | Formate Salt |
| 88A-4 | H | CH$_3$/—CH$_2$-(3-oxo-2,4-dihydro-1,2,4-triazol-5-yl) | +++ | 477.1 | Formate Salt |
| 88A-5 | H | H/3-tetrahydrothienyl 1,1-dioxide | +++ | 484.1 | Formate Salt |
| 88A-6 | H | H/—CH$_2$-(3-Me-3-oxetanyl) | +++ | 450.1 | Formate Salt |
| 88A-7 | H | CH$_3$/—CH(cPr)$_2$ | +++ | 474.1 | Formate Salt |
| 88A-8 | H | H/—CH$_2$C(=CH$_2$)F | +++ | 424.1 | Formate Salt |
| 88A-9 | H | H/—CH(CH$_3$)-2-pyridyl | +++ | 471.1 | Formate Salt |
| 88A-10 | H | H/1-iPr-1,2,3-4-triazolyl | +++ | 475.1 | Formate Salt |
| 88A-11 | H | H/—CH$_2$CH$_2$SO$_2$NH$_2$ | +++ | 473.1 | Formate Salt |
| 88A-12 | H | CH$_3$/—CH$_2$CH$_2$OH | +++ | 424.1 | Formate Salt |
| 88A-13 | H | —CH$_2$CH$_2$OH/—CH$_2$CH$_2$OH | +++ | 454.1 | Formate Salt |
| 88A-14 | H | H/—C(CH$_2$OH)$_2$CH$_3$ | +++ | 454.1 | Formate Salt |
| 88A-15 | H | H/CH(CH$_2$OH)CH$_3$ | +++ | 424.1 | Formate Salt |
| 88A-16 | H | H/CH(CH$_2$OH)Et | +++ | 438.1 | Formate Salt |
| 88A-17 | H | H/—CH$_2$CH(OH)CH$_3$ | +++ | 424.1 | Formate Salt |
| 88A-18 | H | H/—CH$_2$CH$_2$OH | +++ | 410.1 | Formate Salt |
| 88A-19 | H | H/—(CH$_2$)$_3$OH | +++ | 424.1 | Formate Salt |
| 88A-20 | H | H/—(CH$_2$)$_4$OH | +++ | 438.1 | Formate Salt |
| 88A-21 | H | H/1-CO$_2$H—cPr | +++ | 450.1 | Formate Salt |
| 88A-22 | H | H/—CH$_2$CONH$_2$ | +++ | 423.1 | Formate Salt |
| 88A-23 | H | H/—CH$_2$CH$_2$CONH$_2$ | +++ | 437.1 | Formate Salt |
| 88A-24 | H | H/—CH$_2$CH$_2$SO$_2$CH$_3$ | +++ | 472.0 | Formate Salt |
| 88A-25 | H | CH$_3$/—CH$_2$CH$_2$SO$_2$CH$_3$ | +++ | 486.1 | Formate Salt |
| 88A-26 | H | H/1-Et-1,2,3-triazol-4-yl | +++ | 461.1 | Formate Salt |
| 88A-27 | H | H/1-CO$_2$H—cBu | +++ | 464.1 | Formate Salt |
| 88A-28 | H | CH$_3$/—CH$_2$CH(OH)CH$_2$OH | +++ | 454.1 | Formate Salt |
| 88A-29 | H | H/2-oxo-3-azepanyl | +++ | 477.2 | Formate Salt |
| 88A-30 | H | H/CH$_2$CH$_2$-(3-oxo-1-piperazinyl) | +++ | 492.1 | TFA Salt |
| 88A-31 | H | H/—CH$_2$CH$_2$SO$_2$NHCH$_3$ | +++ | 487.1 | TFA Salt |
| 88A-32 | H | H/3-CO$_2$H-5-pyrazolyl | +++ | 476.1 | TFA Salt |
| 88A-33 | H | H/—CH$_2$C(CH$_3$)$_2$OH | +++ | 438.1 | TFA Salt |
| 88A-34 | H | H/1-(CH$_2$CH$_2$OH)-3-Me-5-pyrazolyl | +++ | 490.1 | TFA Salt |
| 88A-35 | H | H/2-oxo-3-pyrrolidinyl | +++ | 448.7 | Free Base |
| 88A-36 | H | H/2-oxo-4-pyrrolidinyl | +++ | 448.7 | Free Base |
| 88A-37 | CH$_3$ | H/2-oxo-3-pyrrolidinyl | +++ | 463.1 | Free Base |
| 88A-38 | CH$_3$ | CH$_3$/CH$_3$ | +++ | 408.1 | Free Base |
| 88A-39 | CH$_3$ | H/2-oxo-4-pyrrolidinyl | +++ | 463.1 | Free Base |
| 88A-40 | H | H/H | +++ | 366.2 | Free Base |
| 88A-41 | H | H/CH$_2$CH(OH)CH$_2$OH | +++ | 440.1 | TFA Salt |
| 88A-42 | H | H/CH$_2$CH$_2$OCH$_2$CH$_2$OH | +++ | 454.1 | TFA Salt |
| 88A-43 | H | H/CH(CH$_2$OH)CH(OH)CH$_3$ (Enantiomer 1) | +++ | 454.1 | TFA Salt |
| 88A-44 | H | H/CH(CH$_2$OH)CH(OH)CH$_3$ (Enantiomer 2) | +++ | 454.1 | TFA Salt |
| 88A-45 | H | H/C(CH$_3$)$_2$CH$_2$CH(OH)CH$_3$ | +++ | 466.2 | TFA Salt |
| 88A-46 | H | H/CH$_2$-(3-CH$_2$OH)-3-oxetanyl | +++ | 466.1 | TFA Salt |
| 88A-47 | H | H/C(CH$_2$OH)$_3$ | +++ | 470.1 | TFA Salt |
| 88A-48 | H | CH$_3$/CH$_2$-2-dioxanyl | +++ | 480.1 | TFA Salt |

TABLE 88A-continued

| Example | R¹ | R²/R³ | rhSYK Activity | [M + H]+ Observed | Form(s) |
|---|---|---|---|---|---|
| 88A-49 | H | H/CH$_2$-(4-CH$_2$OH)-4-tetrahydropyranyl | +++ | 494.2 | TFA Salt |
| 88A-50 | H | H/CH$_2$CH$_2$-(1-Me-4-OH)-4-piperidinyl | +++ | 507.1 | TFA Salt |
| 88A-51 | H | H/(CH$_2$)$_3$N(CH$_2$CH$_2$OH)$_2$ | +++ | 511.2 | TFA Salt |
| 88A-52 | H | CH$_3$CH$_2$OH/CH$_2$CH$_2$SO$_3$H | +++ | 518.1 | TFA Salt |
| 88A-53 | H | H/(4-OH)-3-tetrahydrofuranyl | +++ | 452.1 | TFA Salt |
| 88A-54 | H | CH$_3$/(4-OH)-3-tetrahydrofuranyl (S,R) | +++ | 466.1 | TFA Salt |
| 88A-55 | H | H/2-CH$_2$OH-1-CH$_3$-cHex | +++ | 492.2 | TFA Salt |
| 88A-56 | H | H/3-CH$_2$OH-7-oxobicyclo[2.2.1]-hept-2-yl | +++ | 492.1 | TFA Salt |
| 88A-57 | H | H/(4-OH)-3-tetrahydrothienyl 1,1-dioxide | +++ | 500.1 | TFA Salt |
| 88A-58 | H | Et/(4-OH)-3-tetrahydrothienyl 1,1-dioxide | +++ | 528.1 | TFA Salt |
| 88A-59 | H | CH$_2$CH$_2$OH/3-tetrahydrothienyl 1,1-dioxide | +++ | 528.1 | TFA Salt |
| 88A-60 | H | CH$_2$CH$_2$OH/(4-OH)-3-tetrahydrothienyl 1,1-dioxide | +++ | 544.1 | TFA Salt |
| 88A-61 | H | H/C(O)NHCH$_3$ | +++ | 423.2 | Free Base |
| 88A-62 | H | H/C(O)NHCH$_2$CH$_3$ | +++ | 437.1 | Free Base |
| 88A-63 | H | H/C(O)NHCH(CH$_3$)$_2$ | +++ | 451.1 | Free Base |
| 88A-64 | H | H/C(O)NHCH(CH$_3$)CO$_2$Et | +++ | 509.2 | Free Base |

TABLE 88B

| Example | R¹ | rhSYK Activity | [M + H]+ Observed | Form(s) |
|---|---|---|---|---|
| 88B-1 | 3-Me-3-OH-1-piperidinyl | +++ | 464.1 | Formate Salt |
| 88B-2 | 3-Me-3-OH-1-pyrrolidinyl | +++ | 450.2 | Formate Salt |
| 88B-3 | 4-thiomorpholinyl S-oxide | +++ | 468.1 | Formate Salt |
| 88B-4 | N-(1,4-thiazepanyl) SO | +++ | 482.1 | Formate Salt |
| 88B-5 | 4-Me-4-OH-1-piperidyl | +++ | 464.1 | Formate Salt |
| 88B-6 | 4-acetyl-1-piperazinyl | +++ | 477.2 | Formate Salt |
| 88B-7 | 4-methyl-1,4-diazepanyl | +++ | 463.1 | Formate Salt |
|  | 3-oxo-1-piperazinyl | +++ | 449.1 | Formate Salt |
| 88B-8 | 3-oxo-1,4-diazepanyl | +++ | 463.1 | Formate Salt |
| 88B-9 | 4-(SO$_2$CH$_3$)-1-piperazinyl | +++ | 513.1 | TFA Salt |
| 88B-10 | 3-C(O)NH$_2$-1-piperidinyl | +++ | 477.1 | TFA Salt |

TABLE 88B-continued

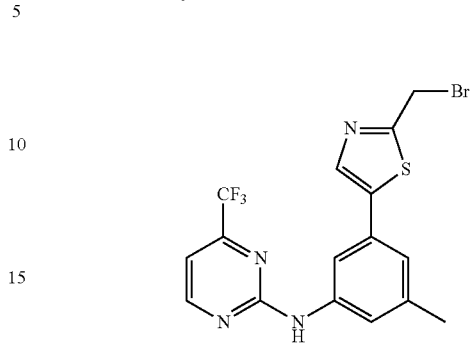

| Example | R¹ | rhSYK Activity | [M + H]+ Observed | Form(s) |
|---|---|---|---|---|
| 88B-11 | 2-(CH$_2$CH$_2$OH)-4-morpholinyl | +++ | 480.1 | TFA Salt |
| 88B-12 | 2-(CH$_2$OH)-1,4-oxazepan-4-yl | +++ | 480.1 | TFA Salt |
| 88B-13 | 2-(CH$_2$OCH$_3$)-4-morpholinyl | +++ | 480.1 | TFA Salt |
| 88B-14 | 2-(CH$_2$CO$_2$H)-4-morpholinyl | +++ | 494.2 | TFA Salt |
| 88B-15 | 3-(P(O)(OH)$_2$)-1-pyrrolidinyl | +++ | 500.1 | TFA Salt |
| 88B-16 | 3-(CH$_2$OP(O)(CH$_3$)$_2$)-1-azetidinyl | +++ | 512.1 | TFA Salt |
| 88B-17 | 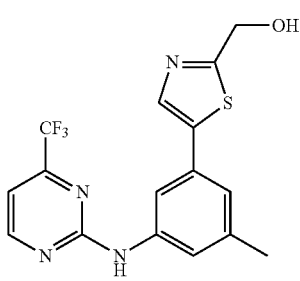 | +++ | 510.1 | TFA Salt |

Examples 89

[5-(3-methyl-5-{[4-(trifluoromethyl)pyrimidin-2-yl]amino}phenyl)-1,3-thiazol-2-yl]methanol

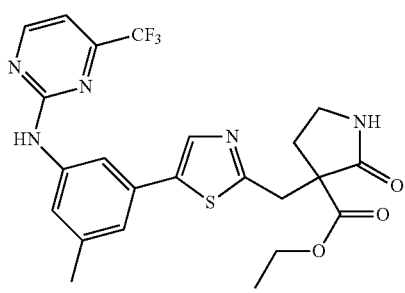 [SMILES: CCOC(=O)C1(Cc2ncc(-c3cc(C)cc(Nc4nccc(C(F)(F)F)n4)c3)s2)CCNC1=O]

To 5-(3-methyl-5-{[4-(trifluoromethyl)pyrimidin-2-yl]amino}phenyl)-1,3-thiazole-2-carbaldehyde (Example 88, Step 1, 0.15 g, 0.41 mmol) was added methanol (4 mL) and sodium borohydride (0.016 g, 0.41 mmol). Once complete, the reaction was diluted with ethyl acetate, washed carefully with aqueous saturated ammonium chloride, dried over magnesium sulfate, filtered and concentrated. The crude product was purified by silica gel column chromatography to yield [5-(3-methyl-5-{[4-(trifluoromethyl)pyrimidin-2-yl]amino}phenyl)-1,3-thiazol-2-yl]methanol (0.13 g, 85%). MS ESI: [M+H]$^+$ m/z 366.7. $^1$H NMR (500 MHz, DMSO-d$_6$) δ 10.26 (s, 1H), 8.83 (d, J=4.8, 1H), 7.98 (s, 2H), 7.45 (s, 1H), 7.28 (d, J=4.9, 1H), 7.17 (s, 1H), 6.10 (t, J=5.8, 1H), 4.71 (d, J=5.8, 2H), 2.31 (s, 3H). rhSYK activity=+++

Examples 90

N-{3-[2-(bromomethyl)-1,3-thiazol-5-yl]-5-methylphenyl}-4-(trifluoromethyl)pyrimidin-2-amine To [5-(3-methyl-5-{[4-(trifluoromethyl)pyrimidin-2-yl]amino}phenyl)-1,3-thiazol-2-yl]methanol (0.13 g, 0.34 mmol) was added dichloromethane (3.5 mL) and triphenylphosphine (0.11 g, 0.41 mmol). The solution was cooled to 0° C. and n-bromosuccinimide (0.067 g, 0.38 mmol) was added and the reaction was allowed to warm slowly to room temperature. Once the reaction was complete, silica gel (1.3 g) was added and the slurry was concentrated. The solid was purified by silica gel chromatography to yield N-{3-[2-(bromomethyl)-1,3-thiazol-5-yl]-5-methylphenyl}-4-(trifluoromethyl)pyrimidin-2-amine (0.072 g, 49%). MS ESI: [M+H]$^+$ m/z 430.9. $^1$H NMR (500 MHz, DMSO-d$_6$) δ 10.29 (s, 1H), 8.84 (d, J=4.9, 1H), 8.07 (s, 1H), 7.99 (s, 1H), 7.49 (s, 1H), 7.29 (d, J=4.9, 1H), 7.21 (s, 1H), 5.04 (s, 2H), 2.32 (s, 3H). rhSYK activity=+++

Example 91

Ethyl 3-{[5-(3-methyl-5-{[4-(trifluoromethyl)pyrimidin-2-yl]amino}phenyl)-1,3-thiazol-2-yl]-methyl}-2-oxopyrrolidine-3-carboxylate To sodium hydride in mineral oil (60%, 0.007 g, 0.33 mmol) was added tetrahydrofuran (1.8 mL) and the suspension was cooled to 0° C. Ethyl 2-oxopyrrolidine-3-carboxylate (0.044 g, 0.28 mmol) was added and the solution was stirred for 15 minutes. N-{3-[2-(bromomethyl)-1,3-thiazol-5-yl]-5-methylphenyl}-4-(trifluoromethyl)pyrimidin-2-amine (0.100 g, 0.23 mmol) was dissolved in tetrahydrofuran (1.8 mL) and then added to the flask. The reaction was allowed to warm to room temperature overnight. The reaction was diluted with ethyl acetate, washed carefully with water, dried over magnesium sulfate, filtered and concentrated. The solid was purified by silica gel chromatography to yield ethyl 3-{[5-(3-methyl-5-{[4-(trifluoromethyl)-pyrimidin-2-yl]amino}phenyl)-1,3-thiazol-2-yl]methyl}-2-oxopyrrolidine-3-carboxylate (0.03 g, 27% yield). MS ESI: [M+H]+ m/z 505.7. 1H NMR (500 MHz, DMSO-d6) δ 10.26 (s, 1H), 8.83 (d, J=5.2, 1H), 8.11 (s, 1H), 8.02-7.84 (m, 2H), 7.47 (s, 1H), 7.28 (d, J=5.2, 1H), 7.14 (s, 1H), 4.11 (q, J=7.4, 2H), 3.58 (m 1H), 3.28-3.21 (m, 2H), 3.15-3.03 (m, 1H), 2.66-2.54 (m, 1H), 2.31 (s, 3H), 2.27-2.16 (m, 1H), 1.15 (t, J=7.3, 3H). rhSYK activity=+++

Example 92

3-{[5-(3-methyl-5-{[4-(trifluoromethyl)pyrimidin-2-yl]amino}phenyl)-1,3-thiazol-2-yl]methyl}-2-oxopyrrolidine-3-carboxylic acid

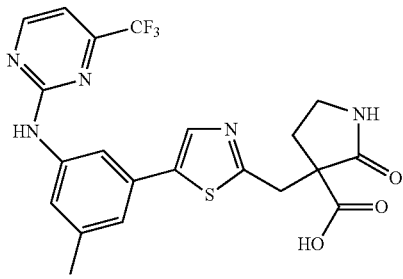 [SMILES: Cc1cc(Nc2nccc(C(F)(F)F)n2)cc(-c2cnc(CC3(C(=O)O)CCNC3=O)s2)c1]

To ethyl 3-{[5-(3-methyl-5-{[4-(trifluoromethyl)pyrimidin-2-yl]amino}phenyl)-1,3-thiazol-2-yl]methyl}-2-oxopyrrolidine-3-carboxylate (0.032 g, 0.063 mmol) was added tetrahydrofuran (0.3 mL), methanol (0.16 mL) and water (0.16 mL). Lithium hydroxide (0.003 g, 0.13 mmol) was added and the reaction was stirred at room temperature. Once complete, the reaction was diluted with ethyl acetate, washed with hydrochloric acid (1N in water), dried over magnesium sulfate, filtered and concentrated to yield 3-{[5-(3-methyl-5-{[4-(trifluoromethyl)pyrimidin-2-yl]amino}phenyl)-1,3-thiazol-2-yl]methyl}-2-oxopyrrolidine-3-carboxylic acid (0.02 g, 66%) without further purification. MS ESI: [M+H]+ m/z 477.7. 1H NMR (500 MHz, CD3OD) δ 8.71 (d, J=5.2, 1H), 7.97 (s, 1H), 7.89 (s, 1H), 7.45 (s, 1H), 7.16-6.98 (m, 2H), 3.67 (m, 1H), 3.54-3.39 (m, 2H), 3.24-3.13 (m, 1H), 2.70-2.52 (m, 1H), 2.36 (s, 3H), 2.00 (d, J=10.4, 1H). rhSYK activity=+++

The following examples were prepared in an analogous manner of that described in Examples 89-92.

TABLE 92

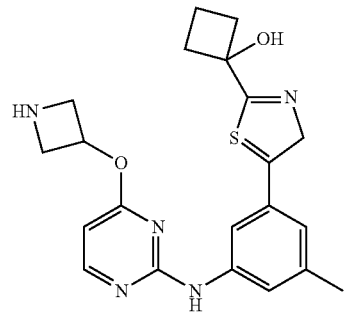

| Example | R | rhSYK Activity | [M + H]+ Observed | Form(s) |
|---|---|---|---|---|
| 92-1 | 2-oxo-3-oxazolidinyl | +++ | 435.7 | Free Base |
| 92-2 | 2-oxo-1-pyrrolidinyl | +++ | 433.8 | Free Base |
| 92-3 | 3-Me-2-oxo-1-imidazolidinyl | +++ | 448.7 | Free Base |

Example 93

1-[5-(3-{[4-(azetidin-3-yloxy)pyrimidin-2-yl]amino}-5-methylphenyl)-1,3-thiazol-2-yl]cyclobutanol Step 1

A flask was charged with a solution of 2,4-dichloropyrimidine (300 mg, 2.0 mmol) in N,N-dimethylformamide (10 mL). tert-Butyl 3-hydroxyazetidine-1-carboxylate (349 mg, 2.0 mmol) and cesium carbonate (1.11 g, 3.42 mmol) were added and the resulting mixture was heated to 80° C. for 2 h. Upon completion, the mixture was diluted with ethyl acetate (20 mL) and washed with 1:1 water:brine (3×40 mL). The organic extracts were dried over sodium sulfate, filtered, and concentrated under reduced pressure. Purification by Chromatography on silica gel (0-80% ethyl acetate in hexanes) afforded tert-butyl 3-[(2-chloropyrimidin-4-yl)oxy]azetidine-1-carboxylate (550 mg, 1.9 mmol, 96%). MS ESI: [M+H]+ m/z 286.1.

Step 2

An oven-dried, cooled, 5 mL microwave vial was charged with INTERMEDIATE 15 (150 mg, 0.58 mmol), cesium carbonate (340 mg, 1.1 mmol), tert-butyl 3-[(2-chloropyrimidin-4-yl)oxy]azetidine-1-carboxylate (150 mg, 0.53 mmol), and dioxane (2.6 mL). The system was purged and flushed with argon (3×) and then XantPhos (46 mg, 0.079 mmol) and palladium(II) acetate (13 mg, 0.058 mmol) were added. The system was then purged and flushed with argon (3×) before sealing and heating to 90° C. for 3 b. Upon completion, the mixture was cooled to room temperature, filtered through celite, and concentrated under reduced pressure. Purification by Chromatography on silica gel (0-60% ethyl acetate in hexanes) provided tert-butyl 3-{[2-({3-[2-(1-hydroxycyclobutyl)-1,3-thiazol-5-yl]-5-methylphenyl}amino)pyrimidin-4-yl]oxy}azetidine-1-carboxylate (200 mg, 0.39 mmol, 75%) as a yellow oil. MS ESI: [M+H]+ m/z 509.8.

Step 3

To a solution of the product from Step 2 (200 mg, 0.39 mmol) in dichloromethane (1.5 mL) was added trifluoroacetic acid (0.49 mL). The mixture was stirred for 1 h at room temperature and then concentrated under reduced pressure. The resulting residue was taken up in dichloromethane and washed with saturated aqueous sodium bicarbonate. The organic layer was dried over sodium sulfate, filtered, and concentrated under reduced pressure to afford 1-[5-(3-{[4-

(azetidin-3-yloxy)pyrimidin-2-yl]amino}-5-methylphenyl)-1,3-thiazol-2-yl]cyclobutanol (158 mg, 0.39 mmol, 98%) as a pale-yellow foam. MS ESI: [M+H]$^+$ m/z 409.8. $^1$H NMR (500 MHz, DMSO-d$_6$) δ 9.53 (s, 1H), 8.23 (d, J=5.6, 1H), 7.98 (s, 1H), 7.80 (s, 1H), 7.52 (s, 1H), 7.09 (s, 1H), 6.64-6.52 (m, 1H), 6.29 (d, J=5.6, 1H), 5.55-5.36 (m, 1H), 3.76 (dd, J=6.7, 9.7, 2H), 3.58-3.45 (m, 2H), 2.56-2.49 (m, 3H), 2.37-2.20 (m, 5H), 1.87 (dt, J=7.0, 10.0, 2H). rhSYK activity=+++

Example 94

1-[5-(3-methyl-5-{[4-(oxetan-3-yloxy)pyrimidin-2-yl]amino}phenyl)-1,3-thiazol-2-yl]cyclobutanol

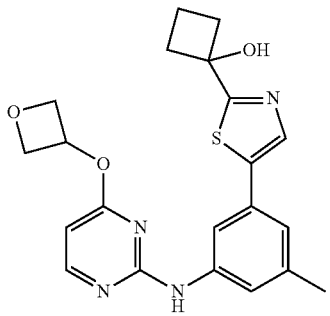 [SMILES: Cc1cc(Nc2nccc(OC3COC3)n2)cc(-c2cnc(C3(O)CCC3)s2)c1]

Step 1

To a suspension of oxetan-3-ol (100 mg, 1.35 mmol) in tetrahydrofuran (1 mL) and N,N-dimethylformamide (1 mL) was added 60% sodium hydride in mineral oil (81 mg, 2.03 mmol). The mixture was stirred for 30 minutes at room temperature. The reaction was then cooled to 0° C. and a solution of 2,4-dichloropyrimidine (300 mg, 2.03 mmol) in tetrahydrofuran (1 mL) and N,N'-dimethylformamide (1 mL) was added. The mixture was warmed to room temperature and stirred for 24 h. The reaction was then diluted with ethyl acetate (20 mL) and washed with 1:1 water:brine (3×40 mL). The organic extracts were dried over sodium sulfate, filtered, and concentrated under reduced pressure. The resulting residue was purified by Chromatography on silica gel (10-60% ethyl acetate in hexanes) to afford 2-chloro-4-(oxetan-3-yloxy)pyrimidine (91 mg, 0.49 mmol, 36% yield) as a white solid. MS ESI: [M+H]$^+$ m/z 186.8.

Step 2

To INTERMEDIATE 15 (140 mg, 0.53 mmol) in an oven-dried, cooled 5 mL vial was added dioxane (2.4 mL), cesium carbonate (320 mg, 0.97 mmol), and the product of Step 1 (91 mg, 0.49 mmol). The system was purged and flushed with argon (3×) before adding XantPhos (42 mg, 0.073 mmol) and palladium(II) acetate (12 mg, 0.053 mmol). The system was purged and flushed with argon (3×) before sealing and heating to 100° C. The reaction was stirred for 4.5 h, cooled to room temperature, filtered through celite and concentrated. The resulting residue was purified by Chromatography on silica gel (10-60% ethyl acetate in hexanes) to afford 1-[5-(3-methyl-5-{[4-(oxetan-3-yloxy)pyrimidin-2-yl]amino}phenyl)-1,3-thiazol-2-yl]cyclobutanol (130 mg, 0.32 mmol, 66%) as a pale yellow foam. MS ESI: [M+H]$^+$ m/z 410.8. $^1$H NMR (500 MHz, d$_6$-DMSO) δ 9.55 (s, 1H), 8.26 (d, J=5.5 Hz, 1H), 8.00 (s, 1H), 7.72 (s, 1H), 7.48 (s, 1H), 7.10 (s, 1H), 6.51 (s, 1H), 6.37 (d, J=5.5 Hz, 1H), 5.65 (m, 1H), 4.85 (m, 2 FT), 4.58 (m, 2H), 2.53 (m, 2H), 2.33 (m, 2H), 2.32 (s, 3H), 1.88 (m, 2H). rhSyk activity=+++

The following examples were prepared in an analogous manner of that described in Examples 93 and 94. Compounds that do not require a BOC-deprotection were made by omitting step 3 in Example 93.

TABLE 94A

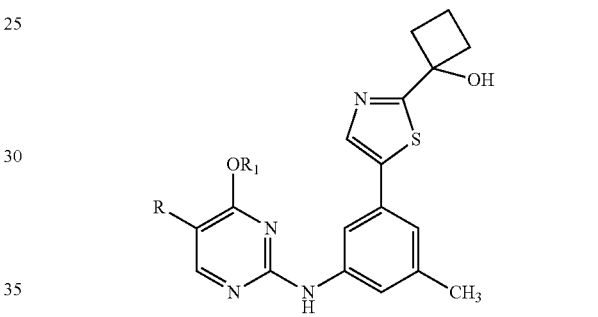

| Example | R | R$^1$ | rhSYK Activity | [M + H]+ Observed | Form(s) |
|---|---|---|---|---|---|
| 94A-1 | H | —CH$_2$-4-pyridyl | +++ | 446.1 | Free Base |
| 94A-2 | H | —CH$_2$-3-pyridyl | +++ | 446.1 | Free Base |
| 94A-3 | H | —CH$_2$-2-pyridyl | +++ | 446.2 | Free Base |
| 94A-4 | H | —CH$_2$-1,4-dioxan-2-yl | +++ | 455.1 | Free Base |
| 94A-5 | H | —CH$_2$CH$_2$-4-tetrahydropyranyl | +++ | 467.2 | Free Base |
| 94A-6 | F | 3-tetrahydrofuranyl | ++ | 443.2 | Free Base |
| 94A-7 | H | —CH$_2$-4-tetrahydropyranyl | +++ | 453.2 | Free Base |
| 94A-8 | H | (3R) 3-tetrahydrofuranyl | +++ | 425.1 | Free Base |
| 94A-9 | H | —(CH$_2$)$_2$OCH$_2$Ph | ++ | 489.2 | Free Base |
| 94A-10 | H | (3S) 3-tetrahydrofuranyl | +++ | 425.1 | Free Base |
| 94A-11 | H | —(CH$_2$)$_4$—OCH$_2$Ph | ++ | 517.2 | Free Base |
| 94A-12 | H | —(CH$_2$)$_3$—OCH$_3$ | +++ | 427.2 | Free Base |
| 94A-13 | H | —(CH$_2$)$_3$—OCH$_2$—Ph | ++ | 503.2 | Free Base |
| 94A-14 | H | —(CH$_2$)$_2$—OCH$_3$ | +++ | 413.1 | Free Base |
| 94A-15 | H | —CH$_2$-(3-tetrahydrofuranyl) | +++ | 438.8 | Free Base |
| 94A-16 | H | 4-CO$_2$Et—cHex | ++ | 508.8 | Free Base |
| 94A-17 | H | 4-tetrahydropyranyl | +++ | 438.8 | Free Base |
| 94A-18 | H | 4-NH$_2$—cHex | +++ | 452.2 | Free Base |
| 94A-19 | H | 3-NH$_2$-8-oxa-bicyclo[3.2.1]oct-6-yl | +++ | 480.2 | Free Base |
| 94A-20 | H | 7-Me-azepan-4-yl | +++ | 466.2 | Free Base |
| 94A-21 | H | azepan-4-yl | +++ | 452.2 | Free Base |
| 94A-22 | H | (2R)-CH(CH$_3$)CO$_2$H | ++ | 427.2 | Free Base |
| 94A-23 | H | —CH$_2$HC$_2$NHCH$_3$ | ++ | 412.2 | Free Base |
| 94A-24 | H | —CH$_2$-4-piperidinyl | ++ | 452.2 | Free Base |
| 94A-25 | H | —C(CH$_3$)$_2$CO$_2$tBu | ++ | 497.3 | Free Base |
| 94A-26 | H | 3-piperidinyl | +++ | 438.2 | Free Base |
| 94A-27 | H | —CH$_2$-3-azetidinyl | +++ | 423.8 | Free Base |
| 94A-28 | H | 3-azetidinyl | +++ | 409.8 | Free Base |
| 94A-29 | H | 3-tetrahydrofuranyl | +++ | 424.8 | Free Base |

TABLE 94A-continued

| Example | R | R[1] | rhSYK Activity | [M + H]+ Observed | Form(s) |
|---|---|---|---|---|---|
| 94A-30 | H | cBu | +++ | 408.8 | Free Base |
| 94A-31 | H | cPen | +++ | 422.8 | Free Base |
| 94A-32 | H | cHex | ++ | 436.8 | Free Base |
| 94A-33 | H | 4-piperidinyl | +++ | 438.1 | TFA Salt |

TABLE 94B

| Example | R[1] | R | R[3]/R[4] | rhSYK Activity | [M + H]+ Observed | Forms(s) |
|---|---|---|---|---|---|---|
| 94B-1 | —CH$_2$Ph | CH$_3$ | CF$_3$/CH$_3$ | +++ | 487.1 | Free Base |
| 94B-2 | 4-Me-4-OH—cHex | CH$_3$ | CF$_3$/CH$_3$ | +++ | 508.8 | Free Base |
| 94B-3 | 4-(OCH$_2$Ph)—cHex | CH$_3$ | CF$_3$/CH$_3$ | ++ | 584.7 | Free Base |
| 94B-4 | 3-F-4-piperidinyl (trans) | CH$_3$ | CF$_3$/CH$_3$ | +++ | 497.7 | Free Base |
| 94B-5 | 3-F-1-tBOC-4-piperidinyl (trans) | CH$_3$ | CF$_3$/CH$_3$ | + | 597.7 | Free Base |
| 94B-6 | 4-piperidinyl | CH$_3$ | CF$_3$/CH$_3$ | +++ | 480.1 | Free Base |
| 94B-7 | 3-F-4-piperdinyl (cis) | CH$_3$ | CF$_3$/CH$_3$ | +++ | 497.8 | TFA Salt |
| 94B-8 | (R) 3-pyrrolidinyl | CH$_3$ | CF$_3$/CH$_3$ | +++ | 465.8 | TFA Salt |
| 94B-9 | (S) 3-pyrrolidinyl | CH$_3$ | CF$_3$/CH$_3$ | +++ | 465.8 | TFA Salt |
| 94B-10 | 4-piperidinyl | H | H/CH$_3$ | +++ | 398.1 | Free Base |

The following compound was analogously prepared using the corresponding amine in place of an alcohol:

| Example | Structure | rhSYK Activity | [M + H]+ Observed | Form(s) |
|---|---|---|---|---|
| 94C-1 | 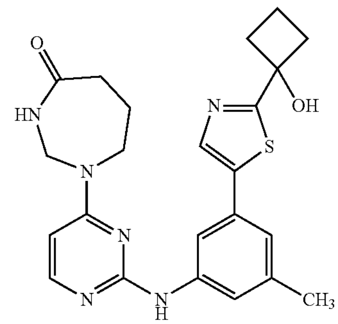 [SMILES: Cc1cc(Nc2nccc(N3CCCC(=O)NC3)n2)cc(-c2cnc(C3(O)CCC3)s2)c1] | +++ | 451.1 | Free Base |

Example 95

2-{[2-({3-[2-(1-hydroxycyclobutyl)-1,3-thiazol-5-yl]-5-methylphenyl}amino)pyrimidin-4-yl]oxy}-2-methylpropanoic acid

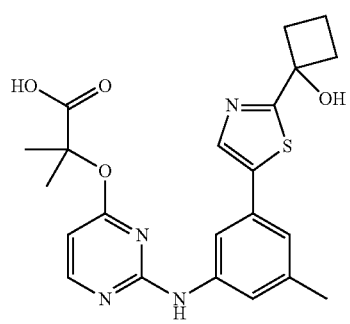 [SMILES: Cc1cc(Nc2nccc(OC(C)(C)C(=O)O)n2)cc(-c2cnc(C3(O)CCC3)s2)c1]

To tert-butyl 2-{[2-({3-[2-(1-hydroxycyclobutyl)-1,3-thiazol-5-yl]-5-methylphenyl}amino)-pyrimidin-4-yl]oxy}-2-methylpropanoate (Example 94A-25, 140 mg, 0.28 mmol) in DCM (1 mL) was added of trifluoroacetic acid (220 µL, 2.8 mmol). The mixture was aged for 2 hours and additional trifluoroacetic acid (500 µL, 6.4 mmol) was added. The reaction was stirred overnight. The reaction was concentrated under reduced pressure. Water was added and the mixture was extracted with ethyl acetate. The organic layer was dried, filtered and solvent removed under reduced pressure to afford 2-{[2-({3-[2-(1-hydroxycyclobutyl)-1,3-thiazol-5-yl]-5-methylphenyl}amino)pyrimidin-4-yl]oxy}-2-methylpropanoic acid (110 mg, 0.25 mmol, 88%) as pale yellow oil. MS ESI: [M+H]+ m/z 441.2. $^1$H NMR (600 MHz. DMSO-$d_6$): δ 9.50 (s, 1H); 8.18 (d, J=6 Hz, 1H); 7.96 (s, 1H); 7.66 (s, 1H); 7.44 (s, 1H); 7.05 (s, 1H); 6.27 (d, J=6 Hz, 1H); 2.52-2.27 (m, 4H); 2.46 (s, 3H); 1.86 (s, 2H); 1.66 (s, 6H). rhSYK activity=++

Example 96

4-{[2-({3-methyl-5-[2-(1,1,1-trifluoro-2-hydroxypropan-2-yl)-1,3-thiazol-5-yl]phenyl}amino)-pyrimidin-4-yl]oxy}cyclohexanol

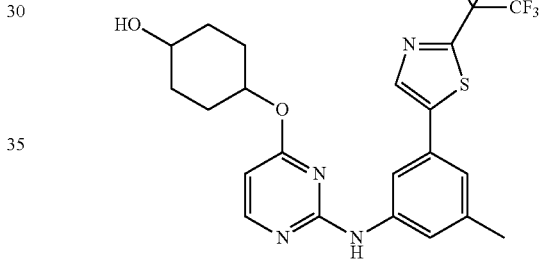

To 2-(5-{3-[(4-{[4-(benzyloxy)cyclohexyl]oxy}pyrimidin-2-yl)amino]-5-methylphenyl}-1,3-thiazol-2-yl)-1,1,1-trifluoropropan-2-ol (Example 94B-3, 0.12 g, 0.21 mmol) was added methanol (0.70 mL) and concentrated hydrochloric acid (6.2 µL, 0.21 mmol). The solution was evacuated and then purged with argon 5 times. 10% Palladium on carbon (0.002 g) was added and the solution was evacuated and then purged with argon 3 times. A balloon filled with hydrogen was placed on top of the reaction and the reaction was evacuated and then backfilled with hydrogen 3 times. The reaction was stirred for four hours. The solution was then filtered carefully through celite. The filtrate was concentrated and purified by reverse phase HPLC (10-100% acetonitrile gradient with water over 12 minutes with a 0.05% trifluoroacetic acid buffer) to afford 4-{[2-({3-methyl-5-[2-(1,1,1-trifluoro-2-hydroxypropan-2-yl)-1,3-thiazol-5-yl]phenyl}amino)pyrimidin-4-yl]oxy}cyclohexanol (30 mg, 0.06 mmol, 30%) as a 60:40 mixture of diastereomers. MS ESI: [M+H]+ m/z 494.7. The following NMR data for the major isomer: $^1$H NMR (500 MHz, DMSO-$d_6$) δ 9.52 (s, 1H), 8.22-8.15 (m, 1H), 8.08 (s, 1H), 7.74 (s, 1H), 7.68-7.60 (m, 2H), 7.11 (s, 1H), 6.31-6.13 (m, 1H), 5.08-4.93 (m, 1H), 4.65-4.53 (m, 1H), 3.54-3.42 (m, 1H), 2.33 (s, 3H), 2.09-1.98 (m, 1H), 1.91-1.72 (m, 5H), 1.59-1.37 (m, 2H), 1.32-1.19 (m, 2H), 1.12-1.03 (m, 1H). rhSYK activity=+++

Example 97

4-{[2-({3-[2-(1-hydroxycyclobutyl)-1,3-thiazol-5-yl]-5-methylphenyl}amino)pyrimidin-4-yl]oxy}cyclohexanecarboxylic acid

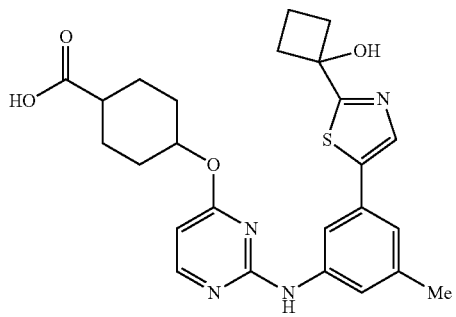 [SMILES: Cc1cc(Nc2nccc(OC3CCC(C(=O)O)CC3)n2)cc(-c2cnc(C3(O)CCC3)s2)c1]

To a solution of ethyl 4-{[2-({3-[2-(1-hydroxycyclobutyl)-1,3-thiazol-5-yl]-5-methylphenyl}-amino)pyrimidin-4-yl]oxy}cyclohexanecarboxylate (Example 94A-16, 40 mg, 0.08 mmol) in tetrahydrofuran (0.52 mL), water (0.13 mL), and methanol (0.13 mL) was added aqueous sodium hydroxide (1.0 M in H$_2$O, 0.2 mL, 0.2 mmol). The mixture was stirred at room temperature until complete. The reaction was then quenched with aqueous hydrochloric acid (1.0 M in H$_2$O, 0.22 mL, 0.22 mmol). The resulting mixture was extracted with dichloromethane. The organic layer was dried over sodium sulfate, filtered, and concentrated under reduced pressure to provide 4-{[2-({3-[2-(1-hydroxycyclobutyl)-1,3-thiazol-5-yl]-5-methylphenyl}amino)pyrimidin-4-yl]oxy}cyclohexanecarboxylic acid (37 mg, 0.08 mmol, 99%) as a pale yellow solid. MS ESI: [M+H]$^+$ m/z 480.8. $^1$H NMR (500 MHz, DMSO-d$_6$) δ 12.12 (s, 1H), 9.52 (s, 1H), 8.19 (m, 1H), 7.97 (s, 1H), 7.88 (s, 1H), 7.73-7.39 (m, 2H), 7.08 (s, 1H), 6.63-6.41 (m, 1H), 6.36-6.15 (m, 1H), 5.38-4.87 (m, 2H), 2.57-2.50 (m, 1H), 2.40-2.26 (m, 4H), 2.19-2.06 (m, 1H), 1.97-1.79 (m, 3H), 1.79-1.68 (m, 2H), 1.67-1.58 (m, 1H), 1.51-1.36 (m, 1H), 1.30-0.74 (m, 2H). rhSyk activity=+++.

Example 98

2-(5-{3-[(4-chloropyrimidin-2-yl)amino]-5-methylphenyl}-1,3-thiazol-2-yl)-1,1,1-trifluoropropan-2-ol

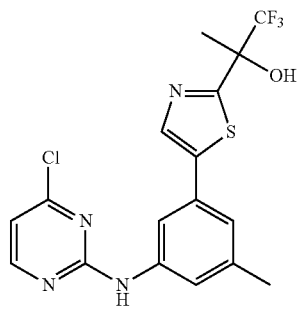 [SMILES: Cc1cc(Nc2nccc(Cl)n2)cc(-c2cnc(C(C)(O)C(F)(F)F)s2)c1]

Step 1

Palladium on carbon (10 wt %) (50 mg, 0.05 mmol) was added to a flask that was evacuated and backfilled with argon (3×). A solution of 2-[5-(3-{[4-(benzyloxy)pyrimidin-2-yl]amino}-5-methylphenyl)-1,3-thiazol-2-yl]-1,1,1-trifluoropropan-2-ol (Example 94B-1, 230 mg, 0.47 mmol) in a mixture of methanol (4 mL), ethanol (3 mL) and ethyl acetate (2 mL) was added followed by the addition of acetic acid (50 μL, 0.87 mmol). A hydrogen balloon was placed on top of the reaction and the reaction was evacuated/backfilled with hydrogen (5×). The reaction was stirred overnight at room temperature. The mixture was then filtered through celite, washing with methanol. The filtrate was concentrated under reduced pressure and purified by Chromatography on silica gel (30-100% ethyl acetate in hexanes) to provide 145 mg (0.367 mmol, 77%) of 2-({3-methyl-5-[2-(1,1,1-trifluoro-2-hydroxypropan-2-yl)-1,3-thiazol-5-yl]phenyl}amino)pyrimidin-4-ol as a white solid.

Step 2

The product of Step 1 (145 mg, 0.37 mmol) was taken up in dioxane (2 mL) and phosphorus oxychloride (1.02 mL, 11 mmol) was added. The mixture was heated at reflux for 1.5 hours. The reaction was then cooled to room temperature, poured over ice, and quenched by dropwise addition of 10 N aqueous sodium hydroxide (until pH=8). Ethyl acetate was added and the layers were separated. The aqueous layer was extracted once more with ethyl acetate. The combined organics were dried over magnesium sulfate, filtered, and concentrated under reduced pressure. The residue was purified by Chromatography on silica gel (0-50% ethyl acetate/hexanes) to afford 114 mg (0.28 mmol, 75%) of 2-(5-{3-[(4-chloropyrimidin-2-yl)amino]-5-methylphenyl}-1,3-thiazol-2-yl)-1,1,1-trifluoropropan-2-ol as a white solid. MS ESI: [M+H]$^+$ m/z 415.0. $^1$H NMR (500 MHz, DMSO-d$_6$) δ 10.10 (s, 1H), 8.47 (d, J=5 Hz, 1H), 8.08 (s, 1H), 7.88 (s, 1H), 7.67 (s, 1H), 7.50 (s, 1H), 7.17 (s, 1H), 6.99 (d, J=5 Hz, 1H), 2.32 (s, 3H), 1.76 (s, 3H). rhSYK activity=+++

Example 99

2-{[2-({3-methyl-5-[2-(1,1,1-trifluoro-2-hydroxypropan-2-yl)-1,3-thiazol-5-yl]phenyl}amino)-pyrimidin-4-yl]oxy}acetamide

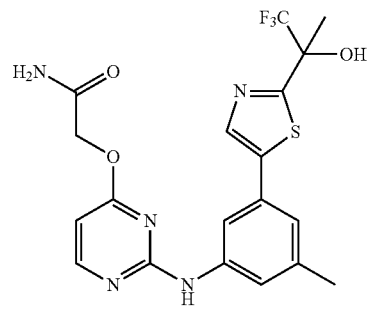 [SMILES: Cc1cc(Nc2nccc(OCC(N)=O)n2)cc(-c2cnc(C(C)(O)C(F)(F)F)s2)c1]

Step 1

Methyl hydroxyacetate (22 mg, 0.24 mmol) and 2-(5-{3-[(4-chloropyrimidin-2-yl)amino]-5-methylphenyl}-1,3-thiazol-2-yl)-1,1,1-trifluoropropan-2-ol (Example 98, 50 mg, 0.12 mmol) were taken up in N,N'-dimethylacetamide (1.2 mL). Cesium carbonate (118 mg, 0.36 mmol) was added and the mixture was stirred for 24 h at 70° C. The reaction was cooled to room temperature, quenched with saturated aqueous ammonium chloride, and extracted with ethyl acetate (2×). The combined organics were concentrated under reduced pressure and purified by reverse phase HPLC (10-80% acetonitrile/water+0.05% TEA modifier). Desired fractions were combined and lyophilized to afford {[2-({3-methyl-5-[2-(1,1,1-trifluoro-2-hydroxypropan-2-yl)-1,3-thiazol-5-yl]phenyl}amino)pyrimidin-4-yl]oxy}acetic acid (10 mg, 0.018 mmol, 15%) as the trifluoroacetic acid salt as a white solid. MS ESI: [M+H]$^+$ m/z 455.1.

Step 2

The product of Step 1 (10 mg, 0.018 mmol), N-hydroxybenzotriazole (5.4 mg, 0.035 mmol), diisopropylethylamine (31 µL, 0.18 mmol), and 1-ethyl-3-(3-dimethylaminopropyl)-carbodiimide hydrochloride (6.7 mg, 0.035 mmol) were taken-up in N,N-dimethylformamide (0.5 mL). Ammonium chloride (6.6 mg, 0.12 mmol) was added in one portion, and the resulting mixture was stirred overnight at room temperature. The resulting mixture was directly purified via reverse phase HPLC (10-80% acetonitrile/water+0.05% TEA modifier). Desired fractions were combined, diluted with ethyl acetate and washed with saturated aqueous sodium bicarbonate (1×) and 10% aqueous ammonium hydroxide (1×). The organic layer was dried over magnesium sulfate, filtered, and concentrated in vacuo to afford 2-{[2-({3-methyl-5-[2-(1,1,1-trifluoro-2-hydroxypropan-2-yl)-1,3-thiazol-5-yl]phenyl}amino)pyrimidin-4-yl]oxy}acetamide (6 mg, 0.013 mmol, 76% yield) as a white solid. MS ESI: [M+H] m/z 454.1. $^1$H NMR (500 MHz, DMSO-d$_6$) δ 9.55 (s, 1H), 8.25 (d, J=5.5 Hz, 1H), 8.07 (s, 1H), 7.70 (s, 1H), 7.68 (s, 1H), 7.64 (s, 1H), 7.49 (s, 1H), 7.31 (s, 1H), 7.09 (s, 1H), 6.35 (d, J=5.5 Hz, 1H), 4.76 (s, 2H), 2.32 (s, 3H), 1.76 (3H).

Example 100

1,1,1-trifluoro-2-(5-(3-methyl-5-[(5-methylpyrimidin-2-yl)amino]phenyl-1,3-thiazol-2-yl)propan-2-ol

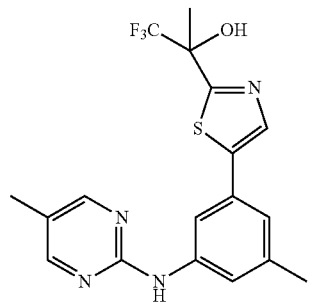

A sealed tube was charged with a stir bar, INTERMEDIATE 17 (100 mg, 0.33 mmol), 2-chloro-5-methylpyrimidine (43 mg, 0.33 mmol), potassium carbonate (91 mg, 0.66 mmol), Pd$_2$dba$_3$ (30 mg, 0.033 mmol), and X-PHOS (79 mg, 0.17 mmol). The tube was evacuated and backfilled with argon three times. Fully degassed t-amyl alcohol (1.1 mL) was added, the tube was sealed, and heated at 90° C. for overnight. Upon completion the mixture was cooled to room temperature, diluted with methanol, and filtered through a celite plug. The filtrate was concentrated under reduced pressure. Purification by Chromatography on silica gel (0-50% ethyl acetate/hexanes) afforded 1,1,1-trifluoro-2-(5-{3-methyl-5-[(5-methylpyrimidin-2-yl)amino]phenyl}-1,3-thiazol-2-yl)propan-2-ol (90 mg, 0.23 mmol, 69%) as an off-white solid. MS ESI: [M+H]$^+$ m/z 395.1. $^1$H NMR (500 MHz, DMSO-d$_6$): δ 9.53 (s, 1H), 8.37 (s, 2H), 8.07 (s, 1H), 7.90 (s, 1H), 7.66 (s, 1H), 7.55 (s, 1H), 7.08 (s, 1H), 2.30 (s, 3H), 2.14 (s, 3H), 1.76 (s, 3H). rhSYK activity=+++

The following examples were prepared in an analogous manner of that described in Example 100.

TABLE 100A

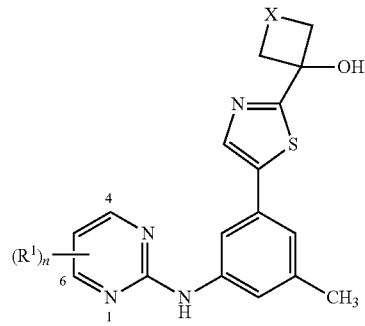

n is 1 or 2 substituents as specified in the Table, or (R$^1$)$_n$ is H, or (R$^1$)$_n$ together with the pyrimidine ring represent 6,7-dihydro-5H-cyclopenta[d]pyrimidine

| Example | R$^1$ | X | rhSYK Activity | [M + H]+ Observed | Form(s) |
|---|---|---|---|---|---|
| 100A-1 | 4-OCH$_3$ | CH$_2$ | +++ | 369.1 | Free Base |
| 100A-2 | 4-CH$_3$ | CH$_2$ | +++ | 353.1 | Free Base |

TABLE 100A-continued

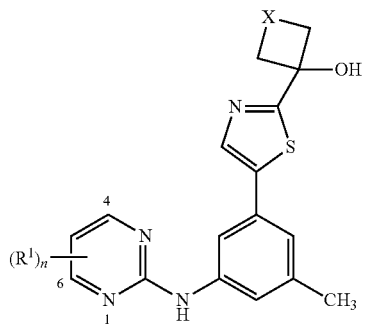

n is 1 or 2 substituents as specified in the Table, or $(R^1)_n$ is H, or $(R^1)_n$ together with the pyrimidine ring represent 6,7- dihydro-5H-cyclopenta[d]pyrimidine

| Example | $R^1$ | X | rhSYK Activity | [M + H]+ Observed | Form(s) |
|---|---|---|---|---|---|
| 100A-3 | H | $CH_2$ | ++ | 338.8 | Free Base |
| 100A-4 | 5-F | $CH_2$ | ++ | 357.1 | Free Base |
| 100A-5 | 5-Cl | $CH_2$ | ++ | 373.1 | Free Base |
| 100A-6 | 5-Et | $CH_2$ | ++ | 367.1 | Free Base |
| 100A-7 | 4-CN | $CH_2$ | +++ | 364.1 | Free Base |
| 100A-8 | $4\text{-}SCH_3$ | $CH_2$ | +++ | 385.1 | Free Base |
| 100A-9 | $4\text{-}CH_3, 6\text{-}CH_3$ | $-CH_2CH(CO_2H)-C(CH_3)_2-$ (cis) | ++ | 467.2 | Free Base |
| 100A-10 | $4\text{-}CH_3, 6\text{-}CH_3$ | $-CH_2CH(CO_2H)-C(CH_3)_2-$ (1S,4F) | ++ | 467.2 | Free Base |
| 100A-11 | $4\text{-}OCH_3, 5\text{-}CF_3$ | $-CH_2CH(OH)CH_2-$ | ++ | 481.1 | Free Base |
| 100A-12 | $4\text{-}CH_3, 6\text{-}CH_3$ | $-CH_2CH(CO_2CH_3)-C(CH_3)_2-$ (cis) | + | 481.2 | Free Base |
| 100A-13 | $4\text{-}OCH_3, 5\text{-}CH_3$ | $-CH_2CH(CO_2H)-C(CH_3)_2-$ (1S,4R) | +++ | 483.2 | Free Base |
| 100A-14 | $4\text{-}CH(OH)CH_3$ | $-CH_2CH(CO_2H)-C(CH_3)_2-$ (Enantiomer 1) | +++ | 483.2 | Free Base |
| 100A-15 | $4\text{-}CH(OH)CH_3$ | $-CH_2CH(CO_2H)-C(CH_3)_2-$ (Enantiomer 2) | +++ | 483.2 | Free Base |
| 100A-16 | $4\text{-}N(CH_3)_2, 5\text{-}CH_3$ | $-CH_2CH(CO_2H)-C(CH_3)_2-$ (1S,4R) | +++ | 496.2 | TFA Salt |
| 100A-17 | $4\text{-}C(CH_3)_2OH$ | $-CH_2CH(CO_2H)-C(CH_3)_2-$ (1S,4R) | +++ | 497.2 | Free Base |
| 100A-18 | 4-(CH(OH)—cPr) | $-CH_2CH(CO_2H)-C(CH_3)_2-$ (Enantiomer 1) | +++ | 509.2 | Free Base |
| 100A-19 | 4-(CH(OH)—cPr) | $-CH_2CH(CO_2H)-C(CH_3)_2-$ (Enantiomer 20 | +++ | 509.2 | Free Base |
| 100A-20 | 4-(CH(F)—cPr) | $-CH_2CH(CO_2H)-C(CH_3)_2-$ | +++ | 511.2 | Free Base |
| 100A-21 | 4-(CH(F)—cPr) | $-CH_2CH(CO_2H)-C(CH_3)_2-$ (Enantiomer 1) | +++ | 511.2 | Free Base |
| 100A-22 | 4-(CH(F)—cPr) | $-CH_2CH(CO_2H)-C(CH_3)_2-$ (Enantiomer 2) | +++ | 511.2 | Free Base |
| 100A-23 | $4\text{-}((E)\text{-}CH=CHC(CH_3)_2OH)$ | $-CH_2CH(CO_2H)-C(CH_3)_2-$ (1S,4R) | +++ | 523.3 | Free Base |
| 100A-24 | $4\text{-}(C(OH)(CH_3)(cPr))$ | $-CH_2CH(CO_2H)-C(CH_3)_2-$ | +++ | 523.3 | Free Base |
| 100A-25 | $4\text{-}(C(OH)(CH_3)(cPr))$ | $-CH_2CH(CO_2H)-C(CH_3)_2-$ (Enantiomer 1) | +++ | 523.2 | Free Base |
| 100A-26 | $4\text{-}(C(OH)(CH_3)(cPr))$ | $-CH_2CH(CO_2)-C(CH_3)_2-$ (Enantiomer 2) | +++ | 523.2 | Free Base |
| 100A-27 | $4\text{-}OCH_3, 5\text{-}CF_3$ | $-CH_2CH(CO_2CH_3)-C(CH_3)_2-$ | + | 551.1 | Free Base |
| 100A-28 | $4\rightarrow 5\ (CH_2)_3$* | $-CH_2CH(CO_2H)-C(CH_3)_2-$ (1S,4R) | +++ | 479.2 | Free Base |
| 100A-29 | $4\rightarrow 5\ (CH_2)_3$* | $-CH_2CH(CO_2CH_3)-C(CH_3)_2-$ (1S,4R) | ++ | 493.3 | TFA Salt |

*forming 6,7- dihydro-5H-cyclopenta[d]pyrimiine

TABLE 100B

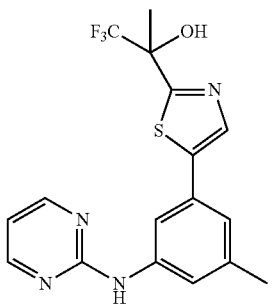 [SMILES: Cc1cc(Nc2ncccn2)cc(-c2cnc(C(C)(O)C(F)(F)F)s2)c1]

| Example | R1 | rhSYK Activity | [M + H]+ Observed | Form(s) |
|---------|-------|----------------|-------------------|-----------|
| 100B-1  | 4-OCH₃ | +++ | 411.1 | Free Base |
| 100B-2  | 5-F    | +++ | 399.0 | Free Base |
| 100B-3  | 5-OCH₃ | ++  | 411.1 | Free Base |
| 100B-4  | 5-cPr  | +   | 421.1 | Free Base |

Example 101

1,1,1-trifluoro-2-{5-[3-methyl-5-(pyrimidin-2-ylamino)phenyl]-1,3-thiazol-2-yl}propan-2-ol

Step 1

A 5 mL microwave vial was charged with INTERMEDIATE 17 (30 mg, 0.10 mmol), 2-chloropyrimidine (12.5 mg, 0.11 mmol), cesium carbonate (65 mg, 0.20 mmol), XantPhos (9 mg, 0.015 mmol), palladium (II) acetate (2.5 mg, 0.011 mmol), and dioxane (0.5 mL). The vial was flushed with argon, sealed, and allowed to react overnight at 100° C. The reaction mixture was filtered through celite and the filtrate was purified by reverse phase HPLC (acetonitrile/water (0.1% Formic Acid). The desired fractions were frozen and lyophilized to afford 1,1,1-trifluoro-2-{5-[3-methyl-5-(pyrimidin-2-ylamino)phenyl]-1,3-thiazol-2-yl}propan-2-ol, formate salt (14 mg, 0.037 mmol, 37%) as an off-white solid. MS ESI: [M+H]⁺ m/z 381.0. $^1$H NMR (500 MHz, DMSO-$d_6$) δ 9.67 (s, 1H), 8.50 (d, J=4.8, 2H), 8.07 (s, 1H), 7.90 (s, 1H), 7.67 (s, 1H), 7.58 (s, 1H), 7.11 (s, 1H), 6.85 (t, 1H), 2.31 (s, 3H), 1.76 (s, 3H). rhSYK activity=++

Compounds in the following Table(s) were prepared in an analogous manner of that described in Example 101:

TABLE 101

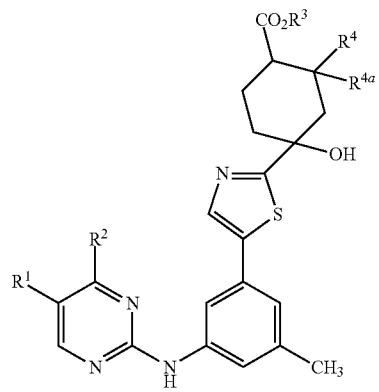

| Ex. | R¹ | R² | R³ | R⁴/R⁴ᵃ | rhSYK Activity | [M + H]+ Observed | Form(s) |
|-------|---|------|-----|-----------------|-----|-------|-----------|
| 101-1 | H | t-Bu | Et  | H/CH₃           | +++ | 509.2 | Free Base |
| 101-2 | H | iPr  | CH₃ | CH₃/CH₃ (1S,4R) | +++ | 495.2 | Free Base |
| 101-3 | H | t-Bu | CH₃ | CH₃/CH₃ (1S,4R) | +++ | 509.2 | Free Base |

TABLE 101-continued

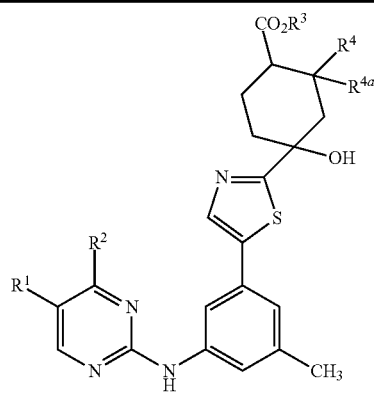

| Ex. | R[1] | R[2] | R[3] | R[4]/R[4a] | rhSYK Activity | [M + H]+ Observed | Form(s) |
|---|---|---|---|---|---|---|---|
| 101-4 | H | O—iPr | CH$_3$ | CH$_3$/CH$_3$ (1S,4R) | +++ | 511.2 | Free Base |
| 101-5 | H | CH=CH2 | CH$_3$ | CH$_3$/CH$_3$ (1S,4R) | +++ | 479.2 | Free Base |
| 101-6 | H | cBu | CH$_3$ | CH$_3$/CH$_3$ (1S,4R) | +++ | 507.2 | Free Base |
| 101-7 | H | CONH$_2$ | CH$_3$ | CH$_3$/CH$_3$ (1S,4R) | +++ | 496.1 | Free Base |
| 101-8 | H | (triazole-CH$_2$-C$_6$H$_4$-OCH$_3$) | t-Bu | H/H (cis) | + | 654.2 | Free Base |
| 101-9 | CF$_3$ | OCH$_3$ | H | CH$_3$/CH$_3$ | +++ | 537.1 | Free Base |
| 101-10 | CF$_3$ | OCH$_3$ | H | CH$_3$/CH$_3$ (1S,4R) | +++ | 537.1 | TFA Salt |

Example 102

1-(5-{3-[(5-chloro-4-methoxypyrimidin-2-yl)amino]-5-methylphenyl}-1,3-thiazol-2-yl)-cyclobutanol

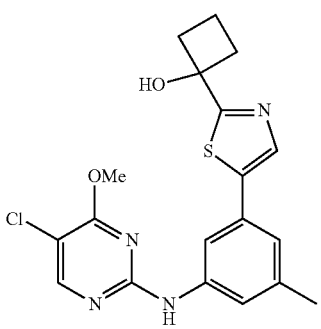 [SMILES: COc1nc(Nc2cc(C)cc(-c3cnc(C4(O)CCC4)s3)c2)ncc1Cl]

Step 1

Sodium methoxide (295 mg, 5.45 mmol) was taken up in methanol (13.6 mL) and 2,4,5-trichloropyrimidine (500 mg, 2.73 mmol) was added. The mixture was stirred at room temperature overnight. The resulting mixture was concentrated under reduced pressure. The resulting residue was diluted with diethyl ether, washed with 1:1 water:saturated aqueous ammonium chloride. The organic layer was dried over magnesium sulfate, filtered, and concentrated under reduced pressure. Purification by Chromatography on silica gel (0-10% diethyl ether/hexanes) afforded 2,5-dichloro-4-methoxypyrimidine (280 mg, 1.56 mmol, 57%) as a white solid.

Step 2

A flask was charged with a stir bar, 2,5-dichloro-4-methoxypyrimidine (69 mg, 0.38 mmol), Intermediate 15 (100 mg, 0.38 mmol), Pd$_2$(dba)$_3$ (35.2 mg, 0.038 mmol), XPhos (92 mg, 0.19 mmol), and potassium carbonate (106 mg, 0.77 mmol). The vial was fully evacuated and backfilled with argon three times. Fully degassed tert-amyl alcohol (1.30 mL) was added to the reaction mixture, which was sealed and stirred at 90° C. overnight. The reaction was then cooled to room temperature. The crude mixture was taken-up in DCM and directly purified by Chromatography on silica gel (0-100% ethyl acetate/hexanes) to provide 1-(5-{3-[(5-chloro-4-methoxypyrimidin-2-yl)amino]-5-methylphenyl}-1,3-thiazol-2-yl)cyclobutanol (93 mg, 0.23 mmol, 60%) as a dark blue solid. MS ESI: [M+H]$^+$ m/z 403.1. $^1$H NMR (500 MHz, dmso) δ 9.78 (s, 1H), 8.32 (s, 1H), 7.98 (s, 1H), 7.89 (s, 1H), 7.46 (s, 1H), 7.10 (s, 1H), 6.50 (s, 1H), 4.05 (s, 3H), 2.56-2.50 (m, 2H), 2.36-2.27 (m, 5H), 1.94-1.82 (m, 2H). rhSYK activity=+++

Example 103

1-(5-{3-[(5-chloro-4-methylpyrimidin-2-yl)amino]-5-methylphenyl}-1,3-thiazol-2-yl)cyclobutanol

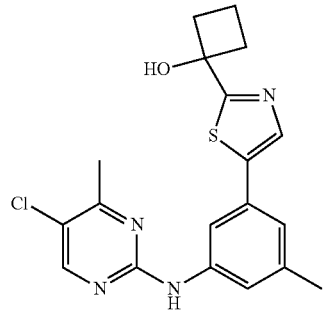 [SMILES: Cc1cc(Nc2ncc(Cl)c(C)n2)cc(-c2cnc(C3(O)CCC3)s2)c1]

Step 1

2,4,5-Trichloropyrimidine (250 mg, 1.36 mmol) and ferric acetylacetonate (24 mg, 0.07 mmol) were taken up in tetrahydrofuran (2.7 mL) and the reaction was cooled to −78° C. Methylmagnesium bromide (0.45 mL of 3 M in THF, 1.36 mmol) was added dropwise and the mixture was stirred at −78° C. for one hour. The mixture was quenched with aqueous ammonium chloride and extracted with ethyl acetate. The combined organic fractions were dried over magnesium sulfate, filtered, and the solvent was evaporated under reduced pressure. The resulting residue was purified by Chromatography on silica gel (0-10% diethylether in hexanes) to provide 2,5-dichloro-4-methylpyrimidine (99 mg, 0.61 mmol, 45%) as a white solid. MS ESI: [M+H]$^+$ m/z 163.0.

Step 2

A flask was charged with a stir bar, 2,5-dichloro-4-methylpyrimidine (63 mg, 0.38 mmol), Intermediate 15 (100 mg, 0.38 mmol), Pd$_2$(dba)$_3$ (35 mg, 0.038 mmol), XPhos (92 mg, 0.19 mmol), and potassium carbonate (106 mg, 0.768 mmol). The vial was evacuated and backfilled with argon three times. Fully degassed tent-amyl alcohol (1.3 mL) was added to the flask, which was sealed and stirred at 90° C. overnight. The reaction was then cooled to room temperature, diluted with DCM and directly purified by Chromatography on silica gel (0-100% ethyl acetate in hexanes) to provide 1-(5-{3-[(5-chloro-4-methylpyrimidin-2-yl)amino]-5-methylphenyl}-1,3-thiazol-2-yl)cyclobutanol (65 mg, 0.17 mmol, 44%) as a dark brown solid. MS ESI: [M+H]$^+$ m/z 387.1 $^1$H NMR (500 MHz, dmso) δ 9.81 (s, 1H), 8.44 (s, 1H), 7.97 (s, 1H), 7.91 (s, 1H), 7.47 (s, 1H), 7.08 (s, 1H), 6.51 (s, 1H), 2.58-2.50 (m, 2H), 2.45 (s, 3H), 2.37-2.27 (m, 5H), 1.93-1.82 (m, 2H). rhSYK activity=+++

Example 104

1-(5-{3-[(4-ethenylpyrimidin-2-yl)amino]-5-methylphenyl}-1,3-thiazol-2-yl)cyclobutanol

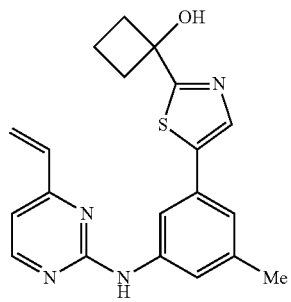 [SMILES: C=Cc1ccnc(Nc2cc(C)cc(-c3cnc(C4(O)CCC4)s3)c2)n1]

Step 1

To a mixture of 2,4-dichloropyrimidine (4.4 g, 29.5 mmol), potassium vinyltrifluoroborate (4.58 g, 32.5 mmol), PdCl$_2$(dppf)-CH$_2$Cl$_2$ (1.21 g, 1.48 mmol) and triethylamine (4.12 mL, 29.5 mmol) in nPrOH (148 mL) was purged with nitrogen for 15 min, heated to 100° C. for 5 h, and then cooled to room temperature. The mixture was treated with water and extracted with EtOAc (×3). The combined organics were washed with brine, dried (sodium sulfate), filtered and concentrated, and purified by flash chromotography to afford 2-chloro-4-ethenylpyrimidine as a colorless oil. $^1$H NMR (500 MHz, CDCl$_3$) δ 8.56 (d, J=5.1, 1H), 7.21 (d, J=5:1, 1H), 6.70 (dd, J=10.6, 17.4, 1H), 6.57-6.51 (m, 1H), 5.79 (dd, J=0.8, 10.6, 1H).

Step 2

A mixture of 2-chloro-4-ethenylpyrimidine (400 mg, 2.85 mmol), Intermediate 15 (815 mg, 3.13 mmol), Pd(OAc)$_2$ (70.3 mg, 0.313 mmol), Xantphos (247 mg, 0.427 mmol) and cesium carbonate (1.85 g, 5.69 mmol) in 1,4-dioxane (14 mL) was purged with nitrogen for 8 min, and heated to 100° C. overnight. The mixture was cooled to room temperature, diluted with water, and extracted with EtOAc (×3). The combined organics were washed with brine, dried (sodium sulfate), concentrated, and purified by flash chromatography to afford 1-(5-{3-[(4-ethenylpyrimidin-2-yl)amino]-5-methylphenyl}-1,3-thiazol-2-yl)cyclobutanol (330 mg, 0.905 mmol). MS ESI: [M+H]$^+$ m/z 365.1. $^1$H NMR (500 MHz, DMSO-d$_6$) δ 9.65 (s, 1H), 8.49 (d, J=4.9, 1H), 8.01 (s, 1H), 7.97 (s, 1H), 7.53 (s, 1H), 7.07 (s, 1H), 6.94 (d, J=5.1, 1H), 6.71 (dd, J=10.5, 17.4, 1H), 6.51 (s, 1H), 6.49 (d, J=16.1, 1H), 5.70 (d, J=10.5, 1H), 2.56-1.85 (m, 6H), 2.31 (s, 3H). rhSYK activity=+++

Compounds in the following Table(s) were prepared in an analogous manner of that described in Example 104:

TABLE 104

[Structure with CO₂R, H₃CO, OH, thiazole, pyrimidine, NH, CH₃]

| Example | R | rhSYK Activity | [M + H]+ Obs'd | Form(s) |
|---------|------|----|-------|-----------|
| 104-1 | t-Bu | ++ | 537.1 | Free Base |
| 104-2 | H | +++ | 481.1 | Free Base |

Example 105

1-[2-({3-[2-(1-hydroxycyclobutyl)-1,3-thiazol-5-yl]-5-methylphenyl}amino)pyrimidin-4-yl]ethane-1,2-diol

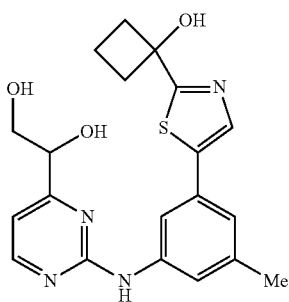 [SMILES: Cc1cc(Nc2nccc(C(O)CO)n2)cc(-c2cnc(C3(O)CCC3)s2)c1]

To a stirred solution of 1-(5-{3-[(4-ethenylpyrimidin-2-yl)amino]-5-methylphenyl}-1,3-thiazol-2-yl)cyclobutanol (200 mg, 0.55 mmol) in THF/water (3.6 mL/1.8 mL) were added osmium tetroxide (4% in water, 0.22 mL, 0.027 mmol) and NMO (77 mg, 0.66 mmol). The reaction mixture was heated to 50° C. overnight. The mixture was cooled to room temperature, treated with aq. Na₂S₂O₃ solution, left to stir overnight, and then extracted with ethyl acetate (3×). The combined organics were washed with brine, dried (sodium sulfate), filtered, concentrated, and purified by column chromatography on silica to afford 1-[2-({3-[2-(1-hydroxycyclobutyl)-1,3-thiazol-5-yl]-5-methylphenyl}amino)pyrimidin-4-yl]ethane-1,2-diol (47 mg, 0.12 mmol). MS ESI: [M+H]⁺ m/z 399.1. ¹H NMR (500 MHz, DMSO-d₆) δ 9.60 (s, 1H), 8.45 (d, J=5.1, 1H), 7.96 (s, 2H), 7.50 (s, 1H), 7.04 (s, 1H), 6.94 (d, J=4.9, 1H), 6.50 (s, 1H), 5.52 (s, 1H), 4.77 (m, 1H), 4.43 (m, 1H), 3.72 (m, 1H), 3.60 (m, 1H), 2.29 (s, 3H), 2.60-1.80 (m, 6H). rhSYK activity=+++

Example 106

1-[2-({3-methyl-5-[2-(1,1,1-trifluoro-2-hydroxypropan-2-yl)-1,3-thiazol-5-yl]phenyl}amino)pyrimidin-4-yl]ethanone

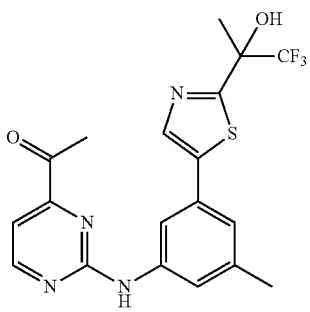 [SMILES: CC(=O)c1ccnc(Nc2cc(C)cc(-c3cnc(C(C)(O)C(F)(F)F)s3)c2)n1]

Step 1

To 2,4-dichloropyrimidine (1.1 g, 7.38 mmol) in a scintillation vial was added toluene (73.8 mL). The system was purged and flushed with Ar(g) three times before adding PdCl₂(dppf)-dichloromethane adduct (0.301 g, 0:369 mmol) and tributyl(1-ethoxyethenyl)stannane (3.74 mL, 11.08 mmol). The system was purged and flushed three times with Ar(g) before sealing the system and heating to 80° C. The reaction was complete after 1.5 hr and was cooled to room temperature before being filtered through celite (washed with dichloromethane) and diluted with water. The organic layer was separated, dried over sodium sulfate, and was concentrated to dryness before purification by column chromatography (5-20% ethyl acetate in hexanes, linear gradient) to yield the ethyl enol ether. The material was subject to hydrolysis (2M HCl in MeOH@50° C.). After 2 hours, the reaction was cooled to room temperature and was diluted with saturated aqueous NaHCO₃ and dichloromethane. The organic layer was dried over sodium sulfate and was concentrated to dryness before purification by column chromatography (10-50% acetone in hexanes) to yield 1-(2-chloropyrimidin-4-yl)-ethanone as a clear oil. ¹H NMR (500 MHz, CDCl₃) δ 8.86 (d, J=4.9, 1H), 7.84 (d, J=4.9, 1H), 2.72 (s, 3H).

Step 2

To Intermediate 17 (500 mg, 1.654 mmol) in a scintillation vial was added dioxane (8.27 mL), cesium carbonate (1078 mg, 3.31 mmol), and 1-(2-chloropyrimidin-4-yl)ethanone (285 mg, 1.819 mmol). The system was purged and flushed with Ar(g) three times before adding Xantphos (144 mg, 0.248 mmol) and Pd(OAc)₂ (40.8 mg, 0.182 mmol). The system was purged and flushed with Ar(g) three times before sealing the system and heating to 100° C. The reaction was stirred overnight and was cooled to room temperature. The reaction mixture was filtered through celite (washed with chloroform) and diluted with water. The organic layer was separated, dried over sodium sulfate, and was concentrated to dryness before purification by column chromatography (10-40% acetone in hexanes, linear gradient) to yield 1-[2-({3-methyl-5-[2-(1,1,1-trifluoro-2-hydroxypropan-2-yl)-1,3-thiazol-5-yl]phenyl}amino)pyrimidin-4-yl]ethanone (250 mg, 0.592 mmol, 36%). MS ESI: [M+H]⁺ m/z 423.1. ¹H NMR (500 MHz, CDCl₃) δ 8.66 (d, J=4.9, 1H), 7.95 (s, 2H), 7.34 (dd, J=8.1, 13.0, 3H), 7.10 (s, 1H), 2.73 (s, 3H), 2.42 (s, 3H), 1.85 (s, 3H). rhSYK activity=+++

Example 107

1-(5-{3-[(4-cyclobutylpyrimidin-2-yl)amino]-5-methylphenyl}-1,3-thiazol-2-yl)cyclobutanol

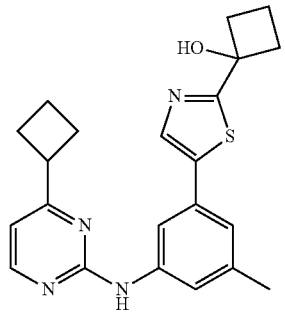 [SMILES: Cc1cc(Nc2nccc(C3CCC3)n2)cc(-c2cnc(C3(O)CCC3)s2)c1]

Step 1

2,4-Dichloropyrimidine (250 mg, 1.68 mmol) and ferric acetylacetonate (30 mg, 0.08 mmol) were taken up in tetrahydrofuran (3.4 mL) and the reaction was cooled to −78° C. Cyclobutylmagnesium chloride (0.5 M, 3.4 mL, 1.68 mmol) was added dropwise and the mixture was stirred at −78° C. for 30 min. The mixture was quenched with aqueous saturated ammonium chloride and extracted with ethyl acetate. The combined organic fractions were washed with aqueous sodium hydrogen carbonate, dried over magnesium sulfate, filtered, and the solvent was evaporated under reduced pressure. The residue was purified by column chromatography on silica gel (0-5% ethyl acetate in hexanes) to provide 121 mg (0.72 mmol, 43%) of 2-chloro-4-cyclobutylpyrimidine as a colorless oil. MS ESI: [M+H]⁺ m/z 169.1.

Step 2

2-Chloro-4-cyclobutylpyrimidine (65 mg, 0.39 mmol), Intermediate 15 (100 mg, 0.39 mmol), and acetic acid (22 µL, 0.39 mmol) were combined in dioxane (1.9 mL) and the mixture was stirred at 120° C. for 3 h. The mixture was cooled to room temperature and directly purified by Combiflash chromatography on silica gel, eluting with ethyl acetate/isohexane to provide 66 mg (0.17 mmol, 44%) of 1-(5-{3-[(4-cyclobutylpyrimidin-2-yl)amino]-5-methylphenyl}-1,3-thiazol-2-yl)cyclobutanol. MS ESI: [M+H]⁺ m/z 393.2. ¹H NMR (600 MHz, DMSO-d₆) δ 9.56 (s, 1H), 8.33 (d, J=4.8, 1H), 8.12 (s, 1H), 7.95 (s, 1H), 7.48 (s, 1H), 7.05 (s, 1H), 6.68 (d, J=5.4, 1H), 6.46 (s, 1H), 3.53-3.50 (m, 1H), 2.52-2.46 (m, 2H), 2.33-2.22 (m, 9H), 1.99 (m, 1H), 1.87-1.83 (m, 3H). rhSYK activity=+++

Compounds in the following Table(s) were prepared in a manner analogous of that described in Example 107:

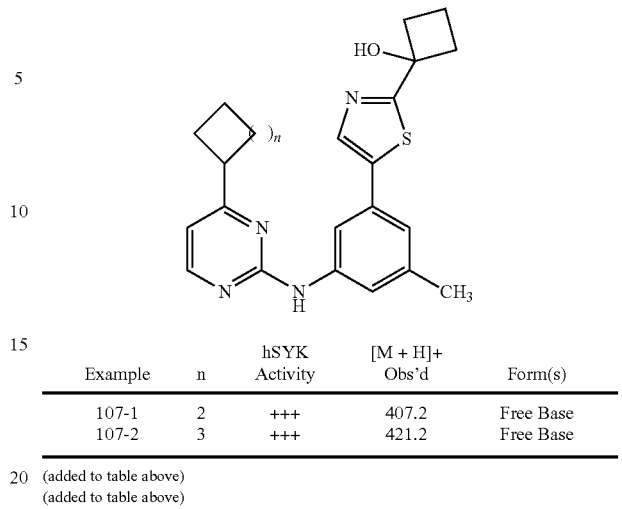

| Example | n | hSYK Activity | [M + H]+ Obs'd | Form(s) |
|---|---|---|---|---|
| 107-1 | 2 | +++ | 407.2 | Free Base |
| 107-2 | 3 | +++ | 421.2 | Free Base |

(added to table above)
(added to table above)

Example 108

1-(5-{3-[(4-ethoxypyrimidin-2-yl)amino]-5-methylphenyl}-1,3-thiazol-2-yl)cyclobutanol

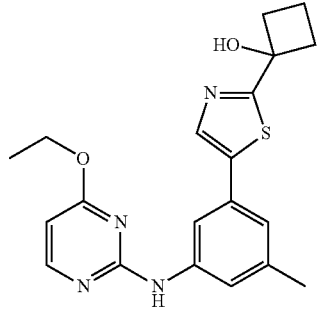 [SMILES: CCOc1ccnc(Nc2cc(C)cc(-c3cnc(C4(O)CCC4)s3)c2)n1]

Step 1

To a mixture of 2-chloro-4-(methylsulfanyl)pyrimidine (Intermediate 28, 500 mg, 3.11 mmol) and Intermediate 15 (810 mg, 3.11 mmol) in dioxane (15 mL) was added palladium(II) acetate (70 mg, 0.311 mmol), XantPhos (270 mg, 0.467 mmol) and cesium carbonate (2 g, 6.23 mmol). The mixture was degassed for 10 min and then heated at 85° C. for 16 h. After cooling to ambient temperature, the reaction mixture was filtered over celite and was washed with DCM/MeOH. After solvent removal, the residue was purified by column chromatography on silica gel (10 to 100% 10:1 ethyl acetate: methanol in hexanes) to afford 1-[5-(3-methyl-5-{[4-(methylsulfanyl)pyrimidin-2-yl]amino}phenyl)-1,3-thiazol-2-yl]cyclobutanol (1.1 g, 2.86 mmol, 92%). MS ESI: [M+H]⁺ m/z 385.1.

Step 2

To a solution of the product from Step 1 (400 mg, 1.040 mmol) in dichloromethane (5 mL) was added mCPBA (527 mg, 2.289 mmol) and the mixture was aged for 1.5 h. Additional mCPBA (400 mg, 1.73 mmol) was added and the reaction was stirred for an additional 2 hr. The solvent was reduced by rotavap and the residue was purified by column chromatography on silica gel (0-100% ethyl acetate in hexanes) to afford 1-[5-(3-methyl-5-{[4-(methylsulfonyl)pyrimidin-2-yl]amino}phenyl)-1,3-thiazol-2-yl]cyclobutanol (210 mg, 0.5 mmol, 49%). MS ESI: [M+H]$^+$ m/z 417.0. $^1$H NMR (600 MHz, DMSO-d$_6$): δ 8.85 (d, J=4.8 Hz, 1H); 7.99 (s, 1H); 7.89 (s, 1H); 7.44 (s, 1H); 7.31 (d, J=4.8 Hz, 1H); 7.13 (s, 1H); 6.49 (s, 1H); 3.31 (s, 3H); 2.49 (m, 2H); 2.31 (m, 5H); 1.85 (m, 2H). Note: By using 1.2 eq of mCPBA, the corresponding sulfoxide can be obtained as major product with similar procedure as above.

Step 3

To a suspension of sodium hydride (60% in mineral oil) (8.6 mg, 0.22 mmol in TIE (1 mL) was added ethyl alcohol (21 μL, 0.36 mmol) and the mixture was stirred at ambient temperature for 40 min followed by addition of the product from Step 2 (30 mg, 0.072 mmol). The reaction mixture stirred for 1 h. To the mixture was added saturated aqueous NH$_4$Cl and the product was extracted with ethyl acetate. The organic layer was dried, filtered and the solvent removed in vacuo. The residue was purified by column chromatography on silica gel (0-100% ethyl acetate in dichloromethane) to afford 1-(5-{3-[(4-ethoxypyrimidin-2-yl)amino]-5-methylphenyl}-1,3-thiazol-2-yl)cyclobutanol (12 mg, 0.03 mmol, 44%) as pale yellow oil. MS ESI: [M+H]$^+$ m/z 383.2. $^1$H NMR (600 MHz, CD$_3$OD): δ 8.11 (d, J=5.4 Hz, 1H); 7.85 (s, 1H); 7.81 (s, 1H); 7.32 (s, 1H); 7.28 (s, 1H); 7.02 (s, 1H); 6.17 (d, J=5.4 Hz, 1H); 4.44 (q, J=7.2 Hz, 2H); 2.67 (m, 2H); 2.47 (m, 2H); 2.35 (s, 3H); 2.04-1.95 (m, 2H); 1.41 (t, J=7.2 Hz, 3H).

The following examples were prepared in an analogous manner of that described in Example 108.

TABLE 108A

| Ex. | X | R$^1$ | R$^2$ | rhSYK Activity | [M + H]+ Observed | Form(s) |
|---|---|---|---|---|---|---|
| 108A-1 | O | H | 1-Me-2-imidazolyl | +++ | 449.2 | Formate Salt |
| 108A-2 | O | H | 4-imidazolyl | +++ | 435.1 | Formate Salt |
| 108A-3 | O | H | —CH$_2$-(3-oxo-4-morpholinyl) | +++ | 482.2 | Formate Salt |
| 108A-4 | O | H | 3-tetrahydropyranyl | +++ | 453.2 | Formate Salt |
| 108A-5 | O | H | —CH$_2$-(3,4-diF-pyrrolidinyl) | +++ | 488.2 | Formate Salt |
| 108A-6 | O | CH$_2$—NH$_2$ | 4-pyrimidinyl | +++ | 476.2 | Formate Salt |
| 108A-7 | O | H | (7-pyrazolo[1,5-a]pyridinyl) | ++ | 485.2 | Formate Salt |
| 108A-8 | O | H | —CH$_2$—(1-Me-4-pyrazolyl) | +++ | 463.2 | Formate Salt |
| 108A-9 | O | H | 3-isoxazolyl | +++ | 436.1 | Formate Salt |
| 108A-10 | O | H | 4-azepanyl (Enantiomer 1) | +++ | 452.2 | Free Base |
| 108A-11 | O | H | 4-azepanyl (Enantiomer 2) | +++ | 452.2 | Free Base |
| 108A-12 | O | H | —CH$_2$-1,2,3-triazol-2-yl | +++ | 450.2 | TFA Salt |
| 108A-13 | O | H | —CH$_2$-1,2,3-triazol-1-yl | +++ | 450.2 | TFA Salt |
| 108A-14 | O | H | —CH$_2$NH-4-(1-Me) piperidyl | ++ | 495.3 | TFA Salt |
| 108A-15 | O | H | 2,3-dihydro-2-indolyl | ++ | 486.2 | TFA Salt |
| 108A-16 | O | H | 1-Me-5-pyrazolyl | +++ | 449.2 | TFA Salt |
| 108A-17 | O | H | —CH$_2$—Me-2-pyrrolidinyl | +++ | 466.2 | TFA Salt |
| 108A-19 | O | H | —CH$_2$-1,4-diazepan-1-yl | +++ | 481.2 | TFA Salt |
| 108A-20 | O | H | 1,4-diMe-2-piperazinyl | +++ | 481.2 | TFA Salt |
| 108A-21 | O | H | CH$_2$-5-tetrazolyl | +++ | 451.1 | TFA Salt |
| 108A-22 | O | H | —C≡C-5-pyrimidinyl | ++ | 471.1 | TFA Salt |
| 108A-23 | O | H | 1-Me-2-oxo-4-pyrrolidinyl | +++ | 466.2 | TFA Salt |
| 108A-24 | O | H | 3-Me-3-piperidinyl | +++ | 466.2 | TFA Salt |
| 108A-25 | O | H | —CH$_2$-(4-Me-2-morpholinyl) | +++ | 482.2 | TFA Salt |

TABLE 108A-continued

Structure with XCHR₁R₂ substituent on pyrimidine core linked via NH to methylphenyl-thiazole-cyclobutanol

| Ex. | X | R¹ | R² | rhSYK Activity | [M + H]+ Observed | Form(s) |
|---|---|---|---|---|---|---|
| 108A-27 | O | CH₃ | —CH₂—(5-Me-2-oxo-3-oxazolidinyl) | +++ | 496.2 | TFA Salt |
| 108A-28 | O | H | —CH₂—O—(3-OH)Ph | ++ | 491.2 | TFA Salt |
| 108A-29 | O | H | —CH₂CH₂-3-pyridyl | +++ | 474.2 | TFA Salt |
| 108A-30 | O | H | —CH₂-(2-oxo-1-pyrrolidinyl) | +++ | 466.2 | TFA Salt |
| 108A-31 | O | H | —(CH₂)₃—OH | +++ | 427.2 | Free Base |
| 108A-34 | O | H | —CH₂OH | +++ | 399.1 | Free Base |
| 108A-35 | O | H | —CH₂CH₂OH | +++ | 413.1 | Free Base |
| 108A-36 | O | H | CH₃ | +++ | 383.2 | Free Base |
| 108A-37 | O | Me | CH₃ | +++ | 397.2 | Free Base |
| 108A-38 | SO | H | H | +++ | 401.1 | Free Base |
| 108A-39 | SO₂ | H | H | +++ | 417.0 | Free Base |
| 108A-40 | S | H | CH₃ | +++ | 399.1 | Free Base |
| 108A-41 | S | H | nPr | ++ | 427.1 | Free Base |
| 108A-42 | S | H | Et | +++ | 413.1 | Free Base |
| 108A-43 | S | CH₃ | CH₃ | +++ | 413.1 | Free Base |
| 108A-44 | S | H | —CH₂OH | +++ | 415.1 | Free Base |
| 108A-45 | S | H | —CH₂CH₂OH | +++ | 429.1 | Free Base |
| 108A-46 | S | H | —(CH₂)₃OH | +++ | 443.2 | Free Base |

TABLE 108B

Structure with OR substituent on pyrimidine core linked via NH to methylphenyl-thiazole-cyclobutanol

| Ex. | R | rhSYK Activity | [M + H]+ Obs'd | Form(s) |
|---|---|---|---|---|
| 108B-1 | 2,2,6,6-tetraMe-4-piperidyl | ++ | 494.3 | TFA Salt |
| 108B-2 | (1R,4R,5S)-2-azabicyclo[2.2.1]hept-5-yl | +++ | 450.2 | Free Base |
| 108B-3 | (1R,4R,5R)-2-azabicyclo[2.2.1]hept-5-yl | ++ | 450.2 | Free Base |

Examples 109(1) and 109(2)

tert-butyl 4-[2-({3-(acetylamino)-5-[2-(1-hydroxycyclobutyl)-1,3-thiazol-5-yl]phenylamino)pyrimidin-4-yl]oxy}piperidine-1-carboxylate N-(3-[2-(1-hydroxycyclobutyl)-1,3-thiazol-5-yl]-5-{[4-(piperidin-4-yloxy)pyrimidin-2-yl]-amino}phenyl)acetamide

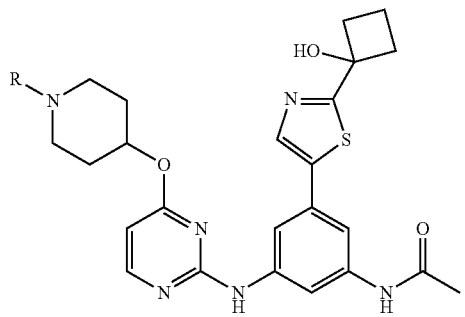

Example 109 (1): R = t-Boc;
Example 109 (2): R = H

Step 1

To tert-butyl 4-hydroxypiperidine-1-carboxylate (389 mg, 1.933 mmol) and 2,4-dichloropyrimidine (240 mg, 1.611 mmol) in DMF (6.4 mL) was added cesium carbonate (1050 mg, 3.22 mmol) and the mixture was heated at 80° C. for 1 h and then to 70° C. overnight. TLC indicated no remaining 2,4-dichloropyrimidine. The reaction was cooled to ambient temperature, diluted with water and extracted with ethyl acetate. The organic layer was washed with water (3×) and brine. The combined organic layer was dried (MgSO$_4$), filtered and solvent was removed under reduced pressure. The residue was purified by column chromatography on silica gel to give tert-butyl 4-[(2-chloropyrimidin-4-yl)oxy]piperidine-1-carboxylate (410 mg, 1.3 mmol, 81%) as white solid. MS ESI: [M+H]$^+$ m/z 314.2.

Step 2

To the product from Step 1 (900 mg, 2.87 mmol) and Intermediate 22 (836 mg, 2.87 mmol) in dioxane (28 mL) was added palladium acetate (129 mg, 0.574 mmol), XantPhos (498 mg, 0.860 mmol) and cesium carbonate (1.87 g, 5.74 mmol). The mixture was degassed with Ar for 10 min and then heated at 100° C. for 20 h. After cooling to ambient temperature, the reaction mixture was filtered through celite and washed with ethyl acetate and methanol. After solvent removal, the residue was purified by column chromatography on silica gel (0-90%, ethyl acetate: 10:1 methanol in hexanes) to afford tert-butyl 4-{[2-({3-[2-(1-hydroxycyclobutyl)-1,3-thiazol-5-yl]-5-nitrophenyl}amino)pyrimidin-4-yl]oxy}piperidine-1-carboxylate (1.15 g, 2.02 mmol, 70%). MS ESI: [M+H]$^+$ m/z 569.2.

Step 3

To the product from Step 2 (320 mg, 0.563 mmol) in MeOH (2.8 mL) was added Pt/C doped with V (3% wt, 110 mg, 0.017 mmol) and the mixture was stirred under H$_2$ balloon for 2 h. The mixture was passed through a silica gel pack and washed with DCM/MeOH. Solvent was removed in vacuo and the residue was purified using column chromatography on silica gel (0-100%, ethyl acetate: 10:1 methanol in DCM) to afford 250 mg (0.46 mmol, 82%) of tert-butyl 4-{[2-({3-amino-5-[2-(1-hydroxycyclobutyl)-1,3-thiazol-5-yl]phenyl}amino)pyrimidin-4-yl]-oxy}piperidine-1-carboxylate as yellow solid. MS ESI: [M+H]$^+$ m/z 539.3.

Step 4

At 0° C., the product from Step 3 (40 mg, 0.074 mmol) in DCM (0.4 mL) was added to acetyl chloride (6.34 μL, 0.089 mmol) and triethylamine (15.53 μL, 0.111 mmol) and the reaction was aged for 1 h. The mixture was then purified directly by column chromatography on silica gel (30-100%, ethyl acetate: 10:1 methanol in hexanes) to afford tert-butyl 4-{[2-({3-(acetylamino)-5-[2-(1-hydroxycyclobutyl)-1,3-thiazol-5-yl]phenyl}amino)pyrimidin-4-yl]oxy}piperidine-1-carboxylate (28 mg, 65% yield). Example 109(1). MS ESI: [M+H]$^+$ m/z 581.3. $^1$H NMR (600 MHz, CDCl$_3$): δ 8.10 (d, J=6.0 Hz, 1H); 7.90 (s, 1H); 7.76 (s, 1H); 7.65 (br s, 1H); 7.53 (s, 1H); 7.11 (s, 1H); 6.14 (d, J=6.0 Hz, 1H); 5.25 (m, 1H); 3.67 (m, 2H); 3.12 (br s, 2H); 2.64 (m, 2H); 2.43 (m, 2H); 2.13 (s, 3H); 1.92 (m, 4H); 1.66 (m, 2H); 1.43 (s, 9H). rhSYK activity=++

Step 5

To the product of Step 4 (20 mg, 0.034 mmol) in DCM (1 mL) was added TFA (133 μL, 1.722 mmol). The mixture was stirred at ambient temperature for 1 hr. LCMS indicated complete reaction. To the reaction was added saturated aqueous NaHCO$_3$ to adjust pH>8 and the product was extracted with ethyl acetate. The combined organic layer was dried, filtered and solvent removed in vacuo to afford 15 mg (0.031 mol, 91%) of N-(3-[2-(1-hydroxycyclobutyl)-1,3-thiazol-5-yl]-5-{[4-(piperidin-4-yloxy)pyrimidin-2-yl]amino}phenyl)acetamide as pale yellow oil. MS ESI: [M+H]$^+$ m/z 481.2. $^1$H NMR (600 MHz, CD$_3$OD): δ 8.16 (m, 2H); 7.90 (s, 1H); 7.55 (s, 1H); 7.30 (s, 1H); 6.26 (d, J=5.4 Hz, 1H); 5.58 (m, 1H); 3.34 (m, 2H); 3.21 (m, 2H); 2.65 (m, 2H); 2.40 (m, 2H); 2.22 (m, al); 2.14 (s, 3H); 2.01 (m, 4H). rhSYK activity=+++

The following examples were prepared in an analogous manner of that described in Examples 109(1)/109(2).

TABLE 109

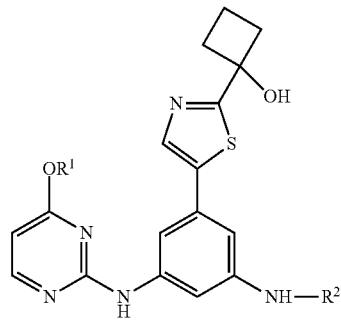

| Example | R$^1$ | R$^2$ | rhSYK Activity | [M + H]+ Observed | Form(s) |
|---------|-------|-------|----------------|-------------------|---------|
| 109-1 | 4-piperidinyl | —C(O)NH-cHex | +++ | 564.3 | TFA Salt |
| 109-2 | 1-(CH$_2$CF$_3$)-4-piperidinyl | H | +++ | 521.2 | Free Base |
| 109-3 | 1-acetyl-4-piperidinyl | —C(O)CH$_3$ | +++ | 523.2 | Free Base |
| 109-5 | 1-(C(O)CF$_3$)-4-piperidiny | H | ++ | 535.2 | Free Base |
| 109-6 | 1-acetyl-4-piperidinyl | H | +++ | 481.2 | Free Base |
| 109-7 | 4-tetrahydropyranyl | —C(O)CF$_3$ | ++ | 536.2 | Free Base |
| 109-8 | 4-tetrahydropyranyl | —C(O)CH$_3$ | +++ | 482.2 | Free Base |
| 109-9 | 4-tetrahydropyranyl | H | +++ | 440.2 | Free Base |
| 109-10 | 1-(Boc)-3-azetidinyl | H | ++ | 511.2 | Free Base |
| 109-11 | 4-piperidinyl | C(O)NH$_2$ | +++ | 482.1 | Free Base |
| 109-12 | 4-piperidinyl | H | +++ | 439.2 | Free Base |
| 109-13 | 1-(CO$_2$Et)-3-azetidinyl | H | +++ | 483.2 | Free Base |
| 109-14 | 3-azetidinyl | H | +++ | 411.2 | Free Base |

Examples 110(1) and 110(2)

Cis-4-(5-(3-[(4-cyclopropylpyrimidin-2-yl)amino]-5-methylphenyl)-1,3-thiazol-2-yl)-4-hydroxycyclohexanecarboxylic acid trans-4-(5-{3-[(4-cyclopropylpyrimidin-2-yl)amino]-5-methylphenyl}-1,3-thiazol-2-yl)-4-hydroxycyclohexanecarboxylic acid

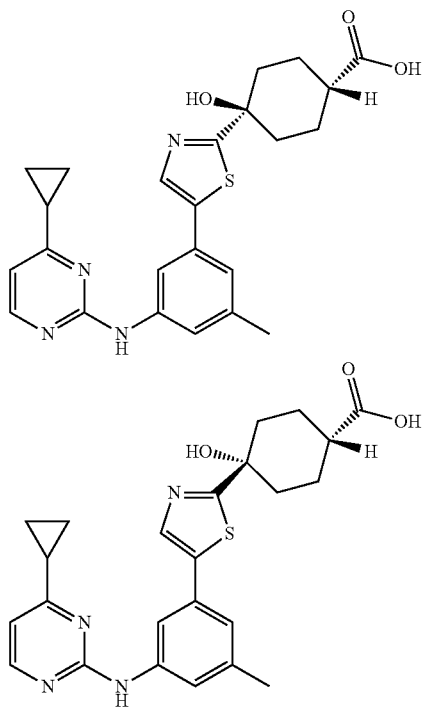

Step 1

To a flask containing tert-butyl trans-4-[5-(3-amino-5-methylphenyl)-1,3-thiazol-2-yl]-4-hydroxycyclohexanecarboxylate (125 mgs, 0.32 mmol) was added a solution of 2-chloro-4-cyclopropylpyrimidine (INTERMEDIATE 29, 57 mgs, 0.37 mmol) in dioxane (1.0 mL). Acetic acid (19 μL, 0.33 mL) was added and the reaction was heated at 100° C. overnight. The reaction was then cooled to room temperature, diluted with ethyl acetate (10 mL), washed with water (10 mL), dried over magnesium sulfate, filtered and concentrated. The residue was purified by flash chromatography to give tert-butyl trans-4-(5-{3-[(4-cyclopropylpyrimidin-2-yl)amino]-5-methylphenyl}-1,3-thiazol-2-yl)-4-hydroxycyclohexanecarboxylate (36 mgs, 0.071 mmol, 22% yield). ESI: [M+H]⁺ m/z 507.2.

Step 2

To a flask containing the product of Step 1 (36 mgs, 0.071 mmol) was added methanol (0.80 mL) and aqueous sodium hydroxide (1M, 0.14 mL, 0.14 mmol). The reaction was heated at 100° C. overnight. The reaction was cooled, acidified with HCl (1M, 0.2 mL, 0.20 mmol) and diluted with water (5 mL) and ethyl acetate (5 mL). The organic layer was separated, dried over magnesium sulfate, filtered and concentrated. During the reaction, the starting material isomerized. The mixture of syn and anti isomers was diluted in DMSO and purified by HPLC to yield:

cis-4-(5-{3-[(4-cyclopropylpyrimidin-2-yl)amino]-5-methylphenyl}-1,3-thiazol-2-yl)-4-hydroxy-cyclohexanecarboxylic acid (example 110(1)). MS ESI: [M+H]⁺ m/z 451.1. ¹H NMR (500 MHz, DMSO-d₆) δ 9.46 (s, 1H), 8.48 (s, 1H), 8.26 (d, J=5.0 Hz, 1H), 7.94 (s, 1H), 7.92 (s, 1H), 7.45 (s, 1H), 7.02 (s, 6.81 (d, J=5.0 Hz, 1H), 5.90 (s, 1H), 2.28 (s, 3H), 2.20 (m 1H), 2.01 (m, 1H), 1.88-1.85 (m 2H), 1.82-1.74 (m, 6H), 1.08-1.05 (m, 4H). rhSYK activity=+++ trans-4-(5-{3-[(4-cyclopropylpyrimidin-2-yl)amino]-5-methylphenyl}-1,3-thiazol-2-yl)-4-hydroxycyclohexanecarboxylic acid (example 110(2)). ESI: [M+H]⁺ m/z 451.1. ¹H NMR (500 MHz, DMSO-d₆) δ 9.46 (s, 1H), 8.47 (s, 1H), 8.26 (d, J=5.0 Hz, 1H), 7.95 (s, 1H), 7.91 (s, 1H), 7.44 (s, 1H), 7.03 (s, 1H), 6.81 (d, J=5.0 Hz, 1H), 5.90 (s, 1H), 2.42 (m, 1H), 2.28 (s, 3H), 2.09-2.06 (m, 2H), 2.02-2.00 (m, 1H), 1.84-1.82 (m, 4H), 1.66-1.63 (m, 2H), 1.08-1.05 (m, 41-1). rhSYK activity=+++

Compounds in the following Table(s) were prepared in a manner analogous of that described in Example 110:

TABLE 110

| Example | Structure | rhSYK Activity | [M + H]+ Observed | Form(s) |
|---|---|---|---|---|
| 110-1 | Enantiomer 1 | +++ | 587.1 | Free Base |
| 110-2 | Enantiomer 2 | +++ | 587.1 | Free Base |

Example 111

(1S,4R)-4-[5-(2-bromo-3-methyl-5-{[4-(trifluoromethyl)pyrimidin-2-yl]amino}phenyl)-1,3-thiazol-2-yl]-4-hydroxy-2,2-dimethylcyclohexanecarboxylic acid

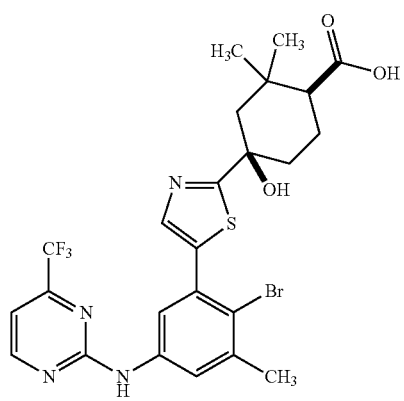 [SMILES: Cc1cc(Nc2nccc(C(F)(F)F)n2)cc(-c2cnc([C@@]3(O)CC[C@H](C(=O)O)C(C)(C)C3)s2)c1Br]

Step 1

To a suspension of (1S,4R)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid (example 42(1), 50 mg, 0.099 mmol) in chloroform (800 µL) was added N-bromosuccinamide (21 mg, 0.12 mmol). The mixture was stirred at room temperature for 15 minutes, and then concentrated under reduced pressure. The residue was purified by column chromatography on silica gel (Biotage 10 G, eluting with 1:99 to 10:90 methanol:dichloromethane) to give (1S,4R)-4-[5-(2-bromo-3-methyl-5-{[4-(trifluoromethyl)pyrimidin-2-yl]amino}phenyl)-1,3-thiazol-2-yl]-4-hydroxy-2,2-dimethylcyclohexanecarboxylic acid (22 mg, 0.038 mmol, 38% yield) as a pale yellow solid. ESI: [M+H]$^+$ m/z 587.1. $^1$H NMR (500 MHz, CD$_3$OD) δ 8.70 (d, J=4.9, 1H), 7.86 (d, J=2.6, 1H), 7.78-7.64 (m, 2H), 7.13 (d, J=4.9, 1H), 2.46 (s, 3H), 2.35 (dd, J=2.9, 12.8, 1H), 2.22 (ddd, J=6.1, 13.2, 24.2, 1H), 2.01 (dd, J=6.7, 14.5, 3H), 1.79 (d, J=14.4, 1H), 1.72 (dd, J=3.2, 13.5, 1H), 1.22 (s, 3H), 1.11 (s, 3H). rhSYK activity=+++

Compounds in the following Table(s) were prepared in a manner analogous of that described in Example 111:

TABLE 111

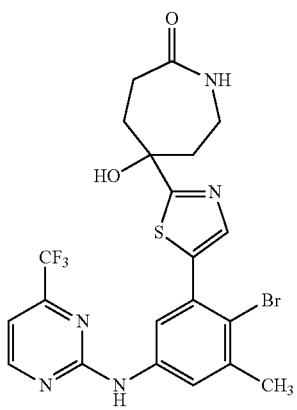 [SMILES: Cc1cc(Nc2nccc(C(F)(F)F)n2)cc(-c2cnc(C3(O)CCNC(=O)CC3)s2)c1Br]

| Example | Structure | rhSYK Activity | [M + H]+ Obs'd | Form(s) |
|---|---|---|---|---|
| 111-1 | Enantiomer 1 | ++ | 542.0 | Free Base |
| 111-2 | Enantiomer 2 | +++ | 542.0 | Free Base |

Example 112

(1S,4R)-4-(hydroxymethyl)-3,3-dimethyl-1-(5-(3-methyl-5-(4-(trifluoromethyl)pyrimidin-2-ylamino)phenyl)thiazol-2-yl)cyclohexanol

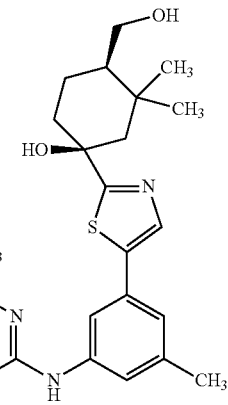

Step 1

(1S,4R)-Methyl 4-(5-bromothiazol-2-yl)-4-hydroxy-2,2-dimethylcyclohexanecarboxylate (110 mg, 0316 mmol) was placed in a 25-mL flask under nitrogen and THF (3 ml) was added. LiAlH$_4$ (1M in THF, 0.6 mL, 0.600 mmol) was added in 1 portion and the reaction mixture turned into a white gel-like suspension. After 2 hours methanol was added and the solvents were evaporated. The residue was purified by reverse phase HPLC (10-50% acetonitrile gradient with water+0.1% TFA) to afford (1S,4R)-4-(hydroxymethyl)-3,3-dimethyl-1-(thiazol-2-yl)cyclohexanol TFA salt (40 mg, 0.113 mmol, 35.6% yield) as a colorless oil.

Step 2

A 4-mL screw-cap pressure vial was charged with N-(3-bromo-5-methylphenyl)-4-(trifluoromethyl)pyrimidin-2-amine (INTERMEDIATE 2, 74.8 mg, 0.225 mmol), stir bar, pivalic acid (2.61 µl, 0.023 mmol), potassium carbonate (46.7 mg, 0.338 mmol), (1S,4R)-4-(hydroxymethyl)-3,3-dimethyl-1-(thiazol-2-yl)cyclohexanol TFA salt (40 mg, 0.113 mmol), and Pd(PPh$_3$)$_4$ (13.01 mg, 0.011 mmol). The vial was closed, evacuated and back-filed with nitrogen 3 times. DMA (0.5 ml) (dry, over molecular sieves, Fluka) was added and the reaction mixture heated to 120° C. for 16 hours, LCMS showed product formation and some remaining starting materials. Filtered and concentrated in vacuo. The residue was purified by reverse phase HPLC (10-60% acetonitrile gradient with water+0.1% TFA) to afford (1S,4R)-4-(hydroxymethyl)-3,3-dimethyl-1-(5-(3-methyl-5-(4-(trifluoromethyl)pyrimidin-2-ylamino)-phenyl)thiazol-2-yl)cyclohexanol (14 mg, 0.023 mmol, 20.51% yield over 2 steps) as a yellow solid. MS ESI: [M+H]$^+$ m/z 492.2. $^1$H NMR (500 MHz, DMSO-d$_6$): δ 10.24 (s, 1H), 8.83 (d, J=4.9 Hz, 1H), 7.94 (s, 1H), 7.92 (m, 1H), 7.46 (s, 1H), 7.28 (d, J=4.9 Hz, 1H), 7.14 (s, 1H), 3.66 (dd, J=10.2, 3.5 Hz, 1H), 3.08 (app t, J=10.2 Hz, 1H), 2.31 (s, 3H), 1.98-1.44 (m, 7H), 0.96 (s, 3H), 0.93 (s, 3H). rhSYK activity=+++

Example 113

(1S,4R)-4-(5-{3-cyclopropyl-5-[(4-methylpyrimidin-2-yl)amino]phenyl}-1,3-thiazol-2-yl)-4-hydroxy-2,2-dimethylcyclohexanecarboxylic acid

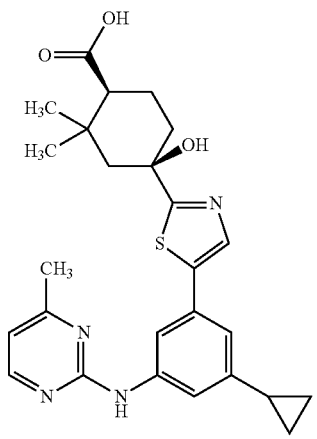 [SMILES: Cc1ccnc(Nc2cc(-c3cnc([C@@]4(O)CC[C@H](C(=O)O)C(C)(C)C4)s3)cc(C3CC3)c2)n1]

Step 1

A reaction mixture containing N-[3-cyclopropyl-5-(4,4,5,5-tetramethyl-1,3,2-dioxaborolan-2-yl)phenyl]-4-methylpyrimidin-2-amine (60 mg, 0.171 mmol), methyl(1S,4R)-4-(5-bromo-1,3-thiazol-2-yl)-4-hydroxy-2,2-dimethylcyclohexanecarboxylate (62.5 mg, 0.179 mmol), PdCl$_2$(dppf)-CH$_2$Cl$_2$ adduct (27.9 mg, 0.034 mmol), 1,4-dioxane (1.2 mL), water (0.1 mL), and aqueous sodium bicarbonate solution (2 M, 0.171 mL, 0.342 mmol) was irradiated in the microwave for 15 minutes at 160° C. The reaction mixture was partitioned between ethyl acetate (30 mL) and saturated aqueous sodium bicarbonate solution (15 mL). The layers were separated and the organic layer was washed with brine, dried over sodium sulfate, filtered, and concentrated. The crude product was purified by silica gel flash column chromatography (25-50% ethyl acetate/hexanes) to afford methyl(1S,4R)-4-(5-{3-cyclopropyl-5-[(4-methylpyrimidin-2-yl)amino]phenyl}-1,3-thiazol-2-yl)-4-hydroxy-2,2-dimethylcyclohexanecarboxylate (41.3 mg, 0.084 mmol, 49% yield) as an off-white, solid.

Step 2

To a solution of the product from Step 1 (41.3 mg, 0.084 mmol) in tetrahydrofuran (0.4 mL) and methanol (0.8 mL) was added sodium hydroxide (1 M in water, 0.153 mL, 0.153 mmol). The reaction mixture was heated to 120° C. for 10 minutes in a microwave oven. An additional charge of sodium hydroxide was added (1 M in water, 0.300 mL, 0.300 mmol) and the vessel was heated again for 10 minutes at 120° C. Upon cooling aqueous hydrogen chloride (2M in water, 0.235 mL, 0.470 mmol) was added and the resulting mixture was diluted with 10% v/v isopropanol/chloroform (20 mL), brine (10 mL), and water (1 mL). The layers were separated and the aqueous layer was re-extracted with 10% v/v isopropanol/chloroform (10 mL). The organic layers were combined, dried over sodium sulfate, filtered, and concentrated. Lyophilization of the residue from methanol/water provided (1S,4R)-4-(5-{3-cyclopropyl-5-[(4-methylpyrimidin-2-yl)amino]phenyl}-1,3-thiazol-2-yl)-4-hydroxy-2,2-dimethylcyclohexanecarboxylic acid (34.3 mg, 0.072 mmol, 84% yield) as an off-white solid. MS ESI: [M+H]$^+$ m/z 461.1.

Compounds in the following Table(s) were prepared in a manner analogous of that described in Example 13:

TABLE 113A

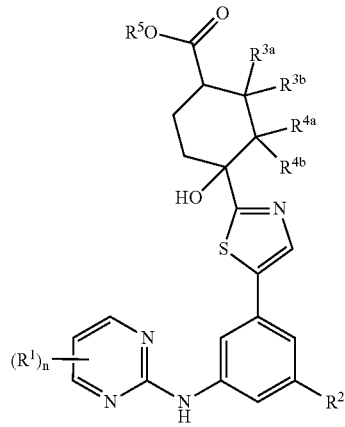

| Example | R$^1$ | R$^2$ | R$^{3a}$/R$^{3b}$ | R$^5$ | rhSYK Activity | [M + H]+ Obs'd | Form(s) |
|---|---|---|---|---|---|---|---|
| R$^{4a}$/R$^{4b}$ = H/H | | | | | | | |
| 113A-1 | 4-O(CH$_2$)$_2$—OCH$_3$ | CH$_3$ | H/H (cis) | H | +++ | 485 | Free Base |
| 113A-2 | 4-O(CH$_2$)$_3$—OCH$_3$ | CH$_3$ | H/H (cis) | H | +++ | 499 | Free Base |

TABLE 113A-continued

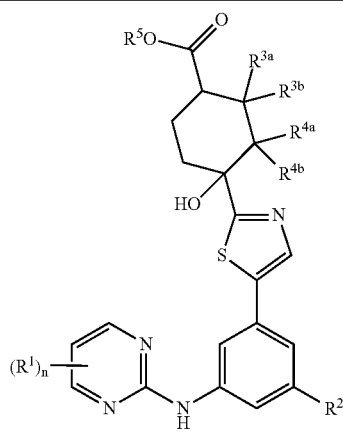

| Example | $R^1$ | $R^2$ | $R^{3a}/R^{3b}$ | $R^5$ | rhSYK Activity | [M + H]+ Obs'd | Form(s) |
|---|---|---|---|---|---|---|---|
| 113A-3 | 4-CF$_3$ | Cl | H/H (cis) | H | +++ | 499.1 | Free Base |
| 113A-4 | 4-CH$_3$ | CH$_3$ | H/CH$_3$ (isomer 1) | H | +++ | 439 | Free Base |
| 113A-5 | 4-CH$_3$ | CH$_3$ | H/CH$_3$ (isomer 2) | H | +++ | 439 | Free Base |
| 113A-6 | 4-CH$_3$ | CH$_3$ | H/CH$_3$ (isomer 3) | H | +++ | 439 | Free Base |
| 113A-7 | 4-CH$_3$ | CH$_3$ | H/CH$_3$ (isomer 4) | H | +++ | 439 | Free Base |
| 113A-8 | 4-CH$_3$ | CH$_3$ | H/CH$_3$ (isomer 1) | CH$_3$ | +++ | 453 | Free Base |
| 113A-9 | 4-CH$_3$ | CH$_3$ | H/CH$_3$ (isomer 2) | CH$_3$ | ++ | 453 | Free Base |
| 113A-10 | 4-CH$_3$ | CH$_3$ | H/CH$_3$ (isomer 3) | CH$_3$ | +++ | 453 | Free Base |
| 113A-11 | 4-CH$_3$ | CH$_3$ | H/CH$_3$ (isomer 4) | CH$_3$ | +++ | 453 | Free Base |
| 113A-12 | 4-CH$_3$ | CH$_3$ | H/CH$_3$ (isomer 5) | CH$_3$ | ++ | 453 | Free Base |
| 113A-13 | 4-CH$_3$ | CH$_3$ | H/CH$_3$ (isomer 6) | CH$_3$ | ++ | 453 | Free Base |
| 113A-14 | 4-Et | CH$_3$ | H/CH$_3$ (isomer 1) | H | +++ | 453.1 | Free Base |
| 113A-15 | 4-Et | CH$_3$ | H/CH$_3$ (isomer 2) | H | +++ | 453.1 | Free Base |
| 113A-16 | 4-OCH$_3$ | CH$_3$ | H/CH$_3$ (1S,2R,4R) | H | +++ | 455 | Formate Salt |
| 113A-17 | 4-OCH$_3$ | CH$_3$ | H/CH$_3$ (1S,2S,4S) | H | +++ | 455 | Formate Salt |
| 113A-18 | 4-CH$_3$, 5-F | CH$_3$ | H/CH$_3$ (1S,2R,4R) | H | +++ | 457 | Formate Salt |
| 113A-19 | 4-CH$_3$, 5-F | CH$_3$ | H/CH$_3$ (1S,2S,4S) | H | +++ | 457 | Formate Salt |
| 113A-20 | 4-cPr | CH$_3$ | H/CH$_3$ (1R,2S,4S) | H | +++ | 465 | Formate Salt |
| 113A-21 | 4-cPr | CH$_3$ | H/CH$_3$ (1S,2R,4R) | H | +++ | 465.1 | Formate Salt |
| 113A-22 | 4-cPr | CH$_3$ | H/CH$_3$ | H | +++ | 465.2 | TFA Salt |
| 113A-23 | 4-CH$_3$ | cPr | H/CH$_3$ (isomer 1) | H | +++ | 465.1 | Free Base |
| 113A-24 | 4-CH$_3$ | cPr | H/CH$_3$ (isomer 2) | H | +++ | 465.1 | Free Base |
| 113A-25 | 4-iPr | CH$_3$ | H/CH$_3$ (1S,2R,4R) | H | +++ | 467.2 | Free Base |
| 113A-26 | 4-iPr | CH$_3$ | H/CH$_3$ (1R,2S,4S) | H | +++ | 467.2 | Free Base |
| 113A-27 | 4-CH$_3$, 5-Cl | CH$_3$ | H/CH$_3$ (1S,2R,4R) | H | +++ | 473 | Formate Salt |
| 113A-28 | 4-CH$_3$, 5-Cl | CH$_3$ | H/CH$_3$ (1R,2S,4S) | H | +++ | 473 | Formate Salt |
| 113A-29 | 4-CH$_3$, 5-F | CH$_3$ | H/CH$_3$ (1S,2R,4R) | H | +++ | 473 | Formate Salt |
| 113A-30 | 4-CH$_3$, 5-F | CH$_3$ | H/CH$_3$ (1R,2S,4S) | H | +++ | 473 | Formate Salt |
| 113A-31 | 4-Et | CH$_3$ | H/CH$_3$ (isomer 1) | Et | +++ | 481.1 | Free Base |
| 113A-32 | 4-Et | CH$_3$ | H/CH$_3$ (isomer 2) | Et | +++ | 481.1 | Free Base |
| 113A-33 | 4-cPr, 5-F | CH$_3$ | H/CH$_3$ (1S,2R,4R) | H | +++ | 483 | Formate Salt |
| 113A-34 | 4-cPr, 5-F | CH$_3$ | H/CH$_3$ (1R,2S,4S) | H | +++ | 483 | Formate Salt |
| 113A-35 | 4-O-iPr | CH$_3$ | H/CH$_3$ (1R,2S,4S) | H | +++ | 483 | Formate Salt |
| 113A-36 | 4-OCH$_3$, 5-Cl | CH$_3$ | H/CH$_3$ (1S,2R,4R) | H | +++ | 489 | Formate Salt |
| 113A-37 | 4-OCH$_3$, 5-Cl | CH$_3$ | H/CH$_3$ (1R,2S,4S) | H | +++ | 489 | Formate Salt |
| 113A-38 | 4-O(CH$_2$)$_2$—OCH$_3$ | CH$_3$ | H/CH$_3$ (isomer 1) | H | +++ | 499 | Free Base |
| 113A-39 | 4-O(CH$_2$)$_2$—OCH$_3$ | CH$_3$ | H/CH$_3$ (isomer 2) | H | +++ | 499 | Free Base |
| 113A-40 | 4-O(CH$_2$)$_3$—OCH$_3$ | CH$_3$ | H/CH$_3$ (isomer 1) | H | +++ | 513 | Free Base |
| 113A-41 | 4-O(CH$_2$)$_3$—OCH$_3$ | CH$_3$ | H/CH$_3$ (isomer 2) | H | +++ | 513 | Free Base |
| 113A-42 | CF$_3$ | CH$_2$—OCH$_3$ | H/CH$_3$ | H | +++ | 523.2 | Free Base |
| 113A-43 | 4-O(CH$_2$)$_2$—OCH$_3$ | CH$_3$ | H/CH$_3$ (isomer 1) | Et | +++ | 527 | Free Base |
| 113A-44 | 4-O(CH$_2$)$_2$—OCH$_3$ | CH$_3$ | H/CH$_3$ (isomer 2) | Et | +++ | 527 | Free Base |
| 113A-45 | 4-CF$_3$ | CH$_3$ | H/CH$_3$ | Et | ++ | 535 | Free Base |
| 113A-47 | 4-O(CH$_2$)$_3$—OCH$_3$ | CH$_3$ | H/CH$_3$ (isomer 1) | Et | +++ | 541 | Free Base |
| 113A-48 | 4-O(CH$_2$)$_3$—OCH$_3$ | CH$_3$ | H/CH$_3$ (isomer 2) | Et | +++ | 541 | Free Base |
| 113A-49 | 4-Et | CH$_3$ | CH$_3$/CH$_3$ (1S,4R) | H | +++ | 467.1 | Free Base |
| 113A-50 | 4-CN | CH$_3$ | CH$_3$/CH$_3$ (1S,4R) | CH$_3$ | +++ | 478.2 | Free Base |
| 113A-51 | 4-cPr | CH$_3$ | CH$_3$/CH$_3$ (cis) | H | +++ | 479 | Free Base |
| 113A-52 | 4-iPr | CH$_3$ | CH$_3$/CH$_3$ (cis) | H | +++ | 481 | Free Base |
| 113A-53 | 4-Et | CH$_3$ | CH$_3$/CH$_3$ (1S,4R) | CH$_3$ | +++ | 481.1 | Free Base |
| 113A-54 | 4-OCH$_3$ | CH$_3$ | CH$_3$/CH$_3$ (1S,4R) | CH$_3$ | +++ | 483.1 | Free Base |
| 113A-55 | 4-OCH$_3$ | CH$_3$ | CH$_3$/CH$_3$ (1R,4S) | CH$_3$ | +++ | 483.2 | Free Base |
| 113A-56 | 4-cPr | CH$_3$ | CH$_3$/CH$_3$ (cis) | CH$_3$ | +++ | 493 | Free Base |
| 113A-57 | 4-cPr, 5-F | CH$_3$ | CH$_3$/CH$_3$ | H | +++ | 497.2 | Free Base |
| 113A-58 | 4-cPr, 5-F | CH$_3$ | CH$_3$/CH$_3$ (1S,4R) | H | +++ | 497.2 | Free Base |
| 113A-59 | 4-CF$_3$ | Cl | CH$_3$/CH$_3$ | H | +++ | 527.1 | Free Base |

TABLE 113A-continued

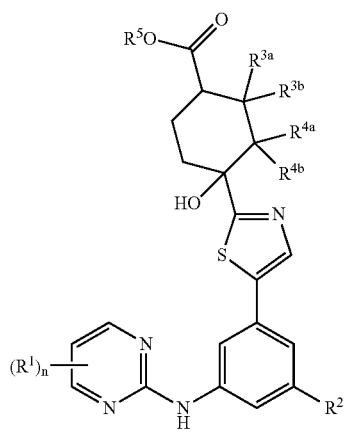

| Example | R¹ | R² | R³ᵃ/R³ᵇ | R⁵ | rhSYK Activity | [M + H]+ Obs'd | Form(s) |
|---|---|---|---|---|---|---|---|
| 113A-60 | 4-CF₃ | Cl | CH₃/CH₃ (1S,4R) | H | +++ | 527.1 | Free Base |
| 113A-61 | 4-CF₃ | Cl | CH₃/CH₃ (1R,4S) | H | +++ | 527.1 | Free Base |
| 113A-62 | 4-CF₃ | CH₂—OCH₃ | CH₃/CH₃ (1S,4R) | H | +++ | 537.2 | TFA Salt |
| 113A-63 | 4-CF₃ | Cl | CH₃/CH₃ | CH₃ | ++ | 541.1 | Free Base |
| 113A-64 | 4-CF₃* | CH₃ | CH₃/CH₃ (1S,4R) | H | +++ | 508.0 | Free Base |
| 113A-65 | 4-CF₃* | CH₃ | CH₃/CH₃ (1S,4R) | CH₃ | +++ | 522.1 | Free Base |

R⁴ᵃ/R⁴ᵇ = H/CH₃

| Example | R¹ | R² | R³ᵃ/R³ᵇ | R⁵ | rhSYK Activity | [M + H]+ Obs'd | Form(s) |
|---|---|---|---|---|---|---|---|
| 113A-66 | 4-CH₃ | CH₃ | H/CH₃ (isomer 1) | H | +++ | 453 | Free Base |
| 113A-67 | 4-CH₃ | CH₃ | H/CH₃ (isomer 2) | H | +++ | 453 | Free Base |
| 113A-68 | 4-CH₃ | CH₃ | H/CH₃ (isomer 3) | H | +++ | 453 | Free Base |
| 113A-69 | 4-CH₃ | CH₃ | H/CH₃ (isomer 4) | H | +++ | 453 | Free Base |
| 113A-70 | 4-CH₃ | CH₃ | H/CH₃ (isomer 1) | Et | +++ | 481 | Free Base |
| 113A-71 | 4-CH₃ | CH₃ | H/CH₃ (isomer 2) | Et | +++ | 481 | Free Base |
| 113A-72 | 4-CH₃ | CH₃ | H/CH₃ (isomer 3) | Et | +++ | 481 | Free Base |
| 113A-73 | 4-CH₃ | CH₃ | H/CH₃ (isomer 4) | Et | +++ | 481 | Free Base |
| 113A-74 | 4-CH₃ | CH₃ | H/CH₃ (isomer 1) | H | +++ | 507 | Free Base |
| 113A-75 | 4-CH₃ | CH₃ | H/CH₃ (isomer 2) | H | +++ | 507 | Free Base |
| 113A-76 | 4-CH₃ | CH₃ | H/CH₃ (isomer 3) | H | +++ | 507 | Free Base |
| 113A-77 | 4-CF₃ | CH₃ | H/CH₃ (isomer 1) | Et | +++ | 535 | Free Base |
| 113A-78 | 4-CF₃ | CH₃ | H/CH₃ (isomer 2) | Et | +++ | 535 | Free Base |
| 113A-79 | 4-CF₃ | CH₃ | H/CH₃ (isomer 3) | Et | +++ | 535 | Free Base |
| 113A-80 | 4-CH₃ | CH₃ | H/H | H | +++ | 439 | Free Base |
| 113A-81 | 4-CH₃ | CH₃ | H/H (isomer 1) | H | +++ | 439 | Free Base |
| 113A-82 | 4-CH₃ | CH₃ | H/H (isomer 2) | H | +++ | 439 | Free Base |
| 113A-83 | 4-CH₃ | CH₃ | H/H (isomer 3) | H | +++ | 439 | TFA Salt |
| 113A-84 | 4-CH₃ | CH₃ | H/H (isomer 4) | H | +++ | 439 | TFA Salt |
| 113A-85 | 4-CH₃ | CH₃ | H/H (isomer 5) | H | +++ | 439 | TFA Salt |
| 113A-86 | 4-CH₃ | CH₃ | H/H (isomer 6) | H | +++ | 439 | TFA Salt |
| 113A-87 | 4-CH₃ | CH₃ | H/H | Et | +++ | 467 | Free Base |
| 113A-88 | 4-CF₃ | CH₃ | H/H | H | +++ | 493 | Free Base |
| 113A-89 | 4-CF₃ | CH₃ | H/H | Et | +++ | 521 | Free Base |

R⁴ᵃ/R⁴ᵇ = H/OH

| Example | R¹ | R² | R³ᵃ/R³ᵇ | R⁵ | rhSYK Activity | [M + H]+ Obs'd | Form(s) |
|---|---|---|---|---|---|---|---|
| 113A-90 | 4-CH₃ | CH₃ | H/H (isomer 1) | H | +++ | 441 | Free Base |
| 113A-91 | 4-CH₃ | CH₃ | H/H (isomer 2) | H | +++ | 441 | Free Base |

R⁴ᵃ/R⁴ᵇ = CH₃/CH₃

| Example | R¹ | R² | R³ᵃ/R³ᵇ | R⁵ | rhSYK Activity | [M + H]+ Obs'd | Form(s) |
|---|---|---|---|---|---|---|---|
| 113A-92 | 4-CH₃ | CH₃ | H/H | H | +++ | 453 | Free Base | n is 1 or 2 substituents as specified in the Table
*deuterated at pyrimidine 6-position

TABLE 113B

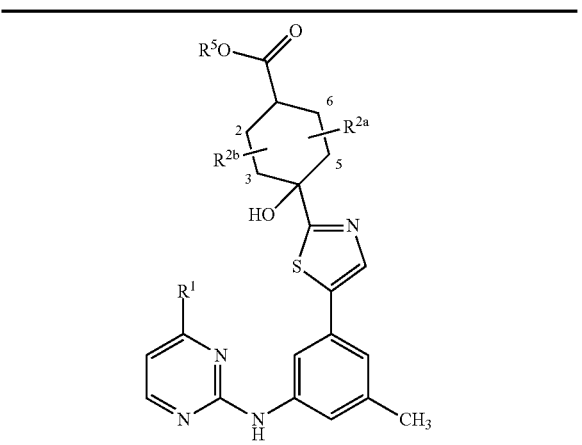

| Example | R¹ | R²ᵃ/R²ᵇ | R³ | rhSYK Activity | [M + H]+ Obs'd | Form(s) |
|---|---|---|---|---|---|---|
| 113B-1 | CH₃ | 2,5-di(CH₃) | H | +++ | 453 | Free Base |
| 113B-2 | CH₃ | 2,5-di(CH₃) (isomer 1) | H | +++ | 453 | Free Base |
| 113B-3 | CH₃ | 2,5-di(CH₃) (isomer 2) | H | +++ | 453 | Free Base |
| 113B-4 | CH₃ | 2,5-di(CH₃) (isomer 3) | H | +++ | 453 | Free Base |
| 113B-5 | CH₃ | 2,5-di(CH₃) (isomer 4) | H | +++ | 453 | Free Base |
| 113B-6 | CH₃ | 2,5-di(CH₃) (isomer 5) | H | +++ | 453 | Free Base |
| 113B-7 | CH₃ | 2,5-di(CH₃) | Et | +++ | 481 | Free Base |
| 113B-8 | CH₃ | 2,5-di(CH₃) (isomer 1) | Et | +++ | 481 | Free Base |
| 113B-9 | CH₃ | 2,5-di(CH₃) (isomer 2) | Et | +++ | 481 | Free Base |
| 113B-10 | CH₃ | 2,5-di(CH₃) (isomer 3) | Et | +++ | 481 | Free Base |
| 113B-11 | CH₃ | 2,5-di(CH₃) (isomer 4) | Et | ++ | 481 | Free Base |
| 113B-12 | CF₃ | 2,5-di(CH₃) | H | +++ | 507 | Free Base |
| 113B-13 | CF₃ | 2,5-di(CH₃) (isomer 1) | H | +++ | 507 | Free Base |
| 113B-14 | CF₃ | 2,5-di(CH₃) (isomer 2) | H | +++ | 507 | Free Base |
| 113B-15 | CF₃ | 2,5-di(CH₃) (isomer 3) | H | +++ | 507 | Free Base |
| 113B-16 | CF₃ | 2,5-di(CH₃) (isomer 4) | H | +++ | 507 | Free Base |
| 113B-17 | CF₃ | 2,5-di(CH₃) | Et | +++ | 535 | Free Base |
| 113B-18 | CF₃ | 2,5-di(CH₃) (isomer 1) | Et | +++ | 535 | Free Base |
| 113B-19 | CF₃ | 2,5-di(CH₃) (isomer 2) | Et | +++ | 535 | Free Base |
| 113B-20 | CF₃ | 2,5-di(CH₃) (isomer 3) | Et | ++ | 535 | Free Base |
| 113B-21 | CH₃ | 2,6-di(CH₃) | H | +++ | 453 | Free Base |
| 113B-22 | CH₃ | 2,6-di(CH₃) (trans,trans,trans) | H | +++ | 453 | Free Base |
| 113B-23 | CH₃ | 2,6-di(CH₃) | iPr | ++ | 495 | Free Base |
| 113B-24 | CF₃ | 2,6-di(CH₃) | H | +++ | 507 | Free Base |
| 113B-25 | CF₃ | 2,6-di(CH₃) (trans,trans,trans) | H | +++ | 507 | Free Base |
| 113B-26 | CF₃ | 2,6-di(CH₃) (isomer 1) | iPr | + | 549 | Free Base |
| 113B-27 | CF₃ | 2,6-di(CH₃) (isomer 2) | iPr | ++ | 549 | Free Base |
| 113B-28 | CH₃ | 3,5-di(CH₃) | H | +++ | 453 | Free Base |
| 113B-29 | CH₃ | 3,5-di(CH₃) | Et | +++ | 481 | Free Base |
| 113B-30 | CF₃ | 3,5-di(CH₃) | H | +++ | 507 | Free Base |
| 113B-31 | CF₃ | 3,5-di(CH₃) | Et | +++ | 535 | Free Base |

TABLE 113C

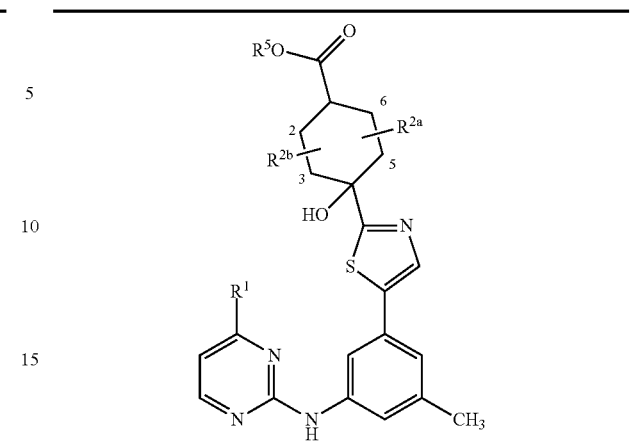

| Ex. | R¹ | R² | R³ | X |
|---|---|---|---|---|
| 113C-1 | 4-CH₃, 5-F | CH₃ | H | C(O) |
| 113C-2 | 4-cPr | CH₃ | H | C(O) |
| 113C-3 | 4-CH(F)—CH₃ | CH₃ | H (enantiomer 1) | C(O) |
| 113C-4 | 4-CH(F)—CH₃ | CH₃ | H (enantiomer 2) | C(O) |
| 113C-5 | 4-CH₃, 5-Cl | CH₃ | H | C(O) |
| 113C-6 | 4-OCH₃, 5-F | CH₃ | H | C(O) |
| 113C-7 | 4-CHF₂ | CH₃ | H | C(O) |
| 113C-8 | 4-CF₃ | H | H | C(O) |
| 113C-9 | 4-tBu | CH₃ | H | C(O) |
| 113C-10 | 4-O-iPr | CH₃ | H | C(O) |
| 113C-11 | 4-OCH₃, 5-Cl | CH₃ | H | C(O) |
| 113C-12 | 4-(2-thienyl) | CH₃ | H | C(O) |
| 113C-13 | 4-cPr | CH₃ | H | CH₂ |
| 113C-14 | 4-iPr | CH₃ | H | CH₂ |
| 113C-15 | 4-OCH₃, 5-Cl | CH₃ | H (enantiomer 1) | CH₂ |
| 113C-16 | 4-OCH₃, 5-Cl | CH₃ | H (enantiomer 2) | CH₂ |
| 113C-17 | 4-cPr | CH₃ | BOC | CH₂ |

TABLE 113C-continued

| Ex. | | | | |
|---|---|---|---|---|
| 113C-18 | 4-cPr | CH₃ | BOC (enantiomer 1) | CH₂ |
| 113C-19 | 4-iPr | CH₃ | BOC | CH₂ |
| 113C-20 | 4-iPr | CH₃ | BOC (enantiomer 1) | CH₂ |
| 113C-21 | 4-iPr | CH₃ | BOC (enantiomer 2) | CH₂ |
| 113C-22 | 4-OCH₃, 5-Cl | CH₃ | H (enantiomer 1) | CH₂ |
| 113C-23 | 4-OCH₃, 5-Cl | CH₃ | H (enantiomer 2) | CH₂ |

| Ex. | rhSYK Activity | [M + H]+ Obs'd | Form(s) |
|---|---|---|---|
| 113C-1 | +++ | 428.0 | TFA Salt |
| 113C-2 | +++ | 436.2 | TFA Salt |
| 113C-3 | +++ | 442.1 | Free Base |
| 113C-4 | +++ | 442.2 | Free Base |
| 113C-5 | +++ | 444.1 | TFA Salt |
| 113C-6 | +++ | 444.1 | TFA Salt |
| 113C-7 | +++ | 446.1 | Free Base |
| 113C-8 | +++ | 450.1 | TFA Salt |
| 113C-9 | +++ | 452.2 | Free Base |
| 113C-10 | +++ | 454.2 | Free Base |
| 113C-11 | +++ | 460.1 | TFA Salt |
| 113C-12 | +++ | 478.0 | Free Base |
| 113C-13 | +++ | 422.2 | Free Base |
| 113C-14 | +++ | 424.2 | Free Base |
| 113C-15 | +++ | 446.1 | Free Base |
| 113C-16 | +++ | 446.1 | Free Base |
| 113C-17 | +++ | 522.3 | Free Base |
| 113C-18 | ++ | 522.3 | Free Base |
| 113C-19 | +++ | 524.3 | Free Base |
| 113C-20 | ++ | 524.3 | Free Base |
| 113C-21 | + | 524.3 | Free Base |
| 113C-22 | + | 546.2 | Free Base |
| 113C-23 | + | 546.2 | Free Base | n is 1 or 2 substituents as specified in the Table.

TABLE 113D

| Ex. | X | Y | R | rhSYK Activity | [M + H]+ Obs'd | Form(s) |
|---|---|---|---|---|---|---|
| 113D-1 | C(=CH₂) | CH | H | +++ | 483.0 | Free Base |
| 113D-2 | C(=CH₂) | CH | CH₃ | ++ | 497.0 | Free Base |

TABLE 113D-continued

| | | | | | | |
|---|---|---|---|---|---|---|
| 113D-3 | (cyclopropyl-1,1-diyl) | CH | H | +++ | 497.1 | Free Base |
| 113D-4 | (E)-CH=CH— | CH | CH₃ | ++ | 497.7 | Free Base |
| 113D-5 | —C(CH₃)₂— | CH | H | +++ | 499.1 | Free Base |
| 113D-6 | —C(OH)(CH₃)— | N | H | +++ | 502.1 | Free Base |
| 113D-7 | —CF₂— | CH | H | +++ | 507.0 | Free Base |
| 113D-8 | (cyclopropyl-1,1-diyl) | CH | CH₃ | ++ | 511.1 | Free Base |
| 113D-9 | —C(CH₃)₂— | CH | CH₃ | ++ | 513.1 | Free Base |
| 113D-10 | —CF₂— | CH | CH₃ | + | 521.1 | Free Base |

| Ex. | Structure | rhSYK Activity | [M + H]+ Obs'd | Form(s) |
|---|---|---|---|---|
| 113D-11 | Isomer 1 | +++ | 481.1 | Free Base |
| 113D-12 | Isomer 2 | +++ | 481.1 | Free Base |
| 113D-13 | (structure shown) | +++ | 443.1 | Free Base |

Example 114

N-{3-methyl-5-[2-(1H-pyrazol-4-yl)-1,3-thiazol-5-yl]phenyl}-4-(trifluoromethyl)pyrimidin-2-amine

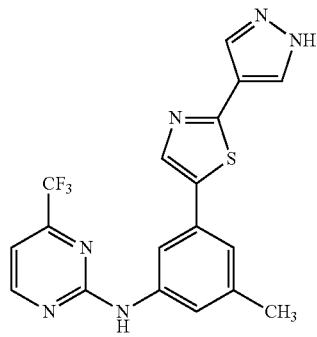 [SMILES: Cc1cc(Nc2nccc(C(F)(F)F)n2)cc(-c2cnc(-c3cn[nH]c3)s2)c1]

To a sealed tube was added INTERMEDIATE 9 (30.0 mg, 0.072 mmol), 4-(4,4,5,5-tetramethyl-1,3,2-dioxaborolan-2-yl)-1H-pyrazole (16.8 mg, 0.087 mmol), Pd(dppf)Cl$_2$—CH$_2$Cl$_2$ (13.2 mg, 0.018 mmol), dioxane (722 μL, 0.1 M), and aqueous Na$_2$CO$_3$ (90 μL, 2 M). The reaction vessel was purged with argon, sealed and heated to 110° C. for 8 hours. The completed reaction was cooled to 60° C. and to the vial was added silica bound Si-2,4,6-trimercaptotriazine (74.5 mg, 0.144 mmol, 1.94 mmol/g) as a Pd(dppf)Cl$_2$ scavenger. The reaction was shaken for 4 hours at 60° C. The completed scavenging reaction was passed through a syringe filter and concentrated in vacuo. Purification by reverse phase preparative HPLC (0:100 to 95:5 acetonitrile:water: 0.1% v/v TFA modifier) afforded the title product (3M mg, 0.0065 mmol, 7.8%). MS ESI: [M+H]$^+$ m/z 403.1. $^1$H NMR (500 MHz, DMSO) δ 10.27 (s, 1H), 8.83 (d, J=4.9, 1H), 8.37-8.07 (m, 1H), 8.03 (s, 1H), 7.98 (s, 1H), 7.47 (s, 1H), 7.28 (d, J=4.9, 1H), 7.18 (s, 1H), 2.32 (s, 3H). rhSTK activity=+++

The following examples were prepared in an analogous manner to that described in Example 114.

TABLE 114

| Example | A | rhSYK Activity | [M + H]+ Observed | Form(s) |
|---|---|---|---|---|
| 114-1 | (tetrahydropyrazolo-pyridinyl) | +++ | 457.1 | Formate Salt |
| 114-2 | 3-pyrazolyl | +++ | 403.1 | Formate Salt |
| 114-3 | 3-pyridyl | +++ | 414.1 | Formate Salt |
| 114-4 | 4-pyridyl | +++ | 414.1 | Formate Salt |
| 114-5 | 2-thienyl | ++ | 419.0 | Formate Salt |

TABLE 114-continued

| Example | A | rhSYK Activity | [M + H]+ Observed | Form(s) |
|---|---|---|---|---|
| 114-6 | 3-thienyl | ++ | 419.0 | Formate Salt |
| 114-7 | 2-furyl | +++ | 403.1 | Formate Salt |
| 114-8 | 2-pyrrolyl | +++ | 402.1 | Formate Salt |

Example 115

2-{4-[5-(3-methyl-5-{[4-(trifluoromethyl)pyrimidin-2-yl]amino}phenyl)-1,3-thiazol-2-yl]-1H-pyrazol-1-yl}ethanol

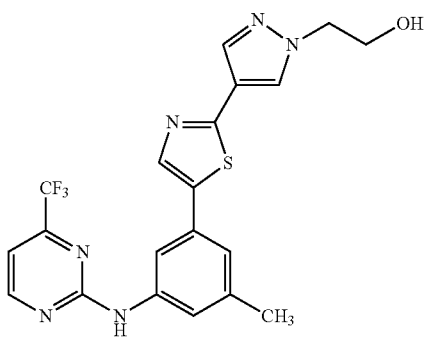 [SMILES: Cc1cc(Nc2nccc(C(F)(F)F)n2)cc(-c2cnc(-c3cnn(CCO)c3)s2)c1]

To a sealed tube was added N-{3-methyl-5-[2-(1H-pyrazol-4-yl)-1,3-thiazol-5-yl]phenyl}-4-(trifluoromethyl)pyrimidin-2-amine (38.0 mg, 0.095 mmol), DMF (950 μL, 0.1 M) and NaH (15.0 mg, 0.380 mmol, 60% wt). The reaction was allowed to age for 20 minutes. Next was added 2-bromo ethanol (11.8 mg, 0.095 mmol) and the reaction was allowed to stir at rt for 4 hours. The completed reaction was quenched with H$_2$O (100 μL) and was concentrated in vacuo. Purification by reverse phase preparative HPLC (0:100 to 95:5 acetonitrile:water: 0.1% v/v formic acid modifier) to afford the title product (2.8 mg, 0.0057 mmol, 6.0%). MS ESI: [M+H]$^+$ m/z 447.1. $^1$H NMR (600 MHz, DMSO) δ 10.24 (s, 1H), 8.82 (d, J=4.9, 1H), 8.28 (s, 1H), 8.01 (s, 1H), 7.97 (s, 1H), 7.91 (s, 1H), 7.44 (s, 1H), 7.26 (d, J=4.9, 1H), 7.16 (s, 1H), 4.18 (t, J=5.5, 2H), 3.74 (s, 2H), 2.30 (s, 3H). rhSTK activity=+++

The following examples were prepared in an analogous manner to that described in Example 115.

TABLE 115

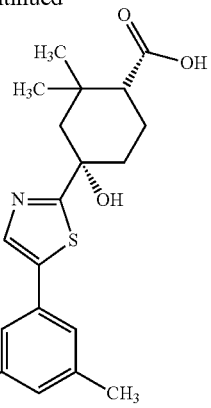

| Example | R | rhSYK Activity | [M + H]+ Obs'd | Form(s) |
|---|---|---|---|---|
| 115-1 | 4-tetrahydropyranyl | +++ | 487.1 | Formate Salt |
| 115-2 | CH$_2$CH$_2$CN | +++ | 456.1 | Formate Salt |
| 115-3 | (CH$_2$)$_3$OH | +++ | 461.1 | Formate Salt |
| 115-4 | (R) —CH$_2$CH(OH)CH$_2$OH | +++ | 477.1 | Formate Salt |
| 115-5 | CH$_2$C(CH$_3$)$_2$OH | +++ | 475.1 | Formate Salt |
| 115-6 | CH(CO2H)CH$_2$CH$_2$OH | +++ | 505.1 | Formate Salt |
| 115-7 | CH$_2$-(2-oxo-5-oxazolidinyl) | +++ | 502.1 | Formate Salt |

Example 116

(1S,4R) and (1R,4S)-4-(5-{3-[(5-fluoro-4-methylpyrimidin-2-yl)amino]-5-methylphenyl}-1,3-thiazol-2-yl)-4-hydroxy-2,2-dimethylcyclohexanecarboxylic acid

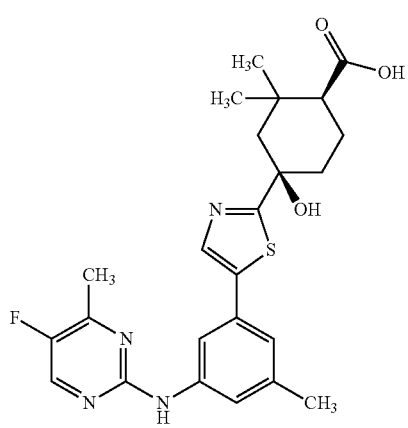

Step 1

Racemic 2-chloro-5-fluoro-4-methylpyrimidine (50.0 mg, 0.341 mmol), methyl-4-[5-(3-amino-5-methylphenyl)-1,3-thiazol-2-yl]-4-hydroxy-2,2-dimethylcyclohexanecarboxylate (128 mg, 0.341 mmol), Pd(OAc)$_2$ (15.3 mg, 0.0680 mmol), Xantphos (59.2 mg, 0.102 mmol), and Cs$_2$CO$_3$ (222 mg, 0.682 mmol) were combined in a flask and degassed with argon. To this solid mixture was added dioxane (2.0 mL), and the resulting mixture was degassed with argon for 5 min. The reaction mixture was heated to 110° C. for 1.5 h. The reaction was cooled to ambient temperature, then diluted with saturated aqueous NaCl and EtOAc. The layers were separated, and the aqueous layer was extracted with EtOAc. The combined organic layers were dried over sodium sulfate, filtered and concentrated in vacuo. The resulting crude product was purified by column chromatography on silica (10-30% EtOAc/hexanes gradient) to afford racemic methyl-4-(5-{3-[(5-fluoro-4-methylpyrimidin-2-yl)amino]-5-methylphenyl}-1,3-thiazol-2-yl)-4-hydroxy-2,2-dimethylcyclohexanecarboxylate (143 mg, 0.295 mmol, 86% yield). MS ESI: [M+H]$^+$ m/z 485.

Step 2

To a solution of racemic methyl(1S,4R)-4-(5-{3-[(5-fluoro-4-methylpyrimidin-2-yl)amino]-5-methylphenyl}-1,3-thiazol-2-yl)-4-hydroxy-2,2-dimethylcyclohexanecarboxylate (70 mg, 0.14 mmol) in Methanol (1 mL) was added sodium hydroxide (1M, 0.87 ml, 0.87 mmol). The resulting suspension was heated to 110° C. for 10 min under microwave irradiation. The reaction was cooled to ambient temperature, and the pH was adjusted to a range of 3-4 (pH paper) using HCl (1 N in water). The resulting mixture was extracted with 10% IPA:CHCl$_3$ (3×). The combined organic layers were dried over Na$_2$SO$_4$ and concentrated in vacuo to provide racemic 4-(5-{3-[(5-fluoro-4-methylpyrimidin-2-yl)amino]-5-methylphenyl}-1,3-thiazol-2-yl)-4-hydroxy-2,2-dimethylcyclohexanecarboxylic acid (58 mg, 0.12 mmol, 58% yield). The racemate was subjected to purification by chiral supercritical fluid chromatography (35%/65% Methanol/CO$_2$, with a flow rate of 70 mL/min and a 4 minute run time).

Enantiomer 1 (26 mg, 0.055 mmol, 38% yield). MS ESI: [M+H]$^+$ m/z 471. $^1$H NMR (500 MHz, DMSO) δ 12.00 (br s, 1H), 9.68 (s, 1H), 8.42 (s, 1H), 7.91 (s, 1H), 7.89 (s, 1H), 7.47 (s, 1H), 7.05 (m, 1H), 5.89 (br s, 1H), 2.41 (s, 3H), 2.29 (s, 3H), 2.16 (br d, J=12.5, 1H), 2.02 (m, 1H), 1.84 (br m, 3H), 1.64 (br d, J=14.0, 1H), 1.58 (br d, J=13.5, 1H), 1.11 (s, 3H), 1.01 (s, 3H).

Enantiomer 2 (27 mg, 0.057 mmol, 40% yield). MS ESI: [M+H]+ m/z 471. ¹H NMR (500 MHz, DMSO) δ 12.00 (br s, 1H), 9.68 (s, 1H), 8.42 (s, 1H), 7.91 (s, 1H), 7.89 (s, 1H), 7.47 (s, 1H), 7.05 (m, 1H), 5.89 (br s, 1H), 2.41 (s, 3H), 2.29 (s, 3H), 2.16 (br d, J=12.5, 1H), 2.02 (m, 1H), 1.84 (br m, 3H), 1.64 (br d, J=14.0, 1H), 1.58 (br d, J=13.5, 1H), 1.11 (s, 3H), 1.01 (s, 31-1).

Compounds in the following Table(s) were prepared in a manner analogous of that described in Example 116:

TABLE 116A

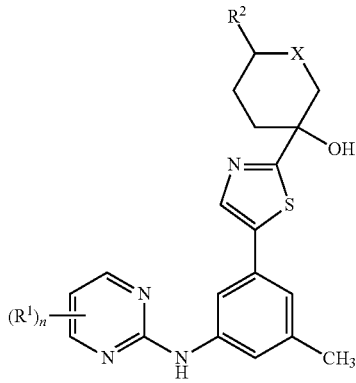

n is 1 or 2 substituents as specified in the Table.

| Ex. | R¹ | R² | X | rhSYK Activity | [M + H] Obs'd | Form(s) |
|---|---|---|---|---|---|---|
| 116A-1 | 4,6-di(CH₃) | OH (cis) | CH₂ | + | 411.2 | Free Base |
| 116A-2 | 4-CH₃, 5-F | CO₂H (cis) | CH₂ | +++ | 443.2 | Free Base |
| 116A-3 | 4-iPr | CO₂H (cis) | CH₂ | +++, +++ | 453.2 | Free Base, TFA Salt |
| 116A-4 | 4-CH₃, 5-Cl | CO₂H (cis) | CH₂ | +++ | 459 | Free Base |
| 116A-5 | 4-OCH₃, 5-F | CO₂H (cis) | CH₂ | +++ | 459 | Free Base |
| 116A-6 | 4-tBu | CO₂H (cis) | CH₂ | +++ | 467.2 | TFA Salt |
| 116A-7 | 4-O—iPr | CO₂H (cis) | CH₂ | +++ | 469.2 | TFA Salt |
| 116A-8 | 4-OCH₃, 5-Cl | CO₂H (cis) | CH₂ | +++ | 475 | Free Base |
| 116A-9 | 4-(2-thienyl) | CO₂H (cis) | CH₂ | +++ | 493.1 | TFA Salt |
| 116A-10 | 4-CH(F)CH₃ | CO₂C(CH₃)₃ | CH₂ | +++ | 513.2 | Free Base |
| 116A-11 | 4-OCH₃, 5-F | CO₂C(CH₃)₃ (cis) | CH₂ | ++ | 515 | Free Base |
| 116A-12 | 4-tBu | CO₂C(CH₃)₃ (cis) | CH₂ | ++ | 523.2 | Free Base |
| 116A-13 | 4-CF₂CF₃ | CO₂H (cis) | CH₂ | +++ | 529.1 | TFA Salt |
| 116A-14 | 4-OCH₃, 5-Cl | CO₂C(CH₃)₃ (cis) | CH₂ | ++ | 531 | Free Base |
| 116A-15 | 4-(2-thienyl) | CO₂C(CH₃)₃ (cis) | CH₂ | ++ | 549.2 | Free Base |
| 116A-16 | 4-CF₂CF₃ | CO₂C(CH₃)₃ (cis) | CH₂ | + | 585.2 | TFA Salt |
| 116A-17 | 4-(1-(4-methoxybenzyl)-1,2,3-triazol-4-yl) | CO₂H (cis) | CH₂ | +++ | 598.2 | TFA Salt |
| 116A-18 | 4-CHF₂ | CO₂H (isomer 10) | CH(CH₃) | +++ | 475.2 | Free Base |
| 116A-19 | 4-CHF₂ | CO₂H (isomer 2) | CH(CH₃) | +++ | 475.2 | Free Base |
| 116A-20 | 4-tBu | CO₂H | CH(CH₃) | +++ | 481.2 | Free Base |
| 116A-21 | 4-O—iPr | CO₂H | CH(CH₃) | +++, +++ | 483.2 | Free Base, Formate Salt |

TABLE 116A-continued n is 1 or 2 substituents as specified in the Table.

| Ex. | R¹ | R² | X | rhSYK Activity | [M + H] Obs'd | Form(s) |
|---|---|---|---|---|---|---|
| 116A-22 | 5-F | CO$_2$CH$_3$ (cis) | C(CH$_3$)$_2$ | ++ | 471 | Free Base |
| 116A-23 | 4-OH, 5-F | CO$_2$H (cis) | C(CH$_3$)$_2$ | ++ | 473 | Free Base |
| 116A-24 | 4-CO$_2$H | CO$_2$H (1S,4R) | C(CH$_3$)$_2$ | +++ | 483.1 | TFA Salt |
| 116A-25 | 4-CH$_3$, 5-F | CO$_2$CH$_3$ | C(CH$_3$)$_2$ | +++ | 485 | Free Base |
| 116A-26 | 4-CH$_3$, 5-Cl | CO$_2$H (1R,4S) | C(CH$_3$)$_2$ | +++ | 487 | Free Base |
| 116A-27 | 4-CH$_3$, 5-Cl | CO$_2$H (1S,4R) | C(CH$_3$)$_2$ | +++ | 487 | Free Base |
| 116A-28 | 4-OCH$_3$, 5-F | CO$_2$H (cis) | C(CH$_3$)$_2$ | +++ | 487 | Free Base |
| 116A-29 | 4-OH, 5-Cl | CO$_2$H (cis) | C(CH$_3$)$_2$ | ++ | 489 | Free Base |
| 116A-30 | 4-CHF$_2$ | CO$_2$H (1S,4R) | C(CH$_3$)$_2$ | +++ | 489.2 | Free Base |
| 116A-31 | 4-cBu | CO$_2$H (1S,4R) | C(CH$_3$)$_2$ | +++ | 493.2 | TFA Salt |
| 116A-32 | 4-tBu | CO$_2$H (cis) | C(CH$_3$)$_2$ | +++ | 495.2 | Free Base |
| 116A-33 | 4-O—iPr | CO$_2$H (1S,4R) | C(CH$_3$)$_2$ | +++ | 497.2 | Free Base |
| 116A-34 | 4-CH$_3$, 5-Cl | CO$_2$CH$_3$ (cis) | C(CH$_3$)$_2$ | ++ | 501 | Free Base |
| 116A-35 | 4-OCH$_3$, 5-F | CO$_2$CH$_3$ (cis) | C(CH$_3$)$_2$ | ++ | 501 | Free Base |
| 116A-36 | 4-OCH$_3$, 5-Cl | CO$_2$H (cis) | C(CH$_3$)$_2$ | +++ | 503 | Free Base |
| 116A-37 | 4-CF$_3$ | CO$_2$H (1S,4R) | C(CH$_3$)$_2$ | +++ | 507.1 | TFA Salt |
| 116A-38 | 4-OCH$_3$, 5-Cl | CO$_2$CH$_3$ (cis) | C(CH$_3$)$_2$ | ++ | 517 | Free Base |
| 116A-39 | (R) 4-CH(F)CH$_3$ | OC$_2$H (1S,4R) | C(CH$_3$)$_2$ | +++ | 485.2 | Free Base |
| 116A-40 | (S) 4-CH(F)CH$_3$ | CO$_2$H (1S,4R) | C(CH$_3$)$_2$ | +++ | 485.2 | Free Base |

TABLE 116B

| Example | R¹ | R² | rhSYK Activity | [M + H]+ obs'd | Forms(s) |
|---|---|---|---|---|---|
| 116B-1 | F | CH$_3$ | +++ | 457 | Free Base |
| 116B-2 | Cl | CH$_3$ | +++ | 473 | Free Base |

Example 117 cis-4-hydroxy-1-methyl-4-[5-(3-methyl-5-{[4-(trifluoromethyl)pyrimidin-2-yl]amino}phenyl)-1,3-thiazol-2-yl]cyclohexanecarboxamide

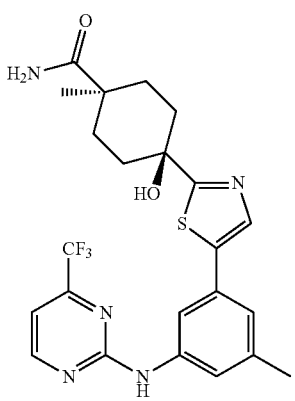 [SMILES: Cc1cc(Nc2nccc(C(F)(F)F)n2)cc(-c2cnc([C@]3(O)CC[C@@](C)(C(N)=O)CC3)s2)c1]

To a stirred solution of cis-4-hydroxy-1-methyl-4-[5-(3-methyl-5-{[4-(trifluoromethyl)pyrimidin-2-yl] amino}phenyl)-1,3-thiazol-2-yl]cyclohexanecarboxylic acid (442 mg, 0.90 mmol) in DMF (9.0 mL) was added ammonium chloride (144 mg, 2.69 mmol), EDC (344 mg, 1.80 mmol), HOBt (243 mg, 1.80 mmol) and diisopropylethylamine (0.94 mL, 5.38 mmol). The solution was allowed to stir at room temperature for 16 h. The reaction was diluted with water and extracted with EtOAc (3×). The combined organic layers were washed with aqueous saturated sodium bicarbonate, brine, then dried (magnesium sulfate), filtered and concentrated. The residue was purified by column chromatography to give the title compound as a white solid. EST: $[M+H]^+$ m/z 492.2. $^1$H NMR (500 MHz, CD$_3$OD) δ 8.71 (d, J=4.9, 1H), 8.03 (s, 1H), 7.91 (s, 1H), 7.44 (s, 1H), 7.13 (s, 2H), 2.37 (s, 3H), 2.22 (d, 13.0, 2H), 2.15 (d, J=12.2, 2H), 1.84 (d, J=14.1, 2H), 1.63 (d, J=13.4, 2H), 1.30 (s, 3H).

Compounds in the following Table(s) were prepared in a manner analogous of that described in Example 117:

TABLE 117

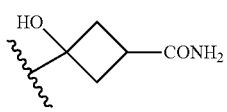 [SMILES: *C1(O)CC(C(N)=O)C1]

| Ex. | R$^1$ | R$^3$ | rhSYK Activity | [M + H]+ Obs'd | Forms(s) |
|---|---|---|---|---|---|
| R$^2$ = H | | | | | |
| 117-1 | CF$_3$ | 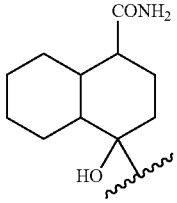 [SMILES: *C1(O)CCC(C(N)=O)C2CCCCC21] | +++ | 450.1 | Free Base |
| 117-2 | CH$_3$ | 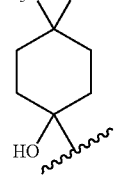 | +++ | 478.3 | TFA Salt |
| 117-3 | CF$_3$ | 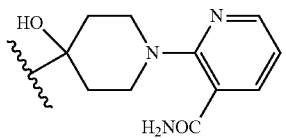 | +++ | 492.2 | Free Base |
| 117-4 | CF$_3$ | 4-CONH$_2$—cHex (cis) | +++ | 462.1 | Free Base |
| 117-5 | CF$_3$ | 4-CONH$_2$—cHex (trans) | +++ | 462.1 | Free Base |
| 117-6 | CF$_3$ | 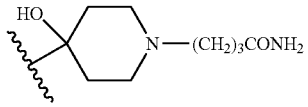 | +++ | 556 | Free Base |
| 117-7 | CF$_3$ | 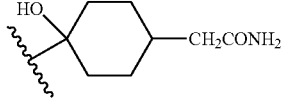 | +++ | 521.1 | Free Base |
| 117-8 | CF$_3$ |  | +++ | 492.2 | Free Base |

TABLE 117-continued

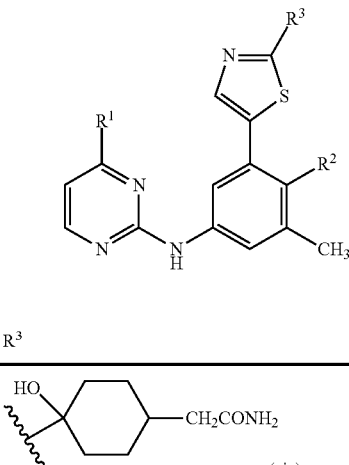

| Ex. | R¹ | R³ | rhSYK Activity | [M + H]+ Obs'd | Forms(s) |
|---|---|---|---|---|---|
| 117-9 | $CF_3$ | 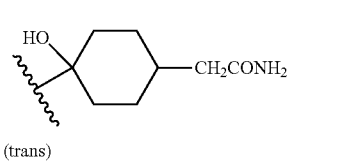(cis) | +++ | 492.2 | Free Base |
| 117-10 | $CF_3$ | (trans) | +++ | 492.2 | Free Base |
| 117-11 | $CF_3$ | 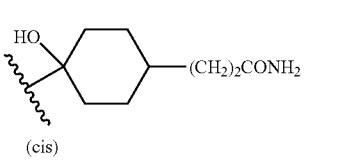(cis) | +++ | 506.2 | Free Base |
| 117-12 | $CF_3$ | (trans) | +++ | 506.2 | Free Base |
| 117-13 | iPr | 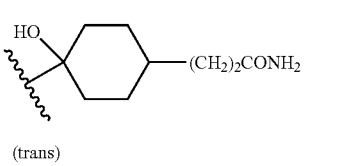 | +++ | 509.2 | Free Base |
| 117-14 | $OCH_2$—$CH_2OH$ | $CH_2CH_2CONH_2$ | +++ | 400.1 | Free Base |
| 117-15 | $CF_3$ | $CH_2CH_2CONH$—$CH(Et)CH_2OH$ | +++ | 480.2 | Free Base |
| 117-16 | $CF_3$ | $CH_2CH_2CONH$—$CH_2CO_2Et$ | +++ | 494.1 | Free Base |
| 117-17 | $CF_3$ | $CH_2CH_2CONH$—$CH(CH_3)CO_2CH_3$ | +++ | 494.1 | Free Base |
| 117-18 | $CF_3$ | $CH_2CH_2CONH$—$CH_2CH_2CO_2CH_3$ | +++ | 494.1 | Free Base |
| 117-19 | $CF_3$ | $CH_2CH_2CONH$—$CH(CH_2CH(CH_3)_2)$$CO_2CH_3$ | ++ | 536.2 | Free Base |
| 117-20 | $CF_3$ | $C(OH)(CH_3)$(4-$CONH_2$—Ph) (enantiomer 1) | +++ | 500.1 | Free Base |
| 117-21 | $CF_3$ | $C(OH)(CH_3)$(4-$CONH_2$—Ph) (enantiomer 2) | +++ | 500.1 | Free Base |
| | | $R^2$ = Br | | | |
| 117-22 | $CF_3$ | 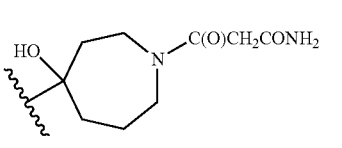(1S,4R) | +++ | 584.0 | Free Base |

Example 118 cis-4-hydroxy-4-[5-(3-methyl-5-{[4-(trifluoromethyl)pyrimidin-2-yl]amino}phenyl)-1,3-thiazol-2-yl]-N-[3-(2-oxopyrrolidin-1-yl)propyl]cyclohexanecarboxamide

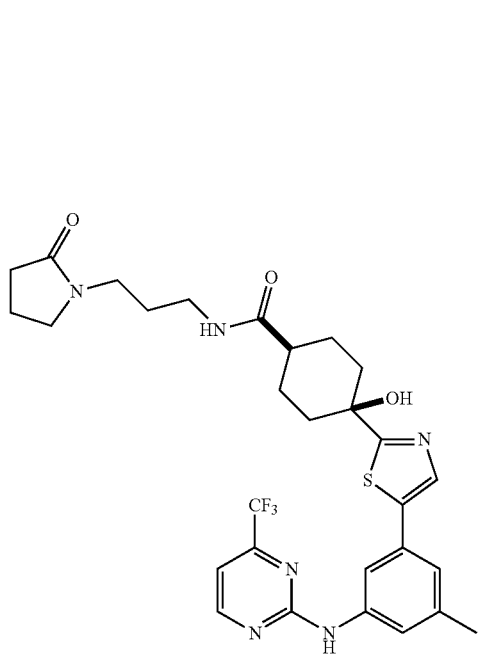 [SMILES: Cc1cc(Nc2nccc(C(F)(F)F)n2)cc(-c2cnc([C@]3(O)CC[C@@H](C(=O)NCCCN4CCCC4=O)CC3)s2)c1]

To N-(3-aminopropyl)-2-pyrrolidinone (14.1 µL, 0.12 mmol) was added a solution of cis-4-hydroxy-4-[5-(3-methyl-5-{[4-(trifluoromethyl)pyrimidin-2-yl]amino}phenyl)-1,3-thiazol-2-yl]cyclohexanecarboxylic acid (48 mg, 0.1 mmol) in N,N-dimethylformamide (1 mL). N,N-diisopropylethylamine (35 µL, 0.2 mmol) was added and the solution was then cooled to 0° C. 1-propanephosphonic acid cyclic anhydride (70 µL, 0.12 mmol) was added and the mixture was warmed to room temperature and stirred for 16 h, filtered, then purified by mass triggered reverse phase (C-18) HPLC to give the title product (21.5 mg, 0.036 mmol, 36% yield) as a pale yellow solid. MS ESI: [M+H]+ m/z 603.2. $^1$H NMR (600 MHz, DMSO) δ 10.22 (s, 1H), 8.80 (d, J=4.9, 1H), 7.91 (s, 2H), 7.73 (s, 1H), 7.43 (s, 1H), 7.25 (d, J=4.9, 1H), 7.12 (s, 1H), 3.29 (t, J=7.0, 1H), 3.13 (t, J=7.2, 2H), 2.98 (d, J=6.0, 2H), 2.29 (s, 3H), 2.17 (t, J=8.1, 3H), 1.91-1.75 (m, 9H), 1.60-1.50 (m, 5H).

Example 119

(1S,4R)-4-hydroxy-2,2-dimethyl-4-[5-(3-methyl-5-{[4-(propan-2-yloxy)pyrimidin-2-yl]amino}phenyl)-1,3-thiazol-2-yl]cyclohexanecarboxamide

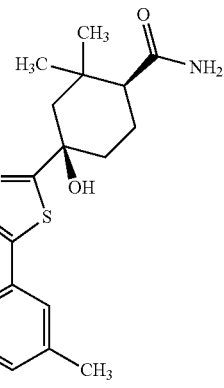

To a solution of (1S,4R)-4-hydroxy-2,2-dimethyl-4-[5-(3-methyl-5-{[4-(propan-2-yloxy)pyrimidin-2-yl]amino}phenyl)-1,3-thiazol-2-yl]cyclohexanecarboxylic acid (30 mg, 0.060 mmol) in DMF (3.0 mL) was added ammonium chloride (19 mg, 0.36 mmol), HATU (35 mg, 0.09 mmol) and Hunig's base (0.13 mL, 0.72 mmol) and the reaction was stirred at rt for 16 hrs. The reaction was then partitioned between 10 mL each of EtOAc and water and the layers were separated. The aqueous phase was extracted once with 10 mL of EtOAc, and the combined organic phases were washed with 10 mL of saturated aqueous sodium chloride, dried over anhydrous MgSO$_4$, filtered, and concentrated under reduced pressure. Purification by reverse phase HPLC (10-100% MeCN gradient in H$_2$O, 0.1% TFA) afforded (1S,4R)-4-hydroxy-2,2-dimethyl-4-[5-(3-methyl-5-{[4-(propan-2-yloxy)pyrimidin-2-yl]amino}phenyl)-1,3-thiazol-2-yl]cyclohexanecarboxamide trifluoroacetate (12 mg, 33%) as a colorless foam. MS ESI: [M+H]+ m/z 496.2. $^1$H NMR (500 MHz, DMSO-d$_6$) δ 9.67 (s, 1H), 8.18 (d, J=5.6 Hz, 1H), 7.92 (s, 1H), 7.86 (s, 1H), 7.45 (s, 1H), 7.14 (s, 1H), 7.11 (s, 1H), 6.71 (s, 1H), 6.24 (d, J=5.9 Hz, 1H), 5.40 (septet, J=6.1 Hz, 1H), 2.30 (s, 3H), 2.04-1.60 (m, 6H), 1.34 (d, J=6.1 Hz, 6H), 1.34 (s, 3H), 1.11 (s, 3H) rhSTK activity=+++

Compounds in the following Table(s) were prepared in a manner analogous of those described in Examples 117 (Method A), 118 (Method B) and 119 (Method C). The particular method used is indicated in the Table(s):

TABLE 119

| Ex. | R¹ | R³/R⁴ or R³ + R⁴ | X | rhSYK Activity | [M + H]+ Obs'd | Form(s) | * |
|---|---|---|---|---|---|---|---|
| | | R² = CH₃ | | | | | |
| 119-1 | CF₃ | H/H | Bond (anti, enantiomer 1) | +++ | 464.1 | Free Base | A |
| 119-2 | CF₃ | H/H | Bond (anti, enantiomer 2) | +++ | 464.1 | Free Base | A |
| 119-3 | CF₃ | H/H | Bond (syn, enantiomer 1) | +++ | 464.1 | Free Base | A |
| 119-4 | CF₃ | H/H | Bond (syn, enantiomer 2) | +++ | 464.1 | Free Base | A |
| 119-5 | CH₃ | H/H | CH(CH₃) (isomer 1) | +++ | 438.2 | Free Base | A |
| 119-6 | CH₃ | H/H | CH(CH₃) (isomer 2) | +++ | 438.2 | Free Base | A |
| 119-7 | CH₃ | H/H | C(CH₃)₂ (cis) | +++ | 452.2 | Free Base | A |
| 119-8 | iPr | H/H | CH₂ (cis) | +++ | 452.2 | Free Base | C |
| 119-9 | tBu | H/H | CH₂ (cis) | +++ | 466.2 | Free Base | C |
| 119-10 | iPr | H/H | CH(CH₃) (isomer 1) | +++ | 466.2 | Free Base | A |
| 119-11 | iPr | H/H | CH(CH₃) (isomer 2) | +++ | 466.2 | Free Base | A |
| 119-12 | O-iPr | H/H | CH(CH₃) (cis) | +++ | 468.2 | Free Base | C |
| 119-13 | OCH₃ | H/H | C(CH₃)₂ (1S,4R) | +++ | 468.2 | Free Base | A |
| 119-14 | OCH₂—CH₂OH | H/H | CH₂ | +++ | 470.2 | Free Base | A |
| 119-15 | CF₃ | H/CH₃ | CH₂ (cis) | +++ | 492.1 | Free Base | A |
| 119-16 | CF₃ | H/OH | CH₂ (cis) | +++ | 494.1 | Free Base | C |
| 119-17 | CF₃ | CH₃/CH₃ | CH₂ (cis) | +++ | 506.2 | Free Base | A |
| 119-18 | CF₃ | H/CH₂CN | CH₂ (cis) | +++ | 517 | Formate Salt | B |
| 119-19 | CF₃ | —(CH₂)₃— | CH₂ (cis) | +++ | 518.2 | Free Base | A |
| 119-20 | CF₃ | H/iPr | CH₂ (cis) | +++ | 520 | Formate Salt | B |
| 119-21 | CF₃ | CH₃/Et | CH₂ (cis) | +++ | 520 | Formate Salt | B |
| 119-22 | CF₃ | H/CH₂CH₂OH | CH₂ (cis) | +++ | 522 | Formate Salt | B |
| 119-23 | CF₃ | H/CH₂—cPr | CH₂ (cis) | +++ | 532 | Formate Salt | B |
| 119-24 | CF₃ | —(CH₂)₄— | CH₂ (cis) | +++ | 532.2 | Free Base | A |
| 119-25 | CF₃ | H/CH₂CH₂OCH₃ | CH₂ (cis) | +++ | 536 | Formate Salt | B |
| 119-26 | CF₃ | H/CH₂CO₂H | CH₂ (cis) | +++ | 536 | Formate Salt | B |
| 119-27 | CF₃ | H/2-imidazolyl | CH₂ (cis) | +++ | 544 | Formate Salt | A |
| 119-28 | CF₃ | CH₃/CH₂CH₂CN | CH₂ (cis) | +++ | 545 | Formate Salt | B |
| 119-29 | CF₃ | —CH₂CH₂OCH₂—CH₂— | CH₂ (cis) | +++ | 548.2 | Free Base | A |
| 119-30 | CF₃ | H/CH₂CH₂CONH₂ | CH₂ (cis) | +++ | 549 | Formate Salt | B |
| 119-31 | CF₃ | H/(CH₂)₃OCH₃ | CH₂ (cis) | +++ | 550 | Formate Salt | B |
| 119-32 | CF₃ | H/CH₂CH(OH)—CH₂OH | CH₂ (cis) | +++ | 552 | Formate Salt | B |
| 191-33 | CF₃ | H/CH(CH₂OH)₂ | CH₂ (cis) | +++ | 552 | Formate Salt | B |
| 119-34 | CF₃ | H/4-pyridyl | CH₂ (cis) | +++ | 555 | Formate Salt | B |
| 119-35 | CF₃ | H/2-pyridyl | CH₂ (cis) | +++ | 555 | Formate Salt | B |

TABLE 119-continued

| Ex. | R[1] | R[3]/R[4] or R[3] + R[4] | X | rhSYK Activity | [M + H]+ Obs'd | Form(s) | * |
|---|---|---|---|---|---|---|---|
| 119-36 | CF$_3$ | H/3-pyridyl | CH$_2$ (cis0 | +++ | 555 | Formate Salt | B |
| 119-37 | CF$_3$ | —CH$_2$CH$_2$CH(CN)—CH$_2$— | CH$_2$ (cis) | +++ | 557 | Formate Salt | B |
| 119-38 | CF$_3$ | H/CH$_2$-2-imidazolyl | CH$_2$ (cis) | +++ | 558 | Formate Salt | A |
| 119-39 | CF$_3$ | H/CH$_2$-3-pyraozlyl | CH$_2$ (cis) | +++ | 558.2 | Free Base | A |
| 119-40 | CF$_3$ | Et/CH$_2$CH$_2$CN | CH$_2$ (cis) | +++ | 559 | Formate Salt | B |
| 119-41 | CF$_3$ | H/CH$_2$-4-isoxazolyl | CH$_2$ (cis) | +++ | 559 | Formate Salt | A |
| 119-42 | CF$_3$ | H/CH$_2$-4-oxazolyl | CH$_2$ (cis) | +++ | 559 | Formate Salt | A |
| 119-43 | CF$_3$ | H/CH$_2$-5-isoxazolyl | CH$_2$ (cis) | +++ | 559 | Formate Salt | A |
| 119-44 | CF$_3$ | H/cHex | CH$_2$ (cis) | +++ | 560 | Formate Salt | B |
| 119-45 | CF$_3$ | H/CH$_2$-1,2,4-oxadiazol-3-yl | CH$_2$ (cis) | +++ | 560 | Formate Salt | A |
| 119-46 | CF$_3$ | —CH$_2$HC$_2$N(CH$_3$)—CH$_2$CH$_2$— | CH$_2$ (cis) | +++ | 561 | Formate Salt | B |
| 119-47 | CF$_3$ | —CH$_2$CH$_2$CH(OH)—CH$_2$CH$_2$— | CH$_2$ (cis) | +++ | 562 | Formate Salt | B |
| 119-48 | CF$_3$ | CH$_3$/3-tetrahydrofuranyl | CH$_2$ (cis) | +++ | 562 | Formate Salt | B |
| 119-49 | CF$_3$ | H/CH$_2$CH$_2$NHCOCH$_3$ CH$_3$ | CH$_2$ (cis) | +++ | 563 | Formate Salt | B |
| 119-50 | CF$_3$ | CH$_2$CH$_2$OH/CH$_2$—CH$_2$OH | CH$_2$ (cis) | +++ | 566 | Formate Salt | B |
| 119-51 | CF$_3$ | H/benzyl | CH$_2$ (cis) | +++ | 568 | Formate Salt | B |
| 191-52 | CF$_3$ | H/CH$_2$-3-pyridyl | CH$_2$ (cis) | +++ | 569 | Formate Salt | B |
| 191-53 | CF$_3$ | H/CH$_2$-4-pyridyl | CH$_2$ (cis) | +++ | 569 | Formate Salt | B |
| 119-54 | CF$_3$ | H/CH$_2$-2-pyridyl | CH$_2$ (cis0 | +++ | 569 | Formate Salt | B |
| 119-55 | CF$_3$ | H/4-OH—Ph | CH$_2$ (cis) | +++ | 570 | Formate Salt | B |
| 119-56 | CF$_3$ | H/2-OH—Ph | CH$_2$ (cis) | +++ | 570 | Formate Salt | B |
| 119-57 | CF$_3$ | H/CH$_2$-5-pyrimidinyl | CH$_2$ (cis) | +++ | 570 | Formate Salt | A |
| 119-58 | CF$_3$ | H/CH$_2$-3-pyridazinyl | CH$_2$ (cis) | +++ | 570 | Formate Salt | A |
| 119-59 | CF$_3$ | —CH$_2$CH$_2$CH(CN)—CH$_2$CH$_2$— | CH$_2$ (cis) | +++ | 571 | Formate Salt | B |
| 119-60 | CF$_3$ | —CH$_2$CH(CN)CH$_2$—CH$_2$CH$_2$— | CH$_2$ (cis) | +++ | 571 | Formate Salt | B |
| 119-61 | CF$_3$ | H/6-OH-3-pyridyl | CH$_2$ (cis) | +++ | 571 | Formate Salt | B |
| 119-62 | CF$_3$ | H/4-F—Ph | CH$_2$ (cis) | +++ | 572 | Formate Salt | B |
| 119-63 | CF$_3$ | H/CH$_2$-2-thienyl | CH$_2$ (cis) | +++ | 574 | Formate Salt | B |
| 119-64 | CF$_3$ | H/CH$_2$CH$_2$-1-pyrrolidinyl | CH$_2$ (cis) | +++ | 575 | Formate Salt | B |
| 119-65 | CF$_3$ | H/CH$_2$-(3-OH-5-isoxazolyl) | CH$_2$ (cis) | +++ | 575 | Formate Salt | A |
| 119-66 | CF$_3$ | H/CH$_2$(5-isothiazolyl) | CH$_2$ (cis) | +++ | 575 | Formate Salt | A |

TABLE 119-continued

| Ex. | R¹ | R³/R⁴ or R³ + R⁴ | X | rhSYK Activity | [M + H]+ Obs'd | Form(s) | * |
|---|---|---|---|---|---|---|---|
| 119-67 | CF₃ | H/CH₂-(1,3,4-thiadiazol-2-yl) | CH₂ (cis) | +++ | 576 | Formate Salt | A |
| 119-68 | CF₃ | H/CH₂CH₂N(CH₃)COCH₃ | CH₂ (cis) | +++ | 577 | Formate Salt | B |
| 119-69 | CF₃ | CH₃/benzyl | CH₂ (cis) | +++ | 582 | Formate Salt | B |
| 119-70 | CF₃ | H/CH₂CH₂Ph | CH₂ (cis) | +++ | 582 | Formate Salt | B |
| 119-71 | CF₃ | H/CH₂-(3-OH)—Ph | CH₂ (cis) | +++ | 584 | Formate Salt | B |
| 119-72 | CF₃ | H/(4-CH₂OH)—Ph | CH₂ (cis) | +++ | 584 | Formate Salt | B |
| 119-73 | CF₃ | H/(3-CH₂OH)—Ph | CH₂ (cis) | +++ | 584 | Formate Salt | B |
| 119-74 | CF₃ | H/CH₂-(2-OH)—Ph | CH₂ (cis) | +++ | 584 | Formate Salt | B |
| 119-75 | CF₃ | H/CH₂-(4-OH)—Ph | CH₂ (cis) | +++ | 584 | Formate Salt | B |
| 119-76 | CF₃ | H/(2,4-diOH)—Ph | CH₂ (cis) | +++ | 586 | Formate Salt | B |
| 119-77 | CF₃ | H/CH₂-(4-F)—Ph | CH₂ (cis) | +++ | 586 | Formate Salt | B |
| 119-78 | CF₃ | H/CH₂CH₂-(2-oxo-1-pyrrolidinyl) | CH₂ (cis) | +++ | 589 | Formate Salt | B |
| 119-79 | CF₃ | H/CH₂CH₂-(2-oxo-1-imidazolidinyl) | CH₂ (cis) | +++ | 590 | Formate Salt | B |
| 119-80 | CF₃ | H/CH₂CH₂-(4-morpholinyl) | CH₂ (cis) | +++ | 591 | Formate Salt | B |
| 119-81 | CF₃ | H/(CH₂)₄NHCO—CH₃ | CH₂ (cis) | +++ | 591 | Formate Salt | B |
| 119-82 | CF₃ | H/5-indolyl | CH₂ (cis) | +++ | 593.1 | Free Base | A |
| 119-83 | CF₃ | H/(CH₂)₃Ph | CH₂ (cis) | +++ | 596 | Formate Salt | B |
| 119-84 | CF₃ | H/CH₂CH₂OPh | CH₂ (cis) | +++ | 598 | Formate Salt | B |
| 119-85 | CF₃ | H/CH₂-(4-CH₂OH)—Ph | CH₂ (cis) | +++ | 598 | Formate Salt | B |
| 119-86 | CF₃ | H/CH₂-(3,4-diOH)—Ph | CH₂ (cis) | +++ | 600 | Formate Salt | B |
| 119-87 | CF₃ | H/CH₂-(4-Cl)—Ph | CH₂ (cis) | +++ | 602 | Formate Salt | B |
| 119-88 | CF₃ | H/(CH₂)₃-(2-oxo-1-pyrrolidinyl) | CH₂ (cis) | +++ | 603 | Formate Salt | B |
| 119-89 | CF₃ | H/CH₂CH₂-(2-oxo-1-piperidinyl) | CH₂ (cis) | +++ | 603 | Formate Salt | B |
| 119-90 | CF₃ | H/4-CONH₂—cHex | CH₂ | +++ | 603.2 | Free Base | A |
| 119-91 | CF₃ | H/4-CO₂H-cHex | CH₂ | +++ | 604 | Formate Salt | B |
| 119-92 | CF₃ | —CH₂CH₂N—(CO₂CH₃)CH₂CH₂— | CH₂ | +++ | 605 | Formate Salt | B |
| 119-93 | CF₃ | H/ (1,2,3,4-tetrahydronaphthalen-1-yl) | CH₂ (cis) | +++ | 608 | Formate Salt | B |

TABLE 119-continued

| Ex. | R¹ | R³/R⁴ or R³ + R⁴ | X | rhSYK Activity | [M + H]+ Obs'd | Form(s) | * |
|---|---|---|---|---|---|---|---|
| 119-94 | CF₃ | H/ imidazo[1,2-a]pyridinylmethyl | CH₂ (cis) | +++ | 608 | Formate Salt | A |
| 119-95 | CF₃ | H/ 2-hydroxyindanyl | CH₂ (cis) | +++ | 610 | Formate Salt | B |
| 119-96 | CF₃ | (isoindolinon-7-yl)methyl /H | CH₂ (cis0 | +++ | 623 | Formate Salt | A |
| 119-97 | CF₃ | H/ (isoindolinon-6-yl)methyl | CH₂ (cis) | +++ | 623 | Formate Salt | A |
| 119-98 | CF₃ | (isoindolinon-4-yl)methyl /H | CH₂ (cis) | +++ | 623 | Formate Salt | A |
| 119-99 | CF₃ | H/ (isoindolinon-5-yl)methyl | CH₂ (cis) | +++ | 623 | Formate Salt | A |
| 119-100 | CF₃ | H/CH₂-(4-CF₃)Ph | CH₂ (cis) | +++ | 636 | Formate salt | B |

TABLE 119-continued

| Ex. | R¹ | R³/R⁴ or R³ + R⁴ | X | rhSYK Activity | [M + H]+ Obs'd | Form(s) | * |
|---|---|---|---|---|---|---|---|
| 119-101 | CF₃ | H/CH2-(3-(2-pyridyl)-isoxazol-5-yl) | CH₂ (cis) | +++ | 636 | Formate Salt | A |
| 119-102 | CF₃ | —CH₂CH₂CH(Bn)—CH₂CH₂— | CH₂ (cis) | ++ | 636 | Formate Salt | B |
| 119-103 | CF₃ | H/ (3,4-dihydroquinolin-2(1H)-one-7-ylmethyl) | CH₂ (cis) | +++ | 637 | Formate Salt | A |
| 119-104 | CF₃ | H/CH₂-(4-SO₂NH₂)Ph | CH₂ (cis) | +++ | 647 | Formate Salt | A |
| 119-105 | CF₃ | H/ (4-(4-(hydroxymethyl)-1H-pyrazol-1-yl)benzyl) | CH₂ (cis) | +++ | 664 | Formate Salt | A |
| 119-106 | CF₃ | H/ (4-((2-oxooxazolidin-4-yl)methyl)benzyl) | CH₂ (cis) | +++ | 667 | Formate Salt | A |
| 119-107 | CF₃ | H/CH₂-(4-OCH₂CF₃)Ph | CH₂ (cis) | ++ | 667 | Formate Salt | A |
| 119-108 | CH₃ | H/CH₂CN | CH(CH₃) (cis) | +++ | 477.2 | Free Base | A |
| 119-109 | tBu | H/H | CH(CH₃) | +++ | 480.2 | TFA Salt | C |
| 119-110 | O—iPr | H/H | CH(CH₃) | +++ | 482.2 | TFA Salt | C |
| 119-111 | CF₃ | H/H | CH(CH₃) (isomer 1) | +++, +++ | 492.1 | Free Base, Free Base | A |
| 119-112 | CF₃ | H/H | CH(CH₃) (isomer 2) | +++ | 492.1 | Free Base | A |
| 119-113 | iPr | H/CH₂CN | CH(CH₃) | +++ | 505.2 | Free Base | A |
| 119-114 | CH₃ | H/CH₂-3-pyridyl | CH(CH₃) | +++ | 529.2 | Free Base | A |
| 119-115 | iPr | H/CH₂-3-pyridyl | CH(CH₃) | +++ | 557.3 | Free Base | A |
| 119-116 | CH₃ | H/(CH₂)₃-(2-oxo-1-pyrrolidinyl) | CH(CH₃) | +++ | 563.3 | Free Base | A |
| 119-117 | OCH₃ | H/H | C(CH₃)₂ (1S,4R) | +++ | 468.2 | Free Base | A |
| 119-118 | cPr | H/H | C(CH₃)₂ (1S,4R) | +++ | 478.2 | Free Base | A |
| 119-119 | iPr | H/H | C(CH₃)₂ (1S,4S) | +++ | 480.2 | TFA Salt | C |
| 119-120 | (S)—CH(OH)CH₃ | H/H | C(CH₃)₂ (1S,4R) | +++ | 482.2 | TFA Salt | A |

TABLE 119-continued

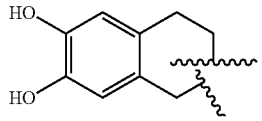 [SMILES: *CCc1cc(O)c(O)cc1C*]

| Ex. | R¹ | R³/R⁴ or R³ + R⁴ | X | rhSYK Activity | [M + H]+ Obs'd | Form(s) | * |
|---|---|---|---|---|---|---|---|
| 119-121 | (R)-CH(OH)CH₃ | H/H | C(CH₃)₂ (1S,4R) | +++ | 482.2 | TFA Salt | A |
| 119-122 | (S)—CH(F)—CH₃ | H/H | C(CH3)₂ (1S,4R) | +++ | 484.2 | TFA Salt | A |
| 119-123 | (R)-CH(F)—CH₃ | H/H | C(CH₃)₂ (1S,4R) | +++ | 484.2 | TFA Salt | A |
| 119-124 | CH₃ | H/CH₂CN | C(CH₃)₂ (cis) | +++ | 491.2 | Formate Salt | A |
| 119-125 | tBu | H/H | C(CH₃)₂ (1S,4R) | +++ | 494.2 | TFA Salt | C |
| 119-126 | O—iPr | H/H | C(CH₃)₂ (1S,4R) | +++ | 496.2 | TFA Salt | C |
| 119-127 | C(CH₃)₂—OH | H/H | C(CH₃)₂ (1S,4R) | +++ | 496.3 | TFA Salt | A |
| 119-128 | OCH₂—CH₂OH | H/H | C(CH₃)₂ | +++ | 498.2 | Free Base | A |
| 119-129 | OCH₂—CH₂OH | H/H | C(CH₃)₂ (1S,4R) | +++ | 498.2 | Free Base | A |
| 119-130 | OCH₂—CH₂OH | H/H | C(CH₃)₂ (1R,4S) | +++ | 498.2 | Free Base | A |
| 119-131 | CF₃ | H/H | C(CH₃)₂ (1R,4S) | +++ | 506.2 | Free Base | A |
| 119-132 | CF₃ | H/H | C(CH₃)₂ (1S,4R) | +++ | 506.2 | Free Base | A |
| 119-133 | OCH₃ | H/CH₂CN | C(CH₃)₂ (1S,4R) | +++ | 507.2 | Free Base | A |
| 119-134 | OCH₃ | H/CH₂-3-pyridyl | C(CH₃)₂ (1S,4R) | +++ | 559.2 | Free Base | A |
| 119-135 | CH₃ | H/(CH₂)₃-(2-oxo 1-pyrrolidinyl) | C(CH₃)₂ (1S,4R) | +++, +++ | 577.3 | Free Base, Formate Salt | A |
| 119-136 | CF₃ | H/3-pyridyl | C(CH₃)₂ (1S,4R) | +++ | 583.2 | Free Base | B |
| 119-137 | OCH₃ | H/(CH₂)₃-(2-oxo-1-pyrrolidinyl) | C(CH₃)₂ (1S,4R) | +++ | 593.3 | Free Base | A |
| 119-138 | CF₃ | 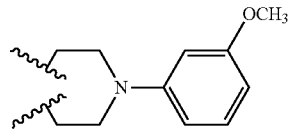 [SMILES: *CCN(CC*)c1cccc(OC)c1] | CH₂ (cis) | +++ | 626 | Formate Salt | B |
| 119-139 | CF₃ | 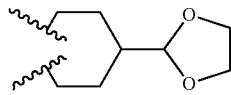 | CH₂ (cis) | +++ | 653 | Formate Salt | B |
| 119-140 | CF₃ | (1,3-dioxolan-2-yl cyclohexyl) R² = CH₂OH | CH₂ (cis) | +++ | 604 | Formate Salt | B |
| 191-141 | CF₃ | H/H | C(CH₃)₂ (1S,4R) | +++ | 522.0 | Free Base | A |

TABLE 119-continued

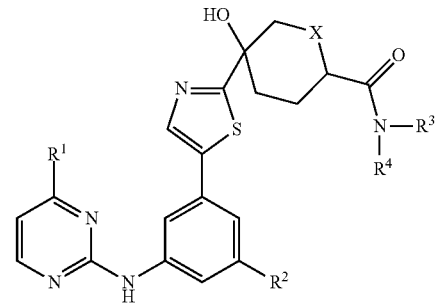

| Ex. | $R^1$ | $R^3/R^4$ or $R^3 + R^4$ | X | rhSYK Activity | [M + H]+ Obs'd | Form(s) | * |
|---|---|---|---|---|---|---|---|
| | | | $R^2 = CH_2OCH_3$ | | | | |
| 119-142 | $CF_3$ | H/H | $CH(CH_3)$ | +++ | 522.1 | Free Base | A |
| 119-143 | $CF_3$ | H/H | $C(CH_3)_2$ (1S,4R) | +++ | 536.1 | Free Base | A |
| | | | $R^2 = Cl$ | | | | |
| 119-144 | $CF_3$ | H/H | $C(CH_3)_2$ (1S,4R) | +++ | 526.1 | Free Base | A |
| 119-145 | $CF_3$ | H/H | $CH_2$ (cis) | +++ | 498.1 | Free Base | A |
| | | | $R^2 = CH_2NHCOCH_3$ | | | | |
| 119-146 | $CF_3$ | H/H | $C(CH_3)_2$ (cis) | +++ | 563.2 | Free Base | A |

*synthetic method A, B, or C

Example 120

Ethyl(1R,4S)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylate

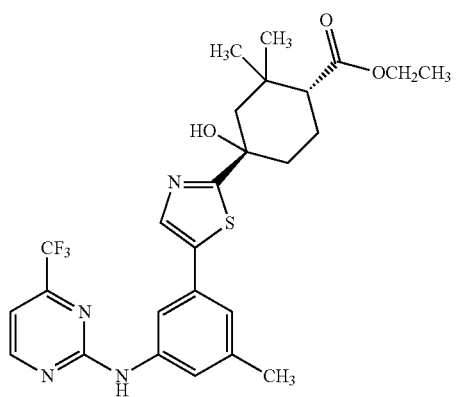 [SMILES: CCOC(=O)[C@@H]1CC[C@@](O)(c2ncc(-c3cc(C)cc(Nc4nccc(C(F)(F)F)n4)c3)s2)CC1(C)C]

(1R,4S)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid (100 mg, 0.197 mmol) was dissolved in ethanol (3 ml) and concentrated sulfuric acid (10.52 μl, 0.197 mmol) added. The reaction mixture was stirred for 16 hours. The reaction mixture was extracted with ethyl acetate (3×) and washed with saturated aqueous sodium bicarbonate. Solvent evaporation gave the title compound (88 mg, 0.165 mmol, 83% yield). ESI: [M+H]+ m/z 535.2. $^1$H NMR (500 MHz, DMSO-d$_6$) δ 10.25 (s, 1H), 8.82 (d, J=4.9, 1H), 7.93 (d, J=9.6, 2H), 7.46 (s, 1H), 7.27 (d, J=4.9, 1H), 7.14 (s, 1H), 4.07 (dt, J=10.8, 17.9, 2H), 2.31 (s, 3H), 2.05 (s, 3H), 1.96-1.78 (m, 3H), 1.65 (m, 2H), 1.18 (m, 3H), 1.09 (s, 3H), 0.97 (s, 3H). rhSYK activity=+++

Example 121

Methyl(1R,4S)-4-hydroxy-2,2-dimethyl-4-[5-(3-methyl-5-{[4-(trifluoromethyl)pyrimidin-2-yl]-amino}phenyl)-1,3-thiazol-2-yl]cyclohexanecarboxylate (1R,4S)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid (100 mg, 0.197 mmol) was dissolved in methanol (3 ml) and concentrated sulfuric acid (10.52 μl, 0.197 mmol) added. The reaction mixture was stirred for 16 hours. The reaction mixture was diluted with water, extracted with ethyl acetate (3×) and washed with saturated aqueous sodium bicarbonate. Solvent evaporation gave the title compound (85 mg, 0.163 mmol, 83% yield). MS ESI: [M+H]+ m/z 521.1. $^1$H NMR (500 MHz, DMSO-$d_6$) $^1$H NMR δ 10.25 (s, 1H), 8.83 (d, J=4.9, 1H), 7.93 (s, 2H), 7.46 (s, 1H), 7.28 (d, J=4.9, 1H), 7.14 (s, 1H), 5.92 (s, 1H), 3.59 (s, 3H), 2.31 (s, 4H), 1.84 (s, 3H), 1.65 (m, 3H), 1.08 (s, 3H), 0.96 (s, 3H). rhSYK activity=+++

Example 122 tert-butyl 4-hydroxy-4-[5-(3-{[4-(3-methoxypropyl)pyrimidin-2-yl]amino}-5-methylphenyl)-1,3-thiazol-2-yl]cyclohexanecarboxylate

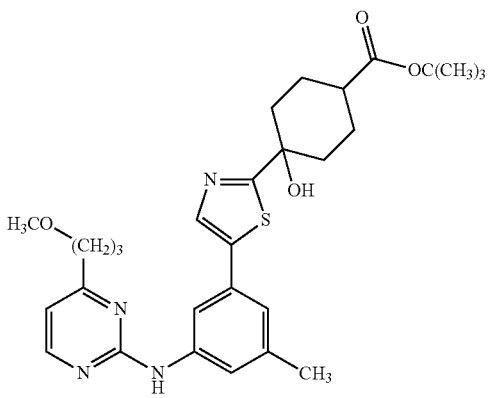

A solution of tert-butyl 4-hydroxy-4-{5-[3-({4-[(1E)-3-methoxyprop-1-en-1-yl]pyrimidin-2-yl}amino)-5-methylphenyl]-1,3-thiazol-2-yl}cyclohexanecarboxylate (100 mg, 0.19 mmol, 1.0 equiv) was dissolved in absolute EtOH (10 ml), deoxygenated, and treated with 10% Pd on carbon (50 mg, 0.47 mmol, 2.5 equiv). The mixture was deoxygenated further before being placed under hydrogen balloon and stirred for at 23° C. for 1 h. The reaction was 50% complete so it was maintained under H2 at 23° C. for another 1 h. The black mixture was filtered through a pad of Celite, which was then washed with EtOAc, dichloromethane, and MeOH. The filtrate was concentrated in vacuo, then purified by reverse-phase HPLC (acetonitrile/water gradient with 0.05% TFA present). The TFA salt was converted to the free base by partitioning between EtOAc (60 ml) and saturated aqueous NaHCO$_3$ (70 ml). The organic layers were dried over MgSO$_4$, filtered and concentrated to afford the title compound (29.1 mg, 27.5%) as a yellow-orange oil. MS ESI: [M+H]+ m/z 539.1. $^1$H NMR (500 MHz, CDCl$_3$) δ 8.29 (d, J=3.4 Hz, 1H), 7.90 (m, 1H), 7.84 (s, 1H), 7.32 (s, 1H), 7.00 (s, 1H), 6.61 (m, 1H), 3.46-3.45 (m, 5H), 2.74-2.72 (m, 2H), 2.36 (s, 3H), 2.30 (m, 1H), 2.15-2.00 (m, 6H), 1.92-1.85 (m, 4H), 1.45 (s, 9H). rhSYK activity=++

Example 123

(1S,4R)-4-{5-[3-(aminomethyl)-5-{[4-(trifluoromethyl)pyrimidin-2-yl]amino}phenyl]-1,3-thiazol-2-yl}-4-hydroxy-2,2-dimethylcyclohexanecarboxylic acid

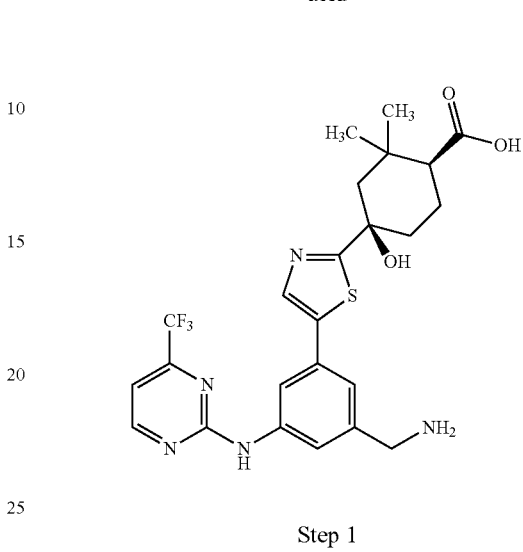

Step 1

Triethylamine (0.200 ml, 1.434 mmol, 1.5 equiv) was added to a stirring solution of methyl(1S,4R)-4-hydroxy-4-{5-[3-(hydroxymethyl)-5-{[4-(trifluoromethyl)pyrimidin-2-yl]amino}phenyl]-1,3-thiazol-2-yl}-2,2-dimethylcyclohexanecarboxylate (513 mg, 0.956 mmol) in anhydrous dichloromethane (15 mL). The orange solution was cooled to 0° C. (water/ice) then charged with methanesulfonyl chloride (0.089 ml, 1.147 mmol, 1.2 equiv). The reaction mixture was allowed to slowly warm to 23° C. and stir for 5 d. The mixture was partitioned between methylene chloride (2×90 ml) and water (95 ml). The combined organic layers were dried over Na$_2$SO$_4$, filtered and concentrated to afford methyl(1S,4R)-4-hydroxy-2,2-dimethyl-4-[5-(3-{[(methylsulfonyl)oxy]methyl}-5-{[4-(trifluoromethyl)pyrimidin-2-yl]amino}phenyl)-1,3-thiazol-2-yl]cyclohexanecarboxylate (520 mg, 71%), as an orange-yellow oil. $^1$H NMR (500 MHz, CDCl$_3$) δ 8.79 (bs, 1H), 8.66 (d, J=4.9 Hz, 1H), 7.95 (s, 1H), 7.85 (s, 1H), 7.61 (s, 1H), 7.23 (s, 1H), 7.06 (d, J=4.9 Hz, 1H), 4.59 (s, 1H), 3.90 (s, 2H), 3.69 (s, 3H), 3.01 (s, 2H), 2.38-2.25 (m, 2H), 2.01 (m, 3H), 1.95-1.77 (m, 4H), 1.35-1.20 (m, 6H).

Step 2

A solution of the product of Step 1 (250 mg, 0.407 mmol) in anhydrous NMP (5 ml) was treated with sodium azide (132 mg, 2.034 mmol, 5.0 equiv) and stirred at 23° C. for 18 h. The reaction was partitioned between EtOAc (2×75 ml) and water (85 ml) and the combined organic layers were dried over Na$_2$SO$_4$, filtered and concentrated to afford methyl(1S,4R)-4-{5-[3-(azidomethyl)-5-{[4-(trifluoromethyl)pyrimidin-2-yl]amino}phenyl]-1,3-thiazol-2-yl}-4-hydroxy-2,2-dimethylcyclohexanecarboxylate (220 mg, 96%), as an orange oil. MS ESI: [M+H]+ m/z 562.1

Step 3

To a solution of the product from Step 2 (220 mg, 0.392 mmol) in THF (4 ml) and water (2 ml), was added resin-bound triphenylphosphine (154 mg, 0.588 mmol, 1.5 equiv). The resulting mixture was stirred at 23° C. for 18 h. The resin-bound triphenylphosphine was removed by filtration, and the residual biphasic, orange-maroon mixture was partitioned between EtOAc (45 ml) and water (55 ml). The separated organic layer was dried over $Na_2SO_4$, filtered and concentrated. The crude orange oil was purified via reverse-phase HPLC (acetonitrile/water gradient with 0.1% TFA present). The TFA salt was converted to the free base by partitioning between EtOAc (55 ml) and saturated aqueous $NaHCO_3$ (45 ml). The organic layer was dried over $Na_2SO_4$, filtered and concentrated. The organic layer was filtered and concentrated, yielding methyl(1S,4R)-4-{5-[3-(aminomethyl)-5-{[4-(trifluoromethyl)pyrimidin-2-yl]amino}phenyl]-1,3-thiazol-2-yl}-4-hydroxy-2,2-dimethylcyclohexanecarboxylate (55 mg, 25%), as an orange oil. MS ESI: [M+H]+ m/z 536.2

Step 4

A microwave vessel was charged with a solution of the compound of Step 3 (10 mg, 0.019 mmol) in MeOH, and sodium hydroxide (1.0 N in $H_2O$, 56 µl, 0.056 mmol, 3 equiv) was added. The resultant cloudy orange suspension was irradiated in the microwave at 110° C. for 15 min. The reaction was not complete. Additional sodium hydroxide (1.0 N in $H_2O$, 190 µL, 0.19 mmol, 10 eq) was added and the faintly yellow solution was irradiated at 150° C. for 30 min. The reaction mixture was concentrated in vacuo, then partitioned between diethyl ether (75 ml) and water (85 ml). The aqueous layer was acidified with 1N aqueous HCl to pH ~3-4, then washed with EtOAc (2×35 ml). The combined organic layers were dried over $Na_2SO_4$, filtered and concentrated, affording the title compound (3.6 mg, 35%) as an orange oil. MS ESI: [M+H]+ m/z 522.2 $^1$H NMR (500 MHz, DMSO-$d_6$) δ 10.5 (s, 1H), 8.85 (d, J=4.9 Hz, 1H), 8.24 (bs, 1H), 8.14 (s, 1H), 7.93 (s, 1H), 7.65 (s, 1H), 7.46 (s, 1H), 7.33 (d, J=4.9 Hz, 1H), 5.94 (bs, 1H), 4.03-3.99 (m, 3H), 3.14 (m, 2H), 2.19-2.16 (m, 2H), 1.86-1.83 (m, 2H), 1.66-1.60 (m, 2H), 1.17-1.11 (m, 6H). rhSYK activity=+++

Example 124

(1S,4R)-4-[5-(3-[(carbamoylamino)methyl]-5-{[4-(trifluoromethyl)pyrimidin-2-yl]amino}phenyl)-1,3-thiazol-2-yl]-4-hydroxy-2,2-dimethylcyclohexanecarboxylic acid

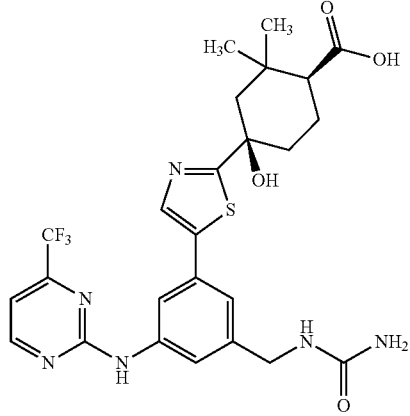 [SMILES: CC1(C)C[C@@](O)(c2ncc(-c3cc(CNC(N)=O)cc(Nc4nccc(C(F)(F)F)n4)c3)s2)CC[C@@H]1C(=O)O]

Step 1

To a solution of methyl(1S,4R)-4-{5-[3-(aminomethyl)-5-{[4-(trifluoromethyl)pyrimidin-2-yl]amino}phenyl]-1,3-thiazol-2-yl}-4-hydroxy-2,2-dimethylcyclohexanecarboxylate (40 mg, 0.075 mmol) in anhydrous THF (1.5 ml) was added potassium cyanate (12.12 mg, 0.149 mmol, 2.0 equiv), acetic acid (8.55 µl, 0.149 mmol, 2.0 equiv), and water (4.5 ml). The mixture was stirred at 50° C. for 14 h. The reaction mixture was quenched with saturated aqueous $NaHCO_3$ and extracted with EtOAc (40 ml). The organic layer were dried over $Na_2SO_4$, filtered and concentrated to provide the desired product, methyl (1S,4R)-4-[5-(3-[(carbarnoylamino)methyl]-5-{[4-(trifluoromethyl)pyrimidin-2-yl] amino}phenyl)-1,3-thiazol-2-yl]-4-hydroxy-2,2-dimethyl-cyclohexanecarboxylate (40 mg, 88%), as an orange oil. MS ESI: [M+H]+ m/z 579.2. $^1$H NMR (500 MHz, DMSO) δ 10.3 (s, 1H), 8.83 (d, J=4.9 Hz, 1H), 8.03 (bs, 1H), 7.88 (s, 1H), 7.50 (s, 1H), 7.28 (d, 1H, J=4.9 Hz), 7.17 (s, 1H), 6.46 (m, 1H), 5.55 (s, 2H), 4.16 (m, 2H), 3.59 (s, 3H), 2.31 (m, 1H), 1.87-1.84 (m, 4H), 1.75-1.73 (m, 2H), 1.17 (s, 3H), 0.96 (s, 3H).

Step 2

A microwave vessel was charged with a solution of the product from Step 1 (40 mg, 0.069 mmol) and MeOH (2 ml). Sodium hydroxide (1.0 N in $H_2O$, 0.207 ml, 0.207 mmol, 3.0 equiv) was added and the resultant cloudy orange suspension was irradiated in the microwave at 110° C. for 15 min. Only partial conversion was observed, so additional sodium hydroxide (1.0 N in $H_2O$, 0.207 ml, 0.207 mmol, 3.0 equiv) was introduced and the orange-maroon mixture was again irradiated in the microwave at 110° C. for 15 min. The reaction mixture was concentrated in vacuo then partitioned between diethyl ether (75 ml) and water (85 ml). The aqueous layer was acidified with 1N aqueous HCl to pH ~3-4 and washed with EtOAc (2×35 ml). The combined organic layers were dried over $Na_2SO_4$ and concentrated to afford the title compound (26 mg, 64%) as an tan solid. MS ESI: [M+H]+ m/z 565.2. $^1$H NMR (500 MHz, dmso) δ 12.00 (s, 1H), 10.32 (s, 1H), 8.82 (d, J=4.9, 1H), 8.03 (s, 1H), 7.88 (s, 1H), 7.50 (s, 1H), 7.28 (d, J=4.9, 1H), 7.17 (s, 1H), 6.45 (t, J=6.0, 1H), 5.90 (s, 1H), 5.55 (s, 2H), 4.12 (d, J=5.9, 2H), 3.15 (d, J=3.7, 1H), 2.16 (d, J=12.6, 1H), 2.07-1.98 (m, 1H), 1.86-1.83 (m, 2H), 1.69 (d, J=14.3, 1H), 1.62 (d, J=10.5, 1H), 1.13 (s, 3H), 1.02 (s, 3H). rhSYK activity=+++

Example 125

(1S,4R)-4-[5-(3-[(acetylamino)methyl]-5-{[4-(trifluoromethyl)pyrimidin-2-yl]amino}phenyl)-1,3-thiazol-2-yl]-4-hydroxy-2,2-dimethylcyclohexanecarboxylic acid

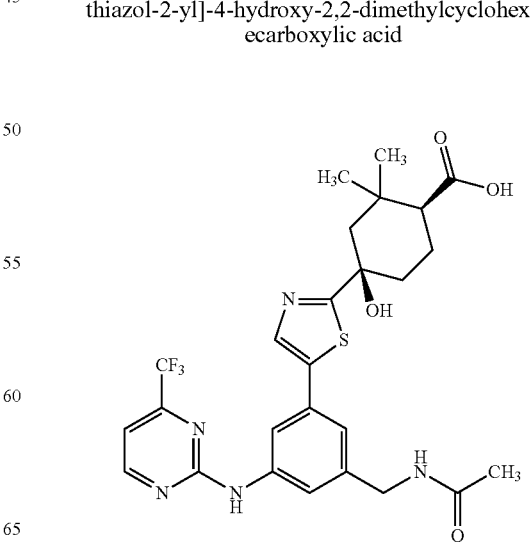

Step 1

A solution of (1S,4R)-4-{5-[3-(aminomethyl)-5-{[4-(trifluoromethyl)pyrimidin-2-yl]amino}phenyl]-1,3-thiazol-2-yl}-4-hydroxy-2,2-dimethylcyclohexanecarboxylic acid (40 mg, 0.075 mmol) in anhydrous THF (5 ml) was added acetic acid (6.41 µl, 0.112 mmol, 1.5 equiv), EDC (21.48 mg, 0.112 mmol, 1.5 equiv), HOBt (17.16 mg, 0.112 mmol, 1.5 equiv) and then triethylamine (0.031 ml, 0.224 mmol, 3.0 equiv). The mixture was stirred at 23° C. for 14 h. The reaction mixture was partitioned between EtOAc (2×40 ml) and water (45 ml). The combined organic layers were dried over $Na_2SO_4$ and concentrated, affording the desired product, methyl (1S,4R)-4-[5-(3-[(acetylamino)methyl]-5-{[4-(trifluoromethyl)pyrimidin-2-yl]amino}phenyl)-1,3-thiazol-2-yl]-4-hydroxy-2,2-dimethylcyclohexanecarboxylate (40 mg, 74%) as a yellow oil. $^1$H NMR (500 MHz, DMSO) 10.3 (s, 1H), 8.83 (d, J=4.9 Hz, 1H), 8.38 (m, 1H), 8.02 (bs, 1H), 7.90 (s, 1H), 7.68-7.66 (m, 2H), 7.52 (s, 1H), 7.28 (d, J=4.9 Hz, 1H), 5.94 (s, 1H), 4.24 (d, J=5.9 Hz, 2H), 4.12 (t, J=5.8 Hz, 1H), 3.60 (s, 3H), 3.31 (m, 2H), 1.97-1.88 (m, 5H), 1.75-1.73 (m, 2H), 1.24-1.22 (m, 6H).

Step 2

A microwave vessel was charged with a solution of the compound of Step 1 (40 mg, 0.069 mmol) in MeOH, and sodium hydroxide (1.0 N in $H_2O$, 0.485 ml, 0.485 mmol, 7 equiv) was added. The resultant cloudy, orange suspension was irradiated in the microwave at 110° C. for 15 min. Due to poor conversion to the desired product, additional sodium hydroxide (1.0 N in $H_2O$, 0.50 mL, 0.49 mmol, 7.0 eq) was made and the orange-maroon mixture was irradiated in the microwave at 150° C. for 30 min. The reaction mixture was concentrated in vacuo, then partitioned between diethyl ether (75 ml) and water (85 ml). The aqueous layer was acidified with HCl (1.0 N in $H_2O$) to pH ~3-4 then re-extracted with EtOAc (2×35 ml). The combined organic layers were dried over $Na_2SO_4$, filtered and concentrated to provide the title compound (18 mg, 39%) as an off-white, tan solid. MS ESI: [M+H]+ m/z 564.2 $^1$H NMR (500 MHz, DMSO) δ 10.8 (s, 1H), 8.82 (d, 1H, J=4.9 Hz), 8.39-8.37 (m, 1H), 8.02 (bs, 1H), 7.96 (m, 1H), 7.69-7.64 (m, 1H), 7.53 (s, 1H), 7.28 (d, 1H, J=4.9 Hz), 7.17 (s, 1H), 5.91 (bs, 1H), 4.24 (d, 2H, J=5.9 Hz), 3.31 (m, 2H), 3.21 (m, 1H), 1.97-1.82 (m, 5H), 1.66-1.61 (m, 2H), 1.08-0.97 (m, 61-1). rhSYK activity=+++

Example 126

5-(aminomethyl)-5-[5-(3-methyl-5-{[4-(trifluoromethyl)pyrimidin-2-yl]amino}phenyl)-1,3-thiazol-2-yl]azepan-2-one

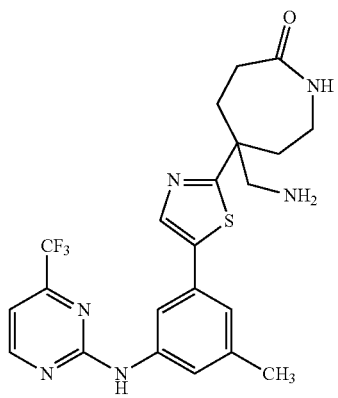 [SMILES: Cc1cc(Nc2nccc(C(F)(F)F)n2)cc(-c2cnc(C3(CN)CCNC(=O)CC3)s2)c1]

Step 1

Diisobutylaluminum hydride (1M in Hexanes, 0.239 ml, 0.239 mmol, 1.2 equiv) was added to a solution of 8-[5-(3-methyl-5-{[4-(trifluoromethyl)pyrimidin-2-yl]amino}phenyl)-1,3-thiazol-2-yl]-1,4-dioxaspiro[4.5]decane-8-carbonitrile (100 mg, 0.20 mmol) at −10° C. and the resulting cloudy mixture was stirred at −10° C. for 1 h. A second addition of DIBAL (1M in Hexanes, 0.239 ml, 0.239 mmol, 1.2 equiv) was made at −10° C. and the reaction was allowed to slowly warm to 23° C. and then stir for 4 days. The reaction was quenched with 1:1:3 mixture of water:aqueous 6N NaOH and the particulate matter was removed via filtration. The remaining filtrate was partitioned between EtOAc (2×55 ml) and water (65 ml). The combined organic layers were dried over $Na_2SO_4$, filtered and concentrated to afford N-(3-{2-[8-(aminomethyl)-1,4-dioxaspiro[4.5]dec-8-yl]-1,3-thiazol-5-yl}-5-methylphenyl)-4-(trifluoromethyl)pyrimidin-2-amine (39 mg, 39%), as an off-white solid. MS ESI: [M+H]+ m/z 506.1. $^1$H NMR (500 MHz, CDCl$_3$) δ 8.66 (d, J=4.6 Hz, 1H), 7.93 (s, 1H), 7.45 (bs, 1H), 7.28 (s, 1H), 7.08-7.04 (m, 2H), 4.06-3.95 (m, 6H), 2.51-2.35 (m, 7H), 1.95-1.71 (m, 4H).

Step 2

Sodium azide (20.45 mg, 0.315 mmol, 3.0 equiv) was added to a stirring solution of the product of Step 1 (53 mg, 0.11 mmol) in chloroform (5 ml). Methanesulfonic Acid (0.082 ml, 1.258 mmol, 12 equiv) was added and the reaction was capped and stirred at 65° C. for 1 h. The yellow mixture was partitioned between EtOAc (2×85 ml) and saturated aqueous NaHCO$_3$ (90 ml), and the combined organic layers were dried over MgSO$_4$ and concentrated. The residual colorless oil was purified via reverse-phase HPLC (Acetonitrile/Water gradient with 0.1% TFA present). The desired fractions were partitioned between EtOAc (2×55 ml) and saturated aqueous NaHCO$_3$ (65 ml). The combined organic layers were dried over Na$_2$SO$_4$ and concentrated, providing the desired title compound (1.3 mg, 2.5%) as a colorless solid-oil. MS ESI: [M+H]+ m/z 477.21. $^1$H NMR (500 MHz, CD$_3$OD) δ 8.72 (d, 1H, J=4.6 Hz), 8.19 (bs, 1H), 7.98 (s, 1H), 7.44 (s, 1H), 7.16 (s, 1H), 7.13 (d, 1H, J=4.6 Hz), 3.45 (s, 2H), 2.95 (m, 2H), 2.05 (s, 3H), 1.90-1.57 (m, 6H). rhSYK activity=+++

Example 127

5-(2-hydroxyethoxy)-5-[5-(3-methyl-5-{[4-(trifluoromethyl)pyrimidin-2-yl]amino}phenyl)-1,3-thiazol-2-yl]azepan-2-one

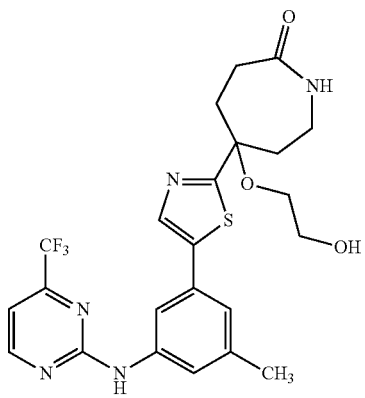 [SMILES: Cc1cc(Nc2nccc(C(F)(F)F)n2)cc(-c2cnc(C3(OCCO)CCNC(=O)CC3)s2)c1]

Step 1

A flame dried microwave vessel was charged with a solution of sodium hydride (4.26 mg, 0.106 mmol, 2.0 equiv) in anhydrous DMF (1 ml). tert-butyl {3-[2-(4-hydroxy-7-oxoazepan-4-yl)-1,3-thiazol-5-yl]-5-methylphenyl}[4-(trifluoromethyl)pyrimidin-2-yl]carbamate (30 mg, 0.05 mmol) and (2-bromoethoxy)-tert-butyldimethylsilane (19.1 mg, 0.08 mmol, 1.5 equiv) were added, causing an exotherm and color change from tan to dark orange. This mixture was heated at 125° C. for 30 min. The resulting mixture of products was purified via reverse-phase HPLC (acetonitrile/water gradient with 0.05% TFA present), to afford tert-butyl (3-{2-[4-(2-hydroxyethoxy)-7-oxoazepan-4-yl]-1,3-thiazol-5-yl}-5-methylphenyl)[4-(trifluoromethyl)pyrimidin-2-yl]carbamate (14 mg, 33%), as an orange oil. MS ESI: [M+H]$^+$ m/z 7222

Step 2

A bi-phasic mixture of the product from Step 1 (15 mg, 0.02 mmol) in acetonitrile and water with 0.05% TFA (reverse-phase HPLC solvent system) was heated at 125° C. for 10 minutes. The reaction was concentrated in vacuo, and the residual oil was partitioned between EtOAc (2×40 ml) and saturated aqueous NaHCO$_3$ (55 ml). The combined organic layers were dried over MgSO$_4$, filtered and concentrated to afford the desired title product (8.1 mg, 77%) as a yellow oil. MS ESI: [M+H]$^+$ m/z 508.2 $^1$H NMR (500 MHz, DMSO) δ 10.3 (m, 1H), 8.82 (m, 1H), 8.04 (m, 1H), 7.98 (s, 1H), 7.54 (m, 1H), 7.45 (s, 1H), 7.17 (s, 1H), 4.68 (m, 1H), 3.98 (m, 2H), 3.55 (m, 2H), 3.00-2.79 (m, 2H), 2.38 (s, 3H), 2.37-1.82 (m, 3H), 1.37-1.01 (m, 3H). rhSYX activity=+++

Example 128

1-[5-(3-methyl-5-{[4-(trifluoromethyl)pyrimidin-2-yl]amino}phenyl)-1,3-thiazol-2-yl]cyclohexanecarbonitrile

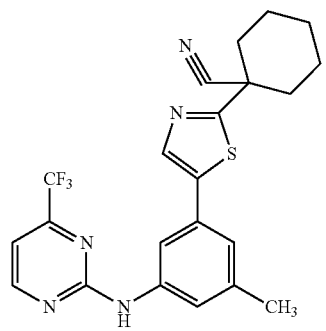 [SMILES: Cc1cc(Nc2nccc(C(F)(F)F)n2)cc(-c2cnc(C3(C#N)CCCCC3)s2)c1]

Step 1

To a solution of cyclohexanecarbonitrile (0.913 g, 8.36 mmol) in toluene (25 ml) at 0° C. was added sodium bis (trimethylsilyl)amide (1M solution in THF, 10.0 ml, 10.0 mmol) and the resulting mixture was stirred for 1 hr at 0° C. 2-Chlorothiazole (1 g, 8.36 mmol) was then added dropwise as a solution in toluene (0.5 mL) over a period of 5 minutes and the resulting mixture was allowed to warm up from 0° C. to room temperature over 16 hrs. The reaction mixture was quenched with saturated aqueous NH$_4$Cl (20 mL), and extracted with EtOAc (2×50 mL). The combined organic layers were washed with brine (60 mL, dried (Na$_2$SO$_4$), filtered and concentrated under reduced pressure. The residue was purified by column chromatography on silica (gradient elution 2% to 12% EtOAc in Hexanes) to afford 1-(1,3-thiazol-2-yl)cyclohexanecarbonitrile (686 mg, 3.57 mmol, 42.7% yield) as a pale yellow oil which solidified upon standing. MS ESI: [M+H]$^+$ m/z 193.

Step 2

N-Bromosuccinimide (0.33 g, 1.87 mmol) was added to a solution of the product from Step 1 (300 mg, 1.56 mmol) in DMF (5 ml) and the resulting reaction mixture was stirred at room temperature for 2 hrs. 2 aliquots of N-bromosuccinimide (0.33 g, 1.87 mmol) were added over a period of 23 hrs before addition of saturated aqueous Na$_2$S$_2$O$_3$ (10 mL). The mixture was then extracted with EtOAc (2×20 mL) and the combined organic layers were washed with brine (50 mL), dried (Na$_2$SO$_4$), filtered and concentrated under reduced pressure. The residue was purified by column chromatography on silica (gradient elution 7% to 60% EtOAc in Hexanes) to afford 1-(5-bromo-1,3-thiazol-2-yl)cyclohexanecarbonitrile (96 mg, 0.35 mmol, 22.7% yield) as a pale yellow oil. MS ESI: [M+H]$^+$ m/z 272.

Step 3

N-[3-methyl-5-(4,4,5,5-tetramethyl-1,3,2-dioxaborolan-2-yl)phenyl]-4-(trifluoromethyl)pyrimidin-2-amine (INTERMEDIATE 3, 134 mg, 0.35 mmol), the compound from Step 2 (96 mg, 0.35 mmol), cesium carbonate (346 mg, 1.06 mmol), X-Phos (16.9 mg, 0.035 mmol) and Pd$_2$(dba)$_3$ (16.2 mg, 0.018 mmol) were placed in a flask and evacuated/purged with N$_2$ for three times. Dioxane (1.5 mL) and water (0.15 mL) were degassed by undersurface N$_2$ bubbling and added to the reaction vessel. The resulting reaction mixture was stirred at 100° C. for 5 hrs and then diluted with EtOAc (5 mL), washed with brine (5 mL), dried (Na$_2$SO$_4$), filtered and concentrated under reduced pressure. The residue was purified by column chromatography on silica (gradient elution 7% to 60% EtOAc in Hexanes) to give the title compound (128 mg, 0.289 mmol, 82% yield) as an off white foam. MS ESI: [M+H]$^+$ m/z 444.1. $^1$H NMR (500 MHz, CD3-OD) δ 8.72 (d, J=5.0, 1H), 8.06 (bs, 1H), 8.00 (s, 1H), 7.48 (bs, 1H), 7.16 (bs, 1H), 7.14 (d, J=4.9, 1H), 2.41-2.37 (m, 5H), 2.06-2.00 (m, 2H), 1.94-1.89 (m, 2H), 1.85-1.73 (m, 3H), 1.40 (m, 1H). rhSYK activity=++

Example 129

1-[5-(3-methyl-5-{[4-(trifluoromethyl)pyrimidin-2-yl]amino}phenyl)-1,3-thiazol-2-yl]cyclohexanecarboxamide

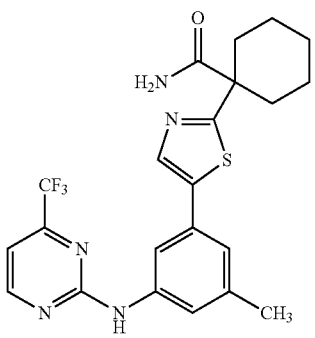 [SMILES: Cc1cc(Nc2nccc(C(F)(F)F)n2)cc(-c2cnc(C3(C(N)=O)CCCCC3)s2)c1]

A mixture of 1-[5-(3-methyl-5-{[4-(trifluoromethyl)pyrimidin-2-yl]amino}phenyl)-1,3-thiazol-2-yl]cyclohexanecarbonitrile (45 mg, 0.10 mmol) and NaOH (1M in MeOH, 0.5 ml, 0.50 mmol) was heated at 100° C. in the microwave for 16 hrs. The mixture was brought to pH=3 by addition of HCl (1.0 N in $H_2O$) and then partitioned between EtOAc (5 mL) and brine (5 mL). The organic layer was separated, dried ($Na_2SO_4$), filtered and the volatiles were removed under reduced pressure. The residue was purified by HPLC (gradient elution 40% to 100% $CH_3CN$ in $H_2O$/0.1% TFA, 20 mins, 20 ml/min) to give the title compound (4.0 mg, 8.67 μmol, 8.5% yield) as a white solid.

MS ESI: $[M+H]^+$ m/z 462.1. $^1H$ NMR (500 MHz, DMSO-$d_6$) δ 10.25 (s, 1H), 8.83 (d, J=5.3, 1H), 7.97 (s, 2H), 7.46 (bs, 1H), 7.28 (d, J=5.2, 1H), 7.20 (bs, 1H), 7.15 (bs, 2H), 2.31-2.24 (m, 5H), 2.00-1.94 (m, 2H), 1.51-1.41 (m, 5H), 1.33 (m, 1H). rhSYK activity=+++.

Example 130

N-[3-(2-cyclohexyl-1,3-thiazol-5-yl)-5-methylphenyl]-4)pyrimidin-2-amine

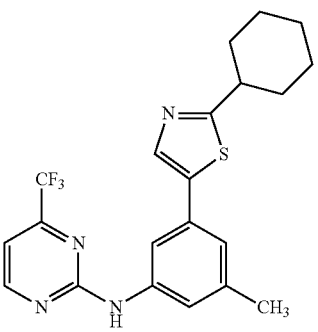 [SMILES: Cc1cc(Nc2nccc(C(F)(F)F)n2)cc(-c2cnc(C3CCCCC3)s2)c1]

A suspension of 1-[5-(3-methyl-5-{[4-(trifluoromethyl)pyrimidin-2-yl]amino}phenyl)-1,3-thiazol-2-yl]cyclohexanecarbonitrile (46 mg, 0.104 mmol) in concentrated aq. HCl (37% w/w, 0.50 mL, 6.09 mmol) was heated at 100° C. until complete dissolution of the starting material was observed (2 hrs). The reaction mixture was allowed to cool to room temperature, and partitioned between EtOAc (5 mL) and water (5 mL). The organic layer was separated, washed with water (2×5 mL) and brine (5 mL), dried ($Na_2SO_4$), filtered and concentrated under reduced pressure. The residue was purified by column chromatoghraphy on silica (gradient elution, 1% to 10% MeOH in DCM) to give the title product (6 mg, 14%). MS ESI: $[M+H]^+$ m/z 419.1. $^1H$ NMR (500 MHz, $CDCl_3$) δ 8.66 (d, J=4.7, 1H), 7.86 (s, 2H), 7.33 (bs, 1H), 7.27 (s, 1H), 7.09 (s, 1H), 7.05 (d, J=4.7, 1H), 3.02 (m, 1H), 2.40 (s, 3H), 2.19 (m, 2H), 1.90-1.85 (m, 2H), 1.62-1.54 (m, 2H), 1.47-1.35 (m, 2H), 1.26-1.23 (m, 2H). rhSYK activity=++.

Example 131

1-[4-(methylsulfonyl)phenyl]-1-[5-(3-methyl-5-{[4-(trifluoromethyl)pyrimidin-2-yl]amino}phenyl)-1,3-thiazol-2-yl]ethanol

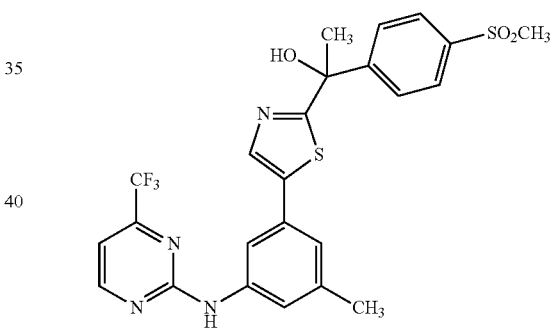

To a solution of 1-[4-(methylsulfanyl)phenyl]-1-[5-(3-methyl-5-{[4-(trifluoromethyl)pyrimidin-2-yl]amino}phenyl)-1,3-thiazol-2-yl]ethanol (Table 4A-57, 33 mg, 0.066 mmol) in DCM (0.5 ml) at 0° C. was added 3-chloroperoxybenzoic acid (22.7 mg, 0.13 mmol). The resulting mixture was stirred for 30 minutes at 0° C. then diluted with AcOEt (5 mL), washed with brine (5 mL), dried ($Na_2SO_4$), filtered, and concentrated under reduced pressure. The residue was purified by reverse phase HPLC (20 ml/min, gradient elution, 20% to 100% AcCN in $H_2O$/0.1% TFA, 20 mins) to give the title compound (28 mg, 0.052 mmol, 80% yield) as a pale yellow solid. MS ESI: $[M+H]^+$ m/z 535.1. $^1H$ NMR (500 MHz, DMSO-$d_6$) δ 10.24 (s, 1H), 8.81 (d, J=4.9, 1H), 7.97 (bs, 1H), 7.92 (bs, 1H), 7.88 (d, J=9.2, 1H), 7.83 (d, J=9.2, 1H), 7.44 (bs, 1H), 7.26 (d, J=4.9, 1H), 7.12 (s, 1H), 7.06 (bs, 1H), 3.16 (s, 3H), 2.29 (s, 3H), 1.94 (s, 3H). rhSYK activity=+++.

Example 132

N-{3-[2-(4-fluorotetrahydro-2H-thiopyran-4-yl)-1,3-thiazol-5-yl]-5-methylphenyl}-4-(trifluoromethyl)pyrimidin-2-amine

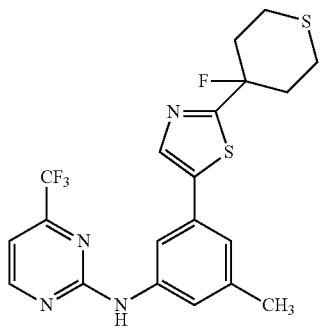 [SMILES: Cc1cc(Nc2nccc(C(F)(F)F)n2)cc(-c2cnc(C3(F)CCSCC3)s2)c1]

Step 1

A solution of N-[3-methyl-5-(1,3-thiazol-5-yl)phenyl]-4-(trifluoromethyl)pyrimidin-2-amine (Intermediate 4, 1.50 g, 4.46 mmol) in THF (10 mL) was added dropwise to a solution of lithium diisopropylamide (7.43 ml, 13.38 mmol) in THF (15 mL) at −78° C. and the resulting mixture was stirred at −78° C. for 30 minutes. Tetrahydrothiopyran-4-one (0.57 g, 4.91 mmol) in THF (5 mL) was then added, the dry ice bath was removed and the reaction was allowed to warm to room temperature. The reaction was quenched with aqueous saturated NH$_4$Cl solution, and extracted with EtOAc (2×). The combined organic layers were washed with brine, dried (MgSO$_4$), filtered and evaporated. Flash chromatography (SiO$_2$, gradient elution 0 to 30% EtOAc in toluene) afforded 4-[5-(3-methyl-5-{[4-(trifluoromethyl)pyrimidin-2-yl]amino}-phenyl)-1,3-thiazol-2-yl]tetrahydro-2H-thiopyran-4-ol (1.21 g, 2.67 mmol, 60% yield) as a yellow foam. MS ESI: [M+H]$^+$ m/z 453.0.

Step 2

To a solution of the product of Step 1 (250 mg, 0.552 mmol) in CH$_2$Cl$_2$ (5 ml) were added EtOH (0.05 mL) and Deoxofluor (0.509 ml, 2.76 mmol). The reaction was stirred at room temperature for 30 minutes, diluted with water (5 mL) and extracted with EtOAc (2×10 mL). The combined organic layers were washed with brine, dried (MgSO$_4$), filtered and evaporated. Column chromatography on silica (gradient elution, 0 to 25% EtOAc in hexanes) afforded the title compound (0.186 g, 0.409 mmol, 74% yield) as a pale yellow foam. MS ESI: [M+H]$^+$ m/z 455.0. $^1$H NMR (500 MHz, DMSO-d$_6$) δ 10.29 (s, 1H), 8.83 (d, J=4.9, 1H), 8.10 (d, J=2.7, 1H), 8.03 (bs, 1H), 7.47 (bs, 1H), 7.28 (d, J=4.9, 1H), 7.20 (bs, 1H), 2.94-2.89 (m, 2H), 2.69-2.66 (m, 2H), 2.39-2.75 (m, 7H). rhSYK activity=++.

Example 133

N-{3-[2-(3,6-dihydro-2H-thiopyran-4-yl)-1,3-thiazol-5-yl]-5-methylphenyl}-4-(trifluoromethyl)pyrimidin-2-amine

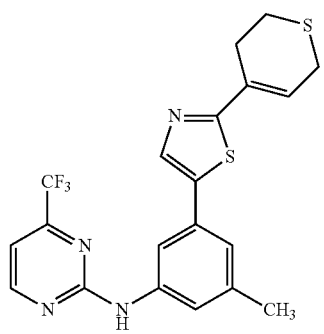 [SMILES: Cc1cc(Nc2nccc(C(F)(F)F)n2)cc(-c2cnc(C3=CCSCC3)s2)c1]

4-[5-(3-methyl-5-{[4-(trifluoromethyl)pyrimidin-2-yl]amino}phenyl)-1,3-thiazol-2-yl]tetrahydro-2H-thiopyran-4-ol (Step 1, Example 132, 250 mg, 0.552 mmol) was combined with Eaton's reagent (1.0 mL, 6.3 mmol) and stirred at 70° C. for 3 hrs. The dark brown reaction mixture was cooled to room temperature, carefully neutralized/diluted with aqueous saturated NaHCO$_3$ (4 mL) and extracted with EtOAc (2×5 mL). The combined organic layers were washed with brine, dried (MgSO$_4$), filtered and evaporated. Column chromatography on silica (gradient elution, 0 to 40% EtOAc in hexanes) afforded the title compound (0.100 g, 0.23 mmol, 41.7% yield) as a yellow foam. MS ESI: [M+H]$^+$ m/z 435.0. $^1$H NMR (500 MHz, DMSO-d$_6$) δ 10.27 (s, 1H), 8.83 (d, J=4.9, 1H), 8.06 (s, 1H), 8.01 (bs, 1H), 7.45 (bs, 1H), 7.28 (d, J=4.9, 1H), 7.18 (bs, 1H), 6.81 (m, 1H), 3.39-3.35 (m, 2H), 2.85-2.83 (m, 2H), 2.77-2.75 (m, 2H), 2.31 (s, 3H). rhSYK activity=+++.

Example 134

N-{3-[2-(4-fluoro-1,1-dioxidotetrahydro-2H-thiopyran-4-yl)-1,3-thiazol-5-yl]-5-methylphenyl}-4-(trifluoromethyl)pyrimidin-2-amine

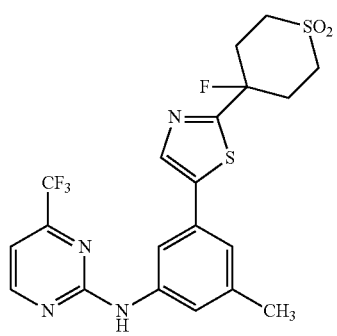 [SMILES: Cc1cc(Nc2nccc(C(F)(F)F)n2)cc(-c2cnc(C3(F)CCS(=O)(=O)CC3)s2)c1]

N-{3-[2-(4-fluorotetrahydro-2H-thiopyran-4-yl)-1,3-thiazol-5-yl]-5-methylphenyl}-4-(trifluoromethyl)pyrimidin-2-amine (Example 132, 140 mg, 0.308 mmol) was dissolved in a 2:1 v/v CH$_2$Cl$_2$/MeOH mixture (6 mL) and magnesium monoperoxyphthalate hexahydrate (286 mg, 0.462 mmol)

was added. The reaction was stirred at room temperature for 2 hrs, diluted with aqueous 10% Na$_2$S$_2$O$_3$ and water and extracted with CH$_2$Cl$_2$ (2×). The combined organic layers were washed with brine, dried (MgSO$_4$), filtered and evaporated. Column chromatography on silica (gradient elution, 0 to 50% EtOAc in hexanes) afforded the title compound (0.118 g, 0.243 mmol, 79% yield) as a white solid. MS ESI: [M+H]$^+$ m/z 487.0. $^1$H NMR (500 MHz, DMSO-d$_6$) δ 10.30 (s, 1H), 8.84 (d, J=4.9, 1H), 8.14 (d, J=2.7, 1H), 8.04 (bs, 1H), 7.48 (bs, 1H), 7.29 (d, J=4.9, 1H), 7.22 (bs, 1H), 3.48-3.40 (m, 2H), 3.28-3.24 (m, 2H), 2.75-2.60 (m, 4H), 2.32 (s, 3H). rhSYK activity=+++.

Example 135

N-{3-[2-(1,1-dioxido-3,6-dihydro-2H-thiopyran-4-yl)-1,3-thiazol-5-yl]-5-methylphenyl}-4-(trifluoromethyl)pyrimidin-2-amine NaHCO$_3$ (4 mL). It was then diluted with water (4 mL) and extracted with EtOAc (2×15 mL). The combined organic layers were washed with brine, dried (MgSO$_4$), and evaporated. Upon addition of CH$_2$Cl$_2$, the title compound precipitated and was isolated by filtration (0.185 g, 0.397 mmol, 91% yield). MS ESI: [M+H]$^+$ m/z 467.0. $^1$H NMR (500 MHz, DMSO-d$_6$) δ 10.29 (s, 1H), 8.83 (d, J=4.9, 1H), 8.12 (d, J=2.7, 1H), 8.03 (bs, 1H), 7.47 (bs, 1H), 7.29 (d, J=4.9, 1H), 7.21 (bs, 1H), 6.53 (m, 1H), 4.00 (m, 2H), 3.39 (m, 2H), 3.14 (m, 2H), 2.32 (s, 3H). rhSYK activity=+++.

Example 136

N-{3-methyl-5-[2-(tetrahydro-2H-thiopyran-4-yl)-1,3-thiazol-5-yl]phenyl}-4-(trifluoromethyl)pyrimidin-2-amine

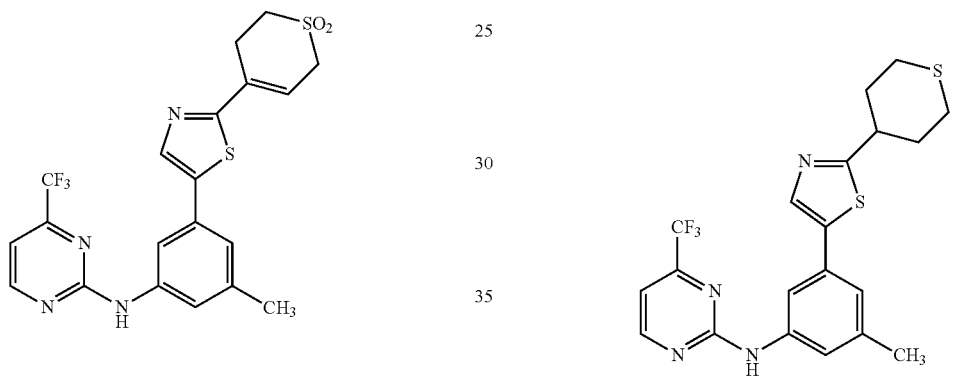

Step 1

4-[5-(3-Methyl-5-{[4-(trifluoromethyl)pyrimidin-2-yl]amino}phenyl)-1,3-thiazol-2-yl]tetrahydro-2H-thiopyran-4-ol (Step 1, Example 132, 300 mg, 0.663 mmol) was taken up in a 2:1 v/v CH$_2$Cl$_2$/MeOH mixture (6 mL) and magnesium monoperoxyphthalate hexahydrate (615 mg, 0.994 mmol) was added. The reaction was stirred at room temperature for 2 h, diluted with aqueous 10% Na$_2$S$_2$O$_3$ and water and extracted with CH$_2$Cl$_2$ (2×). The combined organic layers were washed with brine, dried (MgSO$_4$), filtered and evaporated. Column chromatography on silica (gradient elution, 0 to 75% EtOAc in hexanes) afforded 4-[5-(3-methyl-5-{[4-(trifluoromethyl)pyrimidin-2-yl]amino}phenyl)-1,3-thiazol-2-yl]tetrahydro-2H-thiopyran-4-ol 1,1-dioxide (0.216 g, 0.446 mmol, 67% yield) as a yellow solid. MS ESI: [M+H]$^+$ m/z 485.0.

Step 2

The product from Step 1 (210 mg, 0.433 mmol) was combined with Eaton's reagent (1.00 ml, 6.30 mmol) and stirred at 100° C. for 16 hrs. The reaction was cooled to room temperature and slowly neutralized with aqueous saturated N-{3-[2-(3,6-dihydro-2H-thiopyran-4-yl)-1,3-thiazol-5-yl]-5-methylphenyl}-4-(trifluoromethyl)pyrimidin-2-amine (Example 133, 85 mg, 0.196 mmol) was dissolved in EtOAc (5 ml) and flushed with nitrogen (3×). Palladium on carbon (20.8 mg, 0.020 mmol) was added, and the reaction was flushed with hydrogen (3×) via a hydrogen balloon. The reaction was stirred at room temperature for 16 hrs under hydrogen atmosphere. A further aliquot of palladium on carbon (208 mg, 0.196 mmol) was added, the reaction was purged again with hydrogen, and stirred under hydrogen atmosphere for additional 72 hrs. The reaction mixture was subsequently filtered through a pad of Celite and concentrated under reduced pressure. Column chromatography on silica (gradient elution, 0 to 50% EtOAc in hexanes) afforded N-{3-methyl-5-[2-(tetrahydro-2H-thiopyran-4-yl)-1,3-thiazol-5-yl]phenyl}-4-(trifluoromethyl)pyrimidin-2-amine (0.041 g, 0.094 mmol, 48% yield) as a colorless foam. MS ESI: [M+H]$^+$ m/z 437.0. $^1$H NMR (500 MHz, DMSO-d$_6$) δ 10.26 (s, 1H), 8.83 (d, J=4.9, 1H), 7.96 (m, 2H), 7.42 (bs, 1H), 7.28 (d, J=4.9, 1H), 7.18 (bs, 1H), 3.15 (m, 2H), 2.80 (m, 1H), 2.68 (m, 2H), 2.48 (m, 5H), 1.92 (m, 2H). rhSYK activity=+++.

Example 137

N-{3-[2-(1,1-dioxidotetrahydro-2H-thiopyran-4-yl)-1,3-thiazol-5-yl]-5-methylphenyl}-4-(trifluoromethyl)pyrimidin-2-amine

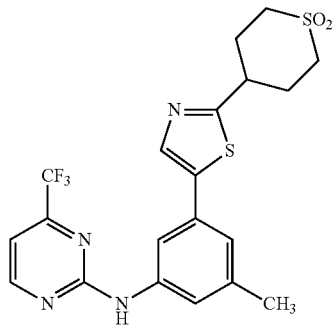 [SMILES: Cc1cc(Nc2nccc(C(F)(F)F)n2)cc(-c2cnc(C3CCS(=O)(=O)CC3)s2)c1]

N-{3-[2-(1,1-Dioxido-3,6-dihydro-2H-thiopyran-4-yl)-1,3-thiazol-5-yl]-5-methylphenyl}-4-(trifluoromethyl)pyrimidin-2-amine (Example 135, 100 mg, 0.214 mmol) was dissolved in a 1:2 v/v mixture MeOH/EtOH (15 mL). Palladium on carbon (57.0 mg, 0.054 mmol) was added, and the reaction was flushed with hydrogen (3×). The reaction was stirred under hydrogen atmosphere at room temperature for 72 hrs. The reaction was filtered through a pad of Celite and concentrated under reduced pressure. Column chromatography on silica (gradient elution, 0 to 75% EtOAc in hexanes) afforded the title compound (0.073 g, 0.156 mmol, 72% yield) as a colorless foam. MS ESI: [M+H]$^+$ m/z 469.0. $^1$H NMR (500 MHz, DMSO-$d_6$) δ 10.27 (s, 1H), 8.83 (d, J=4.9, 1H), 7.99 (m, 2H), 7.45 (bs, 1H), 7.28 (d, J=4.9, 1H), 7.16 (bs, 1H), 3.43 (m, 1H), 3.34 (m, 2H), 3.18 (m, 2H), 2.39 (m, 2H), 2.26 (s, 3H), 2.31 (m, 2H). rhSYK activity=+++.

Example 138

(1S,4R)-4-methoxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid

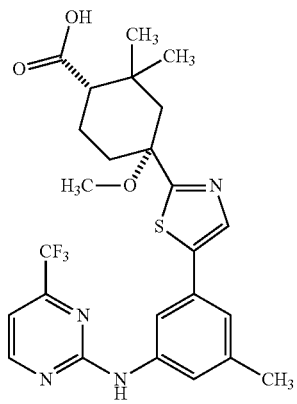 [SMILES: CO[C@]1(c2ncc(-c3cc(C)cc(Nc4nccc(C(F)(F)F)n4)c3)s2)CC[C@H](C(=O)O)C(C)(C)C1]

Step 1

A mixture of methyl cis-4-(5-bromo-1,3-thiazol-2-yl)-4-hydroxycyclohexanecarboxylate (416 mg, 1.195 mmol) and iodomethane (112 μl, 1.792 mmol) in DMF (5500 μl) was cooled to 0° C. and aged while stirring for 10 min. Sodium hydride (47.8 mg, 1.195 mmol) was then added and the reaction aged at 0° C. for 5 min before warming to rt. The reaction was aged at rt for 2 h. The reaction was cooled to 0° C. and quenched with methanol. The mixture was warmed back to room temperature, mixed with water, and extracted with CH$_2$Cl$_2$ (3×). The combined organic layers were dried under reduced pressure and purified by silica gel column chromatography (0-100% EtOAc:Hexanes) afforded methyl cis-4-(5-bromo-1,3-thiazol-2-yl)-4-methoxycyclohexanecarboxylate (306 mg, 71%) as a colorless oil. ESI: [M+H-MeOH]+ m/z 330, 332.

Step 2

N-[3-methyl-5-(4,4,5,5-tetramethyl-1,3,2-dioxaborolan-2-yl)phenyl]-4-(trifluoromethyl)pyrimidin-2-amine (INTERMEDIATE 3, 320 mg, 0.845 mmol), the product of Step 1 (306 mg, 0.845 mmol), and sodium carbonate (845 μL, 1.689 mmol) in 2-Methyl THF (5631 μl) were degassed by sparging with Ar for 5 minutes. PdCl$_2$(dppf)-CH$_2$Cl$_2$ Adduct (34.5 mg, 0.042 mmol) was added and the temperature increased to 85° C. The reaction was aged for 5 hours. The cooled reaction was mixed with water and extracted with CH$_2$Cl$_2$ (3×). The organic layers were dried under reduced pressure. The crude product was purified by silica gel column chromatography (0-100% EtOAc:Hexanes) afforded methyl (1S,4R)-4-methoxy-2,2-dimethyl-4-[5-(3-methyl-5-{[4-(trifluoromethyl)pyrimidin-2-yl]amino}phenyl)-1,3-thiazol-2-yl]cyclohexanecarboxylate (156 mg, 29%) as a colorless oil. MS ESI: [M+H]+ m/z 535.

Step 3

Potassium hydroxide in methanol (3.0 mL, 3.0 mmol) was added to the product of Step 2 (150 mg, 0.23 mmol) and the reaction mixture heated to 65° C. for 110 h. The reaction mixture was cooled and then quenched with HCl (2N in H$_2$O). The mixture was filtered and washed with ~20 mL of water to obtain an off-white solid. The solid was dried under reduced pressure at 40° C. in a vacuum oven for 1.5 h to provide the title compound (95 mg, 79%) as a yellow solid. ESI: [M+H]$^+$ m/z 521. $^1$H NMR (500 MHz, DMSO-$d_6$) δ 12.15-11.94 (m, 1H), 10.26 (s, 1H), 8.83 (d, J=4.9, 1H), 8.00 (s, 1H), 7.96 (s, 1H), 7.45 (s, 1H), 7.28 (d, J=4.9, 1H), 7.16 (s, 1H), 3.07 (s, 3H), 2.31 (s, 3H), 2.22-2.09 (m, 2H), 1.99-1.80 (m, 3H), 1.72 (d, J=14.5, 1H), 1.62 (s, 1H), 1.07 (s, 3H), 1.01 (s, 3H). rhSYK activity=+++

Example 139

Cis-5,5-dimethyl-1-[5-(3-methyl-5-{[4-(trifluoromethyl)pyrimidin-2-yl]amino}phenyl)-1,3-thiazol-2-yl]-2-oxabicyclo[2.2.2]octan-3-one

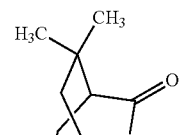

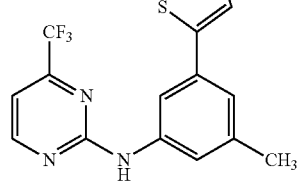

A solution of N,N-Diisopropylamine (13.98 mL, 98 mmol) in THF (55 mL) was cooled to −78° C. n-butyllithium (1.6M in hexanes, 61.3 mL, 98 mmol) was added portionwise via syringe, maintaining an internal temperature lower than −65° C. The reaction mixture warmed to −60° C. and aged for 45 min. and then cooled back to −78° C. A solution of N-[3-methyl-5-(1,3-thiazol-5-yl)phenyl]-4-(trifluoromethyl)pyrimidin-2-amine (INTERMEDIATE 4, 2.113 g, 6.28 mmol) in THF (55 mL) was transferred via cannula (using positive pressure) to the freshly made LDA over the course of 30 min, maintaining the internal temperature below −70° C. The reaction mixture was aged at −78° C. for 35 min, warmed to −50° C. and aged for another 15 min., then cooled to −70° C. A solution of methyl 2,2-dimethyl-4-oxocyclohexanecarboxylate (9.04 g, 49.1 mmol) in THF (50 mL) was transferred via cannula (using positive pressure) to the flask containing the lithium salt, over the course of 45 min, maintaining the internal temperature below −65° C. The reaction was aged at −65° C. for 20 min. The cold bath was removed and the reaction allowed to warm to rt. The solution was cooled to 0° C. and quenched using ethanol (1 mL) and water (1 mL). The mixture was diluted with EtOAc (1 L) and washed with saturated ammonium chloride (3 times, total volume of wash 1.5 L). The organic layer was concentrated under reduced pressure and purified by column chromatography on silica (0-30% EtOAc:Hexanes) to afford the title compound (149 mg, 0.8%) as a yellow solid. MS ESI: [M+H]+ m/z 489. $^1$H NMR (600 MHz, CDCl$_3$) δ 8.66 (d, J=4.8, 1H), 7.89 (d, J=7.0, 2H), 7.39 (s, 1H), 7.29-7.22 (m, 1H), 7.11-7.01 (m, 2H), 2.40 (m, 1H) 2.39 (s, 3H), 2.29 (m, 2H), 2.15 (m, 2H), 2.05-1.90 (m, 2H), 1.24 (s, 3H), 1.15 (s, 3H). rhSYK activity=++

Examples 140(1) and 140(2)

Trans-1,4-dihydroxy-4-[5-(3-methyl-5-{[4-(trifluoromethyl)pyrimidin-2-yl]amino}phenyl)-1,3-thiazol-2-yl]cyclohexanecarboxylic acid and cis-1,4-dihydroxy-4-[5-(3-methyl-5-{[4-(trifluoromethyl)pyrimidin-2-yl]amino}phenyl)-1,3-thiazol-2-yl]cyclohexanecarboxylic acid

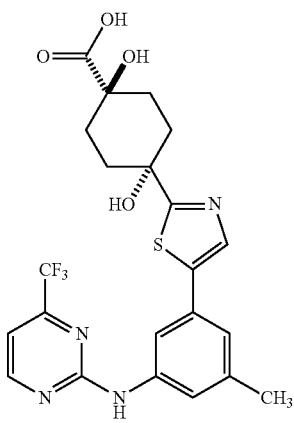

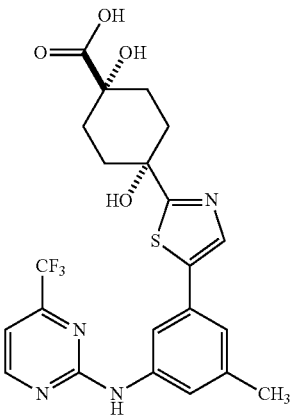

To a suspension of 4-Hydroxy-4-[5-(3-methyl-5-{[4-(trifluoromethyl)pyrimidin-2-yl]amino}phenyl)-1,3-thiazol-2-yl]cyclohexanone (77 mg, 0.17 mmol) and zinc iodide (10 mg, 0.033 mmol) in CH$_2$Cl$_2$ (1 mL), was added trimethylsilyl cyanide (115 pt, 0.858 mL). The resultant suspension was stirred for 14 h at rt. Additional zinc iodide (10 mg, 0.033 mmol) and trimethylsilyl cyanide (115 μL, 0.858 mL) were added, and the resultant suspension was stirred for 5 d at room temperature. HCl (1 mL, 12 N) was then added and stirring continued for 14 h at room temperature. The reaction was quenched with saturated aqueous sodium bicarbonate, extracted with EtOAc (3×), dried over Na$_2$SO$_4$ and concentrated in vacuo. The cis- and trans-isomers were separated via HPLC (20-75% CH$_3$CN:H$_2$O with a 0.1% TFA modifier). The fractions containing the desired product were diluted with ethyl acetate, washed with aqueous saturated sodium hydrogen carbonate, dried over MgSO$_4$, filtered and concentrated to afford provide trans-1,4-dihydroxy-4-[5-(3-methyl-5-{[4-(trifluoromethyl)pyrimidin-2-yl]amino}-phenyl)-1,3-thiazol-2-yl]cyclohexanecarboxylic acid (6 mg, 7%) as a white solid and cis-1,4-dihydroxy-4-[5-(3-methyl-5-{[4-(trifluoromethyl)pyrimidin-2-yl]amino}phenyl)-1,3-thiazol-2-yl]cyclohexanecarboxylic acid (5 mg, 6%) as a white solid. Characterization data for the trans isomer: MS ESI: [M+H]+ m/z 495. $^1$H NMR (500 MHz, DMSO-d$_6$) δ 10.25 (s, 1H), 8.83 (d, J=4.8, 1H), 7.93 (d, J=14.9, 2H), 7.46 (s, 1H), 7.27 (d, J=4.9, 1H), 7.14 (s, 1H), 2.31 (s, 3H), 2.07-1.91 (m, 4H), 1.85 (s, 2H), 1.72 (d, J=9.9, 2H). rhSYK activity=+++. Characterization data for the cis isomer: MS ESI: [M+H]+ m/z 495. $^1$H NMR (500 MHz, DMSO-d$_6$) δ 10.25 (s, 1H), 8.83 (d, J=4.8, 1H), 7.94 (s, 2H), 7.46 (s, 1H), 7.27 (d, J=4.9, 1H), 7.15 (s, 1H), 2.31 (s, 3H), 2.20 (d, 13.0, 2H), 2.09 (d, J=10.4, 2H), 1.57 (m, 4H). rhSYK activity=+++

Example 141

1-{Cis-4-hydroxy-4-[5-(3-methyl-5-{[4-(trifluoromethyl)pyrimidin-2-yl]amino}phenyl)-1,3-thiazol-2-yl]cyclohexyl}pyrrolidin-2-one

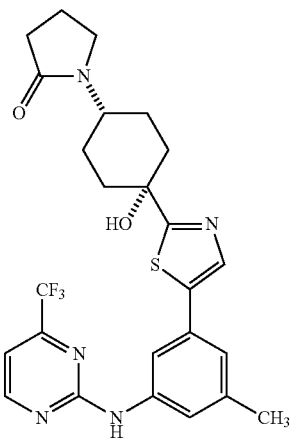 [SMILES: Cc1cc(Nc2nccc(C(F)(F)F)n2)cc(-c2cnc([C@]3(O)CC[C@@H](N4CCCC4=O)CC3)s2)c1]

Step 1

To a solution of cis-4-amino-1-[5-(3-methyl-5-{[4-(trifluoromethyl)pyrimidin-2-yl]amino}phenyl)-1,3-thiazol-2-yl]cyclohexanol (50 mg, 0.111 mmol) in dichloromethane (1 mL) was added triethylamine (0.047 ml, 0.334 mmol) and 4-chlorobutyryl chloride (0.015 ml, 0.133 mmol) sequentially. The resultant white suspension was stirred 1 h at room temperature, filtered, washed with THF, and concentrated in vacuo to afford 4-chloro-N-{cis-4-hydroxy-4-[5-(3-methyl-5-{[4-(trifluoromethyl)pyrimidin-2-yl]amino}phenyl)-1,3-thiazol-2-yl]cyclohexyl}butanamide as an off-white solid (61 mg) which was used in the subsequent reaction without further purification.

Step 2

To a solution of the product from Step 1 (61 mg, 0.110 mmol) in THF (2 mL) was added sodium hydride (14.5 mg, 0.363 mmol) at 0° C. The suspension was stirred 15 min at 0° C., then allowed to warm to rt and stirred 14 h at rt. The reaction was quenched with saturated aqueous ammonium chloride, extracted with EtOAc (3×), dried over $Na_2SO_4$ and concentrated in vacuo. Purification via silica gel column chromatography (0%10% $MeOH:CH_2Cl_2$) gave the title compound (33 mg, 58%) as a white solid. ESI: $[M+H]^+$ m/z 518. $^1$H NMR (500 MHz, DMSO-d6) δ 10.25 (s, 1H), 8.83 (d, J=4.9, 1H), 7.95 (d, J=6.4, 2H), 7.46 (s, 1H), 7.28 (d, J=4.9, 1H), 7.15 (s, 1H), 6.03 (s, 1H), 3.83 (s, 1H), 2.31 (s, 3H), 2.21 (m, 3H), 1.91 (m, 9H), 1.45 (m, 2H). rhSYK activity=+++

Examples 142(1) and 142(2)

1,4-Trans, 1,5-trans-4,5-dihydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid and 1,4-cis, 1,5-cis-4,5-dihydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid

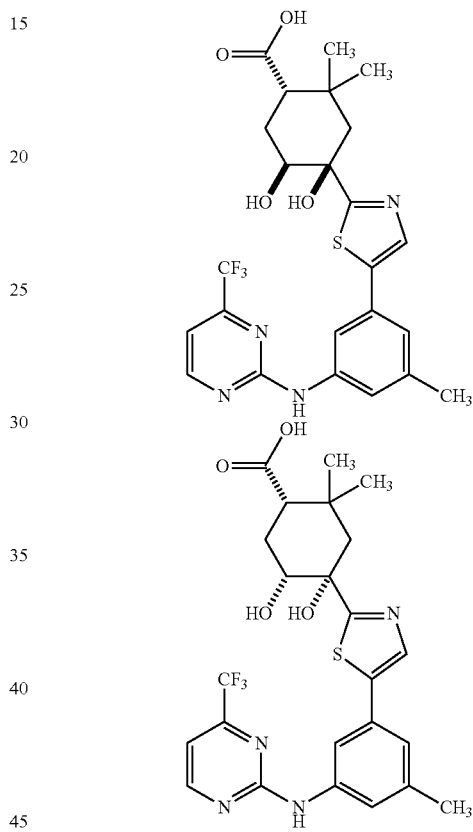

Step 1

Methyl cis-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylate (570 mg, 1.095 mmol) was suspended in Eaton's Reagent (4.14 mL, 21.9 mmol) and heated to 60° C. for 1.5 h. The reaction mixture was allowed to cool to rt, and the reaction quenched via the slow addition of aqueous sodium bicarbonate. The reaction mixture was extracted with EtOAc (3×), dried over $Na_2SO_4$ and concentrated in vacuo. Purification via silica gel column chromatography (10%-35% EtOAc:hexanes) and separation of the diastereomers via HPLC gave 6,6-dimethyl-4-[5-(3-methyl-5-{[4-(trifluoromethyl)pyrimidin-2-yl]amino}phenyl)-1,3-thiazol-2-yl]cyclohex-3-ene-1-carboxylic acid (127 mg, 23%) as a colorless foam. ESI: $[M+H]^+$ m/z 503.

Step 2

The product of Step 1 (41 mg, 0.082 mmol) was dissolved in acetone (800 μL) and water (100 μL), Osmium tetroxide (4% in water, 199 μL, 0.033 mmol) and 4-methylmorpholine N-oxide (38.2 mg, 0.326 mmol) were added, and the suspension was stirred 1 h at rt. The reaction was quenched with 5% aqueous $Na_2S_2O_5$ and stirred for 15 min at rt, extracted with EtOAc (3×), dried over $Na_2SO_4$ and concentrated in vacuo. Purification via silica gel column chromatography (20%-75% EtOAc:Hexanes) gave methyl 1,4-trans, 1,5-trans-4,5-dihydroxy-2,2-dimethyl-4-[5-(3-methyl-5-{[4-(trifluoromethyl)pyrimidin-2-yl]amino}phenyl)-1,3-thiazol-2-yl]cyclohexanecarboxylate and methyl 1,4-cis, 1,5-cis-4,5-dihydroxy-2,2-dimethyl-4-[5-(3-methyl-5-{[4-(trifluoromethyl)pyrimidin-2-yl]amino}phenyl)-1,3-thiazol-2-yl]cyclohexanecarboxylate (28 mg, 64%) as a colorless oil as an apparent ~4:1 mixture of diastereomers. ESI: $[M+H]^+$ m/z 537.

Step 3

4,5-Dihydroxy-2,2-dimethyl-4-[5-(3-methyl-5-{[4-(trifluoromethyl)pyrimidin-2-yl]amino}phenyl)-1,3-thiazol-2-yl]cyclohexanecarboxylate (43 mg, 0.080 mmol) was dissolved in methanol (500 μL). Sodium hydroxide (1.0 M in water, 481 μL, 0.481 mmol) was added, and the suspension was heated in a microwave to 100° C. for 20 min. The mixture was acidified to a pH of 3-4 with HCl (1 M in water) and diluted with water and 10% IPA:CHCl$_3$. The layers were separated and the aqueous layer was re-extracted with 10% IPA:CHCl$_3$(2×). The combined organic layers were washed with water, dried over $Na_2SO_4$, filtered and concentrated in vacuo. Purification via reversed phase HPLC (40-90% $CH_3CN:H_2O$) afforded 1,4-trans, 1,5-trans-4,5-dihydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid (13 mg, 31%) as a white solid and 1,4-cis, 1,5-cis-4,5-dihydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid (17 mg, 41%) as a white solid. Characterization data for the 1,4-cis, 1,5-cis compound: MS ESI: $[M+H]^+$ m/z 523. $^1$H NMR (500 MHz, CD$_3$OD) δ 8.71 (d, J=4.9, 1H), 8.01 (s, 1H), 7.97 (s, 2H), 7.45 (s, 1H), 7.13 (d, J=4.8, 2H), 4.06 (dd, J=4.5, 11.9, 1H), 2.50 (dd, J=3.0, 13.1, 1H), 2.37 (s, 3H), 2.24 (q, J=13.0, 1H), 2.01 (d, J=14.7, 1H), 1.84 (d, J=14.7, 2H), 1.22 (s, 3H), 1.10 (s, 3H). rhSYK activity=+++. Characterization data for the 1,4-trans, 1,5-trans compound: MS ESI: $[M+H]^+$ m/z 523. $^1$H NMR (500 MHz, CD$_3$OD) δ 8.71 (d, J=4.9, 1H), 8.01 (s, 1H), 7.96 (s, 2H), 7.46 (s, 1H), 7.13 (d, J=5.0, 2H), 4.61 (dd, J=4.5, 10.9, 1H), 2.58-2.44 (m, 2H), 2.38 (s, 3H), 2.28-2.16 (m, 1H), 1.96 (d, J=13.7, 1H), 1.75 (d, J=14.0, 1H), 1.30 (s, 3H), 0.98 (s, 3H), rhSYK activity=+++

Examples 143(A) and 143(B)

7-[5-(3-methyl-5-{[4-(trifluoromethyl)pyrimidin-2-yl]amino}phenyl)-1,3-thiazol-2-yl]spiro[2.5]octane-4,7-diol and 9-[5-(3-methyl-5-{[4-(trifluoromethyl)pyrimidin-2-yl]amino}phenyl)-1,3-thiazol-2-yl]dispiro[2.1.2.3]decane-4,9-diol

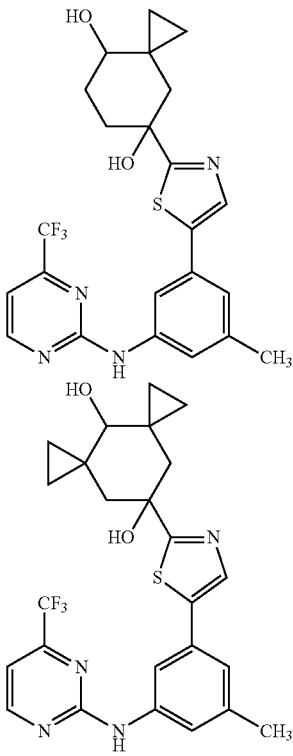

Step 1

4-Hydroxy-4-[5-(3-methyl-5-{[4-(trifluoromethyl)pyrimidin-2-yl]amino}phenyl)-1,3-thiazol-2-yl]cyclohexanone (1 g, 2.230 mmol) was added to a mixture of potassium t-butoxide (0.751 g, 6.69 mmol) in t-butanol (4.96 ml). The reaction was stirred for 30 min before adding 1-chloro-2-[iodo(dimethyl)-λ4-sulfanyl]ethane (0.845 g, 3.34 mmol). The reaction was aged at rt for 14 h, then diluted with water and extracted with $CH_2Cl_2$ (3×). The combined organic layers were concentrated under reduced pressure and purified by silica gel column chromatography (0-100% EtOAc:Hexanes) to give a mixture of 7-hydroxy-7-[5-(3-methyl-5-{[4-(trifluoromethyl)pyrimidin-2-yl]amino}phenyl)-1,3-thiazol-2-yl]spiro[2.5]octan-4-one (MS ESI: $[M+H]^+$ m/z 475) and 9-hydroxy-9-[5-(3-methyl-5-{[4-(trifluoromethyl)pyrimidin-2-yl]amino}phenyl)-1,3-thiazol-2-yl]dispiro[2.1.2.3]decan-4-one (MS ESI: $[M+H]^+$ m/z 501) (676 mg, 64%) as a yellow oil.

Step 2

To the product mixture from Step 1 (676 mg) in methanol (14 mL) was added sodium borohydride (52.5 mg, 1.387 mmol) and the reaction mixture was maintained at room temperature for 30 min. Water and HCl (2 N in water) were added and the mixture was extracted with $CH_2Cl_2$ (3×). The combined organic layers were dried under reduced pressure and purified by column chromatography on silica (0-100% EtOAc:Hexanes) to afford 7-[5-(3-methyl-5-{[4-(trifluoromethyl)pyrimidin-2-yl]amino}phenyl)-1,3-thiazol-2-yl]spiro[2.5]octane-4,7-diol (186 mg) as a colorless oil and 9-[5-(3-methyl-5-{[4-(trifluoromethyl)pyrimidin-2-yl]amino}phenyl)-1,3-thiazol-2-yl]dispiro[2.1.2.3]decane-4,9-diol (194 mg) as a colorless oil. Characterization data for Example 143(A): MS ESI: [M+H]+ m/z 477. ¹H NMR (500 MHz, $CDCl_3$) δ 8.66 (d, J=4.8, 1H), 7.90 (m, 2H), 7.27 (m, 1H), 7.10-7.02 (m, 2H), 3.74 (s, 1H), 2.43 (m, 3H), 2.28 (d, J=14.3, 1H), 2.17 (m, 1H), 2.04 (m, 1H), 1.89-1.57 (m, 2H), 1.26 (t, J=7.5, 1H), 0.78 (m, 1H), 0.61 (m, 1H), 0.55-0.42 (m, 1H), 0.17 (d, J=4.4, 1H). rhSYK activity=+++. Characterization data for Example 143(B): MS ESI: [M+H]+ m/z 485. ¹H NMR (500 MHz, $CDCl_3$) δ 8.66 (d, J=4.8, 1H), 7.88 (s, 2H), 7.27 (m, 1H), 7.11-7.02 (m, 2H), 3.99 (dd, J=3.9, 6.7, 1H), 2.53 (m, 1H), 2.40 (s, 3H), 1.90-1.65 (m, 1H), 1.21 (m, 2H), 0.79 (m, 2H), 0.58 (m, 2H), 0.52 (m, 2H), 0.26 (m, 2H). rhSYK activity=+++.

Example 144

3-[5-(3-methyl-5-{[4-(trifluoromethyl)pyrimidin-2-yl]amino}phenyl)-1,3-thiazol-2-yl]azepan-2-one

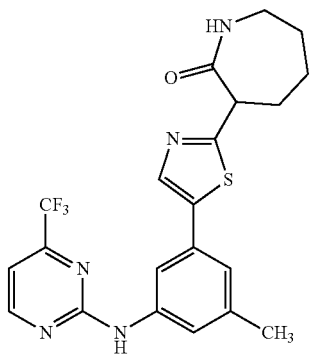 [SMILES: Cc1cc(Nc2nccc(C(F)(F)F)n2)cc(-c2cnc(C3CCCCNC3=O)s2)c1]

Step 1

To a solution of 3-bromoazepan-2-one (1.398 g, 7.28 mmol) in tetrahydrofuran (10 ml), was added sodium hydride (0.48 g, 12.00 mmol) at 0° C. The mixture was stirred at 0° C. for 1 hour, and 1-(bromomethyl)-4-methoxybenzene (1.610 g, 8.01 mmol) was added. The mixture was warmed to room temperature over the span of 2 hours. The reaction was quenched with saturated aqueous ammonium chloride and extracted with ethyl acetate. The organic phase was washed with brine, dried and concentrated to afford crude product, which was purified by chromatography on silica gel (ethyl acetate/hexanes=2/8) to afford 3-bromo-1-(4-methoxybenzyl)azepan-2-one (1.403 g, 4.49 mmol, 61.7% yield). MS ESI: [M+H]+ m/z 313.2.

Step 2

To a solution of N-[3-methyl-5-(1,3-thiazol-5-yl)phenyl]-4-(trifluoromethyl)pyrimidin-2-amine (INTERMEDIATE 4, 150 mg, 0.446 mmol) in THF (5 ml) at −78° C., was added lithium diisopropylamide (1.8M in tetrahydrofuran, 0.75 ml, 1.350 mmol). The mixture was stirred at −78° C. for 1 h, and 3-bromo-1-(4-methoxybenzyl)azepan-2-one (146 mg, 0.468 mmol) was added. The mixture was stirred at −78° C. for 2 hr, and the reaction was quenched with saturated aqueous ammonium chloride solution and extracted with ethyl acetate. The organic phase was washed with brine, dried and concentrated to afford a residue, which was purified by chromatography on silica gel (ethyl acetate/hexanes=3/7) to afford 1-(4-methoxybenzyl)-3-[5-(3-methyl-5-{[4-(trifluoromethyl)pyrimidin-2-yl]amino}phenyl)-1,3-thiazol-2-yl]azepan-2-one (134.5 mg, 0.237 mmol, 53.1% yield). ESI: [M+H]+ m/z 568.2.

Step 3

To a microwave vial, were added the product of Step 2 (44.4 mg, 0.078 mmol), trifluoroacetic acid (0.3 ml, 3.89 mmol), trifluoromethanesulfonic acid (10 µl, 0.078 mmol) and dichloromethane (1 ml). The mixture was irradiated at 110° C. in the microwave for 40 min. The mixture was then purified by reverse phase HPLC to afford the title compound (12 mg, 0.021 mmol, 27.3% yield).

ESI: [M+H]+ m/z 448.2. ¹H NMR (500 MHz, $CD_3OD$) δ 8.74 (d, J=4.9, 1H), 8.42 (s, 1H), 8.29 (s, 1H), 7.50 (s, 1H), 7.31 (s, 1H), 7.17 (d, J=4.9, 1H), 5.01 (dd, J=3.0, 12.1, 1H), 3.53 (d, J=12.9, 1H), 3.20 (t, J=12.9, 1H), 2.69 (t, J=17.1, 1H), 2.40 (s, 3H), 2.07-1.63 (m, 5H). rhSYK activity=+++

Example 145(a) and 145(b)

(R)4-{1,2-dihydroxy-1-[5-(3-methyl-5-{[4-(trifluoromethyl)pyrimidin-2-yl]amino}phenyl)-1,3-thiazol-2-yl]ethyl}benzoic acid (S)4-{1,2-dihydroxy-1-[5-(3-methyl-5-{[4-(trifluoromethyl)pyrimidin-2-yl]amino}phenyl)-1,3-thiazol-2-yl]ethyl}benzoic acid

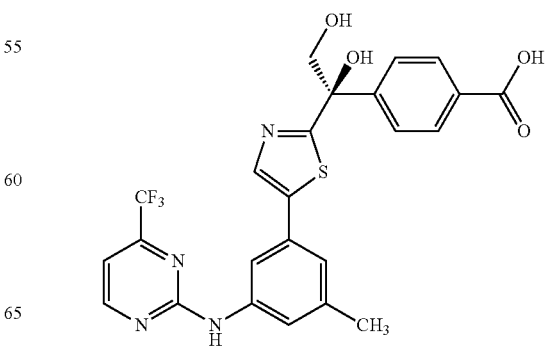

-continued

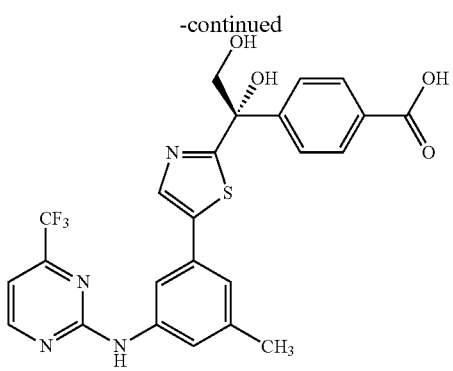

Step 1

A microwave vial was charged with methyl 4-[1-(5-bromo-1,3-thiazol-2-yl)-ethenyl]benzoate (INTERMEDIATE 89, 0.225 g, 0.694 mmol), N-[3-methyl-5-(4,4,5,5-tetramethyl-1,3,2-dioxaborolan-2-yl)phenyl]-4-(trifluoromethyl)pyrimidin-2-amine (INTERMEDIATE 3, 0.263 g, 0.694 mmol), Pd$_2$(dba)$_3$ (0.032 g, 0.035 mmol), cesium carbonate (0.452 g, 1.388 mmol) and X-Phos (0.033 g, 0.069 mmol). The vial was sealed and purged with Argon gas. Dioxane (2.43 mL) and water (0.24 mL) were added and the mixture was stirred at 60° C. for 75 minutes. The temperature was increased to 90° C. and reacted overnight. The resulting solution was cooled and filtered through a celite plug, washing with EtOAc and then concentrated. Chromatography on silica gel (Biotage 100 G SNAP, 10-65% EtOAc/hexanes) afforded methyl 4-{1-[5-(3-methyl-5-{[4-(trifluoromethyl)pyrimidin-2-yl]amino}phenyl)-1,3-thiazol-2-yl]ethenyl}benzoate (103 mg, 0.207 mmol, 29.9% yield). MS ESI: [M+H]$^+$ m/z 497.0.

Step 2

To a solution of the product from Step 1 (0.100 g, 0.201 mmol) and 4-methylmorpholine n-oxide (0.047 g, 0.403 mmol) in acetone (2.98 ml)/water (0.373 ml) was added osmium tetroxide (4% by weight in water, 0.158 ml, 0.020 mmol), and the mixture was stirred at room temperature. Upon completion by LCMS, the mixture was diluted with aqueous 10% Na$_2$SO$_3$ and EtOAc. The aqueous layer was acidified (pH 3-4) with 1 N HCl and extracted with 10% IPA/CHCl$_3$. The combined organic layers were dried (Na$_2$SO$_4$), filtered and concentrated. A combination of chromatography on silica gel (Biotage 250 SNAP, 0-10% MeOH/DCM) and reverse phase HPLC (10-90% ACN/1-120) afforded methyl 4-{1,2-dihydroxy-1-[5-(3-methyl-5-{[4-(trifluoromethyl)pyrimidin-2-yl]amino}phenyl)-1,3-thiazol-2-yl]ethyl}benzoate (70 mg, 0.132 mmol, 65.5% yield). MS ESI: [M+H]$^+$ m/z 531.1.

Step 3

A microwave vial was charged with the product of Step 2 (50 mg, 0.094 mmol), MeOH (666 μl) and then NaOH (700 μl, 0.700 mmol). The mixture was irradiated in the microwave for 20 minutes at 100° C. The pH was adjusted to 3-4 with 1M HCl, then diluted with water and extracted with 10% IPA/CHCl$_3$. The combined organics were washed with water, dried (NaSO$_4$), filtered and concentrated to afford racemic-4-{1,2-dihydroxy-1-[5-(3-methyl-5-{[4-(trifluoromethyl)pyrimidin-2-yl]amino}phenyl)-1,3-thiazol-2-yl]ethyl}benzoic acid (33.4 mg, 0.065 mmol, 68.6% yield). MS ESI: [M+H]$^+$ m/z 517.1. $^1$H NMR (500 MHz, DMSO-d$_6$) δ 12.86 (s, 1H), 10.24 (s, 1H), 8.82 (d, J=4.8, 1H), 7.99 (s, 1H), 7.93-7.85 (m, 3H), 7.74 (d, J=8.3, 2H), 7.45 (s, 1H), 7.26 (d, J=4.8, 1H), 7.12 (s, 1H), 6.73 (s, 1H), 5.11 (t, J=5.8, 1H), 4.10 (dd, J=5.6, 11.2, 1H), 4.04-3.89 (m, 1H), 2.31 (s, 3H).

Step 4

Chiral resolution (Chiral Technology OJ-H 2.1×25 cm, 5 uM, 40%/60% methanol/CO2, 70 mL/Min, 7.5 min run time) of racemic-4-{1,2-dihydroxy-1-[5-(3-methyl-5-{[4-(trifluoromethyl)pyrimidin-2-yl]amino}phenyl)-1,3-thiazol-2-yl]ethyl}benzoic acid (47 mg, 0.091 mmol) afforded enantiomer 1 (14.6 mg, 0.028 mmol, 31.1% yield) and enantiomer 2 (14.9 mg, 0.029 mmol, 31.7% yield) as an off-white powders. Peak 1: MS ESI: [M+H]$^+$ m/z 517.1. $^1$H NMR (500 MHz, DMSO-d$_6$) δ 12.86 (s, 1H), 10.24 (s, 1H), 8.82 (d, J=4.8, 1H), 7.99 (s, 1H), 7.93-7.85 (m, 3H), 7.74 (d, J=8.3, 2H), 7.45 (s, 1H), 7.26 (d, J=4.8, 1H), 7.12 (s, 1H), 6.73 (s, 1H), 5.11 (t, J=5.8, 1H), 4.10 (dd, J=5.6, 11.2, 1H), 4.04-3.89 (m, 1H), 2.31 (s, 3H). Peak 2: MS ESI: [M+H]$^+$ m/z 517.1. $^1$H NMR (500 MHz, DMSO-d$_6$) δ 12.86 (s, 1H), 10.24 (s, 1H), 8.82 (d, J=4.8, 1H), 7.99 (s, 1H), 7.93-7.85 (m, 3H), 7.74 (d, J=8.3, 2H), 7.45 (s, 1H), 7.26 (d, J=4.8, 1H), 7.12 (s, 1H), 6.73 (s, 1H), 5.11 (t, J=5.8, 1H), 4.10 (dd, J=5.6, 11.2, 1H), 4.04-3.89 (m, 1H), 2.31 (s, 3H). rhSYK activity=+++

Example 146

4-{(Cis)-1,2-dihydroxy-2-[5-(3-methyl-5-{[4-(trifluoromethyl)pyrimidin-2-yl]amino}phenyl)-1,3-thiazol-2-yl]ethyl}benzoic acid

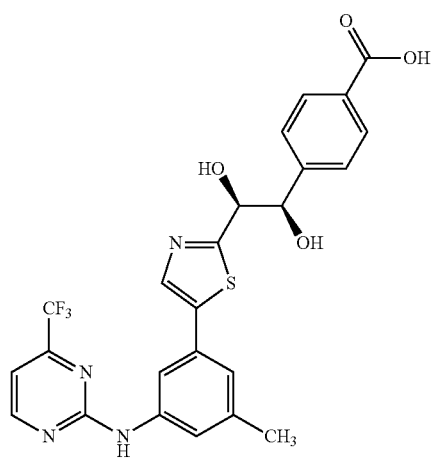 [SMILES: Cc1cc(Nc2nccc(C(F)(F)F)n2)cc(-c2cnc([C@@H](O)[C@H](O)c3ccc(C(=O)O)cc3)s2)c1]

Step 1

Triethyl phosphite (4.58 ml, 26.2 mmol) and methyl 4-(bromomethyl)benzoate (3.00 g, 13.10 mmol) were combined in toluene (25 ml) and stirred at reflux overnight (oil bath set at 140° C. for vigorous reflux). The reaction mixture was concentrated to remove the solvent. Chromatography on silica gel (Biotage 100 g SNAP, 60-100% EtOAc/hexanes) gave a broad product band. Concentration of the product fractions provided the desired product contaminated with phosphite or the corresponding phosphate. The impure product was placed on a high-vac rotovap (at 60° C.) for 2 h. The impurity was removed and afforded methyl 4-[(diethoxyphosphoryl)methyl]benzoate (3.65 g, 12.75 mmol, 97% yield) as a colorless oil. MS ESI: [M+H]$^+$ m/z 287.1.

Step 2

Sodium hydride (49.4 mg, 1.235 mmol) was taken up in THF (4 ml) and cooled to 0° C. Methyl 4-[(diethoxyphosphoryl)methyl]benzoate (141 mg, 0.494 mmol) in THF (1 ml) was added, and the mixture was stirred at 0° C. for 30 min. 5-(3-Methyl-5-{[4-(trifluoromethyl)pyrimidin-2-yl]amino}phenyl)-1,3-thiazole-2-carbaldehyde (described in step 1 of example 88, 150 mg, 0.412 mmol) in THF (1 ml) was subsequently added, and the ice bath was removed. The reaction was warmed to room temperature and stirred for 2 h. The reaction was quenched with saturated aqueous NH$_4$Cl and extracted with EtOAc (2×). The combined organic layers were washed with brine, dried (MgSO$_4$), filtered and evaporated.
Chromatography on silica gel (Biotage 25 g SNAP, 0-50% EtOAc/hexanes) provided methyl 4-{(E)-2-[5-(3-methyl-5-{[4-(trifluoromethyl)pyrimidin-2-yl]amino}phenyl)-1,3-thiazol-2-yl]ethenyl}benzoate (132 mg, 0.266 mmol, 646.% yield) as a bright yellow solid. $^1$H NMR (500 MHz, DMSO-d$_6$) δ 10.29 (s, 1H), 8.84 (d, J=4.8, 1H), 8.19 (s, 1H), 8.02 (s, 1H), 7.95 (d, J=8.2, 2H), 7.84 (d, J=8.3, 2H), 7.65 (d, J=16.3, 1H), 7.54 (d, J=16.2, 1H), 7.49 (s, 1H), 7.29 (d, J=4.9, 1H), 7.23 (s, 1H), 3.84 (s, 3H), 2.33 (s, 3H).

Step 3

The product of Step 2 (105 mg, 0.211 mmol) and 4-methylmorpholine n-oxide (49.5 mg, 0.423 mmol) were taken up in acetone (4 ml) and water (0.500 ml), and osmium tetroxide (4% by weight in water, 0.166 ml, 0.021 mmol) was added. The reaction was stirred at room temperature for 8 h (periodically heated gently to enable dissolution of the starting material). The reaction was diluted with 10% Na$_2$S$_2$O$_3$ solution and extracted with EtOAc (2×). The combined organic layers were washed with brine, dried (MgSO$_4$), filtered and evaporated. Chromatography on silica gel (Biotage 25 g SNAP, dry load, 10-100% EtOAc/hexanes) afforded methyl 4-{cis-1,2-dihydroxy-2-[5-(3-methyl-5-{[4-(trifluoromethyl)pyrimidin-2-yl]amino}phenyl)-1,3-thiazol-2-yl]ethyl}benzoate (54 mg, 0.102 mmol, 48.1% yield) as a colorless solid. MS ESI: [M+H]$^+$ m/z 531.1.

Step 4

The product of Step 3 (84 mg, 0.158 mmol) was taken up in MeOH (5.0 ml) in a microwave vial, and sodium hydroxide (1 M in H$_2$O, 0.475 ml, 0.475 mmol) was added. The sealed reaction was stirred at 100° C. for 1 h in an oil bath. After cooling to room temperature, the yellow solution was adjusted to a pH of 3-4 with 1 N HCl, diluted with water, and extracted with 15% IPA/CHCl$_3$ (3×). The combined organic layers were dried (MgSO$_4$), filtered and evaporated to a tan solid. The material was triturated with Et$_2$O and filtered to afford the title compound (40 mg, 0.077 mmol, 46.9% yield) as a white solid. MS ESI: [M+H]$^+$ m/z 517.1. $^1$H NMR (500 MHz, DMSO-d$_6$) δ 10.24 (s, 1H), 8.82 (d, J=4.7, 1H), 7.94 (m, 2H), 7.87 (d, J=8.1, 2H), 7.55-7.39 (m, 3H), 7.27 (d, J=4.9, 1H), 7.14 (s, 1H), 6.26 (d, J=5.8, 1H), 5.71 (d, J=5.7, 1H), 4.94 (d, J=43.1, 2H), 2.30 (s, 3H). rhSYK activity=+++

Example 147

Methyl 4-{(E)-2-[5-(3-methyl-5-{[4-(trifluoromethyl)pyrimidin-2-yl]amino}phenyl)-1,3-thiazol-2-yl]ethenyl}benzoate

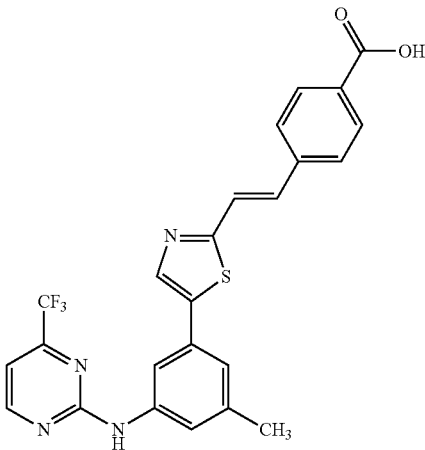 [SMILES: Cc1cc(Nc2nccc(C(F)(F)F)n2)cc(-c2cnc(/C=C/c3ccc(C(=O)O)cc3)s2)c1]

Methyl 4-{(E)-2-[5-(3-methyl-5-{[4-(trifluoromethyl)pyrimidin-2-yl]amino}phenyl)-1,3-thiazol-2-yl]ethenyl}benzoate (40 mg, 0.081 mmol) was taken up in MeOH (1.0 ml) in a microwave vial, and 1.0 M sodium hydroxide (0.161 ml, 0.161 mmol) was added. The reaction was heated to 100° C. for 10 min in the microwave. The bright yellow solution was adjusted to a pH of 3-4 with 1 N HCl, diluted with water, and extracted with 15% IPA/CHCl$_3$ (3×). The combined organic layers were dried (MgSO$_4$) and evaporated to afford the title compound (36 mg, 0.075 mmol, 93% yield) as a bright yellow solid. $^1$H NMR (500 MHz, DMSO-d$_6$) δ 13.01 (s, 1H), 10.29 (s, 1H), 8.84 (d, J=4.8, 1H), 8.18 (s, 1H), 8.02 (s, 1H), 7.93 (d, J=8.3, 2H), 7.82 (d, J=7.8, 2H), 7.63-7.53 (m, 2H), 7.49 (m, 1H), 7.29 (d, J=4.8, 1H), 7.23 (s, 1H), 2.33 (s, 3H). rhSYK activity=+++

Example 148

4-{2-[5-(3-methyl-5-{[4-(trifluoromethyl)pyrimidin-2-yl]amino}phenyl)-1,3-thiazol-2-yl]ethyl}benzoic acid

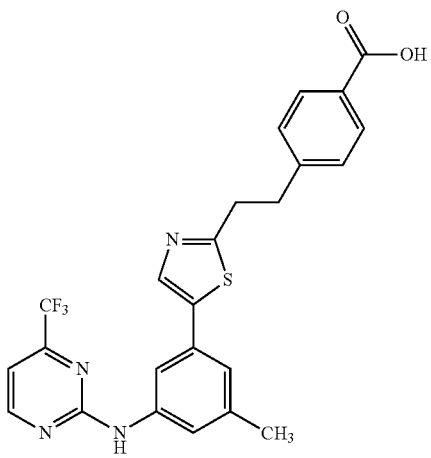 [SMILES: Cc1cc(Nc2nccc(C(F)(F)F)n2)cc(-c2cnc(CCc3ccc(C(=O)O)cc3)s2)c1]

Step 1

Methyl 4-{(E)-2-[5-(3-methyl-5-{[4-(trifluoromethyl)pyrimidin-2-yl]amino}phenyl)-1,3-thiazol-2-yl]ethenyl}benzoate (100 mg, 0.201 mmol) was taken up in EtOAc (5 ml). Palladium on carbon (53.6 mg, 0.050 mmol) was added, and the reaction was purged with hydrogen (3x). The reaction was stirred under a hydrogen balloon at room temperature overnight. Upon complete conversion, the reaction was diluted with EtOAc and filtered through Celite. The filtrate was evaporated to dryness and purified by chromatography on silica gel (Biotage 25 g SNAP, 10-100% EtOAc/hexanes) to give methyl 4-{2-[5-(3-methyl-5-{[4-(trifluoromethyl)pyrimidin-2-yl]amino}phenyl)-1,3-thiazol-2-yl]ethyl}benzoate (82 mg, 0.164 mmol, 82% yield) as a colorless solid.

Step 2

The product of Step 1 (65 mg, 0.130 mmol) was taken up in MeOH (2.0 ml) in a microwave vial, and 1.0M sodium hydroxide (0.261 ml, 0.261 mmol) was added. The reaction was heated to 100° C. for 10 min in the microwave. The colorless solution was adjusted to a pH of 3-4 with 1 N HCl, diluted with water, and extracted with 15% IPA/CHCl$_3$ (2x). The combined organic layers were dried (MgSO$_4$) and evaporated to afford the title compound (60 mg, 0.124 mmol, 95% yield) as a colorless solid. MS ESI: [M+H]$^+$ m/z 485.0 $^1$H NMR (500 MHz, DMSO-d$_6$) δ 12.82 (s, 1H), 10.24 (s, 1H), 8.81 (d, J=4.9, 1H), 7.94 (s, 1H), 7.92 (s, 1H), 7.84 (d, J=8.1, 2H), 7.43 (s, 1H), 7.39 (d, J=8.1, 2H), 7.27 (d, J=4.9, 1H), 7.12 (s, 1H), 3.41-3.20 (m, 2H), 3.13 (t, J=7.6, 2H), 2.29 (s, 3H). rhSYK activity=+++

Example 149

5-{1-Hydroxy-1-[5-(3-methyl-5-{[4-(trifluoromethyl)pyrimidin-2-yl]amino}phenyl)-1,3-thiazol-2-yl]ethyl}pyridine-2-carboxylic acid

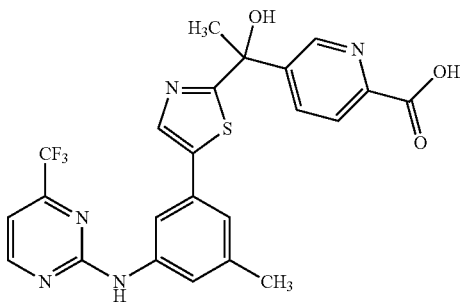 [SMILES: Cc1cc(Nc2nccc(C(F)(F)F)n2)cc(-c2cnc(C(C)(O)c3ccc(C(=O)O)nc3)s2)c1]

Step 1

THF (10 ml) was cooled to −78° C., and lithium diisopropylamide (4.13 ml, 7.43 mmol) was added. N-[3-methyl-5-(1,3-thiazol-5-yl)phenyl]-4-(trifluoromethyl)pyrimidin-2-amine (INTERMEDIATE 4, 1.00 g, 2.97 mmol) in THF (10 ml) was added dropwise, and the reaction was stirred at −78° C. for 30 min. 1-(6-Bromopyridin-3-yl)ethanone (0.595 g, 2.97 mmol) in THF (5 ml) was subsequently added in one portion. The reaction was stirred for 10 min at −78° C. The dry ice bath was removed, and the reaction was allowed to warm to room temperature. The dark brown reaction mixture was quenched with aqueous saturated NH$_4$Cl and extracted with EtOAc (2x). The combined organic layers were washed with brine, dried (MgSO$_4$), filtered and evaporated. Chromatography on silica gel (Biotage 100 g SNAP, 0-30% EtOAc/toluene) afforded 1-(6-bromopyridin-3-yl)-1-[5-(3-methyl-5-{[4-(trifluoromethyl)pyrimidin-2-yl]amino}phenyl)-1,3-thiazol-2-yl]ethanol (348 mg, 0.649 mmol, 21.8% yield) as a yellow solid. MS ESI: [M+H]$^+$ m/z 538.0.

Step 2

The product of Step 1 (175 mg, 0.326 mmol), palladium (II) acetate (7.32 mg, 0.033 mmol), and 1,3-bis(diphenylphosphino)propane (13.46 mg, 0.033 mmol) were combined in a 5 ml microwave vial, sealed, and taken up in DMF (3 ml)/MeOH (1.5 ml). CO was bubbled through the reaction mixture for 5 min. Triethylamine (0.091 ml, 0.653 mmol) was added, a CO balloon was attached, and the reaction was stirred at 70° C. overnight. The reaction was diluted with saturated NH$_4$Cl solution and extracted with EtOAc (2x). The combined organic layers were washed with brine, dried (MgSO$_4$), and evaporated. The crude material was purified by chromatography on silica gel (Biotage 25 g SNAP, 50-100% EtOAc/hexanes, 50-100% EtOAc/toluene) followed by reverse phase HPLC (45-80% MeCN/water w/0.1% TFA). The fractions containing the desired product were combined, partially concentrated to remove MeCN, diluted with saturated NaHCO$_3$, and extracted with CH$_2$Cl$_2$ (2x). The combined organic layers were washed with brine, dried (MgSO$_4$), filtered and evaporated to provide methyl 5-{1-hydroxy-1-[5-(3-methyl-5-{[4-(trifluoromethyl)pyrimidin-2-yl]amino}phenyl)-1,3-thiazol-2-yl]ethyl}pyridine-2-carboxylate (111 mg, 0.215 mmol, 66% yield) as a colorless foam. MS ESI: [M+H]$^+$ m/z 516.1.

Step 3

The product of Step 2 (95 mg, 0.184 mmol) was taken up in MeOH (2.0 ml) in a microwave vial, and sodium hydroxide (1.0 M in H$_2$O, 0.369 ml, 0.369 mmol) was added. The reaction was heated to 100° C. for 10 min in the microwave. The colorless solution was adjusted to a pH of 3-4 with 1 N HCl, diluted with water, and extracted with 15% IPA/CHCl$_3$ (2×). The combined organic layers were dried (MgSO$_4$), filtered and evaporated to afford the title compound (85 mg, 0.169 mmol, 92% yield) as an off-white foam. MS ESI: [M+H]$^+$ m/z 502.1. $^1$H NMR (600 MHz, DMSO-d$_6$) δ 13.12 (s, 1H), 10.23 (s, 1H), 8.89 (d, J=1.9, 1H), 8.80 (d, J=4.9, 1H), 8.09 (dd, J=2.3, 8.2, 1H), 7.99 (d, J=8.2, 1H), 7.97 (s, 1H), 7.92 (s, 1H), 7.44 (s, 1H), 7.25 (d, J=4.9, 1H), 7.13 (d, J=4.5, 2H), 2.28 (s, 3H), 1.95 (s, 3H). rhSYK activity=+++

Example 150

6-{1-Hydroxy-1-[5-(3-methyl-5-{[4-(trifluoromethyl)pyrimidin-2-yl]amino}phenyl)-1,3-thiazol-2-yl]ethyl}pyridine-3-carboxylic acid

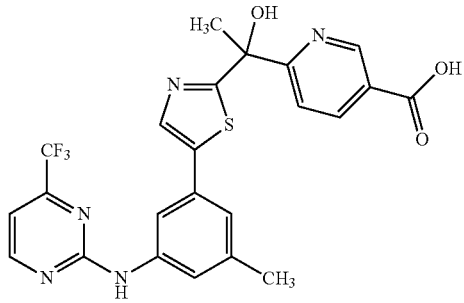 [SMILES: Cc1cc(Nc2nccc(C(F)(F)F)n2)cc(-c2cnc(C(C)(O)c3ccc(C(=O)O)cn3)s2)c1]

Step 1

THF (20 ml) was cooled to −78° C., and lithium diisopropylamide (7.64 ml, 13.75 mmol) was added. N-[3-methyl-5-(1,3-thiazol-5-yl)phenyl]-4-(trifluoromethyl)pyrimidin-2-amine (INTERMEDIATE 4, 1.85 g, 5.50 mmol) in THF (15 ml) was added drop wise, and the reaction was stirred at −78° C. for 30 min. 1-(5-Bromopyridin-2-yl)ethanone (1.100 g, 5.50 mmol) in THF (5 ml) was subsequently added in one portion. The reaction was stirred for 10 min at −78° C. The dry ice bath was removed, and the reaction was allowed to warm to room temperature. The dark brown reaction mixture was quenched with aqueous saturated NH$_4$Cl solution and extracted with EtOAc (2×). The combined organic layers were washed with brine, dried (MgSO$_4$), filtered and evaporated. Chromatography on silica gel (Biotage 100 g SNAP, 0-20% EtOAc/toluene) afforded 1-(5-bromopyridin-2-yl)-1-[5-(3-methyl-5-{[4-(trifluoromethyl)pyridin-2-yl]amino}phenyl)-1,3-thiazol-2-yl]ethanol (1.487 g, 2.77 mmol, 50.4% yield) as a yellow solid. MS ESI: [M+H]$^+$ m/z 538.0.

Step 2

The product of Step 1 (500 mg, 0.932 mmol), palladium (TT) acetate (20.93 mg, 0.093 mmol), and 1,3-bis(diphenylphosphino)propane (38.4 mg, 0.093 mmol) were combined in a 5 ml microwave vial, sealed, and taken up in DMF (4 ml)/MeOH (2.000 ml). CO was bubbled through the reaction mixture for 5 min. Triethylamine (0.260 ml, 1.864 mmol) was added, a CO balloon was attached, and the reaction was stirred at 70° C. for 2 days. The reaction was diluted with aqueous saturated NH$_4$Cl and extracted with EtOAc (2×). The combined organic layers were washed with brine, dried (MgSO$_4$), filtered and evaporated. Chromatography on silica gel (Biotage 100 g SNAP, 0-50% EtOAc/hexanes) provided methyl 6-{1-hydroxy-1-[5-(3-methyl-5-{[4-(trifluoromethyl)pyrimidin-2-yl]amino}phenyl)-1,3-thiazol-2-yl]ethyl}pyridine-3-carboxylate (392 mg, 0.760 mmol, 82% yield) as a pale yellow foam. MS ESI: [M+H]$^+$ m/z 516.1.

Step 3

The product of Step 2 (366 mg, 0.710 mmol) was taken up in MeOH (8.0 ml) in a microwave vial, and sodium hydroxide (1.0 M in H$_2$O, 1.42 ml, 1.42 mmol) was added. The reaction was heated to 100° C. for 10 min in the microwave. The colorless solution was adjusted to a pH of 3-4 with 1 N HCl, diluted with water, and extracted with 15% IPA/CHCl$_3$ (2×). The combined organic layers were dried (MgSO$_4$), filtered and evaporated to a yellow solid that was triturated with CH$_2$Cl$_2$/hexanes, filtered, and dried to provide the title compound (334 mg, 0,666 mmol, 94% yield) as a pale yellow powder. MS ESI: [M+H]$^+$ m/z 502.1. $^1$H NMR (500 MHz, DMSO-d$_6$) δ 13.53-13.21 (s, 1H), δ 10.24 (s, 1H), 8.99 (d, J=2.0, 1H), 8.82 (d, J=4.9, 1H), 8.29 (dd, J=2.2, 8.3, 1H), 7.98-7.90 (m, 2H), 7.85 (d, J=8.3, 1H), 7.45 (s, 1H), 7.27 (d, J=4.9, 1H), 7.13 (s, 1H), 6.95 (s, 1H), 2.29 (s, 3H), 1.98 (s, 3H). rhSYK activity=+++

Examples 151(A) and 151(B)

cis-4-fluoro-4-[5-(3-methyl-5-{[4-(trifluoromethyl)pyrimidin-2-yl]amino}phenyl)-1,3-thiazol-2-yl]cyclohexanecarboxylic acid trans-4-fluoro-4-[5-(3-methyl-5-{[4-(trifluoromethyl)pyrimidin-2-yl]amino}phenyl)-1,3-thiazol-2-yl]cyclohexanecarboxylic acid

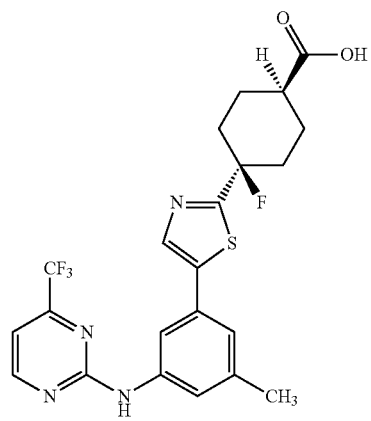

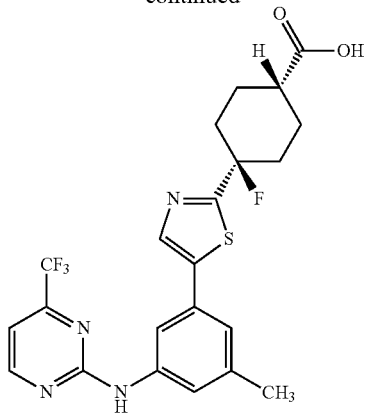

Step 1

To a flask containing tert-butyl 4-hydroxy-4-[5-(3-methyl-5-{[4-(trifluoromethyl)-pyrimidin-2-yl]amino}phenyl)-1,3-thiazol-2-yl]cyclohexanecarboxylate (400 mg, 0.75 mmol) was added dichloromethane (3.7 mL) and ethanol (2.2 mL). Deoxo-fluor (0.69 mL, 3.74 mmol) was added and the reaction was stirred for one hour. The reaction was then diluted with ethyl acetate, washed with water, dried over magnesium sulfate, filtered and concentrated. Flash chromatography was used for purification to yield tert-butyl trans-4-fluoro-4-[5-(3-methyl-5-{[4-(trifluoromethyl)pyrimidin-2-yl]amino}phenyl)-1,3-thiazol-2-yl]cyclohexanecarboxylate (175 mg, 0.33 mmol, 44% yield) and tert-butyl cis-4-fluoro-4-[5-(3-methyl-5-{[4-(trifluoromethyl)pyrimidin-2-yl]amino}phenyl)-1,3-thiazol-2-yl]cyclohexanecarboxylate (140 mg, 0.21 mmol, 28% yield). ESI of trans isomer: [M+H]$^+$ m/z 537. ESI of cis isomer: [M+H]$^+$ m/z 537.

Step 2 with Cis Isomer

To a solution of tert-butyl cis-4-fluoro-4-[5-(3-methyl-5-{[4-(trifluoromethyl)pyrimidin-2-yl]amino}phenyl)-1,3-thiazol-2-yl]cyclohexanecarboxylate (67 mg, 0.13 mmol) in dichloromethane (2.5 mL) was added 2,6-lutidine (0.15 mL, 1.25 mmol) and TBSOTf (0.86 mL, 3.75 mmol). The reaction was stirred for one hour. The mixture was diluted with ethyl acetate, washed with water, dried over magnesium sulfate, filtered and concentrated. Supercritical fluid chromatography (40%/60% methanol/$CO_2$) was used for purification to yield cis-4-fluoro-4-[5-(3-methyl-5-{[4-(trifluoromethyl)pyrimidin-2-yl]amino}phenyl)-1,3-thiazol-2-yl]cyclohexanecarboxylic acid (17 mg, 0.035 mmol, 28% yield). MS ESI: [M+H]$^+$ m/z 461. $^1$H NMR (600 MHz, DMSO-$d_6$) δ 12.20 (s, 1H), 10.26 (s, 1H), 8.81 (d, J=4.8, H), 8.05 (d, J=2.7, 1H), 8.00 (s, 1H), 7.45 (s, 1H), 7.26 (d, J=4.9, 1H), 7.18 (s, 1H), 2.40 (t, J=12.1, 1H), 2.16 (s, 3H), 2.12-1.97 (m, 4H), 1.94-1.87 (m, 2H), 1.67 (dt, J=9.5, 12.9, 2H). rhSYK activity=+++

Step 2 with Trans Isomer

To a solution of tert-butyl trans-4-fluoro-4-[5-(3-methyl-5-{[4-(trifluoromethyl)pyrimidin-2-yl]amino}phenyl)-1,3-thiazol-2-yl]cyclohexanecarboxylate (175 mg, 0.33 mmol) in dichloromethane (6.5 mL) and 2,6-lutidine (0.38 mL, 3.26 mmol) was added TBSOTf (2.25 mL, 9.78 mmol). The reaction was stirred for one hour. The mixture was diluted with ethyl acetate, washed with water, dried over magnesium sulfate, filtered and concentrated. Column chromatography on silica and then reverse phase HPLC was used for purification to yield trans-4-fluoro-4-[5-(3-methyl-5-{[4-(trifluoromethyl)pyrimidin-2-yl]amino}phenyl)-1,3-thiazol-2-yl]cyclohexanecarboxylic acid (70 mg, 0.15 mmol, 45% yield. MS ESI: [M+H]$^+$ m/z 461. $^1$H NMR (600 MHz, DMSO-$d_6$) δ 10.25 (s, 1H), 8.81 (d, J=4.8, 1H), 8.05 (s, 1H), 8.00 (s, 1H), 7.45 (s, 1H), 7.26 (d, J=4.7, 1H), 7.17 (s, 1H), 2.38 (s, 1H), 2.29 (s, 5H), 2.03-1.87 (m, 2H), 1.88-1.71 (m, 4H). rhSYK activity=+++

Example 152

(1S,4R)-4-Hydroxy-2,2-dimethyl-4-{5-[3-methyl-5-(4-methyl-pyrimidin-2-ylamino)-phenyl]-1,3-thiazol-2-yl}-cyclohexanecarboxylic acid

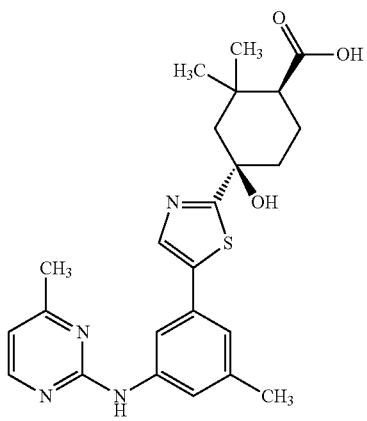 [SMILES: Cc1cc(Nc2nccc(C)n2)cc(-c2cnc([C@@]3(O)CC[C@H](C(=O)O)C(C)(C)C3)s2)c1]

Step 1

To a mixture of (4-methyl-pyrimidin-2-yl)-[3-methyl-5-(4,4,5,5-tetramethyl-[1,3,2]dioxaborolan-2-yl)-phenyl]-amine (20.0 g, 56.9 mmol), (1S,4R)-4-(5-Bromo-thiazol-2-yl)-4-hydroxy-2,2-dimethyl-cyclohexanecarboxylic acid methyl ester (19.8 g, 56.9 mmol), and $PdCl_2(dppf)_2$ (2.33 g, 2.85 mmol) in degassed 2-methyltetrahydrofuran (237 mL), was added sodium carbonate (2 M in $H_2O$, 56.9 mL, 114 mmol). The reaction flask was purged with nitrogen and then heated to 70° C. for 5 hours. The mixture was cooled to room temperature, diluted with ethyl acetate (100 mL) and filtered over celite. The solution was washed with water, dried over $MgSO_4$, filtered and concentrated in vacuo. Purification by chromatography on silica gel (Isco CombiFlash 100:0 to 40:60, hexanes:ethyl acetate), then by Chromatography on silica gel (2:98, methanol:dichloromethane) provided 17.5 g (37.4 mmol 66%) of (1S,4R)-4-hydroxy-2,2-dimethyl-4-{5-[3-methyl-5-(4-methyl-pyrimidin-2-ylamino)-phenyl]-1,3-thiazol-2-yl}-cyclohexanecarboxylic acid methyl ester as a light tan foam.

Step 2

To a solution of the product of Step 1 (16.5 g, 35.3 mmol) in methanol (115 mL) was added sodium hydroxide (1M, 123 mL, 123 mmol) and the mixture was heated to 70° C. for 2.5 hours. The reaction was cooled to 30° C. and hydrochloric acid (1 N, 123 mL, 123 mmol) was added. The reaction was aged for 1.5 hours and filtered to provide 15.3 g (33.7 mmol, 96%) of the title compound as a white solid. MS ESI: [M+H]+ m/z 453.0. $^1$H NMR (600 MHz, DMSO-d$_6$) δ 11.98 (s, 1H), 9.55 (s, 1H), 8.32 (d, J=5.0, 1H), 7.94 (s, 1H), 7.88 (s, 1H), 7.49 (s, 1H), 7.02 (s, 1H), 6.72 (d, J=5.0, 1H), 5.86 (s, 1H), 2.34 (s, 3H), 2.27 (s, 3H), 2.14 (dd, J=12.7, 3.1, 1H), 2.00 (ddd, J=18.6, 13.2, 6.0, 1H), 1.88-1.77 (m, 3H), 1.62 (d, J=14.1, 1H), 1.55 (dq, J=13.5, 3.3, 1H), 1.09 (s, 3H), 0.97 (s, 3H). rhSYK activity=+++

Examples 153(A) and 153(B)

N-(3-{2-[(E)-2-Methoxyethenyl]-1,3-thiazol-5-yl}-5-methylphenyl)-4-(trifluoromethyl)pyrimidin-2-amine N-(3-{2-[(Z)-2-Methoxyethenyl]-1,3-thiazol-5-yl}-5-methylphenyl)-4-(trifluoromethyl)pyrimidin-2-amine

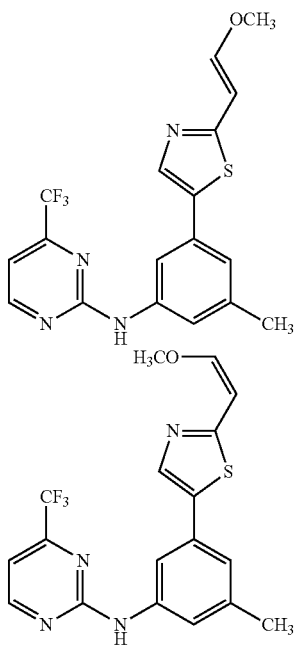

Step 1

Lithium diisopropylamide (1.8M in tetrahydrofuran, 25 ml, 4.46 mmol) was added dropwise to a cooled −78° C. solution of INTERMEDIATE 4 (500 mg, 1.49 mmol) in tetrahydrofuran (7.5 ml). The mixture was stirred at −78° C. for 35 minutes. N,N-dimethylformamide (230 µl, 2.97 mmol) was added, and the resulting mixture was stirred at −78° C. for 1 hour. The mixture then was quenched at −78° C. by the addition of 1 mL of methanol. The mixture was then warmed to room temperature and partitioned between saturated aqueous sodium bicarbonate and ethyl acetate. The layers were separated and the aqueous layer was extracted once more with ethyl acetate. The combined organics were dried over magnesium sulfate, filtered, and concentrated under reduced pressure. Purification via silica gel chromatography (ethyl acetate/hexanes) afforded 5-(3-methyl-5-{[4-(trifluoromethyl)pyrimidin-2-yl]amino}phenyl)-1,3-thiazole-2-carbaldehyde (464 mg, 1.27 mmol, 86% yield) as a yellow solid. ESI: [M+H]+ m/z 365.0.

Step 2

A solution of potassium tert-butoxide (429 mg, 3.82 mmol) in tetrahydrofuran (2 ml) was added dropwise to a cooled −78° C. solution of (methoxymethyl)triphenylphosphonium chloride (1.31 g, 3.82 mmol) in tetrahydrofuran (6 ml). The mixture was warmed to 0° C. and stirred for 20 minutes. A solution of the product of Step 1 (464 mg, 1.27 mmol) in THF (4 ml) was then added, and the resulting mixture was stirred at 0° C. for 1 hour and then warmed to room temperature and stirred overnight. The mixture was then partitioned between saturated aqueous ammonium chloride and ethyl acetate. The layers were separated and the aqueous layer was extracted once more with ethyl acetate. The combined organics were dried over magnesium sulfate, filtered, and concentrated under reduced pressure. Purification via silica gel chromatography (ethyl acetate/hexanes) afforded N-(3-{2-[(E)-2-methoxyethenyl]-1,3-thiazol-5-yl}-5-methylphenyl)-4-(trifluoromethyl)pyrimidin-2-amine (98 mg, 0.25 mmol, 19% yield) as a yellow solid. MS ESI: [M+H]+ m/z 393.1. $^1$H NMR (500 MHz, DMSO-d$_6$) δ 10.23 (s, 1H), 8.80 (d, J=4.0 Hz, 1H), 7.91 (s, 1H), 7.90 (s, 1H), 7.56 (d, J=10.5 Hz, 1H), 7.41 (s, 1H), 7.26 (d, J=4.0 Hz, 1H), 7.11 (s, 1H), 6.14 (d, J=10.5 Hz, 1H), 3.69 (s, 3H), 2.28 (s, 3H). rhSYK activity=+++

N-(3-{2-[(Z)-2-methoxyethenyl]-1,3-thiazol-5-yl}-5-methylphenyl)-4-(trifluoromethyl)-pyrimidin-2-amine (88 mg, 0.22 mmol, 17% yield) as an orange solid. MS ESI: [M+H]+ m/z 393.1. $^1$H NMR (500 MHz, DMSO-d$_6$) δ 10.21 (s, 1H), 8.81 (d, J=4.0 Hz, 1H), 8.03 (s, 1H), 7.96 (s, 1H), 7.39 (s, 1H), 7.26 (d, J=4.0 Hz, 1H), 7.15 (s, 1H), 6.80 (d, J″ 5.5 Hz, 1H), 5.82 (d, J=5.5 Hz, 1H), 3.91 (s, 3H), 2.29 (s, 3H). rhSYK activity=+++

Examples 154(a), 154(b), 154(c) and 154(d)

2,2-Dimethyl-4-[5-(3-methyl-5-{[4-(trifluoromethyl)pyrimidin-2-yl]amino}phenyl)-1,3-thiazol-2-yl]cyclohexanecarboxamide

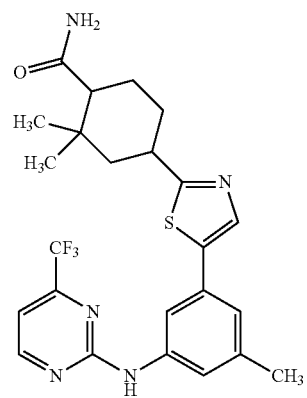

(4 stereoisomers)

Step 1

A suspension of methyl(1S,4R)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid (200 mg, 0.38 mmol) in phosphorous pentoxide (2.2 g, 15.4 mmol) was heated at 65° C. for 3 hours. The resulting mixture was cooled to room temperature, slowly poured into saturated aqueous sodium bicarbonate, and extracted with ethyl acetate (2×). The combined organic layers were dried over magnesium sulfate, filtered, and concentrated under reduced pressure. Purification via silica gel chromatography (ethyl acetate/hexanes) afforded methyl 2,2-dimethyl-4-[5-(3-methyl-5-{[4-(trifluoromethyl)pyrimidin-2-yl]amino}phenyl)-1,3-thiazol-2-yl]cyclohex-3-ene-1-carboxylate (141 mg, 0.28 mmol, 73% yield) as a colorless oil. MS ESI: [M H] m/z 503.1.

Step 2

10% Palladium on carbon (30 mg, 0.028 mmol) was taken up in methanol (1 mL) under argon. A solution of the product from Step 1 (141 mg, 0.281 mmol) in methanol (3 mL) was then added. A hydrogen balloon was attached and the flask was evacuated and backfilled with hydrogen. The mixture was allowed to stir over the weekend. The reaction was filtered through celite and concentrated under reduced pressure. The resulting residue was taken up in methanol (3 mL) and added to a flask containing 10% Palladium on carbon (30 mg, 0.028 mmol) in 1 mL methanol. A hydrogen balloon was attached and the flask was evacuated and backfilled with hydrogen and stirred for 24 hours. The reaction was filtered through celite and concentrated under reduced pressure. The resulting residue was taken up in methanol (3 mL) and added to a flask containing 10% Palladium on carbon (30 mg, 0.028 mmol) in 1 mL methanol. A hydrogen balloon was attached and the flask was evacuated and backfilled with hydrogen and stirred for one week. The mixture was then filtered through a plug of celite and the celite was washed methanol. The filtrate was concentrated under reduced pressure to afford methyl 2,2-dimethyl-4-[5-(3-methyl-5-{[4-(trifluoromethyl)pyrimidin-2-yl]amino}phenyl)-1,3-thiazol-2-yl]cyclohexanecarboxylate (87 mg, 0.17 mmol, 62% yield) as a light yellow oily solid. MS ESI: [M+H]$^+$ m/z 505.1.

Step 3

The product from Step 2 (87 mg, 0.17 mmol) was dissolved in methanol (2.9 ml) and 1 M aqueous sodium hydroxide (0.8 ml, 0.8 mmol) was added. The reaction was heated overnight at 100° C. The reaction was then cooled, acidified with hydrochloric acid (2 M in H$_2$O, 0.4 mL) and then concentrated under reduced pressure to afford crude 2,2-dimethyl-4-[5-(3-methyl-5-{[4-(trifluoromethyl)pyrimidin-2-yl] amino}phenyl)-1,3-thiazol-2-yl]cyclohexanecarboxylic acid that was used in the next step without further purification.

Step 4

The product from Step 3 was taken up in N,N-dimethylformamide (2.9 ml) and EDC (66.1 mg, 0.35 mmol), HOBT (52.8 mg, 0.35 mmol), ammonium chloride (55.3 mg, 1.04 mmol), and N-ethyl-N-(propan-2-yl)propan-2-amine (301 μl, 1.724 mmol) were added. The mixture was stirred at room temperature overnight. The mixture was then diluted with 1 mL of DMSO and directly purified by reverse phase HPLC (acetonitrile/water+0.1% TPA modifier). The desired fractions were combined, diluted with ethyl acetate and washed once with saturated aqueous sodium bicarbonate. The organic layer was dried over magnesium sulfate, filtered, and concentrated under reduced pressure. The resulting residue was subject to purification by chiral supercritical fluid chromatography (4/6 2-Propanol/CO$_2$ with a flow rate of 60 mL/min and a 19 minute run time) to afford the four stereoisomers of 2,2-dimethyl-4-[5-(3-methyl-5-{[4-(trifluoromethyl)pyrimidin-2-yl]amino}phenyl)-1,3-thiazol-2-yl]cyclohexanecarboxamide. Isomer 1 (11 mg, 0.022 mmol, 13% yield). MS ESI: [M+H]$^+$ m/z 490.2. $^1$H NMR (500 MHz, DMSO-d$_6$) δ 10.24 (s, 1H), 8.83 (d, J=5.0 Hz, 1H), 7.95 (s, 1H), 7.92 (s, 1H), 7.45 (s, 1H), 7.27 (d, J=5.0 Hz, 1H), 7.23 (s, 1H), 7.14 (s, 1H), 6.61 (s, 1H), 3.16 (m, 1H), 2.31 (s, 3H), 2:24 (m, 1H), 2.10 (m, 2H), 1.87 (m, 1H), 1.80 (m, 1H), 1.68 (m, 1H), 1.48 (m, 1H), 1.03 (s, 3H), 0.94 (s, 3H). rhSYK activity=+++

Isomer 2 (1.4 mg, 2.9 μmol, 2% yield). MS ESI: [M+H]$^+$ m/z 490.1. $^1$H NMR (500 MHz, DMSO-d$_6$) δ 10.24 (s, 1H), 8.83 (m, 7.95 (s, 1H), 7.92 (s, 1H), 7.45 (s, 1H), 7.27 (m, 1H), 7.23 (s, 1H), 7.14 (s, 1H), 6.61 (s, 1H), 3.15 (m, 1H), 2.30 (s, 3H), 2.24 (m, 1H), 2.10 (m, 2H), 1.87 (m, 1H), 1.81 (m, 1H), 1.68 (m, 1H), 1.49 (m, 1H), 1.03 (s, 3H), 0.94 (s, 3H). rhSYK activity=+++

Isomer 3 (22 mg, 0.045 mmol, 27% yield). MS ESI: [M+H]$^+$ m/z 490.1. $^1$H NMR (500 MHz, DMSO-d$_6$) δ 10.25 (s, 1H), 8.83 (d, J=5.0 Hz, 1H), 7.97 (s, 1H), 7.93 (s, 1H), 7.44 (s, 1H), 7.28 (d, J=5.0 Hz, 1H), 7.17 (s, 1H), 7.14 (s, 1H), 6.72 (s, 1H), 3.18 (m, 1H), 2.30 (s, 3H), 2.11 (m, 1H), 2.01 (m, 1H), 1.79 (m, 2H), 1.56 (m, 1H), 1.39 (m, 2H), 1.01 (s, 3H), 1.00 (s, 3H). rhSYK activity=+++

Isomer 4 (7.2 mg, 0.015 mmol, 9% yield). MS ESI: [M+H]$^+$ m/z 490.1. $^1$H NMR (500 MHz, DMSO-d$_6$) δ 10.25 (s, 1H), 8.83 (d, J=5.0 Hz, 1H), 7.96 (s, 1H), 7.94 (s, 1H), 7.44 (s, 1H), 7.28 (d, J=5.0 Hz, 1H), 7.17 (s, 1H), 7.14 (s, 1H), 6.72 (s, 1H), 3.18 (m, 1H), 2.31 (s, 3H), 2.11 (m, 1H), 2.02 (m, 1H), 1.78 (m, 2H), 1.56 (m, 1H), 1.40 (m, 2H), 1.01 (s, 3H), 1.00 (s, 3H). rhSYK activity=+++

Example 155(A) and 155(B)

Diethyl{cis-1,4-dihydroxy-4-[5-(3-methyl-5-{[4-(trifluoromethyl)pyrimidin-2-yl]amino}phenyl)-1,3-thiazol-2-yl]cyclohexyl}phosphonate Diethyl{trans-1,4-dihydroxy-4-[5-(3-methyl-5-{[4-(trifluoromethyl)pyrimidin-2-yl]amino}phenyl)-1,3-thiazol-2-yl]cyclohexyl}phosphonate

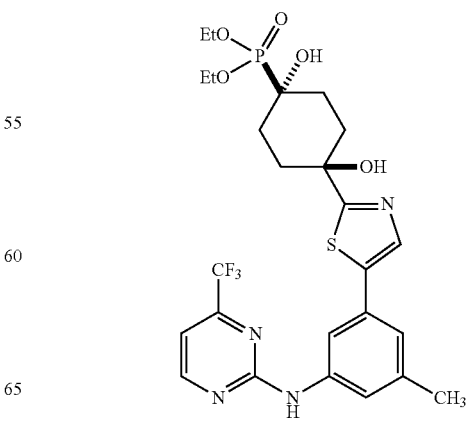

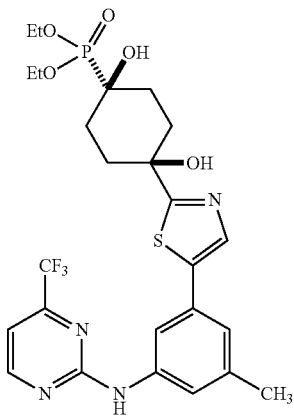

To a stirred solution of 4-hydroxy-4-[5-(3-methyl-5-{[4-(trifluoromethyl)pyrimidin-2-yl]amino}phenyl)-1,3-thiazol-2-yl]cyclohexanone (100 mg, 0.22 mmol) in diethyl phosphite (924 mg, 6.69 mmol) was added 1,1,3,3-tetramethylguanidine (2.6 mg, 0.022 mmol). The reaction mixture was left to stir for 1 h, treated with aqueous saturated sodium bicarbonate solution, and extracted with EtOAc (3×). The combined organics were washed with brine, dried (sodium sulfate), filtered and concentrated, and purified by flash chromatography on silica gel to afford: Diethyl{cis-1,4-dihydroxy-4-[5-(3-methyl-5-{[4-(trifluoromethyl)pyrimidin-2-yl]amino}phenyl)-1,3-thiazol-2-yl]cyclohexyl}phosphonate (9 mg, 0.015 mmol). MS ESI: [M+H]+ m/z 587.1. $^1$H NMR (500 MHz, DMSO-$d_6$) δ 10.26 (s, 1H), 8.84 (d, J=4.9, 1H), 7.96 (s, 1H), 7.95 (s, 1H), 7.47 (s, 1H), 7.29 (d, J=4.9, 1H), 7.16 (s, 1H), 5.94 (s, 1H), 5.17 (s, 1H), 4.06 (q, J=7.1, 4H), 2.33 (s, 3H), 2.22-2.26 (m, 2H), 1.99-2.03 (m, 2H), 1.67-1.70 (m, 2H), 1.57-1.59 (m, 2H), 1.26 (t, J=7.1, 6H). rhSYK activity=+++

Diethyl{trans-1,4-dihydroxy-4-[5-(3-methyl-5-{[4-(trifluoromethyl)pyrimidin-2-yl]amino}phenyl)-1,3-thiazol-2-yl]cyclohexyl}phosphonate (37 mg, 0.063 mmol). MS ESI: [M+H]+ m/z 587.1 $^1$H NMR (500 MHz, DMSO-$d_6$) δ 10.27 (s, 1H), 8.84 (d, J=4.9, 1H), 7.99 (s, 1H), 7.93 (s, 1H), 7.46 (s, 1H), 7.29 (d, J=4.9, 1H), 7.17 (s, 1H), 5.96 (s, 1H), 5.21 (s, 1H), 4.03 (q, J=7.1, 4H), 2.33 (s, 3H), 1.75-2.07 (m, 8H), 1.22 (t, J=7.1, 6H). rhSYK activity=+++.

Example 156

(3E)-3-(Hydroxyimino)-2,2-dimethyl-1-[5-(3-methyl-5-{[4-(trifluoromethyl)pyrimidin-2-yl]amino}phenyl)-1,3-thiazol-2-yl]cyclohexanol

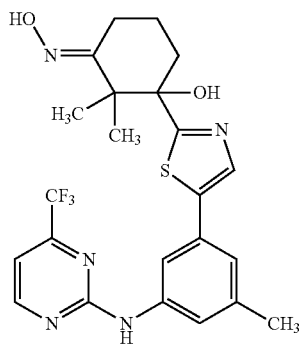 [SMILES: Cc1cc(Nc2nccc(C(F)(F)F)n2)cc(-c2cnc(C3(O)CCC/C(=N\O)C3(C)C)s2)c1]

Step 1

To a stirred solution of INTERMEDIATE 4 (1.09 g, 3.24 mmol) in THF (17 mL) was added LDA (2M, 4.86 mL, 9.72 mmol) dropwise at −78° C. The orange solution was left to stir for 30 min at that temperature, treated with 6,6-dimethyl-1,4-dioxaspiro[4.5]decan-7-one (0.72 g, 3.9 mmol) in THF (4.5 mL) dropwise, and allowed to warm to room temperature as the bath did. The reaction mixture was diluted with saturated ammonium chloride solution, and extracted with EtOAc (3×). The combined organics were washed with brine, dried (sodium sulfate), filtered concentrated, and purified by column chromatography on silica to afford 6,6-dimethyl-7-[5-(3-methyl-5-{[4-(trifluoromethyl)pyrimidin-2-yl]amino}phenyl)-1,3-thiazol-2-yl]-1,4-dioxaspiro[4.5]decan-7-ol (964 mg, 1.85 mmol) as a light yellow foam. MS ESI: [M+H]+ m/z 521.1.

Step 2

To a stirred solution of the product of Step 1 (600 mg, 1.15 mmol) in THF (4 mL) was added HCl (6 M, 3.84 mL, 23.1 mmol). The reaction mixture was allowed to stir at room temperature for 30 min, neutralized with aqueous saturated sodium bicarbonate, and extracted with dichloromethane (3×). The combined organics were dried (sodium sulfate), filtered, concentrated, and purified by flash chromatography on silica to afford 3-hydroxy-2,2-dimethyl-3-[5-(3-methyl-5-{[4-(trifluoromethyl)pyrimidin-2-yl]amino}phenyl)-1,3-thiazol-2-yl]cyclohexanone (534 mg, 1.12 mmol) as a yellow foam. MS ESI: [M+H]+ m/z 477.1.

Step 3

A mixture of the product of Step 2 (300 mg, 0.63 mmol) and hydroxylamine hydrochloride (87 mg, 1.26 mmol) in pyridine (3 mL) was heated to 60° C. for 1 h, concentrated, and purified by flash chromatography to afford the title compound (301 mg, 0.61 mmol). MS ESI: [M+H]+ m/z 492.2. $^1$H NMR (500 MHz, DMSO-$d_6$) δ 10.36 (s, 1H), 10.26 (s, 1H), 8.84 (d, J=4.9, 1H), 7.98 (s, 1H), 7.96 (s, 1H), 7.48 (s, 1H), 7.29 (d, J=4.9, 1H), 7.16 (s, 1H), 5.97 (s, 1H), 2.82 (m, 1H), 2.33 (s, 3H), 2.24:2.38 (m, 2H), 1.65-1.85 (m, 3H), 1.08 (s, 3H), 1.07 (s, 3H). rhSYK activity=+++

Example 157

1-{5-[3-({4-[1-(2-hydroxy-2-methylpropyl)-1H-pyrazol-4-yl]pyrimidin-2-yl}amino)-5-methylphenyl]-1,3-thiazol-2-yl}cyclobutanol

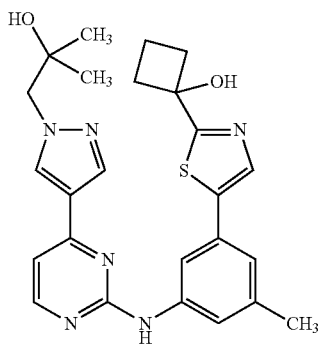 [SMILES: Cc1cc(Nc2nccc(-c3cnn(CC(C)(C)O)c3)n2)cc(-c2cnc(C3(O)CCC3)s2)c1]

Step 1

Isobutylene oxide (101 μL, 1.13 mmol) was added to a solution of 4-(4,4,5,5-tetramethyl-1,3,2-dioxaborolan-2-yl)-1H-pyrazole (200 mg, 1.03 mmol) and cesium carbonate (403 mg, 1.24 mmol) stirring in N,N-dimethylformamide (3.4 mL). The mixture was stirred at 80° C. for 16 h, cooled to room temperature, diluted with diethyl ether, washed with water (3×) and brine, dried over sodium sulfate, filtered, and concentrated to give 2-methyl-1-[4-(4,4,5,5-tetramethyl-1,3,2-dioxaborolan-2-yl)-1H-pyrazol-1-yl]propan-2-ol (84 mg, 0.31 mmol, 31% yield) as a yellow solid. ESI: [M+H]+ m/z 267.0.

Step 2

To a mixture of the product from Step 1 (84 mg, 0.31 mmol), 2,4-dichloropyrimidine (47 mg, 0.31 mmol), potassium phosphate, tribasic (167 mg, 0.79 mmol), and 1,1'-bis(diphenylphosphino)ferrocene-palladium(II)-dichloride dichloromethane complex (26 mg, 0.031 mmol) was added THF (2 mL) and water (0.2 mL). The mixture was heated to 120° C. for 15 minutes under microwave irradiation, cooled to room temperature, quenched with 1:1 water:brine, and extracted with ethyl acetate. The organic layer was dried over sodium sulfate, filtered, and concentrated. Purification by column chromatography on silica gel (Biotage 10 G, eluting with 0:100 to 100:0 ethyl acetate:hexanes) afforded 1-[4-(2-chloropyrimidin-4-yl)-1H-pyrazol-1-yl]-2-methylpropan-2-ol (44 mg, 0.18 mmol, 56% yield) as a yellow solid. MS ESI: [M+H]+ m/z 253.0.

Step 3

A solution containing the product of Step 2 (44 mg, 0.18 mmol), INTERMEDIATE IS (50 mg, 0.19 mmol), and cesium carbonate (114 mg, 0.35 mmol) in dioxane (0.875 mL) was purged and flushed with Ar (g) 3× before the addition of Xantphos (15.2 mg, 0.026 mmol) and palladium(II) acetate (4.3 mg, 0.019 mmol). The system was purged and flushed with Ar (g) 3×, sealed, and heated to 90° C. for 1 h, then cooled to room temperature, filtered through celite, and concentrated. Purification by column chromatography on silica gel (Biotage 10 G, eluting with 0:100 to 70:30 ethyl acetate:hexanes and then 0:100 to 20:80 methanol:dichloromethane) afforded the title compound (63 mg, 0.13 mmol, 76% yield) as a pale yellow solid. MS ESI: [M+H]+ m/z 477.2. 1H NMR (500 MHz, DMSO-d6) δ 9.57 (s, 1H), 8.41 (d, J=5.2, 1H), 8.35 (s, 1H), 8.10 (s, 1H), 7.99 (s, 2H), 7.58 (s, 1H), 7.12 (d, J=5.2, 1H), 7.08 (s, 1H), 6.53 (s, 1H), 4.75 (s, 1H), 4.08 (s, 2H), 2.53 (s, 2H), 2.33 (m, 5H), 1.89 (s, 2H), 1.08 (s, 6H). rhSYX activity=+++

Example 158

2-[5-(3-{[4-(2-hydroxyethoxy)pyrimidin-2-yl]amino}-5-methylphenyl)-1,3-thiazol-2-yl]propane-1,2,3-triol

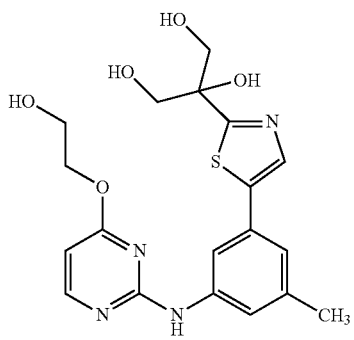 [SMILES: Cc1cc(Nc2nccc(OCCO)n2)cc(-c2cnc(C(O)(CO)CO)s2)c1]

Step 1

3-Chloroperoxybenzoic acid (3.9 g, 17.5 mmol) was added to 2-chloro-4-(methylsulfanyl)pyrimidine (INTERMEDIATE 28, 1.5 g, 7.0 mmol) and dissolved in dichloromethane (35 mL) at 0° C. The reaction mixture was warmed to room temperature and stirred for 1.5 h. The reaction mixture was quenched with aqueous sodium thiosulfate and stirred for 10 minutes. Saturated aqueous sodium bicarbonate was added and the mixture extracted with dichloromethane. The organic layer was washed with brine, dried over sodium sulfate, filtered, and concentrated. Purification by column chromatography on silica gel (Biotage 50 G, eluting with 0:100 to 100:0 ethyl acetate:hexanes) afforded 2-chloro-4-(methylsulfonyl)pyrimidine (1.13 g, 5.86 mmol, 84% yield) as a white solid. MS ESI: [M+H]+ m/z 193.0.

Step 2

To a suspension of ethylene glycol (865 μL, 15.5 mmol) in tetrahydrofuran (19 mL) was added sodium bis(trimethylsilyl)amide (2.0 M in tetrahydrofuran, 4.66 mL, 4.7 mmol) at room temperature. The mixture was stirred for 15 minutes, then 2-chloro-4-(methylsulfonyl)pyrimidine (747 mg, 3.88 mmol) was added. The reaction mixture was stirred for 1 h at room temperature, concentrated, then purified by column chromatography on silica gel (Biotage 50 G, eluting with 0:100 to 100:0 ethyl acetate:hexanes) to give 2-[(2-chloropyrimidin-4-yl)oxy]ethanol (416 mg, 2.37 mmol, 61% yield) as a white solid. MS ESI: [M+H]+ m/z 175.0.

Step 3

Imidazole (389 mg, 5.72 mmol) was added to a suspension of 2-[(2-chloropyrimidin-4-yl)oxy]ethanol (416 mg, 2.38 mmol) in dichloromethane (9.5 mL) at 0° C. tert-Butyldimethylsilyl chloride (424 mg, 2.81 mmol) was added and the reaction mixture stirred at room temperature for 2 h. The reaction was quenched with water and the organic layer separated. The organic layer was dried over sodium sulfate, filtered, and concentrated to give 4-(2-{[tert-butyl(dimethyl) silyl]oxy}ethoxy)-2-chloropyrimidine (678 mg, 2.35 mmol, 99% yield) as a clear, yellow oil. MS ESI: [M+H]$^+$ m/z 289.1.

Step 4

4-(2-{[tert-butyl(dimethyl)silyl]oxy}ethoxy)-2-chloropyrimidine (508 mg, 1.8 mmol), INTERMEDIATE 16 (369 mg, 1.94 mmol), and cesium carbonate (1148 mg, 3.5 mmol) were suspended in dioxane (8.8 mL). The system was purged and flushed with Argon 3× before adding Xantphos (153 mg, 0.26 mmol) and palladium(II) acetate (43 mg, 0.19 mmol). The system was purged and flushed with argon 3×, sealed, and heated to 90° C. for 1.5 h. The reaction was cooled to room temperature, filtered through celite, and concentrated. Purification by column chromatography on silica gel (Biotage 25 G, eluting with 0:100 to 100:0 ethyl acetate:hexanes) afforded 4-(2-{[tert-butyl(dimethyl)silyl]oxy}ethoxy)-N-[3-methyl-5-(1,3-thiazol-5-yl)phenyl]pyrimidin-2-amine (609 mg, 1.76 mmol, 78% yield) as a yellow foam. MS ESI: [M+H]$^+$ m/z 443.2.

Step 5

To diisopropyl amine (185 μL, 1.29 mmol) in tetrahydrofuran (2.2 mL) at 0° C. was added n-butyllithium (2.2 M in hexanes, 589 μL, 1.29 mmol). The mixture was stirred for 15 minutes, then cooled to −78° C. 4-(2-{[tert-butyl(dimethyl) silyl]oxy}ethoxy)-N-[3-methyl-5-(1,3-thiazol-5-yl)phenyl] pyrimidin-2-amine (191 mg, 0.43 mmol), dissolved in tetrahydrofuran (1 mL), was added dropwise over 5 minutes. The mixture was stirred for 30 minutes at −78° C., then 2,2-dimethyl-1,3-dioxan-5-one (57 μL, 0.47 mmol) was added dropwise. The reaction was stirred for 2 h, and then quenched with saturated aqueous ammonium chloride. The mixture was extracted with ethyl acetate (3×), and the combined organic fractions were dried over sodium sulfate, filtered, and concentrated. Purification by column chromatography on silica gel (Biotage 25 G, eluting with 0:100 to 100:0 ethyl acetate:hexanes) gave 5-[5-(3-{[4-(2-{[tert-butyl(dimethyl)silyl]oxy}ethoxy)pyrimidin-2-yl]amino}-5-methylphenyl)-1,3-thiazol-2-yl]-2,2-dimethyl-1,3-dioxan-5-ol (185 mg, 0.32 mmol, 75% yield) as a pale yellow solid. MS ESI: [M+H]$^+$ m/z 573.3.

Step 6

To a solution of 5-[5-(3-{[4-(2-{[tert-butyl(dimethyl)silyl] oxy}ethoxy)pyrimidin-2-yl]amino}-5-methylphenyl)-1,3-thiazol-2-yl]-2,2-dimethyl-1,3-dioxan-5-ol (185 mg, 0.32 mmol) in tetrahydrofuran (1.6 mL) was added hydrochloric acid (1.0 N, 970 μL, 0.97 mmol) at room temperature. The mixture was stirred at room temperature for 2.5 h, then diluted with methanol, filtered, and purified by reverse phase HPLC (10:90 to 90:10 acetonitrile:water with a 0.1% trifluoroacetic acid modifier). The combined fractions were dried on a lyophilizer, dissolved in methanol, and the TEA salt converted to the free base using StratoSpheres SPE PL-HCO$_3$ MP-Resin (0.9 mmol) cartridges to give 2-[5-(3-{[4-(2-hydroxyethoxy) pyrimidin-2-yl]amino}-5-methylphenyl)-1,3-thiazol-2-yl] propane-1,2-triol (75 mg, 0.18 mmol, 56% yield) as a white foam. MS ESI: [M+H]$^+$ m/z 419.1. $^1$H NMR (500 MHz, DMSO-d$_6$) δ 9.65 (dd, J=4.3, 15.1, 1H), 8.21 (d, J=5.7, 1H), 7.96 (s, 1H), 7.90 (s, 1H), 7.47 (s, 1H), 7.09 (s, 1H), 6.31 (s, 1H), 4.39 (s, 2H), 3.79-3.72 (m, 2H), 3.72-3.63 (m, 4H), 2.30 (s, 3H). rhSYK activity=+++

Example 159

4-hydroxy-4-[5-(3-{[4-(2-hydroxyethoxy)pyrimidin-2-yl]amino}-5-methylphenyl)-1,3-thiazol-2-yl]-2,2-dimethylcyclohexanecarboxylic acid

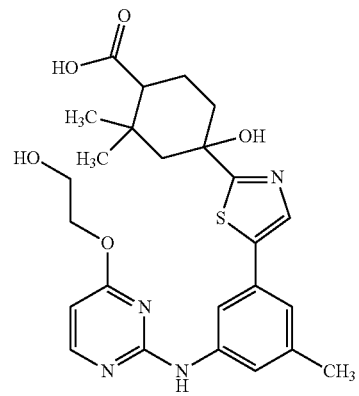 [SMILES: Cc1cc(Nc2nccc(OCCO)n2)cc(-c2cnc(C3(O)CCC(C(=O)O)C(C)(C)C3)s2)c1]

The title compound was prepared in an analogous manner to Example 158. MS ESI: [M+H]$^+$ m/z 499.2. $^1$H NMR (500 MHz, dmso) δ 9.56 (s, 1H), 8.21 (d, J=5.6, 1H), 7.91 (s, 1H), 7.90 (s, 1H), 7.49 (s, 1H), 7.06 (s, 1H), 6.28 (d, J=5.6, 1H), 5.83 (s, 1H), 4.47-4.31 (m, 2H), 3.81-3.69 (m, 2H), 3.15 (s, 1H), 2.29 (s, 3H), 1.94 (s, 2H), 1.88-1.70 (m, 3H), 1.58 (s, 1H), 1.49 (s, 1H), 1.09 (s, 3H), 0.98 (s, 3H). rhSYK activity=+++

Examples 160(a) and 160(b)

4,5-dihydroxy-5-[5-(3-methyl-5-{[4-(trifluoromethyl)pyrimidin-2-yl]amino}phenyl)-1,3-thiazol-2-yl]azepan-2-one 5,6-dihydroxy-5-[5-(3-methyl-5-{[4-(trifluoromethyl)pyrimidin-2-yl]amino}phenyl)-1,3-thiazol-2-yl]azepan-2-one

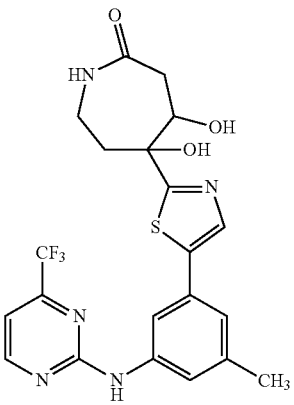

509

-continued

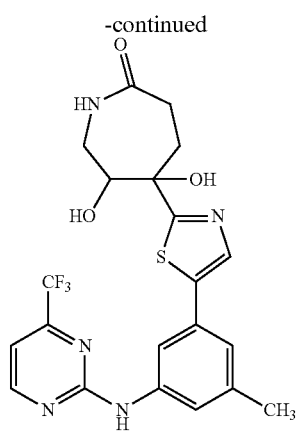

Step 1

5-Hydroxy-5-[5-(3-methyl-5-{[4-(trifluoromethyl)pyrimidin-2-yl]amino}phenyl)-1,3-thiazol-2-yl]azepan-2-one (Example 10, 300 mg, 0.65 mmol) was suspended neat in phosphorus pentoxide (1.2 mL, 12.9 mmol) and stirred at 65° C. for 2 h., then cooled to room temperature, and carefully poured into saturated aqueous sodium bicarbonate. After the exotherm ceased, the mixture was extracted with ethyl acetate (2×). The combined organic layers were dried over sodium sulfate, filtered, and concentrated. The residue was purified by reverse phase HPLC (45:55 to 85:15 acetonitrile:water with a 0.1% trifluoroacetic acid modifier) to afford 5-[5-(3-methyl-5-{[4-(trifluoromethyl)pyrimidin-2-yl]amino}phenyl)-1,3-thiazol-2-yl]-1,3,6,7-tetrahydro-2H-azepin-2-one and 5-[5-(3-methyl-5-{[4-(trifluoromethyl)pyrimidin-2-yl]amino}phenyl)-1,3-thiazol-2-yl]-1,3,4,7-tetrahydro-2H-azepin-2-one (70:30 mixture, 119 mg, 0.26 mmol, 41% yield) as a yellow solid. MS ESI: [M+H]$^+$ m/z 446.1.

Step 2

The 70:30 mixture of products from Step 1 (100 mg, 0.22 mmol) was dissolved in acetone (1 mL) and water (125 μL). Osmium tetroxide (4% in H$_2$O, 548 μL, 0.09 mmol) and 4-methylmorpholine N-oxide (105 mg, 0.90 mmol) were added and the suspension was stirred for 1 h at room temperature. The reaction was quenched with 5% aqueous sodium thiosulfate and stirred for 15 minutes. The mixture was washed with ethyl acetate (3×), and the combined organic layers were dried over sodium sulfate, filtered, and concentrated to give a mixture of 4,5-dihydroxy-5-[5-(3-methyl-5-{[4-(trifluoromethyl)pyrimidin-2-yl]amino}phenyl)-1,3-thiazol-2-yl]azepan-2-one and 5,6-dihydroxy-5-[5-(3-methyl-5-{[4-(trifluoromethyl)pyrimidin-2-yl]amino}phenyl)-1,3-thiazol-2-yl]azepan-2-one (70:30, 40 mg, 0.084 mmol 37% yield) as a brownish-yellow solid. MS ESI: [M+H]$^+$ m/z 480.1. $^1$H NMR (600 MHz, DMSO-d$_6$) δ 10.13 (s, 1H), 8.80 (d, J=4.9, 1H), 7.93 (s, 1H), 7.90 (s, 1H), 7.53-7.36 (m, 2H), 7.23 (d, J=4.9, 1H), 7.11 (s, 1H), 5.92 (s, 1H), 5.86 (s, 1H), 5.12-5.01 (m, 1H), 4.04-3.99 (m, 1H), 3.58-3.36 (m, 1H), 3.19-3.09 (m, 1H), 2.96-2.75 (m, 1H), 2.30 (s, 3H), 2.04-1.82 (m, 2H) rhSYK activity=+++

510

Examples 161(A), 161(B), 161(C) and 161(D)

4,5-dihydroxy-5-[5-(3-methyl-5-{[4-(trifluoromethyl)pyrimidin-2-yl]amino}phenyl)-1,3-thiazol-2-yl]azepan-2-one 5,6-dihydroxy-5-[5-(3-methyl-5-{[4-(trifluoromethyl)pyrimidin-2-yl]amino}phenyl)-1,3-thiazol-2-yl]azepan-2-one

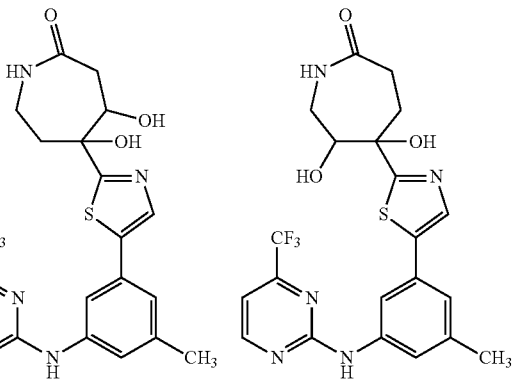

Two stereoisomers each

Step 1

The 70:30 mixture of 4,5-dihydroxy-5-[5-(3-methyl-5-{[4-(trifluoromethyl)pyrimidin-2-yl]amino}phenyl)-1,3-thiazol-2-yl]azepan-2-one and 5,6-dihydroxy-5-[5-(3-methyl-5-{[4-(trifluoromethyl)pyrimidin-2-yl]amino}phenyl)-1,3-thiazol-2-yl]azepan-2-one (30 mg; Examples 160(a) and 160(b)) was subjected to purification by chiral supercritical fluid chromatography (4/6 2-propanol/CO$_2$ with a flow rate of 50 mL/min and a 19 minute run time) to afford the stereoisomers of 4,5-dihydroxy-5-[5-(3-methyl-5-{[4-(trifluoromethyl)pyrimidin-2-yl]amino}phenyl)-1,3-thiazol-2-yl]azepan-2-one and 5,6-dihydroxy-5-[5-(3-methyl-5-{[4-(trifluoromethyl)pyrimidin-2-yl]amino}phenyl)-1,3-thiazol-2-yl]azepan-2-one. Enantiomer 1 [cis]5,6-dihydroxy-5-[5-(3-methyl-5-{[4-(trifluoromethyl)pyrimidin-2-yl]amino}phenyl)-1,3-thiazol-2-yl]azepan-2-one (3.2 mg, 6.25 μmol, 10% yield). MS ESI: [M+H]$^+$ m/z 480. $^1$H NMR (500 MHz, DMSO-d$_6$) δ 10.25 (s, 1H), 8.83 (d, J=4.9, 1H), 7.96 (s, 1H), 7.93 (s, 1H), 7.53 (s, 1H), 7.47 (s, 1H), 7.27 (d, J=4.9, 1H), 7.13 (s, 1H), 6.01 (s, 1H), 5.17 (d, J=5.9, 1H), 3.81-3.73 (m, 1H), 3.54 (m, 1H), 2.82 (m, 2H), 2.31 (s, 3H), 2.04-1.93 (m, 2H), 1.93-1.86 (m, 1H). rhSYK activity=+++

Enantiomer 2 [cis]-4,5-dihydroxy-5-[5-(3-methyl-5-{[4-(trifluoromethyl)pyrimidin-2-yl]amino}phenyl)-1,3-thiazol-2-yl]azepan-2-one (9.0 mg, 0.019 mmol, 30% yield). MS ESI: [M+H]$^+$ m/z 480. $^1$H NMR (500 MHz, DMSO-d$_6$) δ 10.25 (s, 1H), 8.83 (d, J=4.9, 1H), 7.96 (s, 1H), 7.93 (s, 1H), 7.61 (s, 1H), 7.47 (s, 1H), 7.27 (d, J=4.9, 1H), 7.13 (s, 1H), 6.06 (s, 1H), 5.18 (d, J=5.7, 1H), 4.04-4.00 (m, 1H), 3.47-3.40 (m, 1H), 3.15 (d, J=5.3, 1H), 2.90 (s, 1H), 2.31 (s, 3H), 2.18 (s, 1H), 1.97-1.82 (m, 2H). rhSYK activity=+++

Enantiomer 3 [cis]5,6-dihydroxy-5-[5-(3-methyl-5-{[4-(trifluoromethyl)pyrimidin-2-yl]amino}phenyl)-1,3-thiazol-2-yl]azepan-2-one (3.3 mg, 6.88 μmol, 11% yield). MS ESI: [M+H]$^+$ m/z 480. $^1$H NMR (500 MHz, DMSO-d$_6$) δ 10.26 (s, 1H), 8.83 (d, J=4.9, 1H), 7.96 (s, 1H), 7.93 (s, 1H), 7.53 (s, 1H), 7.47 (s, 1H), 7.28 (d, J=4.9, 1H), 7.14 (s, 1H), 6.01 (s, 1H), 5.17 (d, J=5.9, 1H), 3.82-3.71 (m, 1H), 3.53 (m, 1H), 2.91-2.75 (m, 2H), 2.31 (s, 3H), 2.04-1.93 (m, 2H), 1.93-1.86 (m, 1H). rhSYK activity=+++

Enantiomer 4 [cis]4,5-dihydroxy-5-[5-(3-methyl-5-{[4-(trifluoromethyl)pyrimidin-2-yl]amino}phenyl)-1,3-thiazol-2-yl]azepan-2-one (5.1 mg, 0.011 mmol, 17% yield). MS ESI: [M+H]$^+$ m/z 480. $^1$H NMR (500 MHz, DMSO-d$_6$) δ 10.25 (s, 1H), 8.83 (d, J=4.9, 1H), 7.96 (s, 1H), 7.93 (s, 1H), 7.60 (s, 1H), 7.46 (s, 1H), 7.27 (d, J=4.9, 1H), 7.13 (s, 1H), 6.06 (s, 1H), 5.18 (d, J=5.7, 1H), 4.05-4.00 (m, 1H), 3.44 (s, 1H), 3.15 (d, J=5.2, 1H), 2.90 (s, 1H), 2.31 (s, 3H), 2.18 (s, 1H), 1.97-1.84 (m, 2H). rhSYK activity=+++

Example 162

5-amino-5-[5-(3-methyl-5-{[4-(trifluoromethyl)pyrimidin-2-yl]amino}phenyl)-1,3-thiazol-2-yl]azepan-2-one

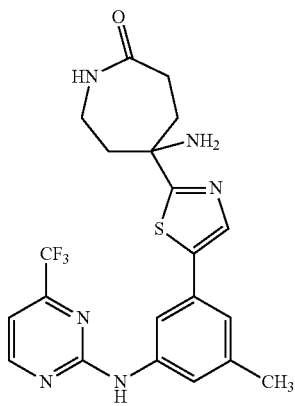 [SMILES: Cc1cc(Nc2nccc(C(F)(F)F)n2)cc(-c2cnc(C3(N)CCNC(=O)CC3)s2)c1]

Step 1

To a stirred solution of (S)-(−)-2-methyl-2-propanesulfinamide (854 mg, 7 mmol) and 1,4-dioxaspiro[4,5]decan-8-one (1 g, 6.40 mmol) in tetrahydrofuran (13 mL) was added titanium(IV) ethoxide (5.11 mL, 16 mmol). The mixture was stirred for 4 h at room temperature, poured over stirring saturated aqueous sodium bicarbonate (10 mL) and acetonitrile (10 mL), and stirred for 20 minutes. Magnesium sulfate was added and the mixture was stirred for 20 minutes, filtered over celite and concentrated. The residue was purified by column chromatography on silica gel (10:90 to 70:30 ethyl acetate:hexanes gradient) to afford N-(1,4-dioxaspiro[4,5]dec-8-ylidene)-2-methylpropane-2-sulfinamide (466 mg, 1.8 mmol, 28% yield) as a white solid. MS ESI: [M+H]$^+$ m/z 260.

Step 2

To diisopropyl amine (318 µL, 2.23 mmol) in tetrahydrofuran (3.7 mL) at 0° C. was added N-butyllithium (2.5 M in hexanes, 892 µL, 2.23 mmol). The mixture was stirred for 15 minutes, then cooled to −78° C. INTERMEDIATE 4 (250 mg, 0.74 mmol) dissolved in tetrahydrofuran (1 mL) was added dropwise over 5 minutes. The mixture was stirred for 30 minutes at −78° C., then the product of Step 1 (212 mg, 0.82 mmol) dissolved in tetrahydrofuran (1 mL) was added dropwise. The reaction mixture was stirred for 2h, and then quenched with saturated aqueous ammonium chloride, extracted with ethyl acetate (3×), and the combined organic fractions were dried over sodium sulfate, filtered, and concentrated. Purification by column chromatography on silica gel (0:100 to 80:20 ethyl acetate:hexanes gradient, then 0:100 to 15:85 methanol:dichloromethane gradient) afforded 2-methyl-N-{8-[5-(3-methyl-5-{[4-(trifluoromethyl)pyrimidin-2-yl]amino}phenyl)-1,3-thiazol-2-yl]-1,4-dioxaspiro[4.5]dec-8-yl}propane-2-sulfinamide (318 mg, 0.40 mmol, 75% yield) as a brown solid. MS ESI: [M+H]$^+$ m/z 596.

Step 3

To the product of Step 2 (100 mg, 0.13 mmol) was added chloroform (630 pt), sodium azide (24.5 mg, 0.38 mmol), and methanesulfonic acid (98 µL, 1.51 mmol). The mixture was heated to 65° C. for 1.5 h., cooled to room temperature, diluted with water, and extracted with ethyl acetate (2×). The combined organic layers were dried over sodium sulfate, filtered, and concentrated. The residue was purified by reverse phase HPLC (35:65 to 70:30 acetonitrile:water with a 0.1% trifluoroacetic acid modifier). The fractions containing the desired product were diluted with ethyl acetate and free based with saturated aqueous sodium bicarbonate. The separated organic layer was dried over magnesium sulfate, filtered and concentrated to afford the title compound (38 mg, 0.083 mmol, 66% yield) as an orange oil. MS ESI: [M+H]$^+$ m/z 463. $^1$H NMR (500 MHz, DMSO-d$_6$) δ 10.26 (s, 1H), 8.83 (s, 1H), 8.75 (s, 1H), 8.02 (s, 1H), 7.93 (s, 1H), 7.49 (s, 1H), 7.28 (d, J=4.7, 1H), 7.16 (s, 1H), 2.39-2.08 (m, 9H), 1.30-0.99 (m, 4H). rhSYK activity=+++

Biological Assay

Homogeneous Time-Resolved Fluorescence (HTRF) Assay for the Recombinant Human SYK Enzyme:

A recombinant GST-hSYK fusion protein was used to measure potency of compounds to inhibit human SYK activity. The recombinant human GST-SYK (Carna Biosciences #08-176) (5 pM final concentration) was incubated with various concentrations of the inhibitor diluted in DMSO (0.1% final concentration) for 10 minutes at room temperature in 15 mM Tris-HCl (pH 7.5), 0.01% tween 20, 2 mM DTT in 384 well plate format. To initiate the reaction the biotinylated substrate peptide (250 nM final concentration) that contains the phosphorylation site for SYK was added with magnesium (5 mM final concentration) and ATP (25 µM final concentration). Final volume of the reaction was 10 µL. Phosphorylation of the peptide was allowed to proceed for 45' at room temperature. To quench the reaction and detect the phosphorylated product, 2 nM of a Europium-anti-phosphotyrosine antibody (Perkin Elmer #AD0161) and 70 nM SA-APC (Perkin-Elmer #CR130-100) were added together in 15 mM Tris pH 7.5, 40 mM EDTA, 0.01% tween 20. Final volume of the quenching solution was 10 µL. The resulting HTRF signal was measured after 30 minutes on a EnVision (Perkin-Elmer) reader using a time-resolved fluorescence protocol. IC$_{50}$ was determined following 10-dose titration (10 µM to 0.508 nM) and four parameter logistic curve fitting using the Merck Assay Data Analyzer. The rhSYK activity (IC50) is expressed as +++ (100 nM or less), ++ (between 100 and 1000 nM), + (between 1 and 10 µM). IC50 for representative compounds of the present invention are provided as follows:

| Compound Name | Syk IC50 |
|---|---|
| 4-{1-hydroxy-1-[5-(3-methyl-5-{[4-(trifluoromethyl)pyrimidin-2-yl]amino}-phenyl)-1,3-thiazol-2-yl]ethyl}benzoic acid | <0.5 nM |
| (1S,4R)-4-[5-(3-cyclopropyl-5-{[4-(trifluoromethyl)pyrimidin-2-yl]amino}phenyl)-1,3-thiazol-2-yl]-4-hydroxy-2,2-dimethylcyclohexanecarboxylic acid | 1 nM |
| 6-hydroxy-6-[5-(3-methyl-5-{[4-(trifluoromethyl)pyrimidin-2-yl]amino}phenyl)-1,3-thiazol-2-yl]spiro[3.3]heptane-2-carboxylic | 2 nM |
| tert-butyl 3-hydroxy-3-[5-(3-methyl-5-{[4-(trifluoromethyl)pyrimidin-2-yl]amino}-phenyl)-1,3-thiazol-2-yl]azetidine-1-carboxylate | 628 nM |
| methyl 4-(5-{3-[(5-chloropyrimidin-2-yl)amino]-5-methylphenyl}-1,3-thiazol-2-yl)-4-hydroxy-2,2-dimethylcyclohexanecarboxylate | 3285 nM |
| ethyl 4-hydroxy-4-(5-{3-methyl-5-[(4-methylpyrimidin-2-yl)amino]phenyl}-1,3-thiazol-2-yl)-2-phenylcyclohexanecarboxylate | 596 nM |
| N-{3-[2-(1,4-diaxaspiro[4.5]dec-8-yl)-1,3-thiazol-5-yl]-5-methylphenyl}-4-(trifluoromethyl)pyrimidin-2-amine | 297 nM |
| 3-hydroxy-3-[5-(3-{[4-(trifluoromethyl)pyrimidin-2-yl]amino}phenyl)-1,3-thiazol-2-yl]pyrrolidine-1-carboxamide | 11 nM |
| 2-[5-(3-fluoro-5-{[4-(trifluaromethyl)pyrimidin-2-yl]amino}phenyl)-1,3-thiazol-2-yl]propane-2-sulfonamide | 818 nM |
| N-[2-hydroxy-1-(hydroxymethyl)ethyl]-5-(3-methyl-5-{[4-(trifluoromethyl)-pyrimidin-2-yl]amino}phenyl)-1,3-thiazole-2-carboxamide | 26 nM |
| methyl (1S,4R)-4-(5-{3-[(4,6-dimethylpyrimidin-2-yl)amino]-5-methylphenyl}-1,3-thiazol-2-yl)-4-hydroxy-2,2-dimethylcyclohexanecarboxylate | 8887 nM |
| 2-(5-{3-[(5-fluoro-4-methoxypyrimidin-2-yl)amino]-5-methylphenyl}-1,3-thiazol-2-yl)propane-1,2-dial | 22 nM |
| {4-hydroxy-4-[5-(3-methyl-5-{[4-(trifluoromethyl)pyrimidin-2-yl]amino}phenyl)-1,3-thiazol-2-yl]azepan-1-yl}acetic acid | 216 nM |
| tert-butyl cis-4-hydroxy-4-{5-[3-({4-[1-(4-methoxybenzyl)-1H-1,2,3-triazol-4-yl]-pyrimidin-2-yl}amino)-5-methylphenyl]-1,3-thiazol-2-yl}cyclohexanecarboxylate | 5912 nM |
| (1S,4R)-4-hydroxy-4-[5-(3-{[4-methoxy-5-(trifluoromethyl)pyrimidin-2-yl]amino}-5-methylphenyl)-1,3-thiazol-2-yl]-2,2-dimethylcyclahexanecarboxylic acid | 20 nM |
| (1S,4R)-4-hydroxy-2,2-dimethyl-4-(5-{3-methyl-5-[(4-methylpyrimidin-2-yl)-amino]phenyl}-1,3-thiazol-2-yl)cyclohexanecarboxylic acid | 1 nM |
| 1-(5-{3-[(4-tert-butylpyrimidin-2-yl)amino]-5-methylphenyl}-1,3-thiazol-2-yl)-cyclobutanol | 25 nM |
| cis-4-hydroxy-4-[5-(3-methyl-5-{[4-(trifluoromethyl)pyrimidin-2-yl]amino}-phenyl)-1,3-thiazol-2-yl]-N-{[6-(2,2,2-trifluoroethoxy)pyridin-3-yl]methyl}-cyclohexanecarboxamide | 222 nM |
| (1S,4R)-N-(cyanomethyl)-4-hydroxy-2,2-dimethyl-4-(5-{3-methyl-5-[(4-methylpyrimidin-2-yl)amino]phenyl}-1,3-thiazol-2-yl)cyclohexanecarboxamide | 2 nM |
| (1S,4R)-4-hydroxy-4-[5-(3-{[4-(2-hydroxyethoxy)pyrimidin-2-yl]amino}-5-methylphenyl)-1,3-thiazol-2-yl]-2,2-dimethylcyclohexanecarboxamide | 3 nM |
| (1S,4R)-4-[5-(3-[(acetylamino)methyl]-5-{[4-(trifluoromethyl)pyrimidin-2-yl]-amino}phenyl)-1,3-thiazol-2-yl]-4-hydroxy-2,2-dimethylcyclohexanecarboxamide | 6 nM |
| N-{3-methyl-5-[2-(1H-pyrazol-5-yl)-1,3-thiazol-5-yl]phenyl}-4-(trifluoromethyl)-pyrimidin-2-amine | 21 nM |
| methyl 4-{difluoro[5-(3-methyl-5-{[4-(trifluoromethyl)pyrimidin-2-yl]amino}-phenyl)-1,3-thiazol-2-yl]methyl}benzoate | 6079 nM |
| (1S,4R)-4-[5-(3-chloro-5-{[4-(trifluoromethyl)pyrimidin-2-yl]amino}phenyl)-1,3-thiazol-2-yl]-4-hydroxy-2,2-dimethylcyclohexanecarboxylic acid | 1 nM |
| Cis-tert-butyl cis-4-hydroxy-4-[5-(3-methyl-5-{[4-(pentafluoroethyl)pyrimidin-2-yl]amino}phenyl)-1,3-thiazol-2-yl]cyclohexanecarboxylate | 2427 nM |
| cis-4-hydroxy-4-(5-{3-methyl-5-[(4-thiophen-2-ylpyrimidin-2-yl)amino]phenyl}-1,3-thiazol-2-yl)cyclohexanecarboxylic acid | 1 nM |
| 3-[5-(3-methyl-5-{[4-(trifluoromethyl)pyrimidin-2-yl]amino}phenyl)-1,3-thiazol-2-yl]propanoic acid | 3 nM |
| N-(3-methyl-5-{2-[2-methyl-2-(1,3,4-oxadiazol-2-yl)propyl]-1,3-thiazol-5-yl}-phenyl)-4-(trifluoromethyl)pyrimidin-2-amine | 7 nM |
| 4-{[5-(3-methyl-5-{[4-(trifluoromethyl)pyrimidin-2-yl]amino}phenyl)-1,3-thiazol-2-yl]carbonyl}piperazin-2-one | 314 nM |
| N-(dicyclopropylmethyl)-N-methyl-5-(3-methyl-5-{[4-(trifluoromethyl)pyrimidin-2-yl]amino}phenyl)-1,3-thiazole-2-carboxamide | 1253 nM |
| (1S,4R)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid | <0.5 nM |
| (1-methyl-1H-pyrazol-5-yl)[5-(3-{[4-(trifluoromethyl)pyrimidin-2-yl]amino}-phenyl)-1,3-thiazol-2-yl]methanol | 237 nM |
| 2-({[5-(3-methyl-5-{[4-(trifluoromethyl)pyrimidin-2-yl]amino}phenyl)-1,3-thiazol-2-yl]methyl}amino)ethanesulfonamide | 5 nM |
| 1-({[5-(3-methyl-5-{[4-(trifluoromethyl)pyrimidin-2-yl]amino}phenyl)-1,3-thiazol-2-yl]methyl}amino)cyclobutanecarboxylic acid | 12 nM |
| trans-4-hydroxy-1-methyl-4-[5-(3-{[4-(trifluoromethyl)pyrimidin-2-yl]amino}-phenyl)-1,3-thiazol-2-yl]cyclohexanecarboxylic acid | 4 nM |
| cis-4-hydroxy-1-methyl-4-[5-(3-{[4-(trifluoromethyl)pyrimidin-2-yl]amino}-phenyl)-1,3-thiazol-2-yl]cyclohexanecarboxylic acid | 2 nM |
| 1-[5-(3-methyl-5-{[4-(methylsulfanyl)pyrimidin-2-yl]amino}phenyl)-1,3-thiazol-2-yl]cyclobutanol | 24 nM |
| 8-[2-(2,2-difluoro-1-hydroxyethyl)-1,3-thiazol-5-yl]-2,2-dimethyl-6-{[4-(trifluoromethyl)pyrimidin-2-yl]amino}-2H-1,4-benzoxazin-3(4H)-one | 15 nM |

-continued

| Compound Name | Syk IC50 |
|---|---|
| 1-{5-[3-(morpholin-4-yl)-5-{[4-(trifluoromethyl)pyrimidin-2-yl]amino}phenyl]-1,3-thiazol-2-yl}cyclobutanol | 13 nM |
| cis-4-[(hydroxyacetyl)amino]-1-[5-(3-methyl-5-{[4-(trifluoromethyl)pyrimidin-2-yl]amino}phenyl)-1,3-thiazol-2-yl]cyclohexanecarboxamide | 2 nM |
| (1S,4R)-4-hydroxy-2,2-dimethyl-4-[5-(3-methyl-5-{[4-(trifluoromethyl)pyrimidin-2-yl]amino}phenyl)-1,3-thiazol-2-yl]-N-[3-(2-oxopyrrolidin-1-yl)propyl]-cyclohexanecarboxamide | 1 nM |
| (1S,2R,4R)-4-hydroxy-2-methyl-4-[5-(3-methyl-5-{[4-(trifluoromethyl)pyrimidin-2-yl]amino}phenyl)-1,3-thiazol-2-yl]cyclohexanecarboxylic acid and enantiomer | 1 nM, <0.5 nM |
| (1S,4R)-4-methoxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid | 2 nM |
| (1R,4S)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid | 2 nM |
| N-{3-[2-(1-aminocyclobutyl)-1,3-thiazol-5-yl]-5-methylphenyl}-4-cyclopropyl-pyrimidin-2-amine hydrochloride | 3 nM |
| 1-{Cis-4-hydroxy-4-[5-(3-methyl-5-{[4-(trifluoromethyl)pyrimidin-2-yl]amino}-phenyl)-1,3-thiazol-2-yl]cyclohexyl}pyrrolidin-2-one | 4 nM |
| (1S,4R)-4-(hydroxymethyl)-3,3-dimethyl-1-(5-(3-methyl-5-(4-(trifluoromethyl)-pyrimidin-2-ylamino)phenyl)thiazol-2-yl)cyclohexanol | 13 nM |
| Ethyl (1R,4S)-4-hydroxy-2,2-dimethyl-4-[5-(3-methyl-5-{[4-(trifluoromethyl)-pyrimidin-2-yl]amino}phenyl)-1,3-thiazol-2-yl]cyclohexanecarboxylate | 49 nM |
| 5-(aminomethyl)-5-[5-(3-methyl-5-{[4-(trifluoromethyl)pyrimidin-2-yl]amino}-phenyl)-1,3-thiazol-2-yl]azepan-2-one | 50 nM |
| (1S,4R)-4-{5-[3-({4-[(1S)-1-fluoroethyl]pyrimidin-2-yl}amino)-5-methylphenyl]-1,3-thiazol-2-yl}-4-hydroxy-2,2-dimethylcyclohexanecarboxylic acid | <0.5 nM |
| (1S,4R)-4-{5-[3-({4-[(1R)-1-fluoroethyl]pyrimidin-2-yl}amino)-5-methylphenyl]-1,3-thiazol-2-yl}-4-hydroxy-2,2-dimethylcyclohexanecarboxylic acid | <0.5 nM |

What is claimed is:
1. A compound having the formula (Ib) or a pharmaceutically acceptable salt thereof:

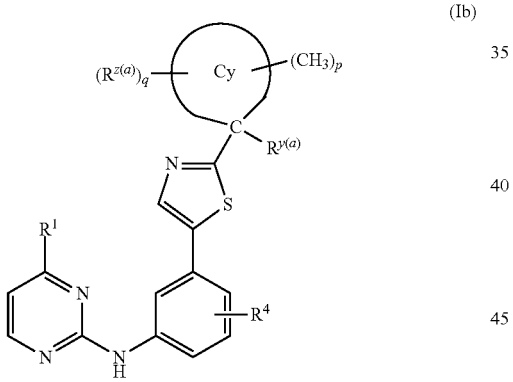

(Ib)

wherein
$R^1$ is selected from H, $C_{1-4}$alkyl, $C_{1-4}$haloalkyl, $C_{3-6}$cycloalkyl, and $OC_{1-4}$alkyl;
$R^4$ is selected from H, $C_{1-4}$alkyl, and $C_{3-4}$cycloalkyl;
Cy is selected from $C_{4-7}$cycloalkyl, oxetanyl, pyrrolidinyl, piperidinyl, and azepanyl;
$R^{y(a)}$ is aminomethyl, OH, $OCH_3$, $OCH_2CH_2OH$, F, CN, $CO_2R^{a(a)}$, $CONR^{b(a)}R^{c(a)}$, $NR^{a(a)}R^{a(a)}$, NHC(O)$C_{1-3}$alkyl (optionally substituted with OH), NHC(O)$NH_2$, $NHSO_2NH_2$, $NHSO_2C_{1-3}$alkyl, or $NHSO_2C_{1-3}$haloalkyl;
$R^{z(a)}$ is selected from (A) $C_{1-4}$ alkyl optionally substituted with one to three groups independently selected from OH, $NH_2$, CN, $CO_2R^{a(a)}$ and $CONH_2$, (B) $C_{1-3}$-fluoroalkyl, (C) halogen, (D) CN, (E) $COC_{1-4}$alkyl (optionally substituted with one or two groups independently selected from $OR^{a(a)}$, CN, $CO_2R^{a(a)}$, $CONR^{a(a)}R^{a(a)}$, and $NR^{a(a)}R^{a(a)}$), (F) CO-phenyl (optionally substituted with one or two groups independently selected from ethynyl, $CO_2R^{a(a)}$, CN, F and OH), (G) CO—$C_{3-6}$cycloalkyl (optionally substituted with OH or $CO_2R^{a(a)}$), (H) $C_{0-3}$alkyl-$CO_2R^{a(a)}$, (I) —C(O)$NR^{b(a)}R^{c(a)}$, (J) —$OR^{a(a)}$, (K) —OC(O)$R^{a(a)}$, (L) —$NR^{b(a)}R^{c(a)}$, (M) —NHC(O)$C_{1-4}$alkyl (optionally substituted with one to three OH or a $CONR^{a(a)}R^{a(a)}$), (N) —$NHSO_2C_{1-3}$alkyl, (O) —$NHSO_2NH_2$, (P) oxo, (Q) 1,3,4-oxadiazole-2(3H)-one, (R) 1,2,4-oxadiazole-5(4H)-one, (S) $SO_2NH_2$, (T) $SO_2C_{1-3}$alkyl, (U) $SO_2C_{1-3}$haloalkyl, and (V) $SO_2Ph$;
$R^{a(a)}$ is H or $C_{1-4}$alkyl;
$R^{b(a)}$ and $R^{c(a)}$ are independently selected from (A) H, (B) $C_{3-6}$cycloalkyl optionally substituted with OH, (C) heteroaryl selected from imidazolyl, pyridyl and indolyl, (D) tetrahydrofuranyl, (E) benzyl, (F) phenyl optionally substituted with one or two groups independently selected from $(CH_2)_{0-2}OH$ and F, (G1) $C_{1-4}$alkyl and (G2) $C_{1-4}$haloalkyl, wherein (G1) and (G2) are each optionally substituted with one to three groups independently selected from (i) OH, (ii) $C_{3-6}$cycloalkyl optionally substituted with one or two groups independently selected from $C_{1-4}$alkyl, $CONH_2$, $CO_2H$ and $CH_2OH$, (iii) $CONH_2$, (iv) $SO_2NH_2$, (v) $SO_2C_{1-4}$alkyl, (vi) 4- to 7-membered monocyclic heterocyclyl optionally substituted with one or two groups independently selected from oxo, $(CH_2)_{0-2}OH$, and $C_{1-4}$alkyl, (vii) a 5- or 6-membered heteroaryl optionally substituted with one or two groups independently selected from carboxy, $(CH_2)_{0-2}OH$, and $C_{1-4}$alkyl, (viii) CN, (x) $OC_{1-4}$alkyl, (ix) $CO_2H$, (xii) $NR^{a(a)}C(O)C_{1-4}$alkyl, (x) phenyl optionally substituted with one or two groups independently selected from $(CH_2)_{0-2}OH$, $SO_2NH_2$, $CF_3$, F and Cl, (xi) 1-pyrrolidinyl optionally substituted with oxo, (xii) 1-imidazolidinyl optionally substituted with oxo, (xiii) 1-piperidinyl optionally substituted with oxo, and (xiv) 4-morpholinyl; or
$R^{b(a)}$ and $R^{c(a)}$ together with the nitrogen atom to which they are attached form a 6- or 7-membered heterocycle having 0 to 1 additional heteroatom selected from N, O and S, wherein said heterocycle is optionally substituted with one or two groups independently selected from oxo, CN, $(CH_2)_{0-2}OH$, acetyl, benzyl, $SO_2C_{1-4}$alkyl, $CONH_2$, methoxymethyl, carboxymethyl, $CO_2R^{a(a)}$ and $C_{1-4}$alkyl;

p is 0 to 4; and q is 0, 1 or 2.

2. The compound of claim 1 or a pharmaceutically acceptable salt thereof wherein Cy is cyclohexyl.

3. The compound of claim 1 or a pharmaceutically acceptable salt thereof wherein Cy is cyclohexyl, q is 1, p is 0, 1 or 2, and $R^{z(a)}$ is selected from $CO_2R^{a(a)}$, $CONR^{b(a)}R^{c(a)}$ and $NHC(O)C_{1-4}$alkyl optionally substituted with OH.

4. The compound of claim 3 or a pharmaceutically acceptable salt thereof wherein $R^{y(a)}$ is OH.

5. The compound of claim 3 or a pharmaceutically acceptable salt thereof wherein $R^{y(a)}$ is $CONH_2$.

6. The compound of claim 1 or a pharmaceutically acceptable salt thereof wherein Cy is azepanyl, p is 0, q is 1, and $R^{z(a)}$ is oxo.

7. The compound of claim 6 or a pharmaceutically acceptable salt thereof wherein $R^{y(a)}$ is OH.

8. A compound having the formula (Ic) or a pharmaceutically acceptable salt thereof:

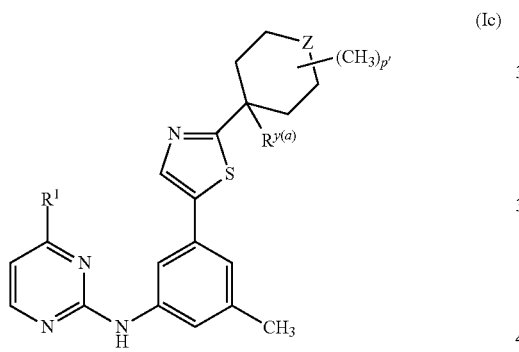

(Ic)

wherein

Z is $-CR^{z(b)}R^{z(c)}-$, $-N(R^{z(d)})-$, $-CH_2-N(R^{z(d)})-$, or $-NHC(O)-$;

p' is 0 to 3, with the proviso that p' is 0 when Z is $-NHC(O)-$;

$R^{z(b)}$ is selected from (A) H, (B) $C_{1-4}$ alkyl optionally substituted with one to three groups independently selected from OH, $NH_2$, CN, $CO_2R^{a(a)}$ and $CONH_2$, (C) halogen, (D) CN, (E) $-C(O)R^{a(a)}$, (F) $-C(O)_2R^{a(a)}$, (G) $-C(O)NR^{b(a)}R^{c(a)}$, (H) $-OR^{a(a)}$, (I) $-OC(O)R^{a(a)}$, (J) $-NR^{b(a)}R^{c(a)}$, (K) $-NHC(O)C_{1-4}$alkyl (optionally substituted with OH), (L) $-NHSO_2C_{1-3}$alkyl, (M) $-NHSO_2NH_2$, (N) 1,3,4-oxadiazole-2(3H)-one, and (O) 1,2,4-oxadiazole-5(4H)-one;

$R^{z(c)}$ is H or methyl;

$R^{z(d)}$ is selected from (A) H, (B) $C_{1-3}$ alkyl optionally substituted with a group selected from $CO_2R^{a(a)}$ and $CONH_2$, (C) $C_{1-3}$fluoroalkyl, (D) $COC_{1-4}$alkyl (optionally substituted with one or two groups independently selected from $OR^{a(a)}$, CN, $CO_2R^{a(a)}$, $CONR^{a(a)}R^{a(a)}$, and $NR^{a(a)}R^{a(a)}$), (E) CO-phenyl (optionally substituted with one or two groups independently selected from ethynyl, $CO_2R^{a(a)}$, CN, F and OH), (F) $CO-C_{3-6}$cycloalkyl (optionally substituted with OH or $CO_2R^{a(a)}$), (G) $C_{0-3}$alkyl-$CO_2R^{a(a)}$, (H) $CONR^{a(a)}R^{a(a)}$, (I) CONH-phenyl (optionally substituted with one or two groups independently selected from $C_{1-4}$alkyl, CN, and Cl), (J) $CONH-C_{3-6}$cycloalkyl, (K) $SO_2NH_2$, (L) $SO_2C_{1-3}$alkyl, (M) $SO_2C_{1-3}$haloalkyl, and (N) $SO_2Ph$;

$R^1$ is selected from H, $C_{1-4}$alkyl, $C_{1-4}$haloalkyl, $C_{3-6}$cycloalkyl, and $OC_{1-4}$alkyl;

$R^4$ is selected from H, $C_{1-4}$alkyl, and $C_{3-4}$cycloalkyl;

$R^{y(a)}$ is aminomethyl, OH, $OCH_3$, $OCH_2CH_2OH$, F, CN, $CO_2R^{a(a)}$, $CONR^{b(a)}R^{c(a)}$, $NR^{a(a)}R^{a(a)}$, $NHC(O)C_{1-3}$alkyl (optionally substituted with OH), $NHC(O)NH_2$, $NHSO_2NH_2$, $NHSO_2C_{1-3}$alkyl, or $NHSO_2C_{1-3}$haloalkyl;

$R^{a(a)}$ is H or $C_{1-4}$alkyl; and $R^{b(a)}$ and $R^{c(a)}$ are independently selected from (A) H, (B) $C_{3-6}$cycloalkyl optionally substituted with OH, (C) heteroaryl selected from imidazolyl, pyridyl and indolyl, (D) tetrahydrofuranyl, (E) benzyl, (F) phenyl optionally substituted with one or two groups independently selected from $(CH_2)_{0-2}OH$ and F, (G1) $C_{1-4}$alkyl and (G2) $C_{1-4}$haloalkyl, wherein (G1) and (G2) are each optionally substituted with one to three groups independently selected from (i) OH, (ii) $C_{3-6}$cycloalkyl optionally substituted with one or two groups independently selected from $C_{1-4}$alkyl, $CONH_2$, $CO_2H$ and $CH_2OH$, (iii) $CONH_2$, (iv) $SO_2NH_2$, (v) $SO_2C_{1-4}$alkyl, (vi) 4- to 7-membered monocyclic heterocyclyl optionally substituted with one or two groups independently selected from oxo, $(CH_2)_{0-2}OH$, and $C_{1-4}$alkyl, (vii) a 5- or 6-membered heteroaryl optionally substituted with one or two groups independently selected from carboxy, $(CH_2)_{0-2}OH$, and $C_{1-4}$alkyl, (viii) CN, (x) $OC_{1-4}$alkyl, (ix) $CO_2H$, (xii) $NR^{a(a)}C(O)C_{1-4}$alkyl, (x) phenyl optionally substituted with one or two groups independently selected from $(CH_2)_{0-2}OH$, $SO_2NH_2$, $CF_3$, F and Cl, (xi) 1-pyrrolidinyl optionally substituted with oxo, (xii) 1-imidazolidinyl optionally substituted with oxo, (xiii) 1-piperidinyl optionally substituted with oxo, and (xiv) 4-morpholinyl; or $R^{b(a)}$ and $R^{c(a)}$ together with the nitrogen atom to which they are attached form a 6- or 7-membered heterocycle having 0 to 1 additional heteroatom selected from N, O and S, wherein said heterocycle is optionally substituted with one or two groups independently selected from oxo, CN, $(CH_2)_{0-2}OH$, acetyl, benzyl, $SO_2C_{1-4}$alkyl, $CONH_2$, methoxymethyl, carboxymethyl, $CO_2R^{a(a)}$ and $C_{1-4}$alkyl.

9. The compound of claim 8 or a pharmaceutically acceptable salt thereof wherein Z is $-CHR^{z(b)}-$, and p' is 0, 1 or 2.

10. The compound of claim 8 or a pharmaceutically acceptable salt thereof wherein Z is $-NHC(O)-$.

11. The compound of claim 9 or a pharmaceutically acceptable salt thereof wherein $R^{z(b)}$ is $-C(O)_2R^{a(a)}$, $-C(O)NHR^{b(a)}$ or $-C(O)NH_2$.

12. The compound of claim 8 or a pharmaceutically acceptable salt thereof wherein $R^{z(b)}$ is $-C(O)_2R^{a(a)}$, $-C(O)NHR^{b(a)}$ or $-C(O)NH_2$, and $R^{y(a)}$ is OH or $CONH_2$.

13. The compound of claim 1 having the formula (Id) or a pharmaceutically acceptable salt thereof:

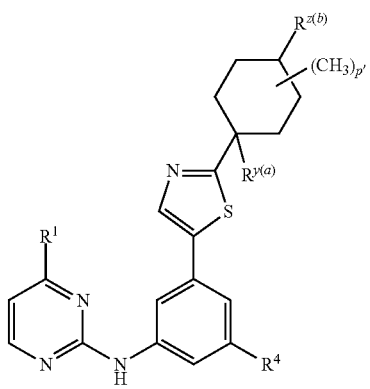

(Id)

wherein
p' is 0, 1 or 2;
$R^{y(a)}$ is selected from OH, OCH$_3$, F, CN and CONH$_2$;
$R^{z(b)}$ is selected from (a) C$_{1-4}$ alkyl optionally substituted with one or more groups independently selected from OH, NH$_2$, CN, CO$_2$R$^{a(a)}$ and CONH$_2$, (b) CN, (c) —C(O)$_2$R$^{a(a)}$, (d) —C(O)NHR$^{b(a)}$, (e) —NHC(O) C$_{1-4}$alkyl (optionally substituted with OH), (f) 1,3,4-oxadiazole-2(3H)-one, and (g) 1,2,4-oxadiazole-5(4H)-one;
R$^1$ is selected from H, methyl, isopropyl, difluoromethyl, trifluoromethyl, 1-fluoroethyl, cyclopropyl and isopropyloxy;
R$^4$ is selected from H, methyl and cyclopropyl;
R$^{a(a)}$ is H or C$_{1-4}$ alkyl; and
R$^{b(a)}$ is H, C$_{1-4}$ alkyl optionally substituted 2-oxo-1-pyrrolidinyl.

14. The compound of claim 13 or a pharmaceutically acceptable salt thereof, wherein R$^{y(a)}$ is OH.

15. The compound of claim 13 or a pharmaceutically acceptable salt thereof, wherein R$^{z(b)}$ is CO$_2$H, CONH$_2$, CONH(CH$_2$)$_3$-(2-oxo-1-pyrrolidinyl), or NHC(O)CH$_2$OH.

16. The compound of claim 1 selected from the group consisting of:
(1R,4S)-4-[5-(3-cyclopropyl-5-{[4-(trifluoromethyl)pyrimidin-2-yl]amino}phenyl)-1,3-thiazol-2-yl]-4-hydroxy-2,2-dimethylcyclohexanecarboxylic acid;
(1S,4R)-4-[5-(3-cyclopropyl-5-{[4-(trifluoromethyl)pyrimidin-2-yl]amino}phenyl)-1,3-thiazol-2-yl]-4-hydroxy-2,2-dimethylcyclohexanecarboxylic acid;
(1S,4R)-4-[5-(3-{[4-(difluoromethyl)pyrimidin-2-yl]amino}-5-methylphenyl)-1,3-thiazol-2-yl]-4-hydroxy-2,2-dimethylcyclohexanecarboxylic acid;
trans-4-hydroxy-4-[5-(3-methyl-5-{[4-(trifluoromethyl)pyrimidin-2-yl]amino}phenyl)-1,3-thiazol-2-yl]cyclohexanecarboxylic acid;
cis-4-hydroxy-4-[5-(3-methyl-5-{[4-(trifluoromethyl)pyrimidin-2-yl]amino}phenyl)-1,3-thiazol-2-yl]cyclohexanecarboxylic acid;
5-hydroxy-5-[5-(3-methyl-5-{[4-(trifluoromethyl)pyrimidin-2-yl]amino}phenyl)-1,3-thiazol-2-yl]azepan-2-one;
cis-4-[(hydroxyacetyl)amino]-1-[5-(3-methyl-5-{[4-(trifluoromethyl)pyrimidin-2-yl]amino}phenyl)-1,3-thiazol-2-yl]cyclohexanecarboxamide; and
(1S,4R)-4-hydroxy-2,2-dimethyl-4-[5-(3-methyl-5-{[4-(trifluoromethyl)pyrimidin-2-yl]amino}phenyl)-1,3-thiazol-2-yl]-N-[3-(2-oxopyrrolidin-1-yl)propyl]cyclohexanecarboxamide;

(1S,4R)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid;
(1R,4S)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid;
(1S,4S)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid;
(1R,4R)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid;
(1R,4S)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxamide;
(1S,4R)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxamide;
(1S,4R)4-{5-[3-({4-[(1R)-1-fluoroethyl]pyrimidin-2-yl}amino)-5-methylphenyl]-1,3-thiazol-2-yl}-4-hydroxy-2,2-dimethylcyclohexanecarboxylic acid; and
(1S,4R)4-{5-[3-({4-[(1S)-1-fluoroethyl]pyrimidin-2-yl}amino)-5-methylphenyl]-1,3-thiazol-2-yl}-4-hydroxy-2,2-dimethylcyclohexanecarboxylic acid;
or a pharmaceutically acceptable salt thereof.

17. The compound of claim 1 selected from the group consisting of:
trans-4-hydroxy-4-[5-(3-methyl-5-{[4-(trifluoromethyl)pyrimidin-2-yl]amino}phenyl)-1,3-thiazol-2-yl]cyclohexanecarboxylic acid;
cis-4-hydroxy-4-[5-(3-methyl-5-{[4-(trifluoromethyl)pyrimidin-2-yl]amino}phenyl)-1,3-thiazol-2-yl]cyclohexanecarboxylic acid;
5-hydroxy-5-[5-(3-methyl-5-{[4-(trifluoromethyl)pyrimidin-2-yl]amino}phenyl)-1,3-thiazol-2-yl]azepan-2-one;
cis-4-[(hydroxyacetyl)amino]-1-[5-(3-methyl-5-{[4-(trifluoromethyl)pyrimidin-2-yl]amino}phenyl)-1,3-thiazol-2-yl]cyclohexanecarboxamide;
4-hydroxy-2,5-dimethyl-4-(5-{3-methyl-5-[(4-methylpyrimidin-2-yl)amino)]phenyl}-1,3-thiazol-2-yl}cyclohexanecarboxylic acid;
4-hydroxy-2,5-dimethyl-4-[5-{3-methyl-5-{[4-(trifluoromethyl)pyrimidin-2-yl]amino}phenyl}-1,3-thiazol-2-yl]cyclohexanecarboxylic acid; or
a pharmaceutically acceptable salt thereof.

18. A compound which is 5-hydroxy-5-[5-(3-methyl-5-{[4-(trifluoromethyl)pyrimidin-2-yl]amino}phenyl)-1,3-thiazol-2-yl]azepan-2-one, or a pharmaceutically acceptable salt thereof.

19. A compound which is (1S,4R)-4-hydroxy-2,2-dimethyl-4-[5-(3-methyl-5-{[4-(trifluoromethyl)pyrimidin-2-yl]amino}phenyl)-1,3-thiazol-2-yl]-N-[3-(2-oxopyrrolidin-1-yl)propyl]cyclohexanecarboxamide, or a pharmaceutically acceptable salt thereof.

20. A compound which is cis-4-[(hydroxyacetyl)amino]-1-[5-(3-methyl-5-{[4-(trifluoromethyl)pyrimidin-2-yl]amino}phenyl)-1,3-thiazol-2-yl]cyclohexanecarboxamide, or a pharmaceutically acceptable salt thereof.

21. A compound which is (1S,4R)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid, or a pharmaceutically acceptable salt thereof.

22. A compound which is (1S,4R)-4-{5-[3-({4-[(1S)-1-fluoroethyl]pyrimidin-2-yl}amino)-5-methylphenyl]-1,3-thiazol-2-yl}-4-hydroxy-2,2-dimethylcyclohexanecarboxylic acid, or a pharmaceutically acceptable salt thereof.

23. A compound which is (1S,4R)-4-{5-[3-({4-[(1R)-1-fluoroethyl]pyrimidin-2-yl}amino)-5-methylphenyl]-1,3-thiazol-2-yl}-4-hydroxy-2,2-dimethylcyclohexanecarboxylic acid, or a pharmaceutically acceptable salt thereof.

24. A compound which is 4-hydroxy-2,5-dimethyl-4-(5-{3-methyl-5-[(4-methylpyrimidin-2-yl)amino)]phenyl]-1,3-thiazol-2-yl}cyclohexanecarboxylic acid, or a pharmaceutically acceptable salt thereof.

25. A compound which is 4-hydroxy-2,5-dimethyl-4-[5-{3-methyl-5-{[4-(trifluoromethyl)pyrimidin-2-yl]amino}phenyl}-1,3-thiazol-2-yl]cyclohexanecarboxylic acid, or a pharmaceutically acceptable salt thereof.

26. A compound, which is 5-hydroxy-5-[5-(3-methyl-5-{[4-(trifluoromethyl)pyrimidin-2-yl]amino}phenyl)-1,3-thiazol-2-yl]azepan-2-one.

27. A compound, which is (1S,4R)-4-hydroxy-2,2-dimethyl-4-[5-(3-methyl-5-{[4-(trifluoromethyl)pyrimidin-2-yl]amino}phenyl)-1,3-thiazol-2-yl]-N-[3-(2-oxopyrrolidin-1-yl)propyl]cyclohexanecarboxamide.

28. A compound, which is cis-4-[(hydroxyacetyl)amino]-1-[5-(3-methyl-5-{[4-(trifluoromethyl)pyrimidin-2-yl]amino}phenyl)-1,3-thiazol-2-yl]cyclohexanecarboxamide.

29. A compound, which is (1S,4R)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid.

30. A compound, which is (1S,4R)-4-{5-[3-({4-[(1S)-1-fluoroethyl]pyrimidin-2-yl}amino)-5-methylphenyl]-1,3-thiazol-2-yl}-4-hydroxy-2,2-dimethylcyclohexanecarboxylic acid.

31. A compound, which is (1S,4R)-4-{5-[3-({4-[(1R)-1-fluoroethyl]pyrimidin-2-yl}amino)-5-methylphenyl]-1,3-thiazol-2-yl}-4-hydroxy-2,2-dimethylcyclohexanecarboxylic acid.

32. The pharmaceutical composition comprising a therapeutically effective amount of the compound of claim 1 or a pharmaceutically acceptable salt thereof and a pharmaceutically acceptable carrier.

33. A method for the treatment of rheumatoid arthritis which comprises administering to a mammal in need thereof a therapeutically effective amount of the compound of claim 1 or a pharmaceutically acceptable salt thereof.

34. A method for the treatment of asthma which comprises administering to a mammal in need thereof a therapeutically effective amount of a compound of claim 1, or a pharmaceutically acceptable salt thereof.

35. The method of claim 33, wherein the compound administered is 5-hydroxy-5-[5-(3-methyl-5-{[4-(trifluoromethyl)pyrimidin-2-yl]amino}phenyl)-1,3-thiazol-2-yl]azepan-2-one, or a pharmaceutically acceptable salt thereof.

36. The method of claim 33, wherein the compound administered is (1S,4R)-4-hydroxy-2,2-dimethyl-4-[5-(3-methyl-5-{[4-(trifluoromethyl)pyrimidin-2-yl]amino}phenyl)-1,3-thiazol-2-yl]-N-[3-(2-oxopyrrolidin-1-yl)propyl]cyclohexanecarboxamide, or a pharmaceutically acceptable salt thereof.

37. The method of claim 33, wherein the compound administered is (1S,4R)-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylic acid, or a pharmaceutically acceptable salt thereof.

38. The method of claim 33, wherein the compound b administered is (1S,4R)-4-{5-[3-({4-[(1S)-1-fluoroethyl]pyrimidin-2-yl}amino)-5-methylphenyl]-1,3-thiazol-2-yl}-4-hydroxy-2,2-dimethylcyclohexanecarboxylic acid, or a pharmaceutically acceptable salt thereof.

39. The method of claim 33, wherein the compound administered is (1S,4R)-4-{5-[3-({4-[(1R)-1-fluoroethyl]pyrimidin-2-yl}amino)-5-methylphenyl]-1,3-thiazol-2-yl}-4-hydroxy-2,2-dimethylcyclohexanecarboxylic acid, or a pharmaceutically acceptable salt thereof.

40. A method for the treatment of systemic lupus erythematosis which comprises administering to a mammal in need thereof a therapeutically effective amount of a compound of claim 1, or a pharmaceutically acceptable salt thereof.

* * * * *